US006706867B1

(12) United States Patent
Lorenz

(10) Patent No.: US 6,706,867 B1
(45) Date of Patent: Mar. 16, 2004

(54) DNA ARRAY SEQUENCE SELECTION

(75) Inventor: Matthias Lorenz, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 132 days.

(21) Appl. No.: 09/741,238

(22) Filed: Dec. 19, 2000

(51) Int. Cl.$^7$ ............................. C07H 21/04; C12Q 1/68
(52) U.S. Cl. ................. 536/23.1; 536/24.32; 536/24.31; 536/24.3; 435/6
(58) Field of Search .......................... 435/6; 536/24.32, 536/24.31, 24.33, 23.1

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91.2 |
| 4,965,188 A | 10/1990 | Mullis et al. | 435/6 |
| 5,744,305 A | 4/1998 | Fodor et al. | 435/6 |
| 5,753,788 A | 5/1998 | Fodor et al. | 536/22.1 |
| 5,770,456 A | 6/1998 | Holmes | 435/518 |
| 6,077,693 A | 6/2000 | Tang et al. | 435/69.5 |

FOREIGN PATENT DOCUMENTS

| | | |
|---|---|---|
| WO | WO 95/11995 | 5/1995 |
| WO | WO 99/37774 | 7/1999 |
| WO | WO/9942813 | 8/1999 |

OTHER PUBLICATIONS

Anderson and Young (1985) Quantitative Filter Hybridization in *Nucleic Acid Hybridization*.
Kacian et al. (1972) "A Replicating RNA Molecule Suitable for a Detailed Analysis of Extracellular Evolution and Replication," Proc. Natl. Acad. Sci. USA 69:3038.
Chamberlin et al. (1970) "New RNA Polymerase from *Escherichia coli* infected with Bacteriophage T7," Nature 228:227.
Wu and Wallace (1989) "The Ligation Amplification Reaction (LAR)—Amplification of Specific DNA Sequences Using Sequential Rounds of Template–Dependent Ligation," Genomics 4:560.
H.A. Erlich (ed.), PCR Technology, Stockton Press [1989].
Emmert–Buck et al. (1996) "Laser Capture Microdissection," Science 274:998.
Lorenz (2000) NIH Lab Book, NIH, Gaithersburg, MD.
Staudt and Brown (2000) "Genomic Views of the Immune System,"Ann. Rev. Immunol. 18:829–859.
Manger and Relman (2000) "How the host "sees"pathogens: global gene expression responses to infection," Curr. Opin. Immunol. 12:215–218.
Lockhart et al. (1996) "Expression monitoring by hybridization to high–density oligonucleotide arrays," Nat. Biotechnol. 14:1675–1680.
Kelly and Rizzino (200) "DNA Microarray Analyses of Genes Regulated During the Differentiation of Embryonic Stem Cells," Mol. Repro. Dev. 56:113–123.
Tanaka et al. (2000) "Genome–wide expression profiling of mid–gestation placenta and embryo using a 15,000 mouse developmental cDNA microarray," Proc. Natl. Acad. Sci. 97:9127–9132.
Foster and Chanock (200) "Mining variations in genes of innate and phagocytic immunity: current status and future prospects," Curr. Opin. Hematol. 7:9–15.
Walker and Rigley (200) "Gene expression profiling in human peripheral blood mononuclear cells using high–density filter–based cDNA microarrays," J. Immunol. Meth. 239:167–179.
Heller et al. (1997) "Discovery and analysis of inflammatory disease–related genes using cDNA microarrays," Proc. Natl. Acad. Sci. USA 94:2150–2155.
Ramsay (1998) "DNA chips: State–of–the–art," Nat. Biotechnol. 16:40–44.
Schena et al. (1998) "Microarrays: biotechnology's discovery platform for functional genomics," Trends Biotechnol. 16:301–306.
Epstein and Butow (2000) "Microarray technology—enhanced versatility, persistent challenge," Curr. Opin. Biotechnol. 11:36–41.
Sherlock (2000) "Analysis of large–scale gene expression data," Curr. Opin. Biotechnol. 12:201–205.
Schena et al. (1996) "Parallel human genome analysis: Microarray–based expression moniotoring of 1,000 genes," Proc. Natl. Acad. Sci. USA 93:10614–10619.
Kurian et al. (1999) "DNA Chip Technology," J. Pathol. 187:267–271.
Ferguson et al.(1996) "A fiber–optic DNA biosensor microarray for the analysis of gene expression," Nat. Biotechnol. 14:1681–1684.
Zweiger (1999) "Knowledge discovery in gene–expression–microarray data: mining the information output of the genome," Trends Biotechnl. 17:429–436.
Lennon and Lehrach (1991) "Hybridization analyses of arrayed cDNA libraries," Trends Genet. 7:314–317.
Chang and Laimins (2000) "Microarray Analysis Identifies Interferon–Inducible Genes and Stat–1 as Major Transcriptional Targets of Human Papillomavirus Type 31," J. Virol. 74:4174–4182.

(List continued on next page.)

*Primary Examiner*—Kenneth R. Horlick
*Assistant Examiner*—Cynthia Wilder
(74) *Attorney, Agent, or Firm*—Leydig, Voit & Mayer, Ltd.

(57) ABSTRACT

The present invention provides methods and compositions for the construction of custom cDNA microarrays. In particular, the methods involve the selection of relevant clusters based on knowledge and expression patterns using public database information and the identification of the best representative cDNA clones within the selected cluster. The methods facilitate the construction of custom microarrays suitable for use in any biotechnological art. In preferred embodiments, the present invention provides the the ImmunoChip.

8 Claims, 29 Drawing Sheets

OTHER PUBLICATIONS

Abdellatif (2000) "Leading the Way Using Microarray," Cir. Res. 86:919–920.

Gress et al. (1992) "Hybridization fingerprinting of high–density cDNA–library arrays with cDNA pools derived from whole tissues," Mammal. Genome 3:609–619.

Brazma et al. (2000) "One–stop ship for microarray data," Nature 403:699–700.

Lee and Lee (2000) "Genomic analysis," Curr. Opin. Biotechnol. 11:171–175.

Carulli et al. (1998) "High Throughput Analysis of Differential Gene Expression," J. Cell. Biochem. Suppl. 30/31:286–296.

Khan et al. (1999) "DNA microarray technology: the anticipated impact on the study of human disease," Biochim. Biophys. Acta 1423:M17–M–28.

Jain (2000) "Biotechnological applications of lab–chips and microarrays," Trends Biotechnol. 18:278–280.

Fodor et al. (1993) "Multiplexed biochemical assays with biological chips," Nature 364:555–556.

Cheung et al. (1999) Making and reading microarrays, Nat. Genet. Suppl. 21:15–19.

Battaglia et al. (2000) "Analysis of DNA Microarrays by Non–Destrictove Fluorescent Staining Using SYBR® Green II," BioTech. 29:78–81.

Borrebaeck (1998) "Tapping the potential of molecular libraries in functional genomics," Immunol. Today 19:524–527.

Borrebaeck (2000) "Antibodies in diagnostics—from immunoassays to protein chips," Immunol. Today 21:379 382.

Lueking et al. (1999) "Protein Microarrays for Gene Expression and Antibody Screening," Anal. Biochem. 270:103–111.

Joos et al. (2000) "A microarray enzyme–linked immunosorbent assay for automimmune diagnostics," Electrophor. 21:2641–2650.

Mendoza et al. (1999) "High–Thoughput Microarray–Based Enzyme–Linked Immunosorbent Assay (ELISA)," BioTech. 27:778–788.

Claverie (1999) "Computational methods for the identification of differential and coordinated gene expression," Hum. Mol. Genet. 8:1821–1832.

Marra et al. (1999) "An encyclopedia of mouse genes," Nat. Genet. 21:191–194.

Capone et al. (1996) Identification through bioinformatics of cDNAs encoding human thymic shared Ag–1 stem cell Ag–2. A new member of the human Ly–6 family, J. Immunol. 157:969–973.

Strivens et al. (2000) "Informatics for mutagenesis the design of Mutabase—a distributed data recording system for animal husbandry, mutagenesis, and phenotypic analysis," Mammal. Genome 11:577–583.

de Lalla et al. (1999) "Cutting Edge: Identification of Novel T Cell Epitopes in Lol p5 a by Computational Prediction," J. Immunol. 163:1725–1729.

Rebhan et al. (1998) "GeneCards: a novel functional genomics compendium with automated data mining and query reformulation support," Bioinform. 14:656–664.

Rossi et al. (1997) "Identification Through Bioinformatics of Two New Macrophage Proinflammatory Human Chemokines MIP–3α and MIP–3β," J. Immunol. 158:1033–1036.

Mallios (1999) "Class II MHC quantitative binding motifs derived from a large molecular database with a versatile iterative stepwise discriminant analysis meta–algorithm," Bioinform. 15:432–439.

Immervoll and Wjst (1999) "Current status of the Asthma and Allergy Database," Nuc. Acids Res. 27:213–214.

Bard (1999) "A bioinformatics approach to investigating developmental pathways in the kidney and other tissues," Int. J. Dev. Biol. 43:397–403.

Zhang (1999) "Large–Scale Gene Expression Data Analysis: A New Challenge to Computational Biologists," Genome Res. 9:681–688.

Rawlings and Searls (1997) "Computational gene discovery and human disease," Curr. Opin. Genet. Develop. 7:416–423.

Boguski (1994) "Bioinformatics," Curr. Opin. Genet. Develop. 4:383–388.

Bourne (2000) "Bioinformatics meets data mining: time to dance?" Trends Biotechnol. 18:228–230.

Construction of the ImmunoChip
a. Identification of immunological-relevant clusters Construction of the ImmunoChip
b. Identification of the best representative clone within a selected cluster

FIG. 3

SEQ ID NO:1

*Mus musculus* bcl-2 mRNA

```
  1 atggcgcaag ccgggagaac aggtatgat aaccgggaga tcgtgatgaa gtacatacat
 61 tataagctgt cacagagggg ctacgagtgg gatgctggag atgcggacgc ggcgccctg
121 ggggctgccc ccacccctgg catcttctcc ttccagcctg agagcaaccc aatgcccgct
181 gtgcacgggg agatggctgc caggacgtct cctctcaggc ccctcgttgc cacggctggg
241 cctgcgctca gccctgtgcc accatgtgtc catctgaccc tccgccggc tggggatgac
301 ttctctcgtc gctaccgtcg tgacttcgca gagatgtcca gtcagctgca cctgacgccc
361 ttcaccgcga gggacgctt tgccacggtg gtggaggaac tcttcaggga tggggtgaac
421 tgggggagga ttgtggcctt ctttgagttc ggtggggtca tgtgtgtgga gagcgtcaac
481 agggagatgt caccccttgt ggacaacatc gcccctgtga tgactgagta cctgaaccgg
541 catctgcaca cctggatcca ggataacgga ggctgggatg ccttttgtga actatatggc
601 cccagcatgc gacctctgtt tgatttctcc tggctgtctc tggctgtctc tgaagaccct gctcagcctg
661 ccctgggtcg gggcctgcat cactctgggt gcatacctgg gccacaagtg a
```

SEQ ID NO:2

*Mus musculus* bcl-2 Image clone

TAGCAAACTACAAACTCGACTTAATTTCATCTGCTCAATGCCCATTTTGACCCAGAATC
CACTCACACCCCAACCTGGCATCTTGGCCTTGAGATCAAAGCCCAGACTCATTCAACCA
GACATGCACCTACCCAGCCTCCGTTATCCTGGATCCAGTGTGTGCAGATGCCGGTTCAGT
ACTCAGTCATCCACAGGGCGATGTTGTCCACCAGGGTGACATCTCCCTGTTGACGCTCT
CCACACACATGACCCCACGAACTCAAAGAAGGCCACAATCCTCCCCCAGTTCACCCAT
CCCTGAAAGAGTTCCTCCACAGTGGCAAAGCGTCCCTGGTGAAGGGCGTCAGGT
GCAGCTGACTGGACATCTCTGCGAAGTCACGACGGTAGCACGGTCACGAGAAGTCATCCCAG
CCCGGCGAGGGTCAGATGGAGCACAGGTGGCACAGGCTGAGCGCAGGCCCAAGCGGTGG
AACGAGGGGGCTGAGAGGAGACGTCTGCAGCCAT

FIG. 3 (Continued)

SEQ ID NO:3 mRNA

*Mus musculus* beta-2 microglobulin

```
  1 atttcagtgg ctgctactcg gcgcttcagt cgcggtcgct tcagtcgtca gcatggctcg
 61 ctcggtgacc ctagtctttc tggtgcttgt ctcactgacc ggcttgtatg ctatccagaa
121 aacccctcaa attcaagtat actcacgcca cccaccggag aatgggaagc cgaacatact
181 gaactgctac gtaacacagt tccaccgcc tcacattgaa atccaaatgc tgaagaacgg
241 gaaaaaaatt cctaaagtag agatgtcaga tatgtccttc agcaaggact ggtctttcta
301 tatcctggct cacactgaat tcacccccac tgagactgat acatacgcct gcagagttaa
361 gcatgacagt atggccgagc ccaagaccgt ctactgggat cgagacatgt gatcaagcat
421 catgatgctc tgaagattca tttgaacctg cttaattaca aatccagttt ctaatatgct
481 atacaattta tgcacgcaga aagaaatagc aatgtacaca tcaccttctt tatatcttac
541 tttaaatgtt ttatgcatgt tttcaaaaat tggaaatatc ctagatagct gagcaataaa
601 tcttcaataa gtatttgat cagaataata aatataattt taagaac
```

SEQ ID NO:4

*Mus musculus* beta-2 microglobulin Image clone

```
TTTTTTTTTAGTTTTTTATTTTAGTAAAAGTAACAAAAGCAGAAGTAGCCACAGGGTT
GGGGGTGAGAATTGCTAAGCATTGGGCACAGTGGCACAGACTTCAATTAGCCCTCTTTGCTT
TACCAAAAGGAAAGTATGTCACTTATGTTGTGATAGACCAAAGATGAGTAACTGCATCCA
AGTAATGAGAAGTACAGAGGGTTTGGCATATGATGATCAACTATTGTTCTTAAAATTATATTT
ATTATTCTGATCAAATACTTATTGAAGATTTATTGCTCAGCTATCTAGGATATTTCCAA
TTTTTGAAAAACATGCATAAAATATTAAAGTAAGATATAAAGAAGGTGATGTGTACATT
GCTATTCTTTCTGCGTGCATAAATTGTATAGCATATTAGAAACTGGATTTGTAATTAAG
CAGGTTCAAATGAATCTTCAGAGCATCATGATGCTTGATCACATGTCTCGATCCCAGTAG
ACGGTCTTGGGCTCGG
```

FIG. 3 (Continued)

SEQ ID NO:5

*Mus musculus* beta-2 microglobulin Image clone

```
TTTCAGTGGTGCTGCTACTCGGCGCTTCAGTCGCGGTCGCTTCAGTGTCGTCAGCATGGCTCGC
TCGGTGACCCTGGTCTTTCTGGTCCTTGTCTCACTGAGCGGCCTGTATGCTATCCAGAAA
ACCCCTCAAATTCAAGTATACTCACGCCACCCACCGGAGAATGGAAGCCGAACATACTG
AACTGCTACGTAACACAGTTCCACCCGCCTCACATTGAAATCCAAATGCTGAAGAACGGG
AAAATAATTCCTAAAGTAGAGATGTCAGATATGTCCTTCAGCAAGGACTGGTCTTTCTAT
ATCCTGGCTCACACTGAATTCACCCCCACTGAGACTGATACATACGCCTGCAGAGTTAAG
CATGCCAGTATGGCCGAGCCCAAGACCGTCTACTGGATCGAGACATGTGATCAAGCATC
ATGATGCTCTGAAGATTCATTTGAACCTGCTTAATTACAATCCAGTTTCTAATATGCTA
TACAATTTATGCACGCAGAAAGAAATAGCAATGTACACATCCACCTTCTTATATCTTACT
TTAAATATTTTATGCATGTTTTCAAAAATTGGAAATATCCTAGATAGCTGAGCAATAAA
TCTTCAATAAGTATTTGATCAGAATAATAATAATTTTAAGAAC
```

SEQ ID NO:6

*Mus musculus* Calnexin mRNA

```
  1 atggaaggga agtggttact gtgtttgctg ctggtccttg gaactgcagc tgttgaggct
 61 catgatggac atgatgatga cgcgattgat attgaagatg atcttgatga tgttattgaa
121 gaggtagaag attcaaaatc taaatcagat gccagcactc ctccatctcc aaaggtcacc
181 tacaaagctc cagttccaac aggggaggtt tatttgctg actctttga cagagggtct
241 ctgtcagggt ggatttatc taaagccaaa aaagatgaca ctgatgatga aattgccaaa
301 tatgatggaa agtgggaagt agatgagatg caagcatcat gccatctctg agcttccagg ggataaagga
361 cttgtactga tgtctcgggc caagcatcat gccatctctg ctaaactgaa taagcccttc
421 ctgtttgata ccaagcctct cattgttcag tatgaggtta attttcagaa tggaatagaa
481 tgtggtggtg cctatgtgaa gctgctttcc aagacggcag agctcagcct ggatcaattc
541 cacgacaaga ctccctatac tattatgttt ggtccagata agtgtggaga ggactacaaa
601 ctgcatttca tctttcgaca caaaaatccc aagacaggtg tatatgaaga aaaacatgct
661 aagaggccag atgcagatct gaagacctat ttcactgaca agaaaacgca tctttataca
```

FIG. 3 (Continued)

```
 721 ttaatcttga atccagacaa tagttttgaa atattagttg accagtctgt tgtgaacagt
 781 ggaaatctgc taaatgacat gactcctcct gtaaaccctt cacgtgaaat tgaagaccca
 841 gaagaccgga agcctgaaga ttgggatgaa aggcccaaaa tagcagatcc agatgctgtc
 901 aagccagatg actgggatga agacgcccct tctaagatcc cagatgaaga ggccaccaag
 961 cctgaaggct ggctagacga cgaacctgag tatattccag accctgatgc agagaagcca
1021 gaggattggg atgaggatat ggacggagaa tgggaggctc ctcagattgc caacccaag
1081 tgtgagtcag cccctggtg tggtgtctgg cagcgaccta tgattgacaa ccccaattat
1141 aagggcaaat ggaagcctcc aatgattgac aaccctaact accaggaat ctggaaacca
1201 aggaaaatac caaatccaga tttcttgaa gacctagaac cttttaagat gactcctttc
1261 agtgctattg gtttggagct ctggtccatg acatccgaca tcttttttga caactttatc
1321 attagtggtg accgaagagt agttgatgat tgggccaatg atgggtgggg cctgaagaaa
1381 gctgctgatg gggctgctga gccaggtgta gtgctgcaga tgctggaggc agctgaagag
1441 cgtccatggc tttgggtggt ctatatttg actgtagctt tgccagtgtt ccttgtgatc
1501 ctcttctgct gttctggaaa gaaacagtcc aatgctatgg agtacaagaa gacggatgct
1561 cccagccag atgtgaagga tgaagaaggg aaggaagaag agaagaacaa gagggatgaa
1621 gaggaagaag aggagaagct gaagagagaa cagaagagtg atgctgaaga gaggtgaa
1681 actggcagtc aagatgagga agatagcaag cctaaagcag cctaaagcag aattttgaac
1741 agatcgccaa gaaacagaaa gccacgaaga gagtga
```

FIG. 3 (Continued)

SEQ ID NO:7

*Mus musculus* Calnexin Image clone GenBank Acc: AA870492

```
ATTCGTCTGACAAGCTGGAAAGAAACAGTCCAATGCTATGGAGTACAAGAAGACGGATGCT
CCCAGCCAGATGTGAAGGATGAAGGAAGAAGAAGAAGAAGAACAAGAGGGATGAA
GAGGAAGAGAGAGAAGCTTGAAGAGAAACAGAAGAGTGATGCTGAAGAAGATGGTGTT
ACTGGCAGTCAAGATGAGGAAGATAGCAAGCCTAAAGCAGAGCCTAAAGCAGAGGAGGATGAAATTTGAAC
AGATCGCCAAGAAACAGAAGGCCACGAAGAGTGAAACAATCTTTAAGAACTTGATCTG
TGATTTCCTCCTCCCCTTCCCCTGCAAATGTGGTCTAGGAGAGGCCTGGTGTACC
TTAGTGGGAGCTCAAAACCTCAGATGTCACCATCCACAGGTTCCAGTGGATACTAGCC
TGTAATTTTAAACATCTAGCAGTAAATAATTGCAGTTGTAATGTAAAGGACCCTGTTTCT
GTAGAAGGAAAAACATTAACATAACATTTTCCAGGTTTGTCTT
GTTTGTGTTGTTTTAAAATTTTCCAGGTTTGTCTT
```

SEQ ID NO:8

*Mus musculus* CD19 mRNA GenBank Acc: NM_009844

```
  1 atgccatctc ctctccctgt ctccttcctc ctcttcctta ccttagtagg aggcaggccc
 61 cagaagtcct tactggtgga gtagaagag ggaggcaatg ttgtgctgcc atgcctcccg
121 gactcctcac ctgtctcttc tgagaagctg gcttggtatc gaggtaacca gtcaacaccc
181 ttcctggagc tgagcccggg gtcccctggc ctggattgc acgtggggtc cctggcatc
241 ttgctagtga ttgtcaatgt ctcagaccat atggggggct tctacctgtg ccagaaagg
301 cccccttca aggacatctg gcagcctgcc tggacagtga agtggagga tagtggggag
361 atgttccggt ggaatgcttc agacgtcttc ttctgttcc cagctgtatg tgtgggctaa gaacaggtcc
421 tctgggagcc acaggtccac ttctggttcc cagctgtatg tgtgggctaa agaccatcct
481 aagtctggg gaacaaagcc tgtatgtgcc cctcggggga gcagtttgaa tcagagtcta
541 atcaaccaag atctcactgt ggcacccggc tccacacttt ggctgtcctg tgggtaccc
601 cctgtcccag tggccaaagc gtccatctcc tggacctctcc tgcatcctag gagacctaat
661 gtttcactac tgagcctaag cctgggga gagcaccgg tgcaccccgg tcagagagat gtgggttttgg
721 gggctctctc tgcttctgcc ccaagccaca gctttagatg aaggcaccta ttattgtctc
```

FIG. 3 (Continued)

```
 781 cgaggaaacc tgaccatcga gaggcacgtg aaggtcattg caaggtcagc agtgtggctc
 841 tggctgttga gaactggtgg atggatagtc ccagtggtga ctttagtata tgtcatcttc
 901 tgtatggttt ctctggtggc ttttctctat tgtcaaagag cctttatcct gagaaggaaa
 961 aggaagcgaa tgactgaccc cgccaggaga ttcttcaaag tgacgcctcc ctcgggaaac
1021 gggacccaga accagtacgg gaatgtgctc tcccttccta catctacctc tggccaggcc
1081 catgctcagc gttgggctgc tggcctaggg agtgtccctg ggtcctatgg aaatccacgc
1141 attcaagtcc aggatactgg agctcagagc catgaaacag gactggaaga agaaggggag
1201 gcctatgaag gccagacag tctgaattct atgagaacga ctccaacctt
1261 gggcaggacc aggtttccca ggatgggagt ggctatgaga accccgagga tgagcccatg
1321 ggtccagagg aagaagactc cttctccaat gctgagtctt atgaaaatgc agatgaggag
1381 ctggcccaac cagttggcag gatgatggac ttcctgagcc cccatgggtc tgcgtggac
1441 cccagccggg aagcatcctc gcttgggtcc cagtcctatg aagatatgag agggatcctc
1501 tatgcagctc ctcagctcca ctcaattcag tccggtccca gtcatgaaga agatgcagac
1561 tcttatgaaa acatggataa gtctgacgac ctagaaccag catgggaagg agagggccac
1621 atgggaactt ggggaaccac gtgactccca agtgactagc ctggacttcg ttaggtccca
1681 agaaccacat ctgattctga aatctggaga tcccagatgg tgtcagtcag tgaaatgacc
1741 ttgatcagga tgtgtgctag ctgacacaca cacactcata tgcatgttca agcaaagctt
1801 cctttttgacc cttttgcttttc cccaaataaa cccaattagc cactcaaatt ctctgaagcc
1861 ggcccttgtg tgggatagga agatggggtt gaatccagcc ctgagtcacc cagaggaagg
1921 agaactgagg tctgagtaca tcctggctct agccttccca tggcctggca tttagccacc
1981 taacatccag tgatgcaaat atgtccagcc gctacattcc atggtgtccc acaagggaga
2041 gacagtgatg ggactagcag actgttttggt tgtaacccat cctgctcac cctgcacaaa
2101 ctgggaaaca ctgtctgcct ctcttttaat cctgcctgct ccaggctaac aggccagtac
2161 cctcaccttc gagttctgg caacactacc tgagtgcctg ctcaggggt tcagctcctg
2221 accatatgta gacaccaccc cagctctgag tttacacatc atcaccctt gcctaagacc
2281 tgaaacccc ctttaccttc gcccaggtgt gccattcc tgctccctcc tggatccttg
2341 ggacctgtga acctactcaa gtgctgctct caataaatct gcctttatac tttc
```

FIG. 3 (Continued)

SEQ ID NO:9

*Mus musculus* CD19 Image clone GenBank Acc: AW496107

```
AGCCCCCATGGGTCTGCGTGGGACCCCAGCCGGAAGCATCCTCGCTTGGGTCCCAGTCC
TATGAAGATATGAGAGGGATCCTCAGCTCCTCAGCTCCACTCAATTCAGTCCGT
CCCAGTCATGAAGAAGATGCAGACTCTTATGAAAACATGGATAAGTCTGACGACCTAGAA
CCAGCATGGGAAGGAGGAGGGCCACATGGGACTTGGGGAACCACGTGACTCCCAAGTGAC
TAGCCTGGACTTCGTTAGGTCCCAAGAACCACATCTGATTCTGAAATCTGAGATCCCAG
ATGGTGTCAGTCAGTGAAATGACCTTGATCAGGATGTGTGCATGCTGACACACACACT
CATATGCATGTTCAAGCAAAGCTTCCTTTGACCCCTTTGCTTTCCCAAATAAACCCAAT
TAGCCACTCAAATTCTCTGAAGCCCGGCCCCTGAGTCACCCAGAGGAAGGAGAACTGAGGTC
TGAGTACATCC
```

SEQ ID NO:10

*Mus musculus* CD19 Image clone GenBank Acc: AW495831

```
TTTAGAAAGTATAAAGGCAGATTTATTGAGAGAGCAGCACTTGAGTAGGTTCACAGAGTCCCA
AGGATGCAGGAGGGAGCAGGAGCAGGAAATGCCACACCTGGGCGAAGGTAAAGGGGGTTTCAGG
TCTTAGGCAAGGGTGATGATGTGTAAACTCAGAGCTGGGGTGGTGTCTACATATGGTCA
GAAGCTGAACCTGAAACCCCTGAGCCAGGCACTCAGGTAGTGTTGCCAGAAACTCGAAGGTGAGGGT
ACTGGCCTGTTAGCCTGGAGCAGGCAGGATTAAAAGAGAGCAGACAGTGTTTCCCAGTT
TGTGCAGGGTGAGGGTGAGGGATGGGTTACAACCAAACAGTCTGCTAGTCCCATCACTGTCTC
TCCCTTGTGTGGACACCATGGAATGTAGCGGCTGACATATTGCATCACTGGATGTTAGG
TGGCTAAATGCCANGCCATGGGAAGGCTAGAGCCAGGATGTACTCAGACCTTCAGTTCTCC
TTCCCTCTGGGTGACTCA
```

FIG. 3 (Continued)

SEQ ID NO:11

*Mus musculus* CD28 mRNA GenBank Acc: NW_007642

```
   1 acacactctg ccttgctcac agaggagggg ctgcagccct ggccctcatc agaacaatga
  61 cactcaggct gctgttcttg gctcctcaact tcttctcagt tcaagtaaca gaaaacaaga
 121 tttggtaaa gcagtcgccc ctgcttgtgg tagatagcaa cgaggtcagc ctcagctgca
 181 ggtattccta caacctcttc gcaaaggaat tccgggcatc cctgtacaag ggcgtgaaca
 241 gcgacgtgga agtctgtgtc gggaatggga atttaccta tcagccccag tttcgctcga
 301 atgccgagtt caactgcgac ggggatttcg acaacgaaac agtgacgttc cgtctctgga
 361 atctgcacgt caatcacaca gatatttact tctgcaaaat tgagttcatg taccctccgc
 421 cttacctaga caacgagagg agcaatgaag ctattattca cataaaagag aaacatcttt
 481 gtcatactca gtcatctcct aagctgtttt gggcactggt cgtggttgct ggagtcctgt
 541 tttgttatgg cttgctagtg acagtggctc tttgtgttat ctggacaaat agtagaagga
 601 acagactcct tcaagtgact accatgaaca cctgccagag tgactcccccg gaggcctgaa ctcactcgaa
 661 agccttacca gccctacgcc cctgccagag acttttgcagc gtaccgcccc tgacaggac
 721 ccctatccag aagcccgccg gctggtaccc gtctacctgc tcatcatcac tgctctggat
 781 aggaaaggac agcctcatct tcagccggcc actttggacc tctactgggc caccaatgcc
 841 aactatttta gagtgtctag atctaacatc atgatcatct tgagactctg gaatgaatga
 901 cagaagcttc tatgcagga taaagtctgt gtggcttgac ccaaactcaa gcttaataca
 961 tttattgact tgattgggga agttagagta gagcaatcaa aaagatcatt cattcagcct
1021 tgggaagtca atttgcaggc tcctgatga gccctgcccc gttttcactt gccagcacat
1081 ttcagtcatg tggtgtgata gccaaagatg ttttggacag aggagaaagg atagaaaaac
1141 ctctcttg gctaagttgg tgtttgggt ggggataggt tagagtatag tacttaacta
1201 tttgaaaaat aatgaaaaca ctttttcac tcatgaaatg agccacttag ctcctaaata
1261 gtgttttcct gttagtttag aaagttgtgg acatattttt ttaatgattt ctgaccattt
1321 ttaatcacat tgactcatgg aatggcctca aagcacccccc cagtgcttct ttcctcattc
1381 ccggtcatgg gaactcagta ttattaatag tcacaacatg atttcagaac tagatagccc
1441 tcccacacca agaagaatgt gagaggaagt aaggtcactt tatgtaaaaa cg
```

FIG. 3 (Continued)

SEQ ID NO:12

*Mus musculus* CD28 Image clone GenBank Acc: AI327367

ACATAAAGTGACCTTACTTCCTCTCACATTCTCTGTTGTGGAGGCTATCTAGTTCT
GAAATCATGTTGTGACTATTAATAATACTGAGTTCCCATGACCGGGAATGAGGAAAGAAG
CACTGGGGGTGCTTTGAGCCATTCCATGAGTCAATGTGATTAAAAATGGTCAGAAATC
ATTAAAAAATATGTCCACACTTTCTAAACTAACAGAGAAAACACTATTTAGGAGCTAAG
TGGCTCATTTCATGAGTGAAAAAAGTGTTTTCATTATTTTCAAATAGTTAAGTACTATA
CTCTAACCTATCCCACCCCAAACACCAACTTAGCCAAACTTAGCCAAAGAGAAGTTTTTCTATCCTTT
CTTCTCTGTCTCCAAAACATCTTGGCTCTATCACACCACATGACTTGAGCTGTGGCAAGTG
AAAACGGNGCAGGCTCATCCAGGAGCCTGCAAATTGACTTCCCAAGCTGAATGAATGA
TCTTTTTGATGCTCTACTCTAACTTCCCAATCAAGTCAAGTCAATAAAGTTATTAAGCTTGAG
TTTGGGTCAAGCCACAGCCACAGACTNTATCCTGCCATAGAAGCTTCGTCATTCCAGAG
TCTCAAGATGATCATGATGGTAGATCTAGACACTCTAAAATAGTTGGCATTGGTGCCCA
GTAGAGGTCCAAAGTCCGGGCCGGGCTGAAGATGAGGCTGTCGTTTCCTATCCAGAGCAGTGA
TGATGAGCAGGTAGCCCGGGTACCAGCCCGGCTTTCTGGAATAGGGTTCCTGTCAGGG
GCGGT

FIG. 3 (Continued)

SEQ ID NO:13

*Mus musculus* CD28 Image clone GenBank Acc: AI386096

```
GTGACTTCAGTTCACACCACACTCTGCCTTGCTCACAGAGGAGGGGCTGCAGCCCTGCC
CTCATCAGAACACAATGACACTCAGCTGCTGTGTTCTTGGCTCTCAACTTCTTCTCAGTTCAA
GTAACAGAAAAACAAGATTTGGTAAAGCAGTCGCCCCTGCTTGTGTAGATAGCAACGAG
GTCAGCCTCAGTCTGCAGGTATTCCTACAACCTTCTCGCAAAGGAATTCCGGCATCCCTG
TACAAGGGCGTGAACAGCGACGTGGAAGTCTGTGTCGGGAACGGGATTTCGACAACGAAACAGTG
CCCCAGTTTCGCTCTCTGGAATCTGCACGTCAATCACACAGATATTTACTTCTGCAAAATTGAG
AGTTCCGTCTCTGAAGTCCGCCTTACCTCATACTCAGTCATCTCCTAAGCTGTTTTGGCACTGGTGTGG
TTGCTGGAGTCCTGTTGTTTGTATGGCTCTAGTGACAGTGGGCTCTTTGTTATCTGGAC
CAATAGTAGAAGGAACCAGACTCTTTCAAGTGACTACATGAACATGAACTCCCCGAGCC
TGGGCTCAACTGACAAGCCTTACCAGCCCTACGCCCCCTGCCAGAGACTTTGCAGGTACCC
GCCCTGACAAGGACCCCCTATNCAAAAGCCCGGCGGNTACCGTCTACCTGCTCATCA
TCACTGCTCTTGAAAGGAAAGGACAGCTTATCTTCAGCCCACTTGAACTTTACTGG
NCCACCAATGCAACTTATTTAAGAGGCTAGATCCACCTTATGACATCTTGAAACTTTGGA
```

FIG. 3 (Continued)

SEQ ID NO:14

*Mus musculus* CD28 Image clone GenBank Acc: AA117418

```
CACTCTGCCTTGCTCACAGAGAGGGGCTGCAGCTGGCGCCTCATCAGAACAATGACACT
CAGGCTGCTGTTCCTGGGCTCTCAACTTCCTCTCAGTTCAAGGTACAGGAAACCAGATTT
TTGGTAAAGAGTCGCCCTTGCTTGTGTGATACAACGAGGCAGCCTAAGTTCGAGGAAT
CCTACAACCCTCTGCAAAGGAATTCCGGAATCCCTGTAAAAGGGCCTTAAAAGCCAAG
TGGAAATTTGTGTTCGGGAATGGGAATTTTACCTTCTAACCCCGGTTTGCGCCGAATGCC
CGGTTCAACTTGAACGGGAATTCGGCACAGGAACAGTGAGCTTTCCGTCTCGGAA
```

SEQ ID NO:15

*Mus musculus* CD4 mRNA GenBank Acc: NM_013488

```
  1 tttcattta cgaacatctg tgaaggcaaa gcaagactct cttcttcact aggtacctgt
 61 ttgcaaagtc tcgagccctc atatacacac acctgtgcaa gaagcagagt gaaggaagga
121 ctggccagag gctcagattc ccaaccaaca agagctcaag gagaccacca tgtgccgagc
181 catctctctt aggcgcttgc tgctgctgct gctgcagctg agggaatca gcagaactgc tagctgtcac
241 tcaagggaag acgctggtgc tggggaagga tcttcacctg gaagttctct gaccagagga cctgcgagag
301 ttcccagaag aagatcacag aaaggtgtat taattagagg aggttcgcct tcgcagtttg atcgtttga
361 gcagcatggc aaaggtgtat gggcatggg agaaaggatc gtttcctctc atcatcaata aacttaagat
421 ttccaaaaaa gggcatggg agaaaggatc tctgtgagct ggagaacagg aaagaggagg tggagttgtg
481 ggaagactct cagacttata gtgaccttca caggggcaga gcctgaccct
541 ggtgttcaaa gtgaccttca cagcctgttg caggggcaga gcctgaccct
```

FIG. 3 (Continued)

```
 601 gaccttggat agcaactcta aggtctctaa cccccttgaca gagtgcaaac acaaaaaggg
 661 taaagttgtc agtggttcca aagttctctc catgtccaac ctaaggttc aggacagcga
 721 cttctggaac tgcaccgtga ccctggacca gaaaaagaac tggttcggca tgacactctc
 781 agtgctgggt tttcagagca cagctatcac ggcctataag agtgagggag agtcagcgga
 841 gttctccttc ccactcaact ttgcagagga aaacggggtgg ggagagctga tgtggaaggc
 901 agagaaggat tctttcttcc agccctggat ctccttctcc ataaagaaca aagaggtgtc
 961 cgtacaaaag tccaccaaag acctcaagct ccagctgaag gaaacgctcc cactcaccct
1021 caagataccc caggtctcgc ttcagtttgc tggttctggc aacctgactc tgactctgga
1081 caagggaca ctgcatcagg aagtgaacct ggtggtgatg aaagtggctc agctcaacaa
1141 tactttgacc tgtgagtga tgggacctac ctctcccaag atgagactga ccctgaagca
1201 ggagaaccag gaggccaggg tctctgagga gcagaaagta gttcaagtgg tggccccctga
1261 gacaggctg tggcagtgtc tactgagtga aggtgataag gtcaagatgg actccaggat
1321 ccaggttta tccagagggg tgaaccagac agtgttcctg gcttgcgtgc tgggtggctc
1381 cttcggcttt ctgggtttcc ttgggctctg catcctctgc tgtgtcaggt gccggcacca
1441 acagcgccag gcagcacgaa tgtctcagat caagaggctc ctcagtgaga agaagaccctg
1501 ccagtgcccc caccggatgc agaagagcca taatctcatc ccgaggcctag gccccacctg
1561 cagcccacca cctgcgtcct gtctcatcgc ccgaggcctg gggaccagat gaatgtagca
1621 cagacgctgc ctccggcctt ctgctctcct cttccacaac cggccaacgg tttccctccc
1681 tctgttccca agcctgtctg tctgcagagc ttgcccctg cgtttcagac actcaagcac
1741 accccatcag cttattatt cttcgctgct gcctttctgc cagagcctcg gcccttctcg
```

FIG. 3 (Continued)

```
1801 gactaaggtc ctggaaccct tttccagctg tctgcttgga tcaaagggca gtgtatagca
1861 cctggcacgg atggtgggac tggtgtctgg aaatacacag cacagtttac gagagggctc
1921 tgggaccaag ctgagtgggg cagggagggc cgggaggttg tgcatgtcac acatgaagca
1981 tgtcagggc  aaatgaagac tgagaggctg cgggagtcag cctcagcttc ccatgatgcc
2041 tgcttctctt ttgaatttgc aagaccagac tcacattcta accagtgcac caacacacat
2101 ccaagccaca cacctgtcca tatatccaaa cagcatatct taattcataa gccactttaa
2161 tgtcccaggc attcgaccct tacaaaaacc ttacaagtgg ttgagcggta aaaagcctca
2221 tgaactgagt ggaaggagag gattaactct tgaaagttgt cccctatgta tgtaccatga
2281 ccctcatgtg tacagaacac acacacacac acacacacac acacacacac gaacagacgc
2341 atgttgcaca cactgcatcg acgctaaatc ctagcaagct gacagtgatg actaagatgg
2401 cagagataac cagtcatccc tagtgaaatg gcaacttggt gtgaatgact acccaaggtt
2461 acccagctaa caactgctga tgtcagggcc aacccaggc  tcctgatccc tagagccaag
2521 ccactacatg aacacagg   atgaatacca cacagatctg tggagctagt tccaggccct
2581 cggtatacac acacacacac acactggagc gcacccctgg cagagatctt
2641 gagaggatgg aggagccatt ctggtttcaa atccctcctt gatcactgct gttctcaccc
2701 cccctcctt  cccccaaaac cctagttctc ttagagtgag gctgggagag atgcacagag
2761 acctgccgca gtgtgtgcag agcctgggaa gtgaccatg  ccaggaggtc ctggggtcct ttatggagag
2821 agcattgtgg caggtggctg tgccttccat ccaggaggtc aggggtctaa gggctctccc
2881 tgagtcttt  gatctgtttc tcatagatcc acagcctcct ctgcctctgt cgtttgcctg
2941 cttcagcact tccttcccct tttttcctct tttcttccca gctgcctctct tctagaaaca
3001 tcccttcccc acttctcttc attattcact tctattcttt gcccactccc cactcctgct
3061 tcctgagctg acagaaaaat aaggctata  aataaaatgc
```

FIG. 3 (Continued)

SEQ ID NO:16

*Mus musculus* CD4 Image clone GenBank Acc: AA210044

```
GCAAGACTCTCTCTTCACTAGGTACCTGTTGCAAAGTCTCGAGCCCTCATATACACAC
ACCTGTGCAAGAAGCAGAGTGAAGGAAGACTGGCCAGAGCGTCAGATTCCCAACAACA
AGAGCTCAAGGAGACCACCATGTGCCGAGCCATCTCTCTTAGGCGCTGTCGCTGTGCT
GCTGCAGTGTCACAACTCCTAGCTGTCACTCAAGGGAAGACGCTGGTGCTGGGGTCCTTT
ATGGAGAGAGCATTGTGGCAGGTGGCTGTGTTCTCATAGATCCAGGAGGTCAGGGTCTAAGGG
CTCTCCCTGAGAGTCTTGATCTGTTTCTCATAGATCCACAGCCTCCTCTGCCTCTGTCGT
TTGCCTGCTTCAGCACTTCCCTTTCCCCTTTTTTCCTGCTTCTCCAGCTGGCCTCTCT
AGAAACATCCCTTCCCACTTCTCTTCATTATTCACTTCTTATTTTGCCCACTCCCAC
TCCTGCTTCCTG
```

FIG. 3 (Continued)

SEQ ID NO:17

*Mus musculus* CD40 mRNA GenBank Acc: NM_011611

```
   1 tgccctgcat ggtgtctttg cctcggctgt gcgcgctatg gggctgcttg ttgacagcgg
  61 tccatctagg gcagtgtgtt acgtgcagtg acaaacagta cctccacgat ggccagtgct
 121 gtgatttgtg ccagccagga agccgactga agccactga caagccactg cacagtcctt gagaagaccc
 181 aatgccaccc atgtgactca ggcgaattct cagcccagtg gaacagggag attcgctgtc
 241 accagcacac acactgtgaa cccaatcaag ggcttcgggt taagaaggag ggcaccgcag
 301 aatcagacac tgtctgtacc tgtaaggaag gacaacactg caccagcaag gattgcgagg
 361 catgtgctca gcacacgccc tgtatccctg gctttggagt tatggagatg gccactgaga
 421 ccactgatac cgtctgtcat ccctgcccag tcggcttctt ctccaatcag tcatcacttt
 481 tcgaaaagtg ttatcccctgg acaagctgtg aggataagaa cttggaggtc ctacagaaag
 541 gaacgagtca gactaatgtc atctgtggtt taaagtcccg gatgcgagcc ctgctggtca
 601 ttcctgtcgt gatggcatc ctcatcacca tttcggggt gttctctcat atcaaaaagg
 661 tggtcaagaa accaaaggat aatgagatgt tacccccctgc ggctcgacgg caagatcccc
 721 aggagatgga agattatccc ggtcataaca ccgctgctcc agtgcaggag acactgcacg
 781 ggtgtcagcc tgtcacacag aggatggta gagagagtcg catctcagtg caggagcggc
 841 aggtgacaga cagcatagcc ttgaggcccc tggtctgaac cctggaactg ctttggaggc
 901 gatggctgct tgctgacctt tgcctgacct tga tgaagtttga gatgagccaa gacagagccc agtgcagcta
 961 actctcatgc ctgcccctg tcattctca acttgctctt taaggatgga gggaaagctc
1021 gggcatcggg aggtccacag tgatatctac caagtgcagc agtgcaggac ccagagttgt
1081 cttgctgcgg cgttcactgt cgttacctg ggctacagga gtccgtgcc cgcagcttgt
1141 gctcgtagag ggcacctggt tgccatcagc agggtactgg ctaaataaat ctgtaattat
1201 ttatacaatg gcatctcaga aactctagca ggtggggcag aaaacaggta gtggaatgat
1261 gggtagagaa acagctttta caaggcaggt aagatggctt ttgtgggtaa
1321 aggagcttgc tgcccaaacc cggttacctg atttgatcc ctgggacttc atggtaaaag
1381 ggagagaacc aaatccagag ggttgtcatt tgacctccat gtgtgctctg tggtaatgta
1441 gctcgtgtgt gcacatgtgc acatatccta aaatgatgt ggtggtgtat tgtagaaatt
1501 atttaatccg ccctgggttt ctacctgtgt gttaccattt agttccttga taaagacaca
1561 ctcaaccttt atatttaca
```

FIG. 3 (Continued)

SEQ ID NO:18

*Mus musculus* CD40 Image clone GenBank Acc: AI385482

```
TTTTCGAAAAGTGTTATCCCTGGACAAGGTTTAAAGTCCCGGATGCGAGCCCTGCTGGTC
ATCCTGTCGTGATGGGCATCCTCATCACCATTTTCGGGGTGTTTCTCTATATCAAAAAG
GTGGTCAAGAAACCAAAGAAAGGATAATGAGATCTTACCCCCTGCGGCTCGACGGCAAGATCCC
CAGGAGATGGAAGATTATCCCGGTCATAACACCGCTGCTCCAGTGCAGGAGACGCTGCAC
GGGTGTCAGCCCTGTGTCACACAGGAGGATGTAAAGAGAGTCGCATCTCAGTGCAGGAGCGG
CAGGTGACAGACAGACATAGCCTTGAGGCCCTGAGGCCCTGGCTCTGAGGAGGGGCAGGG
CGATGGCTCGGCTCGGGAGCAAGACAGAACCCAGTGCAGTCAGCTAACTCTCATGCCTGCC
TTGAGATGAGCCAAGCCAGTGCAGTCAGCTAACTCTCATGCCTGCC
```

SEQ ID NO:19

*Mus musculus* CD40 Image clone GenBank Acc: AA060117

```
TTTAAAGTCCCGGATGCGAGCCCTGCTGGTCATTCCTGTCGTGATGGGCATCCTCATCAC
CATTTTCGGGGTGTTTCTCTATATCAAAAAGGTGTTCAAGATCCCAAGGTGTAATGAGAT
TTTTCCCCTGGGGCTTCAAGGGCAATTTCCCAGAAGTTGAAGTATTTCCCGGGTAATA
ACACGGCTGCTC
```

FIG. 3 (Continued)

SEQ ID NO:20

*Mus musculus* CD45 mRNA GenBank Acc: NM_011210

```
   1 ttgttcttag ggttagagag taggaaaact tgctccccat ctgataagac agagtgcaaa
  61 ggagcccta tttcttaggg gcacagctga tctccagata tgaccatggg tttgtggctc
 121 aaacttctgg cctttggatt tgcccttctg gacacagaag tctttgtcac agggcaaaca
 181 cctacaccca gtgatggtgc cagcctcaca actcttacac catccactct gggccttgca
 241 agcactgacc ctccaagcac aaccatagct accacaacga agcaaacatg tgctgccatg
 301 tttgggaaca ttactgtgaa ttacacctat gaatctagta atcagacttt taaggcagac
 361 ctcaaagatg tccaaaatgc taagtgtgga aatgaggatt gtgaaaacgt gttaaataat
 421 ctagaagaat gctcacagat aaaaaacatc agtgtgtcta atgactcatg tgctccagct
 481 acaactatag attatatgt accaccaggg actgacaagt tttcgctaca tgactgcaca
 541 ccaaaagaaa aggctaatac ttcaatttgt ttggagtgga aaacaaaaaa ccttgatttc
 601 agaaaatgca acagtgacaa tatttcatat gtactccact gtgagccaga aaataataca
 661 aaatgcatta gaagaaatac attcatacct gaaagatgtc agttggacaa ccttcgtgcc
 721 caaacaaatt acacatgtgt agcagaaatc ttatatcgcg gtgtaaaact cgtcaaaaat
 781 gttataaaatg tgcagacaga tttggggatt ccagaaacgc ctaagcctag ttgtggggat
 841 ccagctgcaa gaaaaacgtt agtctcttgg cctgagcctg tatctaaaac tgagtctgca
 901 tctaaacccc atggatatgt tttatgctat aagaacaatt cagaaaaatg taaaagtttg
 961 cctaataatg tgaccagttt tgaggtggaa agcttgaaac cttataaata ctatgaagtg
1021 tccctacttg cctatgtcaa tggaaagatt caaagaaatg ggactgctga gaagtgcaat
1081 tttcacacaa aagcagatcg tccggacaag gtcaatggaa tgaaaacctc ccggccgaca
1141 gacaatagta taaatgttac atgtggtcct cctatgtaaa ctaatgcccc taaaacctt
1201 tacatttttg tagtcagaag tggaggttct tttgttacaa atacaacaaa gacaaactgt
1261 cagttttatg gagataatct ctactattca actgactatg agtttctggt ctcttttcac
1321 aatggagtgt acgagggaga ttcagttata agaagtgagt caacaaattt taatgctaaa
1381 gcactgatta tattcctggt gtttctgatt attgtgacat caatagcctt gcttgttgtt
1441 ttgtataaaa gcgcaagaaa agatccagca atttagatga agatcaggaa acaacaggaa
1501 ctcgttgaaa gggatgatga aaagcagctg atggatgtgg agccaatcca ttctgacatt
```

FIG. 3 (Continued)

```
1561 ttgttggaaa catacaaaag gaagattgct gatgagggca gactgttcct ggctgaattt
1621 cagagcattc cacgggtatt cagcaagttt cccatcaaag atgcccgaaa gcccacaat
1681 cagaataaaa accgttatgt tgacattctt ccctatgatt ataaccgtgt ggaactctct
1741 gaaataaatg gagatgcagg gtccacctac ataaatgcca gctacattga tggcttcaag
1801 gaacccagga aatacattgc tgcacaaggg ccccgggatg agacagttga tgacttctgg
1861 aggatgatct gggagcaaaa ggccacagtt attgtcatgg tcacacgatg tgaagaagga
1921 aacaggaaca agtgcgcaga atactggcca agcatggagg aaggcactcg ggctttcaaa
1981 gatattgttg tgacaatcaa cgatgtcctg attacatcat tcagaagctg
2041 aacgttgcac ataaaaaaga aaaagcaact ggaagagaag tgactcatat ccaattcacc
2101 agctggccag accatggggt tcctgaagac cctcacctgc tcctcaaact tcgacggaga
2161 gttaatgctt ttagcaactt cttcagtggt tgcactgtgg tgcactgcag tgctggtgtt
2221 gggcgtacag gtacctacat tggaattgat gccatgctgg aaggcctggg agcagagggc
2281 aaagtggatg tctatggtta tgttgtcaag ctaaggcgac agaggtgtct gatggtgcaa
2341 gtggaggcac ctttgtgat gagttactgg ctttagtgg aatacaatca gtttggagaa
2401 acacaagtga acttgtctga gttacattca tgcctacaca acatgaagaa gagagatcca
2461 cccagtgacc cctcccctcg tgaggctgaa taccagagac ttccttcata caggagttgg
2521 aggacacagc acattggaaa tcaaggagag aataagagaa agaagaggaa ttctaatgtt
2581 gttccatatg actttaacag agtgccactt aagcatgaac tggagatgag caaagagagt
2641 gagcctgaat cagatgagtc ttcagatgat gacaggact cagaagaaac cagcaaatac
2701 attaatgcat cctttgtgat gagttactgg aaaccagaaa tgatgattgc tgctcagggg
2761 ccactaaaag aaacgatcgg aaccagaagtt cagatgatat tccaaagaaa agtcaaagtt
2821 attgtgatgt tgacagagtt agtgaatgga cagcaggaag tctgtgctca gtactggggc
2881 gaaggaaagc agacttatgg agacatgga gaccaggaga gtggagatga aagacacaaa cagagcctca
2941 gcctcactc tccgaacttt tgagctgaga cattccaaga ggaaggagcc cagaactgtg
3001 taccagtacc agtgtaccac atggaaaggg gaagagctcc ctgcagaacc caaagacctg
```

FIG. 3 (Continued)

```
3061 gtgtctatga ttcaggacct caaacagaag cttcccaagg cttccccaga agggatgaag
3121 tatcacaagc atgcatccat cctcgtccac tgcagagatg gatcccagca gacagggttg
3181 ttctgtgcct tgttcaatct cttggaaagt gcagaaacag aagatgtggt tgatgttttc
3241 caagtggtaa agtctctacg caaagcacgg cctggggtgg tgtgcagcta tgagcaatac
3301 cagttcctct atgacatcat cgccagcatc tatcccgccc agaatggaca agtcaagaaa
3361 acaaacagcc aagacaaaat tgaatttcat aatgaagtgg atggaggcaa gcaggatgct
3421 aactgtgtcc gtccagatgg tcctctgaat aaagcccagg aagacagcag aggggtggga
3481 accccggagc ctaccaatag tgctgaggaa ccagaacatg ctgccaatgg ttctgcgagc
3541 ccagctccaa cccagagttc ataggaaagg agtcatgtgg gacaacgcag actctcacat
3601 tagttcctttc tattttccta gacctaatga aagaacatgg ctgtgcagtg gttatgaa
3661 tctgtgttca cctttgccac tgtataaaaa tatttaagtt tgtcaaaaca ttttgtacag
3721 tttatgctt attttaaaag tgtatctatg tcattcagca ggaatgtata tgtgacagag
3781 ggtgtctgtg tgtgtgagag tgtgtttatg tatgagtgac tatgagtgat tgtgtgtgtg catgtttgtg
3841 cgtgtgtatg acatctaaat gtgattggag aatactttca agccatttca aatgctttcg
3901 agaaacagtg tgcctttct cctcttgagg aaactataca tttatatct aaactgttaa
3961 tttgtttgag ggattaattt tttaaaatcc cattgaaagt ggattcagtt gtaagaataa
4021 caatgtgtac cattctggaa tgacctcaag gtgtcctcct tgtcctgttg atgatcttgt
4081 agtttaagat gctcttttg gatatagata agcgtatgta agagtgctgt gggtgtgtac
4141 agctgatctg ggacgtgaac aaaatcaaca tgtgagactt atgttccata tactgtcatt
4201 tcatcactat ctcttaatgc atatttaatc aaacatgaaa atctcaaggg agactatttt
4261 tgtatccaca tgggaagtag aacattgcaa gtcagttgct gtctacacaa tagataaaaa
4321 ttactagtta atgctcttgg tcatatcgat atatgctatg aacctaaata attgcccctta
4381 gccaaatata atgtatgtta aaaacacata gaataaaaac aggggcatga aaacttgttt
4441 gtactgaata tttacatagg taacctcgta cagttagttc tgttatggaa ttcaccattt
4501 atgggaaatg taaaattgac tatggccatt tcctatgctt aagaccatct ttgacttgca
4561 ttactgtgta tttatcttga atttcccac tgttttgttt actcttactg agatataata
4621 ttgataacca taataaactt tcaactatta tcttc
```

FIG. 3 (Continued)

SEQ ID NO:21

*Mus musculus* CD45  Image clone  GenBank Acc: AA178615

```
GCTTTCGAGAAACAGTGTGCCCTTTCTCCTCTGAGGAAACTATACATTTATATCTAAA
CTGTTAATTTGTTGAGGGATTAATTTTTAAAATCCCATTGAAAGTGGATTCAGTTGTA
AGAATACAATGTGTACCATTCTGGAATGACCTCAAGGTGTCCTCGTCCTGTCGTGATG
ATCTTGTAGTTTAAGATGCTCTTTTTGGATATAGATAAGCGTATGTAAGAGTGCTGTGGG
TGTGTACAGCTGATCTGGGACGTGAACAAAATCAACATGTGAGACTTATGTTCCATATAC
TGTCATTTCATCACTATCTCTTAATGCATATTTAATCAAACATTAAATCTCAAGGGAGA
CTATTTTGTATCCACATAGTTAATGCTCTGTTGGTCATGAACATTGCAAGTCAGTTGCGTGTCTACACAATAG
ATAAAATTACTAGTTAATGCTCTGTTGGTCATCGATATATGCTATGAACCTAAATAATT
GCCCTTAGCCAAATATAATGTATGTTAAAACACATAGAATAAAAACAGGGCATGAAAA
CTTGTTTGTACTGAATATTTACATAGGTAACCTCGTACAGTTAGTTCTGTTATGGAATTC
ACCATTTATGGGAAATGTAAAATTGACTATGGCCCATTTCTATGCTTAAGACCATCTTTG
ACTTGCATTACTGTGTATTTATCCTGAATTGCGCACTGTTTGTTTACTCTACTGAGAT
ATAATATTGATACCCATAATAACTTCCACTATT
```

FIG. 3 (Continued)

SEQ ID NO:22

*Mus musculus* Fas mRNA GenBank Acc: NM_007987

```
   1 gccgcaggct gcccacacag gccgcccgct gttttcccctt gctgcagaca tgctgtggat
  61 ctggctgtc  ctgcctctgg tgcttgctgg ctcacagtta agagttcata ctcaaggtac
 121 taatagcatc tccgagagtt taaagctgag gaggcgggtt catgaaactg ataaaaactg
 181 ctcagaagga ttatatcaag gaggcccatt ttgctgtcaa ccatgccaac ctggtaaaaa
 241 aaaagttgag gactgcaaaa tgaatggggg tacaccaacc tgtgccccat gcacagaagg
 301 gaaggagtac atggacaaga accattatgc tgataaatgc agaagatgca cactcctgcga
 361 tgaagagcat ggtttagaag tggaaacaaa ctgcaccctg acccagaata ccaagtgcaa
 421 gtgcaaacca gacttctact gcgattctcc tggctgtgaa cactgtgttc gctgcgcctc
 481 gtgtgaacat ggaaccctg  agccatgcac agcaaccagc aatacaaact gcaggaaaca
 541 aagtcccaga aatcgcctat ggttgttgac catccttgtt ttgttaattc cacttgtatt
 601 tatatatcga aagtaccgga aagaaaagtg ctggaaaagg agacaggatg accctgaatc
 661 tagaacctcc agtcgtgaaa ccataccaat gaatgcctca aatcttagct tgagtaaata
 721 catcccgaga attgctgaag acatgacaat ccaggaagct aaaaaatttg ctcgagaaaa
 781 taacatcaag gagggcaaga tagatgagat catgcatgac agcatccaag acacagctga
 841 gcagaaagtc cagctgctcc tgtgctggta ccaatctcat gggaagagtg atgcatatca
 901 agatttaatc aagggtctca aaaaagccga atgtcgcaga acccttagata aatttcagga
 961 catggtccag aaggaccttg gaaaatcaac cccagacact ggaaatgaaa atgaaggaca
1021 atgtctggag tgaaaactac ctcagttcca gccatgaaga gaggagagag cctgccaccc
1081 atgatggaaa caaaatgaat gccaactgta ttgacattgg caactcctgg tgtgttctct
1141 ttgccagcaa atggtagttg atactcagtg agggtcaaat gactagcagg ttccagggac
1201 tgcttctgtt atttctctgca gttgctgaga tgaaccattt tctctgtcta ctgcaatttt
1261 tacattcaaa tgtccatgaa atttgtatta aatgtgaagt ggaatctgca gtgtttgtgt
1321 ttatattcat atactatgaa ctgaggagaa ttataaactg aaacaaatac tcgcagttaa
1381 ttgaagacct tccattgatg gacagttctt ttcctctcta tatggaaatg tataatagaa
1441 gaaataattt ttaaattaaa gtatctcttt ttgcatttca
```

FIG. 3 (Continued)

SEQ ID NO:23

*Mus musculus* Fas Image clone GenBank Acc: AA178126

```
CGCAGAACCTTAGATAAATTTCAGGACACATGGTCCAGAAGGACCTTGGAAAATCAACCCCA
GACACTGGAAATGAAAATGAAGGACACAATGTCTGGAGTGAAAACTACCTCAGTTCCAGCCA
TGAAGAGAGGAGAGCCTGCCACCCATGATGGAAACAAAAATGATGCCAACTGTATTGA
CATTGGCAACTCCTGGTGTCTCTTTGCCAGCAAATGGTAGTTGATACTCAGTGAGGG
TCAAATGACTAGCAGGTCCAGGGACTGCTTCTGTTATTCTCTGCAGTTGCTGAGATGAA
CCATTTTCTCTGTCTACTGCAATTTTACATTCAAATGTCCATGAAATTTGTATTAAATG
TGAAGTGGAATCTGCAGTGTTTGTGTTTATATTCATATACTATGAACTGAGGAGAATTAT
AAACTGAAACAAATACTCGCAGTTAATTGAAGACCTTCCATTGATGGACAGTTCTTTTCC
TCTCTATGTGGAAATGTATAATAGAAGAGATAATTTTTAAATTAGAGTATCTCTTTTTGC
ATTTC
```

FIG. 3 (Continued)

SEQ ID NO:24

*Mus musculus* Fyn mRNA GenBank Acc: NM_008054

```
   1 cctgggcccc gccgcggacg cgcggagccg cctggccgc gccggaggag ggcggggaga
  61 ggaccatgtg aatgtgctcc ggagctgagc gccaagccaa gcagtgtttg aaaggaagca
 121 ggatgctgat ctaatcgtgg caaaaagtca gtccgaccgc tggtttcgaa gacatgtggt
 181 gtatataaag tttgtgatag ttggtggaaa tttgggagct tggataatgg gctgtgtgca
 241 atgtaaggat aaagaagcag cgaaactgac cagaccccac agaggagagg gacggcagcc tgaaccagag
 301 ctctgggtac cgctatggca cagacccac ccctcagcac tacccagct tcggcgtgac
 361 ctccatcccg aactacaaca acttccacgc agctggggc cagggactca ccgtctttgg
 421 gggtgtgaac tcctcctctc acactgggac cctacgcacg agaggaggga caggagtgac
 481 actgtttgtg gcgctttatg actatgaagc acggacggaa gatgacctga gttttcacaa
 541 aggagaaaaa tttcaaatat tgaacagctc ggaaggagat tggtgggaag cccgctcctt
 601 gacaaccggg gaaactggtt acattcccag caattacgtg gctccagttg actccatcca
 661 ggcagaaagag tggtactttg gaaaacttgg cgcaaagat ccgcgagagc gctgagagac agctcctgtc
 721 ctttgaaaac ccaagaggta cctttcttat gggatgatat ccgcgagagc caaaccacca aaggtgccta
 781 ctcactttcc atccgtgatt gatactatat gaaaggggac cacgtcaaac attataaaat
 841 ccgcaagctt gacaatggtg cagagaaagc cacaacgcgg gcccagtttg aaacacttca
 901 gcaactggta cagcattact aaacttctgg tgatggtttg tgttttaact taactgtggt
 961 ttcatcaagt tgtaccccac aaacttctgg attggctaaa gatgcttggg aagttgcacg
1021 tgactcgttg tttctggaga agaagctggg gcaggggtgt ttcgctgaag tgtggcttgg
1081 tacctggaat ggaaatacaa aagtagccat aaagacccttaagccaggca ccatgtctcc
1141 ggagtccttc ctgagggagg cgcagatcat gaagaagctg aagcatgaca agctggtgca
1201 gctctacgcg gtcgtgtctg aggagcccat ttacatcgtc acggagtaca tgagcaaagg
1261 aagtttgctt gacttcttaa aagatggtga aggaagagct ctgaagttgc caaaccttgt
1321 ggacatggcg gcacaggttg ctgcaggaat ggcttacatc gagcgcatga attatatcca
1381 cagagatctc cgatcagca acattctagt gggaatgga ctaatttgca agattgctga
1441 ctttggattg gctcggttga ttgaagacaa tgaatacaca gcaagacaag gtgcgaagtt
```

FIG. 3 (Continued)

```
1501 tcccattaag tggacagccc ccgaagcggc cctgtatgga aggttcacaa tcaagtctga
1561 cgtatggtct tttggaatct tactcacaga gctggtcacc aaaggaagag tgccataccc
1621 aggcatgaac aaccgggagg tgctggagca ggtggagaga ggctatagga tgccctgccc
1681 acaggactgc ccgatctccc tgcacgagct catgatccac tgctggaaaa aggatccgga
1741 agagcgcccg acttcgagt acttgcaggg cttcctggag gactacttta cggccacaga
1801 gccccagtat cagcccggtg aaaacctgtg agagcctgcg cttcagacgc ctcttcccga
1861 ggcctccccta cccctcccca ttagcttcca atctgtagc cagctgcccc agagcaggag
1921 aaccgtccag gatcagattg ccccagtcc gaacctcctc ttgaagctga acttccacgg ccctcattaa
1981 tgacacttgt ccccagtcc catgtgactc tgtgaaccat ctgagacaga agcgtgttat
2041 ttctcagact tggaaatgca ttgtatcgat gttatgtcaa aggccaaacc tctgttcagt
2101 gtaaatagct gctcctgtgc caacaatccc agtgctttcc tttttaaaa aagaaaaagc
2161 aaatcctatg tgattttaac tctgatttca cctgattcaa ctaaaaaaaa aaaagtatta
2221 ttttccaaaa gtggcctctt tgtctaaaac aataaaattt tttttcatgt tttaacaaaa
2281 aaatgatcag gacaggtgtt tgggtttttt ttccctttt tatacatatg atatatatgt
2341 taacatatgt tcctgtacat acaccatgtg ggtgctacca tggagactgg ccagcgtagg
2401 ccacatagct acaggaccgg agtgggatt actgcagcgt gatcatgcaa gctcaccccc
2461 ttccagcaaa acactgtgt cagcctgcaa gccggtggct catttttga cttctacgaa
2521 gcatgacgtc ctctccattt ggactttta ataacctaat catacctata gattgttcat
2581 gtgactttt tcaggtccag ggcctagtca cgagttttag tgccagtttt tagtccagct
2641 caactgtgat tcgtcttgaa acttaggagt gagcattta gcaaaaagca gccagccagt
2701 tctaccacaa gagctgcaag acggagacca cactaacttc ctgtataaat atgaatgctg
2761 aagggttcag gtgttttcct tttatttaat aaatcctgta accacattta aatggtctaa
2821 acccatagca ttggtcatgg gcaacctaaa ctttctcat gcaactaaaa ttatgggaag
2881 gctaagggtg gggggttggt acacgtccca ttgtaaaata agtgttttac tgtcctgtac
2941 tgctaatgac tgactctccg tgtcaggagt gctccagtga ataactatgc actactttac
3001 atttcatggg ggtgcacaaa aaaaaaaagg tattacagtt tttagttgct gtttgtacca
3061 acctcgaatt acgtatgttt aacaacaaat caattcctat tctattgagt tttaatactg
3121 actagcaatt ctgaagtctt aattccttt tttgttaat gattacttg tgagtttaca
3181 tttttaaatt gtttaacttt ccctaattag taattaaaaa gagagcattt tacatttgaa
3241 aaaaaaaaaa aaaaaaa
```

FIG. 3 (Continued)

SEQ ID NO:25

*Mus musculus* Fyn Image clone GenBank Acc: AI448320

TTTTTTTTTTTTTTTTTCAAATGTAAAATGCTCTCTTTTAATTACTAAATTAGAA
AAGTAAACAATTAAAAATGTAAACTCACAAGTAAATCATTAACAAAAAAAGAATTA
AGACTTCAGAAATGCTAGTACATTAAAAACTCAATAGAAATAGGAATTGATTGTTG
TTAAACATACGTAATTCGAGGTTGGTACAAACAGCAACTAAAAATGTAATACTTTTTT
TTTGTGCACCCCATGAAATGTAAAGTAAGTGCATAGTTATTCACTGGAGCACTCCTGAC
ACGGAGAGTCACTCATTAGCAGTCAGGACAGTAAAACACTTATTTTACAATGGGACGTG
TACAACCCCCCACCCTTGCCTCCATAATTTTAGTTGCATGAGAAAGTTTAGTAGTT
GCCATGACTACAATGCTATGGGTTTAGACCATTTAAATGTGGTTACAAGATTTATTAAAT
AAAAGGAAAACACCTGAACCCTTCAGCATTCATAT

SEQ ID NO:26

*Mus musculus* Fyn Image clone GenBank Acc: AI510621

GCCAACAATCCCAGTGCTTCCTTTTTTAAAAAGAAAAGGCAAATCCTATGTGATTTTA
ACTCTGTCTTCACCTGATTCAACTAAAAAAAAAAAGTATTATTTTCCAAAAGTGGCCTC
TTTGTCTAAAACAATAAAATTTTTTCATGTTTAACAAAAATGATCAGGACAGGTGT
TTGGGTTTTTTTCCCTTTTTTTATACATATGATATATATGTTAACATATGTTCCTGTACA
TACACCATGTGGGTGCTACCATGGAGACTGGCCAGCGTAGGCCACATAGCTACAGGACCG
GAGTGGGATTACTGCAGAACCCTGCCAGCAAGCACTGGTGTCAGCCTGCAAGCCGGTG
GCCTCATTTTTGACTTCTACGAAGCATGACGTCCTCTCCATTTGACTGCACTTTTTG
GGTCCCTAACAAACACCATTAGATGGGTACATGGACTTT

FIG. 3 (Continued)

SEQ ID NO:27

*Mus musculus* Fyn Image clone GenBank Acc: AA119262

```
GCCAACAATCCCAGTGCTTCCTTTTTAAAAAGAAAAAGCAAATCCTATGTGATTTTA
ACTCTGTCTTCACCTGATTCAACTAAAAAAAAAAGTATTATTTTCCAAAAGTGGCCTC
TTTGTCTAAAACAATAAATTTTTTCATGTTTTAACAAAAATGATCAGGACAGGTGT
TTGGGTTTTTTTCCCTTTTTATACATATATATATGTTAACATATGTTCCTGTACA
TACACCATGTGGGTGCTACCATGGAGACTGGCCAGCTGGCTAGGCACATAGCTACAGGACCGG
AGTGGGGATTACTGCAGAACCCTGCCAAAGCACTGGTGTCAGCCTGCAAGCCGGTGG
CTCATTTTTGACTTCTAGAAGCATGAGCTCCTCTCCATTGGACTGCACTTTTTGGT
TCCTAATC
```

SEQ ID NO:28

*Mus musculus* IL4 mRNA GenBank Acc: M25892

```
  1 ggatccccgg gcagagctgg gggggattt gttagcatct cttgataaac ttaattgtct
 61 ctcgtcactg acggcacaga gctattgatg ggtctcaacc cccagctagt tgtcatccctg
121 ctcttcttc tcgaatgtac caggagccat atccacggat gcgacaaaaa tcacttgaga
181 gagatcatcg gcattttgaa cgaggtcaca ggagaaggga cgccatgcac ggagatggat
241 gtgccaaacg tcctcacagc aacgaagaga accacagaga gtgagctcgt ctgtagggct
301 tccaaggtgc ttccgcatatt ttatttaaaa catgggaaaa ctccatgctt gaagaagaac
361 tctagtgtc tcatggagct gcagagactc tttcgggctt ttcgatgcct ggattcatcg
421 ataagctgca ccatgaatga gtccaagtcc acatcactga aagacttcct ggaaagccta
481 aagagcatca tgcaaatgca ttactcgtag tactgagcca ccatgcttta acttatgaat
541 ttttaatggt ttatttttaa tattatata tttataattc ataaaataaa atatttgtat
601 aatgt
```

FIG. 3 (Continued)

SEQ ID NO:29

*Mus musculus* IL4  Image clone GenBank Acc: AA124283

```
ACTTAATTGTCTCTCGTCACTGACGGCACAGAGCTATAGATGGGTCTCAACCCCAGCTA
GTTGTCATCCTGCTCTTCTTTCTCGAATGTACCAGGAGCCATATCCACGGATGCGACAAA
AATCACTTGAGAGAGATCATGCGGATCATTTGAACGAGGTCACAGGAGAAGGGACGCCATGC
ACGGAGATGGATGTGCCAAACGTCCTCACAGCAAGAACACCACAGAGAGTGAGCTC
GTCTGTAGGGCTTCCAAGTGCTTGCATATTTATTTAACACATGGGAAAACTCCATGCT
TGAAGAAGAACTCTAGTGTTTCTCATGGAGCTGCAGAGACTCTTTCGGGCTTTTCGATGCC
TGGATTCATCGATAAGCTGCACCATGAGTGAGTCCCAGTCCACATCACTGTTAGACTTCC
TGGTAAGCCTAAATGAGCTTCCTGCCAATGGATTACTCGTAGTACTGAGCACACATGGCT
TAACCTAGTGTATTCTTAATGGGCTTAATTTAATA
```

DNA ARRAY SEQUENCE SELECTION

FIELD OF THE INVENTION

The present invention provides methods for the construction of custom microarrays using information from public databases. One preferred embodiment provides the novel cDNA array, the ImmunoChip. The ImmunoChip is useful for diagnostic procedures and screening involving immunological-based sample materials. In preferred embodiments, the ImmunoChip is used in experiments and screens in innate and adaptive basic immunology, tumor immunology, cancer biology of immune cells, aging, drug testing, infection immunology, autoimmune diseases, arthritis, allergy, and vaccine development against these diseases.

BACKGROUND

The purpose of the microarray technology is to associate gene functions with sequences obtained by genome or expressed sequence tags (EST) projects (e.g., the Human Genome Project). Since the genome projects for most model organisms are not yet completed, EST databases are presently the ultimate source for construction of custom microarrays. Currently, more than 6.4 million different ESTs from cDNA libraries representing diverse cells and tissues for various model organisms are publicly available. Bioinformatics algorithms such as Unigene, assemble these ESTs into clusters that tentatively define distinct genes. However, despite these rich resources, a method is missing that would allow for the selection of relevant clusters and to identify the biological best representative EST clone within these clusters for the construction of a microarray. In other words, current methods for the selection of DNA clones for incorporation into an array do not allow for the efficient selection of clones that are specific for cell type, tissue type, etc., without undue redundancy What is needed is a method for the efficient construction of microarrays that are specific for cell types, tissues, organs and diseases (e.g., cancer) without redundancy.

SUMMARY OF THE INVENTION

The present invention provides methods for the selection of DNA sequences for incorporation into DNA arrays, in which the methods comprises novel algorithms. The methods of the present invention facilitate the construction of DNA microarrays that are non-redundant and specific for the desired tissue, organ, species, developmental stage or disease. By using this method, the "ImmunoChip" was constructed. The construction of this immunologically relevant microarray integrates (non-redundantly) the expression information of ESTs from known and unknown genes from all immune cells and lymphoid organs in the developing and adult organism.

The present invention contemplates the utilization of sequences selected by the methods of the present invention specific for any tissue type, cell type, organ and/or disease. Indeed, the present invention is not limited to any specific type of tissue, cell or disease. For example, tissue types that find use with the present invention include, but are not limited to lung, heart, muscle, liver, skin, brain, testicle, thymus, kidney, spleen, breast, etc., or a combination of thereof. Thus, many types of tissue will find use with the present invention. In a preferred embodiment, immune tissue (i.e., tissue that is involved in the immune response in some manner) is contemplated. In addition, the present invention is not limited to any particular type of cell. Indeed, many cell types are contemplated. For example, cells including, but not limited to blood cells, skeletal muscle cells, cardiac muscle cells, smooth muscle cells, fibroblastic cells, chondrocytes, epithelial cells, cells of the reticuloendothelial system, etc., will find use in the present invention. In a preferred embodiment, immune cells are utilized. In addition, the present invention is not limited to any specific or particular type of disease. Indeed, many types of disease are contemplated. In a preferred embodiment, the disease is cancer. However, the present invention is not limited to any specific types of cancer, as many types of cancer are contemplated. For example, cancers such as leukemia, as well as those of the lung, stomach, skin, brain, liver, prostate, testes, bone marrow, bone, breast, intestinal, etc., will find use with the present invention. In other embodiments, other diseases are contemplated. Furthermore, in some embodiments, the present invention finds use in monitoring the progression of a particular disease by assessing changes in the detection and/or levels of various cell markers associated with the disease.

The present invention also provides methods and compositions for screening drug treatments for diseases. The present invention is not limited to any particular drug treatment. Drugs identified using the methods of the present invention include newly recognized compounds, as well as compounds that have already been established for treatment (e.g., compounds used for other purposes), as well as experimental treatments. In alternative embodiments, the present invention provides methods and compositions to monitor the effect of a particular drug or drugs by studying the change in detection of various cell markers following administration of the drug(s) to a subject or in cell culture.

The present invention also provides compositions and methods for the construction of non-redundant DNA microarrays using a bioinformatics approach. Additionally, the present invention provides means for the selection of DNA sequences from public and private databases. However, the present invention is not limited to any particular databases, as many public and private databases find use with the present invention. For example, databases, including, but not limited to gene databases (e.g., GenBank), image clone databases, bacterial clone databases, viral databases, EST databases and phage databases find use with the present invention. Additionally, the present invention provides means for the selection of DNA sequences from the literature.

The present invention provides methods and compositions for the construction of an ImmunoChip for any species of animal having an immune system. Thus, it is not intended that the ImmunoChip be limited to any particular species of animal having an immune system. For example, the present invention contemplates the production of ImmunoChips from various species (e.g., bovines, ovines, lagomorphs, caprines, porcines, primates, including humans, canines, felines, rodents [e.g., mice and rats], equines, avians, reptiles, etc.). In a preferred embodiment, the organism is a murine species.

In addition, the present invention provides methods and compositions for the construction of a DNA array for any species of organism. Indeed, the present invention is not limited to any particular species. For example, the species include plants, animals, bacteria, viruses, and any other organisms. However, in a preferred embodiment, the species is an animal species, and in a particularly preferred embodiment, the species is a murine species.

The present invention provides bioinformatics approaches using public and private databases to generate specific and customizable microarrays. In a preferred embodiment, the array is a unique cDNA microarray specifically designed for immunology research. In a particularly preferred embodiment, a microarray of the present invention was constructed in two steps. First, immunological relevant clusters were selected using literature and expression information. Second, the best representative clones for each of the selected clusters were identified. The array comprised representative clones for more than 13,389 different immunological clusters (See, Table 1, attached hereto), or a portion thereof. Thus, the present invention is suitable for many applications, including experiments and screens addressing questions pertaining to innate and adaptive basic immunology, tumor immunology, oncology (e.g., as associated with immune cells), aging, drug testing, immunology associated with infection disease, autoimmune diseases, arthritis, and allergy, as well as for drug and vaccine development against these diseases. The present invention further provides methods and compositions for selecting cDNA clones for DNA arrays, wherein the clones are selected from diseased organisms, tissues, and/or cells.

In one embodiment, the clonal sequences necessary for the detection of changes in immune function in mice for inclusion on to the ImmunoChip have been deduced. In some embodiments, the ImmunoChip is a DNA microarray wherein the effects of disease progression and treatment protocols are monitored.

The arrays of the present invention are not limited to any particular means of construction. Indeed, the present invention contemplates arrays constructed by any suitable means. Many means of construction of arrays are known in the art (See e.g., the Detailed Description of the Invention).

The present invention contemplates that the arrays may be read by any suitable means, including manual and automated reading. In embodiments involving manual reading, typically reading is conducted visually "by eye" (e.g., the results are read by someone looking at and evaluating them). In alternative embodiments, instrumentation, such as microscopes or manual plate readers are used. Automated readers, for example scanners, are available commercially and are known to those in the art.

In one embodiment the present invention provides an array comprising the sequences of FIG. 3 (i.e., FIG. 3 shows the sequences of SEQ IN NOS: 1–29).

In one embodiment, the present invention provides a composition comprising an array of cDNA probes immobilized on a solid support, wherein the array comprises at least 100 probes and no more than 100,000 probes, which are approximately 100 to 2000 nucleotides in length occupying separate known sites in the array, and wherein at least a portion of the cDNA probes are selected from the sequences in FIG. 3. In another embodiment, the present invention contemplates that the probes are oligodeoxyribonuclotides. In yet another embodiment, the present invention provides oligodeoxynucleotide probes. In still another embodiment, the present invention provides an array that contains between 1,000 and 50,000 probes. In yet still another embodiment, the present invention provides an array that contains between 2,000 and 20,000 probes. In yet still another embodiment, the present invention provides an array that contains between 5,000 and 15,000 probes. In yet still another embodiment, the present invention provides a solid support that is selected from the group consisting of glass, plastic and metal.

The present invention provides compositions and devices comprising cDNA probe elements, probe sites or a plurality of probe molecules affixed to a solid microarray substrate. In one embodiment, the present invention comprises 10 probes selected from FIG. 3. In another embodiment, the present invention comprises 20 probes selected from FIG. 3. In most embodiments, probe elements containing different characteristic molecules are typically arranged in a two-dimensional array, for example, by microfluidic spotting techniques or by patterned photolithographic synthesis. In some embodiments, the present invention provides oligodeoxynulceotide probes, while in other embodiments, the probes are oligodeoxyribonucleotides In some embodiments, the present invention provides methods of selecting cDNA clones for DNA arrays, wherein the array has between 1,000 and 50,000 probes. In another embodiment, the present invention provides arrays having between 2,000 and 20,000 probes. In yet another embodiment, the present invention provides arrays having between 5,000 and 15,000 probes. In still further embodiments, the present invention provides a solid support that is selected from a group comprising glass, plastic and metal.

The present invention further provides methods of selecting DNA sequences for non-redundant microarrays, wherein the methods comprise: a) providing sequence database(s), b) screening the database(s) for DNA sequences specific for a species and/or a tissue found in the species, to generate a redundant sequence list; c) removing redundant sequences from the list to generate a non-redundant cluster list; d) categorizing selected sequences from non-redundant cluster list into at least one module list, and e) selecting the best representative clones based on the characteristics used to establish the parameters of the module list. In some embodiments of the present invention, the genes are screened from databases (for example, Unigen, GenBank, Locuslink, etc.) based on gene name or homolog name, the LL description, the PubMed indicated function, etc., (i.e., indicating the function or tissue desired). Redundant clones and duplicates are removed by importing the sequences into software programs designed for this purpose (for example, Panorama, ProVue, Huntington Beach, Calif.). The categorizing of the nonredundant clones is performed by putting clones with similar characteristics (e.g., whole genes, gene fragments, degrees of homology) into grouped called "modules." Selecting the best representative clones is performed by cluster score, blast score and/or physical parameters (e.g., size).

The present invention also provides methods selecting cDNA clones for DNA arrays, wherein the databases from which the clones are selected are from gene, bacterial, viral, phage, EST and image clone databases and literature sources, or any other suitable data source.

FIGURES

FIG. 3 shows the sequences of cDNA probes (SEQ ID NOS: 1–29) used in the construction of a preferred embodiment of the ImmunoChip cDNA array.

DEFINITIONS

Figure 1:
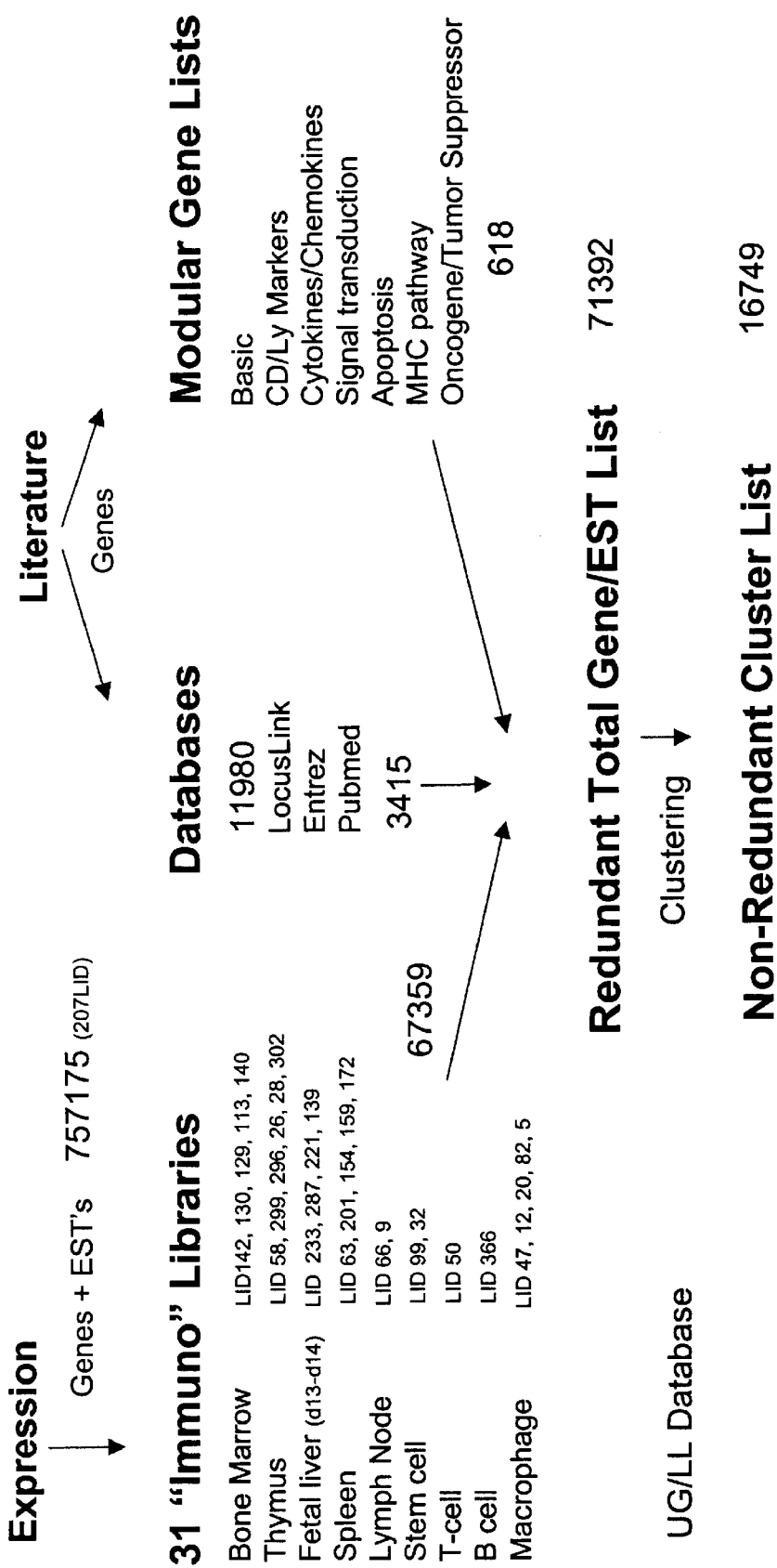
FIG. 1 shows the selection of immunologically relevant clusters.

To facilitate an understanding of the present invention, a number of terms and phrases are defined below:

As noted above, the present invention is directed to non-redundant arrays. By "non-redundant" it is meant that at least the majority of probes (i.e., 51%) in the array have less than 60% homology (more preferably less than 50% homology, and still more preferably less than 40% homology) with any other probe also present in the array. In a preferred embodiment of a non-redundant array of the present invention, at least 75% of probes on the array have less than 60% homology (more preferably less than 50% homology, and still more preferably less than 40% homology) with any other probe also in the array. In still another preferred embodiment of a non-redundant array of the present invention, at least 90% of probes on the array have less than 60% homology (more preferably less than 50% homology, and still more preferably less than 40% homology) with any other probe also on the array. In yet another preferred embodiment of a non-redundant array of the present invention, greater than 95% of the probes on the array have less than 50% homology (more preferably less than 40% homology, and still more preferably less than 30% homology) with any other probe also on the array. It should be clear from the above, that some redundancy is permitted in the "non-redundant" arrays of the present invention. For example, a one intent on using the present invention cannot practice outside the scope of the claims merely by introducing a handful of redundant probes (e.g., probes with 60% homology or greater to other probes on the array) on the otherwise non-redundant array.

As used herein, "immune tissue" refers to any component of the body that functions in the generation, maturation, or temporary sequestering of immune cells. Such components include, but are not limited to bone marrow, thymus, blood, lymph nodes, lymph ducts, lymph, Peyer's patches, spleen, and the like and all fluids comprising cells within these tissues.

As used herein, "immuno function" and "immunological function" refer to tissues, cells, organs, etc. that indicate to one practiced in the art that the tissue, cell, organ, etc. function in conjunction with the immune system to produce an immune response.

As define herein, "module list" refers to cDNA clones that have been selected by the methods of the present invention and organized into groups (modules) based on the physical features of the clones. For example, in one embodiment of the present invention, the GENE module contains genes murine genes but no gene fragments, the HOM module contains genes with >90% homology to other known genes from human, rat, Drosophila, Saccharomyces, Caenorhabditis and *E. coli*, and the EST module contains moderate, weakly or nonhomolgous gene fragments.

As used herein, "light beam" refers to directed light, for example, comprised of either a continuous cross-section or a plurality of convergent or divergent sub-beams (e.g., a patterned beam). This term-is meant to include, but is not limited to, light emitted from a light source, light reflected upon striking a reflecting device (e.g., a micromirror), and the like.

As used herein, the term "collimated light" refers to a beam of light having substantially parallel rays. It is intended that the term also encompasses quasi-collimated light.

As used herein, "optical signal" refers to any energy (e.g., photodetectable energy) from a sample (e.g., produced from a microarray that has one or more optically excited [i.e., by electromagnetic radiation] molecules bound to its surface).

As used herein, "filter" refers to a device or coating that preferentially allows light of a characteristic spectra to pass through it (e.g., the selective transmission of light beams).

As used herein, the term "spatial light modulator" refers to devices that are capable of producing controllable (e.g., programmable by a processor, or pre-directed by a user), spatial patterns of light from a light source. Spatial light modulators include, but are not limited to, Digital Micromirror Devices (DMDs) and Liquid Crystal Devices (LCDs). In some embodiments, the LCD is reflective, while in other embodiments, it is transmissive of the directed (e.g., spatially modulated) light. "Polychromatic" and "broadband" as used herein, refer to a plurality of electromagnetic wavelengths emitted from a light source.

As used herein, "microarray" refers to a substrate with a plurality of molecules (e.g., nucleotides) bound to its surface. Microarrays, for example, are described generally in Schena, *Microarray Biochip Technology*, Eaton Publishing, Natick, MA, (2000). Additionally, the term "patterned microarrays" refers to microarray substrates with a plurality of molecules non-randomly bound to its surface.

As used herein, the term "micromirror array" refers to a plurality of individual light reflecting surfaces that are addressable (e.g., electronically addressable in any combination), such that one or more individual micromirrors can be selectively tilted, as desired.

As used herein, the terms "optical detector" and "photodetector" refers to a device that generates an output signal when irradiated with optical energy. Thus, in its broadest sense, the term "optical detector system" refers devices for converting energy from one form to another for the purpose of measurement of a physical quantity and/or for information transfer. Optical detectors include but are not limited to photomultipliers and photodiodes.

As used herein, the terms "photomultiplier" and "photomultiplier tube" refer to optical detection components that convert incident photons into electrons via the photoelectric effect and secondary electron emission. It is intended that the term "photomultiplier tube" encompasses devices that contain separate dynodes for current multiplication, as well as devices that contain one or more channel electron multipliers.

As used herein, the term "photodiode" refers to solid-state light detector types including, but not limited to PN, PIN, APD and CCD.

As used herein, the term "TTL" stands for Transistor-Transistor Logic, a family of digital logic chips that comprise gates, flip/flops, counters etc. The family uses zero Volt and five Volt signals to represent logical "0" and "1" respectively.

As used herein, the term "dynamic range" refers to the range of input energy over which a detector and data acquisition system is useful. This range encompasses the lowest level signal that is distinguishable from noise to the highest level that can be detected without distortion or saturation.

As used herein, the term "noise" in its broadest sense refers to any undesired disturbances (i.e., signal not directly resulting from the intended detected event) within the frequency band of interest. Noise is the summation of unwanted or disturbing energy introduced into a system from man-made and natural sources. Noise may distort a signal such that the information carried by the signal becomes degraded or less reliable.

As used herein, the term "signal-to-noise ratio" refers the ability to resolve true signal from the noise of a system. Signal-to-noise ratio is computed by taking the ratio of levels of the desired signal to the level of noise present with the signal. In preferred embodiments of the present invention, phenomena affecting signal-to-noise ratio include, but are not limited to, detector noise, system noise, and background artifacts. As used herein, the term "detector noise" refers to undesired disturbances (i.e., signal not directly resulting from the intended detected energy) that originate within the detector. Detector noise includes dark current noise and shot noise. Dark current noise in an optical detector system results from the various thermal emissions from the photodetector. Shot noise in an optical system is the product of the fundamental particle nature (i.e., Poisson-distributed energy fluctuations) of incident photons as they pass through the photodetector.

As used herein, the term "system noise" refers to undesired disturbances that originate within the system. System noise includes, but is not limited to noise contributions from signal amplifiers, electromagnetic noise that is inadvertently coupled into the signal path, and fluctuations in the power applied to certain components (e.g., a light source)

As used herein, the-term "background artifacts" include signal components caused by undesired optical emissions from the microarray. These artifacts arise from a number of sources, including: non-specific hybridization, intrinsic fluorescence of the substrate and/or reagents, incompletely attenuated fluorescent excitation light, and stray ambient light. In some embodiments, the noise of an optical detector system is determined by measuring the noise of the background region and noise of the signal from the microarray feature.

As used herein, the term "processor" refers to a device that performs a set of steps according to a program (e.g., a digital computer). Processors, for example, include Central Processing Units ("CPUs"), electronic devices, and systems for receiving, transmitting, storing and/or manipulating digital data under programmed control.

As used herein, the terms "memory device," and "computer memory" refer to any data storage device that is readable by a computer, including, but not limited to, random access memory, hard disks, magnetic (e.g., floppy) disks, zip disks, compact discs, DVDs, magnetic tape, and the like.

The term "gene" refers to a nucleic acid (e.g., DNA) sequence that comprises coding sequences necessary for the production of a polypeptide or precursor. It is intended that the term encompass polypeptides encoded by a full length coding sequence, as well as any portion of the coding sequence, so long as the desired activity and/or functional properties (e.g., enzymatic activity, ligand binding, etc.) of the full-length or fragmented polypeptide are retained. The term also encompasses the coding region of a structural gene and the sequences located adjacent to the coding region on both the 5' and 3' ends for a distance of about 1 kb on either end such that the gene corresponds to the length of the full-length MRNA. The sequences that are located 5' of the coding region and which are present on the MRNA are referred to as "5' untranslated sequences." The sequences that are located 3' (i.e., "downstream") of the coding region and that are present on the MRNA are referred to as "3' untranslated sequences." The term "gene" encompasses both cDNA and genomic forms of a gene. A genomic form of a genetic clone contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

Where "amino acid sequence" is recited herein to refer to an amino acid sequence of a naturally occurring protein molecule, "amino acid sequence" and like terms, such as "polypeptide" and "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified", "mutant", and "variant" refer to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3'oxygen of its neighbor in one direction via a phosphodiester linkage. Therefore, an end of an oligonucleotide or polynucleotide, referred to as the "5' end" if its 5'phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in either a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" and "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification and hybridization reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (e.g., Southern and/or Northern blots, solution hybridization and the like) under conditions of low stringency. A substantially homologous sequence or probe competes for and inhibits the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85–100% identity, preferably about 70–100% identity). With medium stringency conditions, nucleic acid base pairing will occur between nucleic acids with an intermediate frequency of complementary base sequences (e.g., hybridization under "medium stringency" conditions may occur between homologs with about 50–70% identity). Thus, conditions of "weak" or "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q-replicase, MDV-1 RNA is the specific template for the replicase (Kacian et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to a molecule (e.g., an oligonucleotide, whether occurring naturally as in a purified restriction digest or produced synthetically, recombinantly or by PCR amplification), that is capable of hybridizing to another molecule of interest (e.g., another oligonucleotide). When probes are oligonucleotides they may be single-stranded or double-stranded. Probes are useful in the detection, identification and isolation of particular targets (e.g., gene sequences). In some embodiments, it is contemplated that probes used in the present invention are labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular label. With respect to microarrays, the term probe is used to refer to any hybrididizable material that is affixed to the microarray for the purpose of detecting "target" sequences in the analyte.

As used herein "probe element" and "probe site" refer to a plurality of probe molecules (e.g., identical probe molecules) affixed to a microarray substrate. Probe elements containing different characteristic molecules are typically arranged in a two-dimensional array, for example, by microfluidic spotting techniques or by patterned photolithographic synthesis.

As used herein, the term "target," when used in reference to hybridization assays, refers to the molecules (e.g., nucleic acid) to be detected. Thus, the "target" is sought to be sorted out from other molecules (e.g., nucleic acid sequences) or is to be identified as being present in a sample through its specific interaction (e.g., hybridization) with another agent (e.g., a probe oligonucleotide). A "segment" is defined as a region of nucleic acid within the target sequence.

As used herein, the term "polymerase chain reaction" ("PCR") refers to the method of K. B. Mullis U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified." In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications. With PCR, it is possible to amplify a single copy of a specific target sequence in genomic DNA to a level detectable by the device and systems of the present invention.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the terms "reverse-transcriptase" and "RT-PCR" refer to a type of PCR where the starting material is MRNA. The starting MRNA is enzymatically converted to complementary DNA or "cDNA" using a reverse transcriptase enzyme. The cDNA is then used as a "template" for a "PCR" reaction.

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "coding region" when used in reference to a structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets which specify stop codons (i.e., TA, TAG, TGA).

As used herein, the terms "purified" and "to purify" refer to the removal of contaminants from a sample.

The term "recombinant DNA molecule" as used herein refers to a DNA molecule that is comprised of segments of DNA joined together by means of molecular biological techniques.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (e.g., 4, 5, 6, . . . , 100, . . . ).

The terms "recombinant protein" and "recombinant polypeptide" as used herein refer to a protein molecule that are expressed from a recombinant DNA molecule.

As used herein the term "biologically active polypeptide" refers to any polypeptide which maintains a desired biological activity.

As used herein the term "portion" when in reference to a protein (as in "a portion of a given protein") refers to fragments of that protein. The fragments may range in size from four amino acid residues to the entire amino acid sequence minus one amino acid (e.g., 4, 5, 6, . . . , 100, . . . ).

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "test compound" refers to any chemical entity, pharmaceutical, drug, and the like that can be or might be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention.

As used herein, the term "sample" is used in its broadest sense. In one sense it can refer to a tissue sample. In another sense, it is meant to include a specimen or and/or culture obtained from any source, as well as biological. Biological samples may be obtained from animals (including humans) and encompass fluids, solids, tissues, and gases. Biological samples include, but are not limited to blood products, such as plasma, serum and the like. T and B cell samples are meant to include any such cells obtained from an animal. The cells may be partly or substantially isolated from the other tissue or fluid constituents. These examples are not to be construed as limiting the sample types applicable to the present invention.

GENERAL DESCRIPTION OF THE INVENTION

The primary function of the immune system is to discriminate self from non-self antigens. This fine balance determines whether infections or tumors can be successfully defeated and whether autoimmune diseases can be prevented. To fulfill this task, the immune system involves cells distributed throughout the body in primary (bone marrow, thymus) and secondary lymphoid organs (spleen, lymph node). The most dominant cell types are thymus derived (T) lymphocytes, bone marrow derived (B) lymphocytes, and antigen presenting cells (e.g., macrophages and dendritic cells). The immune response involves the expression of immune specific intracellular transcription factors, signal transduction molecules, cell surface molecules (MHC) and secreted mediators (e.g., cytokines and chemokines). In some preferred embodiments, the ImmunoChip contains probes for all of these components.

While it is not necessary to know the precise mechanisms in order to practice the present invention, it is believed that both B and T cells are clonally produced by a process is called clonal selection. During clonal selection, cells that are nonfunctional or autoreactive are eliminated by apoptotic mechanisms. This process is called "negative selection." Each surviving clone (i.e., clones that are positively selected) is able to recognize a specific antigenic epitope. B cells recognize antigenic epitopes via interaction via cell surface bound antibodies (e.g., surface-bound IgM). Interaction of the IgM antibody with the appropriate antigen results in the activation of the cell. After activation, the B cell clone secretes antibodies that are then capable of recognizing foreign antigens and help combat disease. If, however, the B cell responds to components of the host, autoimmune disease may result.

In a similar chain of events, T cells are activated upon interaction of an antigen with the surface bound T cell receptor in conjunction with the major histocompatibility (MHC) receptor. Once activated, T cells either secret cytokines and thereby stimulate and attract other cells (both B and T cells and other immune system cells such as monocytes and neutrophils) or destroy the invading organisms. Like B cells, self-reactive T cells are also responsible for autoimmune reactions. What is troubling, however, is that most of the immunologically based diseases have not been well characterized in regard to the specific B and T cell clones that are activated. The present invention provides DNA arrays that will find use in characterizing these and other immunologically based diseases.

Thus, the present invention provides novel "DNA arrays" useful for diagnostic procedures and in particular for screening methods involving immunologically-based sample materials. The present invention is suitable, for example, for use in experiments and screens addressing questions in innate and adaptive basic immunology, tumor immunology, cancer biology of immune cells, aging, drug testing, infection immunology, autoimmune diseases, arthritis, allergy, and vaccine development against these diseases.

DNA microarrays typically consist of thousands of immobilized DNA sequences present on a miniaturized surface the size of a business card or smaller. Typically, arrays are used to analyze a sample for the presence of gene variations or mutations (genotyping), or for patterns of gene expression, performing the equivalent of about 100 to 100,000 individual "test tube" experiments.

Robotic technology is employed in the preparation of many arrays. The DNA sequences are bound to a surface such as a nylon membrane or glass slide at precisely defined locations on a grid. Using an alternate method, some arrays are produced using laser lithographic processes and are referred to as "biochips" or "gene chips."

DNA samples are prepared from the cells or tissues of interest. In preferred embodiments involving genotyping analysis, the sample is genomic DNA, while in other embodiments, such as for expression analysis, the sample is cDNA (i.e., DNA copies of RNA). In preferred embodiments, the DNA samples are tagged with a radioactive and/or fluorescent label and applied to the array. Single stranded DNA will bind to a complementary strand of DNA. Thus, at positions on the array where the immobilized DNA recognizes a complementary DNA in the sample, binding or hybridization occurs. The labeled sample DNA marks the exact positions on the array where binding occurs, allowing automatic detection. The output consists of a list of hybridization events, indicating the presence or the relative abundance of specific DNA sequences that are present in the sample. In preferred embodiments of the present invention, the hybridization events indicate the relative abundance, for example, of various immune cells via immune cell specific markers or cytokines present in the sample material.

It is contemplated that the present invention will be modified for use in facilitating the diagnosis of diseases for which a specific immune cell or cytokine has been identified. In other embodiments, the present invention is used in custom drug selection studies. The presence of various immune cells or cytokines after treatment with a test drug provide an indication the effectiveness of the drug on limiting the generation of expression profiles. Similarly, the identification of specific clones is indicative of a target for therapeutic intervention.

The present invention also finds use in predicting drug toxicity. In preferred embodiments, drugs for any condition or treatment are screened to see if they, for example, adversely affect the generation of expression profiles known to be beneficial to the drug recipient. Such drug toxicity screening is useful, for example, in testing drugs for treatment of HIV infection. This facilitates the selection of compounds for further investigation and may reduce the need for animal testing. Such in vitro screens for potential toxicity have the additional advantages of reducing drug-screening costs, preventing human suffering, avoiding the necessity of using experimental animals, and reducing product liability.

The present invention also finds use in determining the pharmacologic mechanisms of drug action. For example, analysis of T and B cell gene expression profiles assists in determining the mechanism of action of a drug or toxin. Given that there may be a multitude of events triggered by the initial action of a drug, screening thousands of T and B cell clones at one time facilitates the rapid and efficient identification of multiple potential drug effectors. This allows robust hypotheses of drug mechanism to be formed and tested in subsequent investigations.

The present invention will also find use in disease monitoring. For example, in rheumatoid arthritis, the presence of specific gene expression profiles are monitored to determine if the suspected autoreactive clone(s) is (are) responding to treatment(s) administered to a subject.

DETAILED DESCRIPTION OF THE INVENTION

The present invention utilizes specific oligonucleotides for the construction of [a] DNA array[s] that allows for the detection of populations. The array[s] of the present invention may be used for screening and diagnostic purposes. For example, in one embodiment, the present invention provides an array that can be used to detect and identify B cell gene expression profiles responsible for the inflammatory response found in patients suffering from rheumatoid arthritis. Certain preferred embodiments of the systems, devices, and methods of the present invention are described in more detail below in the following sections: I) Synthesis of Microarrys; II) Hybridization and; III) Detection. The following sections are provided in order to demonstrate and further illustrate certain embodiments and aspects of the present invention and are not to be construed as limiting the scope thereof.

I. Synthesis of Microarrays

Microarrays represent a powerful tool for the analysis of numerous types of biomolecules, as well as other organic and inorganic samples. Analysis of nucleic acids is one main area of microarray development. Microarray techniques have been developed for comparative studies of DNA, RNA, and MRNA from a number of organisms (e.g., vertebrate animals, invertebrate animals, plants, yeasts, fungi, bacteria, and viruses). Some microarray applications use the "polymerase chain reaction" (PCR) for generating sufficient quantities of target or probe molecules. Alternatively, nucleic acid synthesis methods are used for generating precise oligonucleotide target and probe sequences. Microarrays can also be fabricated with purified or synthetic polypeptides targets and probes. Similarly, the microarray format is suitable for assaying whole cells or fragments of cells. For example, techniques such as laser capture microdissection (LCM) technology (Emmert-Buck, et al. Science 274:998 [1996]), in combination with T7-based RNA amplification, allows for functional analysis of human cells. It is contemplated that further refinements of these techniques will ultimately allow for the building of 3-D databases of gene expression profiles from whole organisms. Adding a fourth dimension (e.g., a temporal component) provides 4-D databases such that the interaction of drugs, hormones, and other stimuli are monitored quantitatively on a cell-by-cell basis in intact cells and organisms.

In preferred embodiments, the microarray elements of the present invention are supported by association with one or more solid or semi-solid substrates. For example, in some embodiments, test array supporting substrates comprise planar (i.e., 2 dimensional) glass, metal, composite, or plastic slides and wafers, biocompatible or biologically unreactive compositions, and porous or structured (i.e., 3 dimensional) substrates of the same, or similar, composition as those utilized in 2 dimensional substrates. For example, common planar arrays include 1 in.×3 in. microscope slides (1×25×76 mm) and yield approximately 19 $cm^2$ of surface area (i.e., enough surface area for >100,000 array features using current microspotting and ink-jetting arraying technologies). Currently microscope slides are being manufactured using ultraflat substrates (ultraflat, also known as "optically flat,") surfaces that help to eliminate data acquisition errors resulting from out of focus array elements on uneven substrate surfaces) (TeleChem, Sunnyvale, Calif.). Specially manufactured, or chemically derivitized, low background fluorescence substrates (e.g., glass slides) are also commercially available. In yet other embodiments, planar microarray substrates further comprise cover slips, gaskets, or other enclosures that protect the array elements and provide channels for the flow of chemical and reagents for microarray preparation, hybridization, labelling, etc. Microarray elements may be prepared and analyzed on either the top or bottom surface of the planar substrate (i.e., relative to the orientation of the substrate in the data acquisition device of the present invention).

In those embodiments that make use of 3-dimensional microarray substrates, the present invention contemplates substrates comprising spheres, waffled structures, rods, cones, tubes (e.g., capillary tubes), or other geometric forms suitable for supporting microarrays. In other embodiments of the present invention, common commercially available or chemically derivitized microwells (e.g., 96 well plastic substrates, such as microtiter plates) support the microarray elements.

Other embodiments of the present invention comprise microarray reaction chambers (e.g., machined, fabricated, or otherwise formed metal or plastic surfaces) that support microarray element production (e.g., light directed maskless microarray fabrication) and data acquisition. For example, commercially available microarray cassettes and modules optimized for data acquisition by the methods and compositions of the present invention are contemplated for use with the present invention (e.g., GENECHIP probe arrays, Affymetrix, Inc., Santa Clara, Calif.; FLOW-THRU CHIP, Gene Logic, Inc., Gaithersburg, Md.). In especially prefelTed embodiments, the microarray substrates and light directed maskless array fabrication techniques are those described in WO/9942813 (hereby incorporated by reference in its entirety).

Those skilled in the art well appreciate that certain substrate preparation are sometimes necessary in order to prepare the chosen substrate for receiving microarray element features. For example, glass or plastic substrate slides are often treated under harsh conditions with strong acids or detergents to remove undesired organic compounds and lipids prior to association with microarray probe features (e.g., nucleic acid sequences).

In some embodiments, the microarray substrates (e.g., glass slides) are associated or derivitized with one or more coatings and/or films that increase microarray element probe-to-substrate binding affinity. Increased microarray probe binding to substrates leads to increased microarray probe retention during the various stages of microarray preparation and analysis (e.g., hybridization, staining, washing, scanning stages, and the like, of microarray preparation and analysis). Additionally, any coatings or films applied to the microarray substrates should be able to withstand any subsequent treatment steps (e.g., photoexposure, boiling, baking, soaking in warm detergent-containing liquids, and the like) without substantial degradation or disassociation from the microarray substrate. Examples of substrate coatings and films include, vapor phase coatings of 3-aminopropyltrimethoxysilane, as applied to glass slide products from Molecular Dynamics, Sunnyvale, Calif. Generally, hydrophobic substrate coatings and films aid in the uniform distribution of hydrophilic probes on the microarray substrate surfaces. Importantly, in those embodiments of the present invention that employ substrate coatings or films, those coatings or films are substantially non-interfering with microarray processing steps (e.g., nonfluorescent), additionally, any coatings or films applied to the substrates either increase target binding to the microarray probes or at least do not substantially impair target binding. While an understanding of the mechanisms is not necessary for practicing the present invention and the present invention is not limited to any particular mechanism, it is believed that hydrophobic microarray substrate coatings contribute to uniform microarray probe distribution by providing increased surface tension that retards the spread of microarray probe material after its application to the substrate. Other applied substrate coatings and films approaches comprise associating chemical agents to the microarray substrate selected for their reactivity with microarray probes or targets. For example, TeleChem, Sunnyvale, Calif., provides organo-amine and organo-aldehyde reactive groups at a concentration of about $5 \times 10^{12}$ reactive groups/cm$^2$. Such reactive groups increase the binding affinity of nucleic acids, proteins, small molecules, extracts, and whole or fragmented cells, etc. to microarray substrates. Substrate coatings and films are preferentially applied as monolayers.

In other embodiments, where two or more coatings or films are associated with a microarray substrate, the coatings may be applied simultaneously or sequentially, such that the layers form a substantially confluent monolayer, or such that the coatings remain separated as distinct features. In particular embodiments, amine- or lysine-coated substrates absorb/adsorb nucleic acid probe element molecules, especially when glass substrates are utilized. In other embodiments, nitrocellulose derivitized substrates are contemplated as suitable microarray substrates.

The present invention is not limited to substrates derivitized by addition or modification of organo-amine or organo-aldehyde, as any derivitization that results in desired sample binding affinity, or improved microarray handling and test results are also contemplated. The utility of proposed microarray substrate coating, film, or deritivization, can be determined by 1) preparing one or more microarray substrates comprising the proposed coating, film or deritivization, that further comprise a plurality of known microarray element features; 2) preparing one or more identical microarray substrate(s), comprising control substrates that omit the proposed microarray substrate coating, film or derivitization; 3) performing like reaction steps (e.g., nucleic acid hybridization and staining) on the substrates; 4) acquiring data from the respective microarrays substrates; and 5) interpreting a change in the data acquired from control (i.e., nonderivitized substrates) and those substrates comprising the proposed microarray substrate coating, film, or deritivization.

As known in the art, a variety of environmental conditions affect microarray fabrication, including but not limited to humidity, temperature, exposure to light or chemical, and dust. For example, low ambient humidity may cause excessive loss of probe element from freshly printed microarrays or from the print or pin heads prior to deposition. In embodiments that utilize printing or contact methodologies for depositing probe elements, measures are taken to minimize probe carry over (e.g., washing deposition devices between depositions of dissimilar chemicals). In preferred embodiments, after microarray elements are deposited on the substrates, unbound probe molecules are usually removed (e.g., washed from the substrate surface).

In preferred embodiments, the characteristics of substrate coatings or films associated with microarrays substrates are analyzed by surface analysis tools and techniques (e.g., electron spectroscopy for chemical analysis [ESCA], and/or spectroscopic ellipsometry). In those embodiments employing ESCA techniques for substrate surface analysis, the substrate surface is bombarded with photons in the form of X-rays. Electrons are emitted from the surface with an energy characteristic (i.e., profile) of their atomic source. The detection of surface emitted electrons bearing energy profiles similar to nitrogen can be used to quantify the presence of amine groups in microarray substrate surface coatings and films. Spectroscopic ellipsometry is an optical technique for quantifying surface characteristics. This technique measures the change in polarization of light reflected from a surface to provide a determination of surface coating thickness. This technique is capable of resolving surface film thicknesses from ten to several thousand angstroms.

In preferred embodiments of the present invention directed to microarray synthesis, the present invention contemplates the reuse of individual microarray substrates in multiple assays. In certain of these embodiments, the microarray substrate remains fixed to the device (e.g., immobilized in a microarray holder) after being read, and the fabricated probes, synthesis and detecting chemicals and other reagents are then substantially removed (e.g., flushed away) from the substrate such that subsequent microarray probes may be fabricated on the substrate (i.e., the substrated is re-used or recycled). It is contemplated that the sensitivity of some probe molecules (e.g., oligonucleotides) to short wavelength light will be exploited for removing fabricated probes from the microarray substrate. For example, in preferred embodiments, a short wavelength UV (e.g., 280 nm) filter is employed to select a "cleaning light" from the light source. In some embodiments, the "cleaning light" is directed by a spatial light modulator to any or all probe sites while suitable wash buffers and/or detergents are contacted to the microarray substrate.

In some embodiments of the present invention, the microarray substrates comprise identifying markers. The present invention contemplates that such identification be either integral to the microarray substrate or otherwise affixed to the substrates (e.g., tags, stickers, stamps, and the like). For example, in some embodiments, the microarray substrates comprise imprinted, or affixed, alphanumeric, mathematical, or other symbols and characters that represent characteristics about the particular microarray, test sample, or about the source of the microarray targets. More particularly, in some preferred embodiments, the microarray substrates comprise machine readable encoding (e.g., bar codes). The present invention contemplates that microarray substrates marked with machine readable encoding convey information about one or more of the characteristics of the microarray, for example, batch number, reagents and hybridization reaction conditions, microarray feature information, microarray tracking information, diagnostic information about a particular subject or experiment, and the like. In some embodiments comprising machine readable microarray substrates, the present invention comprises one device, while in other embodiments, the present invention comprises more than one device selected to perceive the information represented in the machine readable encoding. In yet other embodiments of the present invention, the microarray substrates comprise raised or tactile identifying markers. The present invention contemplates that the embodiments of microarray substrates that comprise tactile markers comprise either raised areas or indentations that represent alphanumeric, mathematical or other symbols and characters that represent characteristics about the particular microarray, test sample, or about the source of the microarray targets.

In some embodiments of the present invention, the microarray substrate comprises one or more chamfers, grooves, pins, cleats, coupling, or ferrules, and the like, for securing the substrate during preparation and processing steps, and/or for immobilizing the microarray substrate during reading or synthesis of the microarray.

Numerous techniques for associating microarray elements with microarray substrates exist. For example, in some embodiments, microarray elements are located on suitable substrates by non-contact systems, while in other embodiments, they are positioned on suitable substrates using contact systems. In particular, non-contact systems typically comprise ink-jet like, or piezoelectric printing technologies. Target microarray elements in solution are associated with a print head which is then moved to an appropriate coordinate above the substrate. The solution comprising the target elements is then forced onto the substrate. In preferred embodiments, the substrate is prepared or derivitized to better adhere the target elements. In certain of these embodiments, target deposition is accomplished by piezoelectric printing technologies. Piezoelectric printing equipment suitable for fabricating microarrays is commercially available (e.g., from Packard Instrument Co., Meridan, Conn., and Incyte Pharmaceuticals, Palo Alto, Calif.). In certain other of these embodiments, target deposition is accomplished by syringe-solenoid printing technologies. Syringe-Solenoid printing technology suitable for fabricating microarrays is also commercially available (e.g., from Cartesian Technologies, Irvine, Calif.). In some embodiments, non-contact printing technologies fabricate microarrays on porous on semi-solid substrates.

In particularly preferred embodiments, contacting microarray printing technologies utilize slender pins, with or without fluid retaining grooves and wells, that are contacted (i.e., "tapped") directly to the surface of the microarray substrate. Examples of rigid contact type printing devices include, quills, capillaries, tweezers, split pins (e.g., TeleChem International, Inc., Sunnyvale, Calif.), and PIN-and-RING (Genetic MicroSystems, Inc., Alameda, Calif.).

In some preferred embodiments of the present invention, the microarrays are fabricated using photolithographic technologies. For example, U.S. Pat. Nos. 5,744,305, 5,753,788, and 5,770,456 (herein incorporated by reference in their entireties) describe photolithographic techniques for directly fabricating microarray elements on a rigid substrate using photolabile protecting groups and a number of fixed-pattern light masks for selectively deprotecting array elements for nucleoside concatenation at each base addition step. "Maskless" microarray fabrication technology is also known (See e.g., WO/9942813). In a preferred embodiment, the present invention is used to acquire data sets from microarrays fabricated utilizing the maskless array fabrication technology disclosed in WO/9942813. In another embodiment, microarrays are fabricated in a manner, in whole, or in part, similar to that described in WO/9942813 by the system of the present invention, and then "read" (i.e., data is acquired from the microarray) by the system of the present invention.

The present invention is not intended to be limited to acquiring data sets from any one of the particular types of arraying technologies briefly described herein. Indeed, the present invention contemplates use with any microarray substrate with probe elements suitable, or optimizable, for data acquisition by the methods and apparatuses of the present invention.

The present invention contemplates microarray elements comprising one or more biologically, or industrially important molecules. For example, target elements may comprise, but are not limited to, nucleic acids either partially or wholly single or double stranded, or combinations additionally of DNA and RNA, proteins or fragments of proteins, polysachrides, lipids and fatty acids, steroids, polysachrides, etc. In preferred embodiments, the target elements comprise cDNA. In other preferred embodiments, the target elements comprise proteins or molecules that selectively bind to proteins.

A range of microarray substrate sizes and shapes are contemplated. In some embodiments, the substrates are rigid (e.g., slides and the like). In yet other embodiments, the microarray substrates are gels or polymers. In still other embodiments, microarray substrates further comprise chambers, vessels or channels (e.g., for target or sample fabrication, labeling, or delivery).

In embodiments where nucleic acids (e.g., DNA) comprise the probe elements, a hybridization step is typically carried out to bind a target, either labeled or unlabeled, to the probe elements. More generally, the probe elements are used to determine the existence and or the extent of appearance of a particular complementary molecule in a sample contacted to the microarray and its probe elements. Typically the probe elements bound to the microarray substrate themselves interact with binding partners when contacted with a solution containing a sample. One or more labeling steps are performed to produce an optically detectable change on the surface of the microarray where hybridization has occurred.

II. Hybridization

In preferred embodiments of the present invention, methods are provided for the hybridization of microarray probes to labeled or unlabeled targets. In some cases the probes are oligonucleotides fabricated on the microarray substrate by the device and system of the present invention. The present invention is not intended to be limited by the type or kind of probe associated with the microarray substrate. In other embodiments, microarray substrates with associated probe elements are provided and optimized for use in the devices and system of the present invention. Alternative embodiments of the microarray targets and probes contemplated by the present invention are provided herein in other sections.

The particular hybridization reaction conditions can be controlled to alter hybridization (e.g., increase or decrease probe/target binding stringency). For example, reaction temperature, concentrations of anions and cations, addition of detergents, and the like, can all alter the hybridization characteristics of microarray probe and target molecules.

Using the detection method described below, one or more specific array sites can be monitored while the array is being exposed to a sample. The monitored sites may be special sites with characteristics (e.g., sequences) known to hybridize with material naturally in or added to the sample. One or more groups of analytical (normal) probe sites may also be monitored together, to provide an average signal representing a relative level of hybridization across the microarray.

In some embodiments of the present invention, it is contemplated that special hybridization monitoring sites may be created by "corrupting" the synthesis at those sites during light-directed synthesis of the microarray by the present invention. These sites are created during synthesis of the microarray by limiting the amount of light provided to these sites for deprotection. This may be effected by briefly pulsing the "on" state of the spatial light modulator elements associated with these sites under programmed control. If, for example, the deprotection is manifest at only one-fourth of the molecules in these probe sites during each nucleotide addition step, a quasi-random collection of oligonucleotide sequences of varying lengths will be created in these probe sites. It is further contemplated that probe sites with these characteristics will exhibit a particularly non-specific hybridization to target material. This lack of specificity may provide hybridization monitor sites which are relatively consistent between different target-bearing samples.

Regardless of the type of hybridization monitoring sites used, the hybridization signal detected from these sites is compared to a pre-determined threshold, thereby providing an endpoint signal that can be used to indicate sufficient hybridization. The endpoint signal may be used to automatically terminate the delivery of sample-containing fluid to a flow cell.

III. Detection

To generate data from microarray assays some signal is detected that signifies the presence of, or absence of, the sequence of, or the quantity of the assayed compound or event. In preferred embodiments, the signal involves a measurement of fluorescence. Briefly, fluorescence occurs when light is absorbed from an external (excitation) source by a fluorescent molecule (a fluorophore) and subsequently emitted. The emitted light is of a lower energy (longer wavelength) than the absorbed light because some of the excitation energy is dissipated upon absorption. The characteristic spectral shift between excitation and emission wavelengths of a particular fluorophore is called the Stokes shift. Discrimination between excitation wavelengths and emission wavelengths improves the signal to noise ratio and dynamic range of the detector system by substantially removing background fluorescence and scattered excitation light from fluorophore-specific emission. The present invention contemplates a number of fluorescence techniques. For example, in some embodiments, one or more spectrums of excitation or emission light are passed through linearly polarizing filters to selectively excite fluorophores in a particular orientation. In other embodiments of the present invention, time-resolved fluorescence is utilized to obtain information on the reaction kinetics of macromolecules.

In embodiments where the microarray comprises nucleic acids, the present invention further contemplates direct and indirect labeling techniques. For example, direct labeling incorporates fluorescent dyes directly into the targets that hybridize to the microarray associated probes (e.g., dyes are incorporated into targets by enzymatic synthesis in the presence of labeled nucleotides or PCR primers). Direct labeling schemes yield strong hybridization signals, typically using families of fluorescent dyes with similar chemical structures and characteristics, and are simple to implement. In preferred embodiments comprising direct labeling of nucleic acid targets, cyanine or alexa analogs are utilized in multiple-fluor comparative microarray analyses. In other embodiments, indirect labeling schemes are utilized to incorporate epitopes into the nucleic acid targets either prior to or after hybridization to the microarray probes. One or more staining procedures and reagents are used to label the hybridized complex (e.g., a fluorescent molecule that binds to the epitopes, thereby providing a fluorescent signal by virtue of the conjugation of dye molecule to the epitope of the hybridized species). In particular embodiments, a biotin epitope and a fluorescent streptavidin-phycoerythrin conjugate are contemplated. Another contemplated indirect labeling scheme employs the Tyramide Signal Amplification (TSA) procedure developed by NEN Life Science Products (Boston, Mass.). In particular, the TSA scheme utilizes biotin and dinitrophenol (DNP) epitopes as well as streptavidin and antibody conjugates linked to horseradish peroxidase (HRP) for labeling molecules of interest. In preferred embodiments, indirect labeling techniques provide 10 to 100-fold signal amplification relative to direct labeling approaches.

The present invention is not limited by the nature of the label chosen, including, but not limited to, labels which comprise a dye, fluorescein moiety, a biotin moiety, luminogenic, fluorogenic, phosphorescent, or fluors in combination with moieties that can suppress emission by fluorescence resonance energy transfer (FRET). Further, the probe oligonucleotide and particularly the target oligonucleotides may contain positively charged adducts (e.g., the Cy3 and Cy5 dyes, and the like). The oligonucleotides may be labeled with different labels (e.g., one or more probe oligonucleotides may each bear a different label).

It is also contemplated that similar sequences from different samples may be detected in a single microarray hybridization step. Material within different samples may be differently labeled. For example, targets within different samples may incorporate different dyes or fluorophores. When differently labeled in one of these ways, the contribution of each specific target sequence to hybridization at a particular probe site can be distinguished. This labeling scheme has several applications. In gene expression studies, for example, the relative rates of transcription of one or more particular sequences within a sample can be measured.

Additionally, in some embodiments, the detection capabilities of the present invention can be used for detecting the quantities of different versions of a gene within a mixture. Different genes in a mixture to be detected and quantified may be wild type and mutant genes (e.g., as may be found in a tumor sample, such as a biopsy) or different genetic variants of microorganisms. In this embodiment, one might design two sets of one or more probes to be complementary to characteristic sequences in one region of the genome, but one probe set to match the wild-type sequence and one probe set to match the mutant. Quantitative detection of the fluorescence from a microarray reaction performed for a set amount of time will reveal the ratio of the two genes in the mixture. Such analysis may also be performed on unrelated genes in a mixture. This type of analysis is not intended to be limited to two genes. Many variants within a mixture may be similarly measured.

In still other embodiments, different sites on a single gene or sequence may be monitored and quantified by different probes to verify the presence of that gene or sequence. In this embodiment, the signal from each probe would be expected to be the same, or follow a characteristic intensity profile (i.e., providing confirmatory information).

It is also contemplated that multiple probes may be used that are similarly labeled upon hybridization, such that the aggregate signal is measured. This may be desirable when using many probes when identical or different sequences are used to detect a single gene or sequence to boost the signal from that gene. This configuration may also be used for detecting unrelated sequences within a mix.

The specificity of the detection reaction is influenced by the aggregate length of the target nucleic acid sequences involved in the hybridization of the complete set of the detection (probe) oligonucleotides. For example, there may be applications in which it is desirable to detect a single region within a complex genome. In other instances, it may be desirable to have the set of oligonucleotide probes interact with multiple sites within a particular sample target. In these cases, one approach would be to use a set of microarray elements that recognize a smaller, and thus statistically more common, segment of target nucleic acid sequence.

There exist many fluorescent indicators which operate in the dual excitation, single emission ratio mode; for example, Fura-2 and BTC for calcium and BCECF for pH. Multiple wavelength excitation also finds use when multiple single-excitation labels are used. Devices for switching between multiple excitation wavelengths from a broadband source include filter wheels and other mechanical devices (e.g., shutters, oscillating filters, etc.) and acousto-optics modulators or tunable filters. If a monochromatic light source is used (e.g., a laser or LED), it is contemplated that manual or automated switching between two or more light sources may be employed. Beamsplitters and/or moveable mirrors may, for example, be used to direct light with different excitation wavelengths into the optical system. The different excitation wavelengths may be utilized simultaneously or in a sequential manner.

The present invention contemplates a simple concordance test for determining the suitability of a particular dye or combination of dyes. The following test is useful in both direct and indirect multiemission (e.g., color) labeling schema. A single nucleic acid is labeled separately with one or more flours or epitopes and then hybridized to a single microarray. The fluorescent signals from all of the elements on the microarray are then determined at each particular emission wavelength. This data is then plotted as ratios as a function of signal intensity. Ideally, a ratio of 1.0 should be obtained for each labeled microarray element such that the data cluster tightly along the "sameness" line. Deviations from 1.0 suggest discordance or imbalance between the two channels that may be due to differences in incorporation or staining of the flours or epitopes, or to inaccuracies in detection and quantitation. Examples of fluorophores suitable for labeling microarray samples include but are not limited to those found in Table 2 from "Microarray Biochip Technology" Schena et al., Eaton Publishing 2000.

TABLE 2

Fluorophores Suitable For Labelling Microarray Samples

| Fluorophore | Aprox. Absorbance (nm) | Aprox. Emission (nm) | Structural Partner | Comments |
| --- | --- | --- | --- | --- |
| FITC[†] | 494 | 518 | | 5-FAM derivative used for DNA sequencing |
| Flour X | 494 | 520 | | Less bright than FITC |
| Alexa 488 | 495 | 520 | Alexa 432, 546, 568, and 594 | |
| Oregon Green 488 | 496 | 524 | | |
| JOE | 522 | 550 | | 6-JOE used for DNA sequencing |
| Alexa 532 | 531 | 554 | Alexa 488, 546, 568, and 594 | |
| Cy3 | 550 | 570 | Cy2, −3.5, −5, and −5.5 | |
| Alexa 546 | 556 | Alexa 488, 532, 568, and 594 | | |
| TMR[‡] | 555 | 580 | | 6-TAMRA used for DNA sequencing |
| Alexa 568 | 578 | 603 | Alexa 488, 532, 546, and 594 | |
| ROX* | 580 | 605 | | 6-ROX used for DNA sequencing |
| Alexa 594 | 590 | 617 | Alexa 488, 532, 546, and 568 | |
| Texas Red | 595 | 615 | | |
| Bodipy 630/650 | 625 | 640 | Bopidy Series | |
| Cy5 | 649 | 670 | Cy2, −3, −3.5, and −5.5 | Less soluble in aqueous than Cy3 |

[†]fluorescein isothiocynate
[‡]tetramethylrhodamine
*X-rhodamine

EXPERIMENTAL

EXAMPLE 1

Selection of Immunologically Relevant Clusters

In these experiments, immunologically relevant genes and ESTs were selected according to literature and expression information as detailed below. This selection strategy ensured that all basic and specific genes expressed in immune cells are included in the ImmunoChip. A flow diagram for the method is provided in FIG. 1.

1. Selection of Genes Prepared from the Literature
   a. Touch Up selection

Gene lists were prepared using scientific literature from the following categories: basic genes, CD/Ly surface markers, cytokines and chemokines, signal transduction, apoptosis, MHC pathway and oncogene/tumor suppressors. The GenBank (GB) accession numbers of all selected genes were identified by literature and PubMed search. The GB accession numbers were used to identify the cluster ID of the Unigene database. In total 618 named genes were selected using this strategy.

b. Touch Down Selection

The Locuslink database was used to perform a touch down selection of immunologically relevant genes. The mouse LocusLink (LL) database contains 11980 genes. Each gene in this database was analyzed due to its immunological function. Genes were selected and determined as immunologically relevant, if (in this order)

1. Mouse Name indicates immuno function
   2. A Human, rat homologue name indicates immuno function
   3. The LL description of the mouse gene indicates immuno function
   4. The LL description of the homologue human, rat gene indicates immunofunction
   5. The PubMed search indicated immuno function.

3415 putative immunologicallt relevant genes were selected. Locuslink and Genbank accession nurbersand Uni-Gene cluster information were obtained from the Locuslink database.

C. Expression Pattern Selection

The UniGene Database (built #75, Feb. 2000) was used to select genes and ESTs according to its expression information. The UniGene database was downloaded, reformatted by using text-editors and imported into an Excel# spreadsheet. The information of each cluster was organized in separate lines. A cluster was determined as immunologically relevant, if at least one of the cluster members (genes or ESTs) was physically derived from a immunological library. A library was defined as immunologically relevant, if it represents a primary lymphoid organ (fetal liver (LID139, LID233, LID287, LID221) thymus (LID26, LID28, LID58, LID296, LID299, LID302), bone marrow (LID113, LID129, LID130, LID140, LID142)) a secondary lymphoid organ (spleen (LID63, LID152, LID159, LID172, LID201), lymph node (LID66)) or a immune cell (B-cell (LID366), T-cell (LID50), macrophage (LID5, LID12, LID20, LID47. LID82), stem cell (LID32, LID99), lymphocyte (LID9)). The library LID366 is present in Unigene built #76 (April 2000).

2. Generation of the Redundant Total Gene/EST List

The selected genes of the touch-up, touch down and expression pattern lists were combined and a redundant total gene/EST list generated. In total, 71392 ESTs were selected for the construction of the ImmunoChip.

3. Generation of a Non-Redundant Cluster List

The UniGene cluster and LocusLink cluster information attached to each record of the redundant gene/EST list was used to identify 16749 non-redundant immunologically relevant clusters by depletion of duplicates (Panorama, ProVue, Huntington Beach, Calif.).

EXAMPLE 2

Figure 2:
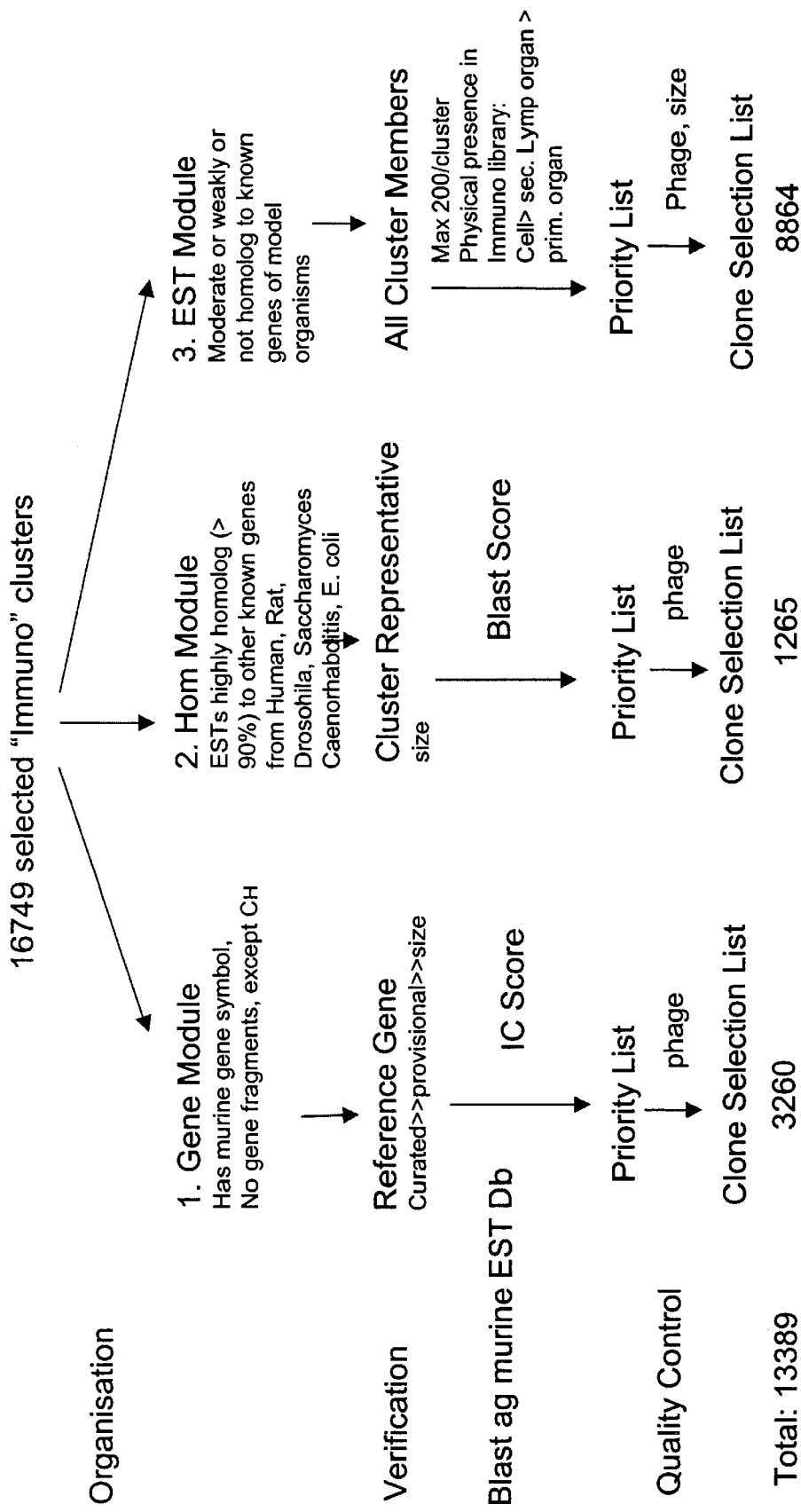
FIG. 2 shows the identification of the best representative clones.

Identification of the Best Representative Clone Within the Selected Immunologically Relevant Cluster 1. Categorization of Selected Clusters into Modules The 16749 selected immunologically relevant clusters were categorized into one of three modules: the gene (GENE) module, the homologous gene (HOM) module and the EST module (See, FIG. 2 for a flow chart of this method). A record was classified as gene, if the cluster was named and had at least one named sequence information including gene name or symbol in it. However, gene fragments such as B cell or T cell variable gene fragments and fragments generated by virus integration but not CH gene fragments (isotypes) were excluded from the gene module. In addition, records with a gene name and or a gene symbol were excluded from the module, if a gene sequence was not identified yet. A record was categorized into the HOM module, if the murine EST was highly homologue (>90% homology) to other known genes of the species *Homo sapiens*, Rat, Drosophila, *Saccharomyces cerevisae*, Caenorhabditis or *Escherichia coli*. A record was classified into the EST module if a sequence was available, but if it could not be classified into the Gene or HOM module. Thus, ESTs which show moderate, weakly or no homology to other known genes from other model organisms are present in the EST module. Selected clusters were excluded from further analysis (NONE module), if a sequence information was not available.

2. Identification of the Best Representative Clone Within the Cluster

The strategy to identify the best representative clone for each selected immunologically relevant cluster was dependent on the module a record belonged to and is detailed below.

a. Gene Module

A reference gene was determined for each selected cluster. The reference gene was obtained from the LocusLink database (RefSeq, 04/03/00). Curated reference genes for a particular cluster had higher preference than a provisional, non-curated reference gene. In the case that a curated or provisional reference gene was not available, a Unique.seq record or a Genbank record was used as reference gene.

The selected reference genes were analyzed to verify that they truly represent the selected immunologically relevant cluster. A batch Entrez search using the GI of the reference gene was performed, the header of the result extracted and compared to the Unigene title. The reference gene for a particular cluster was defined as to be correct, if the FASTA header was identical to the Unigene title. In the case of a discrepancy, the UniGene cluster was analyzed. In the case that the UniGene cluster was mixed with other homologous genes, each of the genes within the cluster was re-evaluated if it is immunologically relevant due to known function or expression. The immunologically relevant gene within the cluster was then used as reference gene.

The selected and verified reference genes were used to Blast against the murine EST database. The GI was used in a batch Entrez search to obtain the annoted sequence of the reference gene. These FASTA sequences were then blasted against the murine EST database using Blast 2.0 Network (Macintosh G3) client (blastcl3.hqx, Blast parameter (program: blastn, database: est, E: 4e-49. Number of one-line description: 0, number of alignments to show: 250, restricted Database: Mus_musculus.n.gil). The resulting hits were exported as text file, reformatted using text-editors, and IMAGE clone hits imported into spreadsheets (Excel™). The Blast score and start of query information were extracted and the end of the alignment information calculated. In addition, an IC score was calculated as the sum of the BLAST score and the 3' query of the alignment. ESTs within the same cluster were sorted according to their IC score and evaluated by hand using the available parameters and scores. The IC score list builds up the priority list with the hand-selected clone as best representative clone within a cluster.

The quality of the clone with the highest priority for a specific cluster was verified. In the case that a clone was reported in the IMAGE consortium problematic database, it was dismissed and the second preference clone within a cluster was analyzed. In the case that also the second preference clone was defined as problematic, the third preference clone was analyzed for its quality. A cluster was rejected totally, if a non-problematic clone was not available.

b. Hom Module

The unique.seq record from the UniGene database was used as the reference gene to construct a priority list for the HOM module. The GI of the reference gene was used to retrieve the sequence from the Entrez batch database. The sequence was then used to Blast against the murine EST database. A clone priority list was generated according to the Blast score.

The quality of the clone with the highest priority for a specific cluster was verified. It was determined, whether the clone had an entry in the IMAGE consortium problematic database. In the case that a clone was defined as problematic, it was rejected and the second preference clone within a cluster was analyzed. In the case that also the second preference clone was defined as problematic, the third preference clone was analyzed for its quality. A cluster was rejected totally, if a non-problematic clone was not available.

c. EST Module

Clones within the EST module were selected by its physical presence in immunological libraries. A priority list was generated in the following order: LID50>LID366>LID47>LID99>LID63>LID154>LID66>LID58>LID296>LID299>LID26>LID221>LID287>LID142.

The clone with the highest priority within a cluster according to the priority list was evaluated according to phage-contamination and sequence length. Clones with records in the IMAGE consortium problematic database were excluded and the $2^{nd}$, $3^{rd}$ . . . clone within the priority list was examined. The sequence of the selected non-problematic clones were retrieved (batch entrez) and the length determined. Clones, which had a known sequence less than 100 bp were excluded from further analyses and the next preference clone was evaluated. A cluster was rejected totally, if a non-problematic clone with a known sequence greater than 100 bp was not available.

In total, 13389 clones were selected for the construction of the ImmunoChip (See, Table 1), with 3260 clones represented in the GENE module, 1265 clones in the HOM module, and 8864 clones in the EST module.

Is is evident from the above that the present invention will allow for the rapid screening of T and B and other immune cell gene expression markers. This rapid screening will be utilized in, for example, diagnosis, drug effect testing, drug screening and monitoring disease progression.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, genetics, bioinformatics, and/or related fields are intended to be within the scope of the following claims.

TABLE 1

| IC ID | IC Selection method | Module | UniGene | UniGene/LocusLink Title | Gene Symbol | Alias | Selected Reference | IMAGE |
|---|---|---|---|---|---|---|---|---|
| IC00001 | 00/02 Literature | GENE | Mm.6826 | apoptosis-associated tyrosine kinase | Aatk | | NM_007377 | 607235 |
| IC00002 | 00/02 Literature | GENE | Mm.89919 | actin, beta, cytoplasmic | Actb | | gi = 49865 | 1921229 |
| IC00003 | 00/02 Literature | GENE | Mm.56893 | angiotensin receptor-like 1 | Agtrl1 | | NM_011784 | 1498919 |
| IC00004 | 00/02 Literature | GENE | Mm.24663 | angiogenin related protein | Angl | | NM_007448 | 1053402 |
| IC00005 | 00/04/26 UG#76 00/02 Literature | GENE | Mm.57058 | angiogenin related protein | Angrp | msr/apj| | NM_007449 | 681634 |
| IC00006 | 17Lid Expansion | GENE | Mm.4996 | ADP-ribosylation factor 5 | Arf5 | | gi = 1565214 | 2645353 |
| IC00007 | UG75 Expansion | GENE | Mm.3181 | Rho guanine nucleotide exchange factore (GEF) 1 | Arhgef1 | Lbcl|Lsc|lymphoid blast crisis like 2| | NM_008488 | 1247621 |
| IC00008 | 00/02 Literature | GENE | Mm.50710 | X52991 Mouse mRNA for homologue of the rat T cell differentiation marker RT6 | Art2a | ADP ribosyltransferase 2a|rat homolog of transplantable antigen gene RT6|rat homolog Rt6, locus 1|Rt-6|Rt6|Rt6-1| | NM_007490 | 1067825 |
| IC00009 | 00/02 Literature | GENE | Mm.14460 | androgen regulated vas deferens protein | Avdp | MVDP| | NM_009731 | 373131 |
| IC00010 | 00/02 Literature | GENE | Mm.12930 | BcL6-associated zinc finger protein | Bazf | | NM_007528 | 1314656 |
| IC00011 | 00/02 Literature | GENE | Mm.87855 | B-cell leukemia/lymphoma 2 related protein A1a | Bcl2a1a | A1|Bcl-2-related protein A1|Bcl2a1|Bfl-1|Hbpa|hematopoietic Bcl-2-related protein A1| | gi = 293273 | 1363928 |
| IC00012 | 00/02 Literature | GENE | Mm.87856 | B-cell leukemia/lymphoma 2 related protein A1c | Bcl2a1c | A1-c| | NM_007535 | 577642 |
| IC00013 | 00/02 Literature | GENE | Mm.87857 | B-cell leukemia/lymphoma 2 related protein A1d | Bcl2a1d | A1-d| | NM_007536 | 1363928 |
| IC00014 | 00/02 Literature | GENE | Mm.3882 | Bcl2-like | Bcl2l | bcl-x|Bcl-XL|Bcl-Xs|BclX| | NM_009743 | 478723 |
| IC00015 | 00/02 Literature | GENE | Mm.25988 | Bcl2-like 10 | Bcl2l10 | Boo|Diva| | NM_013479 | 1123720 |
| IC00016 | 00/02 Literature | GENE | Mm.4800 | B lymphocyte induced maturation protein | Blimp1 | | NM_007548 | 1165721 |
| IC00017 | 00/02 Literature | GENE | Mm.3962 | B lymphoid kinase | Blk | | NM_007549 | 1347570 |
| IC00018 | 00/02 Literature | GENE | Mm.89727 | CD8beta opposite strand | Bop | | gi = 1809321 | 586052 |
| IC00019 | 00/02 Literature | GENE | Mm.30262 | basic transcription element binding protein 2 | Bteb2 | | NM_009769 | 468464 |
| IC00020 | 00/02 Literature | GENE | Mm.14087 | complement component 4 binding protein | C4bp | | NM_007576 | 676656 |
| IC00021 | 00/02 Literature | GENE | Mm.89564 | calcium/calmodulin-dependent protein kinase 1, beta | Camk1b | | NM_012040 | 1493838 |
| IC00022 | 00/02 Literature | GENE | Mm.4857 | calcium/calmodulin-dependent protein kinase II, beta | Camk2b | | NM_007595 | 1138142 |
| IC00023 | 00/02 Literature | GENE | Mm.42163 | caspase 12 | Casp12 | | NM_009808 | 1511485 |
| IC00024 | 00/02 Literature | GENE | Mm.20940 | caspase 14 | Casp14 | MICE|mini-ICE| | NM_009809 | 2259052 |
| IC00025 | 00/02 Literature | GENE | Mm.12829 | calsequestrin 1 | Casq1 | | NM_009813 | 3025509 |
| IC00026 | 00/02 Literature | GENE | Mm.15343 | calsequestrin 2 | Casq2 | Cardiac calsequestrin| | NM_009814 | 2247572 |
| IC00027 | 00/02 Literature | GENE | Mm.4815 | cyclin A1 | Ccna1 | cyclin A1|NM_007628 | 513856 | |
| IC00028 | 00/02 Literature | GENE | Mm.35867 | cyclin E 2 | Ccne2 | | NM_009830 | 2631788 |
| IC00029 | 00/02 Literature | GENE | Mm.31308 | CD39 antigen-like 1 | Cd39l1 | | NM_009849 | 864751 |
| IC00030 | 00/02 Literature | GENE | Mm.87863 | CD39 antigen-like 3 | Cd39l3 | | gi = 4407969 | 737994 |
| IC00031 | 00/02 Literature | GENE | Mm.88200 | CD72 antigen | Cd72 | B-lymphocyte antigen 2|Ly-19|Ly-32|Ly-m19|Lyb-2|lymphocyte antigen 19|lymphocyte antigen 32|lymphocyte antigen m19|B7-1|CD28 antigen ligand|Cd28|Ly-53|lymphocyte antigen 53|MIC17|TS/A-1| | NM_007654 | 637067 |
| IC00032 | 00/02 Literature | GENE | Mm.89474 | CD80 antigen | Cd80 | | gi = 191841 | 1263968 |
| IC00033 | 00/02 Literature | GENE | Mm.57175 | CD83 antigen | Cd83 | | NM_009856 | 1244054 |
| IC00034 | 00/02 Literature | GENE | Mm.19423 | cadherin 16 | Cdh16 | | NM_007663 | 2099212 |
| IC00035 | 00/02 Literature | GENE | Mm.14897 | cadherin 2 | Cdh2 | cadherin, N-|N-cadherin|NCAD| | NM_007664 | 1222753 |
| IC00036 | 00/02 Literature | GENE | Mm.8046 | cyclin-deptendent kinase inhibitor 1B (P27) | Cdkn1b | Kip1|p27Kip1|bb-1|Bgp1|biliary glycoprotein|biliary glycoprotein 1|carcinoembryonic antigen 1|carcinoembryonic antigen 7|CD66a|Cea-7|Cea1|Cea7|mmCEA1|MHVR|mmCGM1|mmCGM1a|mmCGM2 | NM_009875 | 2520004 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00037 | 00/02 Literature | GENE | Mm.14114 | CEA-related cell adhesion molecule 1 | Ceacam1 | |mouse hepatitis virus receptor| | gi = 50170 | 1970468 |
| IC00038 | 00/02 Literature | GENE | Mm.30300 | CEA-related cell adhesion molecule 10 | Ceacam10 | Bgn3|carcinoembryonic antigen 10|Cea10| | NM_007675 | 2649998 |
| IC00039 | 00/02 Literature | GENE | Mm.89819 | CEA-related cell adhesion molecule 2 | Ceacam2 | Bgp2|biliary glycoprotein 2| | NM_007543 | 1164365 |
| IC00040 | 00/04/26 UG#76 | GENE | Mm.4863 | CCAAT/enhancer binding protein (C/EBP), beta | Cebpb | | NM_009883 | 2615752 |
| IC00041 | 17Lid Expansion | GENE | Mm.1736 | close homolog of L1 | Chl1 | | gi = 1532034 | 602970 |
| IC00042 | 00/02 Literature | GENE | Mm.10737 | cell death-inducing DNA fragmentation factor, alpha subunit-like effector B | Cideb | CIDE-B, cell death-inducing DFF45-like effector B| | NM_009894 | 2520169 |
| IC00043 | 00/02 Literature | GENE | Mm.11756 | chemokine (C-X-C) receptor 2 | Cmkar2 | beta|mIL-8RH| | NM_009909 | 793184 |
| IC00044 | 00/02 Literature | GENE | Mm.57051 | chemokine (C-C) receptor 1 | Cmkbr1 | CCR1|MIP-1 alphaR|Mip-1a-R| | NM_009912 | 876482 |
| IC00045 | 00/02 Literature | GENE | Mm.17493 | CASP2 and RIPK1 domain containing adaptor with death domain | Cradd | RAIDD| | NM_009950 | 520277 |
| IC00046 | 00/02 Literature | GENE | Mm.88295 | complement receptor related protein | Crry | Mcp|mCRY|membrane cofactor protein (Cd46)| | NM_013499 | 617624 |
| IC00047 | 00/02 Literature | GENE | Mm.87867 | colony stimulating factor 1 receptor (granulocyte), pseudogene | Csf1r-ps | | gi = 47451 | 973095 |
| IC00048 | 00/02 Literature | GENE | Mm.1238 | colony stimulating factor 3 (granulocyte) | Csf3 | colony stimulating factor, granulocyte|Csfg| | NM_009971 | 1314427 |
| IC00049 | 00/02 Literature | GENE | Mm.56915 | colony stimulating factor 3 receptor (granulocyte) | Csf3r | colony stimulating factor, granulocyte receptor|Csfgr| | NM_007782 | 1514824 |
| IC00050 | 00/02 Literature | GENE | Mm.88188 | DEAD (aspartate-glutamate-alanine-aspartate) box polypeptide 3 | Ddx3 | D1Pas1 related sequence 2|D1Pas1-rs2| | NM_010028 | 619692 |
| IC00051 | 00/02 Literature | GENE | Mm.5082 | DEAD (aspartate-glutamate-alanine-aspartate) box polypeptide 6 | Ddx6 | mRCK|P54| | NM_007841 | 2519760 |
| IC00052 | 00/02 Literature | GENE | Mm.6979 | DNA methyltransferase 2 | Dnmt2 | | NM_010067 | 989119 |
| IC00053 | 00/02 Literature | GENE | Mm.86948 | eosinophil-associated ribonuclease 1 | Ear1 | | NM_007894 | |
| IC00054 | 00/04/26 UG#76 | GENE | Mm.30282 | early B-cell factor 3 | Ebf3 | O/E-2|OIf-1/EBF-like 2| | NM_010096 | |
| IC00055 | 17Lid Expansion | GENE | Mm.30029 | eukaryotic elongation factor-2 kinase | Eef2k | | gi = 2104700 | 2225200 |
| IC00056 | 00/02 Literature | GENE | Mm.28543 | embryonal Fyn-associated substrate | Efs | | NM_010112 | 747044 |
| IC00057 | 00/02 Literature | GENE | Mm.56911 | epidermal growth factor binding protein type A | Egfbp1 | Egfbp-|mGk-22| | gi=32 193472 | 581222 |
| IC00058 | 00/02 Literature | GENE | Mm.87852 | epidermal growth factor binding protein type B | Egfbp2 | Egfbp-2|mGk-13| | NM_010115 | 581222 |
| IC00059 | UG75 Expression | GENE | Mm.20949 | Eukaryotic translation initiation factor 2 alpha kinase 1 | EIf2ak1 | heme-regulated inhibitor|Hri| | NM_013557 | 634851 |
| IC00060 | 00/02 Literature | GENE | Mm.2012 | epidermal growth factor receptor kinase substrate 8 | Eps8 | | NM_007945 | 233266 |
| IC00061 | 00/04/26 UG#76 | GENE | Mm.56990 | excision repair 2 | Ercc2 | Ercc-2|XPD| | NM_007949 | 2811163 |
| IC00062 | 17Lid Expansion | GENE | Mm.2578 | coagulation factor X | F10 | Cf10|fx| bacterially expressed kinase|Bek|Fgfr-2|Fgfr7| fibroblast growth factor receptor 7| | gi = 3641315 | 473290 |
| IC00063 | 00/02 Literature | GENE | Mm.16340 | fibroblast growth factor receptor 2 | Fgfr2 | | NM_010207 | 1230977 |
| IC00064 | 00/02 Literature | GENE | Mm.4912 | fibroblast growth factor receptor 4 | Fgfr4 | Fgfr-4| | NM_008011 | 406823 |
| IC00065 | 00/02 Literature | GENE | Mm.5378 | fibroblast growth factor regulated protein | Fgfrp | Fgrp|FR-1| | NM_008012 | 1924350 |
| IC00066 | 00/02 Literature | GENE | Mm.2565 | interleuken-four induced gene 1 | Fig1 | Fig1-ps|interleukin-four induced gene 1, pseudogene| | NM_010215 | 1349135 |
| IC00067 | 00/02 Literature | GENE | Mm.5043 | FBJ osteosarcoma oncogene | Fos | c-fos|D12Rfj1|DNA segment, Chr 12, Russel F. JAcoby 1| | NM_010234 | 3026051 |
| IC00068 | 00/02 Literature | GENE | Mm.23704 | fos-like antigen 2 | Fosl2 | Fra-2| | NM_008037 | 445817 |
| IC00069 | 00/02 Literature | GENE | Mm.33783 | GATA-binding protein 6 | Gata6 | | gi = 1289501 | 805829 |
| IC00070 | 00/02 Literature | GENE | Mm.4799 | germinal center expressed transcript | Gcet | M17| bp|brachypodism|cartilage-derived morphogenetic protein-1|CDMP-1| | NM_008099 | 2698933 |
| IC00071 | 00/02 Literature | GENE | Mm.4744 | growth differentiation factor 5 | Gdf5 | | NM_008109 | 1244244 |
| IC00072 | 00/02 Literature | GENE | Mm.9714 | growth differentiation factor 9 | Gdf9 | | NM_008110 | 825757 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00073 | UG75 Expression | GENE | Mm.1890 | TITLE non-agouti | GENEa | A<y>|agouti suppressor|As|yellow|yellow; pseudoallele of agouti locus| | gi = 191797 | 482132 |
| IC00074 | UG75 Expression | GENE | Mm.2210 | TITLE ATP-binding cassette 2 | GENE Abc2 | DOS1474E] | gi = 495258 | 949522 |
| IC00075 | UG75 Expression | GENE | Mm.4739 | TITLE ATP-binding cassette 7 | GENE Abc7 | | gi = 1167981 | 1348327 |
| IC00076 | UG75 Expression | GENE | Mm.15691 | TITLE ATP-binding cassette 8 | GENE Abc8 | | NM_009593 | 2650497 |
| IC00077 | UG75 Expression | GENE | Mm.20845 | TITLE ATP-binding cassette, sub-family C (CFTR/MRP), member 5a | GENE Abcc55a | | NM_013790 | 552280 |
| IC00078 | UG75 Expression | GENE | Mm.365 | TITLE ATP-binding cassette, sub-family D (ALD), member 1 | GENE Abcd1 | Aldgh|ALDP|X-linked adrenoleukodystrophy (ALD) gene homolog| | NM_007435 | 420294 |
| IC00079 | UG75 Expression | GENE | Mm.1519 | TITLE ATP-binding cassette, sub-family D (ALD), member 3 | GENE Abcd3 | peroxisomal membrane protein, 70 kDa|PMP70|Pxmp1| | NM_008991 | 1195768 |
| IC00080 | UG75 Expression | GENE | Mm.7458 | TITLE ATP-binding cassette, sub-family G (WHITE), member 2 | GENE Abcg2 | ABC15|ABCP|BCRP|MXR|MXR1| | NM_011920 | 1971542 |
| IC00081 | UG75 Expression | GENE | Mm.695 | TITLE abl-interactor 1 | GENE Abi1 | | NM_007380 | 596953 |
| IC00082 | UG75 Expression | GENE | Mm.1318 | TITLE Abelson murine leukemia oncogene | GENE Abl | | gi = 191566 | 2803502 |
| IC00083 | UG75 Expression | GENE | Mm.2445 | TITLE acetyl-Coenzyme A dehydrogenase, long chain | GENE Acadl | LCAD| | NM_007381 | 1972791 |
| IC00084 | UG75 Expression | GENE | Mm.10530 | TITLE acetyl-Coenzyme A dehydrogenase, short chain | GENE Acadm | MCAD| | NM_007382 | 2236131 |
| IC00085 | UG75 Expression | GENE | Mm.18759 | TITLE acid phosphatase 2, lysosomal | GENE Acads | SCAD| | NM_007383 | 1434306 |
| IC00086 | UG75 Expression | GENE | Mm.45570 | TITLE acetylcholine receptor epsilon | GENE Acp2 | Acp-2| | gi = 52870 | 514537 |
| IC00087 | UG75 Expression | GENE | Mm.4980 | | GENE Acre | | NM_009603 | 1247588 |
| IC00088 | UG75 Expression | GENE | Mm.3969 | TITLE adipocyte complement related protein of 30 kDa | GENE Acrp30 | adipoQ| | gi = 1051267 | 1247588 |
| IC00089 | UG75 Expression | GENE | Mm.89137 | TITLE actin, alpha 1, skeletal muscle | GENE Acta1 | Acta-2|actin, skeletal alpha-actin|Acts|Actsk-1|alpha actin, skeletal-2 | gi = 191572 | 2225608 |
| IC00090 | UG75 Expression | GENE | Mm.29913 | TITLE actin, gamma, cytoplasmic | GENE Actg | | NM_009609 | 1971186 |
| IC00091 | UG75 Expression | GENE | Mm.16537 | TITLE actin, alpha, vascular smooth muscle | GENE Actvs | | NM_007392 | 1224519 |
| IC00092 | UG75 Expression | GENE | Mm.297 | TITLE melanoma X-actin | GENE Actx | | NM_007393 | 1921229 |
| IC00093 | UG75 Expression | GENE | Mm.4839 | TITLE activin A receptor, type II-like 1 | GENE Acvrl1 | activin A receptor type II-like kinase 1|Acvrk|Alk1| | NM_009612 | 2939277 |
| IC00094 | UG75 Expression | GENE | Mm.388 | TITLE adenosine deaminase | GENE Ada | | NM_007398 | 1478338 |
| IC00095 | UG75 Expression | GENE | Mm.89854 | TITLE a disintegrin and metalloprotease domain (ADAM) 11 | GENE Adam11 | Mdc|metalloprotease-like, disintegrin-like, cysteine rich| | NM_009613 | 603264 |
| IC00096 | UG75 Expression | GENE | Mm.41158 | TITLE a disintegrin and metalloproteinase domain 12 (meltrin alpha) | GENE Adam12 | ADAM12|M[a]|meltrin, alpha|Mltna| | NM_007400 | 374232 |
| IC00097 | UG75 Expression | GENE | Mm.27681 | TITLE a disintegrin and metalloproteinase domain 17 | GENE Adam17 | | NM_009615 | 3025313 |
| IC00098 | UG75 Expression | GENE | Mm.1453 | TITLE a disintegrin and metalloproteinase domain 1a (fertilin alpha) | GENE Adam1a | ADAM1|fertilin alpha|Ftna|Ph-30 alpha| | gi = 965009 | 619528 |
| IC00099 | UG75 Expression | GENE | Mm.39533 | TITLE a disintegrin and metalloproteinase domain 23 | GENE Adam23 | | NM_011780 | 1178116 |
| IC00100 | UG75 Expression | GENE | Mm.15969 | TITLE a disintegrin and metalloproteinase domain 8 | GENE Adam8 | CD156|MS2] | NM_007403 | 963560 |
| IC00101 | UG75 Expression | GENE | Mm.28908 | TITLE a disintegrin and metalloprotease domain 9 (meltrin gamma) | GENE Adam9 | ADAM9|MDC9|meltrin, gamma|Mltng| | NM_007404 | 1247777 |
| IC00102 | UG75 Expression | GENE | Mm.10706 | TITLE adenylate cyclase 6 | GENE Adcy6 | | NM_007405 | 747397 |
| IC00103 | UG75 Expression | GENE | Mm.18658 | TITLE adenylate cyclase 7 | GENE Adcy7 | | NM_007406 | 1332523 |
| IC00104 | UG75 Expression | GENE | Mm.381 | TITLE adipose differentiation related protein | GENE Adfp | Adrp| | NM_007408 | 520945 |
| IC00105 | UG75 Expression | GENE | Mm.2409 | TITLE alcohol dehydrogenase 1, complex | GENE Adh1 | Adh-1|alcohol dehydrogenase 1 complex| | NM_007409 | 1886506 |
| IC00106 | UG75 Expression | GENE | Mm.3874 | TITLE alcohol dehydrogenase 5 | GENE Adh5 | Adh-5| | NM_007410 | 2812535 |
| IC00107 | UG75 Expression | GENE | Mm.2857 | TITLE adrenomedullin receptor | GENE Admr | G-protein coupled receptor 22|Gpcr17|G-protein coupled receptor 22|Gpcr22|MB10] | NM_007412 | 1924362 |
| IC00108 | UG75 Expression | GENE | Mm.4407 | TITLE adipsin | GENE Adn | | NM_013459 | 1068126 |
| IC00109 | UG75 Expression | GENE | Mm.25135 | TITLE activity-dependent neuroprotective protein | GENE Adnp | | NM_009628 | 351645 |
| IC00110 | UG75 Expression | GENE | Mm.68974 | TITLE adenosine A2a receptor | GENE Adora2a | A2aR] | gi = 2347034 | 330989 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00111 | UG75 Expression | GENE | Mm.20047 | TITLE ADP-ribosylarginine hydrolase | GENE Adprh | | NM_007414 | 385062 |
| IC00112 | UG75 Expression | GENE | Mm.9248 | TITLE ADP-ribosyltransferase (NAD+; poly (ADP-ribose) polymerase) 1 | GENE Adprt1 | Adprp|PARP|PARP-1|[PARP1][poly (ADP-ribose) polymerase] | NM_007415 | 437616 |
| IC00113 | UG75 Expression | GENE | Mm.5728 | TITLE ADP-ribosyltransferase (NAD+; poly (ADP-ribose) polymerase) 2 | GENE Adpr2 | | NM_009632 | 424224 |
| IC00114 | UG75 Expression | GENE | Mm.5598 | TITLE adrenergic receptor, beta 2 | GENE Adrb2 | Adrb-2|B-adrenergic binding|badm|beta 2-AR|G protein coupled receptor 7|[gpcr7] | gi = 50100 | 573046 |
| IC00115 | UG75 Expression | GENE | Mm.38151 | TITLE adenylosuccinate lyase | GENE Adsl | | NM_009634 | 368729 |
| IC00116 | UG75 Expression | GENE | Mm.3440 | TITLE adenylosuccinate synthetase 1, muscle | GENE Adss1 | adenylosuccinate synthetase|Adss| | NM_007421 | 585228 |
| IC00117 | UG75 Expression | GENE | Mm.39061 | TITLE adenylosuccinate synthetase 2, non muscle | GENE Adss2 | | NM_007422 | 640646 |
| IC00118 | UG75 Expression | GENE | Mm.10739 | TITLE advillin | GENE Advil-per | DOC6| | NM_009635 | 973265 |
| IC00119 | UG75 Expression | GENE | Mm.86453 | TITLE AE-binding protein 2 | GENE Aebp2 | | NM_009637 | 1446003 |
| IC00120 | UG75 Expression | GENE | Mm.4452 | TITLE aryl-hydrocarbon receptor | GENE Ahr | Ah|Ahh|aromatic hydrocarbon responsiveness|aryl hydrocarbon hydroxylase|dioxin receptor|in|inflammatory reactivity| | NM_013464 | 747265 |
| IC00121 | UG75 Expression | GENE | Mm.32398 | TITLE activation induced eaminase | GENE Aid | | NM_009645 | 621244 |
| IC00122 | UG75 Expression | GENE | Mm.35300 | TITLE autoimmune regulator (autoimmune polyendocrinopathy candidiasis ectodermal dystrophy) | GENE Aire | | NM_009646 | 1265557 |
| IC00123 | UG75 Expression | GENE | Mm.27450 | TITLE adenylate kinase 3 | GENE Ak3 | Ak-3| | gi = 4760599 | 1885862 |
| IC00124 | UG75 Expression | GENE | Mm.2969 | TITLE A kinase anchor protein | GENE Akap | S-AKAP84| | NM_009648 | 989053 |
| IC00125 | UG75 Expression | GENE | Mm.1265 | TITLE alkaline phosphatase 2, liver | GENE Akp2 | Akp-2|Tissue Non-Specific Alkaline Phosphatase|TNAP| | NM_007431 | 1007094 |
| IC00126 | UG75 Expression | GENE | Mm.27447 | TITLE aldo-keto reductase AKR1C13 | GENE Akr1c13 | | NM_013778 | 1891393 |
| IC00127 | UG75 Expression | GENE | Mm.6645 | TITLE thymoma viral proto-oncogene | GENE Akt | | NM_009652 | 736089 |
| IC00128 | UG75 Expression | GENE | Mm.8901 | TITLE thymoma viral proto-oncogene 2 | GENE Akt2 | | NM_007434 | 616283 |
| IC00129 | UG75 Expression | GENE | Mm.1217 | TITLE aminolevulinic acid synthase 2, erythroid | GENE Alas2 | Alas-2| | gi = 1220399 | 586194 |
| IC00130 | UG75 Expression | GENE | Mm.4514 | TITLE aldehyde dehydrogenase 1, liver cytosolic (class 1) | GENE Aldh1 | Ahd-2|Ahd2|aldehyde dehydrogenase 1, liver cytosolic (class 1)|aldehyde dehydrogenase 2, cytoplasmic|Aldh1| | NM_013467 | 1885764 |
| IC00131 | UG75 Expression | GENE | Mm.2621 | TITLE aldehyde dehydrogenase 2, mitochondrial | GENE Aldh2 | Ahd-5|Ahd5|aldehyde dehydrogenase 5| | NM_009656 | 1907756 |
| IC00132 | UG75 Expression | GENE | Mm.4210 | Title: Alcohol dehydrogenase family 3, subfamily A2 | GENE Aldh3a | (UG76 renamed) | NM_007437 | 1886469 |
| IC00133 | UG75 Expression | GENE | Mm.14609 | TITLE Aldehyde dehydrogenase 1 (phenobarbital) inducible) | GENE Aldhpb-pending | | NM_011921 | 2182555 |
| IC00134 | UG75 Expression | GENE | Mm.16763 | TITLE aldolase 1, A isoform | GENE Aldo 1 | Aldo-1|aldolase 1|[Aldo-A isoform, skeletal muscle, brain]] | NM_007438 | 735537 |
| IC00135 | UG75 Expression | GENE | Mm.645 | TITLE aldehyde reductase 1 | GENE Aldr1 | | NM_009658 | 1973158 |
| IC00136 | UG75 Expression | GENE | Mm.1122 | TITLE arachidonate 12-lipoxygenase, pseudogene 2 | GENE Alox12-ps2 | | gi = 1845576 | 2655887 |
| IC00137 | UG75 Expression | GENE | Mm.6332 | TITLE arachidonate 15-lipoxygenase, second type | GENE Alox15b | 8S-lipoxygenase|Alox8|arachidonate 8-lipoxygenase| | gi = 2439986 | 972959 |
| IC00138 | UG75 Expression | GENE | Mm.2197 | TITLE alpha 1 microglobulin/bikunin | GENE Ambp | inter-alpha (globulin)inhibitor, H4 polypeptide|inter-alpha-trypsin inhibitor light chain|ntin4|iti| | NM_007443 | 1891439 |
| IC00139 | UG75 Expression | GENE | Mm.7880 | TITLE s-adenosylmethionine decarboxylase 1 | GENE Amd1 | AdoMetDC|Amd-1| | gi = 5821357 | 615962 |
| IC00140 | UG75 Expression | GENE | Mm.13944 | TITLE amelogenin | GENE Amel | Amg| | gi = 1321650 | 493049 |
| IC00141 | UG75 Expression | GENE | Mm.34641 | TITLE autocrine motility factor receptor | GENE Amfr | | NM_011787 | 2648993 |
| IC00142 | UG75 Expression | GENE | Mm.3238 | TITLE AMP deaminase 3 | GENE Ampd3 | | NM_009667 | 1399666 |
| IC00143 | UG75 Expression | GENE | Mm.4383 | TITLE amphiphysin-like | GENE Amphl | | gi = 1914840 | 2748941 |
| IC00144 | UG75 Expression | GENE | Mm.14064 | TITLE S-adenosylmethionine synthetase | GENE Ams | AdoMet| | gi = 388196 | 1450806 |
| IC00145 | UG75 Expression | GENE | Mm.324 | TITLE amylase 2, pancreatic | GENE Amy2 | Amy-2| | NM_009669 | 719662 |
| IC00146 | UG75 Expression | GENE | Mm.4789 | TITLE ankyrin 1, erythroid | GENE Ank1 | Ank-1|nb|normoblastic anemia| | gi = 311816 | 424956 |
| IC00147 | UG75 Expression | GENE | Mm.3526 | TITLE ankyrin 3, epithelial | GENE Ank3 | Ank-3|ankyrin 3, brain| | NM_009670 | 2065335 |
| IC00148 | UG75 Expression | GENE | Mm.10313 | TITLE ankyrin repeat hooked to zinc finger motif | GENE Ankhzn | | NM_009671 | 3167603 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00149 | UG75 Expression | GENE | Mm.16228 | TITLE adenine nucleotide translocator 1, skeletal muscle | GENE Ant1 | | gi = 902007 | 1152260 |
| IC00150 | UG75 Expression | GENE | Mm.658 | TITLE adenine nucleotide translocator 2, fibroblast | GENE Ant2 | | gi = 1816494 | 1891139 |
| IC00151 | UG76 LID366 B cell | GENE | Mm.42179 | TITLE annexin A10 | GENE Anxa10 | | NM_011922 | 2699206 |
| IC00152 | UG75 Expression | GENE | Mm.1427 | TITLE annexin A11 | GENE Anxa11 | Anx11| | NM_013469 | 2064887 |
| IC00153 | UG75 Expression | GENE | Mm.7214 | TITLE annexin A3 | GENE Anxa3 | Anx3| | NM_013470 | 676572 |
| IC00154 | UG75 Expression | GENE | Mm.619 | TITLE annexin A4 | GENE Anxa4 | Anx4| | NM_013471 | 2236429 |
| IC00155 | UG75 Expression | GENE | Mm.1620 | TITLE annexin A5 | GENE Anxa5 | Anx5| | NM_009673 | 576596 |
| IC00156 | UG75 Expression | GENE | Mm.22619 | TITLE annexin A6 | GENE Anxa6 | Annexin VI|Anxa6|AnxVI|Cabm|calcium binding membrane-associated protein|Camb| | NM_013472 | 1884981 |
| IC00157 | UG75 Expression | GENE | Mm.20794 | TITLE annexin A7 | GENE Anxa7 | Anx7|synexin| | NM_009674 | 605420 |
| IC00158 | UG75 Expression | GENE | Mm.3267 | TITLE annexin A8 | GENE Anxa8 | Anx8| | NM_013473 | 481958 |
| IC00159 | UG75 Expression | GENE | Mm.29821 | TITLE anti-oxidant protein 1 | GENE Aop1 | D0Tohi1|Ef2l|Mer5|mitochondrial thioredoxin dependent peroxide reductase precursor|mitochondrial Trx dependent peroxide reductase precursor|TDXM| | NM_007452 | 1363431 |
| IC00160 | UG75 Expression | GENE | Mm.6587 | TITLE anti-oxidant protein 2 | GENE Aop2 | acidic calcium-independent phospholipase A2|aiPLA2|brain protein 12|Brp-12|GPx|liver|20–30 thousand M.Wt. protein 4|liver|20–30 thousand M.Wt. protein 4|Ltw-4|Ltw4|Lvtw-4| | NM_007453 | 1888848 |
| IC00161 | UG75 Expression | GENE | Mm.29699 | TITLE adaptor-related protein complex AP-1, beta 1 subunit | GENE Ap1b1 | adaptin beta 1|Adtb1|beta-prime adaptin| | NM_007454 | 2182363 |
| IC00162 | UG75 Expression | GENE | Mm.10698 | TITLE adaptor-related protein complex AP-1, gamma 2 subunit | GENE Ap1g2 | adaptin, gamma 2|Adtg2|gamma 2-adaptin| | NM_007455 | 642332 |
| IC00163 | UG75 Expression | GENE | Mm.2237 | TITLE adaptor-related protein complex AP-1, mu subunit 1 | GENE Ap1m1 | [m]1A|AP47|clatherin medium chain-associated protein|Cltnm|mu1A| | NM_007456 | 596614 |
| IC00164 | UG75 Expression | GENE | Mm.22239 | TITLE adaptor-related protein complex AP-1, sigma 1 subunit | GENE Ap1s1 | [m]1B|mu1B|AP19| | NM_009678 | 976025 |
| IC00165 | UG75 Expression | GENE | Mm.833 | TITLE adipocyte protein aP2 | GENE Ap2 | | NM_007457 | 572331 |
| IC00166 | UG75 Expression | GENE | Mm.582 | TITLE adaptor-related protein complex AP-2, alpha 1 subunit | GENE Ap2a1 | AKAP-KL| | gi = 198716 | 2225650 |
| IC00167 | UG75 Expression | GENE | Mm.6877 | TITLE adaptor-related protein complex AP-2, alpha 2 subunit | GENE Ap2a2 | adaptin, alpha A|Adtaa| | NM_007458 | 439728 |
| IC00168 | UG75 Expression | GENE | Mm.14555 | TITLE adaptor-related protein complex AP-2, alpha 2 subunit | GENE Ap2m1 | adaptin, alpha B|Adtab|alpha-adaptin C|alpha-C adaptin| | NM_007459 | 1480904 |
| IC00169 | UG75 Expression | GENE | Mm.18946 | TITLE adaptor-related protein complex AP-2, mu 1 subunit | GENE Ap3b1 | pe|pearl|recombination induced mutgation 2|rim2| | NM_009679 | 1920407 |
| IC00170 | UG75 Expression | GENE | Mm.21185 | TITLE adaptor-related protein complex AP-3, beta 1 subunit | GENE Ap3b1 | | NM_009680 | 991277 |
| IC00171 | UG75 Expression | GENE | Mm.28463 | TITLE adaptor-related protein complex AP-3, sigma 1 subunit | GENE Ap3d | Bolvr|bovine leukemia virus receptor|mBLVR1|mh|mocha|[s]3A| | NM_007460 | 442176 |
| IC00172 | UG75 Expression | GENE | Mm.27171 | TITLE adaptor-related protein complex AP-3, sigma 1 subunit | GENE Ap3s1 | | NM_009681 | 1381822 |
| IC00173 | UG75 Expression | GENE | Mm.23861 | TITLE adaptor-related protein complex AP-4, beta 1 subunit | GENE Ap4b1 | NM_009683 | 1922245 | 575596 |
| IC00174 | UG75 Expression | GENE | Mm.20836 | TITLE apoptotic protease activating factor 1 | GENE Apaf1 | Apaf1|apoptotic protease activating factor 1 like| | NM_009684 | 1969901 |
| IC00175 | UG75 Expression | GENE | Mm.5159 | TITLE amyloid beta (A4) precursor protein-binding, family B, member 2 | GENE Apbb2 | retrovirus integrase related-like 1|Riri1|TR21| | gi = 1572734 | 585017 |
| IC00176 | UG75 Expression | GENE | Mm.203 | TITLE apurinic/apyrimidinic endonuclease | GENE Apex | APE|HAP1|Ref-1| | NM_009687 | 850042 |
| IC00177 | UG75 Expression | GENE | Mm.2026 | TITLE apoptosis inhibitor 1 | GENE Api1 | IAP1|MIAP1| | NM_007464 | 597715 |
| IC00178 | UG75 Expression | GENE | Mm.14483 | TITLE apoptosis inhibitor 2 | GENE Api2 | IAP2|mcIAP|MIAP2| | NM_007465 | 793152 |
| IC00179 | UG75 Expression | GENE | Mm.6299 | TITLE apoptosis inhibitor 3 | GENE Api3 | Aip|apaptosis inhibitory protein A|IAP3|MIHA|mXIAP| | NM_009688 | 604782 |
| IC00180 | UG75 Expression | GENE | Mm.8552 | TITLE apoptosis inhibitor 4 | GENE Api4 | survivin|TIAP| | NM_009689 | 1887717 |
| IC00181 | UG75 Expression | GENE | Mm.692 | TITLE apoptosis inhibitor 5 | GENE Api5 | AAC-11| | NM_007466 | 1450657 |
| IC00182 | UG75 Expression | GENE | Mm.6676 | TITLE apoptosis inhibitory 6 | GENE Api6 | AAC-11| | NM_009690 | 25645429 |
| IC00183 | UG75 Expression | GENE | Mm.19133 | TITLE amyloid beta (A4) precursor-like protein 2 | GENE Aplp2 | | NM_009691 | 1891161 |
| IC00184 | UG75 Expression | GENE | Mm.43677 | TITLE apolipoprotein A-II | GENE Apoa2 | Alp-2|Apoa-2|Hdl-1|high density lipoprotein 1| | NM_013474 | |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00185 | UG75 Expression | GENE | Mm.4533 | TITLE apolipoprotein A-IV | GENE Apoa4 | Apoa-4| | NM_007468 | 1096764 |
| IC00186 | UG75 Expression | GENE | Mm.3333 | TITLE apolipoprotein B editing complex 1 | GENE Apobec1 | | gi = 899504 | 484168 |
| IC00187 | UG75 Expression | GENE | Mm.28897 | TITLE apolipoprotein CI | GENE Apoc1 | | NM_007469 | 423556 |
| IC00188 | UG75 Expression | GENE | Mm.28394 | TITLE apolipoprotein CII | GENE Apoc2 | | NM_009695 | 670784 |
| IC00189 | UG75 Expression | GENE | Mm.2082 | TITLE apolipoprotein D | GENE Apod | | NM_007470 | 1382000 |
| IC00190 | UG75 Expression | GENE | Mm.2266 | TITLE apolipoprotein H | GENE Apoh | beta-2-glycoprotein 1|beta-2-GPI|beta2-GPI| Adap|Alzheimer disease amyloid beta protein|betaAPP|cerebrovascular amyloid peptide|Cvap| | NM_013475 | 1889053 |
| IC00191 | UG75 Expression | GENE | Mm.15571 | TITLE amyloid beta (A4) precursor protein | GENE App | | NM_007471 | 1972378 |
| IC00192 | UG75 Expression | GENE | Mm.18625 | TITLE aquaporin 1 | GENE Aqp1 | | NM_007472 | 1481206 |
| IC00193 | UG75 Expression | GENE | Mm.2545 | TITLE aquarius | GENE Aqr | | gi = 1899231 | 466656 |
| IC00194 | UG75 Expression | GENE | Mm.4470 | TITLE androgen receptor | GENE Ar | RED1| | NM_013476 | 1920712 |
| IC00195 | UG75 Expression | GENE | Mm.5286 | TITLE acidic ribosomal phosphoprotein P0 | GENE Arbp | 36B4| | NM_007475 | 1139131 |
| IC00196 | UG75 Expression | GENE | Mm.6836 | TITLE ADP-ribosylation factor 1 | GENE Arf1 | | NM_007476 | 762508 |
| IC00197 | UG75 Expression | GENE | Mm.5061 | TITLE ADP-ribosylation factor 2 | GENE Arf2 | | NM_007477 | 438431 |
| IC00198 | UG75 Expression | GENE | Mm.1486 | TITLE ADP-ribosylation factor 4 | GENE Arf4 | | NM_007479 | 618236 |
| IC00199 | UG75 Expression | GENE | Mm.4898 | TITLE ADP-ribosylation factor 6 | GENE Arf6A | | NM_007481 | 617973 |
| IC00200 | UG75 Expression | GENE | Mm.16423 | TITLE arginase 1, liver | GENE Arg1 | Arg-1|PGIF| | NM_007482 | 1482661 |
| IC00201 | UG75 Expression | GENE | Mm.687 | TITLE aplysia ras-related homolog B (RhoB) | GENE Arhb | RhoB| | NM_007483 | 524899 |
| IC00202 | UG75 Expression | GENE | Mm.262 | TITLE aplysia ras-related homolog 9 (RhoC) | GENE Arhc | Arh9| | NM_007484 | 466539 |
| IC00203 | UG75 Expression | GENE | Mm.27701 | TITLE aplysia ras-related homolog D (RhoD) | GENE Arhd | RhoD| | NM_007485 | 921614 |
| IC00204 | UG75 Expression | GENE | Mm.2241 | TITLE rho, GDP dissociation inhibitor (GDI) beta | GENE Arhgdib | D4|Gdid4|GDP dissociation inhibitor, D4|Ly-GDI| | gi = 193461 | 619689 |
| IC00205 | UG75 Expression | GENE | Mm.27934 | TITLE ariadne 2 | GENE Ari2-pen | UIP48| | NM_011790 | 1069014 |
| IC00206 | UG75 Expression | GENE | Mm.12723 | TITLE ADP-ribosylation-like 4 | GENE Arl4 | | NM_007487 | 426165 |
| IC00207 | UG75 Expression | GENE | Mm.12177 | TITLE aryl hydrocarbon receptor nuclear translocator-like | GENE Arntl | Arnt3|Bmal1|MOP3|NM_007489 | | 943879 |
| IC00208 | UG75 Expression | GENE | Mm.19081 | TITLE angiopoetin related protein 2 | GENE Arp2-pending | | NM_011923 | 1510670 |
| IC00209 | UG75 Expression | GENE | Mm.31099 | TITLE ADP-ribosyltransferase 1 | GENE Art1 | ADPRT| | NM_009710 | 400733 |
| IC00210 | UG75 Expression | GENE | Mm.620 | TITLE arylsulfatase A | GENE As2 | Alas-2 | gi = 312271 | 678544 |
| IC00211 | UG75 Expression | GENE | Mm.27706 | TITLE ash2 (absent, small, or homeotic)-like (Drosophila) | GENE Ash21 | | gi = 4417210 | 934596 |
| IC00212 | UG75 Expression | GENE | Mm.22430 | TITLE activator of S phase kinase | GENE Ask-pen | Dbf4| | NM_013726 | 944255 |
| IC00213 | UG75 Expression | GENE | Mm.2942 | TITLE asparagine synthetase | GENE Asns | | gi = 1147604 | 733867 |
| IC00214 | UG75 Expression | GENE | Mm.3217 | TITLE arginosuccinate synthetase 1 | GENE Ass1 | Ass-1| | NM_007494 | 1891401 |
| IC00215 | UG75 Expression | GENE | Mm.21907 | TITLE arginine-tRNA-protein transferase 1 | GENE Ate1 | | NM_013799 | 1135453 |
| IC00216 | UG75 Expression | GENE | Mm.676 | TITLE activating transcription factor 1 | GENE Atf1 | | NM_007497 | 943972 |
| IC00217 | UG75 Expression | GENE | Mm.3466 | TITLE activating transcription factor 2 | GENE Atf2 | ATF-2|cAMP responsive element binding protein 2|CRE-BP|Creb2|mXBP| | gi = 201819 | 596792 |
| IC00218 | UG75 Expression | GENE | Mm.2706 | TITLE activating transcription factor 3 | GENE Atf3 | LRG-21| | NM_007498 | 515974 |
| IC00219 | UG75 Expression | GENE | Mm.641 | TITLE activating transcription factor 4 | GENE Atf4 | Atf-4|C/ATF|CREB2|TAXREB67| | NM_009716 | 1885646 |
| IC00220 | UG75 Expression | GENE | Mm.9703 | TITLE ATX1 (antioxicant protein 1, yeast) homolog 1 | GENE Atox1 | ATX1| | NM_009720 | 355942 |
| IC00221 | UG75 Expression | GENE | Mm.4550 | TITLE ATPase, Na+/K+ transporting, beta 1 polypeptide | GENE Atp1b2 | | NM_009721 | 2182691 |
| IC00222 | UG75 Expression | GENE | Mm.424 | TITLE ATPase, NA+/K+ beta 3 polypeptide | GENE Atp1b3 | Atpb|Atpb-1|Na, K-ATPase beta|Na, K-ATPase beta 1| | NM_007502 | 792041 |
| IC00223 | UG75 Expression | GENE | Mm.22742 | TITLE ATPase, Ca++ transporting, cardiac muscle, slow twitch 2 | GENE Atp1g1 | | NM_007503 | 848636 |
| IC00224 | UG75 Expression | GENE | Mm.42255 | polypeptide | GENE Atp2a2 | SERCA2| | NM_009722 | 3155757 |
| IC00225 | UG75 Expression | GENE | Mm.4069 | TITLE ATPase synthase, H+ transporting, mitochondrial F1 complex, alpha subunit, isoform 1 | GENE Atp5a1 | ATPase, mitochondrial|Atpm| | NM_007505 | 2225600 |
| IC00226 | UG75 Expression | GENE | Mm.30112 | TITLE ATP synthase, H+ transporting, mitochondrial F0 complex, subunit b, isoform 1 | GENE Atp5f1 | | gi = 1282394 | 1365755 |
| IC00227 | UG75 Expression | GENE | Mm.258 | TITLE ATP synthase, H+transporting, mitochondrial F0 complex, subunit c (subunit 9), isoform 1 | GENE Atp5g1 | | NM_007506 | 888863 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00228 | UG75 Expression | GENE | Mm.19370 | TITLE ATP synthase, H+ transporting, mitochondrial F1F0 complex, subunit e | GENE Atp5k | Lfm1|low fat mammary 1 (may = F1F0-ATPase subunit 3)| | NM_007507 | 1885128 |
| IC00229 | UG75 Expression | GENE | Mm.14663 | TITLE ATP synthase, H+ transporting, mitochondrial F0 complex, subunit g | GENE Atp5l | F1F0-ATP synthase g subunit| | NM_013795 | 1244691 |
| IC00230 | UG75 Expression | GENE | Mm.29771 | TITLE ATPase, H+ transporting, lysosomal (vacuolar proton pump), alpha 70 kDa, isoform 2 | GENE Atp6a2 | 70-kDa subunit| | NM_007508 | 1907680 |
| IC00231 | UG75 Expression | GENE | Mm.10727 | TITLE ATPase, H+ transporting, lysosomal (vacuolar proton pump), beta 56/58 kDa, isoform 2 | GENE Atp6b2 | | NM_007509 | 408000 |
| IC00232 | UG75 Expression | GENE | Mm.1081 | TITLE ATPase, H+ transporting, lysosomal (vacuolar proton pump), 42 kDa | GENE Atp6d | Ac39| | NM_013477 | 440739 |
| IC00233 | UG75 Expression | GENE | Mm.29045 | TITLE ATPase, H+ transporting lysosomal (vacuolar proton pump), 32 kDa | GENE Atp6e | | NM_007510 | 1431445 |
| IC00234 | UG75 Expression | GENE | Mm.22602 | TITLE ATPase, H+ transporting lysosomal (vacuolar proton pump) 9.2 kDa | GENE Atp6k | M9.2| | gi = 3164633 | 903102 |
| IC00235 | UG76 LID366 B cell | GENE | Mm.87029 | TITLE ATPase, class 1 | GENE Atpc1-pe | Class I| | NM_009727 | 761013 |
| IC00236 | UG75 Expression | GENE | Mm.2171 | TITLE ATPase inhibitor | GENE Atpi | If1| | NM_007512 | 313557 |
| IC00237 | UG75 Expression | GENE | Mm.30155 | TITLE ATPase-like vacuolar proton channel | GENE Atpl | Atp6c|PL16|proteolipid, PL16| | NM_009729 | 1887677 |
| IC00238 | UG75 Expression | GENE | Mm.22617 | TITLE AU-rich element RNA-binding protein 1 | GENE Auf1 | | NM_007516 | 1434544 |
| IC00239 | UG75 Expression | GENE | Mm.2146 | TITLE ancient ubiquitous protein | GENE Aup1 | | NM_007517 | 3167531 |
| IC00240 | UG75 Expression | GENE | Mm.23684 | TITLE axin | GENE Axin | axis inhibition|Fu|fused|Kb|Ki|kinky|knoblly| | gi≤2252815 | 2648290 |
| IC00241 | UG75 Expression | GENE | Mm.4128 | TITLE axl | GENE Axl | Ark|ax|Tyro7|Ufo|ufo oncogene homolog| | NM_009465 | 1153248 |
| IC00242 | UG75 Expression | GENE | Mm.30061 | TITLE alpha-2-glycoprotein 1, zinc | GENE Azgp1 | | NM_013478 | 1924024 |
| IC00243 | UG75 Expression | GENE | Mm.2179 | TITLE 5-azacytidine induced gene 2 | GENE Azi2 | AZ2| | NM_013727 | 2599102 |
| IC00244 | UG75 Expression | GENE | Mm.163 | TITLE beta-2 microglobulin | GENE B2m | Ly-m11|lymphocyte antigen m11| | NM_119735 | 1451474 |
| IC00245 | UG75 Expression | GENE | Mm.5183 | TITLE BTB and CNC homology 1 | GENE Bach1 | | NM_007520 | 524824 |
| IC00246 | UG75 Expression | GENE | Mm.21908 | TITLE BTB and CNC homology 2 | GENE Bach2 | | NM_007521 | 2101518 |
| IC00247 | UG75 Expression | GENE | Mm.4387 | TITLE Bcl-associated death promoter | GENE Bad | | NM_007522 | 554143 |
| IC00248 | UG75 Expression | GENE | Mm.4811 | TITLE Bcl2-associated athanogene 1 | GENE Bag1 | | NM_009736 | 2938203 |
| IC00249 | UG75 Expression | GENE | Mm.688 | TITLE Bcl2 homologous antagonist/killer | GENE Bak | | NM_007523 | 864330 |
| IC00250 | UG75 Expression | GENE | Mm.2443 | TITLE BRCA1 associated RING domain 1 | GENE Bard1 | | NM_007525 | 1329476 |
| IC00251 | UG75 Expression | GENE | Mm.10764 | TITLE Bcl2-associated X protein | GENE Bax | | NM_007527 | 1348660 |
| IC00252 | UG75 Expression | GENE | Mm.19904 | TITLE B-cell receptor-associated protein 29 | GENE Bcap29 | Bap29|BCR-associated protein 29| | NM_007530 | 719184 |
| IC00253 | UG75 Expression | GENE | Mm.4236 | TITLE B-cell receptor-associated protein 31 | GENE Bcap31 | BAP31| | NM_012060 | 1889655 |
| IC00254 | UG75 Expression | GENE | Mm.17 | TITLE B-cell receptor-associated protein 37 | GENE Bcap37 | Bap37|BCR-associated protein 37| | NM_007531 | 2646826 |
| IC00255 | UG75 Expression | GENE | Mm.36241 | TITLE branched chain aminotransferase 1, cytosolic | GENE Bcat1 | c-myc regulatory gene|Eca39| | NM_007532 | 616071 |
| IC00256 | UG75 Expression | GENE | Mm.4606 | TITLE branched chain aminotransferase 2, mitochondrial | GENE Bcat2 | Eca40| | gi = 3298878 | 351533 |
| IC00257 | UG75 Expression | GENE | Mm.25848 | TITLE branched chain ketoacid dehydrogenase E1, alpha polypeptide | GENE Bckdha | BCKAD E1[a]| | NM_007533 | 1383215 |
| IC00258 | UG75 Expression | GENE | Mm.12819 | TITLE branched chain keto acid dehydrogenase E1, beta polypeptide | GENE Bckdhb | gi = 293303 | 1888416 | |
| IC00259 | UG75 Expression | GENE | Mm.8903 | TITLE branched chain keto acid dehydrogenase kinase | GENE Bckdk | BCKD-kinase| | NM_009739 | 578018 |
| IC00260 | UG75 Expression | GENE | Mm.28782 | TITLE B-cell leukemia/lymphoma 10 | GENE Bcl10 | CARMEN|CIPER|CLAP|ME10| | NM_009740 | 1379061 |
| IC00261 | UG75 Expression | GENE | Mm.5155 | TITLE B-cell leukemia/lymphoma 2 | GENE Bcl2 | Bcl-2| | NM_009741 | 1344668 |
| IC00262 | UG75 Expression | GENE | Mm.16105 | TITLE B-cell leukemia/lymphoma 2 related protein A1b | GENE Bcl2a1B | A1-b| | NM_007534 | 1363928 |
| IC00263 | UG75 Expression | GENE | Mm.6967 | TITLE Bcl2-like 2 | GENE Bcl2l2 | bcl-w|BC1W|gene trap ROSA 41|gene trap ROSA b-gal 2|Grtgral2|Gtrosa41| | NM_007537 | 975210 |
| IC00264 | UG75 Expression | GENE | Mm.1068 | TITLE B-cell leukemia/lymphoma 3 | GENE Bcl3 | Bcl-3| | gi = 3928844 | 1230937 |
| IC00265 | UG75 Expression | GENE | Mm.15811 | TITLE B-cell leukemia/lymphoma 6 | GENE Bcl6 | | NM_009744 | 1445854 |
| IC00266 | UG75 Expression | GENE | Mm.31 | TITLE B-cell CLL/lymphoma 7B | GENE Bcl7b | | NM_009745 | 793962 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00267 | UG75 Expression | GENE | Mm.2898 | TITLE B-cell CLL/lymphoma 7C | GENE Bcl7c | | NM_009746 | 735097 |
| IC00268 | UG75 Expression | GENE | Mm.7508 | TITLE breakpoint cluster region protein 1 | GENE Bcrp-1-pe | | NM_011793 | 1498630 |
| IC00269 | UG75 Expression | GENE | Mm.8392 | TITLE Bet3 homolog (S. cerevisiae) | GENE Bet3 | | NM_013718 | 406013 |
| IC00270 | UG75 Expression | GENE | Mm.94160 | TITLE brain expressed X-linked 2 | GENE Bex2 | | NM_009749 | 316656 |
| IC00271 | UG75 Expression | GENE | Mm.2040 | TITLE beta-galactosidase complex | GENE Bgl | | NM_009752 | 1051168 |
| IC00272 | UG75 Expression | GENE | Mm.2608 | TITLE biglycan | GENE Bgn | | NM_007542 | 846321 |
| IC00273 | UG75 Expression | GENE | Mm.34384 | TITLE BH3 interacting domain death agonist | GENE bid | | NM_007544 | 1225087 |
| IC00274 | UG75 Expression | GENE | Mm.17912 | TITLE Bcl2-interacting killer-like | GENE Biklk | Blk| | NM_007546 | 2537292 |
| IC00275 | UG75 Expression | GENE | Mm.12932 | TITLE Bloom syndrome homolog (human) | GENE Blm | | NM_007550 | 577228 |
| IC00276 | UG75 Expression | GENE | Mm.6246 | TITLE Burkitt lymphoma receptor 1 | GENE Blr1 | CXCR5|G-protein coupled receptor 6|gpcr6| | NM_007551 | 1330376 |
| IC00277 | UG75 Expression | GENE | Mm.7719 | TITLE B lymphoma Mo-MLV insertion region 1 | GENE Bmi1 | B lymphoma MO-MLV insertion region 1|Bmi-1| | NM_007552 | 1347589 |
| IC00278 | UG75 Expression | GENE | Mm.27757 | TITLE bone morphogenetic protein 1 | GENE bmp1 | TLD| | gi = 439606 | 492502 |
| IC00279 | UG75 Expression | GENE | Mm.504 | TITLE BMX non-receptor tyrosine kinase | GENE Bmx | | NM_009759 | 596729 |
| IC00280 | UG75 Expression | GENE | Mm.2159 | TITLE BCL2/adenovirus E1B 19 kDa-interacting protein 1, NIP3 | GENE Bnip3 | Nip3| | NM_009760 | 805932 |
| IC00281 | UG75 Expression | GENE | Mm.29820 | TITLE BCL2/adenovirus E1B 19 kDa-interacting protein 3-like | GENE Bnip3| | Nix| | NM_009761 | 1450780 |
| IC00282 | UG75 Expression | GENE | Mm.4283 | TITLE block of proliferation 1 | GENE Bop1 | Kiaa0124| | NM_013481 | 2247532 |
| IC00283 | UG75 Expression | GENE | Mm.24612 | TITLE BP-3 alloantigen | GENE Bp3 | 114A10|bone marrow stromal cell antigen 1|BP-3|Bst|Bsta1|Ly65|lymphocyte antigen 65| | NM_009763 | 1971326 |
| IC00284 | UG75 Expression | GENE | Mm.22706 | TITLE 2,3-bisphosphoglycerate mutase | GENE Bpgm | | NM_007563 | 515091 |
| IC00285 | UG75 Expression | GENE | Mm.18096 | TITLE bisphosphate 3'-nucleotidase 1 | GENE Bpnt1 | BPntase| | NM_001794 | 2123582 |
| IC00286 | UG75 Expression | GENE | Mm.8807 | TITLE Braf transforming gene | GENE Braf | Braf transforming gene 2|Braf-2|Braf2| | NM_013801 | 119315 |
| IC00287 | UG75 Expression | GENE | Mm.1889 | TITLE breast cancer 1 | GENE Brca1 | | gi = 1049262 | 608026 |
| IC00288 | UG75 Expression | GENE | Mm.161 | TITLE breast cancer 2 | GENE Brca2 | RAB163| | NM_009765 | 804266 |
| IC00289 | UG75 Expression | GENE | Mm.18571 | TITLE butyrate response factor 1 | GENE Brf1 | TIS11b| | NM_007564 | 671377 |
| IC00290 | UG75 Expression | GENE | Mm.12921 | TITLE baculovirus inhibitor of apoptosis repeat containing ubiquitin-conjugating enzyme | GENE Bruce | | gi = 3319989 | 875563 |
| IC00291 | UG75 Expression | GENE | Mm.726 | TITLE basigin | GENE Bsg | CD147|neurothelin| | gi = 2808467 | 1886456 |
| IC00292 | UG75 Expression | GENE | Mm.16596 | TITLE B-cell translocation gene 1, anti-proliferative | GENE Btg1 | | gi = 50187 | 2802813 |
| IC00293 | UG75 Expression | GENE | Mm.903 | TITLE B-cell translocation gene 2, anti-proliferative | GENE Btg2 | TIS21| | NM_007570 | 316773 |
| IC00294 | UG75 Expression | GENE | Mm.2823 | TITLE B-cell translocation gene 3 | GENE Btg3 | | NM_009770 | 790218 |
| IC00295 | UG75 Expression | GENE | Mm.4475 | TITLE Bruton agammaglobulinemia tyrosine kinase | GENE Btk | X-linked immune deficiency|xid| | gi = 193016 | 597683 |
| IC00296 | UG75 Expression | GENE | Mm.28734 | TITLE beta-transducin repeat containing protein | GENE Btrc | b-TrCP|FWD1|mSlimb|SCF b-TRCP|slimb| | NM_009771 | 375414 |
| IC00297 | UG75 Expression | GENE | Mm.2185 | TITLE budding uninhibited by benzimidazoles 1 homolog (S. cerevisiae) | GENE Bub1 | cerevisiae) homolog|D2Xrf87|DNA segment, Chr 2, XEFdb 87| | gi = 2335137 | 718292 |
| IC00298 | UG75 Expression | GENE | Mm.29133 | TITLE budding uninhibited by benzimidazoles 1 homolog, beta (S. cerevisiae) | GENE Bub1b | | NM_009773 | 2616235 |
| IC00299 | UG75 Expression | GENE | Mm.927 | TITLE budding uninhibited by benzimidazoles 3 homolog (S. cerevisiae) | GENE Bub3 | | NM_009774 | 387161 |
| IC00300 | UG75 Expression | GENE | Mm.1508 | TITLE benzodiazepine receptor, peripheral | GENE Bzrp | | NM_009775 | 1853323 |
| IC00301 | UG75 Expression | GENE | Mm.38888 | TITLE complement component 1 inhibitor | GENE C1nh | | NM_009776 | 1891424 |
| IC00302 | UG75 Expression | GENE | Mm.370 | TITLE complement component 1, q subcomponent, alpha polypeptide | GENE C1qa | | NM_007572 | 1889735 |
| IC00303 | UG75 Expression | GENE | Mm.2570 | TITLE complement component 1, q subcomponent, beta polypeptide | GENE C1qb | | NM_009777 | 2647334 |
| IC00304 | UG75 Expression | GENE | Mm.30049 | TITLE complement component 1, q subcomponent binding protein | GENE C1qbp | gC1qBP| | NM_007573 | 1480291 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00305 | UG75 Expression | GENE | Mm.3453 | TITLE complement component 1, q subcomponent, c polypeptide | GENE C1gc | | NM_007574 | 426010 |
| IC00306 | UG75 Expression | GENE | Mm.2081 | TITLE complement component 2 (within H-2S) | GENE C2 | D0S1474E| | NM_013484 | 2076190 |
| IC00307 | UG75 Expression | GENE | Mm.1619 | TITLE class II transactivator | GENE C2ta | CIITA| | NM_0007575 | 1430808 |
| IC00308 | UG75 Expression | GENE | Mm.19131 | TITLE complement component 3 | GENE C3 | semicarbazide-sensitive amine oxidase|SSAO|VAP1| | gi = 192278 | 1889596 |
| IC00309 | UG75 Expression | GENE | Mm.16106 | TITLE complement component 4 (within H-2S) | GENE C4 | serum substance|Ss| | NM_0009780 | 1510703 |
| IC00310 | UG75 Expression | GENE | Mm.29095 | TITLE complement component 9 | GENE C9 | sulfonylurea receptor 2|Sur2|SUR2A|SUR2B| | gi = 50253 | 1431691 |
| IC00311 | UG75 Expression | GENE | Mm.3544 | TITLE calcium channel beta 3 subunit | GENE Cacnb3 | calcium channel, B3 subunit|Cchb3| | NM_007581 | 58365 |
| IC00312 | UG75 Expression | GENE | Mm.10702 | TITLE calcyclin binding protein | GENE Cacybp | | gi = 313917 | 1922118 |
| IC00313 | UG75 Expression | GENE | Mm.2442 | TITLE calcium binding protein, intestinal | GENE Cai | ERp72| | NM_009787 | 438171 |
| IC00314 | UG75 Expression | GENE | Mm.501 | TITLE cell adhesion kinase | GENE Cak | Nep|neuroepithelial tyrosine kinase II| | NM_007584 | 746728 |
| IC00315 | UG75 Expression | GENE | Mm.584 | TITLE calpactin I heavy chain | GENE cal1h | | NM_007585 | 1228117 |
| IC00316 | UG75 Expression | GENE | Mm.4361 | TITLE calcitonin | GENE Calc | alpha CGRP|CA|calcitonin/alpha CGRP|Cgrp|C|Ctn| | gi = 144303 | 1178118 |
| IC00317 | UG75 Expression | GENE | Mm.2648 | TITLE calmodulin | GENE Calm | | NM_009790 | 1972189 |
| IC00318 | UG75 Expression | GENE | Mm.18041 | TITLE calmodulin 2 | GENE Calm2 | | NM_007589 | 2650369 |
| IC00319 | UG75 Expression | GENE | Mm.1147 | TITLE calmodulin 3 | GENE Calm3 | CaMA| | NM_007590 | 421574 |
| IC00320 | UG75 Expression | GENE | Mm.12940 | TITLE calmodulin binding protein 1 | GENE Calmbp1 | Sha1| | NM_007591 | 439518 |
| IC00321 | UG75 Expression | GENE | Mm.1971 | TITLE calreticulin | GENE Calr | | NM_007591 | 1180181 |
| IC00322 | UG75 Expression | GENE | Mm.7515 | TITLE calumenin | GENE Calu | | NM_007594 | 2503285 |
| IC00323 | UG75 Expression | GENE | Mm.2951 | TITLE calcium/calmodulin-dependent protein kinase IV | GENE Camk4 | | NM_009793 | 1344831 |
| IC00324 | UG75 Expression | GENE | Mm.2313 | TITLE calcium modulating ligand | GENE Caml | | NM_007596 | 427258 |
| IC00325 | UG75 Expression | GENE | Mm.23929 | TITLE calnexin | GENE Canx | | NM_007597 | 1094979 |
| IC00326 | UG75 Expression | GENE | Mm.8687 | TITLE adenylyl cyclase-associated CAP protein, yeist homolog 1 | GENE Cap1 | | NM_007598 | 805363 |
| IC00327 | UG75 Expression | GENE | Mm.18626 | TITLE capping protein (actin filament), gelsolin-like | GENE Capg | gCap39|mbh1| | NM_007599 | 2936735 |
| IC00328 | UG75 Expression | GENE | Mm.6221 | TITLE calpain 1 | GENE Capn1 | calpain 1, large subunit|Capa-1|CPB1|CPB2|CPbeat2|CPbeta1| | NM_007600 | 1349339 |
| IC00329 | UG75 Expression | GENE | Mm.6958 | TITLE calpain 2 | GENE Capn2 | Capa-2|Capa2|m-calpin| | NM_009794 | 524277 |
| IC00330 | UG75 Expression | GENE | Mm.6534 | TITLE calpain 4 | GENE Capn4 | | NM_009795 | 2259062 |
| IC00331 | UG75 Expression | GENE | Mm.10682 | TITLE calpain 5 | GENE Capn5 | | NM_007602 | 977024 |
| IC00332 | UG75 Expression | GENE | Mm.24778 | TITLE calpain 7 | GENE Capn7 | | NM_009796 | 583039 |
| IC00333 | UG75 Expression | GENE | Mm.29544 | TITLE calpain 8 | GENE Capn8 | | NM_011796 | 1002921 |
| IC00334 | UG75 Expression | GENE | Mm.19142 | TITLE capping protein alpha 1 | GENE Cappa1 | | gi = 595916 | 3167026 |
| IC00335 | UG75 Expression | GENE | Mm.3529 | TITLE capping protein alpha 2 | GENE Cappa2 | | NM_007604 | 749169 |
| IC00336 | UG75 Expression | GENE | Mm.2945 | TITLE capping proein beta 1 | GENE Cappb1 | [b]1 cDNA|[b]2 cDNA|capping protein (actin filament) muscle Z line, beta 1|CPB1|CPB2|CPbeat2|CPbeta1| | NM_009798 | 670783 |
| IC00337 | UG75 Expression | GENE | Mm.3471 | TITLE carbonic anydrase 1 | GENE Car1 | CA I|Car-1| | NM_009799 | 1136013 |
| IC00338 | UG75 Expression | GENE | Mm.34556 | TITLE carbonic anydrase 14 | GENE Car14 | CA XIV| | NM_011797 | 680269 |
| IC00339 | UG75 Expression | GENE | Mm.1186 | TITLE carbonic anydrase 2 | GENE Car2 | CA II|Car-2|liver 20–30 thousand M.Wt protein 5|Ltw-5|Ltw-5| | NM_009801 | 1972570 |
| IC00340 | UG75 Expression | GENE | Mm.300 | TITLE carbonic anydrase 3 | GENE Car3 | AND-34| | NM_007606 | 521648 |
| IC00341 | UG75 Expression | GENE | Mm.1641 | TITLE carbonic anydrase 4 | GENE Car4 | CA IV| | NM_007607 | 1079540 |
| IC00342 | UG75 Expression | GENE | Mm.35538 | TITLE carbonic anydrase 5, mitochondrial | GENE Car5 | CAV| | NM_007608 | 1482074 |
| IC00343 | UG75 Expression | GENE | Mm.4215 | TITLE catalase 1 | GENE Cas1 | Cas-1|Cs-1| | NM_009805 | 1480960 |
| IC00344 | UG75 Expression | GENE | Mm.1993 | TITLE caspase homolog | GENE Cash | | NM_009806 | 2123529 |
| IC00345 | UG75 Expression | GENE | Mm.10735 | TITLE calcium/calmodulin-dependent serine protein kinase | GENE Cask | DNA segment, Chr X, Princeton 1|DXPri1| | NM_009807 | 2698979 |
| IC00346 | UG75 Expression | GENE | Mm.1051 | TITLE caspase 1 | GENE Casp1 | ICE|IL-1B converting enzyme|Il11bc|interleukin 1 beta convertase| | NM_009807 | 2645841 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00347 | UG75 Expression | GENE | Mm.1569 | TITLE caspase 11 | GENE Casp11 | caspase-like|Caspl|ich-3| | NM_007609 | 1248291 |
| IC00348 | UG75 Expression | GENE | Mm.3921 | TITLE caspase 2 | GENE Casp2 | ICH-1|Nedd2|neural precursor cell expressed, developmentally down-regulated gene 2| | NM_007610 | 3154786 |
| IC00349 | UG75 Expression | GENE | Mm.34405 | TITLE caspase 3, apoptosis related cystein protease | GENE Casp3 | Apopain|CPP32|Lice|Yama | NM_009810 | 2352568 |
| IC00350 | UG75 Expression | GENE | Mm.28814 | TITLE caspase 6 | GENE Casp6 | mCASP-6|Mch2| | NM_009811 | 1382841 |
| IC00351 | UG75 Expression | GENE | Mm.35687 | TITLE caspase 7 | GENE Casp7 | CMH-1|ICE-IAP3|mCASP-7|Mch3| | NM_007611 | 1499194 |
| IC00352 | UG75 Expression | GENE | Mm.10736 | TITLE caspase 8 | GENE casp8 | Fas-linked ICE-like protease|FLICE|MACH|Mch5| | gi = 3193166 | 1002469 |
| IC00353 | UG75 Expression | GENE | Mm.22279 | TITLE caspase 8 associated protein 2 | GENE Casp8ap2 | | NM_011997 | 636943 |
| IC00354 | UG75 Expression | GENE | Mm.18962 | TITLE catenin alpha 1 | GENE Catna1 | | NM_009818 | 2616326 |
| IC00355 | UG75 Expression | GENE | Mm.3476 | TITLE catenin beta | GENE Catnb | cadherin associated protein| | NM_007614 | 1154334 |
| IC00356 | UG75 Expression | GENE | Mm.35738 | TITLE catenin src | GENE Catns | catenin, delta|Ctnnd|P120| | NM_007615 | 1349430 |
| IC00357 | UG75 Expression | GENE | Mm.28278 | TITLE caveolin, caveolae protein, 22 kDa | GENE Cav | Cav-1| | NM_007616 | 1480732 |
| IC00358 | UG75 Expression | GENE | Mm.12429 | TITLE CBFA2T3 identified gene homolog (human) | GENE Cbfa2t3 | ETO-2|MTGR1| | NM_009824 | 1180816 |
| IC00359 | UG75 Expression | GENE | Mm.2018 | TITLE core binding factor beta | GENE Cbfb | PEA2|Pebp2|Pebp2| | gi = 303695 | 617493 |
| IC00360 | UG75 Expression | GENE | Mm.2874 | TITLE corticosteroid binding globulin | GENE Cbg | | NM_007618 | 367132 |
| IC00361 | UG75 Expression | GENE | Mm.22708 | TITLE callogen bidning protein 1 | GENE Cpb1 | colligin|gp46|heat shock protein 47 kDa|Hsp47|J6| | NM_009825 | 615760 |
| IC00362 | UG75 Expression | GENE | Mm.26940 | TITLE carbonyl reductase | GENE Cbr | | NM_007620 | 2332267 |
| IC00363 | UG75 Expression | GENE | Mm.21454 | TITLE carbonyl reductase 2 | GENE Cbr2 | | NM_007621 | 552719 |
| IC00364 | UG75 Expression | GENE | Mm.29055 | TITLE chromobox homolog (Drosophila HP1 beta) | GENE Cbx | Cbx-rs2|chromobox related sequence 2 (Drosophila HP1 class)|M31|MOD1| | NM_007622 | 1890892 |
| IC00365 | UG75 Expression | GENE | Mm.46536 | TITLE chromobox homolog 3 (Drosophila HP1 gamma) | GENE Cbx3 | M32| | NM_007624 | 1885726 |
| IC00366 | UG75 Expression | GENE | Mm.8556 | TITLE chromobox homolog 4 (Drosophila Pc class) | GENE Cbx4 | MPc2| | NM_007625 | 635635 |
| IC00367 | UG75 Expression | GENE | Mm.28408 | TITLE chromobox homolog 5 (Drosophila HP1a) | GENE Cbx5 | heterochromatin protein 1 alpha|Hp1a|mHP1 (alpha)| | NM_007626 | 538257 |
| IC00368 | UG75 Expression | GENE | Mm.4189 | TITLE cyclin A2 | GENE Ccna2 | Ccn-1|Ccna|Cyca|cyclin A| | NM_009828 | 2087970 |
| IC00369 | UG75 Expression | GENE | Mm.22569 | TITLE cyclin B1, related sequence 1 | GENE Ccnb1-rs | Cyb-4|cyclin B4| | NM_007629 | 1499176 |
| IC00370 | UG75 Expression | GENE | Mm.22592 | TITLE cyclin B2 | GENE Ccnb2 | | NM_007630 | 2939185 |
| IC00371 | UG75 Expression | GENE | Mm.22288 | TITLE cyclin D1 | GENE Ccnd1 | Cyl-1| | NM_007631 | 761652 |
| IC00372 | UG75 Expression | GENE | Mm.3141 | TITLE cyclin D2 | GENE Ccnd2 | Vin-1|viral integration site, radiation leukemia| | NM_009829 | 2064983 |
| IC00373 | UG75 Expression | GENE | Mm.7417 | TITLE cyclin D3 | GENE Ccnd3 | | NM_007632 | 2259264 |
| IC00374 | UG75 Expression | GENE | Mm.16110 | TITLE cyclin E | GENE Ccne | | NM_007633 | 3154251 |
| IC00375 | UG75 Expression | GENE | Mm.4008 | TITLE cyclin F | GENE Ccnf | | NM_007634 | 3025731 |
| IC00376 | UG75 Expression | GENE | Mm.2103 | TITLE cyclin G | GENE Ccng | cyclin G| | NM_009831 | 760728 |
| IC00377 | UG75 Expression | GENE | Mm.3527 | TITLE cyclin G2 | GENE Ccng2 | | NM_007635 | 2749098 |
| IC00378 | UG75 Expression | GENE | Mm.86538 | TITLE cyclin T1 | GENE Ccnt1 | Cyct1| | NM_009833 | 2259329 |
| IC00379 | UG75 Expression | GENE | Mm.3670 | TITLE chaperonin subunit 2 (beta) | GENE Cct2 | Cctb| | NM_007636 | 390866 |
| IC00380 | UG75 Expression | GENE | Mm.390 | TITLE chaperonin subunit 3 (gamma) | GENE Cct3 | | NM_009836 | 538594 |
| IC00381 | UG75 Expression | GENE | Mm.6821 | TITLE chaperonin subunit 4 (delta) | GENE Cct4 | P5| | NM_009837 | 615872 |
| IC00382 | UG75 Expression | GENE | Mm.1813 | TITLE chaperonin subunit 5 (epsilon) | GENE Cct5 | A45| | NM_007637 | 1499044 |
| IC00383 | UG75 Expression | GENE | Mm.398 | TITLE chaperonin subunit 6a (zeta) | GENE Cct6a | Cct6|chaperonin subunit 6 (zeta)| | NM_009838 | 333402 |
| IC00384 | UG75 Expression | GENE | Mm.914 | TITLE chaperonin subunit 7 (eta) | GENE Cct7 | | NM_007638 | 1480264 |
| IC00385 | UG75 Expression | GENE | Mm.17989 | TITLE chaperonin subunit 8 (theta) | GENE Cct8 | Cctz| | NM_009840 | 2192571 |
| IC00386 | UG75 Expression | GENE | Mm.3460 | TITLE CD14 antigen | GENE Cd14 | | NM_009841 | 2937162 |
| IC00387 | UG75 Expression | GENE | Mm.30246 | TITLE CD151 antigen | GENE Cd151 | PETA-3|SFA-1| | NM_009842 | 1970391 |
| IC00388 | UG75 Expression | GENE | Mm.390 | TITLE CD152 antigen | GENE Cd152 | Ctla-4|Ctla4|cytotoxic T lymphocyte-associated protein 4| | NM_009843 | 575713 |
| IC00389 | UG75 Expression | GENE | Mm.4360 | TITLE CD19 antigen | GENE Cd19 | | NM_007640 | 2749233 |
| IC00390 | UG75 Expression | GENE | Mm.1894 | TITLE CD1d1 antigen | GENE Cd1d1 | CD1.1|Cd1a|CD1a antigen|Cd1d|CD1d antigen|Ly-38|lymphocyte antigen 38| | NM_007639 | 2581931 |
| IC00391 | UG75 Expression | GENE | Mm.88779 | TITLE CD1d2 antigen | GENE Cd1d2 | CD1.2|Cd1b|CD1b antigen|Ly-38|lymphocyte antigen 38| | NM_007640 | 963025 |
| IC00392 | UG75 Expression | GENE | Mm.4046 | TITLE CD20 antigen | GENE Cd20 | Ly-44|lymphocyte antigen 44| | NM_007641 | 598478 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00393 | UG75 Expression | GENE | Mm.1708 | TITLE CD22 antigen | GENE Cd22 | B-lymphocyte antigen B|Lyb-8|Lyb8| | NM_009845 | 1230835 |
| IC00394 | UG75 Expression | GENE | Mm.6417 | TITLE CD24a antigen | GENE Cd24a | heat stable antigen|HSA|Ly-52|lymphocyte antigen 52| | NM_009846 | 1382246 |
| IC00395 | UG75 Expression | GENE | Mm.1060 | TITLE CD28 antigen | GENE Cd28 | | NM_007642 | 5476501 |
| IC00396 | UG75 Expression | GENE | Mm.20882 | TITLE CD2-associated protein GENE Cd2ap | | | NM_009847 | 1225807 |
| IC00397 | UG75 Expression | GENE | Mm.18628 | TITLE CD36 antigen | GENE Cd36 | FAT|fatty acid translocase| | NM_007643 | 2811866 |
| IC00398 | UG75 Expression | GENE | Mm.7176 | TITLE CD36 antigen (collagen type I receptor, thrombospondin receptor)-like 2 | GENE Cd36l2 | LGP85|LIMP II|MLGP85| | NM_007644 | 749794 |
| IC00399 | UG75 Expression | GENE | Mm.3689 | TITLE CD37 antigen | GENE 37 | | NM_007645 | 403475 |
| IC00400 | UG75 Expression | GENE | Mm.996 | TITLE CD38 antigen | GENE CD38 | CD38 antigen, related sequence 1|CD38-rs1| | NM_007646 | 750428 |
| IC00401 | UG75 Expression | GENE | Mm.2824 | TITLE CD39 antigen | GENE Cd39 | | NM_009848 | 402959 |
| IC00402 | UG75 Expression | GENE | Mm.102111 | TITLE CD39 antigen-like 4 | GENE Cd39l4 | mNTPase1 | NM_007647 | 597299 |
| IC00403 | UG75 Expression | GENE | Mm.4527 | TITLE CD3 antigen, delta polypeptide | GENE Cd3d | T3-delta chain|T3d| | NM_013487 | 1246607 |
| IC00404 | UG75 Expression | GENE | Mm.1848 | TITLE CD3 antigen, epsilon polypeptide | GENE Cd3e | T3-epsilon chain|T3e| | NM_007648 | 972662 |
| IC00405 | UG75 Expression | GENE | Mm.4513 | TITLE CD3 antigen, gamma polypeptide | GENE Cd3g | Ctg-3|Ctg3|T3-gamma chain|T3g| | NM_009850 | 1193414 |
| IC00406 | UG75 Expression | GENE | Mm.209 | TITLE CD4 antigen | GENE Cd4 | peroxisomal membrane protein 1-like|Pxmp1| | NM_013488 | 641964 |
| IC00407 | UG75 Expression | GENE | Mm.15643 | TITLE CD44 antigen | GENE Cd44 | Ly-24|lymphocyte antigen 24|Pgp-1|phagocyte glycoprotein 1| | gi = 6491803 | 1097108 |
| IC00408 | UG75 Expression | GENE | Mm.1738 | TITLE CD48 antigen | GENE Cd48 | B-cell membrane protein 1|BCM-1|BLAST-1|Sgp-60|Ly-1|Ly-12|Ly-A|lymphocyte antigen 1|lymphocyte antigen 12|Lyt-1|T-lymphocyte antigen 1| | gi = 50134 | 622989 |
| IC00409 | UG75 Expression | GENE | Mm.779 | TITLE CD5 antigen | GENE Cd5 | | NM_007650 | 596064 |
| IC00410 | UG75 Expression | GENE | Mm.24130 | TITLE CD52 antigen | GENE Cd52 | B7|CLS1|MB7| | gi = 200225 | 1137587 |
| IC00411 | UG75 Expression | GENE | Mm.2692 | TITLE CD53 antigen | GENE Cd53 | Ox-44| | NM_007651 | 1295893 |
| IC00412 | UG75 Expression | GENE | Mm.8457 | TITLE CD59 antigen | GENE Cd59 | | NM_007652 | 1382392 |
| IC00413 | UG75 Expression | GENE | Mm.34133 | TITLE CD6 antigen | GENE Cd6 | | NM_009852 | 820137 |
| IC00414 | UG75 Expression | GENE | Mm.4426 | TITLE CD63 antigen | GENE Cd63 | ME491|melanoma 1 antigen| | NM_007653 | 400440 |
| IC00415 | UG75 Expression | GENE | Mm.15819 | TITLE CD68 antigen | GENE Cd68 | macrosialin| | NM_009853 | 679645 |
| IC00416 | UG75 Expression | GENE | Mm.4100 | TITLE CD7 antigen | GENE Cd7 | | NM_009854 | 1263105 |
| IC00417 | UG75 Expression | GENE | Mm.1355 | TITLE CD79a antigen | GENE Cd79a | Ig alpha|Igalla|Ly-54|Ly54|lymphocyte antigen 54|mb-1| | NM_007655 | 1349446 |
| IC00418 | UG75 Expression | GENE | Mm.806 | TITLE CD81 antigen | GENE Cd81 | CD81|Tapa-1|Tapa|target of antiproliferative antibody 1| | gi = 53037 | 351113 |
| IC00419 | UG75 Expression | GENE | Mm.4261 | TITLE CD82 antigen | GENE Cd82 | C33|KAI1| | NM_007656 | 2937052 |
| IC00420 | UG75 Expression | GENE | Mm.1452 | TITLE CD86 antigen | GENE Cd86 | B7|B7-2|B7|CD28 antien ligand|Cd282|CLS1|Ly-58|Ly58|lymphocyte antigen 58|MB7|TS/A-2|Ly-2|Ly-35|Ly-B|lymphocyte antigen 2|lymphocyte antigen 35|Lyt-2|T-lymphocyte antigen 2|lymphocyte antigen 3|Ly-3|Ly-C|lymphocyte antigen 3|T-lymphocyte antigen 3| | gi = 432478 | 2317900 |
| IC00421 | UG75 Expression | GENE | Mm.1858 | TITLE CD8 antigen, alpha chain | GENE Cd8a | | gi = 52967 | 1263157 |
| IC00422 | UG75 Expression | GENE | Mm.21764 | TITLE CD8 antigen, beta chain | GENE Cd8b | | NM_009858 | 1493746 |
| IC00423 | UG75 Expression | GENE | Mm.2956 | TITLE CD9 antigen | GENE Cd9 | | NM_007657 | 1885943 |
| IC00424 | UG75 Expression | GENE | Mm.28222 | TITLE CD97 antigen | GENE Cd97 | | NM_011925 | 420765 |
| IC00425 | UG75 Expression | GENE | Mm.2858 | TITLE cell division cycle 10 homolog (S. cerevisiae) | GENE Cdc10 | | gi = 2827746 | 1921439 |
| IC00426 | UG75 Expression | GENE | Mm.29800 | TITLE cell division cycle 25 homolog A (S. cerevisiae) | GENE Cdc25a | | NM_007658 | 313376 |
| IC00427 | UG75 Expression | GENE | Mm.4761 | TITLE cell division cycle 2 homolog A (S. pombe) | GENE Cdc2a | Cdc2| | NM_007659 | 2076258 |
| IC00428 | UG75 Expression | GENE | Mm.4414 | TITLE cell division cycle 2 homolog (S. pombe)-like 2 | GENE Cdc2l2 | | NM_007661 | 1480554 |
| IC00429 | UG75 Expression | GENE | Mm.1022 | TITLE cell division cycle 42 homolog (S. cerevisiae) | GENE Cdc42 | | NM_009861 | 2182207 |
| IC00430 | UG75 Expression | GENE | Mm.1248 | TITLE cell division cycle 45 homolog (S. cerevisiae)-like | GENE Cdc45l | | NM_009862 | 475506 |
| IC00431 | UG75 Expression | GENE | Mm.20912 | TITLE cell division cycle 6 homolog (S. cerevisiae) | GENE Cdc6 | CDC18(S. pombe)|CDC18L|cell division cycle 18 homolog (S. pombe)-like| | NM_011799 | 571931 |
| IC00432 | UG75 Expression | GENE | Mm.20842 | 1 | GENE Cdc7l1 | Cdc-7|muCdc7| | NM_009863 | 638732 |
| IC00433 | UG75 Expression | GENE | Mm.35605 | TITLE cadherin 1 | GENE Cdh1 | E-cadherin|Ecad|Um|UVO|uvomorulin| | NM_009864 | 2182160 |
| IC00434 | UG75 Expression | GENE | Mm.4525 | TITLE cadherin 11 | GENE Cdh11 | Cad11|OB-cadherin|osteoblast-cadherin| | NM_009866 | 600853 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00435 | UG75 Expression | GENE | Mm.4658 | TITLE cadherin 3 | GENE Cdh3 | Cad|P-cadherin|Pcad|placental cadherin| | gi = 50267 | 474757 |
| IC00436 | UG75 Expression | GENE | Mm.21767 | TITLE cadherin 5 | GENE Cdh5 | 7B4|VE-cadherin|VEC| | NM_009868 | 385761 |
| IC00437 | UG75 Expression | GENE | Mm.6839 | TITLE cyclin-dependent kinase 4 | GENE Cdk4 | CDC2-related kinase 3[Crk3]p34<PSK-J3>/cdk4| | NM_009870 | 481851 |
| IC00438 | UG75 Expression | GENE | Mm.4818 | TITLE cyclin-dependent kinase 5 | GENE Cdk5 | CDC2-related kinase 6[Crk6] | NM_007668 | 480815 |
| IC00439 | UG75 Expression | GENE | Mm.21056 | TITLE cyclin-dependent kinase 7 (homolog of Xenopus MO15 cdk-activating kinase) | GENE Cdk7 | CDC2-related-kinase-4 protein kinase]|cyclin dependent kinase 7 (homolog of Xenopus MO15 cdk-activating kinase)| | gi = 395047 | 479857 |
| IC00440 | UG75 Expression | GENE | Mm.34446 | TITLE cyclin-dependent kinase inhibitor 1A (P21) | GENE Cdkn1a | CAP20|Cdkn1|CIP1|cyclin dependent kinase inhibitor|mda6|P21|p21Cip1|p21WAF|SDI1|Waf1| | NM_007669 | 533961 |
| IC00441 | UG75 Expression | GENE | Mm.2480 | TITLE cyclin-dependent kinase inhibitor 1C (P57) | GENE Cdkn1c | Kip2|p57(kip2)|p57Kip2| | NM_009876 | 2101855 |
| IC00442 | UG75 Expression | GENE | Mm.1912 | TITLE cyclin-dependent kinase inhibitor 2C (p18, inhibits CDK4) | GENE Cdkn2c | INK4c|p18| | NM_007671 | 571858 |
| IC00443 | UG75 Expression | GENE | Mm.29020 | TITLE cyclin-dependent kinase inhibitor 2D (p19, inhibits CDK4) | GENE Cdkn2d | INK4d|p19| | NM_009878 | 426387 |
| IC00444 | UG75 Expression | GENE | Mm.1640 | TITLE cerebellar degeneration-related 2 | GENE Cdr2 | | NM_007672 | 2182163 |
| IC00445 | UG75 Expression | GENE | Mm.29002 | TITLE chromodomain protein, Y chromosome-like | GENE Cdyl | | NM_009881 | 876407 |
| IC00446 | UG75 Expression | GENE | Mm.34537 | TITLE CCAAT/enhancer binding protein (C/EBP), alpha | GENE Cebpa | C/EBP alpha|CBF-A|CCAAT/enhancer binding protein (C/EBP)|Cebp| | NM_007678 | 1450358 |
| IC00447 | UG75 Expression | GENE | Mm.28845 | TITLE CCAAT/enhancer binding protein alpha (C/EBP), related sequence 1 | GENE Cebpa-rs | Cbf| | NM_009882 | 1499028 |
| IC00448 | UG75 Expression | GENE | Mm.4639 | TITLE CCAAT/enhancer binding protein (C/EBP), delta | GENE Cebpd | | NM_007679 | 1401026 |
| IC00449 | UG75 Expression | GENE | Mm.3402 | TITLE CCAAT/enhancer binding protein (C/EBP), gamma | GENE Cebpg | C/EBP[g||g/EBP| | gi = 51788 | 1001742 |
| IC00450 | UG75 Expression | GENE | Mm.22680 | TITLE cadherin EGF LAG seven-pass G-type receptor | GENE Celsr1 | | NM_009886 | 2938799 |
| IC00451 | UG75 Expression | GENE | Mm.6579 | TITLE centromere autoantigen A | GENE Cenpa | centrosomin A| | NM_007681 | 3157202 |
| IC00452 | UG75 Expression | GENE | Mm.41454 | TITLE centromere autoantigen B | GENE Cenpb | | NM_007682 | 523440 |
| IC00453 | UG75 Expression | GENE | Mm.12481 | TITLE centrin 3 | GENE Cetn3 | MmCEN3| | NM_007684 | 1481913 |
| IC00454 | UG75 Expression | GENE | Mm.21310 | TITLE craniofacial development protein 1 | GENE Cfdp | Bcnt|Bucentaur|cp27| | NM_011801 | 902374 |
| IC00455 | UG75 Expression | GENE | Mm.4322 | TITLE complement component factor i | GENE Cfi | | NM_007686 | 722456 |
| IC00456 | UG75 Expression | GENE | Mm.4024 | TITLE cofilin 1, non-muscle | GENE Cfl1 | Cof|cofilin| | NM_007687 | 989980 |
| IC00457 | UG75 Expression | GENE | Mm.3823 | TITLE cofilin 2, muscle | GENE Cfl2 | | NM_007688 | 2939435 |
| IC00458 | UG75 Expression | GENE | Mm.30824 | TITLE cholesterol 25-hydroxylase | GENE Ch25h-p | m25OH| | NM_009890 | 750976 |
| IC00459 | UG75 Expression | GENE | Mm.8137 | TITLE chromodomain helicase DNA binding protein 1 | GENE Chd1 | | NM_007690 | 582689 |
| IC00460 | UG75 Expression | GENE | Mm.16753 | TITLE checkpoint kinase 1 homolog (S. pombe) | GENE Chek1 | | NM_007691 | 960989 |
| IC00461 | UG75 Expression | GENE | Mm.10124 | TITLE choline/ethanolamine kinase | GENE Chetk | CK/EK| | NM_007692 | 2064929 |
| IC00462 | UG75 Expression | GENE | Mm.4376 | TITLE chitinase 3-like 1 | GENE Chi3l3 | brp-39|Brp39|glycoprotein 39|Gp39| | gi = 1085065 | 268812 |
| IC00463 | UG75 Expression | GENE | Mm.4571 | TITLE chitinase 3-like 3 | GENE Chi3l3 | Ym1| | NM_009892 | 973032 |
| IC00464 | UG75 Expression | GENE | Mm.5262 | TITLE choline kinase | GENE Chk | | NM_013490 | 2123748 |
| IC00465 | UG75 Expression | GENE | Mm.3996 | TITLE conserved helix-loop-helix ubiquitous kinase | GENE Chuk | CHuk1|IKK-1|IKK-alpha|IKK[a]1IKK1| | NM_007700 | 2536709 |
| IC00466 | UG75 Expression | GENE | Mm.17898 | TITLE cold inducible RNA-binding protein | GENE Cirbp | Cirp| | NM_007705 | 1923147 |
| IC00467 | UG75 Expression | GENE | Mm.4592 | TITLE cytokine inducible SH2-containing protein | GENE Cish | Cis|F17| | NM_009895 | 335058 |
| IC00468 | UG75 Expression | GENE | Mm.4132 | TITLE cytokine inducible SH2-containing protein 2 | GENE Cish2 | JAB|SOCS-1| | NM_007706 | 2225582 |
| IC00469 | UG75 Expression | GENE | Mm.3468 | TITLE cytokine inducible SH2-containing protein 3 | GENE Cish3 | EF-10|SOCS-2| | NM_007707 | 466123 |
| IC00470 | UG75 Expression | GENE | Mm.130 | TITLE cytokine inducible SH2-containing protein 7 | GENE Cish7 | SOCS-3|SSI-1| | NM_009896 | 2939707 |
| IC00471 | UG75 Expression | GENE | Mm.8321 | TITLE citron | GENE Cit | CRIK|CRIK-SK| | gi = 3599502 | 532799 |
| IC00472 | UG75 Expression | GENE | Mm.2390 | TITLE Cbp/p300-interacting transactivator with Glu/Asp-rich carboxy-terminal domain 1 | GENE Cited1 | melanocyte specific gene|Msg1| | NM_007709 | 1224295 |
| IC00473 | UG75 Expression | GENE | Mm.16831 | TITLE creatine kinase, brain | GENE Ckb | CCK-B/gastrin receptor| | gi = 19727 | 736251 |
| IC00474 | UG75 Expression | GENE | Mm.2375 | TITLE creatine kinase, muscle | GENE Ckmm | | NM_007710 | 467093 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00475 | UG75 Expression | GENE | Mm.30465 | TITLE cysteine know superfamily 1, BMP antagonist 1 | GENE Cktsf1b1 | down-regulated in v-mos-transformed cells\|Drm\|gremlin\| | NM_011824 | 596225 |
| IC00476 | UG75 Expression | GENE | Mm.20897 | TITLE chloride channel calcium activated 1 | GENE Clca1 | | NM_009899 | 2648257 |
| IC00477 | UG75 Expression | GENE | Mm.40955 | TITLE chloride channel 2 | GENE Clcn2 | Clc2\| | NM_009900 | 775900 |
| IC00478 | UG75 Expression | GENE | Mm.28842 | TITLE chloride channel 3 | GENE Clcn3 | Clc3\| | NM_007711 | 2082194 |
| IC00479 | UG75 Expression | GENE | Mm.7339 | TITLE claudin 4 | GENE Cldn4 | Clostridium perfringens exterotoxin receptor 1\|Clostridium perfringens exterotoxin receptor\|Cpetr\|Cpetr1\| | NM_009903 | 876728 |
| IC00480 | UG75 Expression | GENE | Mm.22768 | TITLE claudin 5 | GENE Cldn5 | MBEC1\|TMVCF\| | NM_013805 | 765658 |
| IC00481 | UG75 Expression | GENE | Mm.47384 | TITLE C-type (calcium dependent, carbohydrate recognition domain) lectin, superfamily member 6 | GENE Clecsf6 | DCIR\|dendritic cell immunoreceptor\| | NM_011999 | 820216 |
| IC00482 | UG75 Expression | GENE | Mm.1761 | TITLE CDC-like kinase | GENE Clk | | NM_009905 | 2088087 |
| IC00483 | UG75 Expression | GENE | Mm.18268 | TITLE CDC-like kinase 2 | GENE Clk2 | | NM_007712 | 1328634 |
| IC00484 | UG75 Expression | GENE | Mm.18476 | TITLE CDC-like kinase 3 | GENE Clk3 | | gi = 2645853 | 1280829 |
| IC00485 | UG75 Expression | GENE | Mm.9488 | TITLE CDC-like kianse 4 | GENE Clk4 | | NM_007714 | 2182654 |
| IC00486 | UG75 Expression | GENE | Mm.20837 | TITLE ceroid-lipofuscinosis, neuronal 2 | GENE Cln2 | | NM_009906 | 2225325 |
| IC00487 | UG75 Expression | GENE | Mm.135 | TITLE ceroid-lipofuscinosis, neuronal 3, juvenile (Batten, Spielmeyer-Vogt disease) | GENE Cln3 | | NM_009907 | 3155702 |
| IC00488 | UG75 Expression | GENE | Mm.21578 | TITLE ceroid-lipofuscinoses, neuronal 8 | GENE Cln8 | | NM_012000 | 1480365 |
| IC00489 | UG75 Expression | GENE | Mm.3552 | TITLE circadian locomoter output cycles kaput | GENE Clock | | NM_007715 | 554823 |
| IC00490 | UG75 Expression | GENE | Mm.30088 | TITLE caseinolytic protease X (E. coli) | GENE Clpx- | pending | NM_011802 | 693510 |
| IC00491 | UG75 Expression | GENE | Mm.18700 | TITLE clusterin | GENE Clu | Cli\|complement lysis inhibitor\|Sgp-2\|SP-40, 40 sulfated glycoprotein 2\|Sugp-2\|sulfated glycoprotein 2\|testosterone repressed prostate message\| | NM_013492 | 617298 |
| IC00492 | UG75 Expression | GENE | Mm.8396 | TITLE cytidine monophospho-N-acetylneuraminic acid hydroxylase | GENE Cmah | CMP-NeuAc hydroxylase\| | NM_007717 | 679492 |
| IC00493 | UG75 Expression | GENE | Mm.3820 | TITLE cytidine monophospho-N-acetylneuraminic acid synthetase | GENE Cmas | CMP-NeuSAc\|D6Bwg0250e\|DNA segment, Chr 6, Brigham & Women's Genetics 0250 expressed CXCR4\|fusin\|LESTR\|leukocyte-expressed seven-transmembrane-domain\|PB-CKR\|PBSF/SDF-1\| | gi = 3413319 | 2647420 |
| IC00494 | UG75 Expression | GENE | Mm.1401 | TITLE chemokine (C-X-C) receptor 4 | GENE Cmkar4 | | NM_009911 | 636505 |
| IC00495 | UG75 Expression | GENE | Mm.6272 | TITLE chemokine (C-C) receptor 2 | GENE Cmkbr2 | CCR2\|MIP-1 alpha\|mJE-R\| | NM_009915 | 875523 |
| IC00496 | UG75 Expression | GENE | Mm.14302 | TITLE chemokine (C-C) receptor 5 | GENE Cmkbr5 | AM4-7\|CCR5 | NM_009917 | 947959 |
| IC00497 | UG75 Expression | GENE | Mm.2932 | TITLE chemokine (C-C) receptor 7 | GENE Cmkbr7 | EB11\|Ebi1h\|Epstein-Barr virus induced gene 1 homolog\| | NM_007719 | 637327 |
| IC00498 | UG75 Expression | GENE | Mm.8000 | TITLE chemokine (C-C) receptor 8 | GENE Cmkbr8 | CCR8\|mCCR8\| | NM_007720 | 1149855 |
| IC00499 | UG75 Expression | GENE | Mm.42158 | TITLE chemokine (C-C) receptor 9 | GENE Cmkbr9 | D6\| | NM_007721 | 850473 |
| IC00500 | UG75 Expression | GENE | Mm.6522 | TITLE chemokine orphan receptor 1 | GENE Cmkor1 | Rdc1\| | NM_007722 | 1958612 |
| IC00501 | UG75 Expression | GENE | Mm.7335 | TITLE cellular nucleic acid binding protein | GENE Cnbp | | NM_013493 | 2225469 |
| IC00502 | UG75 Expression | GENE | Mm.3261 | TITLE cornichon homolog (Drosophila) | GENE Cnih | | gi = 3114215 | 1498832 |
| IC00503 | UG75 Expression | GENE | Mm.3834 | TITLE cathelin-like protein | GENE Cnlp | cathelin related antimicrobial peptide\|Cramp\|MCLP\| | NM_009921 | 478131 |
| IC00504 | UG75 Expression | GENE | Mm.21776 | TITLE calponin 2 | GENE Cnn2 | h2-calponin\| | NM_007725 | 2749216 |
| IC00505 | UG75 Expression | GENE | Mm.15711 | TITLE cyclic nucleotide phosphodiesterase 1 | GENE Cnp1 | Cnp\|Cnp-1\| | NM_009923 | 2247570 |
| IC00506 | UG75 Expression | GENE | Mm.1378 | TITLE cannabinoid receptor 2 (macrophage) | GENE Cnr2 | CB2-R\| | NM_009924 | 1163004 |
| IC00507 | UG75 Expression | GENE | Mm.22066 | TITLE ciliary neurotropic factor | GENE Cntf | | gi = 453372 | 639933 |
| IC00508 | UG75 Expression | GENE | Mm.20230 | TITLE procollagen, type XI, alpha 2 | GENE Col11a2 | | NM_009926 | 425385 |
| IC00509 | UG75 Expression | GENE | Mm.41332 | TITLE procollagen, type XIV, alpha 1 | GENE Col14a1 | | gi = 5042293 | 2192739 |
| IC00510 | UG75 Expression | GENE | Mm.4352 | TITLE procollagen, type XV | GENE Col15a1 | | gi = 2558824 | 479752 |
| IC00511 | UG75 Expression | GENE | Mm.2423 | TITLE procollagen, type II, alpha 1 | GENE Col2a1 | Col2a\|Col2a-1\|disproportionate micromelia\|Dmm\|procollagen, type II\| | gi = 854650 | 555603 |
| IC00512 | UG75 Expression | GENE | Mm.4271 | TITLE procollagen, type III, alpha 1 | GENE Col3a1 | | gi = 575321 | 735073 |
| IC00513 | UG75 Expression | GENE | Mm.738 | TITLE procollagen, type IV, alpha 1 | GENE Col4a1 | Col4a-1\|procollagen type IV, alpha 1\| | gi = 556296 | 832251 |
| IC00514 | UG75 Expression | GENE | Mm.6954 | TITLE procollagen, type IV, alpha 2 | GENE Col4a2 | Col4a-2\|procollagen type IV, alpha 2\| | gi = 556298 | 1515807 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00515 | UG75 Expression | GENE | Mm.2509 | TITLE procollagen, type VI, alpha 1 | Col6a1 | Col6a-1\|procollagen type VI, alpha 1\| | NM_009933 | 2076587 |
| IC00516 | UG75 Expression | GENE | Mm.1949 | TITLE procollagen, type VI, alpha 2 | Col6a2 | Col6a-2\|procollagen type VI, alpha 2\| | gi = 49808 | 586391 |
| IC00517 | UG75 Expression | GENE | Mm.22621 | TITLE procollagen, type I, alpha 1 | Col1a1 | Col1a-1\|Cola-1\|Moloney leukemia virus 13\|Mov-13\| | gi = 470673 | 2647439 |
| IC00518 | UG75 Expression | GENE | Mm.4482 | TITLE procollagen, type I, alpha 2 | Cola2 | Col1a-2\|Cola-2\|oinjlosteogenesis imperfecta\|procollagen type I, alpha 2\| | NM_007743 | 614993 |
| IC00519 | UG75 Expression | GENE | Mm.89475 | TITLE collagen-like tail subunit (single strand of homotrimer) of asymmetric acetylcholinesterase | Colq | | gi = 2460054 | 1378262 |
| IC00520 | UG75 Expression | GENE | Mm.35853 | TITLE catechol-O-methyltransferase | Comt | | NM_007743 | 1499700 |
| IC00521 | UG75 Expression | GENE | Mm.30041 | TITLE coatomer protein complex subunit alpha | Copa | | gi = 3602405 | 1481257 |
| IC00522 | UG75 Expression | GENE | Mm.3596 | TITLE COP9 (constitutive photomorphogenic, subunit 2 (Arabidopsis) | Cops2 | | NM_009939 | 1891417 |
| IC00523 | UG75 Expression | GENE | Mm.40 | TITLE COP9 (constitutive photomorphogenic), subunit 3 (Arabidopsis) | Cops3 | COP9 complex S3\|Sgn3 | NM_011991 | 2646841 |
| IC00524 | UG75 Expression | GENE | Mm.957 | TITLE COP9 (constitutive photomorphogenic), subunit 4 (Arabidopsis) | Cops4 | COP9 complex S4 | NM_012001 | 2581930 |
| IC00525 | UG75 Expression | GENE | Mm.2472 | TITLE COP9 (constitutive photomorphogenic), subunit 5 (Arabidopsis) | Cops5 | COP9 complex S5\|Jab1\|JUN activation binding protein\|Sgn5\| | NM_013715 | 1887904 |
| IC00526 | UG75 Expression | GENE | Mm.3981 | TITLE COP9 (constitutive photomorphogenic, subunit 6 (Arabidopsis) | Cops6 | COP9 complex S6\|Sgn3\|VIP/MOV34\| | gi = 3309171 | 872929 |
| IC00527 | UG75 Expression | GENE | Mm.1444 | TITLE COP9 (constitutive photomorphogenic), subunit 7a (Arabidopsis) | Cops7a | COP9 complex S7a\| | NM_012003 | 680467 |
| IC00528 | UG75 Expression | GENE | Mm.12973 | TITLE COP9 (constitutive photomorphogenic), subunit 7b (Arabidopsis) | Cops7b | COP9 complex S7b\| | NM_012004 | 2192703 |
| IC00529 | UG75 Expression | GENE | Mm.27317 | TITLE coronin, actin binding protein 1A | Coro1a | Clabp\|coronin 1\|coronin-like actin binding protein\|p57\|TACO | NM_009898 | 2698685 |
| IC00530 | UG75 Expression | GENE | Mm.28652 | TITLE coronin, actin binding protein 1B | Coro1b | coronin 2\| | NM_011778 | 2645581 |
| IC00531 | UG75 Expression | GENE | Mm.2136 | TITLE cytochrome c oxidase, subunit IV | Cox4 | | NM_009941 | 1053681 |
| IC00532 | UG75 Expression | GENE | Mm.360 | TITLE cytochrome c oxidase, subunit Va | Cox5a | | NM_007747 | 1970061 |
| IC00533 | UG75 Expression | GENE | Mm.167698 | TITLE cytochrome c oxidase, subunit Vb | Cox5b | | NM_009942 | 426910 |
| IC00534 | UG75 Expression | GENE | Mm.43415 | TITLE cytochrome c oxidase, subunit VI a, polypeptide 1 | Cox6a1 | | NM_007748 | 2136787 |
| IC00535 | UG75 Expression | GENE | Mm.548 | TITLE cytochrome c oxidase, subunit VIc | Cox6c | | gi = 2305662 | 934103 |
| IC00536 | UG75 Expression | GENE | Mm.2151 | TITLE cytochrome c oxidase, subunit VIIa3 | Cox7a3 | | NM_009945 | 1248366 |
| IC00537 | UG75 Expression | GENE | Mm.43786 | TITLE cytochrome c oxidase, subunit VIIc | Cox7c | COXVIIc\| | gi ≤ 50524 | 1025650 |
| IC00538 | UG75 Expression | GENE | Mm.14022 | TITLE cytochrome c oxidase, subunit VIIIa | Cox8a | COX VIII-L\|COX8L\| | NM_007750 | 481408 |
| IC00539 | UG75 Expression | GENE | Mm.13787 | TITLE ceruloplasmin | Cp | | NM_007752 | 1885765 |
| IC00540 | UG75 Expression | GENE | Mm.43603 | TITLE carboxypeptidase E | Cpe | Acp-1\| | NM_013494 | 3155556 |
| IC00541 | UG75 Expression | GENE | Mm.22062 | TITLE carboxypeptidase E | Cpeb | carboxypeptidase H\|Cph-1\|Cph1\|fat\|mCPEB\| | NM_007755 | 793977 |
| IC00542 | UG75 Expression | GENE | Mm.35820 | TITLE coproporphyrinogen oxidase protein | Cpo | clone 560\| | NM_007757 | 406647 |
| IC00543 | UG75 Expression | GENE | Mm.18522 | TITLE carnitine palmitoyltransferase 1, liver | Cpt1a | carnitine palmitoyltransferase 1\|Cpt1\|CPTI | gi = 2388721 | 747226 |
| IC00544 | UG75 Expression | GENE | Mm.34881 | TITLE carnitine palmitoyltransferase 1, muscle | Cpt1b | carnitine palmitoyltransferase 1\|Cpt1\|CPTI | NM_009948 | 846098 |
| IC00545 | UG75 Expression | GENE | Mm.1226 | TITLE complement receptor 2 | Cr2 | CD21\|complement receptor 1\|Cr-1\|Cr-2\|Cr1\| | gi = 192687 | 3167720 |
| IC00546 | UG75 Expression | GENE | Mm.18072 | TITLE calcitonin gene-related peptide receptor component protein | Crcp | | NM_007761 | 1888269 |
| IC00547 | UG75 Expression | GENE | Mm.1376 | TITLE cAMP responsive element binding protein 1 | Creb1 | Creb\|Creb-1\|cyclic AMP responsive element binding protein\| | gi = 192713 | 1447005 |
| IC00548 | UG75 Expression | GENE | Mm.459 | TITLE cellular repressor of E1A-stimulated genes | Creg | | NM_0111804 | 1923186 |
| IC00549 | UG75 Expression | GENE | Mm.5244 | TITLE cAMP responsive element modulator | Crem | | NM_013498 | 387753 |
| IC00550 | UG75 Expression | GENE | Mm.1892 | TITLE corticotropin releasing hormone receptor | Crhr | | NM_007762 | 643358 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00551 | UG75 Expression | GENE | Mm.22049 | TITLE cystein rich intestinal protein | GENE Crip | | NM_007763 | 473801 |
| IC00552 | UG75 Expression | GENE | Mm.22695 | TITLE collapsin response mediator protein 1 | GENE Crmp1 | Dpysl1|DRP-1|Ulip3| | NM_007765 | 1225897 |
| IC00553 | UG75 Expression | GENE | Mm.42032 | TITLE cofactor required for Sp1 transcriptional activation subunit 2 (150 kDa) | GENE Crsp2 | Orf1| | NM_012005 | 2631513 |
| IC00554 | UG75 Expression | GENE | Mm.26237 | TITLE cryptochrome 1 (photolyase-like) | GENE Cry1 | Phll1|photolyase-like 1| | NM_007771 | 1265113 |
| IC00555 | UG75 Expression | GENE | Mm.1228 | TITLE crystallin, alpha 1 | GENE Crya1 | Acry-1|alpha-A-crystallin|Crya-1|Cryaa|DAcry-1| | gi = 192760 | 481224 |
| IC00556 | UG75 Expression | GENE | Mm.178 | TITLE crystallin, alpha 2 | GENE Crya2 | Crya-2| | NM_009964 | 1227204 |
| IC00557 | UG75 Expression | GENE | Mm.4808 | TITLE crystallin, alpha binding protein 1 | GENE Cryabp1 | | NM_007772 | 1096946 |
| IC00558 | UG75 Expression | GENE | Mm.22830 | TITLE crystallin, beta A1 | GENE Cryba1 | beta crystallin|Cryb| | gi = 5725421 | 582437 |
| IC00559 | UG75 Expression | GENE | Mm.15973 | TITLE crystallin, gamma E | GENE Cryge | Cryg-6|Eloleye lens obsolescence|gamma crystallin 6| | NM_0077 | 480274 |
| IC00560 | UG75 Expression | GENE | Mm.3534 | TITLE crystallin, zeta | GENE Cryz | quinone reductase| | gi = 546493 | 2537346 |
| IC00561 | UG75 Expression | GENE | Mm.795 | TITLE colony stimulating factor 1 (macrophage) | GENE Csf1 | colony stimulating factor, macrophage|CSF-1|Csfm|M-CSF|lop|osteopetrosis| c-fms oncogene|CD115|CSF-1R|Csfmr|Fim-2|Fms|Friend | NM_007778 | 620960 |
| IC00562 | UG75 Expression | GENE | Mm.22574 | TITLE colony stimulating factor 1 receptor | GENE Csf1r | MuLV integration site 2|M-CSFR| | NM_007779 | 401574 |
| IC00563 | UG75 Expression | GENE | Mm.4922 | TITLE colony stimulating factor 2 (granulocyte-macrophage) | GENE Csf2 | colony stimulating factor, granulocyte macrophae|Csfgm|Gm-CSf| | gi = 51100 | 1428783 |
| IC00564 | UG75 Expression | GENE | Mm.14595 | TITLE colony stimulating factor 2 receptor, beta 1, low-affinity (granulocyte-macrophage) | GENE Csf2rb1 | AIC2B|CDw131|colony stimulating factor, granulocyte macrophage receptor, beta chain|common beta chain|Csfgmrb|Il3r|Il3rb1|Il5rb|interleuken 3 receptor beta chain|interleuken 3 receptor, beta chain 1|interleukin 5 receptor beta| | NM_007780 | 637511 |
| IC00565 | UG75 Expression | GENE | Mm.1940 | TITLE colony stimulating factor 2 receptor, beta 2, low-affinity (granulocyte-macrophage) | GENE Csf2rb2 | AIC2A|colony stimulating factor, granulocyte macrophage receptor, beta chain|Csfgmrb|Il3rb2|interleukin 3 receptor beta chain|interleukin 3 receptor, beta chain 2| | NM_007781 | 550903 |
| IC00566 | UG75 Expression | GENE | Mm.21974 | TITLE c-src tyrosine kinase | GENE Csk | | NM_007783 | 2698813 |
| IC00567 | UG75 Expression | GENE | Mm.4105 | TITLE casein beta | GENE Csnb | | NM_009972 | 2647077 |
| IC00568 | UG75 Expression | GENE | Mm.30199 | TITLE casein kinase 1, epsilon | GENE Csnk1e | CKI, epsilon| | NM_013767 | 978065 |
| IC00569 | UG75 Expression | GENE | Mm.23692 | TITLE casein kinase II, alpha 1, related sequence 4 | GENE Csnk2a-1-rs4 | | NM_007788 | 1971824 |
| IC00570 | UG75 Expression | GENE | Mm.28881 | TITLE casein kinase II, alpha 2, polypeptide | GENE Csnk2a2 | | NM_009974 | 634434 |
| IC00571 | UG75 Expression | GENE | Mm.26789 | TITLE casein kinase II, beta subunit | GENE Csnk2b | | NM_009975 | 571216 |
| IC00572 | UG75 Expression | GENE | Mm.4575 | TITLE chondroitin sulfate proteoglycan 2 Bamacan|HCAP|Max dimerization protein member-interacting | GENE Cspg2 | hdf|heart defect|NG2|PG-M(V0)|PG-M(V1)|versican| | gi = 862459 | 1434374 |
| IC00573 | UG75 Expression | GENE | Mm.14910 | TITLE chondroitin sulfate proteoglycan 6 | GENE Cspg6 | protein 1|Mmip1|SmcD| | NM_007790 | 574398 |
| IC00574 | UG75 Expression | GENE | Mm.10919 | TITLE cysteine rich protein | GENE Csrp | CRP1|CSRP1|cysteine and glycine-rich protein| | NM_007791 | 316436 |
| IC00575 | UG75 Expression | GENE | Mm.2020 | TITLE cystein-rich protein 2 | GENE Csrp2 | Crp2|cysteine and glycine-rich protein 2|SmLim| | NM_007792 | 1923078 |
| IC00576 | UG75 Expression | GENE | Mm.4263 | TITLE cystatin 3 | GENE Cst3 | cystatin C| | NM_009976 | 748121 |
| IC00577 | UG75 Expression | GENE | Mm.12965 | TITLE cystatin 7 | GENE Cst7 | CMAP|cystatin-like metastasis-associated protein|Leukocystatin| | NM_009977 | 557989 |
| IC00578 | UG75 Expression | GENE | Mm.6095 | TITLE cystatin B | GENE Cstb | stefin B (cystatin B)|Stfb| | NM_007793 | 1382899 |
| IC00579 | UG75 Expression | GENE | Mm.6626 | TITLE cystatin F | GENE Cstf3 | | gi = 2282794 | 944187 |
| IC00580 | UG75 Expression | GENE | Mm.7286 | TITLE cleavage stimulation factor, 3' pre-RNA, subunit 3 | GENE Ctbp1 | | NM_013502 | 2076709 |
| IC00581 | UG75 Expression | GENE | Mm.10172 | TITLE C-terminal binding protein 1 | GENE Ctbp2 | | NM_009980 | 467669 |
| IC00582 | UG75 Expression | GENE | Mm.493 | TITLE C-terminal binding protein 2 | GENE Ctcf | | NM_007794 | 2225615 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00583 | UG75 Expression | GENE | Mm.1978 | TITLE acyl-CoA thioesterase 1, cytosolic | GENE Cte1-per ACH2|CTE-1|D12U|cla1| | | NM_012006 | 2650643 |
| IC00584 | UG75 Expression | GENE | Mm.1616 | TITLE cardiotrophin 1 | GENE Ctf1 | CT-1| | NM_007795 | 315363 |
| IC00585 | UG75 Expression | GENE | Mm.30144 | TITLE cytotoxic T lymphocyte-associated protein 2 alpha | gene Ctla2a | Ctla-2a| | NM_007796 | 1277814 |
| IC00586 | UG75 Expression | GENE | Mm.22715 | TITLE cytotoxic T lymphocyte-associated protein 2 beta | gene Ctla2b | Ctla-2b| | gi = 50590 | 604394 |
| IC00587 | UG75 Expression | GENE | Mm.22753 | TITLE cathepsin B | GENE Ctsb | | NM_007798 | 1179427 |
| IC00588 | UG75 Expression | GENE | Mm.684 | TITLE cathepsin C | GENE Ctsc | | NM_009982 | 1383584 |
| IC00589 | UG75 Expression | GENE | Mm.2147 | TITLE cathepsin D | GENE Ctsd | | NM_009983 | 606272 |
| IC00590 | UG75 Expression | GENE | Mm.33671 | TITLE cathepsin E | GENE Ctse | | NM_007799 | 1247224 |
| IC00591 | UG75 Expression | GENE | Mm.4858 | TITLE cathepsin G | GENE Ctsg | | NM_007800 | 1279678 |
| IC00592 | UG75 Expression | GENE | Mm.2277 | TITLE cathepsin H | GENE Ctsh | | NM_007801 | 595917 |
| IC00593 | UG75 Expression | GENE | Mm.3109 | TITLE cathepsin K | GENE Ctsk | | NM_007802 | 348668 |
| IC00594 | UG75 Expression | GENE | Mm.930 | TITLE cathepsin L | GENE Ctsl | | NM_009984 | 533814 |
| IC00595 | UG75 Expression | GENE | Mm.3619 | TITLE cathepsin S | GENE Ctss | | gi = 2746722 | 1450749 |
| IC00596 | UG75 Expression | GENE | Mm.34367 | TITLE cathepsin W | GENE Ctsw | lymphopain|cortactin|Ems1|ems1 sequence|mammary tumor and squamous cell carcinoma associated (p80/85 src substrate)| | NM_009985 | 1265309 |
| IC00597 | UG75 Expression | GENE | Mm.22024 | TITLE cortactin | GENE Cttn | | NM_007803 | 661099 |
| IC00598 | UG75 Expression | GENE | Mm.89583 | TITLE cullin 1 | GENE Cul1 | | NM_012042 | 960946 |
| IC00599 | UG75 Expression | GENE | Mm.448 | TITLE cytochrome b-245, alpha polypeptide | GENE Cyba | b558| | gi = 192913 | 1052415 |
| IC00600 | UG75 Expression | GENE | Mm.35389 | TITLE cytochrome c, *somatic* | GENE Cycs | | NM_007808 | 3026027 |
| IC00601 | UG75 Expression | GENE | Mm.4443 | TITLE cytochrome P450, 1b1 inducible | GENE Cyp1b1 | | NM_009994 | 1481299 |
| IC00602 | UG75 Expression | GENE | Mm.14781 | TITLE cytochrome P450, 2a4 | GENE Cyp2a4 | Cyp15a1|cytochrome P450, 15a1| | gi = 201970 | 577190 |
| IC00603 | UG75 Expression | GENE | Mm.876 | TITLE cytochrome P450, 2b9, phenobarbital inducible, type a | GENE Cyp2b9 | 16/alphaoh-a|Cyp2b|cytochrome P450, 2b, phenobarbitol inducible| | NM_010000 | 1890135 |
| IC00604 | UG75 Expression | GENE | Mm.29973 | TITLE cytochrome P450, 2c40 | GENE P450, 2c40 | GENE Cyp2c40 | NM_010004 | 1885770 |
| IC00605 | UG75 Expression | GENE | Mm.29064 | TITLE cytochrome P450, 2d9 | GENE Cyp2d9 | cyp2d|cytochrome P450, 2d|P450-2D| | NM_010006 | 335442 |
| IC00606 | UG75 Expression | GENE | Mm.21758 | TITLE cytochrome P450, 2e1, ethanol inducible | GENE Cyp2e1 | Cyp2e|cytochrome P450, 2e, ethanol inducible| | gi = 200194 | 1921235 |
| IC00607 | UG75 Expression | GENE | Mm.4515 | TITLE cytochrome P450, 2f2 | GENE Cyp2f2 | Cyp2f|cytochrome P450, 2f| | NM_007817 | 1889215 |
| IC00608 | UG75 Expression | GENE | Mm.21193 | TITLE cytochrome P450, steroid inducible 3a11 | GENE Cyp3a11 | Cyp3a|cytochrome P450, 3, steroid inducible|IIIAm1|Pcn| | NM_007818 | 1431151 |
| IC00609 | UG75 Expression | GENE | Mm.10742 | TITLE cytochrome P450, 4a10 | GENE Cyp4a10 | Cyp4a|cytochrome P450, 4a|D4Rp1|DNA segment, Chr 4, Roswell Park 1|Roswell Park 1, DNA polymorphism|RP1| | gi = 3738262 | 1886987 |
| IC00610 | UG75 Expression | GENE | Mm.1840 | TITLE cytochrome P450, subfamily IV B, polypeptide 1 | GENE Cyp4b1 | | NM_007823 | 1970575 |
| IC00611 | UG75 Expression | GENE | Mm.34248 | TITLE disabled homolog 2 (Drosophila) | GENE Dab2 | | gi = 1176369 | 1383227 |
| IC00612 | UG75 Expression | GENE | Mm.2547 | TITLE defender against cell death 1 | GENE Dad1 | | NM_010015 | 1922255 |
| IC00613 | UG75 Expression | GENE | Mm.20236 | TITLE decay accelaring factor 1 | GENE Daf1 | defender against-cell death 1|CD55|complement-glycosylphosphatidylinositol|Daf-GPI|GPI-DAF|D9Wsu13e|DNA segment, Chr9, Wayne State University 13, expressed|dystrophin associated glycoprotein 1 | NM_010016 | 1248321 |
| IC00614 | UG75 Expression | GENE | Mm.7524 | TITLE dystroglycan 1 | GENE Dag1 | | gi = 1155350 | 1182029 |
| IC00615 | UG75 Expression | GENE | Mm.20115 | TITLE D-amino acid oxidase | GENE Dao1 | Dao-1| | NM_010018 | 848642 |
| IC00616 | UG75 Expression | GENE | Mm.41755 | TITLE death-associated kinase 2 | GENE Dapk2 | | gi = 6521216 | 1095097 |
| IC00617 | UG75 Expression | GENE | Mm.10294 | TITLE death-associated kinase 3 | GENE Dapk3 | ZIP kinase| | NM_007828 | 1294095 |
| IC00618 | UG75 Expression | GENE | Mm.33987 | TITLE dual adaptor for phosphotyrosine and 3-phosphoinositides 1 | GENE Dapp1 | | NM_007828 | 1294095 |
| IC00619 | UG75 Expression | GENE | Mm.28118 | TITLE Fas death domain-associated protein | GENE Daxx | | NM_007829 | 3154888 |
| IC00620 | UG75 Expression | GENE | Mm.2785 | TITLE diazepam binding inhibitor | GENE Dbi | Acbp|acyl-CoA-binding protein| | NM_007830 | 532989 |
| IC00621 | UG75 Expression | GENE | Mm.3636 | TITLE dihydrolipoamide branched chain transacylase E2 | GENE Dbt | BCKAD E2| | NM_010022 | 1921113 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00622 | UG75 Expression | GENE | Mm.20950 | TITLE DEAD (aspartate-glutamate-alanine-aspartate) box polypeptide, Y chromosome | GENE Dby | | gi = 3790185 | 573643 |
| IC00623 | UG75 Expression | GENE | Mm.35833 | TITLE dodecenoyl-coenzyme A delta isomerase (3,2 trans-enoyl-Coenzyme A isomerase) | GENE Dci | | NM_010023 | 2921806 |
| IC00624 | UG75 Expression | GENE | Mm.3446 | TITLE deoxycytidine kinase | GENE Dck | | NM_007832 | 3156898 |
| IC00625 | UG75 Expression | GENE | Mm.1987 | TITLE decorin | GENE Dcn | | NM_007833 | 329684 |
| IC00626 | UG75 Expression | GENE | Mm.7472 | TITLE Down syndrome critical region GENE a | GENE Dcra | | NM_007834 | 2088150 |
| IC00627 | UG75 Expression | GENE | Mm.6919 | TITLE dynactin 1 | GENE Dctn1 | Asap1|PAP|phosphatidylinositol 4,5-biphosphate (PIP>2<)-dependent Art GTPase-activating protein 1, 130 kDa|s19| | NM_007835 | 1480914 |
| IC00628 | UG75 Expression | GENE | Mm.5237 | TITLE development and differentiation enhancing | GENE Ddef1 | | gi = 4063613 | 1450538 |
| IC00629 | UG75 Expression | GENE | Mm.5341 | TITLE DNA-damage inducible transcript 1 | GENE Ddit1 | GADD45|Gadd45|a|Gadd45a| | nm_007836 | 556400 |
| IC00630 | UG75 Expression | GENE | Mm.7549 | TITLE DNA-damage inducible transcript 3 | GENE Ddit3 | C/EBP homoologous protein 10|chop|CHOP-10|gadd153| | NM_007837 | 1078300 |
| IC00631 | UG75 Expression | GENE | Mm.7236 | TITLE dolichyol-di-phosphooligosaccharide-protein glycotransferase | GENE Ddost | | NM_007838 | 576598 |
| IC00632 | UG75 Expression | GENE | Mm.5731 | TITLE D-dopachrome tautomerase | GENE Ddt | | NM_010027 | 670968 |
| IC00633 | UG75 Expression | GENE | Mm.993 | TITLE DEAD/H (Asp-Glu-Ala-Asp/His) box polypeptide 15 | GENE Ddx15 | mDEAH9| | NM_007839 | 1921242 |
| IC00634 | UG75 Expression | GENE | Mm.19101 | TITLE DEAD (aspartate-glutamate-alanine-aspartate) box polypeptide 5 | GENE Ddx5 | helicase, RNA, nuclear 1|Hlr1|p68| | NM_007840 | 2225522 |
| IC00635 | UG75 Expression | GENE | Mm.20000 | TITLE DEAD (aspartate-glutamate-alanine-aspartate) box polypeptide 9 | GENE Ddx9 | | gi = 2961455 | 478642 |
| IC00636 | UG75 Expression | GENE | Mm.35760 | TITLE 2-4-dienoyl-Coenzyme A reductase 2, peroxisomal | GENE Decr2 | | NM_011933 | 1888282 |
| IC00637 | UG75 Expression | GENE | Mm.5341 | TITLE defensin beta 1 | GENE Defb1 | | NM_007843 | 2285954 |
| IC00638 | UG75 Expression | GENE | Mm.29648 | TITLE degenerative spermatocyte homolog (Drosophila) | GENE Degs | Mdes| | NM_007853 | 944114 |
| IC00639 | UG75 Expression | GENE | Mm.6712 | TITLE desmin | GENE Des | | gi = 348971 | 1153462 |
| IC00640 | UG75 Expression | GENE | Mm.41433 | TITLE DNA fragmentation factor, alpha subunit | GENE Dffa | Dff45|CAD|ICAD-L|ICAD-S| | NM_010044 | 615712 |
| IC00641 | UG75 Expression | GENE | Mm.6393 | TITLE Duffy blood group | GENE Dfy | DARC| | NM_010045 | 1151785 |
| IC00642 | UG75 Expression | GENE | Mm.22633 | TITLE diacylglycerol acyltransferase | GENE Dgat | | NM_010046 | 2939157 |
| IC00643 | UG75 Expression | GENE | Mm.27155 | TITLE DiGeorge syndrome chromosome region 6 | GENE Dgcr6 | | gi = 2582382 | 1498173 |
| IC00644 | UG75 Expression | GENE | Mm.4891 | TITLE DiGeorge syndrome GENE c | GENE Dgsc | Dgcr2|Idd|Lan|seizure related gene 12|Sez12| | NM_010048 | 313732 |
| IC00645 | UG75 Expression | GENE | Mm.42234 | TITLE deoxyguanosine kinase | GENE Dguok | dGK| | NM_013764 | 560118 |
| IC00646 | UG75 Expression | GENE | Mm.23695 | TITLE dihydrofolate reductase | GENE Dhfr | diaphorase 4 (NADH)|menadione oxidoreductase 1|NAD(P)H menadione oxidoreductase 1, dioxin inducible|NMO1|Nmor1|Ox-1|Ox1| | NM_010049 | 1399654 |
| IC00647 | UG75 Expression | GENE | Mm.252 | TITLE diaphorase 4 (NADH/NADPH) | GENE Dia4 | | NM_008706 | 532186 |
| IC00648 | UG75 Expression | GENE | Mm.3282 | TITLE diaphanous homolog 1 (Drosophila) | GENE Diap1 | p140mDia| | NM_007858 | 388213 |
| IC00649 | UG75 Expression | GENE | Mm.86386 | TITLE DNase inhibited by DNA fragmentation factor | GENE Didff | CAD| | NM_007859 | 765890 |
| IC00650 | UG75 Expression | GENE | Mm.22480 | TITLE D-interacting myb-like protein | GENE Dimp-pe | DMp1| | NM_011806 | 1134856 |
| IC00651 | UG75 Expression | GENE | Mm.3131 | TITLE dihydrolipoamide dihydrogenase | GENE Dld | | NM_007861 | 1971034 |
| IC00652 | UG75 Expression | GENE | Mm.382 | TITLE discs, large homolog 1 (Drosophila) | GENE Dlgh1 | | NM_007862 | 1327749 |
| IC00653 | UG75 Expression | GENE | Mm.27256 | TITLE discs, large homolog 4 (Drosophila) | GENE Dlgh4 | PSD-95|SAP90| | NM_007864 | 819983 |
| IC00654 | UG75 Expression | GENE | Mm.90029 | TITLE delta-like homolog (Drosophila) | GENE Dlk1 | Ly107|pref-1| | NM_010052 | 553756 |
| IC00655 | UG75 Expression | GENE | Mm.4875 | TITLE delta-like 1 homolog (Drosophila) | GENE Dll1 | | NM_007865 | 721396 |
| IC00656 | UG75 Expression | GENE | Mm.6529 | TITLE dystrophia myotonica kinase, B15 | GENE Dm15 | DM|DMPK| | gi = 311886 | 1886603 |
| IC00657 | UG75 Expression | GENE | Mm.742 | TITLE dystrophin, muscular dystrophy | GENE Dmd | Duchenne muscular dystrophy|mdx|kel|pyruvate kinase expression|X-linked muscular dystrophy| | NM_007868 | 1886154 |
| IC00658 | UG75 Expression | GENE | Mm.18237 | TITLE DnaJ-like protein 1 | GENE Dnajl1 | MTJ1| | NM_007869 | 1973203 |
| IC00659 | UG75 Expression | GENE | Mm.41853 | TITLE deoxyribonuclease II | GENE Dnase2 | | NM_010062 | 640308 |
| IC00660 | UG75 Expression | GENE | Mm.6441 | TITLE dynein, cytoplasmic, intermediate chain 2 | GENE Dncic2 | | NM_010064 | 1066700 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00661 | UG76 LID366 B cell | GENE | Mm.7814 | TITLE DNA methyltransferase (cytosine-5) | Gene Dnmt | Dnmt1|Met-1|Met1|methyltransferase 1|MTase| | gi = 2665785 | 851859 |
| IC00662 | UG75 Expression | GENE | Mm.5001 | TITLE DNA methyltransferase 3A | GENE Dnmt3a | | NM_007872 | 573934 |
| IC00663 | UG75 Expression | GENE | Mm.35847 | TITLE deleted in oral cancer 1 | GENE Doc1 | | gi = 2305225 | 640009 |
| IC00664 | UG75 Expression | GENE | Mm.156 | TITLE downstream of tyrosine kinase 1 | GENE Dok1 | p62DOK|DokR|Frip|IL-Four Receptor Interacting Protein|interleukin four receptor interacting protein|p56 dok-2| | NM_010070 | 1246827 |
| IC00665 | UG75 Expression | GENE | Mm.10761 | TITLE downstream of tyrosine kinase 2 | GENE Dok2 | | NM_010071 | 1499282 |
| IC00666 | UG75 Expression | GENE | Mm.2698 | TITLE deleted in polyposis 1 | GENE Dp1 | DP1/TB2|TB2|DP1| | NM_007874 | 1382845 |
| IC00667 | UG75 Expression | GENE | Mm.18353 | TITLE dolichyl-phosphate alpha-N-acetylglucosaminephosphotransferase 2 | GENE Dpagt2 | | NM_007875 | 676356 |
| IC00668 | UG75 Expression | GENE | Mm.12969 | TITLE dolichol-phosphate (beta-D) mannosyltransferase 1 | | | | |
| IC00669 | UG75 Expression | GENE | Mm.22001 | TITLE dolichol-phosphate (beta-D) mannosyltransferase 2 | gene Dpm2 | | NM_010073 | 2648752 |
| IC00670 | UG75 Expression | GENE | Mm.1151 | TITLE dipeptidylpeptidase 4 | GENE Dpp4 | Cd26|CD26 antigen|Dpp-4|THAM| | NM_010074 | 1481246 |
| IC00671 | UG75 Expression | GENE | Mm.8180 | TITLE dihydropyrimidinase-like 3 | GENE Dpysl3 | Ulip|Ulip1|unc-33-like phosphoprotein|Nedd3|neural precursor cell expressed, developmentally down-regulateed gene 3| | NM_009468 | 669754 |
| IC00672 | UG75 Expression | GENE | Mm.3250 | TITLE developmentally regulated GTP-binding protein 1 | GENE Drg1 | | NM_007879 | 1482502 |
| IC00673 | UG75 Expression | GENE | Mm.2230 | TITLE dead ringer homolog 1 (Drosophila) | GENE Dri1 | | NM_007880 | 406231 |
| IC00674 | UG75 Expression | GENE | Mm.100195 | TITLE developmentall regulated repeat element containing transcript 3 | GENE Drr3 | | gi = 1502407 | 803943 |
| IC00675 | UG75 Expression | GENE | Mm.4163 | TITLE desmocollin 2 | GENE Dsc2 | Dsc2a|Dsc2b| | NM_013505 | 622376 |
| IC00676 | UG75 Expression | GENE | Mm.3386 | TITLE dystrobrevin | GENE Dtn | 87K protein|A1|alpha-dystrobrevin| | NM_007880 | 775144 |
| IC00677 | UG75 Expression | GENE | Mm.10088 | TITLE dystrobrevin, beta | GENE Dtnb | | NM_007886 | 3154900 |
| IC00678 | UG75 Expression | GENE | Mm.1645 | TITLE deltex 1 homolog (Drosophila) | GENE Dtx1 | | NM_008052 | 598729 |
| IC00679 | UG75 Expression | GENE | Mm.4729 | TITLE dual specificity phosphatase 2 | GENE Dusp2 | PAC1| | NM_010090 | 760695 |
| IC00680 | UG75 Expression | GENE | Mm.3400 | TITLE dishevelled, dsh homolog (Drosophila) | GENE Dvl | | NM_010091 | 862760 |
| IC00681 | UG75 Expression | GENE | Mm.5114 | TITLE dishevelled 2, dsh homolog (Drosophila) | GENE Dvl2 | | NM_007888 | 477875 |
| IC00682 | UG75 Expression | GENE | Mm.43239 | TITLE DNA segment, Chr X, human DXS648E | GENE DXHXS648E | | gi = 410741 | 1498423 |
| IC00683 | UG75 Expression | GENE | Mm.18036 | TITLE E2F transcription factor 1 | GENE E2f1 | | NM_007891 | 751755 |
| IC00684 | UG75 Expression | GENE | Mm.6333 | TITLE E2F transcription factor 3 | GENE E2f3 | | gi = 2454575 | 2939046 |
| IC00685 | UG75 Expression | GENE | Mm.20370 | TITLE eosinophil-associated ribonuclease 2 | GENE Ear2 | | NM_007895 | 891131 |
| IC00686 | UG75 Expression | GENE | Mm.18418 | TITLE adenomatosis polyposis coli binding protein Eb1 | GENE Eb1 | | NM_007896 | 1383398 |
| IC00687 | UG75 Expression | GENE | Mm.1120 | TITLE LEFTA|lefty|lefty-1|stimulated by retinoic acid gene LEFTA| endometrial bleeding associated factor | GENE Ebaf | 3|Stra3|Tgfb4|transforming growth factor, beta 4|ACLP| | NM_010094 | 604996 |
| IC00688 | UG75 Expression | GENE | Mm.27183 | TITLE endometrial bleeding associated factor binding protein | GENE Ebp | | NM_007898 | 1890034 |
| IC00689 | UG75 Expression | GENE | Mm.3433 | TITLE extracellular matrix protein 1 | GENE Ecm1 | | NM_007899 | 717050 |
| IC00690 | UG75 Expression | GENE | Mm.29027 | TITLE exrracellular matrix protein 2 | GENE Ecm2 | Sc1| | NM_010097 | 1884972 |
| IC00691 | UG75 Expression | GENE | Mm.32744 | TITLE encephalopsin | GENE Ecpn | | NM_010098 | 777428 |
| IC00692 | UG75 Expression | GENE | Mm.2995 | TITLE ect2 oncogene | GENE Ect2 | | NM_007900 | 943823 |
| IC00693 | UG75 Expression | GENE | Mm.982 | TITLE endothelial differentiation sphingolipid G-protein-coupled receptor 1 | GENE Edg1 | endothelial differentiation spingolipid G-protein-coupled receptor 1|pB1| | NM_007901 | 1498047 |
| IC00694 | UG75 Expression | GENE | Mm.33065 | TITLE endothelial differentiation, G-protein-coupled receptor 6 | GENE Edg6 | | NM_010102 | 723078 |
| IC00695 | UG75 Expression | GENE | Mm.6822 | TITLE early development regulator | GENE Edr | Mph1|Rae-28|rae28| | NM_007905 | 989179 |
| IC00696 | UG75 Expression | GENE | Mm.18203 | TITLE embryonic ectoderm development | GENE eed | | gi = 1710987 | 540416 |
| IC00697 | UG75 Expression | GENE | Mm.16317 | TITLE eukaryotic translation elongation factor 1 alpha 1 | GENE Eef1a1 | | gi = 556300 | 2225630 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00698 | UG75 Expression | GENE | Mm.16332 | ephrin A4 | Efna4 | eph-related receptor tyrosine kinase ligand 4|Epl4|Cek ligand|eph-related receptor tyrosine kinase ligand 2|Epl2|LERK-2|Stra1| | NM_007910 | 440708 |
| IC00699 | UG75 Expression | GENE | Mm.3374 | ephrin B1 | Efnb1 | | NM_010110 | 420424 |
| IC00700 | UG75 Expression | GENE | Mm.4005 | ephrin B2 | Efnb2 | eph-related receptor tyrosine kinase ligand 5|Epl5| | NM_010111 | 535881 |
| IC00701 | UG75 Expression | GENE | Mm.1341 | epidermal growth factor | Egf | | NM_010113 | 1907957 |
| IC00702 | UG75 Expression | GENE | Mm.89945 | epidermal growth factor binding protein type C | Egfbp3 | Egfbp-3|Klk9|mGk-9| | gi = 192997 | 2182745 |
| IC00703 | UG75 Expression | GENE | Mm.8534 | epidermal growth factor receptor | Egfr | avian erythroblastic leukemia viral (v-erb-b) oncogene homolog|avian erythroblastosis oncogene B|Erbb|wa-2|wa2|waved 2| | NM_007912 | 2088092 |
| IC00704 | UG75 Expression | GENE | Mm.3765 | early growth response 1 | Egr1 | egr|Egr-1|Krox-1|Krox-24|Krox24|Kruppel box 1|Kruppel box 24|NGFI-A|NGFIA|TIS8|Zenk|Zfp-6|Zif268|zinc finger protein 6| | NM_007913 | 576284 |
| IC00705 | UG75 Expression | GENE | Mm.1353 | early growth response 2 | Egr2 | Egr-2|Krox-20|Krox20|Kruppel box 2|Zfp-25|Zfp-6|zinc finger protein 25| | gi = 52812 | 1209893 |
| IC00706 | UG75 Expression | GENE | Mm.4337 | etoposide induced 2.4 mRNA | Ei24 | PIG8| | NM_007915 | 3153470 |
| IC00707 | UG75 Expression | GENE | Mm.23375 | eukaryotic translation initiation factor 2 alpha kinase 3 | Eif2ak3 | PEK|perk| | NM_010121 | 1383581 |
| IC00708 | UG75 Expression | GENE | Mm.29128 | eukaryotic translation initiation factor 2B | Eif2b | | NM_010122 | 779696 |
| IC00709 | UG75 Expression | GENE | Mm.22387 | eukaryotic translation initiation factor 2, subunit 2, structural gene X-linked | Eif2s3x | Eif-2gx| | NM_012010 | 1050037 |
| IC00710 | UG75 Expression | GENE | Mm.20831 | eukaryotic translation initiation factor 2, subunit 3, structural gene Y-linked | Eif2s3y | Eif-2gy|Tfy| | NM_012011 | 573320 |
| IC00711 | UG75 Expression | GENE | Mm.2238 | eukaryotic translation initiation factor 3 | Eif3 | centrosomin A|Csma| | NM_010123 | 779016 |
| IC00712 | UG75 Expression | GENE | Mm.3880 | eukaryotic translation initiation factor 4A related sequence 1 | Eif4a-rs1 | | NM_007916 | 735572 |
| IC00713 | UG75 Expression | GENE | Mm.12858 | eukaryotic translation initiation factor 4A1 | Eif4a1 | Eif4|eukaryotic translation factor 4| | gi = 556307 | 3025934 |
| IC00714 | UG75 Expression | GENE | Mm.16323 | eukaryotic translation initiation factor 4A2 | Eif4a2 | Eif4a|eukaryotic translation factor 4| | NM_013506 | 1889722 |
| IC00715 | UG75 Expression | GENE | Mm.3941 | eukaryotic translation initiation factor 4E | Eif4e | Eif4e||4e| | NM_007917 | 793341 |
| IC00716 | UG75 Expression | GENE | Mm.6700 | eukaryotic translation initiation factor 4E binding protein 1 | Eif4ebp1 | PHAS-I| | NM_007918 | 371746 |
| IC00717 | UG75 Expression | GENE | Mm.2521 | eukaryotic translation initiation factor 4E binding protein 2 | Eif4ebp2 | 4E-BP2|PHAS-II| | NM_010124 | 1482299 |
| IC00718 | UG75 Expression | GENE | Mm.525 | eukaryotic translation initiation factor 4, gamma 2 | Eif4g2 | 4E-BP2|PHAS-II| | NM_013507 | 2655020 |
| IC00719 | UG75 Expression | GENE | Mm.24876 | E74-like factor 1 | Elf1 | mEif-1| | NM_007920 | 1970377 |
| IC00720 | UG75 Expression | GENE | Mm.4454 | ELK3, member of ETS oncogene family | Elk3 | Etrp| | NM_013508 | 699191 |
| IC00721 | UG75 Expression | GENE | Mm.1552 | eleven-nineteen lysine-rich leukemia GENE | Ell | | NM_007924 | 959447 |
| IC00722 | UG75 Expression | GENE | Mm.10507 | endothelial monocyte activating polypeptide 2 | Emap2 | EMAPII| | NM_007926 | 515462 |
| IC00723 | UG75 Expression | GENE | Mm.18892 | emerin | Emd | | NM_007927 | 2650889 |
| IC00724 | UG75 Expression | GENE | Mm.4082 | ELKL motif kinase | Emk | | NM_007928 | 574316 |
| IC00725 | UG75 Expression | GENE | Mm.20829 | epithelial membrane protein 3 | Emp3 | HNMP-1| | NM_010129 | 1094955 |
| IC00726 | UG75 Expression | GENE | Mm.2252 | EGF-like module containing, mucin-like, hormone receptor-like sequence 1 | Emr1 | DD7A5-7|F4/80 glycoprotein f4/80 protein|Gpf480| | gi = 4061490 | 737993 |
| IC00727 | UG75 Expression | GENE | Mm.4449 | endonuclease G | Endog | | NM_007931 | 1891207 |
| IC00728 | UG75 Expression | GENE | Mm.4851 | endoglin | Eng | CD105| | NM_007932 | 597174 |
| IC00729 | UG75 Expression | GENE | Mm.3913 | enolase 2, gamma neuronal | Eno2 | Eno-2| | NM_013509 | 1165522 |
| IC00730 | UG75 Expression | GENE | Mm.29994 | enolase 3, beta muscle | Eno3 | Eno-3| | NM_007933 | 1969945 |
| IC00731 | UG75 Expression | GENE | Mm.1193 | glutamy aminopeptidase | Enpep | Bp-1/6C3|Ly-51|Ly51|lymphocyte antigen 51| | NM_007934 | 681802 |
| IC00732 | UG75 Expression | GENE | Mm.1415 | endothelial PAS domain protein 1 | Epas1 | HIF-2alpha|HIF1alpha-like factor|HLF|MOP2| | NM_010137 | 817935 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00733 | UG75 Expression | GENE | Mm.30038 | TITLE erythrocyte protein band 4.1 | GENE Epb4.1 | 4.1R|elliptocytosis 1|Elp-1|Ep1| | gi = 191520 | 963118 |
| IC00734 | UG75 Expression | GENE | Mm.20852 | TITLE erythrocyte protein band 4.1-like 1 | GENE Epb4.1 | |14.1N|NBL1| | NM_013510 | 875293 |
| IC00735 | UG75 Expression | GENE | Mm.3465 | TITLE erythrocyte protein band 4.1-like 4 | GENE Epb4.1 | |4NBL4| | NM_013512 | 3157923 |
| IC00736 | UG75 Expression | GENE | Mm.15802 | TITLE erythrocyte protein band 4.2 | GENE Epb4.2 | | NM_013513 | 554571 |
| IC00737 | UG75 Expression | GENE | Mm.4441 | TITLE erythrocyte protein band 7.2 | GENE Epb7.2 | protein 7.2b|stomatin| | gi = 972906 | 847159 |
| IC00738 | UG75 Expression | GENE | Mm.20828 | TITLE enhancer of polycomb homolog 1, (Drosophila) | GENE Epc1 | | NM_007935 | 621870 |
| IC00739 | UG75 Expression | GENE | Mm.2581 | TITLE Eph receptor A2 | GENE Epha2 | Eck|epithelial cell kinase|Sek-2| | NM_010139 | 1365167 |
| IC00740 | UG75 Expression | GENE | Mm.9075 | TITLE epoxide hydrolase 1,microsomal | GENE Ephx1 | Eph-1|Eph1| | NM_010145 | 1886084 |
| IC00741 | UG75 Expression | GENE | Mm.15295 | TITLE eopxide hydrolase 2, cytoplasmic | GENE Ephx2 | Eph2|epoxide hydrolase 2, soluble| | NM_007940 | 1890201 |
| IC00742 | UG75 Expression | GENE | Mm.3003 | TITLE epimorphin | GENE Epim | | NM_007941 | 479304 |
| IC00743 | UG75 Expression | GENE | Mm.3091 | TITLE epsin 1 | GENE Epn1 | |bp1| | gi = 3063646 | 519671 |
| IC00744 | UG75 Expression | GENE | Mm.10754 | TITLE epsin 2 | GENE Epn2 | |bp2| | gi = 3063648 | 1348424 |
| IC00745 | UG75 Expression | GENE | Mm.2653 | TITLE erythropoietin receptor | GENE Epor | | NM_010149 | 3026171 |
| IC00746 | UG75 Expression | GENE | Mm.35677 | TITLE epidermal growth factor receptor pathway substrate 15, related sequence | GENE Eps15-rs | Eps15R| | NM_007944 | 1230586 |
| IC00747 | UG75 Expression | GENE | Mm.4700 | TITLE excision repair 1 | GENE Ercc1 | Ercc-1| | NM_007948 | 475399 |
| IC00748 | UG75 Expression | GENE | Mm.8068 | TITLE Est2 repressor factor | GENE Erf | | NM_010155 | 2065071 |
| IC00749 | UG75 Expression | GENE | Mm.21952 | TITLE enhancer of rudimentary homolog (Drosophila) | GENE Erh | Mer| | NM_007951 | 1006210 |
| IC00750 | UG75 Expression | GENE | Mm.709 | TITLE endoplasmic reticulum protein | GENE Erp | PLC[a]| | NM_007952 | 1885684 |
| IC00751 | UG75 Expression | GENE | Mm.43005 | TITLE endogenous retroviral sequence 4 (with leucine t-RNA primer) | GENE Erv4-per | MuERV-L| | gi = 2065208 | 833222 |
| IC00752 | UG75 Expression | GENE | Mm.4450 | TITLE embryonic stem cell phosphatase | GENE Esp | | NM_007955 | 2936789 |
| IC00753 | UG75 Expression | GENE | Mm.9213 | TITLE estrogen receptor 1 | GENE Esr1 | ER[a]|ERa|ERalpha|ESR|Estr|Estra|estrogen receptor|estrogen receptor alpha|Nr3a1| | NM_007955 | 2936789 |
| IC00754 | UG75 Expression | GENE | Mm.2563 | TITLE estrogen related receptor, alpha | GENE Esrra | Err1|estrogen receptor related 1|Estrra|Nr3b1| | NM_007953 | 571597 |
| IC00755 | UG76 LID366 B cell | GENE | Mm.88477 | TITLE expressed sequence tag mouse EST 19 | GENE ESTM 19 | | gi = 949956 | 1121627 |
| IC00756 | UG75 Expression | GENE | Mm.17964 | TITLE etoile | GENE Etle | SLM-2|T-STAR| | NM_010158 | 637059 |
| IC00757 | UG75 Expression | GENE | Mm.27700 | TITLE ethanol induced 1 | GENE Etohi1 | | gi = 6078351 | 643636 |
| IC00758 | UG75 Expression | GENE | Mm.27880 | TITLE elav-type RNA-binding protein 3 | GENE Etr3-pending | | NM_010160 | 584897 |
| IC00759 | UG75 Expression | GENE | Mm.14115 | TITLE E26 avian leukemia oncogene 1, 5' domain | GENE Ets1 | Ets-1|Tp1|tumor progression locus 1| | NM_011808 | 13330354 |
| IC00760 | UG75 Expression | GENE | Mm.22365 | TITLE E26 avian leukemia oncogene 2, 3' domain | GENE Ets2 | Ets-2| | NM_011809 | 949055 |
| IC00761 | UG75 Expression | GENE | Mm.2017 | TITLE ets variant GENE 6 (TEL oncogene) | GENE Etv6 | Tel|translocation-ets-leukemia| | NM_007961 | 465999 |
| IC00762 | UG75 Expression | GENE | Mm.3266 | TITLE ecotropic viral integration site 2 | GENE Evi2 | Evi-2| | NM_010161 | 749410 |
| IC00763 | UG75 Expression | GENE | Mm.35796 | TITLE ecotropic viral integration site 5 | GENE Evi5 | | NM_007964 | 569682 |
| IC00764 | UG75 Expression | GENE | Mm.2144 | TITLE Ena-vasodilator stimulated phosphoprotein | GENE Evl | | NM_007965 | 602806 |
| IC00765 | UG75 Expression | GENE | Mm.22691 | TITLE Ewing sarcoma homolog | GENE Ewsh | Ews| | NM_007968 | 1383582 |
| IC00766 | UG75 Expression | GENE | Mm.34988 | TITLE exonuclease 1 | GENE Exo1 | | NM_012012 | 906024 |
| IC00767 | UG75 Expression | GENE | Mm.1650 | TITLE extracellular proteinase inhibitor | GENE Expi | | NM_007969 | 2647351 |
| IC00768 | UG75 Expression | GENE | Mm.4336 | TITLE exostoses (multiple) 2 | GENE Ext2 | WDNM1| | NM_010163 | 577494 |
| IC00769 | UG75 Expression | GENE | Mm.2229 | TITLE eyes absent 2 homolog (Drosophila) | GENE Eya2 | | gi = 1816530 | 426524 |
| IC00770 | UG75 Expression | GENE | Mm.41949 | TITLE eyes absent 4 homolog (Drosophila) | GENE Eya4 | | NM_010167 | 2123740 |
| IC00771 | UG75 Expression | GENE | Mm.5027 | TITLE enhancer of zeste homolog 1 (Drosophila) | GENE Ezh1 | | NM_0079710 | 1969487 |
| IC00772 | UG75 Expression | GENE | Mm.4303 | TITLE enhancer of zeste homolog 2 (Drosophila) | gen eEzh2 | enhancer of zeste homolog (Drosophila)|Enx-1|Enx1h| | NM_007971 | 1400348 |
| IC00773 | UG75 Expression | GENE | Mm.1614 | TITLE coagulation factor II (thrombin) receptor-like 1 | GENE F2rl1 | G-protein coupled receptor 11|Gpcr11|PAR-2|Par2 | NM_007974 | 1400929 |
| IC00774 | UG75 Expression | GENE | Mm.1612 | TITLE coagulation factor II (thrombin) receptor-like 2 | GENE F2rl2 | PAR3| | NM_010170 | 620379 |
| IC00775 | UG75 Expression | GENE | Mm.12900 | TITLE coagulation factor V | GENE F5 | | NM_007976 | 720000 |
| IC00776 | UG75 Expression | GENE | Mm.1805 | TITLE coagulation factor VIII | GENE F8 | | NM_007977 | 637486 |
| IC00777 | UG75 Expression | GENE | Mm.5154 | TITLE factor 8-associated GENE A | GENE F8a | DNA segment, Chr X, UCal San Francisco 1|DXUcsf1| | NM_007978 | 572416 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00778 | UG75 Expression | GENE | Mm.2915 | TITLE fatty acid amide hydrolase | GENE Faah | | NM_010173 | 680059 |
| IC00779 | UG75 Expression | GENE | Mm.22220 | TITLE fatty acid binding protein heart 1 | GENE Fabph1 | Fabh-1|mammary derived growth inhibitor|Mdgi| | NM_010174 | 571084 |
| IC00780 | UG75 Expression | GENE | Mm.28962 | TITLE fatty acid Coenzyme A ligase, long chain 2 | GENE Facl2 | FACS| | NM_007981 | 1432102 |
| IC00781 | UG75 Expression | GENE | Mm.5126 | TITLE Fas-associating protein with death domain | GENE Fadd | Mort1/FADD| | NM_010175 | 419798 |
| IC00782 | UG75 Expression | GENE | Mm.29674 | TITLE focal adhesion kinase | GENE FAdk | | NM_007982 | 2088084 |
| IC00783 | UG75 Expression | GENE | Mm.3722 | TITLE Fas-associated factor 1 | GENE Faf1 | | NM_007983 | 1265326 |
| IC00784 | UG75 Expression | GENE | Mm.3798 | TITLE fumarylacetoacetate hydrolase | GENE Fah | | NM_010176 | 1481444 |
| IC00785 | UG75 Expression | GENE | Mm.74605 | TITLE Fas apoptotic inhibitory molecule | GENE Faim-pending | | NM_011810 | 1107754 |
| IC00786 | UG75 Expression | GENE | Mm.4683 | TITLE Fanconi anemia, complementation group C | GENE Fancc | Facc|Fanconi anaemi, complementation group C| | NM_007985 | 2135781 |
| IC00787 | UG75 Expression | GENE | Mm.1626 | TITLE Fas antigen | GENE Fas | APO-1|CD95|prl|lymphoproliferation| | NM_007987 | 621020 |
| IC00788 | UG75 Expression | GENE | Mm.3355 | TITLE Fas antigen ligand | GENE Fasl | Fas Ligand|generalized lymphoproliferative disease|gld| | NM_010177 | 75124 |
| IC00789 | UG75 Expression | GENE | Mm.3760 | TITLE fatty acid synthase | GENE Fasn | FAS| | gi = 50947 | 607664 |
| IC00790 | UG75 Expression | GENE | Mm.10229 | TITLE Fus-associated protein with serine-arginine repeats | GENE Fasr-per | TASR| | NM_010178 | 539764 |
| IC00791 | UG75 Expression | GENE | Mm.4890 | TITLE Finkel-Biskis-Reilly murine sarcoma virus (FBR-MuSV) ubiquitously expressed (fox derived) | GENE Fau | | NM_007990 | 947532 |
| IC00792 | UG75 Expression | GENE | Mm.4595 | TITLE fibrillarin | GENE Fbl | | NM_007991 | 1448899 |
| IC00793 | UG75 Expression | GENE | Mm.22626 | TITLE fibulin 1 | GENE Fbln1 | | NM_010180 | 603537 |
| IC00794 | UG75 Expression | GENE | Mm.6120 | TITLE fibulin 2 | GENE Fbln2 | | NM_007992 | 568770 |
| IC00795 | UG75 Expression | GENE | Mm.735 | TITLE fibrillin 1 | GENE Fbn1 | tight skin|Tsk| | NM_007993 | 1248284 |
| IC00796 | UG75 Expression | GENE | Mm.20271 | TITLE fibrillin 2 | GENE Fbn2 | | NM_010181 | 375004 |
| IC00797 | UG75 Expression | GENE | Mm.22673 | TITLE Fc receptor, IgE, high affinity I, gamma polypeptide | GENE Fcer1g | Fc epsilon high affinity receptor gamma|Fce1g|FcR-gamma|FcR[g]|Ly-50|lymphocyte antigen 50| | NM_010185 | 534161 |
| IC00798 | UG75 Expression | GENE | Mm.1233 | TITLE Fc receptor, IgE, low affinity II, alpha polypeptide | GENE Fcer2a | Fc epsilon low affinity receptor (IgE)|FC epsilon RII|Fce2|low-affinity IgE receptor|LyA|lymphocyte antigen 42|CD64| | NM_013517 | 1482690 |
| IC00799 | UG75 Expression | GENE | Mm.150 | TITLE Fc receptor, IgG, high affinity I | Gene Fcgr1 | CD32|Fc gamma RIIB|Fc receptor, IgG, low affinity IIb|Fc receptor, IgG, low affinity IIa|Fc-gamma receptor 2|Fc-gamma receptor 3|Fc-gamma-RII|Fce|gRII|Fcgr2|Fcgr2a|FcgRII|Fcr-2|Fcr-3|Ly-17|Ly-m20|LyM-1|lymphocyte antigen 17|lymphocyte antigen m20| | NM_010186 | 575540 |
| IC00800 | UG75 Expression | GENE | Mm.10809 | TITLE Fc receptor, IgG, low affinity IIb | GENE Fcgr2b | CD16|Fcg receptor III | NM_010187 | 596644 |
| IC00801 | UG75 Expression | GENE | Mm.22220 | TITLE Fc receptor, IgG, low affinity III | GENE Fcgr3 | FcRn| | NM_010188 | 780100 |
| IC00802 | UG75 Expression | GENE | Mm.3303 | TITLE Fc receptor, IgG, alpha chain transporter | GENE Fcgt | Fcn1|ficolin A| | NM_010189 | 1499422 |
| IC00803 | UG75 Expression | GENE | Mm.10510 | TITLE ficolin A | GENE Fcna | | NM_007995 | 483804 |
| IC00804 | UG75 Expression | GENE | Mm.3204 | TITLE farnesyl diphosphate farnesyl transferase 1 | GENE Fdft1 | squalene sythase|SS| | NM_010191 | 2581989 |
| IC00805 | UG75 Expression | GENE | Mm.1061 | TITLE farredoxin 1 | GENE Fdx1 | ADRENODOXIN| | NM_007996 | 1383314 |
| IC00806 | UG75 Expression | GENE | Mm.4719 | TITLE ferredoxin reductase | GENE Fdxr | | NM_007997 | 1230740 |
| IC00807 | UG75 Expression | GENE | Mm.1070 | TITLE ferrochelatase | GENE Fech | fch|Fc| | NM_007998 | 1891413 |
| IC00808 | UG75 Expression | GENE | Mm.27723 | TITLE feminization 1 a homolog (C. elegans) | GENE Fem1a | | NM_010192 | 818916 |
| IC00809 | UG75 Expression | GENE | Mm.2952 | TITLE flap structure specific endonuclease 1 | GENE Fen1 | | NM_007999 | 732284 |
| IC00810 | UG75 Expression | GENE | Mm.3394 | TITLE feline sarcoma oncogene | GENE Fes | | gi = 50955 | 2938035 |
| IC00811 | UG75 Expression | GENE | Mm.42103 | TITLE follicle expressed hormone | GENE Fex-pen | FEX| | NM_010195 | 638118 |
| IC00812 | UG75 Expression | GENE | Mm.3157 | TITLE fibroblast growth factor receptor 1 | GENE Fgfr1 | Fgfr-1|FLG|Flt-2|FMS-like tyrosine kinase 2|has been called Flg in some refs; but Flg=filaggrin| | NM_010206 | 2609909 |
| IC00813 | UG75 Expression | GENE | Mm.6904 | TITLE fibroblast growth factor receptor 3 | GENE Fgfr3 | Fgfr-3|HBGFR| | NM_008010 | 2609751 |
| IC00814 | UG75 Expression | GENE | Mm.3040 | TITLE fibrinogen-like protein 2 | GENE Fgl2 | | NM_008013 | 1024302 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00815 | UG75 Expression | GENE | Mm.3126 | TITLE four and a half LIM domains 1 | GENE Fhl1 | KyoT|KyoT1|KyoT2 | NM_010211 | 1969943 |
| IC00816 | UG75 Expression | GENE | Mm.6799 | TITLE four and a half LIM domains 2 | GENE Fhl2 | | NM_010212 | 1434060 |
| IC00817 | UG75 Expression | GENE | Mm.3983 | TITLE c-fos induced growth factor | GENE Figf | VEGF-D1 | NM_010216 | 614347 |
| IC00818 | UG75 Expression | GENE | Mm.14501 | TITLE fibroblast growth factor inducible 13 | GENE Fin13 | | NM_008014 | 2655296 |
| IC00819 | UG75 Expression | GENE | Mm.18459 | TITLE fibroblast growth factor inducible 14 | GENE Fin14 | | NM_008015 | 2331922 |
| IC00820 | UG75 Expression | GENE | Mm.3421 | TITLE fibroblast growth factor inducible 15 | GENE Fin15 | | NM_008016 | 750018 |
| IC00821 | UG75 Expression | GENE | Mm.2999 | TITLE fibroblast growth factor inducible 16 | GENE Fin16 | | NM_008017 | 2582037 |
| IC00822 | UG75 Expression | GENE | Mm.1810 | TITLE fibroblast inducible secreted protein | GENE Fisp12 | CTGF | NM_010217 | 1247552 |
| IC00823 | UG75 Expression | GENE | Mm.27941 | TITLE FK506 binding protein 1a (12kDa) | GENE Fkbp1a | FK506 binding protein|FK506 binding protein 1, 12 kDa|Fkbp|Fkbp1|mFKBP1|mFKBP12| | NM_008019 | 1383557 |
| IC00824 | UG75 Expression | GENE | Mm.12758 | TITLE FK506 binding protein 4 (59 kDa) | GENE Fkbp4 | FK506 bidning protein 4, 59 kDa|FKBP-52|p59| | NM_010219 | 2645974 |
| IC00825 | UG75 Expression | GENE | Mm.22595 | TITLE FK506 binding protein 5 (51 kDa) | GENE Fkbp5 | dexamethasone induced transcript 1|Dit1|FK506 binding protein 5, 51 kDa|FKBP51| | NM_010220 | 737401 |
| IC00826 | UG75 Expression | GENE | Mm.24720 | TITLE FK506 binding protein 7 (23 kDa) | GENE Fkbp7 | FK506 binding protein 7|FKBP23| | NM_010222 | 1451065 |
| IC00827 | UG75 Expression | GENE | Mm.6565 | TITLE FK506 binding protein 8 (38 kDa) | GENE Fkbp8 | Fkbp-38| | NM_010223 | 1499139 |
| IC00828 | UG75 Expression | GENE | Mm.20943 | TITLE FK506 binding protein 9 | GENE Fkbp9 | FKBP60| | gi = 3860028 | 948533 |
| IC00829 | UG75 Expression | GENE | Mm.4685 | TITLE filaggrin | GENE Flg | | gi = 193307 | 492647 |
| IC00830 | UG75 Expression | GENE | Mm.1342 | TITLE Friend leukemia integration 1 | GENE Fli1 | Fli-1| | NM_008026 | 717781 |
| IC00831 | UG75 Expression | GENE | Mm.2931 | TITLE flotilin 1 | GENE Flot1 | | NM_008027 | 3154486 |
| IC00832 | UG75 Expression | GENE | Mm.194 | TITLE FMS-like tyrosine kinase 3 | GENE Flt3 | CD135|fetal liver kinase 2|Flk-2|Flt-3|Ly72| | NM_010229 | 576267 |
| IC00833 | UG75 Expression | GENE | Mm.976 | TITLE flavin containing monooxygenase 1 | GENE Fmo1 | | NM_010231 | 1920979 |
| IC00834 | UG75 Expression | GENE | Mm.1668 | TITLE flavin containing monooxygenase 5 | GENE Fmo5 | | NM_010232 | 1431306 |
| IC00835 | UG75 Expression | GENE | Mm.3451 | TITLE fragile X mental retardation syndrome 1 homolog | GENE Fmr1 | Fmr-1| | NM_008031 | 2631385 |
| IC00836 | UG75 Expression | GENE | Mm.3496 | TITLE farnesyltransferase, CAAX box, alpha | GENE Fnta | FTA| | NM_008033 | 603387 |
| IC00837 | UG75 Expression | GENE | Mm.26091 | TITLE FBJ osteosarcoma oncogene B | GENE Fosb | | NM_008036 | 875302 |
| IC00838 | UG75 Expression | GENE | Mm.6215 | TITLE fos-like antigen 1 | GENE Fosl1 | fra-1|Fra1| | NM_010235 | 1498182 |
| IC00839 | UG75 Expression | GENE | Mm.12949 | TITLE forkhead box C1 | GENE Foxc1 | ch|congenital hydrocephalus|fkh-1|Fkh1|forkhead homolog 1, (Drosophila)|FREAC3|frkhda|mesoderm/mesenchyme forkhead 1|mesoderm/mesenchyme forkhead 4|Mf1|Mf4|Fkh14|forkhead homolog 14, (Drosophila)|Hfhbf3|HNF-3/forkhead homolog, brain factor 3|MFH-1|Mfh1| | NM_008592 | 372142 |
| IC00840 | UG75 Expression | GENE | Mm.14092 | TITLE forkhead box C2 | GENE Foxc2 | Mn|myocyte nuclear factor| | gi = 1869968 | 639750 |
| IC00841 | UG75 Expression | GENE | Mm.24214 | TITLE forkhead box K1 | GENE Foxk1 | Fkh16|forkhead homolog 16 (Drosophila)|HFH-11B|Mpm2|Trident|WIN| | NM_010812 | 607496 |
| IC00842 | UG75 Expression | GENE | Mm.42148 | TITLE forkhead box M1 | GENE Foxm1 | | NM_008021 | 2699038 |
| IC00843 | UG75 Expression | GENE | Mm.3830 | TITLE folylpolyglutamy synthetase | GENE Fpgs | | gi = 1345105 | 2352532 |
| IC00844 | UG75 Expression | GENE | Mm.56951 | TITLE formyl peptid receptor 1 | GENE Fpr1 | FPR| | NM_013521 | 636543 |
| IC00845 | UG75 Expression | GENE | Mm.4573 | TITLE frequently rearranged in advanced T-cell lymphomas | GENE Frat1 | | NM_008043 | 1510933 |
| IC00846 | UG75 Expression | GENE | Mm.7319 | TITLE Friedreich ataxia | GENE Frda | frataxin| | NM_008044 | 1052345 |
| IC00847 | UG75 Expression | GENE | Mm.67 | TITLE FSHD region GENE 1 | GENE Frg1 | | NM_013522 | 2936725 |
| IC00848 | UG75 Expression | GENE | Mm.13194 | TITLE fascin homolog 1 (actin bunding protein, Strongylocentrotus purpuratus) | GENE Fscn1 | Fan1|fascin homolog 1 (actin bunding protein, Strongylocentrotus purpuratus)| | NM_007984 | 660162 |
| IC00849 | UG75 Expression | GENE | Mm.10026 | TITLE fat specific GENE 27 | GENE Fsp27 | | gi-32 201107 | 1025498 |
| IC00850 | UG75 Expression | GENE | Mm.3444 | TITLE female sterile homeotic-related GENE 1 | GENE Fsrg1 | D17H6S113E|DNA segment, Chr 17, human D6S113|ring finger protein 3|Ring3|Rnf3| | NM_010238 | 751650 |
| IC00851 | UG75 Expression | GENE | Mm.22763 | TITLE follistatin-like | GENE Fstl | TSC-36| | NM_008047 | 1969707 |
| IC00852 | UG75 Expression | GENE | Mm.1776 | TITLE ferritin heavy chain | GENE Fth | | NM_010239 | 1139151 |
| IC00853 | UG75 Expression | GENE | Mm.7500 | TITLE ferritin light chain 1 | GENE Ftl1 | ferritin, light chain|ferritin, light chain 1|Ftl|Ftl-1| | NM_010240 | 1920900 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00854 | UG75 Expression | GENE | Mm.34778 | TITLE fatso | GENE Fto | | NM_011936 | 1195720 |
| IC00855 | UG75 Expression | GENE | Mm.1203 | TITLE fucosyltransferase 7 | GENE Fut7 | Fuc-TVII| | NM_013524 | 619197 |
| IC00856 | UG75 Expression | GENE | Mm.4038 | TITLE fragile X mental retardation GENE, autosomal homolog | GENE Fxr1h | FXR1| | gi = 1122421 | 1970464 |
| IC00857 | UG75 Expression | GENE | Mm.41930 | TITLE fragile X mental retardation GENE 2, autosomal homolog | GENE Fxr2h | | NM_011814 | 385956 |
| IC00858 | UG75 Expression | GENE | Mm.4848 | TITLE Fyn proto-oncogene | GENE Fyn | | NM_008054 | 573495 |
| IC00859 | UG75 Expression | GENE | Mm.3283 | TITLE G0/G1 switch GENE 2 | GENE G0s2 | | NM_008059 | 864447 |
| IC00860 | UG75 Expression | GENE | Mm.16147 | TITLE thyroid autoantigen 70 kDa | GENE G22p1 | Ku p70|Ku70| | NM_010247 | 576986 |
| IC00861 | UG75 Expression | GENE | Mm.3196 | TITLE alpha glucosidase 2, alpha neutral subunit | GENE G2an | | NM_008060 | 2065085 |
| IC00862 | UG75 Expression | GENE | Mm.2038 | TITLE Ras-GTPase-activating protein SH3-domain binding protein | GENE G3bp-pe | GAP SH3 binding protein| | NM_013716 | 390832 |
| IC00863 | UG75 Expression | GENE | Mm.2411 | TITLE ras-GTPase-activating protein (GAP<120s>) SH3-domain-binding protein 2 | GENE G3bp2-p | G3BP| | NM_011816 | 721020 |
| IC00864 | UG75 Expression | GENE | Mm.27210 | TITLE glucose-6-phosphate dehydrogenase X-linked | GENE G6pdx | G28A|G6pd|glucose-6-phosphate dehydrogenase 1 X-linked|Gpdx| | NM_008062 | 1499110 |
| IC00865 | UG75 Expression | GENE | Mm.30087 | TITLE glucose-6-phosphatase, transport protein 1 | GENE G6pt1 | GSD-1b| | NM_008063 | 1248232 |
| IC00866 | UG75 Expression | GENE | Mm.4793 | TITLE glucosidase, alpha, acid | GENE Gaa | | NM_008065 | 960707 |
| IC00867 | UG75 Expression | GENE | Mm.18974 | TITLE GA repeat binding protein, alpha | GENE Gabpa | | NM_008065 | 960707 |
| IC00868 | UG75 Expression | GENE | Mm.1764 | TITLE GA repeat binding protein, beta 1 | GENE Gabpb1 | | NM_010249 | 1003892 |
| IC00869 | UG75 Expression | GENE | Mm.4784 | TITLE glutamic acid decarboxylase 2 | GENE Gad2 | Gad-2|GAD65| | NM_008078 | 905588 |
| IC00870 | UG75 Expression | GENE | Mm.9653 | TITLE growth arrest and DNA-damage-inducible, gamma | GENE Gadd45 | CR6|OIG37| | NM_011817 | 581254 |
| IC00871 | UG75 Expression | GENE | Mm.5120 | TITLE galactosylceramidase | GENE Galc | Gacy|tw|twicher| | NM_008079 | 2395239 |
| IC00872 | UG75 Expression | GENE | Mm.1853 | TITLE UDP-N-acetyl-alpha-D-galactosamine:(N-acetylneuraminyl)-galactosylglucosylceramide-beta-1,4-N-acetylgalactosaminyltransferase | GENE Galgt1 | Gal-NAc-T|Gga|NAc T|ganglioside expression 2|Ggm-2|Ggm2|GM2/GD2 synthase|UDP-N-acetyl-alpha-D-galactosamine:(N-acetylneuraminyl)-galactosylglucosylceramide-beta-1,4-Nacetylgalactosaminyltransferase| | NM_008080 | 932962 |
| IC00873 | UG75 Expression | GENE | Mm.30249 | TITLE UDP-N-acetyl-alpha-D-galactosamine:polypeptide N-acetylgalactosaminyltransferase 1 | GENE Gaint1 | ppGaNTase-T1| | NM_013814 | 57041 |
| IC00874 | UG75 Expression | GENE | Mm.5289 | TITLE glyceraldehyde-3-phosphate dehydrogenase | GENE Gapd | Gapdh| | NM_008084 | 547017 |
| IC00875 | UG75 Expression | GENE | Mm.4505 | TITLE phosphoribosylglycinamide formyltransferase | GENE Gart | Gaps|phosphoribosyl glycinamide synthetase|Prgs| | NM_010256 | 1068047 |
| IC00876 | UG75 Expression | GENE | Mm.22701 | TITLE growth arrest specific 1 | GENE Gas1 | Gas-1| | NM_008086 | 576995 |
| IC00877 | UG75 Expression | GENE | Mm.25 | TITLE growth arrest specific 2 | GENE Gas2 | Gas-2| | _008087 | 1907936 |
| IC00878 | UG75 Expression | GENE | Mm.884 | TITLE growth arrest specific 5 | GENE Gas5 | Gas-5| | NM_013525 | 1363926 |
| IC00879 | UG75 Expression | GENE | Mm.3257 | TITLE growth arrest specific 7 | GENE Gas7 | Gas7-cb| | NM_008088 | 1434386 |
| IC00880 | UG75 Expression | GENE | Mm.1344 | TITLE GATA-binding protein 1 | GENE Gata1 | Gata-1|Gf-1|globin factor 1| | _008089 | 468938 |
| IC00881 | UG75 Expression | GENE | Mm.1391 | TITLE GATA-binding protein 2 | GENE Gata2 | Gata-2| | NM_008090 | 657678 |
| IC00882 | UG75 Expression | GENE | Mm.606 | TITLE GATA-binding protein 3 | GENE Gata3 | Gata-3| | NM_008091 | 1971401 |
| IC00883 | UG75 Expression | GENE | Mm.5031 | TITLE acid beta glucosidase | GENE Gba | GC|glucocerebrosidase| | NM_008094 | 421616 |
| IC00884 | UG75 Expression | GENE | Mm.12468 | TITLE glioblastoma amplified sequence | GENE Gbas | 4-nitrophenylphosphatase domain and non-neuronal SNAP25-like protein 2|Nipsnap2| | NM_008095 | 1364495 |
| IC00885 | UG75 Expression | GENE | Mm.24038 | TITLE guanylate nucleotide binding protein 2 | GENE GBP2 | ETR-3|Napor-2| | _010260 | 618810 |
| IC00886 | UG75 Expression | GENE | Mm.22473 | TITLE GTP binding protein associated protein 1 | GENE Gbpap1 | PRA1| | gi = 722666 | 2648646 |
| IC00887 | UG75 Expression | GENE | Mm.4205 | TITLE group specific component | GENE Gc | cartilage matrix deficiency|cmd| | gi = 193445 | 1924234 |
| IC00888 | UG75 Expression | GENE | Mm.2475 | TITLE glutaryl-Coenzyme A dehydrogenase | GENE Gcdh | | NM_008097 | 1891317 |
| IC00889 | UG75 Expression | GENE | Mm.4143 | TITLE granule cell differnetiation protein | GENE Gcdp | V1| | NM_008098 | 225744 |
| IC00890 | UG75 Expression | GENE | Mm.10651 | TITLE GTP cyclohydrolase 1 | GENE Gch | GTP-CH|GTPCH| | NM_008102 | 481354 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00891 | UG75 Expression | GENE | Mm.26931 | Eukaryotic translation initiation factor 2 alpha kinase 4 | GENE GCN2 | | NM_013719 | 440053 |
| IC00892 | UG75 Expression | GENE | Mm.12950 | TITLE ganglioside-induced differentiation-associated-protein 10 | GENE Gdap10 | | NM_010268 | 423021 |
| IC00893 | UG75 Expression | GENE | Mm.22080 | TITLE ganglioside-induced differentiation-associated-protein 2 | GENE Gdap2 | | gi = 3378455 | 1451237 |
| IC00894 | UG75 Expression | GENE | Mm.12962 | TITLE ganglioside-induced differentiation-associated-protein 3 | GENE Gdap3 | | gi = 3378457 | 1382889 |
| IC00895 | UG75 Expression | GENE | Mm.10669 | TITLE glycerolphosphate dehydrogenase 1, cytoplasmic adult | GENE Gdc1 | Gdc-1| | NM_010271 | 1886586 |
| IC00896 | UG75 Expression | GENE | Mm.28084 | TITLE guanosine diphosphate (GDP) dissociation inhibitor 3 | gene Gdi1 | | gi = 493526 | 540164 |
| IC00897 | UG75 Expression | GENE | Mm.19123 | | GENE Gdi3 | GD1 beta|GD1-B|GDIB| | NM_008112 | 522453 |
| IC00898 | UG75 Expression | GENE | Mm.3711 | TITLE glycerol phosphate dehydrogenase 1, mitochondrial | GENE Gdm1 | | NM_010274 | 351221 |
| IC00899 | UG75 Expression | GENE | Mm.4362 | TITLE GTP binding protein (GENE overexpressed in skeletal muscle) | GENE Gem | | NM_010276 | 622432 |
| IC00900 | UG75 Expression | GENE | Mm.2078 | TITLE growth factor independent 1 | GENE Gfi1 | Pal-1|Pal1|proviral insertion Pal1| | NM_010278 | 2749246 |
| IC00901 | UG75 Expression | GENE | Mm.10804 | TITLE growth factor independent 1B | GENE Gfi1b | Gfi-1B| | NM_008114 | 718609 |
| IC00902 | UG75 Expression | GENE | Mm.88367 | TITLE glial cell line derived neurotrophic factor family receptor alpha 1 | GENE Gfra1 | GDNFR-alpha|GFR alpha-1| | NM_010279 | 680894 |
| IC00903 | UG75 Expression | GENE | Mm.20461 | TITLE gamma-glutamyl hydrolase | GENE Ggh | gamma-GH| | NM_010281 | 905706 |
| IC00904 | UG75 Expression | GENE | Mm.36520 | TITLE geranylgeranyl diphosphate synthase 1 | GENE Ggps1 | GGPP synthase1 | NM_010282 | 749906 |
| IC00905 | UG75 Expression | GENE | Mm.1548 | TITLE glycoprotein galactosyltransferase alpha 1,3 | GENE Ggta1 | alpha1-3-galactosyltransferase|Ggta|Ggta-1|glycoprotein alpha galactosidase| | NM_010283 | 585565 |
| IC00906 | UG75 Expression | GENE | Mm.15622 | TITLE glycoprotein galactosyltransferase beta 1,4 | GENE Ggtb | B-1,4-GalT|beta-1,4-GalT| | gi_192195 | 3155838 |
| IC00907 | UG75 Expression | GENE | Mm.18263 | TITLE gamma-glutamyltrasnferase-like activity 1 | GENE Ggtla1 | gamma-glutamyl leukotrienase|GGL|GGT-REL| | NM_0118820 | 1434243 |
| IC00908 | UG75 Expression | GENE | Mm.4559 | TITLE gamma-glutamyl transpeptidase | GENE Ggtp | GGT| | NM_008116 | 2065258 |
| IC00909 | UG75 Expression | GENE | Mm.6317 | TITLE growth hormone releasing hormone | GENE Ghrh | Ghrf| | NM_010285 | 1496474 |
| IC00910 | UG75 Expression | GENE | Mm.22216 | TITLE glucocorticoid-induced leucine zipper | GENE Gilz | | NM_010286 | 3154382 |
| IC00911 | UG75 Expression | GENE | Mm.4504 | TITLE gap junction membrane channel protein alpha 1 | GENE Gja1 | alpha 1 cvonnexin|Cnx43|connexin 43|Cx43|Gja-1| | NM_010288 | 977188 |
| IC00912 | UG75 Expression | GENE | Mm.23886 | TITLE gap junction membrane channel protein alpha 4 | GENE Gja4 | Cnx37|connexin 37|Cx37|Gja-4| | NM_008120 | 746939 |
| IC00913 | UG75 Expression | GENE | Mm.34118 | TITLE gap junction membrane channel protein beta 2 | GENE Gjb2 | Cnx26|connexin 26|Cx26|Gjb-2| | NM_008125 | 1383007 |
| IC00914 | UG75 Expression | GENE | Mm.1114 | TITLE galactosidase, alpha | GENE Gla | | NM_013463 | 1433168 |
| IC00915 | UG75 Expression | GENE | Mm.4368 | TITLE glutamate cysteine ligase (gamma-glutamylcystein synthetase), catalytic | GENE Glclc | | gi = 1945069 | 1431969 |
| IC00916 | UG75 Expression | GENE | Mm.29340 | TITLE glutamate cysteine ligase (gamma-glutamylcystein synthetase), regulatory | GENE Glclr | | NM_008129 | 1265118 |
| IC00917 | UG75 Expression | GENE | Mm.2338 | TITLE glutamine synthetase | GENE Glns | | NM_008131 | 333093 |
| IC00918 | UG75 Expression | GENE | Mm.41660 | TITLE glutamine synthetase pseudoGENE 1 anonymous DNA segment, Chr 14|Gdh-X|Glud||glutamate | GENE Glns-ps1 | | gi = 193654 | 617802 |
| IC00919 | UG75 Expression | GENE | Mm.10600 | TITLE glutamate dehydrogenase | GENE Glud | dehydrogenase like sequence| | NM_008133 | 1482659 |
| IC00920 | UG75 Expression | GENE | Mm.34411 | TITLE glycosylation dependent cell adhesion molecule 1 | GENE Glycam1 | Sele ligand|Sgp50| | gi = 193561 | 1265549 |
| IC00921 | UG75 Expression | GENE | Mm.2834 | TITLE glycine transporter 1 | GENE Glyt1 | Glty-1| | NM_008135 | 477981 |
| IC00922 | UG75 Expression | GENE | Mm.4140 | TITLE GM2 ganglioside activator protein | GENE Gm2a | | NM_010299 | 747616 |
| IC00923 | UG75 Expression | GENE | Mm.33575 | TITLE guanine nucleotide binding protein, related sequence 1 | GENE Gna-rs1 | | NM_008136 | 533185 |
| IC00924 | UG75 Expression | GENE | Mm.989 | TITLE guanine nucleotide binding protein, alpha 11 | GENE Gna11 | | NM_010301 | 2647242 |
| IC00925 | UG75 Expression | GENE | Mm.5238 | TITLE guanine nucleotide binding protein, alpha 13 | GENE Gna13 | | NM_010303 | 1002337 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00926 | UG75 Expression | GENE | Mm.1546 | TITLE guanine nucleotide binding protein, alpha 15 | GENE Gna15 | G[a]15[Galpha15] | NM_010304 | 989202 |
| IC00927 | UG75 Expression | GENE | Mm.4284 | TITLE guanine nucleotide binding protein, alpha inhibiting 2 | GENE Gnai2 | Gi protein, alpha chain (inhib. reg. adenylate cyclase)[Gia[Gnai-2] | NM_008138 | 1265579 |
| IC00928 | UG75 Expression | GENE | Mm.4446 | TITLE guanine nucleotide binding protein, alpha q polypeptide | GENE Gnaq | G alpha q| | NM_008139 | 963649 |
| IC00929 | UG75 Expression | GENE | Mm.17446 | TITLE guanine nucleotide binding protein, alpha stimulating | GENE Gnas | G alpha s[Gnas1[Gs alpha[Gs protein, alpha chain (stim. reg. adenylate cyclase)[Gsa[Gsa-alpha[Gsa[NESP55[XL alpha s] | NM_010309 | 2225511 |
| IC00930 | UG75 Expression | GENE | Mm.88955 | TITLE guanine nucleotide binding protein, alpha stimulating, extra large | GENE Gnasxl | | NM_010310 | 2225511 |
| IC00931 | UG75 Expression | GENE | Mm.2344 | TITLE guanine nucleotide binding protein, beta 1 | GENE Gnb1 | Gnb-1| | NM_008142 | 605669 |
| IC00932 | UG75 Expression | GENE | Mm.5305 | TITLE guanine nucleotide binding protein, beta-2, related sequence 1 | GENE Gnb2-rs | p205| | NM_008143 | 1887673 |
| IC00933 | UG75 Expression | GENE | Mm.9336 | TITLE guanine nucleotide binding protein, beta 4 | GENE Gnb4 | G(beta)4| | NM_013531 | 457406 |
| IC00934 | UG75 Expression | GENE | Mm.4702 | TITLE guanine nucleotide binding protein, beta 5 | GENE Gnb5 | GB5[hug| | NM_010313 | 478224 |
| IC00935 | UG75 Expression | GENE | Mm.46767 | TITLE guanine nucleotide binding protein (G protein), gamma 2 subunit | GENE Gng2 | 82| | NM_010315 | 406684 |
| IC00936 | UG75 Expression | GENE | Mm.15985 | TITLE G protein gamma 3 linked GENE | GENE Gng3lg | | NM_008144 | 1450986 |
| IC00937 | UG75 Expression | GENE | Mm.29395 | TITLE glycine N-methyltransferase | GENE Gnmt | | NM_010321 | 463485 |
| IC00938 | UG75 Expression | GENE | Mm.29114 | TITLE glycerone phosphate O-acyltransferase | GENE Gnpat | DAPAT[DHAPAT] | NM_010322 | 1887197 |
| IC00939 | UG75 Expression | GENE | Mm.5736 | TITLE glucosamine-6-phosphate deaminase | GENE Gnpi | glucose-6-phosphate isomerase, oscillin[GNPDA| Ret-II| | NM_011937 | 318298 |
| IC00940 | UG75 Expression | GENE | Mm.20885 | TITLE golgi autoantigen, golgin subfamily a, 5 | GENE Golga5 | | NM_013747 | 1451105 |
| IC00941 | UG75 Expression | GENE | Mm.19039 | TITLE glutamate oxaloacetate transaminase 1, soluble | GENE Got1 | cAspAT[cytosolic aspartate aminotransferase[Got-1] | NM_010324 | 1451105 |
| IC00942 | UG75 Expression | GENE | Mm.18916 | TITLE glutamate oxaloacetate transaminase 2, mitochondrial | GENE Got2 | GABP-pm[Got-2][mAspA[mitochondrial aspartate aminotransferase[plasma membrane fatty acid binding protein] | NM_010325 | 1499328 |
| IC00943 | UG75 Expression | GENE | Mm.20365 | TITLE glycoprotein Ib, beta polypeptide | GENE Gp1bb | | NM_010327 | 2938190 |
| IC00944 | UG75 Expression | GENE | Mm.5903 | TITLE GPI anchor attachment protein 1 | GENE Gpaa1 | mGAA1| | NM_010331 | 1093798 |
| IC00945 | UG75 Expression | GENE | Mm.1528 | TITLE glypican 4 | GENE Gpc4 | k-glypican| | NM_008150 | 619020 |
| IC00946 | UG75 Expression | GENE | Mm.2840 | TITLE G-protein coupled receptor 25 | GENE Gpcr25 | TDAG8| | NM_008152 | 619907 |
| IC00947 | UG75 Expression | GENE | Mm.4772 | TITLE G-protein coupled receptor 26 | GENE Gpcr26 | clone 4.9[Kdt2]kidney cell line derived transcript 2][lpA1[vzg-1] | NM_010336 | 404566 |
| IC00948 | UG75 Expression | GENE | Mm.589 | TITLE glucose phosphate isomerase 1 complex | GENE Gpi1 | Gpi-1| | NM_008155 | 846367 |
| IC00949 | UG75 Expression | GENE | Mm.6354 | TITLE glycosylphosphatidylinositol 1 homolog (human) | GENE Gpi1h | Gpi1| | NM_011822 | 1195046 |
| IC00950 | UG75 Expression | GENE | Mm.2779 | TITLE phospholipase D1 | GENE Gpld1 | | NM_008156 | 1450433 |
| IC00951 | UG75 Expression | GENE | Mm.35009 | TITLE G protein-coupled receptor 27 | GENE Gpr27 | | NM_008158 | 1265023 |
| IC00952 | UG75 Expression | GENE | Mm.12890 | TITLE G protein-coupled receptor 33 | GENE Gpr33 | | gi = 3282841 | 575313 |
| IC00953 | UG75 Expression | GENE | Mm.20522 | TITLE G protein-coupled receptor 44 | GENE Gpr44 | | NM_009962 | 2225539 |
| IC00954 | UG75 Expression | GENE | Mm.57065 | TITLE G protein-coupled receptor 66 | GENE Gpr66 | FM-3| | NM_010341 | 973369 |
| IC00955 | UG75 Expression | GENE | Mm.10193 | TITLE G protien-coupled receptor kinase 6 | GENE Gprk6 | GRK6| | NM_011938 | 1366179 |
| IC00956 | UG75 Expression | GENE | Mm.1090 | TITLE glutathione peroxidase 1 | GENE Gpx1 | cellular GPx[CGPx[glutathione peroxidase[Gpx] | NM_008160 | 1891141 |
| IC00957 | UG75 Expression | GENE | Mm.7156 | TITLE glutathione peroxidase 3 | GENE Gpx3 | extracellular GPx[GPx[plasma Gpx] | NM_008161 | 1481200 |
| IC00958 | UG75 Expression | GENE | Mm.2400 | TITLE glutathione peroxidase 4 | GENE Gpx4 | | NM_008162 | 420345 |
| IC00959 | UG75 Expression | GENE | Mm.6900 | TITLE growth factor receptor bound protein 2 | GENE Grb2 | | NM_008163 | 578106 |
| IC00960 | UG75 Expression | GENE | Mm.17500 | TITLE growth factor receptor bound protein 7 | GENE Grb7 | | NM_010346 | 3154043 |
| IC00961 | UG75 Expression | GENE | Mm.2514 | TITLE gene rich cluster, A GENE | GENE Grca | | NM_013533 | 420054 |
| IC00962 | UG75 Expression | GENE | Mm.22195 | TITLE gene rich cluster, C10 GENE | GENE Grcc10 | | NM_013535 | 677106 |
| IC00963 | UG75 Expression | GENE | Mm.6390 | TITLE gene rich cluster, C2f GENE | GENE Grcc2f | | NM_013536 | 390914 |
| IC00964 | UG75 Expression | GENE | Mm.3634 | TITLE gene rich cluster, C3f GENE | GENE Grcc3f | | gi = 3287367 | 1229070 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC00965 | UG75 Expression | GENE | Mm.22228 | TITLE gene rich cluster, C8 GENE | GENE Grcc8 | | NM_013538 | 2780960 |
| IC00966 | UG75 Expression | GENE | Mm.2624 | TITLE gene rich cluster, C9 GENE | GENE Grcc9 | | NM_013539 | 1247887 |
| IC00967 | UG75 Expression | GENE | Mm.2626 | TITLE related to Drosophila groucho GENE | GENE Grg | AES|Grg5| | _010347 | 2582059 |
| IC00968 | UG75 Expression | GENE | Mm.1568 | TITLE granulin | GENE Grn | | NM_008175 | 1397208 |
| IC00969 | UG75 Expression | GENE | Mm.918 | TITLE glucose regulated protein, 78 kDa | GENE Grp78 | Bip|glucose-regulated protein (78 kDa)|Hsce70|SEZ-7| | gi = 1304156 | 1431906 |
| IC00970 | UG75 Expression | GENE | Mm.42045 | TITLE germ cell-specific GENE 2 | GENE Gsg2 | | NM_010353 | 636238 |
| IC00971 | UG75 Expression | GENE | Mm.21109 | TITLE gelsolin | GENE Gsn | | NM_010354 | 1969741 |
| IC00972 | UG75 Expression | GENE | Mm.20925 | TITLE G1 to phase transition 1 | GENE Gspt1 | G1-to-S transition GTP binding protein|G1st|Gst-1|GTP binding protein| | gi = 3461879 | 1280578 |
| IC00973 | UG75 Expression | GENE | Mm.7504 | TITLE glutathione synthetase | GENE Gss | GS-A/GS-B| | NM_008180 | 1921065 |
| IC00974 | UG75 Expression | GENE | Mm.87907 | TITLE glutathione-S-transferase, alpha 2 (Yc2) | GENE Gsta2 | alpha glutathione S-transferase 2-2|glutathione S-transferase Yc2 subunit|glutathione S-transferase, alpha 2 (Yc2)|Gst2-2|Gstc-2|Gstc2| | NM_008182 | 1481167 |
| IC00975 | UG75 Expression | GENE | Mm.14719 | TITLE glutathione-S-transferase, alpha 3 | GENE Gsta3 | alpha glutathione S-transferase 2-3|Gst2-3| | NM_010356 | 18889998 |
| IC00976 | UG75 Expression | GENE | Mm.2662 | TITLE glutathione-S-transferase, alpha 4 | GENE Gsta4 | GST 5.7| | NM_010357 | 1432505 |
| IC00977 | UG75 Expression | GENE | Mm.2011 | TITLE glutathione-S-transferase, mu 1 | GENE Gstm1 | glutathione S-transferase Yb1 subunit|glutathione S-transferase, mu 1|Gstb1|Gstb-1| | NM_010358 | 1888999 |
| IC00978 | UG75 Expression | GENE | Mm.14601 | TITLE glutathione-S-transferase, mu 2 | GENE Gstm2 | glutathione S-transferase Yb2 subunit|glutathione S-transferase, mu2|Gstb-2|Gstb2| | NM_008183 | 2182267 |
| IC00979 | UG75 Expression | GENE | Mm.31041 | TITLE glutathione-S-transferase, mu 6 | GENE Gstm6 | | NM_008184 | 1151549 |
| IC00980 | UG75 Expression | GENE | Mm.426 | TITLE glutathione-S-transferase, pi 2 | GENE Gstp2 | | gi = 577418 | 1451284 |
| IC00981 | UG75 Expression | GENE | Mm.2746 | TITLE glutathione-S-transferase, theta 1 | GENE Gstt1 | glutathione S-transferase, theta 1-1|Gstt1-1| | NM_008185 | 1431147 |
| IC00982 | UG75 Expression | GENE | Mm.24118 | TITLE glutathione-S-transferase, theta 2 | GENE Gstt2 | mGSTT2| | NM_010361 | 1891299 |
| IC00983 | UG75 Expression | GENE | Mm.282 | TITLE glutathione-S-transferase like | GENE Gsttl-per | p28| | NM_010362 | 3025757 |
| IC00984 | UG75 Expression | GENE | Mm.29652 | TITLE glutathione transferase zeta 1 (maleylacetoacetate isomerase) | GENE Gstz1 | MAA|maleylacetoacetate isomerase| | NM_010363 | 580925 |
| IC00985 | UG75 Expression | GENE | Mm.22700 | TITLE general transcription factor IIH, polypeptide 1 (62 kD subunit) | GENE Gtf2h1 | p62| | NM_008186 | 424898 |
| IC00986 | UG75 Expression | GENE | Mm.10182 | TITLE general transcription factor IIH, polypeptide 4 | GENE Gtf2h4 | p52|TFIIH| | NM_010364 | 576802 |
| IC00987 | UG75 Expression | GENE | Mm.22593 | TITLE general transcription factor II I | GENE Gtf2i | BAP-135|SPIN|TFII-I|WBSCR6| | NM_010365 | 615993 |
| IC00988 | UG75 Expression | GENE | Mm.23675 | TITLE gene trap locus 2 | GENE Gtl2 | | gi = 2739299 | 661378 |
| IC00989 | UG75 Expression | GENE | Mm.2080 | TITLE gene trap locus 3 | GENE Gtl3 | T10-2A2| | NM_008187 | 3155848 |
| IC00990 | UG75 Expression | GENE | Mm.19080 | TITLE GTP binding protein 1 | GENE Gtpbp | GP-1| | NM_013818 | 902093 |
| IC00991 | UG75 Expression | GENE | Mm.17946 | TITLE gene trap ROSA 26 | GENE Gtrosa26 | GENE trap ROSA b-geo 26|Gtrgeo26| | gi = 1778858 | 619948 |
| IC00992 | UG75 Expression | GENE | Mm.781 | TITLE gene trap ROSA 26 antisense | GENE Gtrosa26as | | NM_0088188 | 3166711 |
| IC00993 | UG75 Expression | GENE | Mm.20858 | TITLE G two S phase expressed protein 1 | GENE Gtse1 | B99| | NM_013882 | 1265282 |
| IC00994 | UG75 Expression | GENE | Mm.16224 | TITLE guanylate cyclase activator 1a (retina) | GENE Guca1a | Gcap1|guanylate cyclase activator 1| | NM_008189 | 793652 |
| IC00995 | UG75 Expression | GENE | Mm.3624 | TITLE guanylate kinase 1 | GENE Guk1 | GMK| | NM_008189 | 1006908 |
| IC00996 | UG75 Expression | GENE | Mm.24593 | TITLE guanylate kinase membrane-associated inverted 1 | GENE Gukmi1 | Magi-1| | gi = 2702346 | 3025587 |
| IC00997 | UG75 Expression | GENE | Mm.3317 | TITLE beta-glucoronidase structural | GENE Gus-s | g|GusB| | NM_010368 | 2076874 |
| IC00998 | UG75 Expression | GENE | Mm.6375 | TITLE glycogenin 1 | GENE Gyg1 | | NM_013755 | 736708 |
| IC00999 | UG75 Expression | GENE | Mm.3242 | TITLE glycerol kinase | GENE Gyk | GK| | NM_008194 | 2331735 |
| IC01000 | UG75 Expression | GENE | Mm.13123 | TITLE glycophorin A | GENE Gypa | | NM_010369 | 734015 |
| IC01001 | UG75 Expression | GENE | Mm.35662 | TITLE glycogen synthase 3, brain | GENE Gys3 | | NM_008195 | 2581965 |
| IC01002 | UG75 Expression | GENE | Mm.15510 | TITLE granzyme A | GENE Gzma | BLT esterase|Ctla-3|Ctla3|cytotoxic T lymphocyte-associated protein 3|Hanukah factor|Hf|serine esterase 1|TSP-1|CCP-1/C11|CCP|Ctla|cytotoxic T lymphocyte- | NM_010370 | 2648572 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01003 | UG75 Expression | GENE | Mm.14874 | TITLE granzyme B | GENE Bzmb | associated protein 1] | NM_013542 | 1247757 |
| IC01004 | UG75 Expression | GENE | Mm.14431 | TITLE granzyme F | GENE Gzmf | AKA granzyme G|CCP4|CTL serine protease 3|Ctla-7|Ctla7|cytotoxic T lymphocyte-associated protein 7|granzyme G|MCSP-3| | NM_010374 | 1434509 |
| IC01005 | UG75 Expression | GENE | Mm.14802 | TITLE H19 fetal liver mRNA | GENE H19 | | gi = 51131 | 2076664 |
| IC01006 | UG75 Expression | GENE | Mm.24350 | TITLE H1-0 histone | GENE H1fv | | NM_008197 | 736630 |
| IC01007 | UG75 Expression | GENE | Mm.14176 | TITLE histocompatibility 2, class II antigen A, alpha | GENE H2-Aa | H-2Aa|histocompaitibility 2, class II antigen A alpha| I region-associated antigen 1|Ia-1|Ia1| | gi = 2555188 | 2646264 |
| IC01008 | UG75 Expression | GENE | Mm.6716 | TITLE histocompatibility 2, class II antigen A, beta 1 | GENE H2-Ab1 | H-2Ab|H2-Ab|histocompatibility 2, class II antigen A beta 1|histocompatibility 2, class II antigen A, beta|I-region-associated antigen 2|Ia-2|Ia2| | NM_010379 | 947701 |
| IC01009 | UG75 Expression | GENE | Mm.653 | TITLE histocompatibility 2, complement component factor B | GENE H2-Bf | B|Bf|complement component factor B|Factor B| | NM_008198 | 2182358 |
| IC01010 | UG75 Expression | GENE | Mm.33263 | TITLE histocompatibility 2, D region locus 1 | GENE H2-D | H-2D| | NM_010380 | 1152166 |
| IC01011 | UG75 Expression | GENE | Mm.16373 | TITLE histocompatibility 2, class II, locus DMa | GENEH2-DMa | | NM_010386 | 1281039 |
| IC01012 | UG75 Expression | GENE | Mm.3322 | TITLE histocompatibility 2, class II, locus Mb1 | GENE H2-DMb | H-2Ma|H2-Ma|histocompatibility 2, class II, locus Ma| | NM_010387 | 330314 |
| IC01013 | UG75 Expression | GENE | Mm.22564 | TITLE histocompatibility 2, class II antigen E beta | GENE H-2EB|I region-associated antigen 4|Ia-4|Ia4| | H-2Mb1|H2-Mb1| | NM_010382 | 1383590 |
| IC01014 | UG75 Expression | GENE | Mm.16771 | TITLE histocompatibility 2, K region | GENE H2-K | H-2K1| | gi = 2182262 | 1513755 |
| IC01015 | UG75 Expression | GENE | Mm.35712 | TITLE histocompatibility 2, K region locus 2 | GENE H2-K2 | H-2K2| | gi = 199435 | 1137264 |
| IC01016 | UG75 Expression | GENE | Mm.2948 | TITLE H2-K region expressed GENE 2 | GENE H2-Ke2 | H-2K region expressed gene 2|H-2Ke2|Ke-2| | NM_010385 | 1195131 |
| IC01017 | UG75 Expression | GENE | Mm.18556 | TITLE H2-K region expressed GENE 4 | GENE H2-Ke4 | H-2K region expressed gene 4|H-2Ke4|Ke-4| | NM_008202 | 1069197 |
| IC01018 | UG75 Expression | GENE | Mm.15479 | TITLE H2-K region expressed GENE 6 | GENE H2-Ke6 | H-2K region expressed gene 6|H-2Ke-6| | NM_013543 | 1243182 |
| IC01019 | UG75 Expression | GENE | Mm.14437 | TITLE histocompatibility 2, M region locus 3 | GENE H2-M3 | H-2M3|Hmt| | NM_013819 | 635710 |
| IC01020 | UG75 Expression | GENE | Mm.116 | TITLE histocompatibility 2, O region alpha locus | GENE H2-Oa | H-2Oa| | NM_008206 | 576900 |
| IC01021 | UG75 Expression | GENE | Mm.29188 | TITLE histocompatibility 2, O region beta locus | GENE H2-Ob | H-2|H-2Ob|H2-Ab|H2-Ab2|histocompatibility 2, class II antigen A, beta|histocompatibility 2, class II antigen A beta 2|Ob| | NM_010389 | 597054 |
| IC01022 | UG75 Expression | GENE | Mm.34421 | TITLE histocompatibility 2, Q region locus 7 | GENE H2-Q7 | H-2Q7|Qa lymphocyte antigen 7|Qa-7|Qa7| | NM_010394 | 1154350 |
| IC01023 | UG75 Expression | GENE | Mm.35016 | TITLE histocompatibility 2, T region locus 23 | GENE H2-T23 | H-2T23| | NM_010398 | 1450553 |
| IC01024 | UG75 Expression | GENE | Mm.14573 | TITLE histocompatibility 2, T region locus 24 | gne eH2-T24 | H-2T24| | NM_008207 | 1149503 |
| IC01025 | UG75 Expression | GENE | Mm.7580 | TITLE histocompatibility-2 complex class 1-like sequence | GENE H2ls | NMR1| | NM_008209 | 577177 |
| IC01026 | UG75 Expression | GENE | Mm.89136 | TITLE H3 histone, family 3A | GENE H3f3a | H3.3A| | NM_008210 | 1887667 |
| IC01027 | UG75 Expression | GENE | Mm.18516 | TITLE H3 histone, family 3B | GENE H3f3b | H3.3B| | NM_008211 | 2064854 |
| IC01028 | UG75 Expression | GENE | Mm.2491 | TITLE hydroxyacyl-Coenzyme A dehydrogenase-dehydrogenase | GENE Hadh | HD|L-bifunctional enzyme|L-PBE|MFP| | NM_008212 | 2236013 |
| IC01029 | UG75 Expression | GENE | Mm.10717 | TITLE hintingtin-associated protein 1 | GENE Hap1 | | NM_010404 | 2598833 |
| IC01030 | UG75 Expression | GENE | Mm.10528 | TITLE histidyl tRNA synthetase | GENE Hars | MMHRS| | NM_008214 | 475357 |
| IC01031 | UG75 Expression | GENE | Mm.7401 | TITLE HS1 binding protein | GENE Hax1-pend-ing | | NM_011826 | 1891175 |
| IC01032 | UG75 Expression | GENE | Mm.16820 | TITLE hemoglobin alpha, adult chain 1 | GENE Hba-a1 | alpha 1 globin| | NM_008218 | 1885025 |
| IC01033 | UG75 Expression | GENE | Mm.2308 | TITLE hemoglobin beta chain complex | GENE Hbb | beta maj|beta major globin| | NM_008219 | 2101237 |
| IC01034 | UG75 Expression | GENE | Mm.35830 | TITLE hemoglobin Y, beta-like embryonic chain | GENE Hbb-y | epsilon Y globin| | NM_008221 | 1315458 |
| IC01035 | UG75 Expression | GENE | Mm.10001 | TITLE holocytochrome c synthetase | GENE Hccs | | NM_008222 | 580968 |
| IC01036 | UG75 Expression | GENE | Mm.6609 | TITLE heparin cofactor II | GENE Hcf2 | HC II| | NM_008223 | 1888683 |
| IC01037 | UG75 Expression | GENE | Mm.715 | TITLE hemopoietic cell kinase | GENE Hck | B-cell myeloid kinase|Bmk|Hck-1|hemopoietic cell kinase 1| | NM_010407 | 597097 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01038 | UG75 Expression | GENE | Mm.4091 | TITLE hematopoietic cell specific Lyn substrate 1 | GENE Hcls1 | HS1| | NM_008225 | 597801 |
| IC01039 | UG75 Expression | GENE | Mm.1484 | TITLE hemopoietic cell phosphatase | GENE Hcph | me|motheaten|PTPN6|SHP-1| | NM_013545 | 597644 |
| IC01040 | UG75 Expression | GENE | Mm.24026 | TITLE hematopoietic cell signal transducer | GENE Hcst | DAP10| | NM_011827 | 640698 |
| IC01041 | UG75 Expression | GENE | Mm.2602 | TITLE histone deacetylase 1 | GENE Hdac1 | HD1|RPD3| | NM_008228 | 3025956 |
| IC01042 | UG75 Expression | GENE | Mm.19806 | TITLE histone deacetylase 2 | GENE Hdac2 | mRPD3|YY1 transcription factor binding protein|Yy1bp| | _008229 | 355035 |
| IC01043 | UG75 Expression | GENE | Mm.18603 | TITLE histidine decarboxylase cluster | GENE Hdc | | NM_008230 | 12225742 |
| IC01044 | UG75 Expression | GENE | Mm.1141 | TITLE hepatoma-derived growth factor | fGENE Hdgf | | NM_008231 | 2939140 |
| IC01045 | UG75 Expression | GENE | Mm.38268 | TITLE hepatoma-derived growth factor, related protein 2 | GENE Hdgfrp2 | HRP-2| | NM_008233 | 329369 |
| IC01046 | UG75 Expression | GENE | Mm.17249 | TITLE heme-binding protein | GENE Hebp-pe | p22 HBP| | NM_013546 | 2921756 |
| IC01047 | UG75 Expression | GENE | Mm.4661 | TITLE heparin binding epidermal growth factor-like growth factor | GENE Hegfl | HB-EGF| | _010415 | 391462 |
| IC01048 | UG75 Expression | GENE | Mm.27494 | TITLE hephaestin | GENE Heph | haphaestin|sex linked anemia|sla|jdf2|juvenile development and fertility 2|rjs|runting, jerky gait, sterility| | NM_010417 | 1382402 |
| IC01049 | UG75 Expression | GENE | Mm.20929 | terminus) domain and RCC1 (CHC1)-like domain (RLD) 2 | GENE Herc2 | | gi = 3414808 | 644973 |
| IC01050 | UG75 Expression | GENE | Mm.4451 | TITLE hairy and enhancer of split 1, (Drosophila) | GENE Hes1 | HTLF1| | NM_008235 | 863393 |
| IC01051 | UG75 Expression | GENE | Mm.4943 | TITLE hairy and enhancer of split 5, (Drosophila) | GENE Hes5 | | NM_010419 | 400761 |
| IC01052 | UG75 Expression | GENE | Mm.2284 | TITLE hexosaminidase A | GENE Hexa | | NM_010421 | 606765 |
| IC01053 | UG75 Expression | GENE | Mm.27816 | TITLE hexosaminidase B | GENE Hexb | Hex-1| | NM_010422 | 2598906 |
| IC01054 | UG75 Expression | GENE | Mm.29581 | TITLE hairy/enhancer-of-split related with YRPW motif 1 | GENE Hey1 | Hairy/E(spl)-related with YRPW motif|hesr-1| | NM_010423 | 2655421 |
| IC01055 | UG75 Expression | GENE | Mm.2681 | TITLE hemochromatosis | GENE Hfe | MR2| | NM_010424 | 693674 |
| IC01056 | UG75 Expression | GENE | Mm.4496 | TITLE HNF-3/forkhead homolog 11 | GENE Hfh11 | nu|nude|Whn| | NM_008238 | 1329145 |
| IC01057 | UG75 Expression | GENE | Mm.3776 | TITLE homogentisate 1, 2-dioxygenase | GENE Hgd | D4|Gdid4|GDP dissociation inhibitor, D4|Ly-GDI| | NM_013547 | 518730 |
| IC01058 | UG75 Expression | GENE | Mm.7919 | TITLE HGF-regulated tyrosine kinase substrate | GENE Hgs | Hrs|Hex|Prh|Prhx|proline-rich homeodomain-containing transcription factor| | NM_008244 | 401297 |
| IC01059 | UG75 Expression | GENE | Mm.33896 | TITLE hematopoietically expressed homeobox | GENE Hhex | | NM_008245 | 1431231 |
| IC01060 | UG75 Expression | GENE | Mm.3792 | TITLE hippocampus abundant GENE transcript 1 | GENE Hiat1 | | NM_008246 | 2648574 |
| IC01061 | UG75 Expression | GENE | Mm.57250 | TITLE hypermethylated in cancer 1 | GENE Hic1 | brain X-linked gene|Brx| | NM_010430 | 1449088 |
| IC01062 | UG75 Expression | GENE | Mm.2598 | TITLE hydrogen peroxide inducible protein 53 | GENE Hic53 | | gi = 1161099 | 1345626 |
| IC01063 | UG75 Expression | GENE | Mm.3879 | TITLE hypoxia inducible factor 1, alpha subunit | GENE Hif1a | | NM_010431 | 2135910 |
| IC01064 | UG75 Expression | GENE | Mm.425 | TITLE histidine triad nucleotide-binding protein | GENE Hint | | gi = 1519045 | 583258 |
| IC01065 | UG75 Expression | GENE | Mm.20827 | TITLE homeodomain interacting protein kinase 1 | GENE Hipk1 | PKCI-1|PRKCNH1, protein kinase C inhibitor 1| | NM_010432 | 1123244 |
| IC01066 | UG75 Expression | GENE | Mm.20934 | TITLE homeodomain interacting protein kinase 2 | GENE Hipk2 | | NM_010433 | 920623 |
| IC01067 | UG75 Expression | GENE | Mm.15694 | TITLE histone cell cycle regulation defective homolog A (S. cerevisiae) | GENE Hira | Tup-like enhancer of split 1|Tuple1| | _010435 | 556524 |
| IC01068 | UG75 Expression | GENE | Mm.15686 | TITLE histone gene complex 2 | GENE Hist2 | | gi = 496635 | 582094 |
| IC01069 | UG75 Expression | GENE | Mm.14775 | TITLE histone 4 protein | GENE Hist4 | | NM_013550 | 479483 |
| IC01070 | UG75 Expression | GENE | Mm.14767 | TITLE histone 5 protein 2ax | GENE Hist5-2a: | H2A.X|H2ax|H2AX histone| | NM_010436 | 2655169 |
| IC01071 | UG75 Expression | GENE | Mm.42157 | TITLE human immunodeficiency virus type I enhancer-binding protein 2 | GENE Hivep2 | MIBP1| | NM_010437 | 438455 |
| IC01072 | UG75 Expression | GENE | Mm.5290 | TITLE hexokinase 1 | GENE Hk1 | Hk-1| | NM_010438 | 603919 |
| IC01073 | UG75 Expression | GENE | Mm.2549 | TITLE hexokinase 2 | GENE Hk2 | HKII| | NM_013820 | 832874 |
| IC01074 | UG75 Expression | GENE | Mm.103 | TITLE house-keeping protein 1 | GENE Hkp1 | | NM_008249 | 1481503 |
| IC01075 | UG75 Expression | GENE | Mm.1710 | TITLE hydroxymethylbilane synthase PBGD|porphobilinogen deaminase|Ups|uroporphyrinogen I synthetase|Uros1| | GENE Hmbs | | gi = 200231 | 1450638 |
| IC01076 | UG75 Expression | GENE | Mm.16421 | TITLE high mobility group protein 1 | GENE Hmg1 | | NM_010439 | 2536708 |
| IC01077 | UG75 Expression | GENE | Mm.2756 | TITLE high mobility group protein 14 | GENE Hmg14 | | NM_008251 | 1888726 |
| IC01078 | UG75 Expression | GENE | Mm.1693 | TITLE high mobility group protein 2 | GENE Hmg2 | | NM_008252 | 2609580 |
| IC01079 | UG75 Expression | GENE | Mm.340 | TITLE high-mobility group protein 4 | GENE Hmg4 | | NM_008253 | 478561 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01080 | UG75 Expression | GENE | Mm.22668 | TITLE 3-hydroxy-3-methylglutaryl-Coenzyme A lyase | GENE Hmgcl | HL| | NM_008254 | 2938195 |
| IC01081 | UG75 Expression | GENE | Mm.2226 | TITLE 3-hydroxy-3-methylglutaryl-Coenzyme A reductase | GENE Hmgcr | | gi = 193881 | 1229971 |
| IC01082 | UG75 Expression | GENE | Mm.10633 | TITLE 3-hydroxy-3-methylglutaryl-Coenzyme A synthase 2 | GENE Hmgcs2 | mHS| | gi = 55836 | 1482021 |
| IC01083 | UG75 Expression | GENE | Mm.35748 | TITLE hyaluronan mediated motility receptor (RHAMM) | GENE Hmmr | receptor for HA-mediated motility|Rhamm| | NM_013552 | 604642 |
| IC01084 | UG75 Expression | GENE | Mm.17980 | TITLE heme oxygenase (decycling) 1 | GENE Hmox1 | HO-1|Hsp32| | NM_010442 | 1229226 |
| IC01085 | UG75 Expression | GENE | Mm.710 | TITLE heme oxygenase (decycling) 2 | GENE Hmox2 | HO-2| | NM_010443 | 602116 |
| IC01086 | UG75 Expression | GENE | Mm.5016 | TITLE H6 homeo box 3 | GENE Hmx3 | Drosophila NK transcription factor related, gene family 5, locus 1|Nkx5-1| | NM_008257 | 583663 |
| IC01087 | UG75 Expression | GENE | Mm.1775 | TITLE hematological and neurological expressed sequence 1 | GENE Hn1 | | NM_008258 | 1446818 |
| IC01088 | UG75 Expression | GENE | Mm.27927 | TITLE heterogenous nuclear ribonucleoprotein A1 | GENE Hnrpa1 | hnrmp-A| | NM_010447 | 402487 |
| IC01089 | UG75 Expression | GENE | Mm.24 | TITLE heterogenous nuclear ribonucleoprotein A/B | GENE Hnrpab | CBF-A| | NM_010448 | 2646987 |
| IC01090 | UG75 Expression | GENE | Mm.30386 | TITLE homer, neuronal immediate early GENE, 1 | GENE Homer1- | Ves-1| | NM_011982 | 642254 |
| IC01091 | UG75 Expression | GENE | Mm.228 | TITLE homer, neuronal immediate early GENE, 2 | GENE Homer2- | qCPD|Cupidin|Vesl-2| | gi = 4150949 | 975789 |
| IC01092 | UG75 Expression | GENE | Mm.10022 | TITLE homer, neuronal immediate early GENE, 3 | GENE Homer3-pending | | gi = 3834612 | 1162828 |
| IC01093 | UG75 Expression | GENE | Mm.131 | TITLE homeo box A2 | GENE Hoxa2 | homeo box-1 cluster, gene 11|Hox-1.11| | NM_010451 | 333548 |
| IC01094 | UG75 Expression | GENE | Mm.173 | TITLE homeo box A5 | GENE Hoxa5 | homeo box-1 cluster, gene 3|Hox-1.3| | NM_010453 | 465937 |
| IC01095 | UG75 Expression | GENE | Mm.1351 | TITLE homeo box C4 | GENE Hoxc4 | homeo box-3 cluster, GENE 5|Hox-3.5| | NM_013553 | 678569 |
| IC01096 | UG75 Expression | GENE | Mm.18832 | TITLE hydroxyprostaglandin dehydrogenase 15 (NAD) | GENE Hpgd | 15-PGDH| | NM_008278 | 1026064 |
| IC01097 | UG75 Expression | GENE | Mm.36 | TITLE hepatic lipase | GENE Hpl | Lipc| | NM_008280 | 1890227 |
| IC01098 | UG75 Expression | GENE | Mm.19182 | TITLE hepsin | GENE Hpn | | NM_008281 | 1972063 |
| IC01099 | UG75 Expression | GENE | Mm.18675 | TITLE hypoxanthine guanine phosphoribosyl transferase | GENE Hprt | | NM_013556 | 718608 |
| IC01100 | UG75 Expression | GENE | Mm.6793 | TITLE Harvey rat sarcoma virus oncogene | GENE Hras1 | Ha-ras|Hras-1| | NM_008284 | 1209604 |
| IC01101 | UG75 Expression | GENE | Mm.6461 | TITLE HIV-1 Rev binding protein | GENE Hrb | RAB|Rip| | gi = 3063650 | 3025955 |
| IC01102 | UG75 Expression | GENE | Mm.2607 | TITLE heat-repsonsive protein 12 | GENE Hrsp12 | HR12|HRP12| | NM_008287 | 1481376 |
| IC01103 | UG75 Expression | GENE | Mm.12559 | TITLE heparan sulfate (glucosamine) 3-O-sulfotransferase 1 | GENE Hs3st1 | 3-OST|heparan sulfate glucosaminyl 3-O-sulfotransferase|Hsg3ost-pending| | NM_010474 | 1891349 |
| IC01104 | UG75 Expression | GENE | Mm.2944 | TITLE heat shock protein cognate 70 | GENE Hsc70 | Hsc73| | gi = 194034 | 2182202 |
| IC01105 | UG75 Expression | GENE | Mm.14287 | TITLE heat shock protein cognate 70, testis | GENE Hsc70t | | NM_013558 | 515296 |
| IC01106 | UG75 Expression | GENE | Mm.5079 | TITLE hydroxysteroid 11-beta dehydrogenase 2 | GENE Hsd11b2 | 11(beta)-HSD2| | NM_008289 | 1001696 |
| IC01107 | UG75 Expression | GENE | Mm.8877 | TITLE hydroxysteroid 17-beta dehydrogenase 2 | GENE Hsd17b2 | 17 HSD type 2| | NM_008290 | 1886664 |
| IC01108 | UG75 Expression | GENE | Mm.3195 | TITLE hydroxysteroid 17-beta dehydrogenase 4 | GENE Hsd17b4 | 17[b]-HSD|MFE-2|perMFE-2| | NM_008292 | 2647287 |
| IC01109 | UG75 Expression | GENE | Mm.16941 | TITLE hydroxysteroid dehydrogenase-1, delta<5>-3-beta | GENE Hsd3b1 | | NM_008293 | 518881 |
| IC01110 | UG75 Expression | GENE | Mm.14309 | TITLE hydroxysteroid dehydrogenase-4, delta<5>-3-beta | GENE Hsd3b4 | | NM_008294 | 1431964 |
| IC01111 | UG75 Expression | GENE | Mm.4841 | TITLE heat shock factor 1 | GENE Hsf1 | | gi = 51445 | 1248225 |
| IC01112 | UG75 Expression | GENE | Mm.27897 | TITLE heat shock protein, DNAJ-like 2 | GENE Hsj2 | | NM_008298 | 1971518 |
| IC01113 | UG75 Expression | GENE | Mm.34828 | TITLE heat shock protein, 105 kDa | GENE Hsp105 | hsp-E7|HSP105 42 C-HSP| | NM_013559 | 1853067 |
| IC01114 | UG75 Expression | GENE | Mm.1032 | TITLE heat shock protein, 110 kDa | GENE Hsp110 | APG02| | NM_008300 | 2136817 |
| IC01115 | UG75 Expression | GENE | Mm.13849 | TITLE heat shock protein, 25 kDa | GENE Hsp25 | | NM_013560 | 2088146 |
| IC01116 | UG75 Expression | GENE | Mm.1777 | TITLE heat shock protein, 60 kDa | GENE Hsp60 | | gi = 51451 | 1450743 |
| IC01117 | UG75 Expression | GENE | Mm.6388 | TITLE heat shock protein, 70 kDa 1 | GENE Hsp70-1 | heat shock protein, 70|hsp68|Hsp70| | gi = 194022 | 1381397 |
| IC01118 | UG75 Expression | GENE | Mm.2180 | TITLE heat shock protein, 84 kDa 1 | GENE Hsp84-1 | heat shock protein, 80 kDa|Hsp80| | NM_008302 | 1920933 |
| IC01119 | UG75 Expression | GENE | Mm.1843 | TITLE heat shock protein, 86 kDa 1 | GENE Hsp86-1 | heat shock protein, 90 kDa|hsp4|Hsp90| | NM_010480 | 2225729 |
| IC01120 | UG75 Expression | GENE | Mm.2849 | TITLE heat shock protein, 74 kDa, A | GENE Hspa9a | heat shock protein cognate 74|heat shock protein, 74 kDa|Hsc74|Hsp74|mortalin|mot2| | NM_010481 | 2064828 |
| IC01121 | UG75 Expression | GENE | Mm.12970 | TITLE heat shock 10 kDa protein 1 (chaperonin 10) | GENE Hspe1 | mt-cpn10| | NM_008303 | 1973362 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01122 | UG75 Expression | GENE | Mm.5128 | TITLE HpaII tiny fragments locus 9c | GENE Htf9c | | NM_010485 | 408100 |
| IC01123 | UG75 Expression | GENE | Mm.21766 | TITLE HU-antigen A | GENE Hua | | NM_010485 | 408100 |
| IC01124 | UG75 Expression | GENE | Mm.10305 | TITLE hyaluronidase 1 | GENE Hyal1 | Hyal-1\| | NM_008317 | 864794 |
| IC01125 | UG75 Expression | GENE | Mm.35835 | TITLE intracisternal A particles | GENE Iap | p140mDia\| | NM_010490 | 1294523 |
| IC01126 | UG75 Expression | GENE | Mm.415 | TITLE islet amyloid polypeptide | GENE Iapp | amylin\| | NM_010491 | 1379049 |
| IC01127 | UG75 Expression | GENE | Mm.3545 | TITLE islet cell autoantigen 1, 69 kDa | GENE Ica1 | ICA69\| | NM_010492 | 438172 |
| IC01128 | UG75 Expression | GENE | Mm.28973 | TITLE intercellulary adhesion molecule | GENE Icam1 | CD54\|CAM-1\|Ly-47\|lymphocyte antigen 47\|MALA-2\| | gi = 194077 | 2225487 |
| IC01129 | UG75 Expression | GENE | Mm.394 | TITLE intercellular adhesion molecule 2 | GENE Icam2 | CD102\|ICAM-2\|Ly-60\| | NM_010494 | 2645551 |
| IC01130 | UG75 Expression | GENE | Mm.3182 | TITLE interferon concensus sequence binding protein | GENE Icsbp | | NM_008320 | 577563 |
| IC01131 | UG75 Expression | GENE | Mm.1466 | TITLE inhibitor of DNA binding 2 | GENE Idb2 | Id2\| | NM_010496 | 2101783 |
| IC01132 | UG75 Expression | GENE | Mm.110 | TITLE inhibitor of DNA binding 3 | GENE Idb3 | HLH462\|Id3\| | NM_008321 | 1499036 |
| IC01133 | UG75 Expression | GENE | Mm.28223 | TITLE inhibitor of DNA binding 4 | GENE Idb4 | Id4\| | gi = 402637 | 1400662 |
| IC01134 | UG75 Expression | GENE | Mm.9925 | TITLE isocitrate dehydrogenase 1 (NADP+), soluble | GENE Idh1 | Id-1\|Idh-1\|isocitrate dehydrogenase 1\| | NM_010497 | 423747 |
| IC01135 | UG75 Expression | GENE | Mm.2966 | TITLE isocitrate dehydrogenase 2 (NAD+), mitochondrial | GENE Idh2 | Id-2\|isocitrate dehydrogenase 2\| | NM_008322 | 1039586 |
| IC01136 | UG75 Expression | GENE | Mm.14825 | TITLE isocitrate dehydrogenase 3 (NAD+), gamma | GENE Idh-2\|isocitrate dehydrogenase 2\] | | NM_008323 | 1886034 |
| IC01137 | UG75 Expression | GENE | Mm.3054 | TITLE alpha-L-iduronidase | GENE Idua | | NM_008325 | 1382816 |
| IC01138 | UG75 Expression | GENE | Mm.399 | TITLE immediate early response 2 | GENE Ier2 | ch1\|pip92\| | NM_010499 | 2936865 |
| IC01139 | UG75 Expression | GENE | Mm.25613 | TITLE immediate early response 3 | GENE Ier3 | gly96\| | gi = 287803 | 1381903 |
| IC01140 | UG75 Expression | GENE | Mm.12246 | TITLE immediate early response 5 | GENE Ier5 | | NM_010500 | 818296 |
| IC01141 | UG75 Expression | GENE | Mm.29938 | TITLE interferon inducible protein 1 | GENE Ifi1 | LRG-47\| | NM_008328 | 1515756 |
| IC01142 | UG75 Expression | GENE | Mm.18530 | TITLE interferon activated GENE 203 | GENE Ifi203 | | NM_008328 | 1515756 |
| IC01143 | UG75 Expression | GENE | Mm.34817 | TITLE interferon activated GENE 204 | GENE Ifi204 | | NM_008329 | 1886499 |
| IC01144 | UG75 Expression | GENE | Mm.24769 | TITLE interferon gamma inducible protein, 47 kDa | GENE Ifi47 | | NM_008330 | 2651285 |
| IC01145 | UG75 Expression | GENE | Mm.6718 | TITLE interferon-induced protein with tetratricopeptide repeats 1 | GENE Ifit1 | Ifi56\|interferon inducible protein 56\| | NM_008331 | 616653 |
| IC01146 | UG75 Expression | GENE | Mm.2036 | TITLE interferon-induced protein with tetratricopeptide repeats 2 | GENE Ifit2 | Ifi54\|interferon inducible protein 54\| | NM_008332 | 717941 |
| IC01147 | UG75 Expression | GENE | Mm.951 | TITLE interferon-induced protein with tetratricopeptide repeats 3 | GENE Ifit3 | Ifi49\|interferon inducible protein 49\| | NM_010501 | 617022 |
| IC01148 | UG75 Expression | GENE | Mm.502 | TITLE interferon (alpha and beta) receptor | GENE Ifnar | CD118\|Ifar\|Ifrc\|INF-a receptor\| | NM_010508 | 2646062 |
| IC01149 | UG75 Expression | GENE | Mm.6834 | TITLE interferon (alpha and beta) receptor 2 | GENE Ifnar2 | | NM_010509 | 2076826 |
| IC01150 | UG75 Expression | GENE | Mm.549 | TITLE interferon gamma receptor | GENE Ifngr | CD119\|Ifgr\|Ifg\|interferon gamma transducer\| | NM_010511 | 920516 |
| IC01151 | UG75 Expression | GENE | Mm.22698 | TITLE interferon gamma receptor 2 | GENE Ifngr2 | PC4\|Tis7\| | NM_008338 | 458720 |
| IC01152 | UG75 Expression | GENE | Mm.168 | TITLE interferon-related developmental regulator 1 | GENE Ifrd1 | | NM_013562 | 943907 |
| IC01153 | UG75 Expression | GENE | Mm.2987 | TITLE immunoglobulin-associated beta | GENE Igb | B29\| | NM_008339 | 596470 |
| IC01154 | UG75 Expression | GENE | Mm.7454 | TITLE immunoglobulin (CD79A) binding protein 1 | GENE Igbp1 | alpha 4\|p52\|Pc52\|phosphoprotein, component, 52 kDa\| | NM_008784 | 2749308 |
| IC01155 | UG75 Expression | GENE | Mm.2770 | TITLE insulin-like growth factor 1 | GENE Igf1 | Igf-1\| | NM_010512 | 2247498 |
| IC01156 | UG75 Expression | GENE | Mm.3862 | TITLE insulin-like growth factor 2 | GENE Igf2 | Igf-2\| | NM_010514 | 614406 |
| IC01157 | UG75 Expression | GENE | Mm.2938 | TITLE insulin-like growth factor 2 receptor | GENE Igf2r | cation-independent mannose 6-phosphate receptor\|cation-independent MPR\|CI-MPR\|IGF-II/CI-MPR\|Mpr300\| | gi = 451552 | 1400527 |
| IC01158 | UG75 Expression | GENE | Mm.3135 | TITLE insulin-like growth factor binding protein, acid labile subunit | GENE Igfals | acid-labile subunit\|Albs\| | NM_008340 | 1922694 |
| IC01159 | UG75 Expression | GENE | Mm.29254 | TITLE insulin-like growth factor binding protein 3 | GENE Igfbp3 | | NM_008343 | 555520 |
| IC01160 | UG75 Expression | GENE | Mm.578 | TITLE insulin-like growth factor binding protein 5 | GENE Igfbp5 | | NM_010518 | 2099710 |
| IC01161 | UG75 Expression | GENE | Mm.534 | TITLE insulin-like growth factor binding protein 7 | GENE Igfbp7 | follistatin-like 2\|Fstl2\|mac25\| | NM_008048 | 2331903 |
| IC01162 | UG75 Expression | GENE | Mm.14721 | TITLE immunoglobulin heavy chain 1 (serum IgG2a) | GENE Igh-1 | | gi = 1799552 | 1166446 |
| IC01163 | UG75 Expression | GENE | Mm.14438 | TITLE immunoglobulin heavy chain 3 (serum IgG2b) | GENE Igh-3 | | gi = 1799552 | 1448206 |

TABLE 1-continued

| IC ID | Module | IC Selection method | UniGene | UniGene/LocusLink Title | Gene Symbol | Alias | Selected Reference | IMAGE |
|---|---|---|---|---|---|---|---|---|
| IC01164 | GENE | UG75 Expression | Mm.2066 | TITLE interferon gamma inducing factor binding protein | GENE Igh-6 | Ig mu|Igh-M|immunoglobulin heavy chain mu| | gi = 194417 | 551003 |
| IC01165 | GENE | UG75 Expression | Mm.45579 | TITLE interferon gamma inducing factor binding protein | GENE Igifbp | IL-18BP|MC541| | NM_010531 | 597161 |
| IC01166 | GENE | UG75 Expression | Mm.16253 | TITLE immunoglobulin kappa chain variable 28 (V28) | GENE Igk-V28 | | gi = 1549272 | 1166424 |
| IC01167 | GENE | UG75 Expression | Mm.7043 | TITLE Ia-associated invariant chain | GENE Ii | Fli1| | gi = 52631 | 1450894 |
| IC01168 | GENE | UG75 Expression | Mm.86427 | TITLE inhibitor of kappa light polypeptide GENE enhancer in B-cells, kinase beta | GENE Ikbkb | IDD-2|KK-beta|KK[b]|IKK2| | gi = 313210 | 987156 |
| IC01169 | GENE | UG75 Expression | Mm.874 | TITLE interleukin 10 | GENE Il10 | CSIF|cytokine synthesis inhibitory factor|IL-10| | NM_010548 | 1002777 |
| IC01170 | GENE | UG75 Expression | Mm.26658 | TITLE interleukin 10 receptor, alpha | GENE Il10ra | Il10r|interleukin 10 receptor|mIL-10R| | NM_008348 | 1498509 |
| IC01171 | GENE | UG75 Expression | Mm.4154 | TITLE interleukin 10 receptor, beta | GENE Il10rb | r|D16H21S58|D21S58h|DNA segment, Chr 16, human D21S58| | NM_008349 | 599133 |
| IC01172 | GENE | UG75 Expression | Mm.15617 | TITLE interleukin 11 receptor, alpha chain 1 | GENE Il11ra1 | Il1ra|interleukin 11 receptor, alpha chain|locus 2|NR1| | NM_010553 | 573472 |
| IC01173 | GENE | UG75 Expression | Mm.979 | TITLE interleukin 12a | GENE Il12a | Il-12a|p35| | NM_008351 | 1278843 |
| IC01174 | GENE | UG75 Expression | Mm.997 | TITLE interleukin 12b | GENE Il12b | Il-12b|Il-12p40|Il12p40|p40| | NM_008352 | 750641 |
| IC01175 | GENE | UG75 Expression | Mm.1284 | TITLE interleukin 13 | GENE Il13 | Il-13| | NM_008355 | 1140097 |
| IC01176 | GENE | UG75 Expression | Mm.20855 | TITLE interleukin 13 receptor, alpha 2 | GENE Il13ra2 | | NM_008356 | 1312091 |
| IC01177 | GENE | UG75 Expression | Mm.4392 | TITLE interleukin 15 | GENE Il15 | | NM_008357 | 1477457 |
| IC01178 | GENE | UG75 Expression | Mm.34704 | TITLE interleukin 15 receptor, alpha chain | GENE Il15ra | | NM_008358 | 1247329 |
| IC01179 | GENE | UG75 Expression | Mm.10137 | TITLE interleukin 16 | GENE Il16 | | NM_010551 | 749833 |
| IC01180 | GENE | UG75 Expression | Mm.4481 | TITLE interleukin 17 receptor | GENE Il17r | | NM_008359 | 303764 |
| IC01181 | GENE | UG75 Expression | Mm.1410 | TITLE interleukin 18 | GENE Il18 | Igif|interferon gamma inducing factor| | NM_008360 | 1150597 |
| IC01182 | GENE | UG75 Expression | Mm.20466 | TITLE interleukin 18 receptor accessory protein | GENE Il18rap | AcPL, accessory protein-like| | NM_010553 | 640615 |
| IC01183 | GENE | UG75 Expression | Mm.22150 | TITLE interleukin 1 beta | GENE Il1b | Il-1b| | NM_008361 | 1139544 |
| IC01184 | GENE | UG75 Expression | Mm.896 | TITLE interleukin 1 receptor, type I | GENE Il1r1 | CD121b|IL-1 receptor alpha chain|Il1r-1| | NM_008362 | 935643 |
| IC01185 | GENE | UG75 Expression | Mm.1349 | TITLE interleukin 1 receptor, type II | GENE Il1r2 | CD121b|IL-1 receptor beta chain|Il1r-2| | NM_010555 | 568661 |
| IC01186 | GENE | UG75 Expression | Mm.38241 | TITLE interleukin 1 receptor-associated inase | GENE Il1rak | IRAK|mPLK|pelle-like protein kinase|Pipk| | NM_008363 | 605302 |
| IC01187 | GENE | UG75 Expression | Mm.2923 | TITLE interleukin 2 receptor, gamma chain | GENE Il2rg | [g|c]common cytokine receptor gamma chain|common gamma chain|gamma C receptor|gamma(c) | NM_013563 | 578022 |
| IC01188 | GENE | UG75 Expression | Mm.371 | TITLE interleukin 4 | GENE Il4 | Il-4| | gi = 533236 | 578022 |
| IC01189 | GENE | UG75 Expression | Mm.1009 | TITLE interleukin 4 receptor, alpha | GENE Il4ra | CD124|IL-4 receptor alpha chain|Il4|interleukin 4 receptor| | NM_010557 | 3166596 |
| IC01190 | GENE | UG75 Expression | Mm.4461 | TITLE interleukin 5 | GENE Il5 | ELP| | NM_010558 | 972705 |
| IC01191 | GENE | UG75 Expression | Mm.3448 | TITLE interleukin 5 receptor, alpha | GENE Il5ra | CD125|IL-5 receptor alpha chain|Il5|interleukin 5 receptor| | NM_008370 | 752483 |
| IC01192 | GENE | UG75 Expression | Mm.2856 | TITLE interleukin 6 receptor, alpha | GENE Il6ra | CD126|IL-6 receptor alpha chain|Il6|interleukin 6 receptor| | NM_010559 | 1195352 |
| IC01193 | GENE | UG75 Expression | Mm.389 | TITLE interleukin 7 receptor | GENE Il7r | CD127|IL-7 receptor alpha chain| | NM_008372 | 578171 |
| IC01194 | GENE | UG75 Expression | Mm.20935 | TITLE interleukin enhancer binding factor 3 | GENE Ilf3 | | NM_010561 | 643826 |
| IC01195 | GENE | UG75 Expression | Mm.8131 | TITLE integrin linked kinase | GENE Ilk | | NM_010562 | 1969843 |
| IC01196 | GENE | UG75 Expression | Mm.42169 | TITLE immunity-associated protein, 38 kDa | GENE Imap38 | IAP38| | NM_010562 | 1969843 |
| IC01197 | GENE | UG75 Expression | Mm.944 | TITLE integral membran glycoprotein | GENE Img | D68wg0781e|DNA segment, Chr6, Brigham & Women's Genetics 0781 expressed|LIG-1| | NM_008377 | 2647236 |
| IC01198 | GENE | UG75 Expression | Mm.8154 | TITLE imprinted and ancient | GENE Impact | | NM_008378 | 1446737 |
| IC01199 | GENE | UG75 Expression | Mm.6065 | TITLE inosine 5′-phosphate dehydrogenase 2 | GENE Impdh2 | IMP dehydrogenase|IMPD| | NM_011830 | 1480902 |
| IC01200 | GENE | UG75 Expression | Mm.16710 | TITLE importin beta | GENE Impnb | | NM_008379 | 1177075 |
| IC01201 | GENE | UG75 Expression | Mm.25709 | TITLE inhibitor of growth family, member 1 | GENE Ing1 | | NM_011919 | 863529 |
| IC01202 | GENE | UG75 Expression | Mm.25777 | TITLE inositol polyphosphate-5-phosphatase, 75 kDa | GENE Inpp5b | | NM_008385 | 749425 |
| IC01203 | GENE | UG75 Expression | Mm.15105 | TITLE inositol polyphosphate-5-phosphatase, 145 kDa | GENE Inpp5d | SHIP|Src homology 2 domain-containing inositol-5-phosphatase| | NM_010566 | 574851 |
| IC01204 | GENE | UG75 Expression | Mm.1531 | TITLE inositol polyphosphate phosphatase-like 1 | GENE Inppl1 | 51C|SHIP2| | gi = 1928963 | 2649030 |
| IC01205 | GENE | UG75 Expression | Mm.100163 | TITLE insulin-like 5 | GENE Insl5 | relaxin/insulin-like factor 2|RIF2| | NM_011831 | 1167437 |
| IC01206 | GENE | UG75 Expression | Mm.46153 | TITLE insulin-like 6 | GENE Insl6 | relaxin/insulin-like factor 1|RIF1| | NM_013754 | 1167056 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01207 | UG75 Expression | GENE | Mm.20896 | TITLE inversin | gnee Invs | inv|inversion of embryonic turning| | NM_010569 | 636902 |
| IC01208 | UG75 Expression | GENE | Mm.1246 | TITLE interferon regulatory factor 1 | GENE Irf1 | Irf-1| | NM_008390 | 1348681 |
| IC01209 | UG75 Expression | GENE | Mm.1149 | TITLE interferon regulatory factor 2 | GENE Irf2 | | NM_008391 | 1382877 |
| IC01210 | UG75 Expression | GENE | Mm.6479 | TITLE interferon regulatory factor 5 | GENE Irf5 | mirf5| | NM_012057 | 598495 |
| IC01211 | UG75 Expression | GENE | Mm.4662 | TITLE immunorespective gene 1 | GENE Irg1 | | gi = 950649 | 577102 |
| IC01212 | UG75 Expression | GENE | Mm.2032 | TITLE interferon dependent positive acting transcription factor 3 gamma | GENE Isgf3g | | NM_008394 | 638627 |
| IC01213 | UG75 Expression | GENE | Mm.38426 | TITLE immunoglobulin superfamily containing leucine-rich repeat | GENE Islr | | NM_012043 | 1397296 |
| IC01214 | UG75 Expression | GENE | Mm.8975 | TITLE itchy | GENE Itch | | NM_008395 | 1497785 |
| IC01215 | UG75 Expression | GENE | Mm.1346 | TITLE integrin alpha 4 (Cd49d) | GENE Itga4 | CD49D|VLA-4 receptor, alpha 4 subunit| | NM_010576 | 1428880 |
| IC01216 | UG75 Expression | GENE | Mm.16234 | TITLE integrin alpha 5 (fibronectin receptor alpha) | GENE Itga5 | fibronectin receptor alpha (Itga5)|fibronectin receptor alpha polypeptide|fnra| | NM_010577 | 476908 |
| IC01217 | UG75 Expression | GENE | Mm.25232 | TITLE integrin alpha 6 | GENE Itga6 | | NM_008397 | 2646625 |
| IC01218 | UG75 Expression | GENE | Mm.15533 | TITLE integrin alpha 7 | GENE Itga7 | CD103| | NM_008399 | 777194 |
| IC01219 | UG75 Expression | GENE | Mm.96 | TITLE integrin, alpha E, epithelial-associated | GENE Itgae | CD103| | NM_008399 | 777194 |
| IC01220 | UG75 Expression | GENE | Mm.1618 | TITLE integrin alpha L (Cd11a) | GENE Itgal | Cd11a|CD11A (p180)|CD11a antigen|LFA-1|Ly-15|Ly-21|lymphocyte antigen 15|lymphocyte antigen 21|lymphocyte function associated antigen 1, alpha polypeptide|CD29, includes MDF2, MSK12|fibronectin receptor beta (integrin)|fibronectin receptor beta polypeptide | gi = 198785 | 1149832 |
| IC01221 | UG75 Expression | GENE | Mm.4712 | TITLE integrin beta 1 (fibronectin receptor beta) | GENE Itgb1 | (FNRB)|Fnrb|gIIa| | gi = 52721 | 597791 |
| IC01222 | UG75 Expression | GENE | Mm.6818 | TITLE integrin beta 1 binding protein 1 | GENE Itgb1bp1 | | NM_008403 | 1478697 |
| IC01223 | UG75 Expression | GENE | Mm.1137 | TITLE integrin beta 2 (Cd18) | GENE Itgb2 | 2F6|Cd18|CD18 antigen|Lfa1||lymphoyte function associated antigen 1|Mac-1 beta|macrophage antigen-1 beta| | NM_008404 | 1430348 |
| IC01224 | UG75 Expression | GENE | Mm.22731 | TITLE integrin beta 4 binding protein | GENE Itgb4bp | eIF6|mc-415|p27BBP|eIF6|mc-415|p27BBP| | gi = 2910994 | 559804 |
| IC01225 | UG75 Expression | GENE | Mm.6424 | TITLE integrin beta 5 | GENE Itgb5 | [b]-5[|b]5A|[b]5B|beta-5|beta5 | NM_010580 | 481681 |
| IC01226 | UG75 Expression | GENE | Mm.58 | TITLE integrin beta 7 | GENE Itgb7 | Ly69| | NM_013566 | 604856 |
| IC01227 | UG75 Expression | GENE | Mm.20183 | TITLE integrin-associated protein | GENE Itgp | CD47|IAP| | NM_010581 | 959204 |
| IC01228 | UG75 Expression | GENE | Mm.2288 | TITLE inter-alpha trypsin inhibitor, heavy chain 2 | GENE Itih2 | inter-alpha (globulin)inhibitor, H2 polypeptide|ntin2|tih-2| | NM_010582 | 1885080 |
| IC01229 | UG75 Expression | GENE | Mm.4517 | TITLE inter-alpha trypsin inhibitor, heavy chain 3 | GENE Itih3 | inter-alpha (globulin) inhibitor, H3 polypeptide|ntin3|tih-3| | NM_008407 | 1480253 |
| IC01230 | UG75 Expression | GENE | Mm.16009 | TITLE IL2-inducible T-cell kinase | GENE Itk | Emt|Tcsk|Tsk| | NM_010583 | 596235 |
| IC01231 | UG75 Expression | GENE | Mm.2863 | TITLE integral membrane protein 1 | GENE Itm1 | | NM_008408 | 1002218 |
| IC01232 | UG75 Expression | GENE | Mm.193 | TITLE integral membrane protein 2 | GENE Itm2 | E25|ttma2a| | NM_008409 | 2225629 |
| IC01233 | UG75 Expression | GENE | Mm.4266 | TITLE integral membrane protein 2 B | GENE Itm2b | D14Sel6|DNA segment, Chr 14, Seldin 6|E25BMM| | NM_008410 | 2192594 |
| IC01234 | UG75 Expression | GENE | Mm.2726 | TITLE inositol 1,4,5-triphosphate receptor 1 | GENE Itpr1 | inositol 1,4,5-triphosphate binding protein|Ipr3|IP3R1|Iptpr-1|opisthotonus|op| | NM_010585 | 2192206 |
| IC01235 | UG75 Expression | GENE | Mm.40546 | TITLE intersection (SH3 domain protein 1A) | GENE Itsn | Eh domain, SH3 domain regulator of endocytosis 1|EH domain/SH3 domain-containing protein|EHSH1|Ese1|Sh3p17| | NM_010587 | 1246139 |
| IC01236 | UG75 Expression | GENE | Mm.809 | TITLE Janus kinase 2 | GENE Jak2 | Fd17| | NM_008413 | 597460 |
| IC01237 | UG75 Expression | GENE | Mm.4181 | TITLE Janus kinase 3 | GENE Jak3 | | NM_010589 | 456994 |
| IC01238 | UG75 Expression | GENE | Mm.25059 | TITLE jumonji | GENE jmj | | gi = 780143 | 1038498 |
| IC01239 | UG75 Expression | GENE | Mm.20971 | TITLE jerky | GENE Jrk | | NM_008415 | 1510925 |
| IC01240 | UG75 Expression | GENE | Mm.13912 | TITLE jumping translocation breakpoint | GENE Jtb-pending | | gi = 3721891 | 1481870 |
| IC01241 | UG75 Expression | GENE | Mm.1167 | TITLE Jun-B oncogene | GENE Junb | | NM_008416 | 556960 |
| IC01242 | UG75 Expression | GENE | Mm.1175 | TITLE Jun proto-oncogene related GENE d1 | GENE Jund1 | Jun-D oncogene|Jund| | NM_010592 | 403617 |
| IC01243 | UG75 Expression | GENE | Mm.21990 | TITLE junction plakoglobin | GENE Jup | junction plakoglobin| | gi = 1389681 | 2937132 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01244 | UG75 Expression | GENE | Mm.13052 | TITLE kidney androgen regulated protein | GENE Kap | S-AKAP84| | NM_010594 | 1908006 |
| IC01245 | UG75 Expression | GENE | Mm.28127 | TITLE katanin p60 (ATPase-containing) subunit A1 | GENE Katna1 | | NM_011835 | 3167683 |
| IC01246 | UG75 Expression | GENE | Mm.6539 | TITLE potassium voltage-gated channel, subfamily H (eag-related), member 2 | GENE Kcnh2 | ether a go-go related|long (electrocardiographic) QT syndrome 2|Lqt2|M-erg|Merg1| | NM_013569 | 475832 |
| IC01247 | UG75 Expression | GENE | Mm.1482 | TITLE potassium inwardly-rectifying channel, subfamily J, GENE Kcnj8 member 8 | | Kir6.1| | NM_008428 | 614956 |
| IC01248 | UG75 Expression | GENE | Mm.57045 | TITLE potassium large conductance calcium-activated channel, subfamily M, alpha member 3 | GENE Kcnma3 | mSlo3|Slo3| | NM_008432 | 534033 |
| IC01249 | UG75 Expression | GENE | Mm.9911 | TITLE potassium intermediate/small conductance calcium-activated channel, subfamily N, member 4 | GENE Kcnn4 | | NM_008433 | 2936774 |
| IC01250 | UG75 Expression | GENE | Mm.9495 | TITLE kidney-derived aspartic protease-like protein | GENE Kdap | KAP| | NM_008437 | 2520251 |
| IC01251 | UG75 Expression | GENE | Mm.1314 | TITLE kidney cell line derived transcript 1 | GENE Kdt1 | clone 1.5| | gi = 987223 | 525101 |
| IC01252 | UG75 Expression | GENE | Mm.4415 | TITLE kinesin heavy chain member 2 | GENE Kif2 | kinesin family member 2|Kns2| | NM_008442 | 636906 |
| IC01253 | UG75 Expression | GENE | Mm.27973 | TITLE kinesin family member 3b | GENE Kif3b | | NM_008444 | 890975 |
| IC01254 | UG75 Expression | GENE | Mm.7688 | TITLE kinesin family member 3c | GENE Kif3c | | NM_008445 | 1078706 |
| IC01255 | UG75 Expression | GENE | Mm.3380 | TITLE kinesin family member 5B | GENE Kif5b | Khcs, KHC| | NM_008448 | 608866 |
| IC01256 | UG75 Expression | GENE | Mm.42170 | TITLE kinesin 9 | GENE Kif9 | | NM_010628 | 595985 |
| IC01257 | UG75 Expression | GENE | Mm.4651 | TITLE kinesin-associated protein 3 | GENE Kifap3 | KAP3| | NM_010629 | 264869 |
| IC01258 | UG75 Expression | GENE | Mm.891 | TITLE kinesin family member C2 | GENE Kifc2 | | NM_010630 | 634870 |
| IC01259 | UG75 Expression | GENE | Mm.42203 | TITLE kinesin-like 1 | GENE Kifl1 | Eg5| | gi = 4160555 | 1379629 |
| IC01260 | UG75 Expression | GENE | Mm.35498 | TITLE antigenic determinant of rec-A protein | GENE Kin | Kin17| | gi = 1045209 | 752229 |
| IC01261 | UG75 Expression | GENE | Mm.4394 | TITLE kit oncogene | GENE Kit | spotting|Fdc|spotted sterile male|ssm|Steel Factor Receptor|W| | gi = 50423 | 3155526 |
| IC01262 | UG75 Expression | GENE | Mm.741 | TITLE keratinocyte lipid binding protein | GENE Klbp | Fabpe E-FAB|mal1| | NM_010634 | 736615 |
| IC01263 | UG75 Expression | GENE | Mm.20354 | TITLE kinesin light chain 1 | GENE Klc1 | | NM_008450 | 2225743 |
| IC01264 | UG75 Expression | GENE | Mm.12958 | TITLE kinesin light chain 2 | GENE Klc2 | | NM_008451 | 2780804 |
| IC01265 | UG75 Expression | GENE | Mm.4847 | TITLE Kruppel-like factor 1 (erythroid) | GENE Klf1 | EKLF|erythroid Kruppel-like factor| | NM_010635 | 423199 |
| IC01266 | UG75 Expression | GENE | Mm.26938 | TITLE Kruppel-like factor 2 (lung) | GENE Klf2 | LKLF|lung Kruppel-like factor| | NM_008452 | 846704 |
| IC01267 | UG75 Expression | GENE | Mm.4549 | TITLE Kruppel-like factor 3 (basic) | GENE Klf3 | basic Kruppel-like factor|BKLF|Tef-2| | NM_008453 | 1448447 |
| IC01268 | UG75 Expression | GENE | Mm.19788 | TITLE kinesin family member 9 | GENE Klf9 | basic transcription element binding protein 1|BTEB-1|Bteb1| | NM_010638 | 975621 |
| IC01269 | UG75 Expression | GENE | Mm.4131 | TITLE killer cell lectin-like receptor, subfamily A, member 7 | GENE Klra7 | LGL-1|Ly49G|lymphocyte antigen 49 complex, locus G| | NM_010654 | 721336 |
| IC01270 | UG75 Expression | GENE | Mm.8186 | TITLE killer cell lectin-like receptor, subfamily D, member 1 | GENE Klrd1 | CD94| | NM_010654 | 721336 |
| IC01271 | UG75 Expression | GENE | Mm.6952 | TITLE karyopherin (importin) alpha 1 | GENE Kpna1 | m-importin-alpha-S1|mSRP1|RAG (recombination activating GENE) cohort 2|Rch2| | NM_008465 | 962092 |
| IC01272 | UG75 Expression | GENE | Mm.12508 | TITLE karyopherin (importin) alpha 2 | GENE Kpna2 | importin|m-importin|m-importin-alpha-P1|pendulin|RAG (recombination activating gene) cohort 1|Rch1| | NM_010655 | 516129 |
| IC01273 | UG75 Expression | GENE | Mm.87443 | TITLE karyopherin (importin) alpha 4 | GENE Kpna4 | | NM_008467 | 1378794 |
| IC01274 | UG75 Expression | GENE | Mm.31530 | TITLE kirsten rat sarcoma oncogene 2, expressed | GENE Kras2 | Ki-ras|Kras-2| | gi = 52798 | 2159411 |
| IC01275 | UG75 Expression | GENE | Mm.39036 | TITLE Kreisler (maf-related) leucine zipper protein | GENE Krml | Kr|Kreisler|MafB| | gi = 625041 | 2099917 |
| IC01276 | UG75 Expression | GENE | Mm.22662 | TITLE keratin complex 1, acidic, GENE 10 | GENE Krt1-10 | K10|K1C1|keratin complex 1 gene 10|Krt-1.10| | gi = 52786 | 1480776 |
| IC01277 | UG75 Expression | GENE | Mm.14046 | TITLE keratin complex 1, acidic, GENE 17 | GENE Krt1-17 | | NM_010663 | 373556 |
| IC01278 | UG75 Expression | GENE | Mm.22479 | TITLE keratin complex 1, acidic, GENE 18 | GENE Krt1-18 | Endo B.|K18| | NM_010664 | 3154596 |
| IC01279 | UG75 Expression | GENE | Mm.14245 | TITLE keratin complex 2, basic, GENE 1 | GENE Krt2-1 | keratin GENE complex 2, gene 1|Mk6a| | NM_008473 | 2076834 |
| IC01280 | UG75 Expression | GENE | Mm.22629 | TITLE keratin complex 2, basic GENE 6a | GENE Krt2-6a | 60-kDa keratin|Mk6a| | NM_008476 | 975221 |
| IC01281 | UG75 Expression | GENE | Mm.22657 | TITLE keratin complex 2, basic GENE 6b | GENE Krt2-6b | mK6[b]| | NM_010669 | 1210102 |
| IC01282 | UG75 Expression | GENE | Mm.6800 | TITLE keratin complex 2, basic, GENE 8 | GENE Krt2-8 | K8|keratin GENE complex 2, gene 8|Krt2.8| | gi = 52788 | 1078343 |
| IC01283 | UG75 Expression | GENE | Mm.3110 | TITLE kinectin 1 | GENE Ktn1 | | NM_008477 | 2645879 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01284 | UG75 Expression | GENE | Mm.42012 | TITLE laminin, alpha 3 | GENE Lama3 | nicin, 150kD | gi = 1922890 | 642217 |
| IC01285 | UG75 Expression | GENE | Mm.1249 | TITLE laminin, gamma 1 | GENE Lamc1 | | gi = 198694 | 2649439 |
| IC01286 | UG75 Expression | GENE | Mm.4717 | TITLE laminin, gamma 2 | GENE Lamc2 | nicein, 100kD | NM_008485 | 663164 |
| IC01287 | UG75 Expression | GENE | Mm.16716 | TITLE lysosomal membrane glycoprotein 1 | GENE Lamp1 | CD107a|LAMP-1| | NM_010684 | 1451112 |
| IC01288 | UG75 Expression | GENE | Mm.486 | TITLE lysosomal membrane glycoprotein 2 | GENE Lamp2 | CD107b|LAMP-2| | NM_010685 | 2649439 |
| IC01289 | UG75 Expression | GENE | Mm.4487 | TITLE leucine arylaminopeptidase 1, intestinal | GENE Lap1 | | NM_008486 | 1096877 |
| IC01290 | UG75 Expression | GENE | Mm.4554 | TITLE lysosomal-associated protein transmembrane 5 | GENE Laptm5 | Bglap|bone gamma carboxyglutamate protein|osteocalcin| R3| | NM_010686 | 577144 |
| IC01291 | UG75 Expression | GENE | Mm.20872 | TITLE like-glycosyltransferase | GENE Large | | NM_010687 | 721627 |
| IC01292 | UG75 Expression | GENE | Mm.21387 | TITLE LIM and SH3 protein 1 | GENE Lasp1 | Def-4|SH3P6| | NM_010688 | 1137938 |
| IC01293 | UG75 Expression | GENE | Mm.10280 | TITLE linker for activation of T cells | GENE Lat | | NM_010689 | 582840 |
| IC01294 | UG75 Expression | GENE | Mm.28110 | TITLE lipopolysaccharide binding protein | GENE Lbp | | NM_008489 | 2647192 |
| IC01295 | UG75 Expression | GENE | Mm.1593 | TITLE lecithin cholesterol acyltransferase | GENE Lcat | B-FABP| | NM_008490 | 1450884 |
| IC01296 | UG75 Expression | GENE | Mm.142 | TITLE lymphocyte protein tyrosine kinase | GENE Lck | Hck-3|hemopoietic cell kinase 3| | gi = 54813 | 1196244 |
| IC01297 | UG75 Expression | GENE | Mm.9537 | TITLE lipocalin 2 | GENE Lcn2 | Clc2| | gi = 1478201 | 1511008 |
| IC01298 | UG75 Expression | GENE | Mm.1781 | TITLE lymphocyte cytosolic protein 2 | GENE Lcp2 | SLP-76| | NM_010696 | 634088 |
| IC01299 | UG75 Expression | GENE | Mm.4524 | TITLE LIM domain binding 1 | GENE Ldb1 | CLIM2|NL1| | NM_010697 | 1511229 |
| IC01300 | UG75 Expression | GENE | Mm.26504 | TITLE lactate dehydrogenase 1, A chain | GENE Ldh1 | Ahd-2|Ahd2|aldehyde dehydrogenase 1, liver cytosolic (class) 1)|aldehyde dehydrogenase 1, liver cytoplasmic|Aldh1| | | |
| IC01301 | UG75 Expression | GENE | Mm.9745 | TITLE lactate dehydrogenase 2, B chain | GENE Ldh2 | 1)|aldehyde dehydrogenase 5| | NM_008492 | 2065018 |
| IC01302 | UG75 Expression | GENE | Mm.99677 | TITLE low density lipoprotein B | GENE Ldlb | LDLB| | NM_013581 | 2650449 |
| IC01303 | UG75 Expression | GENE | Mm.3213 | TITLE low density lipoprotein receptor | GENE Ldlr | | NM_010700 | 618131 |
| IC01304 | UG75 Expression | GENE | Mm.16973 | TITLE leukocyte cell-derived chemotaxin 2 | GENE Lect2 | chondromodulin-II| | NM_010703 | 1431529 |
| IC01305 | UG75 Expression | GENE | Mm.2029 | TITLE lymphoid enhancer binding factor 1 | GENE Lef1 | Lef-1|lymphoid enhancer factor 1| | NM_010703 | 576355 |
| IC01306 | UG75 Expression | GENE | Mm.4756 | TITLE leptin receptor | GENE Lepr | db|diabetes|leptin receptor gene-related protein|OB-RGRP|obese-like|ob|Obr| | gi = 1139592 | 777547 |
| IC01307 | UG75 Expression | GENE | Mm.12834 | TITLE lunatic fringe GENE homolog (Drosophila) | GENE Lfng | | NM_008494 | 1180770 |
| IC01308 | UG75 Expression | GENE | Mm.43831 | TITLE lectin, galactose binding, soluble 1 | GENE Lgals1 | beta galactoside binding protein|Galbp|galectin-1|L-14.5|lactose binding soluble lectin, 14 kDa|Lect14| | NM_008495 | 180770 |
| IC01309 | UG75 Expression | GENE | Mm.2970 | TITLE lectin, galactose binding, soluble 3 | GENE Lgals3 | gal3|galectin-3|L-34|Mac-2| | gi = 52986 | 571813 |
| IC01310 | UG75 Expression | GENE | Mm.17911 | TITLE lectin, galactose binding, soluble 6 | GENE Lgals6 | galectin-6 | NM_010707 | 1052150 |
| IC01311 | UG75 Expression | GENE | Mm.18087 | TITLE lectin, galactose binding, soluble 9 | GENE Lgals9 | galectin-9 | NM_010708 | 374964 |
| IC01312 | UG75 Expression | GENE | Mm.4965 | TITLE LIM homeo box protein 1 | GENE Lhx1 | lim1| | NM_008498 | 1749654 |
| IC01313 | UG75 Expression | GENE | Mm.15530 | TITLE LIM homeo box protein 8 | GENE Lhx8 | L3| | gi = 2285797 | 777339 |
| IC01314 | UG75 Expression | GENE | Mm.1013 | TITLE leukemia inhibitory factor receptor | GENE Lifr | | NM_013584 | 662150 |
| IC01315 | UG75 Expression | GENE | Mm.1013 | TITLE ligase I, DNA, ATP-deptendent | GENE Lig1 | mLig1| | NM_010715 | 1885027 |
| IC01316 | UG75 Expression | GENE | Mm.15409 | TITLE LIM-domain containing, protein kinase | GENE Limk1 | | NM_010717 | 1746478 |
| IC01317 | UG75 Expression | GENE | Mm.42927 | TITLE LIM motif-containing protein kinase 2 | GENE Limk2 | Lim2a|Limk2b| | NM_010718 | 1037992 |
| IC01318 | UG75 Expression | GENE | Mm.1721 | TITLE lipase, hormone sensitive | GENE Lipe | HSL| | NM_010719 | 875976 |
| IC01319 | UG75 Expression | GENE | Mm.3940 | TITLE lethal giant larvae homolog | GENE Llglh | Mgl1| | NM_008502 | 475755 |
| IC01320 | UG75 Expression | GENE | Mm.1129 | TITLE repeat family 3 GENE | GENE Llrep3 | | NM_008498 | 1886295 |
| IC01321 | UG75 Expression | GENE | Mm.3438 | TITLE lamin A | GENE Lmna | | gi = 1838920 | 1970837 |
| IC01322 | UG75 Expression | GENE | Mm.4846 | TITLE lamin B1 | GENE Lmnb1 | | NM_010721 | 576240 |
| IC01323 | UG75 Expression | GENE | Mm.7362 | TITLE lamin B2 | GENE Lmnb2 | | NM_010722 | 2650659 |
| IC01324 | UG75 Expression | GENE | Mm.29266 | TITLE LIM only 2 | GENE Lmo2 | Rbtn-2|Rbtn2|rhombotin 2|Ttg2| | NM_008505 | 404586 |
| IC01325 | UG75 Expression | GENE | Mm.35004 | TITLE LIM only 4 | GENE Lmo4 | | NM_010723 | 2938847 |
| IC01326 | UG75 Expression | GENE | Mm.1055 | TITLE lung carcinoma myc related oncogene 1 | GENE Lmyc1 | Lmyc-1| | NM_008506 | 616319 |
| IC01327 | UG75 Expression | GENE | Mm.380 | TITLE lupus nephritis-associated peptide 1 | GENE Lnap1 | PAHX|PHYH|phytanoyl-CoA hydroxylase gene| | NM_010726 | 2536656 |
| IC01328 | UG75 Expression | GENE | Mm.9036 | TITLE linker of T-cell receptor pathways | GENE Lnk | | NM_008507 | 598499 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01329 | UG75 Expression | GENE | Mm.14860 | TITLE lipocortin 1 | GENE Lpc1 | Lpc-1 | NM_010730 | 1383214 |
| IC01330 | UG75 Expression | GENE | Mm.1514 | TITLE lipoprotein lipase | GENE Lpl | | NM_008509 | 1314022 |
| IC01331 | UG75 Expression | GENE | Mm.190 | TITLE lymphotactin | GENE Lptn | | NM_008510 | 576815 |
| IC01332 | UG75 Expression | GENE | Mm.20920 | TITLE leukemia/lymphoma related factor | GENE Lrf | | qNM_010731 | 2938155 |
| IC01333 | UG75 Expression | GENE | Mm.843 | TITLE lymphoid-restricted membrane protein | GENE Lrmp | Jaw1 | NM_008511 | 1247786 |
| IC01334 | UG75 Expression | GENE | Mm.7221 | TITLE low density lipoprotein receptor related protein | GENE Lrp | carp | NM_008512 | 1138983 |
| IC01335 | UG75 Expression | GENE | Mm.4560 | TITLE low density lipoprotein receptor related protein, associated protein 1 | GENE Lrpap1 | HBP44 low density lipoprotein related protein, associated protein 1 | gi = 220433 | 580767 |
| IC01336 | UG75 Expression | GENE | Mm.3207 | TITLE leucine rich protein, B7 GENE FLAP (FLI LRR associated protein) flightless-I associated | GENE Lrpb7 | | NM_013588 | 574936 |
| IC01337 | UG75 Expression | GENE | Mm.10272 | TITLE leucine rich repeat (in FLII) interacting protein 1 | GENE Lrrfib1 | protein 1 (LRR domain) Fliiap1 | NM_008151 | 2225635 |
| IC01338 | UG75 Expression | GENE | Mm.4640 | TITLE leucine rich repeat protein 1, neuronal | GENE Lrrn1 | NLRR-1 | NM_008516 | 351947 |
| IC01339 | UG75 Expression | GENE | Mm.2183 | TITLE lymphocyte specific 1 | GENE Lsp1 | Lsp-1 | gi = 758359 | 1396205 |
| IC01340 | UG75 Expression | GENE | Mm.19379 | TITLE leucocyte specific transcript 1 | GENE Lst1 | B144 | gi = 2145069 | 846366 |
| IC01341 | UG75 Expression | GENE | Mm.87786 | TITLE lurcher transcript 1 | GENE Lt1 | | gi = 1881702 | 2236201 |
| IC01342 | UG75 Expression | GENE | Mm.533 | TITLE leukotriene A4 hydrolase | GENE Lta4h | LTA4 hydrolase | NM_008517 | 2631658 |
| IC01343 | UG75 Expression | GENE | Mm.1715 | TITLE lymphotoxin B | GENE Ltb | lymphotoxin beta Tnfc tumor necrosis factor C | NM_008518 | 749946 |
| IC01344 | UG75 Expression | GENE | Mm.3900 | TITLE latent transforming growth factor beta binding protein 2 | GENE Ltbp2 | | NM_013589 | 2938219 |
| IC01345 | UG75 Expression | GENE | Mm.21370 | TITLE latent transforming growth factor beta binding protein 3 | GENE Ltbp3 | Ltbp2 | NM_008520 | 1494907 |
| IC01346 | UG75 Expression | GENE | Mm.18888 | TITLE lumican | GENE Lum | Ldc | NM_008524 | 2259107 |
| IC01347 | UG75 Expression | GENE | Mm.6988 | TITLE delta-aminolevulinate dehydratase | GENE Lv | | NM_008525 | 661256 |
| IC01348 | UG75 Expression | GENE | Mm.15889 | TITLE lymphocyte antigen 6 complex | GENE Ly6 | 14/A10 leucine rich repeat protein Lrrp | NM_010738 | 1920915 |
| IC01349 | UG75 Expression | GENE | Mm.681 | TITLE lymphocyte antigen 68 | GENE Ly68 | AA4.1 C1qrp | NM_010740 | 818304 |
| IC01350 | UG75 Expression | GENE | Mm.1583 | TITLE lymphocyte antigen 6 complex, locus C | GENE Ly6c | Ly-6C lymphocyte antigen 6, subunit C | NM_010741 | 1969907 |
| IC01351 | UG75 Expression | GENE | Mm.878 | TITLE lymphocyte antigen 6 complex, locus D | GENE Ly6d | Ly-61 Ly61 lymphocyte antigen 61 Thb ThB cell surface antigen | NM_010742 | 2259243 |
| IC01352 | UG75 Expression | GENE | Mm.788 | TITLE lymphocyte antigen 6 complex, locus E | GENE Ly6e | Ly67 lymphocyte antigen 67 Sca-2 thymic shared antigen 1 Tsa1 | NM_008529 | 670038 |
| IC01353 | UG75 Expression | GENE | Mm.4259 | TITLE lymphocyte antigen 74 | GENE Ly74 | Egn314 Ep-CAM epithelial glycoprotein 314 panepithelial glycoprotein 314 | NM_008532 | 3155338 |
| IC01354 | UG75 Expression | GENE | Mm.2074 | TITLE lymphocyte antigen 75 | GENE Ly75 | DEC-205 | NM_013825 | 1263031 |
| IC01355 | UG75 Expression | GENE | Mm.35692 | TITLE lymphocyte antigen 84 | GENE Ly84 | signal transduction protein 2 signal transduction protein 2, related sequence 1 ST2 St2-rs1 T1 T1 gene T1/ST2 | NM_010743 | 973893 |
| IC01356 | UG75 Expression | GENE | Mm.1044 | TITLE lymphocyte antigen 84 ligand | GENE Ly84l | signal transduction protein 2 ligand St2l | gi = 1223891 | 670207 |
| IC01357 | UG75 Expression | GENE | Mm.2639 | TITLE lymphocyte antigen 86 | GENE Ly86 | MD1 | NM_010745 | 763963 |
| IC01358 | UG75 Expression | GENE | Mm.560 | TITLE lymphocyte antigen 9 | GENE Ly9 | Lgp100 Ly-9 T-100 | NM_008534 | 577717 |
| IC01359 | UG75 Expression | GENE | Mm.41980 | TITLE lymphocyte antigen 94 | GENE Ly94 | MAR1 (mouse activating receptor 1) NKp46 | NM_010746 | 617876 |
| IC01360 | UG75 Expression | GENE | Mm.4925 | TITLE lymphoblastomic leukemia | GENE Lyl1 | Lyl-1 | NM_008535 | 482694 |
| IC01361 | UG75 Expression | GENE | Mm.1834 | TITLE Yamaguchi sarcoma viral (v-yes-1) oncogene homolog | GENE Lyn | Hck-2 hemopoietic cell kinase 2 | gi = 198940 | 3026135 |
| IC01362 | UG75 Expression | GENE | Mm.1423 | TITLE lysophospholipase 1 | GENE Lypla1 | phospholipase 1a Pla1a | NM_008866 | 1970847 |
| IC01363 | UG75 Expression | GENE | Mm.34302 | TITLE lysophospholipase 2 | GENE Lypla2 | Lysoll lysophospholipase II | NM_011942 | 2598876 |
| IC01364 | UG75 Expression | GENE | Mm.856 | TITLE lysosomal trafficking regulator | GENE Lyst | beige bg D13Sfk13 DNA segment, Chr13, Stephen F. Kingsmore 13 | NM_010748 | 1224852 |
| IC01365 | UG75 Expression | GENE | Mm.1358 | TITLE membrane component, surface marker 1 | GENE M3s1 | 12A8 target antigen L6 antigen | NM_008536 | 1890839 |
| IC01366 | UG75 Expression | GENE | Mm.2787 | TITLE membrane-6-phosphate receptor, cation dependent | GENE M6pr | M6pr | NM_010749 | 2247540 |
| IC01367 | UG75 Expression | GENE | | TITLE alpha-methylacyl-Coenzyme A racemase | GENE Macr1 | 2-arylpropionyl-CoA epimerase | NM_008537 | 1248345 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01368 | UG75 Expression | GENE | Mm.30059 | TITLE myristoylated alanine rich protein kinase C substrate | GENE Macs | Marcks|myristoylated alanine rich C protein kinase C substrate| | NM_008538 | 637962 |
| IC01369 | UG75 Expression | GENE | Mm.27250 | TITLE mitotic arrest deficient 1-like 1 | GENE Mad1l1 | | NM_010752 | 1498523 |
| IC01370 | UG75 Expression | GENE | Mm.38795 | TITLE Max dimerization protein 4 | GENE Mad4 | | NM_010753 | 734984 |
| IC01371 | UG75 Expression | GENE | Mm.13866 | TITLE mucosal vascular addressin cell adhesion molecule 1 | GENE Madcam1 | | NM_013591 | 638117 |
| IC01372 | UG75 Expression | GENE | Mm.15185 | TITLE MAD homolog 1 (Drosophila) | GENE Madh1 | Madr1|Mlp1|MusMLP|smad1| | NM_008539 | 620333 |
| IC01373 | UG75 Expression | GENE | Mm.2334 | TITLE MAD homolog 2 (Drosophila) | GENE Madh2 | MAD homolog 2, (Drosophila)|Madr2|Smad2| | NM_010754 | 1054420 |
| IC01374 | UG75 Expression | GENE | Mm.1470 | TITLE MAD homolog 5 (Drosophila) | GENE Madh5 | Dwf-C|Smad5| | NM_008541 | 2352827 |
| IC01375 | UG75 Expression | GENE | Mm.34407 | TITLE MAD homolog 7 (Drosophila) | GENE Madh7 | Smad7| | NM_008543 | 944734 |
| IC01376 | UG75 Expression | GENE | Mm.162 | TITLE nuclear factor, erythroid derived 2, ubiquitous | GENE Mafk | avian musculoaponeurotic fibrosarcoma virus (v-maf) AS42 oncogene, protein K|Nfe2u| | NM_010757 | 576400 |
| IC01377 | UG75 Expression | GENE | Mm.808 | TITLE mago-nashi homolog, proliferation-associated (Drosophila) | GENE Magoh | | NM_010760 | 2225887 |
| IC01378 | UG75 Expression | GENE | Mm.7838 | TITLE maternal inhibition of differentiation | GENE Maid | SECC-s|stage specific embryonic cDNA-8| | NM_010761 | 2651755 |
| IC01379 | UG75 Expression | GENE | Mm.1053 | TITLE mannosidase 1, alpha | GENE Man1a | PCR1| | NM_008548 | 1923559 |
| IC01380 | UG75 Expression | GENE | Mm.4389 | TITLE mannosidase 1, beta | GENE Man1b | PCR2| | NM_010763 | 602358 |
| IC01381 | UG75 Expression | GENE | Mm.2433 | TITLE mannosidase 2, alpha 1 | GENE Man2a1 | alpha mannosidase 2|Mana-2|Mana2| | NM_008549 | 1400626 |
| IC01382 | UG75 Expression | GENE | Mm.4219 | TITLE mannosidase 2, alpha B1 | GENE Man2b1 | LAMAN|lysosomal alpha-mannosidase| | NM_010764 | 818243 |
| IC01383 | UG75 Expression | GENE | Mm.761 | TITLE mannosidase 2, alpha B2 | GENE Man2b2 | 135 kD alph-D-mannosidase| | NM_008550 | 905640 |
| IC01384 | UG75 Expression | GENE | Mm.1059 | TITLE mitogen activated protein kinase kinase 1 | GENE Map2k1 | MAP kinase kinase 1|MAPKK1|MEK1|Prkmk1|protein kinase, | NM_008927 | 634946 |
| IC01385 | UG75 Expression | GENE | Mm.18494 | TITLE mitogen activated protein kinase kinase 3 | GENE Map2k3 | mitogen activated, kinase 1, p45|MAP kinase kinase 3|MEK3|MKK3|mMKK3b|Prkmk3|protein | gi : 1711246 | 1078132 |
| IC01386 | UG75 Expression | GENE | Mm.4412 | TITLE mitogen activated protein kinase kinase 4 | GENE Map2k4 | kinase, mitogen-activated, kinase 3|JNKK1|MEK4|MKK4|PRKMK4|SAPK/Erk/kinase 1|Sek1|Serk1| | gi : 1754530 | 1362893 |
| IC01387 | UG75 Expression | GENE | Mm.19947 | TITLE mitogen activated protein kinase kinase 5 | GENE Map2k5 | MAPK/ERK kinase 5|MEK5| | NM_011840 | 554209 |
| IC01388 | UG75 Expression | GENE | Mm.14487 | TITLE mitogen activated protein kinase kinase 6 | GENE Map2k6 | MAP kinase kinase 6|MEK6|MKK6|Prkmk6|protein kinase, mitogen activated, kinase 6|SAPKK3| | gi : 1209674 | 569028 |
| IC01389 | UG75 Expression | GENE | Mm.15918 | TITLE mitogen activated protein kinase kinase 1 | GENE Map3k1 | MAPKKK1|MEK kinase|Mekk| | gi : 293729 | 751408 |
| IC01390 | UG75 Expression | GENE | Mm.27041 | TITLE mitogen activated protein kinase kinase 3 | GENE Map3k3 | MAPKKK3|MEK kinase 3|Mekk3|D17Rp17|D17R, e|DNA segment, Chr17, Roswell Park 17|DNA segment, Chr 17, Roswell Park-17, expressed|MAPKKK4|MEK kinase 4|Mekk4|MTK1|Roswell | gi : 1223901 | 1314557 |
| IC01391 | UG75 Expression | GENE | Mm.28587 | TITLE mitogen activated protein kinase kinase 4 | GENE Map3k4 | Park 17, DNA polymorphism1RP17|Rp17a| | NM_011948 | 576678 |
| IC01392 | UG75 Expression | GENE | Mm.3968 | TITLE mitogen activated protein kinase kinase 7 | GENE Map3k7 | Tak1|TGF-beta-activated kinase 1| | gi : 1167505 | 634231 |
| IC01393 | UG75 Expression | GENE | Mm.3275 | TITLE mitogen activated protein kinase kinase 8 | GENE Map3k8 | cancer Osaka thyroid, oncogene|Cot| | NM_007746 | 620757 |
| IC01394 | UG75 Expression | GENE | Mm.3313 | TITLE mitogen activated protein kinase kinase kinase 1 | GENE Map4k1 | hematopoietic progenitor kinase 1|Hpk1|mHPK1| | gi : 1654011 | 2699103 |
| IC01395 | UG75 Expression | GENE | Mm.25860 | TITLE mitogen activated protein kinase kinase kinase 2 | GENE Map4k2 | BL44|GCK|RAB8 interacting protein|Rab8ip| | NM_009006 | 2609649 |
| IC01396 | UG75 Expression | GENE | Mm.987 | TITLE mitogen-activated protein kinase kinase kinase 4 | GENE Map4k4 | HGK|HPK/GCK-like kinase|NCK interacting kinase|Nik|elk related tyrosine kinase 2|ERK|Erk2|MAPK2|p41mapk|p42mapk|Prkm1|PRKM|protein | NM_008696 | 541298 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01397 | UG75 Expression | GENE | Mm.1700 | TITLE mitogen activated protein kinase 1 | GENE Mapk1 | kinase, mitogen activated kinase 1\|CDC2-related kinase 1\|Crk1\|Csbp1\|CSBP2\|cytokine suppressive anti-inflammatory drug binding protein | NM_011949 | 907551 |
| IC01398 | UG75 Expression | GENE | Mm.88331 | TITLE mitogen activated protein kinase 14 | GENE Mapk14 | 1\|Mxi2\|p38\|p38 MAP Kinase\|p38-alpha\|PRKM14\|PRKM15\|elk related tyrosine kinase 1\|Erk1\|Erkl\|extra cellular signal regulated kinase 1\|p44\|p44 MAP kinase\|p44erk1\|p44mapk\|Prkm3\|protein kinase, mitogen activated kinase 3\| | gi = 531124 | 352057 |
| IC01399 | UG75 Expression | GENE | Mm.8385 | TITLE mitogen activated protein kinase 3 | GENE Mapk3 | | gi = 50858 | 634370 |
| IC01400 | UG75 Expression | GENE | Mm.38172 | TITLE mitogen-activated protein kinase 7 | GENE Mapk7 | BMK1\|ERK5\|extracellular signal regulated kinase 5\|PRKM7\|MAPKAP kinase 2\|ribosomal protein S6 kinase, 60 kDa, | NM_011841 | 1163242 |
| IC01401 | UG75 Expression | GENE | Mm.29725 | TITLE MAP kinase-activated protein kinase 2 | GENE Mapkapl | polypeptide 1\|Rps6kc1\| | gi = 1078784 | 572979 |
| IC01402 | UG75 Expression | GENE | Mm.22612 | TITLE MAP kinase-activated protein kinase 5 | GENE MAPkapk5 | | NM_010765 | 722986 |
| IC01403 | UG75 Expression | GENE | Mm.1856 | TITLE macrophage receptor with collagenous structure | GENE Marco | Ly112\| | NM_010766 | 637316 |
| IC01404 | UG75 Expression | GENE | Mm.22693 | TITLE mannan-bindjn lectin serine protease 2 | GENE Masp2 | MAp19\|MASP-2\| | NM_010767 | 330679 |
| IC01405 | UG75 Expression | GENE | Mm.1662 | TITLE mammary tumor 8 kDa | GENE Mat8 | | NM_008557 | 1051256 |
| IC01406 | UG75 Expression | GENE | Mm.25339 | TITLE metastasis associated 1-like 1 | GENE Mata1l1 | MTA2\| | NM_011842 | 1149834 |
| IC01407 | UG75 Expression | GENE | Mm.25575 | TITLE matrin 3 | GENE Matr3 | | NM_010771 | 2102064 |
| IC01408 | UG75 Expression | GENE | Mm.3931 | TITLE Max protein | GENE Max | | NM_008558 | 1279687 |
| IC01409 | UG75 Expression | GENE | Mm.29759 | TITLE MYC-associated zinc finger protein (purine-binding transcription factor) | GENE Maz | Pur-1\| | gi = 200590 | 518504 |
| IC01410 | UG75 Expression | GENE | Mm.29010 | TITLE membrane bound C2 domain containing protein | GENE Mbc2 | vp115\| | gi = 4200443 | 1264591 |
| IC01411 | UG75 Expression | GENE | Mm.22522 | TITLE methyl-CpG binding domain protein 1 | GENE Mbd1 | | NM_013594 | 400458 |
| IC01412 | UG75 Expression | GENE | Mm.322 | TITLE methyl-CpG binding domain protein 2 | GENE Mbd2 | | gi = 3800794 | 2599139 |
| IC01413 | UG75 Expression | GENE | Mm.20890 | TITLE methyl-CpG binding domain protein 4 | GENE Mbd4 | | NM_010774 | 1149091 |
| IC01414 | UG75 Expression | GENE | Mm.30045 | TITLE mannose binding lectin, serum (C) | GENE Mbl2 | | NM_010776 | 1450922 |
| IC01415 | UG75 Expression | GENE | Mm.2992 | TITLE myelin basic protein | GENE Mbp | inter-alpha (globulin) inhibitor, H4 polypeptide\|inter-alpha-trypsin inhibitor light chain\|ItIn4\|Itil\| | NM_010777 | 1382930 |
| IC01416 | UG75 Expression | GENE | Mm.1639 | TITLE myeloid cell leukemia sequence 1 | GENE Mcl1\| | | NM_008562 | 1079512 |
| IC01417 | UG75 Expression | GENE | Mm.4502 | TITLE mini chromosome maintenance deficient (S. cerevisiae) | GENE Mcmd | P1\|p1.m\| | gi = 53550 | 422197 |
| IC01418 | UG75 Expression | GENE | Mm.16711 | TITLE mini chromosome maintenance deficient 2 (S. cerevisiae) | GENE Mcmd2 | | NM_008564 | 2937119 |
| IC01419 | UG75 Expression | GENE | Mm.1500 | TITLE mini chromosome maintenace deficient 4 homolog (S. cerevisiae) | GENE Mcmd4 | Cdc21\|cell division cycle 21 (S. pombe)\|mcdc21\| | NM_008565 | 586181 |
| IC01420 | UG75 Expression | GENE | Mm.5048 | TITLE mini chromosome maintenance deficient 5 (S. cerevisiae) | GENE Mcmd5 | Cdc46\|cell division cycle 46 (S. cerevisiae)\|mCD46\| | NM_008566 | 2076778 |
| IC01421 | UG75 Expression | GENE | Mm.4933 | TITLE mini chromosome maintenance deficient 6 (S. cerevisiae) | GENE Mcmd6 | ASP-1\| | NM_008567 | 2225480 |
| IC01422 | UG75 Expression | GENE | Mm.18923 | TITLE mini chromosome maintenance deficient 7 (S. cerevisiae) | GENE Mcmd7 | mCDC47\| | gi = 1136746 | 2088061 |
| IC01423 | UG75 Expression | GENE | Mm.3989 | TITLE meiotic check point regulator | GENE Mcpr | tsg24\| | NM_008569 | 1295992 |
| IC01424 | UG75 Expression | GENE | Mm.4409 | TITLE mast cell protease 2 | GENE Mcpt2 | mast cell protease-2\|Mcp-2\|MMCP-2\| | NM_008571 | 558162 |
| IC01425 | UG75 Expression | GENE | Mm.22693 | TITLE mast cell protease 4 | GENE Mcpt4 | Mcp-4\|MMCP-4\|MMCP-4A\|MMCP-4B\|myonase\| | NM_010779 | 958440 |
| IC01426 | UG75 Expression | GENE | Mm.1252 | TITLE mast cell protease 5 | GENE Mcpt5 | chymase 1, mast cell\|Cma1\|Mcp-5\|MMCP-5\| | NM_010780 | 1245414 |
| IC01427 | UG75 Expression | GENE | Mm.41979 | TITLE mast cell protease 8 | GENE Mcpt8 | MMCP-8\| | NM_008572 | 551493 |
| IC01428 | UG75 Expression | GENE | Mm.14213 | TITLE mast cell protease-like | GENE Mcptl | MMCP-L\| | NM_008573 | 557853 |
| IC01429 | UG75 Expression | GENE | Mm.906 | TITLE midkine | GENE Mdk | Mek\|midgestation embryo & kidney GENE\| | NM_010784 | 736520 |
| IC01430 | UG75 Expression | GENE | Mm.2003 | TITLE transformed mouse 3T3 cell double minute 1 | GENE Mdm1 | Mdm-1\| | NM_010785 | 523900 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01431 | UG75 Expression | GENE | Mm.4114 | TITLE antigen identified by monoclonal antibodies 4F2 | GENE Mdu1 | Mgp-2hc| | NM_008577 | 1907828 |
| IC01432 | UG75 Expression | GENE | Mm.2395 | TITLE male enhanced antigen 1 | GENE Mea1 | male-enhanced antigen 1|Mea-1| | NM_010787 | 1450531 |
| IC01433 | UG75 Expression | GENE | Mm.40984 | TITLE methyl CpG binding protein 2 | GENE Mecp2 | WBP10| | gi = 5419961 | 949357 |
| IC01434 | UG75 Expression | GENE | Mm.24001 | TITLE myocyte enhancer factor 2C | GENE Mef2c |  | gi = 293728 | 303910 |
| IC01435 | UG75 Expression | GENE | Mm.27979 | TITLE melanoma antigen, 80 kDa | GENE Mela |  | NM_008581 | 1296237 |
| IC01436 | UG75 Expression | GENE | Mm.4674 | TITLE maternal embryonic leucine zipper kinase | GENE Melk |  | NM_010790 | 574025 |
| IC01437 | UG75 Expression | GENE | Mm.1178 | TITLE maternal embryonic message 3 | GENE Mem3 |  | NM_008582 | 1382731 |
| IC01438 | UG75 Expression | GENE | Mm.12917 | TITLE multiple endocrine neoplasia 1 | GENE Men1 |  | NM_007472 | 935413 |
| IC01439 | UG75 Expression | GENE | Mm.4346 | TITLE mesenchyme homeobox 2 | GENE Meox2 | Gax|Mox-2|Mox2| | gi = 57949 | 777160 |
| IC01440 | UG75 Expression | GENE | Mm.1089 | TITLE mesoderm specific transcript | GENE Mest | Peg1| | NM_008590 | 2225417 |
| IC01441 | UG75 Expression | GENE | Mm.41667 | TITLE methyltransferase-like 1 (S. cerevisiae) | GENE Mettl1 |  | NM_010792 | 572618 |
| IC01442 | UG75 Expression | GENE | Mm.1451 | TITLE milk fat globule-EGF factor 8 protein | GENE Mfge8 | Mfgm| | NM_008594 | 604907 |
| IC01443 | UG75 Expression | GENE | Mm.517 | TITLE manic fringe homolog (Drosophila) | GENE Mfng |  | NM_008595 | 863219 |
| IC01444 | UG75 Expression | GENE | Mm.2672 | TITLE mannoside acetylglucosaminyl transferase 1 | GENE Mgat1 | Mgat-1| | NM_010794 | 2749198 |
| IC01445 | UG75 Expression | GENE | Mm.4235 | TITLE mast cell growth factor | GENE Mgf | Clo|cloud gray|Con|contrasted|Gb|grizzle-belly|Kit ligand|SCF|SF|SI|SLF|steel|Steel factor|stem cell factor| | NM_013598 | 2649021 |
| IC01446 | UG75 Expression | GENE | Mm.31616 | TITLE monoglyceride lipase | GENE MgII |  | NM_011844 | 1450899 |
| IC01447 | UG75 Expression | GENE | Mm.2326 | TITLE macrophage migration inhibitory factor | GENE Mif | GIF|Glif|glycosylation inhibiting factor| | NM_010798 | 425595 |
| IC01448 | UG75 Expression | GENE | Mm.43580 | TITLE multiple inositol polyphosphate histidine phosphatase 1 | GENE Minpp1 |  | NM_010799 | 722780 |
| IC01449 | UG75 Expression | GENE | Mm.6370 | TITLE Msx-interacting zinc finger | GENE Mizl |  | NM_008602 | 3025433 |
| IC01450 | UG75 Expression | GENE | Mm.20930 | TITLE muskelin 1, intracellular mediator containing kelch motifs | GENE Mkln1 |  | NM_013791 | 1328678 |
| IC01451 | UG75 Expression | GENE | Mm.10414 | TITLE myeloid leukemia factor 1 | GENE Mlf1 |  | NM_010801 | 1193633 |
| IC01452 | UG75 Expression | GENE | Mm.2389 | TITLE myeloid/lymphoid or mixed-lineage leukemia | GENE Mll | acute lymphocytic leukemia|ALL-1|HRX|HTRX|trithorax Drosophila| | gi = 688442 | 1973153 |
| IC01453 | UG75 Expression | GENE | Mm.8866 | TITLE myeloid/lymphoid or mixed lineage-leukemia translocation to 10 homolog (Drosophila) | GENE Mllt10 | Af10| | NM_010804 | 519607 |
| IC01454 | UG75 Expression | GENE | Mm.6949 | TITLE homolog of human MLLT2 unidentified GENE | GENE Mllt2h | Af4| | gi = 3328189 | 442327 |
| IC01455 | UG75 Expression | GENE | Mm.2769 | TITLE MARCKS-like protein | GENE Mlp |  | NM_010807 | 554317 |
| IC01456 | UG75 Expression | GENE | Mm.2055 | TITLE macrophage metalloelastase | GENE Mmel | macrophage elastase|MMP12| | NM_008605 | 2645495 |
| IC01457 | UG75 Expression | GENE | Mm.4561 | TITLE matrix metalloproteinase 11 | GENE Mmp11 | ST3|Stmy3|stromelysin 3|stromelysis 3| | NM_008606 | 657926 |
| IC01458 | UG75 Expression | GENE | Mm.19945 | TITLE matrix metalloproteinase 14 (membrane-inserted) | GENE Mmp14 | Membrane type 1-MMP|MT1-MMP| | NM_008608 | 424959 |
| IC01459 | UG75 Expression | GENE | Mm.29564 | TITLE matrix metalloproteinase 2 | GENE Mmp2 | 72kD gelatinase|72kD type IV collagenase|Clg4a|collagenase IVA, basement membrane, 72 kDa|gelatinase A| | NM_008610 | 2076863 |
| IC01460 | UG75 Expression | GENE | Mm.29373 | TITLE matrix metalloproteinase 23 | GENE Mmp23 | CA-MMP|cystein array matrix metalloproteinase| | NM_011985 | 597664 |
| IC01461 | UG75 Expression | GENE | Mm.4406 | TITLE matrix metalloproteinase 9 | GENE Mmp9 | 92kD gelatinase|92kD type IV collagenase|Clg4b|collagenase IVB, basement membrane, 92 kDa|Gel B|gelatinase B| | NM_013599 | 959144 |
| IC01462 | UG75 Expression | GENE | Mm.3688 | TITLE menage a trois 1 | GENE Mnat1 | p36| | NM_008612 | 480395 |
| IC01463 | UG75 Expression | GENE | Mm.4084 | TITLE mastocytoma N-deacetylase/N-sulfotransferase | GENE Mndns | glucosaminyl N-deacetylase/N-sulphotransferase 2|NDST-2| | NM_008611 | 1195763 |
| IC01464 | UG75 Expression | GENE | Mm.730 | TITLE malic enzyme, supernatant | GENE Mod1 | Mdh-1|Mod-1| | NM_008615 | 2939334 |
| IC01465 | UG75 Expression | GENE | Mm.12947 | TITLE monocytic adapter | GENE Mona | Gads| | NM_010815 | 1447069 |
| IC01466 | UG75 Expression | GENE | Mm.21743 | TITLE malate dehydrogenase, mitochondrial | GENE Mor1 | Mdh-2|Mor-1| | NM_008617 | 2609759 |
| IC01467 | UG75 Expression | GENE | Mm.3156 | TITLE malate dehydrogenase, soluble | GENE Mor2 | Mor-2| | NM_008618 | 1886512 |
| IC01468 | UG75 Expression | GENE | Mm.1597 | TITLE Moloney leukemia virus 10 | GENE Mov10 |  | NM_008620 | 1851985 |
| IC01469 | UG75 Expression | GENE | Mm.5057 | TITLE macrophage expressed GENE 1 | GENE Mpeg1 | Mag-2|Mpa-2| | NM_008620 | 1851985 |
| IC01470 | UG75 Expression | GENE | Mm.3999 | TITLE macrophage activation 2 | GENE Mpg | Mpg-1| | gi = 431419 | 1890126 |
| IC01471 | UG75 Expression | GENE | Mm.2358 | TITLE N-methylpurine-DNA glycosylase | GENE Mpg | Aag|Mid1| | NM_010822 | 513712 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01472 | UG75 Expression | GENE | Mm.4668 | TITLE myeloperoxidase | GENE Mpo | | NM_010824 | 533257 |
| IC01473 | UG75 Expression | GENE | Mm.2814 | TITLE membrane protein, palmitoylated (55 kDa) | GENE Mpp1 | | NM_008621 | 583178 |
| IC01474 | UG75 Expression | GENE | Mm.2045 | TITLE muscle and microspikes RAS | GENE Mras | | NM_008624 | 468878 |
| IC01475 | UG75 Expression | GENE | Mm.2019 | TITLE mannose receptor, C type 1 | GENE Mrc1 | | NM_008625 | 1246598 |
| IC01476 | UG75 Expression | GENE | Mm.4710 | TITLE myeloid ecotropic viral integration site-related GENE 2 | GENE Mrg2 | Meis3 | NM_008627 | 551394 |
| IC01477 | UG75 Expression | GENE | Mm.2701 | TITLE mammalian relative of DnaJ | GENE Mrj-pending | | NM_011847 | 1450634 |
| IC01478 | UG75 Expression | GENE | Mm.5820 | TITLE musculin | GENE Msc | MyoR | NM_010827 | 2076585 |
| IC01479 | UG75 Expression | GENE | Mm.9524 | TITLE melanocyte specific GENE 2 | GENE Msg2 | Er154-like|Mrg1|p35srj | NM_010828 | 455626 |
| IC01480 | UG75 Expression | GENE | Mm.4619 | TITLE mutS homolog 2 (E. coli) | GENE Msh2 | | NM_008628 | 1973034 |
| IC01481 | UG75 Expression | GENE | Mm.43330 | TITLE mutS homolog 3 (E. coli) | GENE Msh3 | D13Em1|Rep-3|Rep3|repair of chromatin damage 3 | NM_010829 | 2802779 |
| IC01482 | UG75 Expression | GENE | Mm.18210 | TITLE mutS homolog 6 (E. coli) | GENE Msh6 | G/T mismatch binding protein|GTBP|Gtmbp|Msh6 | NM_010830 | 1383613 |
| IC01483 | UG75 Expression | GENE | Mm.22248 | TITLE male-specific lethal-3 homolog 1 (Drosophila) | GENE Msl3l1 | | NM_010832 | 1364790 |
| IC01484 | UG75 Expression | GENE | Mm.28687 | TITLE moesin | GENE Msn | | NM_010833 | 2136645 |
| IC01485 | UG75 Expression | GENE | Mm.3514 | TITLE myostatin | GENE Mstn | Cmpt|compact|Gdf8|growth differentiation factor 8 | NM_010834 | 1445968 |
| IC01486 | UG75 Expression | GENE | Mm.870 | TITLE homeo box, msh-like 1 | GENE Msx1 | homeo box-7 cluster, msh-like|Hox-7 | NM_010835 | 616064 |
| IC01487 | UG75 Expression | GENE | Mm.12959 | TITLE GrpE-like 2, mitochondrial | GENE mt-Grpel | mt-GrpE#2 | gi = 3411071 | 482996 |
| IC01488 | UG75 Expression | GENE | Mm.2041 | TITLE metallothionein 1 | GENE Mt1 | | NM_013602 | 1974618 |
| IC01489 | UG75 Expression | GENE | Mm.89170 | TITLE metallothionein 2 | GENE Mt2 | M2 | gi = 199131 | 1511198 |
| IC01490 | UG75 Expression | GENE | Mm.12625 | TITLE microtubule-associated protein 4 | GENE Mtap4 | | NM_008633 | 1212258 |
| IC01491 | UG75 Expression | GENE | Mm.20928 | TITLE microtubule-associated protein 7 | GENE Mtap7 | E-MAP-115 | NM_008635 | 513854 |
| IC01492 | UG75 Expression | GENE | Mm.12871 | TITLE microtubule-associated protein tau | GENE Mtapt | Tau | NM_010838 | 1923982 |
| IC01493 | UG75 Expression | GENE | Mm.16366 | TITLE mature T-cell proliferation 1 | GENE Mtcp1 | | NM_010839 | 749499 |
| IC01494 | UG75 Expression | GENE | Mm.10563 | TITLE metal response element binding transcription factor 2 | GENE Mtf2 | | NM_013827 | 635610 |
| IC01495 | UG75 Expression | GENE | Mm.2539 | TITLE mutT (E. coli) human homolog (8-oxo-dGTPase) | GENE Mth1 | | NM_008637 | 734211 |
| IC01496 | UG75 Expression | GENE | Mm.443 | TITLE methylenetetrahydrofolate dehydrogenase (NAD+ dependent), methenyltetrahydrofolate cyclohydrolase | GENE Mthfd2 | | NM_008638 | 835482 |
| IC01497 | UG75 Expression | GENE | Mm.30071 | TITLE membrane transporter protein | GENE Mtrp | MTP | NM_008640 | 1482882 |
| IC01498 | UG75 Expression | GENE | Mm.9287 | TITLE microtubule associated testis specific serine/threonine protein kinase | GENE Mtssk | | NM_008641 | 478397 |
| IC01499 | UG75 Expression | GENE | Mm.1232 | TITLE mammary tumor virus locus 43 | GENE Mtv43 | | gi = 3132512 | 3155868 |
| IC01500 | UG75 Expression | GENE | Mm.22508 | TITLE metaxin | GENE Mtx | Gcap6|granule cell antiserum positive 6 | NM_013604 | 1886353 |
| IC01501 | UG75 Expression | GENE | Mm.4299 | TITLE methylmalonyl-Coenzyme A mutase | GENE Mut | | NM_008650 | 1383712 |
| IC01502 | UG75 Expression | GENE | Mm.33996 | TITLE myxovirus (influenza virus) resistance 1 | GENE Mx1 | | NM_010846 | 596130 |
| IC01503 | UG75 Expression | GENE | Mm.14157 | TITLE myxovirus (influenza virus) resistance 2 | GENE Mx2 | | NM_013606 | 599128 |
| IC01504 | UG75 Expression | GENE | Mm.2154 | TITLE Max interacting protein 1 | GENE Mxi1 | Mad2 | NM_010847 | 483131 |
| IC01505 | UG75 Expression | GENE | Mm.1202 | TITLE myeloblastosis oncogene | GENE Myb | c-myb | NM_010848 | 721803 |
| IC01506 | UG75 Expression | GENE | Mm.479 | TITLE myeloblastosis oncogene-like 1 | GENE Mybl1 | A-myb | NM_008651 | 2749156 |
| IC01507 | UG75 Expression | GENE | Mm.2444 | TITLE myelocytomatosis oncogene | GENE Myc | | NM_010849 | 3155543 |
| IC01508 | UG75 Expression | GENE | Mm.4048 | TITLE myeloid differentiation primary response GENE 116 | GENE Myd116 | | NM_008654 | 644416 |
| IC01509 | UG75 Expression | GENE | Mm.1360 | TITLE myeloid differentiation primary response GENE 118 | GENE Myd118 | | NM_008655 | 2698942 |
| IC01510 | UG75 Expression | GENE | Mm.12847 | TITLE myeloid differentiation primary response GENE 88 | GENE Myd88 | myeloid differentiation primary response gene | NM_010851 | 1383757 |
| IC01511 | UG75 Expression | GENE | Mm.18535 | TITLE myelin basic protein expression factor 2, repressor | GENE Myef2 | | gi = 536925 | 1498075 |
| IC01512 | UG75 Expression | GENE | Mm.3153 | TITLE myosin heavy chain 11, smooth muscle | GENE Myh11 | | NM_013607 | 737004 |
| IC01513 | UG75 Expression | GENE | Mm.7215 | TITLE myosin heavy chain, cardiac muscle, adult | GENE Myhca | alpha myosin|Myhc-a | NM_010856 | 1260934 |
| IC01514 | UG75 Expression | GENE | Mm.3328 | TITLE myosin light chain, alkali, nonmuscle | GENE Myln | NLC3nm | gi = 1041793 | 1432183 |
| IC01515 | UG75 Expression | GENE | Mm.25194 | TITLE myosin Ic | GENE Myo1c | | NM_008659 | 1958390 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01516 | UG75 Expression | GENE | Mm.3645 | TITLE myosin Va | GENE Myo5a | d|Dbv|dulute|Myo5|myosin V| | NM_010864 | 3025627 |
| IC01517 | UG75 Expression | GENE | Mm.3536 | TITLE myosin Vb | GENE Myo5b | | NM_008661 | 733166 |
| IC01518 | UG75 Expression | GENE | Mm.25903 | TITLE Ngfi-A binding protein 1 | GENE Nab1 | | NM_008667 | 3155795 |
| IC01519 | UG75 Expression | GENE | Mm.6549 | TITLE Ngfi-A binding protein 2 | GENE Nab2 | mKy(beta)1| message|Kcnb3|potassium voltage gated channel, shab-related subfamily, member 3| | NM_008668 | 644224 |
| IC01520 | UG75 Expression | GENE | Mm.3746 | TITLE nascent polypeptide-associated complex alpha polypeptide | GENE Naca | skNAC| | NM_013608 | 1889649 |
| IC01521 | UG75 Expression | GENE | Mm.20325 | TITLE N-acetyl galactosaminidase, alpha | GENE Naga | | NM_008669 | 1078050 |
| IC01522 | UG75 Expression | GENE | Mm.2831 | TITLE nucleosome assembly protein 1 like 4 | GENE Nap1|4 | Nap2| D4H1S1733E|DAN|Dana|differential screening selected gene aberrative in neuroblastoma|DNA segment, Chr 4, human | NM_008672 | 2076916 |
| IC01523 | UG75 Expression | GENE | Mm.9404 | TITLE neuroblastoma, suppression of tumorigenicity 1 | GENE Nbl1 | D1S1733E|NO3| | NM_008675 | 483351 |
| IC01524 | UG75 Expression | GENE | Mm.784 | TITLE next to the Brca1 | GENE Nbr1 | | NM_008676 | 1972988 |
| IC01525 | UG75 Expression | GENE | Mm.10729 | TITLE neutrophil cytosolic factor 2 | GENE Ncf2 | NADPH oxidase subunit (67 kD)/Ncf-2|p67phox| | NM_010877 | 890392 |
| IC01526 | UG75 Expression | GENE | Mm.2068 | TITLE neutrophil cytosolic factor 4 | GENE Ncf4 | p40|phox| | NM_008677 | 641512 |
| IC01527 | UG75 Expression | GENE | Mm.8201 | TITLE non-catalytic region of tyrosine kinase adaptor protein 1 | GENE Nck1 | Nck|non-catalytic region of tyrosine kinase| | NM_010878 | 618165 |
| IC01528 | UG75 Expression | GENE | Mm.9238 | TITLE non-catalytic region of tyrosine kinase adaptor protein 2 | GENE Nck2 | Grb4|growth factor receptor-bound 4|NCK beta| | NM_010879 | 1328963 |
| IC01529 | UG75 Expression | GENE | Mm.4907 | TITLE nucleolin | GENE Ncl | | NM_010880 | 2286068 |
| IC01530 | UG75 Expression | GENE | Mm.2028 | TITLE nuclear receptor coactivator 1 | GENE Ncoa1 | SRC-1|SRC-a/NCoA-1| 1| | NM_010881 | 1209251 |
| IC01531 | UG75 Expression | GENE | Mm.2537 | TITLE nuclear receptor coactivator 2 | GENE Ncoa2 | | NM_008678 | 1055084 |
| IC01532 | UG75 Expression | GENE | Mm.1011 | TITLE nuclear receptor coactivator 3 | GENE Ncoa3 | ACTR|AIB1|p|CIP|RQAC3|TRAM-1| | NM_008679 | 793854 |
| IC01533 | UG75 Expression | GENE | Mm.29412 | TITLE nuclear receptor co-repressor 2 | GENE Ncor2 | silencing mediator of retinoid acid and thyroid hormone receptor|SMRTe| | NM_011424 | 352704 |
| IC01534 | UG75 Expression | GENE | Mm.7089 | TITLE necdin | GENE Ndn | | NM_010882 | 149017 |
| IC01535 | UG75 Expression | GENE | Mm.4941 | TITLE NPC derived proline rich protein 1 | GENE Ndpp1 | glucosaminyl N-deacetylase/N-sulphotransferase 2|NDST-2| | NM_008680 | 751400 |
| IC01536 | UG75 Expression | GENE | Mm.4063 | TITLE N-myc downstream regulated 1 | GENE Ndr1 | WBP8| | NM_010884 | 580263 |
| IC01537 | UG75 Expression | GENE | Mm.26722 | TITLE N-myc downstream regulated 2 | GENE Ndr2 | Ndr1| | NM_013864 | 1181360 |
| IC01538 | UG75 Expression | GENE | Mm.36775 | TITLE N-myc downstream regulated 3 | GENE Ndr3 | | NM_013865 | 2076668 |
| IC01539 | UG75 Expression | GENE | Mm.29867 | TITLE NADH dehydrogenase (ubiquinone) 1 alpha subcomplex 2 (8 kDa) | GENE Ndufa2 | C1-B8| | NM_010885 | 1972967 |
| IC01540 | UG75 Expression | GENE | Mm.14442 | TITLE NADH dehydrogenase (ubiquinone) Fe-S protein 4 (18 kDa) | GENE Ndufs4 | C1-18k| | NM_010887 | 1025396 |
| IC01541 | UG75 Expression | GENE | Mm.2998 | TITLE neural precursor cell expressed, developmentally down regulated GENE 1 | GENE Nedd1 | | NM_008682 | 3154045 |
| IC01542 | UG75 Expression | GENE | Mm.16553 | TITLE neural precursor cell expressed, developmentally down-regulated 4 | GENE Nedd4 | | gi = 2088622 | 2259241 |
| IC01543 | UG75 Expression | GENE | Mm.336 | TITLE neural precursor cell expressed, developmentally down-regulated GENE 5 | GENE Nedd5 | | NM_010891 | 2646342 |
| IC01544 | UG75 Expression | GENE | Mm.196 | TITLE neural precursor cell expressed, developmentally down-regulated GENE 8 | GENE Nedd8 | | NM_008683 | 736082 |
| IC01545 | UG75 Expression | GENE | Mm.5379 | TITLE NIMA-related expressed kinase 2 | GENE Nek2 | | NM_010892 | 959862 |
| IC01546 | UG75 Expression | GENE | Mm.8856 | TITLE neuraminidase 1 | GENE Neu1 | acid phosphatase, liver|Ag|p|alpha glucosidase processing|Ap||mannosidase processing 2|Map-2|Neu-1| | NM_010893 | 332803 |
| IC01547 | UG75 Expression | GENE | Mm.1190 | TITLE neurofibromatosis 2 | GENE Nf2 | | NM_010898 | 1180510 |
| IC01548 | UG75 Expression | GENE | Mm.3107 | TITLE nuclear factor of activated T-cells, cytoplasmic 3 | GENE Nfatc3 | NFAT4|NFATx| | gi = 1906311 | 575541 |
| IC01549 | UG75 Expression | GENE | Mm.3216 | TITLE nuclear factor, erythroid derived 2, 45 kDa | GENE Nfe2 | NF-E2|p45| | gi = 293826 | 373510 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01550 | UG75 Expression | GENE | Mm.6743 | TITLE nuclear factor, erythroid derived 2,-like 1 | GENE Nfe2l1 | LCR-F1|NRF1|TCF-11| | NM_008686 | 1886542 |
| IC01551 | UG75 Expression | GENE | Mm.1025 | TITLE nuclear factor, erythroid derived 2, like 2 | GENE Nfe2l2 | Nrf2| | NM_010902 | 2192413 |
| IC01552 | UG75 Expression | GENE | Mm.2034 | TITLE neurofilament, heavy polypeptide | GENE Nfh | NF-H| | gi = 200021 | 337866 |
| IC01553 | UG75 Expression | GENE | Mm.4025 | TITLE nuclear factor I/B | GENE Nfib |  | NM_008687 | 904019 |
| IC01554 | UG75 Expression | GENE | Mm.3420 | TITLE nuclear factor of kappa light chain GENE enhancer in B-cells 1, p105 | GENE Nfkb1 | NF-kappaB1|NF-KB1|p50 subunit of NF-kappaB1p50/p105| | NM_008689 | 575105 |
| IC01555 | UG75 Expression | GENE | Mm.8884 | TITLE nuclear factor of kappa light chain GENE enhancer in B-cells inhibitor, alpha | GENE Nfkbia | GENE enhancer in B-cells inhibitor| I(Kappa)B(beta|tkB||KB-beta | NM_010907 | 641058 |
| IC01556 | UG75 Expression | GENE | Mm.4448 | TITLE nuclear factor of kappa light chain GENE enhancer in B-cells inhibitor, beta | GENE Nfkbib |  | NM_010908 | 2936874 |
| IC01557 | UG75 Expression | GENE | Mm.29169 | TITLE nitrogen fixation GENE, yeast homolog 1 (S. cerevisiae) | GENE Nfs1 | m-Nfs|NifS-like (sic)| | NM_010911 | 1972350 |
| IC01558 | UG75 Expression | GENE | Mm.4929 | TITLE nuclear transcription factor-Y alpha | GENE Nfya | SEZ-10| | NM_010913 | 719809 |
| IC01559 | UG75 Expression | GENE | Mm.3259 | TITLE nuclear transcription factor-Y beta | GENE Nfyb |  | NM_010914 | 574429 |
| IC01560 | UG75 Expression | GENE | Mm.27220 | TITLE nuclear transcription factor-Y gamma | GENE Nfyc |  | NM_008692 | 582019 |
| IC01561 | UG75 Expression | GENE | Mm.2827 | TITLE neutrophilic granule protein | GENE Ngp |  | NM_008694 | 723612 |
| IC01562 | UG75 Expression | GENE | Mm.4691 | TITLE nidogen | GENE Nid | entactin| | NM_010917 | 636367 |
| IC01563 | UG75 Expression | GENE | Mm.20348 | TITLE nidogen 2 | GENE Nid2 | entactin-2|Ly111| | NM_008695 | 477696 |
| IC01564 | UG75 Expression | GENE | Mm.4569 | TITLE ninein | GENE Nin |  | NM_008697 | 1348257 |
| IC01565 | UG75 Expression | GENE | Mm.18503 | TITLE ninjurin 1 | GENE Ninj1 |  | NM_013610 | 443142 |
| IC01566 | UG75 Expression | GENE | Mm.16958 | TITLE 4-nitrophenylphosphatase domain and non-neuronal SNAP25-like protein homolog 1 (C. elegans) | GENE Nipsnap1 |  | NM_008698 | 1450297 |
| IC01567 | UG75 Expression | GENE | Mm.12915 | TITLE nitrilase 1 | GENE Nit1 |  | NM_012049 | 1888679 |
| IC01568 | UG75 Expression | GENE | Mm.23964 | TITLE natural killer tumor recognition sequence | GENE Nktr |  | NM_010918 | 722840 |
| IC01569 | UG75 Expression | GENE | Mm.5423 | TITLE Drosophila NK transcription factor related, GENE family 6, locus 2 | GENE Nkx6-2 | glial and testis specific homeobox gene|Gtx| | gi = 193715 | 576409 |
| IC01570 | UG75 Expression | GENE | Mm.9001 | TITLE nemo like kinase | GENE Nlk |  | NM_008702 | 2646755 |
| IC01571 | UG75 Expression | GENE | Mm.20918 | TITLE nuclear localization signal protein absent in velo-cardio-facial patients | GENE Nlvcf |  | NM_010922 | 400491 |
| IC01572 | UG75 Expression | GENE | Mm.1260 | TITLE expressed in non-metastatic cells 1, protein (NM23A) | GENE Nme1 |  | gi = 1816593 | 18886411 |
| IC01573 | UG75 Expression | GENE | Mm.1125 | TITLE expressed in non-metastatic cells 2, protein (NM23B) | GENE Nme2 |  | NM_008705 | 550895 |
| IC01574 | UG75 Expression | GENE | Mm.10265 | TITLE N-myristoyltransferase | GENE Nmt1 |  | NM_008707 | 571872 |
| IC01575 | UG75 Expression | GENE | Mm.16469 | TITLE neuroblastoma myc-related oncogene 1 | GENE Nmyc1 | c-nmyc|Nmyc|Nmyc-1| | NM_008709 | 438133 |
| IC01576 | UG75 Expression | GENE | Mm.8362 | TITLE nicotinamide N-methyltransferase | GENE Nnmt |  | NM_010924 | 1889173 |
| IC01577 | UG75 Expression | GENE | Mm.38344 | TITLE novel nuclear protein 1 | GENE Nnp1 | NNP-1| | NM_010925 | 2064806 |
| IC01578 | UG75 Expression | GENE | Mm.22072 | TITLE neighbor of Cox4 | GENE Noc4 |  | NM_010926 | 3167033 |
| IC01579 | UG75 Expression | GENE | Mm.12837 | TITLE nitric oxide synthase 3, endothelial cell | GENE Nos3 | ecNOS|eNOS|nitric oxide synthase 3 (indicible)|Nos-3| | NM_008713 | 620940 |
| IC01580 | UG75 Expression | GENE | Mm.31255 | TITLE Notch GENE homolog 1, (Drosophila) | GENE Notch1 | lin-12|Tan1|translocation-associated Notch| | NM_008714 | 1327877 |
| IC01581 | UG75 Expression | GENE | Mm.4173 | TITLE Notch2-like | GENE Notch2l |  | NM_008715 | 834590 |
| IC01582 | UG75 Expression | GENE | Mm.4503 | TITLE nuclear protein 220 | GENE Np220 | mNP220|nuclear protein| | NM_008717 | 876049 |
| IC01583 | UG75 Expression | GENE | Mm.42196 | TITLE nuclear protein 95 | GENE Np95 |  | NM_010931 | 2582196 |
| IC01584 | UG75 Expression | GENE | Mm.3484 | TITLE Niemann Pick type C1 | GENE Npc1 | npc<nih>|sphingomyelinosis|spm| | NM_008720 | 1055024 |
| IC01585 | UG75 Expression | GENE | Mm.1131 | TITLE neural proliferaiton, differentiation and control GENE 1 | GENE Npdc1 | NPDC-1| | NM_008721 | 1907763 |
| IC01586 | UG75 Expression | GENE | Mm.6343 | TITLE nucleophosmin 1 | GENE Npm1 | B23|NO38|nucleolar protein No38| | NM_008722 | 2812270 |
| IC01587 | UG75 Expression | GENE | Mm.1406 | TITLE nucleoplasmin 3 | GENE Npm3 | Nub1| | NM_008723 | 1973305 |
| IC01588 | UG75 Expression | GENE | Mm.1364 | TITLE neoplastic progression 3 | GENE Npn3 | TX01| | gi = 467582 | 1278439 |
| IC01589 | UG75 Expression | GENE | Mm.16347 | TITLE neuropeptide nociceptin 1 | GENE Npnc1 | N23K| | gi = 1311472 | 456291 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01590 | UG75 Expression | GENE | Mm.6680 | neural plakophilin-related arm-repeat protein | Nprap | D118Bwg1004e|DNA segment, Chr 11, Brigham & Women's | NM_008729 | 765554 |
| IC01591 | UG75 Expression | GENE | Mm.5142 | neuronal pentraxin 1 | Nptx1 | Genetics 1004 expressed| | NM_008730 | 1522292 |
| IC01592 | UG75 Expression | GENE | Mm.968 | nuclear receptor subfamily 1, group H, member 2 | Nr1h2 | LXRB|LXRbeta|NER1|Nr1h2|OR-1|RIP15|ubiquitously-expressed nuclear receptor|ubiquitously-expressed nuclear receptor 2|Unr|Unr2|UR| | NM_009473 | 598300 |
| IC01593 | UG75 Expression | GENE | Mm.8509 | nuclear receptor subfamily 1, group I, member 2 | Nr1i2 | PXR|PXR.1|PXR.2|PXR1| | gi≤2852328 | 737758 |
| IC01594 | UG75 Expression | GENE | Mm.3077 | nuclear receptor subfamily 1, group I, member 3 | Nr1i3 | CAR|CAR1|CAR2|Care2|constitutive androstane receptor 2|constitutively transactivates RAREs|MB67| | NM_009803 | 693202 |
| IC01595 | UG75 Expression | GENE | Mm.3535 | nuclear receptor subfamily 2, group H, member 2 | Nr2c2 | orphan receptor, TR4|TAK1|Tr4| | gi = 2143009 | 1922208 |
| IC01596 | UG75 Expression | GENE | Mm.16519 | nuclear receptor subfamily 2, group F, member 2 | Nr2f2 | apolipoprotein regulatory protein 1|Aporp1|ARP-1|COUP-TFII|COUPTFB|SVP40|Tcfcoup2|transcription factor COUP 2|Gfrp|growth factor response protein|Hbr-1|Hbr1|Hm|hormone | NM_009697 | 2101216 |
| IC01597 | UG75 Expression | GENE | Mm.119 | nuclear receptor subfamily 4, group A, member 1 | geen Nr4a1 | binding receptor 1|hormone receptor|NGFIB|nur77|TIS1|TR3| | NM_01044 | 1265331 |
| IC01598 | UG75 Expression | GENE | Mm.734 | neuroblastoma ras oncogene | Nras | N-ras| | NM_010937 | 1137580 |
| IC01599 | UG75 Expression | GENE | Mm.20895 | nuclear receptor interacting protein 1 | Nrip1 | RIP140| | NM_008735 | 617333 |
| IC01600 | UG75 Expression | GENE | Mm.12964 | nuclear receptor-binding SET-domain protein 1 | Nsd1 | | NM_008739 | 482640 |
| IC01601 | UG75 Expression | GENE | Mm.38792 | NAD(P) dependent steroid dehydrogenase-like | Nsdhl | bare patches|bare-patches|Bpa|H105E3|Str|striated|XAP104| | gi = 2769543 | 963446 |
| IC01602 | UG75 Expression | GENE | Mm.7414 | neuron specific GENE family member 1 | Nsg1 | m234|p21| | NM_010942 | 658942 |
| IC01603 | UG75 Expression | GENE | Mm.3304 | neuron specific GENE family member 2 | Nsg2 | 8.5| | NM_008741 | 1969803 |
| IC01604 | UG75 Expression | GENE | Mm.3059 | neutral sphingomyelinase (N-SMase) activation associated factor | Nsmaf | factor associated with N-SMase activation|Fan| | NM_010945 | 718199 |
| IC01605 | UG75 Expression | GENE | Mm.27378 | N-terminal Asn amidase | Ntan1 | | NM_010946 | 1482861 |
| IC01606 | UG75 Expression | GENE | Mm.29037 | nucleotide binding protein 1 | Nubp1 | D17Wsu11e|DNA segment, Chr 17, Wayne State University 11, expressed| | NM_011955 | 3167196 |
| IC01607 | UG75 Expression | GENE | Mm.36718 | nucleotide binding protein 2 | Nubp2 | | NM_011956 | 1196104 |
| IC01608 | UG75 Expression | GENE | Mm.2283 | nucleobindin | Nucb | | NM_008749 | 2192640 |
| IC01609 | UG75 Expression | GENE | Mm.69 | nuclear distribution GENE C homolog (Aspergillus) | Nudc | NudC|G=SIG-92|Silg92|silica-induced gene 92| | NM_010949 | 949254 |
| IC01610 | UG75 Expression | GENE | Mm.4390 | numb GENE homolog (Drosophila) GENE Numb | m-numb|mnb| | | NM_010949 | 949254 |
| IC01611 | UG75 Expression | GENE | Mm.49224 | numb-like | Numbl | nbl| | NM_010950 | 670806 |
| IC01612 | UG75 Expression | GENE | Mm.27915 | nucleoredoxin | Nxn | | NM_008750 | 1002490 |
| IC01613 | UG75 Expression | GENE | Mm.14301 | 2'-5' oligoadenylate synthetase 1A | Oas1a | 2'-5' oligoadenylate synthetase 1|Oias-1|Oias1| | gi = 49712 | 577664 |
| IC01614 | UG75 Expression | GENE | Mm.683 | ornithine decarboxylase antizyme | Oaz | | NM_008753 | 2247461 |
| IC01615 | UG75 Expression | GENE | Mm.675 | ornithine decarboxylase antizyme 2 | Oaz2 | ornithine decarboxylase antizyme|seizure related gene 15|Sez15| | gi = 1304167 | 2811179 |
| IC01616 | UG75 Expression | GENE | Mm.15259 | ornithine decarboxylase, structural | Odc | | NM_013614 | 1003227 |
| IC01617 | UG75 Expression | GENE | Mm.663 | outer dense fiber of sperm tails 2 | Odf2 | MMTEST29| | NM_013615 | 602081 |
| IC01618 | UG75 Expression | GENE | Mm.45055 | | Odzr1-p | odd-skipped related gene|Osr1| | NM_011859 | 618322 |
| IC01619 | UG75 Expression | GENE | Mm.43612 | 8-oxoguanine DNA-glycosylase 1 | Ogg1 | | NM_010957 | 1382267 |
| IC01620 | UG75 Expression | GENE | Mm.1870 | oncoprotein induced transcript 2 | Oit2 | RIC| | NM_008761 | 637153 |
| IC01621 | UG75 Expression | GENE | Mm.22745 | opioid receptor, sigma 1 | Oprs1 | mSigmaR1| | NM_011014 | 987467 |
| IC01622 | UG75 Expression | GENE | Mm.42024 | origin recognition complex, subunit 1 homolog (S. cerevisiae) | Orc1 | MmORC1| | NM_011015 | 1295828 |
| IC01623 | UG75 Expression | GENE | Mm.3411 | origin recognition complex, subunit 2 homolog (S. cerevisiae) | Orc2 | Orc2|origin recognition complex, subunit 2 (Saccharomyes) homolog-like| | NM_008765 | 598421 |
| IC01624 | UG75 Expression | GENE | Mm.21834 | origin recognition complex, subunit 4 | Orc4 | mMmORC4|oRC4p| | nm_011958 | 572595 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01625 | UG75 Expression | GENE | Mm.566 | TITLE origin recognition complex, subunit 5 homolog (S. cerevisiae) | GENE Orc5 | MmORC5|mouse origin recognition complex 5| | NM_011959 | 577496 |
| IC01626 | UG75 Expression | GENE | Mm.2310 | TITLE open reading frame 6 | GENE ORF6 | C11orf5|chromosome 11 open reading frame 5| | NM_013859 | 2651436 |
| IC01627 | UG75 Expression | GENE | Mm.9846 | TITLE oxidative stress induced | GENE Osi | A170| | NM_011018 | 605631 |
| IC01628 | UG75 Expression | GENE | Mm.10760 | TITLE oncostatin receptor | GENE Osmr | | NM_011019 | 1970578 |
| IC01629 | UG75 Expression | GENE | Mm.4150 | TITLE osmotic stress protein 94 kDa | GENE Osp94 | apg-1| | NM_011020 | 1295907 |
| IC01630 | UG75 Expression | GENE | Mm.16745 | TITLE oxytocin | GENE Oxt | OT|Oxy| | NM_011025 | 640127 |
| IC01631 | UG75 Expression | GENE | Mm.25722 | TITLE purinergic receptor P2X, ligand-gated ion channel, 1 | GENE P2rx1 | P2x|P2X1 receptor| | NM_008771 | 576538 |
| IC01632 | UG75 Expression | GENE | Mm.3000 | TITLE purinergic receptor P2Y, G-protein coupled 2 | GENE P2ry2 | | NM_008773 | 1295191 |
| IC01633 | UG75 Expression | GENE | Mm.4071 | TITLE P40-8, functional | GENE P40-8 | NLR|P40| | NM_011029 | 1886017 |
| IC01634 | UG75 Expression | GENE | Mm.2212 | TITLE procollagen-proline, 2-oxoglutarate 4-dioxygenase (proline 4-hydroxylase), alpha 1 polypeptide | GENE P4ha1 | p4ha|prolyl 4-hydroxylase, alpha polypeptide| | gi = 836897 | 1920914 |
| IC01635 | UG75 Expression | GENE | Mm.3705 | TITLE procollagen-proline, 2-oxoglutarate 4-dioxygenase (proline 4-hydroxylase), alpha II polypeptide | GENE P4ha2 | P4hll|prolyl 4-hydroxylase-like| | NM_011031 | 1434004 |
| IC01636 | UG75 Expression | GENE | Mm.16660 | TITLE prolyl 4-hydroxylase, beta polypeptide | GENE P4hb | ERp59|PDI|Thbp|thyroid hormone binding protein| | gi = 200280 | 1921212 |
| IC01637 | UG75 Expression | GENE | Mm.2642 | TITLE poly A binding protein, cytoplasmic 1 | GENE Pabpc1 | PABP|Pabp1|poly(A)-binding protein-like 1|poly A binding protein 1| | NM_008774 | 2939340 |
| IC01638 | UG75 Expression | GENE | Mm.412 | TITLE proliferation-associated GENE A | GENE Paga | macrophage 23 Kd stress protein|macrophage stress protein 23 kd|MSP23|TDX2|Tdpx2|thioredoxin dependent peroxide reductase 2|Trx dependent peroxide reductase 2| | NM_011034 | 1890166 |
| IC01639 | UG75 Expression | GENE | Mm.2422 | TITLE phenylalanine hydroxylase | GENE Pah | | NM_008777 | 2236422 |
| IC01640 | UG75 Expression | GENE | Mm.3437 | TITLE paladin | GENE Pald | | NM_013753 | 1195794 |
| IC01641 | UG75 Expression | GENE | Mm.18161 | TITLE 3'-phosphoadenosine 5'-phosphosulfate synthase | GENE Papss1 | Asapk|ATP sulfurylase-adenosine 5'-phosphosulfate kinase|SK1| | NM_0111863 | 614816 |
| IC01642 | UG75 Expression | GENE | Mm.27646 | TITLE 3'-phosphoadenosine 5'-phosphosulfate synthase 2 | GENE Papss2 | AtpsU2|bm|brachymorphic|code642|Sk2| | NM_011864 | 888971 |
| IC01643 | UG75 Expression | GENE | Mm.15962 | TITLE poly (ADP-ribose) glycohydrolase | GENE Parg | | NM_011960 | 945431 |
| IC01644 | UG75 Expression | GENE | Mm.3066 | TITLE paired box GENE 1 | GENE Pax1 | hbs|hunchback|Pax-1|un|undulated|wavy tail|wt| | NM_008780 | 1327502 |
| IC01645 | UG75 Expression | GENE | Mm.22675 | TITLE pre B-cell leukemia transcription factor 1 | GENE Pbx1 | pbx-1| | NM_008783 | 1973011 |
| IC01646 | UG75 Expression | GENE | Mm.29089 | TITLE poly(rC)-binding protein 1 | GENE Pcbp1 | [a]CP-1| | NM_011865 | 946083 |
| IC01647 | UG75 Expression | GENE | Mm.111 | TITLE poly(rC)-binding protein 2 | GENE Pcbp2 | alphaCP-2|heterogeneous nuclear ribonucleoprotein X|Hnrpx| | NM_011042 | 992841 |
| IC01648 | UG75 Expression | GENE | Mm.42246 | TITLE phosphoenolpyruvate carboxykinase 1, cytosolic | GENE Pck1 | Pck-1|PEPCK| | NM_011044 | 1970501 |
| IC01649 | UG75 Expression | GENE | Mm.28196 | TITLE pericentriolar material 1 | GENE Pcm1 | | gi = 6505712 | 1162868 |
| IC01650 | UG75 Expression | GENE | Mm.25293 | TITLE protein-L-isoaspartate (D-aspartate)O-methyltransferase 1 | GENE Pcmt1 | PIMT|protein carboxyl methyltransferase| | NM_008786 | 1970313 |
| IC01651 | UG75 Expression | GENE | Mm.7141 | TITLE proliferating cell nuclear antigen | GENE Pcna | | NM_011045 | 1383565 |
| IC01652 | UG75 Expression | GENE | Mm.4379 | TITLE pericentrin | GENE Pcnt | | NM_008787 | 1886419 |
| IC01653 | UG75 Expression | GENE | Mm.18808 | TITLE procollagen C-proteinase enhancer protein | GENE Pcolce | | NM_008788 | 2076666 |
| IC01654 | UG75 Expression | GENE | Mm.5241 | TITLE proprotein convertase subtilisin/kexin type 3 | GENE Pcsk3 | Furi|furin|PACE|SPC1| | NM_011046 | 3025735 |
| IC01655 | UG75 Expression | GENE | Mm.3255 | TITLE proprotein convertase subtilisin/kexin type 7 | GENE Pcsk7 | SPC7| | NM_008794 | 1226389 |
| IC01656 | UG75 Expression | GENE | Mm.1845 | TITLE pyruvate decarboxylase | GENE Pcx | Pc| | NM_008797 | 3154868 |
| IC01657 | UG75 Expression | GENE | Mm.323 | TITLE programmed cell death 2 | GENE Pdcd2 | RP-8| | NM_008799 | 1495609 |
| IC01658 | UG75 Expression | GENE | Mm.1605 | TITLE programmed cell death 4 | GENE Pdcd4 | MA-3|TIS| | gi = 3426154 | 1401011 |
| IC01659 | UG75 Expression | GENE | Mm.24254 | TITLE programmed cell death 6 | GENE Pdcd6 | Alg2|apoptosis linked GENE 2|MA-3|PS2| | NM_011051 | 1247607 |
| IC01660 | UG75 Expression | GENE | Mm.29816 | TITLE programmed cell death 6 interacting protein | GENE Pdcd6ip | AIP1|Alix| | NM_011052 | 2938057 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01661 | UG75 Expression | GENE | Mm.30050 | TITLE programmed cell death 8 (apoptosis inducing factor) | GENE Pdcd8 | mAIF| | NM_012019 | 2159444 |
| IC01662 | UG75 Expression | GENE | Mm.62 | TITLE phosphodiesterase 1B1, Ca2+-calmodulin dependent, 63 kDa | GENE Pde1b1 | | NM_008800 | 557945 |
| IC01663 | UG75 Expression | GENE | Mm.5145 | TITLE phosphodiesterase 1C | GENE Pde1c | | NM_011054 | 1263202 |
| IC01664 | UG75 Expression | GENE | Mm.12925 | TITLE phosphodiesterase 6D, cGMP-specific, rod delta | GENE Pde6d | | NM_008801 | 875119 |
| IC01665 | UG75 Expression | GENE | Mm.5034 | TITLE phosphodiesterase 7A | GENE Pde7a | | NM_008802 | 614429 |
| IC01666 | UG75 Expression | GENE | Mm.9757 | TITLE phosphodiesterase 8 | GENE Pde8 | | NM_008803 | 1066664 |
| IC01667 | UG75 Expression | GENE | Mm.4127 | TITLE testis specific phosphodiesterase | GENE Pdet | | NM_008807 | 514599 |
| IC01668 | UG75 Expression | GENE | Mm.2675 | TITLE platelet derived growth factor, alpha | GENE Pdgfa | | NM_008808 | 388934 |
| IC01669 | UG75 Expression | GENE | Mm.2924 | TITLE platelet derived growth factor receptor, alpha polypeptide | GENE Pdgfra | CD140a|PDGF alpha chain|Pdgfr-2| | NM_011058 | 2609766 |
| IC01670 | UG75 Expression | GENE | Mm.34775 | TITLE pyruvate dehydrogenase E1alpha subunit | GENE Pdha1 | Pdha-1| | NM_008810 | 1400819 |
| IC01671 | UG75 Expression | GENE | Mm.2296 | TITLE peptidyl arginine deiminase, type II | GENE Pdi2 | PAD type IV| | NM_011061 | 638974 |
| IC01672 | UG75 Expression | GENE | Mm.20874 | TITLE peptidyl arginine deiminase, type IV | GENE Pdi4 | PAD type IV| | NM_011061 | 638974 |
| IC01673 | UG75 Expression | GENE | Mm.10283 | TITLE pyruvate dehydrogenase kinase 4 | GENE Pdk4 | | NM_013743 | 1399855 |
| IC01674 | UG75 Expression | GENE | Mm.27254 | TITLE phosphodiesterase I/nucleotide pyrophosphatase 1 | GENE Pdpk1 | pyrophosphatase|Pca|Pca-1|plasma cell alloantigen|plasma cell alloantigen 1|tiptoe walking|tiptoe walking-Pdk1|Pkb kinase| | NM_011062 | 1431858 |
| IC01675 | UG75 Expression | GENE | Mm.10504 | TITLE 3-phosphoinositide deptendent protein kinase-1 | GENE Pdpk1 | Pdk1|Pdk1|Pkb kinase| | NM_011062 | 1431858 |
| IC01676 | UG75 Expression | GENE | Mm.544 | TITLE phosphoprotein enriched in astrocytes 15 | GENE Pea15 | mammary transforming gene 1|Mat1|Pkcs15|protein kinase C substrate 15| | NM_008556 | 1195550 |
| IC01677 | UG75 Expression | GENE | Mm.2822 | TITLE platelet/endothelial cell adhesion molecule | GENE Pecam | CD31|CD31 antigen|PECAM-1| | NM_008816 | 571853 |
| IC01678 | UG75 Expression | GENE | Mm.28883 | TITLE peroxisomal delta 3, delta2-enoyl-Coenzyme A isomerase | GENE Peci-pending | | | |
| IC01679 | UG75 Expression | GENE | Mm.6923 | TITLE placentae and embryos oncogetal GENE | GENE Pem | | NM_008818 | 1149218 |
| IC01680 | UG75 Expression | GENE | Mm.2899 | TITLE preproenkephalin 2 | GENE Penk2 | Penk|preproenkephalin| | gi = 201032 | 481329 |
| IC01681 | UG75 Expression | GENE | Mm.7373 | TITLE period homolog (Drosophila) | GENE Per | m-rigui|mPer1|Per1| | NM_011065 | 949546 |
| IC01682 | UG75 Expression | GENE | Mm.20615 | TITLE peroxisomal biogenesis factor 11a | GENE Pex11a | | NM_011068 | 2123049 |
| IC01683 | UG75 Expression | GENE | Mm.20901 | TITLE peroxisomal biogenesis factor 11b | GENE Pex11b | | NM_011069 | 1383206 |
| IC01684 | UG75 Expression | GENE | Mm.2440 | TITLE peroxisome biogenesis factor 7 | GENE Pex7 | MmPEX7| | NM_008822 | 1925226 |
| IC01685 | UG75 Expression | GENE | Mm.8308 | TITLE properdin factor, complement | GENE Pfc | BCFG| | gi = 53786 | 1887495 |
| IC01686 | UG75 Expression | GENE | Mm.1166 | TITLE phosphofructokinase, liver B-type | GENE Pfkl | | NM_008826 | 3155903 |
| IC01687 | UG75 Expression | GENE | Mm.2647 | TITLE profilin 1 | GENE Pfn1 | Pfn|profilin| | NM_011072 | 1054033 |
| IC01688 | UG75 Expression | GENE | Mm.6456 | TITLE PFTAIRE protein kinase 1 | GENE Pftk1 | | NM_011074 | 635930 |
| IC01689 | UG75 Expression | GENE | Mm.188 | TITLE phosphoglycerate kinase 1 | GENE Pgk1 | Pgk-1| | NM_008828 | 606612 |
| IC01690 | UG75 Expression | GENE | Mm.6404 | TITLE P glycoprotein 1 | GENE Pgy1 | mdr|Mdr1|Mdr1b|multiple drug resistance|Pgy-1| | NM_011075 | 619272 |
| IC01691 | UG75 Expression | GENE | Mm.2355 | TITLE prohibitin | GENE Phb | | NM_008831 | 1973547 |
| IC01692 | UG75 Expression | GENE | Mm.29563 | TITLE PHD finger protein 2 | GENE Phf2 | | NM_011078 | 763234 |
| IC01693 | UG75 Expression | GENE | Mm.42254 | TITLE phosphorylase kinase alpha 1 | GENE Phka1 | Phka|phosphorylase kinase alpha 1| | NM_008832 | 935333 |
| IC01694 | UG75 Expression | GENE | Mm.34346 | TITLE pleckstrin homology-like domain, family A, member 3 | GENE Phlda3 | TDAG/lpl homolog 1|Tth1| | NM_013750 | 735193 |
| IC01695 | UG75 Expression | GENE | Mm.25877 | TITLE putative homeodomain transcription factor | GENE Phtf | | NM_013629 | 577522 |
| IC01696 | UG75 Expression | GENE | Mm.3781 | TITLE phosphatidylinositol glycan, class A | GENE Piga | | gi = 577722 | 637261 |
| IC01697 | UG75 Expression | GENE | Mm.826 | TITLE phosphatidylinositol glycan, class F | GENE Pigf | | NM_008838 | 576174 |
| IC01698 | UG75 Expression | GENE | Mm.37312 | TITLE phosphatidylinositol glycan, class N | GENE Pign | | NM_013784 | 790626 |
| IC01699 | UG75 Expression | GENE | Mm.41943 | TITLE phosphatidylinositol 3-kinase, catalytic, alpha polypeptide | GENE Pik3ca | p110| | NM_008839 | 584258 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01700 | UG75 Expression | GENE | Mm.40613 | phosphatidylinositol 3-kinase, catalytic, delta | Pik3cd | p110delta| | NM_00840 | 620876 |
| IC01701 | UG75 Expression | GENE | Mm.3058 | phosphatidylinositol 3-kinase, regulatory subunit, polypeptide 1 (p85 alpha) | Pik3r1 | | gi = 1621039 | 1429678 |
| IC01702 | UG75 Expression | GENE | Mm.12945 | phosphatidylinositol 3-kinase, regulatory subunit, polypeptide 2 (p85 beta) | Pik3r2 | | NM_008841 | 1383009 |
| IC01703 | UG75 Expression | GENE | Mm.932 | proviral integration site 2 | Pim2 | Pim-2| | gi = 765065 | 540256 |
| IC01704 | UG75 Expression | GENE | Mm.8771 | phosphatidylinositol-4-phosphate 5-kinase, type II alpha | Pip5k2a | | NM_008845 | 1092173 |
| IC01705 | UG75 Expression | GENE | Mm.1945 | phosphatidylinositol-4-phosphate 5-kinase, type I alpha | Pipk5a | PI4P5K-I[a]| | NM_008846 | 573620 |
| IC01706 | UG75 Expression | GENE | Mm.3191 | phosphatidylinositol-4-phosphate 5-kinase, type I beta | Pipk5b | PI4P5K-[l]| | NM_008847 | 2655141 |
| IC01707 | UG75 Expression | GENE | Mm.3189 | paired-Ilo-like receptor B | Pirb | glycoprotein 91|Grp91| | gi = 2138374 | 1066819 |
| IC01708 | UG75 Expression | GENE | Mm.3128 | phosphatidylinositol transfer protein | Pitpn | vb|vibrator| | NM_008850 | 551509 |
| IC01709 | UG75 Expression | GENE | Mm.8211 | phosphatidylinositol membrane-associated | Pitpnm | DRES9|mpt-1|Rd9|RdgB|retinal degeneration 9| | NM_008851 | 3154477 |
| IC01710 | UG75 Expression | GENE | Mm.2635 | praja 1 | Pja1 | | NM_008853 | 2099606 |
| IC01711 | UG75 Expression | GENE | Mm.19111 | pyruvate kinase 3 | Pk3 | ZIP kinase| | NM_011099 | 1884948 |
| IC01712 | UG75 Expression | GENE | Mm.16766 | protein kinase, cAMP dependent, catalytic, alpha | Pkaca | | NM_008854 | 334003 |
| IC01713 | UG75 Expression | GENE | Mm.4182 | protein kinase, cAMP dependent, catalytic, beta | Pkacb | | NM_011100 | 1432083 |
| IC01714 | UG75 Expression | GENE | Mm.2314 | protein kinase C, beta | Pkcb | | NM_008855 | 1617910 |
| IC01715 | UG75 Expression | GENE | Mm.8040 | protein kinase C, delta | Pkcd | PKC[d]|PKCdelta|protein kinase C[d]| | NM_011103 | 1510659 |
| IC01716 | UG75 Expression | GENE | Mm.2921 | protein kinase C, eta | Pkch | | NM_008856 | 1328586 |
| IC01717 | UG75 Expression | GENE | Mm.28561 | protein kinase C, theta | Pkcq | PKC-0| | NM_008859 | 424857 |
| IC01718 | UG75 Expression | GENE | Mm.2973 | protein kinase C, zeta | Pkcz | | NM_008860 | 659127 |
| IC01719 | UG75 Expression | GENE | Mm.6442 | polycystic kidney disease 1 homolog | Pkd1 | polycystin-1| | NM_013630 | 479447 |
| IC01720 | UG75 Expression | GENE | Mm.1499 | polycystic kidney disease 2 | Pkd2 | polycystic kidney disease 2 homolog|polycystin-2| | NM_008861 | 316818 |
| IC01721 | UG75 Expression | GENE | Mm.10091 | protein kinase inhibitor beta, cAMP dependent, testis specific | Pkib | | NM_008863 | 617337 |
| IC01722 | UG75 Expression | GENE | Mm.9277 | protein kinase inhibitor, gamma | Pkig | | NM_011106 | 635374 |
| IC01723 | UG75 Expression | GENE | Mm.22724 | phospholipase A2 group VII (platelet-activating factor acetylhydrolase, plasma) | Pla2g7 | PAF acetylhydrolase| | NM_013737 | 2598862 |
| IC01724 | UG75 Expression | GENE | Mm.5019 | phospholipase A2, activating protein | Plaa | PLAP| | gi = 200394 | 615661 |
| IC01725 | UG75 Expression | GENE | Mm.3170 | plasminogen activator inhibitor, type II | Planh2 | PAI-2| | NM_011111 | 573970 |
| IC01726 | UG75 Expression | GENE | Mm.6888 | poly (A) polymerase | Plap | PAP| | gi = 1256821 | 3167482 |
| IC01727 | UG75 Expression | geen | Mm.6483 | phospholipase C, beta 3 | Plcb3 | | NM_008874 | 644344 |
| IC01728 | UG75 Expression | GENE | Mm.4742 | phospholipase D3 | Pld3 | | NM_011116 | 3155019 |
| IC01729 | UG75 Expression | GENE | Mm.971 | proliferation-associated protein 1 | Plfap | Sam-9| | NM_011119 | 635244 |
| IC01730 | UG75 Expression | GENE | Mm.934 | plasminogen | Plg | | NM_008877 | 1970102 |
| IC01731 | UG75 Expression | GENE | Mm.16525 | plasmin inhibitor alpha 2 | Pli | | NM_008878 | 2087940 |
| IC01732 | UG75 Expression | GENE | Mm.37371 | polo-like kinase homolog, (Drosophila) | Plk | Plk1| | NM_011121 | 480634 |
| IC01733 | UG75 Expression | GENE | Mm.41486 | procollagen-lysine, 2-oxoglutarate 5-dioxygenase 1 | Plod1 | LH1|lysyl hydroxylase 1|procollagen-lysine, 2-oxogluta rate 5-dioxygenase 1| | NM_011122 | 639905 |
| IC01734 | UG75 Expression | GENE | Mm.1268 | procollagen-lysine, 2-oxoglutarate 5-dioxygenase 3 | Plod3 | LH3|lysyl hydroxylase 2| | NM_011962 | 577189 |
| IC01735 | UG75 Expression | GENE | Mm.22510 | proteolipid protein (myelin) | Plp | | gi = 53729 | 747044 |
| IC01736 | UG75 Expression | GENE | Mm.10306 | plastin 2, L | Pls2 | L-fimbrin| | NM_008879 | 3167497 |
| IC01737 | UG75 Expression | GENE | Mm.6105 | phospholipid scramblase 1 | Plscr1 | PL scramblase| | NM_011125 | 1499434 |
| IC01738 | UG75 Expression | GENE | Mm.1685 | phospholipid transfer protein | Pltp | | NM_008880 | 640088 |
| IC01739 | UG75 Expression | GENE | Mm.38497 | plexin 3 | Plxn3 | | NM_008883 | 401253 |
| IC01740 | UG75 Expression | GENE | | promyelocytic leukemia | Pml | | NM_008884 | 577266 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01741 | UG75 Expression | GENE | Mm.18939 | TITLE phosphomannomutase Sec53p homolog mRNA | GENE Pmm1 | Secp53 (yeast) homolog| | gi = 2253429 | 3153981 |
| IC01742 | UG75 Expression | GENE | Mm.30215 | TITLE peroxisomal membrane protein 20 | GENE Pmp20-pending | | NM_012021 | 1498314 |
| IC01743 | UG75 Expression | GENE | Mm.2950 | cerevisiae) | GENE Pms2 | Pmsl2| | NM_008886 | 1345796 |
| IC01744 | UG75 Expression | GENE | Mm.140 | TITLE phospholipase c neighboring | GENE Png | | NM_008889 | 596071 |
| IC01745 | UG75 Expression | GENE | Mm.22347 | TITLE pinin | GENE Pnn | | NM_008891 | 657376 |
| IC01746 | UG75 Expression | GENE | Mm.17932 | TITLE purine-nucleoside phopshorylase | GENE Pnp | Np|Np-1|Np-2|nucleoside phosphorylase| | NM_013632 | 849750 |
| IC01747 | UG75 Expression | GENE | Mm.2214 | TITLE peanut-like 2 homolog (Drosophila) | GENE Pnutl2 | | NM_011129 | 2270185 |
| IC01748 | UG75 Expression | GENE | Mm.1923 | TITLE DNA polymerase alpha 1, 180 kDa | GENE Pola1 | DNA polymerase alpha|Pola| | NM_008892 | 721005 |
| IC01749 | UG75 Expression | GENE | Mm.320 | TITLE DNA polymerase alpha 2, 68 kDa | GENE Pola2 | | NM_008893 | 749541 |
| IC01750 | UG75 Expression | GENE | Mm.16549 | TITLE DNA polymerase delta 1, catalytic domain | GENE Pold1 | | NM_011131 | 659310 |
| IC01751 | UG75 Expression | GENE | Mm.35788 | TITLE DNA polymerase (DNA directed), delta 2, regulatory subunit (50 kDa) | GENE Pold2 | p50|pol2D2| | NM_008894 | 2655384 |
| IC01752 | UG75 Expression | GENE | Mm.35061 | TITLE DNA polymerase epsilon | GENE Pole | DNA polymerase epsilon small subunit| | NM_011132 | 2182223 |
| IC01753 | UG75 Expression | GENE | Mm.9199 | TITLE DNA polymerase epsilon, subunit 2 | GENE Pole2 | DNA polymerase epsilon small subunit| | gi = 2832261 | 875417 |
| IC01754 | UG75 Expression | GENE | Mm.22681 | TITLE paraoxonase 2 | GENE Pon2 | | NM_008896 | 1262741 |
| IC01755 | UG75 Expression | GENE | Mm.89351 | TITLE POP2 homolog (S. cerevisiae) | GENE Pop2 | | NM_011135 | 2076181 |
| IC01756 | UG75 Expression | GENE | Mm.3863 | TITLE P450 (cytochrome) oxidoreductase | GENE Por | | NM_008898 | 579935 |
| IC01757 | UG75 Expression | GENE | Mm.897 | TITLE POU domain, class 2, associating factor | GENE Pou2af1 | BOB.1|OBF-1|OBF.1| | NM_011136 | 636390 |
| IC01758 | UG75 Expression | GENE | Mm.1001 | TITLE placental protein 11 related | GENE Pp11r | T-cell specific protein 30|Tcl-30| | NM_008902 | 1209796 |
| IC01759 | UG75 Expression | GENE | Mm.12926 | TITLE Ppar binding protein | GENE Pparbp | PBP|TRAP 220|NM_013634 | 1362569 | 1180486 |
| IC01760 | UG75 Expression | GENE | Mm.3020 | TITLE peroxisome proliferator activator receptor gamma | GENE Pparg | Nr1c3| | NM_011146 | 337577 |
| IC01761 | UG75 Expression | GENE | Mm.2817 | TITLE protein tyrosine phosphatase, receptor-type, F interacting protein, binding protein 2 | GENE Ppfibp2 | Cclp1|coiled-coil like protein 1|liprin beta 2| | NM_008905 | |
| IC01762 | UG75 Expression | GENE | Mm.7046 | TITLE protective protein for beta-galactosidase | GENE Ppgb | PPCA| | NM_008906 | 1907716 |
| IC01763 | UG75 Expression | GENE | Mm.5246 | TITLE peptidylprolyl isomerase A | GENE Ppia | Cphn|cyclophilin|cyclophilin A|CyP-18| | NM_008907 | 1180129 |
| IC01764 | UG75 Expression | GENE | Mm.22631 | TITLE peptidylprolyl isomerase B | GENE Ppib | Cphn-2|Cphn2|cyclophilin 2|cyclophilin B|CyP-20b| | NM_011149 | 1095790 |
| IC01765 | UG75 Expression | GENE | Mm.4587 | TITLE peptidylprolyl isomerase C | GENE Ppic | cyclophilin C|CyP-20b| | NM_011149 | 1095790 |
| IC01766 | UG75 Expression | GENE | Mm.3152 | TITLE peptidylprolyl isomerase C-associated protein | GENE Ppicap | CyCAP| | NM_011150 | 2088205 |
| IC01767 | UG75 Expression | GENE | Mm.3766 | TITLE protein phosphatase 1A, magnesium dependent, alpha isoform | GENE Ppm1a | | NM_008910 | 792028 |
| IC01768 | UG75 Expression | GENE | Mm.4730 | TITLE protoporphyrinogen oxidase | GENE Ppox | Ppo| | NM_008911 | 482868 |
| IC01769 | UG75 Expression | GENE | Mm.4572 | TITLE protein phosphatase 1, catalytic subunit, beta isoform | GENE Pp1cb | | gi = 471977 | 523632 |
| IC01770 | UG75 Expression | GENE | Mm.7793 | TITLE protein phosphatase 1, catalytic subunit, gamma isoform | GENE Ppp1cc | dis2m1|PP1C gamma|PP1C gamma 1|PP1C gamma 2| | NM_013636 | 643177 |
| IC01771 | UG75 Expression | GENE | Mm.3785 | TITLE protein phosphatase 2, regulatory subunit B (B56), gamma isoform | GENE Pp2r5c | Band 8A| | gi = 2429084 | 1451014 |
| IC01772 | UG75 Expression | GENE | Mm.293 | TITLE protein phosphatase 3, catalytic subunit, alpha isoform | GENE Pp3ca | calcineurin|calcineurin, alpha subunit|Caln| | gi = 192347 | 2123527 |
| IC01773 | UG75 Expression | GENE | Mm.3150 | TITLE protein phosphatase 3, catalytic subunit, beta isoform | GENE Pp3cb | calcineurin, beta subunit|Caln|protein phosphatase 3 | gi = 192537 | 317120 |
| IC01774 | UG75 Expression | GENE | Mm.1567 | TITLE protein phosphatase 3, catalytic subunit, gamma isoform | GENE Pp3cc | calcineurin C, type 3|Calnc | NM_008915 | 513997 |
| IC01775 | UG75 Expression | GENE | Mm.1458 | TITLE putative phosphatase | GENE Pps | C62|PI-5-phosphatase related|putative PI-5-phosphatase| | NM_008916 | 2158878 |
| IC01776 | UG75 Expression | GENE | Mm.43660 | TITLE palmitoyl-protein thioesterase | GENE Ppt | | NM_008917 | 861334 |
| IC01777 | UG75 Expression | GENE | Mm.6735 | TITLE prolyl endopeptidase | GENE Prep | PEP| | NM_011156 | 1294441 |
| IC01778 | UG75 Expression | GENE | Mm.22194 | TITLE proteoglycan, secretory granule | GENE Prg | serglycin|Sgc| | NM_011157 | 420375 |
| IC01779 | UG75 Expression | GENE | Mm.2903 | TITLE DNA primase, p49 subunit | GENE Prim1 | | NM_008921 | 540239 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01780 | UG75 Expression | GENE | Mm.27705 | TITLE DNA primase, p58 subunit | GENE Prim2 | | NM_008922 | 573647 |
| IC01781 | UG75 Expression | GENE | Mm.14244 | TITLE protein kinase C substrate 80K-H | GENE Prkcsh | | NM_008925 | 3154661 |
| IC01782 | UG75 Expression | GENE | Mm.71 | TITLE protein kinase, DNA activated, catalytic polypeptide | GENE Prkdc | DNA-PKcs\|DNAPDcs\|scid\|sever combined immunodeficiency\|slip\| | gi = 1944421 | 524350 |
| IC01783 | UG75 Expression | GENE | Mm.30217 | TITLE protein kinase, DNA activated, catalytic polyprptide interacting protein | GENE Prkdcip-1 | Kip\| | NM_011870 | 699372 |
| IC01784 | UG75 Expression | GENE | Mm.4437 | TITLE protein kinase, mitogen activated kinase,11, p38beta | GENE Prkm11 | | NM_011161 | 352057 |
| IC01785 | UG75 Expression | GENE | Mm.807 | TITLE protein kinase, interferon inducible double stranded RNA dependent | GENE Prkr | RAX\| | NM_011163 | 1477438 |
| IC01786 | UG75 Expression | GENE | Mm.12616 | TITLE protein kinase, interferon inducible double stranded RNA dependent inhibitor | GENE Prkri | p58\|protein kinase, interferon inducible double stranded RNA depenent inhibitor\| | NM_008929 | 442325 |
| IC01787 | UG75 Expression | GENE | Mm.648 | TITLE prion protein | GENE Prnp | prion protein, scrapie incubation time regulation\|prion protein, structural locus\|Prn-i\|Prn-p\|PrP\|PrP-<C>\|PrPC\|scrapie incubation period\|Sinc\| | gi = 200526 | 603591 |
| IC01788 | UG75 Expression | GENE | Mm.3243 | TITLE protein C receptor, endothelial | GENE Procr | Coca\|cell cycle, dependent gene, centrosome-associated\| | NM_011171 | 556873 |
| IC01789 | UG75 Expression | GENE | Mm.28456 | TITLE proline dehydrogenase | GENE Prodh | Pro-1\|Pro1\|proline oxidase 1\| | NM_011172 | 2936783 |
| IC01790 | UG75 Expression | GENE | Mm.24611 | TITLE protein S (alpha) | GENE Pros1 | protein S\| | gi = 487866 | 2645649 |
| IC01791 | UG75 Expression | GENE | Mm.10027 | TITLE pre-mRNA protein kinase | GENE Prpk | | gi = 3236350 | 1970266 |
| IC01792 | UG75 Expression | GENE | Mm.17185 | TITLE protease, cystein, 1 | GENE Prsc1 | legumain\|preprolegumain\| | NM_011175 | 1164616 |
| IC01793 | UG75 Expression | GENE | Mm.28797 | TITLE proline rich protein expressed in brain | GENE Prtb | Brbp\|gt6-12\|prtb\| | NM_011873 | 1969974 |
| IC01794 | UG75 Expression | GENE | Mm.2364 | TITLE proteinase 3 | GENE Prtn3 | myeloblastin\| | NM_011178 | 659861 |
| IC01795 | UG75 Expression | GENE | Mm.29824 | TITLE puromycin-sensitive aminopeptidase | GENE Psa | | NM_008942 | 1229154 |
| IC01796 | UG75 Expression | GENE | Mm.3363 | TITLE prosaposin | GENE Psap | SGP-1\| | NM_011179 | 1050678 |
| IC01797 | UG75 Expression | GENE | Mm.19097 | TITLE pleckstrin homology, Sec7 and coiled/coil domains 2 | GENE Pscd2 | CLM2\|cytohesin 2\| | NM_011181 | 1095413 |
| IC01798 | UG75 Expression | GENE | Mm.19065 | TITLE pleckstrin homology, Sec7 and coiled/coil domains 3 | GENE Pscd3 | cytohesin 3\|Grp1\| | NM_011182 | 1970831 |
| IC01799 | UG75 Expression | GENE | Mm.998 | TITLE presenilin 1 | GENE Psen1 | Ad3h\|alzheimer disease 3 homolog\|PS1\|S182\| | NM_008943 | 669643 |
| IC01800 | UG75 Expression | GENE | Mm.4338 | TITLE presenilin 2 | GENE Psen2 | Ad4h\|ALG-3\|alzheimer disease 4 homolog\|PS-2\|PS2\| | NM_011183 | 1482404 |
| IC01801 | UG75 Expression | GENE | Mm.3428 | TITLE proteasome (prosome, macropain) subunit, alpha type 2 | GENE Psma2 | large multifunctional protease, subunit C3\|Lmpc3\| | NM_008944 | 1886688 |
| IC01802 | UG75 Expression | GENE | Mm.1007 | TITLE proteasome (prosome, macropain) subunit, alpha type 3 | GENE Psma3 | large multifunctional protease, subunit C8\|Lmpc8\| | NM_011184 | 1970488 |
| IC01803 | UG75 Expression | GENE | Mm.30270 | TITLE proteasome (prosome, macropain) subunit, alpha type 4 | GENE Psma4 | C9\| | | |
| IC01804 | UG75 Expression | GENE | Mm.30210 | TITLE proteasome (prosome, macropain) subunit, alpha type 6 | GENE Psma6 | IOTA\| | NM_011968 | 2317839 |
| IC01805 | UG75 Expression | GENE | Mm.34837 | TITLE proteasome (prosome, macropain) subunit, beta type 1 | GENE Psmb1 | large multifunctional protease, subunit C5\|Lmpc5\| | NM_011185 | 605038 |
| IC01806 | UG75 Expression | GENE | Mm.787 | TITLE proteasome (prosome, macropain) subunit, beta type 10 | GENE Psmb10 | Mecl1\| | NM_013640 | 1923220 |
| IC01807 | UG75 Expression | GENE | Mm.22233 | TITLE proteasome (prosome, macropain) subunit, beta type, 2 | GENE Psmb2 | C7-I\| | NM_011970 | 2225654 |
| IC01808 | UG75 Expression | GENE | Mm.21874 | TITLE proteasome (prosome, macropain) subunit, beta type 3 | | | | |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01809 | UG75 Expression | GENE | Mm.368 | TITLE proteasome (prosome, macropain) subunit, beta type 4 | GENE Psmb4 | | gi = 3387638 | 1450603 |
| IC01810 | UG75 Expression | GENE | Mm.8911 | TITLE proteasome beta type subunit 5 | GENE Psmb5 | | NM_011186 | 375209 |
| IC01811 | UG75 Expression | GENE | Mm.98 | TITLE proteasome (prosome, macropain) subunit, beta type 6 | GENE Psmb6 | large multifunctional protease 19|Lmp19|macropain (proteasome), delta subunit|Mpmd|proteasome (prosome, macropain) subunit, beta type, 6|subunit 2| | NM_008946 | 1886792 |
| IC01812 | UG75 Expression | GENE | Mm.2246 | TITLE proteasome (prosome, macropain) subunit, beta type 7 IC01812 | GENE Psmb7 | UG75 Expression MC14 | NM_011187 | 1891177 |
| IC01813 | UG75 Expression | GENE | Mm.13913 | TITLE proteasome (prosome, macropain) subunit, beta type 8 (large multifunctional protease 7) | GENE Psmb8 | large multifunctional protease 7|Lmp-7|Lmp7|low molecular weight polypeptide 7| | NM_010724 | 421919 |
| IC01814 | UG75 Expression | GENE | Mm.16251 | TITLE proteasome (prosomem macropain) subunit, beta type 9 (large multifunctional protease 2) | GENE Psmb9 | large multifunctional protease 2|Lmp-2|Lmp2|low molecular weight polypeptide 2| | gi = 467518 | 1514155 |
| IC01815 | UG75 Expression | GENE | Mm.2222 | TITLE proteasome (prosome, macropain) 26S subunit, ATPase 1 | GENE Psmc1 | P26s4| | NM_008947 | 608679 |
| IC01816 | UG75 Expression | GENE | Mm.20946 | TITLE proteasome (prosome, macropain) 26S subunit, ATPase 3 | GENE Psmc3 | Tat binding protein 1|TBP-1| | NM_008948 | 1890268 |
| IC01817 | UG75 Expression | GENE | Mm.29582 | TITLE proteasome (prosome, macropain) 26S subunit, ATPase, 4 | GENE Psmc4 | CAR interacting protein 21|CIP21|MIP224| | NM_011874 | 1885750 |
| IC01818 | UG75 Expression | GENE | Mm.665 | TITLE proteasome (prosome, macropain) 26S subunit, ATPase 5 | GENE Psmc5 | mSUG1| | NM_008950 | 1482014 |
| IC01819 | UG75 Expression | GENE | Mm.29760 | TITLE peroxisomal sarcosine oxidase | GENE Psmd13 | 26S proteasome subunit p40.5|S11| | NM_011875 | 676110 |
| IC01820 | UG75 Expression | GENE | Mm.2261 | TITLE proteasome (prosome, macropain) 26S subunit, non-ATPase, 13 | GENE Psmd4 | Ncb1, multiubiquitin-chain-binding protein| | NM_008951 | 1139451 |
| IC01821 | UG75 Expression | GENE | Mm.18347 | TITLE proteasome (prosome, macropain) 26S subunit, non-ATPase, 4 | GENE Psmd7 | Moloney leukemia virus 34|Mov-34|Mov34| | NM_010817 | 892327 |
| IC01822 | UG75 Expression | GENE | Mm.830 | TITLE proteasome (prosome, macropain) 26S subunit, non-ATPase, 7 | GENE Psme1 | PA28a| | NM_011189 | 2812288 |
| IC01823 | UG75 Expression | GENE | Mm.626 | TITLE proteasome (prosome, macropain) 28 subunit, alpha | GENE Psme2 | PA28b| | gi = 2351197 | 606382 |
| IC01824 | UG75 Expression | GENE | Mm.2141 | TITLE proteasome (prosome, macropain) 28 subunit, beta | GENE Psme3 | Ki| | NM_011192 | 643625 |
| IC01825 | UG75 Expression | GENE | Mm.8543 | TITLE proteasome (prosome, macropain) 28 subunit, 3 | GENE Pso | | NM_008952 | 519136 |
| IC01826 | UG75 Expression | GENE | Mm.2534 | TITLE proline-serine-threonine phosphatase-interacting protein 1 | GENE Pstpip1 | def-2| | gi = 1857711 | 472995 |
| IC01827 | UG75 Expression | GENE | Mm.10105 | TITLE placenta specific homeobox 1 | GENE Psx1 | | NM_008955 | 1749860 |
| IC01828 | UG75 Expression | GENE | Mm.19117 | TITLE polypyrimidine tract binding protein | GENE Ptb | | NM_008956 | 3154890 |
| IC01829 | UG75 Expression | GENE | Mm.9440 | TITLE phosphatidylserine synthase 1 | GENE Pdss1 | PtdSer Synthase-1| | NM_008959 | 3154459 |
| IC01830 | UG75 Expression | GENE | Mm.1919 | TITLE phosphatase and tensin homolog | GENE Pten | MMAC1| | NM_008960 | 1281657 |
| IC01831 | UG75 Expression | GENE | Mm.4501 | TITLE prostaglandin E receptor EP1 subtype | GENE Ptgerep1 | EP1| | NM_013641 | 1261169 |
| IC01832 | UG75 Expression | GENE | Mm.18509 | TITLE prostaglandin E receptor EP4 subtype | GENE Ptgerep4 | | NM_008965 | 904890 |
| IC01833 | UG75 Expression | GENE | Mm.2339 | TITLE prostaglandin I2 (prostacyclin) synthase | GENE Ptgis | | NM_008968 | 1433961 |
| IC01834 | UG75 Expression | GENE | Mm.2792 | TITLE prostaglandin-endoperoxide synthase 1 | GENE Pghs1 | Cox-1|COX1|cyclooxygenase 1|Pghs1| | NM_008969 | 1433961 |
| IC01835 | UG75 Expression | GENE | Mm.28440 | TITLE parathyroid hormone-like peptide | GENE Pthlh | parathyroid hormone-like hormone|PTH-like|Pthrp| | NM_008970 | 1433961 |
| IC01836 | UG75 Expression | GENE | Mm.21852 | TITLE protein tyrosine kinase 9 related protein | GENE Ptk9r-pe | A6-related| | NM_011876 | 1262462 |
| IC01837 | UG75 Expression | GENE | Mm.19187 | TITLE prothymosin alpha | GENE Ptma | | NM_008972 | 3157018 |
| IC01838 | UG75 Expression | GENE | Mm.22566 | TITLE prothymosin beta 4 | GENE Ptmb4 | Thym|thymosin alpha| | gi = 1072099 | 1078261 |
| IC01839 | UG75 Expression | GENE | Mm.3063 | TITLE pleiotrophin | GENE Ptn | | NM_008973 | 1480918 |
| IC01840 | UG75 Expression | GENE | Mm.28909 | TITLE protein tyrosine phosphatase 4a1 | GENE Ptp4a1 | Prl-1| | NM_011200 | 621373 |
| IC01841 | UG75 Expression | GENE | Mm.6355 | TITLE protein tyrosine phosphatase 4a2 | GENE Ptp4a2 | Prl-2| | NM_008974 | 493485 |
| IC01842 | UG75 Expression | GENE | Mm.4124 | TITLE protein tyrosine phosphatase 4a3 | GENE Ptp4a3 | Prl-3| | NM_008975 | 331144 |
| IC01843 | UG75 Expression | GENE | Mm.2668 | TITLE protein tyrosine phosphatase, non-receptor type 1 | GENE Ptpn1 | | NM_011201 | 335066 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01844 | UG75 Expression | GENE | Mm.14844 | TITLE protein tyrosine phosphatase, non-receptor type 11 | GENE Ptpn11 | PTP1D|PTP2C|SAP-2|SH-PTP2|SH-PTP3|SHP-2|Syp| | NM_011202 | 1039873 |
| IC01845 | UG75 Expression | GENE | Mm.1469 | TITLE protein tyrosine phosphatase, non-receptor type 12 | GENE Ptpn12 | P19-PTP|PTP-P19|PTP-PEST|PTPG1| | NM_011203 | 1331615 |
| IC01846 | UG75 Expression | GENE | Mm.3414 | TITLE protein tyrosine phosphatase, non-receptor type 13 | GENE Ptpn13 | protein tyrosine phosphatase, receptor induced|PTP-BP|Ptpri|RIP| | NM_011204 | 540659 |
| IC01847 | UG75 Expression | GENE | Mm.5400 | TITLE protein tyrosine phosphatase, non-receptor type 13 interacting protein | GENE Ptpn13ip | BP75|bromodomain protein 75 kDa| | NM_012047 | 1080496 |
| IC01848 | UG75 Expression | GENE | Mm.2404 | TITLE protein tyrosine phosphatase, non-receptor type 16 | GENE Ptpn16 | erp|mkp-1| | NM_013642 | 582081 |
| IC01849 | UG75 Expression | GENE | Mm.361 | TITLE protein tyrosine phosphatase, non-receptor type 18 | GENE Ptpn18 | FLP1|HSCF|Ptpk1| | NM_011206 | 576559 |
| IC01850 | UG75 Expression | GENE | Mm.985 | TITLE protein tyrosine phosphatase, non-receptor type 2 | GENE Ptpn2 | | NM_008977 | 557878 |
| IC01851 | UG75 Expression | GENE | Mm.4420 | TITLE protein tyrosine phosphatase, non-receptor type 2 | gene Ptpn21 | PTPD1|PTPRL10| | NM_011877 | 2247664 |
| IC01852 | UG75 Expression | GENE | Mm.395 | TITLE protein tyrosine phosphatase, non-receptor type 8 | GENE Ptpn8 | PEP| | NM_008979 | 574512 |
| IC01853 | UG75 Expression | GENE | Mm.1682 | TITLE protein tyrosine phosphatase, non-receptor type substrate 1 | GENE Ptpns1 | BIT|P84|SHP-1|SHPS-1|SIRP| | nm_011208 | 7515666 |
| IC01854 | UG75 Expression | GENE | Mm.587 | TITLE protein tyrosine phosphatase, receptor type, A | GENE Ptpra | PTP[a]|Ptpa|PTPalpha|RPTR[a]|RPTR alpha| | NM_008980 | 1281653 |
| IC01855 | UG75 Expression | GENE | Mm.70 | TITLE protein tyrosine phosphatase, receptor type, C | GENE Ptprc | B220|CD45|CD45 antigen|CD45R|Ly-5|lymphocyte antigen 5|Lyt-4|T-lymphocyte antigen 4|T200| | NM_011210 | 621350 |
| IC01856 | UG75 Expression | GENE | Mm.41376 | TITLE protein tyrosine phosphatase, receptor type, C polypeptide-associated protein | GENE Ptprcap | CD-45-AP|LPAP|LSM-1| | gi = 454750 | 573361 |
| IC01857 | UG75 Expression | GENE | Mm.945 | TITLE protein tyrosine phosphatase, receptor type, E | GENE Ptpre | PTPe|PTPepsilon| | NM_011212 | 2616346 |
| IC01858 | UG75 Expression | GENE | Mm.5046 | TITLE protein tyrosine phosphatase, receptor type, J | GENE Ptprj | BET|Byp|DEP-1|Ptpb2|PTPbeta2| | gi = 4092840 | 557941 |
| IC01859 | UG75 Expression | GENE | Mm.4220 | TITLE protein tyrosine phosphatase, receptor type, S | GENE Ptprs | PTP-NU3| | gi = 464190 | 614392 |
| IC01860 | UG75 Expression | GENE | Mm.35856 | TITLE 6-pyruvoyl-tetrahydropterin synthase | GENE Pts | PTPS| | NM_011220 | 1067844 |
| IC01861 | UG75 Expression | GENE | Mm.2236 | TITLE purine rich element binding protein A | GENE Pura | CAGER-1|ssCRE-BP| | NM_008989 | 1382922 |
| IC01862 | UG75 Expression | GENE | Mm.7219 | TITLE purine rich element binding protein B | GENE Purb | Cager-2| | NM_011221 | 1193645 |
| IC01863 | UG75 Expression | GENE | Mm.29198 | TITLE peroxisomal farnesylated protein | GENE Pxf | | gi = 6010212 | 974161 |
| IC01864 | UG75 Expression | GENE | Mm.16453 | TITLE peroxisomal membrane protein 3, 35 kDa | GENE Pxmp3 | PMP35| | NM_008994 | 947220 |
| IC01865 | UG75 Expression | GENE | Mm.22418 | TITLE peroxisome receptor 1 | GENE Pxr1 | peroxin 5|Pex5| | NM_008995 | 441054 |
| IC01866 | UG75 Expression | GENE | Mm.2655 | TITLE quaking | GENE qk | | gi = 1181697 | 871163 |
| IC01867 | UG75 Expression | GENE | Mm.14530 | TITLE RAB1, member RAS oncogene family | GENE Rab1 | Gtbp|members RAS oncogene family|name unkown at this time 12/9/992|Rab-1|ypt-1 ras-related GTP binding protein|Ypt1| | NM_008996 | 860450 |
| IC01868 | UG75 Expression | GENE | Mm.35727 | TITLE RAB11B, member RAS oncogene family | GENE Rab11b | | NM_008997 | 1139208 |
| IC01869 | UG75 Expression | GENE | Mm.22660 | TITLE RAB18, member RAS oncogene family | GENE Rab18 | | NM_011225 | 1921493 |
| IC01870 | UG75 Expression | GENE | Mm.18800 | TITLE RAB24, member RAS oncogene family | GENE RAb24 | | NM_009000 | 1449741 |
| IC01871 | UG75 Expression | GENE | Mm.5083 | TITLE RAB3A, member RAS oncogene family | GENE Rab3a | | NM_009000001 | 2938191 |
| IC01872 | UG75 Expression | GENE | Mm.29968 | TITLE RAB3D, member RAS oncogene family | GENE RAb3d | | gi = 200631 | 1365249 |
| IC01873 | UG75 Expression | GENE | Mm.9221 | TITLE RAB4A, member RAS oncogene family | GENE Rab4A | | NM_009003 | 1096140 |
| IC01874 | UG75 Expression | GENE | Mm.4566 | TITLE Rab6, kinesin-like | GENE Rab6kifl | Rabkinesin-6| | NM_009004 | 1969476 |
| IC01875 | UG75 Expression | GENE | Mm.4268 | TITLE RAB7, member RAS oncogene family | GENE Rab7 | | NM_009005 | 1907977 |
| IC01876 | UG75 Expression | GENE | Mm.29211 | TITLE RAB geranylgeranyl transferase, b subunit | GENE Rabggtb | | NM_011231 | 1362856 |
| IC01877 | UG75 Expression | GENE | Mm.889 | TITLE RAS-related C3 botulinum substrate 1 | GENE Rac1 | | gi = 53885 | 1247629 |
| IC01878 | UG75 Expression | GENE | Mm.1972 | TITLE RAS-related C3 botulinum substrate 2 | GENE Rac2 | | NM_009008 | 2749184 |
| IC01879 | UG75 Expression | GENE | Mm.27141 | TITLE Rac GTPase-activating protein 1 | GENE Racgap1 | Band25|GTPase|MgcRacGAP| | NM_012025 | 478181 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01880 | UG75 Expression | GENE | Mm.29014 | TITLE RAS-related C3 botulinum substrate 1, guanine nucleotide exchange factor 1 | GENE Ragef1 | STEF| | NM_011878 | 516082 |
| IC01881 | UG75 Expression | GENE | Mm.20947 | TITLE RAD17 homolog (S. pombe) | GENE Rad17 | MmRad24| | NM_011233 | 1123375 |
| IC01882 | UG75 Expression | GENE | Mm.26879 | TITLE RAD23b homolog (S. cerevisiae) | GENE Rad23b | RAD23 homolog (S. cerevisiae)| | NM_011972 | 1178409 |
| IC01883 | UG75 Expression | GENE | Mm.29300 | TITLE RAD30 (S. cerevisiae) homolog B | GENE Rad30b | | NM_011972 | 1178409 |
| IC01884 | UG75 Expression | GENE | Mm.4888 | TITLE RAD50 homolog (S. cerevisiae) | GENE RAD50 | Mre11|RAD50-like|Rad50| | NM_009012 | 1382134 |
| IC01885 | UG75 Expression | GENE | Mm.231 | TITLE Rad51 homolog (S. cerevisiae) | GENE Rad51 | Rad51a|RAD51|RAD51A homolog (S. cerevisiae)|Reca| recombination and repair of radiation damage, RAD51 homolog| | NM_011234 | 539749 |
| IC01886 | UG75 Expression | GENE | Mm.8156 | TITLE RAD51 associated protein 1 | GENE Rad51ap | RAB22| | NM_009013 | 637179 |
| IC01887 | UG75 Expression | GENE | Mm.25289 | TITLE RAD51 like 1 (S. cerevisiae) | GENE Rad51l1 | mREC2|R51H2|RAD51 homolog B (S. cerevisiae)|RAD51b|R51H3|Rad51l|recombination and repair damage, RAD51 homolog (S. cerevisiae)| | | |
| IC01888 | UG75 Expression | GENE | Mm.9286 | TITLE RAD51 like 3 (S. cerevisiae) | GENE Rad51l3 | | NM_011235 | 1331864 |
| IC01889 | UG75 Expression | GENE | Mm.149 | TITLE RAD52 homolog (S. cerevisiae) | GENE Rad52 | Rad52yh| | NM_011236 | 615958 |
| IC01890 | UG75 Expression | GENE | Mm.3655 | TITLE RAD54 homolog (S. cerevisiae) | GENE Rad54 | | NM_009015 | 1279562 |
| IC01891 | UG75 Expression | GENE | Mm.1970 | TITLE RAD9 homolog (S. pombe) | GENE Rad9 | | NM_011237 | 634960 |
| IC01892 | UG75 Expression | GENE | Mm.828 | TITLE recombination activating gene 1 | GENE Rag1 | | NM_009019 | 582483 |
| IC01893 | UG75 Expression | GENE | Mm.3591 | TITLE hnRNP-associated with lethal yellow | GENE Raly | Rag-1|Merc| | gi = 348995 | 2810841 |
| IC01894 | UG75 Expression | GENE | Mm.3833 | TITLE RAN GTPase activating protein 1 | GENE Rangap1 | failure to undergo gastrulation|Fug1| | NM_011241 | 388633 |
| IC01895 | UG75 Expression | GENE | Mm.18517 | TITLE RAS p21 protein activator 3 | GENE Rasa3 | GAPIII|GAPIII activator 3|Ras GTPase-activating protein III| | NM_009025 | 523995 |
| IC01896 | UG75 Expression | GENE | Mm.41209 | TITLE RAS protein activator like 1 (GAP 1 like) | GENE Rasa11 | MRASAL| | NM_013832 | 1383159 |
| IC01897 | UG75 Expression | GENE | Mm.3903 | TITLE RAS, dexamethasone-induced 1 | GENE Rasd1 | Dexras1| | NM_009026 | 2938637 |
| IC01898 | UG75 Expression | GENE | Mm.20884 | TITLE RAS, guanyl releasing protein 2 | GENE Rasgrp2 | CalDAG-GEFI|CDC251| | NM_011242 | 576487 |
| IC01899 | UG75 Expression | GENE | Mm.304 | TITLE retinoblastoma 1 | GENE Rb1 | RED1| | NM_009029 | 1080656 |
| IC01900 | UG75 Expression | GENE | Mm.12145 | TITLE retinoblastoma binding protein 4 | GENE Rbbp4 | mRbA?| | NM_009030 | 1852774 |
| IC01901 | UG75 Expression | GENE | Mm.14480 | TITLE retinoblastoma binding protein 6 | GENE Rbbp6 | | gi = 1546778 | 1262730 |
| IC01902 | UG75 Expression | GENE | Mm.1603 | TITLE retinoblastoma binding protein 7 | GENE Rbbp7 | mRbAp46| | NM_009031 | 540283 |
| IC01903 | UG75 Expression | GENE | Mm.2994 | TITLE retinoblastoma-like 1 (p107) | GENE Rbl1 | p107| | gi = 1871224 | 1478426 |
| IC01904 | UG75 Expression | GENE | Mm.28027 | TITLE retinoblastoma-like 2 | GENE Rbl2 | p130|Rb2| | NM_011250 | 596171 |
| IC01905 | UG75 Expression | GENE | Mm.2591 | TITLE RNA binding motif protein 3 | GENE Rbm3 | | gi = 3810891 | 920649 |
| IC01906 | UG75 Expression | GENE | Mm.542 | TITLE RNA binding motif protein 4 | GENE Rbm4 | lark|Mlark| | gi = 2078530 | 1888397 |
| IC01907 | UG75 Expression | GENE | Mm.12931 | TITLE RNA binding motif protein 6 | GENE Rbm6 | Def-3|g16|NY-LU-12| | NM_011251 | 1179425 |
| IC01908 | UG75 Expression | GENE | Mm.28275 | TITLE RNA binding motif protein, X chromosome | GENE Rbmx | | NM_011252 | 1888715 |
| IC01909 | UG75 Expression | GENE | Mm.24718 | TITLE RNA binding motif protein, X chromosome retrogene | GENE Rbmxrt | heterogeneous nuclear ribonucleoprotein G|Hnrpg| | NM_009033 | 1886035 |
| IC01910 | UG75 Expression | GENE | Mm.89726 | TITLE recombining binding protein suppressor of hairless (Drosophila) | GENE Rbpsuh | Igk recombining segment binding protein|Igkrsbp|RBP-J|RBP- | gi = 52756 | 1279067 J kappa| |
| IC01911 | UG75 Expression | GENE | Mm.4876 | TITLE reticulocalbin | GENE Rcn | | NM_009037 | 387481 |
| IC01912 | UG75 Expression | GENE | Mm.1782 | TITLE reticulocalbin 2 | GENE Rcn2 | taipoxin-associated calcium binding protein 49|TCBP-49| | NM_011992 | 1432012 |
| IC01913 | UG75 Expression | GENE | Mm.7051 | TITLE radixin | GENE Rdx | | NM_009041 | 1481213 |
| IC01914 | UG75 Expression | GENE | Mm.4280 | TITLE replication factor C, 140 kDa | GENE Recc1 | Alp145|RFC140| | NM_011258 | 1382881 |
| IC01915 | UG75 Expression | GENE | Mm.2588 | TITLE rat regenerating islet-derived, mouse homolog 1 | GENE Reg1 | | NM_009042 | 1053892 |
| IC01916 | UG75 Expression | GENE | Mm.263 | TITLE rat regenerating islet-derived, mouse homolog 3 gamma | GENE Reg3g | RegIII (gamma)| | NM_011260 | 577262 |
| IC01917 | UG75 Expression | GENE | Mm.28170 | TITLE avian reticuloendotheliosis viral (v-rel) oncogene homolog A | GENE Rela | p65 NF-kappa B| | NM_009045 | 1884956 |
| IC01918 | UG75 Expression | GENE | Mm.1741 | TITLE avian reticuloendotheliosis viral (v-rel) oncogene related B | gene Relb | | NM_009046 | 851938 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01919 | UG75 Expression | GENE | Mm.3057 | TITLE reelin | gene Reln | reeler|rl| | NM_011261 | 751423 |
| IC01920 | UG75 Expression | GENE | Mm.4479 | TITLE RalBP1 associated Eps domain containing protein | GENE Reps1 | | NM_009048 | 1328944 |
| IC01921 | UG75 Expression | GENE | Mm.2651 | TITLE requiem | gene Req | Mfreq| | NM_011262 | 1224362 |
| IC01922 | UG75 Expression | GENE | Mm.2167 | TITLE REV3-like, catalytic subunit of DNA polymerase zeta RAD54 like (S. cerevisiae) | GENE Rev3l | seizure related gene 4|Sez4| | gi = 4079830 | 618141 |
| IC01923 | UG75 Expression | GENE | Mm.14768 | TITLE reduced expression 3 | GENE Rex3 | Bex1| | NM_009052 | 401580 |
| IC01924 | UG75 Expression | GENE | Mm.871 | TITLE radical fringe gene homolog, (Drosophila) | GENE Rfng | | NM_009053 | 988249 |
| IC01925 | UG75 Expression | GENE | Mm.55 | TITLE ret finger protein | GENE Rfp | | NM_009054 | 3154902 |
| IC01926 | UG75 Expression | GENE | Mm.102 | TITLE regulatory factor (trans-acting) 2 | GENE Rfx2 | | NM_009056 | 602454 |
| IC01927 | UG75 Expression | GENE | Mm.20848 | TITLE regulatory factor X-associated ankyrin-containing protein | GENE Rfxank | | NM_011266 | 934932 |
| IC01928 | UG75 Expression | GENE | Mm.17958 | TITLE recombination activating gene 1 gene activation | GENE Rga | | NM_009057 | 573247 |
| IC01929 | UG75 Expression | GENE | Mm.5236 | TITLE ral guanine nucleotide dissociation stimulator | GENE Rgds | RalGDS| | NM_009058 | 3154682 |
| IC01930 | UG75 Expression | GENE | Mm.43777 | TITLE | gene Rgl2 | Rif| | NM_009059 | 634926 |
| IC01931 | UG75 Expression | GENE | Mm.2118 | TITLE regucalcin | GENE Rgn | SMP30| | NM_009060 | 1886127 |
| IC01932 | UG75 Expression | GENE | Mm.2555 | TITLE regulator of G-protein signaling 16 | GENE Rgs16 | regulator of G-protein signaling 14|regulator of G-protein signaling-retinal specific|Rgs14|Rgsr| | gi = 2605641 | 1924001 |
| IC01933 | UG75 Expression | GENE | Mm.28262 | TITLE regulator of G-protein signaling 2 | GENE Rgs2 | | NM_009061 | 2135822 |
| IC01934 | UG75 Expression | GENE | Mm.12961 | TITLE Rhesus blood group-associated A glycoprotein | GENE Rhag | Rh50A| | NM_011269 | 750909 |
| IC01935 | UG75 Expression | GENE | Mm.18140 | TITLE Rhesus blood group-like | GENE Rhl1 | | NM_011270 | 334240 |
| IC01936 | UG75 Expression | GENE | Mm.2402 | TITLE Rho interacting protein 3 | GENE Rhoip3-p | p116 Rho interacting protein|p116Rip|RIP3| | gi = 1657836 | 1054488 |
| IC01937 | UG75 Expression | GENE | Mm.20343 | TITLE ring finger protein 1 | GENE Ring1 | Ring1A| | NM_009066 | 476668 |
| IC01938 | UG75 Expression | GENE | Mm.170009 | TITLE Ral-interacting protein 1 | GENE Rip1 | RIP140| | NM_009067 | 2076173 |
| IC01939 | UG75 Expression | GENE | Mm.23997 | TITLE RPB5-mediating protein | GENE Rmp-per | NNX3| | NM_011274 | 747807 |
| IC01940 | UG75 Expression | GENE | Mm.10152 | TITLE ribonuclease H1 | gene Rnaseh1 | | NM_011275 | 1066800 |
| IC01941 | UG75 Expression | GENE | Mm.25228 | TITLE ring finger protein 11 | GENE Rnf11 | | NM_013876 | 525121 |
| IC01942 | UG75 Expression | GENE | Mm.44069 | TITLE ring finger protein 12 | GENE Rnf12 | RLIM| | NM_011276 | 1969644 |
| IC01943 | UG75 Expression | GENE | Mm.9326 | TITLE ring finger protein 13 | GENE Rnf13 | Rzf| | NM_011883 | 574270 |
| IC01944 | UG75 Expression | GENE | Mm.20159 | TITLE ring finger protein 9 | GENE Rnf9 | | NM_011280 | 465060 |
| IC01945 | UG75 Expression | GENE | Mm.26153 | TITLE RNA guanylyltransferase and 5—phosphatase | GENE Rngtt | mouse capping enzyme| | NM_011884 | 1396865 |
| IC01946 | UG75 Expression | GENE | Mm.1951 | TITLE ribonucleic acid binding protein S1 | GENE Rnps1 | | NM_009070 | 2599127 |
| IC01947 | UG75 Expression | GENE | Mm.6710 | TITLE Rho-associated coiled-coil forming kinase 1 | GENE Rock1 | Rock-I| | NM_009071 | 598406 |
| IC01948 | UG75 Expression | GENE | Mm.35815 | TITLE Rho-associated coiled-coil forming kinase 2 | GENE Rock2 | Rock-II| | NM_009072 | 1434337 |
| IC01949 | UG75 Expression | GENE | Mm.4372 | TITLE RAR-related orphan receptor gamma | GENE Rorc | Nr1f3|Thor|thymus orphan receptor|TOR| | NM_011281 | 521908 |
| IC01950 | UG75 Expression | GENE | Mm.2870 | TITLE replication protein A2 | GENE Rpa2 | hnrnp-A| | NM_011284 | 672653 |
| IC01951 | UG75 Expression | GENE | Mm.27720 | TITLE retinitis pigmentosa GTpase regulator | GENE Rpgr | retinitis pigmentosa 3 homolog|Rp3h|RPGR| | NM_011285 | 906429 |
| IC01952 | UG75 Expression | GENE | Mm.17905 | TITLE ribose 5-phosphate isomerase A | GENE Rpia | RPI|Neddo|neural precursor cell expressed, developmentally down-regulated gene 6| | NM_009075 | 617861 |
| IC01953 | UG75 Expression | GENE | Mm.2424 | TITLE ribosomal protein L10A | GENE rpl10a | | NM_011287 | 2236226 |
| IC01954 | UG75 Expression | GENE | Mm.70127 | TITLE ribosomal protein L12 | GENE Rpl12 | tissue specific transplantation antigen P198-7|Tstap 198-7|tum-antigen| | NM_009076 | 3155654 |
| IC01955 | UG75 Expression | GENE | Mm.13020 | TITLE ribosomal protein L13a | GENE Rpl13a | Rpl18-rs16| | NM_009438 | 2939194 |
| IC01956 | UG75 Expression | GENE | Mm.41923 | TITLE ribosomal protein L18 | GENE Rpl18 | | NM_009077 | 1277508 |
| IC01957 | UG75 Expression | GENE | Mm.30806 | TITLE ribosomal protein L19 | GENE Rpl19 | | NM_009078 | 1481593 |
| IC01958 | UG75 Expression | GENE | Mm.13917 | TITLE ribosomal protein L22 | GENE Rpl22 | | NM_009079 | 375220 |
| IC01959 | UG75 Expression | GENE | Mm.12144 | TITLE ribosomal protein L23 | GENE Rpl23 | L23mrp| | NM_011288 | 1922521 |
| IC01960 | UG75 Expression | GENE | Mm.3229 | TITLE ribosomal protein L26 | GENE Rpl26 | SIG-20| | NM_009080 | 1024223 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC01961 | UG75 Expression | GENE | Mm.7277 | TITLE ribosomal protein L27 | GENE Rpl27 | L27A| | gi = 50320 | 2236296 |
| IC01962 | UG75 Expression | GENE | Mm.89853 | TITLE ribosomal protein L27a | GENE Rpl27a | L27A| | gi = 4760603 | 1891091 |
| IC01963 | UG75 Expression | GENE | Mm.3111 | TITLE ribosomal protein L28 | GENE Rpl28 | | NM_009081 | 1969483 |
| IC01964 | UG75 Expression | GENE | Mm.2235 | TITLE ribosomal protein L29 | GENE Rpl29 | ribosomal protein L43|Rpl43| | NM_009082 | 697462 |
| IC01965 | UG75 Expression | GENE | Mm.3486 | TITLE ribosomal protein L3 | GENE Rpl3 | | NM_013762 | 1885733 |
| IC01966 | UG75 Expression | GENE | Mm.3487 | TITLE ribosomal protein L30 | GENE Rpl30 | | NM_009083 | 422486 |
| IC01967 | UG75 Expression | GENE | Mm.42062 | TITLE ribosomal protein L32, pseudogene | GENE Rpl32-ps | | gi = 3228365 | 662938 |
| IC01968 | UG75 Expression | GENE | Mm.21529 | TITLE ribosomal protein L37a | GENE Rpl37a | | NM_009084 | 315860 |
| IC01969 | UG75 Expression | GENE | Mm.588 | TITLE ribosomal protein L6 | GENE Rpl6 | | NM_011290 | 1885738 |
| IC01970 | UG75 Expression | GENE | Mm.37835 | TITLE ribosomal protein L7 | GENE Rpl7 | Taxreb107| | NM_011291 | 1886094 |
| IC01971 | UG75 Expression | GENE | Mm.30066 | TITLE ribosomal protein L8 | GENE Rpl8 | Rpl7a|Surf-3|surfeit gene-3|(L1A ribosomal protein)| | NM_012053 | 1886956 |
| IC01972 | UG75 Expression | GENE | Mm.364 | TITLE ribosomal protein, mitochondrial, S12 | GENE Rpms12 | mitoribosomal protein s12|rps12| | NM_011885 | 577166 |
| IC01973 | UG75 Expression | GENE | Mm.3458 | TITLE RNA polymerase 1-1 (40 kDa subunit) | GENE Rpo1-1 | RPA40| | NM_009085 | 515460 |
| IC01974 | UG75 Expression | GENE | Mm.34589 | TITLE RNA polymerase 1-2 (128 kDa subunit) | GENE Rpo1-02 | RPA2| | NM_009086 | 1134569 |
| IC01975 | UG75 Expression | GENE | Mm.34570 | TITLE RNA polymerase 1-3 (16 kDa subunit) | GENE Rpo1-3 | mRPA16| | NM_009087 | 616379 |
| IC01976 | UG75 Expression | GENE | Mm.16533 | TITLE RNA polymerase II 1 | GENE Rpo2-1 | | NM_009089 | 1383243 |
| IC01977 | UG75 Expression | GENE | Mm.2186 | TITLE RNA polymerase II 3 | GENE Rpo2-3 | mRBP31| | NM_009090 | 1328904 |
| IC01978 | UG75 Expression | GENE | Mm.4896 | TITLE RNA polymerase II 4 (14 kDa subunit) | GENE Rpo2-4 | RNA polymerase II subunit RPB14; mRPB14| | NM_011293 | 616119 |
| IC01979 | UG75 Expression | GENE | Mm.966 | TITLE RNA polymerase II transcriptional coactivator | GENE Rpo2tc1 | P15|P9|Pc4|RNA polymerase II transcription cofactor| | NM_011294 | 722427 |
| IC01980 | UG75 Expression | GENE | Mm.164 | TITLE ribosomal protein S11 | GENE Rps11 | | gi = 6552367 | 1400352 |
| IC01981 | UG75 Expression | GENE | Mm.43452 | TITLE ribosomal protein S12 | GENE Rps12 | | NM_011295 | 1922678 |
| IC01982 | UG75 Expression | GENE | Mm.643 | TITLE ribosomal protein S15 | GENE Rsp15 | | NM_009091 | 2225535 |
| IC01983 | UG75 Expression | GENE | Mm.702 | TITLE ribosomal protein S16 | GENE Rps16 | | NM_013647 | 1972620 |
| IC01984 | UG75 Expression | GENE | Mm.42767 | TITLE ribosomal protein S17 | GENE Rps17 | rig, rat insulinoma gene| | NM_009092 | 616544 |
| IC01985 | UG75 Expression | GENE | Mm.42790 | TITLE ribosomal protein S18 | GENE Rps18 | H-2K region expressed gene E3|H-2Ke3|H2-Ke3|Ke-3| | NM_011297 | 2812563 |
| IC01986 | UG75 Expression | GENE | Mm.16775 | TITLE ribosomal protein S24 | GENE Rps24 | | NM_011297 | 534607 |
| IC01987 | UG75 Expression | GENE | Mm.372 | TITLE ribosomal protein S26 | GENE Rps26 | | NM_013765 | 483060 |
| IC01988 | UG75 Expression | GENE | Mm.35816 | TITLE ribosomal protein S29 | GENE Rps29 | S29 ribosomal protein| | NM_009093 | 116748 |
| IC01989 | UG75 Expression | GENE | Mm.4696 | TITLE ribosomal protein S3 | GENE Rps3 | | NM_012052 | 2225803 |
| IC01990 | UG75 Expression | GENE | Mm.66 | TITLE ribosomal protein S4, X-linked | GENE Rps4x | ribosomal protein S4-1|Rps4-1| | NM_009094 | 1093521 |
| IC01991 | UG75 Expression | GENE | Mm.5291 | TITLE ribosomal protein S5 | GENE Rps5 | S5 ribosomal protein| | NM_009095 | 1480877 |
| IC01992 | UG75 Expression | GENE | Mm.29910 | TITLE ribosomal protein S6 kinase polypeptide 1 | GENE Rps6ka1 | | NM_009097 | 3155766 |
| IC01993 | UG75 Expression | GENE | Mm.32033 | TITLE ribosomal protein S6 kinase, 90 kD, polypeptide 2 | GENE Rps6ka2 | pp90rsk|Rsk3| | NM_011299 | 582077 |
| IC01994 | UG75 Expression | GENE | Mm.5281 | TITLE ribosomal protein S7 | GENE Rps7 | S7| | NM_011300 | 1973447 |
| IC01995 | UG75 Expression | GENE | Mm.3381 | TITLE ribosomal protein S8 | GENE Rps8 | | NM_009098 | 1498231 |
| IC01996 | UG75 Expression | GENE | Mm.257 | TITLE regulatory protein, T lymphocyte 1 | GENE Rpt1 | R-1| | NM_009099 | 638233 |
| IC01997 | UG75 Expression | GENE | Mm.656 | TITLE Harvey rat sarcoma oncogene, subgroup R | GENE Rras | | NM_009101 | 1434722 |
| IC01998 | UG75 Expression | GENE | Mm.656 | TITLE ribonucleotide reductase M1 | GENE Rrm1 | | NM_009103 | 1851949 |
| IC01999 | UG75 Expression | GENE | Mm.99 | TITLE ribonucleotide reductase M2 | GENE Rrm2 | | NM_009104 | 751876 |
| IC02000 | UG75 Expression | GENE | Mm.14063 | TITLE retinal short-chain dehydrogenase/reductase 1 | GENE Rsdr1-p | retSDR1| | NM_011303 | 1973184 |
| IC02001 | UG75 Expression | GENE | Mm.905 | TITLE Ras suppressor protein 1 | GENE Rsu1 | rsp-1| | NM_009105 | 605742 |
| IC02002 | UG75 Expression | GENE | Mm.4139 | TITLE rhotekin | gene Rtkn | AML1|Cbfa2|core binding factor alpha 2|Pebp2a2| runt domain, | NM_009105 | 605742 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02003 | UG75 Expression | GENE | Mm.4081 | TITLE runt related transcription factor 1 | GENE Runx1 | alpha subunit 2\|AKV core binding factor\|AML3\|Cbf\|Cbfa1\|core binding factor\|core binding factor alpha 1\|LS3\|Osf2\|PEBP2 alpha A\|Pebp2a1\|PEBP2aA\|Pebpa2a\|polyomavirus enhancer binding factor 2 (PEBP2)\|runt domain, alpha subunit 1\|SL3-3 enhancer factor 1\| | NM_009821 | 618631 |
| IC02004 | UG75 Expression | GENE | Mm.4509 | TITLE runt related transcription factor 2 | GENE Runx2 | mp47\|p47\| | gi = 391766 | 619252 |
| IC02005 | UG75 Expression | GENE | Mm.34410 | TITLE RuvB-like protein 2 | GENE Ruvbl2 | H-2RIIBP\|Nr2b2\|RCoR-1\| | NM_011304 | 2938212 |
| IC02006 | UG75 Expression | GENE | Mm.1243 | TITLE retinoid X receptor beta | GENE Rxrb | N2b3\| | gi = 337642 | 2631142 |
| IC02007 | UG75 Expression | GENE | Mm.3475 | TITLE retinoid X receptor gamma | GENE Rxrg | RIP110\| | NM_009107 | 479866 |
| IC02008 | UG75 Expression | GENE | Mm.4097 | TITLE retinoid X receptor interacting protein 110 | GENE Rxrip110 | Vik\| | gi = 709960 | 1210518 |
| IC02009 | UG75 Expression | GENE | Mm.3860 | TITLE receptor-like tyrosine kinase | GENE Ryk | calcium release channel isoform 1\|muscle ryanodine receptor\|Ryr\| | gi = 309443 | 1194984 |
| IC02010 | UG75 Expression | GENE | Mm.4519 | TITLE ryanodine receptor 1, skeletal muscle | GENE Ryr1 | | gi = 639812 | 606250 |
| IC02011 | UG75 Expression | GENE | Mm.24662 | TITLE S100 calcium binding protein A1 | GENE S100a1 | Cal1\|calpactin I light chain\|p11\| | NM_011309 | 572494 |
| IC02012 | UG75 Expression | GENE | Mm.1 | TITLE calcium binding protein A11 (calgizzarin) | GENE S100a1 | | NM_009112 | 2520191 |
| IC02013 | UG75 Expression | GENE | Mm.6523 | TITLE S100 calcium-binding protein A13 | GENE S100a13 | | NM_009113 | 576024 |
| IC02014 | UG75 Expression | GENE | Mm.3925 | TITLE S100 calcium-binding protein A4 | GENE S100a4 | 18A2\|42a\|calcium binding protein, placental\|calcium-binding protein, placental\|calvasculin\|CAPL\|FSp1\|malignant transformation suppression 1\|Mts1\|PeL98\|pk9a\| | gi = 220569 | 1094052 |
| IC02015 | UG75 Expression | GENE | Mm.1221 | TITLE calcium binding protein A6 (calcyclin) | GENE S100a6 | Cacy\|calcyclin\| | NM_011313 | 440637 |
| IC02016 | UG75 Expression | GENE | Mm.21567 | TITLE S100 calcium binding protein A8 (calgranulin A) | GENE S100a8 | Cagla\|calgranulin A\|CP-10\|MRP8\| | NM_013650 | 762867 |
| IC02017 | UG75 Expression | GENE | Mm.2128 | TITLE S100 calcium-binding protein A9 (calgranulin B) | GENE S100a9 | Cagb\|calgranulin B\|MRP14\| | NM_009114 | 472993 |
| IC02018 | UG75 Expression | GENE | Mm.1802 | TITLE surface antigen, homeo box of paired rule | GENE S8 | | NM_009116 | 2936967 |
| IC02019 | UG75 Expression | GENE | Mm.14277 | TITLE serum amyloid A 3 | GENE Saa3 | Saa-3\| | NM_011315 | 1278715 |
| IC02020 | UG75 Expression | GENE | Mm.8256 | TITLE src associated in mitosis, 68 kDa | GENE Sam68 | p62\| | NM_011317 | 671158 |
| IC02021 | UG75 Expression | GENE | Mm.2165 | TITLE serum amyloid P-component | GENE Sap | | NM_011318 | 1885785 |
| IC02022 | UG75 Expression | GENE | Mm.35851 | TITLE Sin3-associated polypeptide 18 | GENE Sap18 | EMegR4\|SAP18\|Sinbp1\| | NM_009119 | 3025803 |
| IC02023 | UG75 Expression | GENE | Mm.6698 | TITLE SAR1a gene homolog (S. cerevisiae) | GENE Sara | | gi = 436563 | 661027 |
| IC02024 | UG75 Expression | GENE | Mm.2734 | TITLE spermidine/spermine N1-acetyl transferase | GENE Sat | SSAT\| | NM_009121 | 492959 |
| IC02025 | UG75 Expression | GENE | Mm.4381 | TITLE special AT-rich sequence binding protein 1 | GENE Satb1 | | NM_009122 | 2922248 |
| IC02026 | UG75 Expression | GENE | Mm.1989 | TITLE spinocerebellar ataxia 2 homolog | GENE Sca2 | ataxin 2\|ATX2\|spinocerebellar ataxia 2 (olivopontocerebellar ataxia 2, autosomal dominant, ataxin 2)\| | NM_009125 | 905928 |
| IC02027 | UG75 Expression | GENE | Mm.3230 | TITLE secretory carrier membrane protein 3 | GENE Scamp3 | | NM_011886 | 988499 |
| IC02028 | UG75 Expression | GENE | Mm.22026 | TITLE stearoyl-Coenzyme A desaturase 1 | GENE Scd1 | CLM1\|cytohesin 1\| | NM_009127 | 1381623 |
| IC02029 | UG75 Expression | GENE | Mm.298 | TITLE stearoyl-Coenzyme A desaturase 2 | GENE Scd2 | CLM2\|cytohesin 2\| | NM_009128 | 2332125 |
| IC02030 | UG75 Expression | GENE | Mm.20428 | TITLE stem cell growth factor | GENE Scgf | | NM_009131 | 947754 |
| IC02031 | UG75 Expression | GENE | Mm.1779 | TITLE sterol carrier protein 2, liver | GENE Scp2 | nonspecific lipid transfer protein\|ns-LITP\|NSL-TP\|SCPx\| | gi = 1904220 | 1888688 |
| IC02032 | UG75 Expression | GENE | Mm.4686 | TITLE small inducible cytokine A11 | GENE Scya11 | eotaxin\| | NM_011330 | 577422 |
| IC02033 | UG75 Expression | GENE | Mm.867 | TITLE small inducible cytokine A12 | GENE Scya12 | MCP-5\| | NM_011331 | 777824 |
| IC02034 | UG75 Expression | GENE | Mm.41988 | TITLE small inducible cytokine subfamily A17 | GENE Scya17 | ABCD-2\|TARC\| | NM_011332 | 1398634 |
| IC02035 | UG75 Expression | GENE | Mm.30205 | TITLE small inducible cytokine A19 | GENE Scya19 | EBI-1 ligand chemokine\|ELC\|MIP3B\| | NM_011888 | 949704 |
| IC02036 | UG75 Expression | GENE | Mm.145 | TITLE small inducible cytokine A2 | GENE Scya2 | JE\|MCP-1\|monocyte chemotactic protein\|Sigje\|small inducible gene JE\| | NM_011333 | 573898 |
| IC02037 | UG75 Expression | GENE | Mm.4408 | TITLE small inducible cytokine subfamily A20 | GENE Scya20 | LARC\|MIP-3\|a\|ST38\| | NM_011334 | 2332265 |
| IC02038 | UG75 Expression | GENE | Mm.15780 | TITLE small inducible cytokine A21a (leucine) | GENE Scya21a | 6CKBAC1\|6Ckine\|Exodus-2\|Scya21\|secondary lymphoid organ chemokin\|SLC\|small inducible cytokine A21\| | NM_011335 | 777665 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02039 | UG75 Expression | GENE | Mm.89966 | TITLE small inducible cytokine A21b (serine) | GENE Scya21b | 6CKBAC2|6Ckine|ALP|Exodus-2|paucity of lymph node T-cells|plt|Scya21|secondary lymphoid organ chemokine|SLC|small inducible cytokine A21b (serine)|Tca4| | gi = 2624926 | 777665 |
| IC02040 | UG75 Expression | GENE | Mm.12895 | TITLE small inducible cytokine subfamily A, member 22 | GENE Scya22 | ABCD-1| | NM_009137 | 619257 |
| IC02041 | UG75 Expression | GENE | Mm.7275 | TITLE small inducible cytokine A25 | GENE Scya25 | | NM_009138 | 575567 |
| IC02042 | UG75 Expression | GENE | Mm.6660 | TITLE small inducible cytokine A27 | GENE Scya27 | ALP|CCL27|ESkine|ILC| | NM_011336 | 1281114 |
| IC02043 | UG75 Expression | GENE | Mm.1282 | TITLE small inducible cytokine A3 | GENE Scya3 | macrophage inflammatory protein-1 alpha|MIP-1 alpha|MIP1|NM_011337 (a)|MIP1-alpha|Mip1a| | NM_011337 | 1280073 |
| IC02044 | UG75 Expression | GENE | Mm.1255 | TITLE small inducible cytokine A4 | GENE Scya4 | macrophage inflammatory protein-1 beta|MIP-1 B|Mip1b| | NM_013652 | 621095 |
| IC02045 | UG75 Expression | GENE | Mm.3370 | TITLE small inducible cytokine A5 | GENE Scya5 | RANTES| | NM_013653 | 1366154 |
| IC02046 | UG75 Expression | GENE | Mm.137 | TITLE small inducible cytokine A6 | GENE Scya6 | c10| | NM_009139 | 1383272 |
| IC02047 | UG75 Expression | GENE | Mm.2271 | TITLE small inducible cytokine A9 | GENE Scya9 | CCF18|MIP-1 gamma|MRP-2| | NM_011338 | 2648297 |
| IC02048 | UG75 Expression | GENE | Mm.877 | TITLE small inducible cytokine B subfamily (Cys—X—Cys), member 10 | GENE Scyb10 | CRG-2|Ifi10|interferon activated gene 10|IP-10| | gi = 192720 | 581882 |
| IC02049 | UG75 Expression | GENE | Mm.766 | TITLE small inducible cytokine B subfamily (Cys—X—Cys), member 9 | GENE Scyb9 | Mig|monokine induced by gamma interferon| | NM_008599 | 596559 |
| IC02050 | UG75 Expression | GENE | Mm.3205 | TITLE small inducible cytokine subfamily D, 1 | GENE Scyd1 | ABCD-3|CX3C|Cxc3|D8Bwg0439e|DNA segment, Chr 8, Brigham & Women's Genetics 0439 expressed|fractalkine, neurotactin| | NM_009142 | 761708 |
| IC02051 | UG75 Expression | GENE | Mm.2580 | TITLE syndecan 1 | GENE Sdc1 | CD138|Synd|Synd1|syndecan| | NM_011519 | 3154858 |
| IC02052 | UG75 Expression | GENE | Mm.29350 | TITLE syndecan 2 | GENE Sdc2 | fibroglycan|heparan sulfate proteoglycan 1, cell surface-associated (fibroglycan)|Hspg1|Synd2|syndecan-2| | NM_008304 | 2645606 |
| IC02053 | UG75 Expression | GENE | Mm.3815 | TITLE syndecan 4 | GENE Sdc4 | ryudocan|Synd4| | NM_011521 | 576965 |
| IC02054 | UG75 Expression | GENE | Mm.465 | TITLE stromal cell derived factor 1 | GENE Sdf1 | Sdf1a|Sdf1b|stromal cell derived factor 1A|stromal cell derived factor 1B| | NM_013655 | 1151295 |
| IC02055 | UG75 Expression | GENE | Mm.935 | TITLE stromal cell derived factor 2 | GENE Sdf2 | | NM_009143 | 1248170 |
| IC02056 | UG75 Expression | GENE | Mm.30149 | TITLE stromal cell derived factor 4 | GENE Sdf4 | Cab45|calcium binding protein, 45 kDa| | NM_011341 | 1891202 |
| IC02057 | UG75 Expression | GENE | Mm.19155 | TITLE stromal cell derived factor 5 | GENE Sdf5 | Sfrp2| | NM_009144 | 368879 |
| IC02058 | UG75 Expression | GENE | Mm.15125 | TITLE stromal cell derived factor receptor 1 | GENE Sdfr1 | | NM_009145 | 1481429 |
| IC02059 | UG75 Expression | GENE | Mm.18910 | TITLE stromal cell derived factor receptor 2 | GENE Sdfr2 | | NM_009146 | 1972328 |
| IC02060 | UG75 Expression | GENE | Mm.1164 | TITLE Sec61, gamma subunit | GENE Sec61g | | NM_011343 | 736755 |
| IC02061 | UG75 Expression | GENE | Mm.6925 | TITLE secretory protein SEC8 (S. cerevisiae) | GENE Sec8 | | NM_009148 | 534063 |
| IC02062 | UG75 Expression | GENE | Mm.14352 | TITLE Sel1 (suppressor of lin-12) 1 homolog (C. elegans) | GENE Sel1h | | gi = 4159994 | 623062 |
| IC02063 | UG75 Expression | GENE | Mm.488 | TITLE selectin, endothelial cell, ligand | GENE Selel | CFR|ESL-1| | NM_009149 | 585111 |
| IC02064 | UG75 Expression | GENE | Mm.636 | TITLE selenium binding protein 1 | GENE Selenbp | liver protein, selenium binding, 56 kDa|Lp56|Lpsb| | NM_009150 | 1885704 |
| IC02065 | UG75 Expression | GENE | Mm.1461 | TITLE selectin, lymphocyte | GENE Sell | CD62L|L-selectin|LECAM-1|Lnhr|Ly-22|Lyam-1|Lyam1|lymph node homing receptor|lymphocyte adhesion molecule 1|lymphocyte antigen 22|lymphocyte antigen m22| | NM_011346 | 622487 |
| IC02066 | UG75 Expression | GENE | Mm.22173 | TITLE selectin, platelet (p-selectin) ligand | GENE Selpl | | NM_009151 | 2749107 |
| IC02067 | UG75 Expression | GENE | Mm.4083 | TITLE sema domain, immunoglobulin domain (Ig), short basic domain, secreted, (semaphorin) 3B | GENE Sema3b | LUCA-1|SemA|sema5|SEMAA|semaphorin A|semaV| | NM_009153 | 2646919 |
| IC02068 | UG75 Expression | GENE | Mm.22061 | TITLE sema domain, immunoglobulin domain (Ig), transmembrane domain (TM) and short cytoplasmic domain, (semaphorin) 4A | GENE Sema4a | SEMAB|semaphorin B|SemB| | NM_013658 | 573186 |
| IC02069 | UG75 Expression | GENE | Mm.33903 | TITLE sema domain, immunoglobulin domain (Ig), transmembrane domain (TM) and short cytoplasmic domain, (semaphorin) 4D | GENE Sema4d | CD100|coll-4|M-sema G|Semacl2|SEMAJ|semaphorin C-like 2|semaphorin H|Semcl2| | NM_013660 | 1383840 |

US 6,706,867 B1

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02070 | UG75 Expression | GENE | Mm.23662 | TITLE sema domain, transmembrane domain (TM), and cytoplasmic domain, (semaphorin) 6C | GENE Sema6c | m-Sema Y[Sema Y[semaphorin Y[Semay] | NM_011351 | 642361 |
| IC02071 | UG75 Expression | GENE | Mm.22699 | TITLE selenoprotein P, plasma, 1 | GENE Sepp1 | | gi = 4103141 | 681818 |
| IC02072 | UG75 Expression | GENE | Mm.42829 | TITLE selenoprotein W, muscle 1 | GENE Sepw1 | | NM_009156 | 643267 |
| IC02073 | UG75 Expression | GENE | Mm.1106 | TITLE small EDRK-rich factor 2 | GENE Serf2 | 4F5rel (4F5 related)[m4F5rel] | NM_011354 | 1885135 |
| IC02074 | UG75 Expression | GENE | Mm.1302 | TITLE SFFV proviral integration 1 | GENE Sfpi1 | Dis[PU.1[Sfpi-1[Spi-1[Tcfpu1[Tfpu.1[transcription factor PU.1] | NM_011355 | 736139 |
| IC02075 | UG75 Expression | GENE | Mm.3171 | TITLE secreted frizzled-related sequence protein 1 | GENE Sfrp1 | | NM_013834 | 2182872 |
| IC02076 | UG75 Expression | GENE | Mm.21841 | TITLE splicing factor, arginine/serine-rich 2 (SC-35) | GENE Sfrs2 | | NM_011358 | 2236607 |
| IC02077 | UG75 Expression | GENE | Mm.6787 | TITLE splicing factor, arginine/serine-rich 3 (SRp20) | GENE Sfrs3 | X16] | gi = 2125862 | 1498122 |
| IC02078 | UG75 Expression | GENE | Mm.43331 | TITLE SH3-domain GRB2-like B1 (endophilin) HRS | GENE Sfrs5 | | NM_011359 | 3155853 |
| IC02079 | UG75 Expression | GENE | Mm.8739 | TITLE sarcoglycan, epsilon | GENE Sgce | | NM_011360 | 643823 |
| IC02080 | UG75 Expression | GENE | Mm.72173 | TITLE sarcoglycan, gamma (35 kD dystrophin-associated glycoprotein) | GENE Sgcg | gamma-SG] | NM_011892 | 351420 |
| IC02081 | UG75 Expression | GENE | Mm.28405 | TITLE serum/glucocorticoid regulated kinase | GENE Sgk | | NM_011361 | 2503309 |
| IC02082 | UG75 Expression | GENE | Mm.8538 | TITLE SH2-B PH domain containing signaling mediator 1 | GENE Sh2bpsn | | NM_011363 | 2938189 |
| IC02083 | UG75 Expression | GENE | Mm.20880 | TITLE SH2 domain protein 1A | GENE Sh2d1a | Duncan disease homolog] | NM_011364 | 719479 |
| IC02084 | UG75 Expression | GENE | Mm.4462 | TITLE SH3-domain binding protein 1 | GENE Sh3bp1 | 3BP-1] | NM_009164 | 3167837 |
| IC02085 | UG75 Expression | GENE | Mm.46048 | TITLE SH3-domain binding protein 5 (BTK-associated) | GENE Sh3bp5 | Sab] | NM_011894 | 638538 |
| IC02086 | UG75 Expression | GENE | Mm.40285 | TITLE SH3 domain protein 1B | GENE Sh3d1B | Eh domain, SH3 domain regulator of endocytosis 2[Ese2[Sh3p18] | NM_011365 | 2655624 |
| IC02087 | UG75 Expression | GENE | Mm.1773 | TITLE SH3 domain protein 2B | GENE Sh3d2b | SH3P8] | NM_013664 | 1920799 |
| IC02088 | UG75 Expression | GENE | Mm.2090 | TITLE Sh3 domain YSC-like 1 | GENE Sh3yl1 | Ray[YSC84] | NM_013709 | 1921851 |
| IC02089 | UG75 Expression | GENE | Mm.37801 | TITLE Shc SH2-domain binding protein 1 | GENE Shcbp1 | mPAL] | NM_011369 | 2654132 |
| IC02090 | UG75 Expression | GENE | Mm.2469 | TITLE split hand/foot deleted gene 1 | GENE Shfdg1 | DSS1[Shfg[split hand/foot gene] | NM_009169 | 1106028 |
| IC02091 | UG75 Expression | GENE | Mm.12912 | TITLE selective hybridizing clone | GENE Shyc | | NM_011370 | 1907790 |
| IC02092 | UG75 Expression | GENE | Mm.6765 | TITLE seven in absentia 1A | GENE Siah1a | Sinh1a] | NM_009172 | 1248270 |
| IC02093 | UG75 Expression | GENE | Mm.37215 | TITLE seven in absentia 1B | GENE Siah1b | Sinh1b] | NM_009173 | 616840 |
| IC02094 | UG75 Expression | GENE | Mm.2847 | TITLE seven in absentia 2 | GENE Siah2 | Sinh2] | NM_009174 | 1123783 |
| IC02095 | UG75 Expression | GENE | Mm.2793 | TITLE sialyltransferase 4c | GENE Siat4c | ST3Gal IV] | NM_009178 | 619034 |
| IC02096 | UG75 Expression | GENE | Mm.3947 | TITLE sialyltransferase 7 ((alpha-N-acetylneuraminyl 2,3-beta-galactosyl-1,3)-N-acetyl galactosaminide alpha-2,6-sialyltransferase B | GENE Siat7b | sialyltransferase 7[Siat7[ST6GalNAc II] | NM_009180 | 1971645 |
| IC02097 | UG75 Expression | GENE | Mm.1563 | TITLE sialyltransferase 7 ((alpha-N-acetylneuraminyl 2,3-betagalactosyl-1,3)-N-acetyl galactosaminide alpha-2,6-sialyltransferase) C | GENE Siat7c | ST6GalNAc III] | gi = 4894174 | 619209 |
| IC02098 | UG75 Expression | GENE | Mm.27446 | TITLE sialyltransferase 7 ((alpha-N-acetylneuraminyl 2,3-betagalactosyl-1,3)-N-acetyl galactosaminide alpha-2,6-sialyltransferase) D | GENE Siat7d | ST6GalNAc IV] | NM_011373 | 660287 |
| IC02099 | UG75 Expression | GENE | Mm.10701 | TITLE sialyltransferase 8 (alpha-2, 8-sialyltransferase) D | GENE Siat8d | PST[ST8SiaIV] | NM_009183 | 1020785 |
| IC02100 | UG75 Expression | GENE | Mm.38248 | TITLE sialyltransferase 9 (CMP-NeuAc:lactosylceramide alpha-2,3-sialyltransferase) | GENE Siat9 | [a]2, 3S-T[GM3 synthase[GM3-specific sialyltransferase[mST3Gal V[ST3Gal V] | NM_011375 | 538319 |
| IC02101 | UG75 Expression | GENE | Mm.2984 | TITLE silica-induced gene 41 | GENE Silg41 | SIG-41] | NM_009186 | 1480516 |
| IC02102 | UG75 Expression | GENE | Mm.30072 | TITLE silica-induced gene 81 | GENE Silg81 | SIG-81] | NM_009187 | 1247582 |
| IC02103 | UG75 Expression | GENE | Mm.2137 | TITLE transcriptional regulator, SIN3 yeast homolog B | GENE Sin3b | | gi = 642620 | 1397313 |
| IC02104 | UG75 Expression | GENE | Mm.3072 | TITLE signal-induced proliferation associated gene 1 | GENE Sipa1 | signal-induced proliferation-associated gene 1] | NM_011379 | 372712 |
| IC02105 | UG75 Expression | GENE | Mm.29790 | TITLE signaling intermediate in Toll pathway-evolutionarily conserved | GENE Sitpec-pc | ECSIT] | NM_012029 | 1481217 |
| IC02106 | UG75 Expression | GENE | Mm.18705 | TITLE suppressor of K+ transport defect 1 | GENE Skd1 | | NM_009190 | 2236519 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02107 | UG75 Expression | GENE | Mm.3990 | TITLE suppressor of K+ transport defect 3 | GENE Skd3 | | NM_009191 | 1195049 |
| IC02108 | UG75 Expression | GENE | Mm.7601 | TITLE src-like adapter protein | GENE Slap | | NM_009192 | 1265347 |
| IC02109 | UG75 Expression | GENE | Mm.4172 | TITLE stem-loop binding protein | GENE Slbp | | NM_009193 | 2332210 |
| IC02110 | UG75 Expression | GENE | Mm.35837 | TITLE solute carrier family 10 (sodium/bile acid cotransporter family), member 1 | GENE Slc10a1 | bile acid cotransporting polypeptide|Na+/taurocholate cotransporting polypeptide|Ntcp| | NM_011387 | 1277890 |
| IC02111 | UG75 Expression | GENE | Mm.1304 | TITLE solute carrier family 11 (proton-coupled divalent metal ion transporters), member 2 | GENE Slc11a2 | DCT1|DMT1|microcytic anemia|microcytic anemia, viable anaemia|mk|natural resistance-associated macrophage protein 2|Nramp2|van| | NM_008732 | 1243592 |
| IC02112 | UG75 Expression | GENE | Mm.4190 | TITLE solute carrier family 12, member 4 | GENE Slc12a4 | KCC1|RBCKCC1| | NM_009195 | 634461 |
| IC02113 | UG75 Expression | GENE | Mm.24510 | TITLE solute carrier family 12, member 7 | GENE Slc12a7 | KCC4 | NM_011390 | 719198 |
| IC02114 | UG75 Expression | GENE | Mm.9086 | TITLE solute carrier family 16 (monocarboxylic acid transporters), member 1 | GENE Slc16a1 | MCT1 | NM_009196 | 540170 |
| IC02115 | UG75 Expression | GENE | Mm.5045 | TITLE solute carrier family 16 (monocarboxylic acid transporters), member 2 | GENE Slc16a2 | XPCT | NM_009197 | 427197 |
| IC02116 | UG75 Expression | GENE | Mm.2620 | TITLE solute carrier family 19 (sodium/hydrogen exchanger), member 1 | GENE Slc19a1 | RFC|RFC-1|RFC1| | gi = 1518114 | 1222549 |
| IC02117 | UG75 Expression | GENE | Mm.24741 | TITLE solute carrier family 1, member 1 | GENE Slc1a1 | EAAC1|EAAT3|MEAAC1| | NM_009199 | 2123685 |
| IC02118 | UG75 Expression | GENE | Mm.2861 | TITLE solute carrier family 1, member 2 | GENE Slc1a2 | Eaat2|excitatory amino acid transporter 2|glial high affinity glutamate transporter|GLT1|MGLT1| | NM_011393 | 720240 |
| IC02119 | UG75 Expression | GENE | Mm.1056 | TITLE solute carrier family 1, member 7 | GENE Slc1a7 | AAAT | NM_009201 | 2225686 |
| IC02120 | UG75 Expression | GENE | Mm.42253 | TITLE solute carrier family 22 (organic cation transporter), member 5 | GENE Slc22a5 | juvenile visceral steatosis|jvs|Lstp-like|Lstp|Octn2| | NM_011396 | 992152 |
| IC02121 | UG75 Expression | GENE | Mm.22702 | TITLE solute carrier family 23, (nucleobase transporters) member 1 | GENE Slc23a1 | | gi = 3789786 | 2395251 |
| IC02122 | UG75 Expression | GENE | Mm.34953 | TITLE solute carrier family 25 (mitochondrial carrier, brain) member 14 | GENE Slc25a14 | Bmcp1-pending|brain mitochondrial carrier protein 1| | NM_011398 | 1971657 |
| IC02123 | UG75 Expression | GENE | Mm.306 | TITLE solute carrier family 25 (mitochondrial carrier, peroxisomal membrane protein, 34 kDa), member 17 | GENE Slc25a17 | PMP34 | gi = 3183980 | 571810 |
| IC02124 | UG75 Expression | GENE | Mm.6611 | TITLE solute carrier family 27 (fatty acid transporter), member 2 | GENE Slc27a2 | FATP2 | NM_011978 | 1164648 |
| IC02125 | UG75 Expression | GENE | Mm.30487 | TITLE solute carrier family 27 (fatty acid transporter), member 4 | GENE Slc27a4 | FATP4|fatty acid transport protein 4| | gi = 3335568 | 464463 |
| IC02126 | UG75 Expression | GENE | Mm.21002 | TITLE solute carrier family 2 (facilitated glucose transporter), member 1 | GENE Slc2a1 | glucose transporter 1, erythrocyte|Glut-1|Glut1| | gi = 193704 | 1480612 |
| IC02127 | UG75 Expression | GENE | Mm.10661 | TITLE solute carrier family 2 (facilitated glucose transporter), member 4 | GENE Slc2a4 | glucose transporter 4, muscle and fat|Glut-4|Glut4| | NM_009204 | 1178855 |
| IC02128 | UG75 Expression | GENE | Mm.27801 | TITLE solute carrier family 30 (zinc transporter), member 4 | GENE Slc30a4 | lethal milk|lm|zinc transporter 4|Znt4| | NM_011774 | 1051606 |
| IC02129 | UG75 Expression | GENE | Mm.22684 | TITLE solute carrier family 35 (CMP-sialic acid transporter), member 1 | GENE Slc35a1 | | NM_011895 | 803531 |
| IC02130 | UG75 Expression | GENE | Mm.7248 | TITLE solute carrier family 4 (anion exchanger), member 1 | GENE Slc4a1 | Ae1|anion exchanger 1|Empb3|erythrocyte membrane protein band 3| | NM_011403 | 469103 |
| IC02131 | UG75 Expression | GENE | Mm.20906 | TITLE solute carrier family 7 (cationic amino acid transporter, y+ system), member 7 | GENE Slc7a7 | my+lat1| | NM_011405 | 1973097 |
| IC02132 | UG75 Expression | GENE | Mm.4211 | TITLE solute carrier family 8 (sodium/calcium exchanger), member 1 | GENE Slc8a1 | Ncx1| | NM_011406 | 558549 |
| IC02133 | UG75 Expression | GENE | Mm.27842 | TITLE solute carrier family 9 (sodium/hydrogen exchanger), isoform 3 regulator 1 | GENE Slc9a3r1 | NHE-RF|sodium-hydrogen exchanger regulatory factor| | NM_012030 | 1972939 |
| IC02134 | UG75 Expression | GENE | Mm.10948 | TITLE schlafen 1 | GENE Slfn1 | | NM_011407 | 1379745 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02135 | UG75 Expression | GENE | Mm.42124 | TITLE schlafen 2 | GENE Slfn2 | | NM_011408 | 1329829 |
| IC02136 | UG75 Expression | GENE | Mm.42125 | TITLE schlafen 3 | GENE Slfn3 | | NM_011409 | 638739 |
| IC02137 | UG75 Expression | GENE | Mm.38192 | TITLE schlafen 4 | GENE Slfn4 | | gi = 3983161 | 749416 |
| IC02138 | UG75 Expression | GENE | Mm.1395 | TITLE secretory leukocyte protease inhibitor | GENE Slpi | SLPI| | NM_011414 | 333540 |
| IC02139 | UG75 Expression | GENE | Mm.3909 | TITLE SWI/SNF related, matrix associated, actin dependent regulator of chromatin, subfamily a, member 3 | GENE Smarca3 | P113|SNF2 (sucrose nonfermenting, yeast, homolog)-like 3|[Snf2l3] | NM_009210 | 576531 |
| IC02140 | UG75 Expression | GENE | Mm.26116 | TITLE SWI/SNF related, matrix associated, actin dependent regulator of chromatin, subfamily b, member 1 | GENE Smarcb1 | SNF5/INI1| | NM_011418 | 580874 |
| IC02141 | UG75 Expression | GENE | Mm.1050 | TITLE SWI/SNF related, matrix associated, actin dependent regulator of chromatin, subfamily c, member 1 | GENE Smarcc1 | BAF155|Rsc8| | NM_009211 | 2646003 |
| IC02142 | UG75 Expression | GENE | Mm.3179 | TITLE immunoglobulin S mu binding protein 2 | GENE Smbp2 | Catf1|neuromuscular degeneration|nmd|smal|spinal muscular atrophy| | NM_009212 | 2655616 |
| IC02143 | UG75 Expression | GENE | Mm.2025 | TITLE survival motor neuron | GENE Smn | | NM_011420 | 722027 |
| IC02144 | UG75 Expression | GENE | Mm.29279 | TITLE smoothened homolog (Drosophila) | GENE Smoh | Smo| | gi = 3608491 | 3155765 |
| IC02145 | UG75 Expression | GENE | Mm.4628 | TITLE sphingomyelin phosphodiesterase 1, acid lysosomal | GENE Smpd1 | A-SMase|aSMase| | NM_011421 | 820616 |
| IC02146 | UG75 Expression | GENE | Mm.953 | TITLE sphingomyelin phosphodiesterase 2, neutral | GENE Smpd2 | nSMase| | NM_009213 | 2192870 |
| IC02147 | UG75 Expression | GENE | Mm.3553 | TITLE spermine synthase | GENE Sms | | NM_009214 | 554226 |
| IC02148 | UG75 Expression | GENE | Mm.1374 | TITLE sialoadhesin | GENE Sn | | NM_011426 | 2650862 |
| IC02149 | UG75 Expression | GENE | Mm.100178 | TITLE synaptosomal-associated protein, 25 kDa, binding protein | GENE Snap25b | Snapin| | NM_011429 | 806780 |
| IC02150 | UG75 Expression | GENE | Mm.17484 | TITLE synuclein, alpha | GENE Snca | NACP| | NM_009221 | 2076312 |
| IC02151 | UG75 Expression | GENE | Mm.30197 | TITLE syndet | GENE Sndt | Syndet| | NM_009222 | 2803398 |
| IC02152 | UG75 Expression | GENE | Mm.87023 | TITLE stannin | GENE Snn | | NM_009223 | 2235958 |
| IC02153 | UG75 Expression | GENE | Mm.873 | TITLE U5 small nuclear ribonucleoprotein 116 kDa | GENE Snrp116 | U5-116kD| | NM_011431 | 2699269 |
| IC02154 | UG75 Expression | GENE | Mm.2265 | TITLE U1 small nuclear ribonucleoprotein 1C | GENE Snrp1c | U1-C| | NM_011432 | 1970389 |
| IC02155 | UG75 Expression | GENE | Mm.603 | TITLE small nuclear ribonucleoprotein D1 | GENE Snrpd1 | | NM_009226 | 581863 |
| IC02156 | UG75 Expression | GENE | Mm.27669 | TITLE small nuclear ribonucleoprotein E | GENE Snrpe | | gi = 312004 | 335012 |
| IC02157 | UG75 Expression | GENE | Mm.43721 | TITLE small nuclear ribonucleoprotein N | GENE Snrpn | | NM_013670 | 580121 |
| IC02158 | UG75 Expression | GENE | Mm.30228 | TITLE syntrophin, basic 2 | GENE Sntb2 | Snt2|syntrophin 2| | NM_009229 | 351227 |
| IC02159 | UG75 Expression | GENE | Mm.28099 | TITLE sterol O-acyltransferase 1 | GENE Soat1 | Acact|acetyl coenzyme A cholesterol acyltransferase|adrenocortical lipid depletion|ald| | NM_009230 | 805142 |
| IC02160 | UG75 Expression | GENE | Mm.5274 | TITLE superoxide dismutase 1, soluble | GENE Sod1 | Cu/Zn-SOD|CuZnSOD|indophenol oxidase|lpo-1|lpo1|Sod-1|SODC| | gi = 201005 | 860421 |
| IC02161 | UG75 Expression | GENE | Mm.2597 | TITLE superoxide dismutase 2, mitochondrial | GENE Sod2 | MnSOD|Sod-2| | NM_013671 | 791140 |
| IC02162 | UG75 Expression | GENE | Mm.5396 | TITLE sortilin-related receptor; LDLR class A repeats-containing | GENE Sorl1 | gp250|LR11|mSorLA| | gi = 2654024 | 721295 |
| IC02163 | UG75 Expression | GENE | Mm.6357 | TITLE Son of sevenless homolog 1, (Drosophila) | GENE Sos1 | | NM_009231 | 585263 |
| IC02164 | UG75 Expression | GENE | Mm.3770 | TITLE Son of sevenless homolog 2, (Drosophila) | GENE Sos2 | | gi = 54136 | 735697 |
| IC02165 | UG75 Expression | GENE | Mm.29387 | TITLE SRY-box containing gene 15 | GENE Sox15 | | gi = 3165380 | 577657 |
| IC02166 | UG75 Expression | GENE | Mm.5080 | TITLE SRY-box containing gene 17 | GENE Sox17 | | NM_011441 | 1749381 |
| IC02167 | UG75 Expression | GENE | Mm.18789 | TITLE SRY-box containing gene 4 | GENE Sox4 | Sox| | NM_009238 | 3155166 |
| IC02168 | UG75 Expression | GENE | Mm.4656 | TITLE SRY-box containing gene 6 | GENE Sox6 | Sox-4| | NM_011445 | 821241 |
| IC02169 | UG75 Expression | GENE | Mm.4618 | TITLE nuclear antigen Sp100 | GENE Sp100 | | NM_013672 | 2650249 |
| IC02170 | UG75 Expression | GENE | Mm.8551 | TITLE trans-acting transcription factor 1 | GENE Sp1 | asp-1|[as|inhibition of audiogenic seizure susceptibility| | NM_013673 | 1925132 |
| IC02171 | UG75 Expression | GENE | Mm.28513 | TITLE trans-acting transcription factor 3 | GENE Sp3 | asp-3| | gi = 3132609 | 1025265 |
| IC02172 | UG75 Expression | GENE | Mm.35439 | TITLE secreted acidic cysteine rich glycoprotein | GENE Sparc | osteonectin| | NM_009242 | 1969711 |
| IC02173 | UG75 Expression | GENE | Mm.20944 | TITLE sphingosine kinase 1 | GENE Sphk1 | | gi = 3659691 | 2937093 |
| IC02174 | UG75 Expression | GENE | Mm.89843 | TITLE serine protease inhibitor 1-1 | GENE Spi1-1 | PI1| | NM_009243 | 1450898 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02175 | UG75 Expression | GENE | Mm.89895 | TITLE serine protease inhibitor 1-2 | GENE Spi1-2 | PI2| | gi = 191549 | 1450987 |
| IC02176 | UG75 Expression | GENE | Mm.89363 | TITLE serine protease inhibitor 1-3 | GENE Spi1-3 | PI3| | NM_009245 | 1923185 |
| IC02177 | UG75 Expression | GENE | Mm.16672 | TITLE serine protease inhibitor 1-4 | GENE Spi1-4 | PI4| | NM_009246 | 1923185 |
| IC02178 | UG75 Expression | GENE | Mm.41560 | TITLE serine protease inhibitor 17 | GENE Spi17 | Neuroserpin| | NM_009250 | 1617692 |
| IC02179 | UG75 Expression | GENE | Mm.15085 | TITLE serine protease inhibitor 2-1 | GENE Spi2-1 | | gi = 201037 | 1499338 |
| IC02180 | UG75 Expression | GENE | Mm.22650 | TITLE serine protease inhibitor 2-2 | GENE Spi2-2 | | NM_009252 | 1888347 |
| IC02181 | UG75 Expression | GENE | Mm.3093 | TITLE serine protease inhibitor 4 | GENE Spi4 | nexin|PN-1| | NM_009255 | 481914 |
| IC02182 | UG75 Expression | GENE | Mm.3368 | TITLE serine protease inhibitor 6 | GENE Spi6 | | NM_009256 | 1479969 |
| IC02183 | UG75 Expression | GENE | Mm.4622 | TITLE serine protease inhibitor 7 | GENE Spi7 | Maspin| | NM_009257 | 1383413 |
| IC02184 | UG75 Expression | GENE | Mm.21642 | TITLE Spi-C transcription factor (Spi-1/PU.1 related) | GENE Spic | Spi-C| | NM_011461 | 636018 |
| IC02185 | UG75 Expression | GENE | Mm.42193 | TITLE spindlin | GENE Spin | | NM_011462 | 962008 |
| IC02186 | UG75 Expression | GENE | Mm.4677 | TITLE Sfpi1/PU.1 interaction partner | GENE Spip | LSIRF| | NM_013674 | 330172 |
| IC02187 | UG75 Expression | GENE | Mm.2528 | TITLE alpha-spectrin 1, erythroid | GENE Spna1 | ha|hemolytic anemia|sph|spherocytosis|Spna-1| | NM_011465 | 538325 |
| IC02188 | UG75 Expression | GENE | Mm.20405 | TITLE beta-spectrin 2, non-erythrocytic | GENE Spnb2 | beta fodrin|Spnb-2| | NM_009260 | 860336 |
| IC02189 | UG75 Expression | GENE | Mm.18034 | TITLE spermatid perinuclear RNA-binding protein | GENE Spnr | | NM_009261 | 540421 |
| IC02190 | UG75 Expression | GENE | Mm.89938 | TITLE sporulation protein, meiosis-specific, SPO11 homolog (S. cervisiae) | GENE Spo11 | | NM_012046 | 577547 |
| IC02191 | UG75 Expression | GENE | Mm.321 | TITLE secreted phosphoprotein 1 | GENE Spp1 | 44 kDa bone phosphoprotein|activation protein lymphocyte 1|Apl-1|bone sialoprotein|early T lymphocyte activation|Eta|OPN|Opn|osteopontin|osteopontin-like protein|Ric|rickettsia tsutsugamushi resistance|Spp-1| | NM_009263 | 1432522 |
| IC02192 | UG75 Expression | GENE | Mm.28393 | TITLE sepiapterin reductase | GENE Spr | | NM_011467 | 1482026 |
| IC02193 | UG75 Expression | GENE | Mm.625 | TITLE small proline-rich protein 1A | GENE Sprr1a | | NM_009264 | 606841 |
| IC02194 | UG75 Expression | GENE | Mm.20294 | TITLE selenophosphate synthetase 2 | GENE Sps2 | | NM_009266 | 2646967 |
| IC02195 | UG75 Expression | GENE | Mm.6505 | TITLE serine palmitoyltransferase, long chain base subunit 1 | GENE Splc1 | clone 1000|the SelD gene product|yolk sac gene 3|Ysg3| | NM_009269 | 1922320 |
| IC02196 | UG75 Expression | GENE | Mm.565 | TITLE serine palmitoyltransferase, long chain base subunit 2 | GENE Splc2 | Lcb1| | NM_011479 | 1282816 |
| IC02197 | UG75 Expression | GENE | Mm.22663 | TITLE squalene epoxidase | GENE Sqle | LCB2| | NM_009270 | 524698 |
| IC02198 | UG75 Expression | GENE | Mm.10 | TITLE spermidine synthase | GENE Srm | squalene epoxidase| | NM_009272 | 2938994 |
| IC02199 | UG75 Expression | GENE | Mm.850 | TITLE signal recognition particle 14 kDa (homologous Alu RNA-binding protein) | GENE Srp14 | SpdSy| | NM_009273 | 3167579 |
| IC02200 | UG75 Expression | GENE | Mm.12848 | TITLE signal recognition particle 54 kDa | GENE Srp54 | | NM_011899 | 1432459 |
| IC02201 | UG75 Expression | GENE | Mm.89927 | TITLE signal recognition particle 9 kDa | GENE Srp9 | | NM_012058 | 669719 |
| IC02202 | UG75 Expression | GENE | Mm.8709 | TITLE serine/arginine-rich protein specific kinase 2 | GENE Srpk2 | mSRPK2|WBP6| | NM_009274 | 876627 |
| IC02203 | UG75 Expression | GENE | Mm.7588 | TITLE signal recognition particle receptor, B subunit | GENE Srprb | | NM_009275 | 616300 |
| IC02204 | UG75 Expression | GENE | Mm.19015 | TITLE serine racemase | GENE Srs-penc | | NM_013761 | 475452 |
| IC02205 | UG75 Expression | GENE | Mm.1384 | TITLE Sjogren syndrome antigen A1 | GENE Ssa1 | A-C1| | NM_009277 | 1363803 |
| IC02206 | UG75 Expression | GENE | Mm.10508 | TITLE Sjogren syndrome antigen B | GENE Ssb | Ro52| | NM_009278 | 804742 |
| IC02207 | UG75 Expression | GENE | Mm.29504 | TITLE sperm specific antigen 1 | GENE Ssfa1 | autoantigen La|La protein|SS-B| | NM_011482 | 809008 |
| IC02208 | UG75 Expression | GENE | Mm.831 | TITLE signal sequence receptor, delta | GENE Ssr4 | fertilization antigen 1|Fta1| | NM_009279 | 479133 |
| IC02209 | UG75 Expression | GENE | Mm.4296 | TITLE synovial sarcoma, translocated to X chromosome | GENE Ssxt | | NM_009280 | 2939774 |
| IC02210 | UG75 Expression | GENE | Mm.10815 | TITLE selenocysteine tRNA gene transcription activating factor | GENE Staf | | NM_009281 | 581798 |
| IC02211 | UG75 Expression | GENE | Mm.42135 | TITLE stromal antigen 1 | GENE Stag1 | SA-1| | NM_009282 | 874972 |
| IC02212 | UG75 Expression | GENE | Mm.3965 | TITLE signal transducing adaptor molecule (SH3 domain and ITAM motif) 1 | GENE Stam | | NM_011484 | 657919 |
| IC02213 | UG75 Expression | GENE | Mm.8249 | TITLE signal transducer and activator of transcription 1 | GENE Stat1 | | NM_009283 | 618952 |
| IC02214 | UG75 Expression | GENE | Mm.3948 | TITLE signal transducer and activator of transcription 3 | GENE Stat3 | Aprf| | gi = 473889 | 555559 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02215 | UG75 Expression | GENE | Mm.1550 | TITLE signal transducer and activator of transcription 4 | GENE Stat4 | | NM_011487 | 577343 |
| IC02216 | UG75 Expression | GENE | Mm.4697 | TITLE signal transducer and activator of transcription 5A | GENE Stat5a | | NM_011488 | 1247511 |
| IC02217 | UG75 Expression | GENE | Mm.2489 | TITLE signal transducer and activator of transcription 6 | GENE Stat6 | | NM_009284 | 1227034 |
| IC02218 | UG75 Expression | GENE | Mm.41650 | TITLE staufen (RNA-binding protein) homolog 1 (Drosophila) | GENE Stau1 | | NM_011490 | 1223805 |
| IC02219 | UG75 Expression | GENE | Mm.12904 | TITLE stanniocalcin 2 | GENE Stc2 | mustc2| | NM_011491 | 1196127 |
| IC02220 | UG75 Expression | GENE | Mm.3009 | TITLE sulfotransferase, hydroxysteroid preferring 2 | GENE Sth2 | mSTa2| | NM_009286 | 1891249 |
| IC02221 | UG75 Expression | GENE | Mm.645 | TITLE stromal interaction molecule 1 | GENE Stim1 | SIM|stromal interaction molecule| | NM_009287 | 582664 |
| IC02222 | UG75 Expression | GENE | Mm.8235 | TITLE serine/threonine kinase 10 | GENE Stk10 | Lok| | NM_009288 | 636379 |
| IC02223 | UG75 Expression | GENE | Mm.17461 | TITLE serine/threonine kinase 16 | GENE Stk16 | EDPK|Embryo-Derived Protein Kinase|Krct|PKL12| | NM_011494 | 1888275 |
| IC02224 | UG75 Expression | GENE | Mm.3794 | TITLE serine/threonine kinase 18 | GENE Stk18 | Sak|Smk/Plk-akin kinase| | gi = 487869 | 2698807 |
| IC02225 | UG75 Expression | GENE | Mm.7693 | TITLE serine/threonine kinase 2 | GENE Stk2 | 9A2|Etk4|mSLK| | NM_009289 | 2646334 |
| IC02226 | UG75 Expression | GENE | Mm.3488 | TITLE serine/threonine kinase 5 | GENE Stk5 | AIRK2|Ark2|STK-1| | gi = 2979622 | 2698939 |
| IC02227 | UG75 Expression | GENE | Mm.11738 | TITLE serine/threonine kinase 6 | GENE Stk6 | AIRK1|Ark1|Ayk1|IAK| | gi = 2979620 | 834679 |
| IC02228 | UG75 Expression | GENE | Mm.27364 | TITLE stimulated by retinoic acid 14 | GENE Stra14 | Stra13, eip1 (E47 interaction protein 1)| | NM_011498 | 3155800 |
| IC02229 | UG75 Expression | GENE | Mm.22584 | TITLE stress responsive protein | GENE Strap | | NM_011499 | 641533 |
| IC02230 | UG75 Expression | GENE | Mm.5122 | TITLE syntaxin 3 | GENE Stx3 | syntaxin 3| | gi = 924267 | 989121 |
| IC02231 | UG75 Expression | GENE | Mm.24867 | TITLE syntaxin 4A (placental) | GENE Stx4a | Stx4| | NM_009294 | 1434248 |
| IC02232 | UG75 Expression | GENE | Mm.7247 | TITLE syntaxin binding protein 2 | GENE Stxbp2 | Munc-18b|Sxtbp2|Unc18b| | NM_011503 | 2582194 |
| IC02233 | UG75 Expression | GENE | Mm.12155 | TITLE syntaxin binding protein 3 | GENE Stxbp3 | Munc-18c|Sxtbp3| | NM_011504 | 583180 |
| IC02234 | UG75 Expression | GENE | Mm.88498 | TITLE syntaxin binding protein 4 | GENE Stxbp4 | Synip| | NM_011505 | 1006240 |
| IC02235 | UG75 Expression | GENE | Mm.19154 | TITLE succinate-Coenzyme A ligase, ADP-forming, beta subunit | GENE Sucla2 | | gi = 3766200 | 1510819 |
| IC-02236 | UG76 LID366 B cell | GENE | Mm.100119 | TITLE succinate-Coenzyme A ligase, GDP-forming, beta subunit | GENE Suclg2 | | gi = 202218 | 2748975 |
| IC02237 | UG75 Expression | GENE | Mm.13886 | TITLE suppressor of initiator codon mutations-Yeast homolog related sequence 1 | GENE Sui1-rs1 | | gi = 3335183 | 2503395 |
| IC02238 | UG75 Expression | GENE | Mm.89579 | TITLE suppressor of Lec15 homolog (C. griseus) | GENE Supl15h | SL15| | NM_011900 | 1431355 |
| IC02239 | UG75 Expression | GENE | Mm.622 | TITLE suppressor of Ty 4 homolog (S. cerevisiae) | GENE Supt4h | Supt4h| | NM_009296 | 404500 |
| IC02240 | UG75 Expression | GENE | Mm.460 | TITLE suppressor of Ty 5 homolog (S. cerevisiae) | GENE Supt5h | | gi = 2754751 | 1971842 |
| IC02241 | UG75 Expression | GENE | Mm.20755 | TITLE suppressor of Ty 6 homolog (S. cerevisiae) | GENE Supt6h | SPT6| | NM_009297 | 1481398 |
| IC02242 | UG75 Expression | GENE | Mm.58915 | TITLE surfeit gene 2 | GENE Surf2 | Surf-2|surfeit gene-2 (prov.)| | NM_013678 | 874462 |
| IC02243 | UG75 Expression | GENE | Mm.725 | TITLE surfeit 3 gene. | GENE Surf3 | | NM_013721 | 598592 |
| IC02244 | UG75 Expression | GENE | Mm.2795 | TITLE surfeit gene 4 | GENE Surf4 | Surf-4|surfeit gene-4 (prov.)| | NM_011512 | 1921082 |
| IC02245 | UG75 Expression | GENE | Mm.27364 | TITLE surfeit gene 6 | GENE Surf6 | Surf-6|surfeit gene-6 (prov.)| | NM_009298 | 1885111 |
| IC02246 | UG75 Expression | GENE | Mm.9244 | TITLE suppressor of variegation 3–9 homologue 1 (Drosophila) | GENE Suv39h1 | DNA segment, Chr X, human S7466E, expressed|DXHXS7466e| | NM_011514 | 2936823 |
| IC02247 | UG75 Expression | GENE | Mm.57107 | TITLE SWAP complex protein, 70 kDa | GENE Swap70 | | NM_009302 | 635765 |
| IC02248 | UG75 Expression | GENE | Mm.21754 | TITLE synaptonemal complex protein 3 | GENE Sycp3 | | NM_011517 | 990120 |
| IC02249 | UG75 Expression | GENE | Mm.4708 | TITLE spleen tyrosine kinase | GENE Syk | | NM_011518 | 583475 |
| IC02250 | UG75 Expression | GENE | Mm.20936 | TITLE synapsin I | GENE Syn1 | Syn-1| | NM_013680 | 1513928 |
| IC02251 | UG75 Expression | GENE | Mm.2079 | TITLE synaptogyrin 2 | GENE Syngr2 | | NM_009304 | 3155252 |
| IC02252 | UG75 Expression | GENE | Mm.30717 | TITLE synaptojanin 2 | GENE Synj2 | SJ2| | gi = 3241994 | 1091850 |
| IC02253 | UG75 Expression | GENE | Mm.2397 | TITLE synaptophysin | GENE Syp | | NM_009305 | 613967 |
| IC02254 | UG75 Expression | GENE | Mm.2446 | TITLE synaptotagmin 4 | GENE Syt4 | | NM_009308 | 574704 |
| IC02255 | UG75 Expression | GENE | Mm.1440 | TITLE tachykinin 1 | GENE Tac1 | neurokinin 1|neurokinin A (substance P)|Nkna|PPT-A|preprotachykinin A|substance P| | NM_009311 | 1380603 |
| IC02256 | UG75 Expression | GENE | Mm.27836 | TITLE transforming, acidic coiled-coil containing protein 3 | GENE Tacc3 | | NM_011524 | 2598870 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02257 | UG75 Expression | GENE | Mm.1994 | TITLE TATA box binding protein (Tbp)-associated factor, RNA polymerase II, E | GENE Taf2e | p80| | NM_009315 | 389161 |
| IC02258 | UG75 Expression | GENE | Mm.12001 | TITLE TATA box binding protein (TBP) associated factor, RNA polymerase II, F, 55 kDa | GENE Taf2f | TAFII55| | NM_011901 | 1123357 |
| IC02259 | UG75 Expression | GENE | Mm.2006 | TITLE transgelin | GENE Tagln | Sm22a|smooth muscle protein, alpha, 22 kDa| | NM_011526 | 1511678 |
| IC02260 | UG75 Expression | GENE | Mm.3102 | TITLE T-cell acute lymphocytic leukemia 1 | GENE Tal1 | homolog of human stem-cell leukemia gene (prov.)|Scl|SCL/tal-1| | NM_011527 | 475171 |
| IC02261 | UG75 Expression | GENE | Mm.29182 | TITLE transaldolase 1 | GENE Taldo1 | | gi = 2589165 | 671083 |
| IC02262 | UG75 Expression | GENE | Mm.1803 | TITLE TRAF family member-associated Nf-kappa B activator | GENE Tank | I-TRAF| | NM_011529 | 585550 |
| IC02263 | UG75 Expression | GENE | Mm.16122 | TITLE transporter 1, ABC (ATP binding cassette) | GENE Tap1 | Hacl1|hair follicle specific gene 1 (IFAP keratin family member)|KAP11.1| | NM_013683 | 2937240 |
| IC02264 | UG75 Expression | GENE | Mm.176 | TITLE TAR (HIV) RNA binding protein 2 | GENE Tarbp2 | Prbp|protamine RNA binding protein cofactor A| | NM_009319 | 661071 |
| IC02265 | UG75 Expression | GENE | Mm.1863 | TITLE tubulin cofactor a | GENE Tbca | | NM_009321 | 1383283 |
| IC02266 | UG75 Expression | GENE | Mm.43711 | TITLE TATA box binding protein | GENE Tbp | | gi = 2052376 | 573420 |
| IC02267 | UG75 Expression | GENE | Mm.727 | TITLE T-box 6 | GENE Tbx6 | | NM_011538 | 636895 |
| IC02268 | UG75 Expression | GENE | Mm.4545 | TITLE thromboxane A2 receptor | GENE Tbxa2r | TP|Tp receptor| | NM_009325 | 639506 |
| IC02269 | UG75 Expression | GENE | Mm.4054 | TITLE thromboxane A synthase 1, platelet | GENE Tbxas1 | | NM_011539 | 875135 |
| IC02270 | UG75 Expression | GENE | Mm.24245 | TITLE transcription elongation factor A (SII), 2 | GENE Tcea2 | SII-T1|Tcea|transcription elongation factor A (SID, testis | NM_009326 | 513927 |
| IC02271 | UG75 Expression | GENE | Mm.112 | TITLE transcription elongation factor A (SII), 3 | GENE Tcea3 | S-II| | gi = 220593 | 573147 |
| IC02272 | UG75 Expression | GENE | Mm.42944 | TITLE transcription elongation factor B (SIII), polypeptide 1 (15 kDa), like | GENE Tceb1l | | NM_011543 | 932762 |
| IC02273 | UG75 Expression | GENE | Mm.27663 | TITLE transcription elongation factor B (SIII), polypeptide 3 (110 kD) | GENE Tceb3 | Elongin A| | NM_013736 | 643253 |
| IC02274 | UG75 Expression | GENE | Mm.455 | TITLE transcription factor 1 | GENE Tcf1 | hepatic nuclear factor 1|hepatocyte nuclear factor 1|Hnf-1|HNF1|HNF1-alpha|HNF1[a]|Tcf-1|ALF1|ME1| | NM_009327 | 991667 |
| IC02275 | UG75 Expression | GENE | Mm.36894 | TITLE transcription factor 12 | GENE Tcf12 | capsulin|epc|epicardin|Pod1| | NM_011544 | 405907 |
| IC02276 | UG75 Expression | GENE | Mm.3146 | TITLE transcription factor 20 | GENE Tcf20 | | NM_013836 | 1245286 |
| IC02277 | UG75 Expression | GENE | Mm.16497 | TITLE transcription factor 21 | GENE Tcf21 | Hnf-4|ITF-2|ME2|MITF-2A|MITF-2B|SEF-2|Tcf-4| | NM_011545 | 634816 |
| IC02278 | UG75 Expression | GENE | Mm.4269 | TITLE transcription factor 4 | GENE Tcf4 | T-cell factor 1|TCF-1|Tcf1| | NM_013685 | 618058 |
| IC02279 | UG75 Expression | GENE | Mm.38962 | TITLE transcription factor 7, T-cell specific | GENE Tcf7 | Tcf-3|Tcf3| | NM_009331 | 1378088 |
| IC02280 | UG75 Expression | GENE | Mm.28396 | TITLE transcription factor 7-like 1 | GENE Tcf7l1 | Ap-2.2| | NM_009332 | 349654 |
| IC02281 | UG75 Expression | GENE | Mm.3629 | TITLE transcription factor AP-2, gamma | GENE Tcfap2c | | NM_009335 | 2651416 |
| IC02282 | UG75 Expression | GENE | Mm.1139 | TITLE transcription factor CP2 | GENE Tcfcp2 | ALF2|E12|E2A|E47|ME2| | gi = 191802 | 1890280 |
| IC02283 | UG75 Expression | GENE | Mm.3406 | TITLE transcription factor E2a | GENE Tcfe2a | TFEB| | gi = 54869 | 949516 |
| IC02284 | UG75 Expression | GENE | Mm.2305 | TITLE transcription factor EB | GENE Tcfeb | YL-1| | NM_011549 | 1364912 |
| IC02285 | UG75 Expression | GENE | Mm.2140 | TITLE transcription factor-like 1 | GENE Tcfl1 | | NM_009336 | 583417 |
| IC02286 | UG75 Expression | GENE | Mm.628 | TITLE transcription factor like 4 | GENE Tcfl4 | | NM_011550 | 721169 |
| IC02287 | UG75 Expression | GENE | Mm.2845 | TITLE transcription factor UBF | GENE Tcfubf | | NM_009331 | 2698946 |
| IC02288 | UG75 Expression | GENE | Mm.2215 | TITLE Treacher Collins Franceschetti syndrome 1, homolog | GENE Tcof1 | | NM_011552 | 2581972 |
| IC02289 | UG75 Expression | GENE | Mm.2223 | TITLE t-complex protein 1 | GENE Tcp1 | | NM_013686 | 602648 |
| IC02290 | UG75 Expression | GENE | Mm.6797 | TITLE t-complex protein 1, related sequence 1 | GENE Tcp1-rs1 | Tcp-1x| | gi = 975268 | 583609 |
| IC02291 | UG75 Expression | GENE | Mm.1289 | TITLE T-cell receptor gamma, variable 4 | GENE Tcrg-V4 | | NM_011558 | 551684 |
| IC02292 | UG75 Expression | GENE | Mm.1948 | TITLE t-complex testis expressed 1 | GENE Tctex1 | t complex-testis expressed 1|Tctex-1| | NM_009342 | 2225510 |
| IC02293 | UG75 Expression | GENE | Mm.18643 | TITLE t-complex testis-expressed 3 | GENE Tctex3 | Tctex-3| | NM_009343 | 2922944 |
| IC02294 | UG75 Expression | GENE | Mm.3117 | TITLE T-cell death associated gene | GENE Tdag | PHLDA1|TDAG51| | NM_009344 | 2936986 |
| IC02295 | UG75 Expression | GENE | Mm.4962 | TITLE tumor differentially expressed 1 | GENE Tde1 | DIFF33|TMS-1| | NM_012032 | 2646812 |
| IC02296 | UG75 Expression | GENE | Mm.88099 | TITLE thymine DNA glycosylase | GENE Tdg | Jun zipper-associated 1|JZA-3|jza1| | NM_011561 | 2225276 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02297 | UG75 Expression | GENE | Mm.42948 | TITLE thioredoxin peroxidase 1 | GENE Tdpx1 | protein|thioredoxin dependent peroxide reductase 1|thioredoxin reductase|TPx|TR|Trx dependent peroxide reductase 1|TSA| | NM_011563 | 2076576 |
| IC02298 | UG75 Expression | GENE | Mm.25620 | TITLE terminal deoxynucleotidyl transferase | GENE Tdt | | NM_009345 | 583353 |
| IC02299 | UG75 Expression | GENE | Mm.3019 | TITLE TEA domain family member 2 | GENE Tead2 | embryonic TEA domain containing factor|Etdf|ETF|TEF|TEAD-2|TEF4| | NM_011565 | 806436 |
| IC02300 | UG75 Expression | GENE | Mm.1886 | TITLE Tcra enhancer-binding factor interacting protein 1 | GENE Tebfip-pc | ALY| | NM_011568 | 1345931 |
| IC02301 | UG75 Expression | GENE | Mm.2350 | TITLE cytoplasmic tyrosine kinase, Dscr28C related (Drosophila) | GENE Tec | | NM_013689 | 1889028 |
| IC02302 | UG75 Expression | GENE | Mm.42139 | TITLE tectorin beta | GENE Tectb | [b]-tectorin|Tctnb|tectorin, beta| | NM_009348 | 1150904 |
| IC02303 | UG75 Expression | GENE | Mm.14313 | TITLE endothelial-specific receptor tyrosine kinase | GENE Tek | adhesion structures linked tyrosine kinase|Hyk|Tie2|tyrosine kinase receptor 2| | gi = 220439 | 734615 |
| IC02304 | UG75 Expression | GENE | Mm.299 | TITLE thioether S-methyltransferase | GENE Temt | | NM_009349 | 1451061 |
| IC02305 | UG75 Expression | GENE | Mm.18972 | TITLE telomerase associated protein 1 | GENE Tep1 | telomerase associated protein 1 | NM_009351 | 1433067 |
| IC02306 | UG75 Expression | GENE | Mm.4306 | TITLE telomeric repeat binding factor 1 | GENE Terf1 | Trbf1|Trf1| | NM_009352 | 906058 |
| IC02307 | UG75 Expression | GENE | Mm.6402 | TITLE telomeric repeat binding factor 2 | GENE Terf2 | TRF2| | NM_009353 | 550831 |
| IC02308 | UG75 Expression | GENE | Mm.88645 | TITLE testis derived transcript | GENE Tes | Tes|Tes2| | NM_011570 | 622480 |
| IC02309 | UG75 Expression | GENE | Mm.10154 | TITLE testis specific protein kinase 1 | GENE Teskl | | NM_011571 | 443316 |
| IC02310 | UG75 Expression | GENE | Mm.848 | TITLE testis expressed gene 261 | GENE Tex261 | TEG-261| | NM_009357 | 891288 |
| IC02311 | UG75 Expression | GENE | Mm.88062 | TITLE testis expressed gene 271 | GENE Tex271 | TEG-271| | NM_009358 | 2921930 |
| IC02312 | UG75 Expression | GENE | Mm.41766 | TITLE transcription factor A, mitochondrial | GENE Tfam | specific|Hmgts|mtTFA|sHMG| | NM_009360 | 539693 |
| IC02313 | UG75 Expression | GENE | Mm.925 | TITLE transcription factor Dp 1 | GENE Tfdp1 | Dp1|Drtf1| | NM_009361 | 619129 |
| IC02314 | UG75 Expression | GENE | Mm.1825 | TITLE trefoil factor 2 (spasmolytic protein 1) | GENE Tff2 | mSP| | NM_009363 | 438574 |
| IC02315 | UG75 Expression | GENE | Mm.3601 | TITLE tissue factor pathway inhibitor | GENE Tfpi | EPI|LACI| | gi = 4102790 | 863366 |
| IC02316 | UG75 Expression | GENE | Mm.3992 | TITLE transforming growth factor alpha | GENE Tgfa | wa-1|wa1|waved 1|wwaved 1| | gi = 1518850 | 777327 |
| IC02317 | UG75 Expression | GENE | Mm.9154 | TITLE transforming growth factor, beta 1 | GENE Tgfb1 | Tgfb|Tgb-1| | NM_011577 | 457739 |
| IC02318 | UG75 Expression | GENE | Mm.3248 | TITLE transforming growth factor beta 1 induced transcript 1 | GENE Tgfb1i1 | hic-5|TSC-5| | NM_009365 | 585981 |
| IC02319 | UG75 Expression | GENE | Mm.20927 | TITLE transforming growth factor beta 1 induced transcript 4 | GENE Tgfb1i4 | early growth response 5|Egr5|TSC|TSC-22| | NM_009366 | 1884960 |
| IC02320 | UG75 Expression | GENE | Mm.18213 | TITLE transforming growth factor, beta 2 | GENE Tgfb2 | Tgfb-2| | NM_009367 | 1885695 |
| IC02321 | UG75 Expression | GENE | Mm.1291 | TITLE transforming growth factor, beta 3 | GENE Tgfb3 | Tgfb-3| | NM_009368 | 1054036 |
| IC02322 | UG75 Expression | GENE | Mm.14455 | TITLE transforming growth factor, beta induced, 68 kDa | GENE Tgfbi | big-h3| | NM_009369 | 1972884 |
| IC02323 | UG75 Expression | GENE | Mm.8155 | TITLE TG interacting factor | GENE Tgif | TALE family homeobox| | NM_009372 | 572852 |
| IC02324 | UG75 Expression | GENE | Mm.18843 | TITLE transglutaminase 2, C polypeptide | GENE Tgm2 | C polypeptide|G[a]h|protein-glutamine-gamma-glutamyltransferase|tissue transglutaminase| | NM_009373 | 832159 |
| IC02325 | UG75 Expression | GENE | Mm.15793 | TITLE T-cell specific GTPase | GENE Tgtp | Mg21| | NM_011579 | 597272 |
| IC02326 | UG75 Expression | GENE | Mm.24096 | TITLE thrombomodulin | GENE Thbd | CD141|TM| | NM_009378 | 2159583 |
| IC02327 | UG75 Expression | GENE | Mm.4159 | TITLE thrombospondin 1 | GENE Thbs1 | Thbs-1|TSP1| | NM_011580 | 1294452 |
| IC02328 | UG75 Expression | GENE | Mm.20865 | TITLE thrombospondin 4 | GENE Thbs4 | TSP-4| | NM_011582 | 473150 |
| IC02329 | UG75 Expression | GENE | Mm.4015 | TITLE thyroid hormone receptor alpha | GENE Thra | avian erythroblastosis oncogene A|Erba|Nr1a1|Rev-Erb A(alpha)-related receptor|Rvr|T3R[a]|T3Ralpha|Thra1|Thra2|thyroid hormone receptor alpha 1|thyroid hormone receptor alpha 2| | gi = 537289 | 775457 |
| IC02330 | UG75 Expression | GENE | Mm.28585 | TITLE thyroid hormone responsive SPOT14 homolog (Rattus) | GENE Thrsp | Spot 14| | NM_009381 | 2811774 |
| IC02331 | UG75 Expression | GENE | Mm.3951 | TITLE thymus cell antigen 1, theta | GENE Thy1 | CD90|Thy-1| | NM_009382 | 1510963 |
| IC02332 | UG75 Expression | GENE | Mm.2291 | TITLE | GENE Tia1 | mTIA-1| | NM_011585 | 1040199 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02333 | UG75 Expression | GENE | Mm.4363 | TITLE TIa1l cytotoxic granule-associated RNA-binding protein-like 1 | GENE Tial1 | mTIAR| | NM_009383 | 2938865 |
| IC02334 | UG75 Expression | GENE | Mm.1211 | TITLE T-cell lymphoma invasion and metastasis 1 | GENE Tiam1 | | NM_009384 | 2609690 |
| IC02335 | UG75 Expression | GENE | Mm.4292 | TITLE TGFB inducible early growth response | GENE Tieg | Gdnf|glial cell line derived neurotrophic factor inducible factor|mGIF| | NM_013692 | 1885525 |
| IC02336 | UG75 Expression | GENE | Mm.15701 | TITLE transcriptional intermediary factor 1, beta | GENE Tif1b | KAP-1|KRIP-1| | NM_011588 | 1151659 |
| IC02337 | UG75 Expression | GENE | Mm.6458 | TITLE timeless homolog (Drosophila) | GENE Timeless | tim| | NM_011589 | 2922257 |
| IC02338 | UG75 Expression | GENE | Mm.34791 | TITLE translocator of inner mitochondrial membrane 44 | GENE Timm44 | Mim44|mitochondrial import inner membrane translocase, 44 kDa|Tim44| | gi = 2351409 | 2259246 |
| IC02339 | UG75 Expression | GENE | Mm.8245 | TITLE tissue inhibitor of metalloproteinase | GENE Timp | Clgi|TIMP-1| | NM_011593 | 440922 |
| IC02340 | UG75 Expression | GENE | Mm.19191 | TITLE tissue inhibitor of metalloproteinase 2 | GENE Timp2 | Timp-2| | NM_011594 | 1193903 |
| IC02341 | UG75 Expression | GENE | Mm.4871 | TITLE tissue inhibitor of metalloproteinase 3 | GENE Timp3 | Timp-3| | NM_011595 | 2123734 |
| IC02342 | UG75 Expression | GENE | Mm.1158 | TITLE T-cell expressing clone j6 | GENE Tj6 | TJ6M|TJ6s| | NM_011596 | 477054 |
| IC02343 | UG75 Expression | GENE | Mm.4342 | TITLE tight junction protein 1 | GENE Tjp1 | ZO-1| | NM_009386 | 579645 |
| IC02344 | UG75 Expression | GENE | Mm.27984 | TITLE tight junction protein 3 | GENE Tjp3 | ZO-3| | NM_013769 | 444656 |
| IC02345 | UG75 Expression | GENE | Mm.2661 | TITLE thymidine kinase 1 | GENE Tk1 | | NM_009387 | 556061 |
| IC02346 | UG75 Expression | GENE | Mm.9307 | TITLE transketolase | GENE Tkt | | NM_011388 | 1481356 |
| IC02347 | UG75 Expression | GENE | Mm.24255 | TITLE transducin-like enhancer of split 3, homolog of Drosophila E(spl) | GENE Tle3 | p68|TKT| Grg3a|Grg3b| | NM_009389 | 1327590 |
| IC02348 | UG75 Expression | GENE | Mm.17915 | TITLE transducin-like enhancer of split 4, homolog of Drosophila E(spl) | GENE Tle4 | Grg4| | gi = 4028901 | 1079785 |
| IC02349 | UG75 Expression | GENE | Mm.4557 | TITLE Tousled-like kinase (Arabidopsis) | GENE Tlk | PKUalpha|protein kinase U-alpha| | NM_011903 | 1265334 |
| IC02350 | UG75 Expression | GENE | Mm.4989 | TITLE T lymphoma oncogene | GENE Tlm | | NM_011601 | 2236433 |
| IC02351 | UG75 Expression | GENE | Mm.4053 | TITLE talin | GENE Tln | | NM_011602 | 1139128 |
| IC02352 | UG75 Expression | GENE | Mm.28415 | TITLE TATA box binding protein-like protein | GENE Tlp | TBP-like protein| | NM_011603 | 3167443 |
| IC02353 | UG75 Expression | GENE | Mm.7521 | TITLE toll-like receptor 4 | GENE Tlr4 | lipopolysaccharide response|Lps|Ly87|Ran/M1|RAS-like, family 2, locus 8|Rasl2-8| | gi = 727166 | 516725 |
| IC02354 | UG75 Expression | GENE | Mm.124 | TITLE thymopoietin | GENE Tmpo | | NM_011605 | 1363969 |
| IC02355 | UG75 Expression | GENE | Mm.980 | TITLE tenascin C | GENE Tnc | hexabrachion cell surface molecule|Hxb|Ten| | NM_011607 | 598845 |
| IC02356 | UG75 Expression | GENE | Mm.1293 | TITLE tumor necrosis factor | GENE Tnf | Tnfa|tumor necrosis factor, alpha| | NM_013693 | 3166359 |
| IC02357 | UG75 Expression | GENE | Mm.4348 | TITLE tumor necrosis factor induced protein 2 | GENE Tnfip2 | Tnfaip2|tnfb94|tumor necrosis factor alpha induced protein 2| | NM_009396 | 440275 |
| IC02358 | UG75 Expression | GENE | Mm.3180 | TITLE tumor necrosis factor receptor superfamily, member 18 | GENE Tnfrsf18 | Gitr|glucocorticoid-induced tumor necrosis factor related gene| | NM_009400 | 2647219 |
| IC02359 | UG75 Expression | GENE | Mm.1258 | TITLE tumor necrosis factor receptor superfamily, member 1a | GENE Tnfrsf1a | CD120a|p55|TNF receptor alpha chain|TNF-R1|TNF-R55| Tnfr-2|Tnfr1|TNFRp55|tumor necrosis factor receptor 1|tumor necrosis factor receptor 2| | NM_011609 | 818654 |
| IC02360 | UG75 Expression | GENE | Mm.4966 | TITLE tumor necrosis factor receptor superfamily, member 5 | GENE Tnfrsf5 | Cd40|CD40 antigen| | NM_011611 | 481718 |
| IC02361 | UG75 Expression | GENE | Mm.121 | TITLE tumor necrosis factor receptor superfamily, member 7 | GENE Tnfrsf7 | Cd27|CD27 antigen| | gi = 403146 | 1348188 |
| IC02362 | UG75 Expression | GENE | Mm.6426 | TITLE tumor necrosis factor (ligand) superfamily, member 11 | GENE Tnfsf11 | Ly109|mRANKL|ODF|OPG ligand|OPGL|osteoclast differentiation factor|osteoprotegerin ligand|receptor activator of NF-kappaB ligand|TNF-related activation-induced cytokine|TRANCE| | NM_011613 | 618692 |
| IC02363 | UG75 Expression | GENE | Mm.22585 | TITLE tumor necrosis factor (ligand) superfamily, member 19 | GENE Tnfsf19| | DEDD| | NM_011615 | 1494924 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02364 | UG75 Expression | GENE | Mm.1984 | TITLE troponin I, skeletal, fast 2 | GENE Tnni2 | | NM_009405 | 1068001 |
| IC02365 | UG75 Expression | GENE | Mm.711 | TITLE troponin T1, skeletal, slow | GENE Tnnt1 | Tnt| | NM_011618 | 2247550 |
| IC02366 | UG75 Expression | GENE | Mm.14546 | TITLE troponin T3, skeletal, fast | GENE Tnnt3 | | NM_011620 | 2076591 |
| IC02367 | UG75 Expression | GENE | Mm.4218 | TITLE transducer of ErbB-2,1 | GENE Tob1 | transducer of ErbB-2 | NM_009427 | 1247226 |
| IC02368 | UG75 Expression | GENE | Mm.29663 | TITLE topoisomerase (DNA) I | GENE Top1 | | NM_009408 | 2099885 |
| IC02369 | UG75 Expression | GENE | Mm.4237 | TITLE topoisomerase (DNA) II alpha | GENE Top2a | Top-2|topoisomerase (DNA) II| | NM_011623 | 806374 |
| IC02370 | UG75 Expression | GENE | Mm.4093 | TITLE topoisomerase (DNA) II beta | GENE Top2b | Top-2|topoisomerase (DNA) II| | NM_009409 | 735183 |
| IC02371 | UG75 Expression | GENE | Mm.20915 | TITLE topoisomerase (DNA) III beta | GENE Top3b | Topo III beta| | NM_011624 | 2648272 |
| IC02372 | UG75 Expression | GENE | Mm.790 | TITLE TPA regulated locus | GENE Tparl | pFT27| | NM_011626 | 1281971 |
| IC02373 | UG75 Expression | GENE | Mm.2777 | TITLE tumor protein D52 | GENE Tpd52 | mD52| | NM_009412 | 1066212 |
| IC02374 | UG75 Expression | GENE | Mm.4421 | TITLE tryptophan hydroxylase | GENE Tph | | NM_009414 | 972840 |
| IC02375 | UG75 Expression | GENE | Mm.4222 | TITLE triosephosphate isomerase | GENE Tpi | Ifi| | NM_009415 | 1889285 |
| IC02376 | UG75 Expression | GENE | Mm.87109 | TITLE thiamin pyrophosphokinase | GENE Tpk1 | | NM_013861 | 1970315 |
| IC02377 | UG75 Expression | GENE | Mm.646 | TITLE tropomyosin 2, beta | GENE Tpm2 | Tpm-2|Trop-2|tropomyosin isoform 2|tropomyosin-2 (beta)| | NM_009416 | 607258 |
| IC02378 | UG75 Expression | GENE | Mm.17306 | TITLE tropomyosin 5 | GENE Tpm5 | Tpm-5|Trop-5| | NM_011628 | 463569 |
| IC02379 | UG75 Expression | GENE | Mm.28867 | TITLE tripeptidyl peptidase II | GENE Tpp2 | TppII| | NM_009418 | 616894 |
| IC02380 | UG75 Expression | GENE | Mm.22067 | TITLE transmembrane domain protein regulated in adipocytes 40 kDa | GENE Tpra40-p | TPRA40| | NM_011906 | 1348356 |
| IC02381 | UG75 Expression | GENE | Mm.16084 | TITLE protein-tyrosine sulfotransferase 1 | GENE Tpst1 | | NM_013837 | 582557 |
| IC02382 | UG75 Expression | GENE | Mm.14239 | TITLE protein-tyrosine sulfotransferase 2 | GENE Tpst2 | | NM_009419 | 608597 |
| IC02383 | UG75 Expression | GENE | Mm.4526 | TITLE tumor rejection antigen gp96 | GENE Tra1 | Ctra-1| | NM_011631 | 1921294 |
| IC02384 | UG75 Expression | GENE | Mm.12898 | TITLE Tnf receptor-associated factor 1 | GENE Traf1 | | NM_009421 | 637698 |
| IC02385 | UG75 Expression | GENE | Mm.309 | TITLE Tnf receptor-associated factor 2 | GENE Traf2 | | gi = 532620 | 614108 |
| IC02386 | UG75 Expression | GENE | Mm.27431 | TITLE Tnf receptor-associated factor 3 | GENE Traf3 | am|ammionless|CAP-1|CD40bp|CRAF1|LAP1|T-BAM| | NM_011632 | 2939180 |
| IC02387 | UG75 Expression | GENE | Mm.4521 | TITLE Tnf receptor associated factor 4 | GENE Traf4 | CART1| | NM_009423 | 831673 |
| IC02388 | UG75 Expression | GENE | Mm.2056 | TITLE Tnf receptor-associated factor 5 | GENE Traf5 | | NM_011633 | 616797 |
| IC02389 | UG75 Expression | GENE | Mm.5172 | TITLE Tnf receptor-associated factor 6 | GENE Traf6 | | NM_009424 | 2802349 |
| IC02390 | UG75 Expression | GENE | Mm.1062 | TITLE TNF-related apoptosis inducing ligand | GENE Trail | Ly81| | NM_009425 | 598349 |
| IC02391 | UG75 Expression | GENE | Mm.416 | TITLE TRAF-interacting protein | GENE Traip | | NM_011634 | 555801 |
| IC02392 | UG75 Expression | GENE | Mm.7268 | TITLE thyroid hormone receptor-associated protein 100 kDa | GENE Trap100 | Trap100| | NM_011869 | 615136 |
| IC02393 | UG75 Expression | GENE | Mm.1297 | TITLE tumor rejection antigen P1A | GENE Trap1a | Tra-P1A| | NM_011635 | 933185 |
| IC02394 | UG75 Expression | GENE | Mm.14627 | TITLE transplantability associated gene 1 | GENE Tras1 | MmTRA1a|MmTRA1b|NOR1|TRA1|transplantability associated gene 2|Tras2| | NM_011636 | 1247535 |
| IC02395 | UG75 Expression | GENE | Mm.17632 | TITLE three prime repair exonuclease 1 | GENE Trex1 | 1661|three prime repair exonuclease 2| | NM_011637 | 329698 |
| IC02396 | UG75 Expression | GENE | Mm.222 | TITLE transformation related protein 53 | GENE Trp53 | p53| | NM_011640 | 2937381 |
| IC02397 | UG75 Expression | GENE | Mm.20894 | TITLE transformation related protein 63 | GENE Trp63 | KET protein|KET protein gene|Ket-pending|p53-related protein 1|p63|p73L|Trp53rp1| | NM_011641 | 1262224 |
| IC02398 | UG75 Expression | GENE | Mm.30188 | TITLE transient receptor protein 2 | GENE Trp2 | | NM_011644 | 671965 |
| IC02399 | UG75 Expression | GENE | Mm.254 | TITLE translationally regulated transcript (21 kDa) | GENE Trt | | NM_009429 | 1120661 |
| IC02400 | UG75 Expression | GENE | Mm.14410 | TITLE trypsin 2 | GENE Try2 | TRYP| | NM_011646 | 516518 |
| IC02401 | UG75 Expression | GENE | Mm.6977 | TITLE trypsin 4 | GENE Try4 | | NM_009431 | 516518 |
| IC02402 | UG75 Expression | GENE | Mm.489 | TITLE TPR-containing, SH2-binding phosphoprotein | GENE Tsbp | Tsp| | NM_011647 | 603059 |
| IC02403 | UG75 Expression | GENE | Mm.30435 | TITLE tuberous sclerosis 2 | GENE Tsc2 | tuberin| | NM_011647 | 463053 |
| IC02404 | UG75 Expression | GENE | Mm.22688 | TITLE tumor susceptibility gene 101 | GENE tsg101 | | gi = 3184259 | 1889019 |
| IC02405 | UG75 Expression | GENE | Mm.27481 | TITLE testis specific gene A12 | GENE Tsga12 | Eh domain, SH3 domain regulator of endocytosis 1|EH domain/SH3 domain-containing protein|EHSH1|Ese|Sh3p17| | gi = 4589831 | 775253 |
| IC02406 | UG75 Expression | GENE | Mm.14644 | TITLE translin | GENE Tsn | | NM_011650 | 2182731 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02407 | UG75 Expression | GENE | Mm.15312 | TITLE thiosulfate sulfurtransferase, mitochondrial | GENE Tst | Rhodanese| | NM_009437 | 905176 |
| IC02408 | UG75 Expression | GENE | Mm.22596 | TITLE tissue specific transplantation antigen P35B | GENE Tstap35b | | gi = 199585 | 1890218 |
| IC02409 | UG75 Expression | GENE | Mm.12194 | TITLE tissue specific transplantation antigen P91A | GENE Tstap91a | AntP91a| | gi = 191974 | 3155279 |
| IC02410 | UG75 Expression | GENE | Mm.3679 | TITLE tetratricopeptide repeat domain | GENE Ttc3 | TPRD| | NM_009441 | 1920323 |
| IC02411 | UG76 LID366 B cell | GENE | Mm.63510 | TITLE transcription termination factor 1 | GENE Ttf1 | | NM_009442 | 2749187 |
| IC02412 | UG75 Expression | GENE | Mm.4142 | TITLE trans-golgi network protein 1 | GENE Tgn1 | TGN38|TGN38A| | NM_009443 | 557037 |
| IC02413 | UG75 Expression | GENE | Mm.1904 | TITLE Ttk protein kinase | GENE Ttk | esk|PYT| | NM_009445 | 722497 |
| IC02414 | UG75 Expression | GENE | Mm.2108 | TITLE transthyretin | GENE Ttr | | NM_013697 | 1889331 |
| IC02415 | UG75 Expression | GENE | Mm.88110 | TITLE tubulin alpha 1 | GENE Tuba1 | Tuba-1| | NM_011653 | 1480912 |
| IC02416 | UG75 Expression | GENE | Mm.4591 | TITLE tubulin alpha 2 | GENE Tuba2 | | gi = 202209 | 1921237 |
| IC02417 | UG75 Expression | GENE | Mm.1155 | TITLE tubulin alpha 4 | GENE Tuba4 | | NM_009447 | 1431172 |
| IC02418 | UG75 Expression | GENE | Mm.22774 | TITLE tubulin, beta 2 | GENE Tubb2 | M[a]4| | gi = 202226 | 3155071 |
| IC02419 | UG75 Expression | GENE | Mm.1703 | TITLE tubulin, beta 5 | GENE Tubb5 | M[beta]2| | NM_011655 | 1969782 |
| IC02420 | UG75 Expression | GENE | Mm.10214 | TITLE tuftelin 1 | GENE Tuft1 | M[beta]5| | NM_011656 | 1066939 |
| IC02421 | UG75 Expression | GENE | Mm.12887 | TITLE tubby-like protein 3 | GENE Tulp3 | | NM_011657 | 2631246 |
| IC02422 | UG75 Expression | GENE | Mm.13885 | TITLE tax-transcriptionally activated glycoprotein 1 | GENE Txgp1 | CD134|Ly-70|Ox-40 T-cell antigen|OX40| | NM_011659 | 573690 |
| IC02423 | UG75 Expression | GENE | Mm.3264 | TITLE TXK tyrosine kinase | GENE Txk | Rlk| | NM_013698 | 621896 |
| IC02424 | UG75 Expression | GENE | Mm.90520 | TITLE thioredoxin reductase 2 | GENE Txnrd2 | TrxR2| | NM_013711 | 573010 |
| IC02425 | UG75 Expression | GENE | Mm.46301 | TITLE TYRO protein tyrosine kinase binding protein | GENE Tyrobp | DAP12|KARAP|killer cell activating receptor associated protein|Ly83| | NM_011662 | 553001 |
| IC02426 | UG75 Expression | GENE | Mm.14286 | TITLE U2 small nuclear ribonucleoprotein auxiliary factor (U2AF), 35 kDa, related sequence 1 | GENE U2af1-rs1 | | NM_011663 | 476501 |
| IC02427 | UG75 Expression | GENE | Mm.3358 | TITLE U2 small nuclear ribonucleoprotein auxiliary factor (U2AF), 65 kDa | GENE U2af2 | | gi = 55100 | 373587 |
| IC02428 | UG75 Expression | GENE | Mm.235 | TITLE ubiquitin B | GENE Ubb | jaundice| | NM_011664 | 1924032 |
| IC02429 | UG75 Expression | GENE | Mm.1485 | TITLE ubiquitin-conjugating enzyme 4 | GENE Ubce4 | ubcM2| | NM_009454 | 2599064 |
| IC02430 | UG75 Expression | GENE | Mm.4429 | TITLE ubiquitin-conjugating enzyme 5 | GENE Ubce5 | ubcM2| | NM_011665 | 616812 |
| IC02431 | UG75 Expression | GENE | Mm.3074 | TITLE ubiquitin-conjugating enzyme 7 | GENE Ubce7 | UbcM4| | NM_009455 | 2236301 |
| IC02432 | UG75 Expression | GENE | Mm.12892 | TITLE ubiquitin-activating enzyme E1C | GENE Ube1c | UBA3|ubiquitin activating enzyme 3| | NM_009456 | 1970743 |
| IC02433 | UG75 Expression | GENE | Mm.1104 | TITLE ubiquitin-activating enzyme E1, Chr X | GENE Ube1x | A1S9|Sbx|Sxrb X-homolog|ts A1S9 defective DNA replication gene|Ube-1|ubiquitin 1| | NM_011666 | 1480550 |
| IC02434 | UG75 Expression | GENE | Mm.1920 | TITLE ubiquitin-conjugating enzyme E2B (RAD6 homology) | GENE Ube2b | E2-14k|HR6B| | NM_009457 | 1853271 |
| IC02435 | UG75 Expression | GENE | Mm.5203 | TITLE ubiquitin-conjugating enzyme E2H | GENE Ube2h | E2-20K| | NM_009458 | 873865 |
| IC02436 | UG75 Expression | GENE | Mm.3268 | TITLE ubiquitin-conjugating enzyme E2I | GENE Ube2i | Mmubc9|Ubce9| | NM_009459 | 1080476 |
| IC02437 | UG75 Expression | GENE | Mm.9002 | TITLE ubiquitin conjugating enzyme E3A | GENE Ube3a | E6-AP ubiquitin protein ligase|Hpve6a| | NM_011665 | 1969606 |
| IC02438 | UG75 Expression | GENE | Mm.12953 | TITLE ubiquitin hydrolyzing enzyme 1 | GENE Ubh1 | | gi = 3213206 | 1958335 |
| IC02439 | UG75 Expression | GENE | Mm.7353 | TITLE ubiquitin-like 1 | GENE Ubl1 | Pic1| | NM_011668 | 1432536 |
| IC02440 | UG75 Expression | GENE | Mm.12846 | TITLE ubiquitin-like 3 | GENE Ubl3 | HCG| | NM_009460 | 2225589 |
| IC02441 | UG75 Expression | GENE | Mm.10731 | TITLE ubiquitin-protein ligase e3 componen n-recognin | GENE Ubr1 | | NM_011908 | 2286332 |
| IC02442 | UG75 Expression | GENE | Mm.100465 | TITLE urocortin | GENE Ucn | | NM_009461 | 1051225 |
| IC02443 | UG75 Expression | GENE | Mm.12556 | TITLE uncoupling protein 2, mitochondrial | GENE Ucp2 | | gi = 193144 | 1481400 |
| IC02444 | UG75 Expression | GENE | Mm.1830 | TITLE ubiquitin fusion degradation 1 like | GENE Ufd1l | | NM_011671 | 806772 |
| IC02445 | UG75 Expression | GENE | Mm.12971 | TITLE UDP-glucose ceramide glucosyltransferase | GENE Ugcg | GlcT-1| | NM_011672 | 577841 |
| IC02446 | UG75 Expression | GENE | Mm.10709 | TITLE UDP-glucose dehydrogenase | GENE Ugdh | Udpgdh| | NM_011673 | 478525 |
| IC02447 | UG75 Expression | GENE | Mm.42472 | TITLE UDP-glucuronosyltransferase 1 family, member 1 | GENE Ugt1a1 | glucuronosyltransferase, phenol-UDP|Gnt1|onosyltransferase, phenol-UDP|UDP-glucuronosyltransferase 1a|Udpgt-1a| | NM_009466 | 2182188 |
| IC02448 | UG75 Expression | GENE | Mm.29157 | TITLE UDP-glucuronosyltransferase 2 family, member 5 | GENE Ugt2b5 | phenol-UDP|UDP-glucuronosyltransferase 3|Udpgt-3| | NM_009467 | 1885728 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02449 | UG75 Expression | GENE | Mm.10826 | TITLE uromodulin | GENE Umod | uromucoid, Tamm-Horsfall glycoprotein| | gi = 927202 | 2236432 |
| IC02450 | UG75 Expression | GENE | Mm.2559 | TITLE uridine monophosphate kinase | GENE Umpk | | gi = 471980 | 875710 |
| IC02451 | UG75 Expression | GENE | Mm.802 | TITLE uridine monophosphate synthetase | GENE Umps | | gi = 200138 | 1223250 |
| IC02452 | UG75 Expression | GENE | Mm.27744 | TITLE UNC-119 homolog (C. elegans) | GENE Unc119h | | NM_011676 | 763372 |
| IC02453 | UG75 Expression | GENE | Mm.1393 | TITLE uracil-DNA glycosylase | GENE Ung | UNG1|UNG2| | NM_011677 | 406824 |
| IC02454 | UG75 Expression | GENE | Mm.3974 | TITLE ubiquitous nuclear protein | GENE Unp | | NM_011678 | 458851 |
| IC02455 | UG75 Expression | GENE | Mm.10865 | TITLE urate oxidase | GENE Uox | | NM_009474 | 1891137 |
| IC02456 | UG75 Expression | GENE | Mm.4610 | TITLE uridine phosphorylase | GENE Upp | UdRPase| | NM_009477 | 608590 |
| IC02457 | UG75 Expression | GENE | Mm.22494 | TITLE uroporphyrinogen decarboxylase | GENE Urod | Neurod|neurogenic differentiation| | NM_009478 | 669694 |
| IC02458 | UG75 Expression | GENE | Mm.3160 | TITLE uroporphyrinogen III synthase | GENE Uros3 | | NM_009479 | 2812163 |
| IC02459 | UG75 Expression | GENE | Mm.8 | TITLE upstream transcription factor 1 | GENE Usf1 | upstream stimulatory factor| | NM_009480 | 1180608 |
| IC02460 | UG75 Expression | GENE | Mm.15781 | TITLE upstream transcription factor 2 | GENE Usf2 | | NM_011680 | 537853 |
| IC02461 | UG75 Expression | GENE | Mm.27498 | TITLE ubiquitin specific protease 18 | GENE Usp18 | UBP43| | NM_011909 | 637880 |
| IC02462 | UG75 Expression | GENE | Mm.3571 | TITLE ubiquitin specific protease 5 (isopeptidase T) | GENE Usp5 | ubiquitin carboxy terminal hydrolase T|Uchrt| | NM_013700 | 1247676 |
| IC02463 | UG75 Expression | GENE | Mm.396 | TITLE ubiquitin specific protease 9, X chromosome | GENE Usp9x | Dffrx|Faf|fat-facets like (Drosophila)| | NM_009481 | 1364128 |
| IC02464 | UG75 Expression | GENE | Mm.2258 | TITLE uteroglobin | GENE Utg | Blastokinin|CC10|CCSP|clara cell secretory protein|UG| | NM_011681 | 493435 |
| IC02465 | UG75 Expression | GENE | Mm.42222 | TITLE utrophin | GENE Utrn | Dmdl|dystrophin-like|G-utrophin| | gi = 1934962 | 1429197 |
| IC02466 | UG75 Expression | GENE | Mm.10218 | TITLE ubiquitously transcribed tetratricopeptide repeat gene, X chromosome | GENE Utx | | gi = 3021456 | 2158972 |
| IC02467 | UG75 Expression | GENE | Mm.28643 | TITLE vesicle-associated membrane protein 2 | GENE Vamp2 | Syb-2|Syb2|synaptobrevin 2| | NM_009497 | 2192348 |
| IC02468 | UG75 Expression | GENE | Mm.28420 | TITLE valyl-tRNA synthetase 2 | GENE Vars2 | Bat-6|Bat6|D17H6S56E|DNA segment, Chr 17, human D6S56E|G7a|HLA-B-associated transcript 6| | NM_011690 | 616783 |
| IC02469 | UG75 Expression | GENE | Mm.9684 | TITLE vasodilator-stimulated phosphoprotein | GENE Vasp | | gi = 1617401 | 586602 |
| IC02470 | UG75 Expression | GENE | Mm.5081 | TITLE Vav2 oncogene | GENE Vav2 | | NM_009500 | 875892 |
| IC02471 | UG75 Expression | GENE | Mm.8294 | TITLE von Hippel-Lindau binding protein 1 | GENE Vbp1 | | NM_011692 | 962690 |
| IC02472 | UG75 Expression | GENE | Mm.1021 | TITLE vascular cell adhesion molecule 1 | GENE Vcam1 | CD106|VCAM-1| | NM_011693 | 736519 |
| IC02473 | UG75 Expression | GENE | Mm.12842 | TITLE vinculin | GENE Vcl | | NM_009502 | 1181864 |
| IC02474 | UG75 Expression | GENE | Mm.18921 | TITLE valosin containing protein | GENE Vcp | CDC48|homolog of yeast cdc48|p97| | NM_009503 | 2645826 |
| IC02475 | UG75 Expression | GENE | Mm.3555 | TITLE voltage-dependent anion channel 1 | GENE Vdac1 | Vdac5| | NM_011694 | 3153478 |
| IC02476 | UG75 Expression | GENE | Mm.569 | TITLE voltage-dependent anion channel 2 | GENE Vdac2 | Vdac6| | NM_011695 | 1066447 |
| IC02477 | UG75 Expression | GENE | Mm.15607 | TITLE vascular endothelial growth factor B | GENE Vegfb | vascular endothelial growth factor related protein|VEGF-B|Vrf| | NM_011697 | 890891 |
| IC02478 | UG75 Expression | GENE | Mm.1402 | TITLE vascular endothelial growth factor C | GENE Vegfc | | NM_009506 | 2655127 |
| IC02479 | UG75 Expression | GENE | Mm.13824 | TITLE von Hippel-Lindau syndrome homolog | GENE Vhlh | VHL| | NM_009507 | 573081 |
| IC02480 | UG75 Expression | GENE | Mm.4551 | TITLE villin 2 | GENE Vil2 | ezrin| | NM_009510 | 2655245 |
| IC02481 | UG75 Expression | GENE | Mm.7 | TITLE vimentin | GENE Vim | | NM_011701 | 1021205 |
| IC02482 | UG75 Expression | GENE | Mm.955 | TITLE pre-B lymphocyte gene 3 | GENE Vpreb3 | Vpreb-3| | NM_009514 | 1246296 |
| IC02483 | UG75 Expression | GENE | Mm.2582 | TITLE vacuolar protein sorting-associated protein 45 | GENE Vps45 | mVps45| | NM_013841 | 1383129 |
| IC02484 | UG75 Expression | GENE | Mm.2981 | TITLE vaccinia related kinase 1 | GENE Vrk1 | 51PK| | NM_011705 | 659173 |
| IC02485 | UG75 Expression | GENE | Mm.36248 | TITLE vanilloid receptor-like protein 1 | GENE Vrl1 | | NM_011706 | 2648318 |
| IC02486 | UG75 Expression | GENE | Mm.3667 | TITLE vitronectin | GENE Vtn | Vn| | NM_011707 | 1890267 |
| IC02487 | UG75 Expression | GENE | Mm.38433 | TITLE tryptophanyl-tRNA synthetase | GENE Wars | WRS| | NM_011710 | 367765 |
| IC02488 | UG75 Expression | GENE | Mm.4735 | TITLE Wiskott-Aldrich syndrome protein | GENE Wasp | | NM_009515 | 1432097 |
| IC02489 | UG75 Expression | GENE | Mm.512 | TITLE WW domain binding protein 5 | GENE Wbp5 | | gi = 1914850 | 2236463 |
| IC02490 | UG75 Expression | GENE | Mm.40331 | Bromodomain adjacent to zinc finger domain, 1B | GENE Wbscr9 | | NM_011714 | 777800 |
| IC02491 | UG75 Expression | GENE | Mm.2654 | TITLE WD40 repeat protein 1 | GENE Wdr1 | | NM_011715 | 1248548 |
| IC02492 | UG75 Expression | GENE | Mm.8108 | TITLE wee 1 homolog (S. pombe) | GENE Wee1 | activin A receptor type II-like kinase 1|Acvrlk1|Alk1| | NM_009516 | 474953 |
| IC02493 | UG75 Expression | GENE | Mm.35705 | TITLE wild-type p53-induced gene 1 | GENE Wig1 | | NM_009517 | 1327642 |
| IC02494 | UG75 Expression | GENE | Mm.20878 | TITLE widely-interspaced zinc finger motifs | GENE Wiz | | NM_011717 | 422370 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02495 | UG75 Expression | GENE | Mm.22182 | TITLE wingless-related MMTV integration site 11 | GENE Wnt11 | | NM_009519 | 349486 |
| IC02496 | UG75 Expression | GENE | Mm.15446 | TITLE Werner syndrome homolog (human) | GENE Wrn | | NM_011721 | 1344845 |
| IC02497 | UG75 Expression | GENE | Mm.90496 | TITLE RGD containing protein | GENE Ws3-per | WS-3| | NM_011722 | 1001083 |
| IC02498 | UG75 Expression | GENE | Mm.3043 | TITLE xanthine dehydrogenase | GENE Xdh | xanthine oxidase|Xox-1|Xox1| | NM_011723 | 2938987 |
| IC02499 | UG75 Expression | GENE | Mm.4455 | TITLE X-linked lymphocyte-regulated complex | GENE Xlr | X-linked B-cell surface antigen 1|Xlr-1| | NM_011725 | 1025836 |
| IC02500 | UG75 Expression | GENE | Mm.10141 | TITLE X-linked nuclear protein | GENE Xnp | alpha thalassemia/mental retardation syndrome (X-linked)|ATRX|DXS6677E|DXHXS6677E|heterochromatin protein 2, binding protein 2|Hp1bp2|Hp1bp38|Rad54|RAD54 homolog, (S. cerevisiae)| | NM_009530 | 1328311 |
| IC02501 | UG75 Expression | GENE | Mm.2806 | C | GENE Xpc | | NM_009531 | 1617892 |
| IC02502 | UG75 Expression | GENE | Mm.2213 | G | GENE Xpg | | NM_011729 | 642033 |
| IC02503 | UG75 Expression | GENE | Mm.4347 | TITLE X-ray repair complementing defective repair in Chinese hamster cells 1 | GENE Xrcc1 | X-ray repair complementing defective repair in Chinese hamster|Xrcc-1| | NM_009532 | 519183 |
| IC02504 | UG75 Expression | GENE | Mm.2627 | TITLE X-ray repair complementing defective repair in Chinese hamster cells 5 | GENE Xrcc5 | Ku p80|Ku80|Ku86| | gi = 53585 | 1920904 |
| IC02505 | UG75 Expression | GENE | Mm.42050 | TITLE 5'-3' exoribonuclease 1 | GENE Xrn1 | mXrn1| | NM_011916 | 577388 |
| IC02506 | UG75 Expression | GENE | Mm.3065 | TITLE 5'-3' exoribonuclease 2 | GENE Xrn2 | | NM_011917 | 574486 |
| IC02507 | UG75 Expression | GENE | Mm.30370 | TITLE X transporter protein 2 | GENE Xtrp2 | XT2| | NM_011730 | 2352983 |
| IC02508 | UG75 Expression | GENE | Mm.4885 | TITLE yes-associated protein, 65 kDa | GENE Yap | PACAP| | NM_009534 | 608299 |
| IC02509 | UG75 Expression | GENE | Mm.21054 | TITLE Y box protein 1 | GENE Ybx1 | MSY1| | NM_011732 | 1514775 |
| IC02510 | UG75 Expression | GENE | Mm.22482 | TITLE Y box protein 3 | GENE Ybx3 | | gi = 532212 | 2064809 |
| IC02511 | UG75 Expression | GENE | Mm.23335 | TITLE YME1-like 1 (S. cerevisiae) | GENE Yme1l1 | ATP-dependent metalloprotease FtsH1|Ftsh| | NM_013771 | 775215 |
| IC02512 | UG75 Expression | GENE | Mm.2517 | TITLE yolk sac gene 2 | GENE Ysg2 | clone 165|LSE| | NM_011734 | 2812249 |
| IC02513 | UG75 Expression | GENE | Mm.42972 | TITLE tyrosine 3-monooxygenase/tryptophan 5-monooxygenase activatioprotein, epsilon polypeptide | GENE Ywhae | 14-3-3 epsilon| | NM_009536 | 1515918 |
| IC02514 | UG75 Expression | GENE | Mm.3308 | TITLE tyrosine 3-monooxygenase/tryptophan 5-monooxygenase activation protein, eta polypeptide | GENE Ywhah | 14-3-3 eta| | NM_011738 | 558536 |
| IC02515 | UG75 Expression | GENE | Mm.14722 | TITLE tyrosine 3-monooxygenase/tryptophan 5-monooxygenase activation protein, theta polypeptide | GENE Ywhaq | 14-3-3 theta| | NM_011739 | 1447020 |
| IC02516 | UG75 Expression | GENE | Mm.3360 | TITLE tyrosine 3-monooxygenase/tryptophan 5-monooxygenase activation protein, zeta polypeptide | GENE Ywhaz | | gi = 1304165 | 584061 |
| IC02517 | UG75 Expression | GENE | Mm.3868 | TITLE YY1 transcription factor | GENE Yy1 | delta transcription factor|UCRBP transcription factor| | NM_009537 | 621788 |
| IC02518 | UG75 Expression | GENE | Mm.8022 | TITLE zeta-chain (TCR) associated protein kinase (70 kD) | GENE Zap70 | Srk|syk related kinase|Zap70| | NM_009539 | 832321 |
| IC02519 | UG75 Expression | GENE | Mm.4184 | TITLE zinc finger protein 1 | GENE Zfp1 | finger protein 1|Fnp-1|mkr-1|Zfp-1| | gi = 55482 | 747882 |
| IC02520 | UG75 Expression | GENE | Mm.4340 | TITLE zinc finger protein 100 | GENE Zfp100 | Lp-1|mZl13| | NM_009541 | 2647447 |
| IC02521 | UG75 Expression | GENE | Mm.310 | TITLE zinc finger protein 103 | GENE Zfp103 | kf-1| | NM_009543 | 2247657 |
| IC02522 | UG75 Expression | GENE | Mm.8022 | TITLE zinc finger protein 106 | GENE Zfp106 | Cd-1|H3a|histocompatibility 3a, CTL stimulating| | gi = 3372656 | 573507 |
| IC02523 | UG75 Expression | GENE | Mm.42140 | TITLE Zinc finger protein 118 | GENE Zfp118 | KRAZI| | NM_013843 | 973942 |
| IC02524 | UG75 Expression | GENE | Mm.20857 | TITLE zinc finger protein 125 | GENE Zfp125 | ZT2| | gi = 3646358 | 820660 |
| IC02525 | UG75 Expression | GENE | Mm.146 | TITLE zinc finger protein 127 | GENE Zfp127 | D7H15S9-1|DNA segment, Chr 7, human D15S9| | NM_011746 | 574274 |
| IC02526 | UG75 Expression | GENE | Mm.4973 | TITLE zinc finger protein 147 | GENE Zfp147 | EFP|estrogen-responsive finger protein| | gi = 1088466 | 3154345 |
| IC02527 | UG75 Expression | GENE | Mm.417 | TITLE zinc finger protein 148 | GENE Zfp148 | BERF-1|beta enolase repressor factor 1|BFCOL1| | NM_011749 | 575405 |
| IC02528 | UG75 Expression | GENE | Mm.42240 | TITLE zinc finger protein 162 | GENE Zfp162 | CW17R|MZFM|Sfr1|WBP4| | NM_011750 | 465005 |
| IC02529 | UG75 Expression | GENE | Mm.12236 | TITLE zinc finger protein 207 | GENE Zfp207 | Zep| | NM_011751 | 1972210 |
| IC02530 | UG75 Expression | GENE | Mm.2904 | TITLE zinc finger protein 216 | GENE Zfp216 | | NM_009551 | 891102 |
| IC02531 | UG75 Expression | GENE | Mm.17519 | TITLE zinc finger protein 259 | GENE Zfp259 | ZPR1| | NM_011752 | 1888143 |
| IC02532 | UG75 Expression | GENE | Mm.1176 | TITLE zinc finger protein 26 | GENE Zfp26 | mkr-3|Zfp-26| | gi = 53132 | 620364 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02533 | UG75 Expression | GENE | Mm.4106 | zinc finger protein 260 | Zfp260 | Ozrf1| | NM_011981 | 1281179 |
| IC02534 | UG75 Expression | GENE | Mm.2927 | zinc finger protein 30 | Zfp30 | Zfp-30| | NM_013705 | 1853237 |
| IC02535 | UG75 Expression | GENE | Mm.3297 | zinc finger protein 35 | Zfp35 | Zfp-35| | NM_011755 | 2065091 |
| IC02536 | UG75 Expression | GENE | Mm.1298 | zinc finger protein 36 | Zfp36 | Nup475[TtS1][tris-tetraproline][TTP][Zfp-36] | NM_011756 | 1054074 |
| IC02537 | UG75 Expression | GENE | Mm.2760 | zinc finger protein 38 | Zfp38 | CTfin51[RU49]Zfp-38[Ziprol| | NM_011757 | 513827 |
| IC02538 | UG75 Expression | GENE | Mm.3396 | zinc finger protein 42 | Zfp42 | reduced expression 1[Rex-1][Rex1][Zfp-42] | NM_009556 | 932749 |
| IC02539 | UG75 Expression | GENE | Mm.1504 | zinc finger protein 46 | Zfp46 | Zfp-46| | NM_009557 | 537374 |
| IC02540 | UG75 Expression | GENE | Mm.16650 | zinc finger protein 62 | Zfp62 | | gi = 1061193 | 598234 |
| IC02541 | UG75 Expression | GENE | Mm.2095 | zinc finger protein 64 | Zfp64 | | NM_009564 | 1263981 |
| IC02542 | UG75 Expression | GENE | Mm.29150 | zinc finger protein 67 | Zfp67 | c-Krox| | NM_009565 | 1395362 |
| IC02543 | UG75 Expression | GENE | Mm.27575 | Zinc finger protein 68 | Zfp68 | KRAZ2| | NM_013844 | 1432814 |
| IC02544 | UG75 Expression | GENE | Mm.4906 | zinc finger protein 90 | Zfp90 | NK10|Nk10 expressed protein| | NM_011764 | 463944 |
| IC02545 | UG75 Expression | GENE | Mm.5066 | zinc finger protein 93 | Zfp93 | | NM_009567 | 718197 |
| IC02546 | UG75 Expression | GENE | Mm.3105 | zinc finger protein, multitype 1 | Zfpm1 | FOG|Friend of GATA-1| | NM_009569 | 734017 |
| IC02547 | UG75 Expression | GENE | Mm.919 | zinc finger protein X-linked | Zfx | | NM_011768 | 634652 |
| IC02548 | UG75 Expression | GENE | Mm.3929 | zinc finger homeobox 1a | Zfx1a | [delta]EF1|BZP|MEB1|Nil2|Tcf18|Tcf8|transcription factor 18|transcription factor 8| | NM_011546 | 572837 |
| IC02549 | UG75 Expression | GENE | Mm.37216 | zinc fingers and homeoboxes protein 1 | Zhx1 | | NM_009572 | 1383175 |
| IC02550 | UG75 Expression | GENE | Mm.12396 | zinc finger protein, subfamily 1A, 1 (Ikaros) | Znfn1a1 | early lymphoid specific transcription factor|hlk-1|Ikaros|LyF-1| | NM_009578 | 1281978 |
| IC02551 | UG75 Expression | GENE | Mm.42034 | zinc finger protein, subfamily 1A, 4 | Znfn1a4 | Eos| | NM_011772 | 1429281 |
| IC02552 | UG75 Expression | GENE | Mm.4644 | zona pellucida 3 receptor | Zp3r | SP56| | NM_009581 | 1281391 |
| IC02553 | UG75 Expression | GENE | Mm.4358 | zipper (leucine) protein kinase | Zpk | MUK| | NM_009582 | 367895 |
| IC02554 | UG75 Expression | GENE | Mm.2467 | zuotin related factor 2 | Zrf2 | MIDA1| | NM_009584 | 2631521 |
| IC02555 | UG75 Expression | GENE | Mm.24791 | ZW10 homolog (Drosophila), centromere/kinetochore protein | Zw10 | MmZw10| | gi = 2661219 | 598218 |
| IC02556 | UG75 Expression | GENE | Mm.4895 | zyxin | Zyx | | NM_011777 | 575564 |
| IC02557 | 00/02 Literature | GENE | Mm.3986 | growth hormone receptor | Ghr | | NM_010284 | 1970438 |
| IC02558 | 00/02 Literature | GENE | Mm.8432 | growth factor receptor bound protein 10 | Grb10 | | NM_010345 | 746564 |
| IC02559 | 00/02 Literature | GENE | Mm.57052 | GTP-rho binding protein 1 | Grbp | Rhophilin| | NM_008164 | 1038968 |
| IC02560 | 00/02 Literature | GENE | Mm.14465 | granzyme C | Gzmc | | NM_010371 | 568331 |
| IC02561 | 00/02 Literature | GENE | Mm.14095 | granzyme D | Gzmd | | NM_010372 | 1434509 |
| IC02562 | 00/02 Literature | GENE | Mm.14424 | granzyme E | Gzme | CCP3|Ctla-6|Ctla6|cytotoxic T lymphocyte-associated protein 6|MCSP-2| | NM_010373 | 1434509 |
| IC02563 | 00/02 Literature | GENE | Mm.14868 | granzyme G | Gzmg | AKA granzyme G|CTL serine protease 3|Ctla-7|Ctla7|cytotoxic T lymphocyte-associated protein 7| | NM_010375 | 568643 |
| IC02564 | 00/02 Literature | GENE | Mm.34289 | histocompatibility 2, blastocyst | H2-Bl | blastocyst MHC| | NM_008199 | 904530 |
| IC02565 | 00/02 Literature | GENE | Mm.30377 | histocompatibility 2, D region locus 4 | H2-D4 | H-2D4| | NM_008200 | 1923198 |
| IC02566 | 00/02 Literature | GENE | Mm.87774 | histocompatibility 2, class II, locus Mb2 | H2-DMb2 | H-2Mb2|H2-Mb2| | NM_010388 | 1447352 |
| IC02567 | 00/02 Literature | GENE | Mm.15680 | histocompatibility 2, class II antigen E alpha | H2-Ea | H-2Ea|histocompatibility 2, class II antigen Ealpha|I region-associated antigen 3|Ia-3|Ia3| | NM_010381 | 521720 |
| IC02568 | 00/02 Literature | GENE | Mm.88493 | histocompatibility 2, L region | H2-L | 9.5H| | gi = 199556 | 1363914 |
| IC02569 | 00/02 Literature | GENE | Mm.86686 | histocompatibility 2, M region locus 10.1 | H2-M10.1 | | NM_013544 | 603974 |
| IC02570 | 00/02 Literature | GENE | Mm.56929 | histocompatibility 2, M region locus 2 | H2-M2 | H-2M2|Thy19.4| | gi = 199645 | 1246390 |
| IC02571 | 00/02 Literature | GENE | Mm.34457 | histocompatibility 2, Q region locus 1 | H2-Q1 | H-2Q1|Qa lymphocyte antigen 1|Qa-1|Qa1| | NM_010390 | 904530 |
| IC02572 | 00/02 Literature | GENE | Mm.88795 | histocompatibility 2, Q region locus 10 | H2-Q10 | H-2Q10|Qa10| | NM_010391 | 1888410 |
| IC02573 | 00/02 Literature | GENE | Mm.46812 | histocompatibility 2, Q region locus 2 | H2-Q2 | H-2Q2| | NM_010392 | 1025501 |
| IC02574 | 00/02 Literature | GENE | Mm.87775 | histocompatibility 2, Q region locus 5 | H2-Q5 | H-2Q5|Qa lymphocyte antigen 5|Qa T-cell antigen 5|Qa-5|Qa5|Qat-5| | NM_010393 | 1154350 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02575 | 00/02 Literature | GENE | Mm.87776 | histocompatibility 2, T region locus 10 | H2-T10 | H2-T10 | NM_010395 | 576150 |
| IC02576 | 00/02 Literature | GENE | Mm.88092 | histocompatibility 2, T region locus 17 | H2-T17 | H2-T17 | NM_010396 | 1346428 |
| IC02577 | 00/02 Literature | GENE | Mm.42053 | histocompatibility 2, T region locus 18 | H2-T18 | H2-T18|thymus leukemia antigen|Tla| | gi = 54820 | 861787 |
| IC02578 | 00/02 Literature | GENE | Mm.88783 | histocompatibility 2, T region locus 22 | H2-T22 | H2-T22 | NM_010397 | 1346428 |
| IC02579 | 00/02 Literature | GENE | Mm.14109 | histocompatibility 2, T region locus 3 | H2-T3 | H2-T3 | NM_008208 | 904530 |
| IC02580 | 00/02 Literature | GENE | Mm.88708 | histocompatibility 2, T region locus 9 | H2-T9 | H2-T9 | NM_010399 | 576150 |
| IC02581 | UG75 Expression | GENE | Mm.2329 | TITLE hemoglobin beta, pseudogene bh3 | Hbb-bh3 | | gi = 50155 | 1969583 |
| IC02582 | 00/02 Literature | GENE | Mm.57245 | heat shock protein, 70 kDa 2 | Hsp70-2 | Hspa2 | NM_008301 | 515812 |
| IC02583 | 00/02 Literature | GENE | Mm.88432 | heat shock protein, 70 kDa 3 | Hsp70-3 | | gi = 194014 | 3155158 |
| IC02584 | 00/02 Literature | GENE | Mm.4987 | integrin binding sialoprotein | Ibsp | bone sialoprotein II|BSP| | NM_008318 | 660439 |
| IC02585 | 00/02 Literature | GENE | Mm.16744 | interferon activated gene 202A | Ifi202a | Ifbip-1|Ifi202|interferon activated gene 202|interferon beta induced protein| | NM_008327 | 585716 |
| IC02586 | 00/02 Literature | GENE | Mm.87849 | immunoglobulin heavy chain 4 (serum IgG1) | Igh-4 | | gi = 194361 | 2646928 |
| IC02587 | 00/02 Literature | GENE | Mm.6294 | immunoglobulin kappa chain variable 20 (V20 family) | Igk-V20 | | gi = 55388 | 2749406 |
| IC02588 | 00/02 Literature | GENE | Mm.12967 | inhibitor of kappa light polypeptide gene enhancer in B-cells, kinase gamma | Ikbkg | IKK[g]|NEMO| | NM_010547 | 1399663 |
| IC02589 | 00/02 Literature | GENE | Mm.35814 | interleukin 11 | Il11 | | NM_008350 | 557497 |
| IC02590 | 00/02 Literature | GENE | Mm.88405 | interleukin 11 receptor, alpha chain 2 | Il11ra2 | enhancer trap locus 2|Etl1-2|Etl2|Il11ra-ps1|interleukin 11, receptor alpha, pseudogene 1|locus 2| | NM_010550 | 2609235 |
| IC02591 | 00/02 Literature | GENE | Mm.24771 | interleukin 1 receptor accessory protein | Il1rap | IL-1R AcP| | NM_008364 | 974550 |
| IC02592 | 00/02 Literature | GENE | Mm.931 | interleukin 2 receptor, beta chain | Il2rb | CD122|IL-2 receptor beta chain|p70| | NM_008368 | 1450665 |
| IC02593 | 00/02 Literature | GENE | Mm.4944 | interleukin 3 receptor, alpha chain | Il3ra | CD123|Il-3 alpha subunit|IL-3 receptor alpha chain| | NM_008369 | 3025558 |
| IC02594 | 00/02 Literature | GENE | Mm.4967 | integrin alpha M (Cd11b) | Itgam | CD11B (p170)|complement component receptor 3 alpha-a (CR3A)|Ly-40|lymphocyte antigen 40|Mac-1|Mac-1 alpha Mac-1a|macrophage antigen alpha|macrophage antigen alpha chain (integrin)| | NM_008401 | 483591 |
| IC02595 | 00/02 Literature | GENE | Mm.4427 | integrin alpha V (Cd51) | Itgav | CD51|vitronectin receptor alpha polypeptide (VNRA)| | NM_008402 | 1125496 |
| IC02596 | 00/02 Literature | GENE | Mm.12872 | integrin beta 2-like | Itgb2l | pactolus| | NM_008405 | 1974434 |
| IC02597 | 00/02 Literature | GENE | Mm.21117 | integrin beta 4 | Itgb4 | CD104| | gi = 192151 | 873524 |
| IC02598 | 00/02 Literature | GENE | Mm.89205 | JNK-binding protein 1 | Jnkbp1-pending | | NM_011941 | 2537262 |
| IC02599 | 00/04/26 UG#76 17Lid Expansion | GENE | Mm.482 | Jun oncogene | Jun | c-jun|Jun-C oncogene|Junc| | gi = 6754401 | 2649362 |
| IC02600 | 00/02 Literature | GENE | Mm.87780 | killer cell lectin-like receptor subfamily A, member 10 | Klra10 | Ly49J| | gi = 3483105 | 1226206 |
| IC02601 | 00/02 Literature | GENE | Mm.87781 | killer cell lectin-like receptor subfamily A, member 11 | Klra11 | Ly49K| | gi = 3483119 | 1226206 |
| IC02602 | 00/02 Literature | GENE | Mm.23799 | killer cell lectin-like receptor subfamily A, member 14 | Klra14 | Ly49N| | gi = 3483112 | 874161 |
| IC02603 | 00/02 Literature | GENE | Mm.88397 | killer cell lectin-like receptor subfamily A, member 3 | Klra3 | 5F6|Ly49C|lymphocyte antigen 49 complex, locus C| | gi = 500645 | 874161 |
| IC02604 | 00/02 Literature | GENE | Mm.16749 | killer cell lectin-like receptor subfamily A, member 4 | Klra4 | Chok|Ly49D|lymphocyte antigen 49 complex, locus D| | NM_010649 | 752181 |
| IC02605 | 00/02 Literature | GENE | Mm.14111 | killer cell lectin-like receptor subfamily A, member 5 | Klra5 | Ly49E|lymphocyte antigen 49 complex, locus E| | NM_008463 | 1226206 |
| IC02606 | 00/02 Literature | GENE | Mm.14112 | killer cell lectin-like receptor subfamily A, member 6 | Klra6 | Ly49F|lymphocyte antigen 49 complex, locus F| | NM_008464 | 1226206 |
| IC02607 | 00/02 Literature | GENE | Mm.87782 | killer cell lectin-like receptor subfamily A, member 8 | Klra8 | Ly49H|lymphocyte antigen 49 complex, locus H| | gi = 602407 | 1226206 |
| IC02608 | 00/02 Literature | GENE | Mm.16787 | killer cell lectin-like receptor subfamily A, member 9 | Klra9 | Ly49I| | NM_010651 | 1226206 |
| IC02609 | 00/02 Literature | GENE | Mm.56899 | killer cell lectin-like receptor subfamily C, member 1 | Klrc1 | NKG2A|NKG2B| | NM_010652 | 1381183 |
| IC02610 | 00/02 Literature | GENE | Mm.7634 | lymphoid blast crisis-like 1 | Lbcl1 | Lfc| | NM_008487 | 2609616 |
| IC02611 | 00/02 Literature | GENE | Mm.22302 | lymphocyte Met-ase 1 | Lmet1 | | NM_008504 | 945318 |
| IC02612 | 00/02 Literature | GENE | Mm.87787 | lymphotoxin A | Lta | | NM_010735 | 751270 |
| IC02613 | 00/02 Literature | GENE | Mm.20853 | leukotriene B4 receptor | Ltb4r | mBLTR| | NM_008519 | 1498184 |
| IC02614 | 00/02 Literature | GENE | Mm.16729 | lymphocyte antigen 55 complex, locus A | Ly55a | Ly55-a = gene 2|Nkrp1-a| | NM_010737 | 890417 |
| IC02615 | 00/02 Literature | GENE | Mm.14489 | lymphocyte antigen 55 complex, locus B | Ly55b | Ly55-b = gene 34|Nkrp1-b| | NM_008526 | 1332385 |
| IC02616 | 00/02 Literature | GENE | Mm.6180 | lymphocyte antigen 55 complex, locus C | Ly55c | CD161|Ly55-c = gene 40|NK1.1|Nkrp1-c| | NM_008527 | 1383244 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02617 | 00/02 Literature | GENE | Mm.57179 | lymphocyte antigen 6 complex, locus F | Ly6f | | NM_008530 | 1920915 |
| IC02618 | 00/02 Literature | GENE | Mm.57081 | P lysozyme structural | Lzp-s | | NM_013590 | 1278131 |
| IC02619 | 00/02 Literature | GENE | Mm.39040 | myelin and lymphocyte protein; T-cell differentiation protein | Mal | MPV17|VIP17| | NM_010762 | 2099533 |
| IC02620 | 00/02 Literature | GENE | Mm.6595 | mitogen activated protein kinase kinase 5 | Map3k5 | ASK1|MAPKKK5|MEK kinase 5|Mekk5| | NM_008580 | 678913 |
| IC02621 | 00/02 Literature | GENE | Mm.4936 | mitogen activated protein kinase 10 | Mapk10 | JNK3|p493F12|p54bSAPK|SAPK(beta)|SAPK/Erk/kinase 2|Serk2| | NM_009158 | 2087994 |
| IC02622 | 00/02 Literature | GENE | Mm.27970 | mitogen activated protein kinase 13 | Mapk13 | p38 delta MAP kinase|SAPK/Erk/kinase 4|SAPK4|Serk4| | gi = 4099017 | 368273 |
| IC02623 | 00/02 Literature | GENE | Mm.14135 | mast cell protease 1 | Mcpt1 | Mcp-1| | NM_008570 | 958440 |
| IC02624 | 00/02 Literature | GENE | Mm.7409 | mast cell protease 6 | Mcpt6 | Mcp-6|MMCP-6| | NM_010781 | 351060 |
| IC02625 | 00/02 Literature | GENE | Mm.87791 | mast cell protease 9 | Mcpt9 | | NM_010782 | 557853 |
| IC02626 | 00/04/26 UG#76 17Lid Expansion | GENE | Mm.554 | mitochondrial capsule selenoprotein | Mcs | | gi = 199088 | 603023 |
| IC02627 | 00/02 Literature | GENE | Mm.4582 | c-mer proto-oncogene | Mer | Ves-1| | NM_008587 | 2646667 |
| IC02628 | 00/02 Literature | GENE | Mm.86844 | met proto-oncogene | Met | | NM_008591 | 2609256 |
| IC02629 | UG75 Expression | GENE | Mm.4597 | TITLE M.musculus of PCTAIRE-1 mRNA encoding protein kinase | MGI 97516 | | gi = 53610 | 2651620 |
| IC02630 | 00/04/26 UG#76 17Lid Expansion | GENE | Mm.16415 | matrix metalloproteinase 8 | Mmp8 | Collagenase-2| | gi = 3025474 | 1958234 |
| IC02631 | 00/02 Literature | GENE | Mm.89924 | mitogen regulated protein, proliferin 3 | Mrpplf3 | mrp/plf3| | gi = 53223 | 2300952 |
| IC02632 | 00/02 Literature | GENE | Mm.16193 | mucin 1, transmembrane | Muc1 | EMA|Muc-1|tumor-associated mucin 1| | NM_013605 | 1382544 |
| IC02633 | 00/02 Literature | GENE | Mm.7184 | mucin 3, intestinal | Muc3 | | gi = 2583091 | 1052642 |
| IC02634 | 00/02 Literature | GENE | Mm.57043 | nuclear factor of kappa light polypeptide gene enhancer in B-cells inhibitor, epsilon | Nfkbie | IKBE| | NM_008690 | 2803298 |
| IC02635 | 00/02 Literature | GENE | Mm.4945 | Notch gene homolog 3, (Drosophila) | Notch3 | | NM_008716 | 2655357 |
| IC02636 | 00/02 Literature | GENE | Mm.9493 | poly A binding protein, cytoplasmic 2 | Pabpc2 | PABP|PABP+|Pabp2|poly A binding protein 2| | NM_011033 | 1745619 |
| IC02637 | 00/02 Literature | GENE | Mm.56337 | platelet-activating factor acetylhydrolase, isoform 1b, beta1 subunit | Pafah1b1 | Lis1|Mdsh|Miller-Dieker syndrome homolog|Pafaha|platelet-activating factor acetylhydrolase, alpha subunit| | NM_013625 | 1494293 |
| IC02638 | 00/02 Literature | GENE | Mm.57242 | paired box gene 5 | Pax5 | Pax-5| | NM_008782 | 1745689 |
| IC02639 | 00/02 Literature | GENE | Mm.7988 | platelet derived growth factor, B polypeptide | Pdgfb | simian sarcoma oncogene|Sis| | NM_011057 | 949497 |
| IC02640 | 00/02 Literature | GENE | Mm.4809 | placental growth factor | Pgf | Plgf| | NM_008827 | 1617488 |
| IC02641 | 00/02 Literature | GENE | Mm.10301 | phosphatidylinositol 3-kinase, C2 domain containing, gamma polypeptide | Pik3c2g | | NM_011084 | 520661 |
| IC02642 | 00/02 Literature | GENE | Mm.38370 | phosphoinositide kinase, fyve-containing | Pikfyve | | NM_011086 | 961229 |
| IC02643 | 00/02 Literature | GENE | Mm.10690 | gamma | Pip5k1c | | NM_008844 | 1764588 |
| IC02644 | 00/02 Literature | GENE | Mm.87798 | paired-Ig-like receptor A1 | Pira1 | Ly89|PIR-A1| | NM_011087 | 622850 |
| IC02645 | 00/02 Literature | GENE | Mm.87799 | paired-Ig-like receptor A10 | Pira10 | p91B| | NM_008848 | 622850 |
| IC02646 | 00/02 Literature | GENE | Mm.87800 | paired-Ig-like receptor A2 | Pira2 | | gi = 2138354 | 622850 |
| IC02647 | 00/02 Literature | GENE | Mm.87801 | paired-Ig-like receptor A3 | Pira3 | | NM_011090 | 622850 |
| IC02648 | 00/02 Literature | GENE | Mm.87803 | paired-Ig-like receptor A5 | Pira5 | | gi = 2138360 | 622850 |
| IC02649 | 00/02 Literature | GENE | Mm.87804 | paired-Ig-like receptor A6 | Pira6 | | NM_011093 | 622850 |
| IC02650 | 00/02 Literature | GENE | Mm.87805 | paired-Ig-like receptor A7 | Pira7 | | gi = 2138364 | 622850 |
| IC02651 | 00/02 Literature | GENE | Mm.7980 | protein kinase C, gamma | Pkcc | PKCgamma| | NM_011102 | 3167680 |
| IC02652 | 00/02 Literature | GENE | Mm.12808 | protein kinase C, epsilon | Pkce | PKC[e]| | NM_011104 | 1227189 |
| IC02653 | 00/02 Literature | GENE | Mm.5092 | phospholipase A2, group IB, pancreas, receptor | Pla2g1br | PLA2-I receptor| | NM_008867 | 2123263 |
| IC02654 | 00/02 Literature | GENE | Mm.5189 | phospholipase A2, group IIC | Pla2g2c | | NM_008868 | 513783 |
| IC02655 | 00/02 Literature | GENE | Mm.1263 | plasminogen activator inhibitor, type I | Planh1 | PAI-1| | NM_008871 | 1314695 |
| IC02656 | 00/02 Literature | GENE | Mm.6223 | phospholipase D1 | Pld1 | | gi = 2541939 | 1246490 |
| IC02657 | 00/02 Literature | GENE | Mm.22777 | proliferin | Plf | mrp/plf3| | gi = 200400 | 553572 |

| IC ID | IC Selection method | Module | UniGene | UniGene/LocusLink Title | Gene Symbol | Alias | Selected Reference | IMAGE |
|---|---|---|---|---|---|---|---|---|
| IC02658 | 00/02 Literature | GENE | Mm.88796 | proliferin 2 | Plf2 | PLF-2| | gi = 200398 | 553572 |
| IC02659 | 00/02 Literature | GENE | Mm.15568 | POU domain, class 2, transcription factor 1 | Pou2f1 | Oct-1|Oct-1A|Oct-1B|Oct-1C|octamer binding transcription factor 1|Otf-1|Otf1| | NM_011137 | 2136378 |
| IC02660 | 00/02 Literature | GENE | Mm.37811 | POU domain, class 2, transcription factor 2 | Pou2f2 | Oct-2|Oct-2a|Oct-2b|octamer binding transcription factor 2|Otf-2|Otf2| | NM_011138 | 3167338 |
| IC02661 | 00/02 Literature | GENE | Mm.17031 | POU domain, class 5, transcription factor 1 | Pou5f1 | Oct-3|Oct-4|Oct4|octamer binding transcription factor 3|octamer binding transcription factor 3 related sequence 7|octamer binding transcription factor 4|Otf-3|Otf-4|Otf3|Otf3g|Otf4|rs7|Otf3g|Otf4| | NM_013633 | 835384 |
| IC02662 | 00/02 Literature | GENE | Mm.1373 | peroxisome proliferator activated receptor alpha | Ppara | Nr1c1|peroxisome proliferator activated receptor|PPAR| | NM_011144 | 473047 |
| IC02663 | 00/02 Literature | GENE | Mm.87155 | protein phosphatase, EF hand calcium-binding domain 2 | Ppef2 | | NM_011148 | 482001 |
| IC02664 | 00/02 Literature | GENE | Mm.9334 | protein kinase, cAMP dependent regulatory, type I beta | Prkar1b | | NM_008923 | 736724 |
| IC02665 | 00/02 Literature | GENE | Mm.44410 | protein kinase, cGMP-dependent, type II | Prkg2 | CGKII|Prkgr2|protein kinase, cGMP dependent, regulatory type II| | NM_008926 | 1120767 |
| IC02666 | 00/02 Literature | GENE | Mm.9431 | protease, serine, 12 neurotrypsin, (motopsin) | Prss12 | Bssp-3| | NM_008939 | 614590 |
| IC02667 | 00/02 Literature | GENE | Mm.3944 | protease, serine, 18 | Prss18 | Bssp| | NM_011177 | 1209218 |
| IC02668 | 00/02 Literature | GENE | Mm.57067 | proteasome beta type subunit 5, pseudogene | Psmb5-ps | | gi = 2897807 | 375209 |
| IC02669 | 00/02 Literature | GENE | Mm.18344 | proteasome (prosome, macropain) 26S subunit, ATPase 3, interacting protein | Psmc3ip | | gi = 2578817 | 944886 |
| IC02670 | 00/02 Literature | GENE | Mm.12806 | platelet-activating factor receptor | Ptafr | PAF receptor|PAFR| | gi = 1256924 | 3025645 |
| IC02671 | 00/02 Literature | GENE | Mm.4386 | pre T-cell antigen receptor alpha | Ptcra | pT-alpha|pT[a]|pTalpha| | NM_011195 | 1888464 |
| IC02672 | 00/02 Literature | GENE | Mm.30424 | prostaglandin E receptor EP3 subtype | Ptgerep3 | EP3|Pgerep3| | NM_011196 | 2536643 |
| IC02673 | 00/02 Literature | GENE | Mm.7958 | protein tyrosine kinase 9 | Ptk9 | A6|actin monomer-binding protein|twinfilin| | NM_008971 | 1223029 |
| IC02674 | 00/02 Literature | GENE | Mm.4498 | protein tyrosine phosphatase, non-receptor type 14 | Ptpn14 | PTP36| | NM_008976 | 3025827 |
| IC02675 | 00/02 Literature | GENE | Mm.37213 | protein tyrosine phosphatase, receptor type, B | Ptprb | | gi = 53233 | 2300952 |
| IC02676 | 00/02 Literature | GENE | Mm.89191 | protein tyrosine phosphatase, receptor type, D | Ptprd | | gi = 220487 | 1448630 |
| IC02677 | 00/02 Literature | GENE | Mm.9010 | protein tyrosine phosphatase, receptor type, G | Ptprg | | NM_008981 | 874684 |
| IC02678 | 00/02 Literature | GENE | Mm.27856 | protein tyrosine phosphatase, receptor type, K | Ptprk | | NM_008983 | 615588 |
| IC02679 | 00/02 Literature | GENE | Mm.4860 | protein tyrosine phosphatase, receptor type, L | Ptprl | PTP| | NM_011214 | 386456 |
| IC02681 | 00/02 Literature | GENE | Mm.37854 | protein tyrosine phosphatase, receptor-type, M | Ptprm | | NM_008984 | 1277241 |
| IC02682 | 00/02 Literature | GENE | Mm.4715 | protein tyrosine phosphatase, receptor type, O | Ptpro | | NM_011216 | 1137535 |
| IC02683 | 00/02 Literature | GENE | Mm.40277 | protein tyrosine phosphate, receptor type, Z | Ptprz | DSD-1-PG| | NM_011219 | 1617668 |
| IC02684 | 00/02 Literature | GENE | Mm.8009 | polymerase I and transcript release factor | Ptrf | | NM_008986 | 1885335 |
| IC02685 | 00/02 Literature | GENE | Mm.38889 | RAB17, member RAS oncogene family | Rab17 | | NM_008998 | 1972053 |
| IC02686 | 00/02 Literature | GENE | Mm.86744 | RAB23, member RAS oncogene family | Rab23 | | NM_008999 | 537431 |
| IC02687 | 00/02 Literature | GENE | Mm.87807 | RAB7, member RAS oncogene family, pseudogene 1 | Rab7-ps1 | | gi = 2168154 | 560341 |
| IC02688 | 00/02 Literature | GENE | Mm.27161 | renal tumor antigen | Rage | MAPK|MAK/MRK/ overlapping kinase|MOK|RAGE1| | NM_011973 | 602988 |
| IC02689 | 00/02 Literature | GENE | Mm.42150 | RAS guanyl releasing protein 1 | Rasgrp1 | | NM_011246 | 2802840 |
| IC02690 | 00/02 Literature | GENE | Mm.7892 | regulatory factor (trans-acting) 1 | Rfx1 | | NM_009055 | 1764213 |
| IC02691 | 00/02 Literature | GENE | Mm.20954 | regulator of G-protein signaling 5 | Rgs5 | | NM_009063 | 935524 |
| IC02692 | 00/02 Literature | GENE | Mm.8018 | regulator of G-protein signaling 9 | Rgs9 | | NM_011268 | 3156438 |
| IC02693 | 00/02 Literature | GENE | Mm.3147 | receptor (TNFRSF)-interacting serine-threonine kinase 1 | Ripk1 | receptor interacting protein|Rinp|RIP| | NM_009068 | 422318 |
| IC02694 | 00/02 Literature | GENE | Mm.87812 | 18S RNA | Rn18s | | gi = 50872 | 2646624 |
| IC02695 | 00/02 Literature | GENE | Mm.3901 | receptor protein tyrosine kinase, c-met-related | Ron | Friend virus susceptibility 2|Fv-2|Fv2|STK| | NM_009074 | 1398571 |
| IC02696 | 00/02 Literature | GENE | Mm.7387 | RNA polymerase 1-4 (194 kDa subunit) | Rpol-4 | mRPA1| | NM_009088 | 1209235 |
| IC02697 | 00/02 Literature | GENE | Mm.34039 | spliceosomal protein gene 62 | Sap62 | | NM_013651 | 735485 |
| IC02698 | 00/02 Literature | GENE | Mm.1227 | scavenger receptor | Scvr | Macrophage scavenger receptor|MSR|MSR-A|SR-A|SR-AI|SR-AII| | gi = 293747 | 3026111 |
| IC02699 | 00/02 Literature | GENE | Mm.16091 | small inducible cytokine A7 | Scya7 | fic|marc|mcp3| | NM_013654 | 1181707 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02699 | 00/02 Literature | GENE | Mm.2044 | stromal cell derived factor 3 | Sdf3 | | NM_011340 | 1886967 |
| IC02700 | 00/02 Literature | GENE | Mm.87815 | splicing factor, arginine/serine-rich 10 | Sfrs10 | MRF-1| | gi = 555923 | 860915 |
| IC02701 | 00/02 Literature | GENE | Mm.5012 | SH3-domain binding protein 2 | Sh3bp2 | 3BP2| | NM_011893 | 2938050 |
| IC02702 | 00/02 Literature | GENE | Mm.86595 | src homology 2 domain-containing transforming protein C | Shc | | NM_011368 | 1222897 |
| IC02703 | 00/02 Literature | GENE | Mm.20908 | src homology 2 domain-containing transforming protein D | Shd | | NM_009168 | 401189 |
| IC02704 | 00/02 Literature | GENE | Mm.5073 | trans-acting transcription factor 4 | Sp4 | | NM_009239 | 534549 |
| IC02705 | 00/02 Literature | GENE | Mm.56953 | Rous sarcoma oncogene | Src | Rsp-4| | NM_009271 | 554335 |
| IC02706 | 00/02 Literature | GENE | Mm.89195 | v-src suppressed transcript 5 | Srcs5 | | gi = 558946 | 775253 |
| IC02707 | 00/02 Literature | GENE | Mm.34064 | signal transducer and activator of transcription 5B | Stat5b | | NM_011489 | 763596 |
| IC02708 | 00/02 Literature | GENE | Mm.14097 | TAP binding protein | Tapbp | Tapasin| | NM_009318 | 2650365 |
| IC02709 | 00/02 Literature | GENE | Mm.18154 | T-cell lymphoma breakpoint 1 | Tcl1 | | NM_009337 | 976610 |
| IC02710 | 00/02 Literature | GENE | Mm.57186 | T-cell receptor alpha, variable 8 | Tcra-V8 | | gi = 01166 | 1344798 |
| IC02711 | 00/02 Literature | GENE | Mm.12960 | transforming growth factor, beta receptor III | Tgfbr3 | | gi = 3387819 | 2101554 |
| IC02712 | 00/02 Literature | GENE | Mm.42087 | TGF-beta1-induced anti-apoptotic factor 1 | Tiaf1 | | gi = 4140701 | 1094122 |
| IC02713 | 00/02 Literature | GENE | Mm.57088 | tumor necrosis factor induced protein 1 | Tnfip1 | Edp-1|Edp1|endothelial cell derived protein|Tnfaip1|tumor necrosis factor alpha induced protein 1| | NM_009395 | 3155087 |
| IC02714 | 00/02 Literature | GENE | Mm.56971 | tumor necrosis factor induced protein 3 | Tnfip3 | A20|zinc finger protein A20| | NM_000397 | 1448884 |
| IC02715 | 00/02 Literature | GENE | Mm.12935 | tumor necrosis factor receptor superfamily, member 17 | Tnfrsf17 | BCMA| | NM_011608 | 1349977 |
| IC02716 | 00/02 Literature | GENE | Mm.3720 | tumor necrosis factor receptor superfamily, member 9 | Tnfrsf9 | 4-1BB|CD antigen 137|Cd137|CDw137|Ly63|lymphocyte antigen 63| | NM_011612 | 568845 |
| IC02717 | 00/02 Literature | GENE | Mm.41171 | tumor necrosis factor (ligand) superfamily, member 9 | Tnfsf9 | 4-1BB ligand|CD antigen 137 ligand|Cd137l|Ly63l|lymphocyte antigen 63 ligand| | NM_009404 | 1449661 |
| IC02718 | 00/02 Literature | GENE | Mm.10708 | topoisomerase 3 alpha | Top3a | Top IIIa| | NM_009410 | 1245546 |
| IC02719 | 00/02 Literature | GENE | Mm.89495 | three prime repair exonuclease 2 | Trex2 | | NM_011907 | 480859 |
| IC02720 | 00/02 Literature | GENE | Mm.57191 | vav oncogene | Vav | | NM_011691 | 2802898 |
| IC02721 | 00/02 Literature | GENE | Mm.22730 | vascular endothelial growth factor | Vegf | VEGF-A|VPF| | NM_009505 | 988133 |
| IC02722 | 00/02 Literature | GENE | Mm.87561 | Wilms tumor homolog | Wt1 | Wt-1| | gi = 202413 | 557993 |
| IC02723 | 00/02 Literature | GENE | Mm.16758 | X-linked lymphocyte-regulated 3a | Xlr3a | Xlr3a| | NM_011726 | 621845 |
| IC02724 | 00/02 Literature | GENE | Mm.88311 | X-linked lymphocyte-regulated 3b | Xlr3b | Xlr3b| | NM_011727 | 621845 |
| IC02725 | 00/02 Literature | GENE | Mm.42200 | zinc finger protein regulator of apoptosis and cell cycle arrest | Zac1 | | NM_009538 | 1972868 |
| IC02726 | UG75 Expression | GENE | Mm.14145 | chain | | | gi = 54701 | 1002501 |
| IC02727 | UG75 Expression | GENE | Mm.1963 | TITLE Mus musculus plenty-of-prolines-101 mRNA, complete cds | | | gi = 3153820 | 1020754 |
| IC02728 | UG75 Expression | GENE | Mm.42048 | TITLE Mus musculus mRNA for Septin6, complete cds | | | gi = 5689157 | 1020973 |
| IC02729 | UG75 Expression | GENE | Mm.10102 | TITLE Mus musculus unknown protein mRNA, partial cds | | | gi = 2970116 | 1025649 |
| IC02730 | UG75 Expression | GENE | Mm.14616 | TITLE Mus musculus mRNA for poly-glutamine tract-binding protein (PQBP-1 gene) | | | gi = 6103004 | 1051903 |
| IC02731 | UG75 Expression | GENE | Mm.10699 | TITLE Mus musculus vesicle associated membrane protein 4 (Vamp4) mRNA, complete cds | | | gi = 3108178 | 1052053 |
| IC02732 | 00/02 Literature | GENE | Mm.57178 | Sialophorin | | | NM_009259 | 1053977 |
| IC02733 | 00/02 Literature | GENE | Mm.41064 | MHR23A; Rad23 UV excision repair protein homologue; xeroderma pigmentosum group C (XPC) repair complementing protein | | | NM_009010 | 1054114 |
| IC02734 | UG75 Expression | GENE | Mm.8315 | TITLE Mus musculus neural precursor cell expressed developmentally downregulated Nedd9 (Nedd9) mRNA, complete cds | | | gi = 2454522 | 1054763 |
| IC02735 | UG75 Expression | GENE | Mm.19355 | TITLE Mus musculus mRNA for ribosomal protein L35a | | | gi = 1318345 | 1055042 |
| IC02736 | UG75 Expression | GENE | Mm.34445 | TITLE Mus musculus SH3P9 mRNA, complete cds | | | gi = 1438562 | 1065518 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02737 | UG75 Expression | GENE | Mm.1387 | TITLE Mouse mRNA for Rab 11, partial sequence | | | gi = 1742912 | 1065765 |
| IC02738 | UG75 Expression | GENE | Mm.2437 | TITLE Mus musculus major histocompatibility locus class II region; Fas-binding protein Daxx (DAXX) gene, partial cds; Bing1 (BING1), tapasin (tapasin), RalGDS-like factor (RLF), KE2 (KE2), BING4 (BING4), beta1, 3-galactosyl transferase (beta1,3-galactosyl transferase), ribosomal protein subunit S18 (RPS18), Sacm21 (Sacm21), H2K1(b) (H2-K1(b)), RING1 (RING1), KE6a (KE6a), KE4 (KE4), RXRbeta (RXRbeta), collagen alpha-2 (XI) (COLA11A2), H2-O alpha (H2-Oalpha), RING3 (RING3), H2-M alpha (H2-M alpha), H2-M beta 2 (H2-M beta2), and H2-M beta1 (H2-M beta1) genes, complete cds; and LMP 2 gene, partial cds | | | gi = 3811374 | 1066667 |
| IC02739 | UG75 Expression | GENE | Mm.20926 | TITLE Mus musculus major histocompatibility locus class II region; Fas-binding protein Daxx (DAXX) gene, partial cds; Bing1 (BING1), tapasin (tapasin), RalGDS-like factor (RLF), KE2 (KE2), BING4 (BING4), beta1, 3-galactosyl transferase (beta1,3-galactosyl transferase), ribosomal protein subunit S18 (RPS18), Sacm21 (Sacm21), H2K1(b) (H2-K1(b)), RING1 (RING1), KE6a (KE6a), KE4 (KE4), RXRbeta (RXRbeta), collagen alpha-2 (XI) (COLA11A2), H2-O alpha (H2-Oalpha), RING3 (RING3), H2-M alpha (H2-M alpha), H2-M beta 2 (H2-M beta2), and H2-M beta1 (H2-M beta1) genes, complete cds; and LMP 2 gene, partial cds | | | gi = 3811374 | 1066667 |
| IC02740 | 00/02 Literature | GENE | Mm.1338 | c-Fgr proto-oncogene | | | NM_010208 | 1066790 |
| IC02741 | UG75 Expression | GENE | Mm.6955 | TITLE Mus musculus clipper/cleavage and polyadenylation specificity factor 30 kDa subunit homolog mRNA, partial cds | | | gi = 2687590 | 1066917 |
| IC02742 | UG75 Expression | GENE | Mm.12941 | TITLE Mus musculus metaxin 2 (Mtx2) mRNA, nuclear gene encoding mitochondrial protein, complete cds | | | gi = 3283046 | 1067349 |
| IC02743 | UG75 Expression | GENE | Mm.20938 | TITLE Mus musculus formin binding protein 21 mRNA, complete cds | | | gi = 3550076 | 1077755 |
| IC02744 | UG75 Expression | GENE | Mm.32715 | TITLE Mus musculus KOI-4 gene, partial cds | | | gi = 2623675 | 1078353 |
| IC02745 | UG75 Expression | GENE | Mm.36742 | TITLE Mus musculus mRNA for disintegrin metalloprotease (decysin gene) | | | gi = 5830462 | 1078944 |
| IC02746 | UG75 Expression | GENE | Mm.12966 | TITLE Mus musculus S3-12 mRNA, complete cds | | | gi = 3236367 | 1092902 |
| IC02747 | UG75 Expression | GENE | Mm.20866 | TITLE Mus musculus mRNA for Nibrin, complete cds | | | gi = 3676834 | 1093904 |
| IC02748 | 00/02 Literature | GENE | Mm.4950 | X56602 Mus musculus mRNA Interferon-induced 15-KDa protein | | | gi = 52737 | 1096318 |
| IC02749 | 00/02 Literature | GENE | Mm.14733 | U12565 Mus musculus 129 defensin-like gene 4C-4, complete cds | | | NM_007845 | 1096595 |
| IC02750 | 00/02 Literature | GENE | Mm.14272 | Defensin related cryptdin, related sequence 7 | | | NM_007848 | 1096615 |
| IC02751 | UG75 Expression | GENE | Mm.20945 | TITLE Mus musculus semaF cytoplasmic domain associated protein 1 (Semcap1) mRNA, complete cds | | | gi = 3851519 | 1106337 |
| IC02752 | UG75 Expression | GENE | Mm.25074 | TITLE Mus musculus heterogeneous nuclear ribonucleoprotein C1/C2 mRNA, complete cds | | | gi = 4139187 | 1107673 |
| IC02753 | UG75 Expression | GENE | Mm.30141 | TITLE Mouse G protein beta 2 subunit mRNA, complete cds | | | gi = 984550 | 1120620 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02754 | UG75 Expression | GENE | Mm.10758 | TITLE Mus musculus clone L5 uniform group of 2-cell-stage gene family mRNA, complete cds | | | gi = 3171145 | 1123941 |
| IC02755 | UG75 Expression | GENE | Mm.86541 | TITLE Murine (DBA/2) mRNA fragment for gag related peptide | | | gi = 51495 | 1135520 |
| IC02756 | UG75 Expression | GENE | Mm.22261 | TITLE Mus musculus mRNA for Rho guanine nucleotide-exchange factor, splice variant NET1A | | | gi = 4138206 | 1138348 |
| IC02757 | UG75 Expression | GENE | Mm.9043 | TITLE Mus musculus mRNA for protein L, partial cds | | | gi = 2723394 | 1139508 |
| IC02758 | UG75 Expression | GENE | Mm.29163 | TITLE Mus musculus CAST mRNA for calpastatin, complete cds | | | gi = 6006274 | 1139847 |
| IC02759 | UG75 Expression | GENE | Mm.9699 | TITLE Mus musculus phosphomannomutase (Pmm2) mRNA, complete cds | | | gi = 4105148 | 1149913 |
| IC02760 | UG75 Expression | GENE | Mm.27351 | TITLE Mus musculus AKAP95 mRNA for A kinase anchor protein 95, complete cds | | | gi = 5931617 | 1151259 |
| IC02761 | UG75 Expression | GENE | Mm.34319 | TITLE Mus musculus 14-3-3 protein beta mRNA, complete cds | | | gi = 3065924 | 1162060 |
| IC02762 | UG75 Expression | GENE | Mm.36900 | TITLE Mus musculus mRNA for slow skeletal muscle troponin I (Tnni1 gene) | | | gi = 5457404 | 1162573 |
| IC02763 | UG75 Expression | GENE | Mm.27271 | TITLE Mus musculus tbc1 mRNA, complete cds | | | gi = 988220 | 1163414 |
| IC02764 | UG75 Expression | GENE | Mm.35628 | TITLE Mus musculus mRNA for alpha-1,6-fucosyltransferase, complete cds | | | gi = 4586553 | 1166848 |
| IC02765 | UG75 Expression | GENE | Mm.42185 | TITLE Mus musculus mRNA for OCTN1, complete cds | | | gi = 4126604 | 1177710 |
| IC02766 | UG75 Expression | GENE | Mm.12891 | TITLE Mus musculus ZAN75 mRNA for zinc finger protein, complete cds | | | gi = 3298471 | 1178712 |
| IC02767 | UG75 Expression | GENE | Mm.7562 | TITLE Mus musculus type VI collagen alpha 3 subunit mRNA, complete cds | | | gi = 3236369 | 1180537 |
| IC02768 | UG75 Expression | GENE | Mm.3979 | TITLE UBIQUITIN-LIKE PROTEIN GDX | | | gi = 202256 | 1181214 |
| IC02769 | UG75 Expression | GENE | Mm.19931 | TITLE Mouse housekeeping DXS253E (P3) and DXS254E (GdX) genes, 3' end, and complete cds | | | gi = 202256 | 1181214 |
| IC02770 | UG75 Expression | GENE | Mm.38193 | TITLE Mus musculus Zn-15 transcription factor (Zfp-15) mRNA, complete cds | | | gi = 4102928 | 1194093 |
| IC02771 | UG75 Expression | GENE | Mm.10288 | TITLE Mus musculus putative E1-E2 ATPase mRNA, partial cds | | | gi = 2944186 | 1195779 |
| IC02772 | UG75 Expression | GENE | Mm.22266 | TITLE Mus musculus ultra high sulfur keratin gene, complete cds | | | gi = 341749 | 1196871 |
| IC02773 | UG75 Expression | GENE | Mm.16757 | TITLE Murine Glvr-1 mRNA, complete cds | | | gi = 957211 | 1209595 |
| IC02774 | UG75 Expression | GENE | Mm.27190 | TITLE M.musculus mRNA for glutamyl-tRNA synthetase | | | gi = 5804944 | 1210409 |
| IC02775 | UG75 Expression | GENE | Mm.10119 | TITLE Mus musculus mRNA for L-periaxin | | | gi = 2959887 | 1210429 |
| IC02776 | UG75 Expression | GENE | Mm.20914 | TITLE Mus musculus mitogen- and stress-activated protein kinase-2 (mMSK2) mRNA, complete cds | | | gi = 3786405 | 1225377 |
| IC02777 | 00/02 Literature | GENE | Mm.56942 | Pim-1 proto-oncogene | | | gi = 200352 | 1225382 |
| IC02778 | UG75 Expression | GENE | Mm.33669 | TITLE Mus musculus claudin-1 mRNA, complete cds | | | gi = 3335181 | 1227538 |
| IC02779 | UG75 Expression | GENE | Mm.14843 | TITLE Mus musculus acidic ribosomal phosphoprotein P1 mRNA, complete cds | | | gi = 902557 | 1227647 |
| IC02780 | UG75 Expression | GENE | Mm.21419 | TITLE Mus musculus TAFII30 gene for mTAFII30 protein, exons 1–5 | | | gi = 6119622 | 1227820 |
| IC02781 | UG75 Expression | GENE | Mm.27372 | TITLE Mus musculus mRNA for KIAA312p, partial cds | | | gi = 5931572 | 1228682 |
| IC02782 | UG75 Expression | GENE | Mm.118 | TITLE Mus musculus Sin3-associated protein (sap30) mRNA, complete cds | | | gi = 3309075 | 1243335 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02783 | UG75 Expression | GENE | Mm.38214 | TITLE Mouse germline Ig-lambda chain gene, J3-C3-J1-C1 cluster: J3 region | | | gi = 197602 | 1245651 |
| IC02784 | UG75 Expression | GENE | Mm.30295 | TITLE *Mus musculus* SJL-4E3 T cell receptor alpha chain mRNA, complete cds | | | gi = 476321 | 1246028 |
| IC02785 | UG75 Expression | GENE | Mm.3439 | TITLE *Mus musculus* p85SPR mRNA, complete cds | | | gi = 2098782 | 1246792 |
| IC02786 | UG75 Expression | GENE | Mm.10745 | TITLE *Mus musculus* class I cytokine receptor (Wsx1) mRNA, complete cds | | | gi = 3153242 | 1247177 |
| IC02787 | UG75 Expression | GENE | Mm.23368 | TITLE *Mus musculus* mRNA for U8, complete cds | | | gi = 5102775 | 1247684 |
| IC02788 | UG75 Expression | GENE | Mm.18 | TITLE DIFF6 PROTEIN | | | gi = 193839 | 1247828 |
| IC02789 | UG75 Expression | GENE | Mm.25306 | TITLE *Mus musculus* SID 99 mRNA for small GTP binding protein, complete cds | | | gi = 5931615 | 1247850 |
| IC02790 | UG75 Expression | GENE | Mm.1973 | TITLE *Mus musculus* D9 splice variant 1 mRNA, complete cds | | | gi = 2071990 | 1248198 |
| IC02791 | UG75 Expression | GENE | Mm.41213 | TITLE *Mus musculus* TAPL mRNA for TAP-like ABC transporter, complete cds | | | gi = 6045149 | 1261236 |
| IC02792 | UG75 Expression | GENE | Mm.8540 | TITLE preferentially expressed in LPS-normoresponsive macrophages | | | gi = 4103990 | 1262916 |
| IC02793 | UG75 Expression | GENE | Mm.42152 | TITLE *Mus musculus* lymphocyte specific formin related protein (Frl) mRNA, complete cds | | | gi = 4101719 | 1263246 |
| IC02794 | UG75 Expression | GENE | Mm.31775 | TITLE *Mus musculus* mRNA for SIT protein | | | gi = 4688947 | 1263397 |
| IC02795 | UG75 Expression | GENE | Mm.8012 | TITLE *Mus musculus* Ets transcription factor Spi-B, partial cds | | | gi = 2735134 | 1264777 |
| IC02796 | UG75 Expression | GENE | Mm.6840 | TITLE *M.musculus* ASF mRNA | | | gi = 50027 | 1264935 |
| IC02797 | UG75 Expression | GENE | Mm.7254 | TITLE *M.musculus* cytokine receptor-like molecule (EBI3) mRNA, complete cds | | | gi = 2338440 | 1265208 |
| IC02798 | UG75 Expression | GENE | Mm.3865 | TITLE *M.musculus* seb4 mRNA | | | gi = 407467 | 1265472 |
| IC02799 | UG75 Expression | GENE | Mm.28188 | TITLE *Mus musculus* glucosidase I gene, complete cds | | | gi = 4100635 | 1277506 |
| IC02800 | UG75 Expression | GENE | Mm.2131 | TITLE *Mus musculus* p6-5 gene, 3′ end | | | gi = 200267 | 1277868 |
| IC02801 | UG75 Expression | GENE | Mm.3845 | TITLE *Mus musculus* mRNA for eRF1, partial cds | | | gi = 1542844 | 1280571 |
| IC02802 | UG76 LID366 B cell | GENE | Mm.87730 | TITLE Mouse (strain 129 G-IX+) endogenous murine leukemia virus mRNA, clone E1 | | | gi = 199754 | 1281154 |
| IC02803 | UG75 Expression | GENE | Mm.26894 | TITLE *Mus musculus* mACS4 variant1 mRNA for Acyl-CoA synthetase 4 variant1, complete cds | | | gi = 6172344 | 1293828 |
| IC02804 | UG75 Expression | GENE | Mm.21507 | TITLE *Mus musculus* mRNA for Sid394p, complete cds | | | gi = 5931556 | 1298569 |
| IC02805 | UG75 Expression | GENE | Mm.13081 | TITLE *Mus musculus* mRNA for sterol-C5-desaturase, complete cds | | | gi = 3721883 | 1299121 |
| IC02806 | UG75 Expression | GENE | Mm.10763 | TITLE *Mus musculus* mRNA for dia protein | | | gi = 3171941 | 1313157 |
| IC02807 | UG75 Expression | GENE | Mm.57157 | TITLE *Mus musculus* major histocompatibility locus class II region; Fas-binding protein Daxx (DAXX) gene, partial cds; Bing1 (BING1), tapasin (tapasin), RalGDS-like factor (RLF), KE2 (KE2), BING4 (BING4), beta1, 3-galactosyl transferase (beta1,3-galactosyl transferase), ribosomal protein subunit S18 (RPS18), Sacm21 (Sacm21), H2K1(b) (H2-K1(b)), RING1 (RING1), KE6a (KE6a), KE4 (KE4), RXRbeta (RXRbeta), collagen alpha-2 (XI) (COLA11A2), H2-O alpha (H2-Oalpha), RING3 (RING3), H2-M alpha (H2-M alpha), H2-M beta 2 (H2-M beta2), and H2-M beta1 (H2-M beta1) genes, complete cds; and LMP 2 gene, partial cds | | | gi = 3811374 | 1347649 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02808 | UG75 Expression | GENE | Mm.21905 | TITLE M.musculus mRNA for GTP-binding protein | | | gi = 1177546 | 1348319 |
| IC02809 | UG76 LID366 B cell | GENE | Mm.20869 | TITLE Mus musculus vacuolar adenosine triphosphatase subunit Ac116 mRNA, complete cds | | | gi = 3955095 | 1349514 |
| IC02810 | UG75 Expression | GENE | Mm.38450 | TITLE Mus musculus mRNA for septin-like protein Sint1 (Sint1 gene) | | | gi = 6165418 | 1362556 |
| IC02811 | UG75 Expression | GENE | Mm.20937 | TITLE Mus musculus neural visinin-like protein 3 (NVP-3) mRNA, complete cds | | | gi = 3600082 | 1362647 |
| IC02812 | UG75 Expression | GENE | Mm.35844 | TITLE M.musculus mRNA for gas5 growth arrest specific protein | | | gi = 51049 | 1363926 |
| IC02813 | UG75 Expression | GENE | Mm.7271 | TITLE Mus musculus tip associating protein (Tap) mRNA, complete cds | | | gi = 3719434 | 1365255 |
| IC02814 | UG75 Expression | GENE | Mm.5856 | TITLE Mus musculus BS4 peptide mRNA, complete cds | | | gi = 863013 | 1366633 |
| IC02815 | UG75 Expression | GENE | Mm.28165 | TITLE Mus musculus B cell antigen receptor Ig beta associated protein 1 (IBAP-1) mRNA, complete cds | | | gi = 4101717 | 1380170 |
| IC02816 | UG75 Expression | GENE | Mm.9901 | TITLE Mus musculus mRNA for NEFA protein, complete cds | | | gi = 2612796 | 1381917 |
| IC02817 | UG75 Expression | GENE | Mm.10409 | TITLE Mus musculus golgin-245 (olp-1) mRNA, complete cds | | | gi = 2952521 | 1382122 |
| IC02818 | UG75 Expression | GENE | Mm.29982 | TITLE Mus musculus BUB2-like protein 1 (HBLP1) mRNA, complete cds | | | gi = 4099610 | 1382422 |
| IC02819 | UG75 Expression | GENE | Mm.43760 | TITLE Mus musculus mRNA for sid2895p, complete cds | | | gi = 5931558 | 1382613 |
| IC02820 | UG75 Expression | GENE | Mm.23809 | TITLE Mus musculus mRNA for HIRA-interacting protein (HIRIP5) | | | gi = 6013068 | 1382679 |
| IC02821 | UG75 Expression | GENE | Mm.13859 | TITLE Mus musculus ribosomal protein L41 mRNA, complete cds | | | gi = 1325899 | 1382985 |
| IC02822 | UG75 Expression | GENE | Mm.20922 | TITLE Mus musculus MEK binding partner 1 (Mp1) mRNA, complete cds | | | gi = 3549604 | 1383191 |
| IC02823 | UG75 Expression | GENE | Mm.18502 | TITLE Mus musculus mRNA for oxysterol-binding protein, complete cds | | | gi = 3551522 | 1383199 |
| IC02824 | UG75 Expression | GENE | Mm.6672 | TITLE Mus musculus B-ATF mRNA, complete cds | | | gi = 2394267 | 1383316 |
| IC02825 | UG75 Expression | GENE | Mm.353 | TITLE Mus musculus mitochondrial ATP synthase coupling factor 6 mRNA, nuclear gene encoding mitochondrial protein, complete cds | | | gi = 1679742 | 1383394 |
| IC02826 | UG75 Expression | GENE | Mm.6072 | TITLE Mus musculus clathrin light chain 2 mRNA, complete cds | | | gi = 1916987 | 1383819 |
| IC02827 | UG75 Expression | GENE | Mm.1841 | TITLE M.musculus mRNA for imogen 44 | | | gi = 3520248 | 1398731 |
| IC02828 | 00/02 Literature | GENE | Mm.4771 | Nuclear factor I/A | | | NM_010905 | 1399384 |
| IC02829 | UG75 Expression | GENE | Mm.1676 | TITLE Mouse thymidylate kinase homologue mRNA, complete cds | | | gi = 609542 | 1400538 |
| IC02830 | UG75 Expression | GENE | Mm.3888 | TITLE Mouse (clone RAD11) T-cell receptor rearranged delta-chain mRNA V-D-J-C region, 3′ end | | | gi = 54894 | 1400736 |
| IC02831 | UG75 Expression | GENE | Mm.28580 | TITLE Mus musculus myotubularin (Mtm1) mRNA, complete cds | | | gi = 3882999 | 1400777 |
| IC02832 | UG75 Expression | GENE | Mm.3049 | TITLE Mus musculus mRNA for sid1334p, complete cds | | | gi = 5931566 | 1400818 |
| IC02833 | UG75 Expression | GENE | Mm.27933 | TITLE Mus musculus mRNA for 26S proteasome non-ATPase subunit | | | gi = 2505939 | 1431301 |
| IC02834 | UG75 Expression | GENE | Mm.22757 | TITLE Mus musculus Btk locus, alpha-D-galactosidase A (Ags), ribosomal protein (L44L), and Bruton's tyrosine kinase (Btk) genes, complete cds | | | gi = 1666999 | 1431319 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02835 | UG75 Expression | GENE | Mm.14838 | TITLE *Mus musculus* Btk locus, alpha-D-galactosidase A (Ags), ribosomal protein (L44L), and Bruton's tyrosine kinase (Btk) genes, complete cds | | | gi = 1297626 | 1431319 |
| IC02836 | UG75 Expression | GENE | Mm.7522 | TITLE *Mus musculus* prostate-specific membrane antigen homolog (mopsm) mRNA, complete cds | | | gi = 2565337 | 1432163 |
| IC02837 | UG75 Expression | GENE | Mm.2065 | TITLE *Mus musculus* CTP synthetase homolog (CTPsH) mRNA, complete cds | | | gi = 1654185 | 1432904 |
| IC02838 | UG75 Expression | GENE | Mm.8486 | TITLE *Mus musculus* uterine mRNA, complete cds | | | gi = 1066284 | 1434259 |
| IC02839 | 00/02 Literature | GENE | Mm.57094 | M30644 Mouse basic fibroblast growth factor (Fgfb) mRNA, complete cds | | | NM_008006 | 1447251 |
| IC02840 | 00/02 Literature | GENE | Mm.1329 | Mothers against DPP protein (mad homolog Smad 1, transforming growth factor beta signaling protein) | | | NM_010751 | 1448816 |
| IC02841 | UG75 Expression | GENE | Mm.22570 | TITLE HISTONE H1.1 | | | gi = 193851 | 1448924 |
| IC02842 | UG75 Expression | GENE | Mm.30787 | TITLE *Mus musculus* 85 kDa calcium-independent phospholipase A2 mRNA, complete cds | | | gi = 1857926 | 1449000 |
| IC02843 | UG75 Expression | GENE | Mm.34819 | TITLE *Mus musculus* PK-120 precursor (itih-4) mRNA, complete cds | | | gi = 2739027 | 1450604 |
| IC02844 | UG75 Expression | GENE | Mm.29008 | TITLE *Mus musculus* mRNA for IIGP protein | | | gi = 4158173 | 1450797 |
| IC02845 | UG75 Expression | GENE | Mm.20450 | TITLE *Mus musculus* GARP45 mRNA, complete cds | | | gi = 5263197 | 1451269 |
| IC02846 | UG75 Expression | GENE | Mm.42154 | TITLE *Mus musculus* mRNA for Trif, complete cds | | | gi = 4586406 | 1479185 |
| IC02847 | UG75 Expression | GENE | Mm.22776 | TITLE *Mus musculus* NIPI-like protein (NIPIL(A3)) mRNA, complete cds | | | gi = 1762985 | 1480460 |
| IC02848 | UG75 Expression | GENE | Mm.18728 | TITLE Mouse mRNA for TI-227 | | | gi = 1166394 | 1481165 |
| IC02849 | UG75 Expression | GENE | Mm.1999 | TITLE *Mus musculus* signaling molecule (ATTP) mRNA, complete cds | | | gi = 2098804 | 1481375 |
| IC02850 | UG75 Expression | GENE | Mm.15037 | TITLE *Mus musculus* clone IMAGE:349147 unknown protein mRNA, partial cds | | | gi = 1835752 | 1481574 |
| IC02851 | UG75 Expression | GENE | Mm.25165 | TITLE *Mus musculus* AF1q mRNA, complete cds | | | gi = 1816434 | 1481591 |
| IC02852 | UG75 Expression | GENE | Mm.6994 | TITLE *Mus musculus* amyloid beta-peptide binding protein (ERAB) mRNA, complete cds | | | gi = 2078283 | 1482047 |
| IC02853 | UG75 Expression | GENE | Mm.29453 | TITLE *Mus musculus* Sid329 mRNA, complete cds | | | gi = 5931548 | 1482106 |
| IC02854 | UG75 Expression | GENE | Mm.21482 | TITLE *Mus musculus* chloride ion current inducer protein (CLCI) mRNA, partial cds | | | gi = 1399647 | 1482667 |
| IC02855 | UG75 Expression | GENE | Mm.21961 | TITLE *Mus musculus* mRNA for C7-1 protein, complete cds | | | gi = 5771446 | 1494668 |
| IC02856 | UG75 Expression | GENE | Mm.7491 | TITLE *Mus musculus* Nmi mRNA, complete cds | | | gi = 2425059 | 1494862 |
| IC02857 | UG75 Expression | GENE | Mm.27578 | TITLE *Mus musculus* mRNA for Dlxin-1, complete cds | | | gi = 6520236 | 1499051 |
| IC02858 | UG75 Expression | GENE | Mm.41573 | TITLE *M.musculus* mRNA for fibromodulin | | | gi = 1160193 | 1499097 |
| IC02859 | UG75 Expression | GENE | Mm.7516 | TITLE *Mus musculus* somatic histone binding protein NASP mRNA, complete cds | | | gi = 2645972 | 1499195 |
| IC02860 | UG75 Expression | GENE | Mm.27896 | TITLE *Mus musculus* mRNA for cAMP-regulated phosphoprotein (ARPP-19) | | | gi = 4138189 | 1499311 |
| IC02861 | UG75 Expression | GENE | Mm.4098 | TITLE BRAIN PROTEIN E46 | | | gi = 50794 | 1499589 |
| IC02862 | UG75 Expression | GENE | Mm.7010 | TITLE Untitled | | | gi = 2546994 | 1499691 |
| IC02863 | UG75 Expression | GENE | Mm.25633 | TITLE *Mus musculus* spermatogenesis associated factor (SPAF) mRNA, complete cds | | | gi = 4105618 | 1499779 |
| IC02864 | UG75 Expression | GENE | Mm.28083 | TITLE *Mus musculus* mRNA for cell-surface sialomucin MGc-24, complete cds | | | gi = 5103294 | 1510681 |
| IC02865 | UG75 Expression | GENE | Mm.34869 | TITLE *M.musculus* mRNA for NADH dehydrogenase | | | gi = 2275036 | 1511194 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02866 | UG75 Expression | GENE | Mm.25072 | TITLE *Mus musculus* mRNA for Trf-proximal protein (Trfp gene) | | | gi = 5777875 | 1514761 |
| IC02867 | UG75 Expression | GENE | Mm.42242 | TITLE *Mus musculus* mRNA for Lim-homeodomain protein Islet1 | | | gi = 4469283 | 1616606 |
| IC02868 | UG75 Expression | GENE | Mm.22505 | TITLE *Mus musculus* putative steroid dehydrogenase (KIK-I) mRNA, complete cds | | | gi = 3142701 | 1749973 |
| IC02869 | 00/02 Literature | GENE | Mm.7883 | APC; Adenomatous Polyposis Coli protein | | | NM_007462 | 1764323 |
| IC02870 | UG75 Expression | GENE | Mm.4485 | TITLE *Mus musculus* RGL protein mRNA, complete cds | | | gi = 537276 | 1853422 |
| IC02871 | UG75 Expression | GENE | Mm.4494 | TITLE *M.musculus* mRNA for plakophilin 1 | | | gi = 1707593 | 1885570 |
| IC02872 | UG75 Expression | GENE | Mm.14526 | TITLE *Mus musculus* myosin light chain 2 mRNA, complete cds | | | gi = 1675395 | 1885673 |
| IC02873 | 00/02 Literature | GENE | Mm.1135 | J05118 Mouse mast cell carboxypeptidase A mRNA, complete cds | | | NM_007753 | 1885694 |
| IC02874 | UG75 Expression | GENE | Mm.30201 | TITLE *Mus musculus* short-chain dehydrogenase CRAD2 mRNA, complete cds | | | gi = 5931570 | 1885706 |
| IC02875 | UG75 Expression | GENE | Mm.6696 | cds | | | gi = 3294554 | 1885707 |
| IC02876 | UG75 Expression | GENE | Mm.1017 | TITLE *Mus musculus* mRNA for sid478p, complete cds | | | gi = 5931564 | 1885780 |
| IC02877 | UG75 Expression | GENE | Mm.37217 | TITLE Mouse complement factor H-related protein mRNA, complete cds, clone 13G1 | | | gi = 192559 | 1886334 |
| IC02878 | UG75 Expression | GENE | Mm.13694 | PRECURSOR | | | gi = 53458 | 1886580 |
| IC02879 | UG75 Expression | GENE | Mm.26782 | TITLE *Mus musculus* zinc finger protein 94 (Zfp94) mRNA, complete cds | | | gi = 4097496 | 1886879 |
| IC02880 | UG75 Expression | GENE | Mm.24565 | TITLE *Mus musculus* Tim23 mRNA for translocase of inner mitochondrial membrane, complete cds | | | gi = 4996327 | 1888596 |
| IC02881 | UG75 Expression | GENE | Mm.2379 | TITLE *M.musculus* mRNA for ASM-like phosphodiesterase 3a | | | gi = 1552349 | 1888917 |
| IC02882 | UG75 Expression | GENE | Mm.30076 | TITLE *Mus musculus* nuclear RNA helicase Bat1 mRNA, complete cds | | | gi = 4235115 | 1888985 |
| IC02883 | UG75 Expression | GENE | Mm.3485 | TITLE *Mus musculus* hemopexin mRNA, partial cds | | | gi = 1881767 | 1889460 |
| IC02884 | 00/02 Literature | GENE | Mm.57204 | Z46227 *M.musculus* gene for histone H1 | | | gi = 559479 | 1889637 |
| IC02885 | UG75 Expression | GENE | Mm.29454 | TITLE *Mus musculus* mRNA for epididymal secretory protein, complete cds | | | gi = 4038734 | 1890275 |
| IC02886 | UG75 Expression | GENE | Mm.27230 | TITLE *Mus musculus* mRNA for MSSP, complete cds | | | gi = 4730905 | 1907931 |
| IC02887 | UG75 Expression | GENE | Mm.9052 | TITLE *Mus musculus* putative membrane associated progesterone receptor component mRNA, complete cds | | | gi = 2801792 | 1908257 |
| IC02888 | UG75 Expression | GENE | Mm.18729 | TITLE *Mus musculus* beta prime coatomer protein mRNA, partial cds | | | gi = 2809536 | 1920325 |
| IC02889 | UG75 Expression | GENE | Mm.3716 | TITLE *Mus musculus* nucleolar protein (MSP58) mRNA, complete cds | | | gi = 2384718 | 1921088 |
| IC02890 | UG75 Expression | GENE | Mm.44552 | TITLE *Mus musculus* TXNRD1 mRNA for thioredoxin reductase 1, complete cds | | | gi = 6467192 | 1921276 |
| IC02891 | UG75 Expression | GENE | Mm.27343 | TITLE *Mus musculus* endomucin mRNA, complete cds | | | gi = 4159992 | 1922158 |
| IC02892 | UG75 Expression | GENE | Mm.42795 | TITLE *Mus musculus* mRNA for UBE-1c1, UBE-1c2, UBE-1c3, complete cds | | | gi = 5668736 | 1922266 |
| IC02893 | UG75 Expression | GENE | Mm.16790 | TITLE *Mus musculus* aldo-keto reductase mRNA, complete cds | | | gi = 1698717 | 1922534 |
| IC02894 | UG75 Expression | GENE | Mm.29460 | TITLE *Mus musculus* mRNA for adenylate kinase isozyme 2, complete cds | | | gi = 4760597 | 1923039 |
| IC02895 | UG75 Expression | GENE | Mm.2485 | TITLE *M.musculus* mRNA for C1D protein | | | gi = 1185124 | 1924987 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02896 | UG75 Expression | GENE | Mm.2605 | TITLE Mus musculus retinol binding protein (RBP) mRNA, complete cds | | | gi = 1515449 | 1924998 |
| IC02897 | 00/02 Literature | GENE | Mm.4563 | MRE-binding transcription factor | | | NM_008636 | 1969422 |
| IC02898 | UG75 Expression | GENE | Mm.29698 | TITLE Mus musculus mRNA similar to human Sua1, complete cds | | | gi = 5689241 | 1969668 |
| IC02899 | UG75 Expression | GENE | Mm.2982 | TITLE Mus musculus hsp40 mRNA for heat shock protein 40, complete cds | | | gi = 6531981 | 1969809 |
| IC02900 | UG75 Expression | GENE | Mm.37672 | TITLE Mus musculus IKK-i mRNA for inducible IKappaB kinase, complete cds | | | gi = 6012173 | 1969939 |
| IC02901 | UG75 Expression | GENE | Mm.10818 | TITLE Mus musculus syntaxin 7 (Syn7) mRNA, complete cds | | | gi = 3123923 | 1970284 |
| IC02902 | UG75 Expression | GENE | Mm.34562 | TITLE Mus musculus mRNA for mSART-1(806), complete cds | | | gi = 4126468 | 1970588 |
| IC02903 | UG75 Expression | GENE | Mm.28100 | TITLE Mus musculus mRNA for L-specific multifunctional beta-oxidation protein, partial CDS | | | gi = 5830359 | 1970885 |
| IC02904 | UG75 Expression | GENE | Mm.10133 | TITLE Mus musculus putative ras effector Nore1 mRNA, complete cds | | | gi = 2997697 | 1971377 |
| IC02905 | UG75 Expression | GENE | Mm.13430 | TITLE Mus musculus unknown protein mRNA, complete cds | | | gi = 2183322 | 1971615 |
| IC02906 | UG75 Expression | GENE | Mm.13162 | TITLE Mus musculus ERG-associated protein ESET mRNA, complete cds | | | gi = 3644041 | 1971619 |
| IC02907 | UG75 Expression | GENE | Mm.27783 | TITLE Mus musculus mRNA for Ariadne protein, partial | | | gi = 3925718 | 1972136 |
| IC02908 | 00/02 Literature | GENE | Mm.14105 | DNAse I | | | NM_010061 | 1972180 |
| IC02909 | UG75 Expression | GENE | Mm.29546 | TITLE Mus musculus BAF53a (Baf53a) mRNA, complete cds | | | gi = 4001804 | 1972181 |
| IC02910 | UG75 Expression | GENE | Mm.331 | TITLE Mouse mRNA for TI-225, complete cds | | | gi = 3863211 | 1972252 |
| IC02911 | UG75 Expression | GENE | Mm.6856 | TITLE Mus musculus pituitary tumor transforming gene protein (PTTG) mRNA, complete cds | | | gi = 3978251 | 2064867 |
| IC02912 | UG75 Expression | GENE | Mm.30185 | TITLE Mus musculus mRNA expressed in renal proximal tubles | | | gi = 5030943 | 2064927 |
| IC02913 | UG75 Expression | GENE | Mm.30352 | TITLE Mus musculus mRNA for choline/ethanolamine kinase, complete cds | | | gi = 2897730 | 2064929 |
| IC02914 | UG75 Expression | GENE | Mm.1109 | TITLE Mus musculus WW-domain binding protein 1 mRNA, complete cds | | | gi = 1775576 | 2064966 |
| IC02915 | UG75 Expression | GENE | Mm.1570 | TITLE Mus musculus ubiquitin conjugating enzyme (ubc4) mRNA, complete cds | | | gi = 1480741 | 2064976 |
| IC02916 | UG75 Expression | GENE | Mm.18630 | TITLE M.musculus mitochondrial mRNA for very-long-chain acyl-CoA dehydrogenase | | | gi = 1279564 | 2076597 |
| IC02917 | 00/02 Literature | GENE | Mm.57120 | X16496 Murine H3.1 gene for histone H3.1 | | | gi = 51326 | 2076773 |
| IC02918 | UG75 Expression | GENE | Mm.2112 | TITLE Mus musculus peroxisomal/mitochondrial dienoyl-CoA isomerase ECH1p (Ech1) mRNA, complete cds | | | gi = 2606085 | 2076790 |
| IC02919 | UG75 Expression | GENE | Mm.22676 | TITLE Mouse replication-dependent histone H2A.1 gene | | | gi = 1290268 | 2076817 |
| IC02920 | UG75 Expression | GENE | Mm.5567 | TITLE Mus musculus carboxyl terminal LIM domain protein (Ldb3) mRNA, complete cds | | | gi = 2996195 | 2076828 |
| IC02921 | UG75 Expression | GENE | Mm.3960 | TITLE Mus musculus interferon regulatory factor 3 (mirf3) mRNA, alternatively spliced, complete cds | | | gi = 1658532 | 2088085 |
| IC02922 | UG75 Expression | GENE | Mm.10681 | TITLE Mus musculus osf-2 mRNA for osteoblast specific factor 2, complete cds | | | gi = 393321 | 2088188 |
| IC02923 | UG75 Expression | GENE | Mm.25203 | TITLE MEMBRANE-ASSOCIATED PROTEIN HEM-2 | | | gi = 51135 | 2109309 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02924 | UG75 Expression | GENE | Mm.7013 | TITLE Mus musculus KOI-4 gene, partial cds | | | gi = 2623677 | 2099836 |
| IC02925 | UG75 Expression | GENE | Mm.38470 | TITLE Mus musculus DNaseI precursor mRNA, complete cds | | | gi = 437052 | 2123030 |
| IC02926 | UG75 Expression | GENE | Mm.5831 | TITLE Mus musculus RNAse L inhibitor (Mu-RLI) mRNA, complete cds | | | gi = 3273416 | 2123679 |
| IC02927 | UG75 Expression | GENE | Mm.3118 | TITLE Mus musculus mRNA for actin-related protein 1 alpha-isoform, complete cds | | | gi = 2804291 | 2135509 |
| IC02928 | UG75 Expression | GENE | Mm.28919 | TITLE Mus musculus mRNA for sid23p, complete cds | | | gi = 5931560 | 2135732 |
| IC02929 | UG75 Expression | GENE | Mm.29404 | TITLE Mus musculus Ste-20 related kinase SPAK mRNA, complete cds | | | gi = 3851168 | 2135848 |
| IC02930 | UG75 Expression | GENE | Mm.6670 | TITLE Mus musculus AMP activated protein kinase mRNA, complete cds | | | gi = 2766684 | 2136735 |
| IC02931 | UG75 Expression | GENE | Mm.28761 | TITLE Mus musculus Ste20-like kinase mRNA, complete cds | | | gi = 4101577 | 2158843 |
| IC02932 | UG75 Expression | GENE | Mm.34747 | TITLE Mus musculus pancreas sodium bicarbonate cotransporter mRNA, complete cds | | | gi = 3298571 | 2159587 |
| IC02933 | UG75 Expression | GENE | Mm.28510 | TITLE Mus musculus mRNA for Zinc finger protein s11-6, complete cds | | | gi = 3953592 | 2159854 |
| IC02934 | 00/02 Literature | GENE | Mm.5087 | U67610 Mus musculus fibroblast growth factor 1 (FGF-1) mRNA, complete cds | | | NM_010197 | 2182203 |
| IC02935 | UG75 Expression | GENE | Mm.27330 | TITLE Mus musculus BAF57 (Baf57) gene, complete cds | | | gi = 2914754 | 2182326 |
| IC02936 | UG75 Expression | GENE | Mm.30051 | TITLE Mus musculus mRNA for RIE2, complete cds | | | gi = 5931597 | 2182520 |
| IC02937 | UG75 Expression | GENE | Mm.8655 | TITLE COMPLEMENT FACTOR H PRECURSOR | | | gi = 193724 | 2182630 |
| IC02938 | UG75 Expression | GENE | Mm.19170 | TITLE Mus musculus mRNA for initiation factor 2-associated 67 kDa protein, complete cds | | | gi = 2055253 | 2182835 |
| IC02939 | UG75 Expression | GENE | Mm.1561 | TITLE Mus musculus Nip2l mRNA, complete cds | | | gi = 2911347 | 2192217 |
| IC02940 | UG75 Expression | GENE | Mm.20476 | TITLE Mus musculus vacuolar adenosine triphosphatase subunit C mRNA, complete cds | | | gi = 3955097 | 2192544 |
| IC02941 | UG75 Expression | GENE | Mm.67998 | TITLE Mus musculus mRNA for transcription factor CA150b, complete cds | | | gi = 6329165 | 2225475 |
| IC02942 | 00/02 Literature | GENE | Mm.12286 | Arachidonate 12-lipoxygenase | | | NM_007440 | 2225529 |
| IC02943 | UG75 Expression | GENE | Mm.4438 | TITLE Mouse chromatin nonhistone high mobility group protein (HGM-I(Y), complete cds | | | gi = 193883 | 2225576 |
| IC02944 | UG75 Expression | GENE | Mm.2758 | TITLE Mus musculus 14-3-3 protein sigma mRNA, complete cds | | | gi = 3065926 | 2225735 |
| IC02945 | UG75 Expression | GENE | Mm.29874 | TITLE Mus musculus mRNA for myeloid associated differentiation protein | | | gi = 2463264 | 2225812 |
| IC02946 | UG75 Expression | GENE | Mm.28680 | TITLE Mus musculus prenylated SNARE protein Ykt6 (Ykt6) mRNA, complete cds | | | gi = 3328384 | 2225909 |
| IC02947 | UG75 Expression | GENE | Mm.10808 | TITLE Mus musculus RW1 protein mRNA, complete cds | | | gi = 3091277 | 2235997 |
| IC02948 | UG75 Expression | GENE | Mm.28385 | TITLE Mus musculus mRNA for Clast1, complete cds | | | gi = 5804793 | 2236072 |
| IC02949 | UG75 Expression | GENE | Mm.42578 | TITLE Mus musculus 60S ribosomal protein (A52) mRNA, complete cds | | | gi = 899444 | 2236462 |
| IC02950 | UG75 Expression | GENE | Mm.14255 | TITLE Mus musculus proline-rich protein 48 mRNA, partial cds | | | gi = 2624971 | 2285976 |
| IC02951 | UG75 Expression | GENE | Mm.14744 | TITLE Mus musculus syntenin mRNA, complete cds | | | gi = 2197105 | 2317639 |
| IC02952 | UG75 Expression | GENE | Mm.17167 | TITLE Mus musculus IFN-gamma induced (Mg11) mRNA, complete cds | | | gi = 558902 | 2317689 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02953 | UG75 Expression | GENE | Mm.42960 | TITLE M.musculus (C57 Black/6X CBA) LAL mRNA for lysosomal acid lipase | | | gi = 4456670 | 2331775 |
| IC02954 | UG75 Expression | GENE | Mm.29896 | TITLE Mus musculus ribosomal protein L21 mRNA, complete cds | | | gi = 1938403 | 2331841 |
| IC02955 | UG75 Expression | GENE | Mm.13725 | TITLE Mus musculus Paneth cell enhanced expression PCEE mRNA, complete cds | | | gi = 1276644 | 2332175 |
| IC02956 | UG75 Expression | GENE | Mm.3935 | TITLE Mus musculus ATP-dependent RNA helicase mRNA, partial cds | | | gi = 1262844 | 2372644 |
| IC02957 | UG75 Expression | GENE | Mm.42088 | TITLE Mus musculus fetal globin inducing factor mRNA, complete cds | | | gi = 4103856 | 2395235 |
| IC02958 | UG75 Expression | GENE | Mm.29076 | TITLE Mouse testis abundant mRNA sequence | | | gi = 347399 | 2463233 |
| IC02959 | UG75 Expression | GENE | Mm.6775 | TITLE Mus musculus antizyme inhibitor mRNA, complete cds | | | gi = 2645700 | 2536640 |
| IC02960 | UG75 Expression | GENE | Mm.1815 | TITLE Mus musculus CTP synthetase mRNA, complete cds | | | gi = 1515356 | 2581966 |
| IC02961 | 00/02 Literature | GENE | Mm.5014 | X92397 M.musculus mRNA for Norrie disease gene product | | | NM_010883 | 2582262 |
| IC02962 | UG75 Expression | GENE | Mm.26926 | TITLE Mouse mRNA for neurotrophin receptor interacting factor (Zfp110 gene) | | | gi = 5706478 | 2598965 |
| IC02963 | UG75 Expression | GENE | Mm.22711 | TITLE Mus musculus cyclin I mRNA, complete cds | | | gi = 4101686 | 2599137 |
| IC02964 | UG75 Expression | GENE | Mm.35829 | TITLE Mus musculus mRNA for erythroid differentiation regulator, partial | | | gi = 3336885 | 2615851 |
| IC02965 | UG75 Expression | GENE | Mm.6957 | TITLE M.musculus RPS3a gene | | | gi = 1841931 | 2631380 |
| IC02966 | UG75 Expression | GENE | Mm.1457 | TITLE Mus musculus unknown mRNA, complete cds | | | gi = 2183320 | 2631700 |
| IC02967 | UG75 Expression | GENE | Mm.29025 | TITLE Mus musculus dynactin light chain (P24) mRNA, complete cds | | | gi = 423147 | 2645585 |
| IC02968 | UG75 Expression | GENE | Mm.28082 | TITLE Mus musculus protein phosphatase X (Ppx) mRNA, complete cds | | | gi = 4028534 | 2645893 |
| IC02969 | UG75 Expression | GENE | Mm.25198 | TITLE Mus musculus mRNA for Sid6061p, complete cds | | | gi = 5931550 | 2645948 |
| IC02970 | UG75 Expression | GENE | Mm.3511 | TITLE Mus musculus matrilin-2 precursor mRNA, complete cds | | | gi = 2072791 | 2646608 |
| IC02971 | UG75 Expression | GENE | Mm.1664 | TITLE Mus musculus mRNA for Rab33B, complete cds | | | gi = 2516240 | 2646624 |
| IC02972 | UG75 Expression | GENE | Mm.16784 | TITLE Mus musculus phosphatidylethanolamine binding protein mRNA, complete cds | | | gi = 1517863 | 2646999 |
| IC02973 | UG75 Expression | GENE | Mm.12909 | TITLE Mus musculus X11gamma protein mRNA, complete cds | | | gi = 3264793 | 2647311 |
| IC02974 | UG75 Expression | GENE | Mm.3233 | TITLE Mus musculus interferon regulatory factor 7 (mirf7) mRNA, complete cds | | | gi = 1663639 | 2647806 |
| IC02975 | 00/02 Literature | GENE | Mm.30024 | U25633 Mus musculus tumor-associated membrane protein (TMP) mRNA, complete cds | | | NM_010128 | 2648678 |
| IC02976 | 00/02 Literature | GENE | Mm.5025 | Ets-related protein PEA 3 | | | NM_008815 | 2650132 |
| IC02977 | UG75 Expression | GENE | Mm.44161 | TITLE Mus musculus MHC class III region RD gene, partial cds; Bf, C2, G9A, NG22, G9, HSP70, HSP70, HSC70t, and smRNP genes, complete cds; G7A gene, partial cds; and unknown genes | | | gi = 3986763 | 2650258 |
| IC02978 | UG75 Expression | GENE | Mm.28155 | TITLE Mus musculus MHC class III region RD gene, partial cds; Bf, C2, G9A, NG22, G9, HSP70, HSP70, HSC70t, and smRNP genes, complete cds; G7A gene, partial cds; and unknown genes | | | gi = 3986763 | 2650258 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC02979 | UG75 Expression | GENE | Mm.27218 | TITLE Mus musculus mRNA for Sid393p, complete cds | | | gi = 5931552 | 2650339 |
| IC02980 | UG75 Expression | GENE | Mm.858 | | | | gi = 1806594 | 2654169 |
| IC02981 | UG75 Expression | GENE | Mm.34234 | TITLE Mus musculus mRNA for spastin protein orthologue (Spast gene) | | | gi = 6273571 | 2654382 |
| IC02982 | UG75 Expression | GENE | Mm.29827 | TITLE Mus musculus mRNA for p100 co-activator, complete cds | | | gi = 6009520 | 2654788 |
| IC02983 | UG75 Expression | GENE | Mm.8403 | TITLE Mus musculus peroxisomal acyl-CoA oxidase (muspaox) mRNA, complete cds | | | gi = 2253379 | 2655293 |
| IC02984 | UG75 Expression | GENE | Mm.20921 | TITLE Mus musculus immunosuperfamily protein BI2 mRNA, complete cds | | | gi = 3779241 | 2655411 |
| IC02985 | UG75 Expression | GENE | Mm.4593 | TITLE House mouse; Musculus domesticus mRNA for UDP-galactose transporter related isozyme 1, complete cds | | | gi = 1694638 | 2655782 |
| IC02986 | UG76 LID366 B cell | GENE | Mm.46802 | TITLE Mouse Ig active kappa-chain V-region (V139-J1) mRNA from anti-DNP specific hybridoma TF5-139 | | | gi = 196473 | 2698971 |
| IC02987 | UG75 Expression | GENE | Mm.39082 | TITLE M.musculus mRNA for TAFI68 | | | gi = 1842205 | 2748936 |
| IC02988 | UG75 Expression | GENE | Mm.28746 | TITLE Mus musculus YGR163w mRNA homologue, complete cds | | | gi = 4519622 | 2748938 |
| IC02989 | UG75 Expression | GENE | Mm.10082 | TITLE Mus musculus mRNA for huntingtin interacting protein-2, complete cds | | | gi = 2897817 | 2749158 |
| IC02990 | UG75 Expression | GENE | Mm.2632 | TITLE Mus musculus mRNA for latexin, complete cds | | | gi = 1669620 | 2780939 |
| IC02991 | UG75 Expression | GENE | Mm.7103 | TITLE Mus musculus transcription factor PBX2 (PBX2) mRNA, complete cds | | | gi = 2432012 | 2803152 |
| IC02992 | UG75 Expression | GENE | Mm.2115 | TITLE Mus musculus heterogenous nuclear ribonucleoprotein U (hnRNP U) mRNA, complete cds | | | gi = 3329495 | 2810763 |
| IC02993 | UG75 Expression | GENE | Mm.27657 | TITLE Mus musculus C184L-22 mRNA, complete cds | | | gi = 6469043 | 2810863 |
| IC02994 | UG75 Expression | GENE | Mm.10726 | TITLE Mus musculus mRNA for nuclear protein stag3 | | | gi = 3090422 | 2811449 |
| IC02995 | 00/02 Literature | GENE | Mm.34810 | Mdm2; p53-regulating protein | | | NM_010786 | 2811638 |
| IC02996 | UG75 Expression | GENE | Mm.42029 | TITLE Mus musculus mRNA for monocyte chemoattractant protein-2 (MCP-2) precursor, complete cds | | | gi = 4579906 | 2812116 |
| IC02997 | UG75 Expression | GENE | Mm.28375 | TITLE Mus musculus Sec61 mRNA, complete cds | | | gi = 6012185 | 2937159 |
| IC02998 | UG75 Expression | GENE | Mm.2820 | TITLE Mus musculus galK mRNA for galactokinase, complete cds | | | gi = 5931607 | 2937983 |
| IC02999 | UG75 Expression | GENE | Mm.4312 | TITLE Mus musculus Na+/H+ exchanger (NHE-1) mRNA, complete cds | | | gi = 1236707 | 2938724 |
| IC03000 | UG75 Expression | GENE | Mm.28479 | TITLE M.musculus mRNA for Pr22 protein | | | gi = 1326477 | 2938831 |
| IC03001 | UG75 Expression | GENE | Mm.41434 | TITLE Mus musculus PAR-6 (Par6) mRNA, complete cds | | | gi = 4322035 | 2938880 |
| IC03002 | UG75 Expression | GENE | Mm.86904 | TITLE Mus musculus alpha-endosulfine (complete coding sequence) | | | gi = 4138191 | 2938997 |
| IC03003 | UG75 Expression | GENE | Mm.24680 | TITLE Mus musculus aspartyl aminopeptidase mRNA, complete cds | | | gi = 4101590 | 2939050 |
| IC03004 | UG75 Expression | GENE | Mm.20843 | TITLE Mus musculus mitochondrial outer membrane protein (Tom40) mRNA, nuclear gene encoding mitochondrial protein, complete cds | | | gi = 3941339 | 2939099 |
| IC03005 | UG75 Expression | GENE | Mm.4419 | TITLE M.musculus mRNA for ribosomal protein L5, 3′end | | | gi = 1309668 | 2939259 |
| IC03006 | UG75 Expression | GENE | Mm.18565 | TITLE Mus musculus Plp2 mRNA for proteolipid protein 2, complete cds | | | gi = 5771450 | 2939478 |
| IC03007 | UG75 Expression | GENE | Mm.5181 | TITLE M.musculus GFG-154 mRNA | | | gi = 951301 | 2939653 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03008 | UG75 Expression | GENE | Mm.916 | TITLE *Mus musculus* histone H2A.Z (H2A.Z) mRNA, complete cds | | | gi = 1575712 | 2939696 |
| IC03009 | UG75 Expression | GENE | Mm.10019 | TITLE *Mus musculus* Src-associated adaptor protein (Saps) mRNA, complete cds | | | gi = 4091779 | 3025704 |
| IC03010 | 00/02 Literature | GENE | Mm.57119 | X16495 Murine H2A gene for histone H2A | | | gi = 51324 | 2101892 |
| IC03011 | UG75 Expression | GENE | Mm.42083 | TITLE *Mus musculus* phospholipase C-beta-1a mRNA, complete cds | | | gi = 4099294 | 3025748 |
| IC03012 | UG75 Expression | GENE | Mm.24782 | TITLE *Mus musculus* mRNA for ABINs, (A20-binding inhibitor of NF-kappa B activation (small) | | | gi = 4995752 | 3025922 |
| IC03013 | UG75 Expression | GENE | Mm.28719 | TITLE *Mus musculus* WSB-1 mRNA, complete cds | | | gi = 2766488 | 3025933 |
| IC03014 | UG75 Expression | GENE | Mm.20844 | TITLE *Mus musculus* myotubularin homologous protein 3 mRNA, partial cds | | | gi = 3916225 | 3153414 |
| IC03015 | UG75 Expression | GENE | Mm.60590 | TITLE *Mus musculus* partial mRNA for myosin X (myo 10 gene) | | | gi = 5921504 | 3154667 |
| IC03016 | UG75 Expression | GENE | Mm.22130 | TITLE Mouse MARib mRNA for ribophorin, complete cds | | | gi = 1468960 | 3154859 |
| IC03017 | UG75 Expression | GENE | Mm.27983 | TITLE *M.musculus* es64 mRNA | | | gi = 951299 | 3155179 |
| IC03018 | UG75 Expression | GENE | Mm.1483 | TITLE *Mus musculus* non-receptor protein tyrosine kinase Ack mRNA, complete cds | | | gi = 2921446 | 3155587 |
| IC03019 | UG75 Expression | GENE | Mm.20933 | TITLE *Mus musculus* tuftelin-interacting protein 10 mRNA, complete cds | | | gi = 3851163 | 3155826 |
| IC03020 | UG75 Expression | GENE | Mm.21772 | TITLE Mouse beta-D-galactosidase fusion protein mRNA, complete cds | | | gi = 192154 | 3155846 |
| IC03021 | UG75 Expression | GENE | Mm.42195 | TITLE *Mus musculus* Pontin52 mRNA, complete cds | | | gi = 4106527 | 3155875 |
| IC03022 | UG75 Expression | GENE | Mm.4117 | cds | | | gi = 1375486 | 3167613 |
| IC03023 | UG75 Expression | GENE | Mm.1405 | TITLE *Mus musculus* WW-domain binding protein 2 mRNA, complete cds | | | gi = 1777578 | 317113 |
| IC03024 | UG75 Expression | GENE | Mm.7281 | TITLE *Mus musculus* mRNA for collagen a1(V), complete cds | | | gi = 3219171 | 317811 |
| IC03025 | UG75 Expression | GENE | Mm.43737 | TITLE *M.musculus* mRNA for casein kinase I-alpha | | | gi = 1287794 | 318387 |
| IC03026 | UG75 Expression | GENE | Mm.2299 | TITLE Mouse non-MHC restricted associated molecule (2B4) mRNA, complete cds | | | gi = 309076 | 329566 |
| IC03027 | 00/02 Literature | GENE | Mm.4723 | X73580 *M.musculus* mRNA for secretin | | | NM_011328 | 329994 |
| IC03028 | 00/02 Literature | GENE | Mm.35826 | Cf2r; coagulation factor II (thrombin) receptor | | | NM_010169 | 337258 |
| IC03029 | UG75 Expression | GENE | Mm.4111 | TITLE *M.musculus* mRNA for s17 protein | | | gi = 563530 | 348123 |
| IC03030 | UG75 Expression | GENE | Mm.757 | TITLE *Mus musculus* Rho family GTPase (ArhA) mRNA, complete cds | | | gi = 3237319 | 348274 |
| IC03031 | UG75 Expression | GENE | Mm.44615 | TITLE *Mus musculus* golgi SNARE (GS27) mRNA, complete cds | | | gi = 2316091 | 348869 |
| IC03032 | 00/02 Literature | GENE | Mm.8858 | Nuclear hormone receptor ROR-ALPHA-1 | | | NM_013646 | 350310 |
| IC03033 | UG75 Expression | GENE | Mm.3797 | TITLE NUCLEOSOME ASSEMBLY PROTEIN 1-LIKE 1 | | | gi = 220495 | 351029 |
| IC03034 | UG75 Expression | GENE | Mm.3973 | TITLE *Mus musculus* syntaxin-like protein 3135 mRNA, complete cds | | | gi = 3747021 | 351323 |
| IC03035 | UG75 Expression | GENE | Mm.29467 | TITLE *Mus musculus* Ras-like GTP-binding protein Rad mRNA, complete cds | | | gi = 3462897 | 352112 |
| IC03036 | UG75 Expression | GENE | Mm.7331 | TITLE *Mus musculus* transcription factor PBX3b (PBX3b) mRNA, complete cds | | | gi = 243016 | 353290 |
| IC03037 | UG75 Expression | GENE | Mm.2507 | TITLE *Mus* gene for DJ-1, complete cds | | | gi = 3256342 | 354911 |
| IC03038 | UG75 Expression | GENE | Mm.27065 | TITLE *Mus musculus* mRNA for Sid470p, complete cds | | | gi = 5931554 | 355238 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03039 | UG75 Expression | GENE | Mm.6805 | TITLE Mus musculus p160 myb-binding protein (P160) mRNA, complete cds | | | gi = 2645204 | 355282 |
| IC03040 | UF75 Expression | GENE | Mm.9845 | TITLE Mus musculus thrombospondin 3 (Thbs3) gene, partial cds and mucin 1 (Muc1) gene, complete cds | | | gi = 608488 | 355433 |
| IC03041 | UG76 LID366 B cell | GENE | Mm.42166 | TITLE M. musculus mRNA for map kinase interacting kinase, Mnk2 | | | gi = 1929060 | 355494 |
| IC03042 | UG75 Expression | GENE | Mm.12897 | TITLE Mus musculus mRNA for platelet glycoprotein IX, complete cds | | | gi = 3327259 | 355508 |
| IC03043 | UG75 Expression | GENE | Mm.30098 | TITLE Mus musculus mRNA for GANP protein | | | gi = 4995702 | 367240 |
| IC03044 | 00/02 Literature | GENE | Mm.849 | U09218 Mouse serine/threonine phophatase-2C (PP2C) mRNA, complete cds | | | gi = 484099 | 367507 |
| IC03045 | UG75 Expression | GENE | Mm.1348 | TITLE BRAIN PROTEIN I54 | | | gi = 51480 | 370963 |
| IC03046 | UG75 Expression | GENE | Mm.911 | 17 | | | gi = 51336 | 371160 |
| IC03047 | UG75 Expression | GENE | Mm.3533 | TITLE Mus musculus thioredoxin mRNA, nuclear gene encoding mitochondrial protein, complete cds | | | gi = 1814410 | 372567 |
| IC03048 | UG75 Expression | GENE | Mm.20913 | TITLE Mus musculus suppressor of while apricot homolog 2 (Swap2) mRNA, complete cds | | | gi = 3941323 | 372954 |
| IC03049 | UG75 Expression | GENE | Mm.17869 | TITLE Mus musculus ATP synthase beta-subunit (beta-F1 ATPase) mRNA, nuclear gene encoding mitochondrial protein, complete cds | | | gi = 2623221 | 373127 |
| IC03050 | UG75 Expression | GENE | Mm.20891 | TITLE Mus musculus Hbp mRNA for Hrs binding Protein, complete cds | | | gi = 3721564 | 388453 |
| IC03051 | UG75 Expression | GENE | Mm.20521 | TITLE Mus musculus strain C3H histone deacetylase 3 (Hdac3) mRNA, complete cds | | | gi = 3639053 | 389406 |
| IC03052 | UG75 Expression | GENE | Mm.28392 | TITLE Mus musculus deformed epidermal autoregulatory factor 1 mRNA, complete cds | | | gi = 4063897 | 390207 |
| IC03053 | UG75 Expression | GENE | Mm.10799 | TITLE Mus musculus homeobox protein PKNOX1 (Pknox1) mRNA, complete cds | | | gi = 3126848 | 391583 |
| IC03054 | UG75 Expression | GENE | Mm.3955 | TITLE Mus musculus mRNA for eIF3 p66, complete cds | | | gi = 2992163 | 391597 |
| IC03055 | UG75 Expression | GENE | Mm.4633 | TITLE Mouse small nuclear RNA (Rnu1a-1) mRNA, complete cds | | | gi = 349003 | 403022 |
| IC03056 | UG75 Expression | GENE | Mm.11376 | TITLE M. musculus mRNA for ribosomal protein L36 | | | gi = 443801 | 407241 |
| IC03057 | UG75 Expression | GENE | Mm.4992 | TITLE Mouse 19.5 mRNA, complete cds | | | gi = 6241166 | 420323 |
| IC03058 | 00/02 Literature | GENE | Mm.1347 | H2.0-like homeo box gene | | | NM_008250 | 423176 |
| IC03059 | 00/02 Literature | GENE | Mm.16554 | U24233 Mus musculus huntingtin (Hd) mRNA, complete cds | | | gi = 902003 | 424332 |
| IC03060 | UG75 Expression | GENE | Mm.27291 | TITLE Mus musculus bystin mRNA, complete cds | | | gi = 2738508 | 424948 |
| IC03061 | UG75 Expression | GENE | Mm.10721 | TITLE Mus musculus multiple endocrine neoplasia type 1 candidate protein number 18 mRNA, complete cds | | | gi = 3136115 | 426261 |
| IC03062 | UG75 Expression | GENE | Mm.29710 | TITLE Mouse mRNA for thymic epithelial cell surface antigen, complete cds | | | gi = 2059325 | 437011 |
| IC03063 | UG75 Expression | GENE | Mm.29513 | TITLE Mus musculus major histocompatibility complex region NG27, NG28, RPS28, NADH oxidoreductase. NG29, KIFC1, Fas-binding protein, BING1, tapasin, RalGDS-like, KE2, BING4, beta 1,3-galactosyl transferase, and RPS18 genes, complete cds; Sacm21 gene, partial cds; and unknown gene | | | gi = 4050090 | 439537 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03064 | UG75 Expression | GENE | Mm.29088 | TITLE *Mus musculus* major histocompatibility complex region NG27, NH28, RPS28, NADH oxidoreductase, NH29, KIFC1, Fas-binding protein, BING1, tapasin, RalGDS-like, KE2, BING4, beta 1,3-galactosyl transferase, and RPS18 genes, complete cds; Sacm21 gene, partial cds; and unknown gene | | | gi = 4050090 | 439537 |
| IC03065 | UG75 Expression | GENE | Mm.26992 | TITLE *Mus musculus* major histocompatibility complex region NG27, NG28, RPS28, NADH oxidoreductase, NH29, KIFC1, Fas-binding protein, BING1, tapasin, RalGDS-like, KE2, BING4, beta 1,3-galactosyl transferase, and RPS18 genes, complete cds; Sacm21 gene, partial cds; and unknown gene | | | gi = 4050090 | 439537 |
| IC03066 | UG75 Expression | GENE | Mm.11175 | TITLE *Mus musculus* major histocompatibility complex region NG27, NG28, RPS28, NADH oxidoreductase, NG29, KIFC1, Fas-binding protein, BING1, tapasin, RalGDS-like, KE2, BING4, beta 1,3-galactosyl transferase, and RPS18 genes, complete cds; Sacm21 gene, partial cds; and unknown gene | | | gi = 4050090 | 439537 |
| IC03067 | UG75 Expression | GENE | Mm.19169 | TITLE *Mus musculus* thioredoxin-related protein mRNA, complete cds | | | gi = 2970690 | 440273 |
| IC03068 | 00/02 Literature | GENE | Mm.1359 | uPAR1; urokinase plasminogen activator surface receptor (CD87) | | | NM_011113 | 442112 |
| IC03069 | 00/02 Literature | GENE | Mm.4845 | X74216 *M. musculus* mRNA for transcription activator AP-2 | | | NM_011547 | 456460 |
| IC03070 | UG75 Expression | GENE | Mm.28489 | TITLE Mouse mRNA for KIFC1, complete cds | | | gi = 2766492 | 457100 |
| IC03071 | UG75 Expression | GENE | Mm.29561 | TITLE *Mus musculus* mRNA for cathepsin F | | | gi = 4826564 | 463340 |
| IC03072 | UG75 Expression | GENE | Mm.16779 | TITLE RAS-RELATED PROTEIN RAL-A | | | gi = 1107741 | 463767 |
| IC03073 | UG75 Expression | GENE | Mm.10802 | TITLE *Mus musculus* 14-3-3 protein gamma mRNA, complete cds | | | gi = 3065928 | 464892 |
| IC03074 | UG75 Expression | GENE | Mm.20350 | TITLE *Mus musculus* Max-interacting transcriptional repressor (Mad3) mRNA, complete cds | | | gi = 1184156 | 464953 |
| IC03075 | UG75 Expression | GENE | Mm.18590 | TITLE Mouse mRNA for PE31/TALLA, complete cds | | | gi = 685220 | 465873 |
| IC03076 | 00/02 Literature | GENE | Mm.57097 | X07540 Mouse c-abl gene exon 1 of type II mRNA | | | gi = 49835 | 474966 |
| IC03077 | UG75 Expression | GENE | Mm.29908 | TITLE *Mus musculus* protein inhibitor of nitric oxide synthase (PIN) mRNA, complete cds | | | gi = 4103058 | 475264 |
| IC03078 | UG75 Expression | GENE | Mm.3501 | TITLE Mouse mRNA for KIFC1, complete cds | | | gi = 1944327 | 475904 |
| IC03079 | UG75 Expression | GENE | Mm.24772 | TITLE *Mus musculus* mRNA for MMRP19, complete cds | | | gi = 5103282 | 477887 |
| IC03080 | UG75 Expression | GENE | Mm.9590 | TITLE *Mus musculus* mRNA for NAKAP95, complete cds | | | gi = 5931619 | 478569 |
| IC03081 | UG75 Expression | GENE | Mm.3899 | HCNGP | | | gi = 57911 | 478924 |
| IC03082 | 00/02 Literature | GENE | Mm.57203 | Transcription factor C 1 | | | NM_008224 | 479409 |
| IC03083 | UG75 Expression | GENE | Mm.1838 | TITLE *Mus musculus* endobrevin mRNA, complete cds | | | gi = 2982367 | 479430 |
| IC03084 | UG75 Expression | GENE | Mm.1540 | TITLE *Mus musculus* eIF-1A (eIF-1A) mRNA, complete cds | | | gi = 3746339 | 479742 |
| IC03085 | UG75 Expression | GENE | Mm.20879 | TITLE *Mus musculus* mRNA for leptin receptor gene-related protein | | | gi = 3688429 | 481759 |
| IC03086 | 00/02 Literature | GENE | Mm.15595 | U62675 *Mus musculus* histone H3.2-616 (H3-616), and histone H2b-616 (H2b-616) genes, complete cds | | | gi = 19359 | 481894 |
| IC03087 | UG75 Expression | GENE | Mm.6379 | TITLE *Mus musculus* neutral amino acid transporter mASCT1, mRNA, complete cds | | | gi = 2459560 | 493422 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03088 | UG75 Expression | GENE | Mm.21579 | TITLE Mus musculus histone H2b mRNA, 3– end | | | gi = 556309 | 514032 |
| IC03089 | UG75 Expression | GENE | Mm.654 | TITLE LYSOZYME C, TYPE M PRECURSOR | | | gi = 198950 | 514126 |
| IC03090 | 00/02 Literature | GENE | Mm.18470 | U01840 Mus musculus serine/threonine kinase (tsk-1) mRNA, complete cds | | | NM_009435 | 516363 |
| IC03091 | UG75 Expression | GENE | Mm.34697 | TITLE Mus musculus major histocompatibility locus class III region: complement C4 (C4) and cytochrome P450 hydroxylase A (CYP21OH-A) genes, complete cds; slp pseudogene, complete sequence; NG6, SKI, and complement factor B (Bf) genes, complete cds; and complement factor C2 (C2) gene, partial cds | | | gi = 2944418 | 520507 |
| IC03092 | UG75 Expression | GENE | Mm.18845 | TITLE Mus musculus major histocompatibility locus class III region: complement C4 (C4) and cytochrome P450 hydroxylase A (CYP21OH-A) genes, complete cds; slp pseudogene, complete sequence; NG6, SKI, and complement factor B (Bf) genes, complete cds; and complement factor C2 (C2) gene, partial cds | | | gi = 2944418 | 520507 |
| IC03093 | UG75 Expression | GENE | Mm.30079 | TITLE Mus musculus major histocompatibility locus class III region: complement C4 (C4) and cytochrome P450 hydroxylase A (CYP21OH-A) genes, complete cds; slp pseudogene, complete sequence; NG6, SKI, and complement factor B (Bf) genes, complete cds; and complement factor C2 (C2) gene, partial cds | | | gi = 2944418 | 520507 |
| IC03094 | 00/02 Literature | GENE | Mm.4827 | U44795 Mus musculus coagulation factor VII (fVII) mRNA, complete cds | | | NM_010172 | 522105 |
| IC03095 | UG75 Expression | GENE | Mm.89769 | TITLE Mus musculus mRNA for type II cytokeratin, complete cds | | | gi = 6092074 | 522345 |
| IC03096 | 00/02 Literature | GENE | Mm.57223 | U25691 Mus musculus lymphocyte specific helicase mRNA, complete cds | | | NM_008234 | 524259 |
| IC03097 | UG75 Expression | GENE | Mm.25544 | TITLE Mus musculus putative endo/exonuclease MmMre11b (MmMRE11) mRNA, alternative splicing product, complete cds | | | gi = 1401336 | 524361 |
| IC03098 | UG75 Expression | GENE | Mm.22665 | TITLE Mus musculus histone deacetylase mHDA1 mRNA, complete cds | | | gi = 4165859 | 532157 |
| IC03099 | UG75 Expression | GENE | Mm.16898 | TITLE Mus musculus A10 mRNA, partial cds | | | gi = 398584 | 533608 |
| IC03100 | UG75 Expression | GENE | Mm.4540 | TITLE Mus musculus mSTI1 mRNA, complete cds | | | gi = 881484 | 533631 |
| IC03101 | UG75 Expression | GENE | Mm.9445 | TITLE Mus musculus soluble guanylate cyclase beta-1 subunit (GC-S-beta-1) mRNA, complete cds | | | gi = 2746080 | 536624 |
| IC03102 | UG75 Expression | GENE | Mm.34320 | TITLE Mus musculus antigen containing epitope to monoclonal antibody MMS-85/12 mRNA, partial cds | | | gi = 2384710 | 538456 |
| IC03103 | UG75 Expression | GENE | Mm.2573 | TITLE Mus musculus (clone C7/B9) S-adenosyl homocysteine hydrolase (ahcy) mRNA, complete cds | | | gi = 904131 | 539426 |
| IC03104 | UG75 Expression | GENE | Mm.18637 | TITLE Mus musculus Tera (Tera) mRNA, complete cds | | | gi = 1575504 | 541165 |
| IC03105 | UG75 Expression | GENE | Mm.558 | TITLE Mus musculus stimulated by retinoic acid gene 11 | | | NM_009290 | 541316 |
| IC03106 | 00/02 Literature | GENE | Mm.56927 | M27034 Mouse MHC class I D-region cell surface antigen (D2d) gene, complete cds | | | gi = 19334 | 551203 |
| IC03107 | UG75 Expression | GENE | Mm.19143 | TITLE Mus musculus amino levulinate synthase (ALAS-H) mRNA, 3– end | | | gi = 1220401 | 552191 |
| IC03108 | UG75 Expression | GENE | Mm.27622 | TITLE Mus musculus SH3-containing protein SH3P7 mRNA, complete cds. similar to Human Drebrin | | | gi = 1407654 | 554892 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03109 | 00/02 Literature | GENE | Mm.4822 | Homeo Box protein 2.4 (Hox-2.4) | | | gi = 51389 | 555498 |
| IC03110 | 00/02 Literature | GENE | Mm.87865 | | | | NM_007716 | 557853 |
| IC03111 | UG75 Expression | GENE | Mm.42123 | TITLE *Mus musculus* TSG118.1 (Tsg118) mRNA, complete cds | | | gi = 4104245 | 558025 |
| IC03112 | UG75 Expression | GENE | Mm.11711 | TITLE *Mus musculus* mRNA for phosphatase 2A catalytic subunit, isotype alpha | | | gi = 1246794 | 568134 |
| IC03113 | UG75 Expression | GENE | Mm.20917 | TITLE *Mus musculus* S6 kinase 2 | | | gi = 3901074 | 569218 |
| IC03114 | UG75 Expression | GENE | Mm.26166 | TITLE *Mus musculus* mRNA for protein-tyrosine-phosphatase IF1 | | | gi = 3294228 | 569517 |
| IC03115 | UG75 Expression | GENE | Mm.716 | TITLE *Mus musculus* cleavage and polyadenylation specificity factor (MCPSF) mRNA, complete cds | | | gi = 2331035 | 570966 |
| IC03116 | UG75 Expression | GENE | Mm.20299 | TITLE *Mus musculus* mUGT1 mRNA for UDP-galactose transporter 1, complete cds | | | gi = 6429656 | 573213 |
| IC03117 | UG75 Expression | GENE | Mm.27860 | TITLE *Mus musculus* Ras-binding protein SUR-8 mRNA, complete cds | | | gi = 3252980 | 573245 |
| IC03118 | EG75 Expression | GENE | Mm.8089 | TITLE *Mus musculus* lithium-sensitive myo-inositol monophosphatase A1 (IMPA1) mRNA, complete cds | | | gi = 2801800 | 5733909 |
| IC03119 | UG75 Expression | GENE | Mm.46302 | TITLE *Mus musculus* genomic DNA sequence from clone 573K1 on chromosome 17. Contains the gene for gamma-aminobutyric acid (GABA) B receptor 1, five 7 transmembrane receptor (rhodopsin family, olfactory receptor like) protein genes and one pdeudogene, a novel gene, four unknown pseudogenes, a pseudogene similar to Von Hippel-Lindau disease tumor suppressor gene, and the diubiquitin gene | | | gi = 5051393 | 573650 |
| IC03120 | UG75 Expression | GENE | Mm.32191 | TITLE *Mus musculus* genomic DNA sequence from clone 573K1 on chromosome 17. Contains the gene for gamma-aminobutyric acid (GABA) B receptor 1, five 7 transmembrane receptor (rhodopsin family, olfactory receptor like) protein genes and one pdeudogene, a novel gene, four unknown pseudogenes, a pseudogene similar to Von Hippel-Lindau disease tumor suppressor gene, and the diubiquitin gene | | | gi = 5051393 | 573650 |
| IC03121 | UG75 Expression | GENE | Mm.9455 | TITLE *Mus musculus* small GTPase Rab10 (Rab10) mRNA, complete cds | | | gi = 3406427 | 573868 |
| IC03122 | UG75 Expression | GENE | Mm.25717 | TITLE *Mus musculus* bright and dead ringer gene product homogogous protein Bdp mRNA, complete cds | | | gi = 4185570 | 573991 |
| IC03123 | UG75 Expression | GENE | Mm.4165 | TITLE *Mus musculus* SH3-containing protein SH3P2 mRNA, partial cds | | | gi = 1407662 | 574084 |
| IC03124 | UG75 Expression | GENE | Mm.4877 | TITLE *M. musculus* p16K gene for 16 kDa protein | | | gi = 53546 | 574092 |
| IC03125 | UG75 Expression | GENE | Mm.20863 | TITLE *Mus musculus* calpain Lp82 mRNA, complete cds | | | gi = 3661584 | 574491 |
| IC03126 | UG75 Expression | GENE | Mm.1786 | TITLE Mouse adenine phosphoribosyltransferase (APRT), complete cds | | | gi = 192009 | 575309 |
| IC03127 | UG75 Expression | GENE | Mm.30359 | TITLE *Mus musculus* clone L3 variable group of 2-cell-stage gene family mRNA, complete cds | | | gi = 3171137 | 575653 |
| IC03128 | UG75 Expression | GENE | Mm.38869 | TITLE *Mus musculus* protein inhibitor of activated STAT protein PIAS1 mRNA, complete cds | | | gi = 3643104 | 577047 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03129 | UG75 Expression | GENE | Mm.1034 | TITLE Mus musculus mRNA for PR65 (type 2A serine/threonine protein phosphatase A subunit), complete cds | | | gi = 4514638 | 577833 |
| IC03130 | UG75 Expression | GENE | Mm.9015 | TITLE Mus musculus growth arrest specific mRNA, clone 3546, complete cds | | | gi = 1154619 | 581914 |
| IC03131 | UG75 Expression | GENE | Mm.859 | TITLE Mus musculus mitochondrial DNA polymerase accessory subunit (MtPolB) mRNA, nuclear gene encoding mitochondrial protein, partial cds | | | gi = 2253294 | 581961 |
| IC03132 | UG75 Expression | GENE | Mm.4073 | TITLE Mouse mRNA for proacrosin-binding protein (sp32), complete cds | | | gi = 516783 | 582027 |
| IC03133 | UG75 Expression | GENE | Mm.501 | TITLE Mus musculus mRNA for TBP-binding protein ABT1, complete cds | | | gi = 6518526 | 582582 |
| IC03134 | UG75 Expression | GENE | Mm.23905 | TITLE Mus musculus mRNA for platelet factor 4, complete cds | | | gi = 6070338 | 582960 |
| IC03135 | UG75 Expression | GENE | Mm.2557 | TITLE Mus musculus mRNA for vav-T, complete cds | | | gi = 1913782 | 582976 |
| IC03136 | UG75 Expression | GENE | Mm.23871 | TITLE Mus musculus DNA cytosine methyltransferase mRNA | | | gi = 3435199 | 585513 |
| IC03137 | UG75 Expression | GENE | Mm.736 | TITLE Mus musculus endophilin III mRNA, complete cds | | | gi = 1407660 | 597291 |
| IC03138 | UG75 Expression | GENE | Mm.383 | TITLE Mus musculus endothelial monocyte-activating polypeptide I mRNA, complete cds | | | gi = 1150723 | 598185 |
| IC03139 | UG75 Expression | GENE | Mm.28068 | TITLE Mus musculus diaphanous-related formin (Dia2) mRNA, complete cds | | | gi = 3845724 | 598489 |
| IC03140 | UG75 Expression | GENE | Mm.10116 | TITLE Mus musculus B lymphocyte chemoattractant BLC mRNA, complete cds | | | gi = 2911373 | 598498 |
| IC03141 | UG75 Expression | GENE | Mm.3371 | (mFKBP25) mRNA, partial cds | | | gi = 1480735 | 599045 |
| IC03142 | UG75 Expression | GENE | Mm.4465 | TITLE M. domesticus MD6 mRNA | | | gi = 5907047 | 599275 |
| IC03143 | UG75 Expression | GENE | Mm.21740 | TITLE Mus musculus mRNA for heterogeneous nuclear ribonucleoprotein H | | | gi = 2253040 | 599683 |
| IC03144 | UG75 Expression | GENE | Mm.29794 | TITLE Mouse mRNA for dbpA murine homologue, complete cds | | | gi = 1160330 | 602275 |
| IC03145 | UG75 Expression | GENE | Mm.9114 | TITLE Mus musculus mu-crystallin (Cryn) mRNA, complete cds | | | gi = 2745895 | 606504 |
| IC03146 | UG75 Expression | GENE | Mm.43745 | TITLE Mus musculus major histocompatibility locus class III regions Hsc70t gene, partial cds; smRNP, G7A, NG23, MutS homolog, CLCP, NG24, NG25, and NG26 genes, complete cds; and unknown genes | | | gi = 3986751 | 607435 |
| IC03147 | UG75 Expression | GENE | Mm.37830 | TITLE Mus musculus major histocompatibility locus class III regions Hsc70t gene, partial cds; smRNP, G7A, NG23, MutS homolog, CLCP, NG24, NG25, and NG26 genes, complete cds; and unknown genes | | | gi = 3986751 | 607435 |
| IC03148 | UG75 Expression | GENE | Mm.29524 | TITLE Mus musculus major histocompatibility locus class III regions Hsc70t gene, partial cds; smRNP, G7A, NG23, MutS homolog, CLCP, NG24, NG25, and NG26 genes, complete cds; and unknown genes | | | | |
| IC03149 | UG75 Expression | GENE | Mm.7342 | protein mRNA, alternatively spliced product, complete cds | | | gi = 3138925 | 607565 |
| IC03150 | UG75 Expression | GENE | Mm.671 | TITLE Mus musculus putative lysophosphatidic acid acyltransferase mRNA, complete cds | | | gi = 2317724 | 614425 |
| IC03151 | UG75 Expression | GENE | Mm.4615 | TITLE Mus musculus mRNA for SAP102, complete cds | | | gi = 1507669 | 616606 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03152 | UG75 Expression | GENE | Mm.22262 | TITLE *Mus musculus* (strain C57BI/6) mRNA sequence | | | gi : 198867 | 617538 |
| IC03153 | UG75 Expression | GENE | Mm.41679 | TITLE *Mus musculus* muscle-specific serine kinase 1 mRNA, complete cds | | | gi : 4105090 | 618616 |
| IC03154 | UG75 Expression | GENE | Mm.1927 | TITLE *Mus musculus* drs-1 mRNA for sushi-repeat-containing protein, complete cds | | | gi : 6475030 | 618683 |
| IC03155 | UG75 Expression | GENE | Mm.33962 | TITLE *Mus musculus* cytokine receptor related protein 4 (Cytor4) mRNA, complete cds | | | gi : 4105473 | 619657 |
| IC03156 | 00/02 Literature | GENE | Mm.4300 | U62638 *Mus musculus* cyclin C mRNA, complete cds | | | gi : 1470123 | 620258 |
| IC03157 | UG75 Expression | GENE | Mm.11964 | TITLE *Mus musculus* Pcdh7 mRNA for BH-protocadherin-a, complete cds | | | gb : 3513311 | 620676 |
| IC03158 | UG75 Expression | GENE | Mm.14894 | TITLE *Mus musculus* hematopoietic lineage switch 2 (HLS2) mRNA, complete cds | | | gi : 3169728 | 621445 |
| IC03159 | UG75 Expression | GENE | Mm.4603 | TITLE *Mus musculus* scavenger receptor class B type I (mSR-BI) mRNA, complete cds | | | gi : 1167551 | 621678 |
| IC03160 | UG75 Expression | GENE | Mm.19121 | TITLE Gag..env [*Mus musculus*,MrV, Evi-2, murine AIDS virus-related provirus, Genomic Mutant, 3 genes, 4765 nt] | | | gi : 1245741 | 621746 |
| IC03161 | UG75 Expression | GENE | Mm.22421 | TITLE *Mus musculus* Sid177 mRNA, complete cds | | | gi : 1245741 | 621746 |
| IC03162 | UG75 Expression | GENE | Mm.1098 | TITLE *Mus musculus* glycosyl-phosphatidyl-inositol-anchored protein homolog mRNA, complete cds | | | gi : 1098568 | 634791 |
| IC03163 | UG75 Expression | GENE | Mm.14318 | TITLE *Mus musculus* germline immunoglobulin gamma constant region (IgG3) mRNA | | | gi : 1799549 | 635556 |
| IC03164 | UG75 Expression | GENE | Mm.18651 | TITLE *Mus musculus* mRNA encoding lysine-ketoglutarate reductase/saccharopine dehydrogenase | | | gi : 4107273 | 636116 |
| IC03165 | UG75 Expression | GENE | Mm.3253 | TITLE Mouse mRNA for RNA polymerase I associated factor (PAF53), complete cds | | | gi : 1381028 | 636127 |
| IC03166 | UG75 Expression | GENE | Mm.19981 | TITLE *Mus musculus* alpha diacylglycerol kinase mRNA, complete cds | | | gi : 3493665 | 636572 |
| IC03167 | UG75 Expression | GENE | Mm.1192 | TITLE IMMUNOGLOBULIN J CHAIN PRECURSOR | | | gi : 196378 | 638806 |
| IC03168 | UG75 Expression | GENE | Mm.12440 | TITLE *Mus musculus* RNaseP protein p30 (Rpp30) mRNA, complete cds | | | gi : 349542 | 638902 |
| IC03169 | UG75 Expression | GENE | Mm.10704 | TITLE *Mus musculus* SDP8 mRNA, complete cds | | | gi : 3126980 | 641191 |
| IC03170 | UG75 Expression | GENE | Mm.42197 | TITLE *Mus musculus* proteasome beta-subunit C5 (Psmb1) mRNA, partial cds | | | gi : 4140641 | 6422328 |
| IC03171 | UG75 Expression | GENE | Mm.10303 | TITLE *Mus musculus* SIK similar protein mRNA, complete cds | | | gi : 2996193 | 643463 |
| IC03172 | UG75 Expression | GENE | Mm.10180 | TITLE *Mus musculus* tetraspan TM4SF (Tspan-6) mRNA, complete cds | | | gi : 2995862 | 657408 |
| IC03173 | UG75 Expression | GENE | Mm.29947 | TITLE *Mus musculus* mRNA for LKB1, complete cds | | | gi : 4589403 | 657413 |
| IC03174 | UG75 Expression | GENE | Mm.20931 | TITLE *Mus musculus* 28 kDa cis-Golgi SNARE (GS28) mRNA, complete cds | | | gi : 3421372 | 657872 |
| IC03175 | UG75 Expression | GENE | Mm.15868 | TITLE *Mus musculus* transcytosis associated protein p115 mRNA, partial cds | | | gi : 3860050 | 658342 |
| IC03176 | UG75 Expression | GENE | Mm.10433 | TITLE *Mus musculus* Ah receptor-interacting protein (AIP) mRNA, complete cds | | | gi : 2177173 | 658530 |
| IC03177 | UG75 Expression | GENE | Mm.7138 | TITLE *Mus musculus* pleiotropic regulator 1 (PLRG1) mRNA, complete cds | | | gi : 2832297 | 659341 |
| IC03178 | UG75 Expression | GENE | Mm.7356 | TITLE *Mus musculus* SDP3 mRNA, complete cds | | | gi : 3126976 | 669911 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03179 | UG75 Expression | GENE | Mm.6577 | TITLE Mus musculus putative v-SNARE Vti1b mRNA, complete cds | | | gi = 3213228 | 671050 |
| IC03180 | UG75 Expression | GENE | Mm.27664 | TITLE Mus musculus mRNA for UNC-51-like kinase (ULK) 2, complete cds | | | gi = 4760560 | 672406 |
| IC03181 | UG75 Expression | GENE | Mm.16767 | TITLE Mus musculus heterogenous nuclear ribonucleoprotein A2/B1 (hnRNP A2/B1) mRNA, complete cds | | | gi = 3329497 | 679017 |
| IC03182 | 00/02 Literature | GENE | Mm.1213 | D16492 Mouse mRNA for P100 serine protease of Ra-reactive factor (RaRF), complete cds | | | NM_008555 | 681014 |
| IC03183 | UG75 Expression | GENE | Mm.12914 | TITLE Mus musculus ubiquitin-specific protease UBP41 (Ubp41) mRNA, complete cds | | | gi = 3386551 | 681059 |
| IC03184 | UG75 Expression | GENE | Mm.25121 | TITLE Mus musculus mRNA for acetyl-CoA transporter, complete cds | | | gi = 4589917 | 681508 |
| IC03185 | UG75 Expression | GENE | Mm.28216 | TITLE Mus musculus proapoptotic protein (Siva) gene, complete cds | | | gi = 2921301 | 717588 |
| IC03186 | UG75 Expression | GENE | Mm.2420 | TITLE GALACTOSE-1-PHOSPHATE URIDYLYLTRANSFERASE | | | gi = 193421 | 717639 |
| IC03187 | UG75 Expression | GENE | Mm.7087 | TITLE Mus musculus mRNA for mouse rabaptin-5, complete cds | | | gi = 2696100 | 718521 |
| IC03188 | UG75 Expression | GENE | Mm.27407 | TITLE Mus musculus mRNA for DNA helicase Q1, complete cds | | | gi = 4579743 | 718601 |
| IC03189 | UG75 Expression | GENE | Mm.35645 | TITLE Mus musculus mRNA containing B1 element, clone vario | | | gi = 4138239 | 719223 |
| IC03190 | UG75 Expression | GENE | Mm.34465 | TITLE Mus musculus Cut alternatively spliced product (CASP) mRNA, partial cds | | | gi = 1546824 | 719836 |
| IC03191 | UG75 Expression | GENE | Mm.23502 | TITLE Mus musculus sulfotransferase (SULT1B1) mRNA, partial cds | | | gi = 4103352 | 721406 |
| IC03192 | UG75 Expression | GENE | Mm.260 | TITLE Mus musculus cyclin-dependent kinase-2 alpha (cdk2-alpha) mRNA, complete cds | | | gi = 1695879 | 736019 |
| IC03193 | UG75 Expression | GENE | Mm.19127 | TITLE Mus musculus antioxidant enzyme AOE372 mRNA, complete cds | | | gi = 2104954 | 736561 |
| IC03194 | UG75 Expression | GENE | Mm.12951 | TITLE Mus musculus type 6 nucleoside diphosphate kinase NM23-M6 (Nm23-M6) mRNA, complete cds | | | gi = 3228531 | 737129 |
| IC03195 | 00/02 Literature | GENE | Mm.28767 | X13588 Murine crp gene for C-reactive protein | | | NM_007768 | 738016 |
| IC03196 | UG75 Expression | GENE | Mm.46674 | TITLE Mus musculus mRNA for nuclear protein ZAP, complete cds | | | gi = 6016841 | 749726 |
| IC03197 | UG75 Expression | GENE | Mm.12975 | TITLE Mus musculus mRNA for AMY-1, complete cds | | | gi = 3288715 | 749941 |
| IC03198 | UG75 Expression | GENE | Mm.3441 | TITLE Mouse RyR3 mRNA for brain ryanodine receptor, partial cds | | | gi = 1030711 | 750415 |
| IC03199 | UG75 Expression | GENE | Mm.24399 | TITLE T-CELL SURFACE GLYCOPROTEIN YE1/48 | | | gi = 202437 | 752181 |
| IC03200 | UG75 Expression | GENE | Mm.30080 | TITLE Mus musculus translation initiation factor eIF3-p44 mRNA, complete cds | | | gi = 4097872 | 762606 |
| IC03201 | UG75 Expression | GENE | Mm.34231 | TITLE Mus musculus mRNA for sid2057p, complete cds | | | gi = 5931562 | 762794 |
| IC03202 | UG75 Expression | GENE | Mm.28049 | TITLE Mus musculus ARIP1 mRNA for activin receptor interacting protein1, complete cds | | | gi = 5381219 | 763343 |
| IC03203 | UG75 Expression | GENE | Mm.3272 | TITLE Mus musculus mRNA for receptor activity modifying protein 1 (Ramp1 gene) | | | gi = 4587098 | 763985 |
| IC03204 | UG75 Expression | GENE | Mm.42238 | TITLE Mus musculus mRNA for nuclear protein SA2 | | | gi = 2644956 | 764179 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03205 | UG75 Expression | GENE | Mm.6666 | TITLE Mus musculus krupple-related zinc finger protein (Emzf1) mRNA, complete cds | | | gi = 2645673 | 764361 |
| IC03206 | UG75 Expression | GENE | Mm.10712 | TITLE Mus musculus HMG-box transcription factor TCF4B (Tcf4) mRNA, complete cds | | | gi = 4324630 | 764951 |
| IC03207 | UG75 Expression | GENE | Mm.6678 | TITLE Mus musculus protein-tyrosine phosphatase mRNA, complete cds | | | gi = 2331298 | 765258 |
| IC03208 | UG75 Expression | GENE | Mm.7418 | TITLE M. musculus mRNA for phosphatase 2A catalytic subunit, isotype beta | | | gi = 1246796 | 765781 |
| IC03209 | UG75 Expression | GENE | Mm.10085 | TITLE Mus musculus transcription factor NF-ATc isoform b (Nfatcb) mRNA, complete cds | | | gi = 3643194 | 775149 |
| IC03210 | UG75 Expression | GENE | Mm.11526 | TITLE Mus musculus natural killer cell BY55 precursor, mRNA, complete cds | | | gi = 3687739 | 777492 |
| IC03211 | UG75 Expression | GENE | Mm.20801 | TITLE Mus musculus Tat-interacting protein TIP30 mRNA, complete cds | | | gi = 3820524 | 790058 |
| IC03212 | UG75 Expression | GENE | Mm.20948 | TITLE Mus musculus transcobalmin II (Tcn2) mRNA, complete cds | | | gi = 3659876 | 790188 |
| IC03213 | UG75 Expression | GENE | Mm.14198 | TITLE Mus musculus polyhomeotic (mPh2) mRNA, complete cds | | | gi = 4098992 | 793153 |
| IC03214 | UG75 Expression | GENE | Mm.35854 | TITLE M.musculus mRNA for e1 protein | | | gi = 563507 | 803678 |
| IC03215 | UG75 Expression | GENE | Mm.27541 | TITLE Mus musculus ubiquitin-conjugating enzyme HR6A mRNA, complete cds | | | gi = 3769548 | 804492 |
| IC03216 | UG75 Expression | GENE | Mm.30118 | TITLE Mus musculus GCN5L1 gene, exon 1 and joined CDC | | | gi = 2769584 | 806669 |
| IC03217 | 00/02 Literature | GENE | Mm.14172 | J03398 Mouse mdr gene encoding a multidrug resistance protein mRNA, complete cds | | | NM_008830 | 818518 |
| IC03218 | UG75 Expression | GENE | Mm.43778 | TITLE Mus musculus mRNA for ribosomal protein S14 | | | gi = 1287653 | 819062 |
| IC03219 | UG75 Expression | GENE | Mm.28502 | TITLE Mus musculus double-stranded RNA-specific adenosine deaminase mRNA, complete cds | | | gi = 2981096 | 820627 |
| IC03220 | UG75 Expression | GENE | Mm.33902 | TITLE Mus musculus mRNA for GTPI protein | | | gi = 4158175 | 820635 |
| IC03221 | UG75 Expression | GENE | Mm.38522 | TITLE Mus musculus mRNA for nephrocystin (Nphp1 gene | | | gi = 5262741 | 832514 |
| IC03222 | UG75 Expression | GENE | Mm.20905 | TITLE Mus musculus Keap1 mRNA, complete cds | | | gi = 3894322 | 846747 |
| IC03223 | UG75 Expression | GENE | Mm.21904 | TITLE Mus musculus partial mRNA for hypothetical protein (ORF37 DNA) | | | gi = 5869933 | 847390 |
| IC03224 | UG75 Expression | GENE | Mm.29590 | TITLE Mus musculus E2F-like transcriptional repressor protein mRNA, complete cds | | | gi = 2708789 | 849371 |
| IC03225 | UG75 Expression | GENE | Mm.20862 | TITLE Mus musculus mRECK mRNA, complete cds | | | gi = 3810870 | 849385 |
| IC03226 | UG75 Expression | GENE | Mm.57082 | TITLE Mus musculus calcium/calmodulin-dependent protein kinase II delta mRNA, partial cds | | | gi = 3088550 | 850980 |
| IC03227 | UG75 Expression | GENE | Mm.3982 | TITLE M.musculus GAS 6 mRNA associated with growth-arrest | | | gi = 407060 | 864328 |
| IC03228 | UG75 Expression | GENE | Mm.27609 | TITLE Mus musculus mRNA for chromatin assembly factor-I p150 subunit | | | gi = 5852157 | 864673 |
| IC03229 | UG75 Expression | GENE | Mm.4067 | TITLE Mus musculus B6CBA Lisch7 mRNA, partial cds | | | gi = 1236082 | 866040 |
| IC03330 | UG75 Expression | GENE | Mm.7756 | TITLE Mus musculus mRNA for outer arm dynein light chain 4, complete cds | | | gi = 2754613 | 873112 |
| IC03331 | UG75 Expression | GENE | Mm.8684 | TITLE Mus musculus mRNA for 1-acyl-sn-glycerol-3-phosphate acyltransferase, complete cds | | | gi = 2467309 | 875366 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03332 | UG75 Expression | GENE | Mm.29263 | TITLE Mus musculus mRNA for XPE UV-damaged DNA binding factor, complete cds | | | gi = 5931595 | 876453 |
| IC03333 | UG75 Expression | GENE | Mm.468 | TITLE Mouse mRNA for PAP-1, complete cds | | | gi = 4512329 | 891462 |
| IC03334 | UG75 Expression | GENE | Mm.42027 | | | | gi = 4512329 | 891462 |
| IC03335 | UG75 Expression | GENE | Mm.30084 | TITLE M.musculus mRNA for neuronal protein 15.6 cds | | | gi = 1771305 | 891526 |
| IC03336 | UG75 Expression | GENE | Mm.26584 | TITLE Mus musculus major histocompatibility locus class III region:butyrophilin-like protein gene, partial cds; Notch4, PBX2, RAGE, lysophatidic acid acyl transferase-alpha, palmitoyl-protein thioesterase 2 (PPT2), CREB-RP, and tenascin X (TNX) genes, complete cds; and CYP21OHB pseudogene, complete sequence | | | gi = 2564945 | 904616 |
| IC03337 | UG75 Expression | GENE | Mm.7447 | TITLE Mus musculus major histocompatibility locus class III region:butyrophilin-like protein gene, partial cds; Notch4, PBX2, RAGE, lysophatidic acid acyl transferase-alpha, palmitoyl-protein thioesterase 2 (PPT2), CREB-RP, and tenascin X (TNX) genes, complete cds; and CYP21OHB pseudogene, complete sequence | | | gi = 2564945 | 904616 |
| IC03338 | UG75 Expression | GENE | Mm.29235 | TITLE Mus musculus major histocompatibility locus class III region:butyrophilin-like protein gene, partial cds; Notch4, PBX2, RAGE, lysophatidic acid acyl transferase-alpha, palmitoyl-protein thioesterase 2 (PPT2), CREB-RP, and tenascin X (TNX) genes, complete cds; and CYP21OHB pseudogene, complete sequence | | | gi = 2564945 | 904616 |
| IC03339 | UG75 Expression | GENE | Mm.28124 | TITLE Mus musculus augmenter of liver regeneration (Alr) gene, complete cds | | | gi = 4096809 | 905588 |
| IC03340 | UG75 Expression | GENE | Mm.34650 | TITLE Mus musculus mRNA for paralemmin | | | gi = 4456676 | 920684 |
| IC03341 | UG75 Expression | GENE | Mm.27560 | TITLE Mus musculus anthracycline-associated resistance (Arx) mRNA, complete cds | | | gi = 4096673 | 943883 |
| IC03342 | 00/02 Literature | GENE | Mm.57226 | DCC; netrin receptor; immunoglobulin gene superfamily member; former tumor suppressor protein candidate | | | NM_007831 | 944340 |
| IC03343 | UG75 Expression | GENE | Mm.6160 | TITLE IG ALPHA CHAIN C REGION | | | gi = 194417 | 949235 |
| IC03344 | UG75 Expression | GENE | Mm.34315 | TITLE Mus musculus Golgi SNARE GS15 mRNA, complete cds | | | gi = 4766990 | 949257 |
| IC03345 | UG75 Expression | GENE | Mm.42247 | TITLE Mus musculus mRNA for Scr3, complete cds | | | gi = 4730922 | 949314 |
| IC03346 | UG75 Expression | GENE | Mm.27972 | TITLE Mus musculus RRM RNA binding protein GRY-RBP mRNA, complete cds | | | gi = 3694985 | 958431 |
| IC03347 | UG75 Expression | GENE | Mm.43444 | TITLE Mus musculus mitotic checkpoint component Mad2 mRNA, complete cds | | | gi = 4099130 | 959612 |
| IC03248 | UG75 Expression | GENE | Mm.34143 | TITLE Mus musculus insulin receptor substrate-2 (Irs2) gene, partial cds | | | gi = 3661524 | 973269 |
| IC03249 | UG75 Expression | GENE | Mm.1323 | TITLE M.musculus mRNA for U2-snRNP b" (pRNP11) | | | gi = 840822 | 973631 |
| IC03250 | UG75 Expression | GENE | Mm.25560 | TITLE M.musculus mRNA for transferrin receptor | | | gi = 54914 | 978129 |
| IC03251 | UG75 Expression | GENE | Mm.3616 | TITLE Mus musculus DNA polymerase gamma mRNA, nuclear gene encoding mitochondrial protein, complete cds | | | gi = 1297339 | 988546 |
| IC03252 | UG75 Expression | GENE | Mm.7723 | TITLE Mus musculus poly(A) binding protein II (mPABII) gene, complete cds | | | gi = 2351845 | 989712 |
| IC03253 | 00/02 Literature | GENE | Mm.4594 | B-myb proto-oncogene; myb-related protein B | | | NM_008652 | 990327 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03254 | UG75 Expression | GENE | Mm.3594 | TITLE *Mus musculus* putative transcription factor mRNA, complete cds | | | gi = 3641351 | 990547 |
| IC03255 | UG75 Expression | GENE | Mm.34279 | TITLE *Mus musculus* TLS-associated protein TASR-2 mRNA, complete cds | | | gi = 3327956 | 991364 |
| IC03256 | 00/04/26 UG#76 17Lid Expansion | GENE | Mm.36174 | *Mus musculus* UDP-Gal:betaGlcNAc beta 1,3-galactosyltransferase-III (b3GT3) gene, complete cds | | | gi = 2745738 | 1763312 |
| IC03257 | UG75 Expression | HOM | Mm.10038 | TITLE ESTs, Highly similar to KIAA0691 protein [*H.sapiens*] | | | gi = 4485563 | 903814 |
| IC03258 | UG76 LID366 B cell | HOM | Mm.100845 | TITLE ESTs, Highly similar to hypothetical protein [*H.sapiens*] | | | gi = 7182445 | 2076234 |
| IC03259 | UG75 Expression | HOM | Mm.10188 | TITLE ESTs, Highly similar to G protein-coupled receptor kinase 5 [*M.musculus*] | | | gi = 2850412 | 1244001 |
| IC03260 | UG75 Expression | HOM | Mm.10297 | TITLE ESTs, Highly similar to CGI-58 protein [*H.sapiens*] | | | gi = 6514517 | 2647025 |
| IC03261 | UG75 Expression | HOM | Mm.10314 | BINDING PROTEIN P2 PRECURSOR [*Rattus norvegicus*] | | | gi = 1404964 | 420450 |
| IC03262 | UG75 Expression | HOM | Mm.10474 | TITLE ESTs, Highly similar to 60S RIBOSOMAL PROTEIN L37 [*Homo sapiens*; *Rattus norvegicus*] | | | gi = 1476426 | 440704 |
| IC03263 | UG75 Expression | HOM | Mm.10623 | TITLE ESTs, Highly similar to L-3-phosphoserine phosphatase [*H.sapiens*] | | | gi = 4726526 | 1971895 |
| IC03264 | UG75 Expression | HOM | Mm.1075 | TITLE ESTs, Highly similar to p126 [*H.sapiens*] | | | gi = 1715169 | 580733 |
| IC03265 | UG75 Expression | HOM | Mm.10753 | TITLE ESTs, Highly similar to PANCREATIC LIPASE RELATED PROTEIN 1 PRECURSOR [*Canis familiaris*] | | | gi = 4060800 | 521230 |
| IC03266 | UG75 Expression | HOM | Mm.1103 | TITLE ESTs, Highly similar to NADH-UBIQUINONE OXIDOREDUCTASE B17 SUBUNIT [*Bos taurus*] | | | gi = 2519120 | 846777 |
| IC03267 | UG75 Expression | HOM | Mm.11204 | TITLE ESTs, Highly similar to UNR PROTEIN [*Rattus norvegicus*] | | | gi = 5124656 | 2065269 |
| IC03268 | UG75 Expression | HOM | Mm.11218 | COMPLEMENTING XP-B CELLS HOMOLOG [*M.musculus*] | | | gi = 3373048 | 3153847 |
| IC03269 | UG75 Expression | HOM | Mm.1130 | TITLE ESTs, Highly similar to (defline not available 5916099) [*M.musculus*] | | | gi = 2807845 | 1227997 |
| IC03270 | UG75 Expression | HOM | Mm.11311 | TITLE ESTs, Highly similar to UTR4 PROTEIN [*Saccharomyces cerevisiae*] | | | gi = 6085546 | 1224025 |
| IC03271 | UG75 Expression | HOM | Mm.11660 | TITLE ESTs, Highly similar to tumor suppressing STF cDNA 1 [*H.sapiens*] | | | gi = 1676411 | 573964 |
| IC03272 | UG75 Expression | HOM | Mm.1183 | TITLE ESTs, Highly similar to UBIQUITIN-ACTIVATING ENZYME E1 HOMOLOG [*Homo sapiens*] | | | gi = 6556812 | 2651595 |
| IC03273 | UG75 Expression | HOM | Mm.12051 | TITLE ESTs, Highly similar to similar to *C. elegans* F11A10.5 [*H.sapiens*] | | | gi = 1500846 | 466466 |
| IC03274 | UG75 Expression | HOM | Mm.12091 | TITLE ESTs, Highly similar to HYPOTHETICAL 109.5 KD PROTEIN IN PPA1-DAP2 INTERGENIC REGION [*Saccharomyces cerevisiae*] | | | gi = 2292367 | 948497 |
| IC03275 | UG75 Expression | HOM | Mm.12110 | [*M.musculus*] | | | gi = 1325291 | 350444 |
| IC03276 | UG75 Expression | HOM | Mm.12239 | TITLE ESTs, Highly similar to geminin [*M.musculus*] | | | gi = 4061564 | 424889 |
| IC03277 | UG75 Expression | HOM | Mm.12267 | TITLE ESTs, Highly similar to POLYADENYLATE-BINDING PROTEIN [*Xenopus laevis*] | | | gi = 2273079 | 894590 |
| IC03278 | UG75 Expression | HOM | Mm.12407 | TITLE ESTs, Highly similar to LZIP-1 and LZIP-2 [*M.musculus*] | | | gi = 3981143 | 479740 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03279 | UG75 Expression | HOM | Mm.12441 | TITLE ESTs, Highly similar to 80 KD NUCLEAR CAP BINDING PROTEIN [H.sapiens] | | | gi = 1478905 | 440258 |
| IC03280 | UG75 Expression | HOM | Mm.12479 | TITLE ESTs, Highly similar to ZINC FINGER PROTEIN 18 [Homo sapiens] | | | gi = 3374453 | 1196037 |
| IC03281 | UG75 Expression | HOM | Mm.12553 | TITLE ESTs, Highly similar to ACTIVATOR 1 38 KD SUBUNIT [Homo sapiens] | | | gi = 1282628 | 332501 |
| IC03282 | UG75 Expression | HOM | Mm.12568 | TITLE ESTs, Highly similar to NUCLEAR PORE COMPLEX PROTEIN NUP107 [R.norvegicus] | | | gi = 2517131 | 777779 |
| IC03283 | UG75 Expression | HOM | Mm.12677 | TITLE ESTs, Highly similar to ATP SYNTHASE GAMMA CHAIN, MITOCHONDRIAL [Rattus norvegicus] | | | gi = 3809130 | 1891367 |
| IC03284 | UG75 Expression | HOM | Mm.12706 | TITLE ESTs, Highly similar to RPB17 [R.norvegicus] | | | gi = 4781784 | 660085 |
| IC03285 | UG75 Expression | HOM | Mm.12775 | TITLE ESTs, Highly similar to HYPOTHETICAL 45.3 KD PROTEIN ZK370.5 IN CHROMOSOME III [Caenorhabditis elegans] | | | gi = 3260855 | 1480856 |
| IC03286 | UG75 Expression | HOM | Mm.12864 | RIBOSOMAL PROTEIN YHR148W [Saccharomyces cerevisiae] | | | gi = 3864119 | 1889477 |
| IC03287 | UG75 Expression | HOM | Mm.12980 | TITLE ESTs, Highly similar to sodium bicarbonate cotransporter NBC1 [M.musculus] | | | gi = 4029055 | 1922271 |
| IC03288 | UG75 Expression | HOM | Mm.13148 | TITLE ESTs, Highly similar to KIAA0729 protein [H.sapiens] | | | gi = 2456200 | 1006125 |
| IC03289 | UG75 Expression | HOM | Mm.13356 | TITLE ESTs, Highly similar to nucleoporin p54 [R.norvegicus] | | | gi = 2262656 | 903927 |
| IC03290 | UG75 Expression | HOM | Mm.13427 | TITLE ESTs, Highly similar to EUKARYOTIC INITIATION FACTOR 4 GAMMA [Oryctolagus cuniculus] | | | gi = 1309666 | 337850 |
| IC03291 | UG75 Expression | HOM | Mm.13445 | OXOADIPATE COA-TRANSFERASE SUBUNIT B [Bacillus subtilis] | | | gi = 1282660 | 332084 |
| IC03292 | UG75 Expression | HOM | Mm.13758 | TITLE ESTs, Highly similar to Bdeight protein [R.norvegicus] | | | gi = 3955313 | 1514643 |
| IC03293 | UG75 Expression | HOM | Mm.13799 | TITLE ESTs, Highly similar to (defline not available 6006811) [M.musculus] | | | gi = 4275952 | 388812 |
| IC03294 | UG75 Expression | HOM | Mm.14225 | TITLE ESTs, Highly similar to TUP1-like enhancer [M.musculus] | | | gi = 2517412 | 1378490 |
| IC03295 | UG75 Expression | HOM | Mm.14534 | TITLE ESTs, Highly similar to GLYCOGEN SYNTHASE KINASE-3 ALPHA [Rattus norvegicus] | | | gi = 4273219 | 355707 |
| IC03296 | UG75 Expression | HOM | Mm.14585 | TITLE ESTs, Highly similar to U6 SNRNA-ASSOCIATED PROTEIN [Saccharomyces cerevisiae] | | | gi = 4061822 | 577597 |
| IC03297 | UG75 Expression | HOM | Mm.14712 | TITLE ESTs, Highly similar to RAS-RELATED PROTEIN RAB-20 [M.musculus] | | | gi = 2521504 | 1347712 |
| IC03298 | UG75 Expression | HOM | Mm.14747 | TITLE ESTs, Highly similar to INTERFERON-INDUCIBLE PROTEIN [Rattus norvegicus] | | | gi = 1309599 | 337573 |
| IC03299 | UG75 Expression | HOM | Mm.14796 | TITLE ESTs, Highly similar to GLUTATHIONE S-TRANSFERASE, MICROSOMAL [Rattus norvegicus] | | | gi = 1309667 | 337852 |
| IC03300 | UG75 Expression | HOM | Mm.14798 | TITLE ESTs, Highly similar to 40S RIBOSOMAL PROTEIN S13 [Homo sapiens; Rattus norvegicus] | | | gi = 3718625 | 2158953 |
| IC03301 | UG75 Expression | HOM | Mm.14816 | TITLE ESTs, Highly similar to choline/ethanolaminephosphotransferase [H.sapiens] | | | gi = 5905371 | 2192282 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03302 | UG75 Expression | HOM | Mm.14833 | TITLE ESTs, Highly similar to UBIQUITIN [Homo sapiens; Bos taurus; Sus scrofa; Cavia porcellus; Cricetulus griseus; Cricetulus longicaudatus; Rattus norvegicus; Mus musculus; Oryctolagus cuniculus; Gallus gallus; Xenopus laevis; Drosophila melanogaster; Ceratitis capitata; Spodoptera frugiperda; Manduca sexta] | | | gi = 2192621 | 872972 |
| IC03303 | UG75 Expression | HOM | Mm.1558 | TITLE ESTs, Highly similar to IDN3 [H.sapiens] | | | gi = 1756783 | 619165 |
| IC03304 | UG75 Expression | HOM | Mm.15801 | TITLE ESTs, Highly similar to DIPEPTIDYL-PEPTIDASE I PRECURSOR [Rattus norvegicus] | | | gi = 1934454 | 749038 |
| IC03305 | UG75 Expression | HOM | Mm.15928 | TITLE ESTs, Highly similar to DNA-binding protein PREB [M.musculus] | | | gi = 6078466 | 2225312 |
| IC03306 | UG75 Expression | HOM | Mm.16422 | TITLE ESTs, Highly similar to FIBRINOGEN GAMMA-A AND B CHAIN PRECURSORS [Rattus norvegicus] | | | gi = 3863949 | 1889175 |
| IC03307 | UG75 Expression | HOM | Mm.16963 | TITLE ESTs, Highly similar to MYOCYTE-SPECIFIC ENHANCER FACTOR 2D [M.musculus] | | | gi = 2918889 | 660007 |
| IC03308 | UG75 Expression | HOM | Mm.17035 | TITLE ESTs, Highly similar to CGI-34 protein [H.sapiens] | | | gi = 443931 | 3157520 |
| IC03309 | UG75 Expression | HOM | Mm.17087 | TITLE ESTs, Highly similar to HYPOTHETICAL 19.9 KD PROTEIN IN PUT3-CCE1 INTERGENIC REGION [Saccharomyces cerevisiae] | | | gi = 3031495 | 1297195 |
| IC03310 | UG75 Expression | HOM | Mm.17162 | | | | gi = 3164813 | 422012 |
| IC03311 | UG75 Expression | HOM | Mm.17165 | TITLE ESTs, Highly similar to (defline not available 6013381) [R.norvegicus] | | | gi = 2283962 | 1969792 |
| IC03312 | UG75 Expression | HOM | Mm.17253 | TITLE ESTs, Highly similar to STEROL REGULATORY ELEMENT BINDING PROTEIN 1 [Homo sapiens] | | | gi = 3602444 | 1481355 |
| IC03313 | UG75 Expression | HOM | Mm.17362 | TITLE ESTs, Highly similar to LACTOYLGLUTATHIONE LYASE [Homo sapiens] | | | gi = 4434558 | 1923121 |
| IC03314 | UG75 Expression | HOM | Mm.17403 | TITLE ESTs, Highly similar to GLYCYL-TRNA SYNTHETASE [Homo sapiens] | | | gi = 4968030 | 1498983 |
| IC03315 | UG75 Expression | HOM | Mm.17468 | TITLE ESTs, Highly similar to TRANSCRIPTION FACTOR BTEB [Rattus norvegicus] | | | gi = 4720484 | 1383495 |
| IC03316 | UG75 Expression | HOM | Mm.17533 | TITLE ESTs, Highly similar to BAP2-beta protein [H.sapiens] | | | gi = 4484842 | 483528 |
| IC03317 | UG75 Expression | HOM | Mm.17665 | TITLE ESTs, Highly similar to F23858_1 [H.sapiens] | | | gi = 3719077 | 1211481 |
| IC03318 | UG75 Expression | HOM | Mm.17799 | TITLE ESTs, Highly similar to GALECTIN-4 [Rattus norvegicus] | | | gi = 4060571 | 602304 |
| IC03319 | UG75 Expression | HOM | Mm.17851 | TITLE ESTs, Highly similar to similarto Schizosaccharomyces pombe cut1+ protein which regulates spindle pole body duplication. [H.sapiens] | | | gi = 3978713 | 635713 |
| IC03320 | UG75 Expression | HOM | Mm.1799 | TITLE ESTs, Highly similar to HISTIDINE-RICH GLYCOPROTEIN PRECURSOR [Homo sapiens] | | | gi = 4442485 | 1890253 |
| IC03321 | UG75 Expression | HOM | Mm.18157 | TITLE ESTs, Highly similar to axotrophin [M.musculus] | | | gi = 2305715 | 949081 |
| IC03322 | UG75 Expression | HOM | Mm.18298 | TITLE ESTs, Highly similar to peptidyl-prolyl cis-trans isomerase EPVH [H.sapiens] | | | gi = 3601691 | 1884977 |
| IC03323 | UG75 Expression | HOM | Mm.18472 | TITLE ESTs, Highly similar to 26S PROTEASE REGULATORY SUBUNIT 4 HOMOLOG [Schizosaccharomyces pombe] | | | gi = 1393068 | 403600 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03324 | UG75 Expression | HOM | Mm.18474 | TITLE ESTs, Highly similar to (define not available 5669929) [R.norvegicus] | | | gi = 2918453 | 1082240 |
| IC03325 | UG75 Expression | HOM | Mm.18485 | CONJUGATING ENZYME E2-19 KD [Arabidopsis thaliana] | | | gi = 5598199 | 522819 |
| IC03326 | UG75 Expression | HOM | Mm.18524 | TITLE ESTs, Highly similar to HYPOTHETICAL 94.2 KD PROTEIN C38D4.5 IN CHROMOSOME III [Caenorhabditis elegans] | | | gi = 3978963 | 2654446 |
| IC03327 | UG75 Expression | HOM | Mm.18579 | TITLE ESTs, Highly similar to DNA-DIRECTED RNA POLYMERASE II 23 KD POLYPEPTIDE [Homo sapiens] | | | gi = 6514806 | 2647363 |
| IC03328 | UG75 Expression | HOM | Mm.18588 | TITLE ESTs, Highly similar to PUTATIVE ATP-DEPENDENT RNA HELICASE C22F3.08C [Schizosaccharomyces pombe] | | | gi = 3979147 | 573380 |
| IC03329 | UG75 Expression | HOM | Mm.186 | TITLE ESTs, Highly similar to HYPOTHETICAL 13.5 KD PROTEIN C45G9.7 IN CHROMOSOME III [Caenorhabditis elegans] | | | gi = 3164497 | 572510 |
| IC03330 | UG75 Expression | HOM | Mm.18618 | KETOBUTYRATE COENZYME A LIGASE [Escherichia coli] | | | gi = 3259280 | 1480814 |
| IC03331 | UG75 Expression | HOM | Mm.18634 | TITLE ESTs, Highly similar to vesicle associated protein [R.norvegicus] | | | gi = 2292394 | 949062 |
| IC03332 | UG75 Expression | HOM | Mm.18635 | TITLE ESTs, Highly similar to REGULATOR OF G-PROTEIN SIGNALLING 2 [Homo sapiens] | | | gi = 1309881 | 338063 |
| IC03333 | UG75 Expression | HOM | Mm.18654 | TITLE ESTs, Highly similar to HYPOTHETICAL AMINOTRANSFERASE YIL060W [Saccharomyces cerevisiae] | | | gi = 3749117 | 1887744 |
| IC03334 | UG75 Expression | HOM | Mm.18742 | TITLE ESTs, Highly similar to p8 protein [M.musculus] | | | gi = 3955304 | 860921 |
| IC03335 | UG75 Expression | HOM | Mm.18790 | TITLE ESTs, Highly similar to hypothetical protein [H.sapiens] | | | gi = 3981869 | 2421316 |
| IC03336 | UG75 Expression | HOM | Mm.18795 | TITLE ESTs, Highly similar to RSP5 PROTEIN [Saccharomyces cerevisiae] | | | gi = 6518741 | 2599039 |
| IC03337 | UG75 Expression | HOM | Mm.18798 | TITLE ESTs, Highly similar to HYPOTHETICAL 39.7 KD PROTEIN C34E10.2 IN CHROMOSOME III [Caenorhabditis elegans] | | | gi = 6083594 | 403005 |
| IC03338 | UG75 Expression | HOM | Mm.18803 | TITLE ESTs, Highly similar to putative membrane protein [H.sapiens] | | | gi = 2502993 | 1064669 |
| IC03339 | UG75 Expression | HOM | Mm.18805 | TITLE ESTs, Highly similar to prediabetic NOD sera-reactive autoantigen [M.musculus] | | | gi = 5125279 | 2076589 |
| IC03340 | UG75 Expression | HOM | Mm.18810 | TITLE ESTs, Highly similar to ZINC FINGER PROTEIN 7 [Homo sapiens] | | | gi = 3955602 | 351768 |
| IC03341 | UG75 Expression | HOM | Mm.18847 | TITLE ESTs, Highly similar to HYPOTHETICAL 66.5 KD PROTEIN IN ADE12-RAP1 INTERGENIC REGION [Saccharomyces cerevisiae] | | | gi = 2962526 | 1265273 |
| IC03342 | UG75 Expression | HOM | Mm.18876 | TITLE ESTs, Highly similar to ACTIVATOR 1 37 KD SUBUNIT [Homo sapiens] | | | gi = 5599243 | 408399 |
| IC03343 | UG75 Expression | HOM | Mm.18924 | TITLE ESTs, Highly similar to EUKARYOTIC INITIATION FACTOR 1A [Homo sapiens] | | | gi = 4032958 | 1920695 |
| IC03344 | UG75 Expression | HOM | Mm.1893 | TITLE ESTs, Highly similar to NADH-UBIQUINONE OXIDOREDUCTASE SUBUNIT B14.5B [Bos taurus] | | | gi = 1315502 | 352202 |
| IC03345 | UG75 Expression | HOM | Mm.18941 | TITLE ESTs, Highly similar to CGI-84 protein [H.sapiens] | | | gi = 6083902 | 1889791 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03346 | UG75 Expression | HOM | Mm.18994 | TITLE ESTs, Highly similar to ZRP protein [R.norvegicus] | | | gi = 3978762 | 355289 |
| IC03347 | UG75 Expression | HOM | Mm.19027 | TITLE ESTs, Highly similar to molybdopterin-synthase large subunit [M.musculus] | | | gi = 6826536 | 2938042 |
| IC03348 | UG75 Expression | HOM | Mm.19060 | CONJUGATING ENZYME E2-17 KD 3 [Homo sapiens; Rattus norvegicus] | | | gi = 3685176 | 1494003 |
| IC03349 | UG75 Expression | HOM | Mm.1909 | TITLE ESTs, Highly similar to purine nucleotide binding protein [M.musculus] | | | gi = 1919292 | 777483 |
| IC03350 | UG75 Expression | HOM | Mm.19130 | TITLE ESTs, Highly similar to dJ483K16.1 [H.sapiens] | | | gi = 6084652 | 2076182 |
| IC03351 | UG75 Expression | HOM | Mm.19135 | TITLE ESTs, Highly similar to p63 [H.sapiens] | | | gi = 4729604 | 1970355 |
| IC03352 | UG75 Expression | HOM | Mm.19352 | TITLE ESTs, Highly similar to PUTATIVE ADENOSINE KINASE [Saccharomyces cerevisiae] | | | gi = 5819608 | 2182375 |
| IC03353 | UG75 Expression | HOM | Mm.19440 | TITLE ESTs, Highly similar to HYPOTHETICAL 18.5 KD PROTEIN C12G12.05C IN CHROMOSOME I [Schizosaccharomyces pombe] | | | gi = 2306581 | 944309 |
| IC03354 | UG75 Expression | HOM | Mm.19669 | TITLE ESTs, Highly similar to fructose-6-phosphate 2-kinase/fructose-2,6-bisphosphatase [R.norvegicus] | | | gi = 1826106 | 1244985 |
| IC03355 | UG75 Expression | HOM | Mm.19790 | TITLE ESTs, Highly similar to [Segment 1 of 2] XE169 PROTEIN [M.musculus] | | | gi = 6940311 | 2650040 |
| IC03356 | UG75 Expression | HOM | Mm.19834 | TITLE ESTs, Highly similar to NADH-UBIQUINONE OXIDOREDUCTASE 19 KD SUBUNIT [Bos taurus] | | | gi = 3164850 | 678553 |
| IC03357 | UG75 Expression | HOM | Mm.19839 | TITLE ESTs, Highly similar to TESTIN ½ PRECURSOR [Rattus norvegicus] | | | gi = 4058575 | 445380 |
| IC03358 | UG75 Expression | HOM | Mm.19943 | TITLE ESTs, Highly similar to EOSINOPHIL GRANULE MAJOR BASIC PROTEIN PRECURSOR [Homo sapiens] | | | gi = 1330558 | 354861 |
| IC03359 | UG75 Expression | HOM | Mm.19944 | TITLE ESTs, Highly similar to MELANOMA-ASSOCIATED ANTIGEN XP [Homo sapiens] | | | gi = 4720613 | 1401042 |
| IC03360 | UG75 Expression | HOM | Mm.19958 | TITLE ESTs, Highly similar to KELL BLOOD GROUP GLYCOPROTEIN [Homo sapiens] | | | gi = 4057034 | 468746 |
| IC03361 | UG75 Expression | HOM | Mm.20012 | TITLE ESTs, Highly similar to PROTEIN SEC61 BETA SUBUNIT [Homo sapiens; Canis familiaris] | | | gi = 2803473 | 1224867 |
| IC03362 | UG75 Expression | HOM | Mm.20175 | TITLE ESTs, Highly similar to PHENYLALANYL-TRNA SYNTHETASE MITOCHONDRIAL PRECURSOR [Saccharomyces cerevisiae] | | | gi = 4604502 | 480738 |
| IC03363 | UG75 Expression | HOM | Mm.20181 | TITLE ESTs, Highly similar to CAMP-DEPENDENT 3′,5′-CYCLIC PHOSPHODIESTERASE 4B [Homo sapiens] | | | gi = 6939017 | 2922044 |
| IC03364 | UG75 Expression | HOM | Mm.20188 | ALPHA CHAIN PRECURSOR V REGION [Homo sapiens] | | | gi = 5749153 | 2136586 |
| IC03365 | UG75 Expression | HOM | Mm.20207 | TITLE ESTs, Highly similar to DNA-DIRECTED RNA POLYMERASES I, II, AND III 8.3 KD POLYPEPTIDE [Saccharomyces cerevisiae] | | | gi = 4274645 | 1225603 |
| IC03366 | UG75 Expression | HOM | Mm.20213 | TITLE ESTs, Highly similar to FRUCTOSE-BISPHOSPHATE ALDOLASE A [Mus musculus] | | | gi = 1738646 | 599062 |
| IC03367 | UG75 Expression | HOM | Mm.20214 | TITLE ESTs, Highly similar to DYNEIN BETA CHAIN, CILIARY [Anthocidaris crassispina] | | | gi = 4061753 | 574464 |
| IC03368 | UG75 Expression | HOM | Mm.20216 | TITLE ESTs, Highly similar to GALACTOKINASE 2 [Homo sapiens] | | | gi = 1297621 | 336736 |
| IC03369 | UG75 Expression | HOM | Mm.20225 | TITLE ESTs, Highly similar to NUCLEAR FACTOR NF-KAPPA-B P100 SUBUNIT [Homo sapiens] | | | gi = 4198972 | 482952 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03370 | UG75 Expression | HOM | Mm.20226 | TITLE ESTs, Highly similar to INTERFERON-ACTIVATABLE PROTEIN 204 [Mus musculus] | | | gi = 4600921 | 622037 |
| IC03371 | UG75 Expression | HOM | Mm.20227 | TITLE ESTs, Highly similar to POL POLYPROTEIN [Squirrel monkey retrovirus] | | | gi = 1724878 | 597699 |
| IC03372 | UG75 Expression | HOM | Mm.20279 | TITLE ESTs, Highly similar to MITOCHONDRIAL RESPIRATORY CHAIN COMPLEXES ASSEMBLY PROTEIN RCA1 [Saccharomyces cerevisiae] | | | gi = 4061591 | 426499 |
| IC03373 | UG75 Expression | HOM | Mm.20288 | TITLE ESTs, Highly similar to GLUTATHIONE REDUCTASE [Escherichia coli] | | | gi = 3521714 | 1399649 |
| IC03374 | UG75 Expression | HOM | Mm.20309 | TITLE ESTs, Highly similar to ACYLPHOSPHATASE, ORGAN-COMMON TYPE ISOZYMES A AND B [Sus scrofa] | | | gi = 2646142 | 1179754 |
| IC03375 | UG75 Expression | HOM | Mm.20315 | TITLE ESTs, Highly similar to HYPOTHETICAL 100.3 KD PROTEIN IN MEI4-CAJ1 INTERGENIC REGION [Saccharomyces cerevisiae] | | | gi = 1777088 | 636883 |
| IC03376 | UG75 Expression | HOM | Mm.20320 | TITLE ESTs, Highly similar to DTDP-GLUCOSE 4,6-DEHYDRATASE [Escherichia coli] | | | gi = 4729759 | 1970753 |
| IC03377 | UG75 Expression | HOM | Mm.20323 | TITLE ESTs, Highly similar to RAS-RELATED PROTEIN RAC1 [Caenorhabditis elegans] | | | gi = 1724636 | 581958 |
| IC03378 | UG75 Expression | HOM | Mm.2033 | TITLE ESTs, Highly similar to NADH-UBIQUINONE OXIDOREDUCTASE B12 SUBUNIT [Bos taurus] | | | gi = 4276511 | 352579 |
| IC03379 | UG75 Expression | HOM | Mm.20353 | TITLE ESTs, Highly similar to TYROSYL-TRNA SYNTHETASE, CYTOPLASMIC [Saccharomyces cerevisiae] | | | gi = 6077152 | 2225689 |
| IC03380 | UG75 Expression | HOM | Mm.20377 | TITLE ESTs, Highly similar to SEC PROTEIN [Homo sapiens] | | | gi = 1659955 | 570540 |
| IC03381 | UG75 Expression | HOM | Mm.20399 | TITLE ESTs, Highly similar to HYPOTHETICAL 77.3 KD PROTEIN T05G5.8 IN CHROMOSOME III [Caenorhabditis elegans] | | | gi = 4433900 | 464995 |
| IC03382 | UG75 Expression | HOM | Mm.20414 | | | | gi = 6084704 | 1329408 |
| IC03383 | UG75 Expression | HOM | Mm.20415 | INITIATION FACTOR IIF, BETA SUBUNIT [Rattus norvegicus] | | | gi = 4060744 | 515917 |
| IC03384 | UG75 Expression | HOM | Mm.20420 | TITLE ESTs, Highly similar to BN51 PROTEIN [Homo sapiens] | | | gi = 1681669 | 596063 |
| IC03385 | UG75 Expression | HOM | Mm.2050 | TITLE ESTs, Highly similar to 60S RIBOSOMAL PROTEIN L15 [Rattus norvegicus] | | | gi = 1287301 | 318307 |
| IC03386 | UG75 Expression | HOM | Mm.2060 | TITLE ESTs, Highly similar to NADH-UBIQUINONE OXIDOREDUCTASE ASHI SUBUNIT PRECURSOR [Bos taurus] | | | gi = 1290300 | 333403 |
| IC03387 | UG75 Expression | HOM | Mm.20818 | TITLE ESTs, Highly similar to PROBABLE CALCIUM-BINDING PROTEIN PMP41 [Mus musculus] | | | gi = 1494660 | 464201 |
| IC03388 | UG75 Expression | HOM | Mm.20841 | TITLE ESTs, Highly similar to ATP SYNTHASE EPSILON CHAIN, MITOCHONDRIAL PRECURSOR [Bos taurus] | | | gi = 1284931 | 313581 |
| IC03389 | UG75 Expression | HOM | Mm.20847 | TITLE ESTs, Highly similar to sorting nexin 5 [H.sapiens] | | | gi = 6084393 | 2394942 |
| IC03390 | UG75 Expression | HOM | Mm.20867 | TITLE ESTs, Highly similar to faciogenital dysplasia protein 2 [M.musculus] | | | gi = 4374843 | 876373 |
| IC03391 | UG75 Expression | HOM | Mm.20898 | TITLE ESTs, Highly similar to protein kinase A anchoring protein [M.musculus] | | | gi = 1675405 | 540982 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03392 | UG75 Expression | HOM | Mm.21062 | TITLE ESTs, Highly similar to HYPOTHETICAL 56.6 KD PROTEIN C16C9.03 IN CHROMOSOME I [Schizosaccharomyces pombe] | | | gi = 6515833 | 2101560 |
| IC03393 | UG75 Expression | HOM | Mm.21071 | TITLE ESTs, Highly similar to ADP-RIBOSYLATION FACTOR-LIKE PROTEIN 2 [Homo sapiens] | | | gi = 5598012 | 478516 |
| IC03394 | UG75 Expression | HOM | Mm.21086 | TITLE ESTs, Highly similar to ELONGATION FACTOR 1-DELTA [Homo sapiens] | | | gi = 3809509 | 1891143 |
| IC03395 | UG75 Expression | HOM | Mm.21108 | TITLE ESTs, Highly similar to AMINE OXIDASE [Rattus norvegicus] | | | gi = 6084589 | 864614 |
| IC03396 | UG75 Expression | HOM | Mm.21114 | TITLE ESTs, Highly similar to PROBABLE UBIQUITIN CARBOXYL-TERMINAL HYDROLASE [Mus musculus] | | | gi = 2305617 | 948970 |
| IC03397 | UG75 Expression | HOM | Mm.21118 | TITLE ESTs, Highly similar to ISOLEUCYL-TRNA SYNTHETASE, CYTOPLASMIC [Homo sapiens] | | | gi = 2989115 | 1265150 |
| IC03398 | UG75 Expression | HOM | Mm.21149 | TITLE ESTs, Highly similar to HYPOTHETICAL 45.1 KD PROTEIN IN IMP2-DNA43 INTERGENIC REGION [Saccharomyces cerevisiae] | | | gi = 3054723 | 1327801 |
| IC03399 | UG75 Expression | HOM | Mm.21156 | | | | gi = 4967721 | 1498340 |
| IC03400 | UG75 Expression | HOM | Mm.21158 | TITLE ESTs, Highly similar to FKBP-RAPAMYCIN ASSOCIATED PROTEIN [Rattus norvegicus] | | | gi = 4061497 | 421419 |
| IC03401 | UG75 Expression | HOM | Mm.21203 | TITLE ESTs, Highly similar to (define not available 6164630) [M.musculus] | | | gi = 1919237 | 777412 |
| IC03402 | UG75 Expression | HOM | Mm.21239 | TITLE ESTs, Highly similar to HYPOTHETICAL 24.1 KD PROTEIN ON CHROMOSOME 1 [M.musculus] | | | gi = 1931979 | 764210 |
| IC03403 | UG75 Expression | HOM | Mm.21246 | TITLE ESTs, Highly similar to hypothetical protein [H.sapiens] | | | gi = 3374707 | 618104 |
| IC03404 | UG75 Expression | HOM | Mm.2125 | TITLE ESTs, Highly similar to HYPOTHETICAL 20.1 KD PROTEIN F42H10.6 IN CHROMOSOME III [Caenorhabditis elegans] | | | gi = 6085608 | 1514321 |
| IC03405 | UG75 Expression | HOM | Mm.21285 | TITLE ESTs, Highly similar to hermes [M.musculus] | | | gi = 4375615 | 870794 |
| IC03406 | UG75 Expression | HOM | Mm.21383 | TITLE ESTs, Highly similar to HYPOTHETICAL 37.2 KD PROTEIN C12C2.09C IN CHROMOSOME I [Schizosaccharomyces pombe] | | | gi = 5125679 | 2076851 |
| IC03407 | UG75 Expression | HOM | Mm.21396 | TITLE ESTs, Highly similar to AUXIN-RESISTANCE PROTEIN AXR1 [Arabidopsis thaliana] | | | gi = 1840256 | 660918 |
| IC03408 | UG75 Expression | HOM | Mm.21399 | TITLE ESTs, Highly similar to HAM1 PROTEIN [Saccharomyces cerevisiae] | | | gi = 3981179 | 608869 |
| IC03409 | UG75 Expression | HOM | Mm.21401 | TITLE ESTs, Highly similar to NEDD-4 PROTEIN [Homo sapiens] | | | gi = 6077384 | 2236110 |
| IC03410 | UG75 Expression | HOM | Mm.21435 | TITLE ESTs, Highly similar to (defline not available 6012186) [M.musculus] | | | gi = 4726183 | 1971490 |
| IC03411 | UG75 Expression | HOM | Mm.21444 | TITLE ESTs, Highly similar to nuclear autoantigen of 14 kDa [H.sapiens] | | | gi = 4967648 | 1853392 |
| IC03412 | UG75 Expression | HOM | Mm.21448 | TITLE ESTs, Highly similar to HYPOTHETICAL MYELOID CELL LINE PROTEIN 6 [Homo sapiens] | | | gi = 3748074 | 1886028 |
| IC03413 | UG75 Expression | HOM | Mm.21451 | TITLE ESTs, Highly similar to HSPC012 [H.sapiens] | | | gi = 4316184 | 1383113 |
| IC03414 | UG75 Expression | HOM | Mm.21458 | TITLE ESTs, Highly similar to unknown [H.sapiens] | | | gi = 6748410 | 2373251 |
| IC03415 | UG75 Expression | HOM | Mm.21473 | TITLE ESTs, Highly similar to HYPOTHETICAL 34.7 KD PROTEIN IN SPT10-GCD14 INTERGENIC REGION [Saccharomyces cerevisiae] | | | gi = 3167601 | 1431382 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03416 | UG75 Expression | HOM | Mm.21490 | TITLE ESTs, Highly similar to translocation protein-1 [H.sapiens] | | | gi = 2519526 | 2519903 |
| IC03417 | UG75 Expression | HOM | Mm.21497 | TITLE ESTs, Highly similar to formin binding protein 11 [M.musculus] | | | gi = 5338133 | 2064741 |
| IC03418 | UG75 Expression | HOM | Mm.21515 | TITLE ESTs, Highly similar to zinc finger RNA binding protein [M.musculus] | | | gi = 3374736 | 635639 |
| IC03419 | UG75 Expression | HOM | Mm.21534 | TITLE ESTs, Highly similar to transcription factor NF-AT 45K chain [H.sapiens] | | | gi = 4803588 | 1348640 |
| IC03420 | UG75 Expression | HOM | Mm.21535 | TITLE ESTs, Highly similar to GRPE PROTEIN HOMOLOG PRECURSOR [Drosophila melanogaster] | | | gi = 2643457 | 1039461 |
| IC03421 | UG75 Expression | HOM | Mm.21539 | TITLE ESTs, Highly similar to CARBAMOYL-PHOSPHATE SYNTHASE [Rattus norvegicus] | | | gi = 1309592 | 337546 |
| IC03422 | UG75 Expression | HOM | Mm.21544 | TITLE ESTs, Highly similar to RIS1 PROTEIN [Saccharomyces cerevisiae] | | | gi = 1915146 | 747313 |
| IC03423 | UG75 Expression | HOM | Mm.21569 | TITLE ESTs, Highly similar to sperm acrosomal protein [H.sapiens] | | | gi = 2516911 | 670709 |
| IC03424 | UG75 Expression | HOM | Mm.21580 | TITLE ESTs, Highly similar to ALPHA-L-FUCOSIDASE PRECURSOR [Rattus norvegicus] | | | gi = 1287165 | 316342 |
| IC03425 | UG75 Expression | HOM | Mm.21583 | TITLE ESTs, Highly similar to putative ATP/GTP-binding protein [H.sapiens] | | | gi = 1768522 | 642977 |
| IC03426 | UG75 Expression | HOM | Mm.2160 | TITLE ESTs, Highly similar to T-KININOGEN II PRECURSOR [Rattus norvegicus] | | | gi = 3748635 | 748160 |
| IC03427 | UG75 Expression | HOM | Mm.21608 | TITLE ESTs, Highly similar to spindle pole body protein spc98 homolog GCP3 [H.sapiens] | | | gi = 4729833 | 1970851 |
| IC03428 | UG75 Expression | HOM | Mm.2161 | TITLE ESTs, Highly similar to NG20 [M.musculus] | | | gi = 1806953 | 676182 |
| IC03429 | UG75 Expression | HOM | Mm.21613 | TITLE ESTs, Highly similar to FOCAL ADHESION KINASE 2 [R.norvegicus] | | | gi = 2283963 | 573298 |
| IC03430 | UG75 Expression | HOM | Mm.21622 | TITLE ESTs, Highly similar to DEATH-ASSOCIATED PROTEIN 1 [H.sapiens] | | | gi = 3749251 | 1886125 |
| IC03431 | UG75 Expression | HOM | Mm.21625 | TITLE ESTs, Highly similar to UBIQUINOL-CYTOCHROME C REDUCTASE COMPLEX UBIQUINONE-BINDING PROTEIN QP-C [Bos taurus] | | | gi = 2041309 | 761344 |
| IC03432 | UG75 Expression | HOM | Mm.21634 | TITLE ESTs, Highly similar to ubiquitin-fusion degradation protein 2 [H.sapiens] | | | gi = 6559861 | 2647391 |
| IC03433 | UG75 Expression | HOM | Mm.21639 | TITLE ESTs, Highly similar to karyopherin beta2b homolog [H.sapiens] | | | gi = 2308012 | 959644 |
| IC03434 | UG75 Expression | HOM | Mm.21650 | TITLE ESTs, Highly similar to (define not available 5596626) [M.musculus] | | | gi = 1864623 | 860233 |
| IC03435 | UG75 Expression | HOM | Mm.21667 | TITLE ESTs, Highly similar to 26S proteasome subunit p55 [H.sapiens] | | | gi = 3164392 | 891386 |
| IC03436 | UG75 Expression | HOM | Mm.21669 | TITLE ESTs, Highly similar to NADH-UBIQUINONE OXIDOREDUCTASE 49 KD SUBUNIT [Bos taurus] | | | gi = 6085241 | 555091 |
| IC03437 | UG75 Expression | HOM | Mm.21695 | TITLE ESTs, Highly similar to yeast hypothetical protein ybk4 [H.sapiens] | | | gi = 4373890 | 890883 |
| IC03438 | UG75 Expression | HOM | Mm.21712 | TITLE ESTs, Highly similar to hypothetical protein [H.sapiens] | | | gi = 2307755 | 959500 |
| IC03439 | UG75 Expression | HOM | Mm.21724 | TITLE ESTs, Highly similar to 60S RIBOSOMAL PROTEIN L22 [Tripneustes gratilla] | | | gi = 2273017 | 1230405 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03440 | UG75 Expression | HOM | Mm.21728 | TITLE ESTs, Highly similar to PROTEASOME 28 KD SUBUNIT 1 [Drosophila melanogaster] | | | gi = 3515299 | 1884959 |
| IC03441 | UG75 Expression | HOM | Mm.21739 | TITLE ESTs, Highly similar to Fus1 protein [M.musculus] | | | gi = 6085114 | 596796 |
| IC03442 | UG75 Expression | HOM | Mm.21752 | TITLE ESTs, Highly similar to VESICULAR INTEGRAL-MEMBRANE PROTEIN VIP36 PRECURSOR [Canis familiaris] | | | gi = 5550261 | 1924240 |
| IC03471 | UG75 Expression | HOM | Mm.22144 | TITLE ESTs, Highly similar to COATOMER ZETA SUBUNIT [Bos taurus] | | | gi = 1325497 | 351171 |
| IC03472 | UG75 Expression | HOM | Mm.22149 | TITLE ESTs, Highly similar to SUCCINATE DEHYDROGENASE [Homo sapiens] | | | gi = 4030146 | 1921052 |
| IC03473 | UG75 Expression | HOM | Mm.22162 | TITLE ESTs, Highly similar to 45 kDa splicing factor [H.sapiens] | | | gi = 2692401 | 1180750 |
| IC03474 | UG75 Expression | HOM | Mm.22199 | TITLE ESTs, Highly similar to ISOVALERYL-COA DEHYDROGENASE PRECURSOR [Rattus norvegicus] | | | gi = 2288505 | 949373 |
| IC03475 | UG75 Expression | HOM | Mm.2220 | TITLE ESTs, Highly similar to PROBABLE PROTEIN DISULFIDE ISOMERASE P5 PRECURSOR [Mesocricetus auratus] | | | gi = 434419 | 1888395 |
| IC03476 | UG75 Expression | HOM | Mm.22201 | TITLE ESTs, Highly similar to small zinc finger-like protein [M.musculus] | | | gi = 1872710 | 671757 |
| IC03477 | UG75 Expression | HOM | Mm.22227 | TITLE ESTs, Highly similar to SUCCINATE DEHYDROGENASE CYTOCHROME B560 SUBUNIT PRECURSOR [Bos taurus] | | | gi = 6077751 | 2236464 |
| IC03478 | UG75 Expression | HOM | Mm.22230 | TITLE ESTs, Highly similar to DNA-DIRECTED RNA POLYMERASE II 14.4 KD POLYPEPTIDE [Homo sapiens; Cricetulus griseus] | | | gi = 6075571 | 2236333 |
| IC03479 | UG75 Expression | HOM | Mm.22264 | TITLE ESTs, Highly similar to apoptosis specific protein [H.sapiens] | | | gi = 6749088 | 2352676 |
| IC03480 | UG75 Expression | HOM | Mm.22269 | TITLE ESTs, Highly similar to CHROMOSOME REGION MAINTENANCE PROTEIN 1 [Schizosaccharomyces pombe] | | | gi = 3032480 | 1279722 |
| IC03481 | UG75 Expression | HOM | Mm.22276 | TITLE ESTs, Highly similar to HYPOTHETICAL 92.1 KD PROTEIN C24H6.03 IN CHROMOSOME I [Schizosaccharomyces pombe] | | | gi = 2861309 | 1294669 |
| IC03482 | UG75 Expression | HOM | Mm.22330 | TITLE ESTs, Highly similar to imidazoline receptor 1-1-like protein [M.musculus] | | | gi = 2291710 | 948824 |
| IC03483 | UG75 Expression | HOM | Mm.22339 | TITLE ESTs, Highly similar to VON WILLEBRAND FACTOR PRECURSOR [Homo sapiens] | | | gi = 4483620 | 1055065 |
| IC03484 | UG75 Expression | HOM | Mm.22345 | TITLE ESTs, Highly similar to serine protease [H.sapiens] | | | gi = 4450333 | 576361 |
| IC03485 | UG75 Expression | HOM | Mm.22357 | TITLE ESTs, Highly similar to CH-TOG PROTEIN [H.sapiens] | | | gi = 2521141 | 1263281 |
| IC03486 | UG75 Expression | HOM | Mm.22359 | TITLE ESTs, Highly similar to zinc finger protein [H.sapiens] | | | gi = 3515308 | 1884982 |
| IC03487 | UG75 Expression | HOM | Mm.22363 | TITLE ESTs, Highly similar to ARGINYL-TRNA SYNTHETASE, MITOCHONDRIAL PRECURSOR [Saccharomyces cerevisiae] | | | gi = 4060673 | 468636 |
| IC03488 | UG75 Expression | HOM | Mm.22369 | TITLE ESTs, Highly similar to dipeptidyl peptidase III [R.norvegicus] | | | gi = 3720748 | 1332603 |
| IC03489 | UG75 Expression | HOM | Mm.22385 | TITLE ESTs, Highly similar to GLUCOSE-6-PHOSPHATASE [Homo sapiens] | | | gi = 1793333 | 640146 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03490 | UG75 Expression | HOM | Mm.22399 | TITLE ESTs, Highly similar to TRANSLATIONAL INITIATION FACTOR 2 ALPHA SUBUNIT [Rattus norvegicus; Bos taurus] | | | gi = 4031733 | 1924355 |
| IC03491 | UG75 Expression | HOM | Mm.22417 | TITLE ESTs, Highly similar to cellular apoptosis susceptibility protein [H.sapiens] | | | gi = 1793145 | 640109 |
| IC03492 | UG75 Expression | HOM | Mm.22440 | TITLE ESTs, Highly similar to thyroid hormone receptor-associated protein complex component TRAP150 [H.sapiens] | | | gi = 2804000 | 1227923 |
| IC03493 | UG75 Expression | HOM | Mm.22514 | TITLE ESTs, Highly similar to ATP SYNTHASE DELTA CHAIN, MITOCHONDRIAL PRECURSOR [Rattus norvegicus] | | | gi = 1309717 | 337870 |
| IC03494 | UG75 Expression | HOM | Mm.2252 | TITLE ESTs, Highly similar to P120 PROTEIN [Mus musculus] | | | gi = 6514878 | 2647452 |
| IC03495 | UG75 Expression | HOM | Mm.22543 | TITLE ESTs, Highly similar to brain and reproductive organ-expressed protein [H.sapiens] | | | gi = 1838564 | 751682 |
| IC03496 | UG75 Expression | HOM | Mm.22547 | TITLE ESTs, Highly similar to acid ceramidase [M.musculus] | | | gi = 1337496 | 355962 |
| IC03497 | UG75 Expression | HOM | Mm.22560 | TITLE ESTs, Highly similar to NADH-CYTOCHROME B5 REDUCTASE [Homo sapiens] | | | gi = 4767193 | 1890499 |
| IC03498 | UG75 Expression | HOM | Mm.22573 | TITLE ESTs, Highly similar to ZINC FINGER PROTEIN ZFP-37 [Mus musculus] | | | gi = 2813530 | 1068043 |
| IC03499 | UG75 Expression | HOM | Mm.22579 | TITLE ESTs, Highly similar to RNA-BINDING PROTEIN FUS/TLS [Homo sapiens] | | | gi = 6515151 | 2598827 |
| IC03500 | UG75 Expression | HOM | Mm.22597 | TITLE ESTs, Highly similar to DYNACTIN, 50 KD ISOFORM [H.sapiens] | | | gi = 4316029 | 1382975 |
| IC03501 | UG75 Expression | HOM | Mm.22613 | TITLE ESTs, Highly similar to PERIPHERAL-TYPE BENZODIAZEPINE RECEPTOR [Rattus norvegicus] | | | gi = 4061345 | 478371 |
| IC03502 | UG75 Expression | HOM | Mm.22661 | TITLE ESTs, Highly similar to HYPOTHETICAL 44.2 KD PROTEIN IN SCO2-MRF1 INTERGENIC REGION [Saccharomyces cerevisiae] | | | gi = 3863659 | 1890163 |
| IC03503 | UG75 Expression | HOM | Mm.22667 | TITLE ESTs, Highly similar to NUCLEAR TRANSPORT FACTOR 2 [Homo sapiens; Rattus norvegicus] | | | gi = 3164242 | 762516 |
| IC03504 | UG75 Expression | HOM | Mm.22679 | TRANSPORT PROTEIN PRECURSOR [Rattus norvegicus] | | | gi = 2744918 | 1210158 |
| IC03505 | UG75 Expression | HOM | Mm.22687 | TITLE ESTs, Highly similar to nuclear pore complex glycoprotein p62 [M.musculus] | | | gi = 5338228 | 2064841 |
| IC03506 | UG75 Expression | HOM | Mm.22704 | TITLE ESTs, Highly similar to GUANINE NUCLEOTIDE-BINDING PROTEIN G(K), ALPHA SUBUNIT [Rattus norvegicus] | | | gi = 5598752 | 573100 |
| IC03507 | UG75 Expression | HOM | Mm.22710 | TITLE ESTs, Highly similar to UDP-N-ACETYLGLUCOSAMINE-PEPTIDE N-ACETYLGLUCOSAMINYLTRANSFERASE 110 KD SUBUNIT [R.norvegicus] | | | gi = 3718520 | 583678 |
| IC03508 | UG75 Expression | HOM | Mm.22718 | TITLE ESTs, Highly similar to X box binding protein-1 [M.musculus] | | | gi = 4031924 | 1511586 |
| IC03509 | UG75 Expression | HOM | Mm.22719 | TITLE ESTs, Highly similar to ACETYL-COENZYME A SYNTHETASE [Escherichia coli] | | | gi = 1326465 | 353683 |
| IC03510 | UG75 Expression | HOM | Mm.22723 | TITLE ESTs, Highly similar to 60S RIBOSOMAL PROTEIN L23A [Homo sapiens] | | | gi = 2284400 | 932713 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03511 | UG75 Expression | HOM | Mm.22729 | TITLE ESTs, Highly similar to PROBABLE PEPTIDYL-PROLYL CIS-TRANS ISOMERASE C21E11.05C [Schizosaccharomyces pombe] | | | gi = 4061820 | 577501 |
| IC03512 | UG75 Expression | HOM | Mm.22749 | TITLE ESTs, Highly similar to dJ30M3.2 [H.sapiens] | | | gi = 4434659 | 638294 |
| IC03513 | UG75 Expression | HOM | Mm.22287 | TITLE ESTs, Highly similar to PROTEASOME ZETA CHAIN [Homo sapiens] | | | gi = 1504365 | 464610 |
| IC03514 | UG75 Expression | HOM | Mm.22876 | TITLE ESTs, Highly similar to BLEOMYCIN HYDRO-LASE [R.norvegicus] | | | gi = 3260937 | 1480905 |
| IC03515 | UG75 Expression | HOM | Mm.22884 | TITLE ESTs, Highly similar to (defline not available 6007645) [M.musculus] | | | gi = 4616165 | 316740 |
| IC03516 | UG75 Expression | HOM | Mm.22982 | TITLE ESTs, Highly similar to RSP-1 PROTEIN [Mus musculus] | | | gi = 4060544 | 596028 |
| IC03517 | UG75 Expression | HOM | Mm.23014 | TITLE ESTs, Highly similar to KIAA0663 protein [H.sapiens] | | | gi = 6079199 | 2236009 |
| IC03518 | UG75 Expression | HOM | Mm.23141 | TITLE ESTs, Highly similar to KIAA0622 protein [H.sapiens] | | | gi = 4408879 | 476216 |
| IC03519 | UG75 Expression | HOM | Mm.23454 | TITLE ESTs, Highly similar to unknown [H.sapiens] | | | gi = 4483855 | 1053487 |
| IC03520 | UG75 Expression | HOM | Mm.23653 | TITLE ESTs, Highly similar to pseudouridine synthase 1 [M.musculus] | | | gi = 1804287 | 661413 |
| IC03521 | UG75 Expression | HOM | Mm.23693 | TITLE ESTs, Highly similar to bithoraxoid-like protein [R.norvegicus] | | | gi = 1309574 | 337538 |
| IC03522 | UG75 Expression | HOM | Mm.23702 | TITLE ESTs, Highly similar to KIAA0560 protein [H.sapiens] | | | gi = 1759449 | 620762 |
| IC03523 | UG75 Expression | HOM | Mm.23705 | TITLE ESTs, Highly similar to PUTATIVE ATP-DEPENDENT RNA HELICASE K03H1.2 IN CHROMOSOME III [Caenorhabditis elegans] | | | gi = 1701173 | 597068 |
| IC03524 | UG75 Expression | HOM | Mm.23749 | TITLE ESTs, Highly similar to transcriptional co-activator CRSP70 [H.sapiens] | | | gi = 4258445 | 354936 |
| IC03525 | UG75 Expression | HOM | Mm.23750 | TITLE ESTs, Highly similar to GLUTAMINYL-TRNA SYNTHETASE [Homo sapiens] | | | gi = 4726747 | 1970985 |
| IC03526 | UG75 Expression | HOM | Mm.23755 | TITLE ESTs, Highly similar to GTP-BINDING PROTEIN SARA [Mus musculus] | | | gi = 6085413 | 518712 |
| IC03527 | UG75 Expression | HOM | Mm.23805 | TITLE ESTs, Highly similar to KIAA0221 [H.sapiens] | | | gi = 1504395 | 458332 |
| IC03528 | UG75 Expression | HOM | Mm.23814 | TITLE ESTs, Highly similar to TIP120 [R.norvegicus] | | | gi = 3747611 | 1886701 |
| IC03529 | UG75 Expression | HOM | Mm.23827 | TITLE ESTs, Highly similar to MITOCHONDRIAL RNA SPLICING PROTEIN MSR4 [Saccharomyces cerevisiae] | | | gi = 4061731 | 573684 |
| IC03530 | UG75 Expression | HOM | Mm.23836 | TITLE ESTs, Highly similar to (defline not available 5901572) [R.norvegicus] | | | gi = 1287940 | 331150 |
| IC03531 | UG75 Expression | HOM | Mm.23841 | TITLE ESTs, Highly similar to HYPOTHETICAL TRP-ASP REPEATS CONTAINING PROTEIN IN CPR4-SOL2 INTERGENIC REGION [Saccharomyces cerevisiae] | | | gi = 4434065 | 2101553 |
| IC03532 | UG75 Expression | HOM | Mm.23864 | TITLE ESTs, Highly similar to cbp146 [M.musculus] | | | gi = 3373636 | 1193057 |
| IC03533 | UG75 Expression | HOM | Mm.23869 | TITLE ESTs, Highly similar to ARGININOSUCCINATE LYASE [Homo sapiens] | | | gi = 2962496 | 1265252 |
| IC03534 | UG75 Expression | HOM | Mm.23876 | TITLE ESTs, Highly similar to PROPIONYL-COA CARBOXYLASE ALPHA CHAIN PRECURSOR [Rattus norvegicus] | | | gi = 3863747 | 1890272 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03535 | UG75 Expression | HOM | Mm.23883 | TITLE ESTs, Highly similar to CELL DIVISION CONTROL PROTEIN 23 [Saccharomyces cerevisiae] | | | gi = 2503193 | 1066857 |
| IC03536 | UG75 Expression | HOM | Mm.23884 | PARTICLE RECEPTOR ALPHA SUBUNIT [Homo sapiens] | | | gi = 1713735 | 603798 |
| IC03537 | UG75 Expression | HOM | Mm.23906 | TITLE ESTs, Highly similar to RNA splicing-related protein [R.norvegicus] | | | gi = 2332206 | 972874 |
| IC03538 | UG75 Expression | HOM | Mm.23949 | TITLE ESTs, Highly similar to MUTL PROTEIN HOMOLOG 1 [Homo sapiens] | | | gi = 4513111 | 1262329 |
| IC03539 | UG75 Expression | HOM | Mm.23974 | TITLE ESTs, Highly similar to KIAA0157 gene product is novel. [H.sapiens] | | | gi = 5497319 | 1480657 |
| IC03540 | UG75 Expression | HOM | Mm.24005 | TITLE ESTs, Highly similar to similar to Leucine-rich transmembrane proteins [H.sapiens] | | | gi = 4217159 | 348737 |
| IC03541 | UG75 Expression | HOM | Mm.24021 | TITLE ESTs, Highly similar to FLAVIN REDUCTASE [H.sapiens] | | | gi = 1554525 | 517446 |
| IC03542 | UG75 Expression | HOM | Mm.24042 | TITLE ESTs, Highly similar to PRE-MRNA SPLICING FACTOR SRP75 [Homo sapiens] | | | gi = 6757495 | 2648111 |
| IC03543 | UG75 Expression | HOM | Mm.24059 | TITLE ESTs, Highly similar to unknown [H.sapiens] | | | gi = 1776373 | 637229 |
| IC03544 | UG75 Expression | HOM | Mm.24088 | TITLE ESTs, Highly similar to (defline not available 6063137) [M.musculus] | | | gi = 2305689 | 948538 |
| IC03545 | UG75 Expression | HOM | Mm.24102 | TITLE ESTs, Highly similar to transcription factor E2F-4 [M.musculus] | | | gi = 1826142 | 1005576 |
| IC03546 | UG75 Expression | HOM | Mm.24155 | TITLE ESTs, Highly similar to CYTOCHROME P450 L1 [Saccharomyces cerevisiae] | | | gi = 6084810 | 2136000 |
| IC03547 | UG75 Expression | HOM | Mm.24174 | TITLE ESTs, Highly similar to ALANYL-TRNA SYNTHETASE [Homo sapiens] | | | gi = 4031762 | 1908034 |
| IC03548 | UG75 Expression | HOM | Mm.24178 | TITLE ESTs, Highly similar to QUEUINE TRNA-RIBOSYLTRANSFERASE [Escherichia coli] | | | gi = 4061556 | 424653 |
| IC03549 | UG75 Expression | HOM | Mm.24181 | TITLE ESTs, Highly similar to RN protein [R.norvegicus] | | | gi = 4616595 | 831679 |
| IC03550 | UG75 Expression | HOM | Mm.24202 | TITLE ESTs, Highly similar to (defline not available 5813825) [M.musculus] | | | gi = 6078846 | 2225617 |
| IC03551 | UG75 Expression | HOM | Mm.24220 | TITLE ESTs, Highly similar to huntingtin interacting protein HYPK [H.sapiens] | | | gi = 1330664 | 354926 |
| IC03552 | UG75 Expression | HOM | Mm.24238 | TITLE ESTs, Highly similar to HYPOTHETICAL PROTEIN KIAA0274 [H.sapiens] | | | gi = 2259561 | 904873 |
| IC03553 | UG75 Expression | HOM | Mm.24242 | TITLE ESTs, Highly similar to CARBOXYPEPTIDASE B PRECURSOR [Rattus norvegicus] | | | gi = 4057105 | 477035 |
| IC03554 | UG75 Expression | HOM | Mm.24276 | TITLE ESTs, Highly similar to COMPLEMENT C1R COMPONENT PRECURSOR [Homo sapiens] | | | gi = 3519592 | 1498828 |
| IC03555 | UG75 Expression | HOM | Mm.24293 | TITLE ESTs, Highly similar to ALPHA-1,6-MANNOSYL-GLYCOPROTEIN BETA-1,2-N-ACETYLGLUCOSAMINYLTRANSFERASE [Rattus norvegicus] | | | gi = 1725867 | 599257 |
| IC03556 | UG75 Expression | HOM | Mm.24294 | TITLE ESTs, Highly similar to HYPOTHETICAL PROTEIN KIAA0136 [H.sapiens] | | | gi = 3066019 | 1314774 |
| IC03557 | UG75 Expression | HOM | Mm.24369 | TITLE ESTs, Highly similar to BETA-ARRESTIN 2 [Rattus norvegicus] | | | gi = 3141337 | 1345899 |
| IC03558 | UG75 Expression | HOM | Mm.24383 | TITLE ESTs, Highly similar to hypothetical protein [H.sapiens] | | | gi = 3158998 | 1349324 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03559 | UG75 Expression | HOM | Mm.24431 | TITLE ESTs, Highly similar to TRANSCRIPTION INITIATION FACTOR TFIID 18 KD SUBUNIT [H.sapiens] | | | gi = 4444511 | 1889874 |
| IC03560 | UG75 Expression | HOM | Mm.24433 | CONJUGATING ENZYME E2-18 KD [Saccharomyces cerevisiae] | | | gi = 4434758 | 1885548 |
| IC03561 | UG75 Expression | HOM | Mm.24452 | HYDRATASE, MITOCHONDRIAL PRECURSOR [Rattus norvegicus] | | | gi = 4967979 | 580165 |
| IC03562 | UG75 Expression | HOM | Mm.24455 | TITLE ESTs, Highly similar to REPLICATION PROTEIN A 70 KD DNA-BINDING SUBUNIT [Homo sapiens] | | | gi = 1776563 | 623063 |
| IC03563 | UG75 Expression | HOM | Mm.24457 | TITLE ESTs, Highly similar to ALDEHYDE DEHYDROGENASE, MITOCHONDRIAL X PRECURSOR [Homo sapiens] | | | gi = 3863627 | 1890121 |
| IC03564 | UG75 Expression | HOM | Mm.24483 | TITLE ESTs, Highly similar to KIAA0160 gene product is novel. [H.sapiens] | | | gi = 1794415 | 640237 |
| IC03565 | UG75 Expression | HOM | Mm.24498 | TITLE ESTs, Highly similar to ARP2/3 COMPLEX 21 KD SUBUNIT [H.sapiens] | | | gi = 3165087 | 1972155 |
| IC03566 | UG75 Expression | HOM | Mm.24578 | TITLE ESTs, Highly similar to hypertension-related protein [R.norvegicus] | | | gi = 2187995 | 871334 |
| IC03567 | UG75 Expression | HOM | Mm.24602 | TITLE ESTs, Highly similar to SOH1 PROTEIN [Saccharomyces cerevisiae] | | | gi = 3372065 | 1515757 |
| IC03568 | UG75 Expression | HOM | Mm.2462 | TITLE ESTs, Highly similar to 26S PROTEASE REGULATORY SUBUNIT 7 [Homo sapiens] | | | gi = 4444299 | 1889623 |
| IC03569 | UG75 Expression | HOM | Mm.24627 | TITLE ESTs, Highly similar to KIAA0301 [H. sapiens] INITIATION FACTOR IIF, ALPHA SUBUNIT [Homo sapiens] | | | gi = 1826538 | 653512 |
| IC03570 | UG75 Expression | HOM | Mm.24632 | TITLE ESTs, Highly similar to HSPC004 [H. sapiens] | | | gi = 2517130 | 441284 |
| IC03571 | UG75 Expression | HOM | Mm.24636 | TITLE ESTs, Highly similar to hypothetical protein [H. sapiens] | | | gi = 5910518 | 355253 |
| IC03572 | UG75 Expression | HOM | Mm.24641 | | | | gi = 5549151 | 2099740 |
| IC03573 | UG75 Expression | HOM | Mm.24643 | TITLE ESTs, Highly similar to CALTRACTIN [Homo sapiens] | | | gi = 3373193 | 634823 |
| IC03574 | UG75 Expression | HOM | Mm.24729 | TITLE ESTs, Highly similar to nucleolar protein Nopp140, hepatic [R. norvegicus] | | | gi = 3516225 | 1498960 |
| IC03575 | UG75 Expression | HOM | Mm.24763 | TITLE ESTs, Highly similar to short coiled coil protein SCOCO [M. musculus] | | | gi = 6084691 | 520497 |
| IC03576 | UG75 Expression | HOM | Mm.24805 | CYTOCHROME C REDUCTASE COMPLEX 14 KD PROTEIN [Bos taurus] | | | gi = 4766778 | 1969891 |
| IC03577 | UG75 Expression | HOM | Mm.24830 | TITLE ESTs, Highly similar to (defline not available 5478765) [M. musculus] | | | gi = 4400966 | 1005848 |
| IC03578 | UG75 Expression | HOM | Mm.24831 | TITLE ESTs, Highly similar to INTERFERON-RELATED PROTEIN PC4 [Mus musculus] | | | gi = 1355391 | 367523 |
| IC03579 | UG75 Expression | HOM | Mm.24833 | TITLE ESTs, Highly similar to ZINC FINGER PROTEIN 183 [H. sapiens] [M. musculus] | | | gi = 1792979 | 640083 |
| IC03580 | UG75 Expression | HOM | Mm.24846 | | | | gi = 5126149 | 2065002 |
| IC03581 | UG75 Expression | HOM | Mm.24847 | TITLE ESTs, Highly similar to unknown [H. sapiens] | | | gi = 3864054 | 1889416 |
| IC03582 | UG75 Expression | HOM | Mm.24859 | TITLE ESTs, Highly similar to transcriptional co-activator CRSP34 [H. sapiens] | | | gi = 6937875 | 2646483 |
| IC03583 | UG75 Expression | HOM | Mm.24870 | CARBOXYL-TERMINAL HYDROLASE HAUSP [H. sapiens] | | | gi = 1315280 | 352169 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03584 | UG75 Expression | HOM | Mm.24874 | TITLE ESTs, Highly similar to 26S proteasome subunit p112 [R. norvegicus] | | | gi = 4434618 | 1920967 |
| IC03585 | UG75 Expression | HOM | Mm.24972 | TITLE ESTs, Highly similar to major vault protein [R. norvegicus] | | | gi = 2518195 | 1096248 |
| IC03586 | UG75 Expression | HOM | Mm.24997 | TITLE ESTs, Highly similar to KIAA0585 protein [H. sapiens] | | | gi = 1463760 | 437679 |
| IC03587 | UG75 Expression | HOM | Mm.25018 | TITLE ESTs, Highly similar to KIAA0183 [H. sapiens] | | | gi = 2646474 | 1079729 |
| IC03588 | UG75 Expression | HOM | Mm.25025 | TITLE ESTs, Highly similar to (defline not available 5916179) [M. musculus] | | | gi = 2519637 | 1514287 |
| IC03589 | UG75 Expression | HOM | Mm.25044 | TITLE ESTs, Highly similar to HYPOTHETICAL 153.4 KD PROTEIN B0523.5 IN CHROMOSOME III [Caenorhabditis elegans] | | | gi = 2572768 | 1020962 |
| IC03590 | UG75 Expression | HOM | Mm.25045 | TITLE ESTs, Highly similar to ER LUMEN PROTEIN RETAINING RECEPTOR 1 [Homo sapiens] | | | gi = 1446587 | 426213 |
| IC03591 | UG75 Expression | HOM | Mm.25125 | TITLE ESTs, Highly similar to RIBOSE-PHOSPHATE PYROPHOSPHOKINASE [Schizosaccharomyces pombe] | | | gi = 6084517 | 975982 |
| IC03592 | UG75 Expression | HOM | Mm.25140 | TITLE ESTs, Highly similar to PRE-MRNA SPLICING HELICASE BRR2 [Saccharomyces cerevisiae] | | | gi = 1309600 | 577561 |
| IC03593 | UG75 Expression | HOM | Mm.25148 | TITLE ESTs, Highly similar to hypothetical protein [H. sapiens] | | | gi = 6083547 | 2236359 |
| IC03594 | UG75 Expression | HOM | Mm.25149 | TITLE ESTs, Highly similar to protein p84 [H. sapiens] | | | gi = 2573851 | 1108794 |
| IC03595 | UG75 Expression | HOM | Mm.25154 | TITLE ESTs, Highly similar to HYPOTHETICAL PROTEIN KIAA0105 [H. sapiens] | | | gi = 2040515 | 761010 |
| IC03596 | UG75 Expression | HOM | Mm.25161 | TITLE ESTs, Highly similar to REGULATORY PROTEIN SIR2 [Saccharomyces cerevisiae] | | | gi = 4967457 | 557657 |
| IC03597 | UG76 LID366 B cell | HOM | Mm.25164 | TITLE ESTs, Highly similar to gene trap locus-13 [M. musculus] | | | gi = 2504628 | 934793 |
| IC03598 | UG75 Expression | HOM | Mm.25180 | TITLE ESTs, Highly similar to SODIUM- AND CHLORIDE-DEPENDENT GABA TRANSPORTER 2 [M. musculus] | | | gi = 4059917 | 579596 |
| IC03599 | UG75 Expression | HOM | Mm.25187 | TITLE ESTs, Highly similar to torsinB [H. sapiens] | | | gi = 3371483 | 2937382 |
| IC03600 | UG75 Expression | HOM | Mm.25231 | TITLE ESTs, Highly similar to p53 tumor suppressor-binding protein 1 [H. sapiens] | | | gi = 4602122 | 1211267 |
| IC03601 | UG75 Expression | HOM | Mm.25313 | TITLE ESTs, Highly similar to GLUTHATHIONE S-TRANSFERASE THETA 1 [Homo sapiens] | | | gi = 3685427 | 1885751 |
| IC03602 | UG75 Expression | HOM | Mm.25316 | TITLE ESTs, Highly similar to ATP-CITRATE [Rattus norvegicus] | | | gi = 2518268 | 762531 |
| IC03603 | UG75 Expression | HOM | Mm.25353 | TITLE ESTs, Highly similar to SORCIN [Cricetulus longicaudatus] | | | gi = 1793048 | 639880 |
| IC03604 | UG75 Expression | HOM | Mm.25492 | TITLE ESTs, Highly similar to LCAT-like lysophospholipase [H. sapiens] | | | gi = 2139596 | 809172 |
| IC03605 | UG75 Expression | HOM | Mm.25557 | TITLE ESTs, Highly similar to BETA-UREIDOPROPIONASE [R. norvegicus] | | | gi = 3747629 | 1886717 |
| IC03606 | UG75 Expression | HOM | Mm.25566 | TITLE ESTs, Highly similar to KIAA0650 protein [H. sapiens] | | | gi = 3955699 | 3167357 |
| IC03607 | UG75 Expression | HOM | Mm.25622 | TITLE ESTs, Highly similar to SON PROTEIN [Homo sapiens] | | | gi = 1767810 | 622683 |
| IC03608 | UG75 Expression | HOM | Mm.25642 | TITLE ESTs, Highly similar to Lsm5 protein [H. sapiens] | | | gi = 1769080 | 634355 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03609 | UG75 Expression | HOM | Mm.25691 | TITLE ESTs, Highly similar to complement component C2 [M. musculus] | | | gi = 4297451 | 350628 |
| IC03610 | UG75 Expression | HOM | Mm.25699 | TITLE ESTs, Highly similar to SYNAPTOPORIN [Rattus norvegicus] | | | gi = 6085647 | 1248560 |
| IC03611 | UG75 Expression | HOM | Mm.25732 | TITLE ESTs, Highly similar to SPLICEOSOME ASSOCIATED PROTEIN 114 [H. sapiens] | | | gi = 3515372 | 1885010 |
| IC03612 | UG75 Expression | HOM | Mm.2576 | [H. sapiens] | | | gi = 1287387 | 330213 |
| IC03613 | UG75 Expression | HOM | Mm.25763 | TITLE ESTs, Highly similar to EV12B PROTEIN PRECURSOR TROPIC VIRAL INTEGRATION SITE 2B PROTEIN) [Homo sapiens] | | | gi = 4725443 | 1382865 |
| IC03614 | UG75 Expression | HOM | Mm.25779 | TITLE ESTs, Highly similar to PRE-MRNA SPLICING FACTOR PRP9 [Saccharomyces cerevisiae] | | | gi = 3167713 | 1431947 |
| IC03615 | UG75 Expression | HOM | Mm.25803 | TITLE ESTs, Highly similar to implantation-associated protein [R. norvegicus] | | | gi = 6077284 | 2225900 |
| IC03616 | UG75 Expression | HOM | Mm.25808 | TITLE ESTs, Highly similar to GMP REDUCTASE [Homo sapiens] | | | gi = 1506618 | 467076 |
| IC03617 | UG75 Expression | HOM | Mm.25833 | TITLE ESTs, Highly similar to IDN4-GGTR8 [H. sapiens] | | | gi = 4617320 | 722904 |
| IC03618 | UG75 Expression | HOM | Mm.25837 | TITLE ESTs, Highly similar to U2 SMALL NUCLEAR RIBONUCLEOPROTEIN AUXILIARY FACTOR 35 KD SUBUNIT RELATED-PROTEIN 2 [M. musculus] | | | gi = 2517616 | 734837 |
| IC03619 | UG75 Expression | HOM | Mm.25849 | [H. sapiens] | | | gi = 1326701 | 353803 |
| IC03620 | UG75 Expression | HOM | Mm.26089 | TITLE ESTs, Highly similar to scaffold attachment factor B [R. norvegicus] | | | gi = 3373612 | 763580 |
| IC03621 | UG75 Expression | HOM | Mm.26207 | TITLE ESTs, Highly similar to L-GULONOLACTONE OXIDASE [R. norvegicus] | | | gi = 3447400 | 1482883 |
| IC03622 | UG75 Expression | HOM | Mm.26212 | TITLE ESTs, Highly similar to SRB7 [H. sapiens] | | | gi = 3164934 | 1362574 |
| IC03623 | UG75 Expression | HOM | Mm.26234 | TITLE ESTs, Highly similar to QUEUINE TRNA-RIBOSYLTRANSFERASE [Oryctolagus cuniculus] | | | gi = 6078724 | 2225489 |
| IC03624 | UG75 Expression | HOM | Mm.26242 | TITLE ESTs, Highly similar to KIAA0678 protein [H. sapiens] | | | gi = 1681047 | 579593 |
| IC03625 | UG75 Expression | HOM | Mm.26418 | TITLE ESTs, Highly similar to MITOCHONDRIAL INNER MEMBRANE PROTEASE SUBUNIT 1 [Saccharomyces cerevisiae] | | | gi = 6517809 | 2649406 |
| IC03626 | UG75 Expression | HOM | Mm.26463 | TITLE ESTs, Highly similar to AFLATOXIN 131 ALDEHYDE REDUCTASE [Rattus norvegicus] | | | gi = 6079255 | 2236087 |
| IC03627 | UG75 Expression | HOM | Mm.26486 | TITLE ESTs, Highly similar to RAS GTPASE-ACTIVATING-LIKE PROTEIN IQGAP1 [Homo sapiens] | | | gi = 2850413 | 1244003 |
| IC03628 | UG75 Expression | HOM | Mm.26490 | TITLE ESTs, Highly similar to METHYLMALONATE-SEMIALDEHYDE DEHYDROGENASE PRECURSOR [R. norvegicus] | | | gi = 1755752 | 617478 |
| IC03629 | UG75 Expression | HOM | Mm.265 | TITLE ESTs, Highly similar to 40S RIBOSOMAL PROTEIN S25 [Homo sapiens; Rattus norvegicus] | | | gi = 1290059 | 333032 |
| IC03630 | UG75 Expression | HOM | Mm.26530 | TITLE ESTs, Highly similar to hypothetical protein, similar to [H. sapiens] | | | gi = 3978751 | 1398834 |
| IC03631 | UG75 Expression | HOM | Mm.26540 | TITLE ESTs, Highly similar to ZINC FINGER PROTEIN ZFP-35 [Mus musculus] | | | gi = 4442034 | 1921470 |
| IC03632 | UG75 Expression | HOM | Mm.26560 | TITLE ESTs, Highly similar to HYPOTHETICAL 66.5 KD PROTEIN F02A9.5 IN CHROMOSOME III [Caenorhabditis elegans] | | | gi = 6078763 | 2192674 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03633 | UG75 Expression | HOM | Mm.26585 | TITLE ESTs, Highly similar to ACTIVATOR 1 36 KD SUBUNIT [Homo sapiens] | | | gi = 4061778 | 575667 |
| IC03634 | UG75 Expression | HOM | Mm.26600 | TITLE ESTs, Highly similar to PHOSPHORYLASE B KINASE ALPHA REGULATORY CHAIN, LIVER ISOFORM [Oryctolagus cuniculus] | | | gi = 5598795 | 579660 |
| IC03635 | UG75 Expression | HOM | Mm.26625 | TITLE ESTs, Highly similar to TISSUE ALPHA-L FUCOSIDASE PRECURSOR [Homo sapiens] | | | gi = 4967729 | 2192873 |
| IC03636 | UG75 Expression | HOM | Mm.26644 | TITLE ESTs, Highly similar to HYPOTHETICAL 16.5 KD PROTEIN IN PAS8-EGT2 INTERGENIC REGION [Saccharomyces cerevisiae] | | | gi = 6824429 | 888519 |
| IC03637 | UG75 Expression | HOM | Mm.26792 | TITLE ESTs, Highly similar to pIL2 hypothetical protein [R. norvegicus] | | | gi = 3260864 | 1480855 |
| IC03638 | UG76 LID366 B cell | HOM | Mm.26793 | TITLE ESTs, Highly similar to STEROL 26 HYDROXYLASE MITOCHONDRIAL PRECURSOR [Rattus norvegicus] | | | gi = 3863817 | 1889103 |
| IC03639 | UG75 Expression | HOM | Mm.26835 | TITLE ESTs, Highly similar to hepatocyte growth factor activator inhibitor type 2 [M. musculus] | | | gi = 1309577 | 337560 |
| IC03640 | UG75 Expression | HOM | Mm.26875 | TITLE ESTs, Highly similar to microchidia [M. musculus] | | | gi = 3733798 | 1428933 |
| IC03641 | UG75 Expression | HOM | Mm.26922 | TITLE ESTs, Highly similar to [Human chromosome 3p21.1 gene sequence, complete cds.], gene product [H. sapiens] | | | gi = 2989032 | 1149956 |
| IC03642 | UG75 Expression | HOM | Mm.26947 | TITLE ESTs, Highly similar to leucine zipper-EF-hand containing transmembrane protein 1 [M. musculus] | | | gi = 6638418 | 2331891 |
| IC03643 | UG75 Expression | HOM | Mm.26949 | TITLE ESTs, Highly similar to ELECTRON TRANSFER FLAVOPROTEIN ALPHA-SUBUNIT PRECURSOR [Homo sapiens] | | | gi = 4199416 | 580666 |
| IC03644 | UG75 Expression | HOM | Mm.26991 | TITLE ESTs, Highly similar to HYPOTHETICAL 52.8 KD PROTEIN T05E11.5 IN CHROMOSOME III [Caenorhabditis elegans] | | | gi = 1309517 | 337265 |
| IC03645 | UG75 Expression | HOM | Mm.27070 | AMINOPEPTIDASE ZK353.6 IN CHROMOSOME III [Caenorhabditis elegans] | | | gi = 2917471 | 1383692 |
| IC03646 | UG75 Expression | HOM | Mm.27074 | TITLE ESTs, Highly similar to 54K arginine-rich nuclear protein [H. sapiens] | | | gi = 4434032 | 2331872 |
| IC03647 | UG75 Expression | HOM | Mm.27082 | TITLE ESTs, Highly similar to CGI-11 protein [H. sapiens] | | | gi = 5819604 | 2182390 |
| IC03648 | UG75 Expression | HOM | Mm.27085 | TITLE ESTs, Highly similar to TRANS-1,2-DIHYDROBENZENE-1,2-DIOL DEHYDROGENASE [Homo sapiens] | | | gi = 6078369 | 2155456 |
| IC03649 | UG75 Expression | HOM | Mm.27098 | TITLE ESTs, Highly similar to MVP1 PROTEIN [Saccharomyces cerevisiae] | | | gi = 3718851 | 1885663 |
| IC03650 | UG75 Expression | HOM | Mm.27107 | TITLE ESTs, Highly similar to HYPOTHETICAL 25.7 KD PROTEIN IN MSH1-EPT1 INTERGENIC REGION [Saccharomyces cerevisiae] | | | gi = 2516797 | 1923025 |
| IC03651 | UG75 Expression | HOM | Mm.27128 | TITLE ESTs, Highly similar to HYPOTHETICAL 15.5 KD PROTEIN IN BEM2-SPT2 INTERGENIC REGION [Saccharomyces cerevisiae] | | | gi = 6632540 | 2655850 |
| IC03652 | UG75 Expression | HOM | Mm.27159 | TITLE ESTs, Highly similar to ankyrin repeat-containing protein Asb-2 [M. musculus] | | | gi = 1282136 | 331907 |
| IC03653 | UG75 Expression | HOM | Mm.27162 | TITLE ESTs, Highly similar to 54 kDa oligoadenylate synthetase-like protein p540ASL [M. musculus] | | | gi = 6756992 | 2646375 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03654 | UG75 Expression | HOM | Mm.2718 | TITLE ESTs, Highly similar to ELONGATION FACTOR 1-BETA [Homo sapiens] | | | gi = 1297718 | 336826 |
| IC03655 | UG75 Expression | HOM | Mm.27182 | TITLE ESTs, Highly similar to ELONGATION FACTOR TU, MITOCHONDRIAL PRECURSOR [Bos taurus] | | | gi = 3161302 | 1617623 |
| IC03656 | UG75 Expression | HOM | Mm.27186 | TITLE ESTs, Highly similar to lin-10 protein homolog [R. norvegicus] | | | gi = 3216257 | 1480577 |
| IC03657 | UG75 Expression | HOM | Mm.27195 | TITLE ESTs, Highly similar to heparan-sulfate 6-sulfotransferase [H. sapiens] | | | gi = 1936756 | 790200 |
| IC03658 | UG75 Expression | HOM | Mm.27213 | TITLE ESTs, Highly similar to TRANSCRIPTION INITIATION FACTOR IIB [Rattus norvegicus] | | | gi = 3521605 | 1498432 |
| IC03659 | UG75 Expression | HOM | Mm.27236 | TITLE ESTs, Highly similar to LANOSTEROL SYNTHASE [Rattus norvegicus] | | | gi = 6633497 | 2317834 |
| IC03660 | UG75 Expression | HOM | Mm.27272 | TITLE ESTs, Highly similar to CLATHRIN COAT ASSEMBLY PROTEIN AP17 [Rattus norvegicus] | | | gi = 1309571 | 337515 |
| IC03661 | UG75 Expression | HOM | Mm.27278 | TITLE ESTs, Highly similar to NUCLEOSIDE DIPHOSPHATE KINASE [Ginglymostoma ciratum] | | | gi = 3718462 | 484189 |
| IC03662 | UG75 Expression | HOM | Mm.27283 | TITLE ESTs, Highly similar to DNA-DIRECTED RNA POLYMERASE MITOCHONDRIAL PRECURSOR [Saccharomyces cerevisiae] | | | gi = 1746868 | 608625 |
| IC03663 | UG75 Expression | HOM | Mm.27286 | TITLE ESTs, Highly similar to HYPOTHETICAL 24.5 KD PROTEIN IN SAP185-BCK1 INTERGENIC REGION [Saccharomyces cerevisiae] | | | gi = 3863302 | 1888637 |
| IC03664 | UG75 Expression | HOM | Mm.27294 | TITLE ESTs, Highly similar to PUTATIVE UBIQUITIN CARBOXYL-TERMINAL HYDROLASE C13A11.04C [Schizosaccharomyces pombe] | | | gi = 5549785 | 2099232 |
| IC03665 | UG75 Expression | HOM | Mm.27298 | TITLE ESTs, Highly similar to HSPC005 [H. sapiens] | | | gi = 3371314 | 761083 |
| IC03666 | UG75 Expression | HOM | Mm.27312 | TITLE ESTs, Highly similar to PL6 protein [M. musculus] | | | gi = 251925 | 1434241 |
| IC03667 | UG75 Expression | HOM | Mm.27327 | TITLE ESTs, Highly similar to COATOMER BETA SUBUNIT [Rattus norvegicus] | | | gi = 6521150 | 2645954 |
| IC03668 | UG75 Expression | HOM | Mm.27328 | TITLE ESTs, Highly similar to CGI-31 protein [H. sapiens] | | | gi = 4968310 | 1432040 |
| IC03669 | UG75 Expression 00/04/26 UG#76 17Lid Expansion | HOM | Mm.2733 | ESTs, Highly similar to enoyl-CoA hydratase [H. sapiens] | | | gi = 4604833 | 1925193 |
| IC03670 | UG75 Expression | HOM | Mm.27336 | TITLE ESTs, Highly similar to EXTRACELLULAR RIBONUCLEASE LE PRECURSOR [Lycopersicon esculentum] | | | gi = 1316884 | 350317 |
| IC03671 | UG75 Expression | HOM | Mm.27354 | TITLE ESTs, Highly similar to hypothetical protein [H. sapiens] | | | gi = 2305793 | 948580 |
| IC03672 | UG75 Expression | HOM | Mm.27357 | TITLE ESTs, Highly similar to NARDILYSIN PRECURSOR [Rattus norvegicus] | | | gi = 1291895 | 333931 |
| IC03673 | UG75 Expression | HOM | Mm.27373 | TITLE ESTs, Highly similar to H<BETA>58 PROTEIN [Mus musculus] | | | gi = 2813142 | 1247586 |
| IC03674 | UG75 Expression | HOM | Mm.27387 | TITLE ESTs, Highly similar to cAMP inducible 1 protein [M. musculus] | | | gi = 4443646 | 735109 |
| IC03675 | UG75 Expression | HOM | Mm.27389 | TITLE ESTs, Highly similar to VACUOLAR ASSEMBLY PROTEIN VPS41 HOMOLOG [H. sapiens] | | | gi = 4032613 | 1907942 |
| IC03676 | UG75 Expression | HOM | Mm.27394 | TITLE ESTs, Highly similar to HYPOTHETICAL PROTEIN KIAA0174 [H. sapiens] | | | gi = 3260858 | 1480864 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03677 | UG75 Expression | HOM | Mm.27403 | TITLE ESTs, Highly similar to PHENYLALANYL-TRNA SYNTHETASE BETA CHAIN CYTOPLASMIC [Saccharomyces cerevisiae] | | | gi = 3374424 | 891349 |
| IC03678 | UG75 Expression | HOM | Mm.27415 | TITLE ESTs, Highly similar to Tpr [H. sapiens] | | | gi = 6079244 | 2236082 |
| IC03679 | UG75 Expression | HOM | Mm.27438 | TITLE ESTs, Highly similar to KIAA0676 protein [H. sapiens] | | | gi = 2811710 | 1225731 |
| IC03680 | UG75 Expression | HOM | Mm.27473 | TITLE ESTs, Highly similar to sodium-dependent dicarboxylate, transporter SDCT2 [R. norvegicus] | | | gi = 4409491 | 581007 |
| IC03681 | UG75 Expression | HOM | Mm.27490 | TITLE ESTs, Highly similar to CGI40 protein [H. sapiens] | | | gi = 1324824 | 351956 |
| IC03682 | UG75 Expression | HOM | Mm.27496 | TITLE ESTs, Highly similar to ubiquitin specific protease [H. sapiens] | | | gi = 2519273 | 806085 |
| IC03683 | UG75 Expression | HOM | Mm.27499 | TITLE ESTs, Highly similar to seven transmembrane domain protein [H. sapiens] | | | gi = 1701795 | 585938 |
| | | gi = 1701795 | 585938 | TITLE ESTs, Highly similar to PROBABLE UBIQUITIN CARBOXYL-TERMINAL HYDROLASE [Mus musculus] | | | gi = 6757742 | 2648402 |
| IC03685 | UG75 Expression | HOM | Mm.27526 | TITLE ESTs, Highly similar to ARGINYL-TRNA SYNTHETASE [Cricetulus longicaudatus] | | | gi = 2516804 | 1400494 |
| IC03686 | UG75 Expression | HOM | Mm.27532 | TITLE ESTs, Highly similar to L-A VIRUS GAG PROTEIN N-ACETYLTRANSFERASE [Saccharomyces cerevisiae] | | | gi = 1801013 | 640960 |
| IC03687 | UG75 Expression | HOM | Mm.27544 | TITLE ESTs, Highly similar to KIAA0398 [H. sapiens] | | | gi = 3394227 | 1364287 |
| IC03688 | UG75 Expression | HOM | Mm.27545 | TITLE ESTs, Highly similar to HNRNP METHYLTRANSFERASE [Saccharomyces cerevisiae] | | | gi = 6520881 | 2645661 |
| IC03689 | UG75 Expression | HOM | Mm.27557 | TITLE ESTs, Highly similar to CELL DIVISION CONTROL PROTEIN 2 HOMOLOG 2 [Pisum sativum] | | | gi = 1337516 | 356032 |
| IC03690 | UG75 Expression | HOM | Mm.27570 | TITLE ESTs, Highly similar to NADH-UBIQUINONE OXIDOREDUCTASE B14 SUBUNIT [Bos taurus] | | | gi = 4782377 | 1429015 |
| IC03691 | UG75 Expression | HOM | Mm.27586 | TITLE ESTs, Highly similar to REGULATOR OF G-PROTEIN SIGNALLING 2 [Homo sapiens] | | | gi = 3883589 | 1890663 |
| IC03692 | UG75 Expression | HOM | Mm.27600 | TITLE ESTs, Highly similar to SIGNAL RECOGNITION PARTICLE 72 KD PROTEIN [Canis familiaris] | | | gi = 3516293 | 1498994 |
| IC03693 | UG75 Expression | HOM | Mm.27606 | TITLE ESTs, Highly similar to COP-COATED VESICLE MEMBRANE PROTEIN P24 PRECURSOR [Cricetulus griseus] | | | gi = 1557800 | 483184 |
| IC03694 | UG75 Expression | HOM | Mm.27608 | TITLE ESTs, Highly similar to EST00098 protein [H. sapiens] | | | gi = 6085334 | 3155348 |
| IC03695 | UG75 Expression | HOM | Mm.27624 | TITLE ESTs, Highly similar to HISTONE H2A VARIANT [Gallus gallus] | | | gi = 4967847 | 1515689 |
| IC03696 | UG75 Expression | HOM | Mm.27644 | TITLE ESTs, Highly similar to HYPOTHETICAL PROTEIN KIAA0050 [H. sapiens] | | | gi = -4407376 | 750531 |
| IC03697 | UG75 Expression | HOM | Mm.27649 | TITLE ESTs, Highly similar to PUTATIVE ATP-DEPENDENT RNA HELICASE T26G10.1 IN CHROMOSOME III [Caenorhabditis elegans] | | | gi = 3863802 | 1889088 |
| IC03698 | UG75 Expression | HOM | Mm.27668 | TITLE ESTs, Highly similar to Rabin3 [R. norvegicus] | | | gi = 6633466 | 2317657 |
| IC03699 | UG75 Expression | HOM | Mm.27677 | TITLE ESTs, Highly similar to NADH-UBIQUINONE OXIDOREDUCTASE 13 KD-B SUBUNIT [Bos taurus] | | | gi = 2259585 | 904922 |
| IC03700 | UG75 Expression | HOM | Mm.27685 | TITLE ESTs, Highly similar to EMBRYONIC FIBROBLAST ISOFORM [Rattus norvegicus] | | | gi = 6756735 | 2646065 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03701 | UG75 Expression | HOM | Mm.27689 | TITLE ESTs, Highly similar to Huntingtin interacting protein [*H. sapiens*] | | | gi = 2803044 | 1224468 |
| IC03702 | UG75 Expression | HOM | Mm.27693 | TITLE ESTs, Highly similar to GOLIATH PROTEIN [*Drosophila melanogaster*] | | | gi = 6631571 | 2811539 |
| IC03703 | UG75 Expression | HOM | Mm.27695 | TITLE ESTs, Highly similar to eukaryotic translation initiation factor eIF3, p35 subunit [*H. sapiens*] | | | gi = 6084751 | 525172 |
| IC03704 | UG75 Expression | HOM | Mm.27714 | TITLE ESTs, Highly similar to KIAA0512 protein [*H. sapiens*] | | | gi = 5125708 | 2076901 |
| IC03705 | UG75 Expression | HOM | Mm.27730 | TITLE ESTs, Highly similar to PHOSPHATIDYLINOSITOL 4-KINASE ALPHA [*Homo sapiens*] | | | gi = 4725283 | 1382678 |
| IC03706 | UG75 Expression | HOM | Mm.27740 | TITLE ESTs, Highly similar to MDC-3.13 isoform 1 [*H. sapiens*] | | | gi = 3167913 | 1431997 |
| IC03707 | UG75 Expression | HOM | Mm.27743 | TITLE ESTs, Highly similar to AMIDOPHOSPHORIBOSYLTRANSFERASE PRECURSOR [*Rattus norvegicus*] | | | gi = 1287289 | 318260 |
| IC03708 | UG75 Expression | HOM | Mm.27763 | TITLE ESTs, Highly similar to 130 KD LEUCINE-RICH PROTEIN [*Homo sapiens*] | | | gi = 1661484 | 520358 |
| IC03709 | UG75 Expression | HOM | Mm.27769 | TITLE ESTs, Highly similar to proline rich protein [*R. norvegicus*] | | | gi = 1310565 | 349886 |
| IC03710 | UG75 Expression | HOM | Mm.27771 | TITLE ESTs, Highly similar to KT112 PROTEIN [*Saccharomyces cerevisiae*] | | | gi = 4057094 | 476368 |
| IC03711 | UG75 Expression | HOM | Mm.27796 | TITLE ESTs, Highly similar to HYPOTHETICAL 29.7 KD PROTEIN IN RSP5-PAK1 INTERGENIC REGION [*Saccharomyces cerevisiae*] | | | gi = 6750439 | 2615902 |
| IC03712 | UG75 Expression | HOM | Mm.27797 | TITLE ESTs, Highly similar to The ha3523 gene product is related to *S. cerevisiae* gene product located in chromosome 111. [*H. sapiens*] | | | gi = 4259211 | 354181 |
| IC03713 | UG75 Expression | HOM | Mm.27800 | TITLE ESTs, Highly similar to MICROSOMAL SIGNAL PEPTIDASE 21 KD SUBUNIT [Canis familiaris] | | | gi = 4199908 | 598865 |
| IC03714 | UG75 Expression | HOM | Mm.27818 | TITLE ESTs, Highly similar to CLATHRIN HEAVY CHAIN [*Rattus norvegicus*] | | | gi = 5905272 | 2182811 |
| IC03715 | UG75 Expression | HOM | Mm.27821 | TITLE ESTs, Highly similar to p20-CGGBP [*H. sapiens*] | | | gi = 1429107 | 418554 |
| IC03716 | UG75 Expression | HOM | Mm.27829 | TITLE ESTs, Highly similar to KIAA0368 [*H. sapiens*] | | | gi = 5819415 | 2158973 |
| IC03717 | UG75 Expression | HOM | Mm.27832 | TITLE ESTs, Highly similar to RAS-RELATED PROTEIN RAL-B [*Rattus norvegicus*] | | | gi = 3373647 | 641741 |
| IC03718 | UG75 Expression | HOM | Mm.27835 | TITLE ESTs, Highly similar to DESMOPLAKIN I AND II [*Homo sapiens*] | | | gi = 4513166 | 1227492 |
| IC03719 | UG75 Expression | HOM | Mm.27839 | TITLE ESTs, Highly similar to HYPOTHETICAL 33.4 KD PROTEIN [*H. sapiens*] | | | gi = 5126000 | 2088223 |
| IC03720 | UG75 Expression | HOM | Mm.27846 | TITLE ESTs, Highly similar to INTERFERON-INDUCIBLE PROTEIN [*Rattus norvegicus*] | | | gi = 1309673 | 337874 |
| IC03721 | UG75 Expression | HOM | Mm.27847 | TITLE ESTs, Highly similar to Tera [*M. musculus*] | | | gi = 6938973 | 2921943 |
| IC03722 | UG75 Expression | HOM | Mm.27850 | TITLE ESTs, Highly similar to ACTIVATOR 1 40 KD SUBUNIT [*Homo sapiens*] | | | gi = 4485840 | 1248081 |
| IC03723 | UG75 Expression | HOM | Mm.27855 | | | | gi = 1769184 | 634422 |
| IC03724 | UG75 Expression | HOM | Mm.27881 | TITLE ESTs, Highly similar to myomegalin [*R. norvegicus*] | | | gi = 1286522 | 315787 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03725 | UG75 Expression | HOM | Mm.27899 | TITLE ESTs, Highly similar to CASEIN KINASE I, DELTA ISOFORM [Homo sapiens] | | | gi = 6084449 | 2647264 |
| IC03726 | 00/04/26 UG#76 17Lid Expansion | HOM | Mm.27901 | ESTs, Highly similar to 6.2 kd protein [H. sapiens] | | | gi = 2460543 | 1039950 |
| IC03727 | UG75 Expression | HOM | Mm.27921 | TITLE ESTs, Highly similar to CYCLIN G-ASSOCIATED KINASE [R. norvegicus] | | | gi = 5666000 | 2123767 |
| IC03728 | UG75 Expression | HOM | Mm.27932 | TITLE ESTs, Highly similar to arsenate resistance protein ARS2 [H. sapiens] | | | gi = 3168080 | 1480201 |
| IC03729 | UG75 Expression | HOM | Mm.27939 | TITLE ESTs, Highly similar to phosphorylation regulatory protein HP-10 [H. sapiens] | | | gi = 1287939 | 331148 |
| IC03730 | UG75 Expression | HOM | Mm.27951 | TITLE ESTs, Highly similar to GENSCAN prediction 15E1.1 [H. sapiens] | | | gi = 2288837 | 958480 |
| IC03731 | UG75 Expression | HOM | Mm.27957 | TITLE ESTs, Highly similar to Similar to D. melanogaster parallel sister chromatids protein [H. sapiens] | | | gi = 2306566 | 944297 |
| IC03732 | UG75 Expression | HOM | Mm.27959 | HYDROXYISOBUTYRATE DEHYDROGENASE PRECURSOR [Rattus norvegicus] | | | gi = 4434482 | 1451369 |
| IC03733 | UG75 Expression | HOM | Mm.27964 | [H. sapiens] | | | gi = 2040279 | 789478 |
| IC03734 | UG75 Expression | HOM | Mm.27969 | TITLE ESTs, Highly similar to UDP-N-acetylglucosamine pyrophosphorylase [H. sapiens] | | | gi = 2308454 | 961038 |
| IC03735 | UG75 Expression | HOM | Mm.27985 | TITLE ESTs, Highly similar to CGI-74 protein [H. sapiens] | | | gi = 3373024 | 2615819 |
| IC03736 | UG75 Expression | HOM | Mm.27989 | TITLE ESTs, Highly similar to Cdc5-like protein [R. norvegicus] | | | gi = 2516644 | 1922342 |
| IC03737 | UG75 Expression | HOM | Mm.28001 | TITLE ESTs, Highly similar to HYPOTHETICAL 45.0 KD PROTEIN IN NOT1/CDC39-HMR INTERGENIC REGION [Saccharomyces cerevisiae] | | | gi = 4434105 | 1152503 |
| IC03738 | UG75 Expression | HOM | Mm.28019 | TITLE ESTs, Highly similar to tensin [R. norvegicus] | | | gi = 2813877 | 1067842 |
| IC03739 | UG75 Expression | HOM | Mm.28020 | TITLE ESTs, Highly similar to mediator [H. sapiens] | | | gi = 1793329 | 640123 |
| IC03740 | UG75 Expression | HOM | Mm.28022 | TITLE ESTs, Highly similar to HISTONE H2B [Rattus norvegicus] | | | gi = 4256825 | 355658 |
| IC03741 | UG75 Expression | HOM | Mm.28023 | TITLE ESTs, Highly similar to (defline, not available 5815347) [M. musculus] | | | gi = 2626719 | 1162578 |
| IC03742 | UG75 Expression | HOM | Mm.28044 | TITLE ESTs, Highly similar to ENDOTHELIAL ACTIN-BINDING PROTEIN [Homo sapiens] | | | gi = 1309576 | 337541 |
| IC03743 | UG75 Expression | HOM | Mm.28047 | TITLE ESTs, Highly similar to host cell factor homolog LCP [H. sapiens] | | | gi = 6516054 | 2101822 |
| IC03744 | UG75 Expression | HOM | Mm.2805 | TITLE ESTs, Highly similar to The ha3611 gene product is related to S. cerevisiae SNM1 protein. [H. sapiens] | | | gi = 3387185 | 1498128 |
| IC03745 | UG75 Expression | HOM | Mm.28051 | TITLE ESTs, Highly similar to EUKARYOTIC INITIATION FACTOR 5 [Rattus norvegicus] | | | gi = 3517354 | 1481863 |
| IC03746 | UG75 Expression | HOM | Mm.28052 | TITLE ESTs, Highly similar to NF2d9 [M. musculus] | | | gi = 4061196 | 583883 |
| IC03747 | UG75 Expression | HOM | Mm.28053 | TITLE ESTs, Highly similar to pEachy [R. norvegicus] | | | gi = 2306181 | 944493 |
| IC03748 | UG75 Expression | H6M | Mm.28058 | TITLE ESTs, Highly similar to NADH-UBIQUINONE OXIDOREDUCTASE SGDH SUBUNIT PRECURSOR [Bos taurus] | | | gi = 1291848 | 333765 |
| IC03749 | UG75 Expression | HOM | Mm.28060 | TITLE ESTs, Highly similar to 65 KD YES-ASSOCIATED PROTEIN [Mus musculus] | | | gi = 4029307 | 1920975 |
| IC03750 | UG75 Expression | HOM | Mm.28067 | TITLE ESTs, Highly similar to LAK-1 [H. sapiens] | | | gi = 2291876 | 943888 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03751 | UG75 Expression | HOM | Mm.28080 | TITLE ESTs, Highly similar to PUTATIVE SERYL-TRNA SYNTHETASE YHR011W [Saccharomyces cerevisiae] | | | gi = 3258972 | 1480683 |
| IC03752 | UG75 Expression | HOM | Mm.28091 | TITLE ESTs, Highly similar to DEOXYHYPUSINE SYNTHASE [Homo sapiens] | | | gi = 4199660 | 583332 |
| IC03753 | UG75 Expression | HOM | Mm.28128 | TITLE ESTs, Highly similar to HYPOTHETICAL 35.1 KD PROTEIN IN NAM8-GAR1 INTERGENIC REGION [Saccharomyces cerevisiae] | | | gi = 4032060 | 1853187 |
| IC03754 | UG75 Expression | HOM | Mm.28142 | TITLE ESTs, Highly similar to ERGIC-53 PROTEIN PRECURSOR [Homo sapiens] | | | gi = 4060702 | 513844 |
| IC03755 | UG75 Expression | HOM | Mm.2815 | TITLE ESTs, Highly similar to HYPOTHETICAL 18.5 KD PROTEIN C40H1.6 IN CHROMOSOME III [Caenorhabditis elegans] | | | gi = 4724468 | 1247585 |
| IC03756 | UG75 Expression | HOM | Mm.28150 | TITLE ESTs, Highly similar to spliceosomal protein SAP 155 [H. sapiens] | | | gi = 6519433 | 2582179 |
| IC03757 | UG75 Expression | HOM | Mm.28159 | TITLE ESTs, Highly similar to AUTOANTIGEN PM-SCL [Homo sapiens] | | | gi = 4057115 | 477751 |
| IC03758 | UG75 Expression | HOM | Mm.28162 | GLYCOPROTEIN GP210 PRECURSOR [Rattus norvegicus] | | | gi = 1918787 | 775903 |
| IC03759 | UG75 Expression | HOM | Mm.28173 | TITLE ESTs, Highly similar to METHIONYL-TRNA SYNTHETASE, CYTOPLASMIC [Saccharomyces cerevisiae] | | | gi = 1834214 | 536288 |
| IC03760 | UG75 Expression | HOM | Mm.28179 | TITLE ESTs, Highly similar to fibronectin [M. musculus] | | | gi = 1903519 | 721019 |
| IC03761 | UG75 Expression | HOM | Mm.28187 | TITLE ESTs, Highly similar to S164 [H. sapiens] | | | gi = 2306625 | 944367 |
| IC03762 | UG75 Expression | HOM | Mm.28196 | TITLE ESTs, Highly similar to sorting nexin 4 [H. sapiens] | | | gi = 1315518 | 352251 |
| IC03763 | UG75 Expression | HOM | Mm.28197 | CARNITINE OCTANOYLTRANSFERASE [Rattus norvegicus] | | | gi = 3515501 | 1885094 |
| IC03764 | UG75 Expression | HOM | Mm.28200 | TITLE ESTs, Highly similar to step II splicing factor SLU7 [H. sapiens] | | | gi = 2306175 | 944477 |
| IC03765 | UG75 Expression | HOM | Mm.28202 | TITLE ESTs, Highly similar to SERINE/THREONINE-PROTEIN KINASE PAK-GAMMA [R. norvegicus] | | | gi = 1290303 | 333425 |
| IC03766 | UG75 Expression | HOM | Mm.28219 | TITLE ESTs, Highly similar to phosphatidylinositol synthase [R. norvegicus] | | | gi = 6085303 | 2236355 |
| IC03767 | UG75 Expression | HOM | Mm.28226 | TITLE ESTs, Highly similar to 6-PHOSPHOFRUCTOKINASE, TYPE C [Homo sapiens] | | | gi = 4199741 | 533677 |
| IC03768 | UG75 Expression | HOM | Mm.28228 | TITLE ESTs, Highly similar to HYPOTHETICAL 67.8 KD PROTEIN IN GND1-ERG9 INTERGENIC REGION [Saccharomyces cerevisiae] | | | gi = 6077171 | 2225719 |
| IC03769 | UG75 Expression | HOM | Mm.28235 | TITLE ESTs, Highly similar to zinc RING finger protein SAG [M. musculus] | | | gi = 3164282 | 464271 |
| IC03770 | UG75 Expression | HOM | Mm.28240 | TITLE ESTs, Highly similar to TRAF4-associated factor 2 [H. sapiens] | | | gi = 3374418 | 720735 |
| IC03771 | UG75 Expression | HOM | Mm.28247 | TITLE ESTs, Highly similar to SECRETED PHOSPHOPROTEIN 24 [R. norvegicus] | | | gi = 4444426 | 1889780 |
| IC03772 | UG75 Expression | HOM | Mm.28261 | TITLE ESTs, Highly similar to RFG [M. musculus] | | | gi = 4031325 | 1924471 |
| IC03773 | UG75 Expression | HOM | Mm.28265 | TITLE ESTs, Highly similar to HYPOTHETICAL TRP-ASP REPEATS CONTAINING PROTEIN IN SMY2-RPS101 INTERGENIC REGION [Saccharomyces cerevisiae] | | | gi = 1834173 | 659704 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03774 | UG75 Expression | HOM | Mm.28280 | TITLE ESTs, Highly similar to RENIN-BINDING PROTEIN [Sus scrofa] | | | gi = 1357728 | 368547 |
| IC03775 | UG75 Expression | HOM | Mm.28293 | TITLE ESTs, Highly similar to NADH-UBIQUINONE OXIDOREDUCTASE 42 KD SUBUNIT PRECURSOR [Bos taurus] | | | gi = 6517730 | 2649316 |
| IC03776 | UG75 Expression | HOM | Mm.28295 | gene PC326:GenBank Accession Number M95564 [H. sapiens] | | | gi = 2861187 | 1382161 |
| IC03777 | UG75 Expression | HOM | Mm.28296 | TITLE ESTs, Highly similar to [H. sapiens] | | | gi = 2125738 | 1264784 |
| IC03778 | UG75 Expression | HOM | Mm.28299 | TITLE ESTs, Highly similar to [H. sapiens] | | | gi = 2965554 | 1093989 |
| IC03779 | UG75 Expression | HOM | Mm.28301 | TITLE ESTs, Highly similar to CYSTATHIONINE GAMMA-LYASE [Homo sapiens] | | | gi = 1282103 | 331798 |
| IC03780 | UG75 Expression | HOM | Mm.28327 | TITLE ESTs, Highly similar to hypothetical protein [H. sapiens] | | | gi = 4967984 | 2331864 |
| IC03781 | UG75 Expression | HOM | Mm.28336 | TITLE ESTs, Highly similar to ELECTRON TRANSFER FLAVOPROTEIN-UBIQUINONE OXIDOREDUCTASE PRECURSOR [H. sapiens] | | | gi = 2914986 | 1261096 |
| IC03782 | UG75 Expression | HOM | Mm.28337 | TITLE ESTs, Highly similar to ABC1 PROTEIN PRECURSOR [Saccharomyces cerevisiae] | | | gi = 4782971 | 676768 |
| IC03783 | UG75 Expression | HOM | Mm.28343 | TITLE ESTs, Highly similar to DEK PROTEIN [Homo sapiens] | | | gi = 2855373 | 1151500 |
| IC03784 | UG75 Expression | HOM | Mm.28345 | TITLE ESTs, Highly similar to TRANSLOCON-ASSOCIATED PROTEIN, GAMMA SUBUNIT [Rattus norvegicus] | | | gi = 3692903 | 1885003 |
| IC03785 | UG75 Expression | HOM | Mm.28347 | TITLE ESTs, Highly similar to dJ283E3.6.1 [H. sapiens] | | | gi = 1290060 | 333034 |
| IC03786 | UG75 Expression | HOM | Mm.28349 | TITLE ESTs, Highly similar to NADH-UBIQUINONE OXIDOREDUCTASE 9 KD SUBUNIT PRECURSOR [Bos taurus] | | | gi = 1660011 | 572077 |
| IC03787 | UG75 Expression | HOM | Mm.28353 | TITLE ESTs, Highly similar to 110 KD CELL MEMBRANE GLYCOPROTEIN [H. sapiens] | | | gi = 6514397 | 2646881 |
| IC03788 | UG75 Expression | HOM | Mm.28356 | TITLE ESTs, Highly similar to PEP11 PROTEIN [Saccharomyces cerevisiae] | | | gi = 3164475 | 693883 |
| IC03789 | UG75 Expression | HOM | Mm.28357 | TITLE ESTs, Highly similar to HYPOTHETICAL 13.6 KD PROTEIN IN NUP170-ILS1 INTERGENIC REGION [Saccharomyces cerevisiae] | | | gi = 1309555 | 337459 |
| IC03790 | UG75 Expression | HOM | Mm.28365 | SUCCINYLTRANSFERASE COMPONENT [Homo sapiens] | | | gi = 3718286 | 1498266 |
| IC03791 | UG75 Expression | HOM | Mm.28366 | TITLE ESTs, Highly similar to INSULIN-DEGRADING ENZYME [Rattus norvegicus] | | | gi = 1684142 | 574949 |
| IC03792 | UG75 Expression | HOM | Mm.28382 | TITLE ESTs, Highly similar to katanin p80 subunit [H. sapiens] | | | gi = 2042963 | 750444 |
| IC03793 | UG75 Expression | HOM | Mm.28383 | TITLE ESTs, Highly similar to DOC1 [H. sapiens] | | | gi = 1864320 | 807947 |
| IC03794 | UG75 Expression | HOM | Mm.28386 | TITLE ESTs, Highly similar to MITOTIC KINESIN-LIKE PROTEIN-1 [Homo sapiens] | | | gi = 3521449 | 1498318 |
| IC03795 | UG75 Expression | HOM | Mm.28397 | TITLE ESTs, Highly similar to FGF receptor activating protein FRAG1 [R. norvegicus] | | | gi = 6077788 | 2159528 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03796 | UG75 Expression | HOM | Mm.28401 | TITLE ESTs, Highly similar to HYPOTHETICAL 167.8 KD PROTEIN CCE1-CAP1 INTERGENIC REGION [Saccharomyces cerevisiae] | | | gi = 2272214 | 906265 |
| IC03797 | UG75 Expression | HOM | Mm.28407 | TITLE ESTs, Highly similar to ACYLPHOSPHATASE, MUSCLE TYPE ISOZYME [Rattus norvegicus] | | | gi = 4061767 | 575063 |
| IC03798 | UG75 Expression | HOM | Mm.28423 | TITLE ESTs, Highly similar to THYMIDINE PHOSPHORYLASE [Homo sapiens] | | | gi = 2284049 | 1852997 |
| IC03799 | UG75 Expression | HOM | Mm.28441 | TITLE ESTs, Highly similar to (define not available 5524671) [M. musculus] | | | gi = 4722646 | 1247754 |
| IC03800 | UG75 Expression | HOM | Mm.28464 | TITLE ESTs, Highly similar to ACTIN-LIKE PROTEIN [Bos taurus] | | | gi = 6077157 | 2225701 |
| IC03801 | UG75 Expression | HOM | Mm.28466 | TITLE ESTs, Highly similar to MITOCHONDRIAL 2-OXOGLUTARATE/MALATE CARRIER PROTEIN [Bos taurus] | | | gi = 6084068 | 1481891 |
| IC03802 | UG75 Expression | HOM | Mm.28484 | TITLE ESTs, Highly similar to CELL SURFACE GLYCOPROTEIN A15 [Homo sapiens] | | | gi = 1282456 | 582004 |
| IC03803 | UG75 Expression | HOM | Mm.28491 | TITLE ESTs, Highly similar to (define not available 6013425) [M. musculus] | | | gi = 2812978 | 1229542 |
| IC03804 | UG75 Expression | HOM | Mm.28492 | TITLE ESTs, Highly similar to KIAA0652 protein [H. sapiens] | | | gi = 6085630 | 2803739 |
| IC03805 | UG75 Expression | HOM | Mm.28494 | TITLE ESTs, Highly similar to PROBABLE RIBOSOMAL PROTEIN B0303.15 IN CHROMOSOME III [Caenorhabditis elegans] | | | gi = 3164256 | 762914 |
| IC03806 | UG75 Expression | HOM | Mm.28496 | TITLE ESTs, Highly similar to CENTROMERIC PROTEIN E [Homo sapiens] | | | gi = 4060741 | 515854 |
| IC03807 | UG75 Expression | HOM | Mm.28512 | TITLE ESTs, Highly similar to brefeldin A-inhibited guanine nucleotide-exchange protein 1 [H. sapiens] | | | gi = 4726182 | 1971486 |
| IC03808 | UG75 Expression | HOM | Mm.28515 | TITLE ESTs, Highly similar to PEPTIDYL-PROLYL CIS-TRANS ISOMERASE, RETINAL-SPECIFIC ISOZYME [Bos taurus] | | | gi = 4726592 | 1971986 |
| IC03809 | UG75 Expression | HOM | Mm.28521 | TITLE ESTs, Highly similar to BETA-CENTRACTIN [Homo sapiens] | | | gi = 6083610 | 1248234 |
| IC03810 | UG75 Expression | HOM | Mm.28538 | TITLE ESTs, Highly similar to ALPHA-SOLUBLE NSF ATTACHMENT PROTEIN HOMOLOG [Mus musculus] | | | gi = 1287341 | 329680 |
| IC03811 | UG75 Expression | HOM | Mm.28540 | TITLE ESTs, Highly similar to KIAA0601 protein [H. sapiens] | | | gi = 1287297 | 318306 |
| IC03812 | UG75 Expression | HOM | Mm.28548 | TITLE ESTs, Highly similar to HYPOTHETICAL PROTEIN KIAA0188 [H. sapiens] | | | gi = 1726120 | 676156 |
| IC03813 | UG75 Expression | HOM | Mm.28551 | TITLE ESTs, Highly similar to HYPOTHETICAL 58.6 KD PROTEIN ZK632.3 IN CHROMOSOME III [Caenorhabditis elegans] | | | gi = 6076482 | 2236209 |
| IC03814 | UG75 Expression | HOM | Mm.28560 | TITLE ESTs, Highly similar to CELL GROWTH REGULATING NUCLEOLAR PROTEIN [M. musculus] | | | gi = 4601761 | 634485 |
| IC03815 | UG75 Expression | HOM | Mm.28564 | TITLE ESTs, Highly similar to HYPOTHETICAL 24.5 KD PROTEIN IN SAP185-BCK1 INTERGENIC REGION [Saccharomyces cerevisiae] | | | gi = 1309718 | 337865 |
| IC03816 | UG75 Expression | HOM | Mm.28566 | TITLE ESTs, Highly similar to (define not available 6006813) [M. musculus] | | | gi = 3168575 | 1432049 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03817 | UG75 Expression | HOM | Mm.28571 | TITLE ESTs, Highly similar to HYPOTHETICAL 51.6 KD PROTEIN F59B2.5 IN CHROMOSOME III [Caenorhabditis elegans] | | | gi = 1316698 | 350200 |
| IC03818 | UG75 Expression | HOM | Mm.28574 | TITLE ESTs, Highly similar to BIS(5'-NUCLEOSYL)-TETRAPHOSPHATASE [M. musculus] | | | gi = 3164514 | 575240 |
| IC03819 | UG75 Expression | HOM | Mm.28576 | TITLE ESTs, Highly similar to CGI-35 protein [H. sapiens] | | | gi = 3164643 | 573532 |
| IC03820 | UG75 Expression | HOM | Mm.28582 | TITLE ESTs, Highly similar to RNA polymerase transcriptional regulation mediator [H. sapiens] | | | gi = 2456811 | 1025590 |
| IC03821 | UG75 Expression | HOM | Mm.28584 | TITLE ESTs, Highly similar to dJ341E18.2.1 [H. sapiens] | | | gi = 4967451 | 1480547 |
| IC03822 | UG75 Expression | HOM | Mm.28593 | [H. sapiens] | | | gi = 4722617 | 1247689 |
| IC03823 | UG75 Expression | HOM | Mm.28598 | TITLE ESTs, Highly similar to TYROSINE-PROTEIN KINASE JAK1 [Homo sapiens] | | | gi = 2964837 | 1093568 |
| IC03824 | UG75 Expression | HOM | Mm.28601 | TITLE ESTs, Highly similar to 80 KD NUCLEAR CAP BINDING PROTEIN [H. sapiens] | | | gi = 2855834 | 1080459 |
| IC03825 | UG75 Expression | HOM | Mm.28603 | TITLE ESTs, Highly similar to HYPOTHETICAL 70.2 KD PROTEIN IN GSH1-CHS6 INTERGENIC REGION [Saccharomyces cerevisiae] | | | gi = 4061444 | 483541 |
| IC03826 | UG75 Expression | HOM | Mm.28606 | TITLE ESTs, Highly similar to ANTI-SILENCING PROTEIN 1 [Saccharomyces cerevisiae] | | | gi = 4967626 | 1039329 |
| IC03827 | UG75 Expression | HOM | Mm.28613 | TITLE ESTs, Highly similar to TRANSCRIPTIONAL REPRESSOR NF-X1 [H. sapiens] | | | gi = 3233398 | 1378106 |
| IC03828 | UG75 Expression | HOM | Mm.28618 | TITLE ESTs, Highly similar to PROTEIN PHOSPHATASE PP2A, 55 KD REGULATORY SUBUNIT, ALPHA ISOFORM [Homo sapiens; Oryctolagus cuniculus] | | | gi = 2572824 | 1021207 |
| IC03829 | UG75 Expression | HOM | Mm.28619 | TITLE ESTs, Highly similar to HYPOTHETICAL 67.2 KD PROTEIN T16H12.4 IN CHROMOSOME III [Caenorhabditis elegans] | | | gi = 4061769 | 575067 |
| IC03830 | UG75 Expression | HOM | Mm.28626 | TITLE ESTs, Highly similar to HYPOTHETICAL 64.3 KD GTP-BINDING PROTEIN C02F5.3 IN CHROMOSOME III [Caenorhabditis elegans] | | | gi = 1325785 | 353222 |
| IC03831 | UG75 Expression | HOM | Mm.28630 | TITLE ESTs, Highly similar to HYPOTHETICAL 39.5 KD PROTEIN C12G12.06C IN CHROMOSOME I [Schizosaccharomyces pombe] | | | gi = 5337461 | 1886132 |
| IC03832 | UG75 Expression | HOM | Mm.28632 | TITLE ESTs, Highly similar to putative monocarboxylate transporter [R. norvegicus] | | | gi = 1739237 | 604894 |
| IC03833 | UG75 Expression | HOM | Mm.28650 | TITLE ESTs, Highly similar to RAS-RELATED PROTEIN RAB-6 [Homo sapiens] | | | gi = 1287479 | 331256 |
| IC03834 | UG75 Expression | HOM | Mm.28659 | TITLE ESTs, Highly similar to pescadillo [H. sapiens] TOLERANCE PROTEIN PRECURSOR | | | gi = 2306074 | 949285 |
| IC03835 | UG75 Expression | HOM | Mm.28663 | [Schizosaccharomyces pombe] | | | gi = 1811433 | 677418 |
| IC03836 | UG75 Expression | HOM | Mm.28668 | TITLE ESTs, Highly similar to epsilon-COP [M. musculus] | | | gi = 4967859 | 1511531 |
| IC03837 | UG75 Expression | HOM | Mm.28670 | TITLE ESTs, Highly similar to N-ACETYLGLU-COSAMINE 6-SULFATASE PRECURSOR [Homo sapiens] | | | gi = 2292135 | 935598 |
| IC03838 | UG75 Expression | HOM | Mm.28675 | [H. sapiens] | | | gi = 1682068 | 576994 |
| IC03839 | UG75 Expression | HOM | Mm.28678 | TITLE ESTs, Highly similar to PUTATIVE SERINE/THREONINE-PROTEIN KINASE P78 [Homo sapiens] | | | gi = 2962485 | 1265221 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03840 | UG75 Expression | HOM | Mm.28682 | TITLE ESTs, Highly similar to ENV POLYPROTEIN PRECURSOR [Feline endolgenous virus ece1] | | | gi = 4061815 | 577212 |
| IC03841 | UG75 Expression | HOM | Mm.28684 | TITLE ESTs, Highly similar to DNA POLYMERASE BETA [Rattus norvegicus] | | | gi = 4198940 | 481850 |
| IC03842 | UG75 Expression | HOM | Mm.28685 | TITLE ESTs, Highly similar to L-SERINE DEHYDRATASE [Rattus norvegicus] | | | gi = 3885087 | 1891350 |
| IC03843 | UG75 Expression | HOM | Mm.28688 | TITLE ESTs, Highly similar to SERYL-TRNA SYNTHETASE [Cricetulus griseus] | | | gi = 6083738 | 2099972 |
| IC03844 | UG75 Expression | HOM | Mm.28692 | TITLE ESTs. Highly similar to KIAA0733 protein [H-sapiens] | | | gi = 3393289 | 1247836 |
| IC03845 | UG75 Expression | HOM | Mm.28693 | TITLE ESTs, Highly similar to ASPARTYL-TRNA SYNTHETASE [Rattus norvegicus] | | | gi = 5549589 | 1972356 |
| IC03846 | UG75 Expression | HOM | Mm.28696 | TITLE ESTs, Highly similar to PROTEIN FARNESYLTRANSFERASE BETA SUBUNIT [Rattus norvegicus] | | | gi = 4433908 | 1885443 |
| IC03847 | UG75 Expression | HOM | Mm.28700 | TITLE ESTs, Highly similar to ACYL-COENZYME A OXIDASE 1, PEROXISOMAL, COMPONENT A [Rattus norvegicus] | | | gi = 3286250 | 1432451 |
| IC03848 | UG75 Expression | HOM | Mm.28704 | TITLE ESTs, Highly similar to PROTEIN TRANSPORT PROTEIN SEC23 [Saccharomyces cerevisiae] | | | gi = 4216288 | 678454 |
| IC03849 | UG75 Expression | HOM | Mm.28705 | TITLE ESTs, Highly similar to YSA1 PROTEIN [Saccharomyces cerevisiae] | | | gi = 1315662 | 352442 |
| IC03850 | UG75 Expression | HOM | Mm.28710 | TITLE ESTs, Highly similar to dJ48717.1.1 [H. sapiens] | | | gi = 6756446 | 2648373 |
| IC03851 | UG75 Expression | HOM | Mm.28711 | TITLE ESTs, Highly similar to hypothetical protein 1 [H. sapiens] | | | gi = 4272356 | 518912 |
| IC03852 | UG75 Expression | HOM | Mm.28712 | TITLE ESTs, Highly similar to NUKM_HUMAN, partial CDS [H. sapiens] | | | gi = 3955120 | 1282320 |
| IC03853 | UG75 Expression | HOM | Mm.28715 | TITLE ESTs, Highly similar to R27216_1 [H. sapiens] | | | gi = 3370508 | 573716 |
| IC03854 | UG75 Expression | HOM | Mm.28721 | TITLE ESTs, Highly similar to RING3 PROTEIN [Homo sapiens] | | | gi = 1407047 | 420030 |
| IC03855 | UG75 Expression | HOM | Mm.28725 | TITLE ESTs, Highly similar to lens epithelium-derived growth factor [H. sapiens] | | | gi = 40 32458 | 1853315 |
| IC03856 | UG75 Expression | HOM | Mm.28748 | TITLE ESTs, Highly similar to (defline not available 6110613) [M. musculus] | | | gi = 2919291 | 336241 |
| IC03857 | UG75 Expression | HOM | Mm.28753 | TITLE ESTs, Highly similar to PROTEIN TRANSLATION FACTOR SUI1 HOMOLOG [Anopheles gambiae] | | | gi = 2965904 | 1094939 |
| IC03858 | UG75 Expression | HOM | Mm.28780 | TITLE ESTs, Highly similar to KERATIN, TYPE II CYTOSKELETAL 4 [Homo sapiens] | | | gi = 6517581 | 2649141 |
| IC03859 | UG75 Expression | HOM | Mm.28798 | TITLE ESTs, Highly similar to CDC16 protein [H. sapiens] | | | gi = 6085641 | 387460 |
| IC03860 | UG75 Expression | HOM | Mm.28803 | TITLE ESTs, Highly similar to Lsm3 protein [H. sapiens] | | | gi = 6517366 | 2648877 |
| IC03861 | UG75 Expression | HOM | Mm.28805 | TITLE ESTs, Highly similar to SET PROTEIN [Homo sapiens] | | | gi = 3164835 | 1006307 |
| IC03862 | UG75 Expression | HOM | Mm.28808 | TITLE ESTs, Highly similar to C-1 [H. sapiens] | | | gi = 1826646 | 959978 |
| IC03863 | UG75 Expression | HOM | Mm.28816 | TITLE ESTs, Highly similar to 30 KD PROTEIN KINASE HOMOLOG [Variola virus] | | | gi = 3747520 | 402182 |
| IC03864 | UG75 Expression | HOM | Mm.28821 | TITLE ESTs, Highly similar to Ndr protein kinase [H-sapiens] | | | gi = 2962178 | 1281987 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03865 | UG75 Expression | HOM | Mm.28827 | TITLE ESTs, Highly similar to PHOSPHORYLASE B KINASE BETA REGULATORY CHAIN [*Oryctolagus cuniculus*] | | | gi = 1564448 | 517725 |
| IC03866 | UG75 Expression | HOM | Mm.28830 | TITLE ESTs, Highly similar to PRE-B CELL ENHANCING FACTOR PRECURSOR [*Homo sapiens*] | | | gi = 6076959 | 2225542 |
| IC03867 | UG75 Expression | HOM | Mm.28848 | TITLE ESTs, Highly similar to DTDP-4-DEHYDRORHAMNOSE REDUCTASE [*Salmonella typhimurium*] | | | gi = 1297865 | 337304 |
| IC03868 | UG75 Expression | HOM | Mm.28850 | TITLE ESTs, Highly similar to JM5 [*H. sapiens*] | | | gi = 3518886 | 1481177 |
| IC03869 | UG75 Expression | HOM | Mm.28852 | TITLE ESTs, Highly similar to signal peptidase:SUBUNIT | | | gi = 1282462 | 332831 |
| IC03870 | UG75 Expression | HOM | Mm.28864 | TITLE ESTs, Highly similar to axonemal dynein heavy chain [*H. sapiens*] | | | gi = 2306699 | 933942 |
| IC03871 | UG75 Expression | HOM | Mm.28866 | TITLE ESTs, Highly similar to RNA splicing-related protein [*R. norvegicus*] | | | gi = 3394130 | 2655194 |
| IC03872 | UG75 Expression | HOM | Mm.28872 | TITLE ESTs, Highly similar to RAS-RELATED PROTEIN RAB-5A [*Homo sapiens*] | | | gi = 3216132 | 1480373 |
| IC03873 | UG75 Expression | HOM | Mm.28877 | PHOSPHATE URIDYLYLTRANSFERASE [*Homo sapiens*] | | | gi = 4444348 | 1889683 |
| IC03874 | UG75 Expression | HOM | Mm.28913 | TITLE ESTs, Highly similar to FGFR1 oncogene partner [*H. sapiens*] | | | gi = 6076904 | 2225468 |
| IC03875 | UG75 Expression | HOM | Mm.28935 | TITLE ESTs, Highly similar to DERMATOPONTIN [*Bos taurus*] | | | gi = 4198962 | 482784 |
| IC03876 | UG75 Expression | HOM | Mm.28938 | TITLE ESTs, Highly similar to KIAA0679 protein [*H. sapiens*] | | | gi = 6085301 | 1162651 |
| IC03877 | UG75 Expression | HOM | Mm.28952 | TITLE ESTs, Highly similar to RAS-RELATED PROTEIN RAB-8 [*Homo sapiens; Canis familiaris*] | | | gi = 3718633 | 558482 |
| IC03878 | UG75 Expression | HOM | Mm.28953 | TITLE ESTs, Highly similar to DIHYDROLIPOAMIDE ACETYLTRANSFERASE COMPONENT [*Rattus norvegicus*] | | | gi = 2963326 | 1265202 |
| IC03879 | UG75 Expression | HOM | Mm.28959 | TITLE ESTs, Highly similar to mRNA cleavage factor 125 kDa subunit [*H. sapiens*] | | | gi = 3377146 | 597340 |
| IC03880 | UG75 Expression | HOM | Mm.28961 | [*H. sapiens*] | | | gi = 5125449 | 2076643 |
| IC03881 | UG75 Expression | HOM | Mm.28965 | TITLE ESTs, Highly similar to PROTEIN PHOSPHATASE 2C HOMOLOG 3 [*Schizosaccharomyces pombe*] | | | gi = 4060677 | 468814 |
| IC03882 | UG75 Expression | HOM | Mm.28969 | TITLE ESTs, Highly similar to KIAA0983 protein [*H. sapiens*] | | | gi = 5125407 | 2076567 |
| IC03883 | UG75 Expression | HOM | Mm.28976 | TITLE ESTs, Highly similar to TRANSLOCON-ASSOCIATED PROTEIN, ALPHA SUBUNIT PRECURSOR [*Canis familiaris*] | | | gi = 6083763 | 1920572 |
| IC03884 | UG75 Expression | HOM | Mm.28979 | TITLE ESTs, Highly similar to autoantigen [*H. sapiens*] PROTEIN L27 [*Homo sapiens; Rattus norvegicus; Gallus gallus*] | | | gi = 1909005 | 736611 |
| IC03885 | UG75 Expression | HOM | Mm.28985 | TITLE ESTs, Highly similar to (definline not available 5738222) [*M. musculus*] | | | gi = 2461420 | 1024073 |
| IC03886 | UG75 Expression | HOM | Mm.28986 | | | | gi = 3520835 | 1450454 |
| IC03887 | UG75 Expression | HOM | Mm.28996 | TITLE ESTs, Highly similar to small zinc finger-like protein [*M. musculus*] | | | gi = 3164893 | 1327866 |
| IC03888 | UG75 Expression | HOM | Mm.29000 | TITLE ESTs, Highly similar to carboxy terminus of Hsp70-interacting protein [*M. musculus*] | | | gi = 1446740 | 427079 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03889 | UG75 Expression | HOM | Mm.29001 | TITLE ESTs, Highly similar to URACIL PHOSPHORIBOSYLTRANSFERASE [*Saccharomyces cerevisiae*] | | | gi = 2256460 | 902288 |
| IC03890 | UG75 Expression | HOM | Mm.29015 | TITLE ESTs, Highly similar to armadillo repeat protein [*H. sapiens*] | | | gi = 2403574 | 991023 |
| IC03891 | UG75 Expression | HOM | Mm.29024 | TITLE ESTs, Highly similar to CYTOCHROME C OXIDASE ASSEMBLY PROTEIN COX11 [*Saccharomyces cerevisiae*] | | | gi = 3864354 | 1851973 |
| IC03892 | UG75 Expression | HOM | Mm.29036 | TITLE ESTs, Highly similar to PROTEIN DISULFIDE ISOMERASE PRECURSOR [*Medicago sativa*] | | | gi = 3863421 | 1888988 |
| IC03893 | UG75 Expression | HOM | Mm.29048 | TITLE ESTs, Highly similar to mitogen inducible gene mig-2 [*H. sapiens*] | | | gi = 3680897 | 1478268 |
| IC03894 | UG75 Expression | HOM | Mm.29049 | TITLE ESTs, Highly similar to unknown [*H. sapiens*] | | | gi = 4726558 | 1971952 |
| IC03895 | UG75 Expression | HOM | Mm.29051 | TITLE ESTs, Highly similar to ISOCITRATE DEHYDROGENASE [*Bos taurus*] | | | gi = 5338565 | 1970358 |
| IC03896 | UG75 Expression | HOM | Mm.29052 | TITLE ESTs, Highly similar to ERYTHROCYTE ADDUCIN ALPHA SUBUNIT [*Homo sapiens*] | | | gi = 4306834 | 680443 |
| IC03897 | UG75 Expression | HOM | Mm.29057 | TITLE ESTs, Highly similar to MYOSIN REGULATORY LIGHT CHAIN 2-A, SMOOTH MUSCLE ISOFORM [*Rattus norvegicus*] | | | gi = 1287918 | 331540 |
| IC03898 | UG75 Expression | HOM | Mm.29061 | TITLE ESTs, Highly similar to HYPOTHETICAL PROTEIN KIAA0112 [*H. sapiens*] | | | gi = 4442146 | 1922277 |
| IC03899 | UG75 Expression | HOM | Mm.29065 | TITLE ESTs, Highly similar to NADH-UBIQUINONE OXIDOREDUCTASE B15 SUBUNIT [*Bos taurus*] | | | gi = 1325550 | 351016 |
| IC03900 | UG75 Expression | HOM | Mm.29071 | TITLE ESTs, Highly similar to unknown [*H. sapiens*] | | | gi = 3141784 | 1617167 |
| IC03901 | UG75 Expression | HOM | Mm.29073 | TITLE ESTs, Highly similar to REPLICATION PROTEIN A 14 KD SUBUNIT [*Homo sapiens*] | | | gi = 2811602 | 1243337 |
| IC03902 | UG75 Expression | HOM | Mm.29079 | [*M. musculus*] | | | gi = 6083598 | 574148 |
| IC03903 | UG75 Expression | HOM | Mm.29087 | TITLE ESTs, Highly similar to hypothetical protein [*H. sapiens*] | | | gi = 3164774 | 803695 |
| IC03904 | UG75 Expression | HOM | Mm.29094 | TITLE ESTs, Highly similar to ALPHA-1 ANTIPROTEINASE PRECURSOR [*Rattus norvegicus*] | | | gi = 3987445 | 1888861 |
| IC03905 | UG75 Expression | HOM | Mm.29097 | TITLE ESTs, Highly similar to PINCH PROTEIN [*Homo sapiens*] | | | gi = 3748061 | 1885999 |
| IC03906 | UG75 Expression | HOM | Mm.29105 | TITLE ESTs, Highly similar to TRANSCRIPTION FACTOR IIIA [*Xenopus laevis*] | | | gi = 1284049 | 314664 |
| IC03907 | UG75 Expression | HOM | Mm.29106 | TITLE ESTs, Highly similar to MITOCHONDRIAL LON PROTEASE HOMOLOG PRECURSOR [*Homo sapiens*] | | | gi = 2284203 | 933168 |
| IC03908 | UG75 Expression | HOM | Mm.29122 | TITLE ESTs, Highly similar to CGI-81 protein [*H. sapiens*] | | | gi = 6085210 | 2939732 |
| IC03909 | UG75 Expression | HOM | Mm.29123 | TITLE ESTs, Highly similar to APOLIPOPROTEIN B-100 PRECURSOR [*Homo sapiens*] | | | gi = 4030319 | 1921316 |
| IC03910 | UG75 Expression | HOM | Mm.29135 | TITLE ESTs, Highly similar to SMALL NUCLEAR RIBONUCLEOPROTEIN SM D2 [*Homo sapiens*] | | | gi = 3165029 | 850985 |
| IC03911 | UG75 Expression | HOM | Mm.29141 | TITLE ESTs, Highly similar to SUCCINATE DEHYDROGENASE [*Homo sapiens*] | | | gi = 1315514 | 352248 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03912 | UG75 Expression | HOM | Mm.29145 | TITLE ESTs, Highly similar to 34.7 KD PROTEIN IN SHM1-MRPL37 INTERGENIC REGION [*Saccharomyces cerevisiae*] | | | gi = 2857465 | 1123741 |
| IC03913 | UG75 Expression | HOM | Mm.29151 | TITLE ESTs, Highly similar to HYPOTHETICAL PROTEIN KIAA0025 [*H. sapiens*] | | | gi = 5338461 | 2065079 |
| IC03914 | UG75 Expression | HOM | Mm.29153 | TITLE ESTs, Highly similar to 0-44 PROTEIN [*Rattus norvegicus*] | | | gi = 1325333 | 351057 |
| IC03915 | UG75 Expression | HOM | Mm.29165 | TITLE ESTs, Highly similar to 3-KETOACYL-COA THIOLASE MITOCHONDRIAL [*Rattus norvegicus*] | | | gi = 1297706 | 336782 |
| IC03916 | UG75 Expression | HOM | Mm.29174 | TITLE ESTs, Highly similar to the KIAA0199 gene is expressed ubiquitously. [*H. sapiens*] | | | gi = 4032952 | 1920677 |
| IC03917 | UG75 Expression | HOM | Mm.29180 | TITLE ESTs, Highly similar to ADIPOCYTE P27 PROTEIN [*Mus musculus*] | | | gi = 3517255 | 1481805 |
| IC03918 | UG75 Expression | HOM | Mm.29185 | TITLE ESTs, Highly similar to HYPOTHETICAL 36.7 KD PROTEIN AH6.2 IN CHROMOSOME II [*Caenorhabditis elegans*] | | | gi = 5551418 | 1434656 |
| IC03919 | UG75 Expression | HOM | Mm.29187 | TITLE ESTs, Highly similar to RECOMBINATION SIGNAL SEQUENCE RECOGNITION PROTEIN [*Mus musculus*] TRNA SYNTHETASE DED81 [*Saccharomyces cerevisiae*] | | | gi = 6638518 | 2332115 |
| IC03920 | UG75 Expression | HOM | Mm.29192 | TITLE ESTs, Highly similar to ES18 [*M. musculus*] | | | gi = 3718526 | 2803509 |
| IC03921 | UG75 Expression | HOM | Mm.29193 | TITLE ESTs, Highly similar to potassium channel modulatory factor DEB1-91 [*M. musculus*] | | | gi = 2520442 | 2698737 |
| IC03922 | UG75 Expression | HOM | Mm.29194 | | | | gi = 2956509 | 1282270 |
| IC03923 | UG75 Expression | HOM | Mm.29196 | TITLE ESTs, Highly similar to CYTOCHROME C1, HEME PROTEIN [*Bos taurus*] | | | gi = 4060298 | 422186 |
| IC03924 | UG75 Expression | HOM | Mm.29201 | TITLE ESTs, Highly similar to 1,4-ALPHA-GLUCAN BRANCHING ENZYME [*Homo sapiens*] | | | gi = 4485079 | 520983 |
| IC03925 | UG75 Expression | HOM | Mm.29203 | TITLE ESTs, Highly similar to PROLIFERATING-CELL NUCLEOLAR ANTIGEN P120 [*Homo sapiens*] | | | gi = 4061672 | 552252 |
| IC03926 | UG75 Expression | HOM | Mm.29204 | TITLE ESTs, Highly similar to T-CELL SURFACE PROTEIN TACTILE PRECURSOR [*Homo sapiens*] | | | gi = 1725759 | 597729 |
| IC03927 | UG75 Expression | HOM | Mm.29214 | TITLE ESTs, Highly similar to Unknown [*H. sapiens*] | | | gi = 4729754 | 1970741 |
| IC03928 | UG75 Expression | HOM | Mm.29228 | TITLE ESTs, Highly similar to CATION-TRANSPORTING ATPASE PACL [*Synechococcus pcc7942*] | | | gi = 5598773 | 574893 |
| IC03929 | UG75 Expression | HOM | Mm.29253 | TITLE ESTs, Highly similar to Opa-interacting protein OIP2 [*H. sapiens*] | | | gi = 1309581 | 337565 |
| IC03930 | UG75 Expression | HOM | Mm.29256 | TITLE ESTs, Highly similar to PUTATIVE 2-HYDROXYACID DEHYDROGENASE IN BISC-CSPA INTERGENIC REGION [*Escherichia coli*] | | | gi = 1447168 | 437577 |
| IC03931 | UG75 Expression | HOM | Mm.29283 | TITLE ESTs, Highly similar to KIAA0544 protein [*H. sapiens*] | | | gi = 4 537027 | 1448975 |
| IC03932 | UG75 Expression | HOM | Mm.29296 | TITLE ESTs, Highly similar to PROTEIN TRANSPORT PROTEIN SEC13 [*Saccharomyces cerevisiae*] | | | gi = 3748056 | 1886006 |
| IC03933 | UG75 Expression | HOM | Mm.29317 | TITLE ESTs, Highly similar to ACTIN II [*Plasmodium falciparum*] | | | gi = 4199726 | 737061 |
| IC03934 | UG75 Expression | HOM | Mm.29319 | TITLE ESTs, Highly similar to ERYTHROCYTE ADDUCIN BETA SUBUNIT [*Homo sapiens*] | | | gi = 5338237 | 2064863 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03935 | UG75 Expression | HOM | Mm.29328 | TITLE ESTs, Highly similar to CGI-23 protein [H. sapiens] | | | gi = 6085609 | 2317760 |
| IC03936 | UG75 Expression | HOM | Mm.29341 | TITLE ESTs, Highly similar to unique gene expressed in fibroblasts of periodontal ligament [H. sapiens] | | | gi = 4434436 | 2649067 |
| IC03937 | UG75 Expression | HOM | Mm.29342 | TITLE ESTs, Highly similar to KIAA1002 protein [H. sapiens] | | | gi = 3955497 | 3156497 |
| IC03938 | UG75 Expression | HOM | Mm.29346 | TITLE ESTs, Highly similar to GMP REDUCTASE [Homo sapiens] | | | gi = 1752032 | 615727 |
| IC03939 | UG75 Expression | HOM | Mm.29358 | TITLE ESTs, Highly similar to CGI-38 protein [H. sapiens] | | | gi = 2745185 | 1210372 |
| IC03940 | UG75 Expression | HOM | Mm.29379 | TITLE ESTs, Highly similar to PYRROLINE-5-CARBOXYLATE REDUCTASE [Homo sapiens] | | | gi = 5125923 | 2088123 |
| IC03941 | UG75 Expression | HOM | Mm.29381 | TITLE ESTs, Highly similar to KINESIN-II 85 KD SUBUNIT [Strongylocentrotus purpuratus] | | | gi = 2885305 | 1211169 |
| IC03942 | UG75 Expression | HOM | Mm.29384 | TITLE ESTs, Highly similar to IDN3-B [H. sapiens] | | | gi = 2918120 | 1229736 |
| IC03943 | UG75 Expression | HOM | Mm.29390 | TITLE ESTs, Highly similar to unknown [H. sapiens] | | | gi = 6940169 | 2650580 |
| IC03944 | UG75 Expression | HOM | Mm.29391 | TITLE ESTs, Highly similar to FIBRINOGEN-LIKE PROTEIN [Homo sapiens] | | | gi = 1504772 | 466331 |
| IC03945 | UG75 Expression | HOM | Mm.29392 | TITLE ESTs, Highly similar to MASL1 [H. sapiens] | | | gi = 2745190 | 1210388 |
| IC03946 | UG75 Expression | HOM | Mm.29405 | TITLE ESTs, Highly similar to ring-box protein 1 [M. musculus] | | | gi = 3164330 | 556999 |
| IC03947 | UG75 Expression | HOM | Mm.29415 | TITLE ESTs, Highly similar to NADH-UBIQUINONE OXIDOREDUCTASE AGGG SUBUNIT PRECURSOR [Bos taurus] | | | gi = 3100450 | 1345403 |
| IC03948 | UG75 Expression | HOM | Mm.29418 | TITLE ESTs, Highly similar to PROTEIN DISULFIDE ISOMERASE-RELATED PROTEIN PRECURSOR [Homo sapiens] | | | gi = 2200958 | 874528 |
| IC03949 | UG75 Expression | HOM | Mm.29426 | TITLE ESTs, Highly similar to PRE-MRNA SPLICING FACTOR SF2, P33 SUBUNIT [Homo sapiens] | | | gi = 6938036 | 2812514 |
| IC03950 | UG75 Expression | HOM | Mm.29429 | TITLE ESTs, Highly similar to GASTRULATION SPECIFIC PROTEIN G12 [Danio rerio] | | | gi = 4199592 | 578017 |
| IC03951 | UG75 Expression | HOM | Mm.29432 | TITLE ESTs, Highly similar to HYPOTHETICAL 55.1 KD PROTEIN IN FAB1-PES4 INTERGENIC REGION [Saccharomyces cerevisiae] | | | gi = 3515994 | 1399723 |
| IC03952 | UG75 Expression | HOM | Mm.29440 | TITLE ESTs, Highly similar to lymphocyte specific helicase [M. musculus] | | | gi = 2307794 | 945878 |
| IC03953 | UG75 Expression | HOM | Mm.29442 | TITLE ESTs, Highly similar to R32184_3 [H. sapiens] | | | gi = 1902415 | 716900 |
| IC03954 | UG75 Expression | HOM | Mm.29456 | TITLE ESTs, Highly similar to SOL3 PROTEIN [Saccharomyces cerevisiae] | | | gi = 2256583 | 902124 |
| IC03955 | UG75 Expression | HOM | Mm.29465 | TITLE ESTs, Highly similar to lipoma HMGIC fusion partner [H. sapiens] | | | gi = 4726343 | 1971210 |
| IC03956 | UG75 Expression | HOM | Mm.29471 | TITLE ESTs, Highly similar to nuclear protein E3-3 orf1 [R. norvegicus] | | | gi = 4402950 | 988794 |
| IC03957 | UG75 Expression | HOM | Mm.29473 | TITLE ESTs, Highly similar to COATOMER ZETA SUBUNIT [Bos taurus] | | | gi = 1702690 | 577777 |
| IC03958 | UG75 Expression | HOM | Mm.29475 | TITLE ESTs, Highly similar to c-Jun leucine zipper interactive [M. musculus] | | | gi = 2855781 | 1152145 |
| IC03959 | UG75 Expression | HOM | Mm.29477 | TITLE ESTs, Highly similar to leucine-rich-domain interacting protein 1 [M. musculus] | | | gi = 1309561 | 337504 |
| IC03960 | UG75 Expression | HOM | Mm.29488 | TITLE ESTs, Highly similar to BETA CRYSTALLIN B1 [Rattus norvegicus] | | | gi = 4059283 | 464120 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03961 | UG75 Expression | HOM | Mm.29492 | [M. musculus] | | | gi = 7197727 | 949805 |
| IC03962 | UG75 Expression | HOM | Mm.29497 | TITLE ESTs, Highly similar to NIFU PROTEIN [Anabaena pcc7120] | | | gi = 1287082 | 317782 |
| IC03963 | UG75 Expression | HOM | Mm.29502 | TITLE ESTs, Highly similar to RTS1 PROTEIN [Saccharomyces cerevisiae] | | | gi = 5860669 | 2182730 |
| IC03964 | UG75 Expression | HOM | Mm.29506 | TITLE ESTs, Highly similar to HYPOTHETICAL 38.2 KD PROTEIN IN BEM2-SPT2 INTERGENIC REGION [Saccharomyces cerevisiae] | | | gi = 1792964 | 640034 |
| IC03965 | UG75 Expression | HOM | Mm.29510 | TITLE ESTs, Highly similar to purine-selective Na+ nucleoside cotransporter [M. musculus] | | | gi = 2258595 | 904059 |
| IC03966 | UG75 Expression | HOM | Mm.29511 | TITLE ESTs, Highly similar to THERMOSENSITIVE GLUCONOKINASE [Escherichia coli] | | | gi = 4061463 | 484258 |
| IC03967 | UG75 Expression | HOM | Mm.29522 | TITLE ESTs, Highly similar to PUTATIVE SERINE/THREONINE-PROTEIN KINASE P78 [Homo sapiens] | | | gi = 1840954 | 658531 |
| IC03968 | UG75 Expression | HOM | Mm.29542 | TITLE ESTs, Highly similar to U2 SMALL NUCLEAR RIBONUCLEOPROTEIN AUXILIARY FACTOR 35 KD SUBUNIT RELATED-PROTEIN 1 [M. musculus] | | | gi = 2288430 | 933259 |
| IC03969 | UG75 Expression | HOM | Mm.29547 | TITLE ESTs, Highly similar to DYNEIN HEAVY CHAIN, CYTOSOLIC [Rattus norvegicus] | | | gi = 5600182 | 616392 |
| IC03970 | UG75 Expression | HOM | Mm.29549 | TITLE ESTs, Highly similar to TRANSCRIPTION FACTOR HFS-1 [Rattus norvegicus] | | | gi = 2962181 | 1281993 |
| IC03971 | UG75 Expression | HOM | Mm.29571 | TITLE ESTs, Highly similar to SEC14L [H. sapiens] TETRAHYDROFOLATE SYNTHASE, CYTOPLASMIC [Rattus norvegicus] | | | gi = 4276010 | 390192 |
| IC03972 | UG75 Expression | HOM | Mm.29584 | | | | gi = 5336376 | 1972179 |
| IC03973 | UG75 Expression | HOM | Mm.29591 | TITLE ESTs, Highly similar to SYNDECAN-3 PRECURSOR [Rattus norvegicus] | | | gi = 4968333 | 423353 |
| IC03974 | UG75 Expression | HOM | Mm.29601 | TITLE ESTs, Highly similar to CYTOSOLIC PURINE 5'-NUCLEOTIDASE [H. sapiens] | | | gi = 4967939 | 2598990 |
| IC03975 | UG75 Expression | HOM | Mm.29603 | TITLE ESTs, Highly similar to (defline not available 5916099) [M. musculus] | | | gi = 2057852 | 3155721 |
| IC03976 | UG75 Expression | HOM | Mm.29605 | TITLE ESTs, Highly similar to similar to PID:g3877944 [H. sapiens] | | | gi = 6076686 | 2192844 |
| IC03977 | UG75 Expression | HOM | Mm.29613 | TITLE ESTs, Highly similar to HLA-DR ASSOCIATED PROTEIN I [Homo sapiens] | | | gi = 2308490 | 961088 |
| IC03978 | UG75 Expression | HOM | Mm.29617 | TITLE ESTs, Highly similar to PROTEIN PHOSPHATASE INHIBITOR 2 [Oryctolagus cuniculus] | | | gi = 5125215 | 2076324 |
| IC03979 | UG75 Expression | HOM | Mm.29618 | TITLE ESTs, Highly similar to FIBRILLIN 1 PRECURSOR [Homo sapiens] | | | gi = 1863873 | 692679 |
| IC03980 | UG75 Expression | HOM | Mm.29620 | TITLE ESTs, Highly similar to MITOCHONDRIAL RESPIRATORY CHAIN COMPLEXES ASSEMBLY PROTEIN RCA1 [Saccharomyces cerevisiae] | | | gi = 4061670 | 552230 |
| IC03981 | UG75 Expression | HOM | Mm.29624 | TITLE ESTs, Highly similar to hypothetical protein [H. sapiens] | | | gi = 5908524 | 480616 |
| IC03982 | UG75 Expression | HOM | Mm.29630 | TITLE ESTs, Highly similar to transcription factor IIIC alpha chain [R. norvegicus] | | | gi = 3371389 | 676379 |
| IC03983 | UG75 Expression | HOM | Mm.29641 | TITLE ESTs, Highly similar to RAS-RELATED PROTEIN RAB-14 [Rattus norvegicus] | | | gi = 1325810 | 353426 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC03984 | UG75 Expression | HOM | Mm.29642 | TITLE ESTs, Highly similar to HYPOTHETICAL 46.6 KD PROTEIN IN DAL80-GAP1 INTERGENIC REGION [Saccharomyces cerevisiae] | | | gi = 3518765 | 1482870 |
| IC03985 | UG75 Expression | HOM | Mm.29655 | TITLE ESTs, Highly similar to SIGNAL RECOGNITION PARTICLE 68 KD PROTEIN [Canis familiaris] | | | gi = 4060681 | 468920 |
| IC03986 | UG75 Expression | HOM | Mm.29667 | TITLE ESTs, Highly similar to CGI-36 protein [H. sapiens] | | | gi = 1826938 | 659333 |
| IC03987 | UG75 Expression | HOM | Mm.29675 | TITLE ESTs, Highly similar to HYPOTHETICAL 27.5 KD PROTEIN IN RAD24-BMH1 INTERGENIC REGION [Saccharomyces cerevisiae] | | | gi = 1288812 | 331156 |
| IC03988 | UG75 Expression | HOM | Mm.29683 | TITLE ESTs, Highly similar to NADH-UBIQUINONE OXIDOREDUCTASE B18 SUBUNIT [Bos taurus] | | | gi = 3164292 | 735713 |
| IC03989 | UG75 Expression | HOM | Mm.29697 | TITLE ESTs, Highly similar to OLIGOSACCHARYL TRANSFERASE STT3 SUBUNIT HOMOLOG [Caenorhabditis elegans] | | | gi = 1324780 | 351189 |
| IC03990 | 00/04/26 UG#76 17Lid Expansion | HOM | Mm.29701 | ESTs, Highly similar to HETEROGENEOUS NUCLEAR RIBONUCLEOPROTEIN 27C [Drosophila melanogaster] | | | gi = 1494887 | 457975 |
| IC03991 | UG75 Expression | HOM | Mm.29706 | TITLE ESTs, Highly similar to LEUKOTRIENE A-4 HYDROLASE [Mus musculus] | | | gi = 4316309 | 1383226 |
| IC03992 | UG75 Expression | HOM | Mm.29709 | TITLE ESTs, Highly similar to origin recognition complex subunit 6 [M. musculus] | | | gi = 1309665 | 337848 |
| IC03993 | UG75 Expression | HOM | Mm.29714 | TITLE ESTs, Highly similar to PTD001 [H. sapiens] | | | gi = 2262876 | 904843 |
| IC03994 | UG75 Expression | HOM | Mm.29735 | TITLE ESTs, Highly similar to ASPARTOACYLASE [Homo sapiens] | | | gi = 5905416 | 2192334 |
| IC03995 | UG75 Expression | HOM | Mm.29736 | TITLE ESTs, Highly similar to p53 regulated PA26-T2 nuclear protein [H. sapiens] | | | gi = 2520312 | 602320 |
| IC03996 | UG75 Expression | HOM | Mm.29742 | | | | gi = 4604531 | 481284 |
| IC03997 | UG75 Expression | HOM | Mm.29746 | TITLE ESTs, Highly similar to MITOCHONDRIAL 60S RIBOSOMAL PROTEIN L3 [Rattus norvegicus] | | | gi = 1316249 | 318703 |
| IC03998 | UG75 Expression | HOM | Mm.29747 | TITLE ESTs, Highly similar to 140 KD NUCLEOLAR PHOSPHOPROTEIN [Rattus norvegicus] | | | gi = 6520377 | 2645599 |
| IC03999 | UG75 Expression | HOM | Mm.29749 | TITLE ESTs, Highly similar to 50S RIBOSOMAL PROTEIN L4 [Bacillus stearothermophilus] | | | gi = 6083863 | 1972938 |
| IC04000 | UG75 Expression | HOM | Mm.29755 | TITLE ESTs, Highly similar to inner centromere protein INCENP [M. musculus] | | | gi = 2101770 | 803798 |
| IC04001 | UG75 Expression | HOM | Mm.29766 | TITLE ESTs, Highly similar to GLIA MATURATION FACTOR BETA [Homo sapiens; Bos taurus] | | | gi = 4604009 | 483256 |
| IC04002 | UG75 Expression | HOM | Mm.29778 | TITLE ESTs, Highly similar to ARGININE-RICH PROTEIN [H. sapiens] | | | gi = 4604978 | 1969539 |
| IC04003 | UG75 Expression | HOM | Mm.29787 | TITLE ESTs, Highly similar to dJ347H13.4 [H. sapiens] | | | gi = 3297479 | 1380051 |
| IC04004 | UG75 Expression | HOM | Mm.29791 | TITLE ESTs, Highly similar to subtilisin/kexin isozyme SKI-1 precursor [M. musculus] | | | gi = 2916153 | 1260913 |
| IC04005 | UG75 Expression | HOM | Mm.29795 | TITLE ESTs, Highly similar to HYPOTHETICAL 83.2 KD PROTEIN IN CHA1-APA1/DTP INTERGENIC REGION [Saccharomyces cerevisiae] | | | gi = 695382 | 2101441 |
| IC04006 | UG75 Expression | HOM | Mm.29803 | TITLE ESTs, Highly similar to ALDEHYDE DEHYDROGENASE, E3 ISOZYME [Homo sapiens] | | | gi = 3032399 | 1279665 |
| IC04007 | UG75 Expression | HOM | Mm.29811 | TITLE ESTs, Highly similar to RGC-32 [R. norvegicus] | | | gi = 2138561 | 846942 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04008 | UG75 Expression | HOM | Mm.29814 | [H. sapiens] ADENOSYLMETHIONINE SYNTHETASE GAMMA FORM [Rattus norvegicus] | | | gi = 6638327 | 2331778 |
| IC04009 | UG75 Expression | HOM | Mm.29815 | | | | gi = 2729754 | 1181365 |
| IC04010 | UG75 Expression | HOM | Mm.29829 | TITLE ESTs, Highly similar to RAS-RELATED PROTEIN RAB-5A [Canis familiaris] | | | gi = 5334982 | 1924148 |
| IC04011 | UG75 Expression | HOM | Mm.29830 | TITLE ESTs, Highly similar to RADIAL SPOKE PROTEIN 3 [Chlamydomonas reinhardtii] | | | gi = 3863546 | 1888349 |
| IC04012 | UG75 Expression | HOM | Mm.29845 | TITLE ESTs, Highly similar to SUCCINYL-COA LIGASE [Rattus norvegicus] | | | gi = 3164917 | 1885905 |
| IC04013 | UG75 Expression | HOM | Mm.29849 | TITLE ESTs, Highly similar to HYPOTHETICAL 64.5 KD PROTEIN ZK652.9 IN CHROMOSOME III [Caenorhabditis elegans] | | | gi = 1287066 | 317707 |
| IC04014 | UG75 Expression | HOM | Mm.29859 | INITIATION FACTOR 2 BETA SUBUNIT [Oryctolagus cuniculus] | | | gi = 1310612 | 348518 |
| IC04015 | UG75 Expression | HOM | Mm.29864 | TITLE ESTs, Highly similar to ARP2/3 COMPLEX 16 KD SUBUNIT [H. sapiens] | | | gi = 1293981 | 334687 |
| IC04016 | UG75 Expression | HOM | Mm.29869 | TITLE ESTs, Highly similar to HYPOTHETICAL 28.9 KD PROTEIN C28H8.6 IN CHROMOSOME III [Caenorhabditis elegans] | | | gi = 1531064 | 478666 |
| IC04017 | UG75 Expression | HOM | Mm.29879 | TITLE ESTs, Highly similar to DEOXYURIDINE 5′-TRIPHOSPHATE NUCLEOTIDOHYDROLASE [Homo sapiens] | | | gi = 6078149 | 2192318 |
| IC04018 | UG75 Expression | HOM | Mm.29884 | TITLE ESTs, Highly similar to D-BETA-HYDROXYBUTYRATE DEHYDROGENASE PRECURSOR [Rattus norvegicus] | | | gi = 3749494 | 1886294 |
| IC04019 | UG75 Expression | HOM | Mm.29890 | TITLE ESTs, Highly similar to SERINE HYDROXYMETHYLTRANSFERASE, MITOCHONDRIAL [Oryctolagus cuniculus] | | | gi = 3168451 | 1480529 |
| IC04020 | UG75 Expression | HOM | Mm.29891 | TITLE ESTs, Highly similar to forkhead protein FKHR [M. musculus] | | | gi = 2744989 | 1210247 |
| IC04021 | UG75 Expression | HOM | Mm.29897 | TITLE ESTs, Highly similar to NADH-UBIQUINONE OXIDOREDUCTASE 13 KD-A SUBUNIT PRECURSOR [Bos taurus] | | | gi = 2920157 | 989714 |
| IC04022 | UG75 Expression | HOM | Mm.29900 | ELONGATION FACTOR TS PRECURSOR [Homo sapiens] | | | gi = 1876267 | 699237 |
| IC04023 | UG75 Expression | HOM | Mm.29902 | TITLE ESTs, Highly similar to PROBABLE PHOSPHOSERINE AMINOTRANSFERASE [Oryctolagus cuniculus] | | | gi = 4434103 | 1498348 |
| IC04024 | UG75 Expression | HOM | Mm.29911 | TITLE ESTs, Highly similar to 40S RIBOSOMAL PROTEIN S27 [Homo sapiens] | | | gi = 1805201 | 661966 |
| IC04025 | UG75 Expression | HOM | Mm.29916 | TITLE ESTs, Highly similar to G10 PROTEIN [Xenopus laevis] | | | gi = 6076562 | 2159728 |
| IC04026 | UG75 Expression | HOM | Mm.29919 | TITLE ESTs, Highly similar to 60S RIBOSOMAL PROTEIN L34 [Homo sapiens] | | | gi = 5125078 | 2065400 |
| IC04027 | UG75 Expression | HOM | Mm.29922 | TITLE ESTs, Highly similar to retinoic acid-regulated protein pH 34 [M. musculus] | | | gi = 2519934 | 992452 |
| IC04028 | UG75 Expression | HOM | Mm.29923 | [M. musculus] | | | gi = 3164405 | 874394 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04029 | UG75 Expression | HOM | Mm.29924 | TITLE ESTs, Highly similar to ARL-6 interacting protein-1 [M. musculus] | | | gi = 4434000 | 2192369 |
| IC04030 | UG75 Expression | HOM | Mm.2993 | PROTEIN PHOSPHATASE PPE1 [Schizosaccharomyces pombe] | | | gi = 1715529 | 581656 |
| IC04031 | UG75 Expression | HOM | Mm.29930 | TITLE ESTs, Highly similar to F17127_1 [H. sapiens] | | | gi = 6645850 | 484118 |
| IC04032 | UG75 Expression | HOM | Mm.29931 | TITLE ESTs, Highly similar to CELL DIVISION CONTROL PROTEIN 20 [Saccharomyces cerevisiae] | | | gi = 4061581 | 425838 |
| IC04033 | UG75 Expression | HOM | Mm.29939 | TITLE ESTs, Highly similar to NADH-UBIQUINONE OXIDOREDUCTASE 39 KD SUBUNIT PRECURSOR [Bos taurus] | | | gi = 4409124 | 764749 |
| IC04034 | UG75 Expression | HOM | Mm.29943 | TITLE ESTs, Highly similar to P1.11659_5 [H. sapiens] | | | gi = 4604067 | 515589 |
| IC04035 | UG75 Expression | HOM | Mm.29946 | [H. sapiens] | | | gi = 2272961 | 570620 |
| IC04036 | UG75 Expression | HOM | Mm.29957 | TITLE ESTs, Highly similar to dJ1042K10.2.1 [H. sapiens] | | | gi = 2861760 | 1023941 |
| IC04037 | UG75 Expression | HOM | Mm.29962 | TITLE ESTs, Highly similar to mszf35 [M. musculus] | | | gi = 3720111 | 1885151 |
| IC04038 | UG75 Expression | HOM | Mm.29986 | TITLE ESTs, Highly similar to LEUCINE-RICH ALPHA-2-GLYCOPROTEIN [Homo sapiens] | | | gi = 4061691 | 552581 |
| IC04039 | UG75 Expression | HOM | Mm.29987 | TITLE ESTs, Highly similar to 17.9 KD MEMBRANE PROTEIN C21ORF4 [H. sapiens] | | | gi = 5909293 | 872634 |
| IC04040 | UG75 Expression | HOM | Mm.29989 | TITLE ESTs, Highly similar to dJ465N24.1 [H. sapiens] | | | gi = 1737958 | 604732 |
| IC04041 | UG75 Expression | HOM | Mm.29991 | TITLE ESTs, Highly similar to ALPHA-ACTININ, SMOOTH MUSCLE ISOFORM [Gallus gallus] | | | gi = 3602356 | 3154861 |
| IC04042 | UG75 Expression | HOM | Mm.29998 | TITLE ESTs, Highly similar to unknown [H. sapiens] | | | gi = 4730151 | 1970099 |
| IC04043 | UG75 Expression | HOM | Mm.30001 | TITLE ESTs, Highly similar to TRANSCRIPTION FACTOR BTF3 [Homo sapiens] | | | gi = 3718914 | 1969973 |
| IC04044 | UG75 Expression | HOM | Mm.30004 | TITLE ESTs, Highly similar to hypothetical protein [H. sapiens] | | | gi = 2730063 | 1153886 |
| IC04045 | UG75 Expression | HOM | Mm.30009 | TITLE ESTs, Highly similar to ARL-6 interacting protein-5 [M. musculus] | | | gi = 2720326 | 1166828 |
| IC04046 | UG75 Expression | HOM | Mm.30010 | TITLE ESTs, Highly similar to (define not available 5442444][M. musculus] | | | gi = 1282601 | 332038 |
| IC04047 | UG75 Expression | HOM | Mm.30011 | TITLE ESTs, Highly similar to 40S RIBOSOMAL PROTEIN S23 [Homo sapiens; Rattus norvegicus] | | | gi = 2262676 | 904778 |
| IC04048 | UG75 Expression | HOM | Mm.30012 | TITLE ESTs, Highly similar to caveola-associated protein [R. norvegicus] | | | gi = 1428714 | 423623 |
| IC04049 | UG75 Expression | HOM | Mm.30017 | TITLE ESTs, Highly similar to HYPOTHETICAL 13.6 KD PROTEIN IN NUP170-ILS1 INTERGENIC REGION [Saccharomyces cerevisiae] | | | gi = 3862939 | 1890052 |
| IC04050 | UG75 Expression | HOM | Mm.30018 | ONCOGENE SERINE/THREONINE-PROTEIN KINASE [Homo sapiens] | | | gi = 6079300 | 2236113 |
| IC04051 | UG75 Expression | HOM | Mm.30023 | TITLE ESTs, Highly similar to embryonic lung protein [H. sapiens] | | | gi = 1325610 | 353305 |
| IC04052 | UG75 Expression | HOM | Mm.30025 | TITLE ESTs, Highly similar to ANTITHROMBIN-III PRECURSOR [Mus musculus] | | | gi = 3809557 | 1891216 |
| IC04053 | UG75 Expression | HOM | Mm.30030 | TITLE ESTs, Highly similar to MITOCHONDRIAL PROCESSING PEPTIDASE ALPHA SUBUNIT PRECURSOR [Rattus norvegicus] | | | gi = 2248910 | 891434 |
| IC04054 [H. sapiens] | UG75 Expression | HOM | Mm.30031 | TITLE ESTs, Highly similar to KIAA0831 protein | | | gi = 2517668 | 554401 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04055 | UG75 Expression | HOM | Mm.30036 | TITLE ESTs, Highly similar to EUKARYOTIC INITIATION FACTOR 4 GAMMA [Homo sapiens] | | | gi = 1937424 | 749373 |
| IC04056 | UG75 Expression | HOM | Mm.30039 | TITLE ESTs, Highly similar to CAMP-DEPENDENT PROTEIN KINASE TYPE I-ALPHA REGULATORY CHAIN [Homo sapiens] | | | gi = 6168141 | 2270110 |
| IC04057 | UG75 Expression | HOM | Mm.30040 | TITLE ESTs, Highly similar to Bcl-2-interacting protein beclin [M. musculus] | | | gi = 3519612 | 1498852 |
| IC04058 | UG75 Expression | HOM | Mm.30043 | TITLE ESTs, Highly similar to MICROSOMAL SIGNAL PEPTIDASE 25 KD SUBUNIT [H. sapiens] | | | gi = 6515969 | 2101707 |
| IC04059 | UG75 Expression | HOM | Mm.30062 | TITLE ESTs, Highly similar to p65 protein [R. norvegicus] | | | gi = 1290302 | 333428 |
| IC04060 | UG75 Expression | HOM | Mm.30063 | TITLE ESTs, Highly similar to FIBRINOGEN BETA CHAIN PRECURSOR [Homo sapiens] | | | gi = 3749502 | 1886289 |
| IC04061 | UG75 Expression | HOM | Mm.30064 | TITLE ESTs, Highly similar to HYPOTHETICAL 13.6 KD PROTEIN IN NUP170-ILS1 INTERGENIC REGION [Saccharomyces cerevisiae] | | | gi = 6078122 | 2192267 |
| IC04062 | UG75 Expression | HOM | Mm.30069 | TITLE ESTs, Highly similar to similar to nuclear domain 10 protein NDP52 [H. sapiens] | | | gi = 1310577 | 348114 |
| IC04063 | UG75 Expression | HOM | Mm.30074 | TITLE ESTs, Highly similar to 2-OXOGLUTARATE DEHYDROGENASE E1 COMPONENT PRECURSOR [Homo sapiens] | | | gi = 5336990 | 1972695 |
| IC04064 | UG75 Expression | HOM | Mm.30083 | TITLE ESTs, Highly similar to Unknown [H. sapiens] | | | gi = 1310616 | 348519 |
| IC04065 | UG75 Expression | HOM | Mm.30085 | TITLE ESTs, Highly similar to ALCOHOL DEHYDROGENASE [Homo sapiens] | | | gi = 5598729 | 570836 |
| IC04066 | UG75 Expression | HOM | Mm.30092 | TITLE ESTs, Highly similar to ATP-DEPENDENT PROTEASE LA 2 [Myxococcus xanthus] | | | gi = 4 967410 | 1921569 |
| IC04067 | UG75 Expression | HOM | Mm.30093 | TITLE ESTs, Highly similar to HLA-DR ASSOCIATED PROTEIN I [Homo sapiens] | | | gi = 2516426 | 1295540 |
| IC04068 | UG75 Expression | HOM | Mm.30097 | TITLE ESTs, Highly similar to PROTEASOME COMPONENT C2 [Homo sapiens] | | | gi = 1286295 | 317057 |
| IC04069 | UG75 Expression | HOM | Mm.30100 | HYDROXYANTHRANILATE 3,4-DIOXYGENASE [Homo sapiens] | | | gi = 4061788 | 576135 |
| IC04070 | UG75 Expression | HOM | Mm.30103 | TITLE ESTs, Highly similar to GLYCOPROTEIN 25L PRECURSOR [Canis familiaris] | | | gi = 3718557 | 2225897 |
| IC04071 | UG75 Expression | HOM | Mm.30110 | TITLE ESTs, Highly similar to ALPHA-MANNOSIDASE [Rattus norvegicus] | | | gi = 4722966 | 518334 |
| IC04072 | UG75 Expression | HOM | Mm.30113 | TITLE ESTs, Highly similar to NADH-UBIQUINONE OXIDOREDUCTASE 30 KD SUBUNIT PRECURSOR [Bos taurus] | | | gi = 3863766 | 1890290 |
| IC04073 | UG75 Expression | HOM | Mm.3012 | [H. sapiens] | | | gi = 6526556 | 2650841 |
| IC04074 | UG75 Expression | HOM | Mm.30123 | TITLE ESTs, Highly similar to 30S RIBOSOMAL PROTEIN S7 [Thermotoga maritima] | | | gi = 3068067 | 1328645 |
| IC04075 | UG75 Expression | HOM | Mm.30130 | TITLE ESTs, Highly similar to ALANINE AMINOTRANSFERASE [Rattus norvegicus] | | | gi = 3749121 | 1887752 |
| IC04076 | UG75 Expression | HOM | Mm.30147 | TITLE ESTs, Highly similar to HYPOTHETICAL 47.9 KD PROTEIN B0303.3 IN CHROMOSOME III [Caenorhabditis elegans] | | | gi = 4767162 | 1890476 |
| IC04077 | UG75 Expression | HOM | Mm.30148 | [H. sapiens] | | | gi = 1554651 | 483115 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04078 | UG75 Expression | HOM | Mm.30150 | TITLE ESTs, Highly similar to NADH-UBIQUINONE OXIDOREDUCTASE B9 SUBUNIT [Bos taurus] | | | gi = 1910106 | 736884 |
| IC04079 | UG75 Expression | HOM | Mm.30156 | TITLE ESTs, Highly similar to PROTEASE DO PRECURSOR [Salmonella typhimurium] | | | gi = 5549603 | 1972370 |
| IC04080 | UG75 Expression | HOM | Mm.30165 | TITLE ESTs, Highly similar to CGI-87 protein [H. sapiens] | | | gi = 6167877 | 2247520 |
| IC04081 | UG75 Expression | HOM | Mm.30184 | TITLE ESTs, Highly similar to prefoldin subunit 1 [H. sapiens] | | | gi = 1287291 | 318280 |
| IC04082 | UG75 Expression | HOM | Mm.30194 | TITLE ESTs, Highly similar to HSPC021 [H. sapiens] | | | gi = 6521083 | 2645871 |
| IC04083 | UG75 Expression | HOM | Mm.30195 | TITLE ESTs, Highly similar to FUSCA PROTEIN FUS6 [Arabidopsis thaliana] | | | gi = 6514989 | 2582022 |
| IC04084 | UG75 Expression | HOM | Mm.30200 | TITLE ESTs, Highly similar to ELECTRON TRANSFER FLAVOPROTEIN BETA-SUBUNIT [Paracoccus denitrificans] | | | gi = 1297604 | 336670 |
| IC04085 | UG75 Expression | HOM | Mm.30204 | TITLE ESTs, Highly similar to DIHYDROPTERIDINE REDUCTASE [Rattus norvegicus] | | | gi = 1287567 | 317473 |
| IC04086 | UG75 Expression | HOM | Mm.30206 | TITLE ESTs, Highly similar to VACUOLAR ATP SYNTHASE SUBUNIT D [Bos taurus] | | | gi = 3718762 | 1066743 |
| IC04087 | UG75 Expression | HOM | Mm.30211 | TITLE ESTs, Highly similar to (define not available 6103733) [M. musculus] | | | gi = 3718960 | 2937345 |
| IC04088 | UG75 Expression | HOM | Mm.30230 | TITLE ESTs, Highly similar to ENV POLYPROTEIN PRECURSOR [Moloney murine leukemia virus] | | | gi = 6526173 | 2651089 |
| IC04089 | UG75 Expression | HOM | Mm.30233 | TITLE ESTs, Highly similar to CONJUGATING ENZYME E2-17 KD [Drosophila melanogaster] | | | gi = 5599137 | 387377 |
| IC04090 | UG75 Expression | HOM | Mm.30234 | TITLE ESTs, Highly similar to rer [M. musculus] | | | gi = 6085516 | 2159154 |
| IC04091 | UG75 Expression | HOM | Mm.30236 | TITLE ESTs, Highly similar to (define not available 5931957) [M. musculus] | | | gi = 6558151 | 2655135 |
| IC04092 | UG75 Expression | HOM | Mm.30237 | TITLE ESTs, Highly similar to transactivating protein BRIDGE [R. norvegicus] | | | gi = 3099799 | 1328874 |
| IC04093 | UG75 Expression | HOM | Mm.30241 | TITLE ESTs, Highly similar to INDUCIBLE PROTEIN IP-30 PRECURSOR [Homo sapiens] | | | gi = 2812022 | 1248248 |
| IC04094 | UG75 Expression | HOM | Mm.30242 | TITLE ESTs, Highly similar to 40 KD PEPTIDYL-PROLYL CIS-TRANS ISOMERASE [Homo sapiens] | | | gi = 6084780 | 537282 |
| IC04095 | UG75 Expression | HOM | Mm.30243 | TITLE ESTs, Highly similar to KIAA0890 protein [H. sapiens] | | | gi = 3370215 | 2698940 |
| IC04096 | UG75 Expression | HOM | Mm.30244 | TITLE ESTs, Highly similar to HYPOTHETICAL 13.6 KD PROTEIN IN NUP170-ILS1 INTERGENIC REGION [Saccharomyces cerevisiae] | | | gi = 1910240 | 736870 |
| IC04097 | UG75 Expression | HOM | Mm.30245 | TITLE ESTs, Highly similar to PHOSPHATIDYLSERINE DECARBOXYLASE PROENZYME [Cricetulus griseus] | | | gi = 6083815 | 2099412 |
| IC04098 | UG75 Expression | HOM | Mm.30255 | TITLE ESTs, Highly similar to HISTONE MACRO-H2A.1 [Rattus norvegicus] | | | gi = 1309519 | 337269 |
| IC04099 | UG75 Expression | HOM | Mm.30263 | TITLE ESTs, Highly similar to LONG-CHAIN-FATTY ACID-COA LIGASE 2 [Homo sapiens] | | | gi = 4604731 | 1925071 |
| IC04100 | UG75 Expression | HOM | Mm.3031 | TITLE ESTs, Highly similar to RNA polymerase II transcription factor SIII p18 subunit [R. norvegicus] | | | gi = 3164773 | 1973519 |
| IC04101 | UG75 Expression | HOM | Mm.3035 | TITLE ESTs, Highly similar to [H. sapiens] | | | gi = 443971 | 1923118 |
| IC04102 | UG75 Expression | HOM | Mm.30504 | TITLE ESTs, Highly similar to CYTOCHROME P450 IVF3 [Homo sapiens] | | | gi = 5124779 | 2076172 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04103 | UG75 Expression | HOM | Mm.30552 | TITLE ESTs, Highly similar to HYPOTHETICAL 103.5 KD PROTEIN IN RAD26-GEF1 INTERGENIC REGION [Saccharomyces cerevisiae] | | | gi = 6514608 | 2647132 |
| IC04104 | UG75 Expression | HOM | Mm.30557 | TITLE ESTs, Highly similar to C6.1A PROTEIN [M. musculus] | | | gi = 4316274 | 1383171 |
| IC04105 | UG75 Expression | HOM | Mm.30571 | TITLE ESTs, Highly similar to KIAA0476 protein [H. sapiens] | | | gi = 1309935 | 348029 |
| IC04106 | UG75 Expression | HOM | Mm.30601 | TITLE ESTs, Highly similar to IMPORTIN ALPHA-3 SUBUNIT [M. musculus] | | | gi = 4723598 | 635985 |
| IC04107 | UG75 Expression | HOM | Mm.30602 | TITLE ESTs, Highly similar to PROBABLE UBIQUITIN CARBOXYL-TERMINAL HYDROLASE [Homo sapiens] 5453264] [M. musculus] | | | gi = 2906999 | 1434219 |
| IC04108 | UG75 Expression | HOM | Mm.30657 | TITLE ESTs, Highly similar to (defline not available 5453264) [M. musculus] | | | gi = 4613310 | 619926 |
| IC04109 | UG75 Expression | HOM | Mm.30664 | TITLE ESTs, Highly similar to peroxisome assembly factor-3 [R. norvegicus] | | | gi = 3692691 | 1332756 |
| IC04110 | UG75 Expression | HOM | Mm.30682 | TITLE ESTs, Highly similar to DEOXYHYPUSINE SYNTHASE [H. sapiens] | | | gi = 6574538 | 2811201 |
| IC04111 | UG75 Expression | HOM | Mm.30821 | TITLE ESTs, Highly similar to DNASE I HOMOLOGOUS PROTEIN DHP2 PRECURSOR [M. musculus] | | | gi = 1936182 | 752217 |
| IC04112 | UG75 Expression | HOM | Mm.30826 | TITLE ESTs, Highly similar to BS69 protein [H. sapiens] | | | gi = 1726407 | 634919 |
| IC04113 | UG75 Expression | HOM | Mm.30864 | TITLE ESTs, Highly similar to (defline not available 5823276) [M. musculus] | | | gi = 6631665 | 2811740 |
| IC04114 | UG75 Expression | HOM | Mm.30912 | TITLE ESTs, Highly similar to p68 RNA helicase [M. musculus] | | | gi = 2306031 | 948891 |
| IC04115 | UG75 Expression | HOM | Mm.30926 | TITLE ESTs, Highly similar to SPLICING FACTOR U2AF 35 KD SUBUNIT [Homo sapiens] | | | gi = 1677661 | 539783 |
| IC04116 | UG75 Expression | HOM | Mm.30935 | TITLE ESTs, Highly similar to (defline not available 5689375) [R. norvegicus] | | | gi = 2200721 | 874379 |
| IC04117 | UG75 Expression | HOM | Mm.30991 | TITLE ESTs, Highly similar to PHOSPHORYLASE B KINASE GAMMA CATALYTIC CHAIN, TESTIS ISOFORM [Rattus norvegicus] | | | gi = 4316136 | 1383051 |
| IC04118 | UG75 Expression | HOM | Mm.31170 | TITLE ESTs, Highly similar to msg1-related protein 2 [M. musculus] | | | gi = 5906123 | 1514215 |
| IC04119 | UG75 Expression | HOM | Mm.31417 | TITLE ESTs, Highly similar to zinc finger protein [H. sapiens] | | | gi = 6078460 | 2225299 |
| IC04120 | UG75 Expression | HOM | Mm.31419 | TITLE ESTs, Highly similar to NUCLEAR PORE COMPLEX PROTEIN NUP155 [R. norvegicus] | | | gi = 4288925 | 619994 |
| IC04121 | UG75 Expression | HOM | Mm.31435 | TITLE ESTs, Highly similar to GTP-BINDING ADP RIBOSYLATION FACTOR HOMOLOG 1 PROTEIN [Drosophila melanogaster] | | | gi = 1291867 | 333836 |
| IC04122 | UG75 Expression | HOM | Mm.31523 | TITLE ESTs, Highly similar to KIAA0928 protein [H. sapiens] | | | gi = 6556839 | 2651646 |
| IC04123 | UG75 Expression | HOM | Mm.3154 | TITLE ESTs, Highly similar to dJ434O14.5 [H. sapiens] | | | gi = 4373946 | 891388 |
| IC04124 | UG75 Expression | HOM | Mm.31551 | TITLE ESTs, Highly similar to dJ434O14.5 [H. sapiens] | | | gi = 3377047 | 1430522 |
| IC04125 | UG75 Expression | HOM | Mm.31831 | TITLE EST, Highly similar to similar to AL031532 [H. sapiens] | | | gi = 4303270 | 596659 |
| IC04126 | UG75 Expression | HOM | Mm.31940 | TITLE ESTs, Highly similar to CGMP-INHIBITED 3′,5′-CYCLIC PHOSPHODIESTERASE B [M. musculus] | | | gi = 4307678 | 597524 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04127 | UG75 Expression | HOM | Mm.31976 | TITLE ESTs, Highly similar to putative hydrophobic domain in amino acid positions 373-390. [H. sapiens] | | | gi = 1676321 | 573444 |
| IC04128 | UG75 Expression | HOM | Mm.3199 | TITLE ESTs, Highly similar to HYPOTHETICAL 27.6 KD PROTEIN IN PDX1-SNG1 INTERGENIC REGION [Saccharomyces cerevisiae] | | | gi = 3719054 | 2938161 |
| IC04129 | UG75 Expression | HOM | Mm.32017 | TITLE ESTs, Highly similar to ETS-RELATED PROTEIN TEL [M. musculus] | | | gi = 4374927 | 888471 |
| IC04130 | UG75 Expression | HOM | Mm.3241 | TITLE ESTs, Highly similar to PELOTA [Drosophila melanogaster] | | | gi = 5598710 | 558379 |
| IC04131 | UG75 Expression | HOM | Mm.32488 | TITLE ESTs, Highly similar to KIAA0783 protein [H. sapiens] | | | gi = 4783673 | 642465 |
| IC04132 | UG75 Expression | HOM | Mm.32505 | TITLE ESTs, Highly similar to zinc finger DNA binding protein 99 [H. sapiens] | | | gi = 5191478 | 642898 |
| IC04133 | UG75 Expression | HOM | Mm.32550 | TITLE ESTs, Highly similar to (define not available 5730s898) [M. musculus] | | | gi = 1330742 | 355012 |
| IC04134 | UG75 Expression | HOM | Mm.3256 | TITLE ESTs, Highly similar to CLATHRIN COAT ASSEMBLY PROTEIN AP47 HOMOLOG [Discopyge ommata] | | | gi = 4057084 | 475947 |
| IC04135 | UG75 Expression | HOM | Mm.326 | TITLE ESTs, Highly similar to CYCLIN-DEPENDENT KINASES REGULATORY SUBUNIT 2 [Homo sapiens] | | | gi = 4777768 | 1972263 |
| IC04136 | UG75 Expression | HOM | Mm.32698 | TITLE ESTs, Highly similar to CGI-62 protein [H. sapiens] | | | gi = 6085384 | 1248341 |
| IC04137 | UG75 Expression | HOM | Mm.32920 | TITLE ESTs, Highly similar to CGI-76 protein [H. sapiens] | | | gi = 4485348 | 820523 |
| IC04138 | UG75 Expression | HOM | Mm.32973 | TITLE ESTs, Highly similar to Krit1 [H. sapiens] | | | gi = 2962179 | 1281989 |
| IC04139 | UG75 Expression | HOM | Mm.33019 | TITLE ESTs, Highly similar to -14 [H. sapiens] | | | gi = 6100040 | 1265631 |
| IC04140 | UG75 Expression | HOM | Mm.33038 | TITLE ESTs, Highly similar to JM1 [H. sapiens] | | | gi = 1682699 | 576841 |
| IC04141 | UG75 Expression | HOM | Mm.33120 | TITLE ESTs, Highly similar to HISTAMINE N-METHYLTRANSFERASE [R. norvegicus] | | | gi = 5336085 | 1973008 |
| IC04142 | UG75 Expression | HOM | Mm.33202 | TITLE ESTs, Highly similar to HNRNP METHYLTRANSFERASE [Saccharomyces cerevisiae] | | | gi = 5337051 | 1972765 |
| IC04143 | UG75 Expression | HOM | Mm.33356 | TITLE ESTs, Highly similar to EXCITATORY AMINO ACID TRANSPORTER 1 [M. musculus] | | | gi = 4434274 | 1970005 |
| IC04144 | UG75 Expression | HOM | Mm.3350 | TITLE ESTs, Highly similar to microtubule-actin crosslinking factor [M. musculus] | | | gi = 1282051 | 331699 |
| IC04145 | UG75 Expression | HOM | Mm.33799 | TITLE ESTs, Highly similar to symplekin [H. sapiens] | | | gi = 2262911 | 851754 |
| IC04146 | UG75 Expression | HOM | Mm.33830 | TITLE ESTs, Highly similar to GLUCOSAMINE-6-PHOSPHATE ISOMERASE [Homo sapiens] | | | gi = 5598764 | 574185 |
| IC04147 | UG75 Expression | HOM | Mm.33838 | TITLE ESTs, Highly similar to PCAF-associated factor 400 [H. sapiens] | | | gi = 3809287 | 1498228 |
| IC04148 | UG75 Expression | HOM | Mm.33892 | TITLE ESTs, Highly similar to PROTEINASE ACTIVATED RECEPTOR 2 PRECURSOR [M. musculus] | | | gi = 6079254 | 2236085 |
| IC04149 | UG75 Expression | HOM | Mm.33894 | TITLE ESTs, Highly similar to interferon-inducible protein 203 [M. musculus] | | | gi = 4374694 | 873953 |
| IC04150 | UG75 Expression | HOM | Mm.33907 | TITLE ESTs, Highly similar to hepatitis B virus X interacting protein [H. sapiens] | | | gi = 1840787 | 670237 |
| IC04151 | UG75 Expression | HOM | Mm.33956 | TITLE ESTs, Highly similar to KIAA0449 protein [H. sapiens] | | | gi = 4289829 | 576661 |
| IC04152 | UG75 Expression | HOM | Mm.34034 | TITLE ESTs, Highly similar to CGI-53 protein [H. sapiens] | | | gi = 3168067 | 1432187 |
| IC04153 | UG75 Expression | HOM | Mm.34079 | TITLE ESTs, Highly similar to MYO-INOSITOL-1 (OR 4)-MONOPHOSPHATASE [Xenopus laevis] | | | gi = 6632582 | 2655895 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04154 | UG75 Expression | HOM | Mm.34112 | TITLE ESTs, Highly similar to PV-1 [R. norvegicus] | | | gi = 4029454 | 1908008 |
| IC04155 | UG75 Expression | HOM | Mm.34126 | TITLE ESTs, Highly similar to SERINE CARBOXYPEPTIDASE PRECURSOR [Arabidopsis thaliana] | | | gi = 5749965 | 2158852 |
| IC04156 | UG75 Expression | HOM | Mm.34330 | TITLE ESTs, Highly similar to BLADDER CANCER 10 KD PROTEIN [H. sapiens] | | | gi = 4433940 | 354753 |
| IC04157 | UG75 Expression | HOM | Mm.34333 | TITLE ESTs, Highly similar to protein phosphatase 1 M chain M110 isoform, [R. norvegicus] | | | gi = 1752171 | 614894 |
| IC04158 | UG75 Expression | HOM | Mm.34370 | TITLE ESTs, Highly similar to GLYCOGEN SYNTHASE KINASE-3 BETA [Rattus norvegicus] | | | gi = 4572246 | 988761 |
| IC04159 | UG75 Expression | HOM | Mm.34374 | TITLE ESTs, Highly similar to CHYMOTRYPSINOGEN B PRECURSOR [Rattus norvegicus] | | | gi = 2345819 | 987446 |
| IC04160 | UG75 Expression | HOM | Mm.34389 | TITLE ESTs, Highly similar to macrophage maturation-associated transcript dd3f protein [H. sapiens] | | | gi = 4968102 | 2088140 |
| IC04161 | UG75 Expression | HOM | Mm.34399 | TITLE ESTs, Highly similar to CAAX prenyl protease [H. sapiens] | | | gi = 6084674 | 860351 |
| IC04162 | UG75 Expression | HOM | Mm.34401 | TITLE ESTs, Highly similar to HYPOTHETICAL TRP-ASP REPEATS CONTAINING PROTEIN IN PGI1-KTR4 INTERGENIC REGION [Saccharomyces cerevisiae] | | | gi = 5492926 | 680458 |
| IC04163 | UG75 Expression | HOM | Mm.34463 | TITLE ESTs, Highly similar to KIAA0594 protein [H. sapiens] | | | gi = 5496586 | 894023 |
| IC04164 | UG75 Expression | HOM | Mm.34468 | TITLE ESTs, Highly similar to KIAA0385 [H. sapiens] | | | gi = 3055075 | 1328261 |
| IC04165 | UG75 Expression | HOM | Mm.34485 | TITLE ESTs, Highly similar to LEUKOTRIENE A-4 HYDROLASE [M. musculus] | | | gi = 3393493 | 2598836 |
| IC04166 | UG75 Expression | HOM | Mm.34488 | TITLE ESTs, Highly similar to R31167_1, partial protein [H. sapiens] | | | gi = 5905634 | 2192604 |
| IC04167 | UG75 Expression | HOM | Mm.34490 | TITLE ESTs, Highly similar to RIBOSOMAL PROTEIN S6 KINASE [Homo sapiens] | | | gi = 4304476 | 642183 |
| IC04168 | UG75 Expression | HOM | Mm.34497 | TITLE ESTs, Highly similar to (defline not available 6012071) [R. norvegicus] | | | gi = 6757449 | 2648051 |
| IC04169 | UG75 Expression | HOM | Mm.34507 | TITLE ESTs, Highly similar to class A calcium channel variant riA-I [R. norvegicus] | | | gi = 5492199 | 733370 |
| IC04170 | UG75 Expression | HOM | Mm.34511 | TITLE ESTs, Highly similar to hypothetical protein 384D8_7 [H. sapiens] | | | gi = 2199731 | 874052 |
| IC04171 | UG75 Expression | HOM | Mm.34512 | TITLE ESTs, Highly similar to FARNESYL PYROPHOSPHATE SYNTHETASE [Rattus norvegicus] | | | gi = 3233435 | 1378173 |
| IC04172 | UG75 Expression | HOM | Mm.34515 | TITLE ESTs, Highly similar to dJ347H13.5 [H. sapiens] | | | gi = 2693900 | 1125013 |
| IC04173 | UG75 Expression | HOM | Mm.34526 | TITLE ESTs, Highly similar to D123 [R. norvegicus] | | | gi = 6749200 | 2352981 |
| IC04174 | UG75 Expression | HOM | Mm.34532 | TITLE ESTs, Highly similar to non-muscle alpha-actinin 1 [R. norvegicus] | | | gi = 1876235 | 699420 |
| IC04175 | UG75 Expression | HOM | Mm.34536 | RETICULUM PROTEIN ERP29 PRECURSOR [R. norvegicus] | | | gi = 6514970 | 2581992 |
| IC04176 | UG75 Expression | HOM | Mm.34549 | TITLE ESTs, Highly similar to SMALL NUCLEAR RIBONUCLEOPROTEIN SM D3 [Homo sapiens] | | | gi = 2262970 | 906527 |
| IC04177 | UG75 Expression | HOM | Mm.34577 | TITLE ESTs, Highly similar to Arf-like 2 binding protein BART1 [H. sapiens] | | | gi = 1494891 | 458026 |
| IC04178 | UG75 Expression | HOM | Mm.34579 | TITLE ESTs, Highly similar to KIAA0824 protein [H. sapiens] | | | gi = 5909431 | 2922341 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04179 | UG75 Expression | HOM | Mm.34580 | TITLE ESTs, Highly similar to T2K protein kinase homolog [*M. musculus*] | | | gi = 1901346 | 598120 |
| IC04180 | UG75 Expression | HOM | Mm.34586 | TITLE ESTs, Highly similar to R29515_1 [*H. sapiens*] | | | gi = 3520255 | 1398752 |
| IC04181 | UG75 Expression | HOM | Mm.3459 | TITLE ESTs, Highly similar to D-BINDING PROTEIN [*M. musculus*] | | | gi = 4442672 | 583416 |
| IC04182 | UG75 Expression | HOM | Mm.34647 | TITLE ESTs, Highly similar to NEUROLYSIN PRECURSOR [*Rattus norvegicus*] | | | gi = 4060846 | 524208 |
| IC04183 | UG75 Expression | HOM | Mm.34655 | TITLE ESTs, Highly similar to purine nucleoside phosphorylase [*M. musculus*] | | | gi = 4319509 | 652603 |
| IC04184 | UG75 Expression | HOM | Mm.34662 | TITLE ESTs, Highly similar to KIAA0784 protein [*H. sapiens*] | | | gi = 4258330 | 315878 |
| IC04185 | UG75 Expression | HOM | Mm.34701 | TITLE ESTs, Highly similar to MATERNAL PUMILIO PROTEIN [*Drosophila melanogaster*] | | | gi = 5336274 | 1972062 |
| IC04186 | UG75 Expression | HOM | Mm.34758 | TITLE ESTs, Highly similar to AMP DEAMINASE 2 [*Homo sapiens*] | | | gi = 4408687 | 1265509 |
| IC04187 | UG75 Expression | HOM | Mm.34759 | TITLE ESTs, Highly similar to SERINE HYDROXYMETHYLTRANSFERASE, CYTOSOLIC [*Homo sapiens*] | | | gi = 4199004 | 474977 |
| IC04188 | UG75 Expression | HOM | Mm.34769 | TITLE ESTs, Highly similar to ANKYRIN, BRAIN VARIANT 2 [*Homo sapiens*] | | | gi = 3518225 | 1400401 |
| IC04189 | UG75 Expression | HOM | Mm.34779 | TITLE ESTs, Highly similar to ubiquitously expressed transcript [*M. musculus*] | | | gi = 1380059 | 388843 |
| IC04190 | UG75 Expression | HOM | Mm.3479 | TITLE ESTs, Highly similar to PROTEOLIPID PROTEIN PPA1 [*Saccharomyces cerevisiae*] | | | gi = 2284082 | 933047 |
| IC04191 | UG75 Expression | HOM | Mm.34790 | TITLE ESTs, Highly similar to SPLICING FACTOR U2AF 35 KD SUBUNIT [*Homo sapiens*] | | | gi = 2572829 | 1021219 |
| IC04192 | UG75 Expression | HOM | Mm.34830 | TITLE ESTs, Highly similar to MANNOSE-6-PHOSPHATE ISOMERASE [*Homo sapiens*] | | | gi = 4967613 | 1970816 |
| IC04193 | UG75 Expression | HOM | Mm.34832 | TITLE ESTs, Highly similar to CYTOSOL AMINOPEPTIDASE [*Bos taurus*] | | | gi = 1315624 | 352318 |
| IC04194 | UG75 Expression | HOM | Mm.34847 | TITLE ESTs, Highly similar to HYPOTHETICAL PROTEIN KIAA0144 [*H. sapiens*] | | | gi = 2694098 | 1125193 |
| IC04195 | UG75 Expression | HOM | Mm.34863 | TITLE ESTs, Highly similar to transcription factor AML2/CBFA3 [*M. musculus*] | | | gi = 4290137 | 576925 |
| IC04196 | UG75 Expression | HOM | Mm.34879 | TITLE ESTs, Highly similar to dJ52217.2 [*H. sapiens*] | | | gi = 2284265 | 920640 |
| IC04197 | UG75 Expression | HOM | Mm.35066 | TITLE ESTs, Highly similar to similar to C. elegans protein encoded in cosmid T20D3 [*H. sapiens*] | | | gi = 4729789 | 1970806 |
| IC04198 | UG75 Expression | HOM | Mm.35082 | TITLE ESTs, Highly similar to GLUTAMINASE, KIDNEY ISOFORM PRECURSOR [*Rattus norvegicus*] | | | gi = 4199858 | 573437 |
| IC04199 | UG75 Expression | HOM | Mm.35087 | TITLE ESTs, Highly similar to rA9 [*R. norvegicus*] | | | gi = 7195104 | 3155149 |
| IC04200 | UG75 Expression | HOM | Mm.35105 | TITLE ESTs, Highly similar to hSg11p [*H. sapiens*] | | | gi = 6638332 | 2331788 |
| IC04201 | UG75 Expression | HOM | Mm.35106 | TITLE ESTs, Highly similar to gene PP2A protein [*H. sapiens*] | | | gi = 4284140 | 574514 |
| IC04202 | UG76 LID366 B cell | HOM | Mm.35124 | TITLE ESTs, Highly similar to KIAA1017 protein [*H. sapiens*] | | | gi = 2517975 | 876794 |
| IC04203 | UG75 Expression | HOM | Mm.35139 | TITLE ESTs, Highly similar to putative hydrophobic domain in amino acid positions 373–390. [*H. sapiens*] | | | gi = 4408362 | 1264107 |
| IC04204 | UG75 Expression | HOM | Mm.35169 | TITLE ESTs, Highly similar to aiolos [*M. musculus*] | | | gi = 4482324 | 1263302 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04205 | UG75 Expression | HOM | Mm.35181 | TITLE ESTs, Highly similar to (defline not available 5823129) [M. musculus] | | | gi = 1772163 | 623064 |
| IC04206 | UG75 Expression | HOM | Mm.35193 | TITLE EST, Highly similar to dJ1100H13.1 [H. sapiens] | | | gi = 4482803 | 1264678 |
| IC04207 | UG75 Expression | HOM | Mm.35459 | | | | gi = 4281726 | 573518 |
| IC04208 | UG75 Expression | HOM | Mm.35481 | TITLE ESTs, Highly similar to HYPOTHETICAL PROTEIN KIAA0196 [H. sapiens] | | | gi = 2516793 | 2650870 |
| IC04209 | UG75 Expression | HOM | Mm.35491 | TITLE ESTs, Highly similar to KIAA0332 [H. sapiens] | | | gi = 6083840 | 1970205 |
| IC04210 | UG75 Expression | HOM | Mm.35508 | TITLE ESTs, Highly similar to LZTR-1 [H. sapiens] | | | gi = 1808323 | 641686 |
| IC04211 | UG75 Expression | HOM | Mm.35546 | TITLE ESTs, Highly similar to 60S RIBOSOMAL PROTEIN L21 [M. musculus] | | | gi = 1865590 | 671532 |
| IC04212 | UG75 Expression | HOM | Mm.35575 | TITLE ESTs, Highly similar to tulip 2 [R. norvegicus] | | | gi = 1671532 | 576910 |
| IC04213 | UG75 Expression | HOM | Mm.35590 | TITLE ESTs, Highly similar to T-CELL SURFACE GLYCOPROTEIN CD3 EPSILON CHAIN PRECURSOR [M. musculus] | | | gi = 1769392 | 634532 |
| IC04214 | UG75 Expression | HOM | Mm.35618 | TITLE ESTs, Highly similar to translation initiation factor IF2 [H. sapiens] | | | gi = 2308975 | 944355 |
| IC04215 | UG75 Expression | HOM | Mm.35659 | TITLE ESTs, Highly similar to ABC1 PROTEIN PRECURSOR [Saccharomyces cerevisiae] | | | gi = 1282476 | 332903 |
| IC04216 | UG75 Expression | HOM | Mm.35671 | TITLE ESTs, Highly similar to kinesin light chain 1 [M. musculus] | | | gi = 4402519 | 1096051 |
| IC04217 | UG75 Expression | HOM | Mm.35693 | TITLE ESTs, Highly similar to HYPOTHETICAL 19.7 KD PROTEIN IN SRB6-RIB5 INTERGENIC REGION [Saccharomyces cerevisiae] | | | gi = 5861229 | 2582473 |
| IC04218 | UG75 Expression | HOM | Mm.35698 | TITLE ESTs, Highly similar to nucleoporin Nup84 [R. norvegicus] | | | gi = 6515016 | 2582058 |
| IC04219 | UG75 Expression | HOM | Mm.3572 | PROTEIN S4, X ISOFORM [Homo sapiens; Rattus norvegicus; Mus musculus; Mesocricetus auratus; Felis cattus] | | | gi = 1494856 | 463697 |
| IC04220 | UG75 Expression | HOM | Mm.35753 | TITLE ESTs, Highly similar to KIAA0724 protein [H. sapiens] | | | gi = 2592728 | 1138949 |
| IC04221 | UG75 Expression | HOM | Mm.35779 | TITLE ESTs, Highly similar to TFIIIC2 subunit [H. sapiens] | | | gi = 3372027 | 1382866 |
| IC04222 | UG75 Expression | HOM | Mm.35787 | TITLE ESTs, Highly similar to KIAA0664 protein [H. sapiens] | | | gi = 1286937 | 329828 |
| IC04223 | UG75 Expression | HOM | Mm.35790 | TITLE ESTs, Highly similar to ENDOTHELIN-CONVERTING ENZYME 1 E-1) [Rattus norvegicus] | | | gi = 3387266 | 747316 |
| IC04224 | UG75 Expression | HOM | Mm.35798 | | | | gi = 1726791 | 603854 |
| IC04225 | UG75 Expression | HOM | Mm.35807 | TITLE ESTs, Highly similar to dJ1049G16.1 [H. sapiens] | | | gi = 6516356 | 2102153 |
| IC04226 | UG75 Expression | HOM | Mm.35812 | TITLE ESTs, Highly similar to 26S PROTEASOME REGULATORY SUBUNIT P31 [Homo sapiens] | | | gi = 1288413 | 331529 |
| IC04227 | UG75 Expression | HOM | Mm.35831 | TITLE ESTs, Highly similar to RSP5 PROTEIN [Saccharomyces cerevisiae] | | | gi = 2850623 | 1243928 |
| IC04228 | UG75 Expression | HOM | Mm.35838 | TITLE ESTs, Highly similar to vitamin D receptor-interacting protein [H. sapiens] | | | gi = 1486077 | |
| IC04229 | UG75 Expression | HOM | Mm.35849 | TITLE ESTs, Highly similar to CYTOCHROME B5 [Rattus norvegicus] | | | gi = 4061748 | 574265 |
| IC04230 | UG75 Expression | HOM | Mm.35975 | TITLE ESTs, Highly similar to STRESS-ACTIVATED PROTEIN KINASE JNK3 [M. musculus] | | | gi = 4299352 | 617250 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04231 | UG75 Expression | HOM | Mm.36036 | TITLE ESTs, Highly similar to matrin cyclophilin [R. norvegicus] | | | gi = 6638610 | 2332269 |
| IC04232 | UG75 Expression | HOM | Mm.36088 | TITLE ESTs, Highly similar to transcription factor IIE:SUBUNIT | | | gi = 4316539 | 1383399 |
| IC04233 | UG75 Expression | HOM | Mm.36235 | TITLE ESTs, Highly similar to Arnt [M. musculus] | | | gi = 4304882 | 642664 |
| IC04234 | UG75 Expression | HOM | Mm.36294 | TITLE ESTs, Highly similar to TBP-associated factor TAFII150 [H. sapiens] | | | gi = 4303656 | 641394 |
| IC04235 | UG75 Expression | HOM | Mm.36365 | TITLE ESTs, Highly similar to PAT1 [H. sapiens] | | | gi = 4730099 | 1970229 |
| IC04236 | UG75 Expression | HOM | Mm.36526 | TITLE ESTs, Highly similar to PLACENTAL THROMBIN INHIBITOR [Homo sapiens] | | | gi = 2404991 | 947505 |
| IC04237 | UG75 Expression | HOM | Mm.36569 | TITLE ESTs, Highly similar to PROBABLE UBIQUITIN CARBOXYL-TERMINAL HYDROLASE [Homo sapiens] | | | gi = 4537610 | 1920375 |
| IC04238 | UG75 Expression | HOM | Mm.36605 | TITLE ESTs, Highly similar to PUTATIVE SERINE/THREONINE-PROTEIN KINASE P78 [Homo sapiens] | | | gi = 4482826 | 1264809 |
| IC04239 | UG75 Expression | HOM | Mm.36721 | TITLE ESTs, Highly similar to AE-1 binding protein AEBP2 [M. musculus] | | | gi = 4571899 | 1148493 |
| IC04240 | UG75 Expression | HOM | Mm.36725 | TITLE ESTs, Highly similar to KIAA0095 gene is related to S. cerevisiae NIC96 gene. [H. sapiens] | | | gi = 2116302 | 806461 |
| IC04241 | UG75 Expression | HOM | Mm.3678 | TITLE ESTs, Highly similar to ALPHA-ACTININ 1, CYTOSKELETAL ISOFORM [Homo sapiens] | | | gi = 3681624 | 408265 |
| IC04242 | UG75 Expression | HOM | Mm.36810 | TITLE ESTs, Highly similar to CALCIUM/CALMODULIN DEPENDENT PROTEIN KINASE TYPE II GAMMA CHAIN [Rattus norvegicus] | | | gi = 2503075 | 1066794 |
| IC04243 | UG75 Expression | HOM | Mm.36811 | TITLE ESTs, Highly similar to PUTATIVE SERINE/THREONINE-PROTEIN KINASE A [Trypanosoma brucei brucei] | | | gi = 1474918 | 441501 |
| IC04244 | UG75 Expression | HOM | Mm.36817 | TITLE ESTs, Highly similar to MALATE OXIDOREDUCTASE [Homo sapiens] | | | gi = 1737937 | 614007 |
| IC04245 | UG75 Expression | HOM | Mm.36821 | TITLE ESTs, Highly similar to adenylate kinase isozyme 3 [M. musculus] | | | gi = 4404565 | 1037636 |
| IC04246 | UG75 Expression | HOM | Mm.37473 | TITLE ESTs, Highly similar to hPrp18 [H. sapiens] | | | gi = 5336745 | 1972395 |
| IC04247 | UG75 Expression | HOM | Mm.37486 | TITLE ESTs, Highly similar to CGI-04 protein [H. sapiens] | | | gi = 6632677 | 2811885 |
| IC04248 | UG75 Expression | HOM | Mm.37567 | TITLE ESTs, Highly similar to protein serine/threonine phosphatase 4 regulatory subunit 1 [H. sapiens] | | | gi = 1630331 | 493528 |
| IC04249 | UG75 Expression | HOM | Mm.3757 | TITLE ESTs, Highly similar to HYPOTHETICAL 272.0 KD PROTEIN C50C3.6 IN CHROMOSOME III [Caenorhabditis elegans] | | | gi = 1330774 | 354568 |
| IC04250 | UG75 Expression | HOM | Mm.37643 | TITLE ESTs, Highly similar to CAD PROTEIN [Mesocricetus auratus] | | | gi = 4258047 | 313716 |
| IC04251 | UG75 Expression 00/04/26 UG#76 17Lid Expansion | HOM | Mm.37660 | TITLE ESTs, Highly similar to KIAA0379 [H. sapiens] ESTs, Highly similar to 60S RIBOSOMAL PROTEIN L27A [M. musculus] | | | gi = 4613446 | 620903 |
| IC04252 | UG75 Expression | HOM | Mm.37755 | TITLE ESTs, Highly similar to BCL3 [M. musculus] | | | gi = 1407923 | 1148968 |
| IC04253 | UG75 Expression | HOM | Mm.37961 | TITLE ESTs, Highly similar to exportin t [H. sapiens] | | | gi = 4725133 | 637396 |
| IC04254 | UG75 Expression | HOM | Mm.37962 | TITLE ESTs, Highly similar to CASEIN KINASE I, GAMMA 3 ISOFORM [R. norvegicus] | | | gi = 2807997 | 1228151 |
| IC04255 | UG75 Expression | HOM | Mm.37980 | | | | gi = 6826454 | 736579 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04256 | UG75 Expression | HOM | Mm.38010 | TITLE ESTs, Highly similar to PHOSPHORIBOSYLAMINOIMIDAZOLE-CARBOXAMIDE FORMYLTRANSFERASE [Gallus gallus] | | | gi = 2990285 | 1277395 |
| IC04257 | UG75 Expression | HOM | Mm.38015 | TITLE ESTs, Highly similar to brefeldin A-inhibited guanine nucleotide-exchange protein 1 [H. sapiens] | | | gi = 3956214 | 1243836 |
| IC04258 | UG75 Expression | HOM | Mm.38020 | TITLE ESTs, Highly similar to (defline not available 5525078) [R. norvegicus] | | | gi = 1769063 | 642919 |
| IC04259 | UG75 Expression | HOM | Mm.3805 | TITLE ESTs, Highly similar to snRNA activating protein complex 50kD subunit [H. sapiens] | | | gi = 4257961 | 329883 |
| IC04260 | UG75 Expression | HOM | Mm.38145 | TITLE ESTs, Highly similar to R32184_3 [H. sapiens] [M. musculus] | | | gi = 2049415 | 749763 |
| IC04261 | UG75 Expression | HOM | Mm.38296 | | | | gi = 4290613 | 5**317 |
| IC04262 | UG75 Expression | HOM | Mm.38306 | TITLE ESTs, Highly similar to erythroblast macrophage protein EMP [H. sapiens] | | | gi = 1910803 | 763412 |
| IC04263 | UG75 Expression | HOM | Mm.38320 | TITLE EST, Highly similar to Desert hedgehog protein precursor [M. musculus] | | | gi = 4804713 | 639130 |
| IC04264 | UG75 Expression | HOM | Mm.38335 | TITLE ESTs, Highly similar to Rac GTPase-activating protein [M. musculus] | | | gi = 1793337 | 640147 |
| IC04265 | UG75 Expression | HOM | Mm.38341 | M. musculus] | | | gi = 2518702 | 2536667 |
| IC04266 | UG75 Expression | HOM | Mm.38363 | TITLE ESTs, Highly similar to REGULATORY FACTOR X-ASSOCIATED PROTEIN [H. sapiens] | | | gi = 1542097 | 420557 |
| IC04267 | UG75 Expression | HOM | Mm.38383 | TITLE ESTs, Highly similar to KIAA0546 protein [H. sapiens] | | | gi = 1755617 | 616806 |
| IC04268 | UG75 Expression | HOM | Mm.38412 | TITLE ESTs, Highly similar to CYP4B1 [M. musculus] | | | gi = 1769261 | 643059 |
| IC04269 | UG75 Expression | HOM | Mm.38444 | TITLE ESTs, Highly similar to M-PHASE INDUCER PHOSPHATASE 2 [Mus musculus] | | | gi = 1282475 | 332901 |
| IC04270 | UG75 Expression | HOM | Mm.38475 | TITLE ESTs, Highly similar to ATRIAL NATRIURETIC PEPTIDE CLEARANCE RECEPTOR PRECURSOR [Rattus norvegicus] | | | gi = 1682737 | 577167 |
| IC04271 | UG75 Expression | HOM | Mm.38490 | TITLE ESTs, Highly similar to ADP-ribosylation factor 1-directed GTPase activating protein [R. norvegicus] | | | gi = 6526276 | 2651259 |
| IC04272 | UG75 Expression | HOM | Mm.385 | TITLE ESTs, Highly similar to similar to human DNA-binding protein 5. [H. sapiens] | | | gi = 4296563 | 641008 |
| IC04273 | UG75 Expression | HOM | Mm.38505 | [H. sapiens] | | | gi = 6084182 | 949797 |
| IC04274 | UG75 Expression | HOM | Mm.38521 | [H. sapiens] | | | gi = 2966641 | 1095952 |
| IC04275 | UG75 Expression | HOM | Mm.3856 | TITLE ESTs, Highly similar to THYMIDYLATE KINASE [Homo sapiens] | | | gi = 5600190 | 616445 |
| IC04276 | UG75 Expression | HOM | Mm.38756 | TITLE ESTs, Highly similar to TRANSCRIPTIONAL ACTIVATOR GCN5 [Saccharomyces cerevisiae] | | | gi = 5125580 | 2076837 |
| IC04277 | UG75 Expression | HOM | Mm.38772 | TITLE ESTs, Highly similar to RETINOIC ACID RECEPTOR BETA [M. musculus] | | | gi = 5124727 | 2065364 |
| IC04278 | UG75 Expression | HOM | Mm.38803 | TITLE ESTs, Highly similar to MATERNAL PUMILIO PROTEIN [Drosophila melanogaster] FRUCTOSE-6-PHOSPHATE AMINOTRANSFERASE | | | gi = 6517190 | 2099752 |
| IC04279 | UG75 Expression | HOM | Mm.38852 | [M. musculus] | | | gi = 4058548 | 443380 |
| IC04280 | UG75 Expression | HOM | Mm.38854 | TITLE ESTs, Highly similar to Unknown gene product [H. sapiens] | | | gi = 6519053 | 2647758 |
| IC04281 | UG75 Expression | HOM | Mm.38873 | TITLE ESTs, Highly similar to terra [M. musculus] | | | gi = 3719903 | 1397429 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04282 | UG75 Expression | HOM | Mm.38892 | TITLE ESTs, Highly similar to p58 [R. norvegicus] | | | gi = 5334732 | 1923807 |
| IC04283 | UG76 LID366 B cell | HOM | Mm.38901 | TITLE ESTs, Highly similar to delta-6 fatty acid desaturase [M. musculus] | | | gi = 4725150 | 1382520 |
| IC04284 | UG75 Expression | HOM | Mm.38917 | INITIATION FACTOR TFIID 20/15 KD SUBUNITS [H. sapiens] | | | gi = 1681021 | 577863 |
| IC04285 | UG75 Expression | HOM | Mm.38930 | TITLE ESTs, Highly similar to KIAA0697 protein [H. sapiens] | | | gi = 5497911 | 1383737 |
| IC04286 | UG75 Expression | HOM | Mm.39024 | TITLE ESTs, Highly similar to ZINC FINGER PROTEIN 43 [Homo sapiens] | | | gi = 5598399 | 538942 |
| IC04287 | UG75 Expression | HOM | Mm.39072 | TITLE ESTs, Highly similar to PEPTIDYL-PROLYL CIS-TRANS ISOMERASE [Arabidopsis thaliana] | | | gi = 6077445 | 2236186 |
| IC04288 | UG75 Expression | HOM | Mm.39099 | TITLE ESTs, Highly similar to ZINC FINGER PROTEIN 91 [Homo sapiens] | | | gi = 4060533 | 583687 |
| IC04289 | UG75 Expression | HOM | Mm.39103 | TITLE ESTs, Highly similar to CELL SURFACE GLYCOPROTEIN MUC18 PRECURSOR [H. sapiens] | | | gi = 4767722 | 1497601 |
| IC04290 | UG75 Expression | HOM | Mm.39130 | TITLE ESTs, Highly similar to 40S RIBOSOMAL PROTEIN S10 [Homo sapiens] | | | gi = 1287857 | 318449 |
| IC04291 | UG75 Expression | HOM | Mm.39286 | TITLE ESTs, Highly similar to cleavage stimulation factor 77K chain [H. sapiens] | | | gi = 4434517 | 790813 |
| IC04292 | UG75 Expression | HOM | Mm.39472 | TITLE ESTs, Highly similar to FARNESYL PYROPHOSPHATE SYNTHETASE [Rattus norvegicus] | | | gi = 1509395 | 472349 |
| IC04293 | UG75 Expression | HOM | Mm.39473 | TITLE ESTs, Highly similar to PTERIN-4-ALPHA-CARBINOLAMINE DEHYDRATASE [Homo sapiens; Rattus norvegicus; Mus musculus] | | | gi = 1934446 | 749012 |
| IC04294 | UG75 Expression | HOM | Mm.39999 | TITLE ESTs, Highly similar to similar to tumor suppressor p33ING1 [H. sapiens] | | | gi = 2308320 | 959853 |
| IC04295 | UG75 Expression | HOM | Mm.400 | TITLE ESTs, Highly similar to CYTOCHROME C OXIDASE POLYPEPTIDE VIB [Bos taurus] | | | gi = 1375513 | 388501 |
| IC04296 | UG76 LID366 B cell | HOM | Mm.40120 | TITLE ESTs, Highly similar to MLN 51 [H. sapiens] | | | gi = 7066630 | 2748990 |
| IC04297 | UG75 Expression | HOM | Mm.40307 | TITLE ESTs, Highly similar to HYPOTHETICAL MYELOID CELL LINE PROTEIN 5 [Homo sapiens] | | | gi = 5600208 | 616679 |
| IC04298 | UG75 Expression | HOM | Mm.40350 | TITLE ESTs, Highly similar to METAXIN [M. musculus] | | | gi = 4623943 | 790145 |
| IC04299 | UG75 Expression | HOM | Mm.4050 | TITLE ESTs, Highly similar to small zinc finger-like protein [M. musculus] | | | gi = 5498113 | 874600 |
| IC04300 | UG75 Expression | HOM | Mm.40664 | TITLE ESTs, Highly similar to HYPOTHETICAL 103.6 [H. sapiens] | | | gi = 1756453 | 617911 |
| IC04301 | UG75 Expression | HOM | Mm.41003 | KD PROTEIN IN COX5B-PFK26 INTERGENIC REGION [Saccharomyces cerevisiae] | | | gi = 1554961 | 477730 |
| IC04302 | UG75 Expression | HOM | Mm.41063 | TITLE ESTs, Highly similar to TIF1 protein [M. musculus] | | | gi = 6558051 | 2654994 |
| IC04303 | UG75 Expression | HOM | Mm.41072 | TITLE ESTs, Highly similar to ARACHIDONATE 5-LIPOXYGENASE [M. musculus] | | | gi = 2560721 | 1121463 |
| IC04304 | UG75 Expression | HOM | Mm.41091 | TITLE ESTs, Highly similar to MYLE protein [M. musculus] | | | gi = 6939081 | 2922164 |
| IC04305 | UG75 Expression | HOM | Mm.41124 | TITLE ESTs, Highly similar to transcription factor TFE3 [H. sapiens] | | | gi = 2956168 | 1263731 |
| IC04306 | UG75 Expression | HOM | Mm.4113 | TITLE ESTs, Highly similar to POLY(A) + RNA EXPORT PROTEIN [Schizosaccharomyces pombe] | | | gi = 4061797 | 576512 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04307 | UG75 Expression | HOM | Mm.41139 | TITLE ESTs, Highly similar to INTERLEUKIN ENHANCER-BINDING FACTOR [Homo sapiens] | | | gi = 1481267 | 445576 |
| IC04308 | UG75 Expression | HOM | Mm.41145 | TITLE ESTs, Highly similar to KIAA0483 protein [H. sapiens] | | | gi = 54 98096 | 849539 |
| IC04309 | UG75 Expression | HOM | Mm.41166 | TITLE ESTs, Highly similar to RRP5 PROTEIN HOMOLOG [H. sapiens] | | | gi = 2283272 | 949621 |
| IC04310 | UG75 Expression | HOM | Mm.41224 | TITLE ESTs, Highly similar to GTPASE-ACTIVATING PROTEIN [Homo sapiens] | | | gi = 2990942 | 1265070 |
| IC04311 | UG75 Expression | HOM | Mm.41236 | TITLE ESTs, Highly similar to LACTOPEROXIDASE [Homo sapiens] | | | gi = 5598201 | 522902 |
| IC04312 | UG75 Expression | HOM | Mm.41254 | TITLE ESTs, Highly similar to hypothetical protein [H. sapiens] | | | gi = 2573465 | 821119 |
| IC04313 | UG75 Expression | HOM | Mm.41297 | TITLE ESTs, Highly similar to db83 [R. norvegicus] | | | gi = 4029452 | 1908004 |
| IC04314 | UG75 Expression | HOM | Mm.41300 | TITLE ESTs, Highly similar to PEROXISOMAL ASSEMBLY PROTEIN PEX3 [H. sapiens] | | | gi = 1701422 | 577740 |
| IC04315 | UG75 Expression | HOM | Mm.41373 | GLYCOPROTEIN GP210 PRECURSOR [Rattus norvegicus] | | | gi = 1676398 | 573636 |
| IC04316 | UG75 Expression | HOM | Mm.41380 | TITLE ESTs, Highly similar to DIACYLGLYCEROL KINASE, ZETA [R. norvegicus] | | | gi = 4032127 | 1853263 |
| IC04317 | UG75 Expression | HOM | Mm.41443 | TITLE ESTs, Highly similar to KIAA0782 protein [H. sapiens] | | | gi = 2591287 | 1138997 |
| IC04318 | UG75 Expression | HOM | Mm.41448 | taurus] | | | gi = 4256700 | 349463 |
| IC04319 | UG75 Expression | HOM | Mm.41453 | [H. sapiens] | | | gi = 1375963 | 388895 |
| IC04320 | UG75 Expression | HOM | Mm.41462 | [R. norvegicus] | | | gi = 2461859 | 1066707 |
| IC04321 | UG75 Expression | HOM | Mm.41494 | TITLE ESTs, Highly similar to ribonuclease P protein subunit p20 [H. sapiens] | | | gi = 1553652 | 482012 |
| IC04322 | UG75 Expression | HOM | Mm.41502 | TITLE ESTs, Highly similar to FUMARATE HYDRATASE, MITOCHONDRIAL PRECURSOR [Homo sapiens] | | | gi = 1288374 | 1152776 |
| IC04323 | UG75 Expression | HOM | Mm.41503 | TITLE ESTs, Highly similar to inner centromere protein INCENP [M. musculus] | | | gi = 2990803 | 1264932 |
| IC04324 | UG75 Expression | HOM | Mm.41504 | TITLE ESTs, Highly similar to putative dimethyladenosine transferase [H. sapiens] | | | gi = 2074148 | 779700 |
| IC04325 | UG75 Expression | HOM | Mm.41525 | TITLE ESTs, Highly similar to GAS41 protein [H. sapiens] | | | gi = 5335952 | 2087983 |
| IC04326 | UG75 Expression | HOM | Mm.41536 | TITLE ESTs, Highly similar to PUFF SPECIFIC PROTEIN BX42 [Drosophila melanogaster] | | | gi = 4967808 | 2352761 |
| IC04327 | UG75 Expression | HOM | Mm.41544 | TITLE ESTs, Highly similar to (defline not available 6118541) [M. musculus] | | | gi = 4032519 | 1853383 |
| IC04328 | UG75 Expression | HOM | Mm.41553 | TITLE ESTs, Highly similar to similar to yeast Sec6p, Swiss-Prot Accession Number P32844 [R. norvegicus] | | | gi = 1290287 | 333355 |
| IC04329 | UG75 Expression | HOM | Mm.41555 | TITLE ESTs, Highly similar to RAS-RELATED PROTEIN RAB-11A [Homo sapiens; Rattus norvegicus; Canis familiaris; Oryctolagus cuniculus] | | | gi = 6645314 | 2749219 |
| IC04330 | UG75 Expression | HOM | Mm.41562 | TITLE ESTs, Highly similar to KIAA0116 [H. sapiens] | | | gi = 4768072 | 1495743 |
| IC04331 | UG75 Expression | HOM | Mm.41591 | TITLE ESTs, Highly similar to N4-(BETA-N-ACETYLGLUCOSAMINYL)-L-ASPARAGINASE PRECURSOR [M. musculus] | | | gi = 6008477 | 1401086 |
| IC04332 | UG75 Expression | HOM | Mm.41594 | TITLE ESTs, Highly similar to hypothetical protein [H. sapiens] | | | gi = 1793461 | 1106410 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04333 | UG75 Expression | HOM | Mm.41622 | TITLE ESTs, Highly similar to HYPOTHETICAL 47.4 KD PROTEIN IN PAS1-MST1 INTERGENIC REGION [Saccharomyces cerevisiae] | | | gi = 3164755 | 368546 |
| IC04334 | UG75 Expression | HOM | Mm.41637 | TITLE ESTs, Highly similar to ARFAPTIN 2 [H. sapiens] | | | gi = 6084611 | 2648132 |
| IC04335 | UG75 Expression | HOM | Mm.41673 | TITLE ESTs, Highly similar to (deffine not available 6119709) [R. norvegicus] | | | gi = 1793005 | 640093 |
| IC04336 | UG75 Expression | HOM | Mm.41680 | TITLE ESTs, Highly similar to HSPC003 [H. sapiens] | | | gi = 6645215 | 681056 |
| IC04337 | UG75 Expression | HOM | Mm.41684 | TITLE ESTs, Highly similar to TRANSLOCATION PROTEIN SEC62 [Saccharomyces cerevisiae] | | | gi = 4434484 | 1922564 |
| IC04338 | UG75 Expression | HOM | Mm.41705 | TITLE ESTs, Highly similar to protein arginine methyltransferase [M. musculus] | | | gi = 6638627 | 2332293 |
| IC04339 | UG75 Expression | HOM | Mm.41775 | TITLE ESTs, Highly similar to HYPOTHETICAL 35.9 KD PROTEIN IN VPS27-CSE2 INTERGENIC REGION [Saccharomyces cerevisiae] | | | gi = 6824440 | 596665 |
| IC04340 | UG75 Expression | HOM | Mm.41782 | TITLE ESTs, Highly similar to KIAA0670 protein [H. sapiens] | | | gi = 2288495 | 949376 |
| IC04341 | UG75 Expression | HOM | Mm.41785 | TITLE ESTs, Highly similar to FGF-1 intracellular binding protein [H. sapiens] | | | gi = 1504805 | 466266 |
| IC04342 | UG75 Expression | HOM | Mm.41787 | TITLE ESTs, Highly similar to NUCLEOSIDE DIPHOSPHATE KINASE [Ginglymostoma cirratum] | | | gi = 5598031 | 480596 |
| IC04343 | UG75 Expression | HOM | Mm.41791 | TITLE ESTs, Highly similar to MEMBRANE GLYCOPROTEIN M6-B [Mus musculus] | | | gi = 6083931 | 2225324 |
| IC04344 | UG75 Expression | HOM | Mm.41803 | TITLE ESTs, Highly similar to HYPOTHETICAL 64.3 KD GTP-BINDING PROTEIN C02F5.3 IN CHROMOSOME III [Caenorhabditis elegans] | | | gi = 3862820 | 1889668 |
| IC04345 | UG75 Expression | HOM | Mm.41840 | TITLE ESTs, Highly similar to CALCINEURIN B SUBUNIT ISOFORM 1 [Homo sapiens; Bos taurus; Rattus norvegicus] | | | gi = 5336769 | 1972427 |
| IC04346 | UG75 Expression | HOM | Mm.41880 | TITLE ESTs, Highly similar to ZINC FINGER PROTEIN 46 [Homo sapiens] | | | gi = 1808554 | 641907 |
| IC04347 | UG75 Expression | HOM | Mm.41881 | TITLE ESTs, Highly similar to B-MYC TRANSFORMING PROTEIN [Rattus norvegicus] | | | gi = 2306035 | 948905 |
| IC04348 | UG75 Expression | HOM | Mm.41906 | TITLE ESTs, Highly similar to PTDO14 [H. sapiens] | | | gi = 2813422 | 1067427 |
| IC04349 | UG75 Expression | HOM | Mm.41920 | TITLE ESTs, Highly similar to BETA-ADAPTIN [Homo sapiens; Rattus norvegicus; Bos taurus] | | | gi = 6574369 | 2810963 |
| IC04350 | UG75 Expression | HOM | Mm.41926 | TITLE ESTs, Highly similar to NADH-UBIQUINONE OXIDOREDUCTASE MLRQ SUBUNIT [Bos taurus] | | | gi = 1326560 | 329556 |
| IC04351 | UG75 Expression | HOM | Mm.41936 | TITLE ESTs, Highly similar to N-TERMINAL ACETYLTRANSFERASE COMPLEX ARD1 SUBUNIT HOMOLOG [Leishmania donovani] | | | gi = 1772175 | 623091 |
| IC04352 | UG76 Expression | HOM | Mm.41938 | TITLE ESTs, Highly similar to ADENYLATE CYCLASE, OLFACTIVE TYPE [Rattus norvegicus] | | | gi = 1504509 | 465502 |
| IC04353 | UG75 Expression | HOM | Mm.42187 | TITLE ESTs, Highly similar to probable nocturnin protein [M. musculus] | | | gi = 2333088 | 962917 |
| IC04354 | UG75 Expression | HOM | Mm.42235 | TITLE ESTs, Highly similar to STEFIN 3 [Mus musculus] | | | gi = 1310021 | 348039 |
| IC04355 | UG75 Expression | HOM | Mm.42275 | TITLE ESTs, Highly similar to 3-KETOACYL-COA THIOLASE PEROXISOMAL B PRECURSOR [Rattus norvegicus] | | | gi = 4444538 | 1889883 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04356 | UG75 Expression | HOM | Mm.4230 | TITLE ESTs, Highly similar to (defline not available 6014491) [M. musculus] | | | gi = 2306135 | 944444 |
| IC04357 | UG75 Expression | HOM | Mm.42805 | TITLE ESTs, Highly similar to NADH-UBIQUINONE OXIDOREDUCTASE 15 KD SUBUNIT [Bos taurus] | | | gi = 2065594 | 807003 |
| IC04358 | UG75 Expression | HOM | Mm.43040 | TITLE ESTs, Highly similar to HYPOTHETICAL PROTEIN KIAA0079 [H. sapiens] | | | gi = 2812032 | 1248249 |
| IC04359 | UG75 Expression | HOM | Mm.43152 | TITLE ESTs, Highly similar to unknown [H. sapiens] | | | gi = 6167954 | 2247629 |
| IC04360 | UG75 Expression | HOM | Mm.43157 | TITLE ESTs, Highly similar to KIAA0824 protein [H. sapiens] | | | gi = 1825876 | 722280 |
| IC04361 | UG75 Expression | HOM | Mm.43162 | CYTOCHROME C REDUCTASE COMPLEX 6.4 KD PROTEIN [Bos taurus] | | | gi = 6084651 | 681258 |
| IC04362 | UG75 Expression | HOM | Mm.43167 | TITLE ESTs, Highly similar to TUBULIN GAMMA CHAIN [Homo sapiens] | | | gi = 4967436 | 1347324 |
| IC04363 | UG75 Expression | HOM | Mm.43212 | TITLE ESTs, Highly similar to KIAA0033 [H. sapiens] | | | gi = 5750007 | 2158899 |
| IC04364 | UG75 Expression | HOM | Mm.43213 | TITLE ESTs, Highly similar to PTB-ASSOCIATED SPLICING FACTOR [Homo sapiens] | | | gi = 3862802 | 1889652 |
| IC04365 | UG75 Expression | HOM | Mm.43309 | TITLE ESTs, Highly similar to immunoglobulin kappa-chain [M. musculus] | | | gi = 6757823 | 2648491 |
| IC04366 | UG75 Expression | HOM | Mm.43487 | TITLE ESTs, Highly similar to HYPOTHETICAL 64.5 KD PROTEIN ZK652.9 IN CHROMOSOME III [Caenorhabditis elegans] | | | gi = 2859080 | 1054877 |
| IC04367 | UG75 Expression | HOM | Mm.43681 | TITLE ESTs, Highly similar to RABPHILIN-3A [Rattus norvegicus] | | | gi = 1318141 | 335420 |
| IC04368 | UG75 Expression | HOM | Mm.43749 | TITLE ESTs, Highly similar to PROBABLE 60S RIBOSOMAL PROTEIN L14EB [Saccharomyces cerevisiae] | | | gi = 1497232 | 464761 |
| IC04369 | UG75 Expression | HOM | Mm.43765 | TITLE ESTs, Highly similar to N2,N2-DIMETHYLGUANOSINE TRNA METHYLTRANS-FERASE PRECURSOR [Saccharomyces cerevisiae] | | | gi = 3517954 | 1885638 |
| IC04370 | UG75 Expression | HOM | Mm.43784 | TITLE ESTs, Highly similar to HYPOTHETICAL 23.3 KD PROTEIN ZK688.3 IN CHROMOSOME III [Caenorhabditis elegans] | | | gi = 6084075 | 3025707 |
| IC04371 | UG75 Expression | HOM | Mm.43822 | TITLE ESTs, Highly similar to CITRATE SYNTHASE, MITOCHONDRIAL PRECURSOR [Sus scrofa] | | | gi = 4061757 | 574603 |
| IC04372 | UG75 Expression | HOM | Mm.44089 | TITLE ESTs, Highly similar to KIAA0453 protein [H. sapiens] | | | gi = 5338112 | 2064713 |
| IC04373 | UG75 Expression | HOM | Mm.44106 | TITLE ESTs, Highly similar to ERYTHROCYTE ADDU-CIN BETA SUBUNIT [Homo sapiens] | | | gi = 6084297 | 2064851 |
| IC04374 | UG75 Expression | HOM | Mm.44151 | TITLE ESTs, Highly similar to transcriptional co-activator CRSP77 [H. sapiens] | | | gi = 3374999 | 1383519 |
| IC04375 | UG75 Expression | HOM | Mm.44199 | TITLE ESTs, Highly similar to RIBOSE-PHOSPHATE PYROPHOSPHOKINASE I [Homo sapiens; Rattus norvegicus] | | | gi = 2402843 | 975422 |
| IC04376 | UG75 Expression | HOM | Mm.44202 | TITLE ESTs, Highly similar to unknown [R. norvegicus] | | | gi = 3164584 | 750600 |
| IC04377 | UG75 Expression | HOM | Mm.44219 | TITLE ESTs, Highly similar to PUTATIVE ATP-DEPENDENT RNA HELICASE C1F7.02C [Schizosaccharomyces pombe] | | | gi = 6519407 | 2582151 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04378 | UG75 Expression | HOM | Mm.44220 | TITLE ESTs, Highly similar to (defline not available 6014636) [M. musculus] | | | gi = 1702714 | 586043 |
| IC04379 | UG75 Expression | HOM | Mm.44240 | TITLE ESTs, Highly similar to ATP SYNTHASE SUBUNITS REGION ORF 3 [Rhodobacter blastica] | | | gi = 1282457 | 332828 |
| IC04380 | UG75 Expression | HOM | Mm.4428 | TITLE ESTs, Highly similar to P52rIPK [H. sapiens] | | | gi = 1724628 | 581932 |
| IC04381 | UG75 Expression | HOM | Mm.4436 | TITLE ESTs, Highly similar to RAS-RELATED PROTEIN RAP-1A [Homo sapiens; Rattus norvegicus; Bos taurus] | | | gi = 2813527 | 1068037 |
| IC04382 | UG75 Expression | HOM | Mm.44706 | TITLE ESTs, Highly similar to ZINC FINGER PROTEIN 43 [Homo sapiens] | | | gi = 2256856 | 894269 |
| IC04383 | UG75 Expression | HOM | Mm.44713 | TITLE ESTs, Highly similar to myotubularin homologous protein 2 [M. musculus] | | | gi = 1889527 | 720086 |
| IC04384 | UG75 Expression | HOM | Mm.45116 | TITLE ESTs, Highly similar to ADA3-like protein [H. sapiens] | | | gi = 5819650 | 2182439 |
| IC04385 | UG75 Expression | HOM | Mm.45141 | TITLE ESTs, Highly similar to CLEAVAGE AND POLYADENYLATION SPECIFICITY FACTOR, 160 KD SUBUNIT [H. sapiens] | | | gi = 6514423 | 2646918 |
| IC04386 | UG75 Expression | HOM | Mm.45169 | TITLE ESTs, Highly similar to dJ633O20.1 [H. sapiens] | | | gi = 2283509 | 1345072 |
| IC04387 | UG75 Expression | HOM | Mm.45193 | TITLE ESTs, Highly similar to KIAA0851 protein [H. sapiens] | | | gi = 4967794 | 2270389 |
| IC04388 | UG75 Expression | HOM | Mm.45214 | TITLE ESTs, Highly similar to KIAA0851 protein [H. sapiens] | | | gi = 5910850 | 2802745 |
| IC04389 | UG75 Expression | HOM | Mm.45215 | TITLE ESTs, Highly similar to similar to human transcription factor TFIIS [H. sapiens] | | | gi = 6520327 | 2645568 |
| IC04390 | UG75 Expression | HOM | Mm.4532 | TITLE ESTs, Highly similar to hypothetical protein [H. sapiens] | | | gi = 4297304 | 350400 |
| IC04391 | UG75 Expression | HOM | Mm.4537 | TITLE ESTs, Highly similar to NADH-UBIQUINONE OXIDOREDUCTASE B22 SUBUNIT [Bos taurus] | | | gi = 1309560 | 337487 |
| IC04392 | UG75 Expression | HOM | Mm.45428 | TITLE ESTs, Highly similar to GUANINE NUCLEOTIDE-BINDING PROTEIN G(K), ALPHA SUBUNIT [Rattus norvegicus] | | | gi = 4407211 | 457323 |
| IC04393 | UG75 Expression | HOM | Mm.45516 | TITLE ESTs, Highly similar to hypothetical protein [H. sapiens] | | | gi = 1748800 | 618599 |
| IC04394 | UG75 Expression | HOM | Mm.45558 | TITLE ESTs, Highly similar to INTERFERON-INDUCED 35 KD PROTEIN [Homo sapiens] | | | gi = 4199625 | 582121 |
| IC04395 | UG75 Expression | HOM | Mm.45591 | TITLE ESTs, Highly similar to unnamed protein product [H. sapiens] | | | gi = 2256813 | 893892 |
| IC04396 | UG75 Expression | HOM | Mm.45609 | TITLE ESTs, Highly similar to Wip1 [H. sapiens] | | | gi = 1684094 | 575460 |
| IC04397 | UG75 Expression | HOM | Mm.45762 | TITLE ESTs, Highly similar to PUTATIVE STEROID DEHYDROGENASE KIK-I [M. musculus] | | | gi = 4571740 | 1149721 |
| IC04398 | UG75 Expression | HOM | Mm.45815 | TITLE ESTs, Highly similar to (defline not available 5823528) [M. musculus] | | | gi = 1713756 | 597550 |
| IC04399 | UG75 Expression | HOM | Mm.46014 | TITLE ESTs, Highly similar to APICAL PROTEIN [Xenopus laevis] | | | gi = 4316439 | 1383331 |
| IC04400 | UG75 Expression | HOM | Mm.46025 | TITLE ESTs, Highly similar to Unknown [H. sapiens] | | | gi = 2720321 | 1166816 |
| IC04401 | UG75 Expression | HOM | Mm.46047 | TITLE ESTs, Highly similar to hGCN5 [H. sapiens] | | | gi = 2962457 | 1265540 |
| IC04402 | UG75 Expression | HOM | Mm.4609 | TITLE ESTs, Highly similar to (defline not available 6165614) [M. musculus] | | | gi = 6631404 | 2811326 |
| IC04403 | UG75 Expression | HOM | Mm.46229 | TITLE ESTs, Highly similar to hypothetical protein [H. sapiens] | | | gi = 1325609 | 353310 |
| IC04404 | UG75 Expression | HOM | Mm.46316 | TITLE ESTs, Highly similar to LEUKOCYTE ELASTASE INHIBITOR [Homo sapiens] | | | gi = 4199873 | 596977 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04405 | UG75 Expression | HOM | Mm.46359 | TITLE ESTs, Highly similar to growth factor-responsive protein, vascular smooth muscle [R. norvegicus] | | | gi = 1840675 | 1293718 |
| IC04406 | UG76 LID366 B cell | HOM | Mm.46374 | TITLE ESTs, Highly similar to UBIQUITIN-CONJUGATING ENZYME E2-17 KD 2 [M. musculus] | | | gi = 2232951 | 390625 |
| IC04407 | UG75 Expression | HOM | Mm.464 | TITLE ESTs, Highly similar to HYPOTHETICAL PROTEIN KIAA0103 [H. sapiens] | | | gi = 2306089 | 949307 |
| IC04408 | UG75 Expression | HOM | Mm.46401 | TITLE ESTs, Highly similar to GUANINE NUCLEOTIDE-BINDING PROTEIN BETA SUBUNIT-LIKE PROTEIN 12.3 [Homo sapiens; Mus musculus; Rattus norvegicus; Sus scrofa; Gallus gallus] | | | gi = 1566560 | 532984 |
| IC04409 | UG75 Expression | HOM | Mm.46507 | TITLE ESTs, Highly similar to snRNA activating protein complex 50kD subunit [H. sapiens] | | | gi = 2521307 | 621639 |
| IC04410 | UG75 Expression | HOM | Mm.46533 | TITLE ESTs, Highly similar to CGI-20 protein [H. sapiens] | | | gi = 2041986 | 569370 |
| IC04411 | UG75 Expression | HOM | Mm.46612 | TITLE ESTs, Highly similar to (define not available 6063101) [M. musculus] | | | gi = 6076954 | 2225530 |
| IC04412 | UG75 Expression | HOM | Mm.46613 | TITLE ESTs, Highly similar to protein phosphatase 2A subunit B'-beta [M. musculus] | | | gi = 6077710 | 2236401 |
| IC04413 | UG75 Expression | HOM | Mm.46623 | TITLE ESTs, Highly similar to mm-Mago [M. musculus] | | | gi = 2284557 | 932847 |
| IC04414 | UG75 Expression | HOM | Mm.46676 | TITLE ESTs, Highly similar to Sec22 homolog [R. norvegicus] | | | gi = 2811708 | 1225748 |
| IC04415 | UG75 Expression | HOM | Mm.46690 | TITLE ESTs, Highly similar to 5-aminoimidazole-4-carboxamide ribonucleotide formyltransferase/IMP cyclohydrolase [R. norvegicus] | | | gi = 4571136 | 894493 |
| IC04416 | UG75 Expression | HOM | Mm.46722 | TITLE ESTs, Highly similar to CGI-13 protein [H. sapiens] | | | gi = 1701243 | 596433 |
| IC04417 | UG75 Expression | HOM | Mm.46773 | TITLE ESTs Highly similar to (define not available 6006817) [M. musculus] | | | gi = 4434767 | 2803804 |
| IC04418 | UG75 Expression | HOM | Mm.46774 | TITLE ESTs, Highly similar to KIAA0523 protein [H. sapiens] HYDRATASE, MITOCHONDRIAL [Caenorhabditis elegans] | | | gi = 2891373 | 1226693 |
| IC04419 | UG75 Expression | HOM | Mm.46775 | TITLE ESTs, Highly similar to Rer1 protein [H. sapiens] | | | gi = 6077872 | 2192651 |
| IC04420 | UG75 Expression | HOM | Mm.4859 | TITLE ESTs, Highly similar to cyclin K [M. musculus] | | | gi = 1282046 | 331677 |
| IC04421 | UG75 Expression | HOM | Mm.5202 | TITLE ESTs, Highly similar to HYPOTHETICAL 37.7 KD PROTEIN C06B11.7 IN CHROMOSOME II [Caenorhabditis elegans] | | | gi = 2956439 | 1282194 |
| IC04422 | UG75 Expression | HOM | Mm.52067 | | | | gi = 2523889 | 978183 |
| IC04423 | UG75 Expression | HOM | Mm.52258 | TITLE ESTs, Highly similar to NON-MUSCLE CALDESMON [R. norvegicus] | | | gi = 5125074 | 2065392 |
| IC04424 | UG75 Expression | HOM | Mm.5285 | TITLE ESTs, Highly similar to KIAA0871 protein [H. sapiens] | | | gi = 4286040 | 614648 |
| IC04425 | UG75 Expression | HOM | Mm.5399 | TITLE ESTs, Highly similar to ENV POLYPROTEIN PRECURSOR [Gibbon leukemia virus] | | | gi = 1671623 | 539102 |
| IC04426 | UG75 Expression | HOM | Mm.55078 | TITLE EST, Highly similar to (define not available 5453324) [M. musculus] | | | gi = 4721227 | 1224878 |
| IC04427 | UG75 Expression | HOM | Mm.55679 | TITLE ESTs, Highly similar to similar to calcium-independent phospholipase A2 [H. sapiens] | | | gi = 3054953 | 1328521 |
| IC04428 | UG75 Expression | HOM | Mm.56 | TITLE ESTs, Highly similar to down syndrome candidate region 1 [H. sapiens] | | | gi = 4783388 | 2065207 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04429 | UG75 Expression | HOM | Mm.5612 | TITLE ESTs, Highly similar to EUKARYOTIC INITIATION FACTOR 4B [*Homo sapiens*] | | | gi = 1309698 | 337882 |
| IC04430 | UG75 Expression | HOM | Mm.5624 | TITLE ESTs, Highly similar to PRE-MRNA SPLICING FACTOR RNA HELICASE PRP22 [*Saccharomyces cerevisiae*] | | | gi = 2306593 | 944332 |
| IC04431 | UG75 Expression | HOM | Mm.56685 | TITLE ESTs, Highly similar to RAS GTPASE-ACTIVATING-LIKE PROTEIN IQGAP1 [*Homo sapiens*] | | | gi = 3067125 | 1293652 |
| IC04432 | UG75 Expression | HOM | Mm.5772 | TITLE ESTs, Highly similar to NEDD-4 PROTEIN (Homo sapiens] | | | gi = 4434422 | 596719 |
| IC04433 | UG75 Expression | HOM | Mm.5875 | TITLE ESTs, Highly similar to MAST CELL PROTEASE 7 PRECURSOR [*Mus musculus*] | | | gi = 6077679 | 2236457 |
| IC04434 | UG75 Expression | HOM | Mm.59020 | TITLE ESTs, Highly similar to p71 [*R. norvegicus*] | | | gi = 1726551 | 599123 |
| IC04435 | UG75 Expression | HOM | Mm.5934 | TITLE ESTs, Highly similar to N-TERMINAL ACETYLTRANSFERASE COMPLEX ARD1 SUBUNIT HOMOLOG [*Homo sapiens*] | | | gi = 6638394 | 2331861 |
| IC04436 | UG75 Expression | HOM | Mm.5938 | TITLE ESTs, Highly similar to MYOSIN HEAVY CHAIN, NONMUSCLE [*Gallus gallus*] | | | gi = 2307726 | 945432 |
| IC04437 | UG75 Expression | HOM | Mm.5999 | TITLE ESTs, Highly similar to ETn insert [*M. musculus*] | | | gi = 4444645 | 574844 |
| IC04438 | UG75 Expression | HOM | Mm.6118 | TITLE ESTs, Highly similar to HYPOTHETICAL PROTEIN KIAA0064 [*H. sapiens*] | | | gi = 5338302 | 2064944 |
| IC04439 | UG76 LID366 B cell | HOM | Mm.63466 | TITLE ESTs, Highly similar to Unknown gene product [*H. sapiens*] | | | gi = 3718988 | 1299290 |
| IC04440 | UG75 Expression | HOM | Mm.63500 | TITLE ESTs, Highly similar to KIAA0467 protein [*H. sapiens*] | | | gi = 2259109 | 905059 |
| IC04441 | UG75 Expression | HOM | Mm.63522 | TITLE ESTs, Highly similar to KIAA0467 protein [*H. sapiens*] | | | gi = 4614854 | 314800 |
| IC04442 | UG75 Expression | HOM | Mm.6478 | TITLE ESTs, Highly similar to protein associated with Myc [*H. sapiens*] | | | gi = 1757206 | 620050 |
| IC04443 | UG75 Expression | HOM | Mm.64889 | TITLE ESTs, Highly similar to KIAA0371 [*H. sapiens*] | | | gi = 6084803 | 949321 |
| IC04444 | UG75 Expression | HOM | Mm.6586 | TITLE ESTs, Highly similar to RIBONUCLEASE INHIBITOR [*Rattus norvegicus*] | | | gi = 4434614 | 1921266 |
| IC04445 | UG75 Expression | HOM | Mm.68976 | TITLE ESTs, Highly similar to KIAA0354 [*H. sapiens*] IMPORT RECEPTOR SUBUNIT TOM20 HOMOLOG [*R. norvegicus*] | | | gi = 2248925 | 891456 |
| IC04446 | UG75 Expression | HOM | Mm.6932 | TITLE ESTs, Highly similar to HPV16 E1 protein binding protein [*H. sapiens*] | | | gi = 1310466 | 349830 |
| IC04447 | UG75 Expression | HOM | Mm.6960 | TITLE EST, Highly similar to anticoagulant protein C [*M. Musculus*] | | | gi = 2521099 | 1226752 |
| IC04448 | UG75 Expression | HOM | Mm.70189 | TITLE ESTs, Highly similar to putative mitochondrial outer membrane protein import receptor [*H. sapiens*] | | | gi = 5251135 | 314450 |
| IC04449 | UG75 Expression | HOM | Mm.7039 | TITLE ESTs, Highly similar to TRANSLOCON-ASSOCIATED PROTEIN, BETA SUBUNIT PRECURSOR [*Homo sapiens*] | | | gi = 5907783 | 2803209 |
| IC04450 | UG75 Expression | HOM | Mm.7091 | TITLE ESTs, Highly similar to methyl-CpG binding protein [*M. musculus*] | | | gi = 1316194 | 318800 |
| IC04451 | UG75 Expression | HOM | Mm.7142 | TITLE ESTs, Highly similar to AMINOACYLASE-1 [*Homo sapiens*] | | | gi = 1727083 | 540263 |
| IC04452 | UG75 Expression | HOM | Mm.7165 | | | | gi = 4056724 | 337367 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04453 | UG75 Expression | HOM | Mm.7261 | TITLE ESTs, Highly similar to unknown protein CIT987SK_2A8_1 [*H. sapiens*] | | | gi = 6516088 | 2101843 |
| IC04454 | UG75 Expression | HOM | Mm.7330 | TITLE ESTs, Highly similar to LIGATIN [*M. musculus*] | | | gi = 4968011 | 2609684 |
| IC04455 | UG75 Expression | HOM | Mm.74712 | TITLE ESTs, Highly similar to ARL-6 interacting protein-6 [*M. musculus*] | | | gi = 1932406 | 777740 |
| IC04456 | UG75 Expression | HOM | Mm.74715 | TITLE ESTs, Highly similar to s-tomosyn isoform [*R. norvegicus*] | | | gi = 4320620 | 791579 |
| IC04457 | UG75 Expression | HOM | Mm.749 | TITLE ESTs, Highly similar to RNA helicase HEL117 [*R. norvegicus*] | | | gi = 5749381 | 2136365 |
| IC04458 | UG75 Expression | HOM | Mm.75466 | TITLE ESTs, Highly similar to KIAA0849 protein [*H. sapiens*] | | | gi = 1919749 | 765735 |
| IC04459 | UG75 Expression | HOM | Mm.76081 | TITLE ESTs, Highly similar to similar to human DNA-binding protein 5. [*H. sapiens*] | | | gi = 1309626 | 337605 |
| IC04460 | UG75 Expression | HOM | Mm.76983 | TITLE ESTs, Highly similar to TRANSCRIPTIONAL REGULATOR SPO8 [*Saccharomyces cerevisiae*] | | | gi = 1747163 | 613909 |
| IC04461 | UG75 Expression | HOM | Mm.7729 | TITLE ESTs, Highly similar to FRUCTOSE-BISPHOSPHATE ALDOLASE C [*Homo sapiens*] | | | gi = 4485499 | 902910 |
| IC04462 | UG75 Expression | HOM | Mm.77432 | TITLE ESTs, Highly similar to (define not available 5726647) [*M. musculus*] | | | gi = 1324829 | 351895 |
| IC04463 | UG75 Expression | HOM | Mm.7760 | TITLE ESTs, Highly similar to ADP-RIBOSYLATION FACTOR [*Filobasidiella neoformans*] | | | gi = 6083568 | 2811977 |
| IC04464 | UG75 Expression | HOM | Mm.77707 | TITLE ESTs, Highly similar to polyA binding protein-interacting protein PAIP1 [*M. musculus*] | | | gi = 4604596 | 791070 |
| IC04465 | UG75 Expression | HOM | Mm.7861 | TITLE ESTs, Highly similar to EUKARYOTIC INITIATION FACTOR 4A-LIKE NUK-34 [*Homo sapiens*] | | | gi = 6085169 | 1094059 |
| IC04466 | UG75 Expression | HOM | Mm.78718 | TITLE ESTs, Highly similar to (define, not available 6090975) [*R. norvegicus*] | | | gi = 2291689 | 948804 |
| IC04467 | UG75 Expression | HOM | Mm.7906 | TITLE ESTs, Highly similar to ESS1 PROTEIN [*Saccharomyces cerevisiae*] | | | gi = 3216806 | 1363973 |
| IC04468 | UG75 Expression | HOM | Mm.803 | TITLE ESTs, Highly similar to FYN binding protein FYB-130 [*M. musculus*] | | | gi = 2308188 | 958667 |
| IC04469 | UG75 Expression | HOM | Mm.80527 | TITLE ESTs, Highly similar to CELL DIVISION CONTROL PROTEIN 4 [*Saccharomyces cerevisiae*] | | | gi = 1541251 | 407267 |
| IC04470 | UG75 Expression | HOM | Mm.80773 | TITLE ESTs, Highly similar to PEREGRIN [*H. sapiens*] | | | gi = 7058586 | 1245467 |
| IC04471 | UG75 Expression | HOM | Mm.814 | TITLE ESTs, Highly similar to U2 SMALL NUCLEAR RIBONUCLEOPROTEIN A' [*Homo sapiens*] | | | gi = 1297643 | 337075 |
| IC04472 | UG75 Expression | HOM | Mm.821 | TITLE ESTs, Highly similar to U2 SMALL NUCLEAR RIBONUCLEOPROTEIN A' [*Homo sapiens*] | | | gi = 1714123 | 602987 |
| IC04473 | UG75 Expression | HOM | Mm.836 | TITLE ESTs, Highly similar to c-myc binding protein MM-1 [*M. musculus*] | | | gi = 1286942 | 317838 |
| IC04474 | UG75 Expression | HOM | Mm.84701 | protein L81167.6 of *Saccharomyces cerevisiae*. [*H. sapiens*] | | | gi = 6751105 | 2631297 |
| IC04475 | UG75 Expression | HOM | Mm.85844 | TITLE ESTs, Highly similar to KIAA0186 [*H. sapiens*] | | | gi = 2292445 | 934291 |
| IC04476 | UG75 Expression | HOM | Mm.86261 | TITLE ESTs, Highly similar to POSSIBLE GLOBAL TRANSCRIPTION ACTIVATOR SNF2L1 [*Homo sapiens*] | | | gi = 1672334 | 538390 |
| IC04477 | UG75 Expression | HOM | Mm.86323 | TITLE ESTs, Highly similar to PROTEIN-TYROSINE PHOSPHATASE 10D PRECURSOR [*Drosophila melanogaster*] | | | gi = 1701500 | 577455 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04478 | UG75 Expression | HOM | Mm.86496 | TITLE ESTs, Highly similar to RETINOBLASTOMA-ASSOCIATED PROTEIN [*M. musculus*] | | | gi = 3376611 | 1224980 |
| IC04479 | UG75 Expression | HOM | Mm.86522 | TITLE ESTs, Highly similar to PUTATIVE 30.7 KD METHYLTRANSFERASE IN TSM1-ARE1 INTERGENIC REGION [*Saccharomyces cerevisiae*] | | | gi = 2744352 | 1194013 |
| IC04480 | UG75 Expression | HOM | Mm.86548 | TITLE ESTs, Highly similar to chromosome-associated protein-E [*H. sapiens*] | | | gi = 2861633 | 1294412 |
| IC04481 | UG75 Expression | HOM | Mm.866 | TITLE ESTs, Highly similar to LARGE PROLINE-RICH PROTEIN BAT3 [*Homo sapiens*] | | | gi = 2756140 | 1178767 |
| IC04482 | UG75 Expression | HOM | Mm.86691 | TITLE ESTs, Highly similar to KIAA0714 protein [*H. sapiens*] | | | gi = 1912695 | 764751 |
| IC04483 | UG75 Expression | HOM | Mm.8688 | TITLE ESTs, Highly similar to NADH-UBIQUINONE OXIDOREDUCTASE PDSW SUBUNIT [*Bos taurus*] | | | gi = 1325353 | 351130 |
| IC04484 | UG75 Expression | HOM | Mm.86910 | TITLE ESTs, Highly similar to (definie not available 5714737) [*M. musculus*] | | | gi = 6077538 | 2236312 |
| IC04485 | UG75 Expression | HOM | Mm.86936 | TITLE ESTs, Highly similar to nucleoporin p58 [*R. norvegicus*] | | | gi = 4256941 | 400841 |
| IC04486 | UG75 Expression | HOM | Mm.87216 | TITLE ESTs, Highly similar to RAB GERANYLGERANYLTRANSFERASE ALPHA SUBUNIT [*Rattus norvegicus*] | | | gi = 6750371 | 2615787 |
| IC04487 | UG75 Expression | HOM | Mm.87283 | TITLE ESTs, Highly similar to KIAA0265 [*H. sapiens*] | | | gi = 1662794 | 520325 |
| IC04488 | UG75 Expression | HOM | Mm.87302 | TITLE ESTs, Highly similar to ankyrin repeat-containing protein Asb-1 [*M. musculus*] | | | gi = 4606305 | 907453 |
| IC04489 | UG75 Expression | HOM | Mm.87312 | TITLE ESTs, Highly similar to GLIA MATURATION FACTOR BETA [*Homo sapiens*; *Bos taurus*] | | | gi = 5598039 | 481348 |
| IC04490 | UG75 Expression | HOM | Mm.87319 | TITLE ESTs, Highly similar to PUTATIVE N-ACETYLGLUCOSAMINE-6-PHOSPHATE DEACETYLASE [*Caenorhabditis elegans*] | | | gi = 1680872 | 539843 |
| IC04491 | UG75 Expression | HOM | Mm.87332 | TITLE ESTs, Highly similar to dual specificity phosphatase MKP-5 [*H. sapiens*] | | | gi = 3692053 | 1885032 |
| IC04492 | UG75 Expression | HOM | Mm.87380 | TITLE ESTs, Highly similar to *Rattus norvegicus* jagged protein [*R. norvegicus*] | | | gi = 1765711 | 636540 |
| IC04493 | UG75 Expression | HOM | Mm.87450 | TITLE ESTs, Highly similar to OXYSTEROL-BINDING PROTEIN [*H. sapiens*] | | | gi = 1907597 | 747443 |
| IC04494 | UG75 Expression | HOM | Mm.87471 | TITLE ESTs, Highly similar to 2-5A-DEPENDENT RIBONUCLEASE [*M. musculus*] | | | gi = 5338225 | 2064858 |
| IC04495 | UG75 Expression | HOM | Mm.87637 | TITLE ESTs, Highly similar to KIAA1008 protein [*H. sapiens*] | | | gi = 1931968 | 764190 |
| IC04496 | UG75 Expression | HOM | Mm.87671 | TITLE ESTs, Highly similar to KIAA0461 perotein [*H. sapiens*] | | | gi = 1330546 | 354815 |
| IC04497 | UG75 Expression | HOM | Mm.87720 | TITLE ESTs, Highly similar to ADP-RIBOSYLATION FACTOR 3 [*Arabidopsis thaliana*] | | | gi = 6518470 | 2649462 |
| IC04498 | UG75 Expression | HOM | Mm.87729 | TITLE ESTs, Highly similar to INITIATION FACTOR IF-2, MITOCHONDRIAL PRECURSOR [*Homo sapiens*] | | | gi = 4060867 | 533464 |
| IC04499 | UG75 Expression | HOM | Mm.880 | TITLE ESTs, Highly similar to VIRAL INTEGRATION SITE PROTEIN INT-6 [*M. musculus*] | | | gi = 3987879 | 1887160 |
| IC04500 | UG75 Expression | HOM | Mm.88126 | TITLE ESTs, Highly similar to CALCIUM-DEPENDENT PROTEASE, SMALL [*Oryctolagus cuniculus*] | | | gi = 2745126 | 1210335 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04501 | UG75 Expression | HOM | Mm.88752 | TITLE ESTs, Highly similar to HYPOTHETICAL 30.3 KD PROTEIN IN APE1/LAP4-CWP1 INTERGENIC REGION [Saccharomyces cerevisiae] | | | gi = 3748151 | 1886063 |
| IC04502 | UG75 Expression | HOM | Mm.88753 | TITLE ESTs [H. sapiens] | | | gi = 4729556 | 1970283 |
| IC04503 | UG75 Expression | HOM | Mm.89515 | TITLE ESTs, Highly similar to sorting nexin 9 [H. sapiens] | | | gi = 4605116 | 1969743 |
| IC04504 | UG75 Expression | HOM | Mm.89836 | TITLE ESTs, Highly similar to HYPOTHETICAL 18.5 KD PROTEIN C12G12.05C IN CHROMOSOME I [Schizosaccharomyces pombe] | | | gi = 3164472 | 920549 |
| IC04505 | UG75 Expression | HOM | Mm.89840 | TITLE ESTs, Highly similar to (defline not available 5823146) [R. norvegicus] | | | gi = 6645207 | 573168 |
| IC04506 | UG75 Expression | HOM | Mm.89897 | TITLE ESTs, Highly similar to goodpasture antigen-binding protein [H. sapiens] | | | gi = 6557956 | 2654760 |
| IC04507 | UG75 Expression | HOM | Mm.90587 | TITLE ESTs, Highly similar to ALPHA ENOLASE [Mus musculus] | | | gi = 1315647 | 352391 |
| IC04508 | UG75 Expression | HOM | Mm.90760 | TITLE ESTs, Highly similar to testicular antigen [M. musculus] | | | gi = 2203255 | 875774 |
| IC04509 | UG75 Expression | HOM | Mm.9382 | TITLE ESTs, Highly similar to 5-FORMYLTETRAHYDROFOLATE CYCLO-LIGASE [Oryctolagus cuniculus] | | | gi = 3448302 | 1482627 |
| IC04510 | UG75 Expression | HOM | Mm.946 | TITLE ESTs, Highly similar to zyginII [R. norvegicus] | | | gi = 2520790 | 891207 |
| IC04511 | UG75 Expression | HOM | Mm.9558 | TITLE ESTs, Highly similar to Pax transcription activation domain interacting protein PTIP [M. musculus] | | | gi = 2917029 | 2609633 |
| IC04512 | UG75 Expression | HOM | Mm.9648 | TITLE ESTs, Highly similar to UBIQUINOL-CYTOCHROME-C REDUCTASE COMPLEX CORE PROTEIN I PRECURSOR [Homo sapiens] | | | gi = 5907067 | 1040077 |
| IC04513 | UG75 Expression | HOM | Mm.972 | TITLE ESTs [H. sapiens] | | | gi = 4442149 | 1922282 |
| IC04514 | UG75 Expression | HOM | Mm.9738 | TITLE ESTs, Highly similar to KIAA0765 protein [H. sapiens] | | | gi = 2919244 | 586288 |
| IC04515 | UG75 Expression | HOM | Mm.988 | TITLE ESTs, Highly similar to UBIQUINOL-CYTOCHROME C REDUCTASE COMPLEX CORE PROTEIN 2 PRECURSOR [Bos taurus] | | | gi = 1309884 | 338084 |
| IC04516 | UG75 Expression | HOM | Mm.9909 | TITLE ESTs, Highly similar to KIAA1017 protein [H. sapiens] | | | gi = 2917077 | 1382649 |
| IC04517 | UG75 Expression | HOM | Mm.9945 | TITLE ESTs, Highly similar to THREONYL-TRNA SYNTHETASE, CYTOPLASMIC [Homo sapiens] | | | gi = 6083611 | 2064655 |
| IC04518 | UG75 Expression | HOM | Mm.99776 | TITLE ESTs, Highly similar to HYPOTHETICAL PROTEIN C22G7.01C IN CHROMOSOME I [Schizosaccharomyces pombe] | | | gi = 5598793 | 579547 |
| IC04519 | UG75 Expression | HOM | Mm.99791 | TITLE ESTs, Highly similar to KIAA0462 protein [H. sapiens] | | | gi = 1724358 | 606745 |
| IC04520 | UG75 Expression | HOM | Mm.99943 | TITLE ESTs, Highly similar to Chain A, Crk Sh3 Domain Complexed With Peptoid Inhibitor [M. musculus] | | | gi = 6750193 | 2609797 |
| IC04521 | UG75 Expression | HOM | Mm.99982 | TITLE ESTs, Highly similar to KIAA0679 protein [H. sapiens] | | | gi = 4444664 | 574972 |
| IC04522 | UG75 Expression | EST | Mm.100005 | TITLE ESTs | | | gi = 6822537 | 644864 |
| IC04523 | UG75 Expression | EST | Mm.100059 | TITLE ESTs | | | gi = 1807837 | 644835 |
| IC04524 | UG75 Expression | EST | Mm.100072 | TITLE ESTs | | | gi = 6939486 | 583105 |
| IC04525 | UG75 Expression | EST | Mm.10009 | TITLE DNA segment, Chr 4, University of California at Los Angeles 2 | GENE D4Ucla2 | | | 621759 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04526 | UG75 Expression | EST | Mm.100101 | TITLE ESTs | | | gi = 2234133 | 1363544 |
| IC04527 | UG75 Expression | EST | Mm.100109 | TITLE ESTs, Moderately similar to CMP-N-ACETYLNEURAMINATE-BETA-1,4-GALACTOSIDE ALPHA-2,3-SIALYLTRANSFERASE [Rattus norvegicus] | | | gi = 1915773 | 749414 |
| IC04528 | UG75 Expression | EST | Mm.100110 | TITLE ESTs | | | gi = 1676656 | 576071 |
| IC04529 | UG75 Expression | EST | Mm.100111 | TITLE ESTs | | | gi = 4281686 | 573493 |
| IC04530 | UG75 Expression | EST | Mm.100114 | TITLE ESTs, Moderately similar to ubiquitin specific protease UBP43 [M. musculus] | | | gi = 6939031 | 574619 |
| IC04531 | UG75 Expression | EST | Mm.100117 | TITLE ESTs | | | gi = 177011 | 636873 |
| IC04532 | UG75 Expression | EST | Mm.100123 | TITLE ESTs | | | gi = 6380143 | 721971 |
| IC04533 | UG75 Expression | EST | Mm.100127 | TITLE ESTs | | | gi = 2042995 | 751697 |
| IC04534 | UG75 Expression | EST | Mm.100128 | TITLE ESTs | | | gi = 2049132 | 751691 |
| IC04535 | UG75 Expression | EST | Mm.100145 | TITLE ESTs | | | gi = 1739130 | 634814 |
| IC04536 | UG75 Expression | EST | Mm.100149 | TITLE ESTs | | | gi = 2272092 | 597534 |
| IC04537 | UG75 Expression | EST | Mm.100150 | TITLE ESTs | | | gi = 2331977 | 972690 |
| IC04538 | UG75 Expression | EST | Mm.100162 | TITLE ESTs | | | gi = 2691357 | 764793 |
| IC04539 | UG75 Expression | EST | Mm.100166 | TITLE ESTs | | | gi = 6408018 | 723075 |
| IC04540 | UG75 Expression | EST | Mm.100171 | TITLE DNA segment, Chr 1, Lubeck 1 | GENE D1Lub1 | | gi = 2962467 | 617189 |
| IC04541 | UG75 Expression | EST | Mm.100172 | TITLE ESTs | | | gi = 6756739 | 1265539 |
| IC04542 | UG75 Expression | EST | Mm.100173 | TITLE ESTs, Moderately similar to protein URF1 [M. musculus] | | | gi = 6750293 | 764713 |
| IC04543 | UG75 Expression | EST | Mm.100175 | TITLE ESTs | | | gi = 2955999 | 533400 |
| IC04544 | UG75 Expression | EST | Mm.100177 | TITLE ESTs | | | gi = 316353 | 1263470 |
| IC04545 | UG75 Expression | EST | Mm.100180 | TITLE ESTs | | | gi = 3515958 | 1363190 |
| IC04546 | UG75 Expression | EST | Mm.100183 | TITLE ESTs | | | gi = 4290088 | 1264628 |
| IC04547 | UG75 Expression | EST | Mm.100184 | TITLE ESTs | | | gi = 6363184 | 576887 |
| IC04548 | UG75 Expression | EST | Mm.100185 | TITLE ESTs | | | gi = 1724766 | 1446444 |
| IC04549 | UG75 Expression | EST | Mm.100186 | TITLE ESTs | | | gi = 3685726 | 582552 |
| IC04550 | UG75 Expression | EST | Mm.100188 | TITLE ESTs | | | gi = 7315385 | 1446204 |
| IC04551 | UG76 LID366 B cell | EST | Mm.100190 | TITLE ESTs | | | gi = 1903786 | 721217 |
| IC04552 | UG75 Expression | EST | Mm.100202 | TITLE ESTs | | | gi = 430903 | 721541 |
| IC04553 | UG75 Expression | EST | Mm.100208 | TITLE ESTs | | | gi = 4484891 | 598977 |
| IC04554 | UG75 Expression | EST | Mm.100214 | TITLE ESTs | | | gi = 1479041 | 1265276 |
| IC04555 | UG75 Expression | EST | Mm.100225 | TITLE ESTs | | | gi = 4766331 | 958497 |
| IC04556 | UG75 Expression | EST | Mm.100240 | TITLE ESTs | | | gi = 1487626 | 749575 |
| IC04557 | UG75 Expression | EST | Mm.100245 | TITLE ESTs | | | gi = 627524 | 1395322 |
| IC04558 | UG75 Expression | EST | Mm.100249 | TITLE ESTs | | | gi = 531087 | 777663 |
| IC04559 | UG75 Expression | EST | Mm.100254 | TITLE ESTs | | | gi = 3100202 | 972781 |
| IC04560 | UG75 Expression | EST | Mm.100274 | TITLE DNA segment, Chr 18, Abbott 1 expressed | GENE D18Abb1e | | gi = 1700773 | 764326 |
| IC04561 | UG75 Expression | EST | Mm.10029 | TITLE ESTs | | | gi = 4724668 | 1329785 |
| IC04562 | UG75 Expression | EST | Mm.100299 | TITLE ESTs | | | gi = 6645744 | 596826 |
| IC04563 | UG75 Expression | EST | Mm.100316 | TITLE ESTs, Weakly similar to DNA-binding protein [M. musculus] | | | gi = 1796810 | 638864 |
| IC04564 | UG75 Expression | EST | Mm.100403 | TITLE ESTs | | | gi = 4295681 | 636896 |
| IC04565 | UG75 Expression | EST | Mm.100407 | TITLE ESTs | | | gi = 3980780 | 641364 |
| IC04566 | UG75 Expression | EST | Mm.100408 | TITLE ESTs, Moderately similar to CGI-74 protein [H. sapiens] | | | gi = 4484406 | 637454 |
| IC04567 | UG75 Expression | EST | Mm.10041 | TITLE ESTs | | | gi = 3980780 | 573859 |
| IC04568 | UG75 Expression | EST | Mm.100469 | TITLE ESTs | | | gi = 4484406 | 534116 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04569 | UG75 Expression | EST | Mm.100478 | TITLE ESTs | | | gi = 1895727 | 640754 |
| IC04570 | UG75 Expression | EST | Mm.100483 | TITLE ESTs | | | gi = 4401730 | 620158 |
| IC04571 | UG75 Expression | EST | Mm.100491 | TITLE ESTs | | | gi = 2040523 | 1378830 |
| IC04572 | UG75 Expression | EST | Mm.100502 | TITLE ESTs, Moderately similar to protein COI [*M. musculus*] | | | gi = 444493 | 1148855 |
| IC04573 | UG75 Expression | EST | Mm.100504 | TITLE ESTs | | | gi = 4615976 | 1243714 |
| IC04574 | UG76 LID366 B cell | EST | Mm.100609 | TITLE ESTs | | | gi = 7063718 | 2699247 |
| IC04575 | UG75 Expression | EST | Mm.10061 | TITLE ESTs | | | gi = 3126492 | 1149572 |
| IC04576 | 00/04/26 UG#76 17Lid Expansion | EST | Mm.100628 | ESTs | | | gi = 2259103 | 1327856 |
| IC04577 | UG76 LID366 B cell | EST | Mm.100649 | TITLE ESTs | | | gi = 7315519 | 2699078 |
| IC04578 | UG76 LID366 B cell | EST | Mm.100655 | TITLE ESTs | | | gi = 7315468 | 2698978 |
| IC04579 | UG75 Expression | EST | Mm.10068 | TITLE ESTs | | | gi = 3161541 | 1382085 |
| IC04580 | UG75 Expression | EST | Mm.10076 | TITLE ESTs, Weakly similar to 50S RIBOSOMAL PROTEIN L13 [*Staphylococcus carnosus*] | | | gi = 5549541 | 1001655 |
| IC04581 | UG75 Expression | EST | Mm.10093 | TITLE ESTs, Weakly similar to Similarity to *B. subtilis* YQJC protein [*C. elegans*] | | | gi = 1838555 | 621671 |
| IC04582 | UG75 Expression | EST | Mm.10094 | TITLE DNA segment, Chr 16, human D22S1269E, expressed | GENE D16H22: | 621174 Dgs|DiGeorge syndrome gene i|ES2|T10| | | |
| IC04583 | UG76 LID366 B cell | EST | Mm.100971 | TITLE ESTs | | | gi = 6100340 | 2749528 |
| IC04584 | UG75 Expression | EST | Mm.10153 | TITLE ESTs | | | gi = 1760019 | 550788 |
| IC04585 | UG76 LID366 B cell | EST | Mm.10160 | TITLE ESTs | | | gi = 2308080 | 973142 |
| IC04586 | UG76 LID366 B cell | EST | Mm.101669 | TITLE ESTs | | | gi = 7066533 | 2749620 |
| IC04587 | UG75 Expression | EST | Mm.10167 | TITLE ESTs, Moderately similar to THYROID RECEPTOR INTERACTING PROTEIN 3 [*H. sapiens*] | | | gi = 1290058 | 1429342 |
| IC04588 | UG76 LID366 B cell | EST | Mm.10178 | TITLE ESTs | | | gi = 3260109 | 1282262 |
| IC04589 | UG76 LID366 B cell | EST | Mm.101786 | TITLE ESTs [*M. musculus*] | | | gi = 7063214 | 2748994 |
| IC04590 | UG75 Expression | EST | Mm.10200 | TITLE ESTs | | | gi = 1325788 | 777608 |
| IC04591 | UG75 Expression | EST | Mm.1023 | TITLE ESTs | | | gi = 1777112 | 618913 |
| IC04592 | UG75 Expression | EST | Mm.1024 | TITLE ESTs | | | gi = 2855990 | 598507 |
| IC04593 | UG76 LID366 B cell | EST | Mm.102479 | TITLE ESTs, Weakly similar to Atu [*D. melanogaster*] | | | gi = 7066136 | 2749267 |
| IC04594 | UG76 LID366 B cell | EST | Mm.102480 | TITLE ESTs | | | gi = 7066609 | 2748937 |
| IC04595 | UG76 LID366 B cell | EST | Mm.102481 | TITLE ESTs | | | gi = 7066651 | 2749027 |
| IC04596 | UG76 LID366 B cell | EST | Mm.102482 | TITLE ESTs | | | gi = 7066246 | 2749045 |
| IC04597 | UG76 LID366 B cell | EST | Mm.102483 | TITLE ESTs | | | gi = 7066321 | 2749162 |
| IC04598 | UG76 LID366 B cell | EST | Mm.102484 | TITLE EST | | | gi = 7066410 | 2749261 |
| IC04599 | UG76 LID366 B cell | EST | Mm.102485 | TITLE EST | | | gi = 7066606 | 2748952 |
| IC04600 | UG76 LID366 B cell | EST | Mm.102486 | TITLE EST | | | gi = 7066634 | 2749004 |
| IC04601 | UG76 LID366 B cell | EST | Mm.102487 | TITLE ESTs, Weakly similar to ORF YNL024c [*S. cerevisiae*] | | | gi = 2308758 | 2749053 |
| IC04602 | UG76 LID366 B cell | EST | Mm.102488 | TITLE EST | | | gi = 7066738 | 2749161 |
| IC04603 | UG76 LID366 B cell | EST | Mm.102489 | TITLE EST | | | gi = 7066746 | 2749180 |
| IC04604 | UG76 LID366 B cell | EST | Mm.102490 | TITLE EST | | | gi = 7066757 | 2749181 |
| IC04605 | UG76 LID366 B cell | EST | Mm.102491 | TITLE EST | | | gi = 7066774 | 2749213 |
| IC04606 | UG76 LID366 B cell | EST | Mm.102494 | TITLE EST | | | gi = 7157616 | 2698926 |
| IC04607 | UG76 LID366 B cell | EST | Mm.102495 | TITLE EST | | | gi = 7157739 | 2699135 |
| IC04608 | UG76 LID366 B cell | EST | Mm.102496 | TITLE EST | | | gi = 7157748 | 2699156 |
| IC04609 | UG75 Expression | EST | Mm.10255 | TITLE ESTs | | | gi = 2813209 | 642548 |
| IC04610 | UG76 LID366 B cell | EST | Mm.102671 | TITLE ESTs | | | gi = 7315451 | 2698931 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04611 | UG75 Expression | EST | Mm.10278 | TITLE ESTs | | | gi = 2305855 | 617672 |
| IC04612 | UG75 Expression | EST | Mm.10281 | TITLE ESTs | | | gi = 3520864 | 749094 |
| IC04613 | UG75 Expression | EST | Mm.10285 | TITLE ESTs | | | gi = 2521033 | 973296 |
| IC04614 | UG75 Expression | EST | Mm.1033 | TITLE ESTs | | | gi = 1917863 | 617059 |
| IC04615 | UG75 LID366 B cell | EST | Mm.103305 | TITLE EST | | | gi = 7315361 | 2698644 |
| IC04616 | UG76 LID366 B cell | EST | Mm.103306 | TITLE EST | | | gi = 7315421 | 2698777 |
| IC04617 | UG76 LID366 B cell | EST | Mm.103307 | TITLE EST | | | gi = 5909624 | 2698809 |
| IC04618 | UG76 LID366 B cell | EST | Mm.103308 | TITLE EST | | | gi = 7315459 | 2698954 |
| IC04619 | UG76 LID366 B cell | EST | Mm.103309 | TITLE EST | | | gi = 6079062 | 2698961 |
| IC04620 | UG75 LID366 B cell | EST | Mm.10331 | TITLE ESTs | | | gi = 2965059 | 764121 |
| IC04621 | UG76 LID366 B cell | EST | Mm.103310 | TITLE ESTs, Weakly similar to ZK1058.5 [*C. elegans*] | | | gi = 2306384 | 2699012 |
| IC04622 | UG76 LID366 B cell | EST | Mm.103311 | TITLE ESTs | | | gi = 7315489 | 551479 |
| IC04623 | UG76 LID366 B cell | EST | Mm.103312 | TITLE ESTs | | | gi = 7315564 | 2699230 |
| IC04624 | UG76 LID366 B cell | EST | Mm.103320 | TITLE EST | | | gi = 7066122 | 2749254 |
| IC04625 | UG76 LID366 B cell | EST | Mm.103321 | TITLE ESTs | | | gi = 7066166 | 2749317 |
| IC04626 | UG75 LID366 B cell | EST | Mm.10336 | TITLE EST | | | gi = 4724380 | 598181 |
| IC04627 | UG76 LID366 B cell | EST | Mm.103361 | TITLE ESTs, Weakly similar to synapse-associated protein sap47-1 [*D. melanogaster*] | | | gi = 2527948 | 2698773 |
| IC04628 | UG75 Expression | EST | Mm.10343 | TITLE ESTs | | | gi = 6085138 | 894131 |
| IC04629 | UG76 LID366 B cell | EST | Mm.103454 | TITLE ESTs | | | gi = 7066212 | 2749000 |
| IC04630 | UG76 LID366 B cell | EST | Mm.103459 | TITLE ESTs | | | gi = 7066618 | 2748968 |
| IC04631 | UG76 LID366 B cell | EST | Mm.103545 | TITLE ESTs | | | gi = 7066128 | 2749270 |
| IC04632 | UG75 Expression | EST | Mm.10367 | TITLE ESTs | | | gi = 6079297 | 749717 |
| IC04633 | UG75 Expression | EST | Mm.10374 | TITLE ESTs | | | gi = 1310597 | 557953 |
| IC04634 | UG75 Expression | EST | Mm.1040 | TITLE ESTs | | | gi = 2856668 | 644991 |
| IC04635 | UG75 Expression | EST | Mm.10406 | TITLE ESTs, Moderately similar to SUCCINATE DEHYDROGENASE [*H. sapiens*] | | | gi = 1326470 | 1002453 |
| IC04636 | UG75 Expression | EST | Mm.10407 | TITLE ESTs | | | gi = 1672409 | 1749947 |
| IC04637 | UG75 Expression | EST | Mm.1043 | TITLE ESTs | | | gi = 4779190 | 635707 |
| IC04638 | UG75 Expression | EST | Mm.10460 | TITLE ESTs | | | gi = 3167732 | 596632 |
| IC04639 | UG75 Expression | EST | Mm.10541 | TITLE ESTs | | | gi = 1671651 | 635149 |
| IC04640 | UG75 Expression | EST | Mm.10565 | TITLE ESTs, Weakly similar to Zinc finger protein s11-6 [*M. musculus*] | | | gi = 3167309 | 1193690 |
| IC04641 | UG75 Expression | EST | Mm.1058 | TITLE ESTs | | | gi = 4301441 | 597782 |
| IC04642 | UG75 Expression | EST | Mm.10586 | TITLE ESTs | | | gi = 6167860 | 598527 |
| IC04643 | UG75 Expression | EST | Mm.10621 | TITLE EST | | | gi = 3175816 | 1361809 |
| IC04644 | UG75 Expression | EST | Mm.10622 | TITLE ESTs | | | gi = 4968006 | 1362105 |
| IC04645 | UG75 Expression | EST | Mm.10626 | TITLE ESTs | | | gi = 1684134 | 1429152 |
| IC04646 | UG75 Expression | EST | Mm.10628 | TITLE ESTs | | | gi = 1759378 | 621070 |
| IC04647 | UG75 Expression | EST | Mm.10641 | TITLE ESTs | | | gi = 1427104 | 597946 |
| IC04648 | UG75 Expression | EST | Mm.10643 | TITLE EST | | | gi = 3216504 | 1363487 |
| IC04649 | UG75 Expression | EST | Mm.1065 | TITLE ESTs | | | gi = 1739853 | 598657 |
| IC04650 | UG75 Expression | EST | Mm.10650 | TITLE ESTs, Moderately similar to KIAA0909 protein [*H. sapiens*] | | | gi = 3732122 | 1193659 |
| IC04651 | UG75 Expression | EST | Mm.10665 | TITLE ESTs, Weakly similar to teg292 protein [*M. musculus*] | | | gi = 2520273 | 595853 |
| IC04652 | UG75 Expression | EST | Mm.10711 | TITLE actinin alpha 2 | GENE Actn2 | | gi = 1316339 | 1243839 |
| IC04653 | UG75 Expression | EST | Mm.10750 | TITLE ESTs | | | gi = 2292393 | 1294702 |
| IC04654 | UG75 Expression | EST | Mm.1078 | TITLE ESTs | | | gi = 1740064 | 598332 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04655 | UG75 Expression | EST | Mm.10780 | TITLE ESTs | | | gi = 4616260 | 643437 |
| IC04656 | UG75 Expression | EST | Mm.1079 | TITLE ESTs | | | gi = 1901242 | 598335 |
| IC04657 | UG75 Expression | EST | Mm.10806 | TITLE ESTs | | | gi = 1554694 | 1263647 |
| IC04658 | UG75 Expression | EST | Mm.10814 | TITLE ESTs | | | gi = 5819529 | 642895 |
| IC04659 | UG75 Expression | EST | Mm.10817 | TITLE ESTs | | | gi = 1919439 | 620376 |
| IC04660 | UG75 Expression | EST | Mm.1084 | TITLE ESTs | | | gi = 4601820 | 634922 |
| IC04661 | UG75 Expression | EST | Mm.10844 | TITLE ESTs | | | gi = 4403854 | 973168 |
| IC04662 | UG75 Expression | EST | Mm.10859 | TITLE ESTs, Weakly similar to dJ461P17.1 [*H. sapiens*] | | | gi = 1682818 | 534122 |
| IC04663 | UG75 Expression | EST | Mm.10878 | TITLE ESTs, Weakly similar to All-1 protein + GTE form [*M. musculus*] | | | gi = 6085364 | 1264313 |
| IC04664 | UG75 Expression | EST | Mm.10949 | TITLE ESTs | | | gi = 2272465 | 643268 |
| IC04665 | UG75 Expression | EST | Mm.10954 | TITLE ESTs | | | gi = 5910212 | 1379886 |
| IC04666 | UG75 Expression | EST | Mm.10955 | TITLE ESTs | | | gi = 3684590 | 1226601 |
| IC04667 | UG75 Expression | EST | Mm.10964 | TITLE DNA segment, Chr 17, human D6S45 | GENE D17H6S45 | | | 1294018 |
| IC04668 | UG75 Expression | EST | Mm.10987 | TITLE ESTs | | | gi = 2040396 | 749639 |
| IC04669 | UG75 Expression | EST | Mm.11014 | TITLE ESTs | | | gi = 3370384 | 638978 |
| IC04670 | UG75 Expression | EST | Mm.11022 | TITLE ESTs, Weakly similar to ORF YBL055c [*S. cerevisiae*] | | | gi = 3370482 | 718951 |
| IC04671 | UG75 Expression | EST | Mm.11075 | TITLE ESTs, Moderately similar to fls353 [*H. sapiens*] | | | gi = 3376126 | 1278984 |
| IC04672 | UG75 Expression | EST | Mm.11112 | TITLE ESTs, Weakly similar to predicted using Genefinder [*C. elegans*] | | | gi = 4033056 | 640709 |
| IC04673 | UG75 Expression | EST | Mm.11116 | TITLE ESTs | | | gi = 6749287 | 619576 |
| IC04674 | UG75 Expression | EST | Mm.1116 | TITLE ESTs | | | gi = 5910876 | 642385 |
| IC04675 | UG75 Expression | EST | Mm.11186 | TITLE ESTs | | | gi = 3371857 | 1329002 |
| IC04676 | UG75 Expression | EST | Mm.11223 | TITLE ESTs, Weakly similar to open reading frame [*M. musculus*] | | | gi = 2519161 | 751421 |
| IC04677 | UG75 Expression | EST | Mm.11233 | TITLE ESTs | | | gi = 3372299 | 639347 |
| IC04678 | UG75 Expression | EST | Mm.11331 | TITLE ESTs, Weakly similar to proline-rich protein [*M. musculus*] | | | gi = 5906543 | 620634 |
| IC04679 | UG75 Expression | EST | Mm.11333 | TITLE ESTs | | | gi = 4304889 | 642653 |
| IC04680 | UG75 Expression | EST | Mm.11346 | TITLE ESTs | | | gi = 2919112 | 721459 |
| IC04681 | UG75 Expression | EST | Mm.11360 | TITLE ESTs | | | gi = 3373644 | 1193821 |
| IC04682 | UG75 Expression | EST | Mm.11382 | TITLE ESTs, Moderately similar to KIAA0956 protein [*H. sapiens*] | | | gi = 3863733 | 595914 |
| IC04683 | UG75 Expression | EST | Mm.11428 | TITLE ESTs, Weakly similar to ORF YKR081c [*S. cerevisiae*] | | | gi = 3374096 | 574661 |
| IC04684 | UG75 Expression | EST | Mm.11434 | TITLE ESTs, Moderately similar to SC1 protein [*M. musculus*] | | | gi = 1826530 | 1379534 |
| IC04685 | UG75 Expression | EST | Mm.1144 | TITLE ESTs | | | gi = 6100992 | 598758 |
| IC04686 | UG75 Expression | EST | Mm.11473 | TITLE ESTs | | | gi = 4968380 | 597540 |
| IC04687 | UG75 Expression | EST | Mm.1148 | TITLE ESTs | | | gi = 4601240 | 598860 |
| IC04688 | UG75 Expression | EST | Mm.11480 | TITLE ESTs | | | gi = 3978717 | 1294119 |
| IC04689 | UG75 Expression | EST | Mm.11482 | TITLE DNA segment, Chr 2, Wayne State University 143, expressed | GENE D2Wsu143e | | gi = 3374689 | 596745 |
| IC04690 | UG75 Expression | EST | Mm.115 | TITLE ESTs | | | | 1293890 |
| IC04691 | UG75 Expression | EST | Mm.11513 | TITLE ESTs | | | gi = 3375034 | 635887 |
| IC04692 | UG75 Expression | EST | Mm.1153 | TITLE ESTs | | | gi = 1777126 | 598929 |
| IC04693 | UG75 Expression | EST | Mm.11535 | TITLE DNA segment, Chr 14, University of California at Los Angeles 1 | GENE D14Ucla1 | | | 597865 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04694 | UG75 Expression | EST | Mm.11581 | TITLE ESTs | | | gi = 2857149 | 574706 |
| IC04695 | UG75 Expression | EST | Mm.11593 | TITLE ESTs | | | gi = 2811891 | 617050 |
| IC04696 | UG75 Expression | EST | Mm.11613 | TITLE ESTs | | | gi = 5497572 | 643731 |
| IC04697 | UG75 Expression | EST | Mm.11636 | TITLE ESTs | | | gi = 3235958 | 719315 |
| IC04698 | UG75 Expression | EST | Mm.11680 | TITLE ESTs | | | gi = 5336316 | 637051 |
| IC04699 | UG75 Expression | EST | Mm.11734 | TITLE ESTs | | | gi = 3377154 | 620963 |
| IC04700 | UG75 Expression | EST | Mm.11747 | TITLE ESTs | | | gi = 3374857 | 751152 |
| IC04701 | UG75 Expression | EST | Mm.11778 | TITLE ESTs | | | gi = 2291847 | 1328300 |
| IC04702 | UG75 Expression | EST | Mm.11787 | TITLE ESTs | | | gi = 3394332 | 596743 |
| IC04703 | UG75 Expression | EST | Mm.1181 | TITLE ESTs | | | gi = 443098 | 777798 |
| IC04704 | UG75 Expression | EST | Mm.11815 | TITLE ESTs, Weakly similar to natural killer cell tumor-recognition protein [M. musculus] | | | gi = 5498140 | 1149706 |
| IC04705 | UG75 Expression | EST | Mm.1182 | TITLE ESTs | | | gi = 1504486 | 619404 |
| IC04706 | UG75 Expression | EST | Mm.11827 | TITLE ESTs | | | gi = 6158013 | 523306 |
| IC04707 | UG75 Expression | EST | Mm.11829 | TITLE ESTs | | | gi = 3387269 | 1264301 |
| IC04708 | UG75 Expression | EST | Mm.11833 | TITLE ESTs | | | gi = 6638261 | 1245990 |
| IC04709 | UG75 Expression | EST | Mm.11849 | TITLE ESTs | | | gi = 3394208 | 596500 |
| IC04710 | UG75 Expression | EST | Mm.11862 | TITLE ESTs | | | gi = 3387524 | 616730 |
| IC04711 | UG75 Expression | EST | Mm.11869 | TITLE ESTs | | | gi = 2403710 | 1225147 |
| IC04712 | UG75 Expression | EST | Mm.1187 | TITLE ESTs | | | gi = 1297603 | 616720 |
| IC04713 | UG75 Expression | EST | Mm.11935 | TITLE ESTs | | | gi = 3980547 | 988037 |
| IC04714 | UG75 Expression | EST | Mm.11946 | TITLE ESTs, Moderately similar to a thyroid hormone responsive gene in human skin fibroblasts [H. sapiens] | | | gi = 2406539 | 637279 |
| IC04715 | UG75 Expression | EST | Mm.1196 | TITLE ESTs | | | gi = 2519392 | 618355 |
| IC04716 | UG75 Expression | EST | Mm.11982 | TITLE ESTs | | | gi = 3394358 | 894433 |
| IC04717 | UG75 Expression | EST | Mm.12019 | TITLE ESTs | | | gi = 2591540 | 635634 |
| IC04718 | UG75 Expression | EST | Mm.12055 | TITLE ESTs | | | gi = 2503096 | 718899 |
| IC04719 | UG75 Expression | EST | Mm.12164 | TITLE ESTs | | | gi = 1682277 | 577090 |
| IC04720 | UG75 Expression | EST | Mm.12166 | TITLE ESTs | | | gi = 2102601 | 596286 |
| IC04721 | UG75 Expression | EST | Mm.12180 | TITLE ESTs | | | gi = 6008422 | 597501 |
| IC04722 | UG75 Expression | EST | Mm.12184 | TITLE ESTs | | | gi = 5819789 | 596910 |
| IC04723 | UG75 Expression | EST | Mm.12187 | TITLE ESTs | | | gi = 4801200 | 1263638 |
| IC04724 | UG75 Expression | EST | Mm.12190 | TITLE ESTs | | | gi = 3373641 | 599282 |
| IC04725 | UG75 Expression | EST | Mm.12192 | TITLE ESTs | | | gi = 5548741 | 598465 |
| IC04726 | UG75 Expression | EST | Mm.12193 | TITLE ESTs, Weakly similar to 60S RIBOSOMAL PROTEIN L30A [Saccharomyces cerevisiae] | | | gi = 3718590 | 973400 |
| IC04727 | UG75 Expression | EST | Mm.12219 | TITLE ESTs | | | gi = 3394128 | 622825 |
| IC04728 | UG75 Expression | EST | Mm.12228 | TITLE ESTs | | | gi = 3387675 | 617048 |
| IC04729 | UG75 Expression | EST | Mm.12232 | TITLE ESTs | | | gi = 2256272 | 636920 |
| IC04730 | UG75 Expression | EST | Mm.12248 | TITLE ESTs, Weakly similar to KIAA0586 protein [H. sapiens] | | | gi = 4614944 | 751297 |
| IC04731 | UG75 Expression | EST | Mm.12258 | TITLE ESTs | | | gi = 3167848 | 723256 |
| IC04732 | UG75 Expression | EST | Mm.12261 | TITLE ESTs, Weakly similar to DNA-BINDING PROTEIN MEL-18 [M. musculus] | | | gi = 6083616 | 723200 |
| IC04733 | UG75 Expression | EST | Mm.12265 | TITLE ESTs | | | gi = 3387335 | 1380183 |
| IC04734 | UG75 Expression | EST | Mm.12309 | TITLE ESTs | | | gi = 3681619 | 596023 |
| IC04735 | UG75 Expression | EST | Mm.12329 | TITLE ESTs | | | gi = 4802608 | 634784 |
| IC04736 | UG75 Expression | EST | Mm.12378 | TITLE ESTs | | | gi = 2813369 | 638416 |
| IC04737 | UG75 Expression | EST | Mm.12390 | TITLE ESTs | | | gi = 2730797 | 764171 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04738 | UG75 Expression | EST | Mm.12393 | TITLE ESTs | | | gi = 3393527 | 635263 |
| IC04739 | UG75 Expression | EST | Mm.12411 | TITLE ESTs | | | gi = 4409119 | 764701 |
| IC04740 | UG75 Expression | EST | Mm.12412 | TITLE ESTs | | | gi = 4281918 | 765234 |
| IC04741 | UG75 Expression | EST | Mm.12430 | TITLE ESTs | | | gi = 3387642 | 959100 |
| IC04742 | UG75 Expression | EST | Mm.12436 | TITLE ESTs | | | gi = 3373027 | 1243355 |
| IC04743 | UG75 Expression | EST | Mm.12459 | TITLE ESTs | | | gi = 4725786 | 894564 |
| IC04744 | UG75 Expression | EST | Mm.12573 | TITLE ESTs | | | gi = 3393901 | 1226478 |
| IC04745 | UG75 Expression | EST | Mm.12603 | TITLE ESTs | | | gi = 3297448 | 619783 |
| IC04746 | UG75 Expression | EST | Mm.12648 | TITLE ESTs | | | gi = 2919512 | 596257 |
| IC04747 | UG75 Expression | EST | Mm.12654 | TITLE ESTs | | | gi = 2963084 | 1282108 |
| IC04748 | UG75 Expression | EST | Mm.12665 | TITLE ESTs, Moderately similar to HYPOTHETICAL 92.1 KD PROTEIN C24H6.03 IN CHROMOSOME I [Schizosaccharomyces pombe] | | | gi = 1840197 | 1295023 |
| IC04749 | UG75 Expression | EST | Mm.12705 | TITLE ESTs | | | gi = 3373235 | 1294854 |
| IC04750 | UG75 Expression | EST | Mm.12715 | TITLE ESTs, Weakly similar to ORF YKL026c [S. cerevisiae] | | | gi = 3372067 | 1364499 |
| IC04751 | UG75 Expression | EST | Mm.12716 | TITLE ESTs | | | gi = 3370289 | 1378208 |
| IC04752 | UG75 Expression | EST | Mm.12730 | TITLE ESTs, Weakly similar to alpha integrin binding protein 80 [H. sapiens] | | | gi = 1776829 | 642872 |
| IC04753 | UG75 Expression | EST | Mm.12746 | TITLE ESTs | | | gi = 4783576 | 596157 |
| IC04754 | UG75 Expression | EST | Mm.12752 | TITLE ESTs, Weakly similar to D2092.5 [C. elegans] | | | gi = 3372905 | 557887 |
| IC04755 | UG75 Expression | EST | Mm.12756 | TITLE ESTs, Weakly similar to hypothetical protein 384D8_7 [H. sapiens] | | | gi = 1558528 | 635505 |
| IC04756 | UG75 Expression | EST | Mm.12787 | TITLE ESTs | | | gi = 6638596 | 893872 |
| IC04757 | UG75 Expression | EST | Mm.1279 | TITLE ESTs, Weakly similar to similar to thymidine diphosphoglucose 4,6-dehydratase [C. elegans] | | | gi = 1681749 | 596464 |
| IC04758 | UG75 Expression | EST | Mm.12790 | TITLE ESTs | | | gi = 4729959 | 620730 |
| IC04759 | UG75 Expression | EST | Mm.12831 | TITLE ESTs, Weakly similar to RHO-GAP HEMATOPOIETIC PROTEIN C1 [H. sapiens] | | | gi = 6750773 | 722969 |
| IC04760 | UG75 Expression | EST | Mm.12883 | TITLE ESTs | | | gi = 4723694 | 620130 |
| IC04761 | UG75 Expression | EST | Mm.12983 | TITLE ESTs, Moderately similar to HYPOTHETICAL 36.7 KD PROTEIN AH6.2 IN CHROMOSOME II [Caenorhabditis elegans] | | | gi = 3448307 | 1193117 |
| IC04762 | UG75 Expression | EST | Mm.13036 | TITLE ESTs, Weakly similar to TSC501 [H. sapiens] | | | gi = 5906501 | 722321 |
| IC04763 | UG75 Expression | EST | Mm.13097 | TITLE ESTs | | | gi = 1538956 | 596117 |
| IC04764 | UG75 Expression | EST | Mm.13112 | TITLE ESTs | | | gi = 2917902 | 1295870 |
| IC04765 | UG75 Expression | EST | Mm.13120 | TITLE ESTs | | | gi = 5299968 | 721811 |
| IC04766 | UG75 Expression | EST | Mm.13125 | TITLE ESTs | | | gi = 1767820 | 622646 |
| IC04767 | UG75 Expression | EST | Mm.13146 | TITLE ESTs | | | gi = 1755932 | 617575 |
| IC04768 | UG75 Expression | EST | Mm.13360 | TITLE ESTs | | | gi = 3371208 | 1295990 |
| IC04769 | UG75 Expression | EST | Mm.13433 | TITLE ESTs | | | gi = 2516742 | 1295738 |
| IC04770 | UG75 Expression | EST | Mm.13437 | TITLE ESTs, Weakly similar to UBIQUITIN CARBOXYL-TERMINAL HYDROLASE 13 [Saccharomyces cerevisiae] | | | gi = 2283577 | 620351 |
| IC04771 | UG75 Expression | EST | Mm.13450 | TITLE ESTs | | | gi = 3516334 | 557840 |
| IC04772 | UG75 Expression | EST | Mm.13669 | TITLE ESTs, Weakly similar to PLECTIN [R. norvegicus] | | | gi = 3394889 | 640892 |
| IC04773 | UG75 Expression | EST | Mm.13705 | TITLE ESTs | | | gi = 6633510 | 1149877 |
| IC04774 | UG75 Expression | EST | Mm.13712 | TITLE ESTs | | | gi = 1675438 | 575781 |
| IC04775 | UG75 Expression | EST | Mm.13756 | TITLE ESTs, Weakly similar to similar to S. cerevisiae hypothetical protein RI01 [C. elegans] | | | gi = 6077199 | 1149051 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04776 | UG75 Expression | EST | Mm.13773 | TITLE ESTs, Weakly similar to unknown [*S. cerevisiae*] | | | gi = 3749116 | 641063 |
| IC04777 | UG75 Expression | EST | Mm.13774 | TITLE ESTs, Moderately similar to OS9 [*H. sapiens*] | | | gi = 4257965 | 1395374 |
| IC04778 | UG75 Expression | EST | Mm.13796 | TITLE ESTs | | | gi = 3809437 | 720702 |
| IC04779 | UG75 Expression | EST | Mm.13800 | TITLE ESTs, Weakly similar to T-complex protein 10c [*M. musculus*] | | | gi = 2811492 | 598825 |
| IC04780 | UG75 Expression | EST | Mm.13806 | TITLE ESTs | | | gi = 3957053 | 749730 |
| IC04781 | UG75 Expression | EST | Mm.13823 | TITLE ESTs, Moderately similar to diphthamide biosynthesis protein-2 [*H. sapiens*] | | | gi = 4409083 | 1970040 |
| IC04782 | UG75 Expression | EST | Mm.14155 | TITLE ESTs | | | gi = 3371832 | 1279412 |
| IC04783 | UG75 Expression | EST | Mm.14189 | TITLE ESTs | | | gi = 2813840 | 574794 |
| IC04784 | UG75 Expression | EST | Mm.14253 | TITLE ESTs, Weakly similar to similar to molybdoterin biosynthesis MOEB proteins [*C. elegans*] | | | gi = 2288824 | 959131 |
| IC04785 | UG75 Expression | EST | Mm.144 | TITLE ESTs | | | gi = 2561141 | 1294677 |
| IC04786 | UG75 Expression | EST | Mm.14430 | TITLE ESTs, Weakly similar to scaffold attachment factor B [*R. norvegicus*] | | | gi = 1677755 | 576053 |
| IC04787 | UG75 Expression | EST | Mm.14478 | TITLE ESTs | | | gi = 3394590 | 959398 |
| IC04788 | UG75 Expression | EST | Mm.14486 | TITLE ESTs | | | gi = 1282077 | 1148456 |
| IC04789 | UG75 Expression | EST | Mm.14547 | TITLE ESTs, Weakly similar to crn [*D. melanogaster*] | | | gi = 1808239 | 641670 |
| IC04790 | UG75 Expression | EST | Mm.14569 | TITLE ESTs | | | gi = 4029200 | 894495 |
| IC04791 | UG75 Expression | EST | Mm.14611 | TITLE ESTs | | | gi = 2345928 | 620115 |
| IC04792 | UG75 Expression | EST | Mm.14638 | TITLE ESTs, Moderately similar to HYPOTHETICAL 13.6 KD PROTEIN IN NUP170-ILS1 INTERGENIC REGION [*Saccharomyces cerevisiae*] | | | gi = 2991548 | 717891 |
| IC04793 | UG75 Expression | EST | Mm.1465 | TITLE ESTs | | | gi = 2412014 | 1002454 |
| IC04794 | UG75 Expression | EST | Mm.1468 | TITLE ESTs | | | gi = 5336304 | 619769 |
| IC04795 | UG75 Expression | EST | Mm.14741 | TITLE ESTs, Weakly similar to cypher2 [*M. musculus*] | | | gi = 2964978 | 621768 |
| IC04796 | UG75 Expression | EST | Mm.14787 | TITLE ESTs | | | gi = 3518028 | 973472 |
| IC04797 | UG75 Expression | EST | Mm.1479 | TITLE ESTs | | | gi = 4434343 | 1002781 |
| IC04798 | UG75 Expression | EST | Mm.14864 | TITLE ESTs | | | gi = 1752272 | 1180498 |
| IC04799 | UG75 Expression | EST | Mm.1506 | TITLE ESTs | | | gi = 6078502 | 750204 |
| IC04800 | UG75 Expression | EST | Mm.1511 | TITLE ESTs | | | gi = 5498487 | 973627 |
| IC04801 | UG75 Expression | EST | Mm.1521 | TITLE ESTs | | | gi = 2257214 | 894482 |
| IC04802 | UG75 Expression | EST | Mm.1524 | TITLE ESTs | | | gi = 2626693 | 1162540 |
| IC04803 | UG75 Expression | EST | Mm.15243 | TITLE DNA segment, Chr 17, Wayne State University 160, expressed | GENE D17Wsu160e | | | 533460 |
| IC04804 | UG75 Expression | EST | Mm.153 | TITLE ESTs | | | gi = 3067993 | 572935 |
| IC04805 | UG75 Expression | EST | Mm.15351 | TITLE ESTs, Weakly similar to ankyrin 3 [*M. musculus*] | | | gi = 4032711 | 582082 |
| IC04806 | UG75 Expression | EST | Mm.1538 | TITLE basic transcription factor 3 | GENE Btf3 | | gi = 6084743 | 972481 |
| IC04807 | UG75 Expression | EST | Mm.1543 | TITLE ESTs | | | gi = 1896424 | 637610 |
| IC04808 | UG75 Expression | EST | Mm.155 | TITLE ESTs | | | gi = 2919474 | 617875 |
| IC04809 | UG75 Expression | EST | Mm.1554 | TITLE ESTs | | | gi = 6824674 | 764736 |
| IC04810 | UG75 Expression | EST | Mm.1555 | TITLE ribosomal protein, mitochondrial, L5 | GENE Rpml5 | MRP-L5 | gi = 5906410 | 619401 |
| IC04811 | UG75 Expression | EST | Mm.1560 | TITLE ESTs | | | gi = 5495164 | 619254 |
| IC04812 | UG75 Expression | EST | Mm.1571 | TITLE ESTs | | | gi = 1768201 | 958793 |
| IC04813 | UG75 Expression | EST | Mm.1572 | TITLE ESTs | | | gi = 4286900 | 619710 |
| IC04814 | UG75 Expression | EST | Mm.1581 | TITLE ESTs | | | gi = 2743642 | 621602 |
| IC04815 | UG75 Expression | EST | Mm.1585 | TITLE DNA segment, Chr 13, Abbott 1 expressed | GENE D13Abb1e | | | 637976 |
| IC04816 | UG75 Expression | EST | Mm.1590 | TITLE ESTs | | | gi = 1758718 | 622630 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04817 | UG75 Expression | EST | Mm.15974 | TITLE ESTs | | | gi = 2516421 | 974071 |
| IC04818 | UG75 Expression | EST | Mm.1608 | TITLE ESTs, Weakly similar to zinc finger protein ZNF216 [M. musculus] | | | gi = 3883273 | 622433 |
| IC04819 | UG75 Expression | EST | Mm.1610 | TITLE ESTs | | | gi = 2916386 | 620310 |
| IC04820 | UG75 Expression | EST | Mm.1622 | TITLE ESTs | | | gi = 1553906 | 621023 |
| IC04821 | UG75 Expression | EST | Mm.1627 | TITLE ESTs | | | gi = 2158210 | 620739 |
| IC04822 | UG75 Expression | EST | Mm.1630 | TITLE ESTs | | | gi = 420950 | 620749 |
| IC04823 | UG75 Expression | EST | Mm.1635 | TITLE ESTs | | | gi = 2646036 | 1149803 |
| IC04824 | UG75 Expression | EST | Mm.1643 | TITLE ESTs | | | gi = 1759699 | 620988 |
| IC04825 | UG75 Expression | EST | Mm.1648 | TITLE ESTs | | | gi = 1759838 | 621202 |
| IC04826 | UG75 Expression | EST | Mm.1653 | TITLE ESTs | | | gi = 2521302 | 620640 |
| IC04827 | UG75 Expression | EST | Mm.1654 | TITLE ESTs, Moderately similar to CGI-48 protein [H. sapiens] | | | gi = 4601353 | 621302 |
| IC04828 | UG75 Expression | EST | Mm.1659 | TITLE ESTs | | | gi = 3519828 | 639093 |
| IC04829 | UG75 Expression | EST | Mm.16796 | TITLE ESTs | | | gi = 2283055 | 616727 |
| IC04830 | UG75 Expression | EST | Mm.16813 | TITLE ESTs, Moderately similar to Similar to S. pombe-rad4+/cut5+product [H. sapiens] | | | gi = 1765654 | 638432 |
| IC04831 | UG75 Expression | EST | Mm.1687 | TITLE ESTs | | | gi = 2965596 | 635907 |
| IC04832 | UG75 Expression | EST | Mm.1689 | TITLE ESTs | | | gi = 6939600 | 721087 |
| IC04833 | UG75 Expression | EST | Mm.16925 | TITLE ESTs, Moderately similar to EUKARYOTIC INITIATION FACTOR 4A [Caenorhabditis elegans] | | | gi = 2517461 | 620199 |
| IC04834 | UG75 Expression | EST | mm.16959 | | | | gi = 4726742 | 636563 |
| IC04835 | UG75 Expression | EST | Mm.1706 | TITLE ESTs | | | gi = 1765568 | 575370 |
| IC04836 | UG75 Expression | EST | Mm.17096 | TITLE ESTs | | | gi = 3369505 | 634725 |
| IC04837 | UG75 Expression | EST | Mm.17156 | TITLE ESTs, Weakly similar to HYPOTHETICAL 139.1 KD PROTEIN C08B11.3 IN CHROMOSOME II [Caenorhabditis elegans] | | | gi = 3956554 | 582125 |
| IC04838 | UG75 Expression | EST | Mm.17166 | TITLE ESTs | | | gi = 2919777 | 635918 |
| IC04839 | UG75 Expression | EST | Mm.1717 | TITLE ESTs | | | gi = 6824066 | 1265190 |
| IC04840 | UG75 Expression | EST | Mm.17173 | TITLE ESTs | | | gi = 4602204 | 636244 |
| IC04841 | UG75 Expression | EST | Mm.1719 | TITLE ESTs | | | gi = 297508 | 636419 |
| IC04842 | UG75 Expression | EST | Mm.1722 | TITLE speckle-type POZ protein | GENE Spop | | gi = 6084285 | 533286 |
| IC04843 | UG75 Expression | EST | Mm.17224 | TITLE ESTs | | | gi = 2919734 | 636558 |
| IC04844 | UG75 Expression | EST | Mm.1725 | TITLE ESTs | | | gi = 2305966 | 1280040 |
| IC04845 | UG75 Expression | EST | Mm.17272 | TITLE ESTs, Weakly similar to SIG41 [M. musculus] | | | gi = 6084203 | 973905 |
| IC04846 | UG75 Expression | EST | Mm.17307 | TITLE ESTs | | | gi = 3067221 | 1446262 |
| IC04847 | UG75 Expression | EST | Mm.17331 | TITLE ESTs | | | gi = 2292155 | 643182 |
| IC04848 | UG75 Expression | EST | Mm.17333 | TITLE ESTs | | | gi = 1725891 | 581796 |
| IC04849 | UG75 Expression | EST | Mm.17341 | TITLE ESTs | | | gi = 4300356 | 576038 |
| IC04850 | UG75 Expression | EST | Mm.17343 | TITLE ESTs | | | gi = 3336272 | 1380607 |
| IC04851 | UG75 Expression | EST | Mm.17353 | TITLE ESTs | | | gi = 2192233 | 1447073 |
| IC04852 | UG75 Expression | EST | Mm.17359 | TITLE ESTs | | | gi = 3718542 | 1749195 |
| IC04853 | UG75 Expression | EST | Mm.17436 | TITLE ESTs, Weakly similar to DNA-binding protein [M. musculus] | | | gi = 4614360 | 575358 |
| IC04854 | UG75 Expression | EST | Mm.17448 | TITLE ESTs | | | gi = 1872582 | 765777 |
| IC04855 | UG75 Expression | EST | Mm.17453 | TITLE EST | | | gi = 3079036 | 1329306 |
| IC04856 | UG75 Expression | EST | Mm.17454 | TITLE ESTs | | | gi = 3079719 | 1330086 |
| IC04857 | UG75 Expression | EST | Mm.17456 | TITLE ESTs | | | gi = 3079738 | 1330104 |
| IC04858 | UG75 Expression | EST | Mm.17457 | | | | | |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04859 | UG75 Expression | EST | Mm.17459 | TITLE EST | | | gi = 3079831 | 1330294 |
| IC04860 | UG75 Expression | EST | Mm.17503 | TITLE ESTs | | | gi = 4788723 | 1888266 |
| IC04861 | UG75 Expression | EST | Mm.17523 | TITLE ESTs, Weakly similar to ORF YOL071w [*S. cerevisiae*] | | | gi = 4434125 | 533892 |
| IC04862 | UG75 Expression | EST | Mm.17526 | TITLE ESTs | | | gi = 4968432 | 620302 |
| IC04863 | UG75 Expression | EST | Mm.17537 | TITLE ESTs, Weakly similar to cDNA EST yk47sb4.5 comes from this gene [*C. elegans*] | | | gi = 6633201 | 533761 |
| IC04864 | UG75 Expression | EST | Mm.17580 | TITLE ESTs | | | gi = 4783060 | 572365 |
| IC04865 | UG75 Expression | EST | Mm.1759 | TITLE ESTs | | | gi = 2292165 | 622656 |
| IC04866 | UG75 Expression | EST | Mm.17592 | TITLE ESTs | | | gi = 4601003 | 622879 |
| IC04867 | UG75 Expression | EST | Mm.1760 | TITLE ESTs | | | gi = 1767802 | 622659 |
| IC04868 | UG75 Expression | EST | Mm.17639 | TITLE ESTs | | | gi = 3372920 | 577236 |
| IC04869 | UG75 Expression | EST | Mm.17643 | TITLE ESTs | | | gi = 6633430 | 1329295 |
| IC04870 | UG75 Expression | EST | Mm.17647 | TITLE ESTs | | | gi = 6515820 | 1226539 |
| IC04871 | UG75 Expression | EST | Mm.17706 | TITLE ESTs | | | gi = 4604352 | 721769 |
| IC04872 | UG75 Expression | EST | Mm.17787 | TITLE ESTs | | | gi = 3979831 | 618845 |
| IC04873 | UG75 Expression | EST | Mm.17790 | TITLE ESTs | | | gi = 1904220 | 720677 |
| IC04874 | UG75 Expression | EST | Mm.17794 | TITLE ESTs, Weakly similar to acid sphingomyelinase-like phosphodiesterase [*M. musculus*] | | | gi = 3979429 | 1280101 |
| IC04875 | UG75 Expression | EST | Mm.17804 | TITLE ESTs | | | gi = 3980786 | 2647694 |
| IC04876 | UG75 Expression | EST | Mm.17837 | TITLE ESTs | | | gi = 6167939 | 2182784 |
| IC04877 | UG75 Expression | EST | Mm.17840 | TITLE ESTs, Weakly similar to putative CAMP protein [*M-musculus*] | | | gi = 3982144 | 959313 |
| IC04878 | UG75 Expression | EST | Mm.17846 | TITLE ESTs | | | gi = 5497586 | 635247 |
| IC04879 | UG75 Expression | EST | Mm.17853 | TITLE ESTs | | | gi = 4318977 | 721485 |
| IC04880 | UG75 Expression | EST | Mm.1787 | TITLE ESTs | | | gi = 1932122 | 764122 |
| IC04881 | UG75 Expression | EST | Mm.17870 | TITLE ESTs | | | gi = 3981950 | 893948 |
| IC04882 | UG75 Expression | EST | Mm.17873 | TITLE ESTs | | | gi = 2892562 | 1139700 |
| IC04883 | UG75 Expression | EST | Mm.17875 | TITLE ESTs | | | gi = 3982021 | 749940 |
| IC04884 | UG75 Expression | EST | Mm.17876 | TITLE ESTs | | | gi = 5910874 | 1264806 |
| IC04885 | UG75 Expression | EST | Mm.17880 | TITLE ESTs, Moderately similar to sodium-D-glucose cotransporter [*H. sapiens*] | | | gi = 1915135 | 722064 |
| IC04886 | UG75 Expression | EST | Mm.17881 | TITLE ESTs | | | gi = 1888693 | 597359 |
| IC04887 | UG75 Expression | EST | Mm.1791 | TITLE ESTs, Moderately similar to DUAL SPECIFICITY PROTEIN PHOSPHATASE 6 [*R. norvegicus*] | | | gi = 49468032 | 620249 |
| IC04888 | UG75 Expression | EST | Mm.17917 | TITLE DNA segment, Chr 4, Wayne State University 27, expressed | GENE D4Wsu27e | | | 618967 |
| IC04889 | UG75 Expression | EST | Mm.17918 | TITLE ESTs | | | gi = 6083664 | 1278941 |
| IC04890 | UG75 Expression | EST | Mm.17925 | TITLE ESTs | | | gi = 1699838 | 596187 |
| IC04891 | UG75 Expression | EST | Mm.17929 | TITLE ESTs | | | gi = 2503662 | 596951 |
| IC04892 | UG75 Expression | EST | Mm.17934 | TITLE EST | | | gi = 1725850 | 599212 |
| IC04893 | UG75 Expression | EST | Mm.17940 | TITLE ESTs, Weakly similar to LIPOAMIDE ACYLTRANSFERASE COMPONENT PRECURSOR OF BRANCHED-CHAIN ALPHA-KETO ACID DEHYDROGENASE COMPLEX [*M. musculus*] | | | gi = 5125692 | 619798 |
| IC04894 | UG75 Expression | EST | Mm.17942 | TITLE ESTs | | | gi = 1756937 | 619574 |
| IC04895 | UG75 Expression | EST | Mm.17949 | TITLE ESTs, Weakly similar to cDNA EST EMBL:D70402 comes from this gene [*C. elegans*] | | | gi = 6167942 | 636284 |
| IC04896 | UG75 Expression | EST | Mm.1795 | TITLE ESTs | | | gi = 1769186 | 637010 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04897 | UG75 Expression | EST | Mm.17951 | TITLE ESTs | | | gi = 2272488 | 636468 |
| IC04898 | UG75 Expression | EST | Mm.17957 | TITLE ESTs | | | gi = 1768990 | 636971 |
| IC04899 | UG75 Expression | EST | Mm.17961 | TITLE ESTs | | | gi = 1776598 | 637938 |
| IC04900 | UG75 Expression | EST | Mm.17962 | TITLE ESTs | | | gi = 1776696 | 643446 |
| IC04901 | UG75 Expression | EST | Mm.17963 | TITLE ESTs | | | gi = 1776858 | 637032 |
| IC04902 | UG75 Expression | EST | Mm.17966 | TITLE ESTs | | | gi = 1776975 | 636653 |
| IC04903 | UG75 Expression | EST | Mm.17970 | TITLE ESTs | | | gi = 3522196 | 635347 |
| IC04904 | UG75 Expression | EST | Mm.17977 | TITLE ESTs | | | gi = 2203694 | 719488 |
| IC04905 | UG75 Expression | EST | Mm.1800 | TITLE ESTs | | | gi = 5322311 | 637029 |
| IC04906 | UG75 Expression | EST | Mm.18001 | TITLE ESTs | | | gi = 3980535 | 764639 |
| IC04907 | UG75 Expression | EST | Mm.18009 | TITLE ESTs | | | gi = 1901237 | 598065 |
| IC04908 | UG75 Expression | EST | Mm.18026 | TITLE ESTs, Moderately similar to G protein pathway suppressor 2 [M. musculus] | | | gi = 4403804 | 972891 |
| IC04909 | UG75 Expression | EST | Mm.1804 | TITLE ESTs | | | gi = 1768731 | 637439 |
| IC04910 | UG75 Expression | EST | Mm.18054 | TITLE ESTs | | | gi = 4603465 | 1248158 |
| IC04911 | UG75 Expression | EST | Mm.1806 | TITLE ESTs | | | gi = 1902426 | 718097 |
| IC04912 | UG75 Expression | EST | Mm.18062 | TITLE ESTs | | | gi = 6520978 | 618675 |
| IC04913 | UG75 Expression | EST | Mm.18098 | TITLE ESTs | | | gi = 3954239 | 933804 |
| IC04914 | UG75 Expression | EST | Mm.18104 | TITLE ESTs | | | gi = 3370054 | 973621 |
| IC04915 | UG75 Expression | EST | Mm.18110 | TITLE ESTs | | | gi = 3079710 | 1330067 |
| IC04916 | UG75 Expression | EST | Mm.18113 | TITLE ESTs | | | gi = 4303691 | 641456 |
| IC04917 | UG75 Expression | EST | Mm.1818 | TITLE ESTs | | | gi = 1768998 | 636997 |
| IC04918 | UG75 Expression | EST | Mm.18185 | TITLE ESTs | | | gi = 2956079 | 1243289 |
| IC04919 | UG75 Expression | EST | Mm.18186 | TITLE ESTs | | | gi = 3954061 | 1225343 |
| IC04920 | UG75 Expression | EST | Mm.1819 | TITLE ESTs | | | gi = 1919516 | 777651 |
| IC04921 | UG75 Expression | EST | Mm.18228 | TITLE ESTs, Weakly similar to unknown [H. sapiens] | | | gi = 5125198 | 1293756 |
| IC04922 | UG75 Expression | EST | Mm.1823 | TITLE ESTs | | | gi = 4616499 | 597626 |
| IC04923 | UG75 Expression | EST | Mm.18230 | TITLE ESTs | | | gi = 6084364 | 1312621 |
| IC04924 | UG75 Expression | EST | Mm.18236 | TITLE EST | | | gi = 3031965 | 1278767 |
| IC04969 | UG75 Expression | EST | Mm.18688 | TITLE ESTs, Weakly similar to ENDOSOMAL P24B PROTEIN PRECURSOR [Saccharomyces cerevisiae] | | | gi = 374847 | 1149201 |
| IC04970 | UG75 Expression | EST | Mm.18712 | TITLE ESTs | | | gi = 6084835 | 1226885 |
| IC04971 | UG75 Expression | EST | Mm.18713 | TITLE ESTs | | | gi = 2917569 | 616636 |
| IC04972 | UG75 Expression | EST | Mm.18714 | TITLE ESTs | | | gi = 6079111 | 1295153 |
| IC04973 | UG75 Expression | EST | Mm.18718 | TITLE ESTs | | | gi = 5495524 | 764929 |
| IC04974 | UG75 Expression | EST | Mm.18725 | TITLE ESTs, Weakly similar to estradiol 17beta-dehydrogenase [M. musculus] | | | gi = 4615177 | 642402 |
| IC04975 | UG75 Expression | EST | Mm.1873 | TITLE ESTs | | | gi = 1776319 | 635293 |
| IC04976 | UG75 Expression | EST | Mm.18737 | TITLE ESTs, Moderately similar to HYPOTHETICAL PROTEIN KIAA0166 [H. sapiens] | | | gi = 6514996 | 642153 |
| IC04977 | UG75 Expression | EST | Mm.18739 | TITLE ESTs | | | gi = 3521672 | 1140105 |
| IC04978 | UG75 Expression | EST | Mm.18758 | TITLE ESTs | | | gi = 1936088 | 576855 |
| IC04979 | UG75 Expression | EST | Mm.18761 | TITLE ESTs | | | gi = 2039831 | 1330359 |
| IC04980 | UG75 Expression | EST | Mm.1878 | TITLE ESTs | | | gi = 6096858 | 637196 |
| IC04981 | UG75 Expression | EST | Mm.18783 | TITLE ESTs | | | gi = 1840525 | 717848 |
| IC04982 | UG75 Expression | EST | Mm.18797 | TITLE ESTs | | | gi = 2991038 | 442369 |
| IC04983 | UG75 Expression | EST | Mm.18802 | TITLE ESTs, Weakly similar to lactotransferrin precursor [M. musculus] | | | gi = 4216644 | 636493 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC04984 | UG75 Expression | EST | Mm.1881 | TITLE ESTs, Moderately similar to serine/threonine protein kinase [M. musculus] | | | gi = 4060370 | 637978 |
| IC04985 | UG75 Expression | EST | Mm.18814 | TITLE ESTs | | | gi = 4433885 | 1294467 |
| IC04986 | UG75 Expression | EST | Mm.18818 | TITLE ESTs | | | gi = 5125718 | 1026372 |
| IC04987 | UG75 Expression | EST | Mm.18819 | TITLE ESTs, Moderately similar to serine/threonine protein kinase [M. musculus] | | | gi = 6077743 | 638353 |
| IC04988 | UG75 Expression | EST | Mm.1882 | TITLE ESTs | | | gi = 1776416 | 637886 |
| IC04989 | UG75 Expression | EST | Mm.18821 | TITLE ESTs, Weakly similar to (defline not available 5764393) [M. musculus] | | | gi = 6518316 | 1264516 |
| IC04990 | UG75 Expression | EST | Mm.18822 | TITLE ESTs | | | gi = 2956453 | 618000 |
| IC04991 | UG75 Expression | EST | Mm.18830 | TITLE ESTs, Weakly similar to LOMP protein [H. sapiens] | | | gi = 1793001 | 640092 |
| IC04992 | UG75 Expression | EST | Mm.18834 | TITLE ESTs, Weakly similar to beta-transducin repeat-containing protein [M. musculus] | | | gi = 1522766 | 596052 |
| IC04993 | UG75 Expression | EST | Mm.18838 | TITLE ESTs | | | gi = 2571976 | 1140132 |
| IC04994 | UG75 Expression | EST | Mm.18856 | TITLE ESTs | | | gi = 3956251 | 1265292 |
| IC04995 | UG75 Expression | EST | Mm.18875 | TITLE ESTs, Weakly similar to VRK2 [H. sapiens] | | | gi = 3295355 | 599086 |
| IC04996 | UG75 Expression | EST | Mm.18879 | TITLE ESTs | | | gi = 3979417 | 598191 |
| IC04997 | UG75 Expression | EST | Mm.1891 | TITLE ESTs | | | gi = 3681704 | 972665 |
| IC04998 | UG75 Expression | EST | Mm.18917 | TITLE ESTs | | | gi = 1655143 | 638646 |
| IC04999 | UG75 Expression | EST | Mm.18922 | TITLE ESTs, Weakly similar to Similarity to Yeast YIP1 protein [C. elegans] | | | gi = 3683340 | 1149438 |
| IC05000 | UG75 Expression | EST | Mm.18938 | TITLE ESTs | | | gi = 3685605 | 1446081 |
| IC05001 | UG75 Expression | EST | Mm.18942 | TITLE ESTs | | | gi = 3956538 | 921812 |
| IC05002 | UG75 Expression | EST | Mm.18957 | TITLE ESTs | | | gi = 1808326 | 557969 |
| IC05003 | UG75 Expression | EST | Mm.18959 | TITLE ESTs, Weakly similar to T10H9.3 [C. elegans] | | | gi = 5336674 | 1363121 |
| IC05004 | UG75 Expression | EST | Mm.1896 | TITLE ESTs | | | gi = 1908533 | 597070 |
| IC05005 | UG75 Expression | EST | Mm.18965 | TITLE ESTs | | | gi = 5498157 | 581998 |
| IC05006 | UG75 Expression | EST | Mm.18968 | TITLE ESTs | | | gi = 3234264 | 621402 |
| IC05007 | UG75 Expression | EST | Mm.18979 | TITLE ESTs | | | gi = 2967061 | 643430 |
| IC05008 | UG75 Expression | EST | Mm.1898 | TITLE ESTs | | | gi = 5492482 | 637913 |
| IC05009 | UG75 Expression | EST | Mm.18998 | TITLE ESTs | | | gi = 1725857 | 599236 |
| IC05010 | UG75 Expression | EST | Mm.19000 | TITLE ESTs, Moderately similar to HYPOTHETICAL PROTEIN KIAA0039 [H. sapiens] | | | gi = 3374865 | 576845 |
| IC05011 | UG75 Expression | EST | Mm.19003 | TITLE ESTs | | | gi = 4032442 | 616692 |
| IC05012 | UG75 Expression | EST | Mm.19006 | TITLE ESTs, Weakly similar to Closely related to Arabidopsis thaliana gene T9J22.7 [C. elegans] | | | gi = 2517976 | 973099 |
| IC05013 | UG75 Expression | EST | Mm.1902 | TITLE ESTs | | | gi = 2721691 | 620601 |
| IC05014 | UG75 Expression | EST | Mm.19029 | TITLE ESTs, Moderately similar to HEM45 [H. sapiens] | | | gi = 1282674 | 551661 |
| IC05015 | UG75 Expression | EST | Mm.19031 | TITLE ESTs | | | gi = 4444847 | 575848 |
| IC05016 | UG75 Expression | EST | Mm.1905 | TITLE ESTs | | | gi = 4663921 | 643372 |
| IC05017 | UG75 Expression | EST | Mm.19055 | TITLE ESTs, Weakly similar to contains similarity to Saccharomyces cerevisiae, MAF1 protein [C. elegans] | | | gi = 2305792 | 534108 |
| IC05018 | UG75 Expression | EST | Mm.19059 | TITLE ESTs | | | gi = 1700513 | 596539 |
| IC05019 | UG75 Expression | EST | Mm.19073 | TITLE ESTs | | | gi = 2305863 | 973566 |
| IC05020 | UG75 Expression | EST | Mm.19077 | TITLE ESTs | | | gi = 4276174 | 1282707 |
| IC05021 | UG75 Expression | EST | Mm.19082 | TITLE ESTs | | | gi = 4604485 | 1481053 |
| IC05022 | UG75 Expression | EST | Mm.19091 | TITLE ESTs | | | gi = 3956881 | 635895 |
| IC05023 | UG75 Expression | EST | Mm.19092 | TITLE ESTs | | | gi = 1309554 | 1140221 |
| IC05024 | UG75 Expression | EST | Mm.1911 | TITLE ESTs | | | gi = 6632417 | 643792 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05025 | UG75 Expression | EST | Mm.19126 | TITLE ESTs, Moderately similar to GAMETOGENESIS EXPRESSED PROTEIN GEG-154 [M. musculus] | | | gi = 2282821 | 2655171 |
| IC05026 | UG75 Expression | EST | Mm.1915 | TITLE ESTs | | | gi = 1838672 | 1278902 |
| IC05027 | UG75 Expression | EST | Mm.19168 | TITLE ESTs | | | gi = 3981651 | 1193525 |
| IC05028 | UG75 Expression | EST | Mm.19172 | TITLE ESTs | | | gi = 2744015 | 722367 |
| IC05029 | UG75 Expression | EST | Mm.19184 | TITLE ESTs | | | gi = 1662995 | 636312 |
| IC05030 | UG75 Expression | EST | Mm.19185 | TITLE ESTs, Moderately similar to IMMUNE SUPPRESSOR FACTOR J6B7 [Mus musculus] | | | gi = 4730228 | 1429573 |
| IC05031 | UG75 Expression | EST | Mm.1919 | TITLE ESTs | | | gi = 4725106 | 636699 |
| IC05032 | UG75 Expression | EST | Mm.192 | TITLE ESTs, Moderately similar to putative 13 S Golgi transport complex 90kD subunit brain-specific isoform [H. sapiens] | | | gi = 5337052 | 619406 |
| IC05033 | UG75 Expression | EST | Mm.1921 | TITLE ESTs, Moderately similar to KIAA0826 protein [H. sapiens] | | | gi = 5666318 | 1140280 |
| IC05034 | UG75 Expression | EST | Mm.1925 | TITLE ESTs | | | gi = 1777099 | 636932 |
| IC05035 | UG75 Expression | EST | Mm.19258 | TITLE ESTs | | | gi = 6085030 | 1264675 |
| IC05036 | UG75 Expression | EST | Mm.19271 | TITLE ESTs | | | gi = 4029547 | 1361968 |
| IC05037 | UG75 Expression | EST | Mm.19273 | TITLE ESTs | | | gi = 6167786 | 653227 |
| IC05038 | UG75 Expression | EST | Mm.19281 | TITLE ESTs | | | gi = 2560711 | 577165 |
| IC05039 | UG75 Expression | EST | Mm.19288 | TITLE ESTs | | | gi = 4030173 | 595994 |
| IC05040 | UG75 Expression | EST | Mm.19316 | TITLE ESTs | | | gi = 4030973 | 577992 |
| IC05041 | UG75 Expression | EST | Mm.1939 | TITLE ESTs | | | gi = 1777231 | 637974 |
| IC05042 | UG75 Expression | EST | Mm.19390 | TITLE ESTs, Weakly similar to polypeptide GalNAc transferase-T1 [M. musculus] | | | gi = 4726930 | 634861 |
| IC05043 | UG75 Expression | EST | Mm.19395 | TITLE ESTs | | | gi = 4440816 | 622560 |
| IC05044 | UG75 Expression | EST | Mm.1947 | TITLE ESTs | | | gi = 6008738 | 721443 |
| IC05045 | UG75 Expression | EST | Mm.1960 | TITLE ESTs | | | gi = 3808527 | 1263131 |
| IC05046 | UG75 Expression | EST | Mm.19761 | TITLE ESTs | | | gi = 4726596 | 617338 |
| IC05047 | UG75 Expression | EST | Mm.19799 | TITLE ESTs, Weakly similar to ubiquitin-conjugating enzyme UbcM2 [M. musculus] | | | gi = 1862224 | 599190 |
| IC05048 | UG75 Expression | EST | Mm.198 | TITLE ESTs, Moderately similar to type II membrane protein [H. sapiens] | | | gi = 3394072 | 1433791 |
| IC05049 | UG75 Expression | EST | Mm.19802 | TITLE ESTs | | | gi = 4029287 | 959219 |
| IC05050 | UG75 Expression | EST | Mm.19803 | TITLE DNA segment, Chr 8, Wayne State University 49, expressed | GENE D8Wsu49e | | gi = 3393836 | 637353 |
| IC05051 | UG75 Expression | EST | Mm.19804 | TITLE ESTs | | | gi = 4061585 | 718441 |
| IC05052 | UG75 Expression | EST | Mm.19844 | TITLE ESTs | | | gi = 3956213 | 1329349 |
| IC05053 | UG75 Expression | EST | Mm.1985 | TITLE ESTs, Moderately similar to similar to yeast SSU72 [H. sapiens] | | | gi = 4061233 | 1367254 |
| IC05054 | UG75 Expression | EST | Mm.19895 | TITLE ESTs, Weakly similar to LIGHT-MEDIATED DEVELOPMENT PROTEIN DET1 [Arabidopsis thaliana] | | | gi = 2292516 | 641521 |
| IC05055 | UG75 Expression | EST | Mm.19937 | TITLE ESTs, Weakly similar to VITAMIN K-DEPENDENT GAMMA-CARBOXYLASE [Homo sapiens] | | | gi = 4450425 | 597206 |
| IC05056 | UG75 Expression | EST | Mm.19942 | TITLE ESTs | | | gi = 6526118 | 317039 |
| IC05057 | UG75 Expression | EST | Mm.19962 | TITLE ESTs, Moderately similar to SAV PROTEIN [Sulfolobus acidocaldarius] | | | gi = 4060426 | 958639 |
| IC05058 | UG75 Expression | EST | Mm.19963 | TITLE ESTs, Weakly similar to INTERFERON-INDUCIBLE PROTEIN 9-27 [Homo sapiens] | | | | 597616 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05059 | UG75 Expression | EST | Mm.19967 | TITLE ESTs, Weakly similar to ENV POLYPROTEIN [Mouse mammary tumor virus (strain br6)] | | | gi = 1934544 | 598838 |
| IC05060 | UG75 Expression | EST | Mm.19973 | TITLE ESTs, Weakly similar to HYPOTHETICAL 54.9 KD PROTEIN C02F5.7 IN CHROMOSOME III [Caenorhabditis elegans] | | | gi = 1479110 | 464118 |
| IC05061 | UG75 Expression | EST | Mm.19974 | TITLE ESTs, Moderately similar to ADULT ENHANCER FACTOR 1 [Drosophila melanogaster] | | | gi = 5861137 | 752361 |
| IC05062 | UG75 Expression | EST | Mm.19980 | TITLE ESTs | | | gi = 2272362 | 583540 |
| IC05063 | UG75 Expression | EST | Mm.19992 | TITLE ESTs, Moderately similar to dJ30M3.3 [H. sapiens] | | | gi = 6751147 | 1296063 |
| IC05064 | UG75 Expression | EST | Mm.2000 | TITLE ESTs | | | gi = 1385164 | 657428 |
| IC05065 | UG75 Expression | EST | Mm.2001 | TITLE ESTs, Weakly similar to 1-evidence | | | gi = 2049066 | 751573 |
| IC05066 | UG75 Expression | EST | Mm.20046 | TITLE ESTs, Moderately similar to DEMATIN [Homo sapiens] | | | gi = 4273299 | 635714 |
| IC05067 | UG75 Expression | EST | Mm.2005 | TITLE ESTs | | | gi = 4537664 | 1329464 |
| IC05068 | UG75 Expression | EST | Mm.20064 | TITLE ESTs | | | gi = 4060361 | 582564 |
| IC05069 | UG75 Expression | EST | Mm.20065 | TITLE ESTs | | | gi = 4060390 | 583454 |
| IC05070 | UG75 Expression | EST | Mm.20066 | TITLE ESTs, Weakly similar to PROBABLE PEPTIDYL-TRNA HYDROLASE [Bacillus subtilis] | | | gi = 2967212 | 583513 |
| IC05071 | UG75 Expression | EST | Mm.20074 | TITLE EST, Moderately similar to putative pheromone receptor [M. musculus] | | | gi = 4060521 | 618401 |
| IC05072 | UG75 Expression | EST | Mm.20078 | TITLE EST | | | gi = 4060586 | 635011 |
| IC05073 | UG75 Expression | EST | Mm.20114 | TITLE ESTs | | | gi = 4060906 | 550913 |
| IC05074 | UG75 Expression | EST | Mm.2013 | TITLE ESTs | | | gi = 1318344 | 657458 |
| IC05075 | UG75 Expression | EST | Mm.20138 | TITLE EST | | | gi = 4061707 | 558169 |
| IC05076 | UG75 Expression | EST | Mm.20144 | TITLE EST | | | gi = 4061766 | 575044 |
| IC05077 | UG75 Expression | EST | Mm.20145 | TITLE EST | | | gi = 4061771 | 575308 |
| IC05078 | UG75 Expression | EST | Mm.20147 | TITLE EST, Weakly similar to ARYLSULFATASE B [R. norvegicus] | | | gi = 4061805 | 576780 |
| IC05079 | UG75 Expression | EST | Mm.20148 | TITLE ESTs | | | gi = 4061819 | 577384 |
| IC05080 | UG75 Expression | EST | Mm.20152 | TITLE ESTs, Moderately similar to ELONGATION FACTOR 2 [Drosophila melanogaster] | | | gi = 4765343 | 765431 |
| IC05081 | UG75 Expression | EST | Mm.20156 | TITLE ESTs, Moderately similar to HYPOTHETICAL 29.5 KD PROTEIN C05B5.7 IN CHROMOSOME III [Caenorhabditis elegans] | | | gi = 1297547 | 973563 |
| IC05082 | UG75 Expression | EST | Mm.20169 | TITLE ESTs, Moderately similar to MUSCLE-SPECIFIC DNASE I-LIKE PRECURSOR [Homo sapiens] | | | gi = 4059314 | 642800 |
| IC05083 | UG75 Expression | EST | Mm.20212 | TITLE ESTs | | | gi = 4064798 | 1279899 |
| IC05084 | UG75 Expression | EST | Mm.20219 | TITLE ESTs | | | gi = 4061785 | 616966 |
| IC05085 | UG75 Expression | EST | Mm.20242 | TITLE ESTs | | | gi = 2283122 | 764070 |
| IC05086 | UG75 Expression | EST | Mm.20245 | TITLE ESTs, Moderately similar to N-acetylglucosamine-phosphate mutase [H. sapiens] | | | gi = 6633244 | 1330134 |
| IC05087 | UG75 Expression | EST | Mm.20246 | TITLE ESTs, Moderately similar to L-ASPARAGINASE [Lupinus angustifolius] | | | gi = 3718341 | 550910 |
| IC05088 | UG75 Expression | EST | Mm.20249 | TITLE ESTs | | | gi = 4299453 | 639348 |
| IC05089 | UG75 Expression | EST | Mm.20260 | TITLE ESTs, Moderately similar to MALONYL-COA DECARBOXYLAASE PRECURSOR [Anser anser anser] | | | gi = 1862377 | 349376 |
| IC05090 | UG75 Expression | EST | Mm.20273 | TITLE ESTs, Weakly similar to HYPOTHETICAL 11.0 KD PROTEIN IN FAA3-BET1 INTERGENIC REGION [Saccharomyces cerevisiae] | | | gi = 2248573 | 351184 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05091 | UG75 Expression | EST | Mm.20274 | TITLE ESTs, Weakly similar to SEX-REGULATED PROTEIN JANUS-A [*Drosophila melanogaster*] | | | gi = 1309691 | 721244 |
| IC05092 | UG75 Expression | EST | Mm.20276 | TITLE ESTs | | | gi = 2719875 | 598589 |
| IC05093 | UG75 Expression | EST | Mm.20277 | TITLE ESTs, Weakly similar to natural killer cell tumor-recognition protein [*M. musculus*] | | | gi = 4060797 | 721284 |
| IC05094 | UG75 Expression | EST | Mm.20290 | TITLE ESTs, Weakly similar to similar to leucyl-tRNA synthetase [*C. elegans*] | | | gi = 6077156 | 1002873 |
| IC05095 | UG75 Expression | EST | Mm.20292 | TITLE ESTs | | | gi = 4061411 | 582790 |
| IC05096 | UG75 Expression | EST | Mm.20301 | TITLE ESTs, Weakly similar to ZINC FINGER PROTEIN ZFP-27 [*Mus musculus*] | | | gi = 1393803 | 598984 |
| IC05097 | UG75 Expression | EST | Mm.2035 | TITLE ESTs | | | gi = 2292554 | 959330 |
| IC05098 | UG75 Expression | EST | Mm.20387 | TITLE ESTs, Moderately similar to HYPOTHETICAL 68.7 KD PROTEIN ZK757, 1 IN CHROMOSOME III [*Caenorhabditis elegans*] | | | gi = 2965657 | 717803 |
| IC05099 | UG75 Expression | EST | Mm.204 | TITLE ESTs | | | gi = 6515487 | 1149475 |
| IC05100 | UG75 Expression | EST | Mm.20403 | TITLE ESTs, Moderately similar to ZINC FINGER PROTEIN MFG2 [*Mus musculus*] | | | gi = 4060344 | 581997 |
| IC05101 | UG75 Expression | EST | Mm.20407 | TITLE ESTs, Weakly similar to pancreatic lipase related protein 1 [*M. musculus*] | | | gi = 4060801 | 1077403 |
| IC05102 | UG75 Expression | EST | Mm.20417 | TITLE ESTs | | | gi = 2918518 | 637135 |
| IC05103 | UG75 Expression | EST | Mm.2046 | TITLE ESTs | | | gi = 2139566 | 619399 |
| IC05104 | UG75 Expression | EST | Mm.20488 | TITLE ESTs | | | gi = 3377172 | 596359 |
| IC05105 | UG75 Expression | EST | Mm.20491 | TITLE ESTs | | | gi = 4434110 | 764569 |
| IC05106 | UG75 Expression | EST | Mm.2053 | TITLE ESTs, Weakly similar to cDNA EST yk448c11.3 comes from this gene [*C. elegans*] | | | gi = 1811303 | 638549 |
| IC05107 | UG75 Expression | EST | Mm.20543 | TITLE ESTs | | | gi = 4434104 | 1193664 |
| IC05108 | UG75 Expression | EST | Mm.20592 | TITLE ESTs | | | gi = 5488794 | 568849 |
| IC05109 | UG75 Expression | EST | Mm.20675 | TITLE ESTs | | | gi = 3373679 | 721667 |
| IC05110 | UG75 Expression | EST | Mm.2069 | TITLE ESTs, Weakly similar to ALPHA-1,3-MANNOSYL-GLYCOPROTEIN BETA-1,2-N-ACETYLGLUCOSAMINYLTRANSFERASE [*M. musculus*] | | | gi = 2503015 | 640648 |
| IC05111 | UG75 Expression | EST | Mm.20693 | TITLE ESTs | | | gi = 3978774 | 722651 |
| IC05112 | UG75 Expression | EST | Mm.20697 | TITLE ESTs | | | gi = 6098628 | 618537 |
| IC05113 | UG75 Expression | EST | Mm.20703 | TITLE ESTs | | | gi = 2962577 | 621555 |
| IC05114 | UG75 Expression | EST | Mm.2072 | TITLE ESTs | | | gi = 1913107 | 764641 |
| IC05115 | UG75 Expression | EST | Mm.20722 | TITLE ESTs | | | gi = 3393222 | 1295259 |
| IC05116 | UG75 Expression | EST | Mm.2073 | TITLE ESTs | | | gi = 6822457 | 721476 |
| IC05117 | UG75 Expression | EST | Mm.208 | TITLE ESTs | | | gi = 5749632 | 718826 |
| IC05118 | UG75 Expression | EST | Mm.20805 | TITLE ESTs | | | gi = 3167614 | 636031 |
| IC05119 | UG75 Expression | EST | Mm.20806 | TITLE ESTs | | | gi = 4802562 | 846060 |
| IC05120 | UG75 Expression | EST | Mm.2085 | TITLE EST | | | gi = 1800786 | 643775 |
| IC05121 | UG75 Expression | EST | Mm.20877 | TITLE DNA segment, Chr 5, Abbott 2 expressed | GENE D5Abb2e | | gi = 1800882 | 558038 |
| IC05122 | UG75 Expression | EST | Mm.2089 | TITLE EST | | | gi = 5334979 | 640676 |
| IC05123 | UG75 Expression | EST | Mm.2097 | TITLE ESTs | | | gi = 5498025 | 644422 |
| IC05124 | UG75 Expression | EST | Mm.21048 | TITLE ESTs | | | gi = 6084153 | 1312564 |
| IC05125 | UG75 Expression | EST | Mm.21064 | TITLE ESTs, Weakly similar to osmosis responsive factor [*H. sapiens*] | | | gi = 2192769 | 621834 |
| IC05126 | UG75 Expression | EST | Mm.21065 | TITLE ESTs | | | | 617450 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05127 | UG75 Expression | EST | Mm.21067 | TITLE ESTs, Weakly similar to schwannoma-associated binding protein [M. musculus] | | | gi = 3602337 | 619295 |
| IC05128 | UG75 Expression | EST | Mm.21069 | TITLE ESTs, Moderately similar to heat shock factor binding protein 1 HSBP1 [H. sapiens] | | | gi = 5124721 | 1279900 |
| IC05129 | UG75 Expression | EST | Mm.21072 | TITLE ESTs, Weakly similar to 230k bullous pemphigoid antigen BPM1 [M. musculus] | | | gi = 1287730 | 574182 |
| IC05130 | UG75 Expression | EST | Mm.21079 | TITLE ESTs, Moderately similar to PROPIONYL-COA CARBOXYLASE BETA CHAIN PRECURSOR [Rattus norvegicus] | | | gi = 4056855 | 719007 |
| IC05131 | UG75 Expression | EST | Mm.21081 | TITLE ESTs, Weakly similar to ABC transporter-7 [M. musculus] | | | gi = 5332975 | 621650 |
| IC05132 | UG75 Expression | EST | Mm.21082 | TITLE ESTs | | | gi = 4802596 | 719251 |
| IC05133 | UG75 Expression | EST | Mm.21092 | TITLE ESTs | | | gi = 6078898 | 96101 |
| IC05134 | UG75 Expression | EST | Mm.21093 | TITLE ESTs | | | gi = 2920059 | 765019 |
| IC05135 | UG75 Expression | EST | Mm.21094 | TITLE DNA segment, Chr 9, Wayne State University 138, expressed | GENE D9Wsu138e | | | 973488 |
| IC05136 | UG75 Expression | EST | Mm.21096 | TITLE ESTs, Moderately similar to Era GTPase A protein [H. sapiens] | | | gi = 3375382 | 1294286 |
| IC05137 | UG75 Expression | EST | Mm.21099 | TITLE ESTs | | | gi = 4482516 | 1294594 |
| IC05138 | UG75 Expression | EST | Mm.21103 | TITLE DNA segment, Chr 7, Wayne State University 128, expressed | GENE D7Wsu128e | | | 404256 |
| IC05139 | UG75 Expression | EST | Mm.21104 | TITLE ESTs, Weakly similar to hypothetical protein [H. sapiens] | | | gi = 2990839 | 722522 |
| IC05140 | UG75 Expression | EST | Mm.21105 | TITLE ESTs, Weakly similar to waclaw [D. melanogaster] | | | gi = 2292502 | 1149147 |
| IC05141 | UG75 Expression | EST | Mm.21110 | TITLE ESTs | | | gi = 5338057 | 2064656 |
| IC05142 | UG75 Expression | EST | Mm.21119 | Alpha Factor [H. sapiens] | | | gi = 2812775 | 533592 |
| IC05143 | UG75 Expression | EST | Mm.21126 | TITLE ESTs, Weakly similar to coronin-3 [M. musculus] | | | gi = 6517068 | 1002459 |
| IC05144 | UG75 Expression | EST | Mm.21128 | TITLE ESTs | | | gi = 1539036 | 596628 |
| IC05145 | UG75 Expression | EST | Mm.21130 | TITLE ESTs | | | gi = 1872943 | 643195 |
| IC05146 | UG75 Expression | EST | Mm.21132 | TITLE ESTs, Weakly similar to signal recognition particle 54K protein [M. musculus] | | | gi = 3066474 | 1020778 |
| IC05147 | UG75 Expression | EST | Mm.21135 | TITLE ESTs | | | gi = 2516654 | 850819 |
| IC05148 | UG75 Expression | EST | Mm.21138 | TITLE ESTs | | | gi = 2517219 | 1278766 |
| IC05149 | UG75 Expression | EST | Mm.21146 | TITLE ESTs | | | gi = 2520464 | 805285 |
| IC05150 | UG75 Expression | EST | Mm.21160 | TITLE ESTs, Moderately similar to COLIPASE PRECURSOR [Rattus morvegicus] | | | gi = 4061358 | 481341 |
| IC05151 | UG75 Expression | EST | Mm.21162 | TITLE ESTs, Moderately similar to CGI-39 protein [H. sapiens] | | | gi = 1575965 | 1750038 |
| IC05152 | UG75 Expression | EST | Mm.21173 | TITLE ESTs, Weakly similar to unknown [S. cerevisiae] | | | gi = 1330547 | 634162 |
| IC05153 | UG75 Expression | EST | Mm.21177 | TITLE ESTs | | | gi = 3394226 | 622067 |
| IC05154 | UG75 Expression | EST | Mm.21183 | TITLE ESTs | | | gi = 2307931 | 1282655 |
| IC05155 | UG75 Expression | EST | Mm.21184 | TITLE DNA segment, Chr 2, Wayne State University 58, expressed | GENE D2Wsu58e | | | 621715 |
| IC05156 | UG75 Expression | EST | Mm.21186 | TITLE ESTs, Weakly similar to cDNA EST EMBL:C08125 comes from this gene [C. elegans] | | | gi = 3955507 | 316913 |
| IC05157 | UG75 Expression | EST | Mm.21187 | TITLE ESTs | | | gi = 3522540 | 643886 |
| IC05158 | UG75 Expression | EST | Mm.21199 | TITLE ESTs | | | gi = 4409516 | 718091 |
| IC05159 | UG75 Expression | EST | Mm.21200 | TITLE ESTs | | | gi = 6750317 | 597563 |
| IC05160 | UG75 Expression | EST | Mm.21201 | TITLE ESTs | | | gi = 3955600 | 574861 |

US 6,706,867 B1

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05161 | UG75 Expression | EST | Mm.21207 | TITLE ESTs, Moderately similar to CGI-106 protein [H. sapiens] | | | gi = 4031343 | 1001899 |
| IC05162 | UG75 Expression | EST | Mm.21209 | TITLE ESTs | | | gi = 4303873 | 635138 |
| IC05163 | UG75 Expression | EST | Mm.2121 | TITLE ESTs, Weakly similar to INTERFERON-INDUCED PROTEIN 6-16 PRECURSOR [Homo sapiens] | | | gi = 421714 | 1148909 |
| IC05164 | UG75 Expression | EST | Mm.21211 | TITLE ESTs | | | gi = 3286319 | 644065 |
| IC05165 | UG75 Expression | EST | Mm.21212 | TITLE ESTs, Weakly similar to CARBOXYPEPTIDASE H PRECURSOR [M. musculus] | | | gi = 3294656 | 1451515 |
| IC05166 | UG75 Expression | EST | Mm.21214 | TITLE ESTs, Moderately similar to hypothetical protein [H. sapiens] | | | gi = 3369511 | 551251 |
| IC05167 | UG75 Expression | EST | Mm.21218 | TITLE ESTs, Weakly similar to Ydr327cp [S. cerevisiae] | | | gi = 5819817 | 618927 |
| IC05168 | UG75 Expression | EST | Mm.21228 | TITLE ESTs, Weakly similar to /prediction | | | gi = 4596886 | 616852 |
| IC05169 | UG75 Expression | EST | Mm.21230 | TITLE ESTs | | | gi = 3374299 | 764856 |
| IC05170 | UG75 Expression | EST | Mm.21231 | TITLE ESTs | | | gi = 4450369 | 618551 |
| IC05171 | UG75 Expression | EST | Mm.21241 | TITLE ESTs, Weakly similar to ATP(GTP)-binding protein [H. sapiens] | | | gi = 3955594 | 595997 |
| IC05172 | UG75 Expression | EST | Mm.21265 | TITLE ESTs, Weakly similar to (define not available 6016842) [M. musculus] | | | gi = 4275723 | 1263233 |
| IC05173 | UG75 Expression | EST | Mm.21274 | TITLE ESTs, Weakly similar to C54G7.2 gene product [C. elegans] | | | gi = 1826788 | 1225063 |
| IC05174 | UG75 Expression | EST | Mm.21281 | TITLE ESTs | | | gi = 2516777 | 894169 |
| IC05175 | UG75 Expression | EST | Mm.21284 | TITLE ESTs | | | gi = 3395052 | 1312931 |
| IC05176 | UG75 Expression | EST | Mm.21286 | TITLE ESTs, Weakly similar to HC1 ORF [M. musculus] | | | gi = 1792972 | 618449 |
| IC05177 | UG75 Expression | EST | Mm.21287 | TITLE ESTs, Weakly similar to coded for by C. elegans cDNA yk44f2.5 [C. elegans] | | | gi = 1896310 | 1476860 |
| IC05178 | UG75 Expression | EST | Mm.21288 | TITLE ESTs | | | gi = 2308475 | 777238 |
| IC05179 | UG75 Expression | EST | Mm.21289 | TITLE ESTs | | | gi = 4725285 | 1379633 |
| IC05180 | UG75 Expression | EST | Mm.21291 | TITLE ESTs | | | gi = 1406837 | 639444 |
| IC05181 | UG75 Expression | EST | Mm.21295 | TITLE ESTs | | | gi = 6520398 | 764786 |
| IC05182 | UG75 Expression | EST | Mm.21297 | TITLE ESTs, Moderately similar to NY-REN-45 antigen [H. sapiens] | | | gi = 2518785 | 1265543 |
| IC05183 | UG75 Expression | EST | Mm.21299 | TITLE ESTs | | | gi = 4967862 | 618651 |
| IC05184 | UG75 Expression | EST | Mm.21302 | TITLE ESTs | | | gi = 2518153 | 1125162 |
| IC05185 | UG75 Expression | EST | Mm.21313 | TITLE ESTs | | | gi = 2306618 | 637982 |
| IC05186 | 00/04/26 UG#76 UG75 Expression | EST | Mm.2133 | TITLE ESTs, Weakly similar to KIAA0167 protein [H. sapiens] | | | gi = 4405090 | 480995 |
| IC05187 | 17Lid Expansion | EST | Mm.21331 | ESTs | | | gi = 3979146 | 1383100 |
| IC05188 | UG75 Expression | EST | Mm.21344 | TITLE ESTs | | | gi = 3373151 | 622548 |
| IC05189 | UG75 Expression | EST | Mm.21353 | TITLE ESTs, Weakly similar to contains strong similarity to a DNA-J-like domain [C. elegans] | | | gi = 6078615 | 1140223 |
| IC05190 | UG75 Expression | EST | Mm.21356 | TITLE ESTs [D. melanogaster] | | | gi = 2625718 | 973271 |
| IC05191 | UG75 Expression | EST | Mm.21406 | TITLE ESTs, Moderately similar to antigen NY-CO-3 [H. sapiens] | | | gi = 4271563 | 1139842 |
| IC05192 | UG75 Expression | EST | Mm.21407 | TITLE ESTs | | | gi = 3165015 | 1225937 |
| IC05193 | UG75 Expression | EST | Mm.21409 | TITLE ESTs, Moderately similar to p80 [R. norvegicus] | | | gi = 1309688 | 958780 |
| IC05194 | UG75 Expression | EST | Mm.21414 | TITLE ESTs copper chaperone for superoxide dismutase | GENE Ccsd | CCS| | gi = 3749179 | 851631 |
| IC05195 | UG75 Expression | EST | Mm.21420 | TITLE ESTs | | | gi = 3152904 | 1295800 |
| IC05196 | UG75 Expression | EST | Mm.21421 | SKELETAL MUSCLE ISOFORM PRECURSOR [M. musculus] | | | gi = 2291681 | 558211 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05197 | UG75 Expression | EST | Mm.21428 | TITLE ESTs | | | gi = 5338111 | 1279442 |
| IC05198 | UG75 Expression | EST | Mm.21431 | TITLE ESTs | | | gi = 3718289 | 619928 |
| IC05199 | UG75 Expression | EST | Mm.21439 | TITLE ESTs, Weakly similar to choline-phosphate cytidylyltransferase [M. musculus] | | | gi = 4726481 | 1148644 |
| IC05200 | UG75 Expression | EST | Mm.21440 | TITLE ESTs, Weakly similar to LYSOSOMAL PRO-X CARBOXYPEPTIDASE PRECURSOR [H. sapiens] | | | gi = 2461554 | 596274 |
| IC05201 | UG75 Expression | EST | Mm.21441 | TITLE ESTs | | | gi = 1682390 | 533626 |
| IC05202 | UG75 Expression | EST | Mm.21446 | TITLE ESTs, Weakly similar to sh3bgr protein [M. musculus] | | | gi = 3519287 | 958964 |
| IC05203 | UG75 Expression | EST | Mm.21450 | TITLE ESTs | | | gi = 1493644 | 1279058 |
| IC05204 | UG75 Expression | EST | Mm.21452 | TITLE ESTs | | | gi = 3809206 | 596288 |
| IC05205 | UG75 Expression | EST | Mm.21453 | TITLE ESTs, Moderately similar to HYPOTHETICAL 28.5 KD PROTEIN ZK1236.7 IN CHROMOSOME III [Caenorhabditis elegans] | | | gi = 4316149 | 551579 |
| IC05206 | UG75 Expression | EST | Mm.21455 | TITLE ESTs | | | gi = 2518119 | 577573 |
| IC05207 | UG75 Expression | EST | Mm.21463 | TITLE ESTs, Weakly similar to CALCINEURIN B SUBUNIT [Naegleria gruberi] | | | gi = 4060347 | 623075 |
| IC05208 | UG75 Expression | EST | Mm.21469 | TITLE ESTs | | | gi = 3386684 | 636516 |
| IC05209 | UG75 Expression | EST | Mm.21470 | TITLE ESTs, Weakly similar to M03F8.2 [C. elegans] | | | gi = 6517818 | 1295813 |
| IC05210 | UG75 Expression | EST | Mm.21474 | TITLE ESTs, Weakly similar to COLLAGEN ALPHA 1(XI) CHAIN PRECURSOR [M. musculus] | | | gi = 2067400 | 764199 |
| IC05211 | UG75 Expression | EST | Mm.21475 | TITLE ESTs, Weakly similar to 17-beta-hydroxysteroid dehydrogenase type II [M. musculus] | | | gi = 2520204 | 644893 |
| IC05212 | UG75 Expression | EST | Mm.21480 | TITLE ESTs, Moderately similar to HYPOTHETICAL ADRENODOXIN-LIKE 10.5 KD PROTEIN IN HSP67BC 3'REGION [Drosophila melanogaster] | | | gi = 2292384 | 1149364 |
| IC05213 | UG75 Expression | EST | Mm.21485 | TITLE ESTs | | | gi = 5910536 | 1446268 |
| IC05214 | UG75 Expression | EST | Mm.21489 | TITLE ESTs | | | gi = 3126020 | 764470 |
| IC05215 | UG75 Expression | EST | Mm.21492 | TITLE ESTs, Weakly similar to DNA-BINDING PROTEIN SMUBP-2 [M. musculus] | | | gi = 1826312 | 1279772 |
| IC05216 | UG75 Expression | EST | Mm.21495 | TITLE ESTs | | | gi = 1768376 | 620313 |
| IC05217 | UG75 Expression | EST | Mm.21500 | TITLE ESTs | | | gi = 3167721 | 621562 |
| IC05218 | UG75 Expression | EST | Mm.21501 | TITLE ESTs, Weakly similar to head-elevated expression in 0.9 kb [D. melanogaster] | | | gi = 3286408 | 973598 |
| IC05219 | UG75 Expression | EST | Mm.21503 | TITLE ESTs | | | gi = 6633289 | 636463 |
| IC05220 | UG75 Expression | EST | Mm.21504 | TITLE ESTs | | | gi = 1766770 | 636164 |
| IC05221 | UG75 Expression | EST | Mm.21505 | TITLE ESTs, Moderately similar to CYSTEINYL-TRNA SYNTHETASE [H. sapiens] | | | gi = 4605233 | 636216 |
| IC05222 | UG75 Expression | EST | Mm.21510 | TITLE ESTs | | | gi = 4317530 | 622706 |
| IC05223 | UG75 Expression | EST | Mm.21514 | TITLE ESTs, Weakly similar to KIAA0869 protein [H. sapines] | | | gi = 2306647 | 1279317 |
| IC05224 | UG75 Expression | EST | Mm.21516 | TITLE ESTs | | | gi = 2523615 | 1295994 |
| IC05225 | UG75 Expression | EST | Mm.21518 | TITLE ESTs | | | gi = 1677527 | 722627 |
| IC05226 | UG75 Expression | EST | Mm.21520 | TITLE ESTs, Weakly similar to GARP45 [M. musculus] | | | gi = 2462030 | 959049 |
| IC05227 | UG75 Expression | EST | Mm.2152 | TITLE ESTs [H. sapiens] | | | gi = 4729906 | 642761 |
| IC05228 | UG75 Expression | EST | Mm.21521 | TITLE ESTs | | | gi = 1699565 | 596030 |
| IC05229 | UG75 Expression | EST | Mm.21523 | TITLE ESTs | | | gi = 2917242 | 622334 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05230 | UG75 Expression | EST | Mm.21524 | TITLE ESTs | | | gi = 5490495 | 634607 |
| IC05231 | UG75 Expression | EST | Mm.21532 | TITLE ESTs | | | gi = 1479030 | 749466 |
| IC05232 | UG75 Expression | EST | Mm.21536 | TITLE ESTs | | | gi = 1407897 | 631917 |
| IC05233 | UG75 Expression | EST | Mm.21537 | TITLE ESTs | | | gi = 3954015 | 638641 |
| IC05234 | UG75 Expression | EST | Mm.21538 | TITLE ESTs | | | gi = 1904808 | 643814 |
| IC05235 | UG75 Expression | EST | Mm.21549 | TITLE DNA segment, Chr 5, University of California at Los Angeles 4 | GENE D5Ucla4 | | | 1243513 |
| IC05236 | UG75 Expression | EST | Mm.21551 | TITLE ESTs | | | gi = 2813073 | 638387 |
| IC05237 | UG75 Expression | EST | Mm.21553 | TITLE ESTs, Weakly similar to KIAA0308 [*H. sapiens*] | | | gi = 3393676 | 558214 |
| IC05238 | UG75 Expression | EST | Mm.21556 | TITLE ESTs | | | gi = 4441986 | 1139638 |
| IC05239 | UG75 Expression | EST | Mm.21559 | TITLE ESTs, Moderately similar to PTB-ASSOCIATED SPLICING FACTOR [*Homo sapiens*] | | | gi = 4967687 | 973188 |
| IC05240 | UG75 Expression | EST | Mm.21568 | TITLE ESTs, Weakly similar to CIRP [*M. musculus*] | | | gi = 3393951 | 637174 |
| IC05241 | UG75 Expression | EST | Mm.21571 | TITLE ESTs | | | gi = 6521029 | 617527 |
| IC05242 | UG75 Expression | EST | Mm.21572 | TITLE ESTs | | | gi = 2404035 | 721983 |
| IC05243 | UG75 Expression | EST | Mm.21577 | TITLE ESTs | | | gi = 3981025 | 765815 |
| IC05244 | UG75 Expression | EST | Mm.21586 | TITLE ESTs, Moderately similar to TOM1-like protein [*H. sapiens*] | | | gi = 2520903 | 717939 |
| IC05245 | UG75 Expression | EST | Mm.21593 | TITLE ESTs | | | gi = 1528152 | 722946 |
| IC05246 | UG75 Expression | EST | Mm.21596 | TITLE ESTs, Weakly similar to HYPOTHETICAL 91.2 KD PROTEIN IN RPS7A-SCH9 INTERGENIC REGION [*Saccharomyces cerevisiae*] | | | gi = 2350307 | 972732 |
| IC05247 | UG75 Expression | EST | Mm.21597 | TITLE ESTs | | | gi = 2041034 | 720285 |
| IC05248 | UG75 Expression | EST | Mm.21600 | TITLE ESTs | | | gi = 1484074 | 638619 |
| IC05249 | UG75 Expression | EST | Mm.21606 | TITLE reticulon 3 | GENE Rtn3 | myeloblastin | gi = 6083537 | 1280038 |
| IC05250 | UG75 Expression | EST | Mm.21612 | TITLE ESTs, Weakly similar to striatin [*M. musculus*] | | | gi = 1309573 | 721399 |
| IC05251 | UG75 Expression | EST | Mm.21617 | TITLE ESTs, Weakly similar to EUKARYOTIC TRANSLATION INITIATION FACTOR 3 BETA SUBUNIT [*H. sapiens*] | | | gi = 4968357 | 622486 |
| IC05252 | UG75 Expression | EST | Mm.21623 | TITLE ESTs, Weakly similar to retinal short-chain dehydrogenase/reductase [*M. musculus*] | | | gi = 6077323 | 1139639 |
| IC05253 | UG75 Expression | EST | Mm.21629 | TITLE ATP-binding cassette, sub-family F(GCN20), member 2 | GENE Abcf2 | | gi = 6008438 | 1367279 |
| IC05254 | UG75 Expression | EST | Mm.21630 | TITLE ESTs | | | gi = 3387196 | 1294184 |
| IC05255 | UG75 Expression | EST | Mm.21637 | TITLE ESTs | | | gi = 1759905 | 894152 |
| IC05256 | UG75 Expression | EST | Mm.21640 | TITLE ESTs | | | gi = 1759905 | 894152 |
| IC05257 | UG75 Expression | EST | Mm.21645 | TITLE ESTs, Weakly similar to ring-box protein 1 [*M. musculus*] | | | gi = 2291745 | 1193441 |
| IC05258 | UG75 Expression | EST | Mm.21646 | TITLE ESTs | | | gi = 1725561 | 765669 |
| IC05259 | UG75 Expression | EST | Mm.21649 | TITLE ESTs | | | gi = 3374914 | 749507 |
| IC05260 | UG75 Expression | EST | Mm.21652 | TITLE ESTs | | | gi = 1325792 | 894305 |
| IC05261 | UG75 Expression | EST | Mm.21655 | TITLE ESTs | | | gi = 2039513 | 617818 |
| IC05262 | UG75 Expression | EST | Mm.21659 | TITLE ESTs, Weakly similar to myelin transcription factor 1-like [*M. musculus*] | | | gi = 3167993 | 1312084 |
| IC05263 | UG75 Expression | EST | Mm.21662 | TITLE ESTs | GENE D5Wsu45e | | gi = 1318135 | 551333 |
| IC05264 | UG75 Expression | EST | Mm.21671 | TITLE DNA segment, Chr 5, Wayne State University 45, expressed | GENE D5Wsu45e | | | 958769 |
| IC05265 | UG75 Expression | EST | Mm.21673 | TITLE DNA segment, Chr 2, Wayne State University 101, expressed | GENE D2Wsu101e | | | 749398 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05266 | UG75 Expression | EST | Mm.21679 | TITLE ESTs, Moderately similiar to GENE 33 POLYPEPTIDE [R. norvegicus] | | | gi = 5336471 | 5335595 |
| IC05267 | UG75 Expression | EST | Mm.21684 | TITLE ESTs | | | gi = 6084686 | 551473 |
| IC05268 | UG75 Expression | EST | Mm.21686 | TITLE ESTs, Moderately similar to cofactor E [H. sapiens] | | | gi = 3160623 | 1312856 |
| IC05269 | UG75 Expression | EST | Mm.21687 | TITLE ESTs | | | gi = 4216960 | 749252 |
| IC05270 | UG75 Expression | EST | Mm.21688 | TITLE ESTs | | | gi = 3033197 | 1295086 |
| IC05271 | UG75 Expression | EST | Mm.21690 | TITLE ESTs | | | gi = 5910332 | 1139937 |
| IC05272 | UG75 Expression | EST | Mm.21691 | TITLE ESTs | | | gi = 2074735 | 718974 |
| IC05273 | UG75 Expression | EST | Mm.21693 | TITLE ESTs, Moderately similar to MAK16 PROTEIN [Saccharomyces cerevisiae] | | | gi = 2461335 | 973954 |
| IC05274 | UG75 Expression | EST | Mm.21697 | TITLE ESTs | | | gi = 6719835 | 313367 |
| IC05275 | UG75 Expression | EST | Mm.21698 | TITLE ESTs | | | gi = 1558175 | 765596 |
| IC05276 | UG75 Expression | EST | Mm.21705 | TITLE ESTs, Weakly similar to autoimmunogenic cancer/testis antigen NY-ESO-1 [H. sapiens] | | | gi = 2116485 | 1265170 |
| IC05277 | UG75 Expression | EST | Mm.21707 | TITLE ESTs, Weakly similar to cDNA EST EMBL:D71020 comes from this gene [C. elegans] | | | gi = 1309624 | 1279796 |
| IC05278 | UG75 Expression | EST | Mm.21714 | TITLE ESTs, Weakly similar to H21P03.2 [C. elegans] | | | gi = 2308157 | 1293721 |
| IC05279 | UG75 Expression | EST | Mm.2173 | TITLE ESTs, Moderately similar to similar to a human major CRK-binding protein DOCK180. [H. sapiens] | | | gi = 6097702 | 598105 |
| IC05280 | UG75 Expression | EST | Mm.21735 | TITLE ESTs | | | gi = 2519929 | 765860 |
| IC05281 | UG75 Expression | EST | Mm.21744 | TITLE ESTs | | | gi = 4199023 | 1264028 |
| IC05282 | UG75 Expression | EST | Mm.21749 | TITLE ESTs | | | gi = 1918795 | 1002853 |
| IC05283 | UG75 Expression | EST | Mm.21759 | TITLE ESTs, Weakly similar to RAS-RELATED PROTEIN RAB-3A [M. musculus] | | | gi = 2811526 | 1295875 |
| IC05284 | UG75 Expression | EST | Mm.21761 | TITLE ESTs | | | gi = 4967377 | 973479 |
| IC05285 | UG75 Expression | EST | Mm.21762 | TITLE ESTs, Weakly similar to PROBABLE PROTEIN DISULFIDE ISOMERASE P5 PRECURSOR [Mesocricetus auratus] | | | gi = 6077423 | 551635 |
| IC05286 | UG75 Expression | EST | Mm.21771 | TITLE ESTs, Weakly similar to HYPOTHETICAL 92.1 KD PROTEIN C24H6.03 IN CHROMOSOME I [Schizosaccharomyces pombe] | | | gi = 2991318 | 973655 |
| IC05287 | UG75 Expression | EST | Mm.21773 | TITLE ESTs | | | gi = 2257318 | 596006 |
| IC05288 | UG75 Expression | EST | Mm.21783 | TITLE ESTs | | | gi = 4315291 | 1362472 |
| IC05289 | UG75 Expression | EST | Mm.21787 | TITLE ESTs, Weakly similar to HSPCO34 protein [H. sapiens] | | | gi = 2558833 | 576344 |
| IC05290 | UG75 Expression | EST | Mm.21793 | TITLE ESTs | | | gi = 3068049 | 597857 |
| IC05291 | UG75 Expression | EST | Mm.21798 | TITLE ESTs | | | gi = 2284403 | 751838 |
| IC05292 | UG75 Expression | EST | Mm.21802 | TITLE ESTs, Moderately similar to (define not available 5931553) [M. musculus] | | | gi = 4968131 | 557871 |
| IC05293 | UG75 Expression | EST | Mm.21803 | TITLE ESTs | | | gi = 2519621 | 973130 |
| IC05294 | UG75 Expression | EST | Mm.21819 | TITLE ESTs, Weakly similar to NUCLEAR AND CYTOPLASMIC POLYADENYLATED RNA-BINDING PROTEIN PUB1 [Saccharomyces cerevisiae] | | | gi = 1309774 | 722604 |
| IC05295 | UG75 Expression | EST | Mm.21824 | TITLE ESTs | | | gi = 3375314 | 622748 |
| IC05296 | UG75 Expression | EST | Mm.21832 | TITLE ESTs | | | gi = 3685708 | 1378730 |
| IC05297 | UG75 Expression | EST | Mm.21836 | TITLE ESTs | | | gi = 3370086 | 643376 |
| IC05298 | UG75 Expression | EST | Mm.21848 | TITLE ESTs, Weakly similar to unknown [R. morvegicus] | | | gi = 7200551 | 1002828 |
| IC05299 | UG75 Expression | EST | Mm.21854 | TITLE ESTs | | | gi = 2517363 | 1020733 |
| IC05300 | UG75 Expression | EST | Mm.21859 | TITLE ESTs, Weakly similar to Lpi2p [S. serevisiae] | | | gi = 1826936 | 972832 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05301 | UG75 Expression | EST | Mm.21864 | TITLE ESTs | | | gi = 1325716 | 596892 |
| IC05302 | UG75 Expression | EST | Mm.21873 | TITLE ESTs | | | gi = 3376800 | 1295316 |
| IC05303 | UG75 Expression | EST | Mm.21876 | TITLE ESTs | | | gi = 1504470 | 640017 |
| IC05304 | UG75 Expression | EST | Mm.21881 | TITLE ESTs, Weakly similar to similar to ATPases associated with various cellular activities [*C. elegans*] | | | gi = 1315795 | 618849 |
| IC05305 | UG75 Expression | EST | Mm.21897 | TITLE ESTs, Moderately similar to R31180_1 [*H. sapiens*] | | | gi = 5819379 | 1020922 |
| IC05306 | UG75 Expression | EST | Mm.219 | TITLE ESTs | | | gi = 3521824 | 1294567 |
| IC05307 | UG75 Expression | EST | Mm.2190 | TITLE ESTs | | | gi = 3521824 | 644843 |
| IC05308 | UG75 Expression | EST | Mm.21902 | TITLE ESTs | | | gi = 2080880 | 750857 |
| IC05309 | UG75 Expression | EST | Mm.21912 | TITLE ESTs | | | gi = 3371677 | 634536 |
| IC05310 | UG75 Expression | EST | Mm.21914 | TITLE ESTs | | | gi = 44617271 | 722516 |
| IC05311 | UG75 Expression | EST | Mm.21915 | TITLE ESTs, Weakly similar to ORF YGL231c [*S. cerevisiae*] | | | gi = 4803575 | 551058 |
| IC05312 | UG75 Expression | EST | Mm.21919 | TITLE ESTs | | | gi = 250578 | 958549 |
| IC05313 | UG75 Expression | EST | Mm.21926 | TITLE ESTs | | | gi = 2517817 | 643346 |
| IC05314 | UG75 Expression | EST | Mm.21935 | TITLE ESTs | | | gi = 2664139 | 551127 |
| IC05315 | UG75 Expression | EST | Mm.21936 | TITLE ESTs, Moderately similar to RAS-RELATED | | | gi = 4443576 | 973471 |
| IC05316 | UG75 Expression | EST | Mm.2194 | TITLE ESTs | | | gi = 1807917 | 722443 |
| IC05317 | UG75 Expression | EST | Mm.21950 | TITLE ESTs, Moderately similar to tetraspan NET-2 [*H. sapiens*] | | | gi = 6824170 | 1749303 |
| IC05318 | UG75 Expression | EST | Mm.21954 | TITLE ESTs | | | gi = 2917067 | 863254 |
| IC05319 | UG75 Expression | EST | Mm.21964 | TITLE ESTs | | | gi = 2334859 | 1279338 |
| IC05320 | UG75 Expression | EST | Mm.21965 | TITLE ESTs, Moderately similar to genethonin 1 [*H. sapiens*] | | | gi = 1539971 | 1293752 |
| IC05321 | UG75 Expression | EST | Mm.21966 | TITLE ESTs, Weakly similar to DMR-N9 PROTEIN [*M. musculus*] | | | gi = 5336903 | 1140268 |
| IC05322 | UG75 Expression | EST | Mm.21972 | TITLE ESTs, Weakly similar to KIAA0512 protein [*H. sapiens*] | | | gi = 4604091 | 639226 |
| IC05323 | UG75 Expression | EST | Mm.21976 | TITLE ESTs | | | gi = 1315991 | 718950 |
| IC05324 | UG75 Expression | EST | Mm.21977 | TITLE ESTs | | | gi = 6008465 | 638554 |
| IC05325 | UG75 Expression | EST | Mm.21978 | TITLE ESTs | | | gi = 1330455 | 578394 |
| IC05326 | UG75 Expression | EST | Mm.21994 | TITLE ESTs | | | gi = 2039583 | 764528 |
| IC05327 | UG75 Expression | EST | Mm.32995 | [*M. musculus*] | | | gi = 2140352 | 642133 |
| IC05328 | UG75 Expression | EST | Mm.22021 | TITLE ESTs | | | gi = 1282683 | 750707 |
| IC05329 | UG75 Expression | EST | Mm.22027 | TITLE ESTs | | | gi = 3375234 | 1067108 |
| IC05330 | UG75 Expression | EST | Mm.22028 | TITLE ESTs, Moderately similar to BILIBERDIN REDUCTASE A PRECURSOR [*Rattus norvegicus*] | | | gi = 4060900 | 550841 |
| IC05331 | UG75 Expression | EST | Mm.22029 | TITLE ESTs, Weakly similar to putative mitogen-activated protein kinase kinase kinase [*H. sapiens*] | | | gi = 3375445 | 1265140 |
| IC05332 | UG75 Expression | EST | Mm.22030 | TITLE ESTs | | | gi = 2262580 | 1293617 |
| IC05333 | UG75 Expression | EST | Mm.22031 | TITLE ESTs | | | gi = 2282724 | 618648 |
| IC05334 | UG75 Expression | EST | Mm.22040 | TITLE ESTs | | | gi = 2250185 | 973061 |
| IC05335 | UG75 Expression | EST | Mm.22044 | [*M. musculus*] | | | gi = 6077326 | 958543 |
| IC05336 | UG75 Expression | EST | Mm.22047 | TITLE ESTs | | | gi = 2262896 | 634913 |
| IC05337 | UG75 Expression | EST | Mm.22056 | TITLE ESTs | | | gi = 3372566 | 620127 |
| IC05338 | UG75 Expression | EST | Mm.22073 | TITLE ESTs | | | gi = 2308340 | 1278952 |
| IC05339 | UG75 Expression | EST | Mm.22086 | TITLE ESTs, Weakly similar to Ariadne-2 protein [*M. musculus*] | | | gi = 6805403 | 596073 |
| IC05340 | UG75 Expression | EST | Mm.22103 | TITLE ribosomal protein S19 | GENE Rps19 | | gi = 4603196 | 973642 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05341 | UG75 Expression | EST | Mm.22107 | TITLE ESTs | | | gi = 2919938 | 581834 |
| IC05342 | UG75 Expression | EST | Mm.22108 | TITLE ESTs | | | gi = 2990589 | 1311269 |
| IC05343 | UG75 Expression | EST | Mm.22109 | TITLE ESTs, Weakly similar to (define not available 5852158) [*M. musculus*] | | | gi = 5336550 | 1278697 |
| IC05344 | UG75 Expression | EST | Mm.22111 | TITLE ESTs | | | gi = 2979010 | 1281466 |
| IC05345 | UG75 Expression | EST | Mm.22114 | TITLE ESTs | | | gi = 1325891 | 1279660 |
| IC05346 | UG75 Expression | EST | Mm.22115 | TITLE ESTs | | | gi = 1937015 | 550680 |
| IC05347 | UG75 Expression | EST | Mm.22123 | TITLE DNA segment, Chr 15, Wayne State University 75, expressed | GENE D15Wsu75e | | | 752416 |
| IC05348 | UG75 Expression | EST | Mm.22133 | TITLE ESTs | | | gi = 2258891 | 644929 |
| IC05349 | UG75 Expression | EST | Mm.22136 | TITLE ESTs, Weakly similar to 1-evidence | | | gi = 3395015 | 764789 |
| IC05350 | UG75 Expression | EST | Mm.22145 | TITLE ESTs | | | gi = 2917553 | 1345942 |
| IC05351 | UG75 Expression | EST | Mm.22147 | TITLE ESTs, Weakly similar to putative G-protein [*M. musculus*] | | | gi = 2284523 | 749264 |
| IC05352 | UG75 Expression | EST | Mm.22152 | TITLE ESTs | | | gi = 2861777 | 574966 |
| IC05353 | UG75 Expression | EST | Mm.22161 | TITLE ESTs | | | gi = 2813611 | 972825 |
| IC05354 | UG75 Expression | EST | Mm.22168 | TITLE ESTs, Moderately similar to CALPONIN, ACIDIC ISOFORM [*Rattus norvegicus*] | | | gi = 4316386 | 1295558 |
| IC05355 | UG75 Expression | EST | Mm.22171 | TITLE ESTs | | | gi = 6077027 | 749861 |
| IC05356 | UG75 Expression | EST | Mm.22176 | TITLE ESTs | | | gi = 4291634 | 720860 |
| IC05357 | UG75 Expression | EST | Mm.22179 | TITLE ESTs, Weakly similar to hypothetical 43.2 kDa protein [*H. sapiens*] | | | gi = 2305614 | 972365 |
| IC05358 | UG75 Expression | EST | Mm.22180 | TITLE ESTs | | | gi = 2049105 | 596352 |
| IC05359 | UG75 Expression | EST | Mm.22183 | TITLE ESTs | | | gi = 5333019 | 718539 |
| IC05360 | UG75 Expression | EST | Mm.22185 | TITLE ESTs | | | gi = 3375435 | 973153 |
| IC05361 | UG75 Expression | EST | Mm.22188 | TITLE ESTs | | | gi = 3521279 | 619060 |
| IC05362 | UG75 Expression | EST | Mm.22189 | TITLE ESTs, Moderately similar to NEURONAL Protein [*Felis cattus*] | | | gi = 1910564 | 634943 |
| IC05363 | UG75 Expression | EST | Mm.22192 | TITLE ESTs | | | gi = 3684531 | 723055 |
| IC05364 | UG75 Expression | EST | Mm.22193 | TITLE ESTs | | | gi = 4596938 | 620046 |
| IC05365 | UG75 Expression | EST | Mm.22202 | TITLE ESTs | | | gi = 2647099 | 641611 |
| IC05366 | UG75 Expression | EST | Mm.22213 | TITLE ESTs | | | gi = 2989228 | 749461 |
| IC05367 | UG75 Expression | EST | Mm.22214 | TITLE ESTs | | | gi = 3519465 | 1363791 |
| IC05368 | UG75 Expression | EST | Mm.22218 | TITLE ESTs | | | gi = 2292269 | 643241 |
| IC05369 | UG75 Expression | EST | Mm.22225 | TITLE ESTs, Weakly similar to Trif [*M. musculus*] | | | gi = 1282325 | 973084 |
| IC05370 | UG75 Expression | EST | Mm.22226 | TITLE ESTs | | | gi = 6822520 | 1296042 |
| IC05371 | UG75 Expression | EST | Mm.22238 | TITLE ESTs, Weakly similar to sh2bgr protein | | | gi = 1808569 | 1294862 |
| IC05372 | UG75 Expression | EST | Mm.22240 | TITLE ESTs, Weakly similar to transporter protein [*M. musculus*] | | | gi = 1394179 | 1001364 |
| IC05373 | UG75 Expression | EST | Mm.22242 | TITLE ESTs | | | gi = 6084017 | 1362536 |
| IC05374 | UG75 Expression | EST | Mm.22244 | TITLE ESTs, Moderately similar to DNAJ PROTEIN [*Mycoplasma genitalium*] | | | gi = 6084804 | 958997 |
| IC05375 | UG75 Expression | EST | Mm.22246 | TITLE ESTs, Moderately similar to neuromedin B precursor [*R. norvegicus*] | | | gi = 5906518 | 577022 |
| IC05376 | UG75 Expression | EST | Mm.22248 | TITLE differentially expressed in B16F10.2 | GENE Deb2 | Band 3A| | gi = 1315977 | 621852 |
| IC05377 | UG75 Expression | EST | Mm.22249 | TITLE ESTs | | | gi = 3260063 | 751113 |
| IC05378 | UG75 Expression | EST | Mm.22252 | TITLE ESTs | | | gi = 3394077 | 958737 |
| IC05379 | UG75 Expression | EST | Mm.22260 | TITLE ESTs, Weakly similar to transporter protein [*H. sapiens*] | | | gi = 3296895 | 894468 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05380 | UG75 Expression | EST | Mm.22271 | TITLE ESTs, Weakly similar to 573K1.5 [M. musculus] | | | gi = 4276052 | 643818 |
| IC05381 | UG75 Expression | EST | Mm.22280 | TITLE ESTs | | | gi = 4288792 | 619903 |
| IC05382 | UG75 Expression | EST | Mm.22281 | TITLE ESTs, Moderately similar to PUTATIVE REGULATORY PROTEIN TSC-22 [Mus musculus; Rattus norvegicus] | | | gi = 2283290 | 1395625 |
| IC05383 | UG75 Expression | EST | Mm.22283 | TITLE ESTs | | | gi = 4601751 | 596704 |
| IC05384 | UG75 Expression | EST | Mm.22284 | TITLE ESTs, Moderately similar to Pop4 protein [H. sapiens] | | | gi = 1290115 | 642959 |
| IC05385 | UG75 Expression | EST | Mm.22289 | TITLE ESTs | | | gi = 3369942 | 1327497 |
| IC05386 | UG75 Expression | EST | Mm.22294 | TITLE ESTs | | | gi = 2256590 | 1279713 |
| IC05387 | UG75 Expression | EST | Mm.22297 | TITLE ESTs | | | gi = 3215550 | 1363812 |
| IC05388 | UG75 Expression | EST | Mm.22310 | TITLE ESTs | | | gi = 3718912 | 574116 |
| IC05389 | UG75 Expression | EST | Mm.22315 | TITLE ESTs, Moderately similar to hypothetical protein [H. sapiens] | | | gi = 3371860 | 622864 |
| IC05390 | UG75 Expression | EST | Mm.22317 | TITLE ESTs | | | gi = 2917333 | 1294913 |
| IC05391 | UG75 Expression | EST | Mm.22318 | TITLE ESTs, Moderately similar to HYPOTHETICAL | | | gi = 3387678 | 619644 |
| IC05392 | UG75 Expression | EST | Mm.22327 | TITLE ESTs, Moderately similar to HYPOTHETICAL 167.8 KD PROTEIN CCE1-CAP1 INTERGENIC REGION [Saccharomyces cerevisiae] | | | gi = 4061700 | 557899 |
| IC05393 | UG75 Expression | EST | Mm.22333 | TITLE DNA segment, Chr 6, Wayne State University 137, expressed | GENE D6Wsu137e | | | 637336 |
| IC05394 | UG75 Expression | EST | Mm.22334 | TITLE ESTs | | | gi = 2259939 | 1395047 |
| IC05395 | UG75 Expression | EST | Mm.22336 | TITLE ESTs | | | gi = 2989128 | 642820 |
| IC05396 | UG75 Expression | EST | Mm.22337 | TITLE ESTs | | | gi = 2956080 | 1193470 |
| IC05397 | UG75 Expression | EST | Mm.22338 | TITLE ESTs | | | gi = 3371294 | 652923 |
| IC05398 | UG75 Expression | EST | Mm.22343 | TITLE ESTs | | | gi = 2520048 | 617341 |
| IC05399 | UG75 Expression | EST | Mm.22344 | TITLE ESTs | | | gi = 3518898 | 517440 |
| IC05400 | UG75 Expression | EST | Mm.22351 | TITLE ESTs | | | gi = 3165014 | 751732 |
| IC05401 | UG75 Expression | EST | Mm.22353 | TITLE ESTs | | | gi = 1315649 | 577535 |
| IC05402 | UG75 Expression | EST | Mm.22354 | TITLE ESTs [D. melanogaster] | | | gi = 3164949 | 550639 |
| IC05403 | UG75 Expression | EST | Mm.22355 | TITLE ESTs, Weakly similar to KALIRIN [R. norvegicus] | | | gi = 654932 | 1445733 |
| IC05404 | UG75 Expression | EST | Mm.22358 | TITLE ESTs, Weakly similar to TRANSCRIPTION FACTOR S-II-RELATED PROTEIN [M. musculus] | | | gi = 5910333 | 1395196 |
| IC05405 | UG75 Expression | EST | Mm.22360 | TITLE ESTs | | | gi = 3719007 | 777365 |
| IC05406 | UG75 Expression | EST | Mm.22362 | TITLE ESTs | | | gi = 1290057 | 973388 |
| IC05407 | UG75 Expression | EST | Mm.22372 | TITLE ESTs, Moderately similar to INSULIN-DEGRADING ENZYME [R. norvegicus] | | | gi = 2521670 | 598983 |
| IC05408 | UG75 Expression | EST | Mm.22373 | TITLE ESTs | | | gi = 39560005 | 1344374 |
| IC05409 | UG75 Expression | EST | Mm.22374 | TITLE ESTs | | | gi = 1325054 | 1020850 |
| IC05410 | UG75 Expression | EST | Mm.22378 | TITLE ESTs, Moderately similar to CELL SURFACE GLYCOPROTEIN MAC-1 ALPHA SUBUNIT PRECURSOR [mus musculus] | | | gi = 5599624 | 619955 |
| IC05411 | UG75 Expression | EST | Mm.22379 | TITLE ESTs, Weakly similar to Hsp27 ERE-TATA-binding protein [H. sapiens] | | | gi = 5490521 | 621854 |
| IC05412 | UG75 Expression | EST | Mm.22383 | TITLE ESTs, Weakly similar to R07G3.8 [C. elegans] | | | gi = 6085540 | 617456 |
| IC05413 | UG75 Expression | EST | Mm.22397 | TITLE ESTs, Weakly similar to HYPTHETICAL 51.6 KD PROTEIN ZK353.8 IN CHROMOSOME III [Caenorhabditis elegans] | | | gi = 5336312 | 959234 |
| IC05414 | UG75 Expression | EST | Mm.22398 | TITLE ESTs | | | gi = 6558339 | 851677 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05415 | UG75 Expression | EST | Mm.224 | TITLE ESTs | | | gi = 1677862 | 576363 |
| IC05416 | UG75 Expression | EST | Mm.22405 | TITLE ESTs | | | gi = 2721840 | 576186 |
| IC05417 | UG75 Expression | EST | Mm.22409 | TITLE ESTs, Moderately similar to CHLORINE CHANNEL PROTEIN P64 [Bos taurus] | | | gi = 3718738 | 550934 |
| IC05418 | UG75 Expression | EST | Mm.22413 | TITLE ESTs | | | gi = 1738372 | 577490 |
| IC05419 | UG75 Expression | EST | Mm.22414 | TITLE ESTs | | | gi = 3394479 | 721294 |
| IC05420 | UG75 Expression | EST | Mm.22428 | TITLE ESTs | | | gi = 2519508 | 894063 |
| IC05421 | UG75 Expression | EST | Mm.22435 | TITLE ESTs | | | gi = 6939505 | 1293623 |
| IC05422 | UG75 Expression | EST | Mm.22438 | TITLE ESTs | | | gi = 3387691 | 637038 |
| IC05423 | UG75 Expression | EST | Mm.22448 | TITLE ESTs | | | gi = 6558110 | 750602 |
| IC05424 | UG75 Expression | EST | Mm.22453 | TITLE ESTs, Weakly similar to mannose-binding lectin associated serine protease-2 [M. musculus] | | | gi = 6824370 | 777768 |
| IC05425 | UG75 Expression | EST | Mm.22455 | TITLE ESTs | | | gi = 3160532 | 596091 |
| IC05426 | UG75 Expression | EST | Mm.22456 | TITLE ESTs, Weakly similar to contains similarity to transacylases [C. elegans] | | | gi = 2306723 | 598578 |
| IC05427 | UG75 Expression | EST | Mm.22459 | TITLE ESTs | | | gi = 1757030 | 618565 |
| IC05428 | UG75 Expression | EST | Mm.22466 | TITLE ESTs, Weakly similar to Keap1 [M. musculus] | | | gi = 2647094 | 1429621 |
| IC05429 | UG75 Expression | EST | Mm.22467 | SERINE/THREONINE-PROTEIN KINASE TRANSFORMING PROTEIN [Murine sarcoma virus 3611] | | | gi = 2858865 | 620998 |
| IC05430 | UG75 Expression | EST | Mm.22469 | TITLE ESTs | | | gi = 2057486 | 717951 |
| IC05431 | UG75 Expression | EST | Mm.22470 | TITLE ESTs, Moderately similar to weak similarity to Arabidopsis thaliana ubiquitin-like protein 8 [C. elegans] | | | gi = 2692878 | 1149190 |
| IC05432 | UG75 Expression | EST | Mm.22477 | TITLE ESTs, Weakly similar to aquaporin-3 [M. musculus] | | | gi = 3749384 | 1886176 |
| IC05433 | UG75 Expression | EST | Mm.22478 | TITLE ESTs | | | gi = 1475251 | 1149087 |
| IC05434 | UG75 Expression | EST | Mm.22484 | TITLE ESTs | | | gi = 5910548 | 636856 |
| IC05435 | UG75 Expression | EST | Mm.22485 | TITLE ESTs, Weakly similar to Similarity to Yeast D-lactate dehydrogenase [C. elegans] | | | gi = 2813146 | 1365001 |
| IC05436 | UG75 Expression | EST | Mm.22491 | TITLE ESTs, Moderately similar to UBIQUITIN-CONJUGATING ENZYME E2-17 DK [Drosophila melanogaster] | | | gi = 3216011 | 1279165 |
| IC05437 | UG75 Expression | EST | Mm.225 | TITLE ESTs | | | gi = 1932101 | 764043 |
| IC05438 | UG75 Expression | EST | Mm.22504 | TITLE ESTs | | | gi = 3376606 | 764525 |
| IC05439 | UG75 Expression | EST | Mm.22506 | TITLE DNA segment, Chr 17, human D6S56E 5 | GENE D17H6S56E-5 | | | 616602 |
| IC05440 | UG75 Expression | EST | Mm.22511 | TITLE ESTs, Moderately similar to PUTATIVE KINESIN-LIKE PROTEIN T09A5.2 IN CHROMOSOME III [Caenorhabditis elegans] | | | gi = 6008030 | 596897 |
| IC05441 | UG75 Expression | EST | Mm.22513 | TITLE ESTs | | | gi = 4060874 | 533790 |
| IC05442 | UG75 Expression | EST | Mm.22521 | TITLE ESTs | | | gi = 1326691 | 764397 |
| IC05443 | UG75 Expression | EST | Mm.22525 | TITLE ESTs | | | gi = 6096739 | 1148545 |
| IC05444 | UG75 Expression | EST | Mm.22526 | TITLE ESTs, Weakly similar to Rga [D. melanogaster] | | | gi = 2292213 | 644394 |
| IC05445 | UG75 Expression | EST | Mm.22533 | TITLE ESTs | | | gi = 2519524 | 958829 |
| IC05446 | UG75 Expression | EST | Mm.22537 | TITLE ESTs, Moderately similar to ACYL-COA-BINDING PROTEIN [Homo sapiens] | | | gi = 1310333 | 641774 |
| IC05447 | UG75 Expression | EST | Mm.22538 | TITLE ESTs | | | gi = 3978956 | 1327479 |
| IC05448 | UG75 Expression | EST | Mm.22541 | TITLE ESTs, Moderately similar to TUMOR NECROSIS FACTOR RECEPTOR TYPE 1 ASSOCIATED PROTEIN [H. sapiens] | | | gi = 1796110 | 1429751 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05449 | UG75 Expression | EST | Mm.22546 | TITLE ESTs, Weakly similar to DNA-BINDING PROTEIN BMI-1 [Mus musculus] | | | gi = 2306363 | 1295662 |
| IC05450 | UG75 Expression | EST | Mm.22548 | TITLE ESTs | | | gi = 3954186 | 621564 |
| IC05451 | UG75 Expression | EST | Mm.22550 | TITLE ESTs | | | gi = 3299438 | 617814 |
| IC05452 | UG75 Expression | EST | Mm.22552 | TITLE ESTs | | | gi = 2523868 | 1294374 |
| IC05453 | UG75 Expression | EST | Mm.22554 | TITLE ESTs, Moderately similar to MANNOSE-1-PHOSPHATE GUANYLTRANSFERASE [Saccharomyces cerevisiae] | | | gi = 1769067 | 636226 |
| IC05454 | UG75 Expression | EST | Mm.22559 | TITLE ESTs, Moderately similar to NOF1 [H. sapiens] | | | gi = 1287795 | 620600 |
| IC05455 | UG75 Expression | EST | Mm.22565 | TITLE ESTs | | | gi = 4433991 | 751705 |
| IC05456 | UG75 Expression | EST | Mm.22572 | TITLE DNA segment, WI-11513 | GENE WI-11513 | | gi = 2850443 | 1294067 |
| IC05457 | UG75 Expression | EST | Mm.22577 | TITLE ESTs | | | gi = 2273185 | 577424 |
| IC05458 | UG75 Expression | EST | Mm.22581 | TITLE ESTs, Weakly similar to HYPOTHETICAL 15.3 KD PROTEIN E02H1.6 IN CHROMOSOME II [Caenorhabditis elegans] | | | gi = 4061199 | 634250 |
| IC05459 | UG75 Expression | EST | Mm.22582 | TITLE ESTs | | | gi = 2306045 | 720820 |
| IC05460 | UG75 Expression | EST | Mm.22583 | TITLE ESTs, Weakly similar to (define not available 6014925) [M. musculus] | | | gi = 4605117 | 643234 |
| IC05461 | UG75 Expression | EST | Mm.22587 | TITLE ESTs, Weakly similar to protein phosphatase 2A regulatory subunit PR59 [M. musculus] | | | gi = 2516464 | 765018 |
| IC05462 | UG75 Expression | EST | Mm.22588 | TITLE ESTs, Weakly similar to VILLIN [Gallus gallus] | | | gi = 2305977 | 1345133 |
| IC05463 | UG75 Expression | EST | Mm.22594 | TITLE ESTs, Moderately similar to ZINC FINGER PROTEIN 32 [Homo sapiens] | | | gi = 4057066 | 640232 |
| IC05464 | UG75 Expression | EST | Mm.22599 | TITLE ESTs | | | gi = 2517857 | 749909 |
| IC05465 | UG75 Expression | EST | Mm.22615 | TITLE ESTs | | | gi = 1290295 | 777430 |
| IC05466 | UG75 Expression | EST | Mm.22616 | TITLE ESTs | | | gi = 1529228 | 422536 |
| IC05467 | UG75 Expression | EST | Mm.22623 | TITLE ESTs | | | gi = 4276037 | 750760 |
| IC05468 | UG75 Expression | EST | Mm.22627 | TITLE ESTs | | | gi = 2906882 | 597608 |
| IC05469 | UG75 Expression | EST | Mm.22632 | TITLE transgelin 2 | GENE Tagln2 | | gi = 5124734 | 1020758 |
| IC05470 | UG75 Expression | EST | Mm.22634 | TITLE ESTs | | | gi = 2305796 | 1279667 |
| IC05471 | UG75 Expression | EST | Mm.22635 | TITLE ESTs, Weakly similar to HISTIDINE DECARBOXYLASE [M. musculus] | | | gi = 1287038 | 749282 |
| IC05472 | UG75 Expression | EST | Mm.22637 | TITLE ESTs | | | gi = 3286342 | 1345905 |
| IC05473 | UG75 Expression | EST | Mm.22641 | TITLE ESTs | | | gi = 4605760 | 1447058 |
| IC05474 | UG75 Expression | EST | Mm.22645 | TITLE ESTs, Moderately similar to KIAA0979 protein [H. sapiens] | | | gi = 1769259 | 599194 |
| IC05475 | UG75 Expression | EST | Mm.22649 | TITLE ESTs, Weakly similar to UBIQUITIN-CONJUGATING ENZYME E2-17 KD 2 [M. musculus] | | | gi = 4729798 | 533995 |
| IC05476 | UG75 Expression | EST | Mm.22651 | TITLE ESTs | | | gi = 6083874 | 1001823 |
| IC05477 | UG75 Expression | EST | Mm.22653 | TITLE ESTs, Moderately similar to ataxin-2 related protein [H. sapiens] | | | gi = 1564378 | 637847 |
| IC05478 | UG75 Expression | EST | Mm.22659 | TITLE ESTs | | | gi = 4029203 | 1429523 |
| IC05479 | UG75 Expression | EST | Mm.22670 | TITLE ESTs, Moderately similar to G1/S-SPECIFIC CYCLIN E [Rattus norvegicus] | | | gi = 2308338 | 57923 |
| IC05480 | UG75 Expression | EST | Mm.22682 | TITLE ESTs | | | gi = 2306139 | 634599 |
| IC05481 | UG75 Expression | EST | Mm.227 | TITLE ESTs | | | gi = 2305958 | 619565 |
| IC05482 | UG75 Expression | EST | Mm.22705 | TITLE ESTs, Weakly similar to Sp100 [M. musculus] | | | gi = 2306321 | 550979 |
| IC05483 | UG75 Expression | EST | Mm.22712 | TITLE ESTs | | | gi = 2663134 | 1263959 |
| IC05484 | UG75 Expression | EST | Mm.22716 | TITLE ESTs, Moderately similar to PB39 [H. sapiens] | | | gi = 1365906 | 634575 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05485 | UG75 Expression | EST | Mm.22717 | TITLE ESTs | | | gi = 5493199 | 721260 |
| IC05486 | UG75 Expression | EST | Mm.22721 | TITLE ESTs | | | gi = 1297555 | 751584 |
| IC05487 | UG75 Expression | EST | Mm.22722 | TITLE ESTs | | | gi = 5910470 | 596344 |
| IC05488 | UG75 Expression | EST | Mm.22727 | TITLE DNA segment, Chr 17, Wayne State University 51, expressed | GENE D17Wsu51e | | | 598723 |
| IC05489 | UG75 Expression | EST | Mm.22746 | TITLE ESTs, Weakly similar to non-selective cation channel [*M. musculus*] | | | gi = 4032624 | 534015 |
| IC05490 | UG75 Expression | EST | Mm.2275 | TITLE ESTs | | | gi = 2916149 | 719002 |
| IC05491 | UG75 Expression | EST | Mm.22755 | TITLE ESTs | | | gi = 2919759 | 749576 |
| IC05492 | UG75 Expression | EST | Mm.22758 | TITLE ESTs, Weakly similar to MSI [*M. musculus*] | | | gi = 4405747 | 634994 |
| IC05493 | UG75 Expression | EST | Mm.22759 | TITLE ESTs | | | gi = 3371335 | 973957 |
| IC05494 | UG75 Expression | EST | Mm.22765 | TITLE ESTs | | | gi = 2858888 | 618934 |
| IC05495 | UG75 Expression | EST | Mm.22778 | TITLE ESTs | | | gi = 4273223 | 749231 |
| IC05496 | UG75 Expression | EST | Mm.22779 | TITLE ESTs | | | gi = 1919246 | 621341 |
| IC05497 | UG75 Expression | EST | Mm.22786 | TITLE ESTs | | | gi = 1908150 | 722865 |
| IC05498 | UG75 Expression | EST | Mm.22796 | TITLE ESTs | | | gi = 4216107 | 1379864 |
| IC05499 | UG75 Expression | EST | Mm.22799 | TITLE ESTs | | | gi = 4283596 | 581944 |
| IC05500 | UG75 Expression | EST | Mm.22817 | TITLE ESTs | | | gi = 3370220 | 1243349 |
| IC05501 | UG75 Expression | EST | Mm.22819 | TITLE ESTs | | | gi = 4444623 | 1446386 |
| IC05502 | UG75 Expression | EST | Mm.22825 | TITLE ESTs | | | gi = 2247775 | 721652 |
| IC05503 | UG75 Expression | EST | Mm.22829 | TITLE ESTs | | | gi = 4615286 | 973764 |
| IC05504 | UG75 Expression | EST | Mm.22831 | TITLE ESTs | | | gi = 2305677 | 1293816 |
| IC05505 | UG75 Expression | EST | Mm.22836 | TITLE ESTs | | | gi = 4305343 | 643223 |
| IC05506 | UG75 Expression | EST | Mm.22837 | TITLE ESTs | | | gi = 4216481 | 643719 |
| IC05507 | UG75 Expression | EST | Mm.22844 | TITLE ESTs | | | gi = 4271735 | 635127 |
| IC05508 | UG75 Expression | EST | Mm.22845 | TITLE ESTs | | | gi = 4271737 | 1750022 |
| IC05509 | UG75 Expression | EST | Mm.22847 | TITLE ESTs | | | gi = 4271765 | 1263457 |
| IC05510 | UG75 Expression | EST | Mm.22852 | TITLE ESTs | | | gi = 2308255 | 637476 |
| IC05511 | UG75 Expression | EST | Mm.22856 | TITLE ESTs | | | gi = 4615180 | 642430 |
| IC05512 | UG75 Expression | EST | Mm.22878 | TITLE ESTs | | | gi = 6826678 | 550707 |
| IC05513 | UG75 Expression | EST | Mm.22898 | TITLE ESTs | | | gi = 3692574 | 582919 |
| IC05514 | UG75 Expression | EST | Mm.2290 | TITLE ESTs, Moderately similar to HETEROGENEOUS NUCLEAR RIBONUCLEOPROTEIN L [*Homo sapiens*] | | | gi = 5598831 | 752509 |
| IC05515 | UG75 Expression | EST | Mm.2991 | TITLE ESTs | | | gi = 2405909 | 1278833 |
| IC05516 | UG75 Expression | EST | Mm.22915 | TITLE ESTs | | | gi = 4614920 | 1363375 |
| IC05517 | UG75 Expression | EST | Mm.22916 | TITLE ESTs | | | gi = 1796503 | 643606 |
| IC05518 | UG75 Expression | EST | Mm.22919 | TITLE ESTs, Weakly similar to CBF1 interacting corepressor CIR [*H. sapiens*] | | | gi = 5665960 | 2123728 |
| IC05519 | UG75 Expression | EST | Mm.22925 | TITLE ESTs [*M. musculus*] | | | gi = 5919999 | 1002037 |
| IC05520 | UG75 Expression | EST | Mm.22930 | TITLE ESTs, Moderately similar to kl434O14.3.1 [*H. sapiens*] | | | gi = 1751595 | 620060 |
| IC05521 | UG75 Expression | EST | Mm.22934 | TITLE ESTs | | | gi = 2248743 | 598839 |
| IC05522 | UG75 Expression | EST | Mm.22941 | TITLE ESTs | | | gi = 5477381 | 3147010 |
| IC05523 | UG75 Expression | EST | Mm.22942 | TITLE ESTs | | | gi = 3394156 | 1277131 |
| IC05524 | UG75 Expression | EST | Mm.22955 | TITLE ESTs | | | gi = 4450434 | 717585 |
| IC05525 | UG75 Expression | EST | Mm.22960 | TITLE ESTs | | | gi = 4216967 | 575675 |
| IC05526 | UG75 Expression | EST | Mm.22961 | TITLE ESTs, Weakly similar to PBX3a [*M. musculus*] | | | gi = 2979212 | 718319 |
| IC05527 | UG75 Expression | EST | Mm.22969 | TITLE ESTs | | | gi = 5908563 | 639847 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05528 | UG75 Expression | EST | Mm.22986 | TITLE ESTs, Weakly similar to putative glycolipid transfer protein [*H. sapiens*] | | | gi = 4616186 | 1226029 |
| IC05529 | UG75 Expression | EST | Mm.22990 | TITLE ESTs | | | gi = 5497393 | 573168 |
| IC05530 | UG75 Expression | EST | Mm.23 | TITLE ESTs, Moderately similar to 60S RIBOSOMAL PROTEIN L39 [*Rattus norvegicus*] | | | gi = 4613362 | 973008 |
| IC05531 | UG75 Expression | EST | Mm.23006 | TITLE ESTs | | | gi = 6095814 | 637145 |
| IC05532 | UG75 Expression | EST | Mm.23012 | TITLE ESTs | | | gi = 4258359 | 642225 |
| IC05533 | UG75 Expression | EST | Mm.23018 | TITLE ESTs, Weakly similar to similar to the protein phosphates 2c family [*C. elegans*] | | | gi = 2517580 | 598770 |
| IC05534 | UG75 Expression | EST | Mm.23021 | TITLE ESTs, Moderately similar to cain [*R. norvegicus*] | | | gi = 2892408 | 637648 |
| IC05535 | UG75 Expression | EST | Mm.23030 | TITLE ESTs | | | gi = 2462006 | 597879 |
| IC05536 | UG75 Expression | EST | Mm.23035 | TITLE ESTs | | | gi = 5597485 | 622938 |
| IC05537 | UG75 Expression | EST | Mm.2304 | TITLE ESTs | | | gi = 1825881 | 1225493 |
| IC05538 | UG75 Expression | EST | Mm.23054 | TITLE ESTs | | | gi = 6100017 | 348534 |
| IC05539 | UG75 Expression | EST | Mm.23058 | TITLE ESTs | | | gi = 1357067 | 619807 |
| IC05540 | UG75 Expression | EST | Mm.23060 | TITLE ESTs | | | gi = 5125946 | 636838 |
| IC05541 | UG75 Expression | EST | Mm.23068 | TITLE ESTs, Weakly similar to neuronal-specific septin 3 [*M. musculus*] | | | gi = 2721034 | 639440 |
| IC05542 | UG75 Expression | EST | Mm.23073 | TITLE ESTs | | | gi = 4271538 | 371875/ |
| IC05543 | UG75 Expression | EST | Mm.23082 | TITLE ESTs, Moderately similar to LAMIN B RECEPTOR [*Gallus gallus*] | | | gi = 4258922 | 5596054 |
| IC05544 | UG75 Expression | EST | Mm.23090 | TITLE ESTs | | | gi = 1654993 | 620861 |
| IC05545 | UG75 Expression | EST | Mm.23095 | TITLE ESTs | | | gi = 4434388 | 764738 |
| IC05546 | UG75 Expression | EST | Mm.23103 | TITLE ESTs | | | gi = 4259234 | 576753 |
| IC05547 | UG75 Expression | EST | Mm.23108 | TITLE ESTs, Weakly similar to zipper protein kinase [*M. musculus*] | | | gi = 3067230 | 1244396 |
| IC05548 | UG75 Expression | EST | Mm.23122 | TITLE ESTs | | | gi = 3955642 | 637191 |
| IC05549 | UG75 Expression | EST | Mm.23128 | TITLE ESTs | | | gi = 6079132 | 2235942 |
| IC05550 | UG75 Expression | EST | Mm.23132 | TITLE ESTs | | | gi = 1757029 | 638198 |
| IC05551 | UG75 Expression | EST | Mm.23140 | TITLE ESTs | | | gi = 1479001 | 620415 |
| IC05552 | UG75 Expression | EST | Mm.23142 | TITLE ESTs | | | gi = 4315293 | 1002634 |
| IC05553 | UG75 Expression | EST | Mm.2315 | TITLE ESTs | | | gi = 1826464 | 598513 |
| IC05554 | UG75 Expression | EST | Mm.23168 | TITLE ESTs | | | gi = 4603951 | 764174 |
| IC05555 | UG75 Expression | EST | Mm.23173 | TITLE ESTs, Moderately similar to hTOM34p [*H. sapiens*] | | | gi = 2663480 | 972411 |
| IC05556 | UG75 Expression | EST | Mm.23176 | TITLE ESTs | | | gi = 951129 | 622383 |
| IC05557 | UG75 Expression | EST | Mm.23214 | TITLE ESTs | | | gi = 4031149 | 533259 |
| IC05558 | UG75 Expression | EST | Mm.23216 | TITLE ESTs | | | gi = 4272538 | 433426 |
| IC05559 | UG75 Expression | EST | Mm.23217 | TITLE ESTs | | | gi = 4784785 | 533454 |
| IC05560 | UG75 Expression | EST | Mm.23218 | TITLE ESTs | | | gi = 5495284 | 533455 |
| IC05561 | UG75 Expression | EST | Mm.23219 | TITLE ESTs | | | gi = 2918351 | 533525 |
| IC05562 | UG75 Expression | EST | Mm.2322 | TITLE ESTs | | | gi = 3079374 | 550635 |
| IC05563 | UG75 Expression | EST | Mm.23221 | TITLE ESTs | | | gi = 4272570 | 533893 |
| IC05564 | UG75 Expression | EST | Mm.23226 | TITLE ESTs | | | gi = 2075044 | 635117 |
| IC05565 | UG75 Expression | EST | Mm.23230 | TITLE ESTs, Moderately similar to KIAA0933 protein [*H. sapiens*] | | | gi = 4401097 | 533088 |
| IC05566 | UG75 Expression | EST | Mm.23232 | TITLE ESTs | | | gi = 4767401 | 534050 |
| IC05567 | UG75 Expression | EST | Mm.22235 | TITLE ESTs | | | gi = 7064505 | 620189 |
| IC05568 | UG75 Expression | EST | Mm.23236 | TITLE ESTs | | | gi = 5497765 | 550992 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05569 | UG75 Expression | EST | Mm.2325 | TITLE ESTs, Weakly similar to similar to Phosphoglucomutase and phosphomannomutase phosphoserine [*C. elegans*] | | | gi = 2967230 | 643035 |
| IC05570 | UG75 Expression | EST | Mm.23257 | TITLE ESTs | | | gi = 1493664 | 1080231 |
| IC05571 | UG75 Expression | EST | Mm.23263 | TITLE ESTs | | | gi = 6077577 | 1969540 |
| IC05572 | UG75 Expression | EST | Mm.23265 | TITLE ESTs | | | gi = 5489301 | 718918 |
| IC05573 | UG75 Expression | EST | Mm.23273 | TITLE ESTs | | | gi = 1768504 | 617675 |
| IC05574 | UG75 Expression | EST | Mm.23275 | TITLE ESTs | | | gi = 4273026 | 539726 |
| IC05575 | UG75 Expression | EST | Mm.23286 | TITLE ESTs | | | gi = 7192788 | 1446220 |
| IC05576 | UG75 Expression | EST | Mm.23288 | TITLE ESTs | | | gi = 2520116 | 616781 |
| IC05577 | UG75 Expression | EST | Mm.23302 | TITLE ESTs | | | gi = 1776831 | 642950 |
| IC05578 | UG75 Expression | EST | Mm.23310 | TITLE ESTs, Weakly similar to zinc finger protein/transactivator Zfp-38 [*M. musculus*] | | | gi = 3370481 | 894195 |
| IC05579 | UG75 Expression | EST | Mm.23314 | TITLE ESTs | | | gi = 5910864 | 533584 |
| IC05580 | UG75 Expression | EST | Mm.23319 | TITLE ESTs, Moderately similar to NPAT [*H. sapiens*] | | | gi = 4601027 | 623045 |
| IC05581 | UG75 Expression | EST | Mm.23324 | TITLE ESTs | | | gi = 4283700 | 582016 |
| IC05582 | UG75 Expression | EST | Mm.23325 | TITLE ESTs | | | gi = 4273516 | 522083 |
| IC05583 | UG75 Expression | EST | Mm.23329 | TITLE ESTs, Moderately similar to PACSIN [*M. musculus*] | | | gi = 6939068 | 1329568 |
| IC05584 | UG75 Expression | EST | Mm.23344 | TITLE ESTs | | | gi = 1863861 | 1263575 |
| IC05585 | UG75 Expression | EST | Mm.23346 | TITLE ESTs | | | gi = 4604245 | 1149918 |
| IC05586 | UG75 Expression | EST | Mm.23352 | TITLE ESTs, Weakly similar to SULFITE OXIDASE PRECURSOR [*Rattus norvegicus*] | | | gi = 5749949 | 636972 |
| IC05587 | UG75 Expression | EST | Mm.23365 | TITLE ESTs, Weakly similar to ZK1010.2 [*C. elegans*] | | | gi = 4604189 | 893851 |
| IC05588 | UG75 Expression | EST | Mm.23386 | TITLE ESTs | | | gi = 2917923 | 514594 |
| IC05589 | UG75 Expression | EST | Mm.23406 | TITLE EST | | | gi = 4274106 | 550611 |
| IC05590 | UG75 Expression | EST | Mm.23409 | TITLE ESTs | | | gi = 4483042 | 551115 |
| IC05591 | UG75 Expression | EST | Mm.23410 | TITLE ESTs | | | gi = 4483047 | 551139 |
| IC05592 | UG75 Expression | EST | Mm.23411 | TITLE EST | | | gi = 4274166 | 551141 |
| IC05593 | UG75 Expression | EST | Mm.23412 | TITLE ESTs | | | gi = 4483049 | 551166 |
| IC05594 | UG75 Expression | EST | Mm.23414 | TITLE ESTs | | | gi = 2643973 | 551278 |
| IC05595 | UG75 Expression | EST | Mm.23415 | TITLE ESTs | | | gi = 4483068 | 551320 |
| IC05596 | UG75 Expression | EST | Mm.23416 | TITLE EST | | | gi = 4274187 | 551313 |
| IC05597 | UG75 Expression | EST | Mm.23418 | TITLE EST | | | gi = 4274198 | 551387 |
| IC05598 | UG75 Expression | EST | Mm.23419 | TITLE ESTs | | | gi = 4483093 | 551469 |
| IC05599 | UG75 Expression | EST | Mm.23420 | TITLE ESTs | | | gi = 4483094 | 551494 |
| IC05600 | UG75 Expression | EST | Mm.23421 | TITLE EST | | | gi = 4274223 | 551570 |
| IC05601 | UG75 Expression | EST | Mm.23429 | TITLE ESTs, Weakly similar to Weak similarity to Yeast hypothetical protein L8479.1 [*C. elegans*] | | | gi = 2521252 | 1140098 |
| IC05602 | UG75 Expression | EST | Mm.23430 | TITLE ESTs | | | gi = 5265920 | 553454 |
| IC05603 | UG75 Expression | EST | Mm.23437 | TITLE ESTs | | | gi = 4723749 | 581897 |
| IC05604 | UG75 Expression | EST | Mm.32446 | TITLE ESTs | | | gi = 4274405 | 555526 |
| IC05605 | UG75 Expression | EST | Mm.23448 | TITLE ESTs | | | gi = 4725132 | 637379 |
| IC05606 | UG75 Expression | EST | Mm.23462 | TITLE ESTs | | | gi = 2906414 | 1279138 |
| IC05607 | UG75 Expression | EST | Mm.23466 | TITLE ESTs | | | gi = 2811815 | 1225428 |
| IC05608 | UG75 Expression | EST | Mm.23470 | TITLE ESTs | | | gi = 4274712 | 718528 |
| IC05609 | UG75 Expression | EST | Mm.23488 | TITLE ESTs | | | gi = 4274802 | 572287 |
| IC05610 | UG75 Expression | EST | Mm.23493 | TITLE EST | | | gi = 4274826 | 572811 |
| IC05611 | UG75 Expression | EST | Mm.23494 | TITLE ESTs | | | gi = 4625212 | 583909 |
| IC05612 | UG75 Expression | EST | Mm.23495 | TITLE ESTs | | | gi = 4290781 | 572977 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05613 | UG75 Expression | EST | Mm.23496 | TITLE ESTs | | | gi = 5492247 | 573034 |
| IC05614 | UG75 Expression | EST | Mm.23497 | TITLE EST | | | gi = 4274848 | 573044 |
| IC05615 | UG75 Expression | EST | Mm.23498 | TITLE ESTs | | | gi = 4276378 | 573035 |
| IC05616 | UG75 Expression | EST | Mm.23499 | TITLE ESTs | | | gi = 4274856 | 573091 |
| IC05617 | UG75 Expression | EST | Mm.23500 | TITLE ESTs | | | gi = 4274858 | 573121 |
| IC05618 | UG75 Expression | EST | Mm.23503 | TITLE ESTs | | | gb = 3126018 | 1196942 |
| IC05619 | UG75 Expression | EST | Mm.23526 | TITLE ESTs | | | gi = 3394175 | 637237 |
| IC05620 | UG75 Expression | EST | Mm.23535 | TITLE ESTs, Moderately similar to HREP protein [H. sapiens] | | | gi = 1634586 | 1395084 |
| IC05621 | UG75 Expression | EST | Mm.23543 | TITLE ESTs | | | gi = 4275154 | 1149804 |
| IC05622 | UG75 Expression | EST | Mm.23556 | TITLE ESTs | | | gi = 4275253 | 551615 |
| IC05623 | UG75 Expression | EST | Mm.23557 | TITLE ESTs, Weakly similar to nuclear protein np95 [M. musculus] | | | gi = 2305828 | 1148739 |
| IC05624 | UG75 Expression | EST | Mm.23558 | TITLE ESTs | | | gi = 4483121 | 551665 |
| IC05625 | UG75 Expression | EST | Mm.23566 | TITLE ESTs | | | gi = 1309556 | 721463 |
| IC05626 | UG75 Expression | EST | Mm.23572 | TITLE ESTs | | | gi = 6938123 | 550839 |
| IC05627 | UG75 Expression | EST | Mm.23573 | TITLE ESTs | | | gi = 5471862 | 569336 |
| IC05628 | UG75 Expression | EST | Mm.23582 | TITLE ESTs | | | gi = 4275421 | 1379900 |
| IC05629 | UG75 Expression | EST | Mm.23595 | TITLE ESTs, Moderately similar to P53-BINDING PROTEIN 53BP2 [M. musculus] | | | gi = 5124811 | 638370 |
| IC05630 | UG75 Expression | EST | Mm.23596 | TITLE ESTs | | | gi = 4276159 | 723061 |
| IC05631 | UG75 Expression | EST | Mm.23607 | TITLE ESTs, Weakly similar to KIAA0903 protein [H. sapiens] | | | gi = 1826541 | 722072 |
| IC05632 | UG75 Expression | EST | Mm.23617 | TITLE ESTs, Weaklyl similar to The KIA0146 gene product is novel. [H. sapiens] | | | gi = 1746634 | 598738 |
| IC05633 | UG75 Expression | EST | Mm.23622 | TITLE ESTs | | | gi = 6638617 | 575620 |
| IC05634 | UG75 Expression | EST | Mm.23632 | TITLE ESTs | | | gi = 4276082 | 1226169 |
| IC05635 | UG75 Expression | EST | Mm.23634 | TITLE ESTs | | | gi = 4276457 | 534181 |
| IC05636 | UG75 Expression | EST | Mm.23636 | TITLE ESTs | | | gi = 4276545 | 635593 |
| IC05637 | UG75 Expression | EST | Mm.23642 | TITLE ESTs, Weakly similar to NY-REN-25 antigen [H. sapiens] | | | gi = 4216936 | 573782 |
| IC05638 | UG75 Expression | EST | Mm.23658 | TITLE ESTs | | | gi = 1682666 | 718210 |
| IC05639 | UG75 Expression | EST | Mm.23661 | TITLE ESTs, Weakly similar to (define not available 5668735) [M. musculus] | | | gi = 6526115 | 635871 |
| IC05640 | UG75 Expression | EST | Mm.23672 | TITLE ESTs, Moderately similar to MITOCHONDRIAL IMPORT INNER MEMBRANE TRANSLOCASE SUBUNIT TIM17 Saccharomyces cerevisiae] | | | gi = 6008571 | 1282634 |
| IC05641 | UG75 Expression | EST | Mm.2368 | TITLE ESTs | | | gi = 4782546 | 573599 |
| IC05642 | UG75 Expression | EST | Mm.23682 | TITLE ESTs | | | gi = 2402893 | 599253 |
| IC05643 | UG75 Expression | EST | Mm.23685 | TITLE ESTs, Moderately similar to KIAA0988 protein [H. sapiens] | | | gi = 4030304 | 722408 |
| IC05644 | UG75 Expression | EST | Mm.23686 | TITLE ESTs | | | gi = 6167897 | 1263128 |
| IC05645 | UG75 Expression | EST | Mm.23690 | TITLE ESTs, Moderately similar to 60S RIBOSOMAL PROTEIN L39 [Rattus norvegicus] | | | gi = 2282691 | 1363159 |
| IC05646 | UG75 Expression | EST | Mm.23696 | TITLE ESTs | | | gi = 1464343 | 644302 |
| IC05647 | UG75 Expression | EST | Mm.23706 | TITLE ESTs | | | gi = 3731673 | 1265278 |
| IC05648 | UG75 Expression | EST | Mm.23711 | TITLE ESTs, Moderately similar to HYPOTHETICAL PROTEIN KIAA0076 [H. sapiens] | | | gi = 1290256 | 1395430 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05649 | UG75 Expression | EST | Mm.23713 | TITLE ESTs | | | gi = 2517682 | 1023527 |
| IC05650 | 00/04/26 UG#76 17Lid Expansion | EST | Mm.23720 | ESTs, Weakly similar to similar to nucleotide translocator [C. elegans] | | | gi = 3296829 | 1762872 |
| IC05651 | UG75 Expression | EST | Mm.23723 | TITLE ESTs | | | gi = 4537312 | 749193 |
| IC05652 | UG75 Expression | EST | Mm.23739 | TITLE ESTs, Weakly similar to coded for by C. elegans cDNA yk13g5.3 [C. elegans] | | | gi = 4434321 | 1149700 |
| IC05653 | UG75 Expression | EST | Mm.23744 | TITLE ESTs | | | gi = 437579 | 620135 |
| IC05654 | UG75 Expression | EST | Mm.23751 | TITLE ESTs, Weakly similar to TL132 protein [H. sapiens] | | | gi = 1825947 | 618943 |
| IC05655 | UG75 Expression | EST | Mm.23752 | TITLE ESTs | | | gi = 3394113 | 620737 |
| IC05656 | UG75 Expression | EST | Mm.23758 | TITLE ESTs | | | gi = 2518284 | 1140282 |
| IC05657 | UG75 Expression | EST | Mm.23767 | TITLE ESTs | | | gi = 3297348 | 973564 |
| IC05658 | UG75 Expression | EST | Mm.23774 | TITLE ESTs | | | gi = 2642909 | 750199 |
| IC05659 | UG75 Expression | EST | Mm.23776 | TITLE ESTs | | | gi = 3067095 | 1282813 |
| IC05660 | UG75 Expression | EST | Mm.23781 | TITLE ESTs, Moderately similar to GLUCOSE INHIBITED DIVISION PROTEIN A [Pseudomonas putida] | | | gi = 6748824 | 1279199 |
| IC05661 | UG75 Expression | EST | Mm.23783 | TITLE ESTs | | | gi = 3684037 | 636514 |
| IC05662 | UG75 Expression | EST | Mm.23804 | TITLE ESTs | | | gi = 4060377 | 582977 |
| IC05663 | UG75 Expression | EST | Mm.23808 | TITLE DNA segment, Chr 12, Wayne State University 95, expressed | GENE D12Wsu95e | | | 719461 |
| IC05664 | UG75 Expression | EST | Mm.23811 | TITLE ESTs | | | gi = 4482461 | 558102 |
| IC05665 | UG75 Expression | EST | Mm.23813 | TITLE ESTs | | | gi = 4274128 | 550814 |
| IC05666 | UG75 Expression | EST | Mm.23815 | TITLE ESTs | | | gi = 1675854 | 574558 |
| IC05667 | UG75 Expression | EST | Mm.23816 | TITLE ESTs | | | gi = 1675872 | 574607 |
| IC05668 | UG75 Expression | EST | Mm.21819 | TITLE ESTs | | | gi = 2691015 | 1378447 |
| IC05669 | UG75 Expression | EST | Mm.23822 | TITLE ESTs | | | gi = 2201179 | 718264 |
| IC05670 | UG75 Expression | EST | Mm.23824 | TITLE ESTs | | | gi = 1677154 | 1279531 |
| IC05671 | UG75 Expression | EST | Mm.23825 | TITLE ESTs, Moderately similar to CHLOROPLAST 50S RIBOSOMAL PROTEIN L20 [Odontella sinensis] | | | gi = 2964904 | 550982 |
| IC05672 | UG75 Expression | EST | Mm.23826 | TITLE ESTs | | | gi = 1826756 | 634738 |
| IC05673 | UG75 Expression | EST | Mm.23828 | TITLE ESTs | | | gi = 2917240 | 583901 |
| IC05674 | UG75 Expression | EST | Mm.23829 | TITLE ESTs | | | gi = 6939291 | 640187 |
| IC05675 | UG75 Expression | EST | Mm.23831 | TITLE ESTs | | | gi = 2919304 | 575464 |
| IC05676 | UG75 Expression | EST | Mm.23832 | TITLE ESTs | | | gi = 1485648 | 621638 |
| IC05677 | UG75 Expression | EST | Mm.23833 | TITLE ESTs | | | gi = 4730041 | 576455 |
| IC05678 | UG75 Expression | EST | Mm.23834 | TITLE ESTs | | | gi = 1677248 | 620910 |
| IC05679 | UG75 Expression | EST | Mm.23835 | TITLE ESTs | | | gi = 3395102 | 637845 |
| IC05680 | UG75 Expression | EST | Mm.23837 | TITLE ESTs | | | gi = 3518821 | 1481137 |
| IC05681 | UG75 Expression | EST | Mm.23838 | TITLE ESTs, Weakly similar to ZINC FINGER PROTEIN HF.12 [Homo sapiens] | | | gi = 5819698 | 1193438 |
| IC05682 | UG75 Expression | EST | Mm.23839 | TITLE ESTs, Moderately similar to R27216_1 [H. sapiens] | | | gi = 1282055 | 974036 |
| IC05683 | UG75 Expression | EST | Mm.23840 | TITLE ESTs | | | gi = 6645955 | 972958 |
| IC05684 | UG75 Expression | EST | Mm.23842 | TITLE ESTs | | | gi = 2517176 | 622326 |
| IC05685 | UG75 Expression | EST | Mm.23846 | TITLE ESTs, Weakly similar to TESTIS SPECIFIC PROTEIN A [R. norvegicus] | | | gi = 6084580 | 622800 |
| IC05686 | UG75 Expression | EST | Mm.23851 | TITLE ESTs | | | gi = 1309309 | 1243701 |
| IC05687 | UG75 Expression | EST | Mm.23854 | TITLE ESTs | | | gi = 2504572 | 1149042 |
| IC05688 | UG75 Expression | EST | Mm.23855 | TITLE ESTs | | | gi = 6633440 | 619356 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05689 | UG75 Expression | EST | Mm.23856 | TITLE ESTs, Weakly similar to HYPOTHETICAL 13.4 KD PROTEIN IN ACS1-GCV3 INTERGENIC REGION [*Saccharomyces cerevisiae*] | | | gi = 4434311 | 1149567 |
| IC05690 | UG75 Expression | EST | Mm.23857 | TITLE ESTs | | | gi = 1684527 | 574712 |
| IC05691 | UG75 Expression | EST | Mm.23859 | TITLE ESTs | | | gi = 3516963 | 596497 |
| IC05692 | UG75 Expression | EST | Mm.22860 | TITLE ESTs | | | gi = 1759550 | 620862 |
| IC05693 | UG75 Expression | EST | Mm.23862 | TITLE ESTs, Moderately similar to antigen NY-CO-33 [*H. sapiens*] | | | gi = 6518534 | 622006 |
| IC05694 | UG75 Expression | EST | Mm.23863 | TITLE ESTs | | | gi = 1863238 | 596754 |
| IC05695 | UG75 Expression | EST | Mm.23865 | TITLE ESTs | | | gi = 6078041 | 619793 |
| IC05696 | UG75 Expression | EST | Mm.23867 | TITLE ESTs | | | gi = 3954090 | 598698 |
| IC05697 | UG75 Expression | EST | Mm.2387 | TITLE ESTs | | | gi = 4032537 | 1279901 |
| IC05698 | UG75 Expression | EST | Mm.23870 | TITLE ESTs | | | gi = 2978980 | 577542 |
| IC05699 | UG75 Expression | EST | Mm.23877 | TITLE DNA segment, Chr 9, Wayne State University 20, expressed | GENE D9Wsu20e | | | 617824 |
| IC05700 | UG75 Expression | EST | Mm.23878 | TITLE ESTs | | | gi = 3099817 | 644924 |
| IC05701 | UG75 Expression | EST | Mm.23879 | TITLE ESTs | | | gi = 5493034 | 635506 |
| IC05702 | UG75 Expression | EST | Mm.23880 | TITLE ESTs | | | gi = 3885061 | 718056 |
| IC05703 | UG75 Expression | EST | Mm.23882 | TITLE ESTs, Weakly similar to 1-evidence | | | gi = 1286495 | 581978 |
| IC05704 | UG75 Expression | EST | Mm.23889 | TITLE ESTs, Moderately similar to KIAA0810 protein [*H. sapiens*] | | | gi = 3375428 | 1379085 |
| IC05705 | UG75 Expression | EST | Mm.22890 | TITLE ESTs | | | gi = 4782977 | 777655 |
| IC05706 | UG75 Expression | EST | Mm.23892 | TITLE ESTs | | | gi = 3394489 | 596983 |
| IC05707 | UG75 Expression | EST | Mm.23892 | TITLE ESTs | | | gi = 2521243 | 6174070 |
| IC05708 | UG75 Expression | EST | Mm.23896 | TITLE ESTs, Moderately similar to TB1 [*H. sapiens*] | | | gi = 4060416 | 597172 |
| IC05709 | UG75 Expression | EST | Mm.23897 | TITLE ESTs | | | gi = 1715291 | 575692 |
| IC05710 | UG75 Expression | EST | Mm.23898 | TITLE ESTs | | | gi = 1715383 | 597295 |
| IC05711 | UG75 Expression | EST | Mm.23902 | TITLE ESTs | | | gi = 2200129 | 605179 |
| IC05712 | UG75 Expression | EST | Mm.23904 | TITLE ESTs | | | gi = 2307778 | 635197 |
| IC05713 | UG75 Expression | EST | Mm.23908 | TITLE ESTs | | | gi = 1726395 | 634892 |
| IC05714 | UG75 Expression | EST | Mm.23909 | TITLE ESTs | | | gi = 1726431 | 634705 |
| IC05715 | UG75 Expression | EST | Mm.23910 | TITLE ESTs, Weakly similar to The KIAA0191 gene is expressed ubiquitously. [*H. sapiens*] | | | gi = 3393614 | 958979 |
| IC05716 | UG75 Expression | EST | Mm.23911 | TITLE ESTs | | | gi = 5474346 | 599126 |
| IC05717 | UG75 Expression | EST | Mm.23912 | TITLE ESTs | | | gi = 1726692 | 598360 |
| IC05718 | UG75 Expression | EST | Mm.23913 | TITLE EST | | | gi = 1727024 | 634699 |
| IC05719 | UG75 Expression | EST | Mm.23914 | TITLE ESTs | | | gi = 2305923 | 533755 |
| IC05720 | UG75 Expression | EST | Mm.23917 | TITLE ESTs, Weakly similar to F52C12.1 [*C. elegans*] | | | gi = 2288864 | 958501 |
| IC05721 | UG75 Expression | EST | Mm.23921 | TITLE ESTs, Weakly similar to P1.11659_5 [*H. sapiens*] | | | gi = 2860210 | 599009 |
| IC05722 | UG75 Expression | EST | Mm.23922 | TITLE segregation of mitotic chromosomes b | GENE Smcb-pe | Smcl | gi = 1282319 | 575990 |
| IC05723 | UG75 Expression | EST | Mm.23923 | TITLE ESTs | | | gi = 1739122 | 634790 |
| IC05724 | UG75 Expression | EST | Mm.23924 | TITLE ESTs | | | gi = 3681428 | 634728 |
| IC05725 | UG75 Expression | EST | Mm.23925 | TITLE ESTs [*H. sapiens*] | | | gi = 4782225 | 1312865 |
| IC05726 | UG75 Expression | EST | Mm.23926 | TITLE ESTs, Weakly similar to Similarity to Human MAP kinase phosphatase-1 [*C. elegans*] | | | gi = 4482191 | 1149615 |
| IC05727 | UG75 Expression | EST | Mm.23927 | TITLE ESTs | | | gi = 1908552 | 596686 |
| IC05728 | UG75 Expression | EST | Mm.23928 | TITLE ESTs | | | gi = 3394057 | 618882 |
| IC05729 | UG75 Expression | EST | Mm.23930 | TITLE ESTs | | | gi = 4408481 | 596140 |
| IC05730 | UG75 Expression | EST | Mm.23932 | TITLE ESTs | | | gi = 6750500 | 777474 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05731 | UG75 Expression | EST | Mm.23933 | TITLE ESTs | | | gi = 4725316 | 618973 |
| IC05732 | UG75 Expression | EST | Mm.23934 | TITLE ESTs | | | gi = 4601169 | 598402 |
| IC05733 | UG75 Expression | EST | Mm.23935 | TITLE ESTs | | | gi = 3394886 | 634882 |
| IC05734 | UG75 Expression | EST | Mm.23936 | TITLE ESTs | | | gi = 4306405 | 634981 |
| IC05735 | UG75 Expression | EST | Mm.23937 | TITLE ESTs | | | gi = 6167862 | 599064 |
| IC05736 | UG75 Expression | EST | Mm.23938 | TITLE ESTs | | | gi = 4601150 | 598286 |
| IC05737 | UG75 Expression | EST | Mm.23939 | TITLE ESTs | | | gi = 2918080 | 598220 |
| IC05738 | UG75 Expression | EST | Mm.23940 | TITLE ESTs | | | gi = 5471586 | 635577 |
| IC05739 | UG75 Expression | EST | Mm.23941 | TITLE ESTs, Moderately similar to SKI ONCOGENE [H. sapiens] | | | gi = 2402840 | 1295829 |
| IC05740 | UG75 Expression | EST | Mm.23942 | TITLE ESTs, Moderately similar to multidrug resistance protein [M. musculus] | | | gi = 3374099 | 635617 |
| IC05741 | UG75 Expression | EST | Mm.23943 | TITLE ESTs, Weakly similar to SCS2 PROTEIN [Saccharomyces cerevisiae] | | | gi = 4968295 | 598540 |
| IC05742 | UG75 Expression | EST | Mm.23944 | TITLE ESTs, Weakly similar to LIGATIN [M. musculus] | | | gi = 3692887 | 533496 |
| IC05743 | UG75 Expression | EST | Mm.23946 | TITLE ESTs | | | gi = 5910073 | 617041 |
| IC05744 | UG75 Expression | EST | Mm.23950 | TITLE ESTs | | | gi = 1380704 | 596198 |
| IC05745 | UG75 Expression | EST | Mm.23951 | TITLE ESTs, Moderately similar to MANNOSE-1-PHOSPHATE GUANYLTRANSFERASE [Saccharomyces cerevisiae] | | | gi = 3518723 | 617995 |
| IC05746 | UG75 Expression | EST | Mm.23953 | TITLE ESTs, Moderately similar to PHOSPHATIDATE CYTIDYLYLTRANSFERASE [Saccharomyces cerevisiae] | | | gi = 3720159 | 618162 |
| IC05747 | UG75 Expression | EST | Mm.23954 | TITLE ESTs | | | gi = 1749152 | 619003 |
| IC05748 | UG75 Expression | EST | Mm.23955 | TITLE ESTs | | | gi = 6084298 | 619026 |
| IC05749 | UG75 Expression | EST | Mm.23956 | TITLE ESTs | | | gi = 1749175 | 616798 |
| IC05750 | UG75 Expression | EST | Mm.23957 | TITLE ESTs | | | gi = 1749197 | 777401 |
| IC05751 | UG75 Expression | EST | Mm.23958 | TITLE ESTs | | | gi = 1749239 | 618407 |
| IC05752 | UG75 Expression | EST | Mm.23959 | TITLE ESTs, Moderately similar to tumor suppressor [H. sapiens] | | | gi = 2517867 | 619147 |
| IC05753 | UG75 Expression | EST | Mm.23960 | TITLE ESTs | | | gi = 5908442 | 1281305 |
| IC05754 | UG75 Expression | EST | Mm.23961 | TITLE ESTs | | | gi = 1912728 | 621823 |
| IC05755 | UG75 Expression | EST | Mm.23962 | TITLE ESTs | | | gi = 67492030 | 620303 |
| IC05756 | UG75 Expression | EST | Mm.23965 | TITLE ESTs | | | gi = 6100941 | 619958 |
| IC05757 | UG75 Expression | EST | Mm.23968 | TITLE ESTs | | | gi = 1677537 | 550811 |
| IC05758 | UG75 Expression | EST | Mm.23971 | TITLE ESTs | | | gi = 1917996 | 618581 |
| IC05759 | UG75 Expression | EST | Mm.23972 | TITLE ESTs | | | gi = 3167924 | 618351 |
| IC05760 | UG75 Expression | EST | Mm.23973 | TITLE ESTs | | | gi = 1756619 | 618901 |
| IC05761 | UG75 Expression | EST | Mm.23975 | TITLE ESTs, Weakly similar to zince finger protein [D. melanogaster] | | | gi = 1514867 | 619954 |
| IC05762 | UG75 Expression | EST | Mm.23977 | TITLE ESTs | | | gi = 1756947 | 637930 |
| IC05763 | UG75 Expression | EST | Mm.23978 | TITLE ESTs | | | gi = 3369489 | 618517 |
| IC05764 | UG75 Expression | EST | Mm.23979 | TITLE ESTs | | | gi = 4613337 | 620070 |
| IC05765 | UG75 Expression | EST | Mm.23980 | TITLE ESTs | | | gi = 1757220 | 620100 |
| IC05766 | UG75 Expression | EST | Mm.23981 | TITLE ESTs, Weekly similar to POLY [M.muscules] | | | gi = 1793156 | 598676 |
| IC05767 | UG75 Expression | EST | Mm.23983 | TITLE ESTs | | | gi = 3375417 | 622507 |
| IC05768 | UG75 Expression | EST | Mm.23985 | TITLE ESTs | | | gi = 1777100 | 621652 |
| IC05769 | UG75 Expression | EST | Mm.23986 | TITLE ESTs | | | gi = 1758855 | 622792 |
| IC05770 | UG75 Expression | EST | Mm.23987 | TITLE ESTs | | | gi = 4374002 | 422171 |
| IC05771 | UG75 Expression | EST | Mm.23988 | TITLE ESTs | | | gi = 4604951 | 622892 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05772 | UG75 Expression | EST | Mm.23989 | TITLE ESTs | | | gi = 3259375 | 622268 |
| IC05773 | UG75 Expression | EST | Mm.2399 | TITLE laminin, alpha 4 | GENE Lama4 | laminin [a]4] | | 1001811 |
| IC05774 | UG75 Expression | EST | Mm.23990 | TITLE ESTs | | | gi = 1759088 | 620382 |
| IC05775 | UG75 Expression | EST | Mm.23911 | TITLE ESTs | | | gi = 1727137 | 973406 |
| IC05776 | UG75 Expression | EST | Mm.23992 | TITLE ESTs, Moderately similar to putative hydrophobic domain in amino acid positions 373–390. [H. sapiens] | | | gi = 4724470 | 619835 |
| IC05777 | UG75 Expression | EST | Mm.23993 | TITLE ESTs | | | gi = 3053972 | 620208 |
| IC05778 | UG75 Expression | EST | Mm.23994 | TITLE ESTs | | | gi = 3376601 | 619883 |
| IC05779 | UG75 Expression | EST | Mm.23996 | TITLE ESTs | | | gi = 2849588 | 620000 |
| IC05780 | UG75 Expression | EST | Mm.23998 | TITLE ESTs, Weakly similar to (define not available 5917651) [R. norvegicus] | | | gi = 2308468 | 617183 |
| IC05781 | UG75 Expression | EST | Mm.23999 | TITLE ESTs | | | gi = 1759652 | 620955 |
| IC05782 | UG75 Expression | EST | Mm.24002 | TITLE ESTs, Weakly similar to coded for by C. elegans cDNA yk173c12.5 [C. elegans] | | | gi = 1914894 | 750866 |
| IC05783 | UG75 Expression | EST | Mm.24003 | TITLE ESTs | | | gi = 6005985 | 764706 |
| IC05784 | UG75 Expression | EST | Mm.24004 | TITLE ESTs | | | gi = 1760066 | 621421 |
| IC05785 | UG75 Expression | EST | Mm.24007 | TITLE ESTs | | | gi = 3100472 | 622962 |
| IC05786 | UG75 Expression | EST | Mm.24008 | TITLE ESTs | | | gi = 3682824 | 634174 |
| IC05787 | UG75 Expression | EST | Mm.24009 | TITLE ESTs | | | gi = 1759271 | 620311 |
| IC05788 | UG75 Expression | EST | Mm.24010 | TITLE ESTs, Moderately similar to KIAA0922 protein [H. sapiens] | | | gi = 1765769 | 635799 |
| IC05789 | UG75 Expression | EST | Mm.24011 | TITLE ESTs | | | gi = 1765814 | 636532 |
| IC05790 | UG75 Expression | EST | Mm.24012 | TITLE ESTs | | | gi = 1765835 | 636738 |
| IC05791 | UG75 Expression | EST | Mm.24013 | TITLE ESTs, Weakly similar to ALPHA-1,3(6)-MANNOSYLGLYCOPROTEIN BETA-1,6-N-ACETYL-GLUCOSAMINYLTRANSFERASE V [R. norvegicus] | | | gi = 6645298 | 636007 |
| IC05792 | UG75 Expression | EST | Mm.24014 | TITLE ESTs | | | gi = 4300269 | 636567 |
| IC05793 | UG75 Expression | EST | Mm.24015 | TITLE ESTs, Weakly similar to octamer-binding protein NonO [M. musculus] | | | gi = 1566322 | 894013 |
| IC05794 | UG75 Expression | EST | Mm.24016 | TITLE ESTs | | | gi = 5748957 | 636608 |
| IC05795 | UG75 Expression | EST | Mm.24017 | TITLE ESTs | | | gi = 1776811 | 636012 |
| IC05796 | UG75 Expression | EST | Mm.24018 | TITLE ESTs | | | gi = 1766796 | 636057 |
| IC05797 | UG75 Expression | EST | Mm.24019 | TITLE ESTs | | | gi = 4613964 | 636890 |
| IC05798 | UG75 Expression | EST | Mm.24020 | TITLE ESTs | | | gi = 1889058 | 621126 |
| IC05799 | UG75 Expression | EST | Mm.24022 | TITLE ESTs | | | gi = 1759276 | 619947 |
| IC05800 | UG75 Expression | EST | Mm.24023 | TITLE ESTs | | | gi = 1714673 | 596905 |
| IC05801 | UG75 Expression | EST | Mm.24024 | TITLE ESTs | | | gi = 4316094 | 636437 |
| IC05802 | UG75 Expression | EST | Mm.24025 | TITLE ESTs | | | gi = 2516826 | 620508 |
| IC05803 | UG75 Expression | EST | Mm.24027 | TITLE ESTs | | | gi = 4617088 | 636578 |
| IC05804 | UG75 Expression | EST | Mm.24028 | TITLE ESTs | | | gi = 5819555 | 636607 |
| IC05805 | UG75 Expression | EST | Mm.24029 | TITLE ESTs | | | gi = 3394085 | 636755 |
| IC05806 | UG75 Expression | EST | Mm.24030 | TITLE ESTs, Weakly similar to RENAL SODIUM-DEPENDENT PHOSPHATE TRANSPORT PROTEIN 1 [M. musculus] | | | gi = 4403214 | 636263 |
| IC05807 | UG75 Expression | EST | Mm.24031 | TITLE ESTs | | | gi = 1767069 | 621874 |
| IC05808 | UG75 Expression | EST | Mm.24032 | TITLE ESTs | | | gi = 6526552 | 621951 |
| IC05809 | UG75 Expression | EST | Mm.24033 | TITLE DNA segment, Chr 10, Wayne State University 102, expressed | GENE D10Wsu102e | | | 1295528 |

US 6,706,867 B1

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05810 | UG75 Expression | EST | Mm.24035 | TITLE ESTs | | | gi = 3393120 | 622087 |
| IC05811 | UG75 Expression | EST | Mm.24036 | TITLE ESTs | | | gi = 4720511 | 621798 |
| IC05812 | UG75 Expression | EST | Mm.24037 | TITLE ESTs | | | gi = 5469894 | 533767 |
| IC05813 | UG75 Expression | EST | Mm.24039 | TITLE ESTs | | | gi = 1326781 | 619715 |
| IC05814 | UG75 Expression | EST | Mm.24041 | TITLE ESTs | | | gi = 1767771 | 622261 |
| IC05815 | UG75 Expression | EST | Mm.24043 | TITLE ESTs | | | gi = 4804772 | 642409 |
| IC05816 | UG75 Expression | EST | Mm.24045 | TITLE ESTs | | | gi = 4030461 | 637444 |
| IC05817 | UG75 Expression | EST | Mm.24046 | TITLE ESTs | | | gi = 1897454 | 642722 |
| IC05818 | UG75 Expression | EST | Mm.24048 | TITLE ESTs | | | gi = 1769030 | 642620 |
| IC05819 | UG75 Expression | EST | Mm.24049 | TITLE ESTs | | | gi = 4615196 | 642537 |
| IC05820 | UG75 Expression | EST | Mm.24051 | TITLE ESTs | | | gi = 1776763 | 752482 |
| IC05821 | UG75 Expression | EST | Mm.24053 | TITLE ESTs, Weakly similar to RST [*M. musculus*] | | | gi = 3863343 | 643257 |
| IC05822 | UG75 Expression | EST | Mm.24054 | TITLE ESTs | | | gi = 6085587 | 621396 |
| IC05823 | UG75 Expression | EST | Mm.24055 | TITLE ESTs [*M. musculus*] | | | gi = 4305546 | 643411 |
| IC05824 | UG75 Expression | EST | Mm.24056 | TITLE ESTs | | | gi = 6079041 | 959390 |
| IC05825 | UG75 Expression | EST | Mm.24057 | TITLE ESTs | | | gi = 1772283 | 623028 |
| IC05826 | UG75 Expression | EST | Mm.24058 | TITLE ESTs | | | gi = 1772288 | 623054 |
| IC05827 | UG75 Expression | EST | Mm.24060 | TITLE ESTs | | | gi = 2165114 | 637887 |
| IC05828 | UG75 Expression | EST | Mm.24061 | TITLE ESTs | | | gi = 1776518 | 643095 |
| IC05829 | UG75 Expression | EST | Mm.24062 | TITLE ESTs, Moderately similar to hypothetical protein [*M. musculus*] | | | gi = 2411866 | 1002209 |
| IC05830 | UG75 Expression | EST | Mm.24063 | TITLE ESTs | | | gi = 1776539 | 643317 |
| IC05831 | UG75 Expression | EST | Mm.24064 | TITLE ESTs | | | gi = 1776546 | 643360 |
| IC05832 | UG75 Expression | EST | Mm.24066 | TITLE ESTs | | | gi = 1776815 | 642805 |
| IC05833 | UG75 Expression | EST | Mm.24067 | TITLE ESTs | | | gi = 4271817 | 619079 |
| IC05834 | UG75 Expression | EST | Mm.24068 | TITLE ESTs | | | gi = 2193185 | 643030 |
| IC05835 | UG75 Expression | EST | Mm.24069 | TITLE ESTs | | | gi = 2807200 | 636075 |
| IC05836 | UG75 Expression | EST | Mm.24070 | TITLE EST | | | gi = 1776971 | 636650 |
| IC05837 | UG75 Expression | EST | Mm.24071 | TITLE ESTs | | | gi = 4217093 | 636921 |
| IC05838 | UG75 Expression | EST | Mm.24072 | TITLE ESTs | | | gi = 4295143 | 636923 |
| IC05839 | UG75 Expression | EST | Mm.24073 | TITLE ESTs | | | gi = 4725099 | 636657 |
| IC05840 | UG75 Expression | EST | Mm.24074 | TITLE ESTs, Moderately similar to (define not available 6049254) [*R. norvegicus*] | | | gi = 1876528 | 644873 |
| IC05841 | UG75 Expression | EST | Mm.24075 | TITLE ESTs | | | gi = 4725273 | 635259 |
| IC05842 | UG75 Expression | EST | Mm.24077 | TITLE ESTs | | | gi = 1777190 | 643273 |
| IC05843 | UG75 Expression | EST | Mm.24078 | TITLE ESTs | | | gi = 2520062 | 637926 |
| IC05844 | UG75 Expression | EST | Mm.24082 | TITLE ESTs, Moderately similar to snRNA activating protein complex 19kDa subunit [*H. sapiens*] | | | gi = 4722621 | 765229 |
| IC05845 | UG75 Expression | EST | Mm.24083 | TITLE ESTs | | | gi = 2917041 | 1193251 |
| IC05846 | UG75 Expression | EST | Mm.24084 | TITLE ESTs, Weakly similar to (define not available 5453421) [*M. musculus*] | | | gi = 2518085 | 622811 |
| IC05847 | UG75 Expression | EST | Mm.24085 | TITLE ESTs | | | gi = 1794452 | 639581 |
| IC05848 | UG75 Expression | EST | Mm.24086 | TITLE ESTs | | | gi = 3978746 | 621433 |
| IC05849 | UG75 Expression | EST | Mm.24090 | TITLE ESTs | | | gi = 2516720 | 1481714 |
| IC05850 | UG75 Expression | EST | Mm.24091 | TITLE ESTs | | | gi = 4779152 | 550930 |
| IC05851 | UG75 Expression | EST | Mm.24092 | TITLE ESTs | | | gi = 4032145 | 751781 |
| IC05852 | UG75 Expression | EST | Mm.24093 | TITLE ESTs | | | gi = 2813213 | 638352 |
| IC05853 | UG75 Expression | EST | Mm.24094 | TITLE ESTs | | | gi = 1726397 | 634889 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05854 | UG75 Expression | EST | Mm.24095 | TITLE ESTs | | | gi = 2518784 | 621667 |
| IC05855 | UG75 Expression | EST | Mm.24097 | TITLE ESTs, Moderately similar to WDNM1 PROTEIN [Rattus norvegicus] | | | gi = 1282119 | 972896 |
| IC05856 | UG75 Expression | EST | Mm.24098 | TITLE ESTs, Weakly similar to probable transcription regulator NT fin12 [M. musculus] | | | gi = 3260993 | 749064 |
| IC05857 | UG75 Expression | EST | Mm.24099 | TITLE ESTs | | | gi = 2288468 | 1002038 |
| IC05858 | UG75 Expression | EST | Mm.24100 | TITLE ESTs | | | gi = 3515723 | 638217 |
| IC05859 | UG75 Expression | EST | Mm.24101 | TITLE ESTs | | | gi = 6096665 | 643676 |
| IC05860 | UG75 Expression | EST | Mm.24103 | TITLE ESTs | | | gi = 4405370 | 643889 |
| IC05861 | UG75 Expression | EST | Mm.24104 | TITLE ESTs, Moderately similar to HSPC011 [H. sapiens] | | | gi = 1316296 | 1263563 |
| IC05862 | UG75 Expression | EST | Mm.24105 | TITLE ESTs | | | gi = 3957171 | 750505 |
| IC05863 | UG75 Expression | EST | Mm.24106 | TITLE ESTs | | | gi = 2081546 | 1279308 |
| IC05864 | UG75 Expression | EST | Mm.24107 | TITLE ESTs | | | gi = 2919346 | 643644 |
| IC05865 | UG75 Expression | EST | Mm.24108 | TITLE ESTs, Weakly similar to weak similarity to Bacillus stearothermophilus 30S ribosomal protein S21 [C. elegans] | | | gi = 1662869 | 643666 |
| IC05866 | UG75 Expression | EST | Mm.24109 | TITLE ESTs | | | gi = 2918998 | 1002847 |
| IC05867 | UG75 Expression | EST | Mm.24110 | TITLE ESTs | | | gi = 2517299 | 1193403 |
| IC05868 | UG75 Expression | EST | Mm.24111 | TITLE ESTs | | | gi = 4216464 | 643550 |
| IC05869 | UG75 Expression | EST | Mm.24112 | TITLE ESTs | | | gi = 6277461 | 643855 |
| IC05870 | UG75 Expression | EST | Mm.24113 | TITLE ESTs | | | gi = 3079055 | 1329326 |
| IC05871 | UG75 Expression | EST | Mm.24114 | TITLE ESTs | | | gi = 5336287 | 534019 |
| IC05872 | UG75 Expression | EST | Mm.24115 | TITLE ESTs | | | gi = 2200177 | 717934 |
| IC05873 | UG75 Expression | EST | Mm.24116 | TITLE ESTs | | | gi = 2319743 | 894521 |
| IC05874 | UG75 Expression | EST | Mm.24117 | TITLE ESTs, Weakly similar to similar to 1-acyl-lycerol-3-phosphate acyltransferases [C. elegans] | | | gi = 6083965 | 1279655 |
| IC05875 | UG75 Expression | EST | Mm.24119 | TITLE ESTs | | | gi = 262994 | 1363507 |
| IC05876 | UG75 Expression | EST | Mm.24120 | TITLE ESTs | | | gi = 5909908 | 540905 |
| IC05877 | UG75 Expression | EST | Mm.24123 | TITLE ESTs | | | gi = 3518900 | 618142 |
| IC05878 | UG75 Expression | EST | Mm.24125 | TITLE ESTs | | | gi = 2812742 | 751111 |
| IC05879 | UG75 Expression | EST | Mm.24126 | TITLE ESTs | | | gi = 1290072 | 749458 |
| IC05880 | UG75 Expression | EST | Mm.24128 | TITLE ESTs, Weakly similar to mannose-binding lectin associated serine protease-2 [M. musculus] | | | gi = 4061794 | 617947 |
| IC05881 | UG75 Expression | EST | Mm.24129 | TITLE ESTs | | | gi = 6822511 | 973818 |
| IC05882 | UG75 Expression | EST | Mm.24131 | TITLE ESTs | | | gi = 4274738 | 764681 |
| IC05883 | UG75 Expression | EST | Mm.24132 | TITLE ESTs | | | gi = 1807520 | 644827 |
| IC05884 | UG75 Expression | EST | Mm.24133 | TITLE ESTs | | | gi = 1807561 | 644904 |
| IC05885 | UG75 Expression | EST | Mm.24134 | TITLE ESTs | | | gi = 2521677 | 619000 |
| IC05886 | UG75 Expression | EST | Mm.24136 | TITLE ESTs | | | gi = 5908514 | 644961 |
| IC05887 | UG75 Expression | EST | Mm.24138 | TITLE ESTs | | | gi = 1766995 | 636776 |
| IC05888 | UG75 Expression | EST | Mm.24140 | TITLE ESTs | | | gi = 2906864 | 1002699 |
| IC05889 | UG75 Expression | EST | Mm.24141 | TITLE ESTs | | | gi = 3981308 | 551125 |
| IC05890 | UG75 Expression | EST | Mm.24143 | TITLE ESTs, Weakly similar to (define not available 5901802) [D. melanogaster] | | | gi = 1827237 | 636063 |
| IC05891 | UG75 Expression | EST | Mm.24145 | TITLE ESTs | | | gi = 2990809 | 1264923 |
| IC05892 | UG75 Expression | EST | Mm.24148 | TITLE ESTs | | | gi = 2571246 | 765827 |
| IC05893 | UG75 Expression | EST | Mm.24149 | TITLE ESTs | | | gi = 4217432 | 2655268 |
| IC05894 | UG75 Expression | EST | Mm.24152 | TITLE ESTs | | | gi = 4729787 | 598064 |
| IC05895 | UG75 Expression | EST | Mm.24156 | TITLE ESTs, Weakly similar to cytohesin 2 [M. musculus] | | | gi = 5124738 | 636113 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05896 | UG75 Expression | EST | Mm.24157 | TITLE ESTs | | | gi = 3373670 | 1148442 |
| IC05897 | UG75 Expression | EST | Mm.24158 | TITLE ESTs | | | gi = 4434526 | 558157 |
| IC05898 | UG75 Expression | EST | Mm.24159 | TITLE ESTs, Moderately similar to hMed7 [*H. sapiens*] | | | gi = 4778867 | 777576 |
| IC05899 | UG75 Expression | EST | Mm.24160 | TITLE ESTs | | | gi = 2652132 | 596215 |
| IC05900 | UG75 Expression | EST | Mm.24161 | TITLE ESTs, Weakly similar to DnaJ-like protein [*M. musculus*] | | | gi = 1290119 | 617647 |
| IC05901 | UG75 Expression | EST | Mm.24163 | TITLE ESTs, Weakly similar to KIAA0926 protein [*H. sapiens*] | | | gi = 6756465 | 1265077 |
| IC05902 | UG75 Expression | EST | Mm.24164 | TITLE ESTs | | | gi = 4780102 | 638448 |
| IC05903 | UG75 Expression | EST | Mm.24165 | TITLE ESTs | | | gi = 4726769 | 637584 |
| IC05904 | UG75 Expression | EST | Mm.24166 | TITLE ESTs | | | gi = 2076081 | 595935 |
| IC05905 | UG75 Expression | EST | Mm.24169 | TITLE ESTs | | | gi = 1715679 | 721413 |
| IC05906 | UG75 Expression | EST | Mm.24170 | TITLE ESTs | | | gi = 3068190 | 717709 |
| IC05907 | UG75 Expression | EST | Mm.24176 | TITLE ESTs | | | gi = 3373488 | 574102 |
| IC05908 | UG75 Expression | EST | Mm.24177 | TITLE ESTs | | | gi = 1315496 | 596595 |
| IC05909 | UG75 Expression | EST | Mm.24180 | TITLE ESTs | | | gi = 4723310 | 722962 |
| IC05910 | UG75 Expression | EST | Mm.24186 | TITLE ESTs, Weakly similar to SH3P9 [*M. musculus*] | | | gi = 1772298 | 623096 |
| IC05911 | UG75 Expression | EST | Mm.24187 | TITLE ESTs, Moderately similar to pyridoxine 5'-phosphate oxidase [*R. norvegicus*] | | | gi = 6084384 | 751632 |
| IC05912 | UG75 Expression | EST | Mm.24195 | TITLE ESTs | | | gi = 2813846 | 638209 |
| IC05913 | UG75 Expression | EST | Mm.24196 | TITLE ESTs | | | gi = 4778015 | 329471 |
| IC05914 | UG75 Expression | EST | Mm.24197 | TITLE ESTs | | | gi = 2528206 | 638783 |
| IC05915 | UG75 Expression | EST | Mm.24199 | TITLE ESTs | | | gi = 3749961 | 1149801 |
| IC05916 | UG75 Expression | EST | Mm.24200 | TITLE ESTs | | | gi = 1826737 | 1312464 |
| IC05917 | UG75 Expression | EST | Mm.24201 | TITLE ESTs | | | gi = 4275918 | 373752 |
| IC05918 | UG75 Expression | EST | Mm.24209 | TITLE ESTs, Moderately similar to HYPOTHETICAL PROTEIN KIAA0081 [*H. sapiens*] | | | gi = 6748964 | 764545 |
| IC05919 | UG75 Expression | EST | Mm.24219 | TITLE ESTs | | | gi = 3167538 | 717719 |
| IC05920 | UG75 Expression | EST | Mm.24222 | TITLE ESTs Weakly similar to sphingosine kinase [*M. musculus*] | | | gi = 2517181 | 1148607 |
| IC05921 | UG75 Expression | EST | Mm.24223 | TITLE ESTs, Weakly similar to endothelial lipase [*M. musculus*] | | | gi = 3168437 | 1054242 |
| IC05922 | UG75 Expression | EST | Mm.24228 | TITLE ESTs | | | gi = 1936072 | 575953 |
| IC05923 | UG75 Expression | EST | Mm.24229 | TITLE ESTs | | | gi = 6098932 | 619371 |
| IC05924 | UG75 Expression | EST | Mm.24236 | TITLE ESTs | | | gi = 5338322 | 616994 |
| IC05925 | UG75 Expression | EST | Mm.24241 | TITLE ESTs | | | gi = 1290301 | 620237 |
| IC05926 | UG75 Expression | EST | Mm.24244 | TITLE ESTs, Weakly similar to POSSIBLE 1-ACYL-SN-GLYCEROL-3-PHOSPHATE ACYLTRANSFERASE [*Saccharomyces cerevisiae*] | | | gi = 2979017 | 1281457 |
| IC05927 | UG75 Expression | EST | Mm.24247 | TITLE ESTs | | | gi = 6329009 | 717634 |
| IC05928 | UG75 Expression | EST | Mm.24249 | TITLE ESTs | | | gi = 1917618 | 717623 |
| IC05929 | UG75 Expression | EST | Mm.24250 | TITLE ESTs, Moderately similar to coiled-coil related protein DEEPEST [*H. sapiens*] | | | gi = 5548761 | 717761 |
| IC05930 | UG75 Expression | EST | Mm.24256 | TITLE ESTs | | | gi = 4617238 | 722263 |
| IC05931 | UG75 Expression | EST | Mm.24257 | TITLE ESTs | | | gi = 2042101 | 722348 |
| IC05932 | UG75 Expression | EST | Mm.24258 | TITLE ESTs | | | gi = 1428745 | 722403 |
| IC05933 | UG75 Expression | EST | Mm.24259 | TITLE ESTs | | | gi = 2646416 | 1295075 |
| IC05934 | UG75 Expression | EST | Mm.24260 | TITLE ESTs, Weakly similar to HYPOTHETICAL PROTEIN KIAA0310 [*H. sapiens*] | | | gi = 3394929 | 973673 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05935 | UG75 Expression | EST | Mm.24261 | TITLE ESTs | | | gi = 5492241 | 1280051 |
| IC05936 | UG75 Expression | EST | Mm.24262 | TITLE DNA segment, Human EST 475269 | GENE EST475269 | | gi = 5336518 | 599255 |
| IC05937 | UG75 Expression | EST | Mm.24263 | TITLE ESTs | | | gi = 4317761 | 723067 |
| IC05938 | UG75 Expression | EST | Mm.24264 | TITLE ESTs | | | gi = 1759862 | 621390 |
| IC05939 | UG75 Expression | EST | Mm.24265 | TITLE ESTs | | | gi = 2919364 | 533515 |
| IC05940 | UG75 Expression | EST | Mm.24266 | TITLE ESTs | | | gi = 1827056 | 722826 |
| IC05941 | UG75 Expression | EST | Mm.24267 | TITLE ESTs | | | gi = 6517153 | 777277 |
| IC05942 | UG75 Expression | EST | Mm.24268 | TITLE ESTs, Weakly similar to topoisomerase III [M. musculus] | | | gi = 4290277 | 719423 |
| IC05943 | UG75 Expression | EST | Mm.24269 | TITLE ESTs | | | gi = 4306986 | 596757 |
| IC05944 | UG75 Expression | EST | Mm.24272 | TITLE ESTs | | | gi = 6638620 | 751387 |
| IC05945 | UG75 Expression | EST | Mm.24278 | TITLE ESTs | | | gi = 4405267 | 974050 |
| IC05946 | UG75 Expression | EST | Mm.24280 | UBIQUITIN CARBOXYL-TERMINAL HYDROLASE [Mus musculus] | | | gi = 4720659 | 717999 |
| IC05947 | UG75 Expression | EST | Mm.24282 | TITLE ESTs | | | gi = 1826492 | 619232 |
| IC05948 | UG75 Expression | EST | Mm.24286 | TITLE ESTs | | | gi = 3732451 | 1395499 |
| IC05949 | UG75 Expression | EST | Mm.24288 | TITLE DNA segment, Chr 2, Wayne State University 127, expressed | GENE D2Wsu127e | | | 721044 |
| IC05950 | UG75 Expression | EST | Mm.23289 | TITLE ESTs | | | gi = 2307957 | 1149786 |
| IC05951 | UG75 Expression | EST | Mm.23291 | TITLE ESTs | | | gi = 4764769 | 598094 |
| IC05952 | UG75 Expression | EST | Mm.23292 | TITLE ESTs | | | gi = 1380342 | 635711 |
| IC05953 | UG75 Expression | EST | Mm.24295 | TITLE ESTs | | | gi = 3376387 | 621758 |
| IC05954 | UG75 Expression | EST | Mm.24297 | TITLE ESTs | | | gi = 1901439 | 644359 |
| IC05955 | UG75 Expression | EST | Mm.24298 | TITLE ESTs | | | gi = 2461667 | 644382 |
| IC05956 | UG75 Expression | EST | Mm.24299 | TITLE ESTs | | | gi = 3387483 | 894019 |
| IC05957 | UG75 Expression | EST | Mm.24300 | TITLE ESTs | | | gi = 3515663 | 718682 |
| IC05958 | UG75 Expression | EST | Mm.24302 | TITLE ESTs | | | gi = 2273163 | 642549 |
| IC05959 | UG75 Expression | EST | Mm.24303 | TITLE ESTs | | | gi = 3372982 | 718705 |
| IC05960 | UG75 Expression | EST | Mm.24304 | TITLE ESTs | | | gi = 2517583 | 718723 |
| IC05961 | UG75 Expression | EST | Mm.24205 | TITLE ESTs | | | gi = 1919302 | 777528 |
| IC05962 | UG75 Expression | EST | Mm.24207 | TITLE EST | | | gi = 1902464 | 718242 |
| IC05963 | UG75 Expression | EST | Mm.24308 | TITLE ESTs | | | gi = 1902468 | 718245 |
| IC05964 | UG75 Expression | EST | Mm.24309 | TITLE ESTs | | | gi = 2306037 | 618629 |
| IC05965 | UG75 Expression | EST | Mm.24310 | TITLE ESTs | | | gi = 4404253 | 1001980 |
| IC05966 | UG75 Expression | EST | Mm.24311 | TITLE ESTs | | | gi = 1902583 | 718157 |
| IC05967 | UG75 Expression | EST | Mm.24312 | TITLE ESTs | | | gi = 3372507 | 617257 |
| IC05968 | UG75 Expression | EST | Mm.24313 | TITLE ESTs, Moderately similar to similar to phosphatidylinositol [H. sapiens] | | | gi = 1903753 | 721258 |
| IC05969 | UG75 Expression | EST | Mm.24314 | TITLE ESTs | | | gi = 1530929 | 721367 |
| IC05970 | UG75 Expression | EST | Mm.24315 | TITLE ESTs | | | gi = 1896867 | 620598 |
| IC05971 | UG75 Expression | EST | Mm.24316 | TITLE ESTs | | | gi = 6078284 | 719114 |
| IC05972 | UG75 Expression | EST | Mm.24317 | TITLE ESTs | | | gi = 5498286 | 719173 |
| IC05973 | UG75 Expression | EST | Mm.24318 | TITLE ESTs | | | gi = 3375028 | 719175 |
| IC05974 | UG75 Expression | EST | Mm.24321 | TITLE ESTs, Weakly similar to NG32 [H. sapiens] | | | gi = 1768637 | 721444 |
| IC05975 | UG75 Expression | EST | Mm.24323 | TITLE ESTs | | | gi = 1904410 | 721577 |
| IC05976 | UG75 Expression | EST | Mm.24324 | TITLE ESTs | | | gi = 1713853 | 597623 |
| IC05977 | UG75 Expression | EST | Mm.24326 | TITLE EST | | | gi = 1904610 | 723326 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC05978 | UG75 Expression | EST | Mm.24327 | TITLE ESTs, Weakly similar to signal recognition particle 72 [*H. sapiens*] | | | gi = 2517919 | 1020793 |
| IC05979 | UG75 Expression | EST | Mm.24328 | TITLE ESTs | | | gi = 5668099 | 721854 |
| IC05980 | UG75 Expression | EST | Mm.24329 | TITLE ESTs, Weakly similar to putative seven pass transmembrane protein [*H. sapiens*] | | | gi = 4315739 | 643798 |
| IC05981 | UG75 Expression | EST | Mm.24330 | | | | gi = 1755673 | 599107 |
| IC05982 | UG75 Expression | EST | Mm.24331 | TITLE ESTs, Weakly similar to ankyrin repeat-containing protein Asb-3 [*M. musculus*] | | | gi = 2860807 | 1294481 |
| IC05983 | UG75 Expression | EST | Mm.24332 | TITLE ESTs | | | gi = 5905479 | 722023 |
| IC05984 | UG75 Expression | EST | Mm.24333 | TITLE ESTs | | | gi = 1749351 | 619240 |
| IC05985 | UG75 Expression | EST | Mm.24340 | TITLE ESTs | | | gi = 1908079 | 533543 |
| IC05986 | UG75 Expression | EST | Mm.24342 | TITLE DNA segment, Chr 15, Wayne State University 122, expressed | GENE D15Wsu122e | | | 599270 |
| IC05987 | UG75 Expression | EST | Mm.24343 | TITLE ESTs | | | gi = 2891476 | 635909 |
| IC05988 | UG75 Expression | EST | Mm.24345 | TITLE ESTs | | | gi = 2813536 | 764901 |
| IC05989 | UG75 Expression | EST | Mm.24248 | TITLE ESTs | | | gi = 2503382 | 721690 |
| IC05990 | UG75 Expression | EST | Mm.24349 | TITLE ESTs | | | gi = 2646810 | 1002862 |
| IC05991 | UG75 Expression | EST | Mm.24352 | TITLE ESTs | | | gi = 4274479 | 575122 |
| IC05992 | UG75 Expression | EST | Mm.24353 | TITLE ESTs | | | gi = 6076659 | 575322 |
| IC05993 | UG75 Expression | EST | Mm.24354 | TITLE ESTs | | | gi = 1912817 | 765077 |
| IC05994 | UG75 Expression | EST | Mm.24355 | TITLE ESTs, Moderately similar to unknown [*H. sapiens*] | | | gi = 4482944 | 7646669 |
| IC05995 | UG75 Expression | EST | Mm.24356 | TITLE ESTs, Weakly similar to ORF YKR092c [*S. cerevisiae*] | | | gi = 4766496 | 620332 |
| IC05996 | UG75 Expression | EST | Mm.24358 | TITLE ESTs | | | gi = 1913290 | 764830 |
| IC05997 | UG75 Expression | EST | Mm.24359 | TITLE ESTs | | | gi = 2885671 | 636187 |
| IC05998 | UG75 Expression | EST | Mm.24360 | TITLE ESTs | | | gi = 1913441 | 765239 |
| IC05999 | UG75 Expression | EST | Mm.24362 | TITLE ESTs, Moderately similar to brefeldin A-inhibited guanine nucleotide-exchange protein 2 [*H. sapiens*] | | | gi = 1915152 | 533977 |
| IC06000 | UG75 Expression | EST | Mm.24365 | PHOSPHOGLUCONATE DEHYDROGENASE, DECARBOXYLATING [*Ovis ries*] | | | gi = 1287969 | 534261 |
| IC06001 | UG75 Expression | EST | Mm.24368 | TITLE ESTs | | | gi = 2963263 | 765760 |
| IC06002 | UG75 Expression | EST | Mm.24370 | TITLE ESTs | | | gi = 2259146 | 972624 |
| IC06003 | UG75 Expression | EST | Mm.24372 | TITLE ESTs | | | gi = 2860608 | 764371 |
| IC06004 | UG75 Expression | EST | Mm.24373 | TITLE ESTs | | | gi = 6084729 | 764419 |
| IC06005 | UG75 Expression | EST | Mm.24374 | TITLE ESTs | | | gi = 1309597 | 637514 |
| IC06006 | UG75 Expression | EST | Mm.24379 | TITLE ESTs | | | gi = 1918684 | 1265247 |
| IC06007 | UG75 Expression | EST | Mm.24380 | TITLE ESTs | | | gi = 2813118 | 617589 |
| IC06008 | UG75 Expression | EST | Mm.24381 | TITLE ESTs | | | gi = 3393182 | 777167 |
| IC06009 | UG75 Expression | EST | Mm.24384 | TITLE ESTs | | | gi = 2040627 | 777455 |
| IC06010 | UG75 Expression | EST | Mm.24385 | TITLE ESTs | | | gi = 1759362 | 1002553 |
| IC06011 | UG75 Expression | EST | Mm.24386 | TITLE ESTs | | | gi = 3158829 | 777202 |
| IC06012 | UG75 Expression | EST | Mm.24387 | TITLE ESTs | | | gi = 4720693 | 550700 |
| IC06013 | UG75 Expression | EST | Mm.24393 | TITLE ESTs | | | gi = 1932113 | 764089 |
| IC06014 | UG75 Expression | EST | Mm.24397 | TITLE ESTs, Moderately simimlar to diphosphionositol polyphosphate phosphohydrolase [*H. sapiens*] | | | gi = 1324617 | 1278957 |
| IC06015 | UG75 Expression | EST | Mm.24401 | TITLE ESTs | | | gi = 4537660 | 752323 |
| IC06016 | UG75 Expression | EST | Mm.24403 | TITLE ESTs | | | gi = 6097910 | 750896 |
| IC06017 | UG75 Expression | EST | Mm.24404 | TITLE ESTs | | | gi = 4792184 | 750901 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06018 | UG75 Expression | EST | Mm.24405 | TITLE ESTs, Weakly similar to orphan transporter isoform A10 [M. musculus] | | | gi = 3809644 | 1329890 |
| IC06019 | UG75 Expression | EST | Mm.24408 | TITLE ESTs | | | gi = 1756911 | 619839 |
| IC06020 | UG75 Expression | EST | Mm.24409 | TITLE ESTs | | | gi = 3386805 | 749820 |
| IC06021 | UG75 Expression | EST | Mm.24411 | TITLE ESTs | | | gi = 5125675 | 127924 |
| IC06022 | UG75 Expression | EST | Mm.24413 | TITLE ESTs | | | gi = 3374263 | 764622 |
| IC06023 | UG75 Expression | EST | Mm.24414 | TITLE ESTs | | | gi = 1937496 | 749601 |
| IC06024 | UG75 Expression | EST | Mm.24415 | TITLE ESTs | | | gi = 3376576 | 619586 |
| IC06025 | UG75 Expression | EST | Mm.24416 | TITLE ESTs | | | gi = 3393186 | 621242 |
| IC06026 | UG75 Expression | EST | Mm.24421 | TITLE ESTs | | | gi = 4967890 | 717638 |
| IC06027 | UG75 Expression | EST | Mm.24425 | TITLE ESTs | | | gi = 3394888 | 1395658 |
| IC06028 | UG75 Expression | EST | Mm.24426 | TITLE ESTs | | | gi = 1816954 | 765784 |
| IC06029 | UG75 Expression | EST | Mm.24432 | TITLE ESTs | | | gi = 2041675 | 749882 |
| IC06030 | UG75 Expression | EST | Mm.24434 | TITLE ESTs | | | gi = 3370530 | 619687 |
| IC06031 | UG75 Expression | EST | Mm.24435 | TITLE ESTs | | | gi = 5497211 | 569034 |
| IC06032 | UG75 Expression | EST | Mm.24436 | TITLE ESTs | | | gi = 1766722 | 620877 |
| IC06033 | UG75 Expression | EST | Mm.24437 | TITLE ESTs, Weakly similar to SKD1 PROTEIN [Mus musculus] | | | gi = 1676108 | 1140210 |
| IC06034 | UG75 Expression | EST | Mm.24438 | TITLE ESTs | | | gi = 2042901 | 751554 |
| IC06035 | UG75 Expression | EST | Mm.24440 | TITLE ESTs | | | gi = 2043012 | 751749 |
| IC06036 | UG75 Expression | EST | Mm.24441 | TITLE ESTs | | | gi = 2116456 | 751491 |
| IC06037 | UG75 Expression | EST | Mm.24442 | TITLE ESTs | | | gi = 1919559 | 777316 |
| IC06038 | UG75 Expression | EST | Mm.24443 | TITLE ESTs | | | gi = 2049059 | 751572 |
| IC06039 | UG75 Expression | EST | Mm.24444 | TITLE ESTs | | | gi = 1767177 | 621960 |
| IC06040 | UG75 Expression | EST | Mm.24445 | TITLE ESTs | | | gi = 4571769 | 751736 |
| IC06041 | UG75 Expression | EST | Mm.24446 | TITLE ESTs | | | gi = 2943080 | 751729 |
| IC06042 | UG75 Expression | EST | Mm.24449 | TITLE ESTs, Weakly similar to p140mDia [M. musculus] | | | gi = 4317383 | 638787 |
| IC06043 | UG75 Expression | EST | Mm.24450 | TITLE ESTs | | | gi = 3521365 | 893941 |
| IC06044 | UG75 Expression | EST | Mm.24451 | TITLE ESTs | | | gi = 4615716 | 750362 |
| IC06045 | UG75 Expression | EST | Mm.24456 | TITLA DNA segment, Chr 1, Wayne State University 40, expressed | GENE D1Wsu40e | | | 1282814 |
| IC06046 | UG75 Expression | EST | Mm.24460 | TITLE DNA segment, Chr 9, Wayne State University 18, expressed | GENE D9Wsu18e | | | 597414 |
| IC06047 | UG75 Expression | EST | Mm.24463 | TITEL DNA segment, Chr 16, Wayne State Universtiy 109, expressed | GENE D16Wsu109e | | | 1002322 |
| IC06048 | UG75 Expression | EST | Mm.24464 | TITLE ESTs | | | gi = 1755617 | 622463 |
| IC06049 | UG75 Expression | EST | Mm.24465 | TITLE ESTs | | | gi = 4217282 | 621840 |
| IC06050 | UG75 Expression | EST | Mm.24472 | TITLE ESTs | | | gi = 2067586 | 721638 |
| IC06051 | UG75 Expression | EST | Mm.24474 | TITLE ESTs, Weakly similar to predicted using Genefinder [C. elegans] | | | gi = 3372023 | 722555 |
| IC06052 | UG75 Expression | EST | Mm.24477 | TITLE DNA segment, Chr 14, Wayne Steate University 89, expressed | GENE D14Wsu89e | | | 641243 |
| IC06053 | UG75 Expression | EST | Mm.24482 | TITLE ESTs | | | gi = 1751981 | 61979 |
| IC06054 | UG75 Expression | EST | Mm.24491 | TITLE ESTs | | | gi = 3374059 | 1025382 |
| IC06055 | UG75 Expression | EST | Mm.24495 | TITLE ESTs, Weakly similar to apoptosis related protein APR-5 [H. sapiens] | | | gi = 5551394 | 752164 |
| IC06056 | UG75 Expression | EST | Mm.24496 | TITLE ESTs, Weakly similar to HYPOTHETICAL PROTEIN KIAA0144 [H. sapiens] | | | gi = 6560408 | 642471 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06057 | UG75 Expression | EST | Mm.24499 | TITLE ESTs, Weakly similar to ADP-RIBOSYLATION FACTOR 2 [Saccharomyces cerevisiae] | | | gi = 3216217 | 973744 |
| IC06058 | UG75 Expression | EST | Mm.24501 | TITLE ESTs, Weakly similar to KIAA0690 proteion [H. sapiens] | | | gi = 1290226 | 303694 |
| IC06059 | UG75 Expression | EST | Mm.24502 | TITLE ESTs | | | gi = 1901348 | 598124 |
| IC06060 | UG75 Expression | EST | Mm.24505 | TITLE ESTs | | | gi = 2040399 | 764209 |
| IC06061 | UG75 Expression | EST | Mm.24508 | TITLE ESTs | | | gi = 2068677 | 1262864 |
| IC06062 | UG75 Expression | EST | Mm.24514 | TITLE ESTs | | | gi = 3955985 | 617723 |
| IC06063 | UG75 Expression | EST | Mm.24516 | TITLE ESTs | | | gi = 3395025 | 635224 |
| IC06064 | UG75 Expression | EST | Mm.24517 | TITLE ESTs | | | gi = 1776850 | 1149080 |
| IC06065 | UG75 Expression | EST | Mm.24518 | TITLE ESTs | | | gi = 1726392 | 617786 |
| IC06066 | UG75 Expression | EST | Mm.24527 | TITLE ESTs | | | gi = 1875908 | 764407 |
| IC06067 | UG75 Expression | EST | Mm.24529 | TITLE ESTs | | | gi = 3720012 | 764211 |
| IC06068 | UG75 Expression | EST | Mm.24530 | TITLE ESTs, Moderately similar to Raf responsive zinc finger protein isoform [H. sapiens] | | | gi = 2193074 | 1330082 |
| IC06069 | UG75 Expression | EST | Mm.24537 | TITLE ESTs | | | gi = 4764614 | 719337 |
| IC06070 | UG75 Expression | EST | Mm.24538 | TITLE constitutive photomorphogenic protein 1 (Arabidopsis) | GENE Cop1-pending | | gi = 4199558 | 638638 |
| IC06071 | UG75 Expression | EST | Mm.24540 | TITLE ESTs, Weakly similar to contains similarity to ATP/GTP-binding site motif [C. elegans] | | | gi = 4315718 | 551262 |
| IC06072 | UG75 Expression | EST | Mm.24541 | TITLE ESTs, Weakly similar to F25H9.7 [C. elegans] | | | gi = 2516880 | 617400 |
| IC06073 | UG75 Expression | EST | Mm.24542 | TITLE ESTs, Weakly similar to F25H9.7 [C. elegans] [D. melnogaster] | | | gi = 3374413 | 1970473 |
| IC06074 | UG75 Expression | EST | Mm.24549 | TITLE ESTs, Weakly similar to cDNA EST EMBL:M88812 comes from this gene [C. elegans] | | | gi = 4258516 | 1328765 |
| IC06075 | UG75 Expression | EST | Mm.2455 | TITLE ESTs | | | gi = 1316398 | 596581 |
| IC06076 | UG75 Expression | EST | Mm.24550 | TITLE ESTs | | | gi = 4440649 | 643298 |
| IC06077 | UG75 Expression | EST | Mm.24552 | TITLE ESTs | | | gi = 3375116 | 636525 |
| IC06078 | UG75 Expression | EST | Mm.24554 | TITLE ESTs, Weakly similar to similar to C. elegans lin-19 [C. elegans] | | | gi = 6521047 | 2645850 |
| IC06079 | UG75 Expression | EST | Mm.24562 | TITLE ESTs | | | gi = 4272969 | 777190 |
| IC06080 | UG75 Expression | EST | Mm.24563 | TITLE ESTs | | | gi = 4276211 | 1361788 |
| IC06081 | UG75 Expression | EST | Mm.24569 | TITLE ESTs | | | gi = 1915154 | 973916 |
| IC06082 | UG75 Expression | EST | Mm.24573 | TITLE ESTs | | | gi = 6078038 | 617771 |
| IC06083 | UG75 Expression | EST | Mm.24574 | TITLE ESTs | | | gi = 4059311 | 620900 |
| IC06084 | UG75 Expression | EST | Mm.24575 | TITLE ESTs | | | gi = 1505230 | 595900 |
| IC06085 | UG75 Expression | EST | Mm.24576 | TITLE ESTs, Weakly similar to HORMONE SENSITIVE LIPASE [M. musculus] | | | gi = 5336922 | 1139829 |
| IC06086 | UG75 Expression | EST | Mm.24582 | TITLE ESTs | | | gi = 2807557 | 621045 |
| IC06087 | UG75 Expression | EST | Mm.24583 | TITLE ESTs | | | gi = 3393544 | 643629 |
| IC06088 | UG75 Expression | EST | Mm.24584 | TITLE ESTs, Weakly similar to predicted using Genefinder [C. elegans] | | | gi = 6083660 | 76449 |
| IC06089 | UG75 Expression | EST | Mm.24585 | TITLE ESTs, Moderately similar to serine/threonine protein kinase TAO1 [R. norvegicus] | | | gi = 3394856 | 1380120 |
| IC06090 | UG75 Expression | EST | Mm.24586 | TITLE ESTs | | | gi = 2247330 | 1193042 |
| IC06091 | UG75 Expression | EST | Mm.24589 | TITLE ESTs, Moderately similar to CAMP-DEPENDENT PROTEIN KINASE TYPE II-ALPHA REGULATORY CHAIN [M. musculus] | | | gi = 4029589 | 621258 |
| IC06092 | UG75 Expression | EST | Mm.24591 | TITLE ESTs, Weakly similar to similar to beta transducin proteins containing TRP-ASP domains [C. elegans] | | | gi = 29184002 | 599127 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06093 | UG75 Expression | EST | Mm.24592 | TITLE ESTs | | | gi = 3394095 | 616589 |
| IC06094 | UG75 Expression | EST | Mm.24594 | TITLE ESTs | | | gi = 4484567 | 959261 |
| IC06095 | UG75 Expression | EST | Mm.24600 | TITLE ESTs, Weakly similar to proline-rich protein [*M. musculus*] | | | gi = 2813515 | 718359 |
| IC06096 | UG75 Expression | EST | Mm.24601 | TITLE ESTs, Weakly similar to Yer134cp [*S. cerevisiae*] | | | gi = 4967588 | 636860 |
| IC06097 | UG75 Expression | EST | Mm.24605 | TITLE ESTs | | | gi = 3370208 | 1429885 |
| IC06098 | UG75 Expression | EST | Mm.24608 | TITLE ESTs | | | gi = 5910329 | 642767 |
| IC06099 | UG75 Expression | EST | Mm.24609 | TITLE ESTs | | | gi = 1324828 | 618808 |
| IC06100 | UG75 Expression | EST | Mm.24613 | TITLE ESTs | | | gi = 1888964 | 722849 |
| IC06101 | UG75 Expression | EST | Mm.24614 | TITLE ESTs | | | gi = 2188006 | 618948 |
| IC06102 | UG75 Expression | EST | Mm.24616 | TITLE ESTs | | | gi = 2516732 | 1097096 |
| IC06103 | UG75 Expression | EST | Mm.24621 | TITLE ESTs | | | gi = 2334049 | 551228 |
| IC06104 | UG75 Expression | EST | Mm.24624 | TITLE ESTs, Weakly similar to ANKYRIN [*M. musculus*] | | | gi = 3394116 | 1124144 |
| IC06105 | UG75 Expression | EST | Mm.24628 | TITLE ESTs | | | gi = 6098735 | 1378109 |
| IC06106 | UG75 Expression | EST | Mm.24629 | TITLE ESTs | | | gi = 6822531 | 1002884 |
| IC06107 | UG75 Expression | EST | Mm.24630 | TITLE ESTs | | | gi = 2967318 | 1295804 |
| IC06108 | UG75 Expression | EST | Mm.24633 | TITLE ESTs | | | gi = 5492046 | 750563 |
| IC06109 | UG75 Expression | EST | Mm.24634 | TITLE ESTs | | | gi = 437567 | 596864 |
| IC06110 | UG75 Expression | EST | Mm.24635 | TITLE ESTs, Moderately similar to phosphoenolpyruvate carboxykinase [*M. musculus*] | | | gi = 3299758 | 1380028 |
| IC06111 | UG75 Expression | EST | Mm.24637 | TITLE ESTs | | | gi = 1756097 | 617715 |
| IC06112 | UG75 Expression | EST | Mm.24640 | TITLE ESTs | | | gi = 13900596 | 555508 |
| IC06113 | UG75 Expression | EST | Mm.24642 | TITLE ESTs | | | gi = 6167978 | 1263306 |
| IC06114 | UG75 Expression | EST | Mm.24646 | TITLE ESTs | | | gi = 1505147 | 465219 |
| IC06115 | UG75 Expression | EST | Mm.24647 | TITLE ESTs | | | gi = 5495797 | 749372 |
| IC06116 | UG75 Expression | EST | Mm.24650 | TITLE ESTs | | | gi = 2203681 | 1888676 |
| IC06117 | UG75 Expression | EST | Mm.24655 | TITLE ESTs | | | gi = 2918419 | 621573 |
| IC06118 | UG75 Expression | EST | Mm.24661 | TITLE ESTs, Weakly similar to GASTRULA ZINC FINGER PROTEIN XLCGF62.1 [*Xenopus laevis*] | | | gi = 1619100 | 484215 |
| IC06119 | UG75 Expression | EST | Mm.24666 | TITLE ESTs | | | gi = 4401946 | 1001843 |
| IC06120 | UG75 Expression | EST | Mm.24670 | TITLE ESTs | | | gi = 1681709 | 596226 |
| IC06121 | UG75 Expression | EST | Mm.24671 | TITLE ESTs | | | gi = 2646442 | 777612 |
| | | | | | | | | 4601337 |
| | | | | | | | | 621190 |
| IC06122 | UG75 Expression | EST | Mm.24677 | TITLE ESTs, Weakly similar to PAR-6 [*M. musculus*] | | | gi = 4601337 | 617008 |
| IC06123 | UG75 Expression | EST | Mm.24678 | TITLE ESTs | | | gi = 4317502 | 1295801 |
| IC06124 | UG75 Expression | EST | Mm.24679 | TITLE ESTs, Moderately similar to 5-LIPOXYGENASE ACTIVATING PROTEIN [*Ovis aries*] | | | gi = 4721630 | |
| IC06125 | UG75 Expression | EST | Mm.24684 | TITLE ESTs | | | gi = 22721695 | 1148991 |
| IC06126 | UG75 Expression | EST | Mm.24685 | TITLE ESTs | | | gi = 2256114 | 893983 |
| IC06127 | UG75 Expression | EST | Mm.24686 | TITLE ESTs | | | gi = 2256199 | 1445927 |
| IC06128 | UG75 Expression | EST | Mm.24692 | TITLE ESTs | | | gi = 4317480 | 894357 |
| IC06129 | UG75 Expression | EST | Mm.24701 | TITLE ESTs | | | gi = 6076652 | 1152480 |
| IC06130 | UG75 Expression | EST | Mm.24703 | TITLE ESTs | | | gi = 4434534 | 598804 |
| IC06131 | UG75 Expression | EST | Mm.24707 | TITLE ESTs | | | gi = 4778210 | 973391 |
| IC06132 | UG75 Expression | EST | Mm.24711 | TITLE ESTs | | | gi = 1936958 | 751310 |
| IC06133 | UG75 Expression | EST | Mm.24719 | TITLE ESTs | | | gi = 2670454 | 620402 |
| IC06134 | UG75 Expression | EST | Mm.24725 | TITLE ESTs | | | gi = 3519535 | 641333 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06135 | UG75 Expression | EST | Mm.24731 | TITLE ESTs, Weakly similar to ORF YGR038w [S. cerevisiae] | | | gi = 1888977 | 637266 |
| IC06136 | UG75 Expression | EST | Mm.24736 | TITLE ESTs, Weakly similar to (define not available 5579090) [M. musculus] | | | gi = 5125159 | 616615 |
| IC06137 | UG75 Expression | EST | Mm.24737 | TITLE ESTs | | | gi = 2291683 | 1263877 |
| IC06138 | UG75 Expression | EST | Mm.24739 | TITLE ESTs | | | gi = 2263124 | 958782 |
| IC06139 | UG75 Expression | EST | Mm.24740 | TITLE ESTs | | | gi = 5907780 | 973336 |
| IC06140 | UG75 Expression | EST | Mm.24742 | TITLE ESTs, Weakly similar to C10G11.5 [C. elegans] | | | gi = 3749110 | 1363233 |
| IC06141 | UG75 Expression | EST | Mm.24745 | TITLE ESTs, Moderately similar to unknown [R. norvegicus] | | | gi = 4967977 | 959278 |
| IC06142 | UG75 Expression | EST | Mm.24751 | TITLE ESTs | | | gi = 6438042 | 958666 |
| IC06143 | UG75 Expression | EST | Mm.24752 | TITLE EST | | | gi = 2308186 | 958663 |
| IC06144 | UG75 Expression | EST | Mm.24753 | TITLE ESTs | | | gi = 1282448 | 958677 |
| IC06145 | UG75 Expression | EST | Mm.24758 | TITLE ESTs, Weakly similar to CYTOSKELETAL P17 PROTEIN [Dictyostelium discoideum] | | | gi = 4061507 | 777300 |
| IC06146 | UG75 Expression | EST | Mm.24761 | TITLE ESTs | | | gi = 2917336 | 634950 |
| IC06147 | UG75 Expression | EST | Mm.24765 | TITLE ESTs, Weakly similar to HYPOTHETICAL 97.1 KD PROTEIN R05D3.4 IN CHROMOSOME III [Cainorhabditis elegans] | | | gi = 3955595 | 618646 |
| IC06148 | UG75 Expression | EST | Mm.24770 | TITLE ESTs, Weakly similar to proline-rich protein MP2 [M. musculus] | | | gi = 6084213 | 1282602 |
| IC06149 | UG75 Expression | EST | Mm.24773 | TITLE ESTs | | | gi = 3054704 | 619982 |
| IC06150 | UG75 Expression | EST | Mm.24775 | TITLE ESTs | | | gi = 4059227 | 559113 |
| IC06151 | UG75 Expression | EST | Mm.2478 | TITLE ESTs | | | gi = 6078725 | 750740 |
| IC06152 | UG75 Expression | EST | Mm.24781 | TITLE ESTs, Weakly similar to immune associated protein 38 [M. musculus] | | | gi = 3719051 | 618367 |
| IC06153 | UG75 Expression | EST | Mm.24784 | TITLE ESTs | | | gi = 6854605 | 1148764 |
| IC06154 | UG75 Expression | EST | Mm.24786 | TITLE biotimidase | GENE Btd | | gi = 2262925 | 958649 |
| IC06155 | UG75 Expression | EST | Mm.24788 | TITLE ESTs | | | gi = 1487671 | 719246 |
| IC06156 | UG75 Expression | EST | Mm.24789 | TITLE ESTs, Weakly similar to apoptotic protease activating factor 1 [M. musculus] | | | gi = 1287807 | 894266 |
| IC06157 | UG75 Expression | EST | Mm.24790 | TITLE ESTs, Weakly similar to ANKYRIN, BRAIN VARIANT 2 [Homo sapiens] | | | gi = 6079150 | 1294835 |
| IC06158 | UG75 Expression | EST | Mm.24794 | TITLE ESTs | | | gi = 2516908 | 1278875 |
| IC06159 | UG75 Expression | EST | Mm.24797 | TITLE ESTs | | | gi = 2646429 | 765692 |
| IC06160 | UG75 Expression | EST | Mm.24806 | TITLE ESTs | | | gi = 3297103 | 1328816 |
| IC06161 | UG75 Expression | EST | Mm.24807 | TITLE ESTs | | | gi = 4271706 | 636604 |
| IC06162 | UG75 Expression | EST | Mm.24809 | TITLE ESTs | | | gi = 4276214 | 637147 |
| IC06163 | UG75 Expression | EST | Mm.24816 | TITLE ESTs | | | gi = 1767796 | 1149485 |
| IC06164 | UG75 Expression | EST | Mm.24821 | TITLE ESTs | | | gi = 4766698 | 719460 |
| IC06165 | UG75 Expression | EST | Mm.24826 | TITLE ESTs, Moderately similar to p40 [H. sapiens] | | | gi = 2919268 | 635233 |
| IC06166 | UG75 Expression | EST | Mm.24828 | TITLE ESTs, Weakly similar to 5'-AMP-ACTIVATED PROTEIN KINASE, GAMMA-1 SUBUNIT [M. musculus] | | | gi = 1427693 | 534219 |
| IC06167 | UG75 Expression | EST | Mm.24837 | TITLE ESTs, Weakly similar to C17F3.3 [C. elegans] | | | gi = 5909269 | 1344362 |
| IC06168 | UG75 Expression | EST | Mm.24842 | TITLE ESTs | | | gi = 2404296 | 638401 |
| IC06169 | UG75 Expression | EST | Mm.24848 | TITLE differentially expressed in B16F10 1 | GENE Deb1 | | gi = 241594 | 596370 |
| IC06170 | UG75 Expression | EST | Mm.24855 | TITLE DNA segment, Chr 11, Wayne State University 68, expressed | GENE D11Wsu68e | Band 47B | | 1448561 |
| IC06171 | UG75 Expression | EST | Mm.24860 | TITLE DNA segment, Chr 17, Abbott 1e | GENE D17Abb1e | | | 620293 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06172 | UG75 Expression | EST | Mm.24862 | TITLE ESTs | | | gi = 1672644 | 574447 |
| IC06173 | UG75 Expression | EST | Mm.24864 | TITLE ESTs, Weakly similar to contains similartiy to CDP-alcohol phosphotransferases [*C. elegans*] | | | gi = 2504792 | 576136 |
| IC06174 | UG75 Expression | EST | Mm.24868 | TITLE ESTs, Moderately similar to CGI-147 proteion [*H. sapiens*] | | | gi = 5910289 | 551352 |
| IC06175 | UG75 Expression | EST | Mm.24869 | TITLE ESTs | | | gi = 4408001 | 976095 |
| IC06176 | UG75 Expression | EST | Mm.24873 | TITLE ESTs, Moderately similar to GAR1 PROTEIN [*Saccharomyces cerevisiae*] | | | gi = 1333457 | 717945 |
| IC06176 | UG75 Expression | EST | Mm.24873 | TITLE ESTs, Moderately similar to GAR1 PROTEIN | | | gi = 1333457 | 717 |
| IC06177 | UG75 Expression | EST | Mm.24875 | | | | gi = 3957230 | 721761 |
| IC06176 | UG75 Expression | EST | Mm.24873 | TITLE ESTs, Moderately similar to GAR1 PROTEIN | | | gi = 1333457 | 717 |
| IC06178 | UG75 Expression | EST | Mm.24877 | | | | gi = 3375450 | 596954 |
| IC06176 | UG75 Expression | EST | Mm.24873 | TITLE ESTs, Moderately similar to GAR1 PROTEIN | | | gi = 1333457 | 717 |
| IC06179 | UG75 Expression | EST | Mm.24878 | , Moderately similar to hypothetical protein [*H. sapiens*] | | | gi = 2308504 | 619567 |
| IC06176 | UG75 Expression | EST | Mm.24873 | TITLE ESTs, Moderately similar to GAR1 PROTEIN | | | gi = 1333457 | 717 |
| IC06180 | UG75 Expression | EST | Mm.24883 | , Weakly similar to PYRROLINE-5-CARBOXYLATE REDUCTASE [*Glycine max*] | | | gi = 2850668 | 635280 |
| IC06181 | UG75 Expression | EST | Mm.24886 | [*H. sapiens*] | | | gi = 2516362 | 765247 |
| IC06176 | UG75 Expression | EST | Mm.24873 | TITLE ESTs, Moderately similar to GAR1 PROTEIN | | | gi = 1333457 | 717 |
| IC06182 | UG75 Expression | EST | Mm.24893 | TITLE ESTs | | | gi = 2516428 | 1429174 |
| IC06183 | UG75 Expression | EST | Mm.249 | TITLE ESTs | | | gi = 2039559 | 642920 |
| IC06184 | UG75 Expression | EST | Mm.2490 | TITLE ESTs | | | gi = 2292276 | 717661 |
| IC06185 | UG75 Expression | EST | Mm.24925 | TITLE ESTs | | | gi = 1937222 | 749386 |
| IC06186 | UG75 Expression | EST | Mm.24932 | TITLE ESTs | | | gi = 2517376 | 764298 |
| IC06187 | UG75 Expression | EST | Mm.24937 | TITLE ESTs | | | gi = 6100378 | 1264758 |
| IC06188 | UG75 Expression | EST | Mm.24956 | TITLE ESTs | | | gi = 5909292 | 958373 |
| IC06189 | UG75 Expression | EST | Mm.24974 | TITLE ESTs | | | gi = 2518265 | 617180 |
| IC06190 | UG75 Expression | EST | Mm.2500 | TITLE ESTs | | | gi = 3683309 | 765727 |
| IC06191 | UG75 Expression | EST | Mm.25030 | TITLE ESTs, Weakly similar to 3-7 gene product [*H. sapiens*] | | | gi = 2519745 | 1279579 |
| IC06192 | UG75 Expression | EST | Mm.25042 | TITLE ESTs | | | gi = 2519975 | 1295515 |
| IC06193 | UG75 Expression | EST | Mm.25075 | TITLE ESTs, Moderately similar to putative seven pass transmembrane protein [*H. sapiens*] | | | gi = 2521071 | 1149458 |
| IC06194 | UG75 Expression | EST | Mm.25078 | TITLE ESTs | | | gi = 2520928 | 2225466 |
| IC06195 | UG75 Expression | EST | Mm.25086 | TITLE ESTs | | | gi = 2521061 | 749382 |
| IC06196 | UG75 Expression | EST | Mm.25096 | TITLE ESTs | | | gi = 3982370 | 642368 |
| IC06197 | UG75 Expression | EST | Mm.25116 | TITLE ESTs | | | gi = 2462024 | 533356 |
| IC06198 | UG75 Expression | EST | Mm.25118 | TITLE ESTs | | | gi = 3680517 | 1380410 |
| IC06199 | UG75 Expression | EST | Mm.25119 | [*H. sapiens*] | | | gi = 1404938 | 719072 |
| IC06200 | UG75 Expression | EST | Mm.25122 | TITLE ESTs | | | gi = 3296122 | 718805 |
| IC06201 | UG75 Expression | EST | Mm.25126 | TITLE ESTs, Weakly similar to unknown [*C. elegans*] | | | gi = 2283043 | 765228 |
| IC06202 | UG75 Expression | EST | Mm.25136 | TITLE ESTs | | | gi = 4605228 | 1446731 |
| IC06203 | UG75 Expression | EST | Mm.25137 | TITLE ESTs | | | gi = 1682158 | 723215 |
| IC06204 | UG75 Expression | EST | Mm.25142 | TITLE ESTs | | | gi = 1288763 | 1140350 |
| IC06205 | UG75 Expression | EST | Mm.25143 | TITLE ESTs, Weakly similar to Similarity to Entamoeba elongation factor 1-alpha [*C. elegans*] | | | gi = 1325766 | 1148425 |
| IC06206 | UG75 Expression | EST | Mm.25146 | TITLE ESTs, Weakly similar to SOF1 PROTEIN [*Saccharomyces cerevisiae*] | | | gi = 6079316 | 1148544 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06207 | UG75 Expression | EST | Mm.25150 | TITLE ESTs | | | gi = 3374436 | 574459 |
| IC06208 | UG75 Expression | EST | Mm.25156 | TITLE ESTs | | | gi = 2232932 | 1002856 |
| IC06209 | UG75 Expression | EST | Mm.25157 | TITLE ESTs, Weakly similar to Similarity to S. pombe hypothetical protein C1D4.09C [C. elegans] | | | gi = 2591663 | 1002221 |
| IC06210 | UG75 Expression | EST | Mm.25162 | TITLE ESTs | | | gi = 3370733 | 1001468 |
| IC06211 | UG75 Expression | EST | Mm.25169 | TITLE ESTs | | | gi = 2292171 | 637151 |
| IC06212 | UG75 Expression | EST | Mm.25170 | TITLE ESTs | | | gi = 2192228 | 642521 |
| IC06213 | UG75 Expression | EST | Mm.25181 | TITLE ESTs, Moderately similar to The KIAA0191 gene is express ubiquitously. [H. sapiens] | | | gi = 4305511 | 643380 |
| IC06214 | UG75 Expression | EST | Mm.25188 | TITLE ESTs, Weakly similar to ORF YGL100w [S. cerevisiae] | | | gi = 4606288 | 1313657 |
| IC06215 | UG75 Expression | EST | Mm.2519 | TITLE ESTs | | | gi = 3978771 | 765896 |
| IC06216 | UG75 Expression | EST | Mm.25200 | TITLE ESTs | | | gi = 3372678 | 637844 |
| IC06217 | UG75 Expression | EST | Mm.25204 | TITLE ESTs, Weakly similar to coiled-coil like protein 1 [M. musculus] | | | gi = 2625582 | 1749651 |
| IC06218 | UG75 Expression | EST | Mm.25209 | TITLE ESTs | | | gi = 1724411 | 581890 |
| IC06219 | UG75 Expression | EST | Mm.25210 | TITLE ESTs [R. norvegicus] | | | gi = 2885826 | 576931 |
| IC06220 | UG75 Expression | EST | Mm.25221 | TITLE ESTs | | | gi = 1700055 | 643405 |
| IC06221 | UG75 Expression | EST | Mm.25233 | TITLE ESTs | | | gi = 2518970 | 1224940 |
| IC06222 | UG75 Expression | EST | Mm.25238 | TITLE ESTs | | | gi = 5549095 | 1329923 |
| IC06223 | UG75 Expression | EST | Mm.25239 | TITLE ESTs | | | gi = 3371172 | 1344841 |
| IC06224 | UG75 Expression | EST | Mm.25243 | TITLE ESTs | | | gi = 6555868 | 973017 |
| IC06225 | UG75 Expression | EST | Mm.25245 | TITLE ESTs | | | gi = 3720176 | 1395282 |
| IC06226 | UG75 Expression | EST | Mm.25248 | TITLE ESTs | | | gi = 1801004 | 764777 |
| IC06227 | UG75 Expression | EST | Mm.25261 | TITLE ESTs, Moderately similar to meningioma-expressed antigen 11 [H. sapiens] | | | gi = 2857777 | 1279744 |
| IC06228 | UG75 Expression | EST | Mm.25262 | TITLE ESTs | | | gi = 2917800 | 576374 |
| IC06229 | UG75 Expression | EST | Mm.25263 | TITLE ESTs | | | gi = 2308303 | 750863 |
| IC06230 | UG75 Expression | EST | Mm.25264 | TITLE DNA segment, Chr 10, Wayne State University 42, expressed | GENE D10Wsu42e | | | 1193105 |
| IC06231 | UG75 Expression | EST | Mm.25265 | TITLE ESTs | | | gi = 2201165 | 1279371 |
| IC06232 | UG75 Expression | EST | Mm.25269 | TITLE ESTs, Moderately similar to KIAA0187 [H. sapiens] | | | gi = 3978848 | 1193512 |
| IC06233 | UG75 Expression | EST | Mm.25270 | TITLE ESTs | | | gi = 2744623 | 1193567 |
| IC06234 | UG75 Expression | EST | Mm.25272 | TITLE ESTs | | | gi = 2516488 | 1162087 |
| IC06235 | UG75 Expression | EST | Mm.25277 | TITLE EST | | | gi = 7157832 | 1176911 |
| IC06237 | UG75 Expression | EST | Mm.25279 | TITLE ESTs, Moderately similar to PROTEIN KINASE C INHIBITOR 1 [Bos taurus; Rattus norvegicus] | | | gi = 6084168 | 1280125 |
| IC06238 | UG75 Expression | EST | Mm.25285 | TITLE ESTs | | | gi = 2964994 | 1749093 |
| IC06238 | UG75 Expression | EST | Mm.25287 | TITLE ESTs | | | gi = 2521836 | 596216 |
| IC06239 | UG75 Expression | EST | Mm.25288 | TITLE ESTs | | | gi = 3376135 | 1001873 |
| IC06240 | UG75 Expression | EST | Mm.25290 | TITLE ESTs | | | gi = 2775567 | 1226065 |
| IC06241 | UG75 Expression | EST | Mm.25291 | TITLE EST | | | gi = 2775621 | 1226135 |
| IC06242 | UG75 Expression | EST | Mm.25296 | TITLE ESTs | | | gi = 2516379 | 1092223 |
| IC06243 | UG75 Expression | EST | Mm.25298 | TITLE ESTs, Weakly similar to ORF YGR200c [S. cerevisiae] | | | gi = 3394070 | 1149113 |
| IC06244 | UG75 Expression | EST | Mm.25299 | TITLE ESTs | | | gi = 2068247 | 643943 |
| IC06245 | UG75 Expression | EST | Mm.253 | TITLE ESTs, Weakly similar to rjs [M. musculus] | | | gi = 2652853 | 893918 |
| IC06246 | UG75 Expression | EST | Mm.25307 | TITLE ESTs | | | gi = 6756449 | 634903 |
| IC06247 | UG75 Expression | EST | Mm.25308 | TITLE ESTs | | | gi = 3718498 | 720848 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06248 | UG75 Expression | EST | Mm.25309 | TITLE ESTs, Moderately similar to URIDINE KINASE [Escherichia coli] | | | gi = 2516511 | 642042 |
| IC06249 | UG75 Expression | EST | Mm.25310 | TITLE ESTs | | | gi = 4441954 | 620817 |
| IC06250 | UG75 Expression | EST | Mm.25311 | TITLE ESTs | | | gi = 6748490 | 599228 |
| IC06251 | UG75 Expression | EST | Mm.25315 | TITLE ESTs, Weakly similar to F25B5.3 [C. elegans] | | | gi = 1310013 | 1002180 |
| IC06252 | UG75 Expression | EST | Mm.25319 | TITLE ESTs, Moderately similar to putative ATP-dependent mitochondrial RNA helicase [H. sapiens] | | | gi = 1676504 | 619210 |
| IC06253 | UG75 Expression | EST | Mm.25320 | TITLE ESTs | | | gi = 3395093 | 620932 |
| IC06254 | UG75 Expression | EST | Mm.25321 | TITLE ESTs, Weakly similar to NMUDC protein [M. musculus] | | | gi = 3718127 | 616618 |
| IC06255 | UG75 Expression | EST | Mm.25322 | TITLE ESTs | | | gi = 1315510 | 577920 |
| IC06256 | UG75 Expression | EST | Mm.25326 | TITLE ESTs | | | gi = 3885218 | 1177252 |
| IC06257 | UG75 Expression | EST | Mm.25329 | TITLE ESTs | | | gi = 4613327 | 764365 |
| IC06258 | UG75 Expression | EST | Mm.25330 | TITLE ESTs, Weakly similar to HYPOTHETICAL 20.1 KD PROTEIN IN HSCA 5'REGION [Escherichia coli] | | | gi = 1287613 | 1243968 |
| IC06259 | UG75 Expression | EST | Mm.25331 | TITLE ESTs | | | gi = 2520212 | 576633 |
| IC06260 | UG75 Expression | EST | Mm.25336 | TITLE ESTs | | | gi = 3372918 | 749313 |
| IC06261 | UG75 Expression | EST | Mm.25337 | TITLE ESTs | | | gi = 6096341 | 371256 |
| IC06262 | 00/04/26 UG#76 17Lid Expansion | EST | Mm.25340 | ESTs | | | gi = 2885817 | 2649840 |
| IC06263 | UG75 Expression | EST | Mm.25345 | TITLE ESTs | | | gi = 2516792 | 718535 |
| IC06264 | UG75 Expression | EST | Mm.25350 | TITLE ESTs | | | gi = 1369187 | 1445947 |
| IC06265 | UG75 Expression | EST | Mm.25364 | TITLE ESTs, Weakly similar to damage-specific DNA binding protein 1 [M. musculus] | | | gi = 1407209 | 1293601 |
| IC06266 | UG75 Expression | EST | Mm.25366 | TITLE ESTs | | | gi = 1910239 | 642672 |
| IC06267 | UG75 Expression | EST | Mm.25377 | TITLE ESTs, Weakly similar to MAST CELL CARBOXYPEPTIDASE A PRECURSOR [M. musculus] | | | gi = 2917255 | 1051155 |
| IC06268 | UG75 Expression | EST | Mm.25378 | TITLE ESTs | | | gi = 2917274 | 2101205 |
| IC06269 | UG75 Expression | EST | Mm.25382 | TITLE ESTs | | | gi = 2917371 | 777569 |
| IC06270 | UG75 Expression | EST | Mm.25290 | TITLE ESTs | | | gi = 2917603 | 640659 |
| IC06271 | UG75 Expression | EST | Mm.25393 | TITLE ESTs | | | gi = 6824638 | 1279657 |
| IC06272 | UG75 Expression | EST | Mm.25296 | TITLE ESTs | | | gi = 5910481 | 404026 |
| IC06273 | UG75 Expression | EST | Mm.25412 | TITLE ESTs, Weakly similar to hypthetical protein 1 [R. norvegicus] | | | gi = 3372921 | 636120 |
| IC06274 | UG75 Expression | EST | Mm.25428 | TITLE ESTs | | | gi = 2918423 | 539836 |
| IC06275 | UG75 Expression | EST | Mm.25445 | TITLE ESTs | | | gi = 2918714 | 644933 |
| IC06276 | UG75 Expression | EST | Mm.25450 | TITLE ESTs | | | gi = 2652696 | 721739 |
| IC06277 | UG75 Expression | EST | Mm.25452 | TITLE ESTs | | | gi = 2919563 | 641763 |
| IC06278 | UG75 Expression | EST | Mm.25455 | TITLE ESTs | | | gi = 1759898 | 619148 |
| IC06279 | UG75 Expression | EST | Mm.25457 | TITLE ESTs | | | gi = 2918944 | 1363077 |
| IC06280 | UG75 Expression | EST | Mm.25464 | TITLE ESTs | | | gi = 2919038 | 622618 |
| IC06281 | UG75 Expression | EST | Mm.25483 | TITLE ESTs | | | gi = 2919367 | 634951 |
| IC06282 | UG75 Expression | EST | Mm.25497 | TITLE ESTs | | | gi = 2919521 | 635603 |
| IC06283 | UG75 Expression | EST | Mm.25504 | TITLE ESTs, Weakly similar to unknown [H. sapiens] | | | gi = 5910366 | 551454 |
| IC06284 | UG75 Expression | EST | Mm.25511 | TITLE ESTs | | | gi = 2919706 | 894545 |
| IC06285 | UG75 Expression | EST | Mm.25538 | TITLE ESTs | | | gi = 2920261 | 1328202 |
| IC06286 | UG75 Expression | EST | Mm.25540 | TITLE ESTs | | | gi = 6098782 | 1395606 |
| IC06287 | UG75 Expression | EST | Mm.25542 | TITLE ESTs | | | gi = 3987098 | 749377 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06288 | UG75 Expression | EST | Mm.25543 | TITLE ESTs, Weakly similar to (define not available 5764539) [*M. musculus*] | | | gi = 3749141 | 145991 |
| IC06289 | UG75 Expression | EST | Mm.25546 | TITLE ESTs | | | gi = 3732410 | 1395458 |
| IC06290 | UG75 Expression | EST | Mm.25547 | TITLE ESTs, Moderately similar to GUANINE NUCLEOTIDE-BINDING PROTEIN G(T) GAMMA-1 SUBUNIT [*Homo sapiens*] | | | gi = 4271650 | 847760 |
| IC06291 | UG75 Expression | EST | Mm.25548 | TITLE ESTs | | | gi = 3393433 | 1002569 |
| IC06292 | UG75 Expression | EST | Mm.25549 | TITLE ESTs | | | gi = 3393327 | 619042 |
| IC06293 | UG75 Expression | EST | Mm.25552 | TITLE ESTs | | | gi = 3978767 | 1262013 |
| IC06294 | UG75 Expression | EST | Mm.25553 | TITLE ESTs | | | gi = 3375850 | 1281416 |
| IC06295 | UG75 Expression | EST | Mm.25554 | TITLE ESTs | | | gi = 2979085 | 1281491 |
| IC06296 | UG75 Expression | EST | Mm.25555 | TITLE ESTs | | | gi = 2756628 | 126345 |
| IC06297 | UG75 Expression | EST | Mm.25558 | TITLE ESTs | | | gi = 2405131 | 750205 |
| IC06298 | UG75 Expression | EST | Mm.25559 | TITLE ESTs | | | gi = 1758614 | 974068 |
| IC06299 | UG75 Expression | EST | Mm.25563 | TITLE ESTs | | | gi = 2282743 | 1279766 |
| IC06300 | UG75 Expression | EST | Mm.25564 | TITLE ESTs, Weakly similar to ARL-6 interacting protein-2 [*M. musculus*] | | | gi = 6824763 | 1279795 |
| IC06301 | UG75 Expression | EST | Mm.25565 | TITLE ESTs | | | gi = 4482610 | 1278750 |
| IC06302 | UG75 Expression | EST | Mm.25568 | TITLE ESTs, Moderately similar to The KIAA0147 gene product is related to adenylyl cyclase. [*H. sapiens*] | | | gi = 3518525 | 638628 |
| IC06303 | UG75 Expression | EST | Mm.25573 | TITLE ESTs | | | gi = 2049074 | 638149 |
| IC06304 | UG75 Expression | EST | Mm.25576 | TITLE ESTs | | | gi = 2040272 | 634853 |
| IC06305 | UG75 Expression | EST | Mm.25581 | TITLE ESTs | | | gi = 2519010 | 596506 |
| IC06306 | UG75 Expression | EST | Mm.25583 | TITLE ESTs, Moderately similar to CGI-134 protein | | | gi = 4307205 | 644099 |
| IC06307 | UG75 Expression | EST | Mm.25585 | TITLE ESTs, Moderately similar to CGI-134 protein [*H. sapiens*] | | | gi = 1554365 | 641577 |
| IC06308 | UG75 Expression | EST | Mm.25586 | TITLE DNA segment, Chr 11, Wayne State University 99, expressed | GENE D11Wsu99e | | | 972394 |
| IC06309 | UG75 Expression | EST | Mm.25594 | TITLE ESTs | | | gi = 1838440 | 620715 |
| IC06310 | UG75 Expression | EST | Mm.25595 | TITLE ESTs | | | gi = 4777915 | 1380139 |
| IC06311 | UG75 Expression | EST | Mm.25062 | TITLE ESTs | | | gi = 3684018 | 1245103 |
| IC06312 | UG75 Expression | EST | Mm.25608 | TITLE ESTs | | | gi = 6083904 | 643340 |
| IC06313 | UG75 Expression | EST | Mm.25609 | TITLE ESTs | | | gi = 4030298 | 638412 |
| IC06314 | UG75 Expression | EST | Mm.25614 | TITLE ESTs, Weakly similar to HYPOTHETICAL 16.3 KD PROTEIN IN DUR1,2-NGR1 INTERGENIC REGION [*Saccharomyces cerevisiae*] | | | gi = 1309617 | 534014 |
| IC06315 | UG75 Expression | EST | Mm.25615 | TITLE ESTs | | | gi = 2956233 | 1293856 |
| IC06316 | UG75 Expression | EST | Mm.25616 | TITLE ESTs, Weakly similar to similar to alpha/beta hydrolase fold [*C. elegans*] | | | gi = 6517247 | 1263858 |
| IC06317 | UG75 Expression | EST | Mm.25619 | TITLE ESTs | | | gi = 3158696 | 1263982 |
| IC06318 | UG75 Expression | EST | Mm.25621 | TITLE ESTs | | | gi = 3386837 | 1279827 |
| IC06319 | UG75 Expression | EST | Mm.25624 | TITLE ESTs | | | gi = 6824635 | 620285 |
| IC06320 | UG75 Expression | EST | Mm.25627 | TITLE ESTs | | | gi = 2917910 | 622286 |
| IC06321 | UG75 Expression | EST | Mm.25630 | TITLE ESTs | | | gi = 6009034 | 1282104 |
| IC06322 | UG75 Expression | EST | Mm.25632 | TITLE ESTs | | | gi = 6098609 | 1296124 |
| IC06323 | UG75 Expression | EST | Mm.25634 | TITLE ESTs | | | gi = 5338266 | 641344 |
| IC06324 | UG75 Expression | EST | Mm.25635 | TITLE ESTs | | | gi = 4603118 | 1344710 |
| IC06325 | UG75 Expression | EST | Mm.25640 | TITLE CD39 antigen-like 2 | GENE Cd39l2 | | gi = 6085088 | 894162 |
| IC06326 | UG75 Expression | EST | Mm.25643 | TITLE ESTs | | | gi = 3286296 | 1329479 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06327 | UG75 Expression | EST | Mm.25644 | TITLE ESTs | | | gi = 5493145 | 533614 |
| IC06328 | UG75 Expression | EST | Mm.25645 | TITLE ESTs | | | gi = 1834226 | 1329502 |
| IC06329 | UG75 Expression | EST | Mm.25649 | TITLE ESTs | | | gi = 2518001 | 958851 |
| IC06330 | UG75 Expression | EST | Mm.25661 | TITLE ESTs, Weakly similar to p58 [M. musculus] | | | gi = 1375605 | 533956 |
| IC06331 | UG75 Expression | EST | Mm.25664 | TITLE ESTs | | | gi = 3387143 | 621586 |
| IC06332 | UG75 Expression | EST | Mm.25665 | TITLE ESTs | | | gi = 1917258 | 764387 |
| IC06333 | UG75 Expression | EST | Mm.25669 | TITLE ESTs | | | gi = 4724439 | 434090 |
| IC06334 | UG75 Expression | EST | Mm.2567 | TITLE ESTs | | | gi = 403627 | 718579 |
| IC06335 | UG75 Expression | EST | Mm.25674 | TITLE ESTs | | | gi = 2591769 | 1149285 |
| IC06336 | UG75 Expression | EST | Mm.25677 | TITLE ESTs | | | gi = 4317188 | 1248192 |
| IC06337 | UG75 Expression | EST | Mm.25679 | TITLE ESTs | | | gi = 3295644 | 1263026 |
| IC06338 | UG75 Expression | EST | Mm.25680 | TITLE ESTs | | | gi = 4317202 | 722324 |
| IC06339 | UG75 Expression | EST | Mm.25681 | TITLE ESTs, Moderately similar to PP2C [H. sapiens] | | | gi = 1662882 | 617687 |
| IC06340 | UG75 Expression | EST | Mm.25695 | TITLE ESTs | | | gi = 2965931 | 597229 |
| IC06341 | UG75 Expression | EST | Mm.25700 | TITLE ESTs | | | gi = 3295195 | 1749026 |
| IC06342 | UG75 Expression | EST | Mm.25703 | TITLE ESTs | | | gi = 2049017 | 621409 |
| IC06343 | UG75 Expression | EST | Mm.25705 | TITLE ESTs, Weakly similar to probable transcription regulator NT fin12 [M. musculus] | | | gi = 5910295 | 1001829 |
| IC06344 | UG75 Expression | EST | Mm.25707 | PRECURSOR [M. musculus] | | | gi = 6084327 | 1139752 |
| IC06345 | UG75 Expression | EST | Mm.25710 | TITLE ESTs, Moderately similar to centriole associated protein CEP110 [H. sapiens] | | | gi = 1355643 | 764969 |
| IC06346 | UG75 Expression | EST | Mm.25715 | TITLE ESTs | | | gi = 1853720 | 1279347 |
| IC06347 | UG75 Expression | EST | Mm.25719 | TITLE ESTs, Weakly similar to HYPOTHETICAL PROTEIN HI1723 [Haemophilus influenzae] | | | gi = 5498170 | 718838 |
| IC06348 | UG75 Expression | EST | Mm.25720 | TITLE ESTs | | | gi = 2201835 | 618208 |
| IC06349 | UG75 Expression | EST | Mm.25725 | TITLE ESTs, Moderately similar to KIAA0423 [H. sapiens] | | | gi = 3373243 | 619682 |
| IC06350 | UG75 Expression | EST | Mm.25727 | TITLE DNA segment, Chr 8, Wayne State University 151, GENE D8Wsu151e expressed | | | | 616619 |
| IC06351 | UG75 Expression | EST | Mm.25743 | TITLE ESTs, Weakly similar to Low Density Lipoprotein Receptor Related Protein 4 [M. musculus] | | | gi = 6517383 | 1282496 |
| IC06352 | UG75 Expression | EST | Mm.25753 | TITLE ESTs, Moderately similar to Cdc42 effector protein 3 [H. sapiens] | | | gi = 3519467 | 1429600 |
| IC06353 | UG75 Expression | EST | Mm.25761 | TITLE ESTs | | | gi = 4274774 | 1361472 |
| IC06354 | UG75 Expression | EST | Mm.25762 | TITLE ESTs, Weakly similar to TRANSCRIPTION FACTOR E3 [H. sapiens] | | | gi = 5495446 | 1361949 |
| IC06355 | UG75 Expression | EST | Mm.25764 | TITLE ESTs | | | gi = 3336292 | 1362115 |
| IC06356 | UG75 Expression | EST | Mm.25765 | TITLE ESTs | | | gi = 3079266 | 1329366 |
| IC06357 | 00/04/26 UG#76 17Lid Expansion | EST | Mm.25768 | ESTs | | | gi = 4271553 | |
| IC06358 | UG75 Expression | EST | Mm.25771 | TITLE ESTs | | | gi = 4434537 | 1498813 |
| IC06359 | UG75 Expression | EST | Mm.25773 | TITLE ESTs | | | gi = 3602358 | 1362311 |
| IC06360 | UG75 Expression | EST | Mm.25774 | TITLE ESTs | | | gi = 3216574 | 1362672 |
| IC06361 | UG75 Expression | EST | Mm.25775 | TITLE ESTs | | | gi = 3216703 | 644384 |
| IC06362 | UG75 Expression | EST | Mm.25776 | TITLE ESTs | | | gi = 2893610 | 622753 |
| IC06363 | UG75 Expression | EST | Mm.25781 | TITLE ESTs, Weakly similar to muscle glycogen synthase [M. musculus] | | | gi = 3883744 | 1262875 |
| IC06364 | UG75 Expression | EST | Mm.25783 | TITLE ESTs | | | gi = 6084425 | 1149212 |
| IC06365 | UG75 Expression | EST | Mm.25787 | TITLE ESTs, Moderately similar to KIAA0663 protein [H. sapiens] | | | gi = 2516990 | 1001699 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06366 | UG75 Expression | EST | Mm.25793 | TITLE ESTs | | | gi = 3521520 | 644987 |
| IC06367 | UG75 Expression | EST | Mm.25794 | TITLE ESTs | | | gi = 2919967 | 617042 |
| IC06368 | UG75 Expression | EST | Mm.25799 | TITLE ESTs | | | gi = 2918215 | 617343 |
| IC06369 | UG75 Expression | EST | Mm.25802 | TITLE ESTs | | | gi = 6078426 | 721401 |
| IC06370 | UG75 Expression | EST | Mm.25809 | TITLE ESTs, Weakly similar to ZC328.3 [C. elegans] | | | gi = 5910068 | 534369 |
| IC06371 | UG75 Expression | EST | Mm.25834 | TITLE ESTs | | | gi = 6078048 | 573047 |
| IC06372 | UG75 Expression | EST | Mm.25836 | TITLE ESTs | | | gi = 4726703 | 533613 |
| IC06373 | UG75 Expression | EST | Mm.25840 | TITLE ESTs | | | gi = 4730007 | 642432 |
| IC06374 | UG75 Expression | EST | Mm.25851 | TITLE ESTs | | | gi = 1673223 | 1750074 |
| IC06375 | UG75 Expression | EST | Mm.25854 | TITLE EST | | | gi = 3296767 | 1749438 |
| IC06376 | UG75 Expression | EST | Mm.25856 | TITLE ESTs, Moderately similar to transcription factor IIIC102 [H. sapiens] | | | gi = 3259402 | 1379052 |
| IC06377 | UG75 Expression | EST | Mm.25859 | TITLE ESTs | | | gi = 3259846 | 1379582 |
| IC06378 | UG75 Expression | EST | Mm.25861 | TITLE ESTs | | | gi = 2691433 | 619227 |
| IC06379 | UG75 Expression | EST | Mm.25874 | TITLE ESTs | | | gi = 1756559 | 617913 |
| IC06380 | UG75 Expression | EST | Mm.25875 | TITLE ESTs | | | gi = 2670269 | 636983 |
| IC06381 | UG75 Expression | EST | Mm.25878 | TITLE ESTs | | | gi = 4289570 | 620641 |
| IC06382 | UG75 Expression | EST | Mm.25888 | TITLE ESTs | | | gi = 3373052 | 619810 |
| IC06383 | UG75 Expression | EST | Mm.259 | TITLE ESTs, Weakly similar to glycoprotein specific UDP-glucuronyltransferase [R. norvegicus] | | | gi = 2283115 | 777609 |
| IC06384 | UG75 Expression | EST | Mm.25918 | TITLE ESTs | | | gi = 2965905 | 765617 |
| IC06385 | UG75 Expression | EST | Mm.25937 | TITLE ESTs | | | gi = 1776832 | 642875 |
| IC06386 | UG75 Expression | EST | Mm.25938 | TITLE ESTs | | | gi = 3371547 | 1446143 |
| IC06387 | UG75 Expression | EST | Mm.25941 | TITLE ESTs | | | gi = 2516935 | 1447012 |
| IC06388 | UG75 Expression | EST | Mm.25942 | TITLE ESTs | | | gi = 1676246 | 573063 |
| IC06389 | UG75 Expression | EST | Mm.25946 | TITLE ESTs, Weakly similar to PROTEIN A55 [Vaccinia virus (strain copenhagen)] | | | gi = 4199887 | 597726 |
| IC06390 | UG75 Expression | EST | Mm.25955 | TITLE ESTs | | | gi = 3863554 | 621102 |
| IC06391 | UG75 Expression | EST | Mm.25960 | TITLE ESTs | | | gi = 1913368 | 764638 |
| IC06392 | UG75 Expression | EST | Mm.25976 | TITLE ESTs | | | gi = 1297720 | 622938 |
| IC06393 | UG75 Expression | EST | Mm.25979 | TITLE ESTs, Moderately similar to similar to putative product coded in C. elegans cosmid C01C10. [H. sapiens] | | | gi = 5549470 | 596791 |
| IC06394 | UG75 Expression | EST | Mm.25990 | TITLE ESTs, Weakly similar to cDNA EST EMBL:T01585 comes from this gene [C. elegans] | | | gi = 4482523 | 1344849 |
| IC06395 | UG75 Expression | EST | Mm.25994 | TITLE ESTs | | | gi = 6084583 | 973593 |
| IC06396 | UG75 Expression | EST | Mm.26002 | TITLE ESTs, Moderately similar to KIAA0404 [H. sapiens] | | | gi = 2516748 | 595873 |
| IC06397 | UG75 Expression | EST | Mm.26017 | TITLE ESTs | | | gi = 6519960 | 2689842 |
| IC06398 | UG75 Expression | EST | Mm.26019 | TITLE ESTs | | | gi = 5492006 | 638231 |
| IC06399 | UG75 Expression | EST | Mm.26023 | TITLE ESTs, Moderately similar to ZINC FINGER PROTEIN ZFMSA12A [Micropterus salmoides] | | | gi = 3373610 | 1921209 |
| IC06400 | UG75 Expression | EST | Mm.26040 | TITLE ESTs | | | gi = 6098732 | 583708 |
| IC06401 | UG75 Expression | EST | Mm.26042 | TITLE ESTs | | | gi = 6100978 | 596011 |
| IC06402 | UG75 Expression | EST | Mm.26043 | TITLE ESTs | | | gi = 1853081 | 750382 |
| IC06403 | UG75 Expression | EST | Mm.26062 | TITLE ESTs | | | gi = 4726322 | 642482 |
| IC06404 | UG75 Expression | EST | Mm.26092 | TITLE ESTs | | | gi = 3373623 | 62734 |
| IC06405 | UG75 Expression | EST | Mm.26102 | TITLE ESTs | | | gi = 3373623 | 622734 |
| IC06406 | UG75 LID 366 B cell | EST | Mm.26103 | TITLE pyridoxal (pyridoxine, vitamin B6) kinase | GENE Pdxk | | gi = 4374510 | 849466 |
| IC06407 | UG75 Expression | EST | Mm.26108 | TITLE ESTs, Weakly similar to F41E6.3 [C. elegans] | | | gi = 5860530 | 6216660 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06408 | UG75 Expression | EST | Mm.26143 | TITLE ESTs | | | gi = 3374380 | 1243681 |
| IC06409 | UG75 Expression | EST | Mm.26147 | TITLE ESTs | | | gi = 3377018 | 621418 |
| IC06410 | UG75 Expression | EST | Mm.26148 | TITLE ESTs | | | gi = 6077609 | 637286 |
| IC06411 | UG75 Expression | EST | Mm.26159 | TITLE ESTs | | | gi = 3374797 | 595996 |
| IC06412 | UG75 Expression | EST | Mm.26268 | TITLE ESTs, Weakly similar to acid-rich protein [C. elegans] | | | gi = 1901122 | 1294292 |
| IC06413 | UG75 Expression | EST | Mm.26175 | TITLE ESTs | | | gi = 3376634 | 619426 |
| IC06414 | UG75 Expression | EST | Mm.26181 | TITLE ESTs | | | gi = 1369608 | 751276 |
| IC06415 | UG75 Expression | EST | Mm.26186 | TITLE ESTs | | | gi = 3375400 | 616700 |
| IC06416 | UG75 Expression | EST | Mm.26191 | TITLE ESTs, Weakly similar to KIAA0402 [H. sapiens] | | | gi = 2918633 | 643898 |
| IC06417 | UG75 Expression | EST | Mm.26194 | TITLE ESTs, Moderately similar to hypothetical protein, similar to [H. sapiens] | | | gi = 3067219 | 597905 |
| IC06418 | UG75 Expression | EST | Mm.26196 | TITLE ESTs, Moderately similar to CGMP-DEPENDENT 3',5'-CYCLIC PHOSPHODIESTERASE [R. norvegicus] | | | gi = 3160537 | 619934 |
| IC06419 | UG75 Expression | EST | Mm.26202 | TITLE ESTs | | | gi = 3376156 | 617472 |
| IC06420 | UG75 Expression | EST | Mm.26214 | TITLE ESTs | | | gi = 448430 | 1148960 |
| IC06421 | UG75 Expression | EST | Mm.26217 | TITLE ESTs, Moderately similar to CGI-118 protein [H. sapiens] | | | gi = 3164652 | 576890 |
| IC06422 | UG75 Expression | EST | Mm.26219 | TITLE ESTs | | | gi = 4303904 | 597829 |
| IC06423 | UG75 Expression | EST | Mm.26248 | TITLE ESTs | | | gi = 3376686 | 1263142 |
| IC06424 | UG75 Expression | EST | Mm.26257 | TITLE ESTs | | | gi = 3376888 | 764445 |
| IC06425 | UG75 Expression | EST | Mm.26266 | TITLE ESTs | | | gi = 2519160 | 620272 |
| IC06426 | UG75 Expression | EST | Mm.26268 | TITLE ESTs | | | gi = 3394452 | 1226891 |
| IC06427 | UG75 Expression | EST | Mm.26272 | TITLE ESTs | | | gi = 2517943 | 621236 |
| IC06428 | UG75 Expression | EST | Mm.26304 | TITLE ESTs | | | gi = 4029963 | 621314 |
| IC06429 | UG75 Expression | EST | Mm.26322 | TITLE ESTs, Weakly similar to microtubule-associated serine/threonine protein kinase MAST205 [M. musculus] | | | gi = 3387514 | 538568 |
| IC06430 | UG75 Expression | EST | Mm.26334 | TITLE ESTs | | | gi = 3394558 | 1264892 |
| IC06431 | UG75 Expression | EST | Mm.26362 | TITLE ESTs, Weakly similar to KIAA0946 protein [H. sapiens] | | | gi = 3393636 | 717648 |
| IC06432 | UG75 Expression | EST | Mm.26392 | TITLE ESTs | | | gi = 2919480 | 619603 |
| IC06433 | UG75 Expression | EST | Mm.26404 | TITLE ESTs | | | gi = 3394422 | 1226040 |
| IC06434 | UG75 Expression | EST | Mm.26422 | TITLE ESTs | | | gi = 2518126 | 636462 |
| IC06435 | UG75 Expression | EST | Mm.26435 | TITLE ESTs | | | gi = 3394918 | 597693 |
| IC06436 | UG75 Expression | EST | Mm.2644 | TITLE ESTs, Moderately similar to acetolactate synthase homolog [H. sapiens] | | | gi = 4306386 | 723035 |
| IC06437 | UG76 LID366 B cell | EST | Mm.26465 | TITLE ESTs | | | gi = 7066703 | 1247657 |
| IC06438 | UG75 Expression | EST | Mm.26466 | TITLE ESTs | | | gi = 3448094 | 595860 |
| IC06439 | UG75 Expression | EST | Mm.26468 | TITLE ESTs | | | gi = 3373261 | 752504 |
| IC06440 | UG75 Expression | EST | Mm.26476 | TITLE ESTs | | | gi = 1909014 | 777205 |
| IC06441 | UG75 Expression | EST | Mm.26478 | TITLE ESTs | | | gi = 3294536 | 1002098 |
| IC06442 | UG75 Expression | EST | Mm.26480 | TITLE ESTs | | | gi = 5124676 | 634708 |
| IC06443 | UG75 Expression | EST | Mm.26484 | TITLE ESTs | | | gi = 2775884 | 635531 |
| IC06444 | UG75 Expression | EST | Mm.26488 | TITLE ESTs | | | gi = 3517023 | 717988 |
| IC06445 | UG75 Expression | EST | Mm.26491 | TITLE ESTs | | | gi = 4057878 | 553798 |
| IC06446 | UG75 Expression | EST | Mm.26492 | TITLE ESTs | | | gi = 4032134 | 641658 |
| IC06447 | UG75 Expression | EST | Mm.26495 | TITLE ESTs | | | gi = 3517944 | 1148681 |
| IC06448 | UG75 Expression | EST | Mm.26497 | TITLE ESTs | | | gi = 3518018 | 749078 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06449 | UG75 Expression | EST | Mm.26499 | TITLE ESTs | | | gi = 1936289 | 752344 |
| IC06450 | UG75 Expression | EST | Mm.26506 | TITLE ESTs | | | gi = 2272445 | 575045 |
| IC06451 | UG75 Expression | EST | Mm.26514 | TITLE ESTs, Weakly similar to contains similarity to S. cerevisie YGL211w [C. elegans] | | | gi = 3518792 | 750240 |
| IC06452 | UG75 Expression | EST | Mm.26515 | TITLE ESTs | | | gi = 1760046 | 621147 |
| IC06453 | UG75 Expression | EST | Mm.26520 | TITLE ESTs, Weakly similar to Ubiquinol-cytochrome C reductase 17KD protein [S. cerevisiae] | | | gi = 3518885 | 1002186 |
| IC06454 | UG75 Expression | EST | Mm.26532 | TITLE ESTs, Weakly similar to KINESIN-LIKE PROTEIN KIF1A [M. musculus] | | | gi = 2521232 | 765483 |
| IC06455 | UG75 Expression | EST | Mm.26537 | TITLE ESTs | | | gi = 2918131 | 972994 |
| IC06456 | UG75 Expression | EST | Mm.26542 | TITLE ESTs | | | gi = 3720017 | 721670 |
| IC06457 | UG75 Expression | EST | Mm.26543 | TITLE ESTs | | | gi = 4271247 | 1445669 |
| IC06458 | UG75 Expression | EST | Mm.26546 | TITLE ESTs | | | gi = 3601601 | 621659 |
| IC06459 | UG75 Expression | EST | Mm.26554 | TITLE ESTs | | | gi = 3601723 | 596053 |
| IC06460 | UG75 Expression | EST | Mm.26558 | MEMBRANE PROTEIN SED5 [Saccharomyces cerevisie] | | | gi = 3516226 | 947223 |
| IC06461 | UG75 Expression | EST | Mm.26562 | TITLE ESTs, Weakly similar to cDNA EST yk339a7.5 comes from this gene [C. elegans] | | | gi = 6083607 | 620744 |
| IC06462 | UG75 Expression | EST | Mm.26564 | TITLE ESTs | | | gi = 3602322 | 618270 |
| IC06463 | UG75 Expression | EST | Mm.2658 | TITLE ESTs | | | gi = 4216654 | 634529 |
| IC06464 | UG75 Expression | EST | Mm.26580 | TITLE ESTs | | | gi = 3692162 | 616629 |
| IC06465 | UG75 Expression | EST | Mm.26582 | TITLE ESTs, Weakly similar to /prediction | | | gi = 1769077 | 634354 |
| IC06467 | UG75 Expression | EST | Mm.26587 | TITLE ESTs | | | gi = 4600497 | 619334 |
| IC06468 | UG75 Expression | EST | Mm.26588 | TITLE ESTs | | | gi = 2262923 | 557987 |
| IC06469 | UG75 Expression | EST | Mm.26589 | TITLE ESTs | | | gi = 4304261 | 598250 |
| IC06470 | UG75 Expression | EST | Mm.26591 | TITLE ESTs, Weakly similar to ORF YKR074w [S. cerevisiae] | | | gi = 1324986 | 751673 |
| IC06471 | UG75 Expression | EST | Mm.26593 | TITLE EST | | | gi = 3054096 | 644095 |
| IC06472 | UG75 Expression | EST | Mm.26594 | TITLE ESTs | | | gi = 3681868 | 1429286 |
| IC06473 | UG75 Expression | EST | Mm.26595 | TITLE ESTs | | | gi = 3066784 | 1329379 |
| IC06474 | UG75 Expression | EST | Mm.26598 | TITLE ESTs, Weakly similar to B0507.2 gene product [C. elegans] | | | gi = 2906860 | 597337 |
| IC06475 | UG75 Expression | EST | Mm.26599 | TITLE ESTs | | | gi = 3682535 | 1002044 |
| IC06476 | UG75 Expression | EST | Mm.26603 | TITLE ESTs | | | gi = 2292507 | 765702 |
| IC06477 | UG75 Expression | EST | Mm.26605 | TITLE ESTs | | | gi = 3957009 | 751369 |
| IC06478 | UG75 Expression | EST | Mm.26609 | TITLE ESTs | | | gi = 4271050 | 1227140 |
| IC06479 | UG75 Expression | EST | Mm.26610 | TITLE ESTs | | | gi = 1663176 | 764697 |
| IC06480 | UG75 Expression | EST | Mm.26614 | TITLE ESTs | | | gi = 5668361 | 777291 |
| IC06481 | UG75 Expression | EST | Mm.26617 | TITLE DNA segment, Chr 5, Wayne State University 145, expressed | GENE D5Wsu145e | | gi = 3164708 | 637241 |
| IC06482 | UG75 Expression | EST | Mm.26622 | TITLE ESTs | | | gi = 5338252 | 598254 |
| IC06483 | UG76 LID366 B cell | EST | Mm.26626 | TITLE ESTs | | | gi = 6937855 | 1278782 |
| IC06484 | UG75 Expression | EST | Mm.26627 | TITLE ESTs | | | gi = 3519630 | 2646465 |
| IC06485 | UG75 Expression | EST | Mm.26632 | TITLE ESTs | | | gi = 3719628 | 597808 |
| IC06486 | UG75 Expression | EST | Mm.26633 | TITLE ESTs, Weakly similar to (define not available 6013425) [M. musculus] | | | gi = 6084359 | 2648722 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06487 | UG75 Expression | EST | Mm.26635 | TITLE ESTs, Weakly similar to X-LINKED PROTEIN STS1769 [H. sapiens] | | | gi = 5905248 | 1446229 |
| IC06488 | UG75 Expression | EST | Mm.26639 | TITLE ESTs | | | gi = 3720125 | 1885152 |
| IC06489 | UG75 Expression | EST | Mm.2664 | TITLE ESTs | | | gi = 4296332 | 640686 |
| IC06490 | UG75 Expression 00/04/26 UG#76 | EST | Mm.26652 | TITLE ESTs | | | gi = 1494519 | 720982 |
| IC06491 | 17Lid Expansion | EST | Mm.26665 | EST | | | gi = 3732458 | 1762611 |
| IC06492 | UG75 Expression | EST | Mm.26676 | TITLE ESTs | | | gi = 3733036 | 752324 |
| IC06493 | UG75 Expression | EST | Mm.26685 | TITLE ESTs | | | gi = 4275556 | 1429008 |
| IC06494 | UG75 Expression | EST | Mm.26690 | TITLE ESTs | | | gi = 4275742 | 719417 |
| IC06495 | UG75 Expression | EST | Mm.26694 | TITLE ESTs | | | gi = 3808951 | 1243360 |
| IC06496 | UG75 Expression | EST | Mm.26696 | TITLE ESTs, Weakly similar to GOLIATH PROTEIN [Drosophila melanogaster] | | | gi = 2283046 | 1002307 |
| IC06497 | UG75 Expression | EST | Mm.26697 | TITLE ESTs, Moderately similar to HYPOTHETICAL 9.8 KD PROTEIN ZK652.3 IN CHROMOSOME III [Caenorhabditis elegans] | | | gi = 3448413 | 618121 |
| IC06498 | UG75 Expression | EST | Mm.26699 | TITLE ESTs, Moderately similar to fetal globin inducing factor [M. musculus] | | | gi = 6008685 | 620507 |
| IC06499 | UG75 Expression | EST | Mm.26700 | TITLE ESTs | | | gi = 2813538 | 1329691 |
| IC06500 | UG75 Expression | EST | Mm.26702 | TITLE ESTs | | | gi = 4029347 | 635956 |
| IC06501 | UG75 Expression | EST | Mm.26703 | TITLE ESTs, Weakly similar to protein synthesis initiation factor 4A [M. musculus] | | | gi = 3885217 | 533415 |
| IC06502 | UG75 Expression | EST | Mm.26708 | TITLE ESTs | | | gi = 4663887 | 643131 |
| IC06503 | UG75 Expression | EST | Mm.26709 | TITLE ESTs | | | gi = 4720666 | 637851 |
| IC06504 | UG75 Expression | EST | Mm.26713 | TITLE ESTs | | | gi = 3862949 | 722763 |
| IC06505 | UG75 Expression | EST | Mm.26718 | TITLE ESTs, Weakly similar to YEMANUCLEIN-ALPHA [D. melanogaster] | | | gi = 2306077 | 1886310 |
| IC06506 | UG75 Expression | EST | Mm.26720 | TITLE ESTs | | | gi = 2201243 | 1378176 |
| IC06507 | UG75 Expression | EST | Mm.26726 | TITLE ESTs, Weakly similar to C24B5.4 gene product [C. elegans] | | | gi = 6077614 | 764081 |
| IC06508 | UG75 Expression | EST | Mm.26740 | TITLE ESTs, Weakly similar to HYPOTHETICAL 17.1 KD PROTEIN IN SAH1-MEI4 INTERGENIC REGION [Saccharomyces cerevisiae] | | | gi = 2518185 | 583161 |
| IC06509 | UG75 Expression | EST | Mm.26478 | TITLE ESTs | | | gi = 3883814 | 616663 |
| IC06510 | UG75 Expression | EST | Mm.26754 | TITLE ESTs | | | gi = 3885068 | 598437 |
| IC06511 | UG75 Expression | EST | Mm.26763 | TITLE ESTs | | | gi = 4276104 | 1328905 |
| IC06512 | UG75 Expression | EST | Mm.26765 | TITLE ESTs | | | gi = 3371325 | 958556 |
| IC06513 | UG75 Expression | EST | Mm.26767 | TITLE EST | | | gi = 3079712 | 330071 |
| IC06514 | UG75 Expression | EST | Mm.26771 | TITLE ESTs, Weakly similar to R06C7.6 [C. elegans] | | | gi = 4603344 | 1429123 |
| IC06515 | UG75 Expression | EST | Mm.26772 | TITLE ESTs, Weakly similar to retinal short-chain dehydrogenase/reductase [M. musculus] | | | gi = 4031515 | 597090 |
| IC06516 | UG75 Expression | EST | Mm.26773 | TITLE ESTs, Weakly similar to unknown [S. cerevisiae] | | | gi = 2307971 | 7760587 |
| IC06517 | UG75 Expression | EST | Mm.26775 | TITLE ESTs, Weakly similar to ORF YPL183w-a [S. cerevisiae] | | | gi = 3164831 | 1295068 |
| IC06518 | UG75 Expression | EST | Mm.26780 | TITLE ESTs | | | gi = 3747724 | 721157 |
| IC06519 | UG75 Expression | EST | Mm.26783 | TITLE ESTs, Weakly similar to cDNA EST yk404d1.5 comes from this gene [C. elegans] | | | gi = 24411805 | 557882 |
| IC06520 | UG75 Expression | EST | Mm.26785 | TITLE ESTs | | | gi = 4317325 | 635949 |
| IC06521 | UG75 Expression | EST | Mm.26786 | TITLE ESTs | | | gi = 6638612 | 643301 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06522 | UG75 Expression | EST | Mm.26788 | TITLE ESTs, Weakly similar to FAF1 PROTEIN [M. musculus] | | | gi = 1795218 | 58081 |
| IC06523 | UG75 Expression | EST | Mm.26802 | TITLE ESTs, Weakly similar to PLATELET-ACTIVATING FACTOR ACETYLHDROLASE IB ALPHA SUBUNIT [M. musculus] | | | gi = 1287481 | 1890926 |
| IC06524 | UG75 Expression | EST | Mm.26809 | TITLE ESTs | | | gi = 3954674 | 618484 |
| IC06525 | UG75 Expression | EST | Mm.26817 | TITLE ESTs | | | gi = 2962150 | 1281968 |
| IC06526 | UG75 Expression | EST | Mm.26828 | TITLE ESTs | | | gi = 6518649 | 721421 |
| IC06527 | UG75 Expression | EST | Mm.26834 | TITLE ESTs | | | gi = 4604994 | 871240 |
| IC06528 | UG75 Expression | EST | Mm.26844 | TITLE ESTs | | | gi = 3957022 | 582969 |
| IC06529 | UG75 Expression | EST | Mm.26846 | TITLE ESTs, Weakly similar to Ap-3 complex beta3A subunit [M. musculus] | | | gi = 3957116 | 1263332 |
| IC06530 | UG75 Expression | EST | Mm.26852 | TITLE ESTs, Weakly similar to similar to Zinc finger, C2H2 type [C. elegans] | | | gi = 2346593 | 1001959 |
| IC06531 | UG75 Expression | EST | Mm.26858 | TITLE ESTs | | | gi = 3978825 | 1226577 |
| IC06532 | UG75 Expression | EST | Mm.26870 | TITLE ESTs | | | gi = 6520888 | 618383 |
| IC06533 | UG75 Expression | EST | Mm.26878 | TITLE ESTs | | | gi = 3374850 | 621525 |
| IC06534 | UG75 Expression | EST | Mm.26888 | TITLE ESTs | | | gi = 1671632 | 582575 |
| IC06535 | UG75 Expression | EST | Mm.26893 | TITLE ESTs | | | gi = 3260065 | 598574 |
| IC06536 | UG75 Expression | EST | Mm.26897 | TITLE ESTs | | | gi = 3371474 | 1379363 |
| IC06537 | UG75 Expression | EST | Mm.26903 | TITLE ESTs, Moderately similar to ribonucleasae H1 large subunit [H. sapiens] | | | gi = 5124744 | 1247805 |
| IC06538 | UG75 Expression | EST | Mm.26910 | TITLE ESTs | | | gi = 4030158 | 616980 |
| IC06539 | UG75 Expression | EST | Mm.26936 | TITLE ESTs, Weakly similar to rit [M. musculus] | | | gi = 4373966 | 636728 |
| IC06540 | UG75 Expression | EST | Mm.26939 | TITLE ESTs, Weakly similar to STIMULATION FACTOR, 50 KD SUBUNIT [Homo] | | | gi = 5471939 | 1378768 |
| IC06541 | UG75 Expression | EST | Mm.26944 | PROTEIN 1 [M. musculus] | | | gi = 4315609 | 617421 |
| IC06542 | UG75 Expression | EST | Mm.26945 | TITLE ESTs, Weakly similar to PURKINJE CELL PROTEIN 1 [M. musculus] | | | gi = 6558167 | 621163 |
| IC06543 | UG75 Expression | EST | Mm.26955 | TITLE ESTs | | | gi = 4777988 | 737565 |
| IC06544 | UG75 Expression | EST | Mm.26956 | TITLE DNA segment, Chr 18, Wayne State University 98, expressed | GENE D18Wsu98e | | | 642866 |
| IC06545 | UG75 Expression | EST | Mm.26973 | TITLE ESTs, Weakly similar to HYPOTHETICAL 67.0 KD PROTEIN IN PRE3-SAG1 INTERGENIC REGION [Saccharomyces cerevisie] | | | gi = 4060437 | 597896 |
| IC06546 | UG75 Expression | EST | Mm.2699 | TITLE ESTs, Weakly similar to polymeric immunoglobulin receptor [M. musculus] | | | gi = 1755939 | 617599 |
| IC06547 | UG75 Expression | EST | Mm.26990 | TITLE EST | | | gi = 4060868 | 533576 |
| IC06548 | UG75 Expression | EST | Mm.27001 | TITLE ESTs | | | gi = 2203660 | 750260 |
| IC06549 | UG75 Expression | EST | Mm.27030 | TITLE ESTs | | | gi = 4199179 | 637907 |
| IC06550 | UG75 Expression | EST | Mm.27032 | TITLE ESTs | | | gi = 1590212 | 533816 |
| IC06551 | UG75 Expression | EST | Mm.27033 | TITLE ESTs | | | gi = 2519041 | 534075 |
| IC06552 | UG75 Expression | EST | Mm.27034 | TITLE ESTs, Moderately similar to quiescin [H. sapiens] | | | gi = 3955413 | 639550 |
| IC06553 | UG75 Expression | EST | Mm.27035 | TITLE ESTs, Weakly similar to RENAL SODIUM-DEPENDENT PHOSPHATE TRANSPORT PROTEIN 1 [M. musculus] | | | gi = 1282471 | 1429234 |
| IC06554 | UG75 Expression | EST | Mm.27038 | | | | gi = 6638539 | 522551 |
| IC06555 | UG75 Expression | EST | Mm.27039 | TITLE ESTs, Weakly similar to predicted using Genefinder [C. elegans] | | | gi = 2519211 | 1295379 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06556 | UG75 Expression | EST | Mm.27040 | TITLE ESTs | | | gi = 2906853 | 617594 |
| IC06557 | UG75 Expression | EST | Mm.27042 | TITLE ESTs | | | gi = 1759959 | 621323 |
| IC06558 | UG75 Expression | EST | Mm.27043 | TITLE ESTs | | | gi = 2039694 | 640270 |
| IC06559 | UG75 Expression | EST | Mm.27046 | TITLE ESTs | | | gi = 2411681 | 551164 |
| IC06560 | UG75 Expression | EST | Mm.27047 | TITLE ESTs | | | gi = 1937378 | 551268 |
| IC06561 | UG75 Expression | EST | Mm.27048 | TITLE ESTs | | | gi = 4483080 | 551381 |
| IC06562 | UG75 Expression | EST | Mm.27049 | TITLE ESTs | | | gi = 3067406 | 551497 |
| IC06563 | UG75 Expression | EST | Mm.27050 | TITLE ESTs | | | gi = 3955419 | 551641 |
| IC06564 | UG75 Expression | EST | Mm.27051 | TITLE ESTs, Moderately similar to MEA6 [*H. sapiens*] | | | gi = 618909 | 636719 |
| IC06565 | UG75 Expression | EST | Mm.27053 | TITLE ESTs, Weakly similar to CALPHOTIN [*D. melanogaster*] | | | gi = 4484835 | 620380 |
| IC06566 | UG75 Expression | EST | Mm.27057 | TITLE ESTs | | | gi = 1713365 | 550614 |
| IC06567 | UG75 Expression | EST | Mm.27061 | TITLE ESTs, Weakly similar to LR8 [*M. musculus*] | | | gi = 3954021 | 1346028 |
| IC06568 | UG75 Expression | EST | Mm.27062 | TITLE ESTs | | | gi = 6558317 | 553890 |
| IC06569 | UG75 Expression | EST | Mm.27064 | TITLE ESTs | | | gi = 2247987 | 620472 |
| IC06570 | UG75 Expression | EST | Mm.27067 | TITLE ESTs | | | gi = 2333101 | 973451 |
| IC06571 | UG75 Expression | EST | Mm.27071 | TITLE ESTs | | | gi = 2572676 | 1749354 |
| IC06572 | UG75 Expression | EST | Mm.27075 | TITLE ESTs, Weakly similar to METHIONINE AMINOPEPTIDASE 1 PRECURSOR [*Saccharomyces cerevisiae*] | | | gi = 4288331 | 619558 |
| IC06573 | UG75 Expression | EST | Mm.27083 | TITLE ESTs | | | gi = 1661898 | 1328307 |
| IC06574 | UG75 Expression | EST | Mm.27087 | TITLE ESTs | | | gi = 3164213 | 598940 |
| IC06575 | UG75 Expression | EST | Mm.27088 | TITLE ESTs | | | gi = 3955610 | 576787 |
| IC06576 | UG75 Expression | EST | Mm.27090 | TITLE ESTs | | | gi = 1913120 | 764676 |
| IC06577 | UG75 Expression | EST | Mm.27093 | TITLE ESTs, Moderately similar to HYPOTHETHICAL 90.0 KD PROTEIN T20B12.1 IN CHROMOSOME III [*Caenorhabditis elegans*] | | | gi = 1398067 | 719316 |
| IC06578 | UG75 Expression | EST | Mm.27095 | TITLE ESTs | | | gi = 2920202 | 636146 |
| IC06579 | UG75 Expression | EST | Mm.27100 | TITLE ESTs | | | gi = 1288741 | 718948 |
| IC06580 | UG75 Expression | EST | Mm.27101 | TITLE ESTs, Weakly similar to paraneoplastic neuronal antigen MA1 [*H. sapiens*] | | | gi = 6078022 | 751813 |
| IC06581 | UG75 Expression | EST | Mm.27103 | TITLE ESTs | | | gi = 4482597 | 1446431 |
| IC06582 | UG75 Expression | EST | Mm.27110 | TITLE ESTs | | | gi = 3394437 | 575110 |
| IC06583 | UG75 Expression | EST | Mm.27111 | TITLE ESTs | | | gi = 1889278 | 1293988 |
| IC06584 | UG75 Expression | EST | Mm.27112 | TITLE ESTs, Weakly similar to HYPOTHETICAL 16.1 KD PROTEIN IN SEC17-QCR1 INTERGENIC REGION [*Saccharomyces cerevisiae*] | | | gi = 5333866 | 618128 |
| IC06585 | UG75 Expression | EST | Mm.27114 | TITLE ESTs | | | gi = 1903572 | 973499 |
| IC06586 | UG75 Expression | EST | Mm.27115 | TITLE ESTs | | | gi = 1841253 | 596663 |
| IC06587 | UG75 Expression | EST | Mm.27117 | TITLE ESTs, Weakly similar to K02F3.10 [*C. elegans*] | | | gi = 1475930 | 1296220 |
| IC06588 | UG75 Expression | EST | Mm.27118 | TITLE ESTs | | | gi = 218210 | 574421 |
| IC06589 | UG75 Expression | EST | Mm.27121 | TITLE ESTs | | | gi = 1907924 | 576690 |
| IC06590 | UG75 Expression | EST | Mm.27122 | TITLE ESTs | | | gi = 2516625 | 582146 |
| IC06591 | UG75 Expression | EST | Mm.27123 | TITLE ESTs, Moderately similar to MSP1 PROTEIN [*Saccharomyces cerevisiae*] | | | gi = 6084980 | 973929 |
| IC06592 | UG75 Expression | EST | Mm.27124 | TITLE ESTs | | | gi = 4317565 | 764110 |
| IC06593 | UG75 Expression | EST | Mm.27125 | TITLE ESTs | | | gi = 2519011 | 577018 |
| IC06594 | UG75 Expression | EST | Mm.27126 | TITLE ESTs | | | gi = 4450360 | 575291 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06595 | UG75 Expression | EST | Mm.27127 | TITLE ESTs | | | gi = 5125600 | 642609 |
| IC06596 | UG75 Expression | EST | Mm.27129 | TITLE ESTs | | | gi = 6098617 | 1002612 |
| IC06597 | UG75 Expression | EST | Mm.2713 | TITLE ESTs | | | gi = 1756333 | 617744 |
| IC06598 | 00/04/26 UG#76 17Lid Expansion | EST | Mm.27130 | ESTs | — | | gi = 2075746 | 1196377 |
| IC06599 | UG75 Expression | EST | Mm.27131 | TITLE ESTs | | | gi = 4726284 | 641203 |
| IC06600 | UG75 Expression | EST | Mm.27133 | TITLE ESTs, Weakly similar to RNA binding motif protein 7 [H. sapiens] | | | gi = 3956169 | 621498 |
| IC06601 | UG75 Expression | EST | Mm.27134 | TITLE ESTs, Weakly similar to D1007.5 [C. elegans] | | | gi = 1684271 | 777602 |
| IC06602 | UG75 Expression | EST | Mm.27135 | TITLE ATP-binding cassette, sub-family F (GCN20), member 3 | GENE Abcf3 | | gi = 4967772 | 574680 |
| IC06603 | UG75 Expression | EST | Mm.27136 | TITLE ESTs | | | gi = 1500782 | 718453 |
| IC06604 | UG75 Expression | EST | Mm.27137 | TITLE ESTs | | | gi = 3393353 | 637598 |
| IC06605 | UG75 Expression | EST | Mm.27139 | TITLE ESTs | | | gi = 3731895 | 598925 |
| IC06606 | UG75 Expression | EST | Mm.27140 | TITLE ESTs | | | gi = 5478082 | 1001530 |
| IC06607 | UG75 Expression | EST | Mm.27142 | TITLE ESTs | | | gi = 5909907 | 1279950 |
| IC06608 | UG75 Expression | EST | Mm.27143 | TITLE ESTs | | | gi = 1714772 | 1139699 |
| IC06609 | UG75 Expression | EST | Mm.27144 | TITLE ESTs | | | gi = 3387663 | 597285 |
| IC06610 | UG75 Expression | EST | Mm.27145 | TITLE ESTs | | | gi = 3516123 | 596997 |
| IC06611 | UG75 Expression | EST | Mm.27146 | TITLE ESTs | | | gi = 5333397 | 719440 |
| IC06612 | UG75 Expression | EST | Mm.27147 | TITLE ESTs, Moderately similar to trg [R. norvegicus] | | | gi = 1796133 | 1020761 |
| IC06613 | UG75 Expression | EST | Mm.27151 | TITLE ESTs | | | gi = 4271543 | 1294680 |
| IC06614 | UG75 Expression | EST | Mm.27152 | TITLE ESTs, Weakly similar to Similarity to Yeast D-lactate dehydrogenase [C. elegans] | | | gi = 3956990 | 750941 |
| IC06615 | UG75 Expression | EST | Mm.27153 | TITLE ESTs | | | gi = 3956784 | 1002266 |
| IC06616 | UG75 Expression | EST | Mm.27157 | TITLE ESTs | | | gi = 2233632 | 582593 |
| IC06617 | UG75 Expression | EST | Mm.27160 | TITLE ESTs, Moderately similar to M-phase phosphoprotein 8 [H. sapiens] | | | gi = 6078714 | 719113 |
| IC06618 | UG75 Expression | EST | Mm.27163 | TITLE ESTs | | | gi = 3369742 | 631430 |
| IC06619 | UG75 Expression | EST | Mm.27164 | TITLE ESTs | | | gi = 2142595 | 721551 |
| IC06620 | UG75 Expression | EST | Mm.27165 | TITLE ESTs | | | gi = 1864636 | 722527 |
| IC06621 | UG75 Expression | EST | Mm.27166 | TITLE ESTs, Weakly similar to HYPOTHETICAL 19.3 KD PROTEIN IN STE50 5'REGION [Saccharomyces cerevisiae] | | | gi = 2235886 | 1380448 |
| IC06622 | UG75 Expression | EST | Mm.27167 | TITLE ESTs | | | gi = 4601286 | 599134 |
| IC06623 | UG75 Expression | EST | Mm.27168 | TITLE ESTs, Moderately similar to cote1 [H. sapiens] | | | gi = 2930231 | 1002818 |
| IC06624 | UG75 Expression | EST | Mm.27170 | TITLE ESTs | | | gi = 1318323 | 749529 |
| IC06625 | UG75 Expression | EST | Mm.27172 | TITLE ESTs | | | gi = 1715867 | 596578 |
| IC06626 | UG75 Expression | EST | Mm.27173 | TITLE ESTs | | | gi = 1739803 | 1001397 |
| IC06627 | UG75 Expression | EST | Mm.27175 | TITLE ESTs | | | gi = 2944551 | 634825 |
| IC06628 | UG75 Expression | EST | Mm.27176 | TITLE ESTs | | | gi = 5909234 | 717806 |
| IC06629 | UG75 Expression | EST | Mm.27178 | TITLE ESTs | | | gi = 5551319 | 1380519 |
| IC06630 | UG75 Expression | EST | Mm.27180 | TITLE ESTs | | | gi = 3376446 | 621651 |
| IC06631 | UG75 Expression | EST | Mm.27187 | TITLE ESTs | | | gi = 2918567 | 598318 |
| IC06632 | UG75 Expression | EST | Mm.27188 | TITLE ESTs, Moderately similar to ACTIN-LIKE PROTEIN 14D [Drosophila melanogaster] | | | gi = 5490106 | 635126 |
| IC06633 | UG75 Expression | EST | Mm.27189 | TITLE ESTs | | | gig = 2854697 | 598450 |
| IC06634 | UG75 Expression | EST | Mm.27191 | TITLE ESTs | | | gi = 3371295 | 617730 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06635 | UG75 Expression | EST | Mm.27194 | TITLE DNA segment, Chr 7, Roswell Park 2 complex, expressed | GENE D7Rp2e | D7Rp2|D7Rp2-r|D7Rp2-s|DNA segment, Chr 7, Roswell Park 2 complex|DNA segment, Chr 7, Roswell Park regulator 2|DNA segment, Chr 7, Roswell Park structural 2|Roswell Park 2, regulator|Roswell Park 2, structural |RP2-r|RP2-s| | gi = 4722650 | 638527 |
| IC06636 | UG75 Expression | EST | Mm.27196 | TITLE ESTs | | | gi = 6559644 | 620847 |
| IC06637 | UG75 Expression | EST | Mm.27199 | TITLE ESTs | | | gi = 2967329 | 721365 |
| IC06638 | UG75 Expression | EST | Mm.27206 | TITLE ESTs | | | gi = 2520223 | 765332 |
| IC06639 | UG75 Expression | EST | Mm.27207 | TITLE ESTs | | | gi = 3387403 | 598566 |
| IC06640 | UG75 Expression | EST | Mm.27208 | TITLE ESTs | | | gi = 4726795 | 617207 |
| IC06641 | UG75 Expression | EST | Mm.27209 | TITLE ESTs | | | gi = 4614887 | 619029 |
| IC06642 | UG75 Expression | EST | Mm.27212 | TITLE ESTs | | | gi = 1937491 | 315299 |
| IC06643 | UG75 Expression | EST | Mm.27214 | TITLE ESTs | | | gi = 2258820 | 749581 |
| IC06644 | UG75 Expression | EST | Mm.27215 | TITLE ESTs | | | gi = 2917387 | 952555 |
| IC06645 | UG75 Expression | EST | Mm.27216 | TITLE ESTs | | | gi = 3294947 | 619746 |
| IC06646 | UG75 Expression | EST | Mm.27217 | TITLE ESTs | | | gi = 4216997 | 764468 |
| IC06647 | UG75 Expression | EST | Mm.27219 | TITLE ESTs | | | gi = 2644170 | 764163 |
| IC06648 | UG75 Expression | EST | Mm.27223 | TITLE ESTs | | | gi = 1827031 | 598744 |
| IC06649 | UG75 Expression | EST | Mm.27224 | TITLE ESTs, Moderately similar to CYCLIN-DEPENDENT KINASE INHIBITOR 3 [*H. sapiens*] | | | gi = 2081024 | 723323 |
| IC06650 | UG75 Expression | EST | Mm.27225 | TITLE ESTs | | | gi = 3375022 | 617366 |
| IC06651 | UG75 Expression | EST | Mm.27226 | TITLE ESTs, Weakly similar to cDNA EST EMBL:C07816 comes from this gene [*C. elegans*] | | | gi = 4440903 | 617384 |
| IC06652 | UG75 Expression | EST | Mm.27227 | TITLE ESTs, Weakly similar to Rfxank [*M. musculus*] | | | gi = 1794407 | 636840 |
| IC06653 | UG75 Expression | EST | Mm.27228 | TITLE ESTs | | | gi = 1793347 | 616642 |
| IC06654 | UG75 Expression | EST | Mm.27229 | TITLE ESTs | | | gi = 4060553 | 617987 |
| IC06655 | UG75 Expression | EST | Mm.27231 | TITLE ESTs | | | gi = 1796136 | 972398 |
| IC06656 | UG75 Expression | EST | Mm.27232 | TITLE ESTs | | | gi = 2574188 | 619806 |
| IC06657 | UG75 Expression | EST | Mm.27233 | TITLE ESTs, Weakly similar to similar to yeast heat shock protein STI1 [*C. elegans*] | | | gi = 4601384 | 1295621 |
| IC06658 | UG75 Expression | EST | Mm.27234 | TITLE ESTs | | | gi = 6167970 | 621525 |
| IC06659 | UG75 Expression | EST | Mm.27235 | TITLE ESTs | | | gi = 5819738 | 620329 |
| IC06660 | UG75 Expression | EST | Mm.27238 | TITLE ESTs | | | gi = 6097882 | 635854 |
| IC06661 | UG75 Expression | EST | Mm.27239 | TITLE ESTs | | | gi = 5598439 | 635795 |
| IC06662 | UG75 Expression | EST | Mm.27240 | TITLE ESTs, Weakly similar to coded for by *C. elegans* cDNAs GenBank:M88869 and T01933 [*C. elegans*] | | | gi = 4060822 | 558108 |
| IC06663 | UG75 Expression | EST | Mm.27241 | TITLE ESTs, Moderately similar to R30923_1 [*H. sapiens*] | | | gi = 2644942 | 1020875 |
| IC06664 | UG75 Expression | EST | Mm.27242 | TITLE ESTs, Weakly similar to CELL SURFACE GLYCOPROTEIN EMR1 PRECURSOR [*M. musculus*] | | | gi = 2518288 | 621949 |
| IC06665 | UG75 Expression | EST | Mm.27243 | TITLE ESTs [*D. melanogaster*] | | | gi = 2292458 | 5597124 |
| IC06666 | UG75 Expression | EST | Mm.27245 | TITLE ESTs | | | gi = 1481066 | 622999 |
| IC06667 | UG75 Expression | EST | Mm.27246 | TITLE ESTs, Weakly similar to KIAA1004 protein [*H. sapiens*] | | | gi = 6095862 | 718618 |
| IC06668 | UG75 Expression | EST | Mm.27247 | TITLE ESTs | | | gi = 4615185 | 722223 |
| IC06669 | UG75 Expression | EST | Mm.27248 | TITLE ESTs | | | gi = 2518871 | 642456 |
| IC06670 | UG75 Expression | EST | Mm.27249 | TITLE ESTs, Weakly similar to Ydr412wp [*S. cerevisiae*] | | | gi = 2962176 | 1226904 |
| IC06671 | UG75 Expression | EST | Mm.27252 | TITLE ESTs | | | gi = 1767748 | 635814 |
| IC06672 | UG75 Expression | EST | Mm.27253 | TITLE ESTs | | | | 622274 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06673 | UG75 Expression | EST | Mm.27257 | TITLE ESTs | | | gi = 2918682 | 643098 |
| IC06674 | UG75 Expression | EST | Mm.27259 | TITLE ESTs, Moderately similar to NuMA protein [H. sapiens] | | | gi = 1882497 | 618533 |
| IC06675 | UG75 Expression | EST | Mm.27261 | TITLE ESTs | | | gi = 2990979 | 1002844 |
| IC06676 | UG75 Expression | EST | Mm.27267 | TITLE ESTs, Moderately similar to BRX protein [M. musculus] | | | gi = 1478649 | 1193060 |
| IC06677 | UG75 Expression | EST | Mm.27268 | TITLE DNA segment, Human EST 478828 | GENE EST478828 | | gi = 1793081 | 638631 |
| IC06678 | UG75 Expression | EST | Mm.27269 | TITLE ESTs | | | gi = 3175675 | 749657 |
| IC06679 | UG75 Expression | EST | Mm.27270 | TITLE ESTs | | | gi = 4434433 | 1193732 |
| IC06680 | UG75 Expression | EST | Mm.27273 | TITLE ESTs, Moderately similar to KIAA0947 protein [H. sapiens] | | | gi = 2517575 | 1149788 |
| IC06681 | UG75 Expression | EST | Mm.27274 | TITLE ESTs | | | gi = 3602328 | 635286 |
| IC06682 | UG75 Expression | EST | Mm.27275 | TITLE ESTs, Weakly similar to mRNA capping enzyme [M. musculus] | | | gi = 4601782 | 1193114 |
| IC06683 | UG75 Expression | EST | Mm.27276 | TITLE ESTs | | | gi = 4307007 | 619632 |
| IC06684 | UG75 Expression | EST | Mm.27282 | TITLE ESTs | | | gi = 4766917 | 619410 |
| IC06685 | UG75 Expression | EST | Mm.27284 | TITLE ESTs, Moderately similar to hypothetical protein [H. sapiens] | | | gi = 1872844 | 1265489 |
| IC06686 | UG75 Expression | EST | Mm.27288 | TITLE DNA segment, Chr 3, Wayne State University 133, expressed | GENE D3Wsu133e | | | 622798 |
| IC06687 | UG75 Expression | EST | Mm.27289 | TITLE ESTs, Weakly similar to WDNM1 PROTEIN PRECURSOR [M. musculus] | | | gi = 6167916 | 641555 |
| IC06688 | UG75 Expression | EST | Mm.27290 | TITLE ESTs | | | gi = 4444884 | 1225301 |
| IC06689 | UG75 Expression | EST | Mm.27292 | TITLE DNA segment, Chr 6, Wayne State University 157, expressed | GENE D6Wsu157e | | | 1193540 |
| IC06690 | UG75 Expression | EST | Mm.27293 | TITLE ESTs, Moderately similar to Similar to S. cerevisiae hypothetical protein L3111 [H. sapiens] | | | gi = 2503395 | 1149541 |
| IC06691 | UG75 Expression | EST | Mm.27296 | TITLE ESTs, Weakly similar to ankyrin 3 [M. musculus] | | | gi = 1811439 | 1149092 |
| IC06692 | UG75 Expression | EST | Mm.27302 | TITLE ESTs | | | gi = 6826724 | 621686 |
| IC06693 | UG75 Expression | EST | Mm.27303 | TITLE ESTs, Moderately similar to NSAP1 protein [H. sapiens] | | | gi = 2065770 | 958431 |
| IC06694 | UG75 Expression | EST | Mm.27308 | TITLE ESTs | | | gi = 5336385 | 617360 |
| IC06695 | UG75 Expression | EST | Mm.27309 | TITLE ESTs | | | gi = 620922 | 644388 |
| IC06696 | UG75 Expression | EST | Mm.27310 | TITLE ESTs | | | gi = 6749188 | 973454 |
| IC06697 | UG75 Expression | EST | Mm.27311 | TITLE ESTs | | | gi = 1566029 | 598549 |
| IC06698 | UG75 Expression | EST | Mm.27313 | TITLE ESTs | | | gi = 1827392 | 718061 |
| IC06699 | UG75 Expression | EST | Mm.27314 | TITLE ESTs | | | gi = 1834043 | 635863 |
| IC06700 | UG75 Expression | EST | Mm.27320 | TITLE ESTs | | | gi = 3387493 | 577169 |
| IC06701 | UG75 Expression | EST | Mm.27322 | TITLE ESTs | | | gi = 1325631 | 1020763 |
| IC06702 | UG75 Expression | EST | Mm.27323 | TITLE ESTs | | | gi = 4317512 | 1148826 |
| IC06703 | UG75 Expression | EST | Mm.27324 | TITLE ESTs | | | gi = 4441998 | 621052 |
| IC06704 | UG75 Expression | EST | Mm.27326 | TITLE ESTs | | | gi = 1768362 | 1328691 |
| IC06705 | UG75 Expression | EST | Mm.27332 | TITLE ESTs, Moderately similar to MELANOMA ANTIGEN P15 [H. sapiens] | | | gi = 1659816 | 640538 |
| IC06706 | UG75 Expression | EST | Mm.27337 | TITLE ESTs, Moderately similar to similar to protein U28928 [H. sapiens] | | | gi = 2646459 | 1280802 |
| IC06707 | UG75 Expression | EST | Mm.27338 | TITLE ESTs | | | gi = 3718251 | 721736 |
| IC06708 | UG75 Expression | EST | Mm.27339 | TITLE ESTs, Weakly similar to similar to beta-transducin [C. elegans] | | | gi = 1676043 | 721232 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06709 | UG75 Expression | EST | Mm.27340 | TITLE ESTs | | | gi = 2965761 | 1312864 |
| IC06710 | UG75 Expression | EST | Mm.27341 | TITLE ESTs, Weakly similar to serine/threonine-protein kinase NEK4 [*M. musculus*] | | | gi = 3054906 | 636973 |
| IC06711 | UG75 Expression | EST | Mm.27344 | TITLE ESTs | | | gi = 3296152 | 643448 |
| IC06712 | UG75 Expression | EST | Mm.27348 | TITLE ESTs | | | gb = 6756640 | 723328 |
| IC06713 | UG75 Expression | EST | Mm.27355 | TITLE ESTs | | | gi = 1872574 | 620091 |
| IC06714 | UG75 Expression | EST | Mm.27359 | TITLE ESTs | | | gb = 6078604 | 749856 |
| IC06715 | UG75 Expression | EST | Mm.27363 | TITLE ESTs | | | gi = 4802598 | 596475 |
| IC06716 | UG75 Expression | EST | Mm.27366 | TITLE ESTs, Weakly similar to ZC328.3 [*C. elegans*] | | | gi = 4217330 | 598654 |
| IC06717 | UG75 Expression | EST | Mm.27367 | TITLE ESTs | | | gi = 6078066 | 719159 |
| IC06718 | UG75 Expression | EST | Mm.27374 | TITLE ESTs | | | gi = 3954251 | 722977 |
| IC06719 | UG75 Expression | EST | Mm.27375 | TITLE ESTs, Moderately similar to DNA-DIRECTED RNA POLYMERASES I, II, AND III 7.3 KD POLYPEPTIDE [*Schizosaccharomyces pombe*] | | | gi = 3718563 | 618895 |
| IC06720 | UG75 Expression | EST | Mm.27376 | TITLE ESTs | | | gi = 2248759 | 722797 |
| IC06721 | UG75 Expression | EST | Mm.27380 | TITLE ESTs | | | gi = 1368412 | 583551 |
| IC06722 | UG75 Expression | EST | Mm.27381 | TITLE ESTs | | | gi = 2917135 | 718254 |
| IC06723 | UG75 Expression | EST | Mm.27383 | TITLE ESTs | | | gi = 1895148 | 622165 |
| IC06724 | UG75 Expression | EST | Mm.27384 | TITLE ESTs | | | gi = 4967839 | 597240 |
| IC06725 | UG75 Expression | EST | Mm.27385 | TITLE ESTs | | | gi = 4616147 | 777837 |
| IC06726 | UG75 Expression | EST | Mm.27386 | TITLE ESTs | | | gi = 6649251 | 475119 |
| IC06727 | UG75 Expression | EST | Mm.27388 | TITLE ESTs | | | gi = 2518233 | 637883 |
| IC06728 | UG75 Expression | EST | Mm.2739 | TITLE ESTs | | | gi = 3067283 | 1327617 |
| IC06729 | UG75 Expression | EST | Mm.27390 | TITLE ESTs | | | gi = 2691755 | 692300 |
| IC06730 | UG75 Expression | EST | Mm.27391 | TITLE ESTs | | | gi = 5265655 | 642352 |
| IC06731 | UG75 Expression | EST | Mm.28392 | oncoprotein induced transcript 5 | Oit5 | | gi = 5909620 | 458782 |
| IC06732 | UG75 Expression | EST | Mm.28393 | TITLE ESTs, Moderately similar to MITOCHONDRIAL IMPORT INNER MEMBRANE TRANSLOCASE SUBUNIT TIM17 [*Saccharomyces cerevisiae*] | | | gi = 2461506 | 762921 |
| IC06733 | UG75 Expression | EST | Mm.27395 | TITLE ESTs, Weakly similar to GLUTATHIONE S-TRANSFERASE, MITOCHONDRIAL [*Rattus norvegicus*] | | | gi = 1287489 | 1379255 |
| IC06734 | UG75 Expression | EST | Mm.28396 | TITLE cytochrome c oxidase subunit XVII assembly protein homolog (yeast) | GENE Cox17 | COX17] | gi = 2956470 | 972556 |
| IC06735 | UG75 Expression | EST | Mm.28397 | TITLE ESTs, Moderately similar to myotonic dystrophy kinase-related Cdc42-binding kinase MRCK-beta [*R. norvegicus*] | | | gi = 1330619 | 718639 |
| IC06736 | UG75 Expression | EST | Mm.27399 | TITLE ESTs | | | gi = 4272867 | 644964 |
| IC06737 | UG75 Expression | EST | Mm.27401 | TITLE ESTs, Weakly similar to Pax-6 protein [*R. norvegicus*] | | | gi = 4613277 | 619760 |
| IC06738 | UG75 Expression | EST | Mm.27404 | TITLE ESTs, Weakly similar to HYPOTHETICAL 32.0 KD PROTEIN IN SAP190-SPO14 INTERGENIC REGION [*Saccharomyces cerevisiae*] | | | gi = 1309705 | 551136 |
| IC06739 | UG75 Expression | EST | Mm.27405 | TITLE ESTs, Weakly similar to similar to the beta transducin family [*C. elegans*] | | | gi = 4408908 | 718088 |
| IC06740 | UG75 Expression | EST | Mm.27406 | TITLE ESTs, Weakly similar to Yhr116wp [*S. cerevisiae*] | | | gi = 4803559 | 1226421 |
| IC06741 | UG75 Expression | EST | Mm.27409 | TITLE ESTs | | | gi = 5158490 | 751857 |
| IC06742 | UG75 Expression | EST | Mm.27410 | TITLE ESTs | | | gi = 2068655 | 719248 |
| IC06743 | UG75 Expression | EST | Mm.27412 | TITLE ESTs | | | gi = 3294703 | 720736 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06744 | UG75 Expression | EST | Mm.27413 | TITLE ESTs | | | gi = 2775449 | 638219 |
| IC06745 | UG75 Expression | EST | Mm.27414 | TITLE ESTs | | | gi = 4317787 | 723226 |
| IC06746 | UG75 Expression | EST | Mm.27416 | TITLE ESTs | | | gi = 2990707 | 1264677 |
| IC06747 | UG75 Expression | EST | Mm.27419 | TITLE ESTs | | | gi = 4274470 | 636519 |
| IC06748 | UG75 Expression | EST | Mm.27420 | TITLE ESTs | | | gi = 3518378 | 777637 |
| IC06749 | UG75 Expression | EST | Mm.27421 | TITLE ESTs | | | gi = 2049128 | 973890 |
| IC06750 | UG75 Expression | EST | Mm.27422 | TITLE ESTs | | | gi = 2102035 | 1445967 |
| IC06751 | UG75 Expression | EST | Mm.27423 | TITLE ESTs | | | gi = 3394409 | 619122 |
| IC06752 | UG75 Expression | EST | Mm.27242 | TITLE ESTs, Weakly similar to All-1 protein +GTE form [*M. musculus*] | | | gi = 2291621 | 597267 |
| IC06753 | UG75 Expression | EST | Mm.27249 | TITLE ESTs, Moderately similar to unknown [*H. sapiens*] | | | gi = 6645700 | 893834 |
| IC06754 | UG75 Expression | EST | Mm.27434 | TITLE ESTs, Weakly similar to C13F10.5 [*C. elegans*] | | | gi = 2272440 | 1264054 |
| IC06755 | UG75 Expression | EST | Mm.27440 | TITLE ESTs | | | gi = 2073694 | 765176 |
| IC06756 | UG75 Expression | EST | Mm.27441 | TITLE ESTs | | | gi = 2918145 | 764646 |
| IC06757 | UG75 Expression | EST | Mm.27442 | TITLE ESTs, Weakly similar to Wiskott-Aldrich syndrome protein WASP [*H. sapiens*] | | | gi = 4450486 | 574351 |
| IC06758 | UG75 Expression | EST | Mm.27443 | TITLE DNA segment, Chr 10, Wayne State University 93, expressed | GENE D10Wsu93e | | | 765118 |
| IC06759 | UG75 Expression | EST | Mm.27444 | TITLE ESTs | | | gi = 3395124 | 721126 |
| IC06760 | UG75 Expression | EST | Mm.27445 | NFB42 [*R. norvegicus*] | | | gi = 2517502 | 83919 |
| IC06761 | UG75 Expression | EST | Mm.27449 | TITLE ESTs | | | gi = 1807615 | 598410 |
| IC06762 | UG75 Expression | EST | Mm.2745 | TITLE ESTs, Weakly similar to ELASTASE 2 PRECURSOR [*M. musculus*] | | | gi = 4782077 | 679264 |
| IC06763 | UG75 Expression | EST | Mm.27453 | TITLE DNA segment, Chr 5, Wayne State University 31, expressed | GENE D5Wsu31e | | | 764579 |
| IC06764 | UG75 Expression | EST | Mm.27454 | TITLE ESTs | | | gi = 3386797 | 777384 |
| IC06765 | UG75 Expression | EST | Mm.27455 | TITLE ESTs | | | gi = 6095868 | 620266 |
| IC06766 | UG75 Expression | EST | Mm.27456 | TITLE ESTs | | | gi = 3369573 | 765675 |
| IC06767 | UG75 Expression | EST | Mm.27458 | TITLE ESTs | | | gi = 1929805 | 764249 |
| IC06768 | UG75 Expression | EST | Mm.27462 | TITLE ESTs | | | gi = 4764902 | 777778 |
| IC06769 | UG75 Expression | EST | Mm.27463 | TITLE ESTs | | | gi = 1932530 | 777851 |
| IC06770 | UG75 Expression | EST | Mm.27464 | TITLE ESTs | | | gi = 2164083 | 777834 |
| IC06771 | UG75 Expression | EST | Mm.27466 | TITLE ESTs | | | gi = 2291597 | 777210 |
| IC06772 | UG75 Expression | EST | Mm.27467 | TITLE ESTs | | | gi = 1909543 | 1279344 |
| IC06773 | UG75 Expression | EST | Mm.27469 | TITLE ESTs | | | gi = 5908578 | 752137 |
| IC06774 | UG75 Expression | EST | Mm.27470 | TITLE ESTs | | | gi = 5352695 | 643542 |
| IC06775 | UG75 Expression | EST | Mm.27472 | TITLE ESTs | | | gi = 2965620 | 1278886 |
| IC06776 | UG75 Expression | EST | Mm.27474 | TITLE ESTs | | | gi = 2139582 | 718054 |
| IC06777 | UG75 Expression | EST | Mm.27475 | TITLE ESTs | | | gi = 3373650 | 749288 |
| IC06778 | UG75 Expression | EST | Mm.27476 | TITLE ESTs | | | gi = 1676364 | 598788 |
| IC06779 | UG75 Expression | EST | Mm.27477 | TITLE ESTs, Weakly similar to F15D4.3 [*C. elegans*] | | | gi = 5497770 | 973011 |
| IC06780 | UG75 Expression | EST | Mm.27484 | TITLE ESTs, Moderately similar to tpr protein [*H. sapiens*] | | | gi = 3376376 | 618554 |
| IC06781 | UG75 Expression | EST | Mm.27485 | TITLE ESTs | | | gi = 1681004 | 717637 |
| IC06782 | UG75 Expression | EST | Mm.27486 | TITLE ESTs | | | gi = 2306102 | 1265139 |
| IC06783 | UG75 Expression | EST | Mm.27487 | TITLE ESTs, Weakly similar to (define not available 6013381) [*R. norvegicus*] | | | gi = 6748956 | 1279380 |
| IC06784 | UG75 Expression | EST | Mm.27488 | TITLE ESTs | | | gi = 5906178 | 749681 |
| IC06785 | UG75 Expression | EST | Mm.27489 | TITLE ESTs | | | gi = 6518720 | 617309 |
| IC06786 | UG75 Expression | EST | Mm.27491 | TITLE ESTs | | | gi = 6078836 | 749851 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06787 | UG75 Expression | EST | Mm.27493 | TITLE ESTs | | | gi = 2518633 | 749781 |
| IC06788 | UG75 Expression | EST | Mm.27495 | TITLE ESTs | | | gi = 2518677 | 751424 |
| IC06789 | UG75 Expression | EST | Mm.27497 | TITLE ESTs | | | gi = 4274453 | 764508 |
| IC06790 | UG75 Expression | EST | Mm.27500 | TITLE ESTs | | | gi = 246015 | 617857 |
| IC06791 | UG75 Expression | EST | Mm.27501 | TITLE ESTs | | | gi = 2193075 | 750144 |
| IC06792 | UG75 Expression | EST | Mm.27502 | TITLE DNA segment, Chr 16, human D22S680E, expressed | GENE D16H22: | T10| | | 1279813 |
| IC06793 | UG75 Expression | EST | Mm.27503 | TITLE ESTs | | | gi = 3100217 | 750782 |
| IC06794 | UG75 Expression | EST | Mm.27505 | TITLE ESTs | | | gi = 4615706 | 750285 |
| IC06795 | UG75 Expression | EST | Mm.27509 | TITLE ESTs, Moderately similar to TRANSCRIPTION INITIATION FACTOR TFIID 28 KD SUBUNIT [*H. sapiens*] | | | gi = 2292321 | 972925 |
| IC06796 | UG75 Expression | EST | Mm.27511 | TITLE ESTs | | | gi = 5819826 | 721341 |
| IC06797 | UG75 Expression | EST | Mm.27516 | TITLE ESTs, Weakly similar to coded for by *C. elegans* cDNA yk30c3.5 [*C. elegans*] | | | gi = 1726513 | 595899 |
| IC06798 | UG75 Expression | EST | Mm.27518 | TITLE ESTs, Weakly similar to BcDNA.GH06032 [*D. Melanogaster*] | | | gi = 3956986 | 621844 |
| IC06799 | UG75 Expression | EST | Mm.27520 | TITLE ESTs, Weakly similar to ubiquitin-protein ligase E3-alpha [*M. musculus*] | | | gi = 6084183 | 777143 |
| IC06800 | UG75 Expression | EST | Mm.27523 | TITLE ESTs | | | gi = 2572386 | 1020582 |
| IC06801 | UG75 Expression | EST | Mm.27528 | TITLE ESTs, Weakly similar to cyclin-dependent kinase p130-PITSLRE [*M. musculus*] | | | gi = 1759004 | 1149602 |
| IC06802 | UG75 Expression | EST | Mm.27529 | TITLE ESTs, Moderately similar to protein regulating cytokinesis 1 [*H. sapiens*] | | | gi = 6077256 | 1295418 |
| IC06803 | UG75 Expression | EST | Mm.27533 | TITLE ESTs | | | gi = 3394247 | 598836 |
| IC06804 | UG75 Expression | EST | Mm.27534 | TITLE ESTs | | | gi = 3386833 | 778307 |
| IC06805 | UG75 Expression | EST | Mm.27535 | TITLE ESTs, Weakly similar to HAIRLESS PROTEIN [*M. musculus*] | | | gi = 2074648 | 1193632 |
| IC06806 | UG75 Expression | EST | Mm.27536 | TITLE ESTs | | | gi = 3373673 | 1002877 |
| IC06807 | UG75 Expression | EST | Mm.27539 | TITLE ESTs | | | gi = 1310101 | 637184 |
| IC06808 | UG75 Expression | EST | Mm.27540 | TITLE ESTs | | | gi = 4724198 | 1294029 |
| IC06809 | UG75 Expression | EST | Mm.27542 | TITLE ESTs | | | gi = 6008036 | 643386 |
| IC06810 | UG75 Expression | EST | Mm.27548 | TITLE ESTs | | | gi = 6008218 | 1379969 |
| IC06811 | UG75 Expression | EST | Mm.27552 | TITLE ESTs | | | gi = 1763329 | 634113 |
| IC06812 | UG75 Expression | EST | Mm.27553 | TITLE ESTs | | | gi = 3393445 | 1446254 |
| IC06813 | UG75 Expression | EST | Mm.27556 | TITLE ESTs | | | gi = 3394341 | 719426 |
| IC06814 | UG75 Expression | EST | Mm.27558 | TITLE ESTs, Moderately similar to 26S PROTEASOME SUBUNIT S5B [*H. sapiens*] | | | gi = 6519425 | 972430 |
| IC06815 | UG75 Expression | EST | Mm.27559 | TITLE ESTs, Weakly similar to TRANSCRIPTIONAL ACTIVATOR GCN5 [*Saccharomyces cerevisiae*] | | | gi = 6518839 | 643235 |
| IC06816 | UG75 Expression | EST | Mm.27561 | TITLE ESTs, Weakly similar to weakly similar to gastrula zinc finger protein [*C. elegans*] | | | gi = 4779087 | 749355 |
| IC06817 | UG75 Expression | EST | Mm.27562 | TITLE ESTs | | | gi = 2257329 | 421404 |
| IC06818 | UG75 Expression | EST | Mm.27563 | TITLE ESTs | | | gi = 1749252 | 619123 |
| IC06819 | UG75 Expression | EST | Mm.27566 | TITLE ESTs | | | gi = 2116054 | 597051 |
| IC06820 | UG75 Expression | EST | Mm.27568 | TITLE ESTs, Moderately similar to unknown [*H. sapiens*] | | | gi = 3371185 | 598198 |
| IC06821 | UG75 Expression | EST | Mm.27569 | TITLE ESTs | | | gi = 1699849 | 598461 |
| IC06822 | UG75 Expression | EST | Mm.27571 | TITLE ESTs, Weakly similar to HYPOTHETICAL PROTEIN KIAA0063 [*H. sapiens*] | | | gi = 3987220 | 777207 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06823 | UG75 Expression | EST | Mm.27574 | TITLE ESTs, Weakly similar to asteroid protein [*D. melanogaster*] | | | gi = 4485408 | 1362405 |
| IC06824 | UG75 Expression | EST | Mm.27579 | TITLE ESTs | | | gi = 1794012 | 972703 |
| IC06825 | UG75 Expression | EST | Mm.27580 | TITLE ESTs, Weakly similar to ZK1058.5 [*C. elegans*] | | | gi = 1700116 | 577794 |
| IC06826 | UG75 Expression | EST | Mm.27582 | TITLE ESTs, Weakly similar to HYPOTHETICAL 25.6 KD PROTEIN T20B12.7 IN CHROMOSOME III [*Caenorhabditis elegans*] | | | gi = 5906510 | 958897 |
| IC06827 | UG76 LID366 B cell | EST | Mm.27583 | TITLE ESTs | | | gi = 7157653 | 865442 |
| IC06828 | UG75 Expression | EST | Mm.27584 | TITLE ESTs | | | gi = 2516686 | 765192 |
| IC06829 | UG75 Expression | EST | Mm.27587 | TITLE ESTs | | | gi = 2860541 | 643162 |
| IC06830 | UG75 Expression | EST | Mm.27591 | TITLE ESTs, Weakly similar to G PROTEIN PATHWAY SUPPRESSOR 1 [*R. norvegicus*] | | | gi = 3216196 | 972658 |
| IC06831 | UG75 Expression | EST | Mm.27592 | TITLE ESTs, Moderately similar to KIAA0181 [*H. sapiens*] | | | gi = 4623919 | 1193053 |
| IC06832 | UG75 Expression | EST | Mm.27593 | TITLE ESTs | | | gi = 2291780 | 620018 |
| IC06833 | UG75 Expression | EST | Mm.27597 | TITLE ESTs, Moderately similar to myosin phosphatase target subunit 1 [*H. sapiens*] | | | gi = 4276030 | 1382856 |
| IC06834 | UG75 Expression | EST | Mm.27598 | TITLE ESTs, Moderately similar to KIAA0159 gene product is related to yeast protein L8479.14. [*H. sapiens*] | | | gi = 6518448 | 723286 |
| IC06835 | UG75 Expression | EST | Mm.27599 | TITLE ESTs, Weakly similar to similar to GTP-binding protein [*C. elegans*] | | | gi = 3294964 | 1193588 |
| IC06836 | UG75 Expression | EST | Mm.27601 | TITLE ESTs | | | gi = 1895300 | 958751 |
| IC06837 | UG75 Expression | EST | Mm.27603 | TITLE ESTs | | | gi = 1550986 | 721122 |
| IC06838 | UG75 Expression | EST | Mm.27607 | TITLE ESTs | | | gi = 2039843 | 1139603 |
| IC06839 | UG75 Expression | EST | Mm.27610 | TITLE ESTs | | | gi = 1681776 | 596351 |
| IC06840 | UG75 Expression | EST | Mm.27611 | TITLE ESTs | | | gi = 2918650 | 1293657 |
| IC06841 | UG75 Expression | EST | Mm.27612 | TITLE ESTs | | | gi = 4276562 | 1344619 |
| IC06842 | UG75 Expression | EST | Mm.27614 | TITLE ESTs | | | gi = 1294207 | 619598 |
| IC06843 | UG75 Expression | EST | Mm.27615 | TITLE ESTs, Weakly similar to hypothetical protein [*H. sapiens*] | | | gi = 2462001 | 777486 |
| IC06844 | UG75 Expression | EST | Mm.27621 | TITLE ESTs | | | gi = 4434660 | 1020807 |
| IC06845 | UG75 Expression | EST | Mm.27626 | TITLE ESTs | | | gi = 4482074 | 1139611 |
| IC06846 | UG75 Expression | EST | Mm.27627 | TITLE ESTs | | | gi = 4401231 | 723050 |
| IC06847 | UG75 Expression | EST | Mm.27629 | TITLE ESTs | | | gi = 262854 | 1296099 |
| IC06848 | UG75 Expression | EST | Mm.27631 | TITLE ESTs | | | gi = 2919856 | 751386 |
| IC06849 | UG75 Expression | EST | Mm.27633 | TITLE ESTs | | | gi = 6085009 | 1749477 |
| IC06850 | UG75 Expression | EST | Mm.27635 | TITLE ESTs, Weakly similar to DNA-DIRECTED RNA POLYMERASE I 13.7 KD POLYPEPTIDE [*Saccharomyces cerevisie*] | | | gi = 1330766 | 635545 |
| IC06851 | UG75 Expression | EST | Mm.27637 | TITLE ESTs | | | gi = 1826533 | 617361 |
| IC06852 | UG75 Expression | EST | Mm.27639 | TITLE ESTs | | | gi = 1796118 | 574961 |
| IC06853 | UG75 Expression | EST | Mm.27641 | TITLE ESTs | | | gi = 3863009 | 874820 |
| IC06854 | UG75 Expression | EST | Mm.27647 | TITLE ESTs | | | gi = 4032214 | 973664 |
| IC06855 | UG75 Expression | EST | Mm.27650 | TITLE ESTs | | | gi = 3370359 | 619449 |
| IC06856 | UG75 Expression | EST | Mm.27651 | TITLE ESTs | | | gi = 3371013 | 717779 |
| IC06857 | UG75 Expression | EST | Mm.27652 | TITLE ESTs, Weakly similar to unknown [*M. musculus*] | | | gi = 3369986 | 643236 |
| IC06858 | UG75 Expression | EST | Mm.27653 | TITLE ESTs | | | gi = 5750004 | 972462 |
| IC06859 | UG75 Expression | EST | Mm.27655 | TITLE ESTs | | | gi = 3386754 | 468322 |
| IC06860 | UG75 Expression | EST | Mm.27656 | TITLE ESTs | | | gi = 1853078 | 622144 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06861 | UG75 Expression | EST | Mm.27660 | TITLE ESTs, Moderately similar to copine I [*H. sapiens*] | | | gi = 2305980 | 634745 |
| IC06862 | UG75 Expression | EST | Mm.27662 | TITLE ESTs, Moderately similar to unknown [*H. sapiens*] | | | gi = 3601733 | 534334 |
| IC06863 | UG75 Expression | EST | Mm.27665 | TITLE ESTs, Weakly similar to ARP2/3 COMPLEX 16 KD SUBUNIT [*H. sapiens*] | | | gi = 6077649 | 642762 |
| IC06864 | UG75 Expression | EST | Mm.27667 | TITLE ESTs, Weakly similar to PRAJA1 [*M. musculus*] | | | gi = 1811432 | 1344884 |
| IC06865 | UG75 Expression | EST | Mm.27670 | TITLE ESTs | | | gi = 1309590 | 894555 |
| IC06866 | UG75 Expression | EST | Mm.27671 | TITLE ESTs | | | gi = 3370113 | 583933 |
| IC06867 | UG75 Expression | EST | Mm.27672 | TITLE ESTs | | | gi = 2919549 | 1749247 |
| IC06868 | UG75 Expression | EST | Mm.27673 | TITLE DNA segment, Chr 6, Wayne State University 176, expressed | GENE D6Wsu176e | | | 638688 |
| IC06869 | UG75 Expression | EST | Mm.27683 | TITLE ESTs | | | gi = 4029469 | 599083 |
| IC06870 | UG75 Expression | EST | Mm.27687 | TITLE ESTs, Moderately similar to hypothetical protein [*H. sapiens*] | | | gi = 1841264 | 1148738 |
| IC06871 | UG75 Expression | EST | Mm.27692 | TITLE ESTs, Moderately similar to DNAJ domain-containing protein MCJ [*H. sapiens*] | | | gi = 4779120 | 1380134 |
| IC06872 | UG75 Expression | EST | Mm.27698 | PHOSPHATE PYROPHOSPHOKINASE II [*Rattus norvegicus*] | | | gi = 1538945 | 1295571 |
| IC06873 | UG75 Expression | EST | Mm.27703 | TITLE ESTs | | | gi = 4030325 | 894287 |
| IC06874 | UG75 Expression | EST | Mm.27704 | TITLE ESTs | | | gi = 4061750 | 1296000 |
| IC06875 | UG75 Expression | EST | Mm.27707 | TITLE ESTs | | | gi = 2257399 | 721745 |
| IC06876 | UG75 Expression | EST | Mm.27716 | TITLE ESTs | | | gi = 3394927 | 622135 |
| IC06877 | UG75 Expression | EST | Mm.27717 | TITLE ESTs | | | gi = 2081044 | 635785 |
| IC06878 | UG75 Expression | EST | Mm.27726 | TITLE ESTs, Weakly similar to Unknown [*H. sapiens*] | | | gi = 2306537 | 596426 |
| IC06879 | UG75 Expression | EST | Mm.27728 | TITLE ESTs | | | gi = 2919039 | 638168 |
| IC06880 | UG75 Expression | EST | Mm.27733 | TITLE ESTs | | | gi = 2257439 | 1294783 |
| IC06881 | UG75 Expression | EST | Mm.27737 | TITLE ESTs, Moderately similar to G-rich box-binding protein [*M. musculus*] | | | gi = 4484853 | 599258 |
| IC06882 | UG75 Expression | EST | Mm.27742 | TITLE ESTs | | | gi = 6084900 | 721678 |
| IC06883 | UG75 Expression | EST | Mm.27746 | TITLE ESTs, Moderately similar to leucine rrich protein [*H. sapiens*] | | | gi = 4601644 | 18466 |
| IC06884 | UG75 Expression | EST | Mm.27747 | TITLE ESTs, Weakly similar to ORF YNL059c [*S. cerevisiae*] | | | gi = 3336103 | 1380247 |
| IC06885 | UG75 Expression | EST | Mm.2775 | TITLE ESTs | | | gi = 2259193 | 597149 |
| IC06886 | UG75 Expression | EST | Mm.27750 | TITLE ESTs, Weakly similar to huntingtin interacting protein-2 [*M. musculus*] | | | gi = 2306000 | 638285 |
| IC06887 | UG75 Expression | EST | Mm.27751 | TITLE ESTs | | | gi = 2306033 | 721227 |
| IC06888 | UG75 Expression | EST | Mm.27752 | TITLE ESTs | | | gi = 3376892 | 1002056 |
| IC06889 | UG75 Expression | EST | Mm.27756 | TITLE ESTs | | | gi = 3160725 | 617433 |
| IC06890 | UG75 Expression | EST | Mm.27761 | TITLE ESTs, Moderately similar to (define not available 5714400) [*M. musculus*] | | | gi = 5125333 | 893909 |
| IC06891 | UG75 Expression | EST | Mm.27762 | TITLE ESTs, Weakly similar to RING zinc finger protein [*M. musculus*] | | | gi = 3393640 | 1295022 |
| IC06892 | UG75 Expression | EST | Mm.27764 | TITLE ESTs | | | gi = 6083837 | 1149614 |
| IC06893 | UG75 Expression | EST | Mm.27766 | TITLE ESTs, Weakly similar to 62D9.a [*D. melanogaster*] | | | gi = 2308010 | 958579 |
| IC06894 | UG75 Expression | EST | Mm.27767 | TITLE ESTs | | | gi = 2308148 | 722837 |
| IC06895 | UG75 Expression | EST | Mm.27770 | TITLE ESTs, Weakly similr to cullin 1 [*M. musculus*] | | | gi = 2308471 | 533973 |
| IC06896 | UG75 Expression | EST | Mm.27772 | TITLE ESTs, Weakly similar to RSP-1 PROTEIN [*Mus musculus*] | | | gi = 2625722 | 902985 |
| IC06897 | UG75 Expression | EST | Mm.27773 | TITLE ESTs | | | gi = 4402112 | 1293869 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06898 | UG75 Expression | EST | Mm.27785 | TITLE ESTs | | | gi = 3957057 | 622337 |
| IC06899 | UG75 Expression | EST | Mm.27786 | TITLE ESTs, Weakly similar to similar to nuclear domain 10 protein NDP52 [*H. sapiens*] | | | gi = 3720022 | 972698 |
| IC06900 | UG75 Expression | EST | Mm.27787 | TITLE ESTs, Moderately similar to HYPOTHETICAL PROTEIN KIAA0110 [*H. sapiens*] | | | gi = 4605676 | 970435 |
| IC06901 | UG75 Expression | EST | Mm.27789 | TITLE ESTs | | | gi = 2919332 | 973733 |
| IC06902 | UG75 Expression | EST | Mm.27790 | TITLE ESTs, Weakly similar to rA9 [*R. norvegicus*] | | | gi = 4316484 | 973901 |
| IC06903 | UG75 Expression | EST | Mm.27792 | TITLE ESTs, Weakly similar to H14A12.3 [*C. elegans*] | | | gi = 1288742 | 1362969 |
| IC06904 | UG75 Expression | EST | Mm.27793 | TITLE ESTs | | | gi = 1793998 | 619456 |
| IC06905 | UG75 Expression | EST | Mm.27794 | TITLE ESTs | | | gi = 1282692 | 622367 |
| IC06906 | UG75 Expression | EST | Mm.27799 | TITLE ESTs, Weakly similar to (define not available 5453421) [*M. musculus*] | | | gi = 1751515 | 1296092 |
| IC06907 | UG75 Expression | EST | Mm.27802 | TITLE ESTs | | | gi = 4216196 | 558074 |
| IC06908 | UG75 Expression | EST | Mm.27804 | TITLE ESTs, Weakly similar to Similarity to Yeast hypothetical protein YOR316OW [*C. elegans*] | | | gi = 4434500 | 1193581 |
| IC06909 | UG75 Expression | EST | Mm.27809 | TITLE ESTs | | | gi = 2516765 | 721241 |
| IC06910 | UG75 Expression | EST | Mm.27814 | TITLE ESTs | | | gi = 1519960 | 1279202 |
| IC06911 | UG75 Expression | EST | Mm.27817 | TITLE ESTs, Weakly similar to hypothetical protein [*H. spaiens*] | | | gi = 3517968 | 1429565 |
| IC06912 | UG75 Expression | EST | Mm.27820 | TITLE ESTs | | | gi = 2906961 | 790305 |
| IC06913 | UG75 Expression | EST | Mm.27824 | TITLE ESTs | | | gi = 6633443 | 598138 |
| IC06914 | UG75 Expression | EST | Mm.27827 | TITLE ESTs | | | gi = 2813953 | 777543 |
| IC06915 | UG75 Expression | EST | Mm.27828 | TITLE ESTs, Weakly similar to kinesin-like protein 2beta [*M. musculus*] | | | gi = 2919498 | 437761 |
| IC06916 | UG75 Expression | EST | Mm.27831 | TITLE ESTs, Weakly similar to cDNA EST EMBL:D75703 comes from this gene [*C. elegans*] | | | gi = 6516291 | 722578 |
| IC06917 | UG75 Expression | EST | Mm.27844 | TITLE ESTs | | | gi = 5492615 | 1193036 |
| IC06918 | UG75 Expression | EST | Mm.27845 | TITLE ESTs, Weakly similar to Pro-Pol-dUTPase polyprotein [*M. musculus*] | | | gi = 1749332 | 618479 |
| IC06919 | UG75 Expression | EST | Mm.27848 | TITLE ESTs, Weakly similar to implantation-associated protein [*R. norvegicus*] | | | gi = 4403939 | 973435 |
| IC06920 | UG75 Expression | EST | Mm.27851 | TITLE ESTs, Weakly similar to misato [*D. melanogaster*] | | | gi = 4271625 | 1002222 |
| IC06921 | UG75 Expression | EST | Mm.27852 | TITLE ESTs | | | gi = 3394651 | 1002681 |
| IC06922 | UG75 Expression | EST | Mm.27853 | TITLE DNA segment, Chr 7, Wayne State University 180, expressed | GENE D7Wsu180e | | | 1002691 |
| IC06923 | UG75 Expression | EST | Mm.27854 | TITLE ESTs | | | gi = 2906868 | 721972 |
| IC06924 | UG75 Expression | EST | Mm.27858 | TITLE ESTs | | | gi = 3164733 | 719241 |
| IC06925 | UG75 Expression | EST | Mm.27859 | TITLE ESTs | | | gi = 2292041 | 1040629 |
| IC06926 | UG75 Expression | EST | Mm.27862 | TITLE ESTs, Weakly similar to weakly similar to gastrula zinc finger protein [*C. elegans*] | | | gi = 2081161 | 636741 |
| IC06927 | UG75 Expression | EST | Mm.27863 | TITLE ESTs, Weakly similar to predicted using Genefinder [*C. elegans*] | | | gi = 4726440 | 720981 |
| IC06928 | UG75 Expression | EST | Mm.27867 | TITLE ESTs | | | gi = 1827130 | 1294356 |
| IC06929 | UG75 Expression | EST | Mm.27869 | TITLE ESTs | | | gi = 4726196 | 636991 |
| IC06930 | UG75 Expression | EST | Mm.27871 | TITLE ESTs, Moderately similar to HYPOTHETICAL 27.1 KD PROTEIN CCE1-CAP1 INTERGENIC REGION [*Saccharomyces cerevisiae*] | | | gi = 1318347 | 959126 |
| IC06931 | UG75 Expression | EST | Mm.27872 | TITLE ESTs, Weakly similar to D52 [*M. musculus*] | | | gi = 6560126 | 719448 |
| IC06932 | UG75 Expression | EST | Mm.27876 | TITLE ESTs | | | gi = 6167756 | 582235 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06933 | UG75 Expression | EST | Mm.27878 | TITLE ESTs, Weakly similar to GA BINDING PROTEIN BETA-1 CHAIN [*M. musculus*] | | | gi = 2404690 | 575492 |
| IC06934 | UG75 Expression | EST | Mm.27883 | TITLE ESTs | | | gi = 3684721 | 1378590 |
| IC06935 | UG75 Expression | EST | Mm.27886 | TITLE ESTs, Weakly similar to 13kD differentiation-associated protein [*H. sapiens*] | | | gi = 1407501 | 551217 |
| IC06936 | UG75 Expression | EST | Mm.27887 | TITLE ESTs | | | gi = 2307443 | 959248 |
| IC06937 | UG75 Expression | EST | Mm.27893 | TITLE ESTs | | | gi = 4603072 | 582015 |
| IC06938 | UG75 Expression | EST | Mm.27894 | TITLE ESTs, Moderately similar to INSULIN-INDUCED GROWTH RESPONSE PROTEIN CL-6 [*R. norvegicus*] | | | gi = 4217173 | 1264964 |
| IC06939 | UG75 Expression | EST | Mm.27900 | TITLE ESTs | | | gi = 2919659 | 1379146 |
| IC06940 | UG75 Expression | EST | Mm.27903 | TITLE ESTs | | | gi = 2193170 | 598543 |
| IC06941 | UG75 Expression | EST | Mm.27904 | TITLE ESTs | | | gi = 5492600 | 551426 |
| IC06942 | UG75 Expression | EST | Mm.27908 | TITLE ESTs | | | gi = 3376653 | 958965 |
| IC06943 | UG75 Expression | EST | Mm.27913 | TITLE ESTs, Weakly similar to NUCLEAR PROTEIN STH1/NPS1 [*Saccharomyces cerevisiae*] | | | gi = 5598385 | 893935 |
| IC06944 | UG75 Expression | EST | Mm.27914 | TITLE ESTs, Weakly similar to hypertension-related protein [*R. norvegicus*] | | | gi = 2519841 | 639591 |
| IC06945 | UG75 Expression | EST | Mm.27917 | TITLE ESTs | | | gi = 2192441 | 863000 |
| IC06946 | UG75 Expression | EST | Mm.27918 | TITLE ESTs | | | gi = 230805 | 1294585 |
| IC06947 | UG75 Expression | EST | Mm.27920 | TITLE ESTs | | | gi = 1727176 | 1149661 |
| IC06948 | UG75 Expression | EST | Mm.27922 | TITLE ESTs, Weakly similar to snRNP protein B [*D. melanogaster*] | | | gi = 3165326 | 972361 |
| IC06949 | UG75 Expression | EST | Mm.27923 | TITLE ESTs | | | gi = 4616155 | 1263500 |
| IC06950 | UG75 Expression | EST | Mm.27924 | TITLE ESTs | | | gi = 6645730 | 764687 |
| IC06951 | UG75 Expression | EST | Mm.27928 | TITLE ESTs | | | gi = 2292468 | 722462 |
| IC06952 | UG75 Expression | EST | Mm.27930 | TITLE ESTs | | | gi = 3079021 | 1329179 |
| IC06953 | UG75 Expression | EST | Mm.27936 | TITLE ESTs | | | gi = 2308220 | 1193691 |
| IC06954 | UG75 Expression | EST | Mm.27940 | TITLE ESTs | | | gi = 4730218 | 718504 |
| IC06955 | UG75 Expression | EST | Mm.27942 | TITLE ESTs | | | gi = 2517658 | 642155 |
| IC06956 | UG75 Expression | EST | Mm.27944 | TITLE ESTs, Weakly similar to LONG-CHAIN-FATTY-ACID-COA LIGASE 2 [*M. musculus*] | | | gi = 4767912 | 598075 |
| IC06957 | UG75 Expression | EST | Mm.27945 | TITLE ESTs, Weakly similar to Ydr489wp [*S. cerevisiae*] | | | gi = 4217409 | 533323 |
| IC06958 | UG75 Expression | EST | Mm.27946 | TITLE ESTs, Weakly similar to nucleolar protein p120 [*M. musculus*] | | | gi = 4601368 | 11497004 |
| IC06959 | UG75 Expression | EST | Mm.27947 | TITLE ESTs, Moderately similar to CYTOSKELETON-ASSOCIATED PROTEIN CKAP1 [*H. sapiens*] | | | gi = 1294247 | 1020820 |
| IC06960 | UG75 Expression | EST | Mm.27948 | TITLE ESTs, Weakly similar to GGPP synthase [*M. musculus*] | | | gi = 2519540 | 620738 |
| IC06961 | UG75 Expression | EST | Mm.27952 | TITLE ESTs, Weakly similar to similar to Achlya ambisexualis antheridiol steroid receptor [*C. elegans*] | | | gi = 4604551 | 972927 |
| IC06962 | UG75 Expression | EST | Mm.27953 | TITLE DNA segment, Chr 19, Wayne State University 57, expressed | GENE D19Wsu57e | | | 571599 |
| IC06963 | UG75 Expression | EST | Mm.27954 | TITLE ESTs | | | gi = 4613185 | 1295657 |
| IC06964 | UG75 Expression | EST | Mm.27955 | TITLE ESTs, Weakly similar to EUKARYOTIC INITIATION FACTOR 4B [*Homo sapiens*] | | | gi = 1282474 | 1139711 |
| IC06965 | UG75 Expression | EST | Mm.27956 | TITLE ESTs, Weakly similar to Ylr435wp [*S. cerevisiae*] | | | gi = 2855787 | 1749754 |
| IC06966 | UG75 Expression | EST | Mm.27961 | TITLE ESTs, Weakly similar to B [*M. musculus*] | | | gi = 1864396 | 33916 |
| IC06967 | UG75 Expression | EST | Mm.27962 | TITLE ESTs | | | gi = 3370117 | 595867 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC06968 | UG75 Expression | EST | Mm.27963 | TITLE ESTs, Moderately similar to CREB-BINDING PROTEIN [M. musculus] | | | gi = 4722955 | 975875 |
| IC06969 | UG75 Expression | EST | Mm.27965 | TITLE ESTs, Weakly similar to ZK856.11 [C. elegans] | | | gi = 3374595 | 1140134 |
| IC06970 | UG75 Expression | EST | Mm.27967 | TITLE ESTs | | | gi = 3687178 | 973013 |
| IC06971 | UG75 Expression | EST | Mm.27968 | TITLE ESTs | | | gi = 2201147 | 973145 |
| IC06972 | UG75 Expression | EST | Mm.2797 | TITLE ESTs | | | gi = 312624 | 717601 |
| IC06973 | UG75 Expression | EST | Mm.27971 | TITLE ESTs, Weakly similar to LIM PROTEIN RIL [Rattus norvegicus] | | | gi = 2402736 | 749470 |
| IC06974 | UG75 Expression | EST | Mm.27974 | TITLE ESTs | | | gi = 1801034 | 1345833 |
| IC06975 | UG75 Expression | EST | Mm.27976 | TITLE ESTs | | | gi = 1806942 | 722504 |
| IC06976 | UG75 Expression | EST | Mm.27987 | TITLE ESTs | | | gi = 1876081 | 1149328 |
| IC06977 | UG75 Expression | EST | Mm.27988 | TITLE ESTs | | | gi = 2521582 | 1149321 |
| IC06978 | UG75 Expression | EST | Mm.2799 | TITLE ESTs | | | gi = 1902463 | 718240 |
| IC06979 | UG75 Expression | EST | Mm.27990 | TITLE ESTs | | | gi = 1769206 | 599077 |
| IC06980 | UG75 Expression | EST | Mm.27995 | TITLE ESTs | | | gi = 6520900 | 1001718 |
| IC06981 | UG75 Expression | EST | Mm.27997 | TITLE ESTs, Moderately similar to ACTIVATOR 1 36 KD SUBUNIT [Homo sapiens] | | | gi = 1711761 | 1763434 |
| IC06982 | UG75 Expression | EST | Mm.28 | TITLE ESTs | | | gi = 1672640 | 574446 |
| IC06983 | UG75 Expression | EST | Mm.28000 | TITLE ESTs, Weakly similar to H06H21.6 [C. elegans] | | | gi = 6085634 | 752507 |
| IC06984 | UG75 Expression | EST | Mm.28003 | TITLE ESTs | | | gi = 2521072 | 1295845 |
| IC06985 | UG75 Expression | EST | Mm.28005 | TITLE ESTs | | | gi = 1904375 | 1193603 |
| IC06986 | UG75 Expression | EST | Mm.28012 | TITLE ESTs, Weakly similar to 7-60 [H. sapiens] | | | gi = 6168053 | 572819 |
| IC06987 | UG75 Expression | EST | Mm.28013 | TITLE ESTs, Weakly similar to protein co-factor | | | gi = 6560317 | 959338 |
| IC06988 | UG75 Expression | EST | Mm.28015 | TITLE ESTs | | | gi = 6077443 | 550786 |
| IC06989 | UG75 Expression | EST | Mm.28016 | TITLE ESTs, Weakly similar to cAMP-dependent Rap1 guanine-nucleotide exchange factor [M. musculus] | | | gi = 2647089 | 2159659 |
| IC06990 | UG75 Expression | EST | Mm.28017 | TITLE ESTs, Weakly similar to beta-transducin repeat containing protein [M. musculus] | | | gi = 4273288 | 582032 |
| IC06991 | UG75 Expression | EST | Mm.28018 | TITLE ESTs | | | gi = 2918660 | 1447061 |
| IC06992 | UG75 Expression | EST | Mm.2802 | TITLE ESTs | | | gi = 1882073 | 717593 |
| IC06993 | UG75 Expression | EST | Mm.28021 | TITLE ESTs | | | gi = 6557904 | 618375 |
| IC06994 | UG75 Expression | EST | Mm.28024 | TITLE ESTs | | | gi = 1509115 | 790994 |
| IC06995 | UG75 Expression | EST | Mm.28026 | TITLE ESTs | | | gi = 1675624 | 1193447 |
| IC06996 | UG75 Expression | EST | Mm.28028 | TITLE ESTs, Weakly similar to RNA binding protein [M. musculus] | | | gi = 5336314 | 408692 |
| IC06997 | UG75 Expression | EST | Mm.28029 | TITLE ESTs | | | gi = 2308260 | 765606 |
| IC06998 | UG75 Expression | EST | Mm.28030 | TITLE ESTs | | | gi = 3370485 | 1328054 |
| IC06999 | UG75 Expression | EST | Mm.28031 | TITLE ESTs | | | gi = 4289815 | 620840 |
| IC07000 | UG75 Expression | EST | Mm.28033 | TITLE ESTs | | | gi = 1465013 | 718708 |
| IC07001 | UG75 Expression | EST | Mm.28034 | TITLE ESTs, Weakly similar to inositol 1,4,5-trisphosphate-binding protein, 130K [R. norvegicus] | | | gi = 1747200 | 1001875 |
| IC07002 | UG75 Expression | EST | Mm.28035 | TITLE ESTs | | | gi = 2670843 | 637829 |
| IC07003 | UG75 Expression | EST | Mm.28037 | TITLE ESTs | | | gi = 2521960 | 721250 |
| IC07004 | UG75 Expression | EST | Mm.28038 | TITLE ESTs | | | gi = 2308243 | 574151 |
| IC07005 | UG75 Expression | EST | Mm.28039 | TITLE ESTs, Weakly similar to cDNA EST yk425a6.3 comes from this gene [C. elegans] | | | gi = 1328561 | 1139644 |
| IC07006 | UG75 Expression | EST | Mm.2804 | TITLE ESTs, Weakly similar to 3-OXOACYL-[ACYL-CARRIER PROTEIN] REDUCTASE [Escherichia coli] | | | gi = 4217440 | 1280072 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07007 | UG75 Expression | EST | Mm.28045 | TITLE ESTs | | | gi = 6167971 | 638490 |
| IC07008 | UG75 Expression | EST | Mm.28048 | TITLE ESTs, Weakly similar to Su(P) [D. melanogaster] | | | gi = 6940391 | 600850 |
| IC07009 | UG75 Expression | EST | Mm.28057 | TITLE ESTs, Weakly similar to coded for by C. elegans cDNAs GenBank: [C. elegans] | | | gi = 2283045 | 622887 |
| IC07010 | UG75 Expression | EST | Mm.28059 | TITLE ESTs | | | gi = 2692694 | 644909 |
| IC07011 | UG75 Expression | EST | Mm.28062 | TITLE ESTs | | | gi = 2188011 | 599131 |
| IC07012 | UG75 Expression | EST | Mm.28064 | TITLE ESTs | | | gi = 5125231 | 721957 |
| IC07013 | UG75 Expression | EST | Mm.28065 | TITLE ESTs | | | gi = 5492273 | 1226483 |
| IC07014 | UG75 Expression | EST | Mm.28056 | TITLE ESTs, Weakly similar to extendin [M. musculus] | | | gi = 5124947 | 1279204 |
| IC07015 | UG75 Expression | EST | Mm.28070 | TITLE ESTs, Weakly similar to heterogeneous nuclear ribonucleoprotein H [M. musculus] | | | gi = 6823584 | 616774 |
| IC07016 | UG75 Expression | EST | Mm.28071 | TITLE ESTs | | | gi = 2850444 | 1002748 |
| IC07017 | UG75 Expression | EST | Mm.28077 | TITLE ESTs | | | gi = 3164596 | 750253 |
| IC07018 | UG75 Expression | EST | Mm.28079 | TITLE ESTs | | | gi = 5861418 | 1907900 |
| IC07019 | UG75 Expression | EST | Mm.28085 | TITLE ESTs | | | gi = 2503309 | 972805 |
| IC07020 | UG75 Expression | EST | Mm.28087 | TITLE ESTs | | | gi = 1497514 | 573176 |
| IC07021 | UG75 Expression | EST | Mm.28092 | TITLE ESTs | | | gi = 2721777 | 750262 |
| IC07022 | UG75 Expression | EST | Mm.28094 | TITLE ESTs | | | gi = 3164442 | 643272 |
| IC07023 | UG75 Expression | EST | Mm.28095 | TITLE ESTs, Moderately similar to ENDOTHELIAL ACTIN-BINDING PROTEIN [Homo sapiens] | | | gi = 1710769 | 639597 |
| IC07024 | UG75 Expression | EST | Mm.28097 | TITLE ESTs, Moderately similar to DNA-DIRECTED RNA POLYMERASE II 32KD POLYPEPTIDE [Saccaromyces cerevisiae] | | | gi = 3393411 | 1363467 |
| IC07025 | UG75 Expression | EST | Mm.28101 | TITLE ESTs | | | gi = 4315867 | 636897 |
| IC07026 | UG75 Expression | EST | Mm.28102 | TITLE ESTs | | | gi = 4216375 | 1193220 |
| IC07027 | UG75 Expression | EST | Mm.28103 | TITLE ESTs | | | gi = 2516865 | 1140349 |
| IC07028 | UG75 Expression | EST | Mm.28107 | TITLE ESTs, Moderately similar to PLASMA-CELL MEMBRANE GLYCOPROTEIN PC-1 [Homo sapiens] | | | gi = 4030014 | 533819 |
| IC07029 | UG75 Expression | EST | Mm.28108 | TITLE ESTs, Weakly similar to unknown [S. cerevisiae] | | | gi = 4606345 | 1281487 |
| IC07030 | UG75 Expression | EST | Mm.28109 | TITLE ESTs, Weakly similar to HYPOTHETICAL 15.9 KD PROTEIN IN GLNA-FDHE INTERGENIC REGION [Escherichia coli] | | | gi = 3809086 | 1429120 |
| IC07031 | UG75 Expression | EST | Mm.28111 | TITLE ESTs, Weakly similar to predicted using Genefinder [C. elegans] | | | gi = 5125547 | 1312050 |
| IC07032 | UG75 Expression | EST | Mm.28114 | TITLE ESTs, Weakly similar to ORF YPL191c [S. cerevisiae] | | | gi = 3885254 | 765579 |
| IC07033 | UG75 Expression | EST | Mm.28115 | TITLE ESTs | | | gi = 1634605 | 1265171 |
| IC07034 | UG75 Expression | EST | Mm.28117 | TITLE ESTs, Moderately similar to KIAA0668 protein [H. sapiens] | | | gi = 6519172 | 642679 |
| IC07035 | UG75 Expression | EST | Mm.28119 | TITLE ESTs | | | gi = 2233462 | 575671 |
| IC07036 | UG75 Expression | EST | Mm.28121 | TITLE ESTs, Weakly similar to protein B [M. musculus] | | | gi = 3980826 | 764135 |
| IC07037 | UG75 Expression | EST | Mm.28122 | TITLE ESTs, Weakly similar to cDNA EST yk338f6.5 comes from this gene [C. elegans] | | | gi = 1901839 | 718754 |
| IC07038 | UG75 Expression | EST | Mm.28123 | TITLE ESTs, Moderately similar to FAST kinase [H. sapiens] | | | gi = 6084849 | 596342 |
| IC07039 | UG75 Expression | EST | Mm.28125 | TITLE ESTs, Weakly similar to ASPARTYL-TRNA SYNTHETASE [R. norvegicus] | | | gi = 6078296 | 849781 |
| IC07040 | UG75 Expression | EST | Mm.28129 | TITLE ESTs | | | gi = 2517977 | 581922 |
| IC07041 | UG75 Expression | EST | Mm.28132 | TITLE ESTs | | | gi = 1827257 | 752474 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07042 | UG75 Expression | EST | Mm.28133 | TITLE ESTs | | | gi = 2775379 | 598962 |
| IC07043 | UG75 Expression | EST | Mm.28135 | TITLE ESTs | | | gi = 4272338 | 1226019 |
| IC07044 | UG75 Expression | EST | Mm.28136 | TITLE ESTs | | | gi = 5124718 | 534253 |
| IC07045 | UG75 Expression | EST | Mm.28138 | TITLE ESTs | | | gi = 1282453 | 1361815 |
| IC07046 | UG75 Expression | EST | Mm.28139 | TITLE ESTs | | | gi = 2965083 | 764933 |
| IC07047 | UG75 Expression | EST | Mm.28140 | TITLE ESTs, Weakly similar to Evi-5 [*M. musculus*] | | | gi = 4729921 | 1226950 |
| IC07048 | UG75 Expression | EST | Mm.28144 | TITLE ESTs, Moderately similar to HSPC013 [*H. sapiens*] | | | gi = 1290105 | 1279114 |
| IC07049 | UG75 Expression | EST | Mm.28147 | TITLE ESTs, Moderately similar to POLYPOSIS LOCUS PROTEIN 1 [*Homo sapiens*] | | | gi = 4030324 | 717725 |
| IC07050 | UG75 Expression | EST | Mm.28148 | TITLE ESTs | | | gi = 2520256 | 1149089 |
| IC07051 | UG75 Expression | EST | Mm.28149 | TITLE ESTs | | | gi = 2456529 | 973325 |
| IC07052 | UG75 Expression | EST | Mm.28151 | TITLE ESTs | | | gi = 4433966 | 777404 |
| IC07053 | UG75 Expression | EST | Mm.28152 | TITLE ESTs | | | gi = 1476361 | 1226288 |
| IC07054 | UG75 Expression | EST | Mm.28153 | TITLE ESTs | | | gi = 4029601 | 1265480 |
| IC07055 | UG75 Expression | EST | Mm.28158 | TITLE ESTs | | | gi = 2257197 | 1002581 |
| IC07056 | UG75 Expression | EST | Mm.28161 | TITLE ESTs | | | gi = 2516808 | 972784 |
| IC07057 | UG75 Expression | EST | Mm.28163 | TITLE ESTs | | | gi = 2262574 | 1247519 |
| IC07058 | UG75 Expression | EST | Mm.28164 | TITLE ESTs, Weakly similar to DUAL SPECIFICITY PROTEIN PHOSPHATASE 2 [*M. musculus*] | | | gi = 3167712 | 599016 |
| IC07059 | UG75 Expression | EST | Mm.28166 | TITLE ESTs | | | gi = 2811507 | 1243283 |
| IC07060 | UG75 Expression | EST | Mm.28167 | TITLE ESTs, Weakly similar to ANKYRIN, BRAIN VARIANT 2 [*Homo sapiens*] | | | gi = 4216252 | 1363546 |
| IC07061 | UG75 Expression | EST | Mm.28168 | TITLE ESTs | | | gi = 4625130 | 573378 |
| IC07062 | UG75 Expression | EST | Mm.28169 | TITLE ESTs, Weakly similar to contains similarity to human cyclin A/CDK2-associated protein p19, an RNA polymerase II elongation factor-like protein [*C. elegans*] | | | gi = 1290271 | 635079 |
| IC07063 | UG75 Expression | EST | Mm.28171 | TITLE ESTs | | | gi = 1325324 | 642159 |
| IC07064 | UG75 Expression | EST | Mm.28172 | TITLE DNA segment, Chr 7, Wayne State University 37, expressed | GENE D7Wsu37e | | | 972809 |
| IC07065 | UG75 Expression | EST | Mm.28174 | TITLE ESTs | | | gi = 4315860 | 534206 |
| IC07066 | UG75 Expression | EST | Mm.28175 | TITLE ESTs | | | gi = 5910523 | 619886 |
| IC07067 | UG75 Expression | EST | Mm.2818 | TITLE ESTs, Moderately similar to dachshund variant 2 [*M. musculus*] | | | gi = 2858040 | 621299 |
| IC07068 | UG75 Expression | EST | Mm.28180 | TITLE ESTs, Weakly similar to TDAG51 [*M. musculus*] | | | gi = 1287775 | 1362675 |
| IC07069 | UG75 Expression | EST | Mm.28182 | TITLE ESTs | | | gi = 1325334 | 751959 |
| IC07070 | UG75 Expression | EST | Mm.28184 | TITLE ESTs | | | gi = 3885304 | 752356 |
| IC07071 | UG75 Expression | EST | Mm.28189 | TITLE ESTs | | | gi = 2967357 | 620677 |
| IC07072 | UG75 Expression | EST | Mm.28191 | TITLE ESTs, Weakly similar to LIVER CARBOXYLESTERASE PRECURSOR [*M. musculus*] | | | gi = 4030169 | 1226655 |
| IC07073 | UG75 Expression | EST | Mm.28193 | TITLE ESTs [*H. sapiens*] | | | gi = 1309585 | 720696 |
| IC07074 | UG75 Expression | EST | Mm.28195 | TITLE ESTs | | | gi = 4440754 | 1294869 |
| IC07075 | UG75 Expression | EST | Mm.28198 | TITLE ESTs | | | gi = 2803854 | 620088 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07076 | UG75 Expression | EST | Mm. 28199 | TITLE ESTs, Weakly similar to HYPOTHETICAL PROTEIN KIAA0117 [H. sapiens] | | | gi = 3168018 | 551475 |
| IC07077 | UG75 Expression | EST | Mm. 28203 | TITLE GROUP-LIKE NUCLEAR PROTEIN 2 [Saccharomyces cerevisiae] | | | gi = 1326469 | 1149076 |
| IC07078 | UG75 Expression | EST | Mm. 28205 | TITLE ESTs | | | gi = 2807340 | 973116 |
| IC07079 | UG75 Expression | EST | Mm. 28206 | TITLE ESTs | | | gi = 5337006 | 1002125 |
| IC07080 | UG75 Expression | EST | Mm. 28207 | TITLE DNA segment, Chr 4, Wayne State University 132, expressed | GENE D4Wsu132e | | | 616598 |
| IC07081 | UG75 Expression | EST | Mm. 28209 | TITLE ESTs, Weakly similar to NG22 [M. musculus] | | | gi = 2402914 | 574776 |
| IC07082 | UG75 Expression | EST | Mm. 2821 | TITLE ESTs | | | gi = 3520555 | 722473 |
| IC07083 | UG75 Expression | EST | Mm. 28210 | TITLE ESTs | | | gi = 2075875 | 1002673 |
| IC07084 | UG75 Expression | EST | Mm. 28211 | TITLE ESTs, Weakly similar to IgG Fc binding protein [M. musculus] | | | gi = 2412586 | 574018 |
| IC07085 | UG75 Expression | EST | Mm. 28212 | TITLE DNA segment, Chr 17, Wayne State University 82, expressed | GENE D17Wsu82e | | | 777406 |
| IC07086 | UG75 Expression | EST | Mm. 28213 | TITLE ESTs, Weakly similar to coded for by C. elegans cDNA yk38h3.5 [C. elegans] | | | gi = 2916704 | 1193035 |
| IC07087 | UG75 Expression | EST | Mm. 28214 | TITLE ESTs, Weakly similar to cDNA EST yk23cd4.5 comes from this gene [C. elegans] | | | gi = 4702879 | 618035 |
| IC07088 | UG75 Expression | EST | Mm. 28215 | TITLE ESTs, Moderately similar to growth factor-responsive protein, vascular smooth muscle [R. norvegicus] | | | gi = 3681918 | 1278864 |
| IC07089 | UG75 Expression | EST | Mm. 28217 | TITLE ESTs | | | gi = 1406970 | 1329208 |
| IC07090 | UG75 Expression | EST | Mm. 28221 | TITLE ESTs | | | gi = 1755655 | 617413 |
| IC07091 | UG75 Expression | EST | Mm. 28225 | TITLE ESTs, Weakly similar to BETA-MANNOSIDASE PRECURSOR [H. sapiens] | | | gi = 1682364 | 893915 |
| IC07092 | UG75 Expression | EST | Mm. 28227 | TITLE ESTs | | | gi = 1908863 | 750913 |
| IC07093 | UG75 Expression | EST | Mm. 28230 | TITLE ESTs | | | gi = 2306266 | 622036 |
| IC07094 | UG75 Expression | EST | Mm. 28231 | TITLE ESTs, Weakly similar to tazarotene-induced gene 2 [H. sapiens] | | | gi = 3987266 | 620571 |
| IC07095 | UG75 Expression | EST | Mm. 28232 | TITLE ESTs, Moderately similar to KIAA0797 protein [H. sapiens] | | | gi = 5125437 | 765858 |
| IC07096 | UG75 Expression | EST | Mm. 28233 | TITLE ESTs | | | gi = 2962180 | 751556 |
| IC07097 | 00/04/26 UG#76 17Lid Expansion | EST | Mm. 28236 | ESTs | | — | gi = 3394047 | 778920 |
| IC07098 | UG75 Expression | EST | Mm. 28237 | TITLE ESTs, Weakly similar to syntaxin 7 [M. musculus] | | | gi = 4967863 | 1294647 |
| IC07099 | UG75 Expression | EST | Mm. 28238 | TITLE ESTs, Weakly similar to Hsp70 binding protein HspBP1 [H. sapiens] | | | gi = 2591445 | 1431524 |
| IC07100 | UG75 Expression | EST | Mm. 28239 | TITLE ESTs | | | gi = 2116438 | 638569 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07101 | UG75 Expression | EST | Mm. 28241 | TITLE DNA segment, Chr 1, University of California at Los Angeles 2 | GENE D1Ucla2 | | | 750268 |
| IC07102 | UG75 Expression | EST | Mm. 28242 | TITLE ESTs | | | gi = 2965772 | 597838 |
| IC07103 | 00/04/26 UG#76 17Lid Expansion | EST | Mm. 28243 | ESTs | — | | gi = 7064017 | 1277326 |
| IC07104 | UG75 Expression | EST | Mm. 28244 | TITLE ESTs | | | gi = 1861757 | 1246994 |
| IC07105 | UG75 Expression | EST | Mm. 28245 | TITLE ESTs | | | gi = 1759571 | 638391 |
| IC07106 | UG75 Expression | EST | Mm. 28246 | TITLE ESTs, Weakly similar to envelope polyprotein [*M. musculus*] | | | gi = 4060542 | 749305 |
| IC07107 | UG75 Expression | EST | Mm. 28249 | TITLE ESTs | | | gi = 1676358 | 573482 |
| IC07108 | UG75 Expression | EST | Mm. 28251 | TITLE ESTs | | | gi = 3718735 | 958879 |
| IC07109 | UG75 Expression | EST | Mm. 28254 | TITLE ESTs | | | gi = 3981210 | 1310873 |
| IC07110 | UG75 Expression | EST | Mm. 28256 | TITLE ESTs | | | gi = 2068659 | 533536 |
| IC07111 | UG75 Expression | EST | Mm. 28257 | TITLE ESTs | | | gi = 3371311 | 550906 |
| IC07112 | UG75 Expression | EST | Mm. 28258 | TITLE ESTs, Moderately similar to HYPOTHETICAL 16.7 KD PROTEIN MRP17-MET14 INTERGENIC REGION [*Saccharomyces cerevisiae*] | | | gi = 5598875 | 1362573 |
| IC07113 | UG75 Expression | EST | Mm. 28259 | TITLE ESTs, Moderately similar to acid 82 kDa protein [*H. sapiens*] | | | gi = 5549552 | 1312927 |
| IC07114 | UG75 Expression | EST | Mm. 28260 | TITLE ESTs | | | gi = 2292448 | 1429437 |
| IC07115 | UG75 Expression | EST | Mm. 28268 | TITLE ESTs, Moderately similar to KIAA0648 protein [*H. sapiens*] | | | gi = 4032061 | 618576 |
| IC07116 | UG75 Expression | EST | Mm. 28269 | TITLE ESTs | | | gi = 3602568 | 643813 |
| IC07117 | UG75 Expression | EST | Mm. 28270 | TITLE ESTs, Weakly similar to transforming protein myb [*M. musculus*] | | | gi = 6076991 | 534196 |
| IC07118 | UG75 Expression | EST | Mm. 28271 | TITLE ESTs | | | gi = 3393763 | 621813 |
| IC07119 | UG75 Expression | EST | Mm. 28277 | TITLE ESTs | | | gi = 1808237 | 1002542 |
| IC07120 | UG75 Expression | EST | Mm. 28279 | TITLE ESTs | | | gi = 3054773 | 1327893 |
| IC07121 | UG75 Expression | EST | Mm. 28281 | TITLE ESTs | | | gi = 2915293 | 523183 |
| IC07122 | UG75 Expression | EST | Mm. 28282 | TITLE ESTs | | | gi = 3602325 | 1264659 |
| IC07123 | UG75 Expression | EST | Mm. 28283 | TITLE ESTs | | | gi = 3167687 | 641902 |
| IC07124 | UG75 Expression | EST | Mm. 28285 | TITLE ESTs, Weakly similar to Weak similarity in middle of protein to HIV-1 TAT protein [*S. cerevisiae*] | | | gi = 3373034 | 1293674 |
| IC07125 | UG75 Expression | EST | Mm. 28286 | TITLE ESTs | | | gi = 1843062 | 576509 |
| IC07126 | UG75 Expression | EST | Mm. 28287 | TITLE ESTs, Weakly similar to hepatoma-derived growth factor [*M. musculus*] | | | gi = 3370192 | 621280 |
| IC07127 | UG75 Expression | EST | Mm. 28288 | TITLE ESTs | | | gi = 4316044 | 1002252 |
| IC07128 | UG75 Expression | EST | Mm. 28289 | TITLE ESTs | | | gi = 3164964 | 972487 |
| IC07129 | UG75 Expression | EST | Mm. 2829 | TITLE ESTs | | | gi = 4617264 | 722450 |
| IC07130 | UG75 Expression | EST | Mm. 28290 | TITLE ESTs | | | gi = 2962642 | 635073 |
| IC07131 | UG75 Expression | EST | Mm. 28291 | TITLE ESTs, Weakly similar to PBK1 protein [*H. sapiens*] | | | gi = 3163866 | 550881 |
| IC07132 | UG75 Expression | EST | Mm. 28292 | TITLE ESTs | | | gi = 2693191 | 551369 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07133 | UG75 Expression | EST | Mm. 28294 | TITLE ESTs, Weakly similar to PROBABLE G PROTEIN-COUPLED RECEPTOR G10D [*M. musculus*] | | | gi = 4029885 | 1002127 |
| IC07134 | UG75 Expression | EST | Mm. 28297 | TITLE ESTs | | | gi = 2039551 | 760716 |
| IC07135 | UG75 Expression | EST | Mm. 2830 | TITLE ESTs, Weakly similar to PROBABLE ATP-DEPENDENT RNA HELICASE HRH1 [*H. sapiens*] | | | gi = 3885265 | 637580 |
| IC07136 | UG75 Expression | EST | Mm. 28300 | TITLE ESTs | | | gi = 5909262 | 1749267 |
| IC07137 | UG75 Expression | EST | Mm. 28302 | TITLE ESTs, Weakly similar to R33590_1 [*H. sapiens*] | | | gi = 3602681 | 718585 |
| IC07138 | UG75 Expression | EST | Mm. 28304 | TITLE ESTs | | | gi = 2273311 | 598063 |
| IC07139 | UG75 Expression | EST | Mm. 28305 | TITLE ESTs, Weakly similar to TNF-inducible protein CG12-1 [*H. sapiens*] | | | gi = 3863355 | 972757 |
| IC07140 | UG75 Expression | EST | Mm. 28306 | TITLE ESTs | | | gi = 6646240 | 596722 |
| IC07141 | UG75 Expression | EST | Mm. 28309 | TITLE ESTs | | | gi = 2456676 | 1002157 |
| IC07142 | UG75 Expression | EST | Mm. 28310 | TITLE ESTs, Weakly similar to ankyrin [*D. melanogaster*] | | | gi = 4725173 | 1281408 |
| IC07143 | UG75 Expression | EST | Mm. 28311 | TITLE ESTs | | | gi = 6646420 | 597348 |
| IC07144 | UG75 Expression | EST | Mm. 28312 | TITLE ESTs | | | gi = 1282677 | 1193472 |
| IC07145 | UG75 Expression | EST | Mm. 28315 | TITLE ESTs, Weakly similar to SWI/SNF complex 60 KDa subunit [*M. musculus*] | | | gi = 2462041 | 1281359 |
| IC07146 | UG75 Expression | EST | Mm. 28316 | TITLE ESTs, Weakly similar to HYPOTHETICAL 36.7 KD PROTEIN C2F7.02C IN CHROMOSOME I [*Schizosaccharomyces pombe*] | | | gi = 3053928 | 752471 |
| IC07147 | UG75 Expression | EST | Mm. 28318 | TITLE ESTs | | | gi = 4720714 | 1264038 |
| IC07148 | UG75 Expression | EST | Mm. 28319 | TITLE ESTs | | | gi = 2989123 | 1265145 |
| IC07149 | UG75 Expression | EST | Mm. 28321 | TITLE ESTs | | | gi = 2646198 | 533914 |
| IC07150 | UG75 Expression | EST | Mm. 28323 | TITLE ESTs | | | gi = 1910222 | 894288 |
| IC07151 | UG75 Expression | EST | Mm. 28324 | TITLE ESTs | | | gi = 1811331 | 598173 |
| IC07152 | UG75 Expression | EST | Mm. 28325 | TITLE ESTs | | | gi = 1767793 | 622636 |
| IC07153 | UG75 Expression | EST | Mm. 2833 | TITLE ESTs | | | gi = 1759068 | 622437 |
| IC07154 | UG75 Expression | EST | Mm. 28330 | TITLE ESTs, Weakly similar to heat shock protein hsp40-3 [*M. musculus*] | | | gi = 3720974 | 1296227 |
| IC07155 | UG75 Expression | EST | Mm. 28331 | TITLE ESTs, Weakly similar to BLu protein testis isoform [*H. sapiens*] | | | gi = 2990681 | 1225083 |
| IC07156 | UG75 Expression | EST | Mm. 28332 | TITLE DNA segment, Chr 1, University of California at Los Angeles 4 | GENE D1Ucla4 | | gi = 2262742 | 1002341 |
| IC07157 | UG75 Expression | EST | Mm. 28333 | TITLE ESTs | | | | 722284 |
| IC07158 | UG75 Expression | EST | Mm. 28334 | TITLE ESTs | | | gi = 2646452 | 1225066 |
| IC07159 | UG75 Expression | EST | Mm. 28338 | TITLE ESTs, Moderately similar to 62D9.o [*D. melanogaster*] | | | gi = 5905442 | 1280056 |
| IC07160 | UG75 Expression | EST | Mm. 28339 | TITLE ESTs | | | gi = 6085449 | 959448 |
| IC07161 | UG75 Expression | EST | Mm. 28342 | TITLE ESTs | | | gi = 4615401 | 1278738 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07162 | UG75 Expression | EST | Mm. 28344 | TITLE ESTs, Moderately similar to rab3-GAP regulatory domain [H. sapiens] | | | gi = 2919953 | 1295447 |
| IC07163 | UG75 Expression | EST | Mm. 28348 | TITLE ESTs [D. melanogaster] | | | gi = 4729724 | 1279752 |
| IC07164 | UG75 Expression | EST | Mm. 28350 | TITLE ESTs | | | gi = 5336318 | 582204 |
| IC07165 | UG75 Expression | EST | Mm. 28351 | TITLE ESTs | | | gi = 6518289 | 1295135 |
| IC07166 | UG75 Expression | EST | Mm. 28352 | TITLE ESTs | | | gi = 6168116 | 1148752 |
| IC07167 | UG75 Expression | EST | Mm. 28354 | TITLE ESTs, Weakly similar to cDNA EST yk428d5.3 comes from this gene [C. elegans] | | | gi = 3376980 | 622280 |
| IC07168 | UG75 Expression | EST | Mm. 28355 | TITLE ESTs | | | gi = 3376952 | 618558 |
| IC07169 | UG75 Expression | EST | Mm. 28358 | TITLE ESTs | | | gi = 5497884 | 764248 |
| IC07170 | UG75 Expression | EST | Mm. 28360 | TITLE ESTs, Weakly similar to coded for by C. elegans cDNA CEESW58F [C. elegans] | | | gi = 4768146 | 622805 |
| IC07171 | UG75 Expression | EST | Mm. 28362 | TITLE ESTs | | | gi = 2517908 | 634978 |
| IC07172 | UG75 Expression | EST | Mm. 28364 | TITLE ESTs | | | gi = 4315258 | 1446770 |
| IC07173 | UG75 Expression | EST | Mm. 28367 | TITLE ESTs, Weakly similar to ZIP-kinase [M. musculus] | | | gi = 2643444 | 1328262 |
| IC07174 | UG75 Expression | EST | Mm. 28370 | TITLE ESTs | | | gi = 1680991 | 619651 |
| IC07175 | UG75 Expression | EST | Mm. 28371 | TITLE ESTs, Weakly similar to KIAA0759 protein [H. sapiens] | | | gi = 2894073 | 1296062 |
| IC07176 | UG75 Expression | EST | Mm. 28374 | TITLE ESTs | | | gi = 3259409 | 620408 |
| IC07177 | UG75 Expression | EST | Mm. 28376 | TITLE ESTs | | | gi = 3978658 | 621391 |
| IC07178 | UG75 Expression | EST | Mm. 28378 | TITLE ESTs, Moderately similar to CYANELLE 30S RIBOSOMAL PROTEIN S11 [Cyanophora paradoxa] | | | gi = 2305604 | 635883 |
| IC07179 | UG75 Expression | EST | Mm. 28379 | TITLE nucleoprotein 50 | GENE Nup50 | Npap60\|nuclear pore associated protein 60 kDa| | gi = 3299440 | 550980 |
| IC07180 | UG75 Expression | EST | Mm. 28380 | TITLE ESTs | | | gi = 2857838 | 638441 |
| IC07181 | UG75 Expression | EST | Mm. 28389 | TITLE ESTs, Weakly similar to KIAA0685 protein [H. sapiens] | | | gi = 4968300 | 972987 |
| IC07182 | UG75 Expression | EST | Mm. 28391 | TITLE ESTs | | | gi = 2521146 | 1148973 |
| IC07183 | UG75 Expression | EST | Mm. 28395 | TITLE ESTs | | | gi = 2858901 | 973126 |
| IC07184 | UG75 Expression | EST | Mm. 28399 | TITLE ESTs, Weakly similar to hypothetical protein [H. sapiens] | | | gi = 3376140 | 764698 |
| IC07185 | UG75 Expression | EST | Mm. 28400 | TITLE ESTs, Weakly similar to cDNA EST EMBL:T00743 comes from this gene [C. elegans] | | | gi = 2346585 | 534070 |
| IC07186 | UG75 Expression | EST | Mm. 28402 | TITLE ESTs, Weakly similar to KIAA0280 [H. sapiens] | | | gi = 1908368 | 894161 |
| IC07187 | UG75 Expression | EST | Mm. 28406 | TITLE ESTs, Moderately similar to similar to UNC-93 [H. sapiens] | | | gi = 2860449 | 637291 |
| IC07188 | UG75 Expression | EST | Mm. 28409 | TITLE ESTs | | | gi = 1325425 | 1346018 |
| IC07189 | UG75 Expression | EST | Mm. 2841 | TITLE ESTs | | | gi = 6078262 | 722778 |
| IC07190 | UG75 Expression | EST | Mm. 28410 | TITLE ESTs | | | gi = 2292444 | 620067 |
| IC07191 | UG75 Expression | EST | Mm. 28411 | TITLE ESTs | | | gi = 2857406 | 1279701 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07192 | UG75 Expression | EST | Mm. 28412 | TITLE ESTs, Weakly similar to unknown [*S. cerevisiae*] | | | gi = 2519698 | 1020904 |
| IC07193 | UG75 Expression | EST | Mm. 28413 | TITLE ESTs, Moderately similar to unknown [*H. sapiens*] | | | gi = 3066455 | 619951 |
| IC07194 | UG75 Expression | EST | Mm. 28414 | TITLE ESTs, Weakly similar to female sterile homeotic-related protein Frg-1 [*M. musculus*] | | | gi = 3520065 | 636988 |
| IC07195 | UG75 Expression | EST | Mm. 28418 | TITLE ESTs | | | gi = 2283293 | 1140289 |
| IC07196 | UG75 Expression | EST | Mm. 28421 | TITLE ESTs, Moderately similar to HISTONE ACETYLTRANSFERASE TYPE B CATALYTIC SUBUNIT [*H. sapiens*] | | | gi = 1700206 | 1446371 |
| IC07197 | UG75 Expression | EST | Mm. 28422 | TITLE ESTs | | | gi = 5819807 | 597351 |
| IC07198 | UG75 Expression | EST | Mm. 28424 | TITLE ESTs, Moderately similar to KIAA0978 protein [*H. sapiens*] | | | gi = 6557250 | 1225953 |
| IC07199 | UG75 Expression | EST | Mm. 28426 | TITLE ESTs | | | gi = 3371393 | 958348 |
| IC07200 | UG75 Expression | EST | Mm. 28427 | TITLE ESTs | | | gi = 2517105 | 1361905 |
| IC07201 | UG75 Expression | EST | Mm. 28428 | TITLE ESTs | | | gi = 2139579 | 749984 |
| IC07202 | UG75 Expression | EST | Mm. 28430 | TITLE ESTs, Weakly similar to ACYL-COA DEHYDROGENASE, SHORT-CHAIN SPECIFIC PRECURSOR [*M. musculus*] | | | gi = 5338430 | 1295931 |
| IC07203 | UG75 Expression | EST | Mm. 28431 | TITLE ESTs, Weakly similar to PROTEIN Q300 [*M. musculus*] | | | gi = 3376945 | 620164 |
| IC07204 | UG75 Expression | EST | Mm. 28433 | TITLE ESTs, Moderately similar to voltage-gated ca channel [*R. norvegicus*] | | | gi = 4720627 | 638593 |
| IC07205 | UG75 Expression | EST | Mm. 28435 | TITLE ESTs | | | gi = 2906922 | 390646 |
| IC07206 | UG75 Expression | EST | Mm. 28436 | TITLE ESTs, Weakly similar to KIAA0990 protein [*H. sapiens*] | | | gi = 1795141 | 972798 |
| IC07207 | UG75 Expression | EST | Mm. 28437 | TITLE ESTs, Weakly similar to PLATELET-ACTIVATING FACTOR ACETYLHYDROLASE IB ALPHA SUBUNIT [*M. musculus*] | | | gi = 3165108 | 722850 |
| IC07208 | UG75 Expression | EST | Mm. 28438 | TITLE palate, lung, and nasal epithelium expressed transcript | GENE Plunc | | gi = 3447545 | 1280083 |
| IC07209 | UG75 Expression | EST | Mm. 28439 | TITLE ESTs | | | gi = 3884972 | 1400930 |
| IC07210 | UG75 Expression | EST | Mm. 28442 | TITLE ESTs | | | gi = 4614932 | 1263595 |
| IC07211 | UG75 Expression | EST | Mm. 28443 | TITLE ESTs | | | gi = 3981022 | 1264532 |
| IC07212 | UG75 Expression | EST | Mm. 28444 | TITLE ESTs | | | gi = 4604536 | 620452 |
| IC07213 | UG75 Expression | EST | Mm. 28446 | TITLE ESTs | | | gi = 2517519 | 643088 |
| IC07214 | UG75 Expression | EST | Mm. 28449 | TITLE ESTs | | | gi = 2403417 | 598745 |
| IC07215 | UG75 Expression | EST | Mm. 28450 | TITLE DNA segment, Chr 4, Wayne State University 24, expressed | GENE D4Wsu24e | | | 721935 |
| IC07216 | UG75 Expression | EST | Mm. 28451 | TITLE ESTs | | | gi = 3720150 | 1429018 |
| IC07217 | UG75 Expression | EST | Mm. 28452 | TITLE ESTs, Weakly similar to SNAP45 subunit [*H. sapiens*] | | | gi = 2906409 | 894172 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07218 | UG75 Expression | EST | Mm. 28454 | TITLE ESTs, Weakly similar to Sen34p: tRNA splicing endo-nuclease 34 kDa subunit [S. cerevisiae] | | | gi = 1325831 | 1395603 |
| IC07219 | UG75 Expression | EST | Mm. 28455 | TITLE ESTs | | | gi = 1807676 | 718290 |
| IC07220 | UG75 Expression | EST | Mm. 28458 | TITLE ESTs | | | gi = 2520615 | 1265495 |
| IC07221 | UG75 Expression | EST | Mm. 28459 | TITLE ESTs, Moderately similar to TRANSCRIPTION FACTOR BF-1 [Rattus norvegicus] | | | gi = 2305936 | 617508 |
| IC07222 | UG75 Expression | EST | Mm. 28462 | TITLE ESTs, Weakly similar to aminopeptidase-B [R. norvegicus] | | | gi = 1553408 | 1149498 |
| IC07223 | UG75 Expression | EST | Mm. 28465 | TITLE ESTs, Moderately similar to Unknown [H. sapiens] | | | gi = 4031571 | 894238 |
| IC07224 | UG75 Expression | EST | Mm. 28467 | TITLE ESTs | | | gi = 4444312 | 1282809 |
| IC07225 | UG75 Expression | EST | Mm. 28468 | TITLE ESTs, Weakly similar to C15H9.5 [C. elegans] | | | gi = 2964897 | 621674 |
| IC07226 | UG75 Expression | EST | Mm. 28470 | TITLE ESTs, Moderately similar to R30783_1 [H. sapiens] | | | gi = 2965605 | 1294536 |
| IC07227 | UG75 Expression | EST | Mm. 28472 | TITLE ESTs | | | gi = 4616166 | 1312886 |
| IC07228 | UG75 Expression | EST | Mm. 28473 | TITLE ESTs | | | gi = 4314956 | 1295686 |
| IC07229 | UG75 Expression | EST | Mm. 28474 | TITLE ESTs | | | gi = 2885603 | 534237 |
| IC07230 | UG75 Expression | EST | Mm. 28476 | TITLE ESTs, Moderately similar to CGI-68 protein [H. sapiens] | | | gi = 3957183 | 1312677 |
| IC07231 | UG75 Expression | EST | Mm. 28478 | TITLE ESTs | | | gi = 1908862 | 638164 |
| IC07232 | UG75 Expression | EST | Mm. 2848 | TITLE ESTs | | | gi = 1889338 | 719264 |
| IC07233 | UG75 Expression | EST | Mm. 28480 | TITLE v-src suppressed transcript 1 | GENE Srcs1 | | gi = 2247858 | 1294068 |
| IC07234 | UG75 Expression | EST | Mm. 28481 | TITLE ESTs, Weakly similar to RING zinc finger protein [M. musculus] | | | gi = 3376882 | 1395626 |
| IC07235 | UG75 Expression | EST | Mm. 28482 | TITLE ESTs | | | gi = 3165268 | 764139 |
| IC07236 | UG75 Expression | EST | Mm. 28483 | TITLE ESTs | | | gi = 3373270 | 618232 |
| IC07237 | UG75 Expression | EST | Mm. 28485 | TITLE ESTs | | | gi = 1861390 | 640493 |
| IC07238 | UG75 Expression | EST | Mm. 28486 | TITLE ESTs, Moderately similar to neural plakophilin related arm-repeat protein [M. musculus] | | | gi = 2461858 | 636479 |
| IC07239 | UG75 Expression | EST | Mm. 28487 | TITLE ESTs | | | gi = 3386710 | 619386 |
| IC07240 | UG75 Expression | EST | Mm. 28488 | TITLE ESTs | | | gi = 1913454 | 1294542 |
| IC07241 | UG75 Expression | EST | Mm. 28490 | TITLE ESTs, Weakly similar to KE4 [M. musculus] | | | gi = 3957304 | 1345165 |
| IC07242 | UG75 Expression | EST | Mm. 28497 | TITLE ESTs | | | gi = 3854580 | 1329782 |
| IC07243 | UG75 Expression | EST | Mm. 28498 | TITLE ESTs, Weakly similar to T-complex-associated-testes-expressed-1 protein [M. musculus] | | | gi = 4513179 | 750706 |
| IC07244 | UG75 Expression | EST | Mm. 28499 | TITLE ESTs | | | gi = 5124749 | 596260 |
| IC07245 | UG75 Expression | EST | Mm. 28500 | TITLE ESTs | | | gi = 2891323 | 1265037 |
| IC07246 | UG75 Expression | EST | Mm. 28505 | TITLE ESTs | | | gi = 2247964 | 636940 |
| IC07247 | UG75 Expression | EST | Mm. 28507 | TITLE ESTs | | | gi = 3372546 | 574598 |
| IC07248 | UG75 Expression | EST | Mm. 28508 | TITLE ESTs | | | gi = 3979394 | 619720 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07249 | UG75 Expression | EST | Mm. 28514 | TITLE ESTs, Weakly similar to putative type III alcohol dehydrogenase [D. melanogaster] | | | gi = 6167706 | 777304 |
| IC07250 | UG75 Expression | EST | Mm. 28516 | TITLE ESTs | | | gi = 1756949 | 619618 |
| IC07251 | UG75 Expression | EST | Mm. 28517 | CONTAINING PROTEIN SRPX PRECURSOR [R. norvegicus] | | | gi = 3601925 | 1312484 |
| IC07252 | UG75 Expression | EST | Mm. 28519 | TITLE ESTs | | | gi = 2962560 | 959163 |
| IC07253 | UG75 Expression | EST | Mm. 28520 | TITLE ESTs | | | gi = 1936474 | 617161 |
| IC07254 | UG75 Expression | EST | Mm. 28522 | TITLE ESTs | | | gi = 3375320 | 1446926 |
| IC07255 | UG75 Expression | EST | Mm. 28523 | TITLE ESTs | | | gi = 1676625 | 777587 |
| IC07256 | UG75 Expression | EST | Mm. 28524 | TITLE DNA segment, Chr 6, Wayne State University 116, expressed | GENE D6Wsu116e | | | 1294541 |
| IC07257 | UG75 Expression | EST | Mm. 28525 | TITLE ESTs, Weakly similar to similar to Schizosaccharomyces pombe 4-nitrophenylphosphatase [C. elegans] | | | gi = 6084567 | 764636 |
| IC07258 | UG75 Expression | EST | Mm. 28526 | TITLE ESTs | | | gi = 1766989 | 777813 |
| IC07259 | UG75 Expression | EST | Mm. 28527 | TITLE ESTs | | | gi = 1287011 | 974002 |
| IC07260 | UG75 Expression | EST | Mm. 28528 | TITLE ESTs, Weakly similar to (defline not available 6066585) [M. musculus] | | | gi = 1294015 | 1002580 |
| IC07261 | UG75 Expression | EST | Mm. 28534 | TITLE ESTs | | | gi = 2915599 | 722923 |
| IC07262 | UG75 Expression | EST | Mm. 28535 | TITLE ESTs | | | gi = 3158847 | 644857 |
| IC07263 | UG75 Expression | EST | Mm. 28536 | TITLE ESTs, Weakly similar to predicted using Genefinder [C. elegans] | | | gi = 1497358 | 577003 |
| IC07264 | UG75 Expression | EST | Mm. 28537 | TITLE secretory carrier membrane protein 2 | GENE Scamp2 | | gi = 3718583 | 722801 |
| IC07265 | UG75 Expression | EST | Mm. 28539 | TITLE ESTs, Weakly similar to protein kinase C-binding protein RACK7 [H. sapiens] | | | gi = 1841654 | 1379006 |
| IC07266 | UG75 Expression | EST | Mm. 28541 | TITLE ESTs, Weakly similar to 1-evidence | | | gi = 1366171 | 557888 |
| IC07267 | UG75 Expression | EST | Mm. 28542 | TITLE ESTs, Weakly similar to similar to S. cerevisiae hypothetical protein YKL166 [C. elegans] | | | gi = 2262909 | 894102 |
| IC07268 | UG75 Expression | EST | Mm. 28544 | TITLE ESTs | | | gi = 5125982 | 534025 |
| IC07269 | UG75 Expression | EST | Mm. 28546 | TITLE ESTs | | | gi = 3732996 | 621787 |
| IC07270 | UG75 Expression | EST | Mm. 28549 | TITLE ESTs, Moderately similar to density-regulated protein [H. sapiens] | | | gi = 3167685 | 777427 |
| IC07271 | UG75 Expression | EST | Mm. 28550 | TITLE ESTs | | | gi = 3602357 | 777861 |
| IC07272 | UG75 Expression | EST | Mm. 28552 | TITLE ESTs, Weakly similar to N-terminal region of the protein [M. musculus] | | | gi = 4605270 | 1193535 |
| IC07273 | UG75 Expression | EST | Mm. 28555 | TITLE ESTs, Weakly similar to R01B10.5 [C. elegans] | | | gi = 2291642 | 1890220 |
| IC07274 | UG75 Expression | EST | Mm. 28557 | TITLE ESTs | | | gi = 1315971 | 775635 |
| IC07275 | UG75 Expression | EST | Mm. 28563 | TITLE ESTs | | | gi = 4783131 | 598187 |
| IC07276 | UG75 Expression | EST | Mm. 28567 | TITLE ESTs | | | gi = 4216144 | 1279539 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07277 | UG75 Expression | EST | Mm. 28577 | TITLE ESTs, Weakly similar to weak similarity to ribosomal protein L14 [C. elegans] | | | gi = 1326705 | 1225405 |
| IC07278 | UG75 Expression | EST | Mm. 28578 | TITLE ESTs, Weakly similar to Ric1 [D. melanogaster] | | | gi = 3165322 | 617718 |
| IC07279 | UG75 Expression | EST | Mm. 28579 | TITLE ESTs, Weakly similar to M01F1.6 [C. elegans] | | | gi = 1407888 | 574668 |
| IC07280 | UG75 Expression | EST | Mm. 28581 | TITLE ESTs | | | gi = 3167196 | 617754 |
| IC07281 | UG75 Expression | EST | Mm. 28586 | TITLE ESTs, Weakly similar to fos39554_1 [H. sapiens] | | | gi = 2856100 | 1295182 |
| IC07282 | UG75 Expression | EST | Mm. 28588 | TITLE ESTs | | | gi = 3067348 | 620959 |
| IC07283 | UG75 Expression | EST | Mm. 28589 | TITLE ESTs | | | gi = 3956779 | 619824 |
| IC07284 | UG75 Expression | EST | Mm. 28590 | TITLE ESTs, Weakly similar to serine/threonine kinase [M. musculus] | | | gi = 1530531 | 1193174 |
| IC07285 | UG75 Expression | EST | Mm. 29591 | SYNTHETASE PRECURSOR [Saccharomyces cerevisiae] | | | gi = 251842 | 1279127 |
| IC07286 | UG75 Expression | EST | Mm. 28594 | TITLE ESTs | | | gi = 2256146 | 717987 |
| IC07287 | UG75 Expression | EST | Mm. 28595 | TITLE ESTs, Weakly similar to HYPOTHETICAL PROTEIN KIAA0127 [H. sapiens] | | | gi = 3393444 | 893965 |
| IC07288 | UG75 Expression | EST | Mm. 28596 | TITLE ESTs | | | gi = 2917065 | 1193698 |
| IC07289 | UG75 Expression | EST | Mm. 28597 | TITLE ESTs, Weakly similar to contains similarity to G-coupled protein receptors [C. elegans] | | | gi = 4726479 | 764600 |
| IC07290 | UG75 Expression | EST | Mm. 28600 | TITLE DNA segment, Chr 13, Wayne State University 64, expressed | GENE D13Wsu64e | | | 550657 |
| IC07291 | UG75 Expression | EST | Mm. 28602 | TITLE ESTs | | | gi = 5495487 | 635017 |
| IC07292 | UG75 Expression | EST | Mm. 28604 | TITLE ESTs | | | gi = 3215577 | 616742 |
| IC07293 | UG75 Expression | EST | Mm. 28607 | TITLE ESTs, Weakly similar to HYPOTHETICAL PROTEIN KIAA0182 [H. sapiens] | | | gi = 1287276 | 642406 |
| IC07294 | UG75 Expression | EST | Mm. 28609 | TITLE ESTs | | | gi = 4616949 | 644953 |
| IC07295 | UG75 Expression | EST | Mm. 28611 | TITLE ESTs | | | gi = 3387396 | 598305 |
| IC07296 | UG75 Expression | EST | Mm. 28615 | TITLE ESTs, Moderately similar to unnamed protein product [H. sapiens] | | | gi = 3522189 | 1378352 |
| IC07297 | UG75 Expression | EST | Mm. 28616 | TITLE ESTs | | | gi = 4485345 | 1378471 |
| IC07298 | UG75 Expression | EST | Mm. 29617 | TITLE ESTs | | | gi = 2283627 | 620049 |
| IC07299 | UG75 Expression | EST | Mm. 2862 | TITLE ESTs, Weakly similar to tetracycline transporter-like protein [M. musculus] | | | gi = 3978662 | 1294575 |
| IC07300 | UG75 Expression | EST | Mm. 28622 | TITLE DNA segment, Chr 13, Wayne State University 115, expressed | GENE D13Wsu115e | | | 972913 |
| IC07301 | UG75 Expression | EST | Mm. 28623 | ESTs, Moderately similar to CALMODULIN [Electrophorus electricus] | | | gi = 3518871 | 1481164 |
| IC07302 | UG75 Expression | EST | Mm. 28624 | TITLE ESTs | | | gi = 2519289 | 636393 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07303 | UG75 Expression | EST | Mm. 28625 | TITLE ESTs, Weakly similar to (definline not available 5901818) [D. melanogaster] | | | gi = 2517533 | 893921 |
| IC07304 | UG75 Expression | EST | Mm. 28628 | TITLE ESTs | | | gi = 3164490 | 661425 |
| IC07305 | UG75 Expression | EST | Mm. 28629 | TITLE ESTs | | | gi = 3883812 | 1378856 |
| IC07306 | UG75 Expression | EST | Mm. 28631 | TITLE ESTs, Weakly similar to F29B9.1 [C. elegans] | | | gi = 374846 | 751178 |
| IC07307 | UG75 Expression | EST | Mm. 28633 | TITLE ESTs | | | gi = 2291720 | 1367290 |
| IC07308 | UG75 Expression | EST | Mm. 28634 | TITLE ESTs | | | gi = 3054765 | 622977 |
| IC07309 | UG75 Expression | EST | Mm. 28635 | TITLE ESTs | | | gi = 1841034 | 1380211 |
| IC07310 | UG75 Expression | EST | Mm. 28640 | TITLE ESTs | | | gi = 3395140 | 597274 |
| IC07311 | UG75 Expression | EST | Mm. 28642 | TITLE ESTs | | | gi = 3235959 | 619759 |
| IC07312 | UG75 Expression | EST | Mm. 28645 | TITLE ESTs | | | gi = 2349876 | 622840 |
| IC07313 | UG75 Expression | EST | Mm. 28646 | TITLE ESTs | | | gi = 6515991 | 621462 |
| IC07314 | UG75 Expression | EST | Mm. 28647 | TITLE ESTs | | | gi = 1909676 | 639426 |
| IC07315 | UG75 Expression | EST | Mm. 28651 | TITLE ESTs, Weakly similar to MBNL protein [H. sapiens] | | | gi = 5470790 | 642463 |
| IC07316 | UG75 Expression | EST | Mm. 28654 | TITLE ESTs | | | gi = 1929690 | 1296070 |
| IC07317 | UG75 Expression | EST | Mm. 28658 | TITLE ESTs | | | gi = 3602453 | 749779 |
| IC07318 | UG75 Expression | EST | Mm. 2866 | TITLE ESTs | | | gi = 6645978 | 717962 |
| IC07319 | UG75 Expression | EST | Mm. 28660 | TITLE ESTs | | | gi = 2691436 | 599223 |
| IC07320 | UG75 Expression | EST | Mm. 28661 | TITLE ESTs | | | gi = 3167851 | 597958 |
| IC07321 | UG75 Expression | EST | Mm. 28662 | TITLE ESTs | | | gi = 3067531 | 1282070 |
| IC07322 | UG75 Expression | EST | Mm. 28664 | TITLE ESTs | | | gi = 5749410 | 643290 |
| IC07323 | UG75 Expression | EST | Mm. 28665 | TITLE ESTs, Weakly similar to HYPOTHETICAL 91.2 KD PROTEIN IN RPS7A-SCH9 INTERGENIC REGION [Saccharomyces cerevisiae] | | | gi = 4061783 | 1295270 |
| IC07324 | UG75 Expression | EST | Mm. 28674 | TITLE ESTs, Moderately similar to erythroid differentiation regulator [M. musculus] | | | gi = 2519270 | 1148549 |
| IC07325 | UG75 Expression | EST | Mm. 28676 | TITLE ESTs | | | gi = 1838439 | 596752 |
| IC07326 | UG75 Expression | EST | Mm. 28677 | TITLE ESTs | | | gi = 6168157 | 622722 |
| IC07327 | UG75 Expression | EST | Mm. 28679 | TITLE ESTs, Weakly similar to F42A6.6 [C. elegans] | | | gi = 5550507 | 1749060 |
| IC07328 | UG75 Expression | EST | Mm. 28681 | TITLE ESTs, Moderately similar to OOCYTE ZINC FINGER PROTEIN XLCOF7.1 [Xenopus laevis] | | | gi = 4061307 | 1749841 |
| IC07329 | UG75 Expression | EST | Mm. 28683 | TITLE ESTs | | | gi = 6520981 | 1294683 |
| IC07330 | UG75 Expression | EST | Mm. 28686 | TITLE ESTs | | | gi = 1769365 | 719142 |
| IC07331 | UG75 Expression | EST | Mm. 28689 | TITLE transforming growth factor beta regulated gene 1 | GENE Tbrg1 | TB-5] | gi = 1702107 | 550922 |
| IC07332 | UG75 Expression | EST | Mm. 2869 | TITLE ESTs | | | gi = 1654915 | 718262 |
| IC07333 | UG75 Expression | EST | Mm. 28690 | TITLE ESTs | | | gi = 2288620 | 1749700 |
| IC07334 | UG75 Expression | EST | Mm. 28691 | TITLE ESTs | | | gi = 3296153 | 1294304 |

US 6,706,867 B1

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07335 | UG75 Expression | EST | Mm. 28694 | TITLE ESTs, Moderately similar to HYPOTHETICAL 9.3 KD PROTEIN ZK652.1 IN CHROMOSOME III [Caenorhabditis elegans] | | | gi = 2258890 | 598346 |
| IC07336 | UG75 Expression | EST | Mm. 28695 | TITLE ESTs, Moderately similar to mutY homolog [H. sapiens] | | | gi = 3297355 | 1380122 |
| IC07337 | UG75 Expression | EST | Mm. 28697 | TITLE ESTs | | | gi = 2284086 | 619446 |
| IC07338 | UG75 Expression | EST | Mm. 28698 | TITLE ESTs | | | gi = 1842891 | 1278832 |
| IC07339 | UG75 Expression | EST | Mm. 28701 | TITLE ESTs | | | gi = 1714523 | 597152 |
| IC07340 | UG75 Expression | EST | Mm. 28702 | TITLE ESTs | | | gi = 3159004 | 639035 |
| IC07341 | UG75 Expression | EST | Mm. 28703 | TITLE ESTs, Weakly similar to KIAA0966 protein [H. sapiens] | | | gi = 2918221 | 638156 |
| IC07342 | UG75 Expression | EST | Mm. 28707 | TITLE ESTs | | | gi = 4281662 | 764581 |
| IC07343 | UG75 Expression | EST | Mm. 28708 | TITLE ESTs | | | gi = 6757076 | 973437 |
| IC07344 | UG75 Expression | EST | Mm. 28709 | TITLE DNA segment, Chr 11, Wayne State University 78, expressed | GENE D11Wsu78e | | | 597565 |
| IC07345 | UG75 Expression | EST | Mm. 2871 | TITLE ESTs | | | gi = 1895407 | 718299 |
| IC07346 | UG75 Expression | EST | Mm. 28714 | TITLE ESTs, Weakly similar to endophilin II [M. musculus] | | | gi = 2406405 | 1312393 |
| IC07347 | UG75 Expression | EST | Mm. 28717 | TITLE ESTs, Weakly similar to cDNA EST yk282b7.5 comes from this gene [C. elegans] | | | gi = 6077077 | 599093 |
| IC07348 | UG75 Expression | EST | Mm. 28724 | TITLE ESTs | | | gi = 6749072 | 2352650 |
| IC07349 | UG75 Expression | EST | Mm. 28726 | TITLE ESTs, Weakly similar to testicular antigen [M. musculus] | | | gi = 4440662 | 1001473 |
| IC07350 | UG75 Expression | EST | Mm. 2873 | TITLE ESTs | | | gi = 1908107 | 718023 |
| IC07351 | UG75 Expression | EST | Mm. 28733 | TITLE ESTs | | | gi = 2247833 | 620644 |
| IC07352 | UG75 Expression | EST | Mm. 28738 | TITLE ESTs, Weakly similar to F25B5.3 [C. elegans] | | | gi = 1554155 | 749928 |
| IC07353 | UG75 Expression | EST | Mm. 28742 | TITLE ESTs, Weakly similar to HYPOTHETICAL 86.9 KD PROTEIN ZK945.3 IN CHROMOSOME II [Caenorhabditis elegans] | | | gi = 4029976 | 1149037 |
| IC07354 | UG75 Expression | EST | Mm. 28744 | TITLE ESTs | | | gi = 3376120 | 635025 |
| IC07355 | UG75 Expression | EST | Mm. 28745 | TITLE ESTs | | | gi = 1541908 | 974037 |
| IC07356 | UG75 Expression | EST | Mm. 2875 | TITLE ESTs, Weakly similar to BcDNA.GH11023 [D. melanogaster] | | | gi = 1309545 | 1149802 |
| IC07357 | UG75 Expression | EST | Mm. 28756 | TITLE ESTs | | | gi = 5919871 | 619348 |
| IC07358 | UG75 Expression | EST | Mm. 28757 | TITLE ESTs | | | gi = 3394672 | 620250 |
| IC07359 | UG75 Expression | EST | Mm. 28759 | TITLE ESTs | | | gi = 2906413 | 617815 |
| IC07360 | UG75 Expression | EST | Mm. 28760 | TITLE ESTs | | | gi = 1711760 | 1294806 |
| IC07361 | UG75 Expression | EST | Mm. 28765 | TITLE ESTs | | | gi = 4767412 | 777843 |
| IC07362 | UG75 Expression | EST | Mm. 28768 | TITLE ESTs, Weakly similar to (define not available 5762309) [M. musculus] | | | gi = 1759367 | 621040 |
| IC07363 | UG75 Expression | EST | Mm. 28770 | TITLE ESTs, Weakly similar to junctional adhesion molecule [H. sapiens] | | | gi = 4967331 | 598794 |
| IC07364 | UG75 Expression | EST | Mm. 28771 | | | | gi = 4276020 | 1329285 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07365 | UG75 Expression | EST | Mm. 28772 | TITLE ESTs | | | gi = 1291844 | 721515 |
| IC07366 | UG75 Expression | EST | Mm. 28773 | TITLE ESTs, Weakly similar to HYPOTHETICAL 38.5 KD PROTEIN IN SU12-TDH2 INTERGENIC REGION [Saccharomyces cerevisiae] | | | gi = 4794688 | 597416 |
| IC07367 | UG75 Expression | EST | Mm. 28774 | TITLE ESTs | | | gi = 2989099 | 764878 |
| IC07368 | UG75 Expression | EST | Mm. 28776 | TITLE ESTs, Weakly similar to HYPOTHETICAL 92.1 KD PROTEIN C24H6.03 IN CHROMOSOME I [Schizosaccharomyces pombe] | | | gi = 4061730 | 750962 |
| IC07369 | UG75 Expression | EST | Mm. 28777 | TITLE ESTs, Moderately similar to L-PLASTIN [M. musculus] | | | gi = 2855410 | 617795 |
| IC07370 | UG75 Expression | EST | Mm. 28778 | TITLE ESTs, Weakly similar to ATP-binding cassette transporter [M. musculus] | | | gi = 2518869 | 596492 |
| IC07371 | UG75 Expression | EST | Mm. 28779 | TITLE ESTs | | | gi = 2919351 | 765622 |
| IC07372 | UG75 Expression | EST | Mm. 28785 | TITLE ESTs | | | gi = 2991574 | 1329972 |
| IC07373 | UG75 Expression | EST | Mm. 28786 | TITLE DNA segment, Chr 13, Wayne State University 123, expressed | GENE D13Wsu123e | | | 1020894 |
| IC07374 | UG75 Expression | EST | Mm. 28787 | TITLE ESTs, Weakly similar to Ring3 [M. musculus] | | | gi = 6515042 | 1295116 |
| IC07375 | UG75 Expression | EST | Mm. 28790 | TITLE ESTs, Weakly similar to cleavage and polyadenylation specificity factor [M. musculus] | | | gi = 5905602 | 973359 |
| IC07376 | UG75 Expression | EST | Mm. 28792 | TITLE ESTs, Weakly similar to (define not available 5931573) [M. musculus] | | | gi = 1315625 | 619149 |
| IC07377 | UG75 Expression | EST | Mm. 28793 | TITLE ESTs | | | gi = 1505006 | 621723 |
| IC07378 | UG75 Expression | EST | Mm. 28794 | TITLE ESTs | | | gi = 2561421 | 1362663 |
| IC07379 | UG75 Expression | EST | Mm. 28795 | TITLE ESTs | | | gi = 6822498 | 721770 |
| IC07380 | UG75 Expression | EST | Mm. 28796 | TITLE ESTs | | | gi = 4513187 | 1429840 |
| IC07381 | UG75 Expression | EST | Mm. 28800 | TITLE ESTs | | | gi = 4216841 | 636697 |
| IC07382 | UG75 Expression | EST | Mm. 28804 | TITLE ESTs | | | gi = 4725785 | 749565 |
| IC07383 | UG75 Expression | EST | Mm. 28810 | TITLE ESTs | | | gi = 3720526 | 749599 |
| IC07384 | UG75 Expression | EST | Mm. 28811 | TITLE ESTs | | | gi = 3371456 | 597428 |
| IC07385 | UG75 Expression | EST | Mm. 28817 | TITLE ESTs | | | gi = 4967830 | 1378235 |
| IC07386 | UG75 Expression | EST | Mm. 28818 | TITLE ESTs | | | gi = 2306568 | 750599 |
| IC07387 | UG75 Expression | EST | Mm. 28819 | TITLE ESTs | | | gi = 1660328 | 1294833 |
| IC07388 | UG75 Expression | EST | Mm. 28824 | TITLE ESTs | | | gi = 3864110 | 599301 |
| IC07389 | UG75 Expression | EST | Mm. 28825 | TITLE ESTs | | | gi = 2520743 | 717636 |
| IC07390 | UG75 Expression | EST | Mm. 28828 | TITLE ESTs | | | gi = 5492134 | 777237 |
| IC07391 | UG75 Expression | EST | Mm. 28829 | TITLE ESTs, Moderately similar to KIAA0923 protein [H. sapiens] | | | gi = 4967530 | 1367225 |
| IC07392 | UG75 Expression | EST | Mm. 2883 | TITLE ESTs | | | gi = 3517811 | 1395594 |
| IC07393 | UG75 Expression | EST | Mm. 28831 | TITLE ESTs | | | gi = 2461345 | 718996 |
| IC07394 | UG75 Expression | EST | Mm. 28832 | TITLE ESTs | | | gi = 1795085 | 638826 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07395 | UG75 Expression | EST | Mm. 28833 | TITLE ESTs, Weakly similar to PROLINE-RICH PROTEIN MP-3 [M. musculus] | | | gi = 4450465 | 642899 |
| IC07396 | UG75 Expression | EST | Mm. 28834 | TITLE ESTs, Moderately similar to cysteine-rich protein [H. sapiens] | | | gi = 3371376 | 765558 |
| IC07397 | UG75 Expression | EST | Mm. 28835 | TITLE tumor necrosis factor (ligand) superfamily, member 13b | GENE Tnfsf13b | BAFF| | gi = 291844 | 722549 |
| IC07398 | UG75 Expression | EST | Mm. 28836 | TITLE ESTs, Weakly similar to PTPL-1 associated RhoGAP [H. sapiens] | | | gi = 3954037 | 622214 |
| IC07399 | UG75 Expression | EST | Mm. 28837 | TITLE ESTs, Weakly similar to CELL DIVISION PROTEIN KINASE 8 [Homo sapiens] | | | gi = 2282666 | 621604 |
| IC07400 | UG75 Expression | EST | Mm. 28838 | TITLE ESTs, Moderately similar to KIAA0922 protein [H. sapiens] | | | gi = 1853666 | 751721 |
| IC07401 | UG75 Expression | EST | Mm. 28839 | TITLE ESTs, Moderately similar to HYPOTHETICAL 34.1 KD PROTEIN ZK1098.4 IN CHROMOSOME III [Caenorhabditis elegans] | | | gi = 4374954 | 972514 |
| IC07402 | UG75 Expression | EST | Mm. 28840 | TITLE ESTs | | | gi = 4767496 | 959062 |
| IC07403 | UG75 Expression | EST | Mm. 28843 | TITLE ESTs, Weakly similar to R33423_1 [H. sapiens] | | | gi = 6076645 | 550758 |
| IC07404 | UG75 Expression | EST | Mm. 28844 | TITLE ESTs | | | gi = 2643042 | 617182 |
| IC07405 | UG75 Expression | EST | Mm. 28846 | TITLE ESTs | | | gi = 6008854 | 1294590 |
| IC07406 | UG75 Expression | EST | Mm. 28847 | TITLE ESTs | | | gi = 3387303 | 1446298 |
| IC07407 | UG75 Expression | EST | Mm. 28849 | TITLE ESTs, Weakly similar to skm-BOP2 [M. musculus] | | | gi = 2643856 | 718416 |
| IC07408 | UG75 Expression | EST | Mm. 28851 | TITLE ESTs, Weakly similar to ZnT4 [M. musculus] | | | gi = 3371729 | 1294478 |
| IC07409 | UG75 Expression | EST | Mm. 28853 | TITLE ESTs, Moderately similar to PUTATIVE SURFACE GLYCO-PROTEIN C21ORF1 PRECURSOR [H. sapiens] | | | gi = 5124725 | 973304 |
| IC07410 | UG75 Expression | EST | Mm. 28855 | TITLE ESTs, Weakly similar to hypothetical protein [M. musculus] | | | gi = 2504513 | 1296157 |
| IC07411 | UG75 Expression | EST | Mm. 28857 | TITLE ESTs | | | gi = 3749926 | 550616 |
| IC07412 | UG75 Expression | EST | Mm. 28858 | TITLE ESTs | | | gi = 2282726 | 1295211 |
| IC07413 | UG75 Expression | EST | Mm. 28859 | TITLE ESTs | | | gi = 3982383 | 1429320 |
| IC07414 | UG75 Expression | EST | Mm. 28861 | TITLE ESTs | | | gi = 3718721 | 619646 |
| IC07415 | UG75 Expression | EST | Mm. 28862 | TITLE ESTs, Moderately similar to similar to mouse CC1. [H. sapiens] | | | gi = 4405237 | 972758 |
| IC07416 | UG75 Expression | EST | Mm. 28865 | TITLE ESTs | | | gi = 7197767 | 1429198 |
| IC07417 | UG75 Expression | EST | Mm. 28869 | TITLE ESTs | | | gi = 5338217 | 721432 |
| IC07418 | UG75 Expression | EST | Mm. 28870 | TITLE ESTs | | | gi = 2284353 | 958611 |
| IC07419 | UG75 Expression | EST | Mm. 28871 | TITLE ESTs | | | gi = 3294705 | 616809 |
| IC07420 | UG75 Expression | EST | Mm. 28875 | TITLE ESTs, Moderately similar to BETA GALACTOSIDASE-RELATED PROTEIN PRECURSOR [Homo sapiens] | | | gi = 5905449 | 644906 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07421 | UG75 Expression | EST | Mm. 28876 | TITLE ESTs, Moderately similar to tetraspan TM4SF [H. sapiens] | | | gi = 2519362 | 619290 |
| IC07422 | UG75 Expression | EST | Mm. 28878 | TITLE ESTs | | | gi = 5496310 | 720944 |
| IC07423 | UG75 Expression | EST | Mm. 28879 | TITLE ESTs | | | gi = 3682655 | 1278910 |
| IC07424 | UG75 Expression | EST | Mm. 28882 | TITLE ESTs, Moderately similar to ELONGATION FACTOR 1-ALPHA [Trichoderma reesei] | | | gi = 1297793 | 720984 |
| IC07425 | UG75 Expression | EST | Mm. 28885 | TITLE ESTs | | | gi = 1677293 | 637001 |
| IC07426 | UG75 Expression | EST | Mm. 28887 | TITLE ESTs | | | gi = 3369962 | 619978 |
| IC07427 | UG75 Expression | EST | Mm. 28890 | TITLE ESTs, Weakly similar to acid ceramidase [M. musculus] | | | gi = 2906949 | 618362 |
| IC07428 | UG75 Expression | EST | Mm. 28891 | TITLE ESTs | | | gi = 3683326 | 622071 |
| IC07429 | UG75 Expression | EST | Mm. 28892 | TITLE ESTs | | | gi = 2306519 | 1311333 |
| IC07430 | UG75 Expression | EST | Mm. 28893 | TITLE ESTs | | | gi = 1294212 | 1295089 |
| IC07431 | UG75 Expression | EST | Mm. 28894 | TITLE DNA segment, Chr 12, Wayne State University 118, expressed | GENE D12Wsu118e | | | 894417 |
| IC07432 | UG75 Expression | EST | Mm. 28895 | TITLE ESTs | | | gi = 7200019 | 1002376 |
| IC07433 | UG75 Expression | EST | Mm. 28899 | TITLE ESTs | | | gi = 2920004 | 619602 |
| IC07434 | UG75 Expression | EST | Mm. 28900 | TITLE ESTs | | | gi = 1309758 | 639193 |
| IC07435 | UG75 Expression | EST | Mm. 28901 | TITLE ESTs | | | gi = 6084877 | 622219 |
| IC07436 | UG75 Expression | EST | Mm. 28902 | TITLE ESTs | | | gi = 3956796 | 1749776 |
| IC07437 | UG75 Expression | EST | Mm. 28907 | TITLE ESTs | | | gi = 2305926 | 750999 |
| IC07438 | UG75 Expression | EST | Mm. 28910 | TITLE ESTs, Moderately similar to CCR4-ASSOCIATED FACTOR 1 [M. musculus] | | | gi = 2282809 | 1295128 |
| IC07439 | UG75 Expression | EST | Mm. 28912 | TITLE ESTs, Moderately similar to PEROXISOMAL MEMBRANE PROTEIN PEX13 [H. sapiens] | | | gi = 5336944 | 619474 |
| IC07440 | UG75 Expression | EST | Mm. 28916 | TITLE ESTs, Weakly similar to similarity to yeast UTR3 protein [C. elegans] | | | gi = 2755760 | 1263478 |
| IC07441 | UG75 Expression | EST | Mm. 28917 | TITLE ESTs | | | gi = 4258665 | 718257 |
| IC07442 | UG75 Expression | EST | Mm. 28918 | TITLE ESTs | | | gi = 2854711 | 596579 |
| IC07443 | UG75 Expression | EST | Mm. 28920 | TITLE ESTs | | | gi = 2521696 | 622795 |
| IC07444 | UG75 Expression | EST | Mm. 28922 | TITLE phenylalanine tRNA synthetase alpha | GENE Farsa-pe | PheRS alpha | gi = 1309248 | 622095 |
| IC07445 | UG75 Expression | EST | Mm. 28924 | TITLE ESTs | | | gi = 1316791 | 641852 |
| IC07446 | UG75 Expression | EST | Mm. 28925 | TITLE ESTs | | | gi = 6084807 | 1312500 |
| IC07447 | UG75 Expression | EST | Mm. 28927 | protein | | | gi = 4967952 | 958744 |
| IC07448 | UG75 Expression | EST | Mm. 28928 | TITLE ESTs | | | gi = 4030393 | 597321 |
| IC07449 | UG75 Expression | EST | Mm. 28930 | TITLE ESTs | | | gi = 3394078 | 620933 |
| IC07450 | UG75 Expression | EST | Mm. 28932 | TITLE ESTs | | | gi = 2516559 | 718401 |
| IC07451 | UG75 Expression | EST | Mm. 28933 | TITLE ESTs, Moderately similar to damage-specific DNA binding protein 2 [H. sapiens] | | | gi = 3685053 | 1493929 |
| IC07452 | UG75 Expression | EST | Mm. 28934 | TITLE ESTs | | | gi = 2140348 | 819020 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07453 | UG75 Expression | EST | Mm. 28936 | TITLE ESTs, Weakly similar to CARG-BINDING FACTOR A [*M. musculus*] | | | gi = 1919400 | 551085 |
| IC07454 | UG75 Expression | EST | Mm. 28941 | TITLE ESTs, Moderately similar to YPT1-RELATED PROTEIN 1 [*Schizosaccharomyces pombe*] | | | gi = 4536904 | 551092 |
| IC07455 | UG75 Expression | EST | Mm. 28942 | TITLE ESTs, Moderately similar to KIAA0564 protein [*H. sapiens*] | | | gi = 5749964 | 1294252 |
| IC07456 | UG75 Expression | EST | Mm. 28943 | TITLE ESTs | | | gi = 6558292 | 634517 |
| IC07457 | UG75 Expression | EST | Mm. 28944 | TITLE ESTs, Weakly similar to similar to kinesin-like protein [*C. elegans*] | | | gi = 3294717 | 533848 |
| IC07458 | UG75 Expression | EST | Mm. 28945 | TITLE ESTs | | | gi = 3067199 | 598820 |
| IC07459 | UG75 Expression | EST | Mm. 28947 | TITLE ESTs | | | gi = 2503260 | 1327570 |
| IC07460 | UG75 Expression | EST | Mm. 28948 | TITLE ESTs | | | gi = 6632382 | 598067 |
| IC07461 | UG75 Expression | EST | Mm. 28949 | TITLE ESTs | | | gi = 2520542 | 764919 |
| IC07462 | UG75 Expression | EST | Mm. 2895 | TITLE DNA segment, Chr 13, Wayne State University 50, expressed | GENE D13Wsu50e | | | 643422 |
| IC07463 | UG75 Expression | EST | Mm. 28950 | TITLE ESTs, Weakly similar to PUTATIVE ACID PHOSPHATASE F26C11.1 [*Caenorhabditis elegans*] | | | gi = 6517570 | 534227 |
| IC07464 | UG75 Expression | EST | Mm. 28951 | TITLE ESTs, Moderately similar to (defline not available 5733814) [*M. musculus*] | | | gi = 1909815 | 1429605 |
| IC07465 | UG75 Expression | EST | Mm. 28954 | TITLE ESTs | | | gi = 1827343 | 1429686 |
| IC07466 | UG75 Expression | EST | Mm. 28955 | TITLE ESTs | | | gi = 6083909 | 533707 |
| IC07467 | UG75 Expression | EST | Mm. 28956 | TITLE ESTs | | | gi = 5336716 | 1278936 |
| IC07468 | UG75 Expression | EST | Mm. 28957 | TITLE ESTs, Weakly similar to Pelle associated protein Pellino [*D. melanogaster*] | | | gi = 1662886 | 1149069 |
| IC07469 | UG75 Expression | EST | Mm. 28960 | TITLE ESTs | | | gi = 2334590 | 618644 |
| IC07470 | UG75 Expression | EST | Mm. 28963 | TITLE ESTs | | | gi = 3692255 | 574216 |
| IC07471 | UG75 Expression | EST | Mm. 28964 | TITLE ESTs, Weakly similar to CELL SURFACE ANTIGEN 114/A10 PRECURSOR [*M. musculus*] | | | gi = 2307905 | 764723 |
| IC07472 | UG75 Expression | EST | Mm. 28966 | TITLE ESTs, Weakly similar to transcription factor C1 [*M. musculus*] | | | gi = 3375422 | 718452 |
| IC07473 | UG75 Expression | EST | Mm. 28967 | TITLE ESTs | | | gi = 3686538 | 1447048 |
| IC07474 | UG75 Expression | EST | Mm. 28968 | TITLE ESTs, Weakly similar to rbm3 [*M. musculus*] | | | gi = 2282795 | 551053 |
| IC07475 | UG75 Expression | EST | Mm. 28972 | TITLE ESTs | | | gi = 5191621 | 1020566 |
| IC07476 | UG75 Expression | EST | Mm. 28975 | TITLE ESTs, Weakly similar to CLEAVAGE STIMULATION FACTOR, 50 KD SUBUNIT [*H. sapiens*] | | | gi = 3718540 | 551597 |
| IC07477 | UG75 Expression | EST | Mm. 28978 | TITLE ESTs | | | gi = 5475580 | 638302 |
| IC07478 | UG75 Expression | EST | Mm. 28980 | TITLE ESTs | | | gi = 2915875 | 765205 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07479 | UG75 Expression | EST | Mm. 28981 | TITLE ESTs, Moderately similar to COATOMER DELTA SUBUNIT [Homo sapiens] | | | gi = 3718596 | 635253 |
| IC07480 | UG75 Expression | EST | Mm. 28982 | TITLE ESTs | | | gi = 2516565 | 751892 |
| IC07481 | UG75 Expression | EST | Mm. 28983 | TITLE ESTs | | | gi = 3216792 | 618338 |
| IC07482 | UG75 Expression | EST | Mm. 28984 | TITLE DNA segment, Chr 10, Johns Hopkins University 81 expressed | GENE D10Jhu81e | | | 1445826 |
| IC07483 | UG75 Expression | EST | Mm. 28988 | TITLE ESTs, Moderately similar to CGI-105 protein [H. sapiens] | | | gi = 5905369 | 551458 |
| IC07484 | UG75 Expression | EST | Mm. 28989 | TITLE ESTs | | | gi = 4060451 | 598681 |
| IC07485 | UG75 Expression | EST | Mm. 28991 | TITLE ESTs, Weakly similar to Similarity to Yeast hopothetical 65.2 KD protein [C. elegans] | | | gi = 3296879 | 618063 |
| IC07486 | UG75 Expression | EST | Mm. 28993 | TITLE ESTs | | | gi = 1673234 | 1226365 |
| IC07487 | UG75 Expression | EST | Mm. 28995 | TITLE ESTs, Weakly similar to (define not available 5823131) [M. musculus] | | | gi = 3685608 | 1139895 |
| IC07488 | UG75 Expression | EST | Mm. 28999 | TITLE ESTs | | | gi = 1476417 | 1149160 |
| IC07489 | UG75 Expression | EST | Mm. 29005 | TITLE ESTs | | | gi = 3386708 | 1002659 |
| IC07490 | UG75 Expression | EST | Mm. 29006 | TITLE ESTs | | | gi = 3954673 | 637424 |
| IC07491 | UG75 Expression | EST | Mm. 29011 | TITLE ESTs | | | gi = 3864105 | 1278983 |
| IC07492 | UG75 Expression | EST | Mm. 29012 | TITLE ESTs | | | gi = 5337924 | 1293621 |
| IC07493 | UG75 Expression | EST | Mm. 29016 | TITLE ESTs | | | gi = 2257332 | 1395496 |
| IC07494 | UG75 Expression | EST | Mm. 29017 | TITLE ESTs, Weakly similar to DEOXYRIBONUCLEASE I PRECURSOR [M. musculus] | | | gi = 4405080 | 637141 |
| IC07495 | UG75 Expression | EST | Mm. 29018 | TITLE ESTs | | | gi = 1089006 | 1399133 |
| IC07496 | UG75 Expression | EST | Mm. 29019 | TITLE ESTs, Weakly similar to cDNA EST CEMSA26F comes from this gene [C. elegans] | | | gi = 6558256 | 1312855 |
| IC07497 | UG75 Expression | EST | Mm. 29021 | TITLE ESTs | | | gi = 2193134 | 618981 |
| IC07498 | UG75 Expression | EST | Mm. 29022 | TITLE ESTs | | | gi = 5498587 | 642939 |
| IC07499 | UG75 Expression | EST | Mm. 29023 | TITLE ESTs | | | gi = 2516709 | 576253 |
| IC07500 | UG75 Expression | EST | Mm. 29026 | TITLE ESTs | | | gi = 6083717 | 643668 |
| IC07501 | UG75 Expression | EST | Mm. 29028 | TITLE ESTs, Moderately similar to DEATH-ASSOCIATED PROTEIN 3 [H. sapiens] | | | gi = 3447561 | 635647 |
| IC07502 | UG75 Expression | EST | Mm. 29032 | TITLE ESTs, Weakly similar to similar to kinensin-like protein [C. elegans] | | | gi = 2730264 | 959305 |
| IC07503 | UG75 Expression | EST | Mm. 29033 | TITLE ESTs | | | gi = 4722639 | 777814 |
| IC07504 | UG75 Expression | EST | Mm. 29034 | TITLE ESTs, Moderately similar to unknown [H. sapiens] | | | gi = 1326457 | 636552 |
| IC07505 | UG75 Expression | EST | Mm. 29038 | TITLE ESTs | | | gi = 2801872 | 637250 |
| IC07506 | UG75 Expression | EST | Mm. 29041 | TITLE ESTs, Weakly similar to TRANSLATION INITIATION FACTOR EIF-2B-GAMMA SUBUNIT [Saccharomyces cerevisiae] | | | gi = 5600022 | 622050 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07507 | UG75 Expression | EST | Mm. 29042 | TITLE ESTs, Moderately similar to Unknown gene product [*H. sapiens*] | | | gi = 6517066 | 1149315 |
| IC07508 | UG75 Expression | EST | Mm. 29043 | TITLE ESTs, Weakly similar to lymphocyte specific formin related protein [*M. musculus*] | | | gi = 2181079 | 573632 |
| IC07509 | UG75 Expression | EST | Mm. 29044 | TITLE ESTs | | | gi = 3745603 | 1378100 |
| IC07510 | UG75 Expression | EST | Mm. 29046 | TITLE ESTs, Moderately similar to (define not available 5802543) [*M. musculus*] | | | gi = 3863397 | 1020574 |
| IC07511 | UG75 Expression | EST | Mm. 29047 | TITLE ESTs | | | gi = 1676831 | 616771 |
| IC07512 | UG75 Expression | EST | Mm. 29053 | TITLE ESTs | | | gi = 2920259 | 599088 |
| IC07513 | UG75 Expression | EST | Mm. 29054 | ACETYLTRANSFERASE TYPE B SUBUNIT 2 [*M. musculus*] | | | gi = 1309557 | 577944 |
| IC07514 | UG75 Expression | EST | Mm. 29056 | TITLE transforming growth factor alpha regulated gene 4 | GENE Targ4 | TA-8] | gi = 2517053 | 1001546 |
| IC07515 | UG75 Expression | EST | Mm. 29058 | TITLE ESTs | | | gi = 2518748 | 641559 |
| IC07516 | UG75 Expression | EST | Mm. 29059 | TITLE ESTs, Weakly similar to steroid dehydrogenase [*M. musculus*] | | | gi = 656248 | 972804 |
| IC07517 | UG75 Expression | EST | Mm. 29062 | TITLE ESTs | | | gi = 6518625 | 751393 |
| IC07518 | UG75 Expression | EST | Mm. 29063 | TITLE ESTs | | | gi = 2917389 | 617197 |
| IC07519 | UG75 Expression | EST | Mm. 29066 | TITLE ESTs, Moderately similar to KIAA0701 protein [*H. sapiens*] | | | gi = 3377183 | 1149134 |
| IC07520 | UG75 Expression | EST | Mm. 29067 | TITLE ESTs, Weakly similar to KIAA0681 protein [*H. sapiens*] | | | gi = 2306442 | 894361 |
| IC07521 | UG75 Expression | EST | Mm. 29068 | TITLE ESTs | | | gi = 4290179 | 576964 |
| IC07522 | UG75 Expression | EST | Mm. 29069 | TITLE ESTs | | | gi = 3371178 | 1263189 |
| IC07523 | UG75 Expression | EST | Mm. 29070 | TITLE ESTs | | | gi = 1309908 | 636115 |
| IC07524 | UG75 Expression | EST | Mm. 29072 | TITLE ESTs, Weakly similar to TYROSINE-PROTEIN KINASE JAK3 [*M. musculus*] | | | gi = 2962627 | 1265511 |
| IC07525 | UG75 Expression | EST | Mm. 29075 | TITLE ESTs, Weakly similar to NSP-like 1 [*M. musculus*] | | | gi = 6084019 | 722365 |
| IC07526 | UG75 Expression | EST | Mm. 29078 | TITLE ESTs | | | gi = 6084424 | 1002661 |
| IC07527 | UG75 Expression | EST | Mm. 29081 | TITLE ESTs | | | gi = 4605057 | 1330078 |
| IC07528 | UG75 Expression | EST | Mm. 29082 | TITLE ESTs, Weakly similar to anillin [*D. melanogaster*] | | | gi = 2518431 | 1264178 |
| IC07529 | UG75 Expression | EST | Mm. 29083 | TITLE ESTs | | | gi = 1476351 | 617577 |
| IC07530 | UG75 Expression | EST | Mm. 29090 | TITLE ESTs, Weakly similar to Ydr47wp [*S. cerevisiae*] | | | gi = 440917 | 640891 |
| IC07531 | UG75 Expression | EST | Mm. 29092 | TITLE ESTs, Weakly similar to GOLIATH PROTEIN [*Drosophila melanogaster*] | | | gi = 3718328 | 1328643 |
| IC07532 | UG75 Expression | EST | Mm. 29096 | TITLE nuclear receptor binding factor 1 | GENE Nrbf1 | | gi = 1872998 | 751945 |
| IC07533 | UG75 Expression | EST | Mm. 29098 | TITLE ESTs | | | gi = 4726811 | 1329897 |
| IC07534 | UG75 Expression | EST | Mm. 29099 | TITLE ESTs | | | gi = 2802115 | 777819 |
| IC07535 | UG75 Expression | EST | Mm. 29101 | TITLE ESTs, Weakly similar to SDP8 [*M. musculus*] | | | gi = 5125110 | 1367183 |
| IC07536 | UG75 Expression | EST | Mm. 29102 | TITLE ESTs | | | gi = 3749911 | 1225018 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07537 | UG75 Expression | EST | Mm. 29104 | TITLE ESTs, Weakly similar to cDNA EST yk292d12.3 comes from this gene [C. elegans] | | | gi = 4031934 | 637391 |
| IC07538 | UG75 Expression | EST | Mm. 29107 | TITLE ESTs | | | gi = 6168112 | 894335 |
| IC07539 | UG75 Expression | EST | Mm. 29112 | TITLE ESTs, Weakly similar to similar to S. cerevisiae gene YCR47C, putative 30.7 kd methyltransferase [C. elegans] | | | gi = 4061768 | 575074 |
| IC07540 | UG75 Expression | EST | Mm. 29113 | TITLE ESTs | | | gi = 2917070 | 764702 |
| IC07541 | UG75 Expression | EST | Mm. 29115 | TITLE ESTs | | | gi = 4274796 | 637306 |
| IC07542 | UG75 Expression | EST | Mm. 29116 | TITLE ESTs | | | gi = 2944748 | 597073 |
| IC07543 | UG75 Expression | EST | Mm. 29118 | TITLE ESTs, Weakly similar to Y25C1A.7b [C. elegans] | | | gi = 6632486 | 597663 |
| IC07544 | UG75 Expression | EST | Mm. 29120 | TITLE ESTs | | | gi = 2257314 | 718519 |
| IC07545 | UG75 Expression | EST | Mm. 29126 | TITLE ESTs | | | gi = 1793881 | 973754 |
| IC07546 | UG75 Expression | EST | Mm. 29131 | TITLE ESTs, Moderately similar to HYPOTHETICAL 63.5 KD PROTEIN ZK353.1 IN CHROMOSOME III [Caenorhabditis elegans] | | | gi = 1282690 | 558134 |
| IC07547 | UG75 Expression | EST | Mm. 29138 | TITLE ESTs, Weakly similar to (define not available 6017906) [M. musculus] | | | gi = 6074460 | 973979 |
| IC07548 | UG75 Expression | EST | Mm. 29144 | TITLE DNA segment, Chr 15, Wayne State University 59, expressed | GENE D15Wsu59e | | | 1278873 |
| IC07549 | UG75 Expression | EST | Mm. 29156 | TITLE ESTs | | | gi = 4030603 | 639438 |
| IC07550 | UG75 Expression | EST | Mm. 29159 | TITLE ESTs, Weakly similar to proline rich protein [R. norvegicus] | | | gi = 4031169 | 596388 |
| IC07551 | UG75 Expression | EST | Mm. 29162 | TITLE ESTs, Moderately similar to putative spliceosome associated protein [H. sapiens] | | | gi = 6083796 | 534162 |
| IC07552 | UG75 Expression | EST | Mm. 29164 | TITLE ESTs | | | gi = 3374324 | 721324 |
| IC07553 | UG75 Expression | EST | Mm. 29167 | TITLE ESTs | | | gi = 3692366 | 718298 |
| IC07554 | UG75 Expression | EST | Mm. 29168 | TITLE ESTs, Weakly similar to EPHRIN TYPE-A RECEPTOR 5 PRECURSOR [M. musculus] | | | gi = 3718876 | 573163 |
| IC07555 | UG75 Expression | EST | Mm. 29176 | TITLE ESTs, Moderately similar to HYPOTHETICAL TRP-ASP REPEATS CONTAINING PROTEIN IN CPR4-SOL2 INTERGENIC REGION [Saccharomyces cerevisiae] | | | gi = 5599332 | 637833 |
| IC07556 | UG75 Expression | EST | Mm. 29177 | [M. musculus] | | | gi = 5907093 | 777213 |
| IC07557 | UG75 Expression | EST | Mm. 29181 | TITLE ESTs, Moderately similar to CGI-26 protein [H. sapiens] | | | gi = 5549128 | 1264613 |
| IC07558 | UG75 Expression | EST | Mm. 29183 | TITLE ribosomal protein, mitochondrial, L14 | GENE Rpml14 | MRP-L14 | gi = 6084930 | 575640 |
| IC07559 | UG75 Expression | EST | Mm. 29184 | TITLE ESTs | | | gi = 1740054 | 598285 |
| IC07560 | UG75 Expression | EST | Mm. 29186 | TITLE ESTs, Moderately similar to SIS1 PROTEIN [Saccharomyces cerevisiae] | | | gi = 6077808 | 1139656 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07561 | UG75 Expression | EST | Mm. 29200 | TITLE ESTs, Weakly similar to HYPOTHETICAL 40.4 KD PROTEIN R06F6.5 IN CHROMOSOME II [Caenorhabditis elegans] | | | gi = 4199591 | 620079 |
| IC07562 | UG75 Expression | EST | Mm. 29202 | TITLE ESTs, Weakly similar to PHENYLALANYL-TRNA SYNTHETASE MITOCHONDRIAL PRECURSOR [Saccharomyces cerevisiae] | | | gi = 2528261 | 552225 |
| IC07563 | UG75 Expression | EST | Mm. 29206 | TITLE ESTs | | | gi = 3160441 | 335321 |
| IC07564 | UG75 Expression | EST | Mm. 29208 | TITLE DNA segment, Chr 7, Wayne State University 87, expressed | GENE D7Wsu87e | | | 1279614 |
| IC07565 | UG75 Expression | EST | Mm. 29209 | TITLE ESTs | | | gi = 5478015 | 636055 |
| IC07566 | UG75 Expression | EST | Mm. 29213 | [H. sapiens] | | | gi = 6085486 | 1225741 |
| IC07567 | UG75 Expression | EST | Mm. 29219 | TITLE ESTs | | | gi = 1676758 | 720794 |
| IC07568 | UG75 Expression | EST | Mm. 29224 | TITLE ESTs | | | gi = 1700067 | 1001891 |
| IC07569 | UG75 Expression | EST | Mm. 29230 | TITLE ESTs, Weakly similar to HYDROXYACYLGLUTATHIONE HYDROLASE [R. norvegicus] | | | gi = 1297809 | 1243679 |
| IC07570 | UG75 Expression | EST | Mm. 29234 | TITLE ESTs, Moderately similar to (define not available 5442364) [M. musculus] | | | gi = 4781802 | 1134329 |
| IC07571 | UG75 Expression | EST | Mm. 29236 | TITLE ESTs, Moderately similar to LUTHERAN BLOOD GROUP GLYCOPROTEIN PRECURSOR [H. sapiens] | | | gi = 6514641 | 598382 |
| IC07572 | UG75 Expression | EST | Mm. 29238 | TITLE ESTs | | | gi = 4217123 | 637425 |
| IC07573 | UG75 Expression | EST | Mm. 29241 | TITLE ESTs | | | gi = 3054881 | 1328110 |
| IC07574 | UG75 Expression | EST | Mm. 29242 | TITLE ESTs, Moderately similar to giantin [H. sapiens] | | | gi = 3957187 | 750728 |
| IC07575 | UG75 Expression | EST | Mm. 29243 | TITLE ESTs, Moderately similar to hypothetical protein [H. sapiens] | | | gi = 4605838 | 894522 |
| IC07576 | UG75 Expression | EST | Mm. 29245 | TITLE ESTs | | | gi = 2991840 | 1278904 |
| IC07577 | UG75 Expression | EST | Mm. 29247 | TITLE ESTs, Weakly similar to predicted using Genefinder [C. elegans] | | | gi = 2519304 | 644417 |
| IC07578 | UG75 Expression | EST | Mm. 29248 | TITLE ESTs, Weakly similar to cytosolic sorting protein PACS-1a [R. norvegicus] | | | gi = 4616472 | 619782 |
| IC07579 | UG75 Expression | EST | Mm. 29250 | TITLE ESTs | | | gi = 6748450 | 1445943 |
| IC07580 | UG75 Expression | EST | Mm. 29252 | TITLE ESTs, Weakly similar to estrogen-responsive finger protein [M. musculus] | | | gi = 4967891 | 1362415 |
| IC07581 | UG75 Expression | EST | Mm. 29255 | TITLE ESTs | | | gi = 3100474 | 642345 |
| IC07582 | UG75 Expression | EST | Mm. 29257 | TITLE ESTs, Weakly similar to membrane glycoprotein [M. musculus] | | | gi = 1796252 | 638411 |
| IC07583 | UG75 Expression | EST | Mm. 29258 | TITLE ESTs | | | gi = 2262522 | 751543 |
| IC07584 | UG75 Expression | EST | Mm. 29259 | TITLE ESTs | | | gi = 2307562 | 959287 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07585 | UG75 Expression | EST | Mm. 29262 | TITLE ESTs | | | gi = 5909935 | 348433 |
| IC07586 | UG75 Expression | EST | Mm. 29264 | TITLE ESTs, Moderately similar to putative Rab5-interacting protein {clone L1-57} [H. sapiens] | | | gi = 4374953 | 1296050 |
| IC07587 | UG75 Expression | EST | Mm. 29269 | TITLE ESTs | | | gi = 6518515 | 694126 |
| IC07588 | UG75 Expression | EST | Mm. 29270 | TITLE ESTs | | | gi = 2142611 | 572507 |
| IC07589 | UG75 Expression | EST | Mm. 29273 | TITLE ESTs, Weakly similar to Weak similarity to the yeast KIP1 protein [C. elegans] | | | gi = 4271527 | 576017 |
| IC07590 | UG75 Expression | EST | Mm. 29274 | TITLE ESTs | | | gi = 4271530 | 1001779 |
| IC07591 | UG75 Expression | EST | Mm. 29276 | TITLE ESTs | | | gi = 3885295 | 596882 |
| IC07592 | UG75 Expression | EST | Mm. 29284 | TITLE ESTs | | | gi = 4271692 | 718874 |
| IC07593 | UG75 Expression | EST | Mm. 29288 | TITLE ESTs | | | gi = 4272419 | 721439 |
| IC07594 | UG75 Expression | EST | Mm. 29291 | TITLE ESTs | | | gi = 4273150 | 765212 |
| IC07595 | UG75 Expression | EST | Mm. 29293 | TITLE ESTs, Moderately similar to KIAA0755 protein [H. sapiens] | | | gi = 4273174 | 641112 |
| IC07596 | UG75 Expression | EST | Mm. 29294 | TITLE ESTs | | | gi = 1309141 | 636283 |
| IC07597 | UG75 Expression | EST | Mm. 29297 | TITLE ESTs | | | gi = 2307976 | 1193184 |
| IC07598 | UG75 Expression | EST | Mm. 2930 | [D. melanogaster] | | | gi = 1863941 | 718828 |
| IC07599 | UG75 Expression | EST | Mm. 29301 | TITLE DNA segment, Human S2298E | GENE D0H8S2298E | | | 1921074 |
| IC07600 | UG75 Expression | EST | Mm. 29303 | TITLE ESTs, Weakly similar to cDNA EST yk338g10.5 comes from this gene [C. elegans] | | | gi = 5819675 | 1139755 |
| IC07601 | UG75 Expression | EST | Mm. 29304 | TITLE ESTs, Weakly similar to secretory protein containing thrombospondin motifs [M. musculus] | | | gi = 1796125 | 777529 |
| IC07602 | UG75 Expression | EST | Mm. 29305 | TITLE ESTs | | | gi = 1796548 | 638392 |
| IC07603 | UG75 Expression | EST | Mm. 29306 | TITLE ESTs | | | gi = 2305950 | 635701 |
| IC07604 | UG75 Expression | EST | Mm. 29307 | TITLE ESTs | | | gi = 2663950 | 1225106 |
| IC07605 | UG75 Expression | EST | Mm. 29308 | TITLE ESTs | | | gi = 3718855 | 765044 |
| IC07606 | UG75 Expression | EST | Mm. 29309 | TITLE ESTs | | | gi = 1715479 | 597320 |
| IC07607 | UG75 Expression | EST | Mm. 29313 | TITLE ESTs | | | gi = 1901350 | 618602 |
| IC07608 | UG75 Expression | EST | Mm. 29316 | TITLE ESTs | | | gi = 3521373 | 1750131 |
| IC07609 | UG75 Expression | EST | Mm. 29327 | TITLE ESTs, Weakly similar to Evi-5 [M. musculus] | | | gi = 6079123 | 1294316 |
| IC07610 | UG75 Expression | EST | Mm. 29332 | TITLE ESTs | | | gi = 2917258 | 596843 |
| IC07611 | UG75 Expression | EST | Mm. 29333 | TITLE ESTs | | | gi = 2521675 | 596493 |
| IC07612 | UG75 Expression | EST | Mm. 29337 | TITLE ESTs | | | gi = 1289099 | 621194 |
| IC07613 | UG75 Expression | EST | Mm. 29338 | TITLE ESTs | | | gi = 2807188 | 641676 |
| IC07614 | UG75 Expression | EST | Mm. 29343 | TITLE ESTs, Moderately similar to fractionated X-irradiation-induced 29 thymoma [M. musculus] | | | gi = 2812269 | 791013 |
| IC07615 | UG75 Expression | EST | Mm. 29344 | TITLE ESTs, Moderately similar to (define not available 5853321) [M. musculus] | | | gi = 6083798 | 1279232 |
| IC07616 | UG75 Expression | EST | Mm. 29345 | TITLE ESTs | | | gi = 6084781 | 972712 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07617 | UG75 Expression | EST | Mm. 29348 | TITLE ESTs, Weakly similar to predicted using Genefinder [C. elegans] | | | gi = 6084261 | 720651 |
| IC07618 | UG75 Expression | EST | Mm. 29349 | TITLE ESTs, Moderately similar to OXA1L [H. sapiens] | | | gi = 5600189 | 1226711 |
| IC07619 | UG75 Expression | EST | Mm. 2935 | TITLE ESTs | | | gi = 2990913 | 751146 |
| IC07620 | UG75 Expression | EST | Mm. 29351 | TITLE ESTs, Weakly similar to myosin [M. musculus] | | | gi = 2965665 | 596611 |
| IC07621 | UG75 Expression | EST | Mm. 29352 | TITLE ESTs | | | gi = 5473404 | 1243398 |
| IC07622 | UG75 Expression | EST | Mm. 29353 | TITLE ESTs, Weakly similar to HSPC010 [H. sapiens] | | | gi = 3718591 | 752209 |
| IC07623 | UG75 Expression | EST | Mm. 29354 | REPAIR PROTEIN PROTEIN RAD23 HOMOLOG A [M. musculus] | | | gi = 4402160 | 1380596 |
| IC07624 | UG75 Expression | EST | Mm. 29356 | TITLE ESTs | | | gi = 2523555 | 718294 |
| IC07625 | UG75 Expression | EST | Mm. 29359 | TITLE ESTs | | | gi = 1749032 | 618136 |
| IC07626 | UG75 Expression | EST | Mm. 29360 | TITLE ESTs, Weakly similar to brain mitochondrial carrier protein BMCP1 [M. musculus] | | | gi = 1840932 | 643325 |
| IC07627 | UG75 Expression | EST | Mm. 29361 | TITLE ESTs, Moderately similar to hypothetical protein [H. sapiens] | | | gi = 4275646 | 537862 |
| IC07628 | UG75 Expression | EST | Mm. 29362 | TITLE ESTs | | | gi = 4271891 | 1327548 |
| IC07629 | UG75 Expression | EST | Mm. 29363 | TITLE ESTs, Weakly similar to SIK similar protein [M. musculus] | | | gi = 4967996 | 973713 |
| IC07630 | UG75 Expression | EST | Mm. 29364 | TITLE ESTs | | | gi = 1476191 | 1330105 |
| IC07631 | UG75 Expression | EST | Mm. 29366 | TITLE ESTs | | | gi = 2199649 | 1294120 |
| IC07632 | UG75 Expression | EST | Mm. 29369 | TITLE ESTs, Moderately similar to PROBABLE PEPTIDYL-PROLYL CIS-TRANS ISOMERASE C21E11.05C [Schizosaccharomyces pombe] | | | gi = 3863384 | 972686 |
| IC07633 | UG75 Expression | EST | Mm. 2937 | TITLE ESTs | | | gi = 2288453 | 573120 |
| IC07634 | UG75 Expression | EST | Mm. 29370 | TITLE ESTs, Weakly similar to Ydr482cp [S. cerevisiae] | | | gi = 4483075 | 1002487 |
| IC07635 | UG75 Expression | EST | Mm. 29372 | DIVALENT CAITON TOLERANCE PROTEIN CUTA [Escherichia coli] | | | gi = 1286542 | 973291 |
| IC07636 | UG75 Expression | EST | Mm. 29374 | TITLE ESTs | | | gi = 2988808 | 718983 |
| IC07637 | UG75 Expression | EST | Mm. 29375 | TITLE ESTs | | | gi = 1909519 | 764400 |
| IC07638 | UG75 Expression | EST | Mm. 29377 | TITLE ESTs, Weakly similar to NY-REN-25 antigen [H. sapiens] | | | gi = 2520265 | 1312422 |
| IC07639 | UG75 Expression | EST | Mm. 29382 | TITLE ESTs | | | gi = 2412714 | 1002559 |
| IC07640 | UG75 Expression | EST | Mm. 29385 | TITLE ESTs, Weakly similar to glyceraldehyde 3-phosphate dehydrogenase [M. musculus] | | | gi = 1290236 | 765286 |
| IC07641 | UG75 Expression | EST | Mm. 29386 | TITLE ESTs, Weakly similar to CD63 ANTIGEN [M. musculus] | | | gi = 1908391 | 1001499 |
| IC07642 | UG75 Expression | EST | Mm. 29396 | TITLE ESTs | | | gi = 4663899 | 643245 |
| IC07643 | UG75 Expression | EST | Mm. 29397 | TITLE ESTs, Moderately similar to rA4 [R. norvegicus] | | | gi = 4315297 | 439970 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07644 | UG75 Expression | EST | Mm. 29398 | TITLE DNA segment, Chr 19, Wayne State University 162, expressed | GENE D19Wsu162e | | | 598590 |
| IC07645 | UG75 Expression | EST | Mm. 29402 | TITLE ESTs, Weakly similar to hypothetical protein [H. sapiens] | | | gi = 6938380 | 534040 |
| IC07646 | UG75 Expression | EST | Mm. 29406 | TITLE ESTs, Weakly similar to collagen alpha 1(III) chain precursor [M. musculus] | | | gi = 4601581 | 619118 |
| IC07647 | UG75 Expression | EST | Mm. 29408 | TITLE ESTs, Moderately similar to LEYDIG CELL TUMOR 10 KD PROTEIN [Rattus norvegicus] | | | gi = 1309515 | 533822 |
| IC07648 | UG75 Expression | EST | Mm. 29409 | TITLE ESTs | | | gi = 4604860 | 636986 |
| IC07649 | UG75 Expression | EST | Mm. 29410 | TITLE ESTs | | | gi = 1875698 | 641918 |
| IC07650 | UG75 Expression | EST | Mm. 29413 | TITLE ESTs | | | gi = 1475689 | 638092 |
| IC07651 | UG75 Expression | EST | Mm. 29417 | TITLE ESTs, Weakly similar to (defline not available 5668735) [M. musculus] | | | gi = 4315450 | 642348 |
| IC07652 | UG75 Expression | EST | Mm. 29420 | TITLE ESTs, Weakly similar to nucleolin [R. norvegicus] | | | gi = 2962631 | 550622 |
| IC07653 | UG75 Expression | EST | Mm. 29423 | TITLE ESTs | | | gi = 4614866 | 723134 |
| IC07654 | UG75 Expression | EST | Mm. 29424 | TITLE ESTs | | | gi = 4217352 | 1329896 |
| IC07655 | UG75 Expression | EST | Mm. 29430 | TITLE ESTs, Moderately similar to ARL-6 interacting protein-4 [M. musculus] | | | gi = 2263122 | 972552 |
| IC07656 | UG75 Expression | EST | Mm. 29431 | TITLE ESTs, Moderately similar to gene MAC30 protein [H. sapiens] | | | gi = 6084588 | 1296213 |
| IC07657 | UG75 Expression | EST | Mm. 29433 | TITLE ESTs | | | gi = 1876161 | 1395138 |
| IC07658 | UG75 Expression | EST | Mm. 29434 | TITLE ESTs | | | gi = 2519119 | 598870 |
| IC07659 | UG75 Expression | EST | Mm. 29436 | TITLE ESTs | | | gi = 1489040 | 1139839 |
| IC07660 | UG75 Expression | EST | Mm. 29438 | TITLE ESTs | | | gi = 5749023 | 558136 |
| IC07661 | UG75 Expression | EST | Mm. 29439 | TITLE ESTs, Weakly similar to WW domain binding protein 11 [M. musculus] | | | gi = 4281174 | 573378 |
| IC07662 | UG75 Expression | EST | Mm. 29450 | TITLE Ras and a-factor-converting enzyme 1 homolog (S. cerevisiae) | GENE Rce1 | | gi = 2517382 | 583205 |
| IC07663 | UG75 Expression | EST | Mm. 29451 | TITLE ESTs, Weakly similar to B0414.8 [C. elegans] | | | gi = 4317534 | 1243403 |
| IC07664 | UG75 Expression | EST | Mm. 29452 | RECOGNITION PARTICLE 19 KD PROTEIN [Homo sapiens] | | | gi = 1282275 | 1002088 |
| IC07665 | UG75 Expression | EST | Mm. 29455 | TITLE ESTs, Moderately similar to HSPC035 protein [H. sapiens] | | | gi = 4967405 | 1294718 |
| IC07666 | UG75 Expression | EST | Mm. 29457 | TITLE ESTs | | | gi = 3683704 | 386674 |
| IC07667 | UG75 Expression | EST | Mm. 29458 | TITLE ESTs, Weakly similar to HYPOTHETICAL 19.9 KD PROTEIN C24H6.02C IN CHROMOSOME I [Schizosaccharomyces pombe] | | | gi = 2292475 | 619828 |
| IC07668 | UG75 Expression | EST | Mm. 29459 | TITLE ESTs | | | gi = 3394589 | 721943 |
| IC07669 | UG75 Expression | EST | Mm. 29462 | TITLE ESTs | | | gi = 2307789 | 1278824 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07670 | UG75 Expression | EST | Mm. 29466 | TITLE ESTs | | | gi = 4407208 | 1265319 |
| IC07671 | UG75 Expression | EST | Mm. 29476 | TITLE ESTs | | | gi = 1793067 | 1312049 |
| IC07672 | UG75 Expression | EST | Mm. 29478 | TITLE ESTs, Moderately similar to hypothetical protein [M. musculus] | | | gi = 4408086 | 1345786 |
| IC07673 | UG75 Expression | EST | Mm. 29479 | TITLE ESTs, Weakly similar to (define not available 5931543) [M. musculus] | | | gi = 2647109 | 1446284 |
| IC07674 | UG75 Expression | EST | Mm. 29482 | TITLE DNA segment, Chr 11, KL Mohlke 34 | GENE D11Moh34 | | | 533987 |
| IC07675 | UG75 Expression | EST | Mm. 29483 | TITLE ESTs, Weakly similar to HISTIDINE-RICH PROTEIN KE4 [M. musculus] | | | gi = 3953994 | 749809 |
| IC07676 | UG75 Expression | EST | Mm. 29484 | TITLE ESTs, Moderately similar to PTD017 [H. sapiens] | | | gi = 3165242 | 553092 |
| IC07677 | UG75 Expression | EST | Mm. 29485 | TITLE DNA segment, Chr 10, Johns Hopkins University 12, expressed | GENE D10hu12e | | | 765517 |
| IC07678 | UG75 Expression | EST | Mm. 29487 | TITLE ESTs, Weakly similar to HIGH AFFINITY IMMUNO-GLOBULIN EPSILON RECEPTOR BETA-SUBUNIT [M. musculus] | | | gi = 2288582 | 621956 |
| IC07679 | UG75 Expression | EST | Mm. 29489 | TITLE ESTs, Weakly similar to unknown [S. cerevisiae] | | | gi = 4032830 | 1295735 |
| IC07680 | UG75 Expression | EST | Mm. 29490 | TITLE ESTs, Weakly similar to HYPOTHETICAL 36.7 KD PROTEIN C2F7.02C IN CHROMOSOME I [Schizosaccharomyces pombe] | | | gi = 3953962 | 1227003 |
| IC07681 | UG75 Expression | EST | Mm. 29491 | TITLE ESTs | | | gi = 4217054 | 777329 |
| IC07682 | UG75 Expression | EST | Mm. 29493 | TITLE ESTs | | | gi = 2350301 | 1278827 |
| IC07683 | UG75 Expression | EST | Mm. 29495 | TITLE ESTs | | | gi = 3296808 | 764389 |
| IC07684 | UG75 Expression | EST | Mm. 29496 | TITLE ESTs | | | gi = 4725105 | 598225 |
| IC07685 | UG75 Expression | EST | Mm. 295 | TITLE ESTs | | | gi = 4601217 | 598742 |
| IC07686 | UG75 Expression | EST | Mm. 29500 | TITLE ESTs, Weakly similar to R26660_1, partial CDS [H. sapiens] | | | gi = 4729660 | 973111 |
| IC07687 | UG75 Expression | EST | Mm. 29503 | TITLE ESTs, Weakly similar to P9513.2 gene product [S. cerevisiae] | | | gi = 2517390 | 1378369 |
| IC07688 | UG75 Expression | EST | Mm. 29505 | TITLE ESTs, Moderately similar to 5′-AMP-ACTIVATED PROTEIN KINASE, BETA SUBUNIT [Rattus norvegicus] | | | gi = 3718950 | 1345013 |
| IC07689 | UG75 Expression | EST | Mm. 29508 | TITLE ESTs, Weakly similar to rjs [M. musculus] | | | gi = 3375396 | 1226753 |
| IC07690 | UG75 Expression | EST | Mm. 29512 | [D. melanogaster] | | | g=2562640 | 618792 |
| IC07691 | UG75 Expression | EST | Mm. 29514 | TITLE ESTs, Moderately similar to m6a methyltransferase [M. musculus] | | | gi = 1684543 | 575046 |
| IC07692 | UG75 Expression | EST | Mm. 29515 | TITLE ESTs, Weakly similar to WISKOTT-ALDRICH SYNDROME PROTEIN HOMOLOG [M. musculus] | | | gi = 3374065 | 750893 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07693 | UG75 Expression | EST | Mm. 29516 | TITLE ESTs | | | gi = 1676787 | 573195 |
| IC07694 | UG75 Expression | EST | Mm. 29517 | TITLE ESTs | | | gi = 2283283 | 618262 |
| IC07695 | UG75 Expression | EST | Mm. 29519 | TITLE ESTs | | | gi = 2520729 | 1362580 |
| IC07696 | UG75 Expression | EST | Mm. 29525 | TITLE ESTs, Weakly similar to (define not available 6016530) [*M. musculus*] | | | gi = 6938257 | 641892 |
| IC07697 | UG75 Expression | EST | Mm. 29528 | TITLE ESTs, Weakly similar to N-methyl-D-aspartate receptor glutamate-binding chain [*R. norvegicus*] | | | gi = 2262592 | 751819 |
| IC07698 | UG75 Expression | EST | Mm. 29529 | TITLE ESTs | | | gi = 3957306 | 577974 |
| IC07699 | UG75 Expression | EST | Mm. 29530 | TITLE ESTs | | | gi = 4058505 | 1749442 |
| IC07700 | UG75 Expression | EST | Mm. 29531 | TITLE ESTs | | | gi = 4433882 | 621079 |
| IC07701 | UG75 Expression | EST | Mm. 29534 | TITLE ESTs | | | gi = 1895521 | 621653 |
| IC07702 | UG75 Expression | EST | Mm. 29536 | TITLE ESTs | | | gi = 437399 | 618944 |
| IC07703 | UG75 Expression | EST | Mm. 29537 | TITLE ESTs | | | gi = 4306175 | 871226 |
| IC07704 | UG75 Expression | EST | Mm. 2954 | TITLE ESTs | | | gi = 2979114 | 718800 |
| IC07705 | UG75 Expression | EST | Mm. 29540 | TITLE ESTs | | | gi = 1002166 | 1002166 |
| IC07706 | UG75 Expression | EST | Mm. 29541 | TITLE DNA segment, Chr 13, Wayne State University 177, expressed | GENE D13Wsu177e | | gi = 5124667 | 635166 |
| IC07707 | UG75 Expression | EST | Mm. 29543 | TITLE DNA segment, Chr 17, Wayne State University 166, expressed | GENE D17Wsu166e | | | 894344 |
| IC07708 | UG75 Expression | EST | Mm. 29545 | TITLE ESTs, Weakly similar to homology with 16.7 KD putative viral protein YUB1_NPVAC [*C. elegans*] | | | gi = 4601142 | 598211 |
| IC07709 | UG75 Expression | EST | Mm. 29553 | TITLE ESTs, Weakly similar to HYDROXYACYLGLUTATHIONE HYDROLASE [*R. norvegicus*] | | | gi = 6076517 | 1330108 |
| IC07710 | UG75 Expression | EST | Mm. 29556 | TITLE ESTs, Weakly similar to predicted using Genefinder [*C. elegans*] | | | gi = 2917713 | 638385 |
| IC07711 | UG75 Expression | EST | Mm. 29562 | TITLE expressed sequence tag mouse EST 12 | GENE ESTM12 | | gi = 4434242 | 749275 |
| IC07712 | UG75 Expression | EST | Mm. 29565 | TITLE ESTs | | | gi = 2284349 | 1243976 |
| IC07713 | UG75 Expression | EST | Mm. 29566 | TITLE ESTs | | | gi = 2756181 | 620254 |
| IC07714 | UG75 Expression | EST | Mm. 29568 | TITLE ESTs | | | gi = 7184546 | 577680 |
| IC07715 | UG75 Expression | EST | Mm. 2957 | [*H. sapiens*] | | | gi = 1282482 | 350730 |
| IC07716 | UG75 Expression | EST | Mm. 29572 | TITLE ESTs, Moderately similar to COP9 PROTEIN [*Arabidopsis thaliana*] | | | gi = 2306364 | 1293891 |
| IC07717 | UG75 Expression | EST | Mm. 29573 | TITLE ESTs, Moderately similar to hypothetical protein 384D8_6 [*H. sapiens*] | | | gi = 2284062 | 1139785 |
| IC07718 | UG75 Expression | EST | Mm. 29574 | TITLE ESTs, Weakly similar to dynein light intermediate chain 53/55 [*R. norvegicus*] | | | gi = 2989090 | 972908 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07719 | UG75 Expression | EST | Mm. 29577 | TITLE ESTs, Weakly similar to ORF YGR187c [S. cerevisiae] | | | gi = 3234766 | 1367270 |
| IC07720 | UG75 Expression | EST | Mm. 29578 | TITLE ESTs | | | gi = 1318097 | 1449789 |
| IC07721 | UG75 Expression | EST | Mm. 29579 | TITLE ESTs | | | gi = 1755308 | 1149529 |
| IC07722 | UG75 Expression | EST | Mm. 2958 | TITLE ESTs | | | gi = 5477999 | 765581 |
| IC07723 | UG75 Expression | EST | Mm. 29586 | TITLE ESTs, Moderately similar to BIOTIN CARBOXYLASE [Anabaena pcc7120] | | | gi = 5600034 | 598743 |
| IC07724 | UG75 Expression | EST | Mm. 29588 | TITLE ESTs, Weakly similar to Rab8-interacting protein [M. musculus] | | | gi = 5905468 | 1002242 |
| IC07725 | UG75 Expression | EST | Mm. 29589 | TITLE ESTs | | | gi = 4442702 | 1139819 |
| IC07726 | UG75 Expression | EST | Mm. 29592 | TITLE ESTs, Weakly similar to /prediction | | | gi = 6560003 | 617404 |
| IC07727 | UG75 Expression | EST | Mm. 29594 | TITLE ESTs, Weakly similar to splicing factor U2AF homolog [M. musculus] | | | gi = 1767938 | 893885 |
| IC07728 | UG75 Expression | EST | Mm. 29596 | TITLE ESTs, Moderately similar to JM4 [H. sapiens] | | | gi = 3954137 | 972880 |
| IC07729 | UG75 Expression | EST | Mm. 29599 | TITLE ESTs, Moderately similar to PUTATIVE MITOCHONDRIAL RIBOSOMAL PROTEIN S14 [Caenorhabditis elegans] | | | gi = 3165176 | 419614 |
| IC07730 | UG75 Expression | EST | Mm. 29600 | TITLE ESTs | | | gi = 2892793 | 723567 |
| IC07731 | UG75 Expression | EST | Mm. 29604 | TITLE DNA segment, Chr 5, Wayne State University 46, expressed | GENE D5Wsu46e | | | 1281517 |
| IC07732 | UG75 Expression | EST | Mm. 29606 | TITLE ESTs, Weakly similar to WSB-2 [M. musculus] | | | gi = 3954048 | 894308 |
| IC07733 | UG75 Expression | EST | Mm. 29608 | TITLE ESTs, Moderately similar to hypothetical protein [H. sapiens] | | | gi = 5125332 | 597780 |
| IC07734 | UG75 Expression | EST | Mm. 29609 | TITLE ESTs, Moderately similar to PUTATIVE ORAL CANCER SUPPRESSOR [Mesocricetus auratus] | | | gi = 1309551 | 1002433 |
| IC07735 | UG75 Expression | EST | Mm. 29610 | TITLE ESTs | | | gi = 4061301 | 1243415 |
| IC07736 | UG76 LID366 B cell | EST | Mm. 29614 | TITLE ESTs | | | gi = 7182202 | 871401 |
| IC07737 | UG75 Expression | EST | Mm. 29615 | TITLE ESTs, Weakly similar to GAMMA-ADAPTIN [M. musculus] | | | gi = 4601236 | 777471 |
| IC07738 | UG75 Expression | EST | Mm. 29619 | TITLE ESTs, Weakly similar to GAMMA-ADAPTIN [M. musculus] | | | gi = 1853058 | 1395090 |
| IC07739 | UG75 Expression | EST | Mm. 29621 | TITLE ESTs | | | gi = 3376388 | 596680 |
| IC07740 | UG75 Expression | EST | Mm. 29622 | TITLE ESTs, Weakly similar to Weak similarity with non-histone chromosomal protein HMG-1 [C. elegans] | | | gi = 3233675 | 1378247 |
| IC07741 | UG75 Expression | EST | Mm. 29625 | TITLE ESTs, Moderately similar to CYTOCHROME C OXIDASE POLYPEPTIDE VIB [Homo sapiens] | | | gi = 4790488 | 765293 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07742 | UG75 Expression | EST | Mm. 29627 | TITLE ESTs, Weakly similar to cDNA EST yk416a1.3 comes from this gene [C. elegans] | | | gi = 1827020 | 722933 |
| IC07743 | UG75 Expression | EST | Mm. 29628 | TITLE ESTs, Weakly similar to acetylglucosaminyltransferase-like protein [M. musculus] | | | gi = 1538876 | 1279033 |
| IC07744 | UG75 Expression | EST | Mm. 29629 | TITLE ESTs | | | gi = 2292499 | 642462 |
| IC07745 | UG75 Expression | EST | Mm. 29631 | TITLE ESTs, Moderately similar to DRIM protein [H. sapiens] | | | gi = 6756749 | 894276 |
| IC07746 | UG75 Expression | EST | Mm. 29632 | TITLE ESTs | | | gi = 2192913 | 638685 |
| IC07747 | UG75 Expression | EST | Mm. 29633 | TITLE ESTs | | | gi = 2962472 | 1265212 |
| IC07748 | UG75 Expression | EST | Mm. 29634 | TITLE ESTs | | | gi = 5907813 | 749457 |
| IC07749 | UG75 Expression | EST | Mm. 29635 | TITLE ESTs | | | gi = 1756217 | 622307 |
| IC07750 | UG75 Expression | EST | Mm. 29636 | TITLE ESTs | | | gi = 3374433 | 638185 |
| IC07751 | UG75 Expression | EST | Mm. 29637 | TITLE ESTs, Weakly similar to Hypothetical protein A [C. elegans] | | | gi = 4408950 | 1378777 |
| IC07752 | UG75 Expression | EST | Mm. 29638 | TITLE ESTs | | | gi = 2256956 | 894374 |
| IC07753 | UG75 Expression | EST | Mm. 29639 | TITLE ESTs | | | gi = 1513955 | 473385 |
| IC07754 | UG75 Expression | EST | Mm. 29645 | TITLE ESTs, Weakly similar to cDNA EST EMBL:D69235 comes from this gene [C. elegans] | | | gi = 3394370 | 777552 |
| IC07755 | UG75 Expression | EST | Mm. 29646 | TITLE ESTs, Weakly similar to Similarity to Yeast hypothetical 52.9 KD protein [C. elegans] | | | gi = 1286560 | 551082 |
| IC07756 | UG75 Expression | EST | Mm. 29647 | TITLE ESTs | | | gi = 1287287 | 1279169 |
| IC07757 | UG75 Expression | EST | Mm. 29649 | TITLE ESTs, Weakly similar to ENDOSOMAL P24A PROTEIN PRECURSOR [Saccharomyces cerevisiae] | | | gi = 5599338 | 621251 |
| IC07758 | UG75 Expression | EST | Mm. 29650 | TITLE ESTs, Moderately similar to (define not available 5815343) [M. musculus] | | | gi = 1325025 | 721751 |
| IC07759 | UG75 Expression | EST | Mm. 29651 | TITLE ESTs, Weakly similar to HYPOTHETICAL 43.2 KD PROTEIN C34E10.1 IN CHROMOSOME III [Caenorhabditis elegans] | | | gi = 6078226 | 1312416 |
| IC07760 | UG75 Expression | EST | Mm. 29654 | TITLE ESTs | | | gi = 3393286 | 1263837 |
| IC07761 | UG75 Expression | EST | Mm. 29656 | TITLE ESTs | | | gi = 2039858 | 750556 |
| IC07762 | UG75 Expression | EST | Mm. 29659 | TITLE ESTs, Moderately similar to mel-13a protein [M. musculus] | | | gi = 3167870 | 620542 |
| IC07763 | UG75 Expression | EST | Mm. 29660 | TITLE ESTs | | | gi = 1282567 | 620771 |
| IC07764 | UG75 Expression | EST | Mm. 29662 | TITLE ESTs | | | gi = 2199734 | 597932 |
| IC07765 | UG75 Expression | EST | Mm. 29665 | TITLE ESTs | | | gi = 2292164 | 533560 |
| IC07766 | UG75 Expression | EST | Mm. 29668 | TITLE ESTs, Weakly similar to Y40B1B.7 [C. elegans] | | | gi = 3370358 | 573210 |
| IC07767 | UG75 Expression | EST | Mm. 2967 | TITLE ESTs | | | gi = 4604361 | 721856 |
| IC07768 | UG75 Expression | EST | Mm. 29670 | TITLE ESTs, Weakly similar to TALIN [M. musculus] | | | gi = 250003 | 722570 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07769 | UG75 Expression | EST | Mm. 29671 | TITLE ESTs | | | gi = 1541851 | 637922 |
| IC07770 | UG75 Expression | EST | Mm. 29673 | TITLE ESTs | | | gi = 1801089 | 558061 |
| IC07771 | UG75 Expression | EST | Mm. 29676 | TITLE DNA segment, Chr 19, Wayne State University 54, expressed | GENE D19Wsu54e | | | 550836 |
| IC07772 | UG75 Expression | EST | Mm. 29679 | TITLE ESTs | | | gi = 3520515 | 1749978 |
| IC07773 | UG75 Expression | EST | Mm. 29680 | TITLE ESTs, Moderately similar to ANTI-SILENCING PROTEIN 1 [Saccharomyces cerevisiae] | | | gi = 291812 | 642460 |
| IC07774 | UG75 Expression | EST | Mm. 29681 | TITLE ESTs | | | gi = 2282989 | 1134844 |
| IC07775 | UG75 Expression | EST | Mm. 29682 | TITLE ESTs | | | gi = 4779058 | 636099 |
| IC07776 | UG75 Expression | EST | Mm. 29684 | TITLE ESTs, Weakly similar to coronin-3 [M. musculus] | | | gi = 4968311 | 1380621 |
| IC07777 | UG75 Expression | EST | Mm. 29685 | TITLE ESTs, Weakly similar to DNAJ PROTEIN HOMOLOG MTJ1 [M. musculus] | | | gi = 2333068 | 1149947 |
| IC07778 | UG75 Expression | EST | Mm. 29688 | TITLE ESTs [H. sapiens] | | | gi = 1910578 | 765338 |
| IC07779 | UG75 Expression | EST | Mm. 29689 | TITLE ESTs | | | gi = 4216892 | 1362882 |
| IC07780 | UG75 Expression | EST | Mm. 29690 | TITLE ESTs | | | gi = 6748981 | 718884 |
| IC07781 | UG75 Expression | EST | Mm. 29692 | TITLE ESTs | | | gi = 1282274 | 622381 |
| IC07782 | UG75 Expression | EST | Mm. 29700 | TITLE ESTs | | | gi = 2503081 | 634830 |
| IC07783 | UG75 Expression | EST | Mm. 29702 | TITLE DNA segment, Chr 3, University of California at Los Angeles 1 | GENE D3Ucla1 | | | 1294573 |
| IC07784 | UG75 Expression | EST | Mm. 29703 | TITLE DNA segment, Chr 7, Wayne State University 86, expressed | GENE D7Wsu86e | | | 1001686 |
| IC07785 | UG75 Expression | EST | Mm. 29704 | TITLE ESTs | | | gi = 6008059 | 618514 |
| IC07786 | UG75 Expression | EST | Mm. 29707 | TITLE ESTs, Weakly similar to nuclear poly(C)-binding protein, [M. musculus] | | | gi = 1497260 | 582209 |
| IC07787 | UG75 Expression | EST | Mm. 29711 | TITLE ESTs, Weakly similar to G protein-coupled receptor kinase 6, splice variant A [M. musculus] | | | gi = 4199752 | 534159 |
| IC07788 | UG75 Expression | EST | Mm. 29712 | TITLE ESTs, Weakly similar to neural specific sr protein NSSR 1 [M. musculus] | | | gi = 3164302 | 551601 |
| IC07789 | UG75 Expression | EST | Mm. 29713 | TITLE ESTs, Weakly similar to brain mitochondrial carrier protein BMCP1 [M. musculus] | | | gi = 2663693 | 581727 |
| IC07790 | UG75 Expression | EST | Mm. 29716 | TITLE ESTs | | | gi = 4297514 | 751816 |
| IC07791 | UG75 Expression | EST | Mm. 29717 | TITLE ESTs | | | gi = 1287064 | 1140271 |
| IC07792 | UG75 Expression | EST | Mm. 29718 | TITLE ESTs | | | gi = 1531008 | 635884 |
| IC07793 | UG75 Expression | EST | Mm. 29719 | TITLE ESTs, Moderately similar to Similarity to Yeast LPG22P protein [C. elegans] | | | gi = 2691774 | 1264891 |
| IC07794 | UG75 Expression | EST | Mm. 2972 | TITLE ESTs | | | gi = 1902420 | 718078 |
| IC07795 | UG75 Expression | EST | Mm. 29722 | TITLE ESTs | | | gi = 1565177 | 597476 |
| IC07796 | UG75 Expression | EST | Mm. 29723 | TITLE ESTs | | | gi = 1539711 | 1345647 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07797 | UG75 Expression | EST | Mm. 29724 | TITLE ESTs, Weakly similar to PUTATIVE PRE-MRNA SPLICING FACTOR RNA HELICASE [H. sapiens] | | | gi = 7202362 | 617830 |
| IC07798 | UG75 Expression | EST | Mm. 29728 | TITLE DNA segment, Chr 13, Wayne State University 156, expressed | GENE D13Wsu156e | | | 620554 |
| IC07799 | UG75 Expression | EST | Mm. 29731 | TITLE ESTs, Weakly similar to PARATHYMOSIN [Rattus norvegicus] | | | gi = 1681251 | 573910 |
| IC07800 | UG75 Expression | EST | Mm. 29734 | TITLE ESTs, Moderately similar to HYPOTHETICAL PROTEIN KIAA0253 [H. sapiens] | | | gi = 1756313 | 618796 |
| IC07801 | UG75 Expression | EST | Mm. 29737 | TITLE ESTs, Weakly similar to myelodysplasia/myeloid leukemia factor 1 [M. musculus] | | | gi = 1649082 | 894280 |
| IC07802 | UG75 Expression | EST | Mm. 29738 | TITLE ESTs, Weakly similar to APOLIPOPROTEIN A-IV PRECURSOR [M. musculus] | | | gi = 1282069 | 637308 |
| IC07803 | UG75 Expression | EST | Mm. 29739 | TITLE ESTs | | | gi = 3054435 | 636598 |
| IC07804 | UG75 Expression | EST | Mm. 29741 | TITLE ESTs | | | gi = 4778820 | 617812 |
| IC07805 | UG75 Expression | EST | Mm. 29743 | TITLE ESTs, Weakly similar to B0495.6 [C. elegans] | | | gi = 3165170 | 721448 |
| IC07806 | UG75 Expression | EST | Mm. 29744 | TITLE ESTs, Weakly similar to 36 KD NUCLEOLAR PROTEIN HNP36 [M. musculus] | | | gi = 4434282 | 959247 |
| IC07807 | UG75 Expression | EST | Mm. 29745 | TITLE ESTs, Weakly similar to high affinity immunoglobulin gamma Fc receptor I [M. musculus] | | | gi = 4604532 | 622960 |
| IC07808 | UG75 Expression | EST | Mm. 29748 | TITLE ESTs, Moderately similar to NY-REN-37 antigen [H. sapiens] | | | gi = 1853062 | 638821 |
| IC07809 | UG75 Expression | EST | Mm. 2975 | TITLE ESTs | | | gi = 2256789 | 718080 |
| IC07810 | UG75 Expression | EST | Mm. 29750 | TITLE ESTs | | | gi = 1316271 | 1295050 |
| IC07811 | UG75 Expression | EST | Mm. 29751 | PHOSPHATE REDUCTASE [Corynebacterium glutamicum] | | | gi = 4273177 | 595901 |
| IC07812 | UG75 Expression | EST | Mm. 29752 | TITLE ESTs, Moderately similar to POLLEN SPECIFIC PROTEIN SF3 [Helianthus annuus] | | | gi = 3375460 | 574834 |
| IC07813 | UG75 Expression | EST | Mm. 29761 | TITLE ESTs, Weakly similar to dysferlin [H. sapiens] | | | gi = 1682313 | 576470 |
| IC07814 | UG75 Expression | EST | Mm. 29762 | TITLE ESTs | | | gi = 4729680 | 777320 |
| IC07815 | UG75 Expression | EST | Mm. 29763 | TITLE ESTs, Weakly similar to KIAA0601 protein [H. sapiens] | | | gi = 6514824 | 621335 |
| IC07816 | UG75 Expression | EST | Mm. 29768 | TITLE pyruvate dehydrogenase 2 | GENE Pdk2 | | gi = 4030172 | 533405 |
| IC07817 | UG75 Expression | EST | Mm. 29769 | TITLE ESTs | | | gi = 1282684 | 894218 |
| IC07818 | UG75 Expression | EST | Mm. 29773 | TITLE ESTs | | | gi = 6077356 | 1193609 |
| IC07819 | UG75 Expression | EST | Mm. 29777 | TITLE ESTs | | | gi = 4725398 | 598151 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07820 | UG75 Expression | EST | Mm. 2978 | TITLE ESTs, Weakly similar to Similar to S. cerevisiae hypothetical protein 5 [H. sapiens] | | | gi = 5750055 | 718093 |
| IC07821 | UG75 Expression | EST | Mm. 29780 | TITLE ESTs | | | gi = 3375250 | 1149350 |
| IC07822 | UG75 Expression | EST | Mm. 29782 | TITLE ESTs | | | gi = 1757228 | 1193714 |
| IC07823 | UG75 Expression | EST | Mm. 29784 | TITLE ESTs, Moderately similar to PROTEIN 22A3 [M. musculus] | | | gi = 1282040 | 764138 |
| IC07824 | UG75 Expression | EST | Mm. 29786 | TITLE ESTs, Moderately similar to The ha1438 gene product is related to a C728 protein encoded in S. cerevisiae chromosome II. [H. sapiens] | | | gi = 5125824 | 750574 |
| IC07825 | UG75 Expression | EST | Mm. 29789 | TITLE ESTs | | | gi = 6645514 | 1295760 |
| IC07826 | UG75 Expression | EST | Mm. 29796 | TITLE ESTs | | | gi = 437451 | 718443 |
| IC07827 | UG75 Expression | EST | Mm. 29797 | TITLE ESTs, Weakly similar to FLJ-LRR associated protein-1 [M. musculus] | | | gi = 6084808 | 1279692 |
| IC07828 | UG75 Expression | EST | Mm. 29798 | TITLE ESTs | | | gi = 3216697 | 1380200 |
| IC07829 | UG76 LID366 B cell | EST | Mm. 29802 | TITLE ESTs, Moderately similar to CG1-67 protein [H. sapiens] | | | gi = 1282691 | 1889221 |
| IC07830 | UG75 Expression | EST | Mm. 29804 | TITLE ESTs | | | gi = 3371304 | 1294403 |
| IC07831 | UG75 Expression | EST | Mm. 29805 | TITLE ESTs | | | gi = 2517221 | 777139 |
| IC07832 | UG75 Expression | EST | Mm. 29808 | TITLE ESTs | | | gi = 6097009 | 1224889 |
| IC07833 | UG75 Expression | EST | Mm. 29809 | TITLE ESTs, Weakly similar to predicted using Genefinder [C. elegans] | | | gi = 4726576 | 640716 |
| IC07834 | UG75 Expression | EST | Mm. 29810 | HELICASE IN WAPA-LICT INTERGENIC REGION [Bacillus subtilis] | | | gi = 126476 | 577861 |
| IC07835 | UG75 Expression | EST | Mm. 29812 | TITLE ESTs, Moderately similar to 15 kDa selenoprotein [H. sapiens] | | | gi = 2306401 | 959170 |
| IC07836 | UG75 Expression | EST | Mm. 29822 | TITLE ESTs, Weakly similar to neurofilament triplet H protein [M. musculus] | | | gi = 2057848 | 634410 |
| IC07837 | UG75 Expression | EST | Mm. 29823 | TITLE ESTs, Moderately similar to microsomal glutathione S-transferase 3 [H. sapiens] | | | gi = 2258802 | 723045 |
| IC07838 | UG75 Expression | EST | Mm. 29825 | TITLE ESTs, Weakly similar to POSSIBLE GLOBAL TRANSCRIPTION ACTIVATOR SNF2L [Caenorhabditis elegans] | | | gi = 4060049 | 637492 |
| IC07839 | UG75 Expression | EST | Mm. 29828 | TITLE ESTs, Weakly similar to transforming protein K-ras [M. musculus] | | | gi = 3519383 | 468877 |
| IC07840 | UG75 Expression | EST | Mm. 29831 | TITLE ESTs | | | gi = 1841629 | 1378331 |
| IC07841 | UG75 Expression | EST | Mm. 29832 | TITLE ESTs | | | gi = 5474860 | 634276 |
| IC07842 | UG75 Expression | EST | Mm. 29833 | TITLE ESTs | | | gi = 1826616 | 534185 |
| IC07843 | UG75 Expression | EST | Mm. 29834 | TITLE ESTs | | | gi = 3374414 | 534294 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07844 | UG75 Expression | EST | Mm. 29835 | TITLE DNA segment, Chr 19, Wayne State University 55, expressed | GENE D19Wsu55e | | | 1293791 |
| IC07845 | UG75 Expression | EST | Mm. 29836 | TITLE ESTs | | | gi = 1541801 | 634673 |
| IC07846 | UG75 Expression | EST | Mm. 29841 | TITLE ESTs, Weakly similar to regulatory protein Myef-2 [*M. musculus*] | | | gi = 6518592 | 1278834 |
| IC07847 | UG75 Expression | EST | Mm. 29842 | TITLE NADH dehydrogenase flavoprotein 1 | GENE Ndufv1 | | gi = 4030315 | 638656 |
| IC07848 | UG75 Expression | EST | Mm. 29844 | TITLE ESTs | | | gi = 1901738 | 1378343 |
| IC07849 | UG75 Expression | EST | Mm. 29847 | TITLE ESTs | | | gi = 2503413 | 622737 |
| IC07850 | UG75 Expression | EST | Mm. 29852 | TITLE ESTs, Weakly similar to cDNA EST EMBL:D72691 comes from this gene [*C. elegans*] | | | gi = 3299606 | 959158 |
| IC07851 | UG75 Expression | EST | Mm. 29853 | TITLE ESTs | | | gi = 4315214 | 973164 |
| IC07852 | UG75 Expression | EST | Mm. 29855 | TITLE ESTs, Moderately similar to LAR PROTEIN PRECURSOR [*Homo sapiens*] | | | gi = 5338872 | 636399 |
| IC07853 | UG75 Expression | EST | Mm. 2986 | TITLE ESTs, Weakly similar to Similar to *S. cerevisiae* EMP70 protein precursor [*H. sapiens*] | | | gi = 4032686 | 1001765 |
| IC07854 | UG75 Expression | EST | Mm. 29860 | TITLE ESTs, Weakly similar to F2 alpha prostoglandin regulatory protein [*M. musculus*] | | | gi = 1290239 | 1395436 |
| IC07855 | UG75 Expression | EST | Mm. 29865 | TITLE ESTs, Weakly similar to WW domain binding protein 11 [*M. musculus*] | | | gi = 3718331 | 1002051 |
| IC07856 | UG75 Expression | EST | Mm. 29866 | TITLE ESTs | | | gi = 1751629 | 764762 |
| IC07857 | UG75 Expression | EST | Mm. 29868 | TITLE ESTs, Weakly similar to NG38 [*M. musculus*] | | | gi = 3862992 | 551399 |
| IC07858 | UG75 Expression | EST | Mm. 29870 | TITLE ESTs | | | gi = 6514860 | 1140138 |
| IC07859 | UG75 Expression | EST | Mm. 29873 | TITLE ESTs, Moderately similar to CASEIN KINASE I, GAMMA ISOFORM [*Bos taurus*] | | | gi = 5598895 | 894497 |
| IC07860 | UG75 Expression | EST | Mm. 29877 | TITLE ESTs | | | gi = 6008747 | 1293643 |
| IC07861 | UG75 Expression | EST | Mm. 29878 | TITLE ESTs | | | gi = 2813874 | 620335 |
| IC07862 | UG75 Expression | EST | Mm. 29880 | TITLE ESTs | | | gi = 2811508 | 752216 |
| IC07863 | UG75 Expression | EST | Mm. 29881 | TITLE ESTs | | | gi = 1328736 | 1345373 |
| IC07864 | UG75 Expression | EST | Mm. 29882 | TITLE ESTs, Weakly similar to (define not available 5901816) [*D. melanogaster*] | | | gi = 3394162 | 1261434 |
| IC07865 | UG75 Expression | EST | Mm. 29883 | TITLE ESTs | | | gi = 4272785 | 536337 |
| IC07866 | UG75 Expression | EST | Mm. 29886 | TITLE ESTs, Weakly similar to ZK546.13 [*C. elegans*] | | | gi = 2967244 | 973504 |
| IC07867 | UG75 Expression | EST | Mm. 29887 | TITLE ESTs, Weakly similar to ATP(GTP)-binding protein [*H. sapiens*] | | | gi = 2283059 | 1446299 |
| IC07868 | UG75 Expression | EST | Mm. 29889 | TITLE ESTs, Weakly similar to (define not available 6016842) [*M. musculus*] | | | gi = 1475249 | 1395577 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07869 | UG75 Expression | EST | Mm. 29894 | TITLE ESTs, Weakly similar to hypothetical protein [H. sapiens] | | | gi = 2306186 | 617385 |
| IC07870 | UG75 Expression | EST | Mm. 29895 | BAND 7 INTEGRAL MEMBRANE PROTEIN [Homo sapiens] | | | gi = 1908797 | 1295810 |
| IC07871 | UG75 Expression | EST | Mm. 29898 | TITLE ESTs | | | gi = 3164634 | 894136 |
| IC07872 | UG75 Expression | EST | Mm. 2990 | TITLE ESTs | | | gi = 5907761 | 720955 |
| IC07873 | UG75 Expression | EST | Mm. 29901 | TITLE ESTs | | | gi = 3519927 | 764040 |
| IC07874 | UG75 Expression | EST | Mm. 29903 | TITLE ESTs | | | gi = 4615021 | 641277 |
| IC07875 | UG75 Expression | EST | Mm. 29904 | TITLE ribosomal protein, mitochondrial, L7 | GENE Rpml7 | MRP-L7 | gi = 3165177 | 1279641 |
| IC07876 | UG75 Expression | EST | Mm. 29906 | TITLE ESTs, Moderately similar to HYPOTHETICAL 49.7 KD PROTEIN IN GIN2-STE3 INTERGENIC REGION [Saccharomyces cerevisiae] | | | gi = 6085290 | 1149618 |
| IC07877 | UG75 Expression | EST | Mm. 29909 | TITLE ESTs | | | gi = 2813322 | 1193034 |
| IC07878 | UG75 Expression | EST | Mm. 29912 | TITLE ESTs, Weakly similar to molybdopterin synthase sulfurylase [H. sapiens] | | | gi = 3371310 | 1378999 |
| IC07879 | UG75 Expression | EST | Mm. 29914 | TITLE ESTs | | | gi = 2690684 | 642380 |
| IC07880 | UG75 Expression | EST | Mm. 29915 | SPLICING FACTOR SRP20 [Homo sapiens; Mus musculus] | | | gi = 5550486 | 894462 |
| IC07881 | UG75 Expression | EST | Mm. 29920 | TITLE ESTs | | | gi = 1826555 | 641894 |
| IC07882 | UG75 Expression | EST | Mm. 29925 | TITLE DNA segment, Chr 17, Wayne State University 104, expressed | GENE D17Wsu104e | | | 1149738 |
| IC07883 | UG75 Expression | EST | Mm. 29927 | TITLE ESTs | | | gi = 2651590 | 1002728 |
| IC07884 | UG75 Expression | EST | Mm. 29929 | TITLE ESTs | | | gi = 4604344 | 620359 |
| IC07885 | UG75 Expression | EST | Mm. 29932 | TITLE ESTs, Moderately similar to unknown [H. sapiens] | | | gi = 1794809 | 576892 |
| IC07886 | UG75 Expression | EST | Mm. 29933 | [M. musculus] | | | gi = 4401165 | 1148616 |
| IC07887 | UG75 Expression | EST | Mm. 29936 | TITLE ESTs, Weakly similar to similar to yeast adenylate cyclase [H. sapiens] | | | gi = 3519347 | 551067 |
| IC07888 | UG75 Expression | EST | Mm. 29937 | TITLE ESTs, Weakly similar to predicted using Genefinder [C. elegans] | | | gi = 1853713 | 551186 |
| IC07889 | UG75 Expression | EST | Mm. 29940 | TITLE ESTs | | | gi = 3957054 | 551269 |
| IC07890 | UG75 Expression | EST | Mm. 29941 | TITLE ESTs | | | gi = 3956369 | 958660 |
| IC07891 | UG75 Expression | EST | Mm. 29942 | TITLE ESTs | | | gi = 1794442 | 639553 |
| IC07892 | UG75 Expression | EST | Mm. 29944 | TITLE ESTs | | | gi = 3885280 | 551404 |
| IC07893 | UG75 Expression | EST | Mm. 29945 | TITLE ESTs, Moderately similar to VEGETATIVE SPECIFIC PROTEIN H7 [Dictyostelium discoideum] | | | gi = 2891316 | 557866 |
| IC07894 | UG75 Expression | EST | Mm. 29948 | TITLE ESTs, Weakly similar to Similarity to Human ADP/ATP carrier protein [C. elegans] | | | gi = 1539764 | 551678 |
| IC07895 | UG75 Expression | EST | Mm. 29949 | TITLE DNA segment, Chr 8, Wayne State University 108, expressed | GENE D8Wsu108e | | | 1139680 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07896 | UG75 Expression | EST | Mm. 29950 | TITLE ESTs, Weakly similar to ORF YGR066c [S. cerevisiae] | | | gi = 4604521 | 1380356 |
| IC07897 | UG75 Expression | EST | Mm. 29952 | TITLE ESTs | | | gi = 1630190 | 1293926 |
| IC07898 | UG75 Expression | EST | Mm. 29959 | TITLE ESTs | | | gi = 3957283 | 573148 |
| IC07899 | UG75 Expression | EST | Mm. 29960 | TITLE ESTs, Moderately similar to HYPOTHETICAL 58.5 KD PROTEIN T20B12.3 IN CHROMOSOME III [Caenorhabditis elegans] | | | gi = 2165207 | 765136 |
| IC07900 | UG75 Expression | EST | Mm. 29963 | TITLE ESTs, Weakly similar to HYPOTHETICAL PROTEIN KIAA0029 [H. sapiens] | | | gi = 2962502 | 1263911 |
| IC07901 | UG75 Expression | EST | Mm. 29964 | TITLE ESTs, Weakly similar to polymerase I-transcript release factor [M. musculus] | | | gi = 1297622 | 533441 |
| IC07902 | UG75 Expression | EST | Mm. 29965 | TITLE ESTs, Weakly similar to DNA-DAMAGE-REPAIR/TOLERATION PROTEIN DRT111 PRECURSOR [Arabidopsis thaliana] | | | gi = 1288395 | 618841 |
| IC07903 | UG75 Expression | EST | Mm. 29971 | TITLE ESTs, Weakly similar to sorting nexin 1 [M. musculus] | | | gi = 4029726 | 1295722 |
| IC07904 | UG75 Expression | EST | Mm. 29974 | TITLE ESTs, Weakly similar to PHOSPHATIDYLETHANOL-AMINE-BINDING PROTEIN [R. norvegicus] | | | gi = 4726446 | 1395054 |
| IC07905 | UG75 Expression | EST | Mm. 29975 | TITLE ESTs, Moderately similar to GLYCINE AMIDINOTRANS-FERASE PRECURSOR [R. norvegicus] | | | gi = 6083997 | 533319 |
| IC07906 | UG75 Expression | EST | Mm. 29978 | TITLE ESTs, Weakly similar to growth factor-responsive protein, vascular smooth muscle [R. norvegicus] | | | gi = 6083852 | 894138 |
| IC07907 | UG75 Expression | EST | Mm. 29984 | TITLE ESTs, Moderately similar to BB1 | | | gi = 3374984 | 557885 |
| IC07908 | UG75 Expression | EST | Mm. 29985 | TITLE ESTs | | | gi = 2916208 | 557954 |
| IC07909 | UG75 Expression | EST | Mm. 29990 | TITLE ESTs, Weakly similar to cDNA EST yk194a10.3 comes from this gene [C. elegans] | | | gi = 2991095 | 1314732 |
| IC07910 | UG75 Expression | EST | Mm. 29992 | TITLE ESTs | | | gi = 3518554 | 1279974 |
| IC07911 | UG75 Expression | EST | Mm. 29995 | TITLE DNA segment, Chr 2, University of California at Los Angeles 1 | GENE D2Ucla1 | | | 718037 |
| IC07912 | UG75 Expression | EST | Mm. 29996 | TITLE DNA segment, Chr 18, University of California at Los Angeles 3 | GENE D18Ucla3 | | | 596519 |
| IC07913 | UG75 Expression | EST | Mm. 29999 | TITLE ESTs, Moderately similar to ISOLEUCYL-TRNA SYNTHETASE [Staphylococcus aureus] | | | gi = 6822383 | 1295742 |
| IC07914 | UG75 Expression | EST | Mm. 30 | TITLE ESTs | | | gi = 4605408 | 391880 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07915 | UG75 Expression | EST | Mm. 30000 | TITLE ESTs | | | gi = 2256919 | 1329913 |
| IC07916 | UG75 Expression | EST | Mm. 30003 | TITLE ESTs | | | gi = 1862276 | 641779 |
| IC07917 | UG75 Expression | EST | Mm. 30005 | TITLE ESTs | | | gi = 1310396 | 1001689 |
| IC07918 | UG75 Expression | EST | Mm. 30006 | TITLE ESTs, Weakly similar to (define not available 5929884) [R. norvegicus] | | | gi = 4967787 | 777439 |
| IC07919 | UG75 Expression | EST | Mm. 30007 | TITLE ESTs | | | gi = 3215597 | 551680 |
| IC07920 | UG75 Expression | EST | Mm. 30008 | TITLE ESTs, Weakly similar to cDNA EST yk342h12.5 comes from this gene [C. elegans] | | | gi = 1287560 | 551297 |
| IC07921 | UG75 Expression | EST | Mm. 3001 | TITLE EST | | | gi = 1903862 | 721361 |
| IC07922 | UG75 Expression | EST | Mm. 30013 | TITLE ESTs | | | gi = 1861562 | 643013 |
| IC07923 | UG75 Expression | EST | Mm. 30015 | TITLE ESTs | | | gi = 1330773 | 617268 |
| IC07924 | UG75 Expression | EST | Mm. 30016 | TITLE ESTs, Weakly similar to RHO GDP-DISSOCIATION INHIBITOR 2 [M. musculus] | | | gi = 4967351 | 1149027 |
| IC07925 | UG75 Expression | EST | Mm. 30019 | TITLE ESTs, Weakly similar to CARG-BINDING FACTOR A [Mus musculus] | | | gi = 4967889 | 972742 |
| IC07926 | UG75 Expression | EST | Mm. 3002 | TITLE DNA segment, human D0S6743E | GENE D0HOS6743E | | | 1148980 |
| IC07927 | UG75 Expression | EST | Mm. 30021 | TITLE ESTs, Weakly similar to ORF YKR087c [S. cerevisiae] | | | gi = 6822660 | 1379283 |
| IC07928 | UG75 Expression | EST | Mm. 30026 | TITLE ESTs, Weakly similar to FIG-1 PROTEIN PRECURSOR [M. musculus] | | | gi = 3863159 | 616788 |
| IC07929 | UG75 Expression | EST | Mm. 30028 | TITLE ESTs, Weakly similar to Lpe5p [S. cerevisiae] | | | gi = 2200125 | 1361234 |
| IC07930 | UG75 Expression | EST | Mm. 30033 | TITLE ESTs, Weakly similar to unknown [H. sapiens] | | | gi = 4316398 | 623077 |
| IC07931 | UG75 Expression | EST | Mm. 30034 | TITLE ESTs, Weakly similar to HYPOTHETICAL 11.4 KD PROTEIN C13G6.04 IN CHROMOSOME I [Schizosaccharomyces pombe] | | | gi = 3143507 | 1294676 |
| IC07932 | UG75 Expression | EST | Mm. 30042 | TITLE ESTs, Weakly similar to coded for by C. elegans cDNA yk30b3.5 [C. elegans] | | | gi = 5750070 | 721077 |
| IC07933 | UG75 Expression | EST | Mm. 30047 | TITLE ESTs, Moderately similar to muscle glycogen phosphorylase [M. musculus] | | | gi = 3519095 | 1279639 |
| IC07934 | UG75 Expression | EST | Mm. 30052 | TITLE DNA segment, Chr 4, Wayne State University 125, expressed | GENE D4Wsu125e | | | 721445 |
| IC07935 | UG75 Expression | EST | Mm. 30053 | TITLE ESTs | | | gi = 2262907 | 972848 |
| IC07936 | UG75 Expression | EST | Mm. 30056 | [H. sapiens] | | | gi = 4726649 | 723272 |
| IC07937 | UG75 Expression | EST | Mm. 30057 | TITLE ESTs | | | gi = 1876193 | 1750145 |
| IC07938 | UG75 Expression | EST | Mm. 30060 | TITLE ESTs | | | gi = 1759904 | 972551 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07939 | UG75 Expression | EST | Mm. 30065 | TITLE aconitase 2, mitochondrial | GENE Aco2 | Aco-2\|Aco3\| aconitase 2 mitochondrial\| aconitase 3, mitochondrial\| | gi = 1505109 | 1149687 |
| IC07940 | UG75 Expression | EST | Mm. 30068 | TITLE ESTs | | | gi = 3745488 | 576450 |
| IC07941 | UG75 Expression | EST | Mm. 3007 | TITLE ESTs | | | gi = 1904041 | 719136 |
| IC07942 | UG75 Expression | EST | Mm. 30073 | OUTER MITOCHONDRIAL MEMBRANE [*Rattus norvegicus*] | | | gi = 6084337 | 777466 |
| IC07943 | UG75 Expression | EST | Mm. 30075 | TITLE ESTs, Weakly similar to SERUM PROTEIN MSE55 [*H. sapiens*] | | | gi = 1676137 | 534292 |
| IC07944 | UG75 Expression | EST | Mm. 30077 | TITLE ESTs | | | gi = 4767330 | 722277 |
| IC07945 | UG75 Expression | EST | Mm. 30078 | TITLE dendritic cell protein GA17 | GENE Ga17-pending | | gi = 3862891 | 959012 |
| IC07946 | UG75 Expression | EST | Mm. 30081 | TITLE ESTs | | | gi = 1325888 | 634937 |
| IC07947 | UG75 Expression | EST | Mm. 30091 | TITLE ESTs | | | gi = 1901136 | 635818 |
| IC07948 | UG75 Expression | EST | Mm. 30095 | TITLE ESTs, Weakly similar to similar to YIU2 protein [*C. elegans*] | | | gi = 2517760 | 750178 |
| IC07949 | UG75 Expression | EST | Mm. 30096 | TITLE ESTs, Weakly similar to weak similarity to collagens [*C. elegans*] | | | gi = 2263048 | 618798 |
| IC07950 | UG75 Expression | EST | Mm. 30099 | TITLE ESTs, Weakly similar to cleft lip and palate transmembrane protein 1 [*H. sapiens*] | | | gi = 1682349 | 894453 |
| IC07951 | UG75 Expression | EST | Mm. 3010 | TITLE ESTs, Weakly similar to ORF YNL061w [*S. cerevisiae*] | | | gi = 4766503 | 721046 |
| IC07952 | UG75 Expression | EST | Mm. 30102 | TITLE ESTs | | | gi = 3748138 | 576695 |
| IC07953 | UG75 Expression | EST | Mm. 30104 | TITLE ESTs | | | gi = 6515158 | 642730 |
| IC07954 | UG75 Expression | EST | Mm. 30108 | TITLE ESTs | | | gi = 1310642 | 1002488 |
| IC07955 | UG75 Expression | EST | Mm. 30109 | TITLE ESTs, Weakly similar to receptor DEC-205 [*M. musculus*] | | | gi = 4316384 | 622075 |
| IC07956 | UG75 Expression | EST | Mm. 30111 | TITLE ESTs | | | gi = 6756583 | 2648563 |
| IC07957 | UG75 Expression | EST | Mm. 30114 | TITLE ESTs, Weakly similar to cDNA EST EMBL:D75506 comes from this gene [*C. elegans*] | | | gi = 4726453 | 958767 |
| IC07958 | UG75 Expression | EST | Mm. 30115 | TITLE ESTs | | | gi = 1776623 | 642786 |
| IC07959 | UG75 Expression | EST | Mm. 30116 | TITLE ESTs | | | gi = 2454756 | 643670 |
| IC07960 | UG75 Expression | EST | Mm. 30119 | TITLE ESTs, Weakly similar to cholesterol 25-hydroxylase [*M. musculus*] | | | gi = 6083832 | 618951 |
| IC07961 | UG75 Expression | EST | Mm. 30120 | TITLE ESTs, Moderately similar to 40S RIBOSOMAL PROTEIN S27 [*Rattus norvegicus*] | | | gi = 2284480 | 598562 |
| IC07962 | UG75 Expression | EST | Mm. 30126 | TITLE ESTs, Moderately similar to Unknown gene product [*H. sapiens*] | | | gi = 1287294 | 1379165 |
| IC07963 | UG75 Expression | EST | Mm. 30127 | TITLE ESTs, Weakly similar to Similar to S. cerevisiae hypothetical protein L3111 [*H. sapiens*] | | | gi = 2917426 | 1293705 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07964 | UG75 Expression | EST | Mm. 30132 | TITLE ESTs, Weakly similar to (define not available 5931957) [*M. musculus*] | | | gi = 2305782 | 618609 |
| IC07965 | UG75 Expression | EST | Mm. 30133 | TITLE ethanol induced 6 | GENE Etohi6 | | gi = 1309692 | 1148939 |
| IC07966 | UG75 Expression | EST | Mm. 30136 | TITLE DNA segment, Chr 8, Wayne State University 96, expressed | GENE D8Wsu96e | | | 749526 |
| IC07967 | UG75 Expression | EST | Mm. 30137 | TITLE ESTs | | | gi = 5493234 | 764325 |
| IC07968 | UG75 Expression | EST | Mm. 30138 | TITLE ESTs, Weakly similar to keratin 2 epidermis [*M. musculus*] | | | gi = 1294007 | 750523 |
| IC07969 | UG75 Expression | EST | Mm. 3014 | PROTEIN, MITOCHONDRIAL PRECURSOR [*Neurospora crassa*] | | | gi = 6077904 | 599089 |
| IC07970 | UG75 Expression | EST | Mm. 30142 | TITLE DNA segment, Chr 15, Wayne State University 77, expressed | GENE D15Wsu77e | | | 1395474 |
| IC07971 | UG75 Expression | EST | Mm. 30143 | TITLE ESTs | | | gi = 2040613 | 576840 |
| IC07972 | UG75 Expression | EST | Mm. 30145 | TITLE ESTs | | | gi = 1675963 | 595971 |
| IC07973 | UG75 Expression | EST | Mm. 30152 | TITLE ESTs, Moderately similar to ribosomal protein L33-like protein [*H. sapiens*] | | | gi = 1485658 | 974034 |
| IC07974 | UG75 Expression | EST | Mm. 30153 | TITLE ESTs, Weakly similar to HYPOTHETICAL PROTEIN KIAA0009 [*H. sapiens*] | | | gi = 1318242 | 765522 |
| IC07975 | UG75 Expression | EST | Mm. 30157 | TITLE ESTs, Weakly similar to extendin [*M. musculus*] | | | gi = 2503315 | 1148637 |
| IC07976 | UG75 Expression | EST | Mm. 30158 | TITLE ESTs, Weakly similar to delta-6 fatty acid desaturase [*M. musculus*] | | | gi = 4434303 | 1367084 |
| IC07977 | UG75 Expression | EST | Mm. 30159 | TITLE ESTs | | | gi = 1309872 | 1279408 |
| IC07978 | UG75 Expression | EST | Mm. 30160 | TITLE ESTs | | | gi = 3055117 | 1020637 |
| IC07979 | UG75 Expression | EST | Mm. 30161 | TITLE ESTs, Weakly similar to KIAA0584 protein [*H. sapiens*] | | | gi = 5905544 | 1293929 |
| IC07980 | UG75 Expression | EST | Mm. 30162 | TITLE ESTs, Weakly similar to SPARC-related protein [*M. musculus*] | | | gi = 4603997 | 721826 |
| IC07981 | UG75 Expression | EST | Mm. 30163 | TITLE ESTs | | | gi = 4968106 | 1002264 |
| IC07982 | UG75 Expression | EST | Mm. 30166 | TITLE ESTs, Weakly similar to NADH-CYTOCHROME B5 REDUCTASE [*R. norvegicus*] | | | gi = 2520066 | 534006 |
| IC07983 | UG75 Expression | EST | Mm. 30167 | TITLE ESTs, Weakly similar to rjs [*M. musculus*] | | | gi = 6167937 | 1001433 |
| IC07984 | UG75 Expression | EST | Mm. 30169 | TITLE ESTs, Moderately similar to EPIDERMAL GROWTH FACTOR RECEPTOR SUBSTRATE SUBSTRATE 15 [*Homo sapiens*] | | | gi = 1325117 | 1226140 |
| IC07985 | UG75 Expression | EST | Mm. 30170 | TITLE ESTs | | | gi = 5337969 | 1140103 |
| IC07986 | UG75 Expression | EST | Mm. 30172 | TITLE ESTs | | | gi = 6521162 | 641684 |
| IC07987 | UG75 Expression | EST | Mm. 30173 | TITLE ESTs | | | gi = 6515684 | 619875 |
| IC07988 | UG75 Expression | EST | Mm. 30174 | TITLE ESTs | | | gi = 3161509 | 1362376 |
| IC07989 | UG75 Expression | EST | Mm. 30175 | TITLE ESTs | | | gi = 5493117 | 642816 |
| IC07990 | UG75 Expression | EST | Mm. 30177 | TITLE ESTs | | | gi = 3054734 | 597797 |
| IC07991 | UG75 Expression | EST | Mm. 30179 | TITLE ESTs | | | gi = 2523705 | 973077 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC07992 | UG75 Expression | EST | Mm. 30181 | TITLE ESTs, Moderately similar to epithelial protein up-regulated in carcinoma [*H. sapiens*] | | | gi = 4292650 | 550921 |
| IC07993 | UG75 Expression | EST | Mm. 30183 | TITLE ESTs, Weakly similar to COATOMER GAMMA SUBUNIT [*Saccharomyces cerevisiae*] | | | gi = 6749024 | 973531 |
| IC07994 | UG75 Expression | EST | Mm. 30189 | TITLE ESTs | | | gi = 1902275 | 718411 |
| IC07995 | UG75 Expression | EST | Mm. 30191 | TITLE ESTs, Weakly similar to RAS-RELATED PROTEIN RAB-2 [*M. musculus*] | | | gi = 1908270 | 973777 |
| IC07996 | UG75 Expression | EST | Mm. 30192 | TITLE ESTs | | | gi = 1682555 | 1139851 |
| IC07997 | UG75 Expression | EST | Mm. 30196 | TITLE ESTs, Weakly similar to HYPOTHETICAL UOG-1 PROTEIN [*M. musculus*] | | | gi = 5333765 | 972708 |
| IC07998 | UG75 Expression | EST | Mm. 30198 | TITLE ESTs, Weakly similar to HYPOTHETICAL 20.3 KD PROTEIN IN GCD14-POS18 INTERGENIC REGION [*Saccharomyces cerevisiae*] | | | gi = 4030301 | 1002114 |
| IC07999 | UG75 Expression | EST | Mm. 30202 | TITLE ESTs | | | gi = 4485021 | 551029 |
| IC08000 | UG75 Expression | EST | Mm. 30203 | TITLE ESTs, Weakly similar to unknown [*M. musculus*] | | | gi = 434044 | 1891036 |
| IC08001 | UG75 Expression | EST | Mm. 30208 | TITLE ESTs, Moderately similar to KIAA0264 [*H. sapiens*] | | | gi = 3294630 | 1264479 |
| IC08002 | UG75 Expression | EST | Mm. 30209 | TITLE ESTs | | | gi = 4273338 | 1225973 |
| IC08003 | UG75 Expression | EST | Mm. 3021 | TITLE ESTs | | | gi = 1904345 | 721073 |
| IC08004 | UG75 Expression | EST | Mm. 30212 | TITLE ESTs, Weakly similar to SPORULATION-SPECIFIC PROTEIN 1 [*Saccharomyces cerevisiae*] | | | gi = 2906958 | 973422 |
| IC08005 | UG75 Expression | EST | Mm. 3022 | TITLE ESTs | | | gi = 1771189 | 597825 |
| IC08006 | UG75 Expression | EST | Mm. 30220 | TITLE ESTs, Weakly similar to telencephalin precursor [*M. musculus*] | | | gi = 1330800 | 721470 |
| IC08007 | UG75 Expression | EST | Mm. 30221 | TITLE ESTs | | | gi = 2670783 | 1001976 |
| IC08008 | UG75 Expression | EST | Mm. 30222 | TITLE ESTs, Weakly similar to stromal cell-derived factor 2 [*M. musculus*] | | | gi = 4318908 | 720963 |
| IC08009 | UG75 Expression | EST | Mm. 30223 | TITLE ESTs | | | gi = 4274833 | 572921 |
| IC08010 | UG75 Expression | EST | Mm. 30224 | TITLE ESTs | | | gi = 4276328 | 374691 |
| IC08011 | UG75 Expression | EST | Mm. 30226 | TITLE ESTs, Weakly similar to SECRETORY CARRIER-ASSOCIATED MEMBRANE PROTEIN 3 [*M. musculus*] | | | gi = 1330462 | 598613 |
| IC08012 | UG75 Expression | EST | Mm. 30227 | TITLE ESTs | | | gi = 4274854 | 573071 |
| IC08013 | UG75 Expression | EST | Mm. 30229 | TITLE ESTs | | | gi = 1937314 | 596012 |
| IC08014 | UG75 Expression | EST | Mm. 30231 | TITLE ESTs | | | gi = 4596902 | 572815 |
| IC08015 | UG75 Expression | EST | Mm. 30232 | TITLE ESTs | | | gi = 2049047 | 751537 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08016 | UG75 Expression | EST | Mm. 30235 | TITLE ESTs, Moderately similar to hypothetical protein [H. sapiens] | | | gi = 6083682 | 722932 |
| IC08017 | UG75 Expression | EST | Mm. 30238 | TITLE ESTs | | | gi = 6167866 | 533289 |
| IC08018 | UG75 Expression | EST | Mm. 30239 | TITLE ESTs | | | gi = 3167888 | 573209 |
| IC08019 | UG75 Expression | EST | Mm. 30240 | TITLE ESTs | | | gi = 4798585 | 1137597 |
| IC08020 | UG75 Expression | EST | Mm. 30248 | TITLE ESTs | | | gi = 2518708 | 972386 |
| IC08021 | UG75 Expression | EST | Mm. 3025 | TITLE ESTs | | | gi = 6822381 | 718396 |
| IC08022 | UG75 Expression | EST | Mm. 30250 | TITLE DNA segment, Chr 18, Wayne State University 181, expressed | GENE D18Wsu181e | | | 972676 |
| IC08023 | UG75 Expression | EST | Mm. 30252 | TITLE ESTs | | | gi = 3956233 | 596660 |
| IC08024 | UG75 Expression | EST | Mm. 30256 | TITLE ESTs | | | gi = 2292259 | 972425 |
| IC08025 | UG75 Expression | EST | Mm. 30258 | TITLE ESTs | | | gi = 1699886 | 1295774 |
| IC08026 | UG75 Expression | EST | Mm. 30260 | TITLE ESTs | | | gi = 5819796 | 893978 |
| IC08027 | UG75 Expression | EST | Mm. 30261 | TITLE ESTs | | | gi = 1671400 | 749153 |
| IC08028 | UG75 Expression | EST | Mm. 30264 | TITLE ESTs | | | gi = 1671649 | 1020650 |
| IC08029 | UG75 Expression | EST | Mm. 30265 | TITLE ESTs | | | gi = 4730168 | 644760 |
| IC08030 | UG75 Expression | EST | Mm. 30266 | TITLE ESTs, Moderately similar to CCR4-ASSOCIATED FACTOR 1 [M. musculus] | | | gi = 2306592 | 622655 |
| IC08031 | UG75 Expression | EST | Mm. 30267 | TITLE ESTs | | | gi = 1325458 | 1294521 |
| IC08032 | UG75 Expression | EST | Mm. 30268 | TITLE ESTs | | | gi = 4615765 | 721581 |
| IC08033 | UG75 Expression | EST | Mm. 30272 | TITLE ESTs, Moderately similar to UBIQUITIN-CONJUGATING ENZYME E2-CDC34 COMPLEMENTING [Homo sapiens] | | | gi = 1428948 | 972739 |
| IC08034 | UG75 Expression | EST | Mm. 3028 | TITLE ESTs | | | gi = 2518253 | 637576 |
| IC08035 | UG75 Expression | EST | Mm. 3036 | TITLE ESTs | | | gi = 6515933 | 721861 |
| IC08036 | UG75 Expression | EST | Mm. 3037 | TITLE ESTs | | | gi = 4604374 | 620774 |
| IC08037 | UG75 Expression | EST | Mm. 30444 | TITLE ESTs | | | gi = 1756218 | 618638 |
| IC08038 | UG75 Expression | EST | Mm. 30445 | TITLE ESTs | | | gi = 1772134 | 643407 |
| IC08039 | UG75 Expression | EST | Mm. 30446 | TITLE ESTs | | | gi = 4444750 | 574493 |
| IC08040 | UG75 Expression | EST | Mm. 30448 | TITLE ESTs | | | gi = 3216772 | 1363173 |
| IC08041 | UG75 Expression | EST | Mm. 30449 | TITLE ESTs | | | gi = 4444846 | 575827 |
| IC08042 | UG75 Expression | EST | Mm. 30452 | TITLE ESTs | | | gi = 4444601 | 573864 |
| IC08043 | UG75 Expression | EST | Mm. 30453 | TITLE ESTs | | | gi = 1676891 | 573869 |
| IC08044 | UG75 Expression | EST | Mm. 30454 | TITLE ESTs | | | gi = 4283030 | 573937 |
| IC08045 | UG75 Expression | EST | Mm. 30455 | TITLE ESTs | | | gi = 1796589 | 574161 |
| IC08046 | UG75 Expression | EST | Mm. 30456 | TITLE ESTs, Weakly similar to weak similarity to SP: YAD5_CLOAB [C. elegans] | | | gi = 3100071 | 577174 |
| IC08047 | UG75 Expression | EST | Mm. 30457 | TITLE ESTs | | | gi = 1538808 | 576767 |
| IC08048 | UG75 Expression | EST | Mm. 30458 | TITLE ESTs | | | gi = 1677523 | 576838 |
| IC08049 | UG75 Expression | EST | Mm. 30459 | TITLE ESTs | | | gi = 4483835 | 576271 |
| IC08050 | UG75 Expression | EST | Mm. 30460 | TITLE ESTs | | | gi = 4483846 | 576341 |
| IC08051 | UG75 Expression | EST | Mm. 30462 | TITLE ESTs | | | gi = 1746542 | 620336 |
| IC08052 | UG75 Expression | EST | Mm. 30464 | TITLE ESTs | | | gi = 1287511 | 596108 |
| IC08053 | UG75 Expression | EST | Mm. 30466 | TITLE ESTs | | | gi = 1681747 | 596445 |
| IC08054 | UG75 Expression | EST | Mm. 30467 | TITLE ESTs | | | gi = 1795050 | 638514 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08055 | UG75 Expression | EST | Mm. 30468 | TITLE ESTs | | | gi = 1682350 | 576800 |
| IC08056 | UG75 Expression | EST | Mm. 30470 | TITLE ESTs | | | gi = 4444673 | 575028 |
| IC08057 | UG75 Expression | EST | Mm. 30471 | TITLE ESTs | | | gi = 4290585 | 577256 |
| IC08058 | UG75 Expression | EST | Mm. 30472 | TITLE ESTs | | | gi = 6822436 | 959187 |
| IC08059 | UG75 Expression | EST | Mm. 30474 | TITLE ESTs | | | gi = 4302798 | 596147 |
| IC08060 | UG75 Expression | EST | Mm. 30475 | TITLE ESTs | | | gi = 4302525 | 595907 |
| IC08061 | UG75 Expression | EST | Mm. 30476 | TITLE ESTs | | | gi = 4302560 | 595931 |
| IC08062 | UG75 Expression | EST | Mm. 30478 | TITLE ESTs | | | gi = 2200360 | 597280 |
| IC08063 | UG75 Expression | EST | Mm. 30479 | TITLE ESTs | | | gi = 1700687 | 596777 |
| IC08064 | UG75 Expression | EST | Mm. 30480 | TITLE ESTs | | | gi = 1701162 | 597022 |
| IC08065 | UG75 Expression | EST | Mm. 30481 | TITLE ESTs | | | gi = 4303116 | 596456 |
| IC08066 | UG75 Expression | EST | Mm. 30486 | TITLE ESTs | | | gi = 4299097 | 583004 |
| IC08067 | UG75 Expression | EST | Mm. 30488 | TITLE ESTs | | | gi = 4725775 | 583635 |
| IC08068 | UG75 Expression | EST | Mm. 30489 | TITLE ESTs | | | gi = 1936983 | 752481 |
| IC08069 | UG75 Expression | EST | Mm. 30490 | TITLE ESTs | | | gi = 4625110 | 582472 |
| IC08070 | UG75 Expression | EST | Mm. 30492 | TITLE ESTs | | | gi = 4307307 | 597083 |
| IC08071 | UG75 Expression | EST | Mm. 30495 | TITLE ESTs | | | gi = 4307510 | 597296 |
| IC08072 | UG75 Expression | EST | Mm. 30496 | TITLE ESTs | | | gi = 1715494 | 597372 |
| IC08073 | UG75 Expression | EST | Mm. 30497 | TITLE ESTs | | | gi = 4625080 | 581806 |
| IC08074 | UG75 Expression | EST | Mm. 30498 | TITLE ESTs | | | gi = 4725787 | 583744 |
| IC08075 | UG75 Expression | EST | Mm. 30499 | TITLE ESTs | | | gi = 1715910 | 596630 |
| IC08076 | UG75 Expression | EST | Mm. 3050 | TITLE ESTs | | | gi = 3372848 | 722038 |
| IC08077 | UG75 Expression | EST | Mm. 30500 | TITLE ESTs | | | gi = 1715912 | 596629 |
| IC08078 | UG75 Expression | EST | Mm. 30501 | TITLE ESTs | | | gi = 1724893 | 598231 |
| IC08079 | UG75 Expression | EST | Mm. 30502 | TITLE ESTs | | | gi = 1724959 | 582021 |
| IC08080 | UG75 Expression | EST | Mm. 30503 | TITLE ESTs | | | gi = 4726389 | 582945 |
| IC08081 | UG75 Expression | EST | Mm. 30505 | TITLE ESTs | | | gi = 4601086 | 597685 |
| IC08082 | UG75 Expression | EST | Mm. 30506 | TITLE ESTs | | | gi = 4032152 | 599244 |
| IC08083 | UG75 Expression | EST | Mm. 30507 | TITLE ESTs | | | gi = 1726106 | 581856 |
| IC08084 | UG75 Expression | EST | Mm. 30508 | TITLE ESTs | | | gi = 4301018 | 620976 |
| IC08085 | UG75 Expression | EST | Mm. 3051 | TITLE ESTs | | | gi = 4032078 | 722039 |
| IC08086 | UG75 Expression | EST | Mm. 30510 | TITLE ESTs | | | gi = 4625143 | 583253 |
| IC08087 | UG75 Expression | EST | Mm. 30511 | TITLE ESTs | | | gi = 3167613 | 598470 |
| IC08088 | UG75 Expression | EST | Mm. 30513 | TITLE ESTs | | | gi = 4374993 | 617258 |
| IC08089 | UG75 Expression | EST | Mm. 30515 | TITLE ESTs, Moderately similar to similar to a *C. elegans* protein encoded in cosmid K12D12(Z49069) [*H. sapiens*] | | | gi = 2197550 | 721548 |
| IC08090 | UG75 Expression | EST | Mm. 30516 | TITLE ESTs | | | gi = 4601269 | 598987 |
| IC08091 | UG75 Expression | EST | Mm. 30517 | TITLE ESTs | | | gi = 3160710 | 1226992 |
| IC08092 | UG75 Expression | EST | Mm. 30519 | TITLE ESTs | | | gi = 6559953 | 618584 |
| IC08093 | UG75 Expression | EST | Mm. 30520 | TITLE ESTs | | | gi = 4601200 | 598604 |
| IC08094 | UG75 Expression | EST | Mm. 30521 | TITLE ESTs | | | gi = 1739136 | 635611 |
| IC08095 | UG75 Expression | EST | Mm. 30524 | TITLE ESTs | | | gi = 4281814 | 635065 |
| IC08096 | UG75 Expression | EST | Mm. 30528 | TITLE ESTs | | | gi = 4601205 | 598648 |
| IC08097 | UG75 Expression | EST | Mm. 30529 | TITLE ESTs | | | gi = 1739772 | 597779 |
| IC08098 | UG75 Expression | EST | Mm. 30530 | TITLE ESTs | | | gi = 4601171 | 598397 |
| IC08099 | UG75 Expression | EST | Mm. 30531 | TITLE ESTs | | | gi = 4601823 | 634925 |
| IC08100 | UG75 Expression | EST | Mm. 30532 | TITLE ESTs | | | gi = 6824719 | 621867 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08101 | UG75 Expression | EST | Mm. 30535 | TITLE ESTs | | | gi = 1746601 | 598781 |
| IC08102 | UG75 Expression | EST | Mm. 30537 | TITLE ESTs | | | gi = 4601220 | 598741 |
| IC08103 | UG75 Expression | EST | Mm. 30540 | TITLE ESTs | | | gi = 4601248 | 598879 |
| IC08104 | UG75 Expression | EST | Mm. 30541 | TITLE ESTs, Weakly similar to KIAA0403 [H. sapiens] | | | gi = 4601258 | 598954 |
| IC08105 | UG75 Expression | EST | Mm. 30543 | TITLE ESTs | | | gi = 1752123 | 765244 |
| IC08106 | UG75 Expression | EST | Mm. 30545 | TITLE ESTs | | | gi = 4298639 | 617277 |
| IC08107 | UG75 Expression | EST | Mm. 30546 | TITLE ESTs | | | gi = 4702826 | 617368 |
| IC08108 | UG75 Expression | EST | Mm. 30547 | TITLE ESTs | | | gi = 6084010 | 1193574 |
| IC08109 | UG75 Expression | EST | Mm. 30548 | TITLE ESTs | | | gi = 1827019 | 618088 |
| IC08110 | UG75 Expression | EST | Mm. 30549 | TITLE ESTs | | | gi = 1749015 | 617465 |
| IC08111 | UG75 Expression | EST | Mm. 3055 | TITLE DNA segment, Chr 2, Abbott 2 expressed | GENE D2Abb2e | | | 722152 |
| IC08112 | UG75 Expression | EST | Mm. 30550 | TITLE ESTs | | | gi = 4702847 | 617567 |
| IC08113 | UG75 Expression | EST | Mm. 30553 | TITLE ESTs | | | gi = 4601599 | 619195 |
| IC08114 | UG75 Expression | EST | Mm. 30554 | TITLE ESTs | | | gi = 4613323 | 619988 |
| IC08115 | UG75 Expression | EST | Mm. 30555 | TITLE ESTs | | | gi = 4288946 | 620015 |
| IC08116 | UG75 Expression | EST | Mm. 30556 | TITLE ESTs | | | gi = 6824914 | 721306 |
| IC08117 | UG75 Expression | EST | Mm. 30558 | TITLE ESTs | | | gi = 4613251 | 619624 |
| IC08118 | UG75 Expression | EST | Mm. 30560 | TITLE ESTs | | | gi = 4613275 | 619750 |
| IC08119 | UG75 Expression | EST | Mm. 30561 | TITLE ESTs, Weakly similar to (define not available 5524691) [M. musculus] | | | gi = 1751983 | 619818 |
| IC08120 | UG75 Expression | EST | Mm. 30562 | TITLE ESTs | | | gi = 4703160 | 616682 |
| IC08121 | UG75 Expression | EST | Mm. 30564 | TITLE ESTs | | | gi = 4163423 | 620752 |
| IC08122 | UG75 Expression | EST | Mm. 30565 | TITLE ESTs | | | gi = 4613424 | 620754 |
| IC08123 | UG75 Expression | EST | Mm. 30566 | TITLE ESTs | | | gi = 1738661 | 616656 |
| IC08124 | UG75 Expression | EST | Mm. 30567 | TITLE ESTs | | | gi = 4703234 | 617217 |
| IC08125 | UG75 Expression | EST | Mm. 30568 | TITLE ESTs | | | gi = 1756028 | 617558 |
| IC08126 | UG75 Expression | EST | Mm. 30569 | TITLE ESTs | | | gi = 1756225 | 618662 |
| IC08127 | UG75 Expression | EST | Mm. 30570 | TITLE ESTs | | | gi = 2978912 | 618038 |
| IC08128 | UG75 Expression | EST | Mm. 30572 | TITLE ESTs, Weakly similar to Pro-Pol-dUTPase polyprotein [M. musculus] | | | gi = 4299913 | 618395 |
| IC08129 | UG75 Expression | EST | Mm. 30573 | TITLE ESTs | | | gi = 1756322 | 618823 |
| IC08130 | UG75 Expression | EST | Mm. 30574 | TITLE ESTs | | | gi = 1756326 | 618846 |
| IC08131 | UG75 Expression | EST | Mm. 30575 | TITLE ESTs | | | gi = 4702896 | 618198 |
| IC08132 | UG75 Expression | EST | Mm. 30576 | TITLE ESTs | | | gi = 4307098 | 618483 |
| IC08133 | UG75 Expression | EST | Mm. 30577 | TITLE ESTs | | | gi = 1756415 | 618848 |
| IC08134 | UG75 Expression | EST | Mm. 30579 | TITLE ESTs | | | gi = 1756689 | 619417 |
| IC08135 | UG75 Expression | EST | Mm. 30580 | TITLE ESTs | | | gi = 1756735 | 619381 |
| IC08136 | UG75 Expression | EST | Mm. 30581 | TITLE ESTs | | | gi = 1699774 | 596009 |
| IC08137 | UG75 Expression | EST | Mm. 30582 | TITLE ESTs, Weakly similar to RETROVIRUS-RELATED PROTEASE [H. sapiens] | | | gi = 4601606 | 619239 |
| IC08138 | UG75 Expression | EST | Mm. 30583 | TITLE ESTs | | | gi = 1756885 | 619261 |
| IC08139 | UG75 Expression | EST | Mm. 30584 | TITLE ESTs | | | gi = 4288058 | 619301 |
| IC08140 | UG75 Expression | EST | Mm. 30585 | TITLE ESTs | | | gi = 2989049 | 764399 |
| IC08141 | UG75 Expression | EST | Mm. 30586 | TITLE ESTs | | | gi = 4613267 | 619690 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08142 | UG75 Expression | EST | Mm. 30587 | TITLE ESTs | | | gi = 4613333 | 620047 |
| IC08143 | UG75 Expression | EST | Mm. 30588 | TITLE ESTs, Weakly similar to pIL2 hypothetical protein [R. norvegicus] | | | gi = 4613334 | 620055 |
| IC08144 | UG75 Expression | EST | Mm. 30589 | TITLE ESTs | | | gi = 4601333 | 621160 |
| IC08145 | UG75 Expression | EST | Mm. 30590 | TITLE ESTs | | | gi = 4613370 | 620287 |
| IC08146 | UG75 Expression | EST | Mm. 30591 | TITLE ESTs | | | gi = 4613319 | 619957 |
| IC08147 | UG75 Expression | EST | Mm. 30592 | TITLE ESTs | | | gi = 1759374 | 621047 |
| IC08148 | UG75 Expression | EST | Mm. 30593 | TITLE ESTs | | | gi = 1759419 | 620451 |
| IC08149 | UG75 Expression | EST | Mm. 30594 | TITLE ESTs | | | gi = 4613420 | 620736 |
| IC08150 | UG75 Expression | EST | Mm. 30595 | TITLE ESTs | | | gi = 1759686 | 620936 |
| IC08151 | UG75 Expression | EST | Mm. 30596 | TITLE ESTs, Weakly similar to BAT2 [M. musculus] | | | gi = 4442025 | 621080 |
| IC08152 | UG75 Expression | EST | Mm. 30597 | TITLE ESTs | | | gi = 1760102 | 621486 |
| IC08153 | UG75 Expression | EST | Mm. 30598 | TITLE ESTs, Weakly similar to endocrine regulator [H. sapiens] | | | gi = 1765561 | 636449 |
| IC08154 | UG75 Expression | EST | Mm. 30599 | TITLE ESTs | | | gi = 4483585 | 636564 |
| IC08155 | UG75 Expression | EST | Mm. 30600 | TITLE ESTs, Weakly similar to EGF repeat transmembrane protein [M. musculus] | | | gi = 1700026 | 596238 |
| IC08156 | UG75 Expression | EST | Mm. 30603 | TITLE ESTs | | | gi = 4723605 | 636036 |
| IC08157 | UG75 Expression | EST | Mm. 30604 | TITLE ESTs | | | gi = 4723646 | 636368 |
| IC08158 | UG75 Expression | EST | Mm. 30605 | TITLE ESTs | | | gi = 1767005 | 636804 |
| IC08159 | UG75 Expression | EST | Mm. 30606 | TITLE ESTs | | | gi = 4729842 | 1002281 |
| IC08160 | UG75 Expression | EST | Mm. 30607 | TITLE ESTs, Weakly similar to similar to acid phosphatase [C. elegans] | | | gi = 2292666 | 958523 |
| IC08161 | UG75 Expression | EST | Mm. 30608 | TITLE ESTs, Weakly similar to unknown [H. sapiens] | | | gi = 1514807 | 583256 |
| IC08162 | UG75 Expression | EST | Mm. 30609 | TITLE ESTs | | | gi = 4600881 | 621720 |
| IC08163 | UG75 Expression | EST | Mm. 30610 | TITLE ESTs | | | gi = 4600879 | 621685 |
| IC08164 | UG75 Expression | EST | Mm. 30611 | TITLE ESTs | | | gi = 5475472 | 621793 |
| IC08165 | UG75 Expression | EST | Mm. 30612 | TITLE ESTs | | | gi = 1767599 | 557895 |
| IC08166 | UG75 Expression | EST | Mm. 30613 | TITLE ESTs | | | gi = 4483456 | 622305 |
| IC08167 | UG75 Expression | EST | Mm. 30614 | TITLE ESTs | | | gi = 5214857 | 642958 |
| IC08168 | UG75 Expression | EST | Mm. 30615 | TITLE ESTs | | | gi = 4723693 | 636958 |
| IC08169 | UG75 Expression | EST | Mm. 30616 | TITLE ESTs | | | gi = 4295856 | 637691 |
| IC08170 | UG75 Expression | EST | Mm. 30618 | TITLE ESTs | | | gi = 4663862 | 642860 |
| IC08171 | UG75 Expression | EST | Mm. 30619 | TITLE ESTs | | | gi = 4305120 | 642886 |
| IC08172 | UG75 Expression | EST | Mm. 30620 | TITLE ESTs | | | gi = 4305203 | 643012 |
| IC08173 | UG75 Expression | EST | Mm. 30621 | TITLE ESTs | | | gi = 4663854 | 642793 |
| IC08174 | UG75 Expression | EST | Mm. 30622 | TITLE ESTs | | | gi = 4295276 | 637072 |
| IC08175 | UG75 Expression | EST | Mm. 30623 | TITLE ESTs | | | gi = 1772004 | 597763 |
| IC08176 | UG75 Expression | EST | Mm. 30624 | TITLE ESTs | | | gi = 4305364 | 643248 |
| IC08177 | UG75 Expression | EST | Mm. 30625 | TITLE ESTs | | | gi = 4305371 | 643250 |
| IC08178 | UG75 Expression | EST | Mm. 30626 | TITLE ESTs | | | gi = 1776274 | 637133 |
| IC08179 | UG75 Expression | EST | Mm. 30627 | TITLE ESTs | | | gi = 1776356 | 635274 |
| IC08180 | UG75 Expression | EST | Mm. 30629 | TITLE ESTs | | | gi = 4703230 | 617185 |
| IC08181 | UG75 Expression | EST | Mm. 30630 | TITLE ESTs | | | gi = 4295870 | 637814 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08182 | UG75 Expression | EST | Mm. 30631 | TITLE ESTs | | | gi = 4663909 | 643306 |
| IC08183 | UG75 Expression | EST | Mm. 30632 | TITLE ESTs | | | gi = 1776630 | 637257 |
| IC08184 | UG75 Expression | EST | Mm. 30633 | TITLE ESTs | | | gi = 1776777 | 642492 |
| IC08185 | UG75 Expression | EST | Mm. 30634 | TITLE ESTs | | | gi = 1776787 | 642427 |
| IC08186 | UG75 Expression | EST | Mm. 30636 | TITLE ESTs | | | gi = 4615187 | 642473 |
| IC08187 | UG75 Expression | EST | Mm. 30637 | TITLE ESTs | | | gi = 3956200 | 636337 |
| IC08188 | UG75 Expression | EST | Mm. 30638 | TITLE ESTs, Weakly similar to TYROSINE-PROTEIN KINASE JAK3 [M. musculus] | | | gi = 4725096 | 636648 |
| IC08189 | UG75 Expression | EST | Mm. 30639 | TITLE ESTs | | | gi = 4725102 | 636674 |
| IC08190 | UG75 Expression | EST | Mm. 30640 | TITLE ESTs | | | gi = 4725111 | 1002573 |
| IC08191 | UG75 Expression | EST | Mm. 30641 | TITLE ESTs | | | gi = 4216842 | 637870 |
| IC08192 | UG75 Expression | EST | Mm. 30642 | TITLE ESTs | | | gi = 4305476 | 643323 |
| IC08193 | UG75 Expression | EST | Mm. 30643 | TITLE ESTs | | | gi = 5910392 | 1002757 |
| IC08194 | UG75 Expression | EST | Mm. 30646 | TITLE ESTs | | | gi = 648006 | 638229 |
| IC08195 | UG75 Expression | EST | Mm. 30647 | TITLE ESTs, Moderately similar to HYPOTHETICAL PROTEIN KIAA0036 [H. sapiens] | | | gi = 1794430 | 764657 |
| IC08196 | UG75 Expression | EST | Mm. 30648 | TITLE ESTs, Moderately similar to RIBOSOMAL PROTEIN S6 KINASE [Homo sapiens] | | | gi = 4405233 | 1296107 |
| IC08197 | UG75 Expression | EST | Mm. 30649 | TITLE ESTs [H. sapiens] | | | gi = 4257995 | 1038484 |
| IC08198 | UG75 Expression | EST | Mm. 30650 | TITLE ESTs | | | gi = 1796515 | 643649 |
| IC08199 | UG75 Expression | EST | Mm. 30652 | TITLE ESTs | | | gi = 6283722 | 643887 |
| IC08200 | UG75 Expression | EST | Mm. 30653 | TITLE ESTs | | | gi = 4296374 | 641083 |
| IC08201 | UG75 Expression | EST | Mm. 30654 | TITLE ESTs | | | gi = 4723680 | 643824 |
| IC08202 | UG75 Expression | EST | Mm. 30655 | TITLE ESTs | | | gi = 4296367 | 640718 |
| IC08203 | UG75 Expression | EST | Mm. 30656 | TITLE ESTs | | | gi = 4296395 | 640725 |
| IC08204 | UG75 Expression | EST | Mm. 30658 | TITLE ESTs | | | gi = 1865215 | 643707 |
| IC08205 | UG75 Expression | EST | Mm. 30659 | TITLE ESTs | | | gi = 4216485 | 643739 |
| IC08206 | UG75 Expression | EST | Mm. 30660 | TITLE ESTs | | | gi = 5907993 | 643850 |
| IC08207 | UG75 Expression | EST | Mm. 30661 | TITLE ESTs | | | gi = 4373957 | 641010 |
| IC08208 | UG75 Expression | EST | Mm. 30662 | TITLE ESTs | | | gi = 1801009 | 640937 |
| IC08209 | UG75 Expression | EST | Mm. 30663 | TITLE ESTs | | | gi = 1801097 | 644297 |
| IC08210 | UG75 Expression | EST | Mm. 30665 | TITLE ESTs | | | gi = 1801111 | 644350 |
| IC08211 | UG75 Expression | EST | Mm. 30666 | TITLE ESTs | | | gi = 2406287 | 1225474 |
| IC08212 | UG75 Expression | EST | Mm. 30667 | TITLE ESTs | | | gi = 4291242 | 636618 |
| IC08213 | UG75 Expression | EST | Mm. 30670 | TITLE ESTs | | | gi = 1800958 | 641029 |
| IC08214 | UG75 Expression | EST | Mm. 30678 | TITLE ESTs | | | gi = 5125963 | 749766 |
| IC08215 | UG75 Expression | EST | Mm. 30679 | TITLE ESTs | | | gi = 4307219 | 644118 |
| IC08216 | UG75 Expression | EST | Mm. 30683 | TITLE ESTs | | | gi = 4297206 | 644895 |
| IC08217 | UG75 Expression | EST | Mm. 30684 | TITLE ESTs | | | gi = 4615105 | 641939 |
| IC08218 | UG75 Expression | EST | Mm. 30685 | TITLE ESTs | | | gi = 4615147 | 642176 |
| IC08219 | UG75 Expression | EST | Mm. 30686 | TITLE ESTs | | | gi = 4615140 | 642162 |
| IC08220 | UG75 Expression | EST | Mm. 30687 | TITLE ESTs | | | gi = 1811046 | 642264 |
| IC08221 | UG75 Expression | EST | Mm. 30688 | TITLE ESTs | | | gi = 1309549 | 637894 |
| IC08222 | UG75 Expression | EST | Mm. 30689 | TITLE ESTs | | | gi = 4615171 | 1395706 |
| IC08223 | UG75 Expression | EST | Mm. 3069 | TITLE ESTs | | | gi = 5668381 | 1382342 |
| IC08224 | UG75 Expression | EST | Mm. 30692 | TITLE ESTs | | | gi = 1825953 | 635372 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08225 | UG75 Expression | EST | Mm. 30693 | TITLE ESTs | | | gi = 2646804 | 617452 |
| IC08226 | UG75 Expression | EST | Mm. 30699 | TITLE ESTs | | | gi = 4615128 | 621086 |
| IC08227 | UG75 Expression | EST | Mm. 307 | TITLE ESTs | | | gi = 1756512 | 596179 |
| IC08228 | UG75 Expression | EST | Mm. 30702 | TITLE ESTs | | | gi = 4375020 | 634692 |
| IC08229 | UG75 Expression | EST | Mm. 30703 | TITLE ESTs | | | gi = 4444640 | 574814 |
| IC08230 | UG75 Expression | EST | Mm. 30705 | TITLE ESTs | | | gi = 2523663 | 1001619 |
| IC08231 | UG75 Expression | EST | Mm. 30708 | TITLE ESTs | | | gi = 4723754 | 581913 |
| IC08232 | UG75 Expression | EST | Mm. 30709 | TITLE ESTs | | | gi = 2262687 | 790063 |
| IC08233 | UG75 Expression | EST | Mm. 30710 | TITLE ESTs | | | gi = 2049036 | 1279180 |
| IC08234 | UG75 Expression | EST | Mm. 30713 | TITLE ESTs | | | gi = 1841666 | 717778 |
| IC08235 | UG75 Expression | EST | Mm. 30714 | TITLE ESTs | | | gi = 1936412 | 750932 |
| IC08236 | UG75 Expression | EST | Mm. 30718 | TITLE ESTs, Moderately similar to HYPOTHETICAL 11.4 KD PROTEIN C13G6.04 IN CHROMOSOME I [Schizosaccharomyces pombe] | | | gi = 6085754 | 1367027 |
| IC08237 | UG75 Expression | EST | Mm. 30719 | TITLE ESTs | | | gi = 6100252 | 583033 |
| IC08238 | UG75 Expression | EST | Mm. 30727 | TITLE ESTs | | | gi = 4307202 | 619170 |
| IC08239 | UG75 Expression | EST | Mm. 30734 | TITLE ESTs | | | gi = 2053418 | 1394994 |
| IC08240 | UG75 Expression | EST | Mm. 30735 | TITLE ESTs, Moderately similar to hypothetical protein [H. sapiens] | | | gi = 1756564 | 618221 |
| IC08241 | UG75 Expression | EST | Mm. 30736 | TITLE ESTs | | | gi = 4315524 | 717839 |
| IC08242 | UG75 Expression | EST | Mm. 30737 | TITLE ESTs, Weakly similar to minor expressed alternative spliced form [H. sapiens] | | | gi = 1888045 | 1020822 |
| IC08243 | UG75 Expression | EST | Mm. 30740 | | | | gi = 4297122 | 722326 |
| IC08244 | UG75 Expression | EST | Mm. 30741 | TITLE ESTs | | | gi = 4317765 | 723087 |
| IC08245 | UG75 Expression | EST | Mm. 30742 | TITLE ESTs | | | gi = 4317778 | 723159 |
| IC08246 | UG75 Expression | EST | Mm. 30743 | TITLE ESTs | | | gi = 4317780 | 1001411 |
| IC08247 | UG75 Expression | EST | Mm. 30744 | TITLE ESTs | | | gi = 4783032 | 974004 |
| IC08248 | UG75 Expression | EST | Mm. 30745 | TITLE ESTs | | | gi = 1740181 | 621628 |
| IC08249 | UG76 LID366 B cell | EST | Mm. 30747 | TITLE ESTs | | | gi = 7315475 | 1066373 |
| IC08250 | UG75 Expression | EST | Mm. 30748 | TITLE ESTs | | | gi = 4318782 | 719317 |
| IC08251 | UG75 Expression | EST | Mm. 30749 | TITLE ESTs | | | gi = 4764612 | 719336 |
| IC08252 | UG75 Expression | EST | Mm. 30752 | TITLE ESTs | | | gi = 1527864 | 619663 |
| IC08253 | UG75 Expression | EST | Mm. 30754 | TITLE ESTs | | | gi = 1756088 | 749167 |
| IC08254 | UG75 Expression | EST | Mm. 30755 | TITLE ESTs | | | gi = 4604343 | 617668 |
| IC08255 | UG75 Expression | EST | Mm. 30756 | TITLE ESTs | | | gi = 6638276 | 721729 |
| IC08256 | UG75 Expression | EST | Mm. 30757 | TITLE ESTs | | | gi = 4317801 | 723530 |
| IC08257 | UG75 Expression | EST | Mm. 30758 | TITLE ESTs | | | gi = 2462004 | 764180 |
| IC08258 | UG75 Expression | EST | Mm. 30759 | TITLE ESTs, Weakly similar to PROBABLE ATP-DEPENDENT RNA HELICASE DDX10 [H. sapiens] | | | gi = 4318800 | 719484 |
| IC08259 | UG75 Expression | EST | Mm. 30760 | TITLE ESTs | | | gi = 1901524 | 721348 |
| IC08260 | UG75 Expression | EST | Mm. 30761 | TITLE ESTs | | | gi = 1901530 | 598130 |
| IC08261 | UG75 Expression | EST | Mm. 30762 | TITLE ESTs, Moderately similar to MO25 PROTEIN [Mus musculus] | | | gi = 2503391 | 718633 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08262 | UG75 Expression | EST | Mm. 30763 | TITLE ESTs, Weakly similar to TESTIS-SPECIFIC PROTEIN PBS13 [M. musculus] | | | gi = 1768011 | 622920 |
| IC08263 | UG75 Expression | EST | Mm. 30764 | TITLE ESTs | | | gi = 4315196 | 718152 |
| IC08264 | UG75 Expression | EST | Mm. 30766 | TITLE ESTs | | | gi = 3067369 | 1002697 |
| IC08265 | UG75 Expression | EST | Mm. 30767 | TITLE ESTs, Weakly similar to probably transcription regulator NT fin12 [M. musculus] | | | gi = 4296626 | 622253 |
| IC08266 | UG75 Expression | EST | Mm. 30768 | TITLE ESTs | | | gi = 4318926 | 721063 |
| IC08267 | UG75 Expression | EST | Mm. 30769 | TITLE ESTs | | | gi = 5910461 | 721080 |
| IC08268 | UG75 Expression | EST | Mm. 30770 | TITLE ESTs | | | gi = 4318892 | 720884 |
| IC08269 | UG75 Expression | EST | Mm. 30771 | TITLE ESTs, Weakly similar to K11C4.2 [C. elegans] | | | gi = 2292094 | 721172 |
| IC08270 | UG75 Expression | EST | Mm. 30772 | TITLE ESTs | | | gi = 4318896 | 720890 |
| IC08271 | UG75 Expression | EST | Mm. 30774 | TITLE ESTs | | | gi = 4318864 | 720673 |
| IC08272 | UG75 Expression | EST | Mm. 30775 | TITLE ESTs | | | gi = 3159082 | 764556 |
| IC08273 | UG75 Expression | EST | Mm. 30776 | TITLE ESTs | | | gi = 4317792 | 723370 |
| IC08274 | UG75 Expression | EST | Mm. 30777 | TITLE ESTs | | | gi = 4031799 | 1001446 |
| IC08275 | UG75 Expression | EST | Mm. 30778 | TITLE ESTs | | | gi = 4317798 | 723313 |
| IC08276 | UG75 Expression | EST | Mm. 30780 | TITLE ESTs, Weakly similar to ELASTASE 2 PRECURSOR [M. musculus] | | | gi = 4401851 | 1746111 |
| IC08277 | UG75 Expression | EST | Mm. 30781 | TITLE ESTs | | | gi = 4373868 | 959489 |
| IC08278 | UG75 Expression | EST | Mm. 30782 | TITLE ESTs | | | gi = 1772180 | 764279 |
| IC08279 | UG75 Expression | EST | Mm. 30783 | TITLE ESTs | | | gi = 2292263 | 573473 |
| IC08280 | UG75 Expression | EST | Mm. 30789 | TITLE ESTs | | | gi = 4314953 | 1265049 |
| IC08281 | UG75 Expression | EST | Mm. 30792 | TITLE ESTs | | | gi = 4615760 | 764427 |
| IC08282 | UG75 Expression | EST | Mm. 30794 | TITLE ESTs | | | gi = 4409126 | 621082 |
| IC08283 | UG75 Expression | EST | Mm. 30795 | TITLE ESTs | | | gi = 1912932 | 764607 |
| IC08284 | UG75 Expression | EST | Mm. 30796 | TITLE ESTs | | | gi = 4409163 | 765163 |
| IC08285 | UG75 Expression | EST | Mm. 30797 | TITLE ESTs | | | gi = 4275338 | 765259 |
| IC08286 | UG75 Expression | EST | Mm. 30799 | TITLE ESTs | | | gi = 1777028 | 636925 |
| IC08287 | UG75 Expression | EST | Mm. 3080 | TITLE ESTs | | | gi = 1671486 | 723314 |
| IC08288 | UG75 Expression | EST | Mm. 30800 | TITLE ESTs | | | gi = 1767776 | 622283 |
| IC08289 | UG75 Expression | EST | Mm. 30801 | TITLE ESTs | | | gi = 5497427 | 765600 |
| IC08290 | UG75 Expression | EST | Mm. 30802 | TITLE ESTs | | | gi = 3299377 | 765304 |
| IC08291 | UG75 Expression | EST | Mm. 30803 | TITLE ESTs | | | gi = 4303269 | 765355 |
| IC08292 | UG75 Expression | EST | Mm. 30804 | TITLE ESTs | | | gi = 4303424 | 765497 |
| IC08293 | UG75 Expression | EST | Mm. 30805 | TITLE ESTs, Moderately similar to MEMBRANE-ASSOCIATED PROTEIN HEM-2 [Mus musculus] | | | gi = 2962285 | 765813 |
| IC08294 | UG75 Expression | EST | Mm. 30807 | TITLE ESTs | | | gi = 1911344 | 764395 |
| IC08295 | UG75 Expression | EST | Mm. 30808 | TITLE ESTs | | | gi = 6078316 | 641520 |
| IC08296 | UG75 Expression | EST | Mm. 30809 | TITLE ESTs | | | gi = 6096831 | 1279215 |
| IC08297 | UG75 Expression | EST | Mm. 30810 | TITLE ESTs, Moderately similar to S1-1 protein [R. norvegicus] | | | gi = 5333875 | 777391 |
| IC08298 | UG75 Expression | EST | Mm. 30811 | TITLE ESTs | | | gi = 1756716 | 777225 |
| IC08299 | UG75 Expression | EST | Mm. 30812 | TITLE ESTs | | | gi = 4407812 | 777585 |
| IC08300 | UG75 Expression | EST | Mm. 30813 | TITLE ESTs | | | gi = 5338591 | 777313 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08301 | UG75 Expression | EST | Mm. 30815 | TITLE ESTs | | | gi = 2288615 | 621942 |
| IC08302 | UG75 Expression | EST | Mm. 30816 | TITLE ESTs | | | gi = 4615722 | 764178 |
| IC08303 | UG75 Expression | EST | Mm. 30817 | TITLE ESTs | | | gi = 1931944 | 764137 |
| IC08304 | UG75 Expression | EST | Mm. 30819 | TITLE ESTs | | | gi = 4373725 | 777689 |
| IC08305 | UG75 Expression | EST | Mm. 30822 | TITLE ESTs | | | gi = 4407473 | 752234 |
| IC08306 | UG75 Expression | EST | Mm. 30823 | TITLE ESTs | | | gi = 4316643 | 750935 |
| IC08307 | UG75 Expression | EST | Mm. 30825 | TITLE ESTs | | | gi = 4600721 | 596043 |
| IC08308 | UG75 Expression | EST | Mm. 30827 | TITLE ESTs | | | gi = 1936668 | 750946 |
| IC08309 | UG75 Expression | EST | Mm. 30828 | TITLE ESTs | | | gi = 1936938 | 750995 |
| IC08310 | UG75 Expression | EST | Mm. 30829 | TITLE ESTs | | | gi = 1936952 | 751283 |
| IC08311 | UG75 Expression | EST | Mm. 30830 | TITLE ESTs | | | gi = 4407500 | 752488 |
| IC08312 | UG75 Expression | EST | Mm. 30831 | TITLE ESTs | | | gi = 6168003 | 642347 |
| IC08313 | UG75 Expression | EST | Mm. 30832 | TITLE ESTs | | | gi = 4663910 | 596816 |
| IC08314 | UG75 Expression | EST | Mm. 30833 | TITLE ESTs | | | gi = 4407597 | 751186 |
| IC08315 | UG75 Expression | EST | Mm. 30834 | TITLE ESTs | | | gi = 4831274 | 751190 |
| IC08316 | UG75 Expression | EST | Mm. 30835 | TITLE ESTs | | | gi = 6521192 | 749321 |
| IC08317 | UG75 Expression | EST | Mm. 30836 | TITLE ESTs | | | gi = 2041953 | 637588 |
| IC08318 | UG75 Expression | EST | Mm. 30847 | TITLE ESTs | | | gi = 4441765 | 749273 |
| IC08319 | UG75 Expression | EST | Mm. 30848 | TITLE ESTs | | | gi = 4304188 | 749891 |
| IC08320 | UG75 Expression | EST | Mm. 30849 | TITLE ESTs | | | gi = 1290081 | 620318 |
| IC08321 | UG75 Expression | EST | Mm. 3085 | TITLE ESTs, Weakly similar to plexin 1 [M. musculus] | | | gi = 2966561 | 620652 |
| IC08322 | UG75 Expression | EST | Mm. 30850 | TITLE ESTs | | | gi = 5490475 | 751630 |
| IC08323 | UG75 Expression | EST | Mm. 30851 | TITLE ESTs | | | gi = 3684322 | 616941 |
| IC08324 | UG75 Expression | EST | Mm. 30853 | TITLE ESTs | | | gi = 4407646 | 751618 |
| IC08325 | UG75 Expression | EST | Mm. 30854 | TITLE ESTs | | | gi = 4407652 | 751639 |
| IC08326 | UG75 Expression | EST | Mm. 30857 | TITLE ESTs | | | gi = 4284420 | 574688 |
| IC08327 | UG75 Expression | EST | Mm. 30860 | TITLE ESTs | | | gi = 2065664 | 618312 |
| IC08328 | UG75 Expression | EST | Mm. 30866 | TITLE ESTs | | | gi = 5469196 | 1225163 |
| IC08329 | UG75 Expression | EST | Mm. 30869 | TITLE ESTs | | | gi = 3519827 | 622974 |
| IC08330 | UG75 Expression | EST | Mm. 30874 | TITLE ESTs | | | gi = 1447487 | 596947 |
| IC08331 | UG75 Expression | EST | Mm. 30880 | TITLE ESTs | | | gi = 4730175 | 1002829 |
| IC08332 | UG75 Expression | EST | Mm. 30885 | TITLE ESTs | | | gi = 3686499 | 1446991 |
| IC08333 | UG75 Expression | EST | Mm. 30886 | TITLE ESTs, Weakly similar to KIAA0793 protein [H. sapiens] | | | gi = 6515914 | 1447163 |
| IC08334 | UG75 Expression | EST | Mm. 30888 | TITLE ESTs | | | gi = 5909921 | 1193639 |
| IC08335 | UG75 Expression | EST | Mm. 3089 | TITLE ESTs | | | gi = 4601303 | 599245 |
| IC08336 | UG75 Expression | EST | Mm. 30893 | TITLE ESTs | | | gi = 4725228 | 583375 |
| IC08337 | UG75 Expression | EST | Mm. 30898 | TITLE ESTs | | | gi = 2041225 | 751013 |
| IC08338 | UG75 Expression | EST | Mm. 309 | TITLE ESTs | | | gi = 2075737 | 596253 |
| IC08339 | UG75 Expression | EST | Mm. 30918 | TITLE ESTs | | | gi = 4485287 | 621883 |
| IC08340 | UG75 Expression | EST | Mm. 30921 | TITLE ESTs | | | gi = 1630409 | 720936 |
| IC08341 | UG75 Expression | EST | Mm. 30924 | TITLE ESTs | | | gi = 2187858 | 620818 |
| IC08342 | UG75 Expression | EST | Mm. 30927 | TITLE ESTs [H. sapiens] | | | gi = 4405073 | 634736 |
| IC08343 | UG75 Expression | EST | Mm. 30928 | TITLE ESTs, Weakly similar to MITOCHONDRIAL CARNITINE/ACYLCARNITINE CARRIER PROTEIN [R. norvegicus] | | | gi = 1282271 | 1149831 |
| IC08344 | UG75 Expression | EST | Mm. 30929 | TITLE ESTs | | | gi = 2288303 | 638162 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08345 | UG75 Expression | EST | Mm. 30930 | TITLE ESTs | | | gi = 4625165 | 583443 |
| IC08346 | UG75 Expression | EST | Mm. 30936 | TITLE ESTs | | | gi = 4407375 | 750507 |
| IC08347 | UG75 Expression | EST | Mm. 3094 | TITLE ESTs | | | gi = 4967411 | 752213 |
| IC08348 | UG75 Expression | EST | Mm. 30945 | TITLE ESTs | | | gi = 2202861 | 636569 |
| IC08349 | UG75 Expression | EST | Mm. 30950 | TITLE ESTs | | | gi = 2234619 | 573281 |
| IC08350 | UG75 Expression | EST | Mm. 30954 | TITLE ESTs | | | gi = 4613321 | 619970 |
| IC08351 | UG75 Expression | EST | Mm. 30961 | TITLE ESTs, Moderately similar to hypothetical protein [H. sapiens] | | | gi = 2503261 | 641500 |
| IC08352 | UG75 Expression | EST | Mm. 30965 | TITLE ESTs, Weakly similar to KIAA0971 protein [H. sapiens] | | | gi = 1776402 | 637815 |
| IC08353 | UG75 Expression | EST | Mm. 30969 | TITLE ESTs, Moderately similar to muscle glycogen phosphorylase [M. musculus] | | | gi = 2678473 | 959175 |
| IC08354 | UG75 Expression | EST | Mm. 30970 | TITLE ESTs, Weakly similar to unknown [H. sapiens] | | | gi = 1739435 | 764592 |
| IC08355 | UG75 Expression | EST | Mm. 30977 | TITLE ESTs | | | gi = 4373872 | 1293998 |
| IC08356 | UG75 Expression | EST | Mm. 30984 | TITLE ESTs | | | gi = 4622865 | 894097 |
| IC08357 | UG75 Expression | EST | Mm. 30986 | TITLE ESTs | | | gi = 2101804 | 576488 |
| IC08358 | UG75 Expression | EST | Mm. 30994 | TITLE ESTs, Moderately similar to TURNED ON AFTER DIVISION, 64 KD PROTEIN [Rattus norvegicus] | | | gi = 4604725 | 718815 |
| IC08359 | UG75 Expression | EST | Mm. 30998 | TITLE ESTs | | | gi = 4032081 | 582120 |
| IC08360 | UG75 Expression | EST | Mm. 31001 | TITLE ESTs | | | gi = 4283262 | 574162 |
| IC08361 | UG75 Expression | EST | Mm. 31012 | TITLE ESTs | | | gi = 3370213 | 620805 |
| IC08362 | UG75 Expression | EST | Mm. 31013 | TITLE ESTs | | | gi = 5489257 | 1225241 |
| IC08363 | UG75 Expression | EST | Mm. 31017 | TITLE ESTs | | | gi = 4402667 | 972824 |
| IC08364 | UG75 Expression | EST | Mm. 31018 | TITLE ESTs | | | gi = 3863407 | 972445 |
| IC08365 | UG75 Expression | EST | Mm. 31019 | TITLE ESTs | | | gi = 2331990 | 972695 |
| IC08366 | UG75 Expression | EST | Mm. 31022 | TITLE ESTs | | | gi = 4402777 | 973883 |
| IC08367 | UG75 Expression | EST | Mm. 31023 | TITLE ESTs, Weakly similar to [H. sapiens] | | | gi = 4405260 | 974001 |
| IC08368 | UG75 Expression | EST | Mm. 31024 | TITLE ESTs, Weakly similar to KIAA0704 protein [H. sapiens] | | | gi = 4802634 | 973591 |
| IC08369 | UG75 Expression | EST | Mm. 31025 | TITLE ESTs | | | gi = 2306080 | 617570 |
| IC08370 | UG75 Expression | EST | Mm. 31030 | TITLE ESTs | | | gi = 2333528 | 973319 |
| IC08371 | UG75 Expression | EST | Mm. 31031 | TITLE ESTs | | | gi = 4403821 | 972969 |
| IC08372 | UG75 Expression | EST | Mm. 31032 | TITLE ESTs | | | gi = 4403920 | 973326 |
| IC08373 | UG75 Expression | EST | Mm. 31037 | TITLE ESTs | | | gi = 4317562 | 1327923 |
| IC08374 | UG75 Expression | EST | Mm. 31043 | TITLE ESTs | | | gi = 3719979 | 617455 |
| IC08375 | UG75 Expression | EST | Mm. 31048 | TITLE ESTs | | | gi = 5495464 | 750182 |
| IC08376 | UG75 Expression | EST | Mm. 31051 | TITLE ESTs, Moderately similar to RRM RNA binding protein GRY-RBP [M. musculus] | | | gi = 3053863 | 777791 |
| IC08377 | UG75 Expression | EST | Mm. 31056 | TITLE ESTs, Weakly similar to K02B2.3 gene product [C. elegans] | | | gi = 3685440 | 1434581 |
| IC08378 | UG75 Expression | EST | Mm. 31062 | TITLE ESTs | | | gi = 2850575 | 622025 |
| IC08379 | UG75 Expression | EST | Mm. 31063 | TITLE ESTs | | | gi = 2406487 | 1294804 |
| IC08380 | UG75 Expression | EST | Mm. 31064 | TITLE ESTs | | | gi = 1715952 | 1002458 |
| IC08381 | UG75 Expression | EST | Mm. 31065 | TITLE ESTs | | | gi = 4615507 | 1002558 |
| IC08382 | UG75 Expression | EST | Mm. 31066 | TITLE ESTs | | | gi = 5477953 | 1002593 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08383 | UG75 Expression | EST | Mm. 31072 | TITLE ESTs | | | gi = 2963270 | 1264801 |
| IC08384 | UG75 Expression | EST | Mm. 31076 | TITLE ESTs, Weakly similar to GOB-4 [*M. musculus*] | | | gi = 1852739 | 533330 |
| IC08385 | UG75 Expression | EST | Mm. 31080 | TITLE ESTs | | | gi = 4404659 | 1002731 |
| IC08386 | UG75 Expression | EST | Mm. 31081 | TITLE ESTs | | | gi = 2456369 | 1002756 |
| IC08387 | UG75 Expression | EST | Mm. 31082 | TITLE ESTs | | | gi = 3954592 | 1149761 |
| IC08388 | UG75 Expression | EST | Mm. 31087 | TITLE ESTs | | | gi = 3296664 | 722451 |
| IC08389 | UG75 Expression | EST | Mm. 31091 | TITLE ESTs | | | gi = 1682873 | 578065 |
| IC08390 | UG75 Expression | EST | Mm. 31093 | TITLE ESTs | | | gi = 6940683 | 1149668 |
| IC08391 | UG75 Expression | EST | Mm. 31097 | TITLE ESTs | | | gi = 2200739 | 616685 |
| IC08392 | UG75 Expression | EST | Mm. 31098 | TITLE ESTs | | | gi = 4304083 | 641861 |
| IC08393 | UG75 Expression | EST | Mm. 31114 | TITLE ESTs | | | gi = 4606068 | 718390 |
| IC08394 | UG75 Expression | EST | Mm. 31152 | TITLE ESTs | | | gi = 1772097 | 597085 |
| IC08395 | UG75 Expression | EST | Mm. 31159 | TITLE ESTs | | | gi = 5907592 | 1020772 |
| IC08396 | UG75 Expression | EST | Mm. 3116 | TITLE ESTs | | | gi = 2273074 | 894114 |
| IC08397 | UG75 Expression | EST | Mm. 31160 | TITLE ESTs, Weakly similar to NIFS PROTEIN [*Bacillus subtilis*] | | | gi = 6517526 | 1020846 |
| IC08398 | UG75 Expression | EST | Mm. 31161 | TITLE ESTs | | | gi = 2729458 | 1148870 |
| IC08399 | UG75 Expression | EST | Mm. 31175 | TITLE ESTs | | | gi = 2591261 | 635853 |
| IC08400 | UG75 Expression | EST | Mm. 31176 | TITLE ESTs | | | gi = 2646013 | 1149769 |
| IC08401 | UG75 Expression | EST | Mm. 31183 | TITLE ESTs | | | gi = 2625274 | 1001541 |
| IC08402 | UG75 Expression | EST | Mm. 31184 | TITLE ESTs, Moderately similar to hypothetical protein [*H. sapiens*] | | | gi = 6521113 | 1001567 |
| IC08403 | UG75 Expression | EST | Mm. 31185 | TITLE ESTs | | | gi = 4401917 | 1001675 |
| IC08404 | UG75 Expression | EST | Mm. 31186 | TITLE ESTs | | | gi = 4374435 | 1001633 |
| IC08405 | UG75 Expression | EST | Mm. 31187 | TITLE ESTs | | | gi = 4597033 | 1001733 |
| IC08406 | UG75 Expression | EST | Mm. 31198 | TITLE ESTs | | | gi = 4967865 | 1149375 |
| IC08407 | UG75 Expression | EST | Mm. 31201 | TITLE ESTs | | | gi = 3054688 | 1327766 |
| IC08408 | UG75 Expression | EST | Mm. 31203 | TITLE ESTs | | | gi = 4403202 | 1093051 |
| IC08409 | UG75 Expression | EST | Mm. 31204 | TITLE ESTs | | | gi = 4441401 | 718244 |
| IC08410 | UG75 Expression | EST | Mm. 31206 | TITLE ESTs | | | gi = 2308383 | 764460 |
| IC08411 | UG75 Expression | EST | Mm. 3121 | TITLE ESTs, Weakly similar to PROTEIN PHOSPHATASES PP1 REGULATORY SUBUNIT SDS22 [*Schizosaccharomyces pombe*] | | | gi = 4968362 | 750702 |
| IC08412 | UG75 Expression | EST | Mm. 31213 | TITLE ESTs | | | gi = 4401944 | 1001839 |
| IC08413 | UG75 Expression | EST | Mm. 31215 | TITLE ESTs | | | gi = 5333870 | 619012 |
| IC08414 | UG75 Expression | EST | Mm. 31216 | TITLE ESTs | | | gi = 2670861 | 1002026 |
| IC08415 | UG75 Expression | EST | Mm. 31220 | TITLE ESTs | | | gi = 2690867 | 1226220 |
| IC08416 | UG75 Expression | EST | Mm. 31221 | TITLE ESTs | | | gi = 2288580 | 1193626 |
| IC08417 | UG75 Expression | EST | Mm. 31223 | TITLE ESTs | | | gi = 7194352 | 1378811 |
| IC08418 | UG75 Expression | EST | Mm. 31227 | TITLE ESTs | | | gi = 2811610 | 598272 |
| IC08419 | UG75 Expression | EST | Mm. 31228 | TITLE ESTs | | | gi = 1756649 | 618995 |
| IC08420 | UG75 Expression | EST | Mm. 31229 | TITLE ESTs | | | gi = 5492232 | 1263904 |
| IC08421 | UG75 Expression | EST | Mm. 31233 | TITLE ESTs, Weakly similar to KIAA0539 protein [*H. sapiens*] | | | gi = 5907041 | 576172 |
| IC08422 | UG75 Expression | EST | Mm. 31235 | TITLE ESTs | | | gi = 6645334 | 642379 |
| IC08423 | UG75 Expression | EST | Mm. 31236 | TITLE ESTs, Weakly similar to C30B5.6 [*C. elegans*] | | | gi = 1683974 | 575690 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08424 | UG75 Expression | EST | Mm. 31244 | TITLE ESTs | | | gi = 3099819 | 1329195 |
| IC08425 | UG75 Expression | EST | Mm. 31245 | TITLE ESTs, Moderately similar to BRDT [H. sapiens] | | | gi = 4316528 | 1226138 |
| IC08426 | UG75 Expression | EST | Mm. 31246 | TITLE ESTs | | | gi = 2775731 | 1226752 |
| IC08427 | UG75 Expression | EST | Mm. 31247 | TITLE ESTs | | | gi = 2775983 | 1226883 |
| IC08428 | UG75 Expression | EST | Mm. 31250 | TITLE ESTs | | | gi = 4293841 | 597334 |
| IC08429 | UG75 Expression | EST | Mm. 31253 | TITLE ESTs, Weakly similar to Lpe10p [S. cerevisiae] | | | gi = 1699833 | 596167 |
| IC08430 | UG75 Expression | EST | Mm. 31256 | TITLE ESTs | | | gi = 4317097 | 1428827 |
| IC08431 | UG75 Expression | EST | Mm. 31259 | TITLE ESTs | | | gi = 2720339 | 764050 |
| IC08432 | UG75 Expression | EST | Mm. 31266 | TITLE ESTs | | | gi = 1896405 | 577763 |
| IC08433 | UG75 Expression | EST | Mm. 31273 | TITLE ESTs | | | gi = 1852992 | 1295977 |
| IC08434 | UG75 Expression | EST | Mm. 31274 | TITLE ESTs | | | gi = 2915260 | 597651 |
| IC08435 | UG75 Expression | EST | Mm. 31282 | TITLE ESTs | | | gi = 2075779 | 1001772 |
| IC08436 | UG75 Expression | EST | Mm. 31297 | TITLE ESTs | | | gi = 6168012 | 575049 |
| IC08437 | UG75 Expression | EST | Mm. 31316 | TITLE ESTs | | | gi = 2919735 | 750753 |
| IC08438 | UG75 Expression | EST | Mm. 31319 | TITLE ESTs, Weakly similar to cullin 3 [H. sapiens] | | | gi = 5495468 | 1225623 |
| IC08439 | UG75 Expression | EST | Mm. 31321 | TITLE ESTs, Moderately similar to core promoter binding protein [M. musculus] | | | gi = 5124658 | 1361895 |
| IC08440 | UG75 Expression | EST | Mm. 31331 | TITLE ESTs | | | gi = 2990705 | 1264673 |
| IC08441 | UG75 Expression | EST | Mm. 31333 | TITLE ESTs | | | gi = 445014 | 596331 |
| IC08442 | UG75 Expression | EST | Mm. 31337 | TITLE ESTs | | | gi = 5492870 | 1294080 |
| IC08443 | UG75 Expression | EST | Mm. 31343 | TITLE ESTs | | | gi = 2076203 | 973443 |
| IC08444 | UG75 Expression | EST | Mm. 31344 | TITLE ESTs | | | gi = 3732356 | 1294499 |
| IC08445 | UG75 Expression | EST | Mm. 31345 | TITLE ESTs | | | gi = 4725200 | 574701 |
| IC08446 | UG75 Expression | EST | Mm. 31352 | TITLE ESTs | | | gi = 6558046 | 638216 |
| IC08447 | UG75 Expression | EST | Mm. 31353 | TITLE ESTs, Weakly similar to weakly similar to S. cerevisiae VPS16 protein [C. elegans] | | | gi = 3885047 | 1279934 |
| IC08448 | UG75 Expression | EST | Mm. 31355 | TITLE ESTs, Weakly similar to Weak similarity with myosin proteins [C. elegans] | | | gi = 3067014 | 1243273 |
| IC08449 | UG75 Expression | EST | Mm. 31357 | TITLE ESTs | | | gi = 4726379 | 1328781 |
| IC08450 | UG75 Expression | EST | Mm. 31361 | TITLE ESTs | | | gi = 1901721 | 1345191 |
| IC08451 | UG75 Expression | EST | Mm. 31362 | TITLE ESTs | | | gi = 3167714 | 643447 |
| IC08452 | UG75 Expression | EST | Mm. 31363 | TITLE ESTs | | | gi = 1726409 | 973660 |
| IC08453 | UG75 Expression | EST | Mm. 31367 | TITLE ESTs | | | gi = 4285374 | 599142 |
| IC08454 | UG75 Expression | EST | Mm. 31369 | TITLE ESTs, Moderately similar to pig-c protein [H. sapiens] | | | gi = 4315871 | 749855 |
| IC08455 | UG75 Expression | EST | Mm. 31374 | TITLE ESTs | | | gi = 3215757 | 642575 |
| IC08456 | UG76 LID366 B cell | EST | Mm. 31375 | TITLE ESTs | | | gi = 4766601 | 1248381 |
| IC08457 | UG75 Expression | EST | Mm. 31378 | TITLE ESTs, Weakly similar to regulator of G protein signaling 12 [H. sapiens] | | | gi = 3158715 | 620029 |
| IC08458 | UG75 Expression | EST | Mm. 31380 | TITLE ESTs | | | gi = 3954057 | 620885 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08459 | UG75 Expression | EST | Mm. 31381 | TITLE ESTs, Moderately similar to (defline not available 4092503) [R. norvegicus] | | | gi = 4723628 | 1279315 |
| IC08460 | UG75 Expression | EST | Mm. 31382 | TITLE ESTs | | | gi = 4764754 | 721714 |
| IC08461 | UG75 Expression | EST | Mm. 31392 | TITLE ESTs, Moderately similar to ALDEHYDE DEHYDROGENASE, CYTOSOLIC [Mus musculus] | | | gi = 1700526 | 958506 |
| IC08462 | UG75 Expression | EST | Mm. 31395 | TITLE ESTs, Weakly similar to vimentin protein [M. musculus] | | | gi = 5665841 | 621789 |
| IC08463 | UG75 Expression | EST | Mm. 31396 | TITLE ESTs | | | gi = 2721594 | 1378222 |
| IC08464 | UG75 Expression | EST | Mm. 31399 | TITLE ESTs | | | gi = 1724373 | 597579 |
| IC08465 | UG75 Expression | EST | Mm. 314 | TITLE ESTs | | | gi = 1681766 | 596515 |
| IC08466 | UG75 Expression | EST | Mm. 31400 | TITLE ESTs | | | gi = 3234562 | 752184 |
| IC08467 | UG75 Expression | EST | Mm. 31402 | TITLE ESTs | | | gi = 5819410 | 634522 |
| IC08468 | UG75 Expression | EST | Mm. 31403 | TITLE ESTs | | | gi = 3054783 | 617782 |
| IC08469 | UG75 Expression | EST | Mm. 31404 | TITLE ESTs | | | gi = 1751571 | 619391 |
| IC08470 | UG75 Expression | EST | Mm. 31405 | TITLE ESTs | | | gi = 2644672 | 777204 |
| IC08471 | UG75 Expression | EST | Mm. 31406 | TITLE ESTs | | | gi = 4725229 | 752473 |
| IC08472 | UG75 Expression | EST | Mm. 31407 | TITLE ESTs | | | gi = 4405463 | 1746075 |
| IC08473 | UG75 Expression | EST | Mm. 31408 | TITLE ESTs, Weakly similar to The KIAA0135 gene is related to pim-1 oncogene. [H. sapiens] | | | gi = 4316055 | 1383016 |
| IC08474 | UG75 Expression | EST | Mm. 31411 | TITLE ESTs | | | gi = 2412172 | 1002526 |
| IC08475 | UG75 Expression | EST | Mm. 31412 | TITLE ESTs | | | gi = 3286127 | 597678 |
| IC08476 | UG75 Expression | EST | Mm. 31416 | TITLE ESTs | | | gi = 2291629 | 597360 |
| IC08477 | UG75 Expression | EST | Mm. 31418 | TITLE ESTs | | | gi = 3296809 | 641416 |
| IC08478 | UG75 Expression | EST | Mm. 31420 | TITLE ESTs | | | gi = 3054878 | 1295560 |
| IC08479 | UG75 Expression | EST | Mm. 31421 | TITLE ESTs | | | gi = 5491858 | 972785 |
| IC08480 | UG75 Expression | EST | Mm. 31466 | TITLE ESTs, Weakly similar to HYPOTHETICAL 44.2 KD PROTEIN IN SCO2-MRF1 INTERGENIC REGION [Saccharomyces cerevisiae] | | | gi = 3376194 | 537733 |
| IC08481 | UG75 Expression | EST | Mm. 31486 | TITLE ESTs | | | gi = 3387270 | 598193 |
| IC08482 | UG75 Expression | EST | Mm. 31504 | TITLE ESTs | | | gi = 2965743 | 764550 |
| IC08483 | UG75 Expression | EST | Mm. 31508 | TITLE ESTs | | | gi = 3448973 | 558189 |
| IC08484 | UG75 Expression | EST | Mm. 31512 | TITLE ESTs, Weakly similar to RING1B protein [M. musculus] | | | gi = 3374832 | 636731 |
| IC08485 | UG75 Expression | EST | Mm. 31513 | TITLE ESTs | | | gi = 1842813 | 1378937 |
| IC08486 | UG75 Expression | EST | Mm. 31516 | TITLE ESTs, Weakly similar to ZINC FINGER PROTEIN 91 [H. sapiens] | | | gi = 2292340 | 622786 |
| IC08487 | UG75 Expression | EST | Mm. 31517 | TITLE ESTs | | | gi = 4615723 | 764182 |
| IC08488 | UG75 Expression | EST | Mm. 31524 | TITLE ESTs | | | gi = 4281486 | 1446280 |
| IC08489 | UG75 Expression | EST | Mm. 31527 | TITLE ESTs | | | gi = 1760164 | 621537 |
| IC08490 | UG75 Expression | EST | Mm. 31529 | TITLE ESTs, Weakly similar to BcDNA.LD26050 [D. melanogaster] | | | gi = 3681954 | 1429052 |
| IC08491 | UG75 Expression | EST | Mm. 31533 | TITLE ESTs | | | gi = 2305967 | 1148857 |
| IC08492 | UG75 Expression | EST | Mm. 31536 | TITLE ESTs | | | gi = 3883892 | 621627 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08493 | UG75 Expression | EST | Mm. 31537 | TITLE ESTs | | | gi = 5491871 | 619513 |
| IC08494 | UG75 Expression | EST | Mm. 31538 | TITLE ESTs | | | gi = 1904400 | 858941 |
| IC08495 | UG75 Expression | EST | Mm. 31540 | TITLE ESTs | | | gi = 5191501 | 641220 |
| IC08496 | UG75 Expression | EST | Mm. 31541 | TITLE ESTs | | | gi = 2193616 | 1294110 |
| IC08497 | UG75 Expression | EST | Mm. 31542 | TITLE ESTs | | | gi = 4307037 | 643832 |
| IC08498 | UG75 Expression | EST | Mm. 31543 | TITLE ESTs | | | gi = 2962578 | 1447018 |
| IC08499 | UG75 Expression | EST | Mm. 31544 | TITLE ESTs | | | gi = 4723750 | 1380293 |
| IC08500 | UG75 Expression | EST | Mm. 31546 | TITLE ESTs | | | gi = 5125802 | 718877 |
| IC08501 | UG75 Expression | EST | Mm. 31548 | TITLE ESTs | | | gi = 2080998 | 620345 |
| IC08502 | UG75 Expression | EST | Mm. 31550 | TITLE ESTs | | | gi = 4375619 | 5500855 |
| IC08503 | UG75 Expression | EST | Mm. 31556 | TITLE ESTs | | | gi = 3078870 | 642403 |
| IC08504 | UG75 Expression | EST | Mm. 31557 | TITLE ESTs | | | gi = 5498574 | 1327759 |
| IC08505 | UG75 Expression | EST | Mm. 31563 | TITLE ESTs, Weakly similar to hydrogen peroxide-inducible protein hic-5 [*M. musculus*] | | | gi = 4061735 | 583635 |
| IC08506 | UG75 Expression | EST | Mm. 31571 | TITLE ESTs | | | gi = 3926401 | 616791 |
| IC08507 | UG75 Expression | EST | Mm. 31586 | TITLE ESTs, Weakly similar to p140mDia [*M. musculus*] | | | gi = 6079100 | 621502 |
| IC08508 | UG75 Expression | EST | Mm. 31598 | TITLE ESTs | | | gi = 3979251 | 1294722 |
| IC08509 | UG75 Expression | EST | Mm. 31607 | TITLE ESTs | | | gi = 2906957 | 619087 |
| IC08510 | UG75 Expression | EST | Mm. 31622 | TITLE ESTs | | | gi = 4032410 | 639781 |
| IC08511 | UG75 Expression | EST | Mm. 31626 | TITLE ESTs | | | gi = 2042956 | 616655 |
| IC08512 | UG75 Expression | EST | Mm. 31630 | TITLE ESTs | | | gi = 4058071 | 638691 |
| IC08513 | UG75 Expression | EST | Mm. 31643 | TITLE ESTs, Weakly similar to F37A4.2 [*C. elegans*] | | | gi = 5494311 | 635514 |
| IC08514 | UG75 Expression | EST | Mm. 31650 | TITLE ESTs | | | gi = 4308874 | 558193 |
| IC08515 | UG75 Expression | EST | Mm. 31666 | TITLE ESTs | | | gi = 5819613 | 1002803 |
| IC08516 | UG75 Expression | EST | Mm. 31672 | TITLE ESTs | | | gi = 6749229 | 1001661 |
| IC08517 | UG75 Expression | EST | Mm. 31676 | TITLE ESTs, Moderately similar to KIAA0683 protein [*H. sapiens*] | | | gi = 4614780 | 597482 |
| IC08518 | UG75 Expression | EST | Mm. 31685 | TITLE ESTs | | | gi = 5906131 | 1379692 |
| IC08519 | UG75 Expression | EST | Mm. 31687 | TITLE ESTs | | | gi = 1901379 | 618122 |
| IC08520 | UG75 Expression | EST | Mm. 31695 | TITLE ESTs | | | gi = 4299135 | 540268 |
| IC08521 | UG75 Expression | EST | Mm. 31713 | TITLE ESTs | | | gi = 4275648 | 635962 |
| IC08522 | UG75 Expression | EST | Mm. 31722 | TITLE EST | | | gi = 4298302 | 574938 |
| IC08523 | UG75 Expression | EST | Mm. 31723 | TITLE EST | | | gi = 4298372 | 574982 |
| IC08524 | UG75 Expression | EST | Mm. 31724 | TITLE ESTs | | | gi = 1776262 | 643553 |
| IC08525 | UG75 Expression | EST | Mm. 31725 | TITLE ESTs | | | gi = 4613016 | 575002 |
| IC08526 | UG75 Expression | EST | Mm. 31726 | TITLE ESTs | | | gi = 5472874 | 575011 |
| IC08527 | UG75 Expression | EST | Mm. 31727 | TITLE ESTs, Moderately similar to 6-pyruvoyl-tetrahydropterin synthase [*M. musculus*] | | | gi = 4444672 | 1447044 |
| IC08528 | UG75 Expression | EST | Mm. 31728 | TITLE EST | | | gi = 4298540 | 575100 |
| IC08529 | UG75 Expression | EST | Mm. 31729 | TITLE ESTs | | | gi = 4444783 | 1446596 |
| IC08530 | UG75 Expression | EST | Mm. 31730 | TITLE ESTs, Weakly similar to retinoblastoma-associated protein HEC [*H. sapiens*] | | | gi = 2518306 | 575251 |
| IC08531 | UG75 Expression | EST | Mm. 31731 | TITLE EST | | | gi = 4298727 | 581740 |
| IC08532 | UG75 Expression | EST | Mm. 31732 | TITLE EST | | | gi = 4298888 | 582328 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08533 | UG75 Expression | EST | Mm. 31733 | TITLE ESTs | | | gi = 3522194 | 582417 |
| IC08534 | UG75 Expression | EST | Mm. 31734 | TITLE ESTs | | | gi = 5338478 | 582497 |
| IC08535 | UG75 Expression | EST | Mm. 31735 | TITLE ESTs | | | gi = 6750402 | 582516 |
| IC08536 | UG75 Expression | EST | Mm. 31737 | TITLE EST | | | gi = 4299076 | 582988 |
| IC08537 | UG75 Expression | EST | Mm. 31738 | TITLE ESTs | | | gi = 5299104 | 582997 |
| IC08538 | UG75 Expression | EST | Mm. 31739 | TITLE ESTs | | | gi = 4725758 | 583030 |
| IC08539 | UG75 Expression | EST | Mm. 31740 | TITLE EST | | | gi = 4299174 | 583080 |
| IC08540 | UG75 Expression | EST | Mm. 31751 | TITLE EST | | | gi = 5909744 | 573677 |
| IC08541 | UG75 Expression | EST | Mm. 31752 | TITLE EST | | | gi = 4299564 | 573735 |
| IC08542 | UG75 Expression | EST | Mm. 31753 | TITLE ESTs | | | gi = 4299571 | 573737 |
| IC08543 | UG75 Expression | EST | Mm. 31754 | TITLE EST | | | gi = 4299578 | 573743 |
| IC08544 | UG75 Expression | EST | Mm. 31755 | TITLE EST | | | gi = 4299655 | 573792 |
| IC08545 | UG75 Expression | EST | Mm. 31756 | TITLE ESTs | | | gi = 4444587 | 573796 |
| IC08546 | UG75 Expression | EST | Mm. 31757 | TITLE ESTs | | | gi = 4299690 | 573812 |
| IC08547 | UG75 Expression | EST | Mm. 31758 | TITLE ESTs | | | gi = 4444594 | 573816 |
| IC08548 | UG75 Expression | EST | Mm. 31759 | TITLE ESTs | | | gi = 4408303 | 573827 |
| IC08549 | UG75 Expression | EST | Mm. 31760 | TITLE EST | | | gi = 4299858 | 575523 |
| IC08550 | UG75 Expression | EST | Mm. 31761 | TITLE EST | | | gi = 4299865 | 575529 |
| IC08551 | UG75 Expression | EST | Mm. 31762 | TITLE EST | | | gi = 4299915 | 575580 |
| IC08552 | UG75 Expression | EST | Mm. 31763 | TITLE EST | | | gi = 4299922 | 575571 |
| IC08553 | UG75 Expression | EST | Mm. 31764 | TITLE EST | | | gi = 4299943 | 575603 |
| IC08554 | UG75 Expression | EST | Mm. 31765 | TITLE EST | | | gi = 4300048 | 575685 |
| IC08555 | UG75 Expression | EST | Mm. 31766 | TITLE EST | | | gi = 4300118 | 575763 |
| IC08556 | UG75 Expression | EST | Mm. 31767 | TITLE EST | | | gi = 4300125 | 675783 |
| IC08557 | UG75 Expression | EST | Mm. 31768 | TITLE ESTs, Moderately similar to endothelial cell growth factor 1 [H. sapiens] | | | gi = 4300139 | 575826 |
| IC08558 | UG75 Expression | EST | Mm. 31769 | TITLE EST | | | gi = 4300153 | 575829 |
| IC08559 | UG75 Expression | EST | Mm. 31770 | TITLE ESTs | | | gi = 4300195 | 575895 |
| IC08560 | UG75 Expression | EST | Mm. 31771 | TITLE EST | | | gi = 4300251 | 575939 |
| IC08561 | UG75 Expression | EST | Mm. 31773 | TITLE ESTs | | | gi = 4300405 | 576066 |
| IC08562 | UG75 Expression | EST | Mm. 31776 | TITLE EST | | | gi = 4300454 | 576099 |
| IC08563 | UG75 Expression | EST | Mm. 31777 | TITLE EST | | | gi = 4300489 | 576148 |
| IC08564 | UG75 Expression | EST | Mm. 31778 | TITLE ESTs, Weakly similar to Similar to aldehyde dehydrogenase [C. elegans] | | | gi = 1290279 | 576152 |
| IC08565 | UG75 Expression | EST | Mm. 31779 | TITLE EST | | | gi = 4300545 | 576198 |
| IC08566 | UG75 Expression | EST | Mm. 31780 | TITLE EST | | | gi = 4300629 | 576282 |
| IC08567 | UG75 Expression | EST | Mm. 31781 | TITLE EST | | | gi = 4300643 | 576292 |
| IC08568 | UG75 Expression | EST | Mm. 31782 | TITLE EST | | | gi = 4300685 | 576320 |
| IC08569 | UG75 Expression | EST | Mm. 31783 | TITLE EST | | | gi = 4300713 | 576366 |
| IC08570 | UG75 Expression | EST | Mm. 31785 | TITLE ESTs | | | gi = 4450332 | 576380 |
| IC08571 | UG75 Expression | EST | Mm. 31786 | TITLE EST | | | gi = 4300818 | 576462 |
| IC08572 | UG75 Expression | EST | Mm. 31787 | TITLE ESTs | | | gi = 4887815 | 777446 |
| IC08573 | UG75 Expression | EST | Mm. 31788 | TITLE ESTs | | | gi = 4300902 | 576505 |
| IC08574 | UG75 Expression | EST | Mm. 31789 | TITLE EST | | | gi = 4300909 | 576511 |
| IC08575 | UG75 Expression | EST | Mm. 31790 | TITLE EST | | | gi = 4300916 | 576517 |
| IC08576 | UG75 Expression | EST | Mm. 31791 | TITLE EST | | | gi = 4300958 | 576556 |
| IC08577 | UG75 Expression | EST | Mm. 31792 | TITLE EST | | | gi = 4300993 | 576580 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08578 | UG75 Expression | EST | Mm. 31793 | TITLE ESTs | | | gi = 2919413 | 576593 |
| IC08579 | UG75 Expression | EST | Mm. 318 | TITLE ESTs, Moderately similar to 6.6 KD MITOCHONDRIAL PROTEOLIPID [Bos taurus] | | | gi = 230742 | 596958 |
| IC08580 | UG75 Expression | EST | Mm. 31802 | TITLE ESTs | | | gi = 5749533 | 597209 |
| IC08581 | UG75 Expression | EST | Mm. 31805 | TITLE ESTs | | | gi = 4301553 | 1327528 |
| IC08582 | UG75 Expression | EST | Mm. 31810 | TITLE ESTs | | | gi = 1756164 | 618050 |
| IC08583 | UG75 Expression | EST | Mm. 31811 | TITLE ESTs | | | gi = 1699902 | 595855 |
| IC08584 | UG75 Expression | EST | Mm. 31812 | TITLE ESTs | | | gi = 4302477 | 595858 |
| IC08585 | UG75 Expression | EST | Mm. 31813 | TITLE EST | | | gi = 4302581 | 595953 |
| IC08586 | UG75 Expression | EST | Mm. 31814 | TITLE EST | | | gi = 4302658 | 596025 |
| IC08587 | UG75 Expression | EST | Mm. 31815 | TITLE ESTs | | | gi = 5819801 | 1295193 |
| IC08588 | UG75 Expression | EST | Mm. 31816 | TITLE ESTs | | | gi = 4285774 | 596106 |
| IC08589 | UG75 Expression | EST | Mm. 31817 | TITLE ESTs | | | gi = 1699823 | 596138 |
| IC08590 | UG75 Expression | EST | Mm. 31818 | TITLE ESTs | | | gi = 3375521 | 596176 |
| IC08591 | UG75 Expression | EST | Mm. 31819 | TITLE ESTs | | | gi = 4766004 | 596224 |
| IC08592 | UG75 Expression | EST | Mm. 31820 | TITLE EST | | | gi = 4302875 | 596223 |
| IC08593 | UG75 Expression | EST | Mm. 31821 | TITLE EST | | | gi = 4302924 | 596281 |
| IC08594 | UG75 Expression | EST | Mm. 31823 | TITLE ESTs | | | gi = 4302976 | 596347 |
| IC08595 | UG75 Expression | EST | Mm. 31824 | TITLE ESTs | | | gi = 1701062 | 596366 |
| IC08596 | UG75 Expression | EST | Mm. 31825 | TITLE EST | | | gi = 4450321 | 596357 |
| IC08597 | UG75 Expression | EST | Mm. 31826 | TITLE ESTs | | | gi = 6159335 | 596386 |
| IC08598 | UG75 Expression | EST | Mm. 31827 | TITLE ESTs | | | gi = 6008166 | 596381 |
| IC08599 | UG75 Expression | EST | Mm. 31828 | TITLE ESTs | | | gi = 2718466 | 596411 |
| IC08600 | UG75 Expression | EST | Mm. 31829 | TITLE ESTs | | | gi = 4600698 | 596528 |
| IC08601 | UG75 Expression | EST | Mm. 3183 | TITLE ESTs | | | gi = 6101199 | 765006 |
| IC08602 | UG75 Expression | EST | Mm. 31830 | TITLE EST | | | gi = 4303249 | 596638 |
| IC08603 | UG75 Expression | EST | Mm. 31832 | TITLE ESTs | | | gi = 1715903 | 596694 |
| IC08604 | UG75 Expression | EST | Mm. 31833 | TITLE ESTs | | | gi = 2855197 | 621060 |
| IC08605 | UG75 Expression | EST | Mm. 31834 | GLUCOSYLTRASFERASE ALG8 [Saccharomyces cerevisiae] | | | gi = 1681501 | 576877 |
| IC08606 | UG75 Expression | EST | Mm. 31836 | TITLE ESTs | | | gi = 3732354 | 583275 |
| IC08607 | UG75 Expression | EST | Mm. 31837 | TITLE ESTs | | | gi = 4625145 | 1225379 |
| IC08608 | UG75 Expression | EST | Mm. 31838 | TITLE EST | | | gi = 4303589 | 583296 |
| IC08609 | UG75 Expression | EST | Mm. 31839 | TITLE ESTs, Weakly similar to KIAA0819 protein [H. sapiens] | | | gi = 6340582 | 583371 |
| IC08610 | UG75 Expression | EST | Mm. 31840 | TITLE ESTs | | | gi = 5750062 | 583437 |
| IC08611 | UG75 Expression | EST | Mm. 31841 | TITLE EST | | | gi = 4304771 | 583508 |
| IC08612 | UG75 Expression | EST | Mm. 31842 | TITLE EST | | | gi = 4303785 | 583511 |
| IC08613 | UG75 Expression | EST | Mm. 31843 | TITLE ESTs | | | gi = 4303792 | 583534 |
| IC08614 | UG75 Expression | EST | Mm. 31844 | TITLE ESTs | | | gi = 4303806 | 583527 |
| IC08615 | UG75 Expression | EST | Mm. 31845 | TITLE ESTs | | | gi = 1861196 | 1279526 |
| IC08616 | UG75 Expression | EST | Mm. 31846 | TITLE EST | | | gi = 4303841 | 583575 |
| IC08617 | UG75 Expression | EST | Mm. 31847 | TITLE ESTs | | | gi = 4303855 | 597767 |
| IC08618 | UG75 Expression | EST | Mm. 31848 | TITLE ESTs | | | gi = 4303862 | 597772 |
| IC08619 | UG75 Expression | EST | Mm. 31849 | TITLE ESTs | | | gi = 4295255 | 597856 |
| IC08620 | UG75 Expression | EST | Mm. 31851 | TITLE EST | | | gi = 4601107 | 597874 |
| IC08621 | UG75 Expression | EST | Mm. 31853 | TITLE ESTs | | | gi = 4726877 | 597924 |
| IC08622 | UG75 Expression | EST | Mm. 31854 | TITLE ESTs | | | gi = 4537294 | 598072 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08623 | UG75 Expression | EST | Mm. 31855 | TITLE EST | | | gi - 4304149 | 598138 |
| IC08624 | UG75 Expression | EST | Mm. 31856 | TITLE ESTs | | | gi - 5497940 | 598166 |
| IC08625 | UG75 Expression | EST | Mm. 31857 | TITLE EST | | | gi - 4304345 | 598337 |
| IC08626 | UG75 Expression | EST | Mm. 31858 | TITLE ESTs | | | gi - 4444715 | 574315 |
| IC08627 | UG75 Expression | EST | Mm. 31859 | TITLE EST | | | gi - 4304604 | 574818 |
| IC08628 | UG75 Expression | EST | Mm. 31860 | TITLE EST | | | gi - 4304625 | 574840 |
| IC08629 | UG75 Expression | EST | Mm. 31861 | TITLE EST | | | gi - 4304681 | 575359 |
| IC08630 | UG75 Expression | EST | Mm. 31862 | TITLE EST | | | gi - 6100854 | 575361 |
| IC08631 | UG75 Expression | EST | Mm. 31863 | TITLE EST | | | gi - 4304786 | 575466 |
| IC08632 | UG75 Expression | EST | Mm. 31864 | TITLE EST | | | gi - 1738017 | 598521 |
| IC08633 | UG75 Expression | EST | Mm. 31865 | TITLE ESTs | | | gi - 4601196 | 598561 |
| IC08634 | UG75 Expression | EST | Mm. 31866 | TITLE ESTs | | | gi - 5477712 | 598599 |
| IC08635 | UG75 Expression | EST | Mm. 31867 | TITLE ESTs | | | gi - 4304982 | 598695 |
| IC08636 | UG75 Expression | EST | Mm. 31868 | TITLE EST | | | gi - 4305003 | 598708 |
| IC08637 | UG75 Expression | EST | Mm. 31869 | TITLE EST | | | gi - 5497976 | 598705 |
| IC08638 | UG75 Expression | EST | Mm. 31870 | TITLE ESTs | | | gi - 1738986 | 598748 |
| IC08639 | UG75 Expression | EST | Mm. 31871 | TITLE EST | | | gi - 4305087 | 598772 |
| IC08640 | UG75 Expression | EST | Mm. 31872 | TITLE EST | | | gi - 4305130 | 598796 |
| IC08641 | UG75 Expression | EST | Mm. 31873 | TITLE EST | | | gi - 4305158 | 598793 |
| IC08642 | UG75 Expression | EST | Mm. 31874 | TITLE ESTs | | | gi - 1746744 | 598862 |
| IC08643 | UG75 Expression | EST | Mm. 31875 | TITLE ESTs | | | gi - 6521007 | 598853 |
| IC08644 | UG75 Expression | EST | Mm. 31887 | TITLE ESTs | | | gi - 1738636 | 599032 |
| IC08645 | UG75 Expression | EST | Mm. 31888 | TITLE EST | | | gi - 4305837 | 599091 |
| IC08646 | UG75 Expression | EST | Mm. 31889 | TITLE ESTs | | | gi - 1751911 | 599101 |
| IC08647 | UG75 Expression | EST | Mm. 31890 | TITLE ESTs | | | gi - 1864673 | 621541 |
| IC08648 | UG75 Expression | EST | Mm. 31891 | TITLE EST | | | gi - 4305936 | 599145 |
| IC08649 | UG75 Expression | EST | Mm. 31892 | TITLE EST | | | gi - 4305950 | 599174 |
| IC08650 | UG75 Expression | EST | Mm. 31893 | TITLE ESTs | | | gi - 4305971 | 599203 |
| IC08651 | UG75 Expression | EST | Mm. 31894 | TITLE ESTs | | | gi - 4305992 | 599227 |
| IC08652 | UG75 Expression | EST | Mm. 31895 | TITLE ESTs | | | gi - 6377948 | 599303 |
| IC08653 | UG75 Expression | EST | Mm. 31899 | TITLE ESTs | | | gi - 1796384 | 638580 |
| IC08654 | UG75 Expression | EST | Mm. 31901 | TITLE ESTs | | | gi - 4404624 | 1002498 |
| IC08655 | UG75 Expression | EST | Mm. 31908 | TITLE EST | | | gi - 1739801 | 598351 |
| IC08656 | UG75 Expression | EST | Mm. 31909 | TITLE ESTs | | | gi - 4601164 | 598359 |
| IC08657 | UG75 Expression | EST | Mm. 31910 | TITLE ESTs | | | gi - 4276788 | 598399 |
| IC08658 | UG75 Expression | EST | Mm. 31911 | TITLE EST | | | gi - 4306685 | 598420 |
| IC08659 | UG75 Expression | EST | Mm. 31912 | TITLE EST | | | gi - 4306699 | 598460 |
| IC08660 | UG75 Expression | EST | Mm. 31913 | TITLE ESTs | | | gi - 2850572 | 598883 |
| IC08661 | UG75 Expression | EST | Mm. 31914 | TITLE ESTs | | | gi - 6008360 | 598928 |
| IC08662 | UG75 Expression | EST | Mm. 31915 | TITLE ESTs | | | gi - 2690740 | 598948 |
| IC08663 | UG75 Expression | EST | Mm. 31916 | TITLE EST | | | gi - 4601261 | 598949 |
| IC08664 | UG75 Expression | EST | Mm. 31919 | TITLE EST | | | gi - 4307070 | 596829 |
| IC08665 | UG75 Expression | EST | Mm. 31921 | TITLE EST | | | gi - 4307084 | 596850 |
| IC08667 | UG75 Expression | EST | Mm. 31922 | TITLE ESTs | | | gi - 4307112 | 596869 |
| IC08668 | UG75 Expression | EST | Mm. 31923 | TITLE ESTs | | | gi - 4307133 | 596885 |
| IC08669 | UG75 Expression | EST | Mm. 31924 | TITLE EST | | | gi - 1700799 | 596903 |
| IC08670 | UG75 Expression | EST | Mm. 31925 | TITLE EST | | | gi - 1714682 | 596933 |
| IC08671 | UG75 Expression | EST | Mm. 31926 | TITLE EST | | | gi - 4307189 | 596970 |
| IC08671 | UG75 Expression | EST | Mm. 31927 | TITLE ESTs | | | gi - 5910609 | 596983 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08672 | UG75 Expression | EST | Mm. 31930 | TITLE EST | | | gi = 4307321 | 597102 |
| IC08673 | UG75 Expression | EST | Mm. 31931 | TITLE ESTs | | | gi = 4617691 | 637329 |
| IC08674 | UG75 Expression | EST | Mm. 31932 | TITLE ESTs | | | gi = 1714535 | 597179 |
| IC08675 | UG75 Expression | EST | Mm. 31933 | TITLE EST | | | gi = 4307398 | 597206 |
| IC08676 | UG75 Expression | EST | Mm. 31934 | TITLE ESTs | | | gi = 6098106 | 597254 |
| IC08677 | UG75 Expression | EST | Mm. 31935 | TITLE EST | | | gi = 4307489 | 597269 |
| IC08678 | UG75 Expression | EST | Mm. 31936 | TITLE ESTs | | | gi = 4307524 | 597310 |
| IC08679 | UG75 Expression | EST | Mm. 31937 | TITLE ESTs | | | gi = 1715382 | 597293 |
| IC08680 | UG75 Expression | EST | Mm. 31938 | TITLE ESTs | | | gi = 4307664 | 637878 |
| IC08681 | UG75 Expression | EST | Mm. 31939 | TITLE ESTs | | | gi = 4307671 | 597516 |
| IC08682 | UG75 Expression | EST | Mm. 31941 | TITLE EST | | | gi = 4307712 | 597548 |
| IC08683 | UG75 Expression | EST | Mm. 31942 | TITLE ESTs | | | gi = 3335814 | 597592 |
| IC08684 | UG75 Expression | EST | Mm. 31944 | TITLE EST | | | gi = 4307796 | 597636 |
| IC08685 | UG75 Expression | EST | Mm. 31945 | TITLE EST | | | gi = 4307803 | 597640 |
| IC08686 | UG75 Expression | EST | Mm. 31946 | TITLE ESTs, Weakly similar to BACR37P7.g [D. melanogaster] | | | gi = 5336705 | 597725 |
| IC08687 | UG75 Expression | EST | Mm. 31947 | TITLE EST | | | gi = 4307908 | 597757 |
| IC08688 | UG75 Expression | EST | Mm. 31957 | TITLE EST | | | gi = 4308650 | 557942 |
| IC08689 | UG75 Expression | EST | Mm. 31958 | TITLE ESTs | | | gi = 4308671 | 557959 |
| IC08690 | UG75 Expression | EST | Mm. 31959 | TITLE EST | | | gi = 2333171 | 973497 |
| IC08691 | UG75 Expression | EST | Mm. 31966 | TITLE EST | | | gi = 4309546 | 573231 |
| IC08692 | UG75 Expression | EST | Mm. 31967 | TITLE ESTs | | | gi = 4596955 | 573271 |
| IC08693 | UG75 Expression | EST | Mm. 31968 | TITLE EST | | | gi = 4309616 | 573292 |
| IC08694 | UG75 Expression | EST | Mm. 31969 | TITLE EST | | | gi = 4281126 | 573350 |
| IC08695 | UG75 Expression | EST | Mm. 31971 | TITLE EST | | | gi = 4281166 | 573372 |
| IC08696 | UG75 Expression | EST | Mm. 31972 | TITLE ESTs | | | gi = 2192183 | 573392 |
| IC08697 | UG75 Expression | EST | Mm. 31973 | TITLE EST | | | gi = 4281198 | 573396 |
| IC08698 | UG75 Expression | EST | Mm. 31975 | TITLE EST | | | gi = 4281262 | 573430 |
| IC08699 | UG75 Expression | EST | Mm. 31984 | TITLE ESTs | | | gi = 4281630 | 573453 |
| IC08700 | UG75 Expression | EST | Mm. 31985 | TITLE EST | | | gi = 4281654 | 573476 |
| IC08701 | UG75 Expression | EST | Mm. 31986 | TITLE EST | | | gi = 4281678 | 573481 |
| IC08702 | UG75 Expression | EST | Mm. 31987 | TITLE EST | | | gi = 4281718 | 573512 |
| IC08703 | UG75 Expression | EST | Mm. 31989 | TITLE ESTs | | | gi = 4281910 | 636642 |
| IC08704 | UG75 Expression | EST | Mm. 31990 | LEUKEMIA VIRUS ENHANCER FACTOR [Homo sapiens] | | | gi = 1676436 | 573676 |
| IC08705 | UG75 Expression | EST | Mm. 32 | TITLE ESTs, Weakly similar to zinc finger protein [M. musculus] | | | gi = 4444703 | 574258 |
| IC08706 | UG75 Expression | EST | Mm. 3200 | TITLE ESTs | | | gi = 1913429 | 765214 |
| IC08707 | UG75 Expression | EST | Mm. 32004 | TITLE ESTs | | | gi = 1801176 | 636620 |
| IC08708 | UG75 Expression | EST | Mm. 32007 | TITLE ESTs | | | gi = 4601741 | 581698 |
| IC08709 | UG75 Expression | EST | Mm. 32008 | TITLE EST | | | gi = 4282958 | 573896 |
| IC08710 | UG75 Expression | EST | Mm. 32009 | TITLE ESTs | | | gi = 1407879 | 573926 |
| IC08711 | UG75 Expression | EST | Mm. 32010 | TITLE ESTs | | | gi = 5496594 | 573949 |
| IC08712 | UG75 Expression | EST | Mm. 32011 | TITLE ESTs | | | gi = 4803516 | 573951 |
| IC08713 | UG75 Expression | EST | Mm. 32012 | TITLE EST | | | gi = 4317784 | 723209 |
| IC08714 | UG75 Expression | EST | Mm. 32013 | TITLE ESTs | | | gi = 4283110 | 573991 |
| IC08715 | UG75 Expression | EST | Mm. 32015 | TITLE EST | | | gi = 4283134 | 574011 |
| IC08716 | UG75 Expression | EST | Mm. 32016 | TITLE EST | | | gi = 4283142 | 574015 |
| IC08717 | UG75 Expression | EST | Mm. 32018 | TITLE ESTs | | | gi = 1662884 | 573980 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08718 | UG75 Expression | EST | Mm. 32019 | TITLE EST | | | gi = 4283230 | 574104 |
| IC08719 | UG75 Expression | EST | Mm. 32020 | TITLE EST | | | gi = 4283246 | 574140 |
| IC08720 | UG75 Expression | EST | Mm. 32021 | TITLE EST | | | gi = 4283270 | 574170 |
| IC08721 | UG75 Expression | EST | Mm. 32022 | TITLE ESTs, Weakly similar to RAD54 [M. musculus] | | | gi = 1759951 | 621297 |
| IC08722 | UG75 Expression | EST | Mm. 32023 | TITLE ESTs | | | gi = 4283389 | 574263 |
| IC08723 | UG75 Expression | EST | Mm. 32024 | TITLE ESTs | | | gi = 5337941 | 581861 |
| IC08724 | UG75 Expression | EST | Mm. 32025 | TITLE EST | | | gi = 4283477 | 581888 |
| IC08725 | UG75 Expression | EST | Mm. 32026 | TITLE ESTs | | | gi = 4485944 | 581885 |
| IC08726 | UG75 Expression | EST | Mm. 32027 | TITLE EST | | | gi = 4283524 | 581891 |
| IC08727 | UG75 Expression | EST | Mm. 32028 | TITLE EST | | | gi = 4283580 | 581934 |
| IC08728 | UG75 Expression | EST | Mm. 32029 | TITLE ESTs, Weakly similar to unknown protein [R. norvegicus] | | | gi = 1724630 | 581929 |
| IC08729 | UG75 Expression | EST | Mm. 32030 | TITLE ESTs | | | gi = 1725790 | 581991 |
| IC08730 | UG75 Expression | EST | Mm. 32032 | TITLE EST | | | gi = 4283732 | 582040 |
| IC08731 | UG75 Expression | EST | Mm. 32034 | TITLE ESTs | | | gi = 4283796 | 582091 |
| IC08732 | UG75 Expression | EST | Mm. 32035 | TITLE ESTs, Moderately similar to putative protein B2 [H. sapiens] | | | gi = 6758447 | 582126 |
| IC08733 | UG75 Expression | EST | Mm. 32036 | TITLE ESTs, Moderately similar to beaded filament protein CP49 [H. sapiens] | | | gi = 4283876 | 582139 |
| IC08734 | UG75 Expression | EST | Mm. 32037 | TITLE EST | | | gi = 4283892 | 582150 |
| IC08735 | UG75 Expression | EST | Mm. 32038 | TITLE ESTs | | | gi = 4723801 | 582171 |
| IC08736 | UG75 Expression | EST | Mm. 32039 | TITLE ESTs | | | gi = 2187276 | 574443 |
| IC08737 | UG75 Expression | EST | Mm. 32040 | TITLE EST | | | gi = 4284004 | 574445 |
| IC08738 | UG75 Expression | EST | Mm. 32041 | TITLE EST | | | gi = 4317105 | 574461 |
| IC08739 | UG75 Expression | EST | Mm. 32042 | TITLE EST | | | gi = 4284028 | 574466 |
| IC08740 | UG75 Expression | EST | Mm. 32043 | TITLE ESTs, Moderately similar to thymus specific serine peptidase [H. sapiens] | | | gi = 4444741 | 574482 |
| IC08741 | UG75 Expression | EST | Mm. 32044 | TITLE ESTs | | | gi = 1769307 | 618691 |
| IC08742 | UG75 Expression | EST | Mm. 32045 | TITLE EST | | | gi = 4284124 | 574507 |
| IC08743 | UG75 Expression | EST | Mm. 32046 | TITLE EST | | | gi = 4284132 | 574511 |
| IC08744 | UG75 Expression | EST | Mm. 32047 | TITLE ESTs | | | gi = 1675829 | 618903 |
| IC08745 | UG75 Expression | EST | Mm. 32048 | TITLE EST | | | gi = 4284228 | 574545 |
| IC08746 | UG75 Expression | EST | Mm. 32049 | TITLE EST | | | gi = 4284244 | 574582 |
| IC08747 | UG75 Expression | EST | Mm. 32050 | TITLE EST | | | gi = 4284284 | 574593 |
| IC08748 | UG75 Expression | EST | Mm. 32051 | TITLE EST | | | gi = 4284308 | 574618 |
| IC08749 | UG75 Expression | EST | Mm. 32052 | TITLE ESTs | | | gi = 1675877 | 574627 |
| IC08750 | UG75 Expression | EST | Mm. 32053 | TITLE ESTs | | | gi = 3161114 | 574639 |
| IC08751 | UG75 Expression | EST | Mm. 32054 | TITLE EST | | | gi = 4284364 | 574655 |
| IC08752 | UG75 Expression | EST | Mm. 32055 | TITLE EST | | | gi = 4284380 | 574670 |
| IC08753 | UG75 Expression | EST | Mm. 32056 | TITLE EST | | | gi = 4723814 | 582574 |
| IC08754 | UG75 Expression | EST | Mm. 32057 | TITLE EST | | | gi = 4284540 | 582584 |
| IC08755 | UG75 Expression | EST | Mm. 32059 | TITLE ESTs | | | gi = 4284660 | 582685 |
| IC08756 | UG75 Expression | EST | Mm. 32062 | TITLE EST | | | gi = 4216469 | 643611 |
| IC08757 | UG75 Expression | EST | Mm. 32063 | TITLE EST | | | gi = 4284892 | 582905 |
| IC08758 | UG75 Expression | EST | Mm. 32064 | TITLE EST | | | gi = 4284916 | 582917 |
| IC08759 | UG75 Expression | EST | Mm. 32065 | TITLE ESTs | | | gi = 4284964 | 959122 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08760 | UG75 Expression | EST | Mm. 32073 | TITLE ESTs | | | gi = 4285809 | 614413 |
| IC08761 | UG75 Expression | EST | Mm. 32083 | TITLE ESTs | | | gi = 5494535 | 721633 |
| IC08762 | UG75 Expression | EST | Mm. 32084 | TITLE ESTs | | | gi = 1724512 | 581679 |
| IC08763 | UG75 Expression | EST | Mm. 32098 | TITLE ESTs, Weakly similar to Ras-related protein [R. norvegicus] | | | gi = 4483848 | 576372 |
| IC08764 | UG75 Expression | EST | Mm. 32100 | TITLE ESTs | | | gi = 1793072 | 640074 |
| IC08765 | UG75 Expression | EST | Mm. 32103 | TITLE ESTs | | | gi = 4601544 | 618804 |
| IC08766 | UG75 Expression | EST | Mm. 32104 | TITLE ESTs | | | gi = 1756320 | 618819 |
| IC08767 | UG75 Expression | EST | Mm. 32106 | TITLE ESTs | | | gi = 4601560 | 618941 |
| IC08768 | UG75 Expression | EST | Mm. 32107 | TITLE ESTs | | | gi = 5493104 | 618966 |
| IC08769 | UG75 Expression | EST | Mm. 32108 | TITLE ESTs | | | gi = 1756536 | 618961 |
| IC08770 | UG75 Expression | EST | Mm. 32109 | TITLE EST | | | gi = 4287588 | 618983 |
| IC08771 | UG75 Expression | EST | Mm. 32110 | TITLE EST | | | gi = 4287595 | 618998 |
| IC08772 | UG75 Expression | EST | Mm. 32111 | TITLE ESTs | | | gi = 1749149 | 619004 |
| IC08773 | UG75 Expression | EST | Mm. 32112 | TITLE ESTs | | | gi = 1757051 | 619032 |
| IC08774 | UG75 Expression | EST | Mm. 32113 | TITLE ESTs | | | gi = 4601584 | 619105 |
| IC08775 | UG75 Expression | EST | Mm. 32114 | TITLE EST | | | gi = 4287778 | 619135 |
| IC08776 | UG75 Expression | EST | Mm. 32115 | TITLE EST | | | gi = 4287806 | 619152 |
| IC08777 | UG75 Expression | EST | Mm. 32116 | TITLE EST | | | gi = 4287813 | 619153 |
| IC08778 | UG75 Expression | EST | Mm. 32117 | TITLE EST | | | gi = 4287841 | 619182 |
| IC08779 | UG75 Expression | EST | Mm. 32118 | TITLE EST | | | gi = 4601602 | 619223 |
| IC08780 | UG75 Expression | EST | Mm. 32119 | TITLE ESTs | | | gi = 5488543 | 619224 |
| IC08781 | UG75 Expression | EST | Mm. 32120 | TITLE EST | | | gi = 4287953 | 619249 |
| IC08782 | UG75 Expression | EST | Mm. 32121 | TITLE EST | | | gi = 4601610 | 619255 |
| IC08783 | UG75 Expression | EST | Mm. 32122 | TITLE ESTs | | | gi = 4288051 | 619312 |
| IC08784 | UG75 Expression | EST | Mm. 32123 | TITLE EST | | | gi = 4288079 | 619342 |
| IC08785 | UG75 Expression | EST | Mm. 32124 | TITLE ESTs | | | gi = 1756678 | 619394 |
| IC08786 | UG75 Expression | EST | Mm. 32125 | TITLE ESTs | | | gi = 1751579 | 619415 |
| IC08787 | UG75 Expression | EST | Mm. 32126 | TITLE EST | | | gi = 4726628 | 619505 |
| IC08788 | UG75 Expression | EST | Mm. 32127 | TITLE EST | | | gi = 4613241 | 619562 |
| IC08789 | UG75 Expression | EST | Mm. 32128 | TITLE ESTs | | | gi = 1756952 | 619617 |
| IC08790 | UG75 Expression | EST | Mm. 32129 | TITLE ESTs | | | gi = 4613255 | 619634 |
| IC08791 | UG75 Expression | EST | Mm. 32130 | TITLE EST | | | gi = 4288477 | 619866 |
| IC08792 | UG75 Expression | EST | Mm. 32131 | TITLE ESTs | | | gi = 4288519 | 619702 |
| IC08793 | UG75 Expression | EST | Mm. 32132 | TITLE ESTs | | | gi = 4288596 | 619778 |
| IC08794 | UG75 Expression | EST | Mm. 32133 | TITLE EST | | | gi = 4288603 | 619784 |
| IC08795 | UG75 Expression | EST | Mm. 32134 | TITLE ESTs | | | gi = 4613282 | 619781 |
| IC08796 | UG75 Expression | EST | Mm. 32135 | TITLE EST | | | gi = 1427108 | 619814 |
| IC08797 | UG75 Expression | EST | Mm. 32136 | TITLE EST | | | gi = 4288673 | 619811 |
| IC08798 | UG75 Expression | EST | Mm. 32138 | TITLE EST | | | gi = 4288785 | 619910 |
| IC08799 | UG75 Expression | EST | Mm. 32139 | TITLE ESTs | | | gi = 5496074 | 1294218 |
| IC08800 | UG75 Expression | EST | Mm. 32140 | TITLE ESTs | | | gi = 1759282 | 619974 |
| IC08801 | UG75 Expression | EST | Mm. 32141 | TITLE ESTs | | | gi = 4613326 | 619998 |
| IC08802 | UG75 Expression | EST | Mm. 32142 | TITLE EST | | | gi = 4289002 | 620059 |
| IC08803 | UG75 Expression | EST | Mm. 32144 | TITLE EST | | | gi = 1757215 | 620075 |
| IC08804 | UG75 Expression | EST | Mm. 32145 | TITLE ESTs | | | gi = 4289205 | 620242 |
| IC08805 | UG75 Expression | EST | Mm. 32146 | TITLE EST | | | gi = 4289324 | 620331 |
| IC08806 | UG75 Expression | EST | Mm. 32147 | TITLE EST | | | gi = 4289331 | 620343 |
| IC08807 | UG75 Expression | EST | Mm. 32148 | TITLE ESTs | | | gi = 4613378 | 620371 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08808 | UG75 Expression | EST | Mm. 32149 | TITLE EST | | | gi = 4289429 | 620432 |
| IC08809 | UG75 Expression | EST | Mm. 32150 | TITLE ESTs | | | gi = 4613388 | 620464 |
| IC08810 | UG75 Expression | EST | Mm. 32151 | TITLE EST | | | gi = 4289486 | 620515 |
| IC08811 | UG75 Expression | EST | Mm. 32153 | TITLE ESTs | | | gi = 4613408 | 620684 |
| IC08812 | UG75 Expression | EST | Mm. 32154 | TITLE ESTs | | | gi = 4613409 | 620671 |
| IC08813 | UG75 Expression | EST | Mm. 32156 | TITLE EST | | | gi = 4289647 | 620691 |
| IC08814 | UG75 Expression | EST | Mm. 32157 | TITLE ESTs | | | gi = 4289661 | 620712 |
| IC08815 | UG75 Expression | EST | Mm. 32158 | TITLE EST | | | gi = 4289703 | 620742 |
| IC08816 | UG75 Expression | EST | Mm. 32159 | TITLE ESTs | | | gi = 4613427 | 620768 |
| IC08817 | UG75 Expression | EST | Mm. 32160 | TITLE EST | | | gi = 4613432 | 620812 |
| IC08818 | UG75 Expression | EST | Mm. 32161 | TITLE ESTs | | | gi = 1755849 | 620826 |
| IC08819 | UG75 Expression | EST | Mm. 32162 | TITLE ESTs | | | gi = 4057801 | 620834 |
| IC08820 | UG75 Expression | EST | Mm. 32163 | TITLE EST | | | gi = 4289857 | 576689 |
| IC08821 | UG75 Expression | EST | Mm. 32165 | TITLE ESTs | | | gi = 1794433 | 639534 |
| IC08822 | UG75 Expression | EST | Mm. 32166 | TITLE ESTs | | | gi = 4289927 | 576747 |
| IC08823 | UG75 Expression | EST | Mm. 32167 | TITLE ESTs | | | gi = 4409241 | 576776 |
| IC08824 | UG75 Expression | EST | Mm. 32168 | TITLE ESTs | | | gi = 1681492 | 576854 |
| IC08825 | UG75 Expression | EST | Mm. 32169 | TITLE ESTs | | | gi = 4290025 | 576860 |
| IC08826 | UG75 Expression | EST | Mm. 32170 | TITLE EST | | | gi = 4290032 | 576843 |
| IC08827 | UG75 Expression | EST | Mm. 32171 | TITLE EST | | | gi = 4290067 | 576867 |
| IC08828 | UG75 Expression | EST | Mm. 32172 | TITLE EST | | | gi = 4290109 | 576895 |
| IC08829 | UG75 Expression | EST | Mm. 32173 | TITLE ESTs | | | gi = 4290130 | 576913 |
| IC08830 | UG75 Expression | EST | Mm. 32174 | TITLE EST | | | gi = 4290235 | 577036 |
| IC08831 | UG75 Expression | EST | Mm. 32175 | TITLE EST | | | gi = 4290256 | 577060 |
| IC08832 | UG75 Expression | EST | Mm. 32176 | TITLE EST | | | gi = 4290284 | 577084 |
| IC08833 | UG75 Expression | EST | Mm. 32178 | TITLE EST | | | gi = 4290354 | 577113 |
| IC08834 | UG75 Expression | EST | Mm. 32179 | TITLE ESTs | | | gi = 1671513 | 577125 |
| IC08835 | UG75 Expression | EST | Mm. 32180 | TITLE ESTs | | | gi = 1682382 | 577179 |
| IC08836 | UG75 Expression | EST | Mm. 32181 | TITLE ESTs, Weakly similar to ZINC FINGER PROTEIN 85 [Homo sapiens] | | | gi = 2560666 | 751120 |
| IC08837 | UG75 Expression | EST | Mm. 32182 | TITLE ESTs | | | gi = 5124710 | 577237 |
| IC08838 | UG75 Expression | EST | Mm. 32183 | TITLE ESTs | | | gi = 5488702 | 1330148 |
| IC08839 | UG75 Expression | EST | Mm. 32184 | TITLE ESTs | | | gi = 5492279 | 577252 |
| IC08840 | UG75 Expression | EST | Mm. 32185 | TITLE ESTs | | | gi = 4290571 | 577290 |
| IC08841 | UG75 Expression | EST | Mm. 32186 | TITLE ESTs | | | gi = 4290578 | 577251 |
| IC08842 | UG75 Expression | EST | Mm. 32187 | TITLE ESTs | | | gi = 4274760 | 577291 |
| IC08843 | UG75 Expression | EST | Mm. 32188 | TITLE EST | | | gi = 3681426 | 749571 |
| IC08844 | UG75 Expression | EST | Mm. 32189 | TITLE ESTs | | | gi = 4290662 | 577428 |
| IC08845 | UG75 Expression | EST | Mm. 32190 | TITLE EST | | | gi = 1701504 | 577473 |
| IC08846 | UG75 Expression | EST | Mm. 32192 | TITLE ESTs | | | gi = 4281782 | 573551 |
| IC08847 | UG75 Expression | EST | Mm. 32193 | TITLE ESTs | | | gi = 4290795 | 577565 |
| IC08848 | UG75 Expression | EST | Mm. 32194 | TITLE EST | | | gi = 4290809 | 577575 |
| IC08849 | UG75 Expression | EST | Mm. 32195 | TITLE ESTs | | | gi = 4290948 | 577750 |
| IC08850 | UG75 Expression | EST | Mm. 32196 | TITLE EST | | | gi = 1700112 | 577774 |
| IC08851 | UG75 Expression | EST | Mm. 32197 | TITLE ESTs | | | gi = 4290990 | 577805 |
| IC08852 | UG75 Expression | EST | Mm. 32198 | TITLE ESTs | | | gi = 5475970 | 577809 |
| IC08853 | UG75 Expression | EST | Mm. 32199 | TITLE EST | | | gi = 4291004 | 577826 |
| IC08854 | UG75 Expression | EST | Mm. 32200 | TITLE ESTs | | | gi = 4291102 | 577932 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08855 | UG75 Expression | EST | Mm. 32201 | TITLE EST | | | gi = 4291151 | 577999 |
| IC08856 | UG75 Expression | EST | Mm. 32202 | TITLE ESTs | | | gi = 4409412 | 578064 |
| IC08857 | UG75 Expression | EST | Mm. 32207 | TITLE ESTs | | | gi = 4291445 | 600775 |
| IC08858 | UG75 Expression | EST | Mm. 3221 | TITLE EST | | | gi = 1915841 | 765794 |
| IC08859 | UG75 Expression | EST | Mm. 32217 | TITLE DNA segment, Chr 9, MRC UK Mouse Genome Centre 48 expressed [H. sapiens] | GENE D9Mgc4: | CD20R| | | 576087 |
| IC08860 | UG75 Expression | EST | Mm. 32221 | TITLE EST | | | gi = 4615602 | 1020827 |
| IC08861 | UG75 Expression | EST | Mm. 3224 | TITLE ESTs | | | gi = 7204449 | 1001456 |
| IC08862 | UG75 Expression | EST | Mm. 32247 | TITLE ESTs | | | gi = 6556853 | 751663 |
| IC08863 | UG75 Expression | EST | Mm. 32248 | TITLE ESTs | | | gi = 4444835 | 575727 |
| IC08864 | UG75 Expression | EST | Mm. 32266 | TITLE ESTs | | | gi = 4783395 | 636074 |
| IC08865 | UG75 Expression | EST | Mm. 32267 | TITLE ESTs | | | gi = 4723620 | 636132 |
| IC08866 | UG75 Expression | EST | Mm. 32268 | TITLE EST | | | gi = 4294540 | 636153 |
| IC08867 | UG75 Expression | EST | Mm. 32269 | TITLE ESTs | | | gi = 4723632 | 636258 |
| IC08868 | UG75 Expression | EST | Mm. 32270 | TITLE EST | | | gi = 4294680 | 636333 |
| IC08869 | UG75 Expression | EST | Mm. 32271 | TITLE ESTs | | | gi = 6168143 | 597300 |
| IC08870 | UG75 Expression | EST | Mm. 32274 | TITLE EST | | | gi = 4294967 | 636657 |
| IC08871 | UG75 Expression | EST | Mm. 32275 | TITLE EST | | | gi = 4294974 | 636663 |
| IC08872 | UG75 Expression | EST | Mm. 32276 | TITLE EST | | | gi = 4295009 | 636720 |
| IC08873 | UG75 Expression | EST | Mm. 32279 | TITLE ESTs | | | gi = 2963058 | 636978 |
| IC08874 | UG75 Expression | EST | Mm. 32281 | TITLE ESTs | | | gi = 4723705 | 637017 |
| IC08875 | UG75 Expression | EST | Mm. 32284 | TITLE ESTs | | | gi = 4723737 | 637214 |
| IC08876 | UG75 Expression | EST | Mm. 32285 | TITLE EST | | | gi = 4295472 | 637221 |
| IC08877 | UG75 Expression | EST | Mm. 32286 | TITLE ESTs | | | gi = 1772071 | 637270 |
| IC08878 | UG75 Expression | EST | Mm. 32287 | TITLE ESTs | | | gi = 5493971 | 637302 |
| IC08879 | UG75 Expression | EST | Mm. 32288 | TITLE ESTs | | | gi = 4295612 | 637402 |
| IC08880 | UG75 Expression | EST | Mm. 32290 | TITLE EST | | | gi = 4295653 | 637417 |
| IC08881 | UG75 Expression | EST | Mm. 32291 | TITLE ESTs | | | gi = 4408222 | 637427 |
| IC08882 | UG75 Expression | EST | Mm. 32292 | TITLE ESTs | | | gi = 4295695 | 637464 |
| IC08883 | UG75 Expression | EST | Mm. 32293 | TITLE ESTs | | | gi = 2308670 | 637495 |
| IC08884 | UG75 Expression | EST | Mm. 32295 | TITLE ESTs | | | gi = 4295758 | 637579 |
| IC08885 | UG75 Expression | EST | Mm. 32296 | TITLE EST | | | gi = 4295765 | 637626 |
| IC08886 | UG75 Expression | EST | Mm. 32297 | TITLE ESTs | | | gi = 4295786 | 637634 |
| IC08887 | UG75 Expression | EST | Mm. 32298 | TITLE ESTs | | | gi = 4408246 | 637663 |
| IC08888 | UG75 Expression | EST | Mm. 32299 | TITLE ESTs | | | gi = 1776396 | 637810 |
| IC08889 | UG75 Expression | EST | Mm. 32300 | TITLE ESTs | | | gi = 4318715 | 637856 |
| IC08890 | UG75 Expression | EST | Mm. 32301 | TITLE ESTs | | | gi = 1777171 | 637864 |
| IC08891 | UG75 Expression | EST | Mm. 32302 | TITLE EST | | | gi = 4296017 | 637958 |
| IC08892 | UG75 Expression | EST | Mm. 32303 | TITLE ESTs | | | gi = 4296045 | 638110 |
| IC08893 | UG75 Expression | EST | Mm. 32304 | TITLE EST | | | gi = 4296143 | 638169 |
| IC08894 | UG75 Expression | EST | Mm. 32305 | TITLE ESTs | | | gi = 1796533 | 638240 |
| IC08895 | UG75 Expression | EST | Mm. 32306 | TITLE EST | | | gi = 4296248 | 640587 |
| IC08896 | UG75 Expression | EST | Mm. 32307 | TITLE ESTs | | | gi = 4296290 | 640676 |
| IC08897 | UG75 Expression | EST | Mm. 32308 | TITLE ESTs | | | gi = 1800392 | 640733 |
| IC08898 | UG75 Expression | EST | Mm. 32309 | TITLE ESTs | | | gi = 4408246 | 637663 |
| IC08898 | UG75 Expression | EST | Mm. 32309 | TITLE ESTs | | | gi = 1800995 | 640889 |
| IC08899 | UG75 Expression | EST | Mm. 32310 | TITLE ESTs | | | gi = 5469407 | 640917 |
| IC08900 | UG75 Expression | EST | Mm. 32311 | TITLE EST | | | gi = 4296514 | 640964 |
| IC08901 | UG75 Expression | EST | Mm. 32313 | TITLE EST | | | gi = 4296598 | 641025 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08902 | UG75 Expression | EST | Mm. 32314 | TITLE ESTs | | | gi = 4296633 | 1226912 |
| IC08903 | UG75 Expression | EST | Mm. 32316 | TITLE EST | | | gi = 4296723 | 641128 |
| IC08904 | UG75 Expression | EST | Mm. 32317 | TITLE ESTs | | | gi = 4296751 | 641173 |
| IC08905 | UG75 Expression | EST | Mm. 32318 | TITLE ESTs | | | gi = 6633448 | 641175 |
| IC08906 | UG75 Expression | EST | Mm. 32319 | TITLE EST | | | gi = 4296765 | 641181 |
| IC08907 | UG75 Expression | EST | Mm. 32320 | TITLE ESTs | | | gi = 4297269 | 644983 |
| IC08908 | UG75 Expression | EST | Mm. 32321 | TITLE ESTs | | | gi = 4297668 | 972938 |
| IC08909 | UG75 Expression | EST | Mm. 32322 | TITLE EST | | | gi = 4297752 | 583650 |
| IC08910 | UG75 Expression | EST | Mm. 32323 | TITLE ESTs | | | gi = 4482572 | 583647 |
| IC08911 | UG75 Expression | EST | Mm. 32324 | TITLE ESTs, Weakly similar to KIAA0748 protein [H. sapiens] | | | gi = 4297780 | 750239 |
| IC08912 | UG75 Expression | EST | Mm. 32325 | TITLE EST | | | gi = 4297800 | 583714 |
| IC08913 | UG75 Expression | EST | Mm. 32328 | TITLE ESTs, Weakly similar to UDP-N-ACETYLGLUCOSAMINE-PEPTIDE N-ACETYLGLUCOS-AMINYLTRANSFERASE 110 KD SUBUNIT [R. norvegicus] | | | gi = 4778297 | 777490 |
| IC08914 | UG75 Expression | EST | Mm. 32334 | TITLE ESTs | | | gi = 4482066 | 616594 |
| IC08915 | UG75 Expression | EST | Mm. 32335 | TITLE ESTs | | | gi = 4703149 | 619841 |
| IC08916 | UG75 Expression | EST | Mm. 32336 | TITLE EST | | | gi = 4298548 | 616861 |
| IC08917 | UG75 Expression | EST | Mm. 32337 | TITLE EST | | | gi = 4703185 | 616895 |
| IC08918 | UG75 Expression | EST | Mm. 32338 | TITLE ESTs | | | gi = 1755459 | 617312 |
| IC08919 | UG75 Expression | EST | Mm. 32339 | TITLE ESTs | | | gi = 1755462 | 617313 |
| IC08920 | UG75 Expression | EST | Mm. 32340 | TITLE EST | | | gi = 4298715 | 617352 |
| IC08921 | UG75 Expression | EST | Mm. 32341 | TITLE ESTs | | | gi = 6940507 | 617397 |
| IC08922 | UG75 Expression | EST | Mm. 32342 | TITLE ESTs | | | gi = 4298793 | 617446 |
| IC08923 | UG75 Expression | EST | Mm. 32343 | TITLE ESTs | | | gi = 4702842 | 617518 |
| IC08924 | UG75 Expression | EST | Mm. 32344 | TITLE ESTs | | | gi = 1755929 | 617574 |
| IC08925 | UG75 Expression | EST | Mm. 32345 | TITLE ESTs | | | gi = 1755931 | 617573 |
| IC08926 | UG75 Expression | EST | Mm. 32347 | TITLE ESTs | | | gi = 1749121 | 617634 |
| IC08927 | UG75 Expression | EST | Mm. 3235 | TITLE DNA segment, Chr 3, Wayne State University 161, expressed | GENE D3Wsu161e | | | 1279613 |
| IC08928 | UG75 Expression | EST | Mm. 32350 | TITLE EST | | | gi = 4299212 | 617025 |
| IC08929 | UG75 Expression | EST | Mm. 32351 | TITLE ESTs | | | gi = 4301178 | 617051 |
| IC08930 | UG75 Expression | EST | Mm. 32352 | TITLE ESTs | | | gi = 4703225 | 617165 |
| IC08931 | UG75 Expression | EST | Mm. 32353 | TITLE ESTs | | | gi = 4299387 | 617765 |
| IC08932 | UG75 Expression | EST | Mm. 32354 | TITLE EST | | | gi = 4299429 | 617833 |
| IC08933 | UG75 Expression | EST | Mm. 32355 | TITLE EST | | | gi = 4299436 | 617876 |
| IC08934 | UG75 Expression | EST | Mm. 32356 | TITLE ESTs | | | gi = 6369122 | 617898 |
| IC08935 | UG75 Expression | EST | Mm. 32357 | TITLE ESTs | | | gi = 4767385 | 617908 |
| IC08936 | UG75 Expression | EST | Mm. 32358 | TITLE ESTs | | | gi = 6098552 | 617945 |
| IC08937 | UG75 Expression | EST | Mm. 32359 | TITLE ESTs | | | gi = 4299541 | 618006 |
| IC08938 | UG75 Expression | EST | Mm. 32360 | TITLE EST | | | gi = 4299555 | 618029 |
| IC08939 | UG75 Expression | EST | Mm. 32362 | TITLE EST | | | gi = 4299619 | 618091 |
| IC08940 | UG75 Expression | EST | Mm. 32363 | TITLE EST | | | gi = 4283868 | 618108 |
| IC08941 | UG75 Expression | EST | Mm. 32364 | TITLE ESTs | | | gi = 4730022 | 618242 |
| IC08942 | UG75 Expression | EST | Mm. 32365 | TITLE EST | | | gi = 1749139 | 618283 |
| IC08943 | UG75 Expression | EST | Mm. 32366 | TITLE ESTs | | | gi = 4299899 | 618406 |
| IC08944 | UG75 Expression | EST | Mm. 32368 | TITLE ESTs | | | gi = 4702931 | 618452 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08945 | UG75 Expression | EST | Mm. 32369 | TITLE EST | | | gi = 4299983 | 618488 |
| IC08946 | UG75 Expression | EST | Mm. 32381 | TITLE EST | | | gi = 4300906 | 620906 |
| IC08947 | UG75 Expression | EST | Mm. 32382 | TITLE ESTs, Moderately similar to dl434O14.3.1 [H. sapiens] | | | gi = 4613449 | 620924 |
| IC08948 | UG75 Expression | EST | Mm. 32383 | TITLE ESTs | | | gi = 4300962 | 620928 |
| IC08949 | UG75 Expression | EST | Mm. 32384 | TITLE ESTs | | | gi = 4301011 | 958363 |
| IC08950 | UG75 Expression | EST | Mm. 32385 | TITLE ESTs | | | gi = 1759918 | 621000 |
| IC08951 | UG75 Expression | EST | Mm. 32386 | TITLE EST | | | gi = 4301053 | 621016 |
| IC08952 | UG75 Expression | EST | Mm. 32387 | TITLE ESTs, Weakly similar to plexin 2 [M. musculus] | | | gi = 4301060 | 621001 |
| IC08953 | UG75 Expression | EST | Mm. 32389 | TITLE EST | | | gi = 4301157 | 621084 |
| IC08954 | UG75 Expression | EST | Mm. 32392 | TITLE ESTs | | | gi = 3955984 | 621109 |
| IC08955 | UG75 Expression | EST | Mm. 32393 | TITLE EST | | | gi = 4301234 | 621111 |
| IC08956 | UG75 Expression | EST | Mm. 32394 | TITLE ESTs | | | gi = 4601332 | 621152 |
| IC08957 | UG75 Expression | EST | Mm. 32395 | TITLE ESTs | | | gi = 4601341 | 621211 |
| IC08958 | UG75 Expression | EST | Mm. 32396 | TITLE EST | | | gi = 3521928 | 621233 |
| IC08959 | UG75 Expression | EST | Mm. 32397 | TITLE ESTs | | | gi = 4601346 | 621235 |
| IC08960 | UG75 Expression | EST | Mm. 32399 | TITLE ESTs | | | gi = 1759858 | 621255 |
| IC08961 | UG75 Expression | EST | Mm. 32400 | TITLE ESTs | | | gi = 4301444 | 621261 |
| IC08962 | UG75 Expression | EST | Mm. 32401 | TITLE EST | | | gi = 4301507 | 621351 |
| IC08963 | UG75 Expression | EST | Mm. 32403 | TITLE EST | | | gi = 4301612 | 621451 |
| IC08964 | UG75 Expression | EST | Mm. 32404 | TITLE ESTs | | | gi = 4301619 | 621464 |
| IC08965 | UG75 Expression | EST | Mm. 32405 | TITLE ESTs | | | gi = 4601374 | 621461 |
| IC08966 | UG75 Expression | EST | Mm. 32406 | TITLE EST | | | gi = 4968379 | 621485 |
| IC08967 | UG75 Expression | EST | Mm. 32407 | TITLE ESTs | | | gi = 4601383 | 621513 |
| IC08968 | UG75 Expression | EST | Mm. 32408 | TITLE ESTs | | | gi = 6515003 | 619078 |
| IC08969 | UG75 Expression | EST | Mm. 32409 | TITLE ESTs | | | gi = 6632555 | 621546 |
| IC08970 | UG75 Expression | EST | Mm. 32410 | TITLE EST | | | gi = 4301744 | 621535 |
| IC08971 | UG75 Expression | EST | Mm. 32411 | TITLE ESTs | | | gi = 4600863 | 621580 |
| IC08972 | UG75 Expression | EST | Mm. 32412 | TITLE EST | | | gi = 4301863 | 621673 |
| IC08973 | UG75 Expression | EST | Mm. 32413 | TITLE ESTs | | | gi = 4301905 | 621756 |
| IC08974 | UG75 Expression | EST | Mm. 32414 | TITLE ESTs | | | gi = 4304418 | 621760 |
| IC08975 | UG75 Expression | EST | Mm. 32415 | TITLE EST | | | gi = 1767582 | 1278733 |
| IC08976 | UG75 Expression | EST | Mm. 32416 | TITLE ESTs | | | gi = 651822 | 621805 |
| IC08977 | UG75 Expression | EST | Mm. 32417 | TITLE ESTs | | | gi = 4600900 | 621892 |
| IC08978 | UG75 Expression | EST | Mm. 32418 | TITLE ESTs | | | gi = 1726399 | 634893 |
| IC08979 | UG75 Expression | EST | Mm. 32419 | TITLE EST | | | gi = 1739993 | 634935 |
| IC08980 | UG75 Expression | EST | Mm. 32421 | TITLE ESTs | | | gi = 4601832 | 634974 |
| IC08981 | UG75 Expression | EST | Mm. 32422 | TITLE EST | | | gi = 4304121 | 634988 |
| IC08982 | UG75 Expression | EST | Mm. 32423 | TITLE ESTs | | | gi = 4601836 | 634993 |
| IC08983 | UG75 Expression | EST | Mm. 32425 | TITLE ESTs | | | gi = 4302318 | 635042 |
| IC08984 | UG75 Expression | EST | Mm. 32426 | TITLE EST | | | gi = 4302381 | 635108 |
| IC08985 | UG75 Expression | EST | Mm. 32427 | TITLE EST | | | gi = 4302395 | 635112 |
| IC08986 | UG75 Expression | EST | Mm. 32428 | TITLE ESTs | | | gi = 4302416 | 635124 |
| IC08987 | UG75 Expression | EST | Mm. 32429 | TITLE ESTs | | | gi = 4302423 | 635134 |
| IC08988 | UG75 Expression | EST | Mm. 32430 | TITLE EST | | | gi = 1737752 | 635131 |
| IC08989 | UG75 Expression | EST | Mm. 32432 | TITLE EST | | | gi = 4302507 | 635213 |
| IC08990 | UG75 Expression | EST | Mm. 32433 | TITLE ESTs | | | gi = 4601271 | 599012 |
| IC08991 | UG75 Expression | EST | Mm. 32434 | TITLE ESTs | | | gi = 4302521 | 635227 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08992 | UG75 Expression | EST | Mm.32435 | TITLE ESTs | | | gi = 4302542 | 635256 |
| IC08993 | UG75 Expression | EST | Mm.32436 | TITLE ESTs | | | gi = 6336607 | 635294 |
| IC08994 | UG75 Expression | EST | Mm.32437 | TITLE EST | | | gi = 4302612 | 635500 |
| IC08995 | UG75 Expression | EST | Mm.32438 | TITLE ESTs | | | gi = 2164343 | 635580 |
| IC08996 | UG75 Expression | EST | Mm.32439 | TITLE ESTs | | | gi = 4302682 | 635597 |
| IC08997 | UG75 Expression | EST | Mm.32440 | TITLE ESTs | | | gi = 1739146 | 635658 |
| IC08998 | UG75 Expression | EST | Mm.32441 | TITLE ESTs | | | gi = 6008362 | 635695 |
| IC08999 | UG75 Expression | EST | Mm.32442 | TITLE ESTs | | | gi = 4302871 | 635751 |
| IC09000 | UG75 Expression | EST | Mm.32444 | TITLE EST | | | gi = 4302975 | 635875 |
| IC09001 | UG75 Expression | EST | Mm.32445 | TITLE ESTs | | | gi = 4303003 | 617545 |
| IC09002 | UG75 Expression | EST | Mm.32446 | TITLE ESTs | | | gi = 5909835 | 635960 |
| IC09003 | UG75 Expression | EST | Mm.32447 | TITLE EST | | | gi = 1765611 | 635970 |
| IC09004 | UG75 Expression | EST | Mm.32448 | TITLE ESTs | | | gi = 2918991 | 635961 |
| IC09005 | UG75 Expression | EST | Mm.32449 | TITLE EST | | | gi = 4303087 | 635991 |
| IC09006 | UG75 Expression | EST | Mm.32450 | TITLE ESTs | | | gi = 4303136 | 636029 |
| IC09007 | UG75 Expression | EST | Mm.32451 | TITLE ESTs | | | gi = 1766789 | 636035 |
| IC09008 | UG75 Expression | EST | Mm.32452 | TITLE EST | | | gi = 4303157 | 636050 |
| IC09009 | UG75 Expression | EST | Mm.32453 | TITLE ESTs | | | gi = 5497031 | 1312459 |
| IC09010 | UG75 Expression | EST | Mm.32454 | TITLE ESTs | | | gi = 4723614 | 636065 |
| IC09011 | UG75 Expression | EST | Mm.32455 | TITLE ESTs | | | gi = 1915542 | 765290 |
| IC09012 | UG75 Expression | EST | Mm.32456 | TITLE EST | | | gi = 4303262 | 765347 |
| IC09013 | UG75 Expression | EST | Mm.32457 | TITLE ESTs | | | gi = 4303395 | 765526 |
| IC09014 | UG75 Expression | EST | Mm.32458 | TITLE ESTs, Moderately similar to WD-REPEAT PROTEIN SAZD [H. sapiens] | | | gi = 4483188 | 765589 |
| IC09015 | UG75 Expression | EST | Mm.32459 | TITLE ESTs, Weakly similar to HYPOTHETICAL PROTEIN HI1130 [Haemophilus influenzae] | | | gi = 4303488 | 765624 |
| IC09016 | UG75 Expression | EST | Mm.32460 | TITLE ESTs | | | gi = 6085615 | 641445 |
| IC09017 | UG75 Expression | EST | Mm.32461 | TITLE EST | | | gi = 4303726 | 641508 |
| IC09018 | UG75 Expression | EST | Mm.32462 | TITLE EST | | | gi = 2258942 | 641541 |
| IC09019 | UG75 Expression | EST | Mm.32463 | TITLE ESTs | | | gi = 4615051 | 641584 |
| IC09020 | UG75 Expression | EST | Mm.32465 | TITLE EST | | | gi = 4303866 | 641644 |
| IC09021 | UG75 Expression | EST | Mm.32466 | TITLE ESTs | | | gi = 4615081 | 641801 |
| IC09022 | UG75 Expression | EST | Mm.32467 | TITLE ESTs | | | gi = 4304034 | 641844 |
| IC09023 | UG75 Expression | EST | Mm.32469 | TITLE EST | | | gi = 4304076 | 641878 |
| IC09024 | UG75 Expression | EST | Mm.32470 | TITLE ESTs | | | gi = 4304139 | 1362349 |
| IC09025 | UG75 Expression | EST | Mm.32471 | TITLE ESTs | | | gi = 4304146 | 641924 |
| IC09026 | UG75 Expression | EST | Mm.32472 | TITLE ESTs | | | gi = 4304181 | 641966 |
| IC09027 | UG75 Expression | EST | Mm.32473 | TITLE EST | | | gi = 4304223 | 642018 |
| IC09028 | UG75 Expression | EST | Mm.32474 | TITLE ESTs | | | gi = 4304328 | 642090 |
| IC09029 | UG75 Expression | EST | Mm.32475 | TITLE ESTs | | | gi = 4613988 | 1225859 |
| IC09030 | UG75 Expression | EST | Mm.32476 | TITLE ESTs | | | gi = 1808526 | 642113 |
| IC09031 | UG75 Expression | EST | Mm.32477 | TITLE EST | | | gi = 4304378 | 642121 |
| IC09032 | UG75 Expression | EST | Mm.32478 | TITLE EST | | | gi = 4304420 | 642164 |
| IC09033 | UG75 Expression | EST | Mm.32479 | TITLE ESTs | | | gi = 4615151 | 642195 |
| IC09034 | UG75 Expression | EST | Mm.32480 | TITLE ESTs | | | gi = 5492358 | 642197 |
| IC09035 | UG75 Expression | EST | Mm.32481 | TITLE EST | | | gi = 4304511 | 642218 |
| IC09036 | UG75 Expression | EST | Mm.32482 | TITLE ESTs | | | gi = 4304525 | 642236 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09037 | UG75 Expression | EST | Mm. 32483 | TITLE EST | | | gi = 4304602 | 642308 |
| IC09038 | UG75 Expression | EST | Mm. 32484 | TITLE ESTs | | | gi = 2282947 | 642293 |
| IC09039 | UG75 Expression | EST | Mm. 32485 | TITLE ESTs | | | gi = 1768774 | 642338 |
| IC09040 | UG75 Expression | EST | Mm. 32486 | TITLE ESTs | | | gi = 4615178 | 642391 |
| IC09041 | UG75 Expression | EST | Mm. 32487 | TITLE ESTs | | | gi = 5492277 | 642415 |
| IC09042 | UG75 Expression | EST | Mm. 32489 | TITLE ESTs | | | gi = 4615190 | 642494 |
| IC09043 | UG75 Expression | EST | Mm. 32490 | TITLE EST | | | gi = 4304812 | 642525 |
| IC09044 | UG75 Expression | EST | Mm. 32492 | TITLE ESTs | | | gi = 1768554 | 642610 |
| IC09045 | UG75 Expression | EST | Mm.32493 | TITLE ESTs, Moderately similar to The KIAA0191 gene is expressed ubiquitously. [*H. sapiens*] | | | gi = 4304875 | 642611 |
| IC09046 | UG75 Expression | EST | Mm.32494 | TITLE ESTs | | | gi = 5496584 | 642698 |
| IC09047 | UG75 Expression | EST | Mm.32495 | TITLE EST | | | gi = 4304945 | 642712 |
| IC09048 | UG75 Expression | EST | Mm.32496 | TITLE ESTs | | | gi = 1769217 | 642713 |
| IC09049 | UG75 Expression | EST | Mm.32497 | TITLE ESTs | | | gi = 4296423 | 642728 |
| IC09050 | UG75 Expression | EST | Mm.32498 | TITLE ESTs | | | gi = 4304980 | 642750 |
| IC09051 | UG75 Expression | EST | Mm.32499 | TITLE EST | | | gi = 4304987 | 642753 |
| IC09052 | UG75 Expression | EST | Mm.32501 | TITLE ESTs | | | gi = 4663852 | 642769 |
| IC09053 | UG75 Expression | EST | Mm.32502 | TITLE ESTs | | | gi = 4663853 | 642775 |
| IC09054 | UG75 Expression | EST | Mm.32503 | TITLE ESTs | | | gi = 1776817 | 642826 |
| IC09055 | UG75 Expression | EST | Mm.32504 | TITLE ESTs | | | gi = 4305113 | 642882 |
| IC09056 | UG75 Expression | EST | Mm.32506 | TITLE ESTs | | | gi = 1769243 | 642989 |
| IC09057 | UG75 Expression | EST | Mm.32508 | TITLE ESTs, Moderately similar to signal recognition particle 54K protein [*M. musculus*] | | | gi = 1309587 | 643103 |
| IC09058 | UG75 Expression | EST | Mm.32509 | TITLE EST | | | gi = 4305259 | 643111 |
| IC09059 | UG75 Expression | EST | Mm.32510 | TITLE ESTs | | | gi = 1776525 | 643167 |
| IC09060 | UG75 Expression | EST | Mm.32511 | TITLE EST | | | gi = 4305329 | 643218 |
| IC09061 | UG75 Expression | EST | Mm.32512 | TITLE ESTs, Weakly similar to ORF YNL317w [*S. cerevisiae*] | | | gi = 4305378 | 643249 |
| IC09062 | UG75 Expression | EST | Mm.32513 | TITLE ESTs | | | gi = 1776538 | 643315 |
| IC09063 | UG75 Expression | EST | Mm.32514 | TITLE ESTs | | | gi = 4216455 | 643434 |
| IC09064 | UG75 Expression | EST | Mm.32515 | TITLE ESTs | | | gi = 4216461 | 643487 |
| IC09065 | UG75 Expression | EST | Mm.32518 | TITLE EST | | | gi = 4305706 | 643627 |
| IC09066 | UG75 Expression | EST | Mm.32519 | TITLE EST | | | gi = 4305804 | 643742 |
| IC09067 | UG75 Expression | EST | Mm.32520 | TITLE ESTs | | | gi = 4305832 | 643768 |
| IC09068 | UG75 Expression | EST | Mm.32528 | TITLE ESTs | | | gi = 4305839 | 643775 |
| IC09069 | UG75 Expression | EST | Mm.32529 | TITLE EST | | | gi = 4307100 | 643877 |
| IC09070 | UG75 Expression | EST | Mm.32532 | TITLE ESTs, Weakly similar to DNA-binding protein [*M. musculus*] | | | gi = 4307268 | 644208 |
| IC09071 | UG75 Expression | EST | Mm.32533 | TITLE ESTs | | | gi = 3215769 | 718195 |
| IC09072 | UG75 Expression | EST | Mm.32534 | TITLE ESTs | | | gi = 6097917 | 621876 |
| IC09073 | UG75 Expression | EST | Mm.3254 | TITLE ESTs | | | gi = 1755455 | 617294 |
| IC09074 | UG75 Expression | EST | Mm.32552 | TITLE ESTs | | | gi = 1324851 | 351270 |
| IC09075 | UG75 Expression | EST | Mm.32553 | TITLE ESTs | | | gi = 6758343 | 582936 |
| IC09076 | UG75 Expression | EST | Mm.32567 | TITLE ESTs | | | gi = 2262966 | 618358 |
| IC09077 | UG75 Expression | EST | Mm.32572 | TITLE ESTs, Weakly similar to TAP 2 [*M. musculus*] | | | gi = 6100306 | 1382313 |
| IC09078 | UG75 Expression | EST | Mm.32580 | TITLE ESTs, Moderately similar to KIAA0710 protein [*H. sapiens*] | | | gi = 4316459 | 596736 |
| IC09079 | UG75 Expression | EST | Mm.32581 | TITLE ESTs | | | gi = 1727163 | 550859 |
| IC09080 | UG75 Expression | EST | | | | | gi = 5495268 | 718360 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09081 | UG75 Expression | EST | Mm.32584 | TITLE ESTs | | | gi = 4299584 | 618068 |
| IC09082 | UG75 Expression | EST | Mm.32591 | TITLE ESTs | | | gi = 6520778 | 750798 |
| IC09083 | UG75 Expression | EST | Mm.32592 | TITLE ESTs | | | gi = 1936575 | 750873 |
| IC09084 | UG75 Expression | EST | Mm.32593 | TITLE ESTs | | | gi = 4786002 | 750877 |
| IC09085 | UG75 Expression | EST | Mm.32594 | TITLE ESTs | | | gi = 4407417 | 750917 |
| IC09086 | UG75 Expression | EST | Mm.32595 | TITLE ESTs | | | gi = 5491885 | 750933 |
| IC09087 | UG75 Expression | EST | Mm.32596 | TITLE EST | | | gi = 4316647 | 750955 |
| IC09088 | UG75 Expression | EST | Mm.32597 | TITLE EST | | | gi = 4316660 | 751032 |
| IC09089 | UG75 Expression | EST | Mm.32598 | TITLE ESTs | | | gi = 4316661 | 751102 |
| IC09090 | UG75 Expression | EST | Mm.32599 | TITLE ESTs | | | gi = 4407604 | 751277 |
| IC09091 | UG75 Expression | EST | Mm.32600 | TITLE ESTs | | | gi = 5197050 | 751289 |
| IC09092 | UG75 Expression | EST | Mm.32601 | TITLE ESTs | | | gi = 4407607 | 751300 |
| IC09093 | UG75 Expression | EST | Mm.32609 | TITLE ESTs | | | gi = 6379754 | 751535 |
| IC09094 | UG75 Expression | EST | Mm.32610 | TITLE ESTs | | | gi = 4407647 | 751620 |
| IC09095 | UG75 Expression | EST | Mm.32612 | TITLE ESTs | | | gi = 2692328 | 751744 |
| IC09096 | UG75 Expression | EST | Mm.32613 | TITLE ESTs | | | gi = 4407664 | 751766 |
| IC09097 | UG75 Expression | EST | Mm.32614 | TITLE ESTs | | | gi = 4308195 | 751808 |
| IC09098 | UG75 Expression | EST | Mm.32625 | TITLE EST | | | gi = 4316850 | 752227 |
| IC09099 | UG75 Expression | EST | Mm.32626 | TITLE EST | | | gi = 4316853 | 752242 |
| IC09100 | UG75 Expression | EST | Mm.32627 | TITLE ESTs | | | gi = 4407475 | 752244 |
| IC09101 | UG75 Expression | EST | Mm.32628 | TITLE ESTs | | | gi = 4407476 | 752250 |
| IC09102 | UG75 Expression | EST | Mm.32629 | TITLE EST | | | gi = 4316859 | 752300 |
| IC09103 | UG75 Expression | EST | Mm.32630 | TITLE EST | | | gi = 4316865 | 752336 |
| IC09104 | UG75 Expression | EST | Mm.32631 | TITLE ESTs, Weakly similar to PROTEIN DISULFIDE ISOMERASE PRECURSOR [*M. musculus*] | | | gi = 4407488 | 722782 |
| IC09105 | UG75 Expression | EST | Mm.32632 | TITLE ESTs | | | gi = 1936306 | 752394 |
| IC09106 | UG75 Expression | EST | Mm.32633 | TITLE EST | | | gi = 4316873 | 752425 |
| IC09107 | UG75 Expression | EST | Mm.32634 | TITLE ESTs | | | gi = 4482273 | 622483 |
| IC09108 | UG75 Expression | EST | Mm.32635 | TITLE EST | | | gi = 4316881 | 752489 |
| IC09109 | UG75 Expression | EST | Mm.32636 | TITLE ESTs | | | gi = 4316883 | 752508 |
| IC09110 | UG75 Expression | EST | Mm.32637 | TITLE EST | | | gi = 4316884 | 752514 |
| IC09111 | UG75 Expression | EST | Mm.32638 | TITLE ESTs | | | gi = 5470633 | 752516 |
| IC09112 | UG75 Expression | EST | Mm.32646 | TITLE ESTs | | | gi = 2521586 | 765183 |
| IC09113 | UG75 Expression | EST | Mm.32648 | TITLE ESTs | | | gi = 2040936 | 1243712 |
| IC09114 | UG75 Expression | EST | Mm.3265 | TITLE ESTs | | | gi = 6341257 | 777259 |
| IC09115 | UG75 Expression | EST | Mm.32657 | TITLE ESTs | | | gi = 6516510 | 751376 |
| IC09116 | UG75 Expression | EST | Mm.32658 | TITLE EST | | | gi = 4407612 | 751378 |
| IC09117 | UG75 Expression | EST | Mm.32659 | TITLE ESTs | | | gi = 2049392 | 751460 |
| IC09118 | UG75 Expression | EST | Mm.32660 | TITLE ESTs | | | gi = 4316976 | 751480 |
| IC09119 | UG75 Expression | EST | Mm.32661 | TITLE EST | | | gi = 6364355 | 751500 |
| IC09120 | UG75 Expression | EST | Mm.32662 | TITLE ESTs | | | gi = 4316981 | 751933 |
| IC09121 | UG75 Expression | EST | Mm.32663 | TITLE EST | | | gi = 4316987 | 751982 |
| IC09122 | UG75 Expression | EST | Mm.32664 | TITLE ESTs | | | gi = 4407465 | 752191 |
| IC09123 | UG75 Expression | EST | Mm.32668 | TITLE ESTs | | | gi = 4615724 | 764165 |
| IC09124 | UG75 Expression | EST | Mm.32670 | TITLE ESTs | | | gi = 1715953 | 596790 |
| IC09125 | UG75 Expression | EST | Mm.32671 | TITLE ESTs | | | gi = 1931971 | 764196 |
| IC09126 | UG75 Expression | EST | Mm.32672 | TITLE EST | | | gi = 4317034 | 764214 |
| IC09127 | UG75 Expression | EST | Mm.32673 | TITLE ESTs | | | gi = 1929811 | 764276 |
| IC09128 | UG75 Expression | EST | Mm.32674 | TITLE EST | | | gi = 4317040 | 764275 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09129 | UG75 Expression | EST | Mm.32675 | TITLE ESTs | | | gi = 1808264 | 764277 |
| IC09130 | UG75 Expression | EST | Mm.32676 | TITLE EST | | | gi = 4317044 | 764320 |
| IC09131 | UG75 Expression | EST | Mm.32677 | TITLE ESTs | | | gi = 1917250 | 764362 |
| IC09132 | UG75 Expression | EST | Mm.32678 | TITLE EST | | | gi = 4317054 | 764379 |
| IC09133 | UG75 Expression | EST | Mm.32679 | TITLE ESTs | | | gi = 2823062 | 764404 |
| IC09134 | UG75 Expression | EST | Mm.32680 | TITLE ESTs | | | gi = 4615759 | 764446 |
| IC09135 | UG75 Expression | EST | Mm.32681 | TITLE EST | | | gi = 4317064 | 764433 |
| IC09136 | UG75 Expression | EST | Mm.32683 | TITLE EST | | | gi = 4317070 | 764455 |
| IC09137 | UG75 Expression | EST | Mm.32684 | TITLE ESTs | | | gi = 1912558 | 764472 |
| IC09138 | UG75 Expression | EST | Mm.32685 | TITLE ESTs | | | gi = 1912879 | 764532 |
| IC09139 | UG75 Expression | EST | Mm.32686 | TITLE ESTs | | | gi = 6404078 | 764566 |
| IC09140 | UG75 Expression | EST | Mm.32687 | TITLE ESTs, Moderately similar to predicted using Genefinder [C. elegans] | | | gi = 1756572 | 618247 |
| IC09141 | UG75 Expression | EST | Mm.32700 | TITLE ESTs | | | gi = 4968440 | 597324 |
| IC09142 | UG75 Expression | EST | Mm.32702 | TITLE ESTs | | | gi = 1882096 | 599148 |
| IC09143 | UG75 Expression | EST | Mm.32714 | TITLE ESTs | | | gi = 3522055 | 618207 |
| IC09144 | UG75 Expression | EST | Mm.32732 | TITLE EST | | | gi = 4318240 | 777118 |
| IC09145 | UG75 Expression | EST | Mm.32733 | TITLE ESTs | | | gi = 4318241 | 777109 |
| IC09146 | UG75 Expression | EST | Mm.32734 | TITLE ESTs | | | gi = 4318247 | 777192 |
| IC09147 | UG75 Expression | EST | Mm.32735 | TITLE EST | | | gi = 4318250 | 777206 |
| IC09148 | UG75 Expression | EST | Mm.32736 | TITLE ESTs | | | gi = 4318251 | 777214 |
| IC09149 | UG75 Expression | EST | Mm.32737 | TITLE ESTs | | | gi = 4407775 | 777218 |
| IC09150 | UG75 Expression | EST | Mm.32738 | TITLE ESTs | | | gi = 4318253 | 777220 |
| IC09151 | UG75 Expression | EST | Mm.32739 | TITLE EST | | | gi = 4318254 | 777224 |
| IC09152 | UG75 Expression | EST | Mm.32741 | TITLE ESTs | | | gi = 1919589 | 777258 |
| IC09153 | UG75 Expression | EST | Mm.32742 | TITLE ESTs | | | gi = 4601010 | 777271 |
| IC09154 | UG75 Expression | EST | Mm.32743 | TITLE ESTs, Weakly similar to unknown protein [R. norvegicus] | | | gi = 4318269 | 777325 |
| IC09155 | UG75 Expression | EST | Mm.32746 | TITLE ESTs [R. norvegicus] | | | gi = 2517200 | 573263 |
| IC09156 | UG75 Expression | EST | Mm.32790 | TITLE ESTs | | | gi = 6095806 | 1225479 |
| IC09157 | UG75 Expression | EST | Mm.32792 | TITLE ESTs | | | gi = 4318627 | 718398 |
| IC09158 | UG75 Expression | EST | Mm.32793 | TITLE ESTs | | | gi = 4318630 | 718413 |
| IC09159 | UG75 Expression | EST | Mm.32794 | TITLE ESTs | | | gi = 5472195 | 718431 |
| IC09160 | UG75 Expression | EST | Mm.32795 | TITLE ESTs | | | gi = 4601367 | 621431 |
| IC09161 | UG75 Expression | EST | Mm.32796 | TITLE ESTs | | | gi = 4318664 | 718648 |
| IC09162 | UG75 Expression | EST | Mm.32797 | TITLE ESTs | | | gi = 4318673 | 718680 |
| IC09163 | UG75 Expression | EST | Mm.32798 | TITLE ESTs | | | gi = 3336399 | 718685 |
| IC09164 | UG75 Expression | EST | Mm.32799 | TITLE ESTs | | | gi = 4318682 | 718711 |
| IC09165 | UG75 Expression | EST | Mm.32800 | TITLE ESTs | | | gi = 6076526 | 718934 |
| IC09166 | UG75 Expression | EST | Mm.32801 | TITLE ESTs | | | gi = 6078089 | 718953 |
| IC09167 | UG75 Expression | EST | Mm.32802 | TITLE ESTs | | | gi = 4764894 | 722993 |
| IC09168 | UG75 Expression | EST | Mm.32803 | TITLE ESTs | | | gi = 2861494 | 719069 |
| IC09169 | UG75 Expression | EST | Mm.32804 | TITLE ESTs | | | gi = 4318794 | 719429 |
| IC09170 | UG75 Expression | EST | Mm.32807 | TITLE ESTs | | | gi = 4318863 | 720676 |
| IC09171 | UG75 Expression | EST | Mm.32808 | TITLE ESTs | | | gi = 6078089 | 720957 |
| IC09172 | UG75 Expression | EST | Mm.32809 | TITLE ESTs | | | gi = 4318904 | 721219 |
| IC09173 | UG75 Expression | EST | Mm.3281 | TITLE ESTs | | | gi = 4318939 | 597873 |
| IC09174 | UG75 Expression | EST | Mm.32810 | TITLE ESTs | | | gi = 4805118 | 721280 |
| IC09175 | UG75 Expression | EST | Mm.32811 | TITLE ESTs | | | gi = 4318959 | 721329 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09176 | UG75 Expression | EST | Mm.32821 | TITLE ESTs | | | gi = 1725798 | 718008 |
| IC09177 | UG75 Expression | EST | Mm.32826 | TITLE ESTs | | | gi = 3295335 | 1749759 |
| IC09178 | UG75 Expression | EST | Mm.32832 | TITLE ESTs | | | gi = 6519919 | 644274 |
| IC09179 | UG75 Expression | EST | Mm.32833 | TITLE ESTs | | | gi = 4297094 | 644348 |
| IC09180 | UG75 Expression | EST | Mm.32834 | TITLE ESTs | | | gi = 4319346 | 644412 |
| IC09181 | UG75 Expression | EST | Mm.32835 | TITLE ESTs | | | gi = 4319354 | 644831 |
| IC09182 | UG75 Expression | EST | Mm.32836 | TITLE ESTs | | | gi = 4297220 | 644912 |
| IC09183 | UG75 Expression | EST | Mm.32837 | TITLE ESTs, Moderately similar to megakaryocyte stimulating factor [H. sapiens] | | | gi = 1807679 | 644974 |
| IC09184 | UG75 Expression | EST | Mm.32840 | TITLE ESTs | | | gi = 3926561 | 635643 |
| IC09185 | UG75 Expression | EST | Mm.32842 | TITLE ESTs | | | gi = 4317553 | 1149151 |
| IC09186 | UG75 Expression | EST | Mm.32846 | TITLE ESTs | | | gi = 1765525 | 636308 |
| IC09187 | UG75 Expression | EST | Mm.32860 | TITLE ESTs, Weakly similar to The KIAA0191 gene is expressed ubiquitously. [H. sapiens] | | | gi = 2670927 | 893991 |
| IC09188 | UG75 Expression | EST | Mm.32863 | TITLE EST | | | gi = 4320354 | 764062 |
| IC09189 | UG75 Expression | EST | Mm.32865 | TITLE ESTs | | | gi = 4602943 | 764091 |
| IC09190 | UG75 Expression | EST | Mm.32866 | TITLE ESTs | | | gi = 1932123 | 764124 |
| IC09191 | UG75 Expression | EST | Mm.32867 | TITLE EST | | | gi = 4320370 | 764154 |
| IC09192 | UG75 Expression | EST | Mm.32868 | TITLE ESTs | | | gi = 1931949 | 764151 |
| IC09193 | UG75 Expression | EST | Mm.32869 | TITLE ESTs | | | gi = 6008017 | 764589 |
| IC09194 | UG75 Expression | EST | Mm.32870 | TITLE ESTs | | | gi = 2200303 | 764620 |
| IC09195 | UG75 Expression | EST | Mm.32871 | TITLE ESTs | | | gi = 1913099 | 764631 |
| IC09196 | UG75 Expression | EST | Mm.32872 | TITLE ESTs | | | gi = 4318668 | 764635 |
| IC09197 | UG75 Expression | EST | Mm.32873 | TITLE ESTs | | | gi = 4320394 | 764656 |
| IC09198 | UG75 Expression | EST | Mm.32874 | TITLE ESTs | | | gi = 4302059 | 621910 |
| IC09199 | UG75 Expression | EST | Mm.3289 | TITLE ESTs | | | gi = 2919209 | 764187 |
| IC09200 | UG75 Expression | EST | Mm.32902 | TITLE ESTs, Weakly similar to HC1 ORF [M. musculus] | | | gi = 1902233 | 582948 |
| IC09201 | UG75 Expression | EST | Mm.32906 | TITLE ESTs | | | gi = 1882338 | 749805 |
| IC09202 | UG75 Expression | EST | Mm.32911 | TITLE ESTs | | | gi = 2811766 | 1279949 |
| IC09203 | UG75 Expression | EST | Mm.32916 | TITLE ESTs | | | gi = 1796465 | 638636 |
| IC09204 | UG75 Expression | EST | Mm.32930 | TITLE ESTs | | | gi = 6085054 | 597523 |
| IC09205 | UG75 Expression | EST | Mm.32938 | TITLE ESTs | | | gi = 4373740 | 718352 |
| IC09206 | UG75 Expression | EST | Mm.32947 | TITLE ESTs, Weakly similar to KIAA0993 protein [H. sapiens] | | | gi = 3158655 | 721839 |
| IC09207 | UG75 Expression | EST | Mm.32950 | TITLE ESTs, Weakly similar to putative transcription factor [H. sapiens] | | | gi = 3067096 | 1263425 |
| IC09208 | UG75 Expression | EST | Mm.32957 | TITLE ESTs | | | gi = 6372272 | 1225156 |
| IC09209 | UG75 Expression | EST | Mm.32970 | TITLE ESTs | | | gi = 2248158 | 891231 |
| IC09210 | UG75 Expression | EST | Mm.33001 | TITLE ESTs | | | gi = 2164990 | 598102 |
| IC09211 | UG75 Expression | EST | Mm.33002 | TITLE ESTs | | | gi = 4374188 | 720858 |
| IC09212 | UG75 Expression | EST | Mm.33008 | TITLE ESTs | | | gi = 4374215 | 750597 |
| IC09213 | UG75 Expression | EST | Mm.33032 | TITLE ESTs | | | gi = 4601326 | 621129 |
| IC09214 | UG75 Expression | EST | Mm.33042 | TITLE ESTs | | | gi = 4374458 | 1002018 |
| IC09215 | UG75 Expression | EST | Mm.33057 | TITLE ESTs | | | gi = 4601350 | 621270 |
| IC09216 | UG75 Expression | EST | Mm.33070 | TITLE ESTs | | | gi = 2071507 | 638830 |
| IC09217 | UG75 Expression | EST | Mm.33083 | TITLE ESTs | | | gi = 5910764 | 1020679 |
| IC09218 | UG75 Expression | EST | Mm.3310 | TITLE ESTs | | | gi = 4726197 | 550769 |
| IC09219 | UG75 Expression | EST | Mm.33101 | TITLE ESTs | | | gi = 4374881 | 717711 |
| IC09220 | UG75 Expression | EST | Mm.33103 | TITLE ESTs | | | gi = 4801178 | 599004 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09221 | UG75 Expression | EST | Mm.3311 | TITLE ESTs, Weakly similar to cDNA EST EMBL:D70654 comes from this gene [C. elegans] | | | gi = 2292036 | 636471 |
| IC09222 | UG75 Expression | EST | Mm.33115 | TITLE ESTs | | | gi = 4613394 | 620540 |
| IC09223 | UG75 Expression | EST | Mm.33123 | TITLE ESTs, Weakly similar to/prediction | | | gi = 4730006 | 551192 |
| IC09224 | UG75 Expression | EST | Mm.33125 | TITLE ESTs | | | gi = 4407392 | 750698 |
| IC09225 | UG76 LID366 B cell | EST | Mm.33127 | TITLE ESTs | | | gi = 7066397 | 875235 |
| IC09226 | UG75 Expression | EST | Mm.33131 | TITLE ESTs | | | gi = 1387851 | 1361220 |
| IC09227 | UG75 Expression | EST | Mm.33135 | TITLE ESTs | | | gi = 2158193 | 1361197 |
| IC09228 | UG75 Expression | EST | Mm.33143 | TITLE ESTs | | | gi = 4485597 | 635124 |
| IC09229 | UG75 Expression | EST | Mm.33146 | TITLE EST | | | gi = 4375226 | 893934 |
| IC09230 | UG75 Expression | EST | Mm.33147 | TITLE ESTs | | | gi = 6096039 | 893968 |
| IC09231 | UG75 Expression | EST | Mm.33148 | TITLE ESTs, Weakly similar to zinc finger protein 51 [M. musculus] | | | gi = 5548994 | 893963 |
| IC09232 | UG75 Expression | EST | Mm.33149 | TITLE ESTs | | | gi = 4614806 | 893973 |
| IC09233 | UG75 Expression | EST | Mm.33150 | TITLE ESTs | | | gi = 4375242 | 894111 |
| IC09234 | UG75 Expression | EST | Mm.33151 | TITLE EST | | | gi = 4375244 | 894129 |
| IC09235 | UG75 Expression | EST | Mm.33152 | TITLE ESTs | | | gi = 2256438 | 894146 |
| IC09236 | UG75 Expression | EST | Mm.33153 | TITLE EST | | | gi = 4375248 | 894151 |
| IC09237 | UG75 Expression | EST | Mm.33154 | TITLE EST | | | gi = 4375254 | 894250 |
| IC09238 | UG75 Expression | EST | Mm.33155 | TITLE ESTs | | | gi = 4375258 | 894274 |
| IC09239 | UG75 Expression | EST | Mm.33156 | TITLE ESTs | | | gi = 4316263 | 894273 |
| IC09240 | UG75 Expression | EST | Mm.33157 | TITLE ESTs | | | gi = 4375266 | 894347 |
| IC09241 | UG75 Expression | EST | Mm.33159 | TITLE ESTs | | | gi = 4485651 | 573121 |
| IC09242 | UG75 Expression | EST | Mm.33166 | TITLE ESTs | | | gi = 4485463 | 577654 |
| IC09243 | UG75 Expression | EST | Mm.33167 | TITLE ESTs | | | gi = 4485466 | 847255 |
| IC09244 | UG75 Expression | EST | Mm.33173 | TITLE ESTs | | | gi = 4484513 | 640107 |
| IC09245 | UG75 Expression | EST | Mm.33185 | TITLE ESTs, Weakly similar to DIPEPTIDYL PEPTIDASE IV [M. musculus] | | | gi = 200217 | 533418 |
| IC09246 | UG75 Expression | EST | Mm.33186 | TITLE ESTs [H. sapiens] | | | gi = 4484563 | 1295104 |
| IC09247 | UG75 Expression | EST | Mm.33205 | TITLE ESTs | | | gi = 4271647 | 749480 |
| IC09248 | UG75 Expression | EST | Mm.33206 | TITLE ESTs, Moderately similar to reverse transcriptase [M. musculus] | | | gi = 4276216 | 1149641 |
| IC09249 | UG75 Expression | EST | Mm.33212 | TITLE ESTs | | | gi = 1677570 | 621577 |
| IC09250 | UG75 Expression | EST | Mm.33220 | TITLE ESTs | | | gi = 6079164 | 2599097 |
| IC09251 | UG75 Expression | EST | Mm.3323 | TITLE ESTs | | | gi = 4777305 | 752147 |
| IC09252 | UG75 Expression | EST | Mm.33230 | TITLE ESTs | | | gi = 2560829 | 876162 |
| IC09253 | UG75 Expression | EST | Mm.33238 | TITLE ESTs | | | gi = 4400881 | 583601 |
| IC09254 | UG75 Expression | EST | Mm.33255 | TITLE EST | | | gi = 4401037 | 1020558 |
| IC09255 | UG75 Expression | EST | Mm.33256 | TITLE ESTs | | | gi = 4401039 | 1020553 |
| IC09256 | UG75 Expression | EST | Mm.33257 | TITLE ESTs | | | gi = 2574305 | 1020565 |
| IC09257 | UG75 Expression | EST | Mm.33258 | TITLE EST | | | gi = 4401045 | 1020622 |
| IC09258 | UG75 Expression | EST | Mm.33259 | TITLE ESTs | | | gi = 4401055 | 1020655 |
| IC09259 | UG75 Expression | EST | Mm.3326 | TITLE ESTs | | | gi = 4407481 | 752299 |
| IC09260 | UG75 Expression | EST | Mm.33260 | TITLE ESTs | | | gi = 1701038 | 1020661 |
| IC09261 | UG75 Expression | EST | Mm.33261 | TITLE ESTs | | | gi = 4603219 | 1020769 |
| IC09262 | UG75 Expression | EST | Mm.33262 | TITLE EST | | | gi = 4401067 | 1020806 |
| IC09263 | UG75 Expression | EST | Mm.33264 | TITLE EST | | | gi = 4401079 | 1020872 |
| IC09264 | UG75 Expression | EST | Mm.33265 | TITLE ESTs | | | gi = 4401084 | 1020916 |
| IC09265 | UG75 Expression | EST | Mm.33277 | TITLE ESTs | | | gi = 2262326 | 596273 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09266 | UG75 Expression | EST | Mm.33285 | TITLE ESTs, Moderately similar to basic-leucine zipper nuclear factor [H. sapiens] | | | gi = 2503311 | 550952 |
| IC09267 | UG75 Expression | EST | Mm.33294 | TITTLE ESTs | | | gi = 6097885 | 973024 |
| IC09268 | UG75 Expression | EST | Mm.33295 | TITLE ESTs, Weakly similar to R10D12.12 [C. elegans] | | | gi = 2038595 | 583535 |
| IC09269 | UG75 Expression | EST | Mm.33298 | TITTLE ESTs | | | gi = 4765855 | 583889 |
| IC09270 | UG75 Expression | EST | Mm.3330 | TITTLE ESTs | | | gi = 4316196 | 749306 |
| IC09271 | UG75 Expression | EST | Mm.33301 | TITTLE ESTs | | | gi = 2306036 | 639552 |
| IC09272 | UG75 Expression | EST | Mm.33304 | TITTLE ESTs | | | gi = 2292374 | 551523 |
| IC09273 | UG75 Expression | EST | Mm.3331 | TITTLE ESTs | | | gi = 1936544 | 750823 |
| IC09274 | UG75 Expression | EST | Mm.33317 | TITTLE ESTs | | | gi = 4401717 | 1226212 |
| IC09275 | UG75 Expression | EST | Mm.3332 | TITTLE ESTs | | | gi = 6410288 | 750840 |
| IC09276 | UG75 Expression | EST | Mm.33329 | TITTLE ESTs | | | gi = 4401877 | 1001444 |
| IC09277 | UG75 Expression | EST | Mm.33330 | TITTLE ESTs | | | gi = 4401896 | 1001521 |
| IC09278 | UG75 Expression | EST | Mm.33331 | TITTLE EST | | | gi = 4401906 | 1001587 |
| IC09279 | UG75 Expression | EST | Mm.33332 | TITTLE ESTs | | | gi = 4374868 | 1001670 |
| IC09280 | UG75 Expression | EST | Mm.33333 | TITTLE ESTs | | | gi = 4401916 | 1001674 |
| IC09281 | UG75 Expression | EST | Mm.33334 | TITTLE EST | | | gi = 4401936 | 1001785 |
| IC09282 | UG75 Expression | EST | Mm.33358 | TITTLE ESTs | | | gi = 4720496 | 1225964 |
| IC09283 | UG75 Expression | EST | Mm.3336 | TITTLE ESTs | | | gi = 1936745 | 1020611 |
| IC09284 | UG75 Expression | EST | Mm.33367 | TITTLE ESTs | | | gi = 4730194 | 1379891 |
| IC09285 | UG75 Expression | EST | Mm.33376 | TITTLE ESTs | | | gi = 2812803 | 1229655 |
| IC09286 | UG75 Expression | EST | Mm.33378 | TITLE ESTs, Weakly similar to EPIDERMAL GROWTH FACTOR RECEPTOR KINASE SUBSTRATE EPS8 [M. musculus] | | | gi = 5124816 | 635882 |
| IC09287 | UG75 Expression | EST | Mm.3338 | TITTLE ESTs | | | gi = 3685486 | 750736 |
| IC09288 | UG75 Expression | EST | Mm.33383 | TITTLE ESTs | | | gi = 1385589 | 642104 |
| IC09289 | UG75 Expression | EST | Mm.33394 | TITTLE ESTs | | | gi = 2518352 | 621099 |
| IC09290 | UG75 Expression | EST | Mm.334 | TITLE ESTs, Moderately similar to The ha1539 protein is related to cyclophilin. [H. sapiens] | | | gi = 1800805 | 1295304 |
| IC09291 | UG75 Expression | EST | Mm.33407 | TITTLE EST | | | gi = 4402591 | 972383 |
| IC09292 | UG75 Expression | EST | Mm.33408 | TITTLE ESTs | | | gi = 3980569 | 972477 |
| IC09293 | UG75 Expression | EST | Mm.33409 | TITTLE EST | | | gi = 4402612 | 972529 |
| IC09294 | UG75 Expression | EST | Mm.33410 | TITTLE ESTs | | | gi = 4726330 | 972594 |
| IC09295 | UG75 Expression | EST | Mm.33411 | TITTLE EST | | | gi = 4402648 | 972701 |
| IC09296 | UG75 Expression | EST | Mm.33412 | TITTLE ESTs | | | gi = 4402652 | 972723 |
| IC09297 | UG75 Expression | EST | Mm.33413 | TITTLE EST | | | gi = 4402661 | 972769 |
| IC09298 | UG75 Expression | EST | Mm.33414 | TITTLE ESTs | | | gi = 4402665 | 972797 |
| IC09299 | UG75 Expression | EST | Mm.33420 | TITTLE ESTs | | | gi = 1912978 | 765124 |
| IC09300 | UG75 Expression | EST | Mm.33421 | TITTLE ESTs | | | gi = 5495204 | 1378199 |
| IC09301 | UG75 Expression | EST | Mm.33424 | TITTLE ESTs | | | gi = 5477602 | 638906 |
| IC09302 | UG75 Expression | EST | Mm.33426 | TITTLE ESTs | | | gi = 4402767 | 973819 |
| IC09303 | UG75 Expression | EST | Mm.33427 | TITTLE ESTs | | | gi = 4602068 | 973940 |
| IC09304 | UG75 Expression | EST | Mm.33439 | TITTLE ESTs | | | gi = 4031953 | 958922 |
| IC09305 | UG75 Expression | EST | Mm.3344 | TITTLE ESTs | | | gi = 2067332 | 751286 |
| IC09306 | UG75 Expression | EST | Mm.33443 | TITLE ESTs, Weakly similar to KRAB-containing zinc-finger protein KRAZ1 [M. musculus] | | | gi = 4766055 | 622359 |
| IC09307 | UG75 Expression | EST | Mm.33459 | TITLE ESTs | | | gi = 2456354 | 1002734 |
| IC09308 | UG75 Expression | EST | Mm.3347 | TITLE ESTs | | | gi = 6078055 | 749304 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09309 | UG75 Expression | EST | Mm.33475 | TITLE ESTs, Weakly similar to (define not available 5802698) [M. musculus] | | | gi = 2257220 | 894496 |
| IC09310 | UG75 Expression | EST | Mm.33484 | TITLE ESTs | | | gi = 4403404 | 1293696 |
| IC09311 | UG75 Expression | EST | Mm.33490 | TITLE ESTs | | | gi = 2561511 | 1428817 |
| IC09312 | UG75 Expression | EST | Mm.33493 | TITLE ESTs | | | gi = 4605841 | 373856 |
| IC09313 | UG75 Expression | EST | Mm.33495 | TITLE ESTs | | | gi = 2283103 | 949520 |
| IC09314 | UG75 Expression | EST | Mm.33496 | TITLE ESTs | | | gi = 2283107 | 1361793 |
| IC09315 | UG75 Expression | EST | Mm.33497 | TITLE ESTs | | | gi = 4605849 | 619296 |
| IC09316 | UG75 Expression | EST | Mm.33498 | TITLE ESTs, Weakly similar to GARP PROTEIN PRECURSOR [H. sapiens] | | | gi = 6078469 | 622971 |
| IC09317 | UG75 Expression | EST | Mm.33500 | TITLE ESTs | | | gi = 5906729 | 958865 |
| IC09318 | UG75 Expression | EST | Mm.33502 | TITLE ESTs | | | gi = 2284192 | 595854 |
| IC09319 | UG75 Expression | EST | Mm.33505 | TITLE ESTs | | | gi = 1407874 | 1279781 |
| IC09320 | UG75 Expression | EST | Mm.33509 | TITLE ESTs | | | gi = 4403668 | 959041 |
| IC09321 | UG75 Expression | EST | Mm.33510 | TITLE ESTs | | | gi = 2307437 | 959232 |
| IC09322 | UG75 Expression | EST | Mm.33511 | TITLE ESTs | | | gi = 4571444 | 959296 |
| IC09323 | UG75 Expression | EST | Mm.33512 | TITLE ESTs | | | gi = 4403719 | 959419 |
| IC09324 | UG75 Expression | EST | Mm.33513 | TITLE EST | | | gi = 4403721 | 959444 |
| IC09325 | UG75 Expression | EST | Mm.33517 | TITLE ESTs | | | gi = 4258519 | 972937 |
| IC09326 | UG75 Expression | EST | Mm.33518 | TITLE EST | | | gi = 4403820 | 972961 |
| IC09327 | UG75 Expression | EST | Mm.33521 | TITLE ESTs | | | gi = 4403932 | 973397 |
| IC09328 | UG75 Expression | EST | Mm.33522 | TITLE ESTs | | | gi = 4624951 | 973442 |
| IC09329 | UG75 Expression | EST | Mm.33523 | TITLE ESTs | | | gi = 4403946 | 973513 |
| IC09330 | UG75 Expression | EST | Mm.33524 | TITLE ESTs | | | gi = 4624956 | 973515 |
| IC09331 | UG75 Expression | EST | Mm.33525 | TITLE EST | | | gi = 4403951 | 973565 |
| IC09332 | UG75 Expression | EST | Mm.33526 | TITLE EST | | | gi = 4403953 | 973579 |
| IC09333 | UG75 Expression | EST | Mm.33527 | TITLE ESTs | | | gi = 4403962 | 973620 |
| IC09334 | UG75 Expression | EST | Mm.33528 | TITLE ESTs | | | gi = 6757571 | 973646 |
| IC09335 | UG75 Expression | EST | Mm.33529 | TITLE ESTs, Weakly similar to ZINC FINGER PROTEIN MFG-3 [M. musculus] | | | gi = 2332866 | 973658 |
| IC09336 | UG75 Expression | EST | Mm.33530 | TITLE ESTs | | | gi = 2332866 | 973739 |
| IC09337 | UG75 Expression | EST | Mm.33546 | TITLE ESTs | | | gi = 1904363 | 721416 |
| IC09338 | UG75 Expression | EST | Mm.33558 | TITLE ESTs | | | gi = 5475966 | 1002128 |
| IC09339 | UG75 Expression | EST | Mm.33559 | TITLE EST | | | gi = 4404280 | 1002166 |
| IC09340 | UG75 Expression | EST | Mm.33582 | TITLE EST | | | gi = 2643983 | 595911 |
| IC09341 | UG75 Expression | EST | Mm.33583 | TITLE ESTs | | | gi = 1738119 | 617646 |
| IC09342 | UG75 Expression | EST | Mm.33584 | TITLE ESTs, Weakly similar to probable cell cycle control protein cm [D. melanogaster] | | | gi = 5124570 | 718503 |
| IC09343 | UG75 Expression | EST | Mm.33586 | TITLE ESTs | | | gi = 3393221 | 2646968 |
| IC09344 | UG75 Expression | EST | Mm.33587 | TITLE ESTs | | | gi = 4615471 | 1002236 |
| IC09345 | UG75 Expression | EST | Mm.33588 | TITLE ESTs | | | gi = 2412056 | 1002249 |
| IC09346 | UG75 Expression | EST | Mm.33589 | TITLE ESTs | | | gi = 4404604 | 1002305 |
| IC09347 | UG75 Expression | EST | Mm.33590 | TITLE EST | | | gi = 4404608 | 1002317 |
| IC09348 | UG75 Expression | EST | Mm.33591 | TITLE ESTs | | | gi = 6098062 | 1002353 |
| IC09349 | UG75 Expression | EST | Mm.33592 | TITLE ESTs | | | gi = 2411944 | 1002446 |
| IC09350 | UG75 Expression | EST | Mm.33594 | TITLE EST | | | gi = 4404620 | 1002463 |
| IC09351 | UG75 Expression | EST | Mm.33595 | TITLE EST | | | gi = 4404623 | 1002479 |
| IC09352 | UG75 Expression | EST | Mm.33596 | TITLE ESTs | | | gi = 2412086 | 1002528 |
| IC09353 | UG75 Expression | EST | Mm.33597 | TITLE ESTs | | | gi = 4615509 | 1002567 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09354 | UG75 Expression | EST | Mm.33599 | TITLE ESTs | | | gi = 2412199 | 1002620 |
| IC09355 | UG75 Expression | EST | Mm.33600 | TITLE EST | | | gi = 4404655 | 1002704 |
| IC09356 | UG75 Expression | EST | Mm.33601 | TITLE ESTs | | | gi = 1917699 | 1002709 |
| IC09357 | UG75 Expression | EST | Mm.33608 | TITLE ESTs | | | gi = 4409226 | 573390 |
| IC09358 | UG75 Expression | EST | Mm.33613 | TITLE ESTs | | | gi = 4407603 | 751284 |
| IC09359 | UG75 Expression | EST | Mm.33640 | TITLE ESTs | | | gi = 1701765 | 577657 |
| IC09360 | UG75 Expression | EST | Mm.33649 | TITLE ESTs | | | gi = 4444646 | 574825 |
| IC09361 | UG75 Expression | EST | Mm.33662 | TITLE ESTs | | | gi = 4299118 | 583020 |
| IC09362 | UG75 Expression | EST | Mm.33663 | TITLE ESTs | | | gi = 4405206 | 974194 |
| IC09363 | UG75 Expression | EST | Mm.33697 | TITLE ESTs | | | gi = 4407389 | 750686 |
| IC09364 | UG75 Expression | EST | Mm.33698 | TITLE ESTs | | | gi = 1936561 | 750853 |
| IC09365 | UG75 Expression | EST | Mm.33699 | TITLE ESTs | | | gi = 4407413 | 750891 |
| IC09366 | UG75 Expression | EST | Mm.33700 | TITLE ESTs | | | gi = 4407428 | 751012 |
| IC09367 | UG75 Expression | EST | Mm.33701 | TITLE ESTs, Weakly similar to alternatively spliced form [H. sapiens] | | | gi = 4407459 | 752166 |
| IC09368 | UG75 Expression | EST | Mm.33702 | TITLE ESTs | | | gi = 4407460 | 752182 |
| IC09369 | UG75 Expression | EST | Mm.33703 | TITLE ESTs | | | gi = 2049376 | 751388 |
| IC09370 | UG75 Expression | EST | Mm.33704 | TITLE ESTs | | | gi = 2049112 | 751668 |
| IC09371 | UG75 Expression | EST | Mm.33705 | TITLE ESTs | | | gi = 4318273 | 777345 |
| IC09372 | UG75 Expression | EST | Mm.33707 | TITLE ESTs | | | gi = 4404630 | 1002523 |
| IC09373 | UG75 Expression | EST | Mm.33710 | TITLE ESTs, Weakly similar to putative REX-2 [M. musculus] | | | gi = 4374263 | 635676 |
| IC09374 | UG75 Expression | EST | Mm.33711 | TITLE ESTs | | | gi = 1739486 | 635735 |
| IC09375 | UG75 Expression | EST | Mm.33712 | TITLE ESTs | | | gi = 4302885 | 635760 |
| IC09376 | UG75 Expression | EST | Mm.33713 | TITLE ESTs | | | gi = 4408192 | 635775 |
| IC09377 | UG75 Expression | EST | Mm.33714 | TITLE ESTs | | | gi = 4302996 | 635902 |
| IC09378 | UG75 Expression | EST | Mm.33715 | TITLE ESTs | | | gi = 1768742 | 637462 |
| IC09379 | UG75 Expression | EST | Mm.33716 | TITLE ESTs | | | gi = 1777215 | 637897 |
| IC09380 | UG75 Expression | EST | Mm.33717 | TITLE ESTs, Weakly similar to rjs [M. musculus] | | | gi = 4408556 | 764173 |
| IC09381 | UG75 Expression | EST | Mm.33718 | TITLE ESTs | | | gi = 2963306 | 1295740 |
| IC09382 | UG75 Expression | EST | Mm.33719 | TITLE ESTs | | | gi = 4409125 | 764753 |
| IC09383 | UG75 Expression | EST | Mm.33720 | TITLE ESTs | | | gi = 5497743 | 764771 |
| IC09384 | UG75 Expression | EST | Mm.33721 | TITLE ESTs | | | gi = 6098884 | 1294263 |
| IC09385 | UG75 Expression | EST | Mm.33722 | TITLE ESTs, Moderately similar to RAS-LIKE PROTEIN TC10 [Homo sapiens] | | | gi = 6751134 | 1293650 |
| IC09386 | UG75 Expression | EST | Mm.33723 | TITLE ESTs, Moderately similiar to KIAA0470 protein [H. sapiens] | | | gi = 1682278 | 577092 |
| IC09387 | UG75 Expression | EST | Mm.33728 | TITLE ESTs | | | gi = 4441112 | 1923209 |
| IC09388 | UG75 Expression | EST | Mm.33729 | TITLE ESTs | | | gi = 2305808 | 637432 |
| IC09389 | UG75 Expression | EST | Mm.33738 | TITLE EST | | | gi = 4442862 | 598832 |
| IC09390 | UG75 Expression | EST | Mm.33749 | TITLE ESTs | | | gi = 4703153 | 616623 |
| IC09391 | UG75 Expression | EST | Mm.33750 | TITLE ESTs | | | gi = 1699939 | 596193 |
| IC09392 | UG75 Expression | EST | Mm.33751 | TITLE ESTs | | | gi = 4450310 | 596324 |
| IC09393 | UG75 Expression | EST | Mm.33752 | TITLE ESTs | | | gi = 4450311 | 596325 |
| IC09394 | UG75 Expression | EST | Mm.33753 | TITLE ESTs | | | gi = 4450376 | 576615 |
| IC09395 | UG75 Expression | EST | Mm.33754 | TITLE ESTs, Moderately similar to LONG-CHAIN-FATTY-ACID-COA LIGASE 2 [M. musculus] | | | gi = 4602517 | 1110539 |
| IC09396 | UG75 Expression | EST | Mm.33759 | TITLE ESTs | | | gi = 2670413 | 1293777 |
| IC09397 | UG75 Expression | EST | Mm.33761 | TITLE ESTs | | | gi = 2919109 | 634085 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09398 | UG75 Expression | EST | Mm.33765 | TITLE ESTs | | | gi = 4450575 | 638338 |
| IC09399 | UG75 Expression | EST | Mm.33771 | TITLE ESTs | | | gi = 4300363 | 576027 |
| IC09400 | UG75 Expression | EST | Mm.33773 | TITLE ESTs | | | gi = 5473860 | 597662 |
| IC09401 | UG75 Expression | EST | Mm.33774 | TITLE ESTs | | | gi = 2308562 | 642596 |
| IC09402 | UG75 Expression | EST | Mm.33776 | TITLE ESTs | | | gi = 3215491 | 1363796 |
| IC09403 | UG75 Expression | EST | Mm.33779 | TITLE ESTs | | | gi = 4374966 | 1225815 |
| IC09404 | UG75 Expression | EST | Mm.33786 | TITLE ESTs | | | gi = 4434039 | 2651779 |
| IC09405 | UG75 Expression | EST | Mm.33787 | TITLE ESTs | | | gi = 228816 | 621930 |
| IC09406 | UG75 Expression | EST | Mm.33788 | TITLE ESTs | | | gi = 4601092 | 597752 |
| IC09407 | UG75 Expression | EST | Mm.33793 | TITLE ESTs | | | gi = 5548784 | 723590 |
| IC09408 | UG75 Expression | EST | Mm.33797 | TITLE huntingtin interacting protein 1 related | GENE Hip 1r | | gi = 4272448 | 597630 |
| IC09409 | UG75 Expression | EST | Mm.33808 | TITLE ESTs, Weakly similar to polypeptide GalNAc transferase-T1 [M. musculus] | | | gi = 2591288 | 722806 |
| IC09410 | UG75 Expression | EST | Mm.33814 | TITLE ESTs | | | gi = 1659537 | 582611 |
| IC09411 | UG75 Expression | EST | Mm.33815 | TITLE ESTs, Weakly similar to predicted using Genefinder [C. elegans] | | | gi = 1284924 | 1447168 |
| IC09412 | UG75 Expression | EST | Mm.33816 | TITLE ESTs, Weakly similar to calcium-binding protein CaN19 [H. sapiens] | | | gi = 1662988 | 574078 |
| IC09413 | UG75 Expression | EST | Mm.33817 | TITLE ESTs, Weakly similar to KIAA0980 protein [H. sapiens] | | | gi = 6749717 | 1002041 |
| IC09414 | UG75 Expression | EST | Mm.33818 | TITLE ESTs | | | gi = 1671404 | 578086 |
| IC09415 | UG75 Expression | EST | Mm.33819 | TITLE ESTs | | | gi = 6078024 | 620405 |
| IC09416 | UG75 Expression | EST | Mm.33820 | TITLE ESTs, Weakly similar to molybdenum cofactor biosynthesis protein C [H. sapiens] | | | gi = 4409365 | 577145 |
| IC09417 | UG75 Expression | EST | Mm.33821 | TITLE ESTs | | | gi = 1671634 | 577366 |
| IC09418 | UG75 Expression | EST | Mm.33822 | TITLE ESTs | | | gi = 4444809 | 958400 |
| IC09419 | UG75 Expression | EST | Mm.33823 | TITLE ESTs | | | gi = 448542 | 642528 |
| IC09420 | UG75 Expression | EST | Mm.33824 | TITLE ESTs, Weakly similar to sorting nexin 1 [M. musculus] | | | gi = 5749583 | 616890 |
| IC09421 | UG75 Expression | EST | Mm.33829 | TITLE ESTs | | | gi = 4444588 | 573802 |
| IC09422 | UG75 Expression | EST | Mm.33831 | TITLE ESTs | | | gi = 2041300 | 575685 |
| IC09423 | UG75 Expression | EST | Mm.33832 | TITLE ESTs | | | gi = 1865601 | 721816 |
| IC09424 | UG75 Expression | EST | Mm.33833 | TITLE ESTs | | | gi = 1681482 | 576634 |
| IC09425 | UG75 Expression | EST | Mm.33834 | TITLE ESTs | | | gi = 4603074 | 1279125 |
| IC09426 | UG75 Expression | EST | Mm.33840 | TITLE ESTs | | | gi = 1682340 | 576758 |
| IC09427 | UG75 Expression | EST | Mm.33847 | TITLE ESTs | | | gi = 1684390 | 575427 |
| IC09428 | UG75 Expression | EST | Mm.33848 | TITLE ESTs, Weakly similar to NONHISTONE CHROMOSOMAL PROTEIN HMG-17 [M. musculus] | | | gi = 3160721 | 619854 |
| IC09429 | UG75 Expression | EST | Mm.33849 | TITLE ESTs | | | gi = 4318671 | 596000 |
| IC09430 | UG75 Expression | EST | Mm.33850 | TITLE ESTs | | | gi = 4302770 | 596146 |
| IC09431 | UG75 Expression | EST | Mm.33851 | TITLE ESTs, Weakly similar to PROBABLE PHOSPHATIDYLINOSITOL-4-PHOSPHATE 5-KINASE FAB1 [Saccharomyces cerevisiae] | | | gi = 1700242 | 636708 |
| IC09432 | UG75 Expression | EST | Mm.33853 | TITLE ESTs | | | gi = 1700749 | 638354 |
| IC09433 | UG75 Expression | EST | Mm.33855 | TITLE ESTs | | | gi = 3720896 | 635185 |
| IC09434 | UG75 Expression | EST | Mm.33856 | TITLE ESTs | | | gi = 1558319 | 752513 |
| IC09435 | UG75 Expression | EST | Mm.33858 | TITLE ESTs | | | gi = 2962146 | 638205 |
| IC09436 | UG75 Expression | EST | Mm.33859 | TITLE ESTs | | | gi = 2305979 | 1262901 |
| IC09437 | UG75 Expression | EST | Mm.33860 | TITLE ESTs, Moderately similar to P38IP [H. sapiens] | | | gi = 1807668 | 749089 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09438 | UG75 Expression | EST | Mm.33862 | TITLE ESTs | | | gi = 4601076 | 597619 |
| IC09439 | UG75 Expression | EST | Mm.33865 | TITLE ESTs | | | gi = 4317758 | 723068 |
| IC09440 | UG75 Expression | EST | Mm.33867 | TITLE ESTs | | | gi = 4307370 | 597146 |
| IC09441 | UG75 Expression | EST | Mm.33868 | TITLE ESTs | | | gi = 3067033 | 599277 |
| IC09442 | UG75 Expression | EST | Mm.33869 | TITLE ESTs | | | gi = 1675928 | 1296158 |
| IC09443 | UG75 Expression | EST | Mm.33870 | TITLE ESTs, Weakly similar to C26B2.6 [C. elegans] | | | gi = 4803610 | 641403 |
| IC09444 | UG75 Expression | EST | Mm.33871 | TITLE ESTs | | | gi = 1904020 | 596959 |
| IC09445 | UG75 Expression | EST | Mm.33872 | TITLE ESTs | | | gi = 1528730 | 1263413 |
| IC09446 | UG75 Expression | EST | Mm.33874 | TITLE ESTs | | | gi = 5749892 | 597586 |
| IC09447 | UG75 Expression | EST | Mm.33875 | TITLE ESTs, Weakly similar to torsinA [H. sapiens] | | | gi = 4407965 | 1294641 |
| IC09448 | UG75 Expression | EST | Mm.33876 | TITLE ESTs | | | gi = 1725177 | 1279037 |
| IC09449 | UG75 Expression | EST | Mm.33878 | TITLE ESTs | | | gi = 6826105 | 973814 |
| IC09450 | UG75 Expression | EST | Mm.33879 | TITLE ESTs | | | gi = 1725775 | 581939 |
| IC09451 | UG75 Expression | EST | Mm.3388 | TITLE ESTs, Weakly similar to ADP-RIBOSYLATION FACTOR-LIKE PROTEIN 4 [M. musculus] | | | gi = 5489929 | 1149293 |
| IC09452 | UG75 Expression | EST | Mm.33880 | TITLE ESTs | | | gi = 1726103 | 1361175 |
| IC09453 | UG75 Expression | EST | Mm.33881 | TITLE ESTs | | | gi = 2257042 | 894435 |
| IC09454 | UG75 Expression | EST | Mm.33882 | TITLE ESTs | | | gi = 4605566 | 1279140 |
| IC09455 | UG75 Expression | EST | Mm.33883 | TITLE ESTs | | | gi = 4404964 | 598497 |
| IC09456 | UG75 Expression | EST | Mm.33884 | TITLE ESTs | | | gi = 2906379 | 598544 |
| IC09457 | UG75 Expression | EST | Mm.33885 | TITLE ESTs, Weakly similar to type III collagen [M. musculus] | | | gi = 2249801 | 617584 |
| IC09458 | UG75 Expression | EST | Mm.33887 | TITLE ESTs | | | gi = 4601111 | 597881 |
| IC09459 | UG75 Expression | EST | Mm.33889 | TITLE ESTs | | | gi = 4302717 | 635648 |
| IC09460 | UG75 Expression | EST | Mm.33890 | TITLE ESTs | | | gi = 2965970 | 764601 |
| IC09461 | UG75 Expression | EST | Mm.33891 | TITLE ESTs | | | gi = 2691630 | 598385 |
| IC09462 | UG75 Expression | EST | Mm.33895 | TITLE ESTs | | | gi = 2811471 | 637593 |
| IC09463 | UG75 Expression | EST | Mm.33897 | TITLE ESTs | | | gi = 4702900 | 618212 |
| IC09464 | UG75 Expression | EST | Mm.33898 | TITLE ESTs | | | gi = 4601558 | 618954 |
| IC09465 | UG75 Expression | EST | Mm.33899 | TITLE ESTs | | | gi = 5491293 | 616702 |
| IC09466 | UG75 Expression | EST | Mm.33900 | TITLE ESTs | | | gi = 4702862 | 617662 |
| IC09467 | UG75 Expression | EST | Mm.33901 | TITLE ESTs | | | gi = 1749250 | 619124 |
| IC09468 | UG75 Expression | EST | Mm.33904 | TITLE ESTs | | | gi = 1817033 | 1193602 |
| IC09469 | UG75 Expression | EST | Mm.33905 | TITLE ESTs | | | gi = 1767492 | 622122 |
| IC09470 | UG75 Expression | EST | Mm.33908 | TITLE ESTs, Weakly similar to RNA helicase HEL117 [R. norvegicus] | | | gi = 2920223 | 1193510 |
| IC09471 | UG75 Expression | EST | Mm.33910 | TITLE ESTs | | | gi = 1776991 | 617598 |
| IC09472 | UG75 Expression | EST | Mm.33911 | TITLE ESTs | | | gi = 2813307 | 595989 |
| IC09473 | UG75 Expression | EST | Mm.33912 | TITLE ESTs | | | gi = 4601117 | 617880 |
| IC09474 | UG75 Expression | EST | Mm.33913 | TITLE ESTs | | | gi = 4287820 | 619161 |
| IC09475 | UG75 Expression | EST | Mm.33914 | TITLE ESTs | | | gi = 4300857 | 619615 |
| IC09476 | UG75 Expression | EST | Mm.33915 | TITLE ESTs | | | gi = 1757005 | 618296 |
| IC09477 | UG75 Expression | EST | Mm.33916 | TITLE ESTs | | | gi = 4603272 | 596681 |
| IC09478 | UG75 Expression | EST | Mm.33918 | TITLE ESTs | | | gi = 4287883 | 619200 |
| IC09479 | UG75 Expression | EST | Mm.33920 | TITLE DNA segment, Chr 16, Wayne State University 83, expressed | GENE D16Wsu83e | | | 621618 |
| IC09480 | UG75 Expression | EST | Mm.33921 | TITLE ESTs, Moderately similar to lecithin retinol acyltransferase [H. sapiens] | | | gi = 4613294 | 619832 |
| IC09481 | UG75 Expression | EST | Mm.33922 | TITLE ESTs, Moderately similar to TLR6 [M. musculus] | | | gi = 4299002 | 777805 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09482 | UG75 Expression | EST | Mm.33923 | TITLE ESTs | | | gi = 4723657 | 636454 |
| IC09483 | UG75 Expression | EST | Mm.33924 | TITLE ESTs | | | gi = 4613439 | 620865 |
| IC09484 | UG75 Expression | EST | Mm.33925 | TITLE ESTs | | | gi = 1759623 | 620647 |
| IC09485 | UG75 Expression | EST | Mm.33926 | TITLE ESTs | | | gi = 5125859 | 621175 |
| IC09486 | UG75 Expression | EST | Mm.33928 | TITLE ESTs | | | gi = 4601319 | 621105 |
| IC09487 | UG75 Expression | EST | Mm.33929 | TITLE ESTs | | | gi = 4601327 | 621131 |
| IC09488 | UG75 Expression | EST | Mm.33930 | TITLE ESTs | | | gi = 4723595 | 635976 |
| IC09489 | UG75 Expression | EST | Mm.33931 | TITLE ESTs | | | gi = 4723654 | 636440 |
| IC09490 | UG75 Expression | EST | Mm.33932 | TITLE ESTs | | | gi = 3080062 | 635964 |
| IC09491 | UG75 Expression | EST | Mm.33933 | TITLE ESTs | | | gi = 4284612 | 582635 |
| IC09492 | UG75 Expression | EST | Mm.33934 | TITLE ESTs | | | gi = 1767590 | 621827 |
| IC09493 | UG75 Expression | EST | Mm.33935 | TITLE ESTs | | | gi = 1767815 | 622710 |
| IC09494 | UG75 Expression | EST | Mm.33936 | TITLE ESTs | | | gi = 1768389 | 764479 |
| IC09495 | UG75 Expression | EST | Mm.33937 | TITLE ESTs | | | gi = 4295591 | 637384 |
| IC09496 | UG75 Expression | EST | Mm.33938 | TITLE ESTs | | | gi = 4298597 | 616971 |
| IC09497 | UG75 Expression | EST | Mm.33941 | TITLE ESTs, Weakly similar to U1 SMALL NUCLEAR RIBONUCLEOPROTEIN A [H. sapiens] | | | gi = 1772162 | 598565 |
| IC09498 | UG75 Expression | EST | Mm.33944 | TITLE ESTs | | | gi = 2775636 | 636156 |
| IC09499 | UG75 Expression | EST | Mm.33945 | TITLE ESTs | | | gi = 1777093 | 636910 |
| IC09500 | UG75 Expression | EST | Mm.33946 | TITLE ESTs | | | gi = 4725135 | 637404 |
| IC09501 | UG75 Expression | EST | Mm.33947 | TITLE ESTs | | | gi = 3602724 | 617948 |
| IC09502 | UG75 Expression | EST | Mm.33949 | TITLE ESTs | | | gi = 4967535 | 751160 |
| IC09503 | UG75 Expression | EST | Mm.33950 | TITLE ESTs | | | gi = 2775655 | 972431 |
| IC09504 | UG75 Expression | EST | Mm.33951 | TITLE ESTs | | | gi = 2291824 | 622300 |
| IC09505 | UG75 Expression | EST | Mm.33954 | TITLE ESTs, Weakly similar CCA3 [R. norvegicus] | | | gi = 6574446 | 634502 |
| IC09506 | UG75 Expression | EST | Mm.33955 | TITLE ESTs | | | gi = 4409376 | 597680 |
| IC09507 | UG75 Expression | EST | Mm.33957 | TITLE ESTs, Weakly similar to IgE receptor beta subunit [H. sapiens] | | | gi = 4600986 | 598479 |
| IC09508 | UG75 Expression | EST | Mm.33960 | TITLE ESTs | | | gi = 4724385 | 638964 |
| IC09509 | UG75 Expression | EST | Mm.33961 | TITLE ESTs | | | gi = 1796522 | 638195 |
| IC09510 | UG75 Expression | EST | Mm.33963 | TITLE ESTs, Weakly similar to delta7-sterol reductase [M. musculus] | | | gi = 2308231 | 1380688 |
| IC09511 | UG75 Expression | EST | Mm.33964 | TITLE ESTs | | | gi = 1649824 | 750442 |
| IC09512 | UG75 Expression | EST | Mm.33965 | TITLE ESTs | | | gi = 4216468 | 643612 |
| IC09513 | UG75 Expression | EST | Mm.33966 | TITLE EST | | | gi = 4307142 | 643897 |
| IC09514 | UG75 Expression | EST | Mm.33968 | TITLE ESTs | | | gi = 1801031 | 641110 |
| IC09515 | UG75 Expression | EST | Mm.33969 | TITLE ESTs | | | gi = 4803462 | 644272 |
| IC09516 | UG75 Expression | EST | Mm.33970 | TITLE ESTs | | | gi = 4297080 | 644301 |
| IC09517 | UG75 Expression | EST | Mm.33975 | TITLE ESTs | | | gi = 6008020 | 1193129 |
| IC09518 | UG75 Expression | EST | Mm.33976 | TITLE ESTs, Weakly similar to KIAA1005 protein [H. sapiens] | | | gi = 2520760 | 597708 |
| IC09519 | UG75 Expression | EST | Mm.33977 | TITLE ESTs | | | gi = 1826425 | 644200 |
| IC09520 | UG75 Expression | EST | Mm.33978 | TITLE EST | | | gi = 4307163 | 644057 |
| IC09521 | UG75 Expression | EST | Mm.33979 | TITLE ESTs | | | gi = 4319330 | 644241 |
| IC09522 | UG75 Expression | EST | Mm.33980 | TITLE ESTs | | | gi = 4513376 | 644290 |
| IC09523 | UG75 Expression | EST | Mm.33982 | TITLE ESTs | | | gi = 3223841 | 644926 |
| IC09524 | UG75 Expression | EST | Mm.33983 | TITLE ESTs | | | gi = 4319368 | 644994 |
| IC09525 | UG75 Expression | EST | Mm.33988 | TITLE ESTs | | | gi = 1810955 | 642160 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09526 | UG75 Expression | EST | Mm.33990 | TITLE ESTs, Moderately similar to COP-COATED VESICLE MEMBRANE PROTEIN P24 PRECURSOR [Cricetulus griseus] | | | gi = 4444773 | 574591 |
| IC09527 | UG75 Expression | EST | Mm.34000 | TITLE ESTs | | | gi = 5491863 | 596524 |
| IC09528 | UG75 Expression | EST | Mm.34002 | TITLE ESTs | | | gi = 2259347 | 719013 |
| IC09529 | UG75 Expression | EST | Mm.34007 | TITLE ESTs | | | gi = 1682599 | 718963 |
| IC09530 | UG75 Expression | EST | Mm.34008 | TITLE ESTs, Weakly similar to collagen alpha 1 (III) chain precursor [M. musculus] | | | gi = 1864614 | 1001705 |
| IC09531 | UG75 Expression | EST | Mm.34009 | TITLE ESTs, Weakly similar to similarity to methylases. [C. elegans] | | | gi = 3862975 | 749697 |
| IC09532 | UG75 Expression | EST | Mm.34012 | TITLE ESTs | | | gi = 6084052 | 1279448 |
| IC09533 | UG75 Expression | EST | Mm.34014 | TITLE ESTs | | | gi = 2139791 | 765846 |
| IC09534 | UG75 Expression | EST | Mm.34015 | TITLE ESTs, Weakly similar to endocrine regulator | | | gi = 4614855 | 722948 |
| IC09535 | UG75 Expression | EST | Mm.34019 | TITLE ESTs, Moderately similar to (define not available 5901653) [M. musculus] | | | gi = 3747234 | 734759 |
| IC09536 | UG75 Expression | EST | Mm.34023 | TITLE ESTs | | | gi = 1902467 | 721717 |
| IC09537 | UG75 Expression | EST | Mm.34024 | TITLE ESTs | | | gi = 3159434 | 638136 |
| IC09538 | UG75 Expression | EST | Mm.34026 | TITLE ESTs | | | gi = 2528140 | 622778 |
| IC09539 | UG75 Expression | EST | Mm.34027 | TITLE ESTs, Weakly similar to (define not available 5931616) [M. musculus] | | | gi = 1682537 | 777790 |
| IC09540 | UG75 Expression | EST | Mm.34028 | TITLE ESTs, Moderately similar to KIAA0494 protein [H. sapiens] | | | gi = 2307265 | 959035 |
| IC09541 | UG75 Expression | EST | Mm.34029 | TITLE ESTs | | | gi = 2850698 | 551213 |
| IC09542 | UG75 Expression | EST | Mm.34030 | TITLE ESTs | | | gi = 1794492 | 764197 |
| IC09543 | UG75 Expression | EST | Mm.34031 | TITLE ESTs | | | gi = 3684015 | 719034 |
| IC09544 | UG75 Expression | EST | Mm.34032 | TITLE ESTs | | | gi = 4318931 | 721120 |
| IC09545 | UG75 Expression | EST | Mm.34035 | TITLE ESTs | | | gi = 2049087 | 618477 |
| IC09546 | UG75 Expression | EST | Mm.34038 | TITLE ESTs, Moderately similar to RNA 3'-TERMINAL PHOSPHATE CYCLASE 1 [H. sapiens] | | | gi = 4596945 | 637822 |
| IC09547 | UG75 Expression | EST | Mm.34045 | TITLE ESTs | | | gi = 4724167 | 762621 |
| IC09548 | UG75 Expression | EST | Mm.34046 | TITLE ESTs | | | gi = 1287930 | 551373 |
| IC09549 | UG75 Expression | EST | Mm.34047 | TITLE ESTs | | | gi = 1287206 | 1002782 |
| IC09550 | UG75 Expression | EST | Mm.34048 | TITLE ESTs | | | gi = 2967378 | 616678 |
| IC09551 | UG75 Expression | EST | Mm.34049 | TITLE ESTs, Weakly similar to K02G10.3 gene product [C. elegans] | | | gi = 1889541 | 1295465 |
| IC09552 | UG75 Expression | EST | Mm.34051 | TITLE ESTs | | | gi = 1759252 | 620260 |
| IC09553 | UG75 Expression | EST | Mm.34052 | TITLE ESTs | | | gi = 4303276 | 765364 |
| IC09554 | UG75 Expression | EST | Mm.34054 | TITLE EST | | | gi = 4317049 | 764331 |
| IC09555 | UG75 Expression | EST | Mm.34057 | TITLE ESTs | | | gi = 4316133 | 720877 |
| IC09556 | UG75 Expression | EST | Mm.34059 | TITLE ESTs | | | gi = 4967997 | 534150 |
| IC09557 | UG75 Expression | EST | Mm.34060 | TITLE ESTs, Weakly similar to breast cancer suppressor candidate 1 [H. sapiens] | | | gi = 1876500 | 777125 |
| IC09558 | UG75 Expression | EST | Mm.34062 | TITLE ESTs | | | gi = 1919672 | 973782 |
| IC09559 | UG75 Expression | EST | Mm.34066 | TITLE EST | | | gi = 4304282 | 598266 |
| IC09560 | UG75 Expression | EST | Mm.34067 | TITLE ESTs | | | gi = 2248935 | 751316 |
| IC09561 | UG75 Expression | EST | Mm.34068 | TITLE ESTs | | | gi = 1681783 | 596373 |
| IC09562 | UG75 Expression | EST | Mm.34069 | TITLE ESTs | | | gi = 3692834 | 972704 |
| IC09563 | UG75 Expression | EST | Mm.34070 | TITLE ESTs | | | gi = 1769242 | 642987 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09564 | UG75 Expression | EST | Mm.34071 | TITLE ESTs | | | gi = 1937258 | 777410 |
| IC09565 | UG75 Expression | EST | Mm.34072 | TITLE ESTs | | | gi = 1681062 | 575724 |
| IC09566 | UG75 Expression | EST | Mm.34073 | TITLE ESTs | | | gi = 2039566 | 597852 |
| IC09567 | UG75 Expression | EST | Mm.34075 | TITLE ESTs | | | gi = 296932 | 1001925 |
| IC09568 | UG75 Expression | EST | Mm.34077 | TITLE ESTs | | | gi = 1759921 | 621006 |
| IC09569 | UG75 Expression | EST | Mm.34080 | TITLE ESTs | | | gi = 2721940 | 617847 |
| IC09570 | UG75 Expression | EST | Mm.34081 | TITLE ESTs | | | gi = 4968287 | 749162 |
| IC09571 | UG75 Expression | EST | Mm.34083 | TITLE ESTs | | | gi = 2754962 | 1149634 |
| IC09572 | UG75 Expression | EST | Mm.34086 | TITLE ESTs | | | gi = 4407666 | 751780 |
| IC09573 | UG75 Expression | EST | Mm.34087 | TITLE ESTs | | | gi = 1816964 | 751784 |
| IC09574 | UG75 Expression | EST | Mm.34088 | TITLE ESTs | | | gi = 2283301 | 720808 |
| IC09575 | UG75 Expression | EST | Mm.34091 | TITLE ESTs | | | gi = 1316324 | 751902 |
| IC09576 | UG75 Expression | EST | Mm.34092 | TITLE ESTs | | | gi = 4603479 | 621092 |
| IC09577 | UG75 Expression | EST | Mm.34093 | TITLE ESTs, Weakly similar to Bing1 [M. musculus] | | | gi = 2990525 | 1264031 |
| IC09578 | UG75 Expression | EST | Mm.34096 | TITLE ESTs | | | gi = 2139808 | 720834 |
| IC09579 | UG75 Expression | EST | Mm.34097 | TITLE ESTs | | | gi = 1872763 | 1227137 |
| IC09580 | UG75 Expression | EST | Mm.34098 | TITLE ESTs | | | gi = 2907030 | 574417 |
| IC09581 | UG75 Expression | EST | Mm.34102 | TITLE ESTs | | | gi = 6167890 | 635854 |
| IC09582 | UG75 Expression | EST | Mm.34103 | TITLE ESTs | | | gi = 2308588 | 575050 |
| IC09583 | UG75 Expression | EST | Mm.34104 | TITLE ESTs, Weakly similar to Similarity to [C. elegans] | | | gi = 4440810 | 1020823 |
| IC09584 | UG75 Expression | EST | Mm.34111 | TITLE ESTs, Moderately similar to CGI-90 protein [H. sapiens] | | | gi = 2305931 | 618665 |
| IC09585 | UG75 Expression | EST | Mm.34123 | TITLE ESTs | | | gi = 4320882 | 720802 |
| IC09586 | UG75 Expression | EST | Mm.34125 | TITLE ESTs | | | gi = 1881899 | 717836 |
| IC09587 | UG75 Expression | EST | Mm.34128 | TITLE ESTs | | | gi = 4316160 | 720832 |
| IC09588 | UG75 Expression | EST | Mm.34129 | TITLE ESTs | | | gi = 5910891 | 597871 |
| IC09589 | UG75 Expression | EST | Mm.34130 | TITLE ESTs | | | gi = 4484544 | 1263229 |
| IC09590 | UG75 Expression | EST | Mm.34131 | TITLE ESTs | | | gi = 2517042 | 596866 |
| IC09591 | UG75 Expression | EST | Mm.34134 | TITLE ESTs | | | gi = 1285333 | 749792 |
| IC09592 | UG75 Expression | EST | Mm.34139 | TITLE ESTs | | | gi = 6749494 | 749761 |
| IC09593 | UG75 Expression | EST | Mm.34142 | TITLE ESTs | | | gi = 4296409 | 596896 |
| IC09594 | UG75 Expression | EST | Mm.34144 | TITLE ESTs | | | gi = 2404469 | 1362846 |
| IC09595 | UG75 Expression | EST | Mm.34148 | TITLE ESTs | | | gi = 5908103 | 577154 |
| IC09596 | UG75 Expression | EST | Mm.34151 | TITLE ESTs | | | gi = 2907004 | 597227 |
| IC09597 | UG75 Expression | EST | Mm.34155 | TITLE ESTs | | | gi = 3685473 | 616600 |
| IC09598 | UG75 Expression | EST | Mm.34156 | TITLE ESTs | | | gi = 4283964 | 582206 |
| IC09599 | UG75 Expression | EST | Mm.34157 | TITLE ESTs, Weakly similar to Hrs [M. musculus] | | | gi = 6517441 | 718822 |
| IC09600 | UG75 Expression | EST | Mm.34158 | TITLE ESTs | | | gi = 1681462 | 576562 |
| IC09601 | UG75 Expression | EST | Mm.34159 | TITLE ESTs, Moderately similar to KIAA0977 protein [H. sapiens] | | | gi = 2049296 | 619086 |
| IC09602 | UG75 Expression | EST | Mm.34162 | TITLE ESTs, Moderately similar to GTPASE-ACTIVATING PROTEIN [Bos taurus] | | | gi = 4061764 | 751726 |
| IC09603 | UG75 Expression | EST | Mm.34163 | TITLE ESTs, Weakly similar to immune associated protein 38 [M. musculus] | | | gi = 4374825 | 1149068 |
| IC09604 | UG75 Expression | EST | Mm.34164 | TITLE ESTs, Moderately similar to unknown [R. norvegicus] | | | gi = 2203629 | 958483 |
| IC09605 | UG75 Expression | EST | Mm.34169 | TITLE ESTs | | | gi = 1290064 | 573751 |
| IC09606 | UG75 Expression | EST | Mm.34171 | TITLE ESTs | | | gi = 2857330 | 1195894 |
| IC09607 | UG75 Expression | EST | Mm.34176 | TITLE ESTs | | | gi = 4373840 | 1149273 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09608 | UG75 Expression | EST | Mm.34179 | TITLE ESTs | | | gi = 4723081 | 638857 |
| IC09609 | UG75 Expression | EST | Mm.34182 | TITLE ESTs | | | gi = 1290121 | 644398 |
| IC09610 | UG75 Expression | EST | Mm.34183 | TITLE ESTs | | | gi = 1309870 | 973332 |
| IC09611 | UG75 Expression | EST | Mm.34184 | TITLE ESTs, Weakly similar to matrin cyclophilin [*R. norvegicus*] | | | gi = 248913 | 618451 |
| IC09612 | UG75 Expression | EST | Mm.34189 | TITLE ESTs | | | gi = 2257447 | 620453 |
| IC09613 | UG75 Expression | EST | Mm.3419 | TITLE ESTs, Weakly similar to C1q-related factor [*M. musculus*] | | | gi = 1677131 | 749942 |
| IC09614 | UG75 Expression | EST | Mm.34192 | TITLE ESTs | | | gi = 2262782 | 1361962 |
| IC09615 | UG75 Expression | EST | Mm.34194 | TITLE ESTs | | | gi = 5494743 | 717847 |
| IC09616 | UG75 Expression | EST | Mm.34198 | TITLE ESTs, Weakly similar to BRCA1-associated RING domain protein [*M. musculus*] | | | gi = 2272032 | 622077 |
| IC09617 | UG75 Expression | EST | Mm.34200 | TITLE ESTs | | | gi = 1808451 | 642074 |
| IC09618 | UG75 Expression | EST | Mm.34204 | TITLE ESTs | | | gi = 2273439 | 596874 |
| IC09619 | UG75 Expression | EST | Mm.34205 | TITLE ESTs | | | gi = 4616290 | 1312951 |
| IC09620 | UG75 Expression | EST | Mm.34207 | TITLE ESTs, Weakly similar to Lpg12p [*S. cerevisiae*] | | | gi = 2283256 | 1193529 |
| IC09621 | UG75 Expression | EST | Mm.34212 | TITLE ESTs | | | gi = 2292034 | 641465 |
| IC09622 | UG75 Expression | EST | Mm.34218 | TITLE ESTs | | | gi = 2256451 | 958529 |
| IC09623 | UG75 Expression | EST | Mm.34220 | TITLE ESTs | | | gi = 4401438 | 717756 |
| IC09624 | UG75 Expression | EST | Mm.34222 | TITLE ESTs | | | gi = 2307958 | 804548 |
| IC09625 | UG75 Expression | EST | Mm.34224 | TITLE ESTs | | | gi = 2571910 | 597215 |
| IC09626 | UG75 Expression | EST | Mm.34228 | TITLE ESTs | | | gi = 3749840 | 533597 |
| IC09627 | UG75 Expression | EST | Mm.34232 | TITLE ESTs | | | gi = 1919238 | 557977 |
| IC09628 | UG75 Expression | EST | Mm.34233 | TITLE ESTs, Weakly similar to zinc finger protein [*M. musculus*] | | | gi = 2306710 | 621003 |
| IC09629 | UG75 Expression | EST | Mm.34235 | TITLE ESTs | | | gi = 1768622 | 634467 |
| IC09630 | UG75 Expression | EST | Mm.34236 | TITLE ESTs | | | gi = 4405270 | 974057 |
| IC09631 | UG75 Expression | EST | Mm.34238 | TITLE ESTs | | | gi = 1915736 | 596044 |
| IC09632 | UG75 Expression | EST | Mm.34242 | TITLE ESTs, Moderately similar to PHOSPHOMEVALONATE KINASE [*H. sapiens*] | | | gi = 1287267 | 1294205 |
| IC09633 | UG75 Expression | EST | Mm.34244 | TITLE ESTs, Weakly similar to hypothetical 43.2 kDa protein [*H. sapiens*] | | | gi = 1375725 | 1020934 |
| IC09634 | UG75 Expression | EST | Mm.34246 | TITLE ESTs | | | gi = 1316779 | 619245 |
| IC09635 | UG75 Expression | EST | Mm.34255 | TITLE ESTs | | | gi = 4508411 | 636893 |
| IC09636 | UG75 Expression | EST | Mm.34257 | TITLE ESTs | | | gi = 3718297 | 972947 |
| IC09637 | UG75 Expression | EST | Mm.34259 | TITLE ESTs | | | gi = 1744045 | 718368 |
| IC09638 | UG75 Expression | EST | Mm.34261 | TITLE ESTs, Weakly similar to Similarity with Schizosaccharomyces hypothetical gene [*C. elegans*] | | | gi = 1808566 | 972940 |
| IC09639 | UG75 Expression | EST | Mm.34263 | TITLE ESTs | | | gi = 2040535 | 573268 |
| IC09640 | UG75 Expression | EST | Mm.34264 | TITLE ESTs | | | gi = 4601840 | 635028 |
| IC09641 | 17Lid Expansion 00/04/26 UG#76 | EST | Mm.34265 | ESTs | | | gi = 2454798 | 605280 |
| IC09642 | UG75 Expression | EST | Mm.34282 | TITLE ESTs | | | gi = 4300090 | 575756 |
| IC09643 | UG75 Expression | EST | Mm.34284 | TITLE ESTs | | | gi = 4216979 | 573823 |
| IC09644 | UG75 Expression | EST | Mm.34292 | TITLE ESTs | | | gi = 2307830 | 720741 |
| IC09645 | UG75 Expression | EST | Mm.34293 | TITLE ESTs | | | gi = 2116040 | 1279275 |
| IC09646 | UG75 Expression | EST | Mm.34296 | TITLE ESTs | | | gi = 2516648 | 642152 |
| IC09647 | UG75 Expression | EST | Mm.34298 | TITLE ESTs, Moderately similar to This gene is novel. [*H. sapiens*] | | | gi = 1726804 | 1140170 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09648 | UG75 Expression | EST | Mm.34300 | TITLE ESTs | | | gi = 4319427 | 618649 |
| IC09649 | UG75 Expression | EST | Mm.34310 | TITLE ESTs | | | gi = 4374856 | 643677 |
| IC09650 | UG75 Expression | EST | Mm.34311 | TITLE ESTs | | | gi = 4274652 | 1225644 |
| IC09651 | UG75 Expression | EST | Mm.34314 | TITLE ESTs | | | gi = 2892719 | 1149253 |
| IC09652 | UG75 Expression | EST | Mm.34316 | TITLE ESTs, Moderately similar to modulator recognition factor 1 [H. sapiens] | | | gi = 4404293 | 1002677 |
| IC09653 | UG75 Expression | EST | Mm.34317 | TITLE ESTs | | | gi = 4613360 | 1149568 |
| IC09654 | UG75 Expression | EST | Mm.34322 | TITLE ESTs | | | gi = 3393318 | 972759 |
| IC09655 | UG75 Expression | EST | Mm.34323 | TITLE EST | | | gi = 4401893 | 1001519 |
| IC09656 | UG75 Expression | EST | Mm.34324 | TITLE ESTs, Moderately similar to RAS-RELATED PROTEIN RAP-2A [Home sapiens] | | | gi = 3809326 | 583613 |
| IC09657 | UG75 Expression | EST | Mm.34328 | TITLE ESTs | | | gi = 1895997 | 1749685 |
| IC09658 | UG75 Expression | EST | Mm.34329 | TITLE ESTs, Moderately similar to selenophosphate synthetase 2 [M. musculus] | | | gi = 6824333 | 635586 |
| IC09659 | UG75 Expression | EST | Mm.34338 | TITLE ESTs | | | gi = 5477726 | 972560 |
| IC09660 | UG75 Expression | EST | Mm.34339 | TITLE ESTs | | | gi = 2917082 | 893872 |
| IC09661 | UG75 Expression | EST | Mm.34342 | TITLE ESTs | | | gi = 2346570 | 1279755 |
| IC09662 | UG75 Expression | EST | Mm.34350 | TITLE ESTs | | | gi = 3718112 | 777512 |
| IC09663 | UG75 Expression | EST | Mm.34351 | TITLE ESTs | | | gi = 5336406 | 959487 |
| IC09664 | UG75 Expression | EST | Mm.34356 | TITLE ESTs, Weakly similar to dJ963K23.2 [H. sapiens] | | | gi = 2263027 | 1001815 |
| IC09665 | UG75 Expression | EST | Mm.34357 | TITLE ESTs, Weakly similar to similar to genome polyprotein [C. elegans] | | | gi = 6167899 | 1263212 |
| IC09666 | UG75 Expression | EST | Mm.34358 | TITLE ESTs | | | gi = 4450604 | 634884 |
| IC09667 | UG75 Expression | EST | Mm.34360 | TITLE ESTs | | | gi = 3373621 | 621648 |
| IC09668 | UG75 Expression | EST | Mm.34361 | TITLE ESTs | | | gi = 472054 | 533708 |
| IC09669 | UG75 Expression | EST | Mm.34364 | TITLE ESTs | | | gi = 4303943 | 622190 |
| IC09670 | UG75 Expression | EST | Mm.34365 | TITLE ESTs, Weakly similar to yvh1, len: 364, CAI: 0.17, PVH1_YEAST Q02256 PROTEIN-TYROSINE PHOSPHATASE YVH1 [S. cerevisiae] | | | gi = 1493410 | 637342 |
| IC09671 | UG75 Expression | EST | Mm.34366 | TITLE ESTs, Weakly similar to nuclear protein np95 [M. musculus] | | | gi = 2519319 | 534109 |
| IC09672 | UG75 Expression | EST | Mm.34368 | TITLE ESTs, Weakly similar to MDC-3.13 isoform 1 [H. sapiens] | | | gi = 3235177 | 573953 |
| IC09673 | UG75 Expression | EST | Mm.34371 | TITLE ESTs | | | gi = 5488768 | 598073 |
| IC09674 | UG75 Expression | EST | Mm.34373 | TITLE ESTs | | | gi = 2745434 | 598930 |
| IC09675 | UG75 Expression | EST | Mm.34377 | TITLE ESTs | | | gi = 4783005 | 599271 |
| IC09676 | UG75 Expression | EST | Mm.34378 | TITLE ESTs | | | gi = 2756500 | 1363376 |
| IC09677 | UG75 Expression | EST | Mm.34381 | TITLE ESTs, Weakly similar to ankyrin, erythrocyte [M. musculus] | | | gi = 2775545 | 1225990 |
| IC09678 | UG75 Expression | EST | Mm.34383 | TITLE ESTs, Weakly similar to kinase Myt1 [H. sapiens] | | | gi = 6514999 | 636366 |
| IC09679 | UG75 Expression | EST | Mm.34385 | TITLE ESTs | | | gi = 6085605 | 719467 |
| IC09680 | UG75 Expression | EST | Mm.34386 | TITLE ESTs | | | gi = 3731305 | 636178 |
| IC09681 | UG75 Expression | EST | Mm.34387 | TITLE ESTs, Weakly similar to similar to the protein phosphates 2c family [C. elegans] | | | gi = 3126512 | 642145 |
| IC09682 | UG75 Expression | EST | Mm.34388 | TITLE ESTs | | | gi = 1862673 | 620664 |
| IC09683 | UG75 Expression | EST | Mm.34394 | TITLE ESTs | | | gi = 2813614 | 619566 |
| IC09684 | UG75 Expression | EST | Mm.34396 | TITLE ESTs | | | gi = 1807678 | 635225 |
| IC09685 | UG75 Expression | EST | Mm.34398 | TITLE ESTs | | | gi = 2775894 | 1226854 |
| IC09686 | UG75 Expression | EST | Mm.34400 | TITLE ESTs | | | gi = 2885594 | 635607 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09687 | UG75 Expression | EST | Mm.34402 | TITLE ESTs, Moderately similar to AKAP450 protein [H. sapiens] | | | gi = 4216298 | 1023370 |
| IC09688 | UG75 Expression | EST | Mm.34412 | TITLE ESTs | | | gi = 4720595 | 1282730 |
| IC09689 | UG75 Expression | EST | Mm.34416 | TITLE ESTs, Weakly similar to Ylr350wp [S. cerevisiae] | | | gi = 298941 | 765750 |
| IC09690 | UG75 Expression | EST | Mm.34419 | TITLE ESTs | | | gi = 2528478 | 1294098 |
| IC09691 | UG75 Expression | EST | Mm.34420 | TITLE ESTs | | | gi = 6098719 | 777620 |
| IC09692 | UG75 Expression | EST | Mm.3443 | TITLE ESTs | | | gi = 4216254 | 751607 |
| IC09693 | UG75 Expression | EST | Mm.34431 | TITLE ESTs | | | gi = 2201397 | 832690 |
| IC09694 | UG75 Expression | EST | Mm.34432 | TITLE ESTs, Weakly similar to /prediction | | | gi = 2693201 | 1124262 |
| IC09695 | UG75 Expression | EST | Mm.34433 | TITLE ESTs | | | gi = 2979080 | 1281481 |
| IC09696 | UG75 Expression | EST | Mm.34435 | TITLE ESTs | | | gi = 4307107 | 643879 |
| IC09697 | UG75 Expression | EST | Mm.34437 | TITLE ESTs | | | gi = 1297790 | 619430 |
| IC09698 | UG75 Expression | EST | Mm.34438 | TITLE ESTs | | | gi = 2990954 | 597402 |
| IC09699 | UG75 Expression | EST | Mm.34440 | TITLE ESTs | | | gi = 4444687 | 575096 |
| IC09700 | UG75 Expression | EST | Mm.34443 | TITLE ESTs | | | gi = 431948 | 644419 |
| IC09701 | UG75 Expression | EST | Mm.34449 | TITLE ESTs | | | gi = 4765570 | 641578 |
| IC09702 | UG75 Expression | EST | Mm.3445 | TITLE ESTs | | | gi = 5427929 | 750443 |
| IC09703 | UG75 Expression | EST | Mm.34452 | TITLE ESTs, Weakly similar to trg [R. norvegicus] | | | gi = 6822651 | 751015 |
| IC09704 | UG75 Expression | EST | Mm.34453 | TITLE ESTs [H. sapiens] | | | gi = 3167584 | 550724 |
| IC09705 | UG75 Expression | EST | Mm.34455 | TITLE ESTs | | | gi = 4304251 | 599000 |
| IC09706 | UG75 Expression | EST | Mm.34456 | TITLE ESTs | | | gi = 4968409 | 635791 |
| IC09707 | UG75 Expression | EST | Mm.34461 | TITLE ESTs | | | gi = 4307135 | 643914 |
| IC09708 | UG75 Expression | EST | Mm.34462 | TITLE ESTs | | | gi = 3749955 | 576885 |
| IC09709 | UG75 Expression | EST | Mm.34466 | TITLE ESTs | | | gi = 2956270 | 1263922 |
| IC09710 | UG75 Expression | EST | Mm.34467 | TITLE ESTs | | | gi = 4613383 | 620411 |
| IC09711 | UG75 Expression | EST | Mm.3447 | TITLE ESTs | | | gi = 3125930 | 751798 |
| IC09712 | UG75 Expression | EST | Mm.34470 | TITLE ESTs | | | gi = 2192179 | 1363065 |
| IC09713 | UG75 Expression | EST | Mm.34471 | TITLE ESTs | | | gi = 5338331 | 582456 |
| IC09714 | UG75 Expression | EST | Mm.34472 | TITLE ESTs | | | gi = 3067532 | 1282072 |
| IC09715 | UG75 Expression | EST | Mm.34474 | TITLE ESTs, Moderately similar to cytohesin binding protein HE [H. sapiens] | | | gi = 4450383 | 1345188 |
| IC09716 | UG75 Expression | EST | Mm.34475 | TITLE ESTs | | | gi = 2964945 | 1345676 |
| IC09717 | UG75 Expression | EST | Mm.34476 | TITLE ESTs | | | gi = 3100451 | 1345405 |
| IC09718 | UG75 Expression | EST | Mm.34477 | TITLE ESTs | | | gi = 1801017 | 640963 |
| IC09719 | UG75 Expression | EST | Mm.34479 | TITLE ESTs | | | gi = 4295437 | 618192 |
| IC09720 | UG75 Expression | EST | Mm.34480 | TITLE ESTs | | | gi = 1863779 | 894165 |
| IC09721 | UG75 Expression | EST | Mm.34482 | TITLE ESTs | | | gi = 4723793 | 582658 |
| IC09722 | UG75 Expression | EST | Mm.34483 | TITLE ESTs | | | gi = 5549596 | 635085 |
| IC09723 | UG75 Expression | EST | Mm.34484 | TITLE ESTs | | | gi = 1777153 | 637208 |
| IC09724 | UG75 Expression | EST | Mm.34489 | TITLE ESTs, Weakly similar to hypothetical protein unp [M. musculus] | | | gi = 3517935 | 644898 |
| IC09725 | UG75 Expression | EST | Mm.34492 | TITLE ESTs | | | gi = 2906962 | 1225003 |
| IC09726 | UG75 Expression | EST | Mm.34498 | TITLE ESTs | | | gi = 3167151 | 619909 |
| IC09727 | UG75 Expression | EST | Mm.34500 | TITLE ESTs, Weakly similar to ORF [H. sapiens] | | | gi = 1909759 | 723274 |
| IC09728 | UG75 Expression | EST | Mm.34501 | TITLE ESTs | | | gi = 6748737 | 573573 |
| IC09729 | UG75 Expression | EST | Mm.34506 | TITLE ESTs | | | gi = 1936650 | 750914 |
| IC09730 | UG75 Expression | EST | Mm.34508 | TITLE ESTs | | | gi = 4613284 | 619787 |
| IC09731 | UG75 Expression | EST | Mm.34510 | TITLE ESTs | | | gi = 1725067 | 622922 |
| IC09732 | UG75 Expression | EST | Mm.34514 | TITLE ESTs | | | gi = 2520920 | 599182 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09733 | UG75 Expression | EST | Mm.34516 | TITLE ESTs | | | gi = 1682367 | 577129 |
| IC09734 | UG75 Expression | EST | Mm.34517 | TITLE ESTs, Weakly similar to ZINC FINGER PROTEIN MLZ-4 [M. musculus] | | | gi = 4374522 | 1265071 |
| IC09735 | UG75 Expression | EST | Mm.34521 | TITLE ESTs, Weakly similar to (define not available 5689035) [M. musculus] | | | gi = 4404355 | 1296008 |
| IC09736 | UG75 Expression | EST | Mm.34522 | TITLE ESTs | | | gi = 4373911 | 1367111 |
| IC09737 | UG75 Expression | EST | Mm.34524 | TITLE ESTs | | | gi = 3167642 | 618650 |
| IC09738 | UG75 Expression | EST | Mm.34527 | TITLE ESTs | | | gi = 4301046 | 621008 |
| IC09739 | UG75 Expression | EST | Mm.34530 | TITLE ESTs | | | gi = 1737757 | 777497 |
| IC09740 | UG75 Expression | EST | Mm.34538 | TITLE ESTs, Weakly similar to ADP-ribosylation-like factor homolog ARL6 [M. musculus] | | | gi = 3296945 | 638770 |
| IC09741 | UG75 Expression | EST | Mm.34539 | TITLE ESTs | | | gi = 3053367 | 751749 |
| IC09742 | UG75 Expression | EST | Mm.34540 | TITLE ESTs | | | gi = 4434142 | 643313 |
| IC09743 | UG75 Expression | EST | Mm.34542 | TITLE ESTs | | | gi = 1714063 | 1380629 |
| IC09744 | UG75 Expression | EST | Mm.34545 | TITLE ESTs | | | gi = 4301919 | 621763 |
| IC09745 | UG75 Expression | EST | Mm.34546 | TITLE ESTs | | | gi = 6645216 | 1972712 |
| IC09746 | UG75 Expression | EST | Mm.34550 | TITLE ESTs | | | gi = 3515315 | 1293904 |
| IC09747 | UG75 Expression | EST | Mm.34554 | TITLE ESTs, Weakly similar to HYPOTHETICAL PROTEIN KIAA0281 [H. sapiens] | | | gi = 4374434 | 1395288 |
| IC09748 | UG75 Expression | EST | Mm.34555 | TITLE ESTs | | | gi = 4783389 | 616859 |
| IC09749 | UG75 Expression | EST | Mm.34557 | TITLE ESTs | | | gi = 2918000 | 751839 |
| IC09750 | UG75 Expression | EST | Mm.34561 | TITLE ESTs | | | gi = 1282129 | 1445956 |
| IC09751 | UG75 Expression | EST | Mm.34563 | TITLE ESTs | | | gi = 4604129 | 1445678 |
| IC09752 | UG75 Expression | EST | Mm.34564 | TITLE ESTs, Moderately similar to tetracycline transporter-like protein [H. sapiens] | | | gi = 6520891 | 636977 |
| IC09753 | UG75 Expression | EST | Mm.34567 | TITLE ESTs, Moderately similar to CGI-12 protein [H. sapiens] | | | gi = 1287501 | 638178 |
| IC09754 | UG75 Expression | EST | Mm.34568 | TITLE ESTs, Weakly similar to probable transcription regulator NT fin12 [M. musculus] | | | gi = 2234614 | 1446571 |
| IC09755 | UG75 Expression | EST | Mm.34571 | TITLE ESTs | | | gi = 4484629 | 1344616 |
| IC09756 | UG75 Expression | EST | Mm.34573 | TITLE ESTs | | | gi = 2963301 | 1265166 |
| IC09757 | UG75 Expression | EST | Mm.34576 | TITLE ESTs | | | gi = 4802537 | 751590 |
| IC09758 | UG75 Expression | EST | Mm.34578 | TITLE ESTs | | | gi = 1826942 | 637449 |
| IC09759 | UG75 Expression | EST | Mm.34581 | TITLE ESTs, Weakly similar to similar to beta-mannosyltransferase [C. elegans] | | | gi = 433916 | 1366923 |
| IC09760 | UG75 Expression | EST | Mm.34582 | TITLE ESTs | | | gi = 2201177 | 750590 |
| IC09761 | UG75 Expression | EST | Mm.34583 | TITLE EST | | | gi = 4307517 | 597308 |
| IC09762 | UG75 Expression | EST | Mm.34584 | TITLE ESTs | | | gi = 6008035 | 615062 |
| IC09763 | UG75 Expression | EST | Mm.34585 | TITLE ESTs | | | gi = 1800975 | 641009 |
| IC09764 | UG75 Expression | EST | Mm.34587 | TITLE ESTs | | | gi = 2861334 | 1148761 |
| IC09765 | UG75 Expression | EST | Mm.34590 | TITLE ESTs | | | gi = 3099628 | 638115 |
| IC09766 | UG75 Expression | EST | Mm.34591 | TITLE ESTs | | | gi = 4275966 | 574045 |
| IC09767 | UG75 Expression | EST | Mm.34598 | TITLE ESTs | | | gi = 2988664 | 621294 |
| IC09768 | UG75 Expression | EST | Mm.346 | TITLE ESTs, Weakly similar to (define not available 5478765) [M. musculus] | | | gi = 2861615 | 1193090 |
| IC09769 | UG75 Expression | EST | Mm.34602 | TITLE ESTs | | | gi = 3808369 | 576819 |
| IC09770 | UG75 Expression | EST | Mm.34606 | TITLE ESTs, Moderately similar to GLIOMA PATHOGENESIS-RELATED PROTEIN [Homo sapiens] | | | gi = 3164623 | 1312925 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09771 | UG75 Expression | EST | Mm.34609 | TITLE DNA segment, Chr 5, Wayne State University 111, expressed | GENE D5Wsu111e | | | 1294911 |
| IC09772 | UG75 Expression | EST | Mm.34611 | TITLE ESTs | | | gi = 3078621 | 1328984 |
| IC09773 | UG75 Expression | EST | Mm.34613 | TITLE ESTs, Moderately similar to type III multi-pass transmembrane protein [R. norvegicus] | | | gi = 4725040 | 764104 |
| IC09774 | UG75 Expression | EST | Mm.34614 | TITLE ESTs | | | gi = 3718343 | 1380700 |
| IC09775 | UG75 Expression | EST | Mm.34617 | TITLE ESTs | | | gi = 3926406 | 637188 |
| IC09776 | UG75 Expression | EST | Mm.34618 | TITLE ESTs | | | gi = 2412219 | 1002690 |
| IC09777 | UG75 Expression | EST | Mm.34620 | TITLE ESTs, Weakly similar to C56C10.7 [C. elegans] | | | gi = 3517961 | 643122 |
| IC09778 | UG75 Expression | EST | Mm.34624 | TITLE ESTs | | | gi = 3954223 | 576698 |
| IC09779 | UG75 Expression | EST | Mm.34626 | TITLE ESTs, Weakly similar to (define not available 6014925) [M. musculus] | | | gi = 3956780 | 1329564 |
| IC09780 | UG75 Expression | EST | Mm.34627 | TITLE EST | | | gi = 4304471 | 574426 |
| IC09781 | UG75 Expression | EST | Mm.3463 | TITLE ESTs | | | gi = 2201043 | 751906 |
| IC09782 | UG75 Expression | EST | Mm.34632 | TITLE DNA segment, Chr 6, Wayne State University 120, expressed | GENE D6Wsu120e | | | 1294364 |
| IC09783 | UG75 Expression | EST | Mm.34635 | TITLE ESTs, Weakly similar to MRJ [M. musculus] | | | gi = 4768046 | 1379601 |
| IC09784 | UG75 Expression | EST | Mm.34644 | TITLE ESTs, Weakly similar to growth factor independence [M. musculus] | | | gi = 4615110 | 641967 |
| IC09785 | UG75 Expression | EST | Mm.34652 | TITLE ESTs | | | gi = 4305532 | 643392 |
| IC09786 | UG75 Expression | EST | Mm.34653 | TITLE ESTs | | | gi = 4402481 | 575510 |
| IC09787 | UG75 Expression | EST | Mm.34654 | TITLE ESTs, Weakly similar to thyroid hormone receptor-associated protein complex component TRAP150 [H. sapiens] | | | gi = 4216557 | 722300 |
| IC09788 | UG75 Expression | EST | Mm.34659 | TITLE ESTs | | | gi = 1309622 | 894074 |
| IC09789 | UG75 Expression | EST | Mm.34660 | TITLE ESTs, Moderately similar to LL5 protein [R. norvegicus] | | | gi = 4258676 | 751976 |
| IC09790 | UG75 Expression | EST | Mm.34661 | TITLE ESTs, Moderately similar to KIAA0380 [H. sapiens] | | | gi = 3141160 | 621228 |
| IC09791 | UG75 Expression | EST | Mm.34663 | TITLE ESTs, Moderately similar to (define not available 5880867) [M. musculus] | | | gi = 5549461 | 894411 |
| IC09792 | UG75 Expression | EST | Mm.34669 | TITLE ESTs | | | gi = 2979340 | 1281660 |
| IC09793 | UG75 Expression | EST | Mm.34670 | TITLE ESTs | | | gi = 1776438 | 1139971 |
| IC09794 | UG75 Expression | EST | Mm.34671 | TITLE ESTs | | | gi = 5910917 | 749303 |
| IC09795 | UG75 Expression | EST | Mm.34672 | TITLE ESTs | | | gi = 1724528 | 722315 |
| IC09796 | UG75 Expression | EST | Mm.34673 | TITLE ESTs | | | gi = 2962261 | 616675 |
| IC09797 | UG75 Expression | EST | Mm.34678 | TITLE ESTs, Weakly similar to SOX13 [M. musculus] | | | gi = 1805037 | 1148618 |
| IC09798 | UG75 Expression | EST | Mm.34680 | TITLE ESTs | | | gi = 4624781 | 973025 |
| IC09799 | UG75 Expression | EST | Mm.34682 | TITLE ESTs | | | gi = 4408281 | 761000 |
| IC09800 | UG75 Expression | EST | Mm.34683 | TITLE ESTs | | | gi = 1677286 | 576131 |
| IC09801 | UG75 Expression | EST | Mm.34684 | TITLE ESTs | | | gi = 2109757 | 636446 |
| IC09802 | UG75 Expression | EST | Mm.34686 | TITLE ESTs | | | gi = 4623219 | 1162011 |
| IC09803 | UG75 Expression | EST | Mm.34687 | TITLE ESTs | | | gi = 4297178 | 644841 |
| IC09804 | UG75 Expression | EST | Mm.34689 | TITLE ESTs, Weakly similar to c-type lectin DCL1 [M. musculus] | | | gi = 4724021 | 1361219 |
| IC09805 | UG75 Expression | EST | Mm.34690 | TITLE ESTs | | | gi = 4300874 | 576486 |
| IC09806 | UG75 Expression | EST | Mm.34691 | TITLE ESTs | | | gi = 2042233 | 749926 |
| IC09807 | UG75 Expression | EST | Mm.34692 | TITLE ESTs, Weakly similar to MAST CELL CARBOXYPEPTIDASE A PRECURSOR [M. musculus] | | | gi = 4402721 | 680881 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09808 | UG75 Expression | EST | Mm.34693 | TITLE ESTs | | | gi = 4303277 | 596666 |
| IC09809 | UG75 Expression | EST | Mm.34696 | TITLE ESTs | | | gi = 4374433 | 751674 |
| IC09810 | UG75 Expression | EST | Mm.34698 | TITLE ESTs | | | gi = 4305231 | 643090 |
| IC09811 | UG75 Expression | EST | Mm.34699 | TITLE ESTs | | | gi = 1808509 | 720725 |
| IC09812 | UG75 Expression | EST | Mm.347 | TITLE ESTs, Weakly similar to gc-rich sequence dna-binding factor [H. sapiens] | | | gi = 6756352 | 637556 |
| IC09813 | UG75 Expression | EST | Mm.34700 | TITLE ESTs | | | gi = 3067546 | 719017 |
| IC09814 | UG75 Expression | EST | Mm.34703 | TITLE ESTs | | | gi = 1903772 | 596847 |
| IC09815 | UG75 Expression | EST | Mm.34706 | TITLE ESTs | | | gi = 1904358 | 597207 |
| IC09816 | UG75 Expression | EST | Mm.34707 | TITLE ESTs | | | gi = 4296584 | 641034 |
| IC09817 | UG75 Expression | EST | Mm.34708 | TITLE ESTs | | | gi = 3732335 | 1383837 |
| IC09818 | UG75 Expression | EST | Mm.34711 | TITLE ESTs | | | gi = 4482024 | 973021 |
| IC09819 | UG75 Expression | EST | Mm.34712 | TITLE ESTs | | | gi = 4596972 | 573395 |
| IC09820 | UG75 Expression | EST | Mm.34714 | TITLE ESTs, Moderately similar to CGI-101 protein [H. sapiens] | | | gi = 4216922 | 622713 |
| IC09821 | UG75 Expression | EST | Mm.34715 | TITLE ESTs, Weakly similar to p190-B [M. musculus] | | | gi = 5551534 | 583225 |
| IC09822 | UG75 Expression | EST | Mm.34718 | TITLE ESTs | | | gi = 1739928 | 619347 |
| IC09823 | UG75 Expression | EST | Mm.34720 | TITLE ESTs | | | gi = 1756332 | 618865 |
| IC09824 | UG75 Expression | EST | Mm.34721 | TITLE ESTs | | | gi = 4605007 | 1345883 |
| IC09825 | UG75 Expression | EST | Mm.34723 | TITLE ESTs | | | gi = 2049259 | 637640 |
| IC09826 | UG75 Expression | EST | Mm.34724 | TITLE ESTs | | | gi = 2049354 | 751972 |
| IC09827 | UG75 Expression | EST | Mm.34725 | TITLE ESTs | | | gi = 4407632 | 751505 |
| IC09828 | UG75 Expression | EST | Mm.34726 | TITLE ESTs | | | gi = 2049042 | 751538 |
| IC09829 | UG75 Expression | EST | Mm.34727 | TITLE ESTs | | | gi = 4302913 | 635786 |
| IC09830 | UG75 Expression | EST | Mm.34728 | TITLE ESTs | | | gi = 2990754 | 1346032 |
| IC09831 | UG75 Expression | EST | Mm.34732 | TITLE ESTs | | | gi = 5335268 | 765513 |
| IC09832 | UG75 Expression | EST | Mm.34734 | TITLE ESTs | | | gi = 4409512 | 581685 |
| IC09833 | UG75 Expression | EST | Mm.34740 | TITLE ESTs | | | gi = 4434669 | 620381 |
| IC09834 | UG75 Expression | EST | Mm.34743 | TITLE ESTs | | | gi = 441073 | 620997 |
| IC09835 | UG75 Expression | EST | Mm.34745 | TITLE ESTs | | | gi = 2502496 | 973992 |
| IC09836 | UG75 Expression | EST | Mm.34746 | TITLE ESTs, Weakly similar to ORF YNL039w [S. cerevisiae] | | | gi = 442099 | 641336 |
| IC09837 | UG75 Expression | EST | Mm.34750 | hypothetical protein CET01H8.1, CEC05C12.3, CEF54D1.5. similar to trp and trp-like proteins [H. sapiens] | | | gi = 4316504 | 777777 |
| IC09838 | UG75 Expression | EST | Mm.34751 | TITLE ESTs, Moderately similar to SPLICING FACTOR, ARGININE/SERINE-RICH 8 [H. sapiens] | | | gi = 6518080 | 1193062 |
| IC09839 | UG75 Expression | EST | Mm.34752 | TITLE ESTs | | | gi = 1681070 | 1264653 |
| IC09840 | UG75 Expression | EST | Mm.34753 | TITLE ESTs | | | gi = 4444844 | 1295680 |
| IC09841 | UG75 Expression | EST | Mm.34757 | TITLE ESTs, Moderately similar to TIAP [M. musculus] | | | gi = 1465187 | 721237 |
| IC09842 | UG75 Expression | EST | Mm.34763 | TITLE ESTs, Weakly similar to similar to vacuolar biogenesis protein [C. elegans] | | | gi = 1475258 | 550598 |
| IC09843 | UG75 Expression | EST | Mm.34766 | TITLE ESTs, Moderately similar to TRANSCRIPTION INITIATION FACTOR IIA SMALL CHAIN [Saccharomyces cerevisiae] | | | gi = 2519439 | 1264877 |
| IC09844 | UG75 Expression | EST | Mm.34772 | TITLE ESTs | | | gi = 434094 | 576649 |
| IC09845 | UG75 Expression | EST | Mm.34774 | TITLE ESTs, Weakly similar to F18F11.1 [C. elegans] | | | gi = 5338563 | 641479 |
| IC09846 | UG75 Expression | EST | Mm.34776 | TITLE ESTs | | | gi = 4604078 | 1264072 |
| IC09847 | UG75 Expression | EST | Mm.34777 | TITLE ESTs | | | gi = 1671628 | 720909 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09848 | UG75 Expression | EST | Mm.34785 | TITLE ESTs | | | gi = 3732682 | 575130 |
| IC09849 | UG75 Expression | EST | Mm.34788 | TITLE ESTs, Weakly similar to cDNA EST yk273d8.5 comes from this gene [C. elegans] | | | gi = 3336182 | 1380502 |
| IC09850 | UG75 Expression | EST | Mm.34789 | TITLE ESTs, Moderately similar to KINESIN LIGHT CHAIN [Rattus norvegicus] | | | gi = 6168039 | 717774 |
| IC09851 | UG75 Expression | EST | Mm.34792 | TITLE ESTs | | | gi = 5472844 | 1282792 |
| IC09852 | UG75 Expression | EST | Mm.34796 | TITLE ESTs | | | gi = 3261197 | 1327508 |
| IC09853 | UG75 Expression | EST | Mm.34798 | TITLE ESTs | | | gi = 2461837 | 972833 |
| IC09854 | UG75 Expression | EST | Mm.34801 | TITLE ESTs, Weakly similar to Y66H1A.3 [C. elegans] | | | gi = 1369484 | 582924 |
| IC09855 | UG75 Expression | EST | Mm.34803 | TITLE ESTs, Moderately similar to HOMEOTIC GENE REGULATOR [Drosophila melanogaster] | | | gi = 6560218 | 1193452 |
| IC09856 | UG75 Expression | EST | Mm.34806 | TITLE ESTs | | | gi = 1915497 | 573259 |
| IC09857 | UG75 Expression | EST | Mm.34807 | TITLE ESTs | | | gi = 1677441 | 575932 |
| IC09858 | UG75 Expression | EST | Mm.34811 | TITLE ESTs | | | gi = 4317470 | 534178 |
| IC09859 | UG75 Expression | EST | Mm.34812 | TITLE ESTs, Moderately similar to 60S ACIDIC RIBOSOMAL PROTEIN P1 [M. musculus] | | | gi = 5492009 | 597468 |
| IC09860 | UG75 Expression | EST | Mm.34816 | TITLE ESTs | | | gi = 1316769 | 551338 |
| IC09861 | UG75 Expression | EST | Mm.34818 | TITLE ESTs | | | gi = 1724533 | 1446226 |
| IC09862 | UG75 Expression | EST | Mm.34820 | TITLE ESTs, Moderately similar to LYSOSOMAL PRO-X CARBOXYPEPTIDASE PRECURSOR [H. sapiens] | | | gi = 4305965 | 681298 |
| IC09863 | UG75 Expression | EST | Mm.34823 | TITLE ESTs | | | gi = 4725262 | 634225 |
| IC09864 | UG75 Expression | EST | Mm.34826 | TITLE ESTs | | | gi = 3521921 | 1445644 |
| IC09865 | UG75 Expression | EST | Mm.34840 | TITLE ESTs | | | gi = 4783104 | 1148910 |
| IC09866 | UG75 Expression | EST | Mm.34843 | TITLE ESTs | | | gi = 2331959 | 972651 |
| IC09867 | UG75 Expression | EST | Mm.34845 | TITLE ESTs | | | gi = 4444808 | 575429 |
| IC09868 | UG75 Expression | EST | Mm.34850 | TITLE ESTs | | | gi = 1758701 | 622580 |
| IC09869 | UG75 Expression | EST | Mm.34851 | TITLE ESTs | | | gi = 6645890 | 1293838 |
| IC09870 | UG75 Expression | EST | Mm.34854 | TITLE ESTs | | | gi = 1768857 | 642972 |
| IC09871 | UG75 Expression | EST | Mm.34855 | TITLE ESTs | | | gi = 4522210 | 638577 |
| IC09872 | UG75 Expression | EST | Mm.34857 | TITLE ESTs | | | gi = 4522176 | 638404 |
| IC09873 | UG75 Expression | EST | Mm.34858 | TITLE ESTs | | | gi = 6940407 | 959383 |
| IC09874 | UG75 Expression | EST | Mm.34859 | TITLE ESTs, Moderately similar to T20D3.3 [C. elegans] | | | gi = 2282956 | 617288 |
| IC09875 | UG75 Expression | EST | Mm.34860 | TITLE ESTs | | | gi = 5749958 | 1264117 |
| IC09876 | UG75 Expression | EST | Mm.34864 | TITLE ESTs | | | gi = 4318700 | 718850 |
| IC09877 | UG75 Expression | EST | Mm.34866 | TITLE ESTs | | | gi = 4604368 | 749598 |
| IC09878 | UG75 Expression | EST | Mm.34867 | TITLE ESTs | | | gi = 4804901 | 722128 |
| IC09879 | UG75 Expression | EST | Mm.34870 | TITLE ESTs | | | gi = 1759259 | 620282 |
| IC09880 | UG75 Expression | EST | Mm.34871 | TITLE ESTs | | | gi = 2503317 | 764044 |
| IC09881 | UG75 Expression | EST | Mm.34872 | TITLE ESTs | | | gi = 4408123 | 749441 |
| IC09882 | UG75 Expression | EST | Mm.34873 | TITLE ESTs | | | gi = 1937549 | 749272 |
| IC09883 | UG75 Expression | EST | Mm.34874 | TITLE ESTs | | | gi = 3601587 | 750284 |
| IC09884 | UG75 Expression | EST | Mm.34876 | TITLE DNA segment, Chr 15, Wayne State University 97, expressed | GENE D15Wsu97e | | | 643293 |
| IC09885 | UG75 Expression | EST | Mm.34907 | TITLE ESTs | | | gi = 4726880 | 576351 |
| IC09886 | UG75 Expression | EST | Mm.34908 | TITLE ESTs | | | gi = 5488739 | 619664 |
| IC09887 | UG75 Expression | EST | Mm.34910 | TITLE ESTs | | | gi = 1672496 | 1295514 |
| IC09888 | UG75 Expression | EST | Mm.34912 | TITLE ESTs | | | gi = 2519321 | 1051374 |
| IC09889 | UG75 Expression | EST | Mm.34916 | TITLE ESTs | | | gi = 1776943 | 636073 |
| IC09890 | UG75 Expression | EST | Mm.34923 | TITLE ESTs | | | gi = 1826303 | 637211 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC08891 | UG75 Expression | EST | Mm.34926 | TITLE ESTs | | | gi = 1284978 | 1312633 |
| IC08892 | UG75 Expression | EST | Mm.34938 | TITLE ESTs, Moderately similar to H-REV 107 PROTEIN [R. norvegicus] | | | gi = 218973 | 533604 |
| IC08993 | UG75 Expression | EST | Mm.34951 | TITLE DNA segment, Chr 11, KL Mohike 47 | GENE D11Moh47 | | | 576491 |
| IC08894 | UG75 Expression | EST | Mm.34955 | TITLE ESTs | | | gi = 3685018 | 1193630 |
| IC08895 | UG75 Expression | EST | Mm.34968 | TITLE ESTs | | | gi = 2719841 | 721268 |
| IC08896 | UG75 Expression | EST | Mm.34969 | TITLE ESTs | | | gi = 2722016 | 1282761 |
| IC08897 | UG75 Expression | EST | Mm.34971 | TITLE ESTs | | | gi = 2745175 | 533435 |
| IC08898 | UG75 Expression | EST | Mm.34973 | TITLE ESTs | | | gi = 1700673 | 596732 |
| IC08899 | UG75 Expression | EST | Mm.34977 | TITLE ESTs | | | gi = 3515558 | 1295277 |
| IC08900 | UG75 Expression | EST | Mm.34978 | TITLE ESTs | | | gi = 4485976 | 1224925 |
| IC08901 | UG75 Expression | EST | Mm.34982 | TITLE ESTs | | | gi = 4571345 | 1262894 |
| IC08902 | UG75 Expression | EST | Mm.34984 | TITLE ESTs | | | gi = 2849930 | 1243612 |
| IC08903 | UG75 Expression | EST | Mm.34994 | TITLE ESTs | | | gi = 4408466 | 1263254 |
| IC08904 | UG75 Expression | EST | Mm.34995 | TITLE ESTs | | | gi = 4408663 | 1265371 |
| IC08905 | UG75 Expression | EST | Mm.34996 | TITLE ESTs | | | gi = 2963318 | 1265186 |
| IC08906 | UG75 Expression | EST | Mm.34997 | TITLE ESTs | | | gi = 2978876 | 1281381 |
| IC08907 | UG75 Expression | EST | Mm.34998 | TITLE ESTs | | | gi = 2979209 | 1263380 |
| IC08908 | UG75 Expression | EST | Mm.34999 | TITLE ESTs | | | gi = 2989116 | 1265152 |
| IC08909 | UG75 Expression | EST | Mm.35000 | TITLE ESTs | | | gi = 2990976 | 1265093 |
| IC08910 | UG75 Expression | EST | Mm.35003 | TITLE ESTs | | | gi = 2855041 | 972960 |
| IC08911 | UG75 Expression | EST | Mm.35006 | TITLE ESTs | | | gi = 2906493 | 596591 |
| IC08912 | UG75 Expression | EST | Mm.35011 | TITLE ESTs | | | gi = 4484611 | 1345534 |
| IC08913 | UG75 Expression | EST | Mm.35019 | TITLE ESTs | | | gi = 6079263 | 1364711 |
| IC08914 | UG75 Expression | EST | Mm.35024 | TITLE ESTs | | | gi = 3373609 | 1970456 |
| IC08915 | UG75 Expression | EST | Mm.35039 | TITLE ESTs | | | gi = 6939309 | 375167 |
| IC08916 | UG75 Expression | EST | Mm.35055 | TITLE ESTs | | | gi = 3447564 | 750414 |
| IC08917 | UG75 Expression | EST | Mm.35057 | TITLE ESTs | | | gi = 2504721 | 596292 |
| IC08918 | UG75 Expression | EST | Mm.35060 | TITLE ESTs | | | gi = 6149966 | 1446339 |
| IC08919 | UG75 Expression | EST | Mm.35063 | TITLE ESTs | | | gi = 2978845 | 1281358 |
| IC08920 | UG75 Expression | EST | Mm.35064 | TITLE ESTs, Moderately similar to HYPOTHETICAL PROTEIN KIAA0281 [H. sapiens] | | | gi = 2962427 | 1265500 |
| IC08921 | UG75 Expression | EST | Mm.35084 | TITLE ESTs | | | gi = 2412721 | 958605 |
| IC08922 | UG75 Expression | EST | Mm.35092 | TITLE ESTs, Moderately similar to hypothetical protein [M. musculus] | | | gi = 4057929 | 493124 |
| IC08923 | UG75 Expression | EST | Mm.35096 | TITLE ESTs, Weakly similar to HSPC040 protein [H. sapiens] | | | gi = 4596901 | 572813 |
| IC08924 | UG75 Expression | EST | Mm.35097 | TITLE ESTs, Moderately similar to RAB-R protein [H. sapiens] | | | gi = 2906301 | 720945 |
| IC08925 | UG75 Expression | EST | Mm.35098 | TITLE ESTs | | | gi = 2962628 | 644809 |
| IC08926 | UG75 Expression | EST | Mm.35099 | TITLE ESTs | | | gi = 4483111 | 551576 |
| IC08927 | UG75 Expression | EST | Mm.35101 | TITLE ESTs | | | gi = 4444814 | 575138 |
| IC08928 | UG75 Expression | EST | Mm.35102 | TITLE ESTs | | | gi = 4298872 | 575550 |
| IC08929 | UG75 Expression | EST | Mm.35104 | TITLE ESTs, Weakly similar to cDNA EST CEESW54F comes from this gene [C. elegans] | | | gi = 3067995 | 598951 |
| IC08930 | UG75 Expression | EST | Mm.35107 | TITLE ESTs | | | gi = 4723808 | 1264256 |
| IC08931 | UG75 Expression | EST | Mm.35108 | TITLE ESTs | | | gi = 5497064 | 1265002 |
| IC08932 | UG75 Expression | EST | Mm.35110 | TITLE ESTs, Moderately similar to INTERFERON-ACTIVATABLE PROTEIN 204 [M. musculus] | | | gi = 4617040 | 749130 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09933 | UG75 Expression | EST | Mm.35116 | TITLE ESTs | | | gi = 2292275 | 752276 |
| IC09934 | UG75 Expression | EST | Mm.35118 | TITLE ESTs | | | gi = 4663828 | 618045 |
| IC09935 | UG75 Expression | EST | Mm.35127 | TITTLE ESTs, Weakly similar to (define not available 5901802) [D. melanogaster] | | | gi = 6822562 | 973033 |
| IC09936 | UG75 Expression | EST | Mm.35135 | TITLE ESTs | | | gi = 4404251 | 1001967 |
| IC09937 | UG75 Expression | EST | Mm.35136 | TITLE ESTs | | | gi = 2283643 | 949450 |
| IC09938 | UG75 Expression | EST | Mm.35140 | TITLE ESTs | | | gi = 4408458 | 1263234 |
| IC09939 | UG75 Expression | EST | Mm.35141 | TITLE ESTs | | | gi = 6096672 | 1263237 |
| IC09940 | UG75 Expression | EST | Mm.35142 | TITLE ESTs | | | gi = 2990695 | 1264674 |
| IC09941 | UG75 Expression | EST | Mm.35143 | TITLE ESTs | | | gi = 4482831 | 1264850 |
| IC09942 | UG75 Expression | EST | Mm.35144 | TITLE ESTs | | | gi = 4408572 | 1264889 |
| IC09943 | UG75 Expression | EST | Mm.35145 | TITLE ESTs | | | gi = 2962700 | 1265478 |
| IC09944 | UG75 Expression | EST | Mm.35147 | TITLE ESTs | | | gi = 2916100 | 1282741 |
| IC09945 | UG75 Expression | EST | Mm.35148 | TITLE ESTs | | | gi = 2962257 | 1282542 |
| IC09946 | UG75 Expression | EST | Mm.35149 | TITLE ESTs | | | gi = 2962403 | 1282591 |
| IC09947 | UG75 Expression | EST | Mm.35151 | TITLE EST, Weakly similar to proline-rich protein MP4 [M. musculus] | | | gi = 4482231 | 1262864 |
| IC09948 | UG75 Expression | EST | Mm.35152 | TITLE EST | | | gi = 4482232 | 1262857 |
| IC09949 | UG75 Expression | EST | Mm.35153 | TITLE ESTs | | | gi = 4482238 | 1262881 |
| IC09950 | UG75 Expression | EST | Mm.35154 | TITLE EST | | | gi = 4482239 | 1262883 |
| IC09951 | UG75 Expression | EST | Mm.35155 | TITLE ESTs | | | gi = 4482241 | 1262891 |
| IC09952 | UG75 Expression | EST | Mm.35156 | TITLE EST | | | gi = 4482253 | 1262934 |
| IC09953 | UG75 Expression | EST | Mm.35157 | TITLE EST | | | gi = 4482257 | 1262943 |
| IC09954 | UG75 Expression | EST | Mm.35158 | TITLE EST | | | gi = 4482264 | 1263021 |
| IC09955 | UG75 Expression | EST | Mm.35159 | TITLE ESTs | | | gi = 5497102 | 1263028 |
| IC09956 | UG75 Expression | EST | Mm.35160 | TITLE EST | | | gi = 4482268 | 1263037 |
| IC09957 | UG75 Expression | EST | Mm.35161 | TITLE ESTs | | | gi = 3160997 | 1263077 |
| IC09958 | UG75 Expression | EST | Mm.35162 | TITLE ESTs | | | gi = 2944625 | 1263096 |
| IC09959 | UG75 Expression | EST | Mm.35163 | TITLE EST | | | gi = 4482279 | 1263098 |
| IC09960 | UG75 Expression | EST | Mm.35164 | TITLE ESTs | | | gi = 2944639 | 1263107 |
| IC09961 | UG75 Expression | EST | Mm.35165 | TITLE ESTs | | | gi = 2944676 | 1263158 |
| IC09962 | UG75 Expression | EST | Mm.35166 | TITLE ESTs | | | gi = 1756051 | 617627 |
| IC09963 | UG75 Expression | EST | Mm.35167 | TITLE EST | | | gi = 4271506 | 1193143 |
| IC09964 | UG75 Expression | EST | Mm.35168 | TITLE ESTs | | | gi = 5907742 | 1263282 |
| IC09965 | UG75 Expression | EST | Mm.35170 | TITLE ESTs | | | gi = 4483327 | 1263303 |
| IC09966 | UG75 Expression | EST | Mm.35172 | TITLE EST | | | gi = 4482657 | 1263351 |
| IC09967 | UG75 Expression | EST | Mm.35173 | TITLE ESTs | | | gi = 4408397 | 1263376 |
| IC09968 | UG75 Expression | EST | Mm.35174 | TITLE ESTs | | | gi = 4482683 | 1263520 |
| IC09969 | UG75 Expression | EST | Mm.35175 | TITLE ESTs | | | gi = 2811793 | 1225790 |
| IC09970 | UG75 Expression | EST | Mm.35176 | TITLE ESTs | | | gi = 4482702 | 1264052 |
| IC09971 | UG75 Expression | EST | Mm.35177 | TITLE EST | | | gi = 4482713 | 1264124 |
| IC09972 | UG75 Expression | EST | Mm.35178 | TITLE EST | | | gi = 4482721 | 1264205 |
| IC09973 | UG75 Expression | EST | Mm.35179 | TITLE EST | | | gi = 4482727 | 1264227 |
| IC09974 | UG75 Expression | EST | Mm.35180 | TITLE EST | | | gi = 4482740 | 1264296 |
| IC09975 | UG75 Expression | EST | Mm.35182 | TITLE EST | | | gi = 4482745 | 1264297 |
| IC09976 | UG75 Expression | EST | Mm.35183 | TITLE EST | | | gi = 4482754 | 1264324 |
| IC09977 | UG75 Expression | EST | Mm.35184 | TITLE EST | | | gi = 4482755 | 1264334 |
| IC09978 | UG75 Expression | EST | Mm.35186 | TITLE ESTs | | | gi = 4482761 | 1264331 |
| IC09979 | UG75 Expression | EST | Mm.35187 | TITLE ESTs | | | gi = 4408510 | 1264347 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC09980 | UG75 Expression | EST | Mm.35188 | TITLE ESTs | | | gi = 4482776 | 1264482 |
| IC09981 | UG75 Expression | EST | Mm.35189 | TITLE ESTs | | | gi = 2990685 | 1264483 |
| IC09982 | UG75 Expression | EST | Mm.35190 | TITLE ESTs | | | gi = 5909197 | 1264487 |
| IC09983 | UG75 Expression | EST | Mm.35191 | TITLE EST | | | gi = 4482793 | 1264611 |
| IC09984 | UG75 Expression | EST | Mm.35192 | TITLE ESTs | | | gi = 408541 | 583764 |
| IC09985 | UG75 Expression | EST | Mm.35194 | TITLE EST | | | gi = 4482819 | 1264804 |
| IC09986 | UG75 Expression | EST | Mm.35195 | TITLE EST | | | gi = 4482821 | 1264816 |
| IC09987 | UG75 Expression | EST | Mm.35196 | TITLE EST | | | gi = 4482824 | 1264803 |
| IC09988 | UG75 Expression | EST | Mm.35197 | TITLE EST | | | gi = 4482829 | 1264839 |
| IC09989 | UG75 Expression | EST | Mm.35198 | TITLE ESTs | | | gi = 5498604 | 1264879 |
| IC09990 | UG75 Expression | EST | Mm.35199 | TITLE ESTs | | | gi = 4482849 | 1264921 |
| IC09991 | UG75 Expression | EST | Mm.35200 | TITLE EST | | | gi = 4482851 | 1264941 |
| IC09992 | UG75 Expression | EST | Mm.35201 | TITLE EST | | | gi = 4482867 | 1265018 |
| IC09993 | UG75 Expression | EST | Mm.35203 | TITLE EST | | | gi = 4482876 | 1265066 |
| IC09994 | UG75 Expression | EST | Mm.35204 | TITLE EST | | | gi = 4482878 | 1265100 |
| IC09995 | UG75 Expression | EST | Mm.35205 | TITLE EST | | | gi = 4482883 | 1265109 |
| IC09996 | UG75 Expression | EST | Mm.35207 | TITLE EST | | | gi = 4482901 | 1265169 |
| IC09997 | UG75 Expression | EST | Mm.35212 | TITLE EST | | | gi = 3294866 | 1446581 |
| IC09998 | UG75 Expression | EST | Mm.35227 | TITLE ESTs | | | gi = 4602495 | 1193735 |
| IC09999 | UG75 Expression | EST | Mm.35251 | TITLE ESTs | | | gi = 4483706 | 1278268 |
| IC10000 | UG75 Expression | EST | Mm.35291 | TITLE EST | | | gi = 5497024 | 1362603 |
| IC10001 | UG75 Expression | EST | Mm.35293 | TITLE EST | | | gi = 4484894 | 1265287 |
| IC10002 | UG75 Expression | EST | Mm.35294 | TITLE EST, Weakly similar to ORF2 [M. musculus] | | | gi = 4484896 | 1265301 |
| IC10003 | UG75 Expression | EST | Mm.35295 | TITLE ESTs | | | gi = 2962575 | 1265327 |
| IC10004 | UG75 Expression | EST | Mm.35296 | TITLE EST | | | gi = 4484907 | 1265368 |
| IC10005 | UG75 Expression | EST | Mm.35297 | TITLE ESTs | | | gi = 4484911 | 1265380 |
| IC10006 | UG75 Expression | EST | Mm.35298 | TITLE ESTs | | | gi = 7063813 | 636421 |
| IC10007 | UG75 Expression | EST | Mm.35299 | TITLE EST | | | gi = 4484924 | 1265452 |
| IC10008 | UG75 Expression | EST | Mm.3532 | TITLE ESTs, Moderately similar to THYMOSIN BETA-10 [Homo sapiens; Rattus norvegicus; Equus caballus] | | | gi = 2233107 | 1149816 |
| IC10009 | UG75 Expression | EST | Mm.35321 | TITLE ESTs | | | gi = 3683098 | 1246024 |
| IC10010 | UG75 Expression | EST | Mm.35351 | TITLE EST | | | gi = 4508378 | 1243631 |
| IC10011 | UG75 Expression | EST | Mm.35352 | TITLE ESTs | | | gi = 4508380 | 1243635 |
| IC10012 | UG75 Expression | EST | Mm.35366 | TITLE EST | | | gi = 4512885 | 1281355 |
| IC10013 | UG75 Expression | EST | Mm.35367 | TITLE ESTs | | | gi = 5498057 | 1281440 |
| IC10014 | UG75 Expression | EST | Mm.35368 | TITLE ESTs | | | gi = 6633044 | 1281445 |
| IC10015 | UG75 Expression | EST | Mm.35382 | TITLE EST | | | gi = 5906163 | 1226997 |
| IC10016 | UG75 Expression | EST | Mm.35383 | TITLE EST | | | gi = 4513055 | 1227001 |
| IC10017 | UG75 Expression | EST | Mm.35385 | TITLE EST | | | gi = 4513064 | 1227013 |
| IC10018 | UG75 Expression | EST | Mm.35405 | TITLE ESTs | | | gi = 3234350 | 1378644 |
| IC10019 | UG75 Expression | EST | Mm.35416 | TITLE ESTs | | | gi = 1825963 | 894398 |
| IC10020 | UG75 Expression | EST | Mm.35420 | TITLE EST | | | gi = 4522054 | 1282556 |
| IC10021 | UG75 Expression | EST | Mm.35421 | TITLE EST | | | gi = 4522059 | 1282576 |
| IC10022 | UG75 Expression | EST | Mm.35422 | TITLE EST | | | gi = 4409591 | 1282621 |
| IC10023 | UG75 Expression | EST | Mm.35423 | TITLE ESTs | | | gi = 5498044 | 1282640 |
| IC10024 | UG75 Expression | EST | Mm.35424 | TITLE EST | | | gi = 4522072 | 1282650 |
| IC10025 | UG75 Expression | EST | Mm.35425 | TITLE EST | | | gi = 4522074 | 1282647 |
| IC10026 | UG75 Expression | EST | Mm.35426 | TITLE ESTs | | | gi = 4409184 | 1282676 |
| IC10027 | UG75 Expression | EST | Mm.35427 | TITLE EST | | | gi = 4522096 | 1293895 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10028 | UG75 Expression | EST | Mm.35428 | TITLE ESTs | | | gi = 6167719 | 1295929 |
| IC10029 | UG75 Expression | EST | Mm.35430 | TITLE ESTs | | | gi = 2979156 | 1281541 |
| IC10030 | UG75 Expression | EST | Mm.35433 | TITLE ESTs, Moderately similar to HYPOTHETICAL 21.5 KD PROTEIN C08B11.9 IN CHROMOSOME II [Caenorhabditis elegans] | | | gi = 6084291 | 597455 |
| IC10031 | UG75 Expression | EST | Mm.35443 | TITLE ESTs | | | gi = 4317550 | 534004 |
| IC10032 | UG75 Expression | EST | Mm.35444 | TITLE ESTs | | | gi = 1901108 | 1294066 |
| IC10033 | UG75 Expression | EST | Mm.35445 | TITLE ESTs, Weakly similar to predicted using Genefinder [C. elegans] | | | gi = 3683128 | 1293911 |
| IC10034 | UG75 Expression | EST | Mm.35446 | TITLE ESTs, Weakly similar to DYNACTIN, 150 KD ISOFORM [M. musculus] | | | gi = 2139803 | 574404 |
| IC10035 | UG75 Expression | EST | Mm.35447 | TITLE ESTs | | | gi = 1725673 | 582124 |
| IC10036 | UG75 Expression | EST | Mm.35449 | TITLE ESTs | | | gi = 5471359 | 635966 |
| IC10037 | UG75 Expression | EST | Mm.35450 | TITLE ESTs | | | gi = 4441791 | 622897 |
| IC10038 | UG75 Expression | EST | Mm.35451 | TITLE ESTs | | | gi = 4615198 | 642582 |
| IC10039 | UG75 Expression | EST | Mm.35452 | TITLE ESTs | | | gi = 3032947 | 1279940 |
| IC10040 | UG75 Expression | EST | Mm.35453 | TITLE ESTs | | | gi = 4271613 | 1226703 |
| IC10041 | UG75 Expression | EST | Mm.35454 | TITLE ESTs | | | gi = 1834038 | 641304 |
| IC10042 | UG75 Expression | EST | Mm.35458 | TITLE ESTs | | | gi = 261110 | 1193454 |
| IC10043 | UG75 Expression | EST | Mm.35460 | TITLE ESTs | | | gi = 1796505 | 643603 |
| IC10044 | UG75 Expression | EST | Mm.35463 | TITLE ESTs | | | gi = 1918010 | 765956 |
| IC10045 | UG75 Expression | EST | Mm.35466 | TITLE ESTs, Weakly similar to R26660_1, partial CDS [H. sapiens] | | | gi = 3216728 | 616833 |
| IC10046 | UG75 Expression | EST | Mm.35467 | TITLE ESTs | | | gi = 4316776 | 751776 |
| IC10047 | UG75 Expression | EST | Mm.35470 | TITLE ESTs | | | gi = 4483516 | 749789 |
| IC10048 | UG75 Expression | EST | Mm.35476 | TITLE ESTs | | | gi = 5909982 | 1282661 |
| IC10049 | UG75 Expression | EST | Mm.35478 | TITLE ESTs | | | gi = 2979310 | 752419 |
| IC10050 | UG75 Expression | EST | Mm.35480 | TITLE ESTs | | | gi = 4512888 | 619745 |
| IC10051 | UG75 Expression | EST | Mm.35483 | TITLE ESTs, Moderately similar to nuclear dual-specificity phosphatase [H. sapiens] | | | gi = 1286680 | 1428870 |
| IC10052 | UG75 Expression | EST | Mm.35492 | TITLE ESTs, Weakly similar to myosin heavy chain, cardiac [R. norvegicus] | | | gi = 6077283 | 765237 |
| IC10053 | UG75 Expression | EST | Mm.35493 | TITLE ESTs | | | gi = 2272112 | 619001 |
| IC10054 | UG75 Expression | EST | Mm.35495 | TITLE ESTs | | | gi = 1808263 | 641853 |
| IC10055 | UG75 Expression | EST | Mm.35504 | TITLE ESTs, Weakly similar to cyclic nucleotide-gated channel beta subunit [R. norvegicus] | | | gi = 3393952 | 958938 |
| IC10056 | UG75 Expression | EST | Mm.35505 | TITLE ESTs, Weakly similar to DNA-binding protein [M. musculus] | | | gi = 2962445 | 1265517 |
| IC10057 | UG75 Expression | EST | Mm.35507 | TITLE ESTs | | | gi = 2962398 | 1282596 |
| IC10058 | UG75 Expression | EST | Mm.35509 | TITLE ESTs | | | gi = 1394667 | 1264894 |
| IC10059 | UG75 Expression | EST | Mm.35510 | TITLE ESTs | | | gi = 4613387 | 620445 |
| IC10060 | UG75 Expression | EST | Mm.35514 | TITLE ESTs | | | gi = 2503385 | 1446853 |
| IC10061 | UG75 Expression | EST | Mm.35520 | TITLE ESTs | | | gi = 4058524 | 720871 |
| IC10062 | UG75 Expression | EST | Mm.35522 | TITLE ESTs, Moderately similar to myosin phosphatase target subunit 1 [H. sapiens] | | | gi = 2049131 | 721919 |
| IC10063 | UG75 Expression | EST | Mm.35544 | TITLE ESTs | | | gi = 4703007 | 1243540 |
| IC10064 | UG75 Expression | EST | Mm.35547 | TITLE ESTs | | | gi = 2291674 | 1226791 |
| IC10065 | UG75 Expression | EST | Mm.35559 | TITLE ESTs | | | gi = 2116479 | 1293577 |
| IC10066 | UG75 Expression | EST | Mm.35564 | TITLE ESTs | | | gi = 1917367 | 1225413 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10067 | UG75 Expression | EST | Mm.35569 | TITLE ESTs, Weakly similar to PSD-95/SAP90-associated protein-4 [R. norvegicus] | | | gi = 6750206 | 1293874 |
| IC10068 | UG75 Expression | EST | Mm.35573 | TITLE ESTs | | | gi = 5907109 | 352656 |
| IC10069 | UG75 Expression | EST | Mm.35574 | TITLE ESTs | | | gi = 4409183 | 572918 |
| IC10070 | UG75 Expression | EST | Mm.35577 | TITLE ESTs | | | gi = 1915600 | 596879 |
| IC10071 | UG75 Expression | EST | Mm.35578 | TITLE ESTs | | | gi = 4482293 | 636435 |
| IC10072 | UG75 Expression | EST | Mm.35581 | TITLE ESTs | | | gi = 3601598 | 1263086 |
| IC10073 | UG75 Expression | EST | Mm.35582 | TITLE ESTs, Weakly similar to hepatoma-derived growth factor [M. musculus] | | | gi = 2962464 | 1293839 |
| IC10074 | UG75 Expression | EST | Mm.35583 | TITLE ESTs | | | gi = 4276019 | 1294248 |
| IC10075 | UG75 Expression | EST | Mm.35584 | TITLE ESTs | | | gi = 2963066 | 1264201 |
| IC10076 | UG75 Expression | EST | Mm.35587 | TITLE ESTs | | | gi = 4512893 | 1281395 |
| IC10077 | UG75 Expression | EST | Mm.35588 | TITLE EST | | | gi = 2979076 | 1281494 |
| IC10078 | UG75 Expression | EST | Mm.35589 | TITLE ESTs | | | gi = 2979301 | 1281324 |
| IC10079 | UG75 Expression | EST | Mm.35591 | TITLE ESTs | | | gi = 2990890 | 1345962 |
| IC10080 | UG75 Expression | EST | Mm.35598 | TITLE ESTs | | | gi = 4303551 | 973636 |
| IC10081 | UG75 Expression | EST | Mm.35600 | TITLE ESTs, Weakly similar to (define not available 5771451) [M. musculus] | | | gi = 3164336 | 641886 |
| IC10082 | UG75 Expression | EST | Mm.35604 | TITLE ESTs | | | gi = 4482708 | 1264084 |
| IC10083 | UG75 Expression | EST | Mm.35606 | TITLE ESTs, Weakly similar to myelin transcription factor 1-like [M. musculus] | | | gi = 6646607 | 642333 |
| IC10084 | UG75 Expression | EST | Mm.35607 | TITLE ESTs, Weakly similar to MYELOID CELL SURFACE ANTIGEN CD33 PRECURSOR [H. sapiens] | | | gi = 4299893 | 575555 |
| IC10085 | UG75 Expression | EST | Mm.3561 | TITLE ESTs | | | gi = 1500736 | 622785 |
| IC10086 | UG75 Expression | EST | Mm.35610 | TITLE ESTs | | | gi = 5491297 | 1281627 |
| IC10087 | UG75 Expression | EST | Mm.35616 | TITLE ESTs | | | gi = 2292170 | 616790 |
| IC10088 | UG75 Expression | EST | Mm.35621 | TITLE ESTs | | | gi = 3336050 | 719406 |
| IC10089 | UG75 Expression | EST | Mm.35622 | TITLE ESTs, Moderately similar to AMP DEAMINASE 3 [M. musculus] | | | gi = 6167917 | 1327579 |
| IC10090 | UG75 Expression | EST | Mm.35623 | TITLE ESTs | | | gi = 4408517 | 1264464 |
| IC10091 | UG75 Expression | EST | Mm.35625 | TITLE ESTs | | | gi = 1759044 | 622366 |
| IC10092 | UG75 Expression | EST | Mm.35627 | TITLE ESTs, Weakly similar to KIAA0616 protein [H. sapiens] | | | gi = 2461362 | 777363 |
| IC10093 | UG75 Expression | EST | Mm.35634 | TITLE ESTs | | | gi = 4032044 | 618962 |
| IC10094 | UG75 Expression | EST | Mm.35648 | TITLE ESTs | | | gi = 4301287 | 582726 |
| IC10095 | UG75 Expression | EST | Mm.35650 | TITLE ESTs, Moderately similar to SAS [H. sapiens] | | | gi = 3448065 | 1279193 |
| IC10096 | UG75 Expression | EST | Mm.35651 | TITLE ESTs | | | gi = 2979110 | 1281519 |
| IC10097 | UG75 Expression | EST | Mm.35653 | TITLE ESTs | | | gi = 3517785 | 1264971 |
| IC10098 | UG75 Expression | EST | Mm.35655 | TITLE ESTs | | | gi = 2519222 | 1225511 |
| IC10099 | UG75 Expression | EST | Mm.35658 | TITLE ESTs | | | gi = 4783419 | 619112 |
| IC10100 | UG75 Expression | EST | Mm.35661 | TITLE ESTs, Weakly similar to unnamed protein product [H. sapiens] | | | gi = 2257093 | 1749714 |
| IC10101 | UG75 Expression | EST | Mm.35665 | TITLE ESTs | | | gi = 4408433 | 1263909 |
| IC10102 | UG75 Expression | EST | Mm.35668 | TITLE ESTs | | | gi = 1675710 | 1294288 |
| IC10103 | UG75 Expression | EST | Mm.35674 | TITLE ESTs | | | gi = 5191395 | 777553 |
| IC10104 | UG75 Expression | EST | Mm.35678 | TITLE ESTs | | | gi = 2962468 | 1264275 |
| IC10105 | UG75 Expression | EST | Mm.35679 | TITLE ESTs, Weakly similar to F38A5.1 [C. elegans] | | | gi = 4730180 | 1312035 |
| IC10106 | UG75 Expression | EST | Mm.35680 | TITLE ESTs, Weakly similar to R12C12.6 [C. elegans] | | | gi = 6750415 | 973603 |
| IC10107 | UG75 Expression | EST | Mm.35682 | TITLE ESTs | | | gi = 2647225 | 618238 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10108 | UG75 Expression | EST | Mm.35691 | TITLE ESTs | | | gi = 1282517 | 634917 |
| IC10109 | UG75 Expression | EST | Mm.35694 | TITLE EST | | | gi = 4508365 | 1243546 |
| IC10110 | UG75 Expression | EST | Mm.35695 | TITLE ESTs | | | gi = 1714769 | 596941 |
| IC10111 | UG75 Expression | EST | Mm.35703 | TITLE ESTs | | | gi = 1380557 | 388017 |
| IC10112 | UG75 Expression | EST | Mm.35709 | TITLE ESTs | | | gi = 1724618 | 597636 |
| IC10113 | UG75 Expression | EST | Mm.35714 | TITLE ESTs, Weakly similar to COLLAGEN ALPHA 1(I) CHAIN [R. norvegicus] | | | gi = 4276247 | 618326 |
| IC10114 | UG75 Expression | EST | Mm.35717 | TITLE ESTs | | | gi = 1794924 | 1282486 |
| IC10115 | UG75 Expression | EST | Mm.35724 | TITLE ESTs | | | gi = 5492909 | 1278947 |
| IC10116 | UG75 Expression | EST | Mm.35731 | TITLE ESTs, Weakly similar to LNXp80 [M. musculus] | | | gi = 3260294 | 1263250 |
| IC10117 | UG75 Expression | EST | Mm.35732 | TITLE ESTs | | | gi = 2811536 | 574727 |
| IC10118 | UG75 Expression | EST | Mm.35735 | TITLE ESTs | | | gi = 5495167 | 596822 |
| IC10119 | UG75 Expression | EST | Mm.35736 | TITLE ESTs | | | gi = 4482260 | 1263016 |
| IC10120 | UG75 Expression | EST | Mm.35737 | TITLE ESTs | | | gi = 2849539 | 718512 |
| IC10121 | UG75 Expression | EST | Mm.35742 | TITLE ESTs, Weakly similar to BAT2 [M. musculus] | | | gi = 6520701 | 974016 |
| IC10122 | UG75 Expression | EST | Mm.35744 | TITLE ESTs, Moderately similar to HYPOTHETICAL 22.7 KD PROTEIN C28H8.9 IN CHROMOSOME III [Caenorhabditis elegans] | | | gi = 2966413 | 1295566 |
| IC10123 | UG75 Expression | EST | Mm.35747 | TITLE ESTs | | | gi = 4482836 | 1265018 |
| IC10124 | UG75 Expression | EST | Mm.35749 | TITLE ESTs | | | gi = 2561264 | 1264359 |
| IC10125 | UG75 Expression | EST | Mm.35751 | TITLE ESTs | | | gi = 2333286 | 973070 |
| IC10126 | UG75 Expression | EST | Mm.35754 | TITLE ESTs | | | gi = 2180862 | 959115 |
| IC10127 | UG75 Expression | EST | Mm.35756 | TITLE ESTs | | | gi = 3982282 | 533874 |
| IC10128 | UG75 Expression | EST | Mm.35758 | TITLE ESTs | | | gi = 4408491 | 764645 |
| IC10129 | UG75 Expression | EST | Mm.35769 | TITLE ESTs | | | gi = 2813114 | 1446335 |
| IC10130 | UG75 Expression | EST | Mm.35771 | TITLE ESTs | | | gi = 6632551 | 1293914 |
| IC10131 | UG75 Expression | EST | Mm.35792 | TITLE ESTs | | | gi = 5909779 | 958822 |
| IC10132 | UG75 Expression | EST | Mm.35794 | TITLE ESTs | | | gi = 4484908 | 1265367 |
| IC10133 | UG75 Expression | EST | Mm.35795 | TITLE ESTs | | | gi = 1800862 | 617513 |
| IC10134 | UG75 Expression | EST | Mm.35797 | TITLE ESTs | | | gi = 6756274 | 639356 |
| IC10135 | UG75 Expression | EST | Mm.358 | TITLE ESTs | | | gi = 6085614 | 1311713 |
| IC10136 | UG75 Expression | EST | Mm.35802 | TITLE ESTs, Moderately similar to R26660_2, partial CDS [H. sapiens] | | | gi = 2990645 | 1264372 |
| IC10137 | UG75 Expression | EST | Mm.35808 | TITLE ESTs | | | gi = 4059454 | 622740 |
| IC10138 | UG75 Expression | EST | Mm.35810 | TITLE ESTs | | | gi = 2962165 | 1281983 |
| IC10139 | UG75 Expression | EST | Mm.35823 | TITLE ESTs, Weakly similar to open reading frame [M. musculus] | | | gi = 1768220 | 1294989 |
| IC10140 | UG75 Expression | EST | Mm.35827 | TITLE ESTs | | | gi = 4777802 | 576083 |
| IC10141 | UG75 Expression | EST | Mm.35828 | TITLE ESTs, Moderately similar to R32184_1 [H. sapiens] | | | gi = 3079941 | 482403 |
| IC10142 | UG75 Expression | EST | Mm.35834 | TITLE ESTs | | | gi = 3067914 | 1295582 |
| IC10143 | UG75 Expression | EST | Mm.3584 | TITLE ESTs | | | gi = 1715788 | 720747 |
| IC10144 | UG75 Expression | EST | Mm.35842 | TITLE ESTs | | | gi = 5478013 | 619857 |
| IC10145 | UG75 Expression | EST | Mm.35843 | TITLE ESTs, Moderately similar to HYPOTHETICAL 97.6 KD PROTEIN IN SHP1-SEC17 INTERGENIC REGION [Saccharomyces cerevisiae] | | | gi = 4967395 | 1749713 |
| IC10146 | UG75 Expression | EST | Mm.35850 | TITLE ESTs | | | gi = 4408487 | 1264304 |
| IC10147 | UG75 Expression | EST | Mm.35869 | TITLE ESTs | | | gi = 1672161 | 558124 |
| IC10148 | UG75 Expression | EST | Mm.3587 | TITLE ESTs | | | gi = 2918704 | 1001827 |
| IC10149 | UG75 Expression | EST | Mm.35910 | TITLE ESTs | | | gi = 6749296 | 2373159 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10150 | UG75 Expression | EST | Mm.35926 | TITLE ESTs | | | gi = 4726676 | 1279490 |
| IC10151 | UG75 Expression | EST | Mm.35930 | TITLE ESTs, Weakly similar to ganglioside-induced differentiation associated protein 1 [M. musculus] | | | gi = 1514911 | 1378336 |
| IC10152 | UG75 Expression | EST | Mm.35933 | TITLE EST | | | gi = 4299181 | 583089 |
| IC10153 | UG75 Expression | EST | Mm.35935 | TITLE EST | | | gi = 4300167 | 575876 |
| IC10154 | UG75 Expression | EST | Mm.35936 | TITLE EST | | | gi = 4304947 | 598621 |
| IC10155 | UG75 Expression | EST | Mm.35937 | TITLE EST | | | gi = 4290836 | 577607 |
| IC10156 | UG75 Expression | EST | Mm.35938 | TITLE EST | | | gi = 4299871 | 618362 |
| IC10157 | UG75 Expression | EST | Mm.35949 | TITLE EST | | | gi = 4375227 | 893946 |
| IC10158 | UG75 Expression | EST | Mm.35955 | TITLE EST | | | gi = 4482248 | 1262924 |
| IC10159 | UG75 Expression | EST | Mm.35956 | TITLE EST | | | gi = 4482677 | 1263412 |
| IC10160 | UG75 Expression | EST | Mm.35957 | TITLE EST | | | gi = 4482748 | 1264305 |
| IC10161 | UG75 Expression | EST | Mm.35966 | TITLE EST | | | gi = 4571908 | 1148787 |
| IC10162 | UG75 Expression | EST | Mm.35968 | TITLE ESTs | | | gi = 4572211 | 1149166 |
| IC10163 | UG75 Expression | EST | Mm.35981 | TITLE EST | | | gi = 1915797 | 765521 |
| IC10164 | UG75 Expression | EST | Mm.35986 | TITLE EST | | | gi = 5476118 | 958520 |
| IC10165 | UG75 Expression | EST | Mm.35997 | TITLE ESTs | | | gi = 2258923 | 596528 |
| IC10166 | UG75 Expression | EST | Mm.3600 | TITLE ESTs | | | gi = 2164692 | 779684 |
| IC10167 | UG76 LID366 B cell | EST | Mm.36000 | TITLE ESTs, Weakly similar to B0025.2 [C. elegans] | | | gi = 7066441 | 1167769 |
| IC10168 | UG75 Expression | EST | Mm.36008 | TITLE ESTs | | | gi = 2979189 | 1263339 |
| IC10169 | UG75 Expression | EST | Mm.36025 | TITLE EST | | | gi = 4299139 | 583034 |
| IC10170 | UG75 Expression | EST | Mm.36026 | TITLE EST | | | gi = 4304863 | 598554 |
| IC10171 | UG75 Expression | EST | Mm.36027 | TITLE EST | | | gi = 4282974 | 573893 |
| IC10172 | UG75 Expression | EST | Mm.36029 | TITLE EST | | | gi = 4295311 | 637106 |
| IC10173 | UG75 Expression | EST | Mm.36030 | TITLE EST | | | gi = 4295500 | 637247 |
| IC10174 | UG75 Expression | EST | Mm.36031 | TITLE EST | | | gi = 4296339 | 640689 |
| IC10175 | UG75 Expression | EST | Mm.36032 | TITLE EST | | | gi = 4296388 | 640723 |
| IC10176 | UG75 Expression | EST | Mm.36037 | TITLE EST | | | gi = 4316676 | 751286 |
| IC10177 | UG75 Expression | EST | Mm.36038 | TITLE EST | | | gi = 4317080 | 764544 |
| IC10178 | UG75 Expression | EST | Mm.36054 | TITLE ESTs | | | gi = 4482294 | 1263161 |
| IC10179 | UG75 Expression | EST | Mm.36058 | TITLE EST | | | gi = 4522056 | 1282543 |
| IC10180 | UG75 Expression | EST | Mm.36061 | TITLE EST | | | gi = 4571730 | 1149684 |
| IC10181 | UG75 Expression | EST | Mm.36065 | TITLE EST, Moderately similar to mszf59-2 [M. musculus] | | | gi = 4571857 | 1139622 |
| IC10182 | UG75 Expression | EST | Mm.36066 | TITLE EST | | | gi = 4571937 | 1149020 |
| IC10183 | UG75 Expression | EST | Mm.36078 | TITLE EST | | | gi = 4596923 | 573038 |
| IC10184 | UG75 Expression | EST | Mm.36085 | TITLE ESTs | | | gi = 1826703 | 720902 |
| IC10185 | UG75 Expression | EST | Mm.36087 | TITLE ESTs | | | gi = 2803375 | 719466 |
| IC10186 | UG75 Expression | EST | Mm.36089 | TITLE ESTs | | | gi = 5469722 | 765080 |
| IC10187 | UG75 Expression | EST | Mm.3609 | TITLE EST | | | gi = 3336132 | 618061 |
| IC10188 | UG75 Expression | EST | Mm.36090 | TITLE EST | | | gi = 2049373 | 752028 |
| IC10189 | UG75 Expression | EST | Mm.36097 | TITLE ESTs | | | gi = 4600849 | 1140255 |
| IC10190 | UG75 Expression | EST | Mm.36115 | TITLE ESTs | | | gi = 3680463 | 1446244 |
| IC10191 | UG75 Expression | EST | Mm.36124 | TITLE EST | | | gi = 4060432 | 597742 |
| IC10192 | UG75 Expression | EST | Mm.36132 | TITLE EST | | | gi = 4299146 | 583046 |
| IC10193 | UG75 Expression | EST | Mm.36135 | TITLE EST | | | gi = 4287750 | 619109 |
| IC10194 | UG75 Expression | EST | Mm.36136 | TITLE EST | | | gi = 4968468 | 637928 |
| IC10195 | UG75 Expression | EST | Mm.36137 | TITLE EST, Weakly similar to proline-rich protein 15 [R. norvegicus] | | | gi = 4296772 | 641194 |
| IC10196 | UG75 Expression | EST | Mm.36148 | TITLE ESTs | | | gi = 5907080 | 1225678 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10197 | UG75 Expression | EST | Mm.36157 | TITLE EST | | | gi = 4375243 | 894138 |
| IC10198 | UG75 Expression | EST | Mm.36161 | TITLE EST | | | gi = 4403707 | 959289 |
| IC10199 | UG75 Expression | EST | Mm.36166 | TITLE ESTs | | | gi = 5496980 | 1149792 |
| IC10200 | UG75 Expression | EST | Mm.36167 | TITLE EST | | | gi = 4571938 | 1149001 |
| IC10201 | UG75 Expression | EST | Mm.36173 | TITLE EST | | | gi = 4273113 | 596368 |
| IC10202 | UG75 Expression | EST | Mm.36180 | TITLE ESTs | | | gi = 3956134 | 752309 |
| IC10203 | UG75 Expression | EST | Mm.36187 | TITLE ESTs | | | gi = 4571909 | 1148818 |
| IC10204 | UG75 Expression | EST | Mm.36212 | TITLE EST | | | gi = 3078722 | 1330245 |
| IC10205 | UG75 Expression | EST | Mm.36227 | TITLE EST | | | gi = 4298267 | 574901 |
| IC10206 | UG75 Expression | EST | Mm.36228 | TITLE ESTs | | | gi = 450318 | 596360 |
| IC10207 | UG75 Expression | EST | Mm.36230 | TITLE ESTs | | | gi = 4309581 | 573284 |
| IC10208 | UG75 Expression | EST | Mm.36234 | TITLE EST | | | gi = 4301598 | 621452 |
| IC10209 | UG75 Expression | EST | Mm.36240 | TITLE EST | | | gi = 4318257 | 777254 |
| IC10210 | UG75 Expression | EST | Mm.36253 | TITLE EST | | | gi = 4401902 | 1001590 |
| IC10211 | UG75 Expression | EST | Mm.3626 | TITLE ESTs | | | gi = 6521176 | 536186 |
| IC10212 | UG75 Expression | EST | Mm.36265 | TITLE EST | | | gi = 4571719 | 1149581 |
| IC10213 | UG75 Expression | EST | Mm.36266 | TITLE ESTs | | | gi = 2592280 | 1149694 |
| IC10214 | UG75 Expression | EST | Mm.36267 | TITLE EST | | | gi = 4571766 | 1149950 |
| IC10215 | UG75 Expression | EST | Mm.36273 | TITLE ESTs | | | gi = 4401887 | 1001475 |
| IC10216 | UG75 Expression | EST | Mm.36278 | TITLE ESTs, Moderately similar to human forminotransferase cyclodeaminase [H. sapiens] | | | gi = 3518615 | 1482767 |
| IC10217 | UG75 Expression | EST | Mm.36280 | TITLE ESTs | | | gi = 4788440 | 534045 |
| IC10218 | UG75 Expression | EST | Mm.36283 | TITLE ESTs | | | gi = 1500791 | 597813 |
| IC10219 | UG75 Expression | EST | Mm.36288 | TITLE EST | | | gi = 1724526 | 582700 |
| IC10220 | UG75 Expression | EST | Mm.36290 | TITLE ESTs | | | gi = 1816923 | 637519 |
| IC10221 | UG75 Expression | EST | Mm.36291 | TITLE EST | | | gi = 4725497 | 620080 |
| IC10222 | UG75 Expression | EST | Mm.36292 | TITLE ESTs | | | gi = 241593 | 635953 |
| IC10223 | UG75 Expression | EST | Mm.36293 | TITLE ESTs | | | gi = 1772102 | 643205 |
| IC10224 | UG75 Expression | EST | Mm.36295 | TITLE EST | | | gi = 1801180 | 636621 |
| IC10225 | UG75 Expression | EST | Mm.36298 | TITLE EST | | | gi = 1915844 | 765793 |
| IC10226 | UG75 Expression | EST | Mm.36303 | TITLE ESTs | | | gi = 2331583 | 972466 |
| IC10227 | UG75 Expression | EST | Mm.36304 | TITLE ESTs | | | gi = 4402636 | 972668 |
| IC10228 | UG75 Expression | EST | Mm.36311 | TITLE ESTs | | | gi = 2592123 | 1149206 |
| IC10229 | UG75 Expression | EST | Mm.36314 | TITLE ESTs | | | gi = 4274591 | 1225217 |
| IC10230 | UG75 Expression | EST | Mm.3632 | TITLE DNA segment, Chr 18, Wayne State University 70, expressed | GENE D18Wsu70e | | | 619509 |
| IC10231 | UG75 Expression | EST | Mm.36335 | TITLE ESTs | | | gi = 1908752 | 736272 |
| IC10232 | UG75 Expression | EST | Mm.36354 | TITLE ESTs | | | gi = 4407221 | 1149057 |
| IC10233 | UG75 Expression | EST | Mm.36355 | TITLE EST | | | gi = 4303403 | 583114 |
| IC10234 | UG75 Expression | EST | Mm.36357 | TITLE EST | | | gi = 4290843 | 582136 |
| IC10235 | UG75 Expression | EST | Mm.36358 | TITLE EST | | | gi = 1751868 | 619701 |
| IC10236 | UG75 Expression | EST | Mm.36359 | TITLE EST | | | gi = 4304567 | 642263 |
| IC10237 | UG75 Expression | EST | Mm.36370 | TITLE EST | | | gi = 4401088 | 1020925 |
| IC10238 | UG75 Expression | EST | Mm.36377 | TITLE EST | | | gi = 4404661 | 1002750 |
| IC10239 | UG75 Expression | EST | Mm.36379 | TITLE EST | | | gi = 4482328 | 1263318 |
| IC10240 | UG75 Expression | EST | Mm.36380 | TITLE EST | | | gi = 4482681 | 1263429 |
| IC10241 | UG75 Expression | EST | Mm.36384 | TITLE EST | | | gi = 4512875 | 1281315 |
| IC10242 | UG75 Expression | EST | Mm.36385 | TITLE ESTs | | | gi = 4723416 | 1149396 |
| IC10243 | UG75 Expression | EST | Mm.36402 | TITLE ESTs | | | gi = 4571910 | 1148820 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10244 | UG75 Expression | EST | Mm.36404 | TITLE ESTs | | | gi = 1777073 | 636730 |
| IC10245 | UG75 Expression | EST | Mm.36406 | TITLE ESTs | | | gi = 4723761 | 581968 |
| IC10246 | UG75 Expression | EST | Mm.36408 | TITLE EST | | | gi = 1766869 | 636243 |
| IC10247 | UG75 Expression | EST | Mm.36412 | TITLE EST | | | gi = 1904066 | 719165 |
| IC10248 | UG75 Expression | EST | Mm.36414 | TITLE EST | | | gi = 1915677 | 765642 |
| IC10249 | UG75 Expression | EST | Mm.36417 | TITLE ESTs | | | gi = 3955638 | 1149358 |
| IC10250 | UG75 Expression | EST | Mm.36424 | TITLE ESTs, Weakly similar to KIAA0978 protein [H. sapiens] | | | gi = 4725341 | 1149170 |
| IC10251 | UG75 Expression | EST | Mm.36430 | TITLE ESTs | | | gi = 2518294 | 581927 |
| IC10252 | UG75 Expression | EST | Mm.36434 | TITLE ESTs | | | gi = 5907594 | 1148819 |
| IC10253 | UG75 Expression | EST | Mm.36441 | TITLE ESTs | | | gi = 2041049 | 576043 |
| IC10254 | UG75 Expression | EST | Mm.36462 | TITLE EST | | | gi = 4058060 | 575507 |
| IC10255 | UG75 Expression | EST | Mm.36467 | TITLE ESTs | | | gi = 4258963 | 620390 |
| IC10256 | UG75 Expression | EST | Mm.36471 | TITLE EST | | | gi = 4298323 | 574923 |
| IC10257 | UG75 Expression | EST | Mm.36472 | TITLE EST | | | gi = 4298365 | 574972 |
| IC10258 | UG75 Expression | EST | Mm.36474 | TITLE EST | | | gi = 4302777 | 596150 |
| IC10259 | UG75 Expression | EST | Mm.36475 | TITLE ESTs | | | gi = 1681780 | 596374 |
| IC10260 | UG75 Expression | EST | Mm.36476 | TITLE EST | | | gi = 4303046 | 596410 |
| IC10261 | UG75 Expression | EST | Mm.36477 | TITLE EST | | | gi = 4304660 | 575358 |
| IC10262 | UG75 Expression | EST | Mm.36479 | TITLE EST | | | gi = 4283206 | 574078 |
| IC10263 | UG75 Expression | EST | Mm.36480 | TITLE ESTs | | | gi = 4295290 | 637059 |
| IC10264 | UG75 Expression | EST | Mm.36485 | TITLE EST | | | gi = 4316879 | 752478 |
| IC10265 | UG75 Expression | EST | Mm.36492 | TITLE ESTs | | | gi = 1807572 | 644934 |
| IC10266 | UG75 Expression | EST | Mm.36499 | TITLE EST | | | gi = 4403600 | 959015 |
| IC10267 | UG75 Expression | EST | Mm.36503 | TITLE ESTs | | | gi = 4703223 | 617168 |
| IC10268 | UG75 Expression | EST | Mm.36505 | TITLE ESTs, Weakly similar to contains weak similarity to HIV P17 matrix protein [C. elegans] | | | gi = 2646434 | 973283 |
| IC10269 | UG75 Expression | EST | Mm.36506 | TITLE ESTs | | | gi = 4571721 | 1149612 |
| IC10270 | UG75 Expression | EST | Mm.36509 | TITLE ESTs | | | gi = 2572733 | 1148464 |
| IC10271 | UG75 Expression | EST | Mm.36510 | TITLE ESTs | | | gi = 4571934 | 1148959 |
| IC10272 | UG75 Expression | EST | Mm.36511 | TITLE ESTs, Weakly similar to putative [C. elegans] | | | gi = 1801002 | 750318 |
| IC10273 | UG75 Expression | EST | Mm.36513 | TITLE expressed sequence tag mouse EST 11 | GENE ESTM11 | | gi = 1529911 | 540488 |
| IC10274 | UG75 Expression | EST | Mm.36523 | TITLE ESTs | | | gi = 1876643 | 1294905 |
| IC10275 | UG75 Expression | EST | Mm.36524 | TITLE ESTs | | | gi = 1677321 | 576575 |
| IC10276 | UG75 Expression | EST | Mm.36530 | TITLE ESTs | | | gi = 3371142 | 597596 |
| IC10277 | UG75 Expression | EST | Mm.36533 | TITLE EST | | | gi = 1740035 | 597823 |
| IC10278 | UG75 Expression | EST | Mm.36534 | TITLE ESTs | | | gi = 2991228 | 619696 |
| IC10279 | UG75 Expression | EST | Mm.36535 | TITLE ESTs | | | gi = 4703151 | 616609 |
| IC10280 | UG75 Expression | EST | Mm.36536 | TITLE ESTs | | | gi = 1776403 | 637832 |
| IC10281 | UG75 Expression | EST | Mm.36537 | TITLE ESTs | | | gi = 5498789 | 596323 |
| IC10282 | UG75 Expression | EST | Mm.36541 | TITLE EST | | | gi = 1910231 | 718508 |
| IC10283 | UG75 Expression | EST | Mm.36542 | TITLE ESTs | | | gi = 2775525 | 634972 |
| IC10284 | UG75 Expression | EST | Mm.36543 | TITLE ESTs | | | gi = 5498210 | 572881 |
| IC10285 | UG75 Expression | EST | Mm.36545 | TITLE ESTs | | | gi = 3215626 | 1148861 |
| IC10286 | UG75 Expression | EST | Mm.36547 | TITLE EST | | | gi = 1937004 | 751078 |
| IC10287 | UG75 Expression | EST | Mm.36548 | TITLE EST | | | gi = 2049280 | 751875 |
| IC10288 | UG75 Expression | EST | Mm.36553 | TITLE ESTs, Moderately similar to SON PROTEIN [Homo sapiens] | | | gi = 1672847 | 1149914 |
| IC10289 | UG75 Expression | EST | Mm.36573 | TITLE ESTs | | | gi = 4600860 | 1148478 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10290 | UG75 Expression | EST | Mm.36574 | TITLE ESTs | | | gi = 4723393 | 1149090 |
| IC10291 | UG75 Expression | EST | Mm.36575 | TITLE ESTs, Weakly similar to C43H8.1 [*C. elegans*] | | | gi = 5495132 | 1149452 |
| IC10292 | UG75 Expression | EST | Mm.36582 | TITLE ESTs | | | gi = 2075152 | 1243728 |
| IC10293 | UG75 Expression | EST | Mm.36585 | TITLE ESTs | | | gi = 6645319 | 749447 |
| IC10294 | UG75 Expression | EST | Mm.36591 | TITLE ESTs | | | gi = 3692901 | 573359 |
| IC10295 | UG75 Expression | EST | Mm.36606 | TITLE ESTs | | | gi = 4482181 | 635100 |
| IC10296 | UG75 Expression | EST | Mm.36611 | TITLE ESTs | | | gi = 5498231 | 1363041 |
| IC10297 | UG75 Expression | EST | Mm.36613 | TITLE ESTs | | | gi = 1662075 | 572829 |
| IC10298 | UG75 Expression | EST | Mm.36616 | TITLE ESTs | | | gi = 4721950 | 582796 |
| IC10299 | UG75 Expression | EST | Mm.36618 | TITLE EST | | | gi = 4289850 | 576687 |
| IC10300 | UG75 Expression | EST | Mm.36620 | TITLE EST | | | gi = 4290788 | 577560 |
| IC10301 | UG75 Expression | EST | Mm.36621 | TITLE EST, Weakly similar to proline-rich protein PRB3M [*H. sapiens*] | | | gi = 4291060 | 577892 |
| IC10302 | UG75 Expression | EST | Mm.36622 | TITLE EST | | | gi = 4294666 | 636321 |
| IC10303 | UG75 Expression | EST | Mm.36624 | TITLE ESTs | | | gi = 4307149 | 643899 |
| IC10304 | UG75 Expression | EST | Mm.36626 | TITLE ESTs | | | gi = 4316681 | 751316 |
| IC10305 | UG75 Expression | EST | Mm.36635 | TITLE EST | | | gi = 4375240 | 894083 |
| IC10306 | UG75 Expression | EST | Mm.36636 | TITLE EST | | | gi = 4375276 | 894417 |
| IC10307 | UG75 Expression | EST | Mm.36641 | TITLE EST | | | gi = 440397 | 973744 |
| IC10308 | UG75 Expression | EST | Mm.36654 | TITLE ESTs | | | gi = 2591778 | 1149380 |
| IC10309 | UG75 Expression | EST | Mm.36655 | TITLE ESTs | | | gi = 2591903 | 1149451 |
| IC10310 | UG75 Expression | EST | Mm.36656 | TITLE ESTs | | | gi = 4513167 | 1149038 |
| IC10311 | UG75 Expression | EST | Mm.36665 | TITLE EST | | | gi = 4572236 | 1149344 |
| IC10312 | UG75 Expression | EST | Mm.36667 | TITLE ESTs | | | gi = 1861410 | 617745 |
| IC10313 | UG75 Expression | EST | Mm.36669 | TITLE ESTs | | | gi = 6526080 | 902945 |
| IC10314 | UG75 Expression | EST | Mm.36677 | TITLE ESTs, Weakly similar to Herc2 [*M. musculus*] | | | gi = 1487812 | 551467 |
| IC10315 | UG75 Expression | EST | Mm.36679 | TITLE ESTs, Weakly similar to IG DELTA CHAIN C REGION MEMBRANE-BOUND FORM [*Mus musculus*] | | | gi = 6516176 | 1148970 |
| IC10316 | UG75 Expression | EST | Mm.36682 | TITLE ESTs, Moderately similar to p18 component of aminoacyl-tRNA synthetase complex [*H. sapiens*] | | | gi = 2292002 | 958739 |
| IC10317 | UG75 Expression | EST | Mm.36683 | TITLE ESTs | | | gi = 3686748 | 723076 |
| IC10318 | UG75 Expression | EST | Mm.36684 | TITLE ESTs | | | gi = 1715950 | 596765 |
| IC10319 | UG75 Expression | EST | Mm.36685 | TITLE ESTs | | | gi = 5909793 | 764172 |
| IC10320 | UG75 Expression | EST | Mm.36686 | TITLE ESTs | | | gi = 4831958 | 598439 |
| IC10321 | UG75 Expression | EST | Mm.36687 | TITLE ESTs | | | gi = 4596912 | 572938 |
| IC10322 | UG75 Expression | EST | Mm.36690 | TITLE ESTs | | | gi = 1749240 | 558088 |
| IC10323 | UG75 Expression | EST | Mm.36692 | TITLE ESTs | | | gi = 6097876 | 618936 |
| IC10324 | UG75 Expression | EST | Mm.36693 | TITLE ESTs | | | gi = 2906865 | 751501 |
| IC10325 | UG75 Expression | EST | Mm.36695 | TITLE ESTs | | | gi = 1842633 | 752371 |
| IC10326 | UG75 Expression | EST | Mm.36697 | TITLE ESTs | | | gi = 1290242 | 639931 |
| IC10327 | UG75 Expression | EST | Mm.36699 | TITLE ESTs, Weakly similar to unknown [*R. norvegicus*] | | | gi = 2561594 | 1395614 |
| IC10328 | UG75 Expression | EST | Mm.36700 | TITLE ESTs | | | gi = 2504290 | 718829 |
| IC10329 | UG75 Expression | EST | Mm.36703 | TITLE ESTs | | | gi = 4617022 | 1395147 |
| IC10330 | UG75 Expression | EST | Mm.36705 | TITLE ESTs | | | gi = 1826585 | 620259 |
| IC10331 | UG75 Expression | EST | Mm.36706 | TITLE ESTs | | | gi = 1553622 | 550631 |
| IC10332 | UG75 Expression | EST | Mm.36707 | TITLE ESTs, Weakly similar to Yhr075cp [*S. cerevisiae*] | | | gi = 264092 | 619363 |
| IC10333 | UG75 Expression | EST | Mm.36708 | TITLE ESTs, Weakly similar to p140mDia [*M. musculus*] | | | gi = 1896040 | 1279947 |
| IC10334 | UG75 Expression | EST | Mm.36714 | TITLE ESTs | | | gi = 4407492 | 752436 |
| IC10335 | UG75 Expression | EST | Mm.36715 | TITLE ESTs | | | gi = 1910393 | 533369 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10336 | UG75 Expression | EST | Mm.36716 | TITLE ESTs | | | gi = 3376646 | 583108 |
| IC10337 | UG75 Expression | EST | Mm.36717 | TITLE ESTs, Weakly similar to (define not available 5640017) [*M. musculus*] | | | gi = 2644280 | 1379414 |
| IC10338 | UG75 Expression | EST | Mm.36720 | TITLE ESTs | | | gi = 1726550 | 599121 |
| IC10339 | UG75 Expression | EST | Mm.36722 | TITLE ESTs | | | gi = 1776257 | 1362341 |
| IC10340 | UG75 Expression | EST | Mm.36727 | TITLE ESTs | | | gi = 2305930 | 1149063 |
| IC10341 | UG75 Expression | EST | Mm.36729 | TITLE ESTs | | | gi = 3141293 | 1345844 |
| IC10342 | UG75 Expression | EST | Mm.36733 | TITLE EST | | | gi = 1889251 | 719262 |
| IC10343 | UG75 Expression | EST | Mm.36736 | TITLE ESTs | | | gi = 3125298 | 973712 |
| IC10344 | UG75 Expression | EST | Mm.36737 | TITLE ESTs | | | gi = 4403850 | 973148 |
| IC10345 | UG75 Expression | EST | Mm.36738 | TITLE ESTs, Moderately similar to HYDROXYMETHYLGLUTARYL-COA SYNTHASE, CYTOPLASMIC [*Homo sapiens*] | | | gi = 4537798 | 722519 |
| IC10346 | UG75 Expression | EST | Mm.3674 | TITLE ESTs | | | gi = 1937213 | 749357 |
| IC10347 | UG75 Expression | EST | Mm.36743 | TITLE ESTs, Moderately similar to endogenous superantigen [*M. musculus*] | | | gi = 1089475 | 959188 |
| IC10348 | UG75 Expression | EST | Mm.36746 | TITLE ESTs, Moderately similar to hypothetical protein [*H. sapiens*] | | | gi = 4276070 | 614844 |
| IC10349 | UG75 Expression | EST | Mm.36752 | TITLE ESTs | | | gi = 4601291 | 599135 |
| IC10350 | UG75 Expression | EST | Mm.36753 | TITLE ESTs, Moderately similar to damage-specific DNA binding protein 2 [*H. sapiens*] | | | gi = 3601600 | 1139673 |
| IC10351 | UG75 Expression | EST | Mm.36756 | TITLE ESTs | | | gi = 2192241 | 1149633 |
| IC10352 | UG75 Expression | EST | Mm.36767 | TITLE ESTs | | | gi = 4571749 | 1149790 |
| IC10353 | UG75 Expression | EST | Mm.36768 | TITLE ESTs, Weakly similar to Smarce1-related protein [*M. musculus*] | | | gi = 6083753 | 1020839 |
| IC10354 | UG75 Expression | EST | Mm.36769 | TITLE ESTs, Moderately similar to SLAP-2 homolog [*H. sapiens*] | | | gi = 2456833 | 619267 |
| IC10355 | UG75 Expression | EST | Mm.36770 | TITLE ESTs | | | gi = 6077858 | 550891 |
| IC10356 | UG75 Expression | EST | Mm.36776 | TITLE ESTs, Weakly similar to SH2 domain-containing protein [*M. musculus*] | | | gi = 1287744 | 680957 |
| IC10357 | UG75 Expression | EST | Mm.36781 | TITLE EST | | | gi = 4571940 | 1149023 |
| IC10358 | UG75 Expression | EST | Mm.36785 | TITLE ESTs [*R. norvegicus*] | | | gi = 3053947 | 635645 |
| IC10359 | UG75 Expression | EST | Mm.36786 | TITLE ESTs | | | gi = 2906898 | 1328649 |
| IC10360 | UG75 Expression | EST | Mm.36792 | TITLE ESTs, Weakly similar to ubiquitin-specific protease UBP41 [*M. musculus*] | | | gi = 2263140 | 596702 |
| IC10361 | UG75 Expression | EST | Mm.36793 | TITLE ESTs | | | gi = 4601777 | 577200 |
| IC10362 | UG75 Expression | EST | Mm.36794 | TITLE ESTs | | | gi = 4299090 | 1362016 |
| IC10363 | UG75 Expression | EST | Mm.36798 | TITLE ESTs | | | gi = 1715678 | 622822 |
| IC10364 | UG75 Expression | EST | Mm.3680 | TITLE DNA segment, Chr 14, Wayne State University 146, expressed | GENE D14Wsu146e | | | 1329072 |
| IC10365 | UG75 Expression | EST | Mm.36803 | TITLE ESTs | | | gi = 3519019 | 1263522 |
| IC10366 | UG75 Expression | EST | Mm.36805 | TITLE ESTs | | | gi = 1372720 | 719312 |
| IC10367 | UG75 Expression | EST | Mm.36806 | TITLE ESTs | | | gi = 2306680 | 638296 |
| IC10368 | UG75 Expression | EST | Mm.36808 | TITLE ESTs | | | gi = 3683890 | 1279484 |
| IC10369 | UG75 Expression | EST | Mm.36809 | TITLE ESTs | | | gi = 2461009 | 638336 |
| IC10370 | UG75 Expression | EST | Mm.36822 | TITLE ESTs, Moderately similar to hypothetical protein [*H. sapiens*] | | | gi = 2516829 | 1345100 |
| IC10371 | UG75 Expression | EST | Mm.36824 | TITLE ESTs | | | gi = 3956871 | 620045 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10372 | UG75 Expression | EST | Mm.36832 | TITLE ESTs | | | gi = 4271726 | 1148940 |
| IC10373 | UG75 Expression | EST | Mm.36835 | TITLE ESTs | | | gi = 2222654 | 765108 |
| IC10374 | UG75 Expression | EST | Mm.36840 | TITLE ESTs | | | gi = 1772151 | 623022 |
| IC10375 | UG75 Expression | EST | Mm.36841 | TITLE ESTs | | | gi = 1801099 | 644303 |
| IC10376 | UG75 Expression | EST | Mm.36844 | TITLE ESTs | | | gi = 1282296 | 620965 |
| IC10377 | UG75 Expression | EST | Mm.36846 | TITLE ESTs | | | gi = 3261196 | 622759 |
| IC10378 | UG75 Expression | EST | Mm.36848 | TITLE ESTs | | | gi = 3980537 | 959036 |
| IC10379 | UG75 Expression | EST | Mm.36852 | TITLE ESTs | | | gi = 4726402 | 621412 |
| IC10380 | UG75 Expression | EST | Mm.36855 | TITLE ESTs | | | gi = 4404255 | 1001996 |
| IC10381 | UG75 Expression | EST | Mm.36857 | TITLE ESTs, Moderately similar to AMSH [*H. sapiens*] | | | gi = 4296262 | 750798 |
| IC10382 | UG75 Expression | EST | Mm.36861 | TITLE ESTs | | | gi = 4409373 | 577702 |
| IC10383 | UG75 Expression | EST | Mm.36863 | TITLE ESTs | | | gi = 4726799 | 620608 |
| IC10384 | UG75 Expression | EST | Mm.36866 | TITLE ESTs | | | gi = 2860677 | 934277 |
| IC10385 | UG75 Expression | EST | Mm.36873 | TITLE ESTs | | | gi = 2646935 | 1139627 |
| IC10386 | UG75 Expression | EST | Mm.36879 | TITLE ESTs, Moderately similar to CLATHRIN LIGHT CHAIN B [*Bos taurus*] | | | gi = 5599276 | 616654 |
| IC10387 | UG75 Expression | EST | Mm.36883 | TITLE ESTs, Weakly similar to dithiolethione-inducible gene-1 [*R. norvegicus*] | | | gi = 6632445 | 973306 |
| IC10388 | UG75 Expression | EST | Mm.36884 | TITLE ESTs | | | gi = 4409008 | 636639 |
| IC10389 | UG75 Expression | EST | Mm.36885 | TITLE ESTs | | | gi = 2692630 | 1278704 |
| IC10390 | UG75 Expression | EST | Mm.36904 | TITLE ESTs | | | gi = 4601272 | 599015 |
| IC10391 | UG75 Expression | EST | Mm.36912 | TITLE ESTs | | | gi = 6520866 | 620911 |
| IC10392 | UG75 Expression | EST | Mm.36913 | TITLE ESTs | | | gi = 4299522 | 573718 |
| IC10393 | UG75 Expression | EST | Mm.36962 | TITLE ESTs | | | gi = 4401901 | 1001572 |
| IC10394 | UG75 Expression | EST | Mm.3702 | TITLE ESTs | | | gi = 3373455 | 1152333 |
| IC10395 | UG75 Expression | EST | Mm.37131 | TITLE ESTs | | | gi = 5597454 | 598926 |
| IC10396 | UG75 Expression | EST | Mm.3715 | [*H. sapiens*] | | | gi = 5819582 | 973335 |
| IC10397 | UG75 Expression | EST | Mm.37181 | TITLE EST | | | gi = 4283636 | 581957 |
| IC10398 | UG75 Expression | EST | Mm.37192 | TITLE EST | | | gi = 4284484 | 582525 |
| IC10399 | UG75 Expression | EST | Mm.37214 | TITLE DNA segment, Chr 17, Wayne State University 155, expressed | GENE D17Wsu155e | | gi = 599098 | 599098 |
| IC10400 | UG75 Expression | EST | Mm.37221 | TITLE ESTs | | | gi = 1739301 | 634781 |
| IC10401 | UG75 Expression | EST | Mm.37223 | TITLE ESTs | | | gi = 4614363 | 765713 |
| IC10402 | UG75 Expression | EST | Mm.37256 | TITLE ESTs | | | gi = 6378710 | 722198 |
| IC10403 | UG75 Expression | EST | Mm.37259 | TITLE EST | | | gi = 4765245 | 749106 |
| IC10404 | UG75 Expression | EST | Mm.37262 | TITLE ESTs | | | gi = 1902525 | 718070 |
| IC10405 | UG75 Expression | EST | Mm.37266 | TITLE EST | | | gi = 4766080 | 622779 |
| IC10406 | UG75 Expression | EST | Mm.3727 | TITLE ESTs | | | gi = 2068129 | 551603 |
| IC10407 | UG75 Expression | EST | Mm.37271 | TITLE ESTs | | | gi = 4766329 | 749572 |
| IC10408 | UG75 Expression | EST | Mm.37272 | TITLE EST | | | gi = 4766427 | 750272 |
| IC10409 | UG75 Expression | EST | Mm.37273 | TITLE ESTs | | | gi = 4804620 | 634121 |
| IC10410 | UG75 Expression | EST | Mm.37274 | TITLE ESTs | | | gi = 5550462 | 634205 |
| IC10411 | UG75 Expression | EST | Mm.37275 | TITLE EST | | | gi = 4804662 | 638639 |
| IC10412 | UG75 Expression | EST | Mm.37276 | TITLE EST | | | gi = 4804697 | 638986 |
| IC10413 | UG75 Expression | EST | Mm.37277 | TITLE ESTs | | | gi = 4316413 | 639101 |
| IC10414 | UG75 Expression | EST | Mm.37278 | TITLE ESTs | | | gi = 5478116 | 718432 |
| IC10415 | UG75 Expression | EST | Mm.37279 | TITLE ESTs [*M. musculus*] | | | gi = 4804823 | 639691 |
| IC10416 | UG75 Expression | EST | Mm.37280 | TITLE EST | | | gi = 4804830 | 639779 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10417 | UG75 Expression | EST | Mm.37281 | TITLE EST | | | gi = 4804851 | 639985 |
| IC10418 | UG75 Expression | EST | Mm.37282 | TITLE EST | | | gi = 4804858 | 640048 |
| IC10419 | UG75 Expression | EST | Mm.37284 | TITLE EST | | | gi = 4804902 | 640298 |
| IC10420 | UG75 Expression | EST | Mm.37285 | TITLE EST | | | gi = 4804958 | 640389 |
| IC10421 | UG75 Expression | EST | Mm.37286 | TITLE EST | | | gi = 4805057 | 718673 |
| IC10422 | UG75 Expression | EST | Mm.37287 | TITLE EST | | | gi = 4805064 | 718693 |
| IC10423 | UG75 Expression | EST | Mm.37290 | TITLE ESTs | | | gi = 1751604 | 620086 |
| IC10424 | UG75 Expression | EST | Mm.37291 | TITLE ESTs | | | gi = 1768864 | 622660 |
| IC10425 | UG75 Expression | EST | Mm.37293 | TITLE ESTs | | | gi = 4318895 | 720888 |
| IC10426 | UG75 Expression | EST | Mm.37294 | TITLE ESTs | | | gi = 2049419 | 749784 |
| IC10427 | UG75 Expression | EST | Mm.37295 | TITLE ESTs | | | gi = 4318867 | 958546 |
| IC10428 | UG75 Expression | EST | Mm.37301 | TITLE ESTs | | | gi = 3216662 | 1362966 |
| IC10429 | UG75 Expression | EST | Mm.37304 | TITLE ESTs | | | gi = 1751858 | 619678 |
| IC10430 | UG75 Expression | EST | Mm.37307 | TITLE ESTs | | | gi = 1794390 | 1429044 |
| IC10431 | UG75 Expression | EST | Mm.37311 | TITLE ESTs | | | gi = 1889267 | 719422 |
| IC10432 | UG75 Expression | EST | Mm.37313 | TITLE ESTs | | | gi = 1756009 | 617281 |
| IC10433 | UG75 Expression | EST | Mm.3732 | TITLE ESTs | | | gi = 1726425 | 972535 |
| IC10434 | UG75 Expression | EST | Mm.37323 | TITLE ESTs, Moderately similar to PIG-L [R. norvegicus] | | | gi = 2199755 | 1346152 |
| IC10435 | UG75 Expression | EST | Mm.37324 | TITLE ESTs | | | gi = 1776243 | 634553 |
| IC10436 | UG75 Expression | EST | Mm.37326 | TITLE ESTs | | | gi = 4605519 | 622756 |
| IC10437 | UG75 Expression | EST | Mm.37332 | TITLE ESTs | | | gi = 2962453 | 1265532 |
| IC10438 | UG75 Expression | EST | Mm.37333 | TITLE ESTs | | | gi = 4617310 | 722876 |
| IC10439 | UG75 Expression | EST | Mm.37336 | TITLE ESTs | | | gi = 5498335 | 1153135 |
| IC10440 | UG75 Expression | EST | Mm.37338 | TITLE ESTs | | | gi = 2721676 | 635800 |
| IC10441 | UG75 Expression | EST | Mm.37339 | TITLE ESTs | | | gi = 5338028 | 719280 |
| IC10442 | UG75 Expression | EST | Mm.37340 | TITLE EST | | | gi = 4764690 | 717788 |
| IC10443 | UG75 Expression | EST | Mm.37341 | TITLE EST | | | gi = 4764816 | 722306 |
| IC10444 | UG75 Expression | EST | Mm.37342 | TITLE ESTs | | | gi = 4604371 | 721923 |
| IC10445 | UG75 Expression | EST | Mm.37343 | TITLE EST | | | gi = 4764984 | 723309 |
| IC10446 | UG75 Expression | EST | Mm.37349 | TITLE EST | | | gi = 4765834 | 583761 |
| IC10447 | UG75 Expression | EST | Mm.37350 | TITLE ESTs | | | gi = 1767493 | 622068 |
| IC10448 | UG75 Expression | EST | Mm.37351 | TITLE ESTs | | | gi = 4766059 | 622408 |
| IC10449 | UG75 Expression | EST | Mm.37352 | TITLE ESTs, Moderately similar to putative RNA binding protein KOC [H. sapiens] | | | gi = 4615712 | 750335 |
| IC10450 | UG75 Expression | EST | Mm.37353 | TITLE EST | | | gi = 4804670 | 638731 |
| IC10451 | UG75 Expression | EST | Mm.37355 | TITLE EST | | | gi = 4804796 | 639580 |
| IC10452 | UG75 Expression | EST | Mm.37356 | TITLE EST | | | gi = 4804803 | 639610 |
| IC10453 | UG75 Expression | EST | Mm.37357 | TITLE EST | | | gi = 4804810 | 639666 |
| IC10454 | UG75 Expression | EST | Mm.37358 | TITLE EST | | | gi = 4804845 | 639839 |
| IC10455 | UG75 Expression | EST | Mm.37359 | TITLE EST | | | gi = 4804852 | 639995 |
| IC10456 | UG75 Expression | EST | Mm.37360 | TITLE EST | | | gi = 4804938 | 639910 |
| IC10457 | UG75 Expression | EST | Mm.37361 | TITLE EST | | | gi = 4804945 | 639936 |
| IC10458 | UG75 Expression | EST | Mm.37363 | TITLE EST | | | gi = 4968461 | 640414 |
| IC10459 | UG75 Expression | EST | Mm.37364 | TITLE EST | | | gi = 4805072 | 718719 |
| IC10460 | UG75 Expression | EST | Mm.37369 | TITLE EST | | | gi = 4805100 | 721591 |
| IC10461 | UG75 Expression | EST | Mm.37370 | TITLE EST | | | gi = 3216797 | 596202 |
| IC10462 | UG75 Expression | EST | Mm.37373 | TITLE ESTs | | | gi = 1792997 | 640069 |
| IC10463 | UG75 Expression | EST | Mm.37374 | TITLE ESTs | | | gi = 1888615 | 722484 |
| IC10464 | UG75 Expression | EST | Mm.37374 | TITLE ESTs | | | gi = 4317754 | 723030 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10465 | UG75 Expression | EST | Mm.37375 | TITLE ESTs | | | gi = 1904011 | 721383 |
| IC10466 | UG75 Expression | EST | Mm.37376 | TITLE ESTs | | | gi = 4318917 | 721054 |
| IC10467 | UG75 Expression | EST | Mm.37377 | TITLE ESTs | | | gi = 4604364 | 721853 |
| IC10468 | UG75 Expression | EST | Mm.37380 | TITLE ESTs | | | gi = 6077432 | 2236157 |
| IC10469 | UG75 Expression | EST | Mm.37381 | TITLE ESTs | | | gi = 4407592 | 751119 |
| IC10470 | UG75 Expression | EST | Mm.37383 | TITLE ESTs | | | gi = 2523711 | 1226514 |
| IC10471 | UG75 Expression | EST | Mm.37392 | TITLE ESTs | | | gi = 2461655 | 1279680 |
| IC10472 | UG75 Expression | EST | Mm.37395 | TITLE ESTs, Weakly similar to mCAC [*M. musculus*] | | | gi = 3809847 | 1293680 |
| IC10473 | UG75 Expression | EST | Mm.37397 | TITLE ESTs | | | gi = 3982379 | 1149084 |
| IC10474 | UG75 Expression | EST | Mm.37403 | TITLE ESTs | | | gi = 2203449 | 1002811 |
| IC10475 | UG75 Expression | EST | Mm.37404 | TITLE ESTs | | | gi = 4402655 | 972749 |
| IC10476 | UG75 Expression | EST | Mm.3741 | TITLE ESTs | | | gi = 2068452 | 1429216 |
| IC10477 | UG75 Expression | EST | Mm.37428 | TITLE ESTs | | | gi = 4616596 | 831691 |
| IC10478 | UG75 Expression | EST | Mm.37435 | TITLE EST | | | gi = 4764733 | 721610 |
| IC10479 | UG75 Expression | EST | Mm.37436 | TITLE ESTs | | | gi = 4617201 | 721680 |
| IC10480 | UG75 Expression | EST | Mm.37437 | TITLE ESTs | | | gi = 5908736 | 722047 |
| IC10481 | UG75 Expression | EST | Mm.37438 | TITLE EST | | | gi = 4764873 | 722892 |
| IC10482 | UG75 Expression | EST | Mm.37439 | TITLE EST, Weakly similar to PROLINE-RICH PROTEIN MP-3 [*M. musculus*] | | | gi = 4764936 | 722506 |
| IC10483 | UG75 Expression | EST | Mm.37443 | TITLE ESTs | | | gi = 1895246 | 717965 |
| IC10484 | UG75 Expression | EST | Mm.37444 | TITLE EST | | | gi = 4766032 | 622176 |
| IC10485 | UG75 Expression | EST | Mm.37446 | TITLE ESTs | | | gi = 5472812 | 749973 |
| IC10486 | UG75 Expression | EST | Mm.37447 | TITLE EST | | | gi = 4766401 | 750008 |
| IC10487 | UG75 Expression | EST | Mm.37448 | TITLE EST | | | gi = 4804657 | 634812 |
| IC10488 | UG75 Expression | EST | Mm.37449 | TITLE EST | | | gi = 4804678 | 638839 |
| IC10489 | UG75 Expression | EST | Mm.37451 | TITLE ESTs | | | gi = 4304293 | 642045 |
| IC10490 | UG75 Expression | EST | Mm.37452 | TITLE ESTs | | | gi = 4804748 | 718396 |
| IC10491 | UG75 Expression | EST | Mm.37453 | TITLE EST | | | gi = 4804797 | 639584 |
| IC10492 | UG75 Expression | EST | Mm.37454 | TITLE ESTs | | | gi = 5428829 | 639668 |
| IC10493 | UG75 Expression | EST | Mm.37455 | TITLE ESTs | | | gi = 6008847 | 639792 |
| IC10494 | UG75 Expression | EST | Mm.37456 | TITLE ESTs | | | gi = 5497340 | 639832 |
| IC10495 | UG75 Expression | EST | Mm.37457 | TITLE ESTs | | | gi = 5549628 | 640182 |
| IC10496 | UG75 Expression | EST | Mm.37458 | TITLE EST | | | gi = 4804932 | 639515 |
| IC10497 | UG75 Expression | EST | Mm.37459 | TITLE ESTs | | | gi = 4614966 | 640409 |
| IC10498 | UG75 Expression | EST | Mm.37466 | TITLE ESTs | | | gi = 6515015 | 1749104 |
| IC10499 | UG75 Expression | EST | Mm.37467 | TITLE ESTs | | | gi = 4600935 | 622242 |
| IC10500 | UG75 Expression | EST | Mm.37468 | TITLE EST | | | gi = 4274184 | 551289 |
| IC10501 | UG75 Expression | EST | Mm.37470 | TITLE ESTs | | | gi = 4613345 | 620125 |
| IC10502 | UG75 Expression | EST | Mm.37471 | TITLE ESTs | | | gi = 4616575 | 621946 |
| IC10503 | UG75 Expression | EST | Mm.37472 | TITLE ESTs | | | gi = 4613453 | 620919 |
| IC10504 | UG75 Expression | EST | Mm.37478 | TITLE ESTs | | | gi = 1888707 | 722514 |
| IC10505 | UG75 Expression | EST | Mm.37480 | TITLE ESTs, Weakly similar to CALCINEURIN B SUBUNIT ISOFORM 1 [*M. musculus*] | | | gi = 4604345 | 721744 |
| IC10506 | UG75 Expression | EST | Mm.37488 | TITLE ESTs | | | gi = 6084246 | 749411 |
| IC10507 | UG75 Expression | EST | Mm.37490 | TITLE ESTs | | | gi = 4804676 | 638825 |
| IC10508 | UG75 Expression | EST | Mm.37493 | TITLE ESTs | | | gi = 2593082 | 638756 |
| IC10509 | UG75 Expression | EST | Mm.37499 | TITLE ESTs | | | gi = 6520884 | 1328582 |
| IC10510 | UG75 Expression | EST | Mm.37500 | TITLE ESTs | | | gi = 4318932 | 1295618 |
| IC10511 | UG75 Expression | EST | Mm.37502 | TITLE ESTs, Weakly similar to T25G3.1 [*C. elegans*] | | | gi = 2283038 | 722905 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10512 | UG75 Expression | EST | Mm.37505 | TITLE ESTs, Weakly similar to/prediction | | | gi = 5125443 | 576576 |
| IC10513 | UG75 Expression | EST | Mm.37508 | TITLE ESTs | | | gi = 4600929 | 622149 |
| IC10514 | UG75 Expression | EST | Mm.37510 | TITLE ESTs, Weakly similar to Additional sex combs [*D. melanogaster*] | | | gi = 2860912 | 1281412 |
| IC10515 | UG75 Expression | EST | Mm.37512 | TITLE ESTs | | | gi = 4318708 | 718913 |
| IC10516 | UG75 Expression | EST | Mm.37514 | TITLE ESTs | | | gi = 3515475 | 583623 |
| IC10517 | UG75 Expression | EST | Mm.37516 | TITLE ESTs, Weakly similar to DnaJ-like protein [*M. musculus*] | | | gi = 4485957 | 1149174 |
| IC10518 | UG75 Expression | EST | Mm.37527 | TITLE ESTs | | | gi = 5478034 | 832252 |
| IC10519 | UG75 Expression | EST | Mm.37536 | TITLE ESTs | | | gi = 4615974 | 1243685 |
| IC10520 | UG75 Expression | EST | Mm.37537 | TITLE ESTs | | | gi = 4616002 | 1243988 |
| IC10521 | UG75 Expression | EST | Mm.37541 | TITLE ESTs | | | gi = 5495213 | 831696 |
| IC10522 | UG75 Expression | EST | Mm.37545 | TITLE ESTs | | | gi = 1905330 | 722104 |
| IC10523 | UG75 Expression | EST | Mm.37549 | TITLE ESTs | | | gi = 1904280 | 719106 |
| IC10524 | UG75 Expression | EST | Mm.37550 | TITLE EST | | | gi = 4764586 | 719155 |
| IC10525 | UG75 Expression | EST | Mm.37551 | TITLE ESTs | | | gi = 4764607 | 719297 |
| IC10526 | UG75 Expression | EST | Mm.37553 | TITLE EST | | | gi = 4764671 | 717648 |
| IC10527 | UG75 Expression | EST | Mm.37554 | TITLE ESTs | | | gi = 6150328 | 717758 |
| IC10528 | UG75 Expression | EST | Mm.37555 | TITLE ESTs | | | gi = 1905245 | 722051 |
| IC10529 | UG75 Expression | EST | Mm.37556 | TITLE EST | | | gi = 4764804 | 722228 |
| IC10530 | UG75 Expression | EST | Mm.37557 | TITLE ESTs | | | gi = 4617298 | 722802 |
| IC10531 | UG75 Expression | EST | Mm.37558 | TITLE ESTs | | | gi = 4764993 | 723529 |
| IC10532 | UG75 Expression | EST | Mm.37562 | TITLE ESTs | | | gi = 3981867 | 735374 |
| IC10533 | UG75 Expression | EST | Mm.37565 | TITLE ESTs | | | gi = 1934548 | 749542 |
| IC10534 | UG75 Expression | EST | Mm.37569 | TITLE ESTs | | | gi = 5429104 | 717826 |
| IC10535 | UG75 Expression | EST | Mm.37570 | TITLE EST | | | gi = 4765537 | 718128 |
| IC10536 | UG75 Expression | EST | Mm.37571 | TITLE EST | | | gi = 4765743 | 720904 |
| IC10537 | UG75 Expression | EST | Mm.37572 | TITLE ESTs | | | gi = 4318928 | 721100 |
| IC10538 | UG75 Expression | EST | Mm.37573 | TITLE ESTs | | | gi = 1903768 | 721304 |
| IC10539 | UG75 Expression | EST | Mm.37574 | TITLE ESTs | | | gi = 1715776 | 583796 |
| IC10540 | UG75 Expression | EST | Mm.37576 | TITLE ESTs | | | gi = 4600937 | 622256 |
| IC10541 | UG75 Expression | EST | Mm.37577 | TITLE ESTs | | | gi = 4766118 | 623037 |
| IC10542 | UG75 Expression | EST | Mm.37578 | TITLE EST | | | gi = 4766346 | 749718 |
| IC10543 | UG75 Expression | EST | Mm.37579 | TITLE ESTs, Weakly similar to BIT [*M. musculus*] | | | gi = 6521078 | 750344 |
| IC10544 | UG75 Expression | EST | Mm.37581 | TITLE ESTs, Weakly similar to UDP-N-ACETYLGLUCOSAMINE-PEPTIDE N-ACETYLGLUCOSAMINYLTRANSFERASE 110 KD SUBUNIT [*R. norvegicus*] | | | gi = 4407157 | 1394952 |
| IC10545 | UG75 Expression | EST | Mm.37582 | TITLE EST | | | gi = 4804735 | 639320 |
| IC10546 | UG75 Expression | EST | Mm.37583 | TITLE EST | | | gi = 4804770 | 718562 |
| IC10547 | UG75 Expression | EST | Mm.37584 | TITLE EST | | | gi = 4804784 | 639550 |
| IC10548 | UG75 Expression | EST | Mm.37585 | TITLE EST | | | gi = 4804875 | 640147 |
| IC10549 | UG75 Expression | EST | Mm.37586 | TITLE EST | | | gi = 4804961 | 640436 |
| IC10550 | UG75 Expression | EST | Mm.37588 | TITLE EST | | | gi = 4805032 | 634057 |
| IC10551 | UG75 Expression | EST | Mm.37591 | TITLE ESTs | | | gi = 1793044 | 639857 |
| IC10552 | UG75 Expression | EST | Mm.37592 | TITLE ESTs | | | gi = 4434358 | 550989 |
| IC10553 | UG75 Expression | EST | Mm.37596 | TITLE ESTs | | | gi = 4616494 | 634914 |
| IC10554 | UG75 Expression | EST | Mm.37597 | TITLE ESTs | | | gi = 2518781 | 618534 |
| IC10555 | UG75 Expression | EST | Mm.37598 | TITLE ESTs | | | gi = 4766047 | 622314 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10556 | UG75 Expression | EST | Mm.37599 | TITLE ESTs | | | gi = 3053573 | 619813 |
| IC10557 | UG75 Expression | EST | Mm.37600 | TITLE ESTs | | | gi = 1796219 | 622621 |
| IC10558 | UG75 Expression | EST | Mm.37601 | TITLE ESTs | | | gi = 2234803 | 721938 |
| IC10559 | UG75 Expression | EST | Mm.37602 | TITLE ESTs | | | gi = 1724808 | 597391 |
| IC10560 | UG75 Expression | EST | Mm.37605 | TITLE ESTs, Moderately similar to estradiol 17beta-dehydrogenase [*M. musculus*] | | | gi = 3885139 | 721959 |
| IC10561 | UG75 Expression | EST | Mm.37606 | TITLE ESTs | | | gi = 1888673 | 722291 |
| IC10562 | UG75 Expression | EST | Mm.37607 | TITLE ESTs | | | gi = 4617301 | 722822 |
| IC10563 | UG75 Expression | EST | Mm.37608 | TITLE ESTs | | | gi = 4318693 | 749391 |
| IC10564 | UG75 Expression | EST | Mm.37610 | TITLE ESTs | | | gi = 4318910 | 721006 |
| IC10565 | UG75 Expression | EST | Mm.37611 | TITLE ESTs | | | gi = 1794599 | 616607 |
| IC10566 | UG75 Expression | EST | Mm.37612 | TITLE ESTs | | | gi = 1752253 | 621103 |
| IC10567 | UG75 Expression | EST | Mm.37613 | TITLE ESTs | | | gi = 3053940 | 622968 |
| IC10568 | UG75 Expression | EST | Mm.37615 | TITLE ESTs | | | gi = 4723288 | 749367 |
| IC10569 | UG75 Expression | EST | Mm.37616 | TITLE ESTs | | | gi = 4766324 | 749564 |
| IC10570 | UG75 Expression | EST | Mm.37617 | TITLE ESTs | | | gi = 5549594 | 638599 |
| IC10571 | UG75 Expression | EST | Mm.37618 | TITLE ESTs | | | gi = 2041936 | 749950 |
| IC10572 | UG75 Expression | EST | Mm.37619 | TITLE ESTs | | | gi = 4407638 | 751550 |
| IC10573 | UG75 Expression | EST | Mm.37623 | TITLE ESTs | | | gi = 3680654 | 720801 |
| IC10574 | UG75 Expression | EST | Mm.37628 | TITLE ESTs | | | gi = 4613837 | 1395088 |
| IC10575 | UG75 Expression | EST | Mm.37629 | TITLE ESTs | | | gi = 1908045 | 750854 |
| IC10576 | UG75 Expression | EST | Mm.37632 | TITLE ESTs | | | gi = 4485390 | 1263740 |
| IC10577 | UG75 Expression | EST | Mm.37634 | TITLE ESTs | | | gi = 3295242 | 1749110 |
| IC10578 | UG75 Expression | EST | Mm.37635 | TITLE ESTs | | | gi = 1882081 | 717584 |
| IC10579 | UG75 Expression | EST | Mm.37640 | TITLE ESTs | | | gi = 1792983 | 640020 |
| IC10580 | UG75 Expression | EST | Mm.37642 | TITLE ESTs, Moderately similar to KIAA0240 [*H. sapiens*] | | | gi = 4318665 | 718647 |
| IC10581 | UG75 Expression | EST | Mm.37645 | TITLE ESTs | | | gi = 4272555 | 1294932 |
| IC10582 | UG75 Expression | EST | Mm.37647 | TITLE ESTs | | | gi = 3957296 | 596608 |
| IC10583 | UG75 Expression | EST | Mm.37649 | TITLE ESTs | | | gi = 1727134 | 635009 |
| IC10584 | UG75 Expression | EST | Mm.37650 | TITLE ESTs | | | gi = 4304854 | 642612 |
| IC10585 | UG75 Expression | EST | Mm.37652 | TITLE ESTs | | | gi = 1895261 | 718013 |
| IC10586 | UG75 Expression | EST | Mm.37653 | TITLE ESTs | | | gi = 4317788 | 723229 |
| IC10587 | UG75 Expression | EST | Mm.37654 | TITLE ESTs | | | gi = 4318744 | 719105 |
| IC10588 | UG75 Expression | EST | Mm.37655 | TITLE ESTs | | | gi = 4318772 | 719273 |
| IC10589 | UG75 Expression | EST | Mm.37657 | TITLE ESTs | | | gi = 2041714 | 749677 |
| IC10590 | UG75 Expression | EST | Mm.37675 | TITLE ESTs | | | gi = 1806793 | 1225621 |
| IC10591 | UG75 Expression | EST | Mm.37678 | TITLE ESTs | | | gi = 4276335 | 1446639 |
| IC10592 | UG75 Expression | EST | Mm.37679 | TITLE EST | | | gi = 4615989 | 1243831 |
| IC10593 | UG75 Expression | EST | Mm.37685 | TITLE ESTs | | | gi = 1895310 | 718313 |
| IC10594 | UG75 Expression | EST | Mm.37691 | TITLE ESTs | | | gi = 5495370 | 717613 |
| IC10595 | UG75 Expression | EST | Mm.37695 | TITLE ESTs | | | gi = 1889235 | 719210 |
| IC10596 | UG75 Expression | EST | Mm.37696 | TITLE ESTs, Weakly similar to predicted using Genefinder [*C. elegans*] | | | gi = 1882159 | 717716 |
| IC10597 | UG75 Expression | EST | Mm.37697 | TITLE ESTs | | | gi = 4764686 | 717766 |
| IC10598 | UG75 Expression | EST | Mm.37698 | TITLE ESTs | | | gi = 4604349 | 721762 |
| IC10599 | UG75 Expression | EST | Mm.37699 | TITLE ESTs | | | gi = 4764777 | 721862 |
| IC10600 | UG75 Expression | EST | Mm.37700 | TITLE ESTs | | | gi = 5489457 | 722070 |
| IC10601 | UG75 Expression | EST | Mm.37701 | TITLE EST | | | gi = 4764826 | 722339 |
| IC10602 | UG75 Expression | EST | Mm.37702 | TITLE EST | | | gi = 4764847 | 722730 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10603 | UG75 Expression | EST | Mm.37703 | TITLE ESTs | | | gi = 5489743 | 722887 |
| IC10604 | UG75 Expression | EST | Mm.37704 | TITLE ESTs | | | gi = 4317763 | 723080 |
| IC10605 | UG75 Expression | EST | Mm.37705 | TITLE ESTs | | | gi = 1888721 | 722543 |
| IC10606 | UG75 Expression | EST | Mm.37710 | TITLE ESTs | | | gi = 4968446 | 749090 |
| IC10607 | UG75 Expression | EST | Mm.37711 | TITLE EST | | | gi = 4765249 | 749125 |
| IC10608 | UG75 Expression | EST | Mm.37713 | TITLE ESTs | | | gi = 4765291 | 749420 |
| IC10609 | UG75 Expression | EST | Mm.37718 | TITLE EST | | | gi = 4765751 | 720966 |
| IC10610 | UG75 Expression | EST | Mm.37719 | TITLE ESTs | | | gi = 4318911 | 622552 |
| IC10611 | UG75 Expression | EST | Mm.37720 | TITLE ESTs | | | gi = 3808846 | 721312 |
| IC10612 | UG75 Expression | EST | Mm.37721 | TITLE ESTs | | | gi = 4765837 | 583779 |
| IC10613 | UG75 Expression | EST | Mm.37722 | TITLE ESTs | | | gi = 4625199 | 583827 |
| IC10614 | UG75 Expression | EST | Mm.37723 | TITLE EST | | | gi = 4765858 | 583917 |
| IC10615 | UG75 Expression | EST | Mm.37726 | TITLE ESTs | | | gi = 6084326 | 622829 |
| IC10616 | UG75 Expression | EST | Mm.37727 | TITLE ESTs | | | gi = 4601004 | 622900 |
| IC10617 | UG75 Expression | EST | Mm.37728 | TITLE ESTs | | | gi = 4318712 | 718936 |
| IC10618 | UG75 Expression | EST | Mm.37729 | TITLE ESTs | | | gi = 4318733 | 719042 |
| IC10619 | UG75 Expression | EST | Mm.37732 | TITLE ESTs | | | gi = 2041636 | 749551 |
| IC10620 | UG75 Expression | EST | Mm.37733 | TITLE EST | | | gi = 4766340 | 749634 |
| IC10621 | UG75 Expression | EST | Mm.37734 | TITLE ESTs | | | gi = 4318986 | 749795 |
| IC10622 | UG75 Expression | EST | Mm.37735 | TITLE ESTs | | | gi = 2042112 | 749879 |
| IC10623 | UG75 Expression | EST | Mm.37736 | TITLE ESTs | | | gi = 2042236 | 749925 |
| IC10624 | UG75 Expression | EST | Mm.37737 | TITLE EST | | | gi = 4766410 | 750155 |
| IC10625 | UG75 Expression | EST | Mm.37738 | TITLE EST | | | gi = 4766417 | 750195 |
| IC10626 | UG75 Expression | EST | Mm.37739 | TITLE ESTs | | | gi = 2066263 | 634228 |
| IC10627 | UG75 Expression | EST | Mm.3774 | TITLE ESTs | | | gi = 3394935 | 1226023 |
| IC10628 | UG75 Expression | EST | Mm.37740 | TITLE EST | | | gi = 4804659 | 634826 |
| IC10629 | UG75 Expression | EST | Mm.37741 | TITLE ESTs | | | gi = 1795029 | 639083 |
| IC10630 | UG75 Expression | EST | Mm.37742 | TITLE ESTs, Weakly similar to MAP KINASE-ACTIVATED PROTEIN KINASE 2 [*M. musculus*] | | | gi = 4724409 | 639131 |
| IC10631 | UG75 Expression | EST | Mm.37743 | TITLE ESTs | | | gi = 4724425 | 639261 |
| IC10632 | UG75 Expression | EST | Mm.37744 | TITLE ESTs, Moderately similar to hypothetical protein [*H. sapiens*] | | | gi = 1759054 | 622391 |
| IC10633 | UG75 Expression | EST | Mm.37745 | TITLE ESTs | | | gi = 4724686 | 639849 |
| IC10634 | UG75 Expression | EST | Mm.37748 | TITLE EST | | | gi = 4805054 | 718678 |
| IC10635 | UG75 Expression | EST | Mm.37749 | TITLE ESTs | | | gi = 4318701 | 718862 |
| IC10636 | UG75 Expression | EST | Mm.37753 | TITLE ESTs | | | gi = 1852954 | 643217 |
| IC10637 | UG75 Expression | EST | Mm.37758 | TITLE ESTs | | | gi = 1550994 | 749271 |
| IC10638 | UG75 Expression | EST | Mm.37759 | TITLE ESTs | | | gi = 4766229 | 719006 |
| IC10639 | UG75 Expression | EST | Mm.37763 | TITLE ESTs | | | gi = 1715855 | 596531 |
| IC10640 | UG75 Expression | EST | Mm.37765 | TITLE ESTs | | | gi = 4601067 | 618564 |
| IC10641 | UG75 Expression | EST | Mm.37766 | TITLE ESTs | | | gi = 4613295 | 619829 |
| IC10642 | UG75 Expression | EST | Mm.37767 | TITLE ESTs | | | gi = 5494979 | 622927 |
| IC10643 | UG75 Expression | EST | Mm.37768 | TITLE ESTs | | | gi = 1769370 | 634458 |
| IC10644 | UG75 Expression | EST | Mm.37769 | TITLE ESTs | | | gi = 4601032 | 623109 |
| IC10645 | UG75 Expression | EST | Mm.37770 | TITLE ESTs | | | gi = 1792980 | 596797 |
| IC10646 | UG75 Expression | EST | Mm.37771 | TITLE ESTs | | | gi = 1793351 | 640197 |
| IC10647 | UG75 Expression | EST | Mm.37773 | TITLE ESTs | | | gi = 2248737 | 1312603 |
| IC10648 | UG75 Expression | EST | Mm.37775 | TITLE ESTs | | | gi = 4604342 | 721726 |
| IC10649 | UG75 Expression | EST | Mm.37776 | TITLE ESTs | | | gi = 4318666 | 718658 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10650 | UG75 Expression | EST | Mm.37777 | TITLE ESTs, Weakly similar to Fish protein [*M. musculus*] | | | gi = 2292402 | 718522 |
| IC10651 | UG75 Expression | EST | Mm.37778 | TITLE ESTs | | | gi = 4318646 | 718554 |
| IC10652 | UG75 Expression | EST | Mm.37779 | TITLE ESTs | | | gi = 1903650 | 721277 |
| IC10653 | UG75 Expression | EST | Mm.37780 | TITLE ESTs | | | gi = 1903868 | 721385 |
| IC10654 | UG75 Expression | EST | Mm.37781 | TITLE ESTs | | | gi = 4318877 | 720763 |
| IC10655 | UG75 Expression | EST | Mm.37782 | TITLE ESTs, Weakly similar to transposon LRE2 reverse transcriptase homolog [*H. sapiens*] | | | gi = 1904390 | 721528 |
| IC10656 | UG75 Expression | EST | Mm.37783 | TITLE ESTs | | | gi = 1905355 | 722182 |
| IC10657 | UG75 Expression | EST | Mm.37784 | TITLE ESTs, Moderately similar to KIAA0431 [*H. sapiens*] | | | gi = 4443674 | 894315 |
| IC10658 | UG75 Expression | EST | Mm.37787 | TITLE ESTs | | | gi = 6167738 | 718261 |
| IC10659 | UG75 Expression | EST | Mm.3779 | TITLE ESTs, Weakly similar to ubiquitin C-terminal hydrolase UCH37 [*M. musculus*] | | | gi = 4276009 | 1294318 |
| IC10660 | UG75 Expression | EST | Mm.37790 | TITLE ESTs | | | gi = 4615732 | 764206 |
| IC10661 | UG75 Expression | EST | Mm.37791 | TITLE ESTs | | | gi = 6099569 | 749260 |
| IC10662 | UG75 Expression | EST | Mm.37792 | TITLE ESTs | | | gi = 1937404 | 749109 |
| IC10663 | UG75 Expression | EST | Mm.37793 | TITLE ESTs | | | gi = 2041653 | 749616 |
| IC10664 | UG75 Expression | EST | Mm.37799 | TITLE ESTs | | | gi = 3733250 | 1399282 |
| IC10665 | UG75 Expression | EST | Mm.37800 | TITLE ESTs | | | gi = 4622846 | 893914 |
| IC10666 | UG75 Expression | EST | Mm.37803 | TITLE ESTs | | | gi = 4615789 | 958585 |
| IC10667 | UG75 Expression | EST | Mm.37804 | TITLE ESTs | | | gi = 1908527 | 635397 |
| IC10668 | UG75 Expression | EST | Mm.37810 | TITLE ESTs, Weakly similar to serine-threonine kinase receptor-associated protein [*M. musculus*] | | | gi = 1282598 | 620788 |
| IC10669 | UG75 Expression | EST | Mm.37816 | TITLE ESTs | | | gi = 1768966 | 635834 |
| IC10670 | UG75 Expression | EST | Mm.37825 | TITLE ESTs | | | gi = 2456336 | 1002696 |
| IC10671 | UG75 Expression | EST | Mm.37829 | TITLE ESTs | | | gi = 6756696 | 751861 |
| IC10672 | UG75 Expression | EST | Mm.37831 | TITLE ESTs | | | gi = 4602578 | 722890 |
| IC10673 | UG75 Expression | EST | Mm.37833 | TITLE ESTs, Weakly similar to similar to hypothetical protein D4478 of S. cerevisiae. [*H. sapiens*] | | | gi = 614927 | 1139621 |
| IC10674 | UG75 Expression | EST | Mm.37836 | TITLE ESTs | | | gi = 4764906 | 723070 |
| IC10675 | UG75 Expression | EST | Mm.37838 | TITLE ESTs | | | gi = 1902526 | 718057 |
| IC10676 | UG75 Expression | EST | Mm.37840 | TITLE ESTs | | | gi = 4317768 | 723113 |
| IC10677 | UG75 Expression | EST | Mm.37841 | TITLE EST | | | gi = 2201782 | 723212 |
| IC10678 | UG75 Expression | EST | Mm.37843 | TITLE ESTs | | | gi = 1901996 | 718930 |
| IC10679 | UG75 Expression | EST | Mm.37848 | TITLE ESTs | | | gi = 4600941 | 622276 |
| IC10680 | UG75 Expression | EST | Mm.37870 | TITLE ESTs | | | gi = 5496245 | 1051148 |
| IC10681 | UG75 Expression | EST | Mm.37875 | TITLE ESTs | | | gi = 4616011 | 639334 |
| IC10682 | UG75 Expression | EST | Mm.37886 | TITLE ESTs | | | gi = 5860516 | 722109 |
| IC10683 | UG75 Expression | EST | Mm.37887 | TITLE ESTs | | | gi = 4617293 | 722759 |
| IC10684 | UG75 Expression | EST | Mm.37888 | TITLE ESTs | | | gi = 4617412 | 894541 |
| IC10685 | UG75 Expression | EST | Mm.37897 | TITLE EST | | | gi = 4764588 | 719160 |
| IC10686 | UG75 Expression | EST | Mm.37898 | TITLE ESTs | | | gi = 1649319 | 719311 |
| IC10687 | UG75 Expression | EST | Mm.37899 | TITLE ESTs | | | gi = 2308472 | 719343 |
| IC10688 | UG75 Expression | EST | Mm.37900 | TITLE ESTs | | | gi = 1888858 | 722356 |
| IC10689 | UG75 Expression | EST | Mm.37901 | TITLE EST | | | gi = 4764883 | 722919 |
| IC10690 | UG75 Expression | EST | Mm.37902 | TITLE ESTs | | | gi = 4512956 | 722507 |
| IC10691 | UG75 Expression | EST | Mm.37903 | TITLE ESTs, Moderately similar to KIAA0986 protein [*H. sapiens*] | | | gi = 1905312 | 723564 |
| IC10692 | UG75 Expression | EST | Mm.37908 | TITLE ESTs | | | gi = 4765264 | 749292 |
| IC10693 | UG75 Expression | EST | Mm.37909 | TITLE ESTs | | | gi = 1937104 | 749335 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10694 | UG75 Expression | EST | Mm.37910 | TITLE ESTs | | | gi = 4276134 | 749444 |
| IC10695 | UG75 Expression | EST | Mm.37914 | TITLE ESTs | | | gi = 4315492 | 1429691 |
| IC10696 | UG75 Expression | EST | Mm.37915 | TITLE EST | | | gi = 4765496 | 717827 |
| IC10697 | UG75 Expression | EST | Mm.37916 | TITLE ESTs | | | gi = 2284398 | 717955 |
| IC10698 | UG75 Expression | EST | Mm.37917 | TITLE ESTs | | | gi = 4765518 | 718051 |
| IC10699 | UG75 Expression | EST | Mm.37919 | TITLE ESTs | | | gi = 1903610 | 720976 |
| IC10700 | UG75 Expression | EST | Mm.37920 | TITLE EST | | | gi = 4765766 | 721053 |
| IC10701 | UG75 Expression | EST | Mm.37921 | TITLE EST | | | gi = 4765773 | 721112 |
| IC10702 | UG75 Expression | EST | Mm.37922 | TITLE ESTs, Weakly similar to cDNA EST yk474g3.5 comes from this gene [*C. elegans*] | | | gi = 4318955 | 721318 |
| IC10703 | UG75 Expression | EST | Mm.37924 | TITLE EST | | | gi = 4766014 | 622020 |
| IC10704 | UG75 Expression | EST | Mm.37925 | TITLE ESTs | | | gi = 6079122 | 622984 |
| IC10705 | UG75 Expression | EST | Mm.37926 | TITLE ESTs | | | gi = 1896933 | 746797 |
| IC10706 | UG75 Expression | EST | Mm.37927 | TITLE EST | | | gi = 4766362 | 749801 |
| IC10707 | UG75 Expression | EST | Mm.37928 | TITLE EST | | | gi = 4766432 | 750311 |
| IC10708 | UG75 Expression | EST | Mm.37929 | TITLE ESTs | | | gi = 2292015 | 958764 |
| IC10709 | UG75 Expression | EST | Mm.37930 | TITLE ESTs | | | gi = 4804702 | 639007 |
| IC10710 | UG75 Expression | EST | Mm.37931 | TITLE EST | | | gi = 4804716 | 639146 |
| IC10711 | UG75 Expression | EST | Mm.37932 | TITLE ESTs | | | gi = 3685034 | 639234 |
| IC10712 | UG75 Expression | EST | Mm.37933 | TITLE EST | | | gi = 4804842 | 639821 |
| IC10713 | UG75 Expression | EST | Mm.37934 | TITLE EST | | | gi = 4804907 | 640334 |
| IC10714 | UG75 Expression | EST | Mm.37935 | TITLE ESTs | | | gi = 4804942 | 639922 |
| IC10715 | UG75 Expression | EST | Mm.37937 | TITLE EST | | | gi = 4805034 | 634073 |
| IC10716 | UG75 Expression | EST | Mm.37944 | TITLE ESTs | | | gi = 4318735 | 719060 |
| IC10717 | UG75 Expression | EST | Mm.37946 | TITLE ESTs, Weakly similar to H-2 CLASS I HISTOCOMPATIBILITY ANTIGEN, Q8 ALPHA CHAIN PRECURSOR [*Mus musculus*] | | | gi = 4536766 | 551203 |
| IC10718 | UG75 Expression | EST | Mm.37948 | TITLE ESTs, Weakly similar to major sperm fibrous sheath protein Pro-mAKAP82 [*M. musculus*] | | | gi = 2915096 | 622224 |
| IC10719 | UG75 Expression | EST | Mm.37949 | TITLE ESTs | | | gi = 6100928 | 640312 |
| IC10720 | UG75 Expression | EST | Mm.37950 | TITLE ESTs | | | gi = 1725451 | 749297 |
| IC10721 | UG75 Expression | EST | Mm.37954 | TITLE ESTs, Moderately similar to PMF31 [*R. norvegicus*] | | | gi = 3141117 | 598422 |
| IC10722 | UG75 Expression | EST | Mm.37955 | TITLE ESTs | | | gi = 4723573 | 618516 |
| IC10723 | UG75 Expression | EST | Mm.37956 | TITLE ESTs | | | gi = 4613349 | 620144 |
| IC10724 | UG75 Expression | EST | Mm.37957 | TITLE ESTs | | | gi = 2200208 | 620623 |
| IC10725 | UG75 Expression | EST | Mm.37958 | TITLE ESTs | | | gi = 1767086 | 621944 |
| IC10726 | UG75 Expression | EST | Mm.37959 | TITLE ESTs | | | gi = 4601014 | 622944 |
| IC10727 | UG75 Expression | EST | Mm.37960 | TITLE ESTs | | | gi = 4601717 | 1294931 |
| IC10728 | UG75 Expression | EST | Mm.37963 | TITLE ESTs | | | gi = 4804905 | 640317 |
| IC10729 | UG75 Expression | EST | Mm.37965 | TITLE ESTs | | | gi = 4968542 | 622823 |
| IC10730 | UG75 Expression | EST | Mm.37968 | TITLE ESTs | | | gi = 1881948 | 638709 |
| IC10731 | UG75 Expression | EST | Mm.37969 | TITLE ESTs | | | gi = 1888570 | 722393 |
| IC10732 | UG75 Expression | EST | Mm.37970 | TITLE ESTs | | | gi = 1888668 | 722279 |
| IC10733 | UG75 Expression | EST | Mm.37971 | TITLE ESTs | | | gi = 4617228 | 722199 |
| IC10734 | UG75 Expression | EST | Mm.37972 | TITLE ESTs | | | gi = 6247438 | 722256 |
| IC10735 | UG75 Expression | EST | Mm.37974 | TITLE ESTs | | | gi = 4315551 | 718025 |
| IC10736 | UG75 Expression | EST | Mm.37975 | TITLE ESTs | | | gi = 1896147 | 1395429 |
| IC10737 | UG75 Expression | EST | Mm.37976 | TITLE ESTs | | | gi = 4624088 | 721003 |
| IC10738 | UG75 Expression | EST | Mm.37977 | TITLE ESTs | | | gi = 1904029 | 719120 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10739 | UG75 Expression | EST | Mm.37978 | TITLE ESTs | | | gi = 2906502 | 722045 |
| IC10740 | UG75 Expression | EST | Mm.37981 | TITLE ESTs | | | gi = 6757912 | 764169 |
| IC10741 | UG75 Expression | EST | Mm.37985 | TITLE ESTs | | | gi = 2041945 | 749971 |
| IC10742 | UG75 Expression | EST | Mm.37986 | TITLE ESTs, Weakly similar to N-WASP [*H. sapiens*] | | | gi = 2042219 | 749875 |
| IC10743 | UG75 Expression | EST | Mm.37988 | TITLE ESTs, Moderately similar to hypothetical protein [*M. musculus*] | | | gi = 4614958 | 640323 |
| IC10744 | UG75 Expression | EST | Mm.38001 | | | | gi = 2406061 | 1224903 |
| IC10745 | UG75 Expression | EST | Mm.38002 | TITLE ESTs, Weakly similar to latexin [*M. musculus*] | | | gi = 2502428 | 720662 |
| IC10746 | UG75 Expression | EST | Mm.38009 | TITLE ESTs | | | gi = 5498507 | 765160 |
| IC10747 | UG75 Expression | EST | Mm.38011 | TITLE ESTs, Weakly similar to putative monocarboxylate transporter [*R. norvegicus*] | | | gi = 2308151 | 764690 |
| IC10748 | UG75 Expression | EST | Mm.38014 | TITLE ESTs | | | gi = 2920008 | 721868 |
| IC10749 | UG75 Expression | EST | Mm.38016 | TITLE ESTs | | | gi = 1290291 | 635912 |
| IC10750 | 00/02 Literature | EST | Mm.38017 | single Ig IL-1 receptor related protein | Sigirr-pending | | gi = 4606150 | 1244644 |
| IC10751 | UG75 Expression | EST | Mm.38018 | TITLE ESTs | | | gi = 2860472 | 718094 |
| IC10752 | UG75 Expression | EST | Mm.38019 | TITLE ESTs | | | gi = 1794575 | 622849 |
| IC10753 | UG75 Expression | EST | Mm.38028 | TITLE ESTs, Weakly similar to HC1 ORF [*M. musculus*] | | | gi = 5819520 | 1295479 |
| IC10754 | UG75 Expression | EST | Mm.3804 | TITLE ESTs, Weakly similar to RNA POLYMERASE II ELONGATION FACTOR ELL [*M. musculus*] | | | gi = 2592120 | 1149198 |
| IC10755 | UG75 Expression | EST | Mm.38042 | TITLE ESTs | | | gi = 1768657 | 637005 |
| IC10756 | UG75 Expression | EST | Mm.38043 | TITLE ESTs | | | gi = 4615188 | 642488 |
| IC10757 | UG75 Expression | EST | Mm.38046 | TITLE ESTs | | | gi = 4617303 | 620430 |
| IC10758 | UG75 Expression | EST | Mm.38047 | TITLE ESTs, Weakly similar to activin receptor interacting protein 1 [*M. musculus*] | | | gi = 4318648 | 718559 |
| IC10759 | UG75 Expression | EST | Mm.38048 | TITLE ESTs | | | gi = 6254732 | 718713 |
| IC10760 | UG75 Expression | EST | Mm.38049 | TITLE ESTs | | | gi = 1902109 | 719086 |
| IC10761 | UG75 Expression | EST | Mm.38050 | TITLE ESTs | | | gi = 4318788 | 719360 |
| IC10762 | UG75 Expression | EST | Mm.38060 | TITLE ESTs | | | gi = 4450479 | 1282766 |
| IC10763 | UG75 Expression | EST | Mm.38061 | TITLE ESTs | | | gi = 1756960 | 619641 |
| IC10764 | UG75 Expression | EST | Mm.38075 | TITLE EST | | | gi = 4614612 | 1050093 |
| IC10765 | UG75 Expression | EST | Mm.38084 | TITLE ESTs | | | gi = 4615998 | 1243938 |
| IC10766 | UG75 Expression | EST | Mm.38085 | TITLE EST | | | gi = 2850399 | 1243994 |
| IC10767 | UG75 Expression | EST | Mm.38087 | TITLE ESTs | | | gi = 4605119 | 1363802 |
| IC10768 | UG75 Expression | EST | Mm.38091 | TITLE ESTs | | | gi = 4616895 | 717754 |
| IC10769 | UG75 Expression | EST | Mm.38094 | TITLE ESTs, Weakly similar to | | | gi = 6097886 | 722076 |
| IC10770 | UG75 Expression | EST | Mm.38095 | TITLE EST | | | gi = 4617420 | 894596 |
| IC10771 | UG75 Expression | EST | Mm.38100 | TITLE EST | | | gi = 1904060 | 719168 |
| IC10772 | UG75 Expression | EST | Mm.38101 | TITLE ESTs | | | gi = 4764610 | 719313 |
| IC10773 | UG75 Expression | EST | Mm.38103 | TITLE EST | | | gi = 1309886 | 1148635 |
| IC10774 | UG75 Expression | EST | Mm.38105 | TITLE ESTs | | | gi = 4617208 | 721993 |
| IC10775 | UG75 Expression | EST | Mm.38106 | TITLE EST | | | gi = 4764786 | 722039 |
| IC10776 | UG75 Expression | EST | Mm.38107 | TITLE ESTs | | | gi = 431954l | 722179 |
| IC10777 | UG75 Expression | EST | Mm.38108 | TITLE ESTs | | | gi = 4297794 | 722327 |
| IC10778 | UG75 Expression | EST | Mm.38109 | TITLE ESTs | | | gi = 4617256 | 722366 |
| IC10779 | UG75 Expression | EST | Mm.38110 | TITLE EST | | | gi = 4764835 | 722430 |
| IC10780 | UG75 Expression | EST | Mm.38111 | TITLE ESTs | | | gi = 4615281 | 722478 |
| IC10781 | UG75 Expression | EST | Mm.38117 | TITLE ESTs | | | gi = 1684394 | 575450 |
| IC10782 | UG75 Expression | EST | Mm.38120 | TITLE ESTs | | | gi = 4765272 | 749324 |
| IC10783 | UG75 Expression | EST | Mm.38121 | TITLE ESTs | | | gi = 1937257 | 749437 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10784 | UG75 Expression | EST | Mm.38123 | TITLE ESTs | | | gi = 4482847 | 1264906 |
| IC10785 | UG75 Expression | EST | Mm.38125 | TITLE ESTs | | | gi = 4765490 | 717812 |
| IC10786 | UG75 Expression | EST | Mm.38126 | TITLE ESTs | | | gi = 4765526 | 718090 |
| IC10787 | UG75 Expression | EST | Mm.38127 | TITLE EST | | | gi = 4765533 | 718104 |
| IC10788 | UG75 Expression | EST | Mm.38130 | TITLE EST | | | gi = 4318907 | 720961 |
| IC10789 | UG75 Expression | EST | Mm.38131 | TITLE ESTs | | | gi = 1904116 | 721070 |
| IC10790 | UG75 Expression | EST | Mm.38132 | TITLE ESTs | | | gi = 1903860 | 721364 |
| IC10791 | UG75 Expression | EST | Mm.38133 | TITLE ESTs | | | gi = 1904019 | 619284 |
| IC10792 | UG75 Expression | EST | Mm.38137 | TITLE ESTs | | | gi = 4766057 | 622378 |
| IC10793 | UG75 Expression | EST | Mm.38138 | TITLE EST | | | gi = 4766086 | 622824 |
| IC10794 | UG75 Expression | EST | Mm.38139 | TITLE ESTs | | | gi = 4766145 | 618526 |
| IC10795 | UG75 Expression | EST | Mm.38141 | TITLE EST | | | gi = 4766211 | 718908 |
| IC10796 | UG75 Expression | EST | Mm.38142 | TITLE ESTs | | | gi = 1902094 | 719051 |
| IC10797 | UG75 Expression | EST | Mm.38144 | TITLE ESTs | | | gi = 2041649 | 749593 |
| IC10798 | UG75 Expression | EST | Mm.38146 | TITLE EST | | | gi = 4804619 | 634124 |
| IC10799 | UG75 Expression | EST | Mm.38147 | TITLE ESTs | | | gi = 4804633 | 634200 |
| IC10800 | UG75 Expression | EST | Mm.38148 | TITLE EST | | | gi = 4804661 | 638631 |
| IC10801 | UG75 Expression | EST | Mm.38149 | TITLE ESTs | | | gi = 4724663 | 638816 |
| IC10802 | UG75 Expression | EST | Mm.38152 | TITLE ESTs | | | gi = 4318660 | 718611 |
| IC10803 | UG75 Expression | EST | Mm.38153 | TITLE ESTs | | | gi = 5219255 | 639669 |
| IC10804 | UG75 Expression | EST | Mm.38154 | TITLE ESTs, Weakly similar to F56C9.10 [C. elegans] | | | gi = 1793199 | 639797 |
| IC10805 | UG75 Expression | EST | Mm.38155 | TITLE ESTs | | | gi = 3926462 | 1395182 |
| IC10806 | UG75 Expression | EST | Mm.38156 | TITLE ESTs, Moderately similar to NY-REN-58 antigen [H. sapiens] | | | gi = 1724753 | 582510 |
| IC10807 | UG75 Expression | EST | Mm.38157 | TITLE EST | | | gi = 4804957 | 640380 |
| IC10808 | UG75 Expression | EST | Mm.38158 | TITLE ESTs | | | gi = 3522480 | 1445995 |
| IC10809 | UG75 Expression | EST | Mm.38159 | TITLE ESTs | | | gi = 4805056 | 718671 |
| IC10810 | UG75 Expression | EST | Mm.38162 | TITLE ESTs | | | gi = 1407892 | 576846 |
| IC10811 | UG75 Expression | EST | Mm.38163 | TITLE ESTs | | | gi = 1889655 | 719342 |
| IC10812 | UG75 Expression | EST | Mm.38164 | TITLE ESTs | | | gi = 1684531 | 718165 |
| IC10813 | UG75 Expression | EST | Mm.38166 | TITLE ESTs | | | gi = 3053983 | 750310 |
| IC10814 | UG75 Expression | EST | Mm.38167 | TITLE ESTs, Weakly similar to KIAA0512 protein [H. sapiens] | | | gi = 4766069 | 622545 |
| IC10815 | UG75 Expression | EST | Mm.38168 | PROTEIN IN BDF1 5'REGION [Saccharomyces cerevisiae] | | | gi = 1682514 | 597037 |
| IC10816 | UG75 Expression | EST | Mm.38169 | TITLE ESTs | | | gi = 6097034 | 617015 |
| IC10817 | UG75 Expression | EST | Mm.38170 | TITLE ESTs | | | gi = 2049054 | 599058 |
| IC10818 | UG75 Expression | EST | Mm.38171 | TITLE ESTs | | | gi = 2721603 | 598404 |
| IC10819 | UG75 Expression | EST | Mm.38173 | TITLE ESTs, Weakly similar to ZINC FINGER PROTEIN RP-8 [M. musculus] | | | gi = 3260077 | 1378517 |
| IC10820 | UG75 Expression | EST | Mm.38175 | TITLE ESTs, Weakly similar to GARG-16 [M. musculus] | | | gi = 1937209 | 622973 |
| IC10821 | UG75 Expression | EST | Mm.38177 | TITLE ESTs | | | gi = 4766066 | 622529 |
| IC10822 | UG75 Expression | EST | Mm.38178 | [R. norvegicus] | | | gi = 1758974 | 622291 |
| IC10823 | UG75 Expression | EST | Mm.38179 | TITLE ESTs | | | gi = 4600947 | 638716 |
| IC10824 | UG75 Expression | EST | Mm.38180 | TITLE ESTs | | | gi = 4766061 | 622434 |
| IC10825 | UG75 Expression | EST | Mm.38181 | TITLE ESTs | | | gi = 2305854 | 894426 |
| IC10826 | UG75 Expression | EST | Mm.38182 | TITLE ESTs | | | gi = 2258541 | 621894 |
| IC10827 | UG75 Expression | EST | Mm.38183 | TITLE ESTs | | | gi = 1767869 | 622728 |
| IC10828 | UG75 Expression | EST | Mm.38184 | TITLE ESTs | | | gi = 6097668 | 597190 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10829 | UG75 Expression | EST | Mm.38186 | TITLE ESTs | | | gi = 5335939 | 640082 |
| IC10830 | UG75 Expression | EST | Mm.38187 | TITLE ESTs | | | gi = 1793037 | 639833 |
| IC10831 | UG75 Expression | EST | Mm.38188 | TITLE ESTs | | | gi = 1793317 | 639979 |
| IC10832 | UG75 Expression | EST | Mm.38189 | TITLE ESTs | | | gi = 4724414 | 640175 |
| IC10833 | UG75 Expression | EST | Mm.38195 | TITLE ESTs | | | gi = 1794353 | 1379097 |
| IC10834 | UG75 Expression | EST | Mm.38196 | TITLE ESTs, Weakly similar to DNA-BINDING PROTEIN BMI-1 [*M. musculus*] | | | gi = 2074659 | 620701 |
| IC10835 | UG75 Expression | EST | Mm.38198 | TITLE ESTs | | | gi = 3370185 | 597399 |
| IC10836 | UG75 Expression | EST | Mm.38199 | TITLE ESTs | | | gi = 1919643 | 621569 |
| IC10837 | UG75 Expression | EST | Mm.38204 | TITLE EST | | | gi = 4766208 | 718879 |
| IC10838 | UG75 Expression | EST | Mm.38205 | TITLE ESTs | | | gi = 6278407 | 718059 |
| IC10839 | UG75 Expression | EST | Mm.38206 | TITLE ESTs | | | gi = 3954172 | 718202 |
| IC10840 | UG75 Expression | EST | Mm.38208 | TITLE ESTs | | | gi = 4318898 | 720901 |
| IC10841 | UG75 Expression | EST | Mm.38209 | TITLE EST | | | gi = 4765783 | 721246 |
| IC10842 | UG75 Expression | EST | Mm.38211 | TITLE ESTs | | | gi = 6822652 | 894118 |
| IC10843 | UG75 Expression | EST | Mm.38212 | TITLE ESTs | | | gi = 1834215 | 722869 |
| IC10844 | UG75 Expression | EST | Mm.38213 | TITLE ESTs | | | gi = 1903618 | 619090 |
| IC10845 | UG75 Expression | EST | Mm.38215 | TITLE EST | | | gi = 4764960 | 723150 |
| IC10846 | UG75 Expression | EST | Mm.38216 | TITLE ESTs | | | gi = 2041959 | 750017 |
| IC10847 | UG75 Expression | EST | Mm.38217 | TITLE EST | | | gi = 4766352 | 749745 |
| IC10848 | UG75 Expression | EST | Mm.38218 | TITLE ESTs | | | gi = 4766413 | 750175 |
| IC10849 | UG75 Expression | EST | Mm.38224 | TITLE ESTs | | | gi = 4765782 | 721224 |
| IC10850 | UG75 Expression | EST | Mm.38228 | TITLE ESTs | | | gi = 4764716 | 1294569 |
| IC10851 | UG75 Expression | EST | Mm.38232 | TITLE ESTs | | | gi = 5492293 | 749136 |
| IC10852 | UG75 Expression | EST | Mm.38233 | TITLE ESTs | | | gi = 6078081 | 717613 |
| IC10853 | UG75 Expression | EST | Mm.38235 | TITLE ESTs | | | gi = 1768388 | 972699 |
| IC10854 | UG75 Expression | EST | Mm.38237 | TITLE ESTs, Weakly similar to Unknown gene product [*H. sapiens*] | | | gi = 4766048 | 622318 |
| IC10855 | UG75 Expression | EST | Mm.3824 | TITLE ESTs | | | gi = 2247361 | 619343 |
| IC10856 | UG75 Expression | EST | Mm.38244 | TITLE ESTs, Weakly similar to NIPSNAP1 protein [*M. musculus*] | | | gi = 3164752 | 777692 |
| IC10857 | UG75 Expression | EST | Mm.38245 | TITLE heparan sulfate (glucosamine) 3-O-sulfotransferase 3B | GENE Hs3st3b | heparan sulfate glucosaminyl 3-O-sulfotransferase 3b|Hsg3ost3b-pending| | gi = 1934462 | 640008 |
| IC10858 | UG75 Expression | EST | Mm.38247 | TITLE ESTs | | | gi = 2291991 | 958736 |
| IC10859 | UG75 Expression | EST | Mm.38249 | TITLE ESTs, Weakly similar to sex-determination protein homolog Fem1a [*M. musculus*] | | | gi = 4602853 | 722935 |
| IC10860 | UG75 Expression | EST | Mm.38251 | TITLE ESTs | | | gi = 4804785 | 639539 |
| IC10861 | UG75 Expression | EST | Mm.38252 | TITLE ESTs | | | gi = 4617234 | 750496 |
| IC10862 | UG75 Expression | EST | Mm.38254 | TITLE ESTs | | | gi = 1888727 | 722563 |
| IC10863 | UG75 Expression | EST | Mm.38257 | TITLE ESTs | | | gi = 4663878 | 643076 |
| IC10864 | UG75 Expression | EST | Mm.38259 | TITLE ESTs | | | gi = 4617119 | 1225811 |
| IC10865 | UG75 Expression | EST | Mm.38261 | CONJUGATING ENZYME E2-16 KD [*Saccharomyces cerevisiae*] | | | gi = 2519221 | 973073 |
| IC10866 | UG75 Expression | EST | Mm.38265 | TITLE ESTs, Moderately similar to cadherin-11 [*M. musculus*] | | | gi = 4600988 | 550973 |
| IC10867 | UG75 Expression | EST | Mm.38271 | TITLE ESTs | | | gi = 4616008 | 1243938 |
| IC10868 | UG75 Expression | EST | Mm.38272 | TITLE ESTs | | | gi = 2249835 | 723271 |
| IC10869 | UG75 Expression | EST | Mm.38276 | TITLE ESTs | | | gi = 2041630 | 749546 |
| IC10870 | UG75 Expression | EST | Mm.38277 | TITLE ESTs | | | gi = 4765305 | 749449 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10871 | UG75 Expression | EST | Mm.38279 | TITLE ESTs | | | gi = 3032959 | 1279943 |
| IC10872 | UG75 Expression | EST | Mm.38280 | TITLE ESTs | | | gi = 1759179 | 619589 |
| IC10873 | UG75 Expression | EST | Mm.38283 | TITLE ESTs | | | gi = 2860839 | 749585 |
| IC10874 | UG75 Expression | EST | Mm.38287 | TITLE ESTs | | | gi = 4617302 | 722828 |
| IC10875 | UG75 Expression | EST | Mm.38289 | TITLE ESTs | | | gi = 4315804 | 639570 |
| IC10876 | UG75 Expression | EST | Mm.38291 | TITLE ESTs | | | gi = 5488538 | 1278968 |
| IC10877 | UG75 Expression | EST | Mm.38292 | TITLE ESTs, Moderately similar to p80 [*R. norvegicus*] | | | gi = 1862741 | 1243903 |
| IC10878 | UG75 Expression | EST | Mm.38293 | TITLE ESTs | | | gi = 1903956 | 720925 |
| IC10879 | UG75 Expression | EST | Mm.38294 | TITLE ESTs | | | gi = 2962618 | 749684 |
| IC10880 | UG75 Expression | EST | Mm.38298 | TITLE ESTs | | | gi = 2861133 | 1328636 |
| IC10881 | UG75 Expression | EST | Mm.38300 | TITLE ESTs | | | gi = 5125396 | 1362468 |
| IC10882 | UG75 Expression | EST | Mm.38308 | TITLE EST | | | gi = 4765805 | 721388 |
| IC10883 | UG75 Expression | EST | Mm.38313 | TITLE ESTs, Weakly similar to ATP-BINDING CASSETTE TRANSPORTER 1 [*M. musculus*] | | | gi = 1861800 | 623071 |
| IC10884 | UG75 Expression | EST | Mm.38315 | TITLE ESTs, Weakly similar to ZINC FINGER PROTEIN ZFP-26 [*M. musculus*] | | | gi = 2307930 | 582138 |
| IC10885 | UG75 Expression | EST | Mm.38316 | TITLE ESTs | | | gi = 6645944 | 1429469 |
| IC10886 | UG75 Expression | EST | Mm.38317 | TITLE ESTs | | | gi = 1827003 | 721575 |
| IC10887 | UG75 Expression | EST | Mm.38319 | TITLE ESTs | | | gi = 3685206 | 722477 |
| IC10888 | UG75 Expression | EST | Mm.38324 | TITLE ESTs | | | gi = 4723999 | 639562 |
| IC10889 | UG75 Expression | EST | Mm.38327 | TITLE ESTs | | | gi = 4484357 | 533454 |
| IC10890 | UG75 Expression | EST | Mm.38333 | TITLE ESTs, Weakly similar to mszf 54 [*M. musculus*] | | | gi = 4032050 | 719144 |
| IC10891 | UG75 Expression | EST | Mm.38334 | TITLE ESTs | | | gi = 4057722 | 640222 |
| IC10892 | UG75 Expression | EST | Mm.38336 | TITLE ESTs | | | gi = 6084111 | 637335 |
| IC10893 | UG75 Expression | EST | Mm.38337 | TITLE ESTs | | | gi = 4256948 | 718722 |
| IC10894 | UG75 Expression | EST | Mm.38349 | TITLE ESTs | | | gi = 6167709 | 640941 |
| IC10895 | UG75 Expression | EST | Mm.38351 | TITLE ESTs | | | gi = 4765801 | 973961 |
| IC10896 | UG75 Expression | EST | Mm.38354 | TITLE ESTs | | | gi = 4440880 | 1328550 |
| IC10897 | UG75 Expression | EST | Mm.38355 | TITLE ESTs | | | gi = 4315572 | 718142 |
| IC10898 | UG75 Expression | EST | Mm.38357 | TITLE ESTs | | | gi = 4317793 | 723279 |
| IC10899 | UG75 Expression | EST | Mm.38358 | TITLE ESTs | | | gi = 4317773 | 723154 |
| IC10900 | UG75 Expression | EST | Mm.38361 | TITLE ESTs | | | gi = 4318641 | 718509 |
| IC10901 | UG75 Expression | EST | Mm.38362 | TITLE ESTs | | | gi = 2272008 | 551493 |
| IC10902 | UG75 Expression | EST | Mm.38365 | TITLE ESTs | | | gi = 4482252 | 640240 |
| IC10903 | UG75 Expression | EST | Mm.38366 | TITLE ESTs | | | gi = 4615991 | 1243878 |
| IC10904 | UG75 Expression | EST | Mm.38367 | TITLE ESTs | | | gi = 5498165 | 618637 |
| IC10905 | UG75 Expression | EST | Mm.38369 | TITLE ESTs | | | gi = 4481975 | 639581 |
| IC10906 | UG75 Expression | EST | Mm.38379 | TITLE ESTs, Weakly similar to put. gag and pol gene product [*M. musculus*] | | | gi = 2850635 | 1244088 |
| IC10907 | UG75 Expression | EST | Mm.38381 | TITLE ESTs, Weakly similar to PUTATIVE STEROID DEHYDROGENASE KIK-I [*M. musculus*] | | | gi = 1286961 | 1344897 |
| IC10908 | UG75 Expression | EST | Mm.38385 | TITLE ESTs | | | gi = 4217185 | 1380284 |
| IC10909 | UG75 Expression | EST | Mm.38389 | TITLE ESTs, Moderately similar to KIAA0676 protein [*H. sapiens*] | | | gi = 5124660 | 722346 |
| IC10910 | UG75 Expression | EST | Mm.38390 | TITLE ESTs, Weakly similar to N-copine [*M. musculus*] | | | gi = 4617250 | 1295932 |
| IC10911 | UG75 Expression | EST | Mm.38391 | TITLE ESTs | | | gi = 1841651 | 638356 |
| IC10912 | UG75 Expression | EST | Mm.38392 | TITLE ESTs | | | gi = 4571912 | 1148848 |
| IC10913 | UG75 Expression | EST | Mm.38393 | TITLE ESTs | | | gi = 4596752 | 1379413 |
| IC10914 | UG75 Expression | EST | Mm.38394 | TITLE EST | | | gi = 4804873 | 640131 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10915 | UG75 Expression | EST | Mm.38397 | TITLE ESTs | | | gi = 4615687 | 750134 |
| IC10916 | UG75 Expression | EST | Mm.38398 | TITLE ESTs | | | gi = 4766434 | 750332 |
| IC10917 | UG75 Expression | EST | Mm.38399 | TITLE ESTs | | | gi = 4615762 | 721571 |
| IC10918 | UG75 Expression | EST | Mm.38400 | TITLE ESTs | | | gi = 4616892 | 717726 |
| IC10919 | UG75 Expression | EST | Mm.38401 | TITLE ESTs | | | gi = 4617212 | 722021 |
| IC10920 | UG75 Expression | EST | Mm.38402 | TITLE ESTs | | | gi = 4617240 | 722269 |
| IC10921 | UG75 Expression | EST | Mm.38403 | TITLE ESTs | | | gi = 1888631 | 722529 |
| IC10922 | UG75 Expression | EST | Mm.38404 | TITLE ESTs | | | gi = 5493132 | 623092 |
| IC10923 | UG75 Expression | EST | Mm.38405 | TITLE ESTs | | | gi = 1715218 | 583940 |
| IC10924 | UG75 Expression | EST | Mm.38410 | TITLE ESTs, Weakly similar to alternatively spliced from [D. melanogaster] | | | gi = 4483059 | 551256 |
| IC10925 | UG75 Expression | EST | Mm.38413 | TITLE ESTs | | | gi = 4408131 | 749522 |
| IC10926 | UG75 Expression | EST | Mm.38415 | TITLE ESTs, Weakly similar to putative retrovirus-related gag protein [R. norvegicus] | | | gi = 4318890 | 720866 |
| IC10927 | UG75 Expression | EST | Mm.38417 | TITLE ESTs | | | gi = 4617281 | 722564 |
| IC10928 | UG75 Expression | EST | Mm.38418 | TITLE ESTs | | | gi = 4615697 | 750208 |
| IC10929 | UG75 Expression | EST | Mm.38419 | TITLE ESTs | | | gi = 4615719 | 597095 |
| IC10930 | UG75 Expression | EST | Mm.38427 | TITLE ESTs | | | gi = 4794833 | 536196 |
| IC10931 | UG75 Expression | EST | Mm.38429 | [H. sapiens] | | | gi = 1287234 | 1139761 |
| IC10932 | UG75 Expression | EST | Mm.38434 | TITLE ESTs | | | gi = 1888883 | 722458 |
| IC10933 | UG75 Expression | EST | Mm.38436 | TITLE ESTs, Weakly similar to transcriptional repressor Mpc2 [M. musculus] | | | gi = 5497948 | 734685 |
| IC10934 | UG75 Expression | EST | Mm.38438 | TITLE ESTs | | | gi = 3718908 | 1922474 |
| IC10935 | UG75 Expression | EST | Mm.38439 | TITLE ESTs | | | gi = 1826169 | 1362557 |
| IC10936 | UG75 Expression | EST | Mm.38442 | TITLE ESTs | | | gi = 2528545 | 597615 |
| IC10937 | UG75 Expression | EST | Mm.38443 | TITLE ESTs | | | gi = 4281614 | 573443 |
| IC10938 | UG75 Expression | EST | Mm.38445 | TITLE ESTs | | | gi = 2307910 | 576792 |
| IC10939 | UG75 Expression | EST | Mm.38446 | TITLE ESTs | | | gi = 2461896 | 634757 |
| IC10940 | UG75 Expression | EST | Mm.38449 | TITLE ESTs | | | gi = 5749946 | 583836 |
| IC10941 | UG75 Expression | EST | Mm.38451 | TITLE ESTs | | | gi = 6077477 | 617284 |
| IC10942 | UG75 Expression | EST | Mm.38459 | TITLE ESTs | | | gi = 4032606 | 722530 |
| IC10943 | UG75 Expression | EST | Mm.38460 | TITLE ESTs, Moderately similar to HSPC007 [H. sapiens] | | | gi = 3165247 | 1279123 |
| IC10944 | UG75 Expression | EST | Mm.38461 | TITLE ESTs, Weakly similar to TYROSINE-PROTEIN KINASE JAK3 [M. musculus] | | | gi = 4031366 | 1263887 |
| IC10945 | UG75 Expression | EST | Mm.38463 | TITLE ESTs | | | gi = 4216106 | 639153 |
| IC10946 | UG75 Expression | EST | Mm.38464 | TITLE ESTs, Weakly similar to ORF YPL207w [S. cerevisiae] | | | gi = 1283110 | 622755 |
| IC10947 | UG75 Expression | EST | Mm.38473 | TITLE ESTs, Weakly similar to weak similarity with a B. Flavum translocation protein [C. elegans] | | | gi = 5125929 | 639947 |
| IC10948 | UG75 Expression | EST | Mm.38474 | TITLE ESTs, Weakly similar to Smarce 1-related protein [M. musculus] | | | gi = 1476420 | 440684 |
| IC10949 | UG75 Expression | EST | Mm.38477 | TITLE ESTs | | | gi = 4301514 | 621364 |
| IC10950 | UG75 Expression | EST | Mm.38480 | TITLE ESTs, Weakly similar to predicted using Genefinder [C. elegans] | | | gi = 2057509 | 1263696 |
| IC10951 | UG75 Expression | EST | Mm.38484 | TITLE ESTs | | | gi = 4317797 | 723320 |
| IC10952 | UG75 Expression | EST | Mm.38486 | TITLE ESTs | | | gi = 1309664 | 439445 |
| IC10953 | UG75 Expression | EST | Mm.38488 | TITLE ESTs | | | gi = 1913611 | 621172 |
| IC10954 | UG75 Expression | EST | Mm.38489 | TITLE ESTs | | | gi = 3680987 | 599263 |
| IC10955 | UG75 Expression | EST | Mm.38492 | TITLE ESTs | | | gi = 1794414 | 719298 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10956 | UG75 Expression | EST | Mm.38494 | TITLE ESTs, Weakly similar to tyrosine kinase receptor [*M. musculus*] | | | gi = 4061318 | 599242 |
| IC10957 | UG75 Expression | EST | Mm.38500 | TITLE ESTs | | | gi = 4401895 | 1001536 |
| IC10958 | UG75 Expression | EST | Mm.38503 | TITLE ESTs, Weakly similar to ORF YBR146w [*S. cerevisiae*] | | | gi = 2745120 | 973872 |
| IC10959 | UG75 Expression | EST | Mm.38506 | TITLE ESTs | | | gi = 2283279 | 764572 |
| IC10960 | UG75 Expression | EST | Mm.38509 | TITLE ESTs | | | gi = 1631120 | 640507 |
| IC10961 | UG75 Expression | EST | Mm.38512 | TITLE ESTs | | | gi = 4318703 | 718857 |
| IC10962 | UG75 Expression | EST | Mm.38524 | TITLE ESTs, Weakly similar to cDNA EST EMBL:T01421 comes from this gene [*C. elegans*] | | | gi = 3719038 | 764048 |
| IC10963 | UG75 Expression | EST | Mm.38525 | TITLE ESTs, Weakly similar to SH3 domain-containing adapter protein [*M. musculus*] | | | gi = 1408034 | 765874 |
| IC10964 | UG75 Expression | EST | Mm.38526 | TITLE ESTs | | | gi = 4600922 | 622041 |
| IC10965 | UG75 Expression | EST | Mm.38527 | TITLE ESTs | | | gi = 1901909 | 637811 |
| IC10966 | UG75 Expression | EST | Mm.38529 | TITLE ESTs | | | gi = 5474876 | 1196728 |
| IC10967 | UG75 Expression | EST | Mm.38532 | TITLE ESTs | | | gi = 2041935 | 749948 |
| IC10968 | UG75 Expression | EST | Mm.38533 | TITLE ESTs | | | gi = 1330815 | 721290 |
| IC10969 | UG75 Expression | EST | Mm.3855 | TITLE DNA segment, Chr 6, Wayne State University 113, expressed | GENE D6Wsu113e | | | 959436 |
| IC10970 | UG75 Expression | EST | Mm.38561 | TITLE ESTs | | | gi = 4968502 | 1265001 |
| IC10971 | UG75 Expression | EST | Mm.38562 | TITLE ESTs | | | gi = 4968563 | 1330026 |
| IC10972 | UG75 Expression | EST | Mm.38578 | TITLE ESTs | | | gi = 4968564 | 1294208 |
| IC10973 | UG75 Expression | EST | Mm.38585 | TITLE ESTs | | | gi = 4968559 | 1312024 |
| IC10974 | UG75 Expression | EST | Mm.38587 | TITLE ESTs | | | gi = 1766675 | 636026 |
| IC10975 | UG75 Expression | EST | Mm.38589 | TITLE ESTs, Weakly similar to similar to protein kinase C substrate [*C. elegans*] | | | gi = 4968429 | 582198 |
| IC10976 | UG75 Expression | EST | Mm.38607 | TITLE ESTs, Moderately similar to TRANSDUCIN-LIKE ENHANCER PROTEIN 2 [*Homo sapiens*] | | | gi = 6083633 | 1001986 |
| IC10977 | UG75 Expression | EST | Mm.38608 | TITLE ESTs, Weakly similar to PHOSPHATIDYLINOSITOL [*M. musculus*] | | | gi = 2964877 | 1395103 |
| IC10978 | UG75 Expression | EST | Mm.38610 | TITLE ESTs | | | gi = 4968390 | 581779 |
| IC10979 | UG75 Expression | EST | Mm.38611 | TITLE ESTs | | | gi = 4968560 | 972714 |
| IC10980 | UG75 Expression | EST | Mm.38614 | TITLE EST | | | gi = 4508374 | 1243603 |
| IC10981 | UG75 Expression | EST | Mm.38615 | TITLE ESTs | | | gi = 4060438 | 597945 |
| IC10982 | UG75 Expression | EST | Mm.38651 | TITLE EST | | | gi = 1903576 | 720750 |
| IC10983 | UG75 Expression | EST | Mm.38665 | TITLE ESTs | | | gi = 3393668 | 1193479 |
| IC10984 | UG75 Expression | EST | Mm.38682 | TITLE EST | | | gi = 4804710 | 639099 |
| IC10985 | UG75 Expression | EST | Mm.38713 | TITLE EST | | | gi = 4301021 | 576604 |
| IC10986 | UG75 Expression | EST | Mm.38723 | TITLE EST | | | gi = 4766367 | 749844 |
| IC10987 | UG75 Expression | EST | Mm.38724 | TITLE ESTs | | | gi = 2434122 | 1002836 |
| IC10988 | UG75 Expression | EST | Mm.38725 | TITLE ESTs, Weakly similar to RETROVIRUS-RELATED POL POLYPROTEIN [*M. musculus*] | | | gi = 3956221 | 973987 |
| IC10989 | UG75 Expression | EST | Mm.38736 | TITLE ESTs | | | gi = 2256964 | 1294114 |
| IC10990 | UG75 Expression | EST | Mm.38739 | TITLE ESTs | | | gi = 2292518 | 617968 |
| IC10991 | UG75 Expression | EST | Mm.38746 | TITLE ESTs, Weakly similar to W05H7.3 [*C. elegans*] | | | gi = 4616963 | 1344672 |
| IC10992 | UG75 Expression | EST | Mm.38753 | TITLE ESTs | | | gi = 5125916 | 2088128 |
| IC10993 | UG75 Expression | EST | Mm.38762 | TITLE ESTs | | | gi = 5125189 | 1279283 |
| IC10994 | UG75 Expression | EST | Mm.38763 | TITLE ESTs | | | gi = 5125790 | 1282244 |
| IC10995 | UG75 Expression | EST | Mm.38768 | TITLE ESTs | | | gi = 5125792 | 581942 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC10996 | UG75 Expression | EST | Mm.38774 | TITLE ESTs | | | gi = 5125800 | 599233 |
| IC10997 | UG75 Expression | EST | Mm.38776 | TITLE ESTs | | | gi = 5124586 | 637112 |
| IC10998 | UG75 Expression | EST | Mm.38780 | TITLE ESTs | | | gi = 5125669 | 1312789 |
| IC10999 | UG75 Expression | EST | Mm.38782 | TITLE ESTs, Weakly similar to F57H12.7 [C. elegans] | | | gi = 2292297 | 973134 |
| IC11000 | UG75 Expression | EST | Mm.38783 | TITLE ESTs | | | gi = 5124814 | 750422 |
| IC11001 | UG75 Expression | EST | Mm.38786 | TITLE ESTs | | | gi = 5124550 | 1279000 |
| IC11002 | UG75 Expression | EST | Mm.38791 | TITLE ESTs | | | gi = 5125921 | 1294179 |
| IC11003 | UG75 Expression | EST | Mm.38800 | TITLE ESTs, Weakly similar to (define not available 5566087) [M. musculus] | | | gi = 2965347 | 641896 |
| IC11004 | UG75 Expression | EST | Mm.38801 | TITLE ESTs | | | gi = 5125553 | 720695 |
| IC11005 | UG75 Expression | EST | Mm.38802 | TITLE DNA segment, Chr 11, KL Mohlke 35 | GENE D11Moh35 | | | 1265522 |
| IC11006 | UG75 Expression | EST | Mm.38804 | TITLE ESTs | | | gi = 5125820 | 1279543 |
| IC11007 | UG75 Expression | EST | Mm.38808 | TITLE ESTs | | | gi = 6519081 | 1447057 |
| IC11008 | UG75 Expression | EST | Mm.38810 | TITLE ESTs, Moderately similar to GLYCEROL-3-PHOSPHATE DEHYDROGENASE [M. musculus] | | | gi = 6099232 | 638447 |
| IC11009 | UG75 Expression | EST | Mm.38813 | TITLE ESTs | | | gi = 5336587 | 598128 |
| IC11010 | UG75 Expression | EST | Mm.38816 | TITLE ESTs, Weakly similar to GUANINE NUCLEOTIDE-BINDING PROTEIN G(I)/G(S)/G(T) BETA SUBUNIT 2 [M. musculus] | | | gi = 5338153 | 765209 |
| IC11011 | UG75 Expression | EST | Mm.38831 | TITLE ESTs, Moderately similar to KIAA0646 protein [H. sapiens] | | | gi = 5336250 | 722918 |
| IC11012 | UG75 Expression | EST | Mm.38832 | TITLE ESTs | | | gi = 5338377 | 1294771 |
| IC11013 | UG75 Expression | EST | Mm.38833 | TITLE ESTs | | | gi = 5334719 | 1279847 |
| IC11014 | UG75 Expression | EST | Mm.38847 | TITLE ESTs | | | gi = 5338312 | 1193242 |
| IC11015 | UG75 Expression | EST | Mm.38849 | TITLE ESTs | | | gi = 5332966 | 721659 |
| IC11016 | UG76 LID366 B cell | EST | Mm.38851 | TITLE ESTs, Weakly similar to alpha glucosidase II, alpha subunit [M. musculus] | | | gi = 5337963 | 1970607 |
| IC11017 | UG75 Expression | EST | Mm.38853 | TITLE ESTs | | | gi = 4271973 | 427290 |
| IC11018 | UG75 Expression | EST | Mm.3886 | TITLE ESTs | | | gi = 2306588 | 1264008 |
| IC11019 | UG75 Expression | EST | Mm.38868 | TITLE ESTs | | | gi = 4783418 | 643109 |
| IC11020 | UG75 Expression | EST | Mm.38875 | TITLE ESTs | | | gi = 6084408 | 1445656 |
| IC11021 | UG75 Expression | EST | Mm.38876 | TITLE ESTs, Moderately similar to putative REX-2 [M. musculus] | | | gi = 5337163 | 577242 |
| IC11022 | UG75 Expression | EST | Mm.38877 | TITLE ESTs | | | gi = 1816917 | 717720 |
| IC11023 | UG75 Expression | EST | Mm.38878 | TITLE ESTs | | | gi = 5336493 | 1001398 |
| IC11024 | UG75 Expression | EST | Mm.38879 | TITLE ESTs, Weakly similar to predicted using Genefinder [C. elegans] | | | gi = 5819562 | 765561 |
| IC11025 | UG75 Expression | EST | Mm.38885 | TITLE ESTs | | | gi = 5908572 | 764442 |
| IC11026 | UG75 Expression | EST | Mm.38890 | TITLE ESTs | | | gi = 6156551 | 1265031 |
| IC11027 | UG75 Expression | EST | Mm.38891 | TITLE ESTs, Weakly similar to TYROSINE-PROTEIN KINASE JAK3 [M. musculus] | | | gi = 3375402 | 1225408 |
| IC11028 | UG75 Expression | EST | Mm.38894 | TITLE ESTs | | | gi = 5337440 | 718391 |
| IC11029 | UG75 Expression | EST | Mm.38899 | TITLE ESTs | | | gi = 2962660 | 1265432 |
| IC11030 | UG75 Expression | EST | Mm.38903 | TITLE ESTs | | | gi = 5336513 | 777142 |
| IC11031 | UG75 Expression | EST | Mm.38907 | TITLE ESTs, Weakly similar to R10F2.5 [C. elegans] | | | gi = 5337258 | 574962 |
| IC11032 | UG75 Expression | EST | Mm.38910 | TITLE ESTs | | | gi = 6077543 | 1363731 |
| IC11033 | UG75 Expression | EST | Mm.38911 | TITLE ESTs | | | gi = 5337920 | 751518 |
| IC11034 | UG75 Expression | EST | Mm.38912 | TITLE ESTs | | | gi = 5338022 | 576641 |
| IC11035 | UG75 Expression | EST | Mm.38921 | TITLE ESTs, Weakly similar to C44B9.1 [C. elegans] | | | gi = 4725529 | 1295195 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11036 | UG75 Expression | EST | Mm.38924 | TITLE ESTs | | | gi = 5338048 | 989342 |
| IC11037 | UG75 Expression | EST | Mm.38927 | TITLE ESTs, Weakly similar to peptidylprolyl isomerase [M. musculus] | | | gi = 4434664 | 1148596 |
| IC11038 | UG75 Expression | EST | Mm.38955 | TITLE ESTs | | | gi = 5337982 | 1295406 |
| IC11039 | UG75 Expression | EST | Mm.38957 | TITLE ESTs | | | gi = 5338332 | 749072 |
| IC11040 | UG75 Expression | EST | Mm.38958 | TITLE ESTs | | | gi = 4765293 | 749413 |
| IC11041 | UG75 Expression | EST | Mm.38959 | TITLE DNA segment, Chr 1, University of California at Los Angeles 3 | GENE D1Ucla3 | | | 597150 |
| IC11042 | UG75 Expression | EST | Mm.38976 | TITLE ESTs, Weakly similar to putative deubiquitinating enzyme UBPY [M. musculus] | | | gi = 1309885 | 1193492 |
| IC11043 | UG75 Expression | EST | Mm.38980 | TITLE ESTs | | | gi = 4058303 | 635508 |
| IC11044 | UG75 Expression | EST | Mm.38987 | TITLE EST | | | gi = 4058055 | 575382 |
| IC11045 | UG75 Expression | EST | Mm.38993 | TITLE ESTs | | | gi = 2272699 | 1429224 |
| IC11046 | UG75 Expression | EST | Mm.38994 | TITLE ESTs, Weakly similar to ZW10 interactor Zwint [H. sapiens] | | | gi = 4434492 | 1002751 |
| IC11047 | UG75 Expression | EST | Mm.39006 | TITLE ESTs, Moderately similar to topoisomerase I-binding RS protein [H. sapiens] | | | gi = 6085487 | 1226963 |
| IC11048 | UG75 Expression | EST | Mm.39053 | TITLE ESTs | | | gi = 5336695 | 1445685 |
| IC11049 | UG75 Expression | EST | Mm.39056 | TITLE ESTs, Weakly similar to cDNA EST yk465d10.3 comes from this gene [C. elegans] | | | gi = 3164754 | 598427 |
| IC11050 | UG75 Expression | EST | Mm.39060 | TITLE ESTs | | | gi = 6084901 | 973903 |
| IC11051 | UG75 Expression | EST | Mm.39077 | TITLE ESTs | | | gi = 2918668 | 765157 |
| IC11052 | UG75 Expression | EST | Mm.39079 | TITLE ESTs | | | gi = 4316056 | 635510 |
| IC11053 | UG75 Expression | EST | Mm.39097 | TITLE ESTs | | | gi = 1756491 | 618443 |
| IC11054 | UG75 Expression | EST | Mm.391 | TITLE ESTs, Moderately similar to T-cell activation protein [H. sapiens] | | | gi = 4967423 | 637346 |
| IC11055 | UG75 Expression | EST | Mm.39100 | TITLE ESTs | | | gi = 5498612 | 959480 |
| IC11056 | UG75 Expression | EST | Mm.39112 | TITLE ESTs | | | gi = 5910285 | 534502 |
| IC11057 | UG75 Expression | EST | Mm.39126 | TITLE ESTs | | | gi = 4444737 | 574461 |
| IC11058 | UG75 Expression | EST | Mm.3926 | TITLE ESTs | | | gi = 1795303 | 635566 |
| IC11059 | UG75 Expression | EST | Mm.39279 | TITLE ESTs | | | gi = 3522755 | 720797 |
| IC11060 | UG75 Expression | EST | Mm.39281 | TITLE ESTs, Weakly similar to R32611_2 [H. sapiens] | | | gi = 2519542 | 751478 |
| IC11061 | UG75 Expression | EST | Mm.39285 | TITLE ESTs | | | gi = 5474583 | 621328 |
| IC11062 | UG75 Expression | EST | Mm.39287 | TITLE ESTs | | | gi = 4724895 | 622099 |
| IC11063 | UG75 Expression | EST | Mm.39288 | TITLE ESTs | | | gi = 4441746 | 764678 |
| IC11064 | UG75 Expression | EST | Mm.39290 | TITLE ESTs | | | gi = 2042932 | 750485 |
| IC11065 | UG75 Expression | EST | Mm.39291 | TITLE ESTs | | | gi = 5489574 | 598224 |
| IC11066 | UG75 Expression | EST | Mm.39293 | TITLE ESTs | | | gi = 3100492 | 1344877 |
| IC11067 | UG75 Expression | EST | Mm.39295 | TITLE ESTs | | | gi = 3718195 | 1225070 |
| IC11068 | UG75 Expression | EST | Mm.39296 | TITLE ESTs | | | gi = 1554426 | 1446051 |
| IC11069 | UG75 Expression | EST | Mm.39297 | TITLE ESTs | | | gi = 2139768 | 722602 |
| IC11070 | UG75 Expression | EST | Mm.39299 | TITLE ESTs, Moderately similar to Dyrk3 protein [H. sapiens] | | | gi = 2402621 | 721534 |
| IC11071 | UG75 Expression | EST | Mm.39350 | TITLE ESTs | | | gi = 5493256 | 1362646 |
| IC11072 | UG75 Expression | EST | Mm.39435 | TITLE ESTs | | | gi = 5496702 | 640549 |
| IC11073 | UG75 Expression | EST | Mm.39456 | TITLE EST | | | gi = 5599463 | 577197 |
| IC11074 | UG75 Expression | EST | Mm.39462 | TITLE ESTs, Weakly similar to B120 [H. sapiens] | | | gi = 5497598 | 1281559 |
| IC11075 | UG75 Expression | EST | Mm.39463 | TITLE ESTs, Weakly similar to Additional sex combs [D. melanogaster] | | | gi = 4297395 | 581889 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11076 | UG75 Expression | EST | Mm.39468 | TITLE ESTs | | | gi = 1643700 | 550791 |
| IC11077 | UG75 Expression | EST | Mm.39469 | TITLE ESTs, Moderately similar to similar to human transcription factor THIIS [*H. sapiens*] | | | gi = 6100115 | 1313136 |
| IC11078 | UG75 Expression | EST | Mm.39471 | TITLE ESTs | | | gi = 3054893 | 1328116 |
| IC11079 | UG75 Expression | EST | Mm.39474 | TITLE ESTs | | | gi = 1796661 | 619707 |
| IC11080 | UG75 Expression | EST | Mm.39476 | TITLE ESTs | | | gi = 4616838 | 746512 |
| IC11081 | UG75 Expression | EST | Mm.39477 | TITLE ESTs | | | gi = 2516705 | 616837 |
| IC11082 | UG75 Expression | EST | Mm.39478 | TITLE ESTs | | | gi = 1919250 | 777456 |
| IC11083 | UG75 Expression | EST | Mm.39479 | TITLE ESTs | | | gi = 5469194 | 1265128 |
| IC11084 | UG75 Expression | EST | Mm.39480 | TITLE ESTs | | | gi = 1919733 | 765703 |
| IC11085 | UG75 Expression | EST | Mm.39482 | TITLE ESTs | | | gi = 1852934 | 1378866 |
| IC11086 | UG75 Expression | EST | Mm.39484 | TITLE ESTs | | | gi = 2292661 | 958528 |
| IC11087 | UG75 Expression | EST | Mm.39485 | TITLE ESTs | | | gi = 4031673 | 1263177 |
| IC11088 | UG75 Expression | EST | Mm.39489 | TITLE ESTs | | | gi = 5494104 | 1330039 |
| IC11089 | UG75 Expression | EST | Mm.39490 | TITLE ESTs, Weakly similar to Similarity with snail BR-1 protein [*C. elegans*] | | | gi = 2074756 | 752139 |
| IC11090 | UG75 Expression | EST | Mm.39501 | TITLE ESTs, Weakly similar to HC1 ORF [*M. musculus*] | | | gi = 1675905 | 1148760 |
| IC11091 | UG75 Expression | EST | Mm.39505 | TITLE ESTs | | | gi = 5470797 | 735313 |
| IC11092 | UG75 Expression | EST | Mm.39529 | TITLE ESTs | | | gi = 1794456 | 639604 |
| IC11093 | UG75 Expression | EST | Mm.39700 | TITLE ESTs | | | gi = 2284145 | 717606 |
| IC11094 | UG75 Expression | EST | Mm.39704 | TITLE ESTs | | | gi = 1682370 | 642986 |
| IC11095 | UG75 Expression | EST | Mm.39706 | TITLE ESTs | | | gi = 4441744 | 638477 |
| IC11096 | UG75 Expression | EST | Mm.39709 | TITLE ESTs | | | gi = 1875937 | 1002328 |
| IC11097 | UG75 Expression | EST | Mm.39710 | TITLE ESTs | | | gi = 5910663 | 638097 |
| IC11098 | UG75 Expression | EST | Mm.39711 | TITLE ESTs | | | gi = 3732219 | 638419 |
| IC11099 | UG75 Expression | EST | Mm.39712 | TITLE ESTs | | | gi = 1826837 | 1345653 |
| IC11100 | UG75 Expression | EST | Mm.39713 | TITLE ESTs | | | gi = 5488544 | 636021 |
| IC11101 | UG75 Expression | EST | Mm.39714 | TITLE ESTs, Weakly similar to TRAF4-associated factor 2 [*H. sapiens*] | | | gi = 5469242 | 723108 |
| IC11102 | UG75 Expression | EST | Mm.39715 | TITLE ESTs, Weakly similar to ADP-ribosylation factor-directed GTPase activating protein isoform b [*M. musculus*] | | | gi = 2306687 | 575037 |
| IC11103 | UG75 Expression | EST | Mm.39720 | TITLE ESTs | | | gi = 1447110 | 573578 |
| IC11104 | UG75 Expression | EST | Mm.39723 | TITLE ESTs | | | gi = 1827394 | 1447169 |
| IC11105 | UG75 Expression | EST | Mm.39726 | TITLE ESTs | | | gi = 4605671 | 2123443 |
| IC11106 | UG75 Expression | EST | Mm.39729 | TITLE ESTs | | | gi = 1755387 | 620375 |
| IC11107 | UG75 Expression | EST | Mm.39732 | TITLE ESTs | | | gi = 1671405 | 578081 |
| IC11108 | UG75 Expression | EST | Mm.39733 | TITLE ESTs | | | gi = 5125367 | 1380173 |
| IC11109 | UG75 Expression | EST | Mm.39734 | TITLE ESTs | | | gi = 3336088 | 1380427 |
| IC11110 | UG75 Expression | EST | Mm.39756 | TITLE ESTs | | | gi = 5495437 | 551443 |
| IC11111 | UG75 Expression | EST | Mm.39856 | TITLE ESTs | | | gi = 4726278 | 721017 |
| IC11112 | UG75 Expression | EST | Mm.39872 | TITLE ESTs | | | gi = 1888002 | 640292 |
| IC11113 | UG75 Expression | EST | Mm.39896 | TITLE ESTs | | | gi = 6556921 | 583460 |
| IC11114 | UG75 Expression | EST | Mm.39933 | TITLE ESTs | | | gi = 5497404 | 638329 |
| IC11115 | UG75 Expression | EST | Mm.39934 | TITLE ESTs | | | gi = 4602490 | 1193718 |
| IC11116 | UG75 Expression | EST | Mm.3994 | TITLE ESTs | | | gi = 2187377 | 1295832 |
| IC11117 | UG75 Expression | EST | Mm.39963 | TITLE ESTs | | | gi = 4216868 | 331080 |
| IC11118 | UG75 Expression | EST | Mm.39966 | TITLE ESTs, Weakly similar to ADP-RIBOSYLATION FACTOR-LIKE PROTEIN 2 [*Homo sapiens*] | | | gi = 1476254 | 1750120 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| ICI1119 | UG75 Expression | EST | Mm.39967 | TITLE ESTs | | | gi = 1657070 | 519576 |
| ICI1120 | UG75 Expression | EST | Mm.39972 | TITLE ESTs | | | gi = 5492124 | 575489 |
| ICI1121 | UG75 Expression | EST | Mm.39973 | TITLE ESTs | | | gi = 1683949 | 578097 |
| ICI1122 | UG75 Expression | EST | Mm.39974 | TITLE ESTs, Weakly similar to HP33 [R. norvegicus] | | | gi = 3747855 | 534066 |
| ICI1123 | UG75 Expression | EST | Mm.39976 | TITLE ESTs | | | gi = 2461850 | 599037 |
| ICI1125 | UG75 Expression | EST | Mm.39977 | TITLE ESTs | | | gi = 1739940 | 598695 |
| ICI1126 | UG75 Expression | EST | Mm.39979 | TITLE ESTs | | | gi = 1758867 | 622821 |
| ICI1127 | UG75 Expression | EST | Mm.39980 | TITLE ESTs | | | gi = 5491615 | 597606 |
| ICI1128 | UG75 Expression | EST | Mm.39981 | TITLE ESTs | | | gi = 4602763 | 619730 |
| ICI1129 | UG75 Expression | EST | Mm.39982 | TITLE ESTs | | | gi = 5473848 | 642341 |
| ICI1130 | UG75 Expression | EST | Mm.39983 | TITLE ESTs | | | gi = 4614849 | 644132 |
| ICI1131 | UG75 Expression | EST | Mm.39986 | TITLE ESTs | | | gi = 1918001 | 765928 |
| ICI1132 | UG75 Expression | EST | Mm.39992 | TITLE ESTs | | | gi = 5494209 | 972818 |
| ICI1133 | UG75 Expression | EST | Mm.39994 | TITLE ESTs, Moderately similar to KIAA0007 [H. sapiens] | | | gi = 3885272 | 1002230 |
| ICI1134 | UG75 Expression | EST | Mm.39995 | TITLE ESTs | | | gi = 2235651 | 1295204 |
| ICI1135 | UG75 Expression | EST | Mm.39997 | TITLE ESTs | | | gi = 5473071 | 1263726 |
| ICI1136 | UG75 Expression | EST | Mm.39998 | TITLE ESTs | | | gi = 5492218 | 1328528 |
| ICI1137 | UG75 Expression | EST | Mm.40001 | TITLE ESTs | | | gi = 4601702 | 634065 |
| ICI1138 | UG75 Expression | EST | Mm.40003 | TITLE ESTs | | | gi = 5497529 | 1362318 |
| ICI1139 | UG75 Expression | EST | Mm.40025 | TITLE ESTs | | | gi = 1355205 | 718845 |
| ICI1140 | UG75 Expression | EST | Mm.4011 | TITLE ESTs | | | gi = 1543680 | 1329404 |
| ICI1141 | UG75 Expression | EST | Mm.40122 | TITLE ESTs | | | gi = 2811590 | 1330400 |
| ICI1142 | UG75 Expression | EST | Mm.40151 | TITLE ESTs | | | gi = 1676866 | 573581 |
| ICI1143 | UG75 Expression | EST | Mm.40171 | TITLE ESTs, Weakly similar to RanBP2 protein [M. musculus] | | | gi = 4724426 | 639263 |
| ICI1144 | UG75 Expression | EST | Mm.40177 | TITLE ESTs | | | gi = 5492267 | 717846 |
| ICI1145 | UG75 Expression | EST | Mm.40180 | TITLE ESTs | | | gi = 5492365 | 1429817 |
| ICI1146 | UG75 Expression | EST | Mm.402 | TITLE ESTs | | | gi = 1684335 | 574544 |
| ICI1147 | UG75 Expression | EST | Mm.40217 | TITLE ESTs | | | gi = 3157743 | 634160 |
| ICI1148 | UG75 Expression | EST | Mm.4022 | TITLE ESTs, Moderately similar to R26529_2, partial CDS [H. sapiens] | | | gi = 4571810 | 1139094 |
| ICI1149 | UG75 Expression | EST | Mm.40245 | TITLE ESTs | | | gi = 5498126 | 1380577 |
| ICI1150 | UG75 Expression | EST | Mm.40260 | TITLE ESTs | | | gi = 2272526 | 717970 |
| ICI1151 | UG75 Expression | EST | Mm.40262 | TITLE ESTs | | | gi = 1365635 | 1328979 |
| ICI1152 | UG75 Expression | EST | Mm.40269 | TITLE ESTs | | | gi = 1738454 | 598867 |
| ICI1153 | UG75 Expression | EST | Mm.40272 | TITLE ESTs | | | gi = 2956538 | 1293889 |
| ICI1154 | UG75 Expression | EST | Mm.40273 | TITLE ESTs | | | gi = 5497985 | 597235 |
| ICI1155 | UG75 Expression | EST | Mm.40274 | TITLE ESTs | | | gi = 5549248 | 596799 |
| ICI1156 | UG75 Expression | EST | Mm.40278 | TITLE ESTs | | | gi = 5906407 | 616757 |
| ICI1157 | UG75 Expression | EST | Mm.40279 | TITLE ESTs | | | gi = 3066462 | 764752 |
| ICI1158 | UG75 Expression | EST | Mm.40280 | TITLE ESTs | | | gi = 1768802 | 637646 |
| ICI1159 | UG75 Expression | EST | Mm.40281 | TITLE ESTs, Weakly similar to proline-rich protein [M. musculus] | | | gi = 1769334 | 637094 |
| ICI1160 | UG75 Expression | EST | Mm.40282 | TITLE ESTs, Moderately similar to GEPHYRIN [Rattus norvegicus] | | | gi = 6638381 | 1280036 |
| ICI1161 | UG75 Expression | EST | Mm.40284 | TITLE ESTs | | | gi = 1826017 | 638453 |
| ICI1162 | UG75 Expression | EST | Mm.40288 | TITLE ESTs | | | gi = 5492240 | 572936 |
| ICI1163 | UG75 Expression | EST | Mm.40289 | TITLE ESTs | | | gi = 1915702 | 596637 |
| | UG75 Expression | EST | Mm.40291 | TITLE ESTs | | | gi = 2573027 | 642516 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11164 | UG75 Expression | EST | Mm.40292 | TITLE ESTs, Moderately similar to unknown protein IT12 [*H. sapiens*] | | | gi = 6167913 | 1002840 |
| IC11165 | UG75 Expression | EST | Mm.40293 | TITLE ESTs | | | gi = 5476876 | 833248 |
| IC11166 | UG75 Expression | EST | Mm.40295 | TITLE ESTs | | | gi = 5497999 | 574101 |
| IC11167 | UG75 Expression | EST | Mm.40298 | TITLE ESTs | | | gi = 5597459 | 2581954 |
| IC11168 | UG75 Expression | EST | Mm.40308 | TITLE ESTs | | | gi = 5498147 | 574963 |
| IC11169 | UG75 Expression | EST | Mm.40309 | TITLE ESTs | | | gi = 4271593 | 1345476 |
| IC11170 | UG75 Expression | EST | Mm.40320 | TITLE ESTs | | | gi = 3687016 | 1446958 |
| IC11171 | UG75 Expression | EST | Mm.40321 | TITLE ESTs | | | gi = 4601077 | 597626 |
| IC11172 | UG75 Expression | EST | Mm.40332 | TITLE ESTs | | | gi = 4300384 | 576048 |
| IC11173 | UG75 Expression | EST | Mm.40335 | TITLE ESTs, Moderately similar to 5-METHYLTETRAHYDROFOLATE-HOMOCYSTEINE METHYLTRANSFERASE [*Escherichia coli*] | | | gi = 5600072 | 617269 |
| IC11174 | UG75 Expression | EST | Mm.40336 | TITLE ESTs | | | gi = 4305036 | 765934 |
| IC11175 | UG75 Expression | EST | Mm.40338 | TITLE ESTs | | | gi = 5472064 | 777420 |
| IC11176 | UG75 Expression | EST | Mm.40339 | TITLE ESTs, Weakly similar to P2Y PURINOCEPTOR 1 [*M. musculus*] | | | gi = 5498504 | 973284 |
| IC11177 | UG75 Expression | EST | Mm.40345 | TITLE ESTs, Weakly similar to homeotic protein protein zhx-1 [*M. musculus*] | | | gi = 5492620 | 1265051 |
| IC11178 | UG75 Expression | EST | Mm.40347 | TITLE ESTs | | | gi = 1672048 | 719455 |
| IC11179 | UG75 Expression | EST | Mm.40351 | TITLE ESTs | | | gi = 5477111 | 722450 |
| IC11180 | UG75 Expression | EST | Mm.40352 | TITLE ESTs | | | gi = 1724727 | 583763 |
| IC11181 | UG75 Expression | EST | Mm.40362 | TITLE ESTs, Moderately similar to TRANSLATION INITIATION FACTOR IF-2, MITOCHONDRIAL PRECURSOR [*H. sapiens*] | | | gi = 5336555 | 1279654 |
| IC11182 | UG75 Expression | EST | Mm.40364 | TITLE ESTs [*M. musculus*] | | | gi = 1793023 | 1243396 |
| IC11183 | UG75 Expression | EST | Mm.40365 | TITLE ESTs | | | gi = 3517841 | 1395635 |
| IC11184 | UG75 Expression | EST | Mm.4042 | TITLE ESTs, Moderately similar to NG22 [*M. musculus*] | | | gi = 2291984 | 533974 |
| IC11185 | UG75 Expression | EST | Mm.40452 | TITLE ESTs | | | gi = 2691780 | 720922 |
| IC11186 | UG75 Expression | EST | Mm.40460 | TITLE ESTs | | | gi = 2944563 | 1263009 |
| IC11187 | UG75 Expression | EST | Mm.40466 | TITLE ESTs | | | gi = 223914 | 599149 |
| IC11188 | UG75 Expression | EST | Mm.40490 | TITLE ESTs | | | gi = 2744495 | 1193591 |
| IC11189 | UG75 Expression | EST | Mm.40503 | TITLE ESTs | | | gi = 4296213 | 638232 |
| IC11190 | UG75 Expression | EST | Mm.4052 | TITLE ESTs | | | gi = 4409024 | 551860 |
| IC11191 | UG75 Expression | EST | Mm.40530 | TITLE ESTs | | | gi = 5488998 | 620261 |
| IC11192 | UG75 Expression | EST | Mm.4055 | TITLE ESTs | | | gi = 3748741 | 1263349 |
| IC11193 | UG75 Expression | EST | Mm.40574 | TITLE ESTs | | | gi = 2257334 | 596304 |
| IC11194 | UG75 Expression | EST | Mm.40594 | TITLE ESTs | | | gi = 4726307 | 534101 |
| IC11195 | UG75 Expression | EST | Mm.40601 | TITLE ESTs | | | gi = 3955648 | 573593 |
| IC11196 | UG75 Expression | EST | Mm.40609 | TITLE ESTs | | | gi = 5492126 | 1139766 |
| IC11197 | UG75 Expression | EST | Mm.40611 | TITLE ESTs, Moderately similar to Edp1 protein [*M. musculus*] | | | gi = 2307836 | 1263987 |
| IC11198 | UG75 Expression | EST | Mm.40617 | TITLE ESTs | | | gi = 5749790 | 777519 |
| IC11199 | UG75 Expression | EST | Mm.40620 | TITLE ESTs | | | gi = 1672221 | 558206 |
| IC11200 | UG75 Expression | EST | Mm.40621 | TITLE ESTs | | | gi = 1676355 | 573181 |
| IC11201 | UG75 Expression | EST | Mm.40626 | TITLE ESTs | | | gi = 1767998 | 622598 |
| IC11202 | UG75 Expression | EST | Mm.40627 | TITLE ESTs | | | gi = 2305618 | 642506 |
| IC11203 | UG75 Expression | EST | Mm.40628 | TITLE ESTs | | | gi = 2964534 | 1429443 |
| IC11204 | UG75 Expression | EST | Mm.40629 | TITLE ESTs | | | gi = 1699996 | 577603 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11205 | UG75 Expression | EST | Mm.40633 | TITLE ESTs | | | gi = 2571426 | 717900 |
| IC11206 | UG75 Expression | EST | Mm.40634 | TITLE ESTs | | | gi = 1909973 | 1001725 |
| IC11207 | UG75 Expression | EST | Mm.40635 | TITLE ESTs | | | gi = 1915639 | 765311 |
| IC11208 | UG75 Expression | EST | Mm.40636 | TITLE ESTs | | | gi = 549513 | 894310 |
| IC11209 | UG75 Expression | EST | Mm.40639 | TITLE ESTs | | | gi = 2203174 | 750952 |
| IC11210 | UG75 Expression | EST | Mm.40640 | TITLE ESTs | | | gi = 2967305 | 620442 |
| IC11211 | UG75 Expression | EST | Mm.40641 | TITLE ESTs | | | gi = 2283462 | 617992 |
| IC11212 | UG75 Expression | EST | Mm.40642 | TITLE ESTs | | | gi = 1550882 | 635698 |
| IC11213 | UG75 Expression | EST | Mm.4065 | TITLE ESTs | | | gi = 1680956 | 619526 |
| IC11214 | UG75 Expression | EST | Mm.40650 | TITLE ESTs, Moderately similar to ARPP-21 | | | gi = 2803477 | 576781 |
| IC11215 | UG75 Expression | EST | Mm.40653 | TITLE ESTs, Moderately similar to synaptojanin [R. norvegicus] | | | gi = 1917948 | 765865 |
| IC11216 | UG75 Expression | EST | Mm.40654 | TITLE ESTs | | | gi = 5493064 | 1263908 |
| IC11217 | UG75 Expression | EST | Mm.40655 | TITLE ESTs | | | gi = 3295895 | 1020877 |
| IC11218 | UG75 Expression | EST | Mm.40659 | TITLE ESTs | | | gi = 2180815 | 1265350 |
| IC11219 | UG75 Expression | EST | Mm.40661 | TITLE ESTs | | | gi = 1913445 | 749553 |
| IC11220 | UG75 Expression | EST | Mm.40671 | TITLE ESTs, Weakly similar to HSPC012 [H. sapiens] | | | gi = 4433967 | 1379729 |
| IC11221 | UG75 Expression | EST | Mm.40672 | TITLE ESTs | | | gi = 4058053 | 617596 |
| IC11222 | UG75 Expression | EST | Mm.40673 | TITLE ESTs | | | gi = 4032052 | 1264905 |
| IC11223 | UG75 Expression | EST | Mm.40674 | TITLE ESTs, Weakly similar to weakly similar to S. cerevisiae CBP3 protein precursor [C. elegans] | | | gi = 3732817 | 1282168 |
| IC11224 | UG75 Expression | EST | Mm.40688 | TITLE ESTs | | | gi = 5497691 | 574460 |
| IC11225 | UG75 Expression | EST | Mm.40689 | TITLE ESTs | | | gi = 4613428 | 620772 |
| IC11226 | UG75 Expression | EST | Mm.40695 | TITLE ESTs | | | gi = 2434103 | 1002808 |
| IC11227 | UG75 Expression | EST | Mm.40697 | TITLE ESTs | | | gi = 5666297 | 635728 |
| IC11228 | UG75 Expression | EST | Mm.40700 | TITLE ESTs | | | gi = 5491165 | 1263908 |
| IC11229 | UG75 Expression | EST | Mm.40721 | TITLE ESTs | | | gi = 1538943 | 597826 |
| IC11230 | UG75 Expression | EST | Mm.40723 | TITLE ESTs | | | gi = 2262421 | 1226510 |
| IC11231 | UG75 Expression | EST | Mm.40727 | TITLE ESTs | | | gi = 5496317 | 1225022 |
| IC11232 | UG75 Expression | EST | Mm.40732 | TITLE ESTs | | | gi = 3336335 | 1380718 |
| IC11233 | UG75 Expression | EST | Mm.40746 | TITLE ESTs | | | gi = 4433901 | 636948 |
| IC11234 | UG75 Expression | EST | Mm.4075 | TITLE ESTs, Weakly similar to ZINC FINGER PROTEIN MLZ-4 [Mus musculus] | | | gi = 1862708 | 638245 |
| IC11235 | UG75 Expression | EST | Mm.40750 | TITLE ESTs, Moderately similar to KIAA0415 [H. sapiens] | | | ge = 5471194 | 1225049 |
| IC11236 | UG75 Expression | EST | Mm.40777 | TITLE ESTs, Moderately similar to PTP 35 protein [M. musculus] | | | gi = 1681511 | 638694 |
| IC11237 | UG75 Expression | EST | Mm.40780 | TITLE ESTs | | | gi = 5477290 | 575398 |
| IC11238 | UG75 Expression | EST | Mm.40783 | TITLE ESTs | | | gi = 6749144 | 619756 |
| IC11239 | UG75 Expression | EST | Mm.40818 | TITLE ESTs | | | gi = 2308554 | 636503 |
| IC11240 | UG75 Expression | EST | Mm.40832 | TITLE ESTs | | | gi = 4257049 | 1226192 |
| IC11241 | UG75 Expression | EST | Mm.40854 | TITLE ESTs | | | gi = 5491212 | 718432 |
| IC11242 | UG75 Expression | EST | Mm.40882 | TITLE ESTs, Moderately similar to spindle pole body protein spc97 homolog GCP2 [H. sapiens] | | | gi = 6168166 | 1446293 |
| IC11243 | UG75 Expression | EST | Mm.40888 | TITLE ESTs | | | gi = 2288331 | 719001 |
| IC11244 | UG75 Expression | EST | Mm.40897 | TITLE ESTs | | | gi = 3373003 | 618840 |
| IC11245 | UG75 Expression | EST | Mm.40919 | TITLE ESTs | | | gi = 4512904 | 1281443 |
| IC11246 | UG75 Expression | EST | Mm.40920 | TITLE ESTs, Moderately similar to enhancer of polycomb | | | gi = 4298618 | 617260 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11247 | UG75 Expression | EST | Mm.40923 | TITLE ESTs, Moderately similar to GC-RICH SEQUENCE | | | gi = 2990704 | 1264671 |
| IC11248 | UG75 Expression | EST | Mm.40943 | TITLE ESTs | | | gi = 1751578 | 619413 |
| IC11249 | UG75 Expression | EST | Mm.40946 | TITLE ESTs, Weakly similar to myelin gene expression factor [M. musculus] | | | gi = 4058046 | 575072 |
| IC11250 | UG75 Expression | EST | Mm.40961 | TITLE ESTs | | | gi = 5498324 | 620904 |
| IC11251 | UG75 Expression | EST | Mm.40976 | TITLE ESTs | | | gi = 5599485 | 617615 |
| IC11252 | UG75 Expression | EST | Mm.40982 | TITLE ESTs | | | gi = 1475804 | 1363369 |
| IC11253 | UG75 Expression | EST | Mm.40983 | TITLE ESTs | | | gi = 5497946 | 749212 |
| IC11254 | UG75 Expression | EST | Mm.40985 | TITLE ESTs | | | gi = 1681603 | 576990 |
| IC11255 | UG75 Expression | EST | Mm.40986 | TITLE ESTs | | | gi = 5470168 | 1001889 |
| IC11256 | UG75 Expression | EST | Mm.40987 | TITLE ESTs | | | gi = 1918722 | 620913 |
| IC11257 | UG75 Expression | EST | Mm.40991 | TITLE ESTs | | | gi = 2262577 | 619477 |
| IC11258 | UG75 Expression | EST | Mm.40992 | TITLE ESTs | | | gi = 5906379 | 718627 |
| IC11259 | UG75 Expression | EST | Mm.40993 | TITLE ESTs | | | gi = 2811516 | 573630 |
| IC11260 | UG75 Expression | EST | Mm.40994 | TITLE ESTs | | | gi = 1904496 | 595951 |
| IC11261 | UG75 Expression | EST | Mm.40995 | TITLE ESTs | | | gi = 3682563 | 622028 |
| IC11262 | UG75 Expression | EST | Mm.40999 | TITLE ESTs | | | gi = 2561546 | 616688 |
| IC11263 | UG75 Expression | EST | Mm.41 | TITLE DNA segment, Chr 12, Wayne State University 28, expressed | GENE D12Wsu28e | | gi = 4600877 | 959410 |
| IC11264 | UG75 Expression | EST | Mm.41000 | TITLE ESTs | | | gi = 3981473 | 621690 |
| IC11265 | UG75 Expression | EST | Mm.41002 | TITLE ESTs | | | gi = 5477605 | 1279028 |
| IC11266 | UG75 Expression | EST | Mm.41004 | TITLE ESTs | | | gi = 5496773 | 642459 |
| IC11267 | UG75 Expression | EST | Mm.41005 | TITLE ESTs | | | gi = 1758856 | 642565 |
| IC11268 | UG75 Expression | EST | Mm.41007 | TITLE ESTs | | | gi = 5469262 | 622794 |
| IC11269 | UG75 Expression | EST | Mm.41008 | TITLE ESTs, Weakly similar to clone 22[H. sapiens] | | | gi = 1796680 | 557914 |
| IC11270 | UG75 Expression | EST | Mm.41009 | TITLE ESTs | | | gi = 4831673 | 644215 |
| IC11271 | UG75 Expression | EST | Mm.41010 | TITLE ESTs | | | gi = 5498407 | 643687 |
| IC11272 | UG75 Expression | EST | Mm.41012 | TITLE ESTs, Weakly similar to hypothetical protein [H. sapiens] | | | gi = 2307606 | 617779 |
| IC11273 | UG75 Expression | EST | Mm.41016 | TITLE ESTs, Moderately similar to hypothetical protein [H. sapiens] | | | gi = 6078209 | 959358 |
| IC11274 | UG75 Expression | EST | Mm.41020 | TITLE ESTs | | | gi = 5495689 | 1445921 |
| IC11275 | UG75 Expression | EST | Mm.41021 | TITLE ESTs | | | gi = 5910378 | 644396 |
| IC11276 | UG75 Expression | EST | Mm.41023 | TITLE ESTs | | | gi = 5489787 | 751715 |
| IC11277 | UG75 Expression | EST | Mm.41024 | TITLE ESTs | | | gi = 1913288 | 764792 |
| IC11278 | UG75 Expression | EST | Mm.41025 | TITLE ESTs | | | gi = 1913449 | 764826 |
| IC11279 | UG75 Expression | EST | Mm.41026 | TITLE ESTs | | | gi = 2625420 | 765263 |
| IC11280 | UG75 Expression | EST | Mm.41029 | TITLE ESTs | | | gi = 1738108 | 1001792 |
| IC11281 | UG75 Expression | EST | Mm.41031 | TITLE ESTs, Weakly similar to polyhomeotic 2 [M. musculus] | | | gi = 2978837 | 618890 |
| IC11282 | UG75 Expression | EST | Mm.41033 | TITLE ESTs | | | gi = 5491370 | 642905 |
| IC11283 | UG75 Expression | EST | Mm.41036 | TITLE ESTs, Weakly similar to Ras-binding protein SUR-8 [M. musculus] | | | gi = 5860829 | 575212 |
| IC11284 | UG75 Expression | EST | Mm.41037 | TITLE ESTs, Moderately similar to embryonic lung protein [H. sapiens] | | | gi = 6098578 | 640532 |
| IC11285 | UG75 Expression | EST | Mm.41043 | TITLE ESTs | | | gi = 5336849 | 751469 |
| IC11286 | UG75 Expression | EST | Mm.41046 | TITLE ESTs | | | gi = 2990878 | 642831 |
| IC11287 | UG75 Expression | EST | Mm.41054 | TITLE ESTs | | | gi = 2990878 | 550920 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11288 | UG75 Expression | EST | Mm.41055 | TITLE ESTs | | | gi = 2256456 | 894167 |
| IC11289 | UG75 Expression | EST | Mm.41057 | TITLE ESTs | | | gi = 2272006 | 721293 |
| IC11290 | UG76 LID366 B cell | EST | Mm.41058 | TITLE ESTs, Weakly similar to KIAA0661 protein [H. sapiens] | | | gi = 3395022 | 2123222 |
| IC11291 | UG75 Expression | EST | Mm.41060 | TITLE ESTs | | | gi = 4407216 | 621630 |
| IC11292 | UG75 Expression | EST | Mm.41061 | TITLE ESTs, Weakly similar to contains similarity to Mus musculus probable transcription factor requiem [C. elegans] | | | gi = 2306194 | 637469 |
| IC11293 | UG75 Expression | EST | Mm.41065 | TITLE ESTs | | | gi = 3718513 | 1149605 |
| IC11294 | UG75 Expression | EST | Mm.41067 | TITLE ESTs, Moderately similar to hypothetical protein [H. sapiens] | | | gi = 3387090 | 637501 |
| IC11295 | UG75 Expression | EST | Mm.41068 | TITLE ESTs | | | gi = 2893510 | 1294386 |
| IC11296 | UG75 Expression | EST | Mm.41069 | TITLE ESTs, Weakly similar to C24H11.6 [C. elegans] | | | gi = 1862347 | 577095 |
| IC11297 | UG75 Expression | EST | Mm.41077 | TITLE ESTs | | | gi = 5495000 | 634677 |
| IC11298 | UG75 Expression | EST | Mm.41084 | TITLE ESTs | | | gi = 4031926 | 637968 |
| IC11299 | UG75 Expression | EST | Mm.41090 | TITLE ESTs | | | gi = 3685484 | 1379572 |
| IC11300 | UG75 Expression | EST | Mm.41093 | TITLE ESTs, Moderately similar to LETHAL(2) GIANT LARVAE PROTEIN [Drosophila melanogaster] | | | gi = 2991396 | 722105 |
| IC11301 | UG75 Expression | EST | Mm.41099 | TITLE ESTs | | | gi = 3066869 | 1226102 |
| IC11302 | UG75 Expression | EST | Mm.41101 | TITLE ESTs, Moderately similar to actin-associated protein 2E4/kaptin [H. sapiens] | | | gi = 4702828 | 617380 |
| IC11303 | UG75 Expression | EST | Mm.41102 | TITLE ESTs | | | gi = 4482060 | 620162 |
| IC11304 | UG75 Expression | EST | Mm.41111 | TITLE ESTs | | | gi = 2528200 | 635933 |
| IC11305 | UG75 Expression | EST | Mm.41114 | TITLE ESTs | | | gi = 2288698 | 577167 |
| IC11306 | UG75 Expression | EST | Mm.41117 | TITLE ESTs | | | gi = 3299484 | 1379230 |
| IC11307 | UG75 Expression | EST | Mm.41118 | TITLE ESTs | | | gi = 2907039 | 1002861 |
| IC11308 | UG75 Expression | EST | Mm.41119 | TITLE ESTs | | | gi = 2403404 | 597718 |
| IC11309 | UG75 Expression | EST | Mm.41120 | TITLE ESTs | | | gi = 6083675 | 1328693 |
| IC11310 | UG75 Expression | EST | Mm.41121 | TITLE ESTs | | | gi = 2979123 | 1263889 |
| IC11311 | UG75 Expression | EST | Mm.41122 | TITLE ESTs | | | gi = 2283180 | 1265841 |
| IC11312 | UG75 Expression | EST | Mm.41125 | TITLE ESTs | | | gi = 2744985 | 1264933 |
| IC11313 | UG75 Expression | EST | Mm.41128 | TITLE ESTs, Weakly similar to zinc finger protein 95 [M. musculus] | | | gi = 1479954 | 717996 |
| IC11314 | UG75 Expression | EST | Mm.41132 | TITLE ESTs | | | gi = 5494978 | 1346023 |
| IC11315 | UG75 Expression | EST | Mm.41133 | TITLE ESTs, Moderately similar to KIAA0728 protein [H. sapiens] | | | gi = 2626730 | 1001750 |
| IC11316 | UG75 Expression | EST | Mm.41134 | TITLE ESTs | | | gi = 6526336 | 764997 |
| IC11317 | UG75 Expression | EST | Mm.41135 | TITLE ESTs | | | gi = 2756146 | 972761 |
| IC11318 | UG75 Expression | EST | Mm.41138 | TITLE ESTs, Moderately similar to RETINOBLASTOMA BINDING PROTEIN 1 [H. sapiens] | | | gi = 5474360 | 618571 |
| IC11319 | UG75 Expression | EST | Mm.41140 | TITLE ESTs | | | gi = 5498224 | 1749607 |
| IC11320 | UG75 Expression | EST | Mm.41143 | TITLE ESTs | | | gi = 5498173 | 1749922 |
| IC11321 | UG75 Expression | EST | Mm.41151 | TITLE ESTs | | | gi = 1936475 | 750750 |
| IC11322 | UG75 Expression | EST | Mm.41155 | TITLE ESTs | | | gi = 1752533 | 1225627 |
| IC11323 | UG75 Expression | EST | Mm.41159 | TITLE ESTs | | | gi = 4723157 | 1001983 |
| IC11324 | UG75 Expression | EST | Mm.41160 | TITLE ESTs | | | gi = 2626318 | 959413 |
| IC11325 | UG75 Expression | EST | Mm.41161 | TITLE ESTs | | | gi = 59089945 | 618306 |
| IC11326 | UG75 Expression | EST | Mm.41164 | TITLE ESTs, Weakly similar to cDNA EST EMBL:D32434 comes from this gene [C. elegans] | | | gi = 2308272 | 958932 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11327 | UG75 Expression | EST | Mm.41170 | TITLE ESTs, Moderately similar to RANTES factor of late activated T lymphoctyes-1 [H. sapiens] | | | gi = 4537488 | 643836 |
| IC11328 | UG75 Expression | EST | Mm.41172 | TITLE ESTs, Weakly similar to KRUEPPEL PROTEIN [Drosophila melanogaster] | | | gi = 1529807 | 1446718 |
| IC11329 | UG75 Expression | EST | Mm.41176 | TITLE ESTs, Moderately similar to Rabin3 [R. norvegicus] | | | gi = 3718362 | 637973 |
| IC11330 | UG75 Expression | EST | Mm.41180 | TITLE ESTs, Weakly similar to unknown [M. musculus] | | | gi = 2187895 | 1262915 |
| IC11331 | UG75 Expression | EST | Mm.41181 | Genscan predictions confirmed by EST splicing. [H. sapiens] | | | gi = 608723 | 1264323 |
| IC11332 | UG75 Expression | EST | Mm.41182 | TITLE ESTs | | | gi = 1494446 | 622885 |
| IC11333 | UG75 Expression | EST | Mm.41191 | TITLE ESTs | | | gi = 4276529 | 777356 |
| IC11334 | UG75 Expression | EST | Mm.41192 | TITLE ESTs | | | gi = 3749951 | 637333 |
| IC11335 | UG75 Expression | EST | Mm.41214 | TITLE ESTs, Weakly similar to LIV-1 protein [H. sapiens] | | | gi = 3718283 | 1001929 |
| IC11336 | UG75 Expression | EST | Mm.41216 | TITLE ESTs | | | gi = 2040232 | 1361232 |
| IC11337 | UG75 Expression | EST | Mm.41218 | TITLE ESTs | | | gi = 2306049 | 750536 |
| IC11338 | UG75 Expression | EST | Mm.41221 | TITLE ESTs, Weakly similar to Nbr1 [M. musculus] | | | gi = 5666534 | 1139629 |
| IC11339 | UG75 Expression | EST | Mm.41227 | TITLE ESTs, Weakly similar to Weak similarity with myosin proteins [C. elegans] | | | gi = 4433953 | 1243273 |
| IC11340 | UG75 Expression | EST | Mm.41228 | TITLE ESTs | | | gi = 4443595 | 734275 |
| IC11341 | UG75 Expression | EST | Mm.41229 | TITLE ESTs, Weakly similar to KIAA0386 [H. sapiens] | | | gi = 4276843 | 574836 |
| IC11342 | UG75 Expression | EST | Mm.41242 | TITLE ESTs | | | gi = 5908907 | 1001713 |
| IC11343 | UG75 Expression | EST | Mm.41245 | TITLE ESTs, Weakly similar to coded for by C. elegans cDNA cm21e6 [C. elegans] | | | gi = 2503228 | 634844 |
| IC11344 | UG75 Expression | EST | Mm.41247 | TITLE ESTs | | | gi = 3749974 | 1225559 |
| IC11345 | UG75 Expression | EST | Mm.41257 | TITLE ESTs | | | gi = 1760030 | 621097 |
| IC11346 | UG75 Expression | EST | Mm.41260 | TITLE ESTs, Weakly similar to B7 [M. musculus] | | | gi = 1326545 | 1749286 |
| IC11347 | UG75 Expression | EST | Mm.41261 | TITLE ESTs, Weakly similar to KIAA0386 [H. sapiens] | | | gi = 3216332 | 751143 |
| IC11348 | UG75 Expression | EST | Mm.41263 | TITLE ESTs | | | gi = 4316336 | 1382293 |
| IC11349 | UG75 Expression | EST | Mm.41265 | TITLE ESTs | | | gi = 2305978 | 973393 |
| IC11350 | UG75 Expression | EST | Mm.41267 | TITLE ESTs | | | gi = 1684167 | 639273 |
| IC11351 | UG75 Expression | EST | Mm.41268 | TITLE ESTs, Moderately similar to PEROXISOME BIOSYNTHESIS PROTEIN PAY4 [Yarrowia lipolytica] | | | gi = 3602589 | 636056 |
| IC11352 | UG75 Expression | EST | Mm.41269 | TITLE ESTs | | | gi = 4434584 | 598842 |
| IC11353 | UG75 Expression | EST | Mm.41271 | TITLE ESTs | | | gi = 5499038 | 749537 |
| IC11354 | UG75 Expression | EST | Mm.41272 | TITLE ESTs | | | gi = 2259104 | 2609502 |
| IC11355 | UG75 Expression | EST | Mm.41273 | TITLE ESTs | | | gi = 2807284 | 722893 |
| IC11356 | UG75 Expression | EST | Mm.41274 | TITLE ESTs | | | gi = 2283177 | 1446209 |
| IC11357 | UG75 Expression | EST | Mm.41275 | TITLE ESTs, Weakly similar to NUCLEAR PROTEIN SNF7 [Saccharomyces cerevisiae] | | | gi = 2306129 | 893845 |
| IC11358 | UG75 Expression | EST | Mm.41279 | TITLE ESTs | | | gi = 5125521 | 643060 |
| IC11359 | UG75 Expression | EST | Mm.41304 | TITLE ESTs | | | gi = 1767665 | 621866 |
| IC11360 | UG75 Expression | EST | Mm.41305 | TITLE ESTs | | | gi = 6078896 | 2225655 |
| IC11361 | UG75 Expression | EST | Mm.41307 | TITLE ESTs, Weakly similar to apoptotic protease activating factor 1 [M. musculus] | | | gi = 6167754 | 718339 |
| IC11362 | UG76 LID366 B cell | EST | Mm.41313 | TITLE ESTs, Moderately similar to FGFR1 oncogene partner [H. sapiens] | | | gi = 7066507 | 1195227 |
| IC11363 | UG75 Expression | EST | Mm.41317 | TITLE ESTs | | | gi = 1676538 | 643579 |
| IC11364 | UG75 Expression | EST | Mm.41320 | TITLE ESTs | | | gi = 5472976 | 752183 |
| IC11365 | UG75 Expression | EST | Mm.41328 | TITLE ESTs | | | gi = 6083764 | 777549 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11366 | UG75 Expression | EST | Mm.41331 | TITLE ESTs, Weakly similar to putative ATPase [H. sapiens] | | | gi = 2142724 | 749721 |
| IC11367 | UG75 Expression | EST | Mm.41335 | TITLE ESTs | | | gi = 1793266 | 640190 |
| IC11368 | UG75 Expression | EST | Mm.41336 | TITLE ESTs, Moderately similar to SERINE/THREONINE PROTEIN PHOSPHATASE 6 [R. norvegicus] | | | gi = 1937426 | 749392 |
| IC11369 | UG75 Expression | EST | Mm.41339 | TITLE ESTs | | | gi = 3067209 | 1327583 |
| IC11370 | UG75 Expression | EST | Mm.41340 | TITLE ESTs | | | gi = 6574346 | 621588 |
| IC11371 | UG75 Expression | EST | Mm.41342 | TITLE ESTs | | | gi = 2292014 | 958762 |
| IC11372 | UG75 Expression | EST | Mm.41347 | TITLE ESTs | | | gi = 1519898 | 1225181 |
| IC11373 | UG75 Expression | EST | Mm.41351 | TITLE ESTs | | | gi = 1551096 | 750953 |
| IC11374 | UG75 Expression | EST | Mm.41352 | TITLE ESTs | | | gi = 1683961 | 972777 |
| IC11375 | UG75 Expression | EST | Mm.41353 | TITLE ESTs | | | gi = 2256861 | 894283 |
| IC11376 | UG75 Expression | EST | Mm.41356 | TITLE ESTs | | | gi = 1485731 | 38852 |
| IC11377 | UG75 Expression | EST | Mm.41358 | TITLE ESTs | | | gi = 5124647 | 551029 |
| IC11378 | UG75 Expression | EST | Mm.41360 | TITLE ESTs | | | gi = 3517184 | 620759 |
| IC11379 | UG75 Expression | EST | Mm.41366 | TITLE ESTs, Moderately similar to repressor protein | | | gi = 1290298 | 577692 |
| IC11380 | UG75 Expression | EST | Mm.41367 | TITLE ESTs, Moderately similar to hypothetical protein [H. sapiens] | | | gi = 6749052 | 972820 |
| IC11381 | UG75 Expression | EST | Mm.41368 | TITLE DNA Segment, Chr 15 Massachusetts Institute of Technology 260 | GENE D15Mit260 | | | 597026 |
| IC11382 | UG75 Expression | EST | Mm.41372 | TITLE ESTs | | | gi = 1436007 | 623024 |
| IC11383 | UG75 Expression | EST | Mm.41374 | TITLE Trk-fused gene | GENE Tfg | | gi = 4199331 | 617047 |
| IC11384 | UG75 Expression | EST | Mm.41375 | TITLE guanine nucleotide binding protein (G protein), gamma 12 | GENE Gng12 | | gi = 1912546 | 764426 |
| IC11385 | UG75 Expression | EST | Mm.41382 | TITLE ESTs | | | gi = 1767761 | 622323 |
| IC11386 | UG75 Expression | EST | Mm.41383 | TITLE ESTs | | | gi = 4783412 | 597230 |
| IC11387 | UG75 Expression | EST | Mm.41388 | TITLE ESTs | | | gi = 1912725 | 764488 |
| IC11388 | UG75 Expression | EST | Mm.41390 | TITLE ESTs, Weakly similar to/prediction | | | gi = 5550505 | 722424 |
| IC11389 | UG75 Expression | EST | Mm.41393 | TITLE ESTs | | | gi = 2272697 | 722566 |
| IC11390 | UG75 Expression | EST | Mm.41394 | TITLE ESTs, Moderately similar to PROBABLE ATP-DEPENDENT RNA HELICASE DDX10 [H. sapiens] | | | gi = 4724529 | 749569 |
| IC11391 | UG75 Expression | EST | Mm.41398 | TITLE ESTs, Moderately similar to (define not available 5457150) [M. musculus] | | | gi = 6084222 | 619484 |
| IC11392 | UG75 Expression | EST | Mm.41399 | TITLE ESTs | | | gi = 2813533 | 582543 |
| IC11393 | UG75 Expression | EST | Mm.41404 | TITLE ESTs | | | gi = 3067281 | 1193561 |
| IC11394 | UG75 Expression | EST | Mm.41406 | TITLE ESTs, Weakly similar to (define not available 6016842) [M. musculus] | | | gi = 1677813 | 1362960 |
| IC11395 | UG75 Expression | EST | Mm.41411 | TITLE ESTs | | | gi = 1904606 | 723318 |
| IC11396 | UG75 Expression | EST | Mm.41412 | TITLE ESTs | | | gi = 4407172 | 1278711 |
| IC11397 | UG75 Expression | EST | Mm.41416 | TITLE ESTs | | | gi = 1904955 | 765201 |
| IC11398 | UG75 Expression | EST | Mm.41419 | TITLE ESTs | | | gi = 4600737 | 1328881 |
| IC11399 | UG75 Expression | EST | Mm.41420 | TITLE ESTs, Weakly similar to Evi-5 [M. musculus] | | | gi = 2203451 | 1140172 |
| IC11400 | UG75 Expression | EST | Mm.41423 | TITLE ESTs | | | gi = 5494843 | 1223132 |
| IC11401 | UG75 Expression | EST | Mm.41428 | TITLE ESTs, Moderately similar to Ku70-binding protein [H. sapiens] | | | gi = 2729153 | 719075 |
| IC11402 | UG75 Expression | EST | Mm.41432 | TITLE ESTs, Moderately similar to calcium and DAG-regulated guanine nucleotide exchange factor I [M. musculus] | | | gi = 2646138 | 1225837 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11403 | UG75 Expression | EST | Mm.41438 | TITLE ESTs | | | gi = 1715880 | 596607 |
| IC11404 | UG75 Expression | EST | Mm.41440 | TITLE ESTs, Moderately similar to ZINC FINGER PROTEIN MFG1 [*Mus musculus*] | | | gi = 5474133 | 777635 |
| IC11405 | UG75 Expression | EST | Mm.41441 | TITLE ESTs | | | gi = 4031923 | 1395475 |
| IC11406 | UG75 Expression | EST | Mm.41445 | TITLE ESTs, Weakly similar to a thyroid hormone responsive gene in human skin fibroblasts [*H. sapiens*] | | | gi = 2074642 | 639681 |
| IC11407 | UG75 Expression | EST | Mm.41447 | HELICASE-DNA-BINDING PROTEIN CHD-1 [*Mus musculus*] | | | gi = 4059293 | 472805 |
| IC11408 | UG75 Expression | EST | Mm.41449 | TITLE ESTs | | | gi = 4484613 | 637239 |
| IC11409 | UG75 Expression | EST | Mm.41450 | TITLE ESTs, Weakly similar to F33G12.3 gene product [*C. elegans*] | | | gi = 6077329 | 2270207 |
| IC11410 | UG75 Expression | EST | Mm.41451 | TITLE ESTs | | | gi = 2964833 | 1429736 |
| IC11411 | UG75 Expression | EST | Mm.41452 | TITLE ESTs | | | gi = 5265615 | 440673 |
| IC11412 | UG75 Expression | EST | Mm.41457 | TITLE ESTs | | | gi = 5491455 | 1229472 |
| IC11413 | UG75 Expression | EST | Mm.41458 | TITLE ESTs | | | gi = 2906930 | 617629 |
| IC11414 | UG75 Expression | EST | Mm.41460 | TITLE ESTs, Weakly similar to proline-rich protein 15 [*R. norvegicus*] | | | gi = 1901309 | 573246 |
| IC11415 | UG75 Expression | EST | Mm.41463 | TITLE ESTs, Weakly similar to UbcM4 interacting protein 28[*M. musculus*] | | | gi = 1349119 | 622692 |
| IC11416 | UG75 Expression | EST | Mm.41464 | TITLE ESTs, Weakly similar to F53E2.1 [*C. elegans*] | | | gi = 5478009 | 596333 |
| IC11417 | UG75 Expression | EST | Mm.41465 | TITLE ESTs | | | gi = 2918093 | 749066 |
| IC11418 | UG75 Expression | EST | Mm.41466 | TITLE ESTs | | | gi = 6084812 | 619794 |
| IC11419 | UG75 Expression | EST | Mm.41470 | TITLE ESTs | | | gi = 2720362 | 720988 |
| IC11420 | UG75 Expression | EST | Mm.41472 | TITLE ESTs, Weakly similar to weakly similar to *S. cerevisiae* CBP3 protein precursor [*C. elegans*] | | | gi = 5910569 | 751084 |
| IC11421 | UG75 Expression | EST | Mm.41477 | TITLE ESTs | | | gi = 5124644 | 1379152 |
| IC11422 | UG75 Expression | EST | Mm.41479 | TITLE ESTs | | | gi = 6084344 | 717922 |
| IC11423 | UG75 Expression | EST | Mm.41481 | TITLE staufen (RNA-binding protein) homolog 2 (Drosophila) | GENE Stau2 | | gi = 5630091 | 974076 |
| IC11424 | UG75 Expression | EST | Mm.41488 | TITLE ESTs, Weakly similar to tumor suppressor [*H. sapiens*] | | | gi = 6519322 | 720952 |
| IC11425 | UG75 Expression | EST | Mm.41489 | TITLE ESTs | | | gi = 5475739 | 636947 |
| IC11426 | UG75 Expression | EST | Mm.41491 | TITLE ESTs | | | gi = 4729741 | 750767 |
| IC11427 | UG75 Expression | EST | Mm.41492 | TITLE ESTs | | | gi = 5498115 | 388343 |
| IC11428 | UG75 Expression | EST | Mm.41493 | TITLE ESTs, Weakly similar to SIG41 [*M. musculus*] | | | gi = 4290263 | 577064 |
| IC11429 | UG75 Expression | EST | Mm.41495 | TITLE ESTs, Moderately similar to NY-REN-45 antigen [*H. sapiens*] | | | gi = 2306330 | 1295842 |
| IC11430 | UG75 Expression | EST | Mm.41496 | TITLE ESTs, Weakly similar to OVCA2 | | | gi = 2201624 | 637093 |
| IC11431 | UG75 Expression | EST | Mm.41497 | TITLE ESTs | | | gi = 4032483 | 1429526 |
| IC11432 | UG75 Expression | EST | Mm.41506 | TITLE ESTs, Weakly similar to Dreg-2 protein [*D. melanogaster*] | | | gi = 5333251 | 1225415 |
| IC11433 | UG75 Expression | EST | Mm.41507 | TITLE ESTs | | | gi = 4722609 | 622872 |
| IC11434 | UG75 Expression | EST | Mm.41508 | TITLE ESTs, Weakly similar to Atu [*D. melanogaster*] | | | gi = 5470877 | 1749177 |
| IC11435 | UG75 Expression | EST | Mm.41511 | TITLE ESTs | | | gi = 4726646 | 637305 |
| IC11436 | UG75 Expression | EST | Mm.41512 | TITLE ESTs | | | gi = 1826765 | 721091 |
| IC11437 | UG75 Expression | EST | Mm.41513 | TITLE ESTs | | | gi = 5477955 | 2649595 |
| IC11438 | UG75 Expression | EST | Mm.41518 | TITLE ESTs | | | gi = 1500816 | 973756 |
| IC11439 | UG75 Expression | EST | Mm.4152 | TITLE ESTs | | | gi = 2346360 | 1282649 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11440 | UG75 Expression | EST | Mm.41531 | TITLE ESTs, Moderately similar to AAC-RICH MRNA CLONE AAC3 PROTEIN [Dictyostelium discoideum] | | | gi = 1767936 | 551427 |
| IC11441 | UG75 Expression | EST | Mm.41532 | TITLE ESTs | | | gi = 1758938 | 622914 |
| IC11442 | UG75 Expression | EST | Mm.41533 | TITLE ESTs | | | gi = 1287904 | 1263816 |
| IC11443 | UG75 Expression | EST | Mm.41535 | TITLE ESTs | | | gi = 2893638 | 596707 |
| IC11444 | UG75 Expression | EST | Mm.41538 | TITLE ESTs, Moderately similar to PLATELET BASIC PROTEIN PRECURSOR [Sus scrofa] | | | gi = 1909080 | 752492 |
| IC11445 | UG75 Expression | EST | Mm.41539 | TITLE ESTs, Moderately similar to HYPOTHETICAL 32.7 KD PROTEIN IN NTH2-COQ1 INTERGENIC REGION [Saccharomyces cerevisiae] | | | gi = 6084328 | 973543 |
| IC11446 | UG75 Expression | EST | Mm.41540 | TITLE ESTs | | | gi = 2906762 | 623021 |
| IC11447 | UG75 Expression | EST | Mm.41541 | TITLE ESTs, Moderately similar to protein DS 1,24K [H. sapiens] | | | gi = 1682305 | 1379898 |
| IC11448 | UG75 Expression | EST | Mm.41543 | TITLE ESTs, Weakly similar to C13F10.7 [C. elegans] | | | gi = 2962269 | 1361464 |
| IC11449 | UG75 Expression | EST | Mm.41550 | TITLE ESTs | | | gi = 1407182 | 639462 |
| IC11450 | UG75 Expression | EST | Mm.41551 | TITLE ESTs | | | gi = 2625738 | 640283 |
| IC11451 | UG75 Expression | EST | Mm.41558 | TITLE ESTs | | | gi = 6078305 | 596956 |
| IC11452 | UG75 Expression | EST | Mm.41561 | TITLE ESTs | | | gi = 1768888 | 634438 |
| IC11453 | UG75 Expression | EST | Mm.41563 | TITLE ESTs | | | gi = 4293287 | 751687 |
| IC11454 | UG75 Expression | EST | Mm.41565 | TITLE ESTs, Weakly similar to coded for by C. elegans cDNA yk52e10.5 [C. elegans] | | | gi = 5819448 | 598535 |
| IC11455 | UG75 Expression | EST | Mm.41567 | TITLE ESTs | | | gi = 6938107 | 576453 |
| IC11456 | UG75 Expression | EST | Mm.41568 | TITLE ESTs, Moderately similar to ZINC FINGER PROTEIN HF.12 [Homo sapiens] | | | gi = 2813125 | 1327699 |
| IC11457 | UG75 Expression | EST | Mm.41578 | TITLE ESTs | | | gi = 6645880 | 1149773 |
| IC11458 | UG75 Expression | EST | Mm.41581 | TITLE ESTs | | | gi = 4031963 | 751132 |
| IC11459 | UG75 Expression | EST | Mm.41582 | TITLE ESTs | | | gi = 1919244 | 777434 |
| IC11460 | UG75 Expression | EST | Mm.41583 | TITLE ESTs, Moderately similar to PTD015 [H. sapiens] | | | gi = 2283198 | 1264501 |
| IC11461 | UG75 Expression | EST | Mm.41589 | TITLE ESTs | | | gi = 1682380 | 577182 |
| IC11462 | UG75 Expression | EST | Mm.41593 | TITLE ESTs, Weakly similar to latent TGF-beta binding protein-2 [M. musculus] | | | gi = 1862632 | 481777 |
| IC11463 | UG75 Expression | EST | Mm.41596 | TITLE ESTs | | | gi = 1309508 | 750819 |
| IC11464 | UG75 Expression | EST | Mm.41603 | TITLE ESTs | | | gi = 3718680 | 636912 |
| IC11465 | UG75 Expression | EST | Mm.41608 | TITLE ESTs | | | gi = 3066891 | 1327559 |
| IC11466 | UG75 Expression | EST | Mm.41616 | TITLE ESTs | | | gi = 5488730 | 752204 |
| IC11467 | UG75 Expression | EST | Mm.41617 | TITLE ESTs, Weakly similar to veli 3 [M. musculus] | | | gi = 2592748 | 1148943 |
| IC11468 | UG75 Expression | EST | Mm.41618 | TITLE ESTs | | | gi = 5498334 | 1226067 |
| IC11469 | UG75 Expression | EST | Mm.41621 | TITLE ESTs | | | gi = 1379875 | 597916 |
| IC11470 | UG75 Expression | EST | Mm.41629 | TITLE ESTs | | | gi = 2560942 | 1750111 |
| IC11471 | UG75 Expression | EST | Mm.41631 | TITLE ESTs | | | gi = 2885752 | 1079562 |
| IC11472 | UG75 Expression | EST | Mm.41634 | TITLE ESTs, Moderately similar to KIAA0898 protein [H. sapiens] | | | gi = 5597550 | 2655150 |
| IC11473 | UG75 Expression | EST | Mm.41635 | TITLE ESTs | | | gi = 3682071 | 1293792 |
| IC11474 | UG75 Expression | EST | Mm.41636 | TITLE ESTs | | | gi = 3683052 | 598737 |
| IC11475 | UG75 Expression | EST | Mm.41641 | TITLE ESTs, Weakly similar to XY40 protein [R. norvegicus] | | | gi = 2116469 | 619941 |
| IC11476 | UG75 Expression | EST | Mm.41643 | TITLE ESTs | | | gi = 4305588 | 643455 |
| IC11477 | UG75 Expression | EST | Mm.41647 | TITLE ESTs | | | gi = 2943526 | 1345583 |
| IC11478 | UG75 Expression | EST | Mm.41648 | TITLE ESTs | | | gi = 5495952 | 750228 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11479 | UG75 Expression | EST | Mm.41649 | TITLE ESTs | | | gi = 2561248 | 619419 |
| IC11480 | UG75 Expression | EST | Mm.41654 | TITLE ESTs | | | gi = 1841194 | 1265388 |
| IC11481 | UG75 Expression | EST | Mm.41656 | TITLE ESTs, Moderately similar to PEPTIDYL-PROLYL CIS-TRANS ISOMERASE A [M. musculus] | | | gi = 2962658 | 1148689 |
| IC11482 | UG75 Expression | EST | Mm.41657 | TITLE ESTs | | | gi = 5549713 | 1002843 |
| IC11483 | UG75 Expression | EST | Mm.41658 | TITLE ESTs | | | gi = 2291951 | 1264103 |
| IC11484 | UG75 Expression | EST | Mm.41663 | TITLE ESTs | | | gi = 2591275 | 1293824 |
| IC11485 | UG75 Expression | EST | Mm.41664 | TITLE expressed sequence tag mouse EST 2 | GENE ESTM2 | | gi = 949911 | 1227129 |
| IC11486 | UG75 Expression | EST | Mm.41665 | TITLE ESTs, Weakly similar to proline-rich protein [M. musculus] | | | gi = 4968305 | 764513 |
| IC11487 | UG75 Expression | EST | Mm.41668 | TITLE ESTs | | | gi = 5498143 | 597703 |
| IC11488 | UG75 Expression | EST | Mm.41670 | TITLE ESTs, Weakly similar to SURVIVAL MOTOR NEURON PROTEIN 1 [M. musculus] | | | gi = 2284412 | 1279042 |
| IC11489 | UG75 Expression | EST | Mm.41671 | TITLE ESTs | | | gi = 2775764 | 577783 |
| IC11490 | UG75 Expression | EST | Mm.41676 | TITLE ESTs | | | gi = 1903545 | 718429 |
| IC11491 | UG75 Expression | EST | Mm.41678 | TITLE ESTs, Moderately similar to HYPOTHETICAL 36.7 KD PROTEIN C2F7.02C IN CHROMOSOME I [Schizosaccharomyces pombe] | | | gi = 2158116 | 1295575 |
| IC11492 | UG75 Expression | EST | Mm.41683 | TITLE ESTs | | | gi = 1901502 | 1134750 |
| IC11493 | UG75 Expression | EST | Mm.41686 | TITLE ESTs | | | gi = 1554627 | 765105 |
| IC11494 | UG75 Expression | EST | Mm.41687 | TITLE ESTs, Weakly similar to T28F2.2 [C. elegans] | | | gi = 3168518 | 1294896 |
| IC11495 | UG75 Expression | EST | Mm.41690 | TITLE ESTs | | | gi = 4031782 | 1446147 |
| IC11496 | UG75 Expression | EST | Mm.41693 | TITLE ESTs | | | gi = 4726853 | 598631 |
| IC11497 | UG75 Expression | EST | Mm.41694 | TITLE ESTs | | | gi = 5475713 | 1762656 |
| IC11498 | UG75 Expression | EST | Mm.41695 | TITLE ESTs, Weakly similar to periplakin [M. musculus] | | | gi = 4402628 | 972607 |
| IC11499 | UG75 Expression | EST | Mm.41699 | TITLE ESTs | | | gi = 1755343 | 1279327 |
| IC11500 | UG75 Expression | EST | Mm.41704 | TITLE ESTs | | | gi = 5497113 | 863333 |
| IC11501 | UG75 Expression | EST | Mm.41704 | TITLE ESTs, Weakly similar to hypothetical protein [H. sapiens] | | | gi = 4723873 | 582920 |
| IC11502 | UG75 Expression | EST | Mm.41707 | TITLE ESTs, Moderately similar to putative [C. elegans] | | | gi = 2157904 | 1149163 |
| IC11503 | UG75 Expression | EST | Mm.41711 | TITLE ESTs, Moderately similar to PRAJA1 [M. musculus] | | | gi = 2692715 | 958624 |
| IC11504 | UG75 Expression | EST | Mm.41713 | TITLE ESTs, Weakly similar to coded for by C. elegans cDNA yk20t8.5 [C. elegans] | | | gi = 1309421 | 1265512 |
| IC11505 | UG75 Expression | EST | Mm.41714 | TITLE ESTs | | | gi = 5492291 | 635779 |
| IC11506 | UG75 Expression | EST | Mm.41715 | TITLE ESTs | | | gi = 1808552 | 1149095 |
| IC11507 | UG75 Expression | EST | Mm.41718 | TITLE ESTs | | | gi = 2691612 | 1312097 |
| IC11508 | UG75 Expression | EST | Mm.41719 | TITLE ESTs, Moderately similar to match to ESTs AA307614 [H. sapiens] | | | gi = 2292503 | 2192574 |
| IC11509 | UG75 Expression | EST | Mm.41720 | TITLE ESTs | | | gi = 1755940 | 617616 |
| IC11510 | UG75 Expression | EST | Mm.41722 | TITLE ESTs | | | gi = 5495426 | 1139708 |
| IC11511 | UG75 Expression | EST | Mm.41723 | TITLE ESTs | | | gi = 1672818 | 1329375 |
| IC11512 | UG75 Expression | EST | Mm.41724 | TITLE ESTs | | | gi = 4803612 | 2651637 |
| IC11513 | UG75 Expression | EST | Mm.41725 | TITLE ESTs | | | gi = 1683976 | 1293708 |
| IC11514 | UG75 Expression | EST | Mm.41728 | PEROXISOMAL ENOYL-COA HYDRATASE [M. musculus] | | | gi = 2234868 | 717772 |
| IC11515 | UG75 Expression | EST | Mm.41730 | TITLE ESTs | | | gi = 1853734 | 551447 |
| IC11516 | UG75 Expression | EST | Mm.41733 | TITLE ESTs | | | gi = 1375557 | 1295846 |
| IC11517 | UG75 Expression | EST | Mm.41734 | TITLE ESTs, Weakly similar to HEPATOMA-DERIVED GROWTH FACTOR [M. musculus] | | | gi = 1682862 | 578023 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11518 | UG75 Expression | EST | Mm.41735 | TITLE ESTs, Weakly similar to (define not available 6014493 [M. musculus] | | | gi = 2572272 | 1139803 |
| IC11519 | UG75 Expression | EST | Mm.41738 | TITLE ESTs | | | gi = 6078912 | 777825 |
| IC11520 | UG75 Expression | EST | Mm.41739 | [M. musculus] | | | gi = 2907049 | 621762 |
| IC11521 | UG75 Expression | EST | Mm.41741 | TITLE ESTs | | | gi = 6939469 | 617721 |
| IC11522 | UG75 Expression | EST | Mm.41744 | TITLE ESTs | | | gi = 2990802 | 721109 |
| IC11523 | UG75 Expression | EST | Mm.41745 | TITLE ESTs | | | gi = 5597752 | 583255 |
| IC11524 | UG75 Expression | EST | Mm.41750 | TITLE ESTs, Moderately similar to RAS-RELATED PROTEIN RAB04A [M. musculus] | | | gi = 1919588 | 777256 |
| IC11525 | UG75 Expression | EST | Mm.41751 | TITLE ESTs, Weakly similar to coxsackie and adenovirus receptor homologue [M. musculus] | | | gi = 1290073 | 717904 |
| IC11526 | 00/04/26 UG#76 17 Lid Expansion | EST | Mm.41752 | ESTs | — | | gi = 5491840 | 1762532 |
| IC11527 | 00/04/26 UG#76 | EST | Mm.41756 | ESTs | — | | gi = 1310244 | 1279508 |
| IC11528 | 00/04/26 UG#76 | EST | Mm.4176 | ESTs | | | gi = 7197895 | 861747 |
| IC11529 | UG75 Expression | EST | Mm.41761 | TITLE ESTs | | | gi = 1908782 | 1365850 |
| IC11530 | UG75 Expression | EST | Mm.41762 | TITLE ESTs, Weakly similar to cappuccino [D. melanogaster] | | | gi = 2193184 | 618984 |
| IC11531 | UG75 Expression | EST | Mm.41763 | TITLE ESTs | | | gi = 1929731 | 576821 |
| IC11532 | UG75 Expression | EST | Mm.41767 | TITLE ESTs, Weakly similar to R09B5.12 [C. elegans] | | | gi = 4434011 | 1429582 |
| IC11533 | UG75 Expression | EST | Mm.41768 | TITLE ESTs | | | gi = 6084135 | 1264037 |
| IC11534 | UG75 Expression | EST | Mm.41772 | TITLE ESTs | | | gi = 1755316 | 479071 |
| IC11535 | UG75 Expression | EST | Mm.41773 | TITLE ESTs | | | gi = 5402592 | 554336 |
| IC11536 | UG75 Expression | EST | Mm.41778 | TITLE ESTs | | | gi = 2625734 | 1002129 |
| IC11537 | UG75 Expression | EST | Mm.41779 | TITLE ESTs, Weakly similar to predicted using Genefinder [C. elegans] | | | gi = 7066684 | 737010 |
| IC11538 | UG75 Expression | EST | Mm.41780 | TITLE guanine nucleotide binding protein (G protein), gamma 10 | GENE Gng10 | | gi = 4783511 | 972603 |
| IC11539 | UG75 Expression | EST | Mm.41786 | TITLE ESTs | | | gi = 2456474 | 551529 |
| IC11540 | UG75 Expression | EST | Mm.41788 | TITLE ESTs | | | gi = 5861344 | 1148437 |
| IC11541 | UG75 Expression | EST | Mm.41792 | TITLE ESTs, Moderately similar to 70 KD WD-REPEAT TUMOR-SPECIFIC ANTIGEN [R. norvegicus] | | | gi = 1777025 | 749235 |
| IC11542 | UG75 Expression | EST | Mm.41793 | TITLE ESTs | | | gi = 4726888 | 640434 |
| IC11543 | UG75 Expression | EST | Mm.41797 | TITLE ESTs | | | gi = 1333389 | 533390 |
| IC11544 | UG75 Expression | EST | Mm.41800 | TITLE ESTs, Moderately similar to (define not available 5901862) [D. melanogaster] | | | gi = 6079138 | 1020742 |
| IC11545 | UG75 Expression | EST | Mm.41801 | TITLE ESTs, Moderately similar to ribonuclease P protein subunit p14 [H. sapiens] | | | gi = 6084991 | 1282290 |
| IC11546 | UG75 Expression | EST | Mm.41804 | TITLE ESTs, Weakly similar to K11B4.2 [C. elegans] | | | gi = 1291920 | 1394962 |
| IC11547 | UG75 Expression | EST | Mm.41808 | TITLE ESTs | | | gi = 6084170 | 1749666 |
| IC11548 | UG75 Expression | EST | Mm.41824 | TITLE ESTs, Moderately similar to molybdopterin synthase sulfurylase [H. sapiens] | | | gi = 5473732 | 1225852 |
| IC11549 | UG75 Expression | EST | Mm.41829 | TITLE ESTs | | | gi = 5475963 | 721484 |
| IC11550 | UG75 Expression | EST | Mm.41832 | TITLE ESTs | | | gi = 2327328 | 765814 |
| IC11551 | UG75 Expression | EST | Mm.41833 | TITLE ESTs | | | gi = 6083823 | 1282316 |
| IC11552 | UG75 Expression | EST | Mm.41847 | TITLE ESTs | | | gi = 4434404 | 777827 |
| IC11553 | UG75 Expression | EST | Mm.41851 | TITLE ESTs | | | gi = 5493365 | 1001771 |
| IC11554 | UG75 Expression | EST | Mm.41854 | TITLE ESTs | | | gi = 1661899 | 777762 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11555 | UG75 Expression | EST | Mm.41856 | TITLE ESTs, Weakly similar to cDNA EST EMBL:D70654 comes from this gene [*C. elegans*] | | | gi = 2257325 | 640297 |
| IC11556 | UG75 Expression | EST | Mm.41858 | TITLE ESTs, Weakly similar to GENERAL NEGATIVE REGULATOR OF TRANSCRIPTION SUBUNIT 1 [*Saccharomyces cerevisiae*] | | | gi = 1355402 | 1001479 |
| IC11557 | UG75 Expression | EST | Mm.41862 | TITLE ESTs | | | gi = 6748191 | 576283 |
| IC11558 | UG75 Expression | EST | Mm.41863 | TITLE ESTs, Moderately similar to Nup98-Nup96 precursor [*H. sapiens*] | | | gi = 571318 | 598661 |
| IC11559 | UG75 Expression | EST | Mm.41865 | TITLE ESTs | | | gi = 3522469 | 1445994 |
| IC11560 | UG75 Expression | EST | Mm.41867 | TITLE ESTs | | | gi = 2404392 | 596449 |
| IC11561 | UG75 Expression | EST | Mm.41868 | TITLE ESTs | | | gi = 2192910 | 597246 |
| IC11562 | UG75 Expression | EST | Mm.41869 | TITLE ESTs | | | gi = 1841572 | 722558 |
| IC11563 | UG75 Expression | EST | Mm.41874 | TITLE ESTs | | | gi = 1660573 | 642865 |
| IC11564 | UG75 Expression | EST | Mm.41882 | TITLE ESTs, Weakly similar to FAF1 PROTEIN [*M. musculus*] | | | gi = 6632021 | 1380073 |
| IC11565 | UG75 Expression | EST | Mm.41890 | TITLE ESTs | | | gi = 4779015 | 1279466 |
| IC11566 | UG75 Expression | EST | Mm.41892 | TITLE ESTs | | | gi = 2291598 | 617626 |
| IC11567 | UG75 Expression | EST | Mm.41894 | TITLE ESTs | | | gi = 2292216 | 1263207 |
| IC11568 | UG75 Expression | EST | Mm.41895 | TITLE ESTs | | | gi = 4764772 | 721819 |
| IC11569 | UG75 Expression | EST | Mm.41896 | TITLE ESTs | | | gi = 3683869 | 765116 |
| IC11570 | UG75 Expression | EST | Mm.41902 | TITLE ESTs, Weakly similar to zinc finger transcription factor REST protein [*R. norvegicus*] | | | gi = 2262952 | 1264953 |
| IC11571 | UG75 Expression | EST | Mm.41904 | TITLE ESTs | | | gi = 1756092 | 617695 |
| IC11572 | UG75 Expression | EST | Mm.41907 | TITLE ESTs, Moderately similar to 60S RIBOSOMAL PROTEIN L7 [*Mus musculus*] | | | gi = 3747303 | 1428930 |
| IC11573 | UG75 Expression | EST | Mm.41910 | TITLE ESTs, Moderately similar to CGI-138 protein [*H. sapiens*] | | | gi = 3295607 | 959336 |
| IC11574 | UG75 Expression | EST | Mm.41913 | TITLE expressed sequence tag mouse EST 3 | GENE ESTM3 | | gi = 1765588 | 749168 |
| IC11575 | UG75 Expression | EST | Mm.41916 | TITLE ESTs, Weakly similar to HYPOTHETICAL 37.2 KD PROTEIN C12C2.09C IN CHROMOSOME I [*Schizosaccharomyces pombe*] | | | gi = 1715287 | 582067 |
| IC11576 | UG75 Expression | EST | Mm.41918 | TITLE ESTs | | | gi = 2850515 | 636395 |
| IC11577 | UG75 Expression | EST | Mm.41924 | TITLE ESTs | | | gi = 3894906 | 622145 |
| IC11578 | UG75 Expression | EST | Mm.41928 | TITLE ESTs | | | gi = 1391121 | 749154 |
| IC11579 | UG75 Expression | EST | Mm.41929 | TITLE ESTs, Weakly similar to BRCA1-associated RING domain protein [*M. musculus*] | | | gi = 6516308 | 1295524 |
| IC11580 | UG75 Expression | EST | Mm.41931 | ASSOCIATED GLYCOPROTEIN PRECURSOR [*Bos taurus*] | | | gi = 1282052 | 582564 |
| IC11581 | UG75 Expression | EST | Mm.41932 | TITLE ESTs | | | gi = 3745665 | 1363741 |
| IC11582 | UG75 Expression | EST | Mm.41933 | TITLE ESTs, Moderately similar to metalloprotease 1 [*H. sapiens*] | | | gi = 1478944 | 1001953 |
| IC11583 | UG75 Expression | EST | Mm.41935 | NUCLEOTIDYLTRANSFERASE [*Haemophilus influenzae*] | | | gi = 3978664 | 643233 |
| IC11584 | UG75 Expression | EST | Mm.41937 | TITLE ESTs | | | gi = 5492224 | 972730 |
| IC11585 | UG75 Expression | EST | Mm.41939 | TITLE ESTs | | | gi = 1310568 | 749536 |
| IC11586 | UG75 Expression | EST | Mm.41940 | TITLE ESTs | | | gi = 6100304 | 1149054 |
| IC11587 | UG75 Expression | EST | Mm.41941 | TITLE ESTs | | | gi = 1671387 | 578013 |
| IC11588 | UG75 Expression | EST | Mm.41948 | TITLE ESTs, Weakly similar to es 64 [*M. musculus*] | | | gi = 5668204 | 641908 |
| IC11589 | UG75 Expression | EST | Mm.41959 | TITLE ESTs | | | gi = 1777149 | 637986 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11590 | UG75 Expression | EST | Mm.41961 | TITLE ESTs | | | gi = 4484871 | 1139901 |
| IC11591 | UG75 Expression | EST | Mm.41962 | TITLE ESTs | | | gi = 4307016 | 643787 |
| IC11592 | UG75 Expression | EST | Mm.41966 | TITLE ESTs, Moderately similar to hypothetical protein [*H. sapiens*] | | | gi = 2248525 | 1226305 |
| IC11593 | UG75 Expression | EST | Mm.41968 | TITLE ESTs | | | gi = 3745487 | 676112 |
| IC11594 | UG75 Expression | EST | Mm.4206 | TITLE ESTs | | | gi = 1316203 | 723224 |
| IC11595 | UG75 Expression | EST | Mm.42061 | TITLE ESTs, Weakly similar to unknown [*H. sapiens*] | | | gi = 2915740 | 1262938 |
| IC11596 | UG75 Expression | EST | Mm.42066 | TITLE ESTs | | | gi = 5749744 | 764898 |
| IC11597 | UG75 Expression | EST | Mm.42068 | TITLE ESTs, Weakly similar to CREB-BINDING PROTEIN [*M. musculus*] | | | gi = 6085473 | 622046 |
| IC11598 | UG75 Expression | EST | Mm.42070 | TITLE ESTs | | | gi = 2562137 | 1002312 |
| IC11599 | UG75 Expression | EST | Mm.42072 | TITLE ESTs, Weakly similar to FGFR1 oncogene partner [*H. sapiens*] | | | gi = 4967913 | 1328303 |
| IC11600 | UG75 Expression | EST | Mm.421 | TITLE ESTs | | | gi = 4444618 | 574684 |
| IC11601 | UG75 Expression | EST | Mm.42110 | TITLE ESTs, Weakly similar to cDNA EST yk325c7.5 comes from this gene [*C. elegans*] | | | gi = 5749886 | 638584 |
| IC11602 | UG75 Expression | EST | Mm.42127 | TITLE ESTs | | | gi = 2944830 | 1263315 |
| IC11603 | UG75 Expression | EST | Mm.42129 | TITLE ESTs | | | gi = 4765286 | 749383 |
| IC11604 | UG75 Expression | EST | Mm.42137 | TITLE ESTs | | | gi = 4571947 | 1149062 |
| IC11605 | UG75 Expression | EST | Mm.42144 | TITLE ESTs | | | gi = 3175359 | 1361416 |
| IC11606 | UG75 Expression | EST | Mm.42147 | TITLE ESTs, Weakly similar to schafen3 [*M. musculus*] | | | gi = 5749549 | 764466 |
| IC11607 | UG75 Expression | EST | Mm.42218 | TITLE EST | | | gi = 4482808 | 1264752 |
| IC11608 | UG75 Expression | EST | Mm.423 | TITLE ESTs, Weakly similar to (define not available 5931543) [*M. musculus*] | | | gi = 420517 | 622963 |
| IC11609 | UG75 Expression | EST | Mm.42317 | TITLE EST | | | gi = 4061740 | 573970 |
| IC11610 | UG75 Expression | EST | Mm.42325 | TITLE EST | | | gi = 4289577 | 60645 |
| IC11611 | UG75 Expression | EST | Mm.42340 | TITLE EST | | | gi = 4765258 | 749272 |
| IC11612 | UG75 Expression | EST | Mm.42341 | TITLE ESTs | | | gi = 4306764 | 1193222 |
| IC11613 | UG75 Expression | EST | Mm.42342 | TITLE EST | | | gi = 4805099 | 721587 |
| IC11614 | UG75 Expression | EST | Mm.42404 | TITLE ESTs | | | gi = 4274152 | 551035 |
| IC11615 | UG75 Expression | EST | Mm.42405 | TITLE EST | | | gi = 4274196 | 551390 |
| IC11616 | UG75 Expression | EST | Mm.42414 | TITLE EST | | | gi = 4482887 | 1265119 |
| IC11617 | UG75 Expression | EST | Mm.42466 | TITLE EST | | | gi = 3522641 | 1429745 |
| IC11618 | UG75 Expression | EST | Mm.42478 | TITLE EST | | | gi = 4272566 | 533828 |
| IC11619 | UG75 Expression | EST | Mm.42480 | TITLE EST | | | gi = 4289037 | 620075 |
| IC11620 | UG75 Expression | EST | Mm.42481 | TITLE EST | | | gi = 4297689 | 583599 |
| IC11621 | UG75 Expression | EST | Mm.42491 | TITLE EST | | | gi = 4764591 | 719171 |
| IC11622 | UG75 Expression | EST | Mm.42492 | TITLE ESTs | | | gi = 4764704 | 718301 |
| IC11623 | UG75 Expression | EST | Mm.42493 | TITLE EST | | | gi = 4804085 | 638916 |
| IC11624 | UG75 Expression | EST | Mm.42556 | TITLE EST | | | gi = 4482854 | 1264955 |
| IC11625 | UG75 Expression | EST | Mm.42557 | TITLE EST | | | gi = 4764747 | 721680 |
| IC11626 | UG75 Expression | EST | Mm.42606 | TITLE EST | | | gi = 4766422 | 750239 |
| IC11627 | UG75 Expression | EST | Mm.42607 | TITLE EST | | | gi = 4058490 | 635770 |
| IC11628 | UG75 Expression | EST | Mm.42613 | TITLE EST | | | gi = 4060399 | 583567 |
| IC11629 | UG75 Expression | EST | Mm.42614 | TITLE ESTs | | | gi = 4303659 | 583400 |
| IC11630 | UG75 Expression | EST | Mm.42616 | TITLE EST | | | gi = 6008583 | 573370 |
| IC11631 | UG75 Expression | EST | Mm.42623 | TITLE EST | | | gi = 4302479 | 635186 |
| IC11632 | UG75 Expression | EST | Mm.42626 | TITLE ESTs | | | gi = 4482897 | 1265155 |
| IC11633 | UG75 Expression | EST | Mm.42626 | TITLE EST | | | gi = 4522277 | 1281487 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11634 | UG75 Expression | EST | Mm.42630 | TITLE EST | | | gi = 4766437 | 750344 |
| IC11635 | UG75 Expression | EST | Mm.42666 | TITLE EST | | | gi = 2049271 | 751872 |
| IC11636 | UG75 Expression | EST | Mm.42704 | TITLE EST | | | gi = 4288911 | 619990 |
| IC11637 | UG75 Expression | EST | Mm.42705 | TITLE EST | | | gi = 4290739 | 577495 |
| IC11638 | UG75 Expression | EST | Mm.42826 | TITLE EST, Weakly similar to T12G3.5 [C. elegans] | | | gi = 1290117 | 752442 |
| IC11639 | UG75 Expression | EST | Mm.42850 | TITLE ESTs | | | gi = 2918941 | 752424 |
| IC11640 | UG75 Expression | EST | Mm.42857 | TITLE ESTs | | | gi = 4617324 | 587774 |
| IC11641 | UG75 Expression | EST | Mm.42870 | TITLE ESTs | | | gi = 4271673 | 575994 |
| IC11642 | UG75 Expression | EST | Mm.42873 | TITLE ESTs | | | gi = 1756045 | 617607 |
| IC11643 | UG75 Expression | EST | Mm.4290 | TITLE ESTs, Weakly similar to NSP-like 1 [M. musculus] | | | gi = 6083917 | 1149886 |
| IC11644 | UG75 Expression | EST | Mm.42908 | TITLE ESTs | | | gi = 2262747 | 1279339 |
| IC11645 | UG75 Expression | EST | Mm.42925 | TITLE ESTs, Weakly similar to weak similarity to the yeast SSM4 protein [C. elegans] | | | gi = 2646684 | 972548 |
| IC11646 | UG75 Expression | EST | Mm.42949 | TITLE EST [H. sapiens] | | | gi = 1290286 | 558062 |
| IC11647 | UG75 Expression | EST | Mm.42956 | TITLE ESTs | | | gi = 3167558 | 749711 |
| IC11648 | UG75 Expression | EST | Mm.42967 | TITLE ESTs, Weakly similar to predicted using Genefinder [C. elegans] | | | gi = 4402506 | 721635 |
| IC11649 | UG75 Expression | EST | Mm.43017 | TITLE ESTs | | | gi = 1309510 | 642424 |
| IC11650 | UG75 Expression | EST | Mm.43151 | TITLE EST | | | gi = 1882119 | 717949 |
| IC11651 | UG75 Expression | EST | Mm.43155 | TITLE ESTs | | | gi = 1714852 | 597078 |
| IC11652 | UG75 Expression | EST | Mm.43161 | TITLE ESTs | | | gi = 4296619 | 1243720 |
| IC11653 | UG75 Expression | EST | Mm.43179 | TITLE ESTs | | | gi = 4766320 | 749523 |
| IC11654 | UG75 Expression | EST | Mm.43194 | TITLE ESTs [M. musculus] | | | gi = 3371140 | 617340 |
| IC11655 | UG75 Expression | EST | Mm.43208 | TITLE EST | | | gi = 1919582 | 777236 |
| IC11656 | UG75 Expression | EST | Mm.43225 | TITLE ESTs | | | gi = 4571756 | 1149881 |
| IC11657 | UG75 Expression | EST | Mm.43229 | TITLE ESTs, Moderately similar to Sp100 [M. musculus] | | | gi = 2917609 | 598548 |
| IC11658 | UG75 Expression | EST | Mm.43237 | TITLE EST | | | gi = 4305922 | 599150 |
| IC11659 | UG75 Expression | EST | Mm.43243 | TITLE ESTs | | | gi = 1793254 | 622352 |
| IC11660 | UG75 Expression | EST | Mm.4327 | TITLE ESTs | | | gi = 4060879 | 533963 |
| IC11661 | UG75 Expression | EST | Mm.43289 | TITLE ESTs | | | gi = 4059980 | 576749 |
| IC11662 | UG75 Expression | EST | Mm.43290 | TITLE ESTs, Moderately similar to peptidyl-prolyl cis-trans isomerase EPVH [H. sapiens] | | | gi = 2516543 | 582921 |
| IC11663 | UG75 Expression | EST | Mm.43293 | TITLE ESTs | | | gi = 4408704 | 973943 |
| IC11664 | UG75 Expression | EST | Mm.43297 | TITLE ESTs | | | gi = 297502 | 638565 |
| IC11665 | UG75 Expression | EST | Mm.43322 | TITLE ESTs | | | gi = 5488274 | 638963 |
| IC11666 | UG75 Expression | EST | Mm.43345 | TITLE ESTs | | | gi = 2049275 | 638751 |
| IC11667 | UG75 Expression | EST | Mm.43358 | TITLE EST | | | gi = 3718471 | 617386 |
| IC11668 | UG75 Expression | EST | Mm.43397 | TITLE ESTs, Weakly similar to F25H5.6 [C. elegans] | | | gi = 6008723 | 751048 |
| IC11669 | UG75 Expression | EST | Mm.43477 | TITLE ESTs, Moderately similar to MKR2 PROTEIN [Mus musculus] | | | gi = 5338084 | 958519 |
| IC11670 | UG75 Expression | EST | Mm.43482 | TITLE DNA segment, Chr 6, Wayne State Univeristy 147, expressed | GENE D6Wsu147e | | | 1225219 |
| IC11671 | UG75 Expression | EST | Mm.43499 | TITLE ESTs | | | gi = 4968519 | 723579 |
| IC11672 | UG75 Expression | EST | Mm.435 | TITLE ESTs | | | gi = 3393100 | 575268 |
| IC11673 | UG75 Expression | EST | Mm.43553 | TITLE ESTs | | | gi = 1714849 | 597072 |
| IC11674 | UG75 Expression | EST | Mm.43561 | TITLE EST | | | gi = 4403943 | 973481 |
| IC11675 | UG75 Expression | EST | Mm.43563 | TITLE EST | | | gi = 4484887 | 1265237 |
| IC11676 | UG75 Expression | EST | Mm.43636 | TITLE ESTs | | | gi = 1289053 | 533778 |
| IC11677 | UG75 Expression | EST | Mm.43640 | TITLE ESTs | | | gi = 1318290 | 1312444 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11678 | UG75 Expression | EST | Mm.43671 | TITLE ESTs | | | gi = 3394968 | 617471 |
| IC11679 | UG75 Expression | EST | Mm.43696 | TITLE ESTs | | | gi = 2116468 | 635139 |
| IC11680 | UG75 Expression | EST | Mm.43731 | TITLE ESTs | | | gi = 3374108 | 2646940 |
| IC11681 | UG75 Expression | EST | Mm.4385 | TITLE ESTs | | | gi = 2962757 | 1293816 |
| IC11682 | UG75 Expression | EST | Mm.43871 | TITLE ESTs | | | gi = 1193103 | |
| IC11683 | UG75 Expression | EST | Mm.439 | TITLE DNA segment, Chr 9, Wayne State University 10, expressed | GENE D9Wsu10e | | gi = 2262634 | 1278714 |
| IC11684 | UG75 Expression | EST | Mm.43901 | TITLE EST | | | gi = 2331965 | 972663 |
| IC11685 | UG75 Expression | EST | Mm.43912 | TITLE ESTs | | | gi = 3731823 | 1394974 |
| IC11686 | UG75 Expression | EST | Mm.43914 | TITLE ESTs | | | gi = 5909808 | 581879 |
| IC11687 | UG75 Expression | EST | Mm.43918 | TITLE EST | | | gi = 4805043 | 634108 |
| IC11688 | UG75 Expression | EST | Mm.43926 | TITLE EST | | | gi = 2851212 | 1244030 |
| IC11689 | UG75 Expression | EST | Mm.43934 | TITLE ESTs, Moderately similar to 60S RIBOSOMAL PROTEIN L39 [R. norvegicus] | | | gi = 4307789 | 597632 |
| IC11690 | UG75 Expression | EST | Mm.43949 | TITLE EST | | | gi = 2256439 | 894150 |
| IC11691 | UG75 Expression | EST | Mm.43961 | TITLE EST | | | gi = 4300230 | 575944 |
| IC11692 | UG75 Expression | EST | Mm.43962 | TITLE EST | | | gi = 4284772 | 582793 |
| IC11693 | UG75 Expression | EST | Mm.43976 | TITLE ESTs | | | gi = 5819558 | 721685 |
| IC11694 | UG75 Expression | EST | Mm.43977 | TITLE ESTs | | | gi = 5819725 | 620192 |
| IC11695 | UG75 Expression | EST | Mm.43981 | TITLE EST | | | gi = 1806696 | 644226 |
| IC11696 | UG75 Expression | EST | Mm.44000 | TITLE EST | | | gi = 4272531 | 533298 |
| IC11697 | UG75 Expression | EST | Mm.44001 | TITLE EST | | | gi = 4308608 | 557890 |
| IC11698 | UG75 Expression | EST | Mm.44004 | TITLE ESTs | | | gi = 4299906 | 618385 |
| IC11699 | UG75 Expression | EST | Mm.44026 | TITLE EST | | | gi = 4305943 | 599170 |
| IC11700 | UG75 Expression | EST | Mm.44032 | TITLE ESTs | | | gi = 5819669 | 1380144 |
| IC11701 | UG75 Expression | EST | Mm.44045 | TITLE ESTs | | | gi = 2978866 | 1281361 |
| IC11702 | UG75 Expression | EST | Mm.44053 | TITLE EST | | | gi = 4301213 | 621114 |
| IC11703 | UG75 Expression | EST | Mm.44060 | TITLE ESTs | | | gi = 2918552 | 100259 |
| IC11704 | UG75 Expression | EST | Mm.44064 | TITLE ESTs | | | gi = 5470724 | 1243727 |
| IC11705 | UG75 Expression | EST | Mm.44065 | TITLE ESTs | | | gi = 4287855 | 749242 |
| IC11706 | UG75 Expression | EST | Mm.44067 | TITLE ESTs | | | gi = 554546 | 1281516 |
| IC11707 | UG75 Expression | EST | Mm.44068 | TITLE ESTs | | | gi = 4968044 | 894403 |
| IC11708 | UG75 Expression | EST | Mm.44082 | TITLE ESTs | | | gi = 2920076 | 639781 |
| IC11709 | UG75 Expression | EST | Mm.44084 | TITLE ESTs, Weakly similar to Y38A8.1 gene product [C. elegans] | | | gi = 4765838 | 751595 |
| IC11710 | UG75 Expression | EST | Mm.44092 | [M. musculus] | | | gi = 1519964 | 583273 |
| IC11711 | UG75 Expression | EST | Mm.44094 | TITLE ESTs | | | gi = 3100488 | 1344869 |
| IC11712 | 00/04/26 UG#76 17Lid Expansion | EST | Mm.44101 | ESTs, Moderately similar to (define not available 5457150) [M. musculus] | | | gi = 3447897 | 1762756 |
| IC11713 | UG75 Expression | EST | Mm.44111 | TITLE ESTs | | | gi = 6559425 | 1293838 |
| IC11714 | UG75 Expression | EST | Mm.44112 | TITLE ESTs | | | gi = 5495566 | 1363232 |
| IC11715 | UG75 Expression | EST | Mm.44122 | TITLE ESTs | | | gi = 4315951 | 619335 |
| IC11716 | UG75 Expression | EST | Mm.44123 | TITLE ESTs | | | gi = 1530229 | 577257 |
| IC11717 | UG75 Expression | EST | Mm.44131 | TITLE ESTs, Weakly similar to CREB-RP [M. musculus] | | | gi = 2691095 | 1395564 |
| IC11718 | UG75 Expression | EST | Mm.44147 | TITLE ESTs | | | gi = 5497445 | 1020640 |
| IC11719 | UG75 Expression | EST | Mm.44153 | TITLE ESTs | | | gi = 5549491 | 576810 |
| IC11720 | UG75 Expression | EST | Mm.44162 | TITLE ESTs | | | gi = 2248558 | 973729 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11721 | UG76 LID366 B cell | EST | Mm.44163 | TITLE ESTs, Weakly similar to growth factor-responsive protein, vascular smooth muscle [R. norvegicus] | | | gi = 1290261 | 333165 |
| IC11722 | UG75 Expression | EST | Mm.44167 | TITLE ESTs | | | gi = 3371388 | 622874 |
| IC11723 | UG75 Expression | EST | Mm.44172 | TITLE ESTs | | | gi = 1808549 | 958743 |
| IC11724 | UG75 Expression | EST | Mm.44174 | TITLE ESTs, Weakly similar to Similarity to Bovine NADH-ubiquinone oxidoreductase B8 subunit [C. elegans] | | | gi = 5666503 | 1139883 |
| IC11725 | UG75 Expression | EST | Mm.44177 | TITLE ESTs | | | gi = 5334216 | 641334 |
| IC11726 | UG75 Expression | EST | Mm.44181 | TITLE ESTs, Weakly similar to (define not available 6018823) [D. melanogaster] | | | gi = 1895674 | 644358 |
| IC11727 | UG75 Expression | EST | Mm.44183 | TITLE ESTs | | | gi = 6556926 | 1140085 |
| IC11728 | UG75 Expression | EST | Mm.44184 | TITLE ESTs | | | gi = 1677170 | 765059 |
| IC11729 | UG75 Expression | EST | Mm.44198 | TITLE ESTs | | | gi = 5549283 | 619395 |
| IC11730 | UG75 Expression | EST | Mm.44201 | TITLE ESTs. | | | gi = 2756171 | 1263031 |
| IC11731 | UG76 LID366 B cell | EST | Mm.44204 | TITLE ESTs, Weakly similar to mitochondrial outer membrane protein [M. musculus] | | | gi = 6519409 | 1054503 |
| IC11732 | UG75 Expression | EST | Mm.44207 | TITLE ESTs | | | gi = 6938181 | 550594 |
| IC11733 | UG75 Expression | EST | Mm.44209 | TITLE ESTs | | | gi = 2518721 | 622943 |
| IC11734 | UG75 Expression | EST | Mm.44212 | TITLE ESTs, Weakly similar to proline-rich protein [M. musculus] | | | gi = 6168122 | 577206 |
| IC11735 | UG75 Expression | EST | Mm.44213 | TITLE ESTs, Weakly similar to [Segment 1 of 2] PROCOLLAGEN ALPHA 1(III) CHAIN PRECURSOR [M. musculus] | | | | 617491 |
| IC11736 | UG75 Expression | EST | Mm.44214 | TITLE ESTs, Weakly similar to UBIQUITIN-CONJUGATING ENZYME E2-25 KD [Bos taurus] | | | gi = 6076827 | 1293810 |
| IC11737 | UG75 Expression | EST | Mm.44217 | TITLE ESTs, Weakly similar to All-1 protein +GTE form [M. musculus] | | | gi = 4433845 | 558188 |
| IC11738 | UG75 Expression | EST | Mm.44218 | TITLE ESTs, Weakly similar to ORF YJL004c [S. cerevisiae] | | | gi = 3885122 | 597481 |
| IC11739 | UG75 Expression | EST | Mm.44221 | TITLE ESTs, Weakly similar to ORF YOR258w [S. cerevisiae] | | | gi = 5496982 | 1149023 |
| IC11740 | UG75 Expression | EST | Mm.44223 | TITLE DNA segment, Chr 5, Bucan 26 expressed | GENE D5Buc26|IMAGE:1958590| | | | 1446780 |
| IC11741 | UG75 Expression | EST | Mm.44224 | TITLE ESTs, Weakly similar to CALDESMON [H. sapiens] | | | gi = 3810149 | 574753 |
| IC11742 | UG75 Expression | EST | Mm.44225 | TITLE ribosomal protein, mitochondrial, L26 | GENE Rpml26 MRP-L26| | | gi = 3164683 | 972461 |
| IC11743 | UG75 Expression | EST | Mm.44226 | TITLE ESTs, Moderately similar to CGI-69 protein [H. sapiens] | | | gi = 4443240 | 720817 |
| IC11744 | UG75 Expression | EST | Mm.44228 | TITLE DNA segment, Chr 6, Wayne State University 163, expressed | GENE D6Wsu163e | | | 599294 |
| IC11745 | UG75 Expression | EST | Mm.44236 | TITLE ESTs, Moderately similar to hypothetical protein [H. sapiens] | | | gi = 6518564 | 639236 |
| IC11746 | UG75 Expression | EST | Mm.44239 | TITLE ESTs, Moderately similar to KIAA0873 protein [H. sapiens] | | | gi = 4433925 | 634742 |
| IC11747 | 00/04/26 UG#76 17 Lid Expansion | EST | Mm.44241 | ESTs, Weakly similar to P19 PROTEIN [M. musculus] | | | gi = 5498766 | 1763135 |
| IC11748 | UG75 Expression | EST | Mm.44252 | TITLE ESTs | | | gi = 5910137 | 639476 |
| IC11749 | UG75 Expression | EST | Mm.44319 | TITLE ESTs | | | gi = 5910376 | 1749314 |
| IC11750 | UG75 Expression | EST | Mm.44320 | TITLE ESTs | | | gi = 3683063 | 718092 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11751 | UG75 Expression | EST | Mm.44322 | TITLE ESTs | | | gi = 2516828 | 1446006 |
| IC11752 | UG75 Expression | EST | Mm.44324 | TITLE ESTs | | | gi = 153924 | 1294526 |
| IC11753 | UG75 Expression | EST | Mm.44377 | TITLE ESTs | | | gi = 5600041 | 386198 |
| IC11754 | UG75 Expression | EST | Mm.44400 | TITLE ESTs | | | gi = 5907313 | 958777 |
| IC11755 | UG75 Expression | EST | Mm.44403 | TITLE ESTs | | | gi = 1699877 | 777223 |
| IC11756 | UG75 Expression | EST | Mm.44404 | TITLE ESTs | | | gi = 6098582 | 721825 |
| IC11757 | UG75 Expression | EST | Mm.44405 | TITLE ESTs | | | gi = 1748882 | 618617 |
| IC11758 | UG75 Expression | EST | Mm.44411 | TITLE ESTs, Moderately similar to KIAA0014 [*H. sapiens*] | | | gi = 1901125 | 1749766 |
| IC11759 | UG75 Expression | EST | Mm.44412 | TITLE ESTs | | | gi = 5910524 | 1378377 |
| IC11760 | UG75 Expression | EST | Mm.44432 | TITLE ESTs | | | gi = 3216309 | 1362570 |
| IC11761 | UG75 Expression | EST | Mm.44463 | TITLE ESTs | | | gi = 5600042 | 777437 |
| IC11762 | UG75 Expression | EST | Mm.44473 | TITLE ESTs | | | gi = 5910188 | 1330122 |
| IC11763 | UG76 LID366 B cell | EST | Mm.44487 | TITLE ESTs | | | gi = 7066686 | 1382464 |
| IC11764 | UG75 Expression | EST | Mm.44489 | TITLE ESTs | | | gi = 1807498 | 1263041 |
| IC11765 | UG75 Expression | EST | Mm.44494 | TITLE ESTs | | | gi = 4613317 | 619960 |
| IC11766 | UG75 Expression | EST | Mm.44497 | TITLE ESTs | | | gi = 2283294 | 1265017 |
| IC11767 | UG75 Expression | EST | Mm.44504 | TITLE ESTs | | | gi = 4723860 | 582850 |
| IC11768 | UG75 Expression | EST | Mm.44505 | TITLE ESTs | | | gi = 5905720 | 576818 |
| IC11769 | UG75 Expression | EST | Mm.44578 | TITLE ESTs | | | gi = 4307154 | 596915 |
| IC11770 | UG75 Expression | EST | Mm.44593 | TITLE ESTs | | | gi = 4614727 | 1264043 |
| IC11771 | UG75 Expression | EST | Mm.44596 | TITLE ESTs | | | gi = 3732404 | 595973 |
| IC11772 | UG75 Expression | EST | Mm.44598 | TITLE ESTs | | | gi = 5909302 | 1750129 |
| IC11773 | UG75 Expression | EST | Mm.44599 | TITLE ESTs | | | gi = 450541 | 1002745 |
| IC11774 | UG75 Expression | EST | Mm.446 | TITLE ESTs | | | gi = 1759930 | 619429 |
| IC11775 | UG75 Expression | EST | Mm.44601 | TITLE ESTs | | | gi = 6085444 | 619906 |
| IC11776 | UG75 Expression | EST | Mm.44604 | TITLE ESTs | | | gi = 1539796 | 1193097 |
| IC11777 | UG75 Expression | EST | Mm.44605 | TITLE ESTs | | | gi = 3079265 | 1329364 |
| IC11778 | UG75 Expression | EST | Mm.44609 | TITLE ESTs | | | gi = 4318686 | 718734 |
| IC11779 | UG75 Expression | EST | Mm.44616 | TITLE ESTs, Weakly similar to SERINE/THREONINE-PROTEIN KINASE MAK [*M. musculus*] | | | gi = 5908557 | 574258 |
| IC11780 | UG75 Expression | EST | Mm.44626 | TITLE ESTs | | | gi = 3686533 | 640727 |
| IC11781 | UG75 Expression | EST | Mm.44634 | TITLE ESTs | | | gi = 4602599 | 749949 |
| IC11782 | UG75 Expression | EST | Mm.4467 | TITLE ESTs | | | gi = 1318398 | 1149639 |
| IC11783 | UG75 Expression | EST | Mm.44676 | TITLE ESTs, Weakly similar to predicted using Genefinder [*C. elegans*] | | | gi = 3681701 | 1429148 |
| IC11784 | UG75 Expression | EST | Mm.44696 | TITLE ESTs, Weakly similar to Pontin52 [*M. musculus*] | | | gi = 3167156 | 1362466 |
| IC11785 | UG75 Expression | EST | Mm.447 | TITLE ESTs | | | gi = 1724806 | 597387 |
| IC11786 | UG75 Expression | EST | Mm.44707 | TITLE ESTs | | | gi = 1326699 | 620375 |
| IC11787 | UG75 Expression | EST | Mm.4471 | [*D. melanogaster*] | | | gi = 1539860 | 808954 |
| IC11788 | UG75 Expression | EST | Mm.44710 | TITLE ESTs, Weakly similar to F53F10.1 [*C. elegans*] | | | gi = 2978945 | 1281423 |
| IC11789 | UG75 Expression | EST | Mm.44711 | TITLE ESTs, Moderately similar to similar to human EXLM1 gene [*M. musculus*] | | | gi = 1531247 | 637650 |
| IC11790 | UG75 Expression | EST | Mm.44712 | TITLE ESTs | | | gi = 4217071 | 573370 |
| IC11791 | UG75 Expression | EST | Mm.44714 | TITLE ESTs, Moderatley similar to clathrin assembly protein long form [*R. norvegicus*] | | | gi = 440914 | 597118 |
| IC11792 | UG75 Expression | EST | Mm.44715 | TITLE ESTs | | | gi = 1738730 | 577146 |
| IC11793 | UG75 Expression | EST | Mm.44716 | TITLE ESTs | | | gi = 5908090 | 620058 |
| IC11794 | UG75 Expression | EST | Mm.44718 | TITLE ESTs | | | gi = 3685738 | 618043 |
| IC11795 | UG75 Expression | EST | Mm.44719 | TITLE ESTs | | | gi = 1889149 | 722800 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11796 | UG75 Expression | EST | Mm.44727 | TITLE ESTs | | | gi = 5909658 | 576464 |
| IC11797 | UG75 Expression | EST | Mm.44728 | TITLE ESTs | | | gi = 5907053 | 1379632 |
| IC11798 | UG75 Expression | EST | Mm.44729 | TITLE ESTs | | | gi = 4434399 | 1378245 |
| IC11799 | UG75 Expression | EST | Mm.44730 | TITLE ESTs | | | gi = 5910883 | 1380033 |
| IC11800 | UG75 Expression | EST | Mm.44737 | TITLE ESTs | | | gi = 4305392 | 643276 |
| IC11801 | UG75 Expression | EST | Mm.44757 | TITLE ESTs | | | gi = 1755451 | 617271 |
| IC11802 | UG75 Expression | EST | Mm.44768 | TITLE ESTs | | | gi = 5906810 | 1344339 |
| IC11803 | UG75 Expression | EST | Mm.44782 | TITLE ESTs | | | gi = 4724416 | 639192 |
| IC11804 | UG75 Expression | EST | Mm.44847 | TITLE ESTs | | | gi = 3233724 | 1378576 |
| IC11805 | 00/04/26 UG#76 17Lid Expansion | EST | Mm.44850 | ESTs | | | gi = 6557422 | 2654247 |
| IC11806 | UG75 Expression | EST | Mm.44856 | TITLE ESTs | | | gi = 5905746 | 596748 |
| IC11807 | UG75 Expression | EST | Mm.44857 | TITLE ESTs | | | gi = 306002 | 618083 |
| IC11808 | UG75 Expression | EST | Mm.44858 | TITLE ESTs | | | gi = 1497400 | 533489 |
| IC11809 | UG75 Expression | EST | Mm.44861 | TITLE ESTs | | | gi = 1910167 | 1264817 |
| IC11810 | UG75 Expression | EST | Mm.44863 | TITLE ESTs | | | gi = 1937490 | 749579 |
| IC11811 | UG75 Expression | EST | Mm.44865 | TITLE ESTs | | | gi = 5909911 | 634559 |
| IC11812 | UG75 Expression | EST | Mm.44867 | TITLE ESTs | | | gi = 6008910 | 973154 |
| IC11813 | UG75 Expression | EST | Mm.44872 | TITLE ESTs, Weakly similar to T-LYMPHONA INVASION AND METASTASIS INDUCING PROTEIN 1 [*M. musculus*] | | | gi = 2859485 | 1282123 |
| IC11814 | UG75 Expression | EST | Mm.44873 | TITLE ESTs | | | gi = 2503259 | 1295597 |
| IC11815 | UG75 Expression | EST | Mm.44874 | TITLE ESTs | | | gi = 2263065 | 1224858 |
| IC11816 | UG75 Expression | EST | Mm.44875 | TITLE ESTs | | | gi = 2851118 | 597816 |
| IC11817 | UG75 Expression | EST | Mm.44878 | TITLE ESTs | | | gi = 1682368 | 764106 |
| IC11818 | UG75 Expression | EST | Mm.44879 | TITLE ESTs, Weakly similar to LAMININ ALPHA-2 CHAIN PRECURSOR [*M. musculus*] | | | gi = 4061824 | 577718 |
| IC11819 | UG75 Expression | EST | Mm.44881 | TITLE ESTs | | | gi = 2850549 | 619714 |
| IC11820 | UG75 Expression | EST | Mm.44883 | TITLE ESTs | | | gi = 4601752 | 63446 |
| IC11821 | UG75 Expression | EST | Mm.44888 | TITLE ESTs, Weakly similar to (define not available 5731129) [*D. melanogaster*] | | | gi = 1713455 | 583350 |
| IC11822 | UG75 Expression | EST | Mm.44889 | TITLE ESTs, Weakly similar to Toll-like receptor 3 [*H. sapiens*] | | | gi = 4302437 | 635142 |
| IC11823 | UG75 Expression | EST | Mm.44890 | TITLE ESTs | | | gi = 4409131 | 764838 |
| IC11824 | UG75 Expression | EST | Mm.44892 | TITLE ESTs | | | gi = 4597003 | 1001506 |
| IC11825 | UG75 Expression | EST | Mm.44894 | TITLE ESTs | | | gi = 4724382 | 638924 |
| IC11826 | UG75 Expression | EST | Mm.44906 | TITLE ESTs, Weakly similar to GUANINE NUCLEOTIDE-BINDING PROTEIN G(S), ALPHA SUBUNIT [*Bos taurus*] | | | gi = 1676323 | 573441 |
| IC11827 | UG75 Expression | EST | Mm.44954 | TITLE ESTs | | | gi = 5908183 | 764930 |
| IC11828 | UG75 Expression | EST | Mm.44960 | [*Mus musculus*] | | | gi = 1917537 | 636599 |
| IC11829 | UG75 Expression | EST | Mm.44973 | TITLE ESTs | | | gi = 4723822 | 582601 |
| IC11830 | UG75 Expression | EST | Mm.44976 | TITLE ESTs | | | gi = 4060904 | 550914 |
| IC11831 | UG75 Expression | EST | Mm.44997 | TITLE ESTs | | | gi = 4482737 | 1264282 |
| IC11832 | UG75 Expression | EST | Mm.45001 | TITLE ESTs | | | gi = 6009008 | 1024791 |
| IC11833 | UG75 Expression | EST | Mm.45004 | TITLE ESTs | | | gi = 5910892 | 638756 |
| IC11834 | UG75 Expression | EST | Mm.45008 | TITLE ESTs | | | gi = 1675900 | 574989 |
| IC11835 | UG75 Expression | EST | Mm.45014 | TITLE ESTs | | | gi = 5478196 | 619872 |
| IC11836 | UG75 Expression | EST | Mm.45015 | TITLE ESTs | | | gi = 1767827 | 622668 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11837 | UG75 Expression | EST | Mm.45016 | TITLE ESTs | | | gi = 1932192 | 1294840 |
| IC11838 | UG75 Expression | EST | Mm.45017 | TITLE ESTs | | | gi = 1769269 | 634453 |
| IC11839 | UG75 Expression | EST | Mm.45018 | TITLE ESTs | | | gi = 5909926 | 644839 |
| IC11840 | UG75 Expression | EST | Mm.45019 | TITLE ESTs | | | gi = 1811536 | 677623 |
| IC11841 | UG75 Expression | EST | Mm.45020 | TITLE ESTs | | | gi = 1919460 | 777578 |
| IC11842 | UG75 Expression | EST | Mm.45021 | TITLE ESTs | | | gi = 5906990 | 534060 |
| IC11843 | UG75 Expression | EST | Mm.45024 | TITLE ESTs, Weakly similar to HYDROXYMETHYLGLUTARYL-COA SYNTHASE, MITOCHONDRIAL PRECURSOR [Rattus norvegicus] | | | gi = 2503307 | 634712 |
| IC11844 | UG75 Expression | EST | Mm.45025 | TITLE ESTs, Moderately similar to unknown [H. sapiens] | | | gi = 3374702 | 621427 |
| IC11845 | UG75 Expression | EST | Mm.45031 | TITLE ESTs | | | gi = 2247414 | 573897 |
| IC11846 | UG75 Expression | EST | Mm.45033 | TITLE ESTs, Weakly similar to zinc finger protein 51 [M. musculus] | | | gi = 5910353 | 719250 |
| IC11847 | UG75 Expression | EST | Mm.45034 | TITLE ESTs | | | gi = 2288406 | 1149139 |
| IC11848 | UG75 Expression | EST | Mm.45035 | TITLE ESTs | | | gi = 5908473 | 1149156 |
| IC11849 | UG75 Expression | EST | Mm.45037 | TITLE ESTs | | | gi = 3516296 | 777719 |
| IC11850 | UG75 Expression | EST | Mm.45039 | TITLE ESTs | | | gi = 1700453 | 1193435 |
| IC11851 | UG75 Expression | EST | Mm.45042 | TITLE ESTs | | | gi = 3680445 | 1446230 |
| IC11852 | UG75 Expression | EST | Mm.45043 | TITLE ESTs | | | gi = 2234872 | 721712 |
| IC11853 | UG75 Expression | EST | Mm.45046 | TITLE ESTs | | | gi = 2988668 | 582690 |
| IC11854 | UG75 Expression | EST | Mm.45047 | TITLE ESTs | | | gi = 1715434 | 618607 |
| IC11855 | UG75 Expression | EST | Mm.45048 | TITLE ESTs | | | gi = 6519951 | 596315 |
| IC11856 | UG75 Expression | EST | Mm.45049 | TITLE ESTs | | | gi = 4061756 | 574576 |
| IC11857 | UG75 Expression | EST | Mm.45052 | TITLE ESTs | | | gi = 3054737 | 1327837 |
| IC11858 | UG75 Expression | EST | Mm.45053 | TITLE ESTs | | | gi = 3718364 | 581799 |
| IC11859 | UG75 Expression | EST | Mm.45058 | TITLE ESTs | | | gi = 6085749 | 1446437 |
| IC11860 | UG75 Expression | EST | Mm.45061 | TITLE ESTs | | | gi = 2965604 | 1139594 |
| IC11861 | UG75 Expression | EST | Mm.45063 | TITLE ESTs | | | gi = 2203576 | 1379013 |
| IC11862 | UG75 Expression | EST | Mm.45066 | TITLE ESTs | | | gi = 1487648 | 1362889 |
| IC11863 | UG75 Expression | EST | Mm.45067 | TITLE ESTs, Weakly similar to salivary proline-rich protein [R. norvegicus] | | | gi = 6084595 | 575181 |
| IC11864 | UG75 Expression | EST | Mm.45068 | TITLE ESTs | | | gi = 1675776 | 574409 |
| IC11865 | UG75 Expression | EST | Mm.45070 | TITLE ESTs | | | gi = 5909860 | 1282669 |
| IC11866 | UG75 Expression | EST | Mm.45077 | TITLE ESTs | | | gi = 5906211 | 582890 |
| IC11867 | UG75 Expression | EST | Mm.45078 | TITLE ESTs | | | gi = 5909924 | 620175 |
| IC11868 | UG75 Expression | EST | Mm.45079 | TITLE ESTs | | | gi = 1919386 | 618940 |
| IC11869 | UG75 Expression | EST | Mm.45080 | TITLE ESTs | | | gi = 1919410 | 777200 |
| IC11870 | 00/04/26 UG#76 17Lid Expansion | EST | Mm.45081 | ESTs | | | gi = 434246 | 1762441 |
| IC11871 | UG75 Expression | EST | Mm.45086 | TITLE ESTs | | | gi = 5909584 | 1149222 |
| IC11872 | UG75 Expression | EST | Mm.45088 | TITLE ESTs, Moderately similar to HYPOTHETICAL 251.0 KD PROTEIN IN CRY1-GNS1 INTERGENIC REGION [Saccharomyces cerevisiae] | | | gi = 4303523 | 576958 |
| IC11873 | UG75 Expression | EST | Mm.45092 | TITLE ESTs | | | gi = 1811683 | 1263609 |
| IC11874 | UG75 Expression | EST | Mm.45094 | TITLE ESTs, Weakly similar to KIAA0351 [H. sapiens] | | | gi = 5906690 | 636344 |
| IC11875 | UG75 Expression | EST | Mm.45099 | TITLE ESTs, Moderately similar to R31341_1 [H. sapiens] | | | gi = 6095870 | 764705 |
| IC11876 | UG75 Expression | EST | Mm.45106 | TITLE ESTs, Moderately similar to pig-c protein [H. sapiens] | | | gi = 6518109 | 2649047 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11877 | UG75 Expression | EST | Mm.45108 | TITLE ESTs, Moderately similar to EUKARYOTIC INITIATION FACTOR 4A-3 [Nicotiana plumbaginifolia] | | | gi = 3161345 | 643720 |
| IC11878 | UG75 Expression | EST | Mm.45111 | TITLE ESTs | | | gi = 1826966 | 638247 |
| IC11879 | UG75 Expression | EST | Mm.45113 | TITLE ESTs | | | gi = 1285278 | 765171 |
| IC11880 | UG75 Expression | EST | Mm.45118 | TITLE ESTs | | | gi = 2292190 | 1327489 |
| IC11881 | UG75 Expression | EST | Mm.45122 | TITLE ESTs | | | gi = 5496904 | 597035 |
| IC11882 | UG75 Expression | EST | Mm.45124 | TITLE ESTs | | | gi = 3160713 | 598361 |
| IC11883 | UG75 Expression | EST | Mm.45125 | TITLE ESTs, Moderately similar to HYPOTHETICAL PROTEIN KIAA0009 [H. sapiens] | | | gi = 2308054 | 1295695 |
| IC11884 | UG75 Expression | EST | Mm.45127 | TITLE ESTs, Moderately similar to cell growth regulator rCGR11 [R. norvegicus] | | | gi = 1840673 | 1429470 |
| IC11885 | UG75 Expression | EST | Mm.45128 | TITLE ESTs, Weakly similar to dJ126A5.2.1 [H. sapiens] | | | gi = 4216910 | 391512 |
| IC11886 | UG75 Expression | EST | Mm.45129 | TITLE ESTs | | | gi = 4613366 | 620262 |
| IC11887 | UG75 Expression | EST | Mm.45133 | TITLE ESTs, Weakly similar to Ylr218cp [S. cerevisiae] | | | gi = 1316255 | 620987 |
| IC11888 | UG75 Expression | EST | Mm.45134 | TITLE ESTs | | | gi = 6008586 | 719433 |
| IC11889 | UG75 Expression | EST | Mm.45142 | TITLE ESTs | | | gi = 2907060 | 1329289 |
| IC11890 | UG75 Expression | EST | Mm.45145 | TITLE ESTs, Moderately similar to Similar to D. melanogaster parallel sister chromatids protein [H. sapiens] | | | gi = 6098597 | 1279550 |
| IC11891 | UG75 Expression | EST | Mm.45147 | TITLE ESTs | | | gi = 4720602 | 1510599 |
| IC11892 | UG75 Expression | EST | Mm.45149 | TITLE ESTs | | | gi = 1310392 | 718341 |
| IC11893 | UG75 Expression | EST | Mm.45155 | TITLE ESTs | | | gi = 3099847 | 720991 |
| IC11894 | UG75 Expression | EST | Mm.45157 | TITLE ESTs | | | gi = 5910382 | 1002689 |
| IC11895 | UG75 Expression | EST | Mm.45159 | TITLE ESTs, Moderately similar to hADA2 | | | gi = 3164897 | 722013 |
| IC11896 | UG75 Expression | EST | Mm.45161 | TITLE ESTs, Moderately similar to hypoxis-indicible protein 2 [H. sapiens] | | | gi = 2962635 | 1265400 |
| IC11897 | UG75 Expression | EST | Mm.45168 | TITLE ESTs | | | gi = 6749049 | 1395470 |
| IC11898 | UG75 Expression | EST | Mm.45171 | TITLE ESTs | | | gi = 2574334 | 1020618 |
| IC11899 | UG75 Expression | EST | Mm.45180 | TITLE ESTs | | | gi = 6516305 | 764142 |
| IC11900 | UG75 Expression | EST | Mm.45184 | TITLE ESTs | | | gi = 6008867 | 749249 |
| IC11901 | UG75 Expression | EST | Mm.45186 | TITLE ESTs | | | gi = 1863647 | 637612 |
| IC11902 | UG75 Expression | EST | Mm.45189 | TITLE ESTs | | | gi = 2691640 | 1295218 |
| IC11903 | UG75 Expression | EST | Mm.45194 | TITLE ESTs | | | gi = 1838780 | 583922 |
| IC11904 | UG75 Expression | EST | Mm.45197 | TITLE ESTs | | | gi = 3053463 | 617884 |
| IC11905 | UG75 Expression | EST | Mm.45199 | TITLE ESTs | | | gi = 5910387 | 617883 |
| IC11906 | UG75 Expression | EST | Mm.45208 | TITLE ESTs | | | gi = 2305601 | 752369 |
| IC11907 | UG75 Expression | EST | Mm.45217 | TITLE ESTs, Weakly similar to DNA-binding protein [M. musculus] | | | gi = 5749041 | 722975 |
| IC11908 | UG75 Expression | EST | Mm.45225 | TITLE ESTs, Weakly similar to predicted using Genefinder [C. elegans] | | | gi = 5906494 | 1345465 |
| IC11909 | UG75 Expression | EST | Mm.45233 | TITLE ESTs, Weakly similar to GLYCOPROTEIN 25L PRECURSOR [Canis familiaris] | | | gi = 2776101 | 894372 |
| IC11910 | UG75 Expression | EST | Mm.45237 | TITLE ESTs | | | gi = 1908123 | 1263539 |
| IC11911 | UG75 Expression | EST | Mm.45243 | TITLE ESTs, Weakly similar to calmodulin [M. musculus] | | | gi = 5337238 | 1745752 |
| IC11912 | UG75 Expression | EST | Mm.45252 | TITLE ESTs | | | gi = 2305332 | 1264756 |
| IC11913 | UG75 Expression | EST | Mm.45253 | TITLE ESTs | | | gi = 4303228 | 596616 |
| IC11914 | UG75 Expression | EST | Mm.45254 | TITLE ESTs, Weakly similar to one short region of weak similarity to S. cerevisia protease A inhibitor 3 [C. elegans] | | | gi = 2502662 | 640685 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11915 | UG75 Expression | EST | Mm.45255 | TITLE ESTs | | | gi = 5197132 | 777340 |
| IC11916 | UG75 Expression | EST | Mm.45256 | TITLE ESTs | | | gi = 4300853 | 576479 |
| IC11917 | UG75 Expression | EST | Mm.45258 | TITLE ESTs | | | gi = 1738026 | 607191 |
| IC11918 | UG75 Expression | EST | Mm.45260 | TITLE ESTs | | | gi = 4296227 | 640544 |
| IC11919 | UG75 Expression | EST | Mm.45284 | TITLE ESTs, Weakly similar to coding region determinant binding protein [M. musculus] | | | gi = 4032954 | 1922447 |
| IC11920 | UG75 Expression | EST | Mm.45288 | TITLE ESTs | | | gi = 4967391 | 2135631 |
| IC11921 | UG75 Expression | EST | Mm.45289 | TITLE ESTs | | | gi = 2284380 | 583559 |
| IC11922 | UG75 Expression | EST | Mm.45291 | TITLE ESTs | | | gi = 4777785 | 1225543 |
| IC11923 | UG75 Expression | EST | Mm.45292 | TITLE ESTs | | | gi = 2956520 | 1282276 |
| IC11924 | UG75 Expression | EST | Mm.45294 | TITLE ESTs | | | gi = 2963059 | 1264210 |
| IC11925 | UG75 Expression | EST | Mm.45298 | TITLE ESTs | | | gi = 4730227 | 636682 |
| IC11926 | UG75 Expression | EST | Mm.45314 | TITLE ESTs | | | gi = 4791835 | 2812376 |
| IC11927 | UG75 Expression | EST | Mm.45322 | TITLE ESTs | | | gi = 3374208 | 1446015 |
| IC11928 | UG75 Expression | EST | Mm.45332 | TITLE ESTs | | | gi = 6099460 | 1039028 |
| IC11929 | UG75 Expression | EST | Mm.45333 | TITLE ESTs | | | gi = 5372611 | 749184 |
| IC11930 | UG75 Expression | EST | Mm.45337 | TITLE ESTs, Moderately similar to KIAA1014 protein [H. sapiens] | | | gi = 1776435 | 643240 |
| IC11931 | UG75 Expression | EST | Mm.45345 | TITLE ESTs | | | gi = 1475431 | 619929 |
| IC11932 | UG75 Expression | EST | Mm.45349 | TITLE ESTs | | | gi = 1873216 | 1749102 |
| IC11933 | UG75 Expression | EST | Mm.45350 | TITLE ESTs, Weakly similar to similar to O-sialoglycoprotein endopeptidase [C. elegans] | | | gi = 1663487 | 751494 |
| IC11934 | UG75 Expression | EST | Mm.45352 | TITLE ESTs | | | gi = 6085208 | 1295772 |
| IC11935 | UG75 Expression | EST | Mm.45357 | TITLE ESTs, Weakly similar to PRESYNAPTIC DENSITY PROTEIN 95 [M. musculus] | | | gi = 5567187 | 1294426 |
| IC11936 | UG75 Expression | EST | Mm.45360 | TITLE ESTs | | | gi = 4289086 | 620128 |
| IC11937 | UG75 Expression | EST | Mm.45361 | TITLE ESTs | | | gi = 4804787 | 639549 |
| IC11938 | UG75 Expression | EST | Mm.45367 | TITLE ESTs | | | gi = 1776433 | 722755 |
| IC11939 | UG75 Expression | EST | Mm.4538 | TITLE ESTs | | | gi = 2520069 | 596397 |
| IC11940 | UG75 Expression | EST | Mm.45406 | TITLE ESTs, Moderately similar to Unknown [H. sapiens] | | | gi = 4306456 | 893903 |
| IC11941 | UG75 Expression | EST | Mm.45408 | TITLE ESTs, Moderately similar to unknown protein IT12 [H. sapiens] | | | gi = 1752623 | 1447151 |
| IC11942 | UG75 Expression | EST | Mm.45418 | TITLE ESTs | | | gi = 1649391 | 1446025 |
| IC11943 | UG75 Expression | EST | Mm.45430 | TITLE ESTs | | | gi = 2967200 | 1749924 |
| IC11944 | UG75 Expression | EST | Mm.45432 | TITLE ESTs | | | gi = 6100130 | 573971 |
| IC11945 | UG75 Expression | EST | Mm.45434 | TITLE ESTs, Weakly similar to ankyrin 3 [M. musculus] | | | gi = 5372762 | 1149155 |
| IC11946 | UG75 Expression | EST | Mm.45435 | TITLE ESTs, Moderately similar to (define not available 6094339) [R. norvegicus] | | | gi = 4616000 | 1243966 |
| IC11947 | UG75 Expression | EST | Mm.45437 | TITLE ESTs | | | gi = 4441753 | 749143 |
| IC11948 | UG75 Expression | EST | Mm.45439 | TITLE ESTs | | | gi = 1808570 | 641993 |
| IC11949 | UG75 Expression | EST | Mm.45444 | TITLE ESTs | | | gi = 1727172 | 598292 |
| IC11950 | UG75 Expression | EST | Mm.45479 | TITLE ESTs, Weakly similar to MUCIN 1 PRECURSOR [M. musculus] | | | gi = 6085544 | 575897 |
| IC11951 | UG75 Expression | EST | Mm.45502 | TITLE ESTs | | | gi = 1793004 | 640091 |
| IC11952 | UG75 Expression | EST | Mm.45513 | TITLE ESTs | | | gi = 5298194 | 1229593 |
| IC11953 | UG75 Expression | EST | Mm.45533 | TITLE ESTs | | | gi = 3235925 | 642499 |
| IC11954 | UG75 Expression | EST | Mm.45559 | TITLE ESTs, Weakly similar to NUCLEOSOME ASSEMBLY PROTEIN 1-LIKE 2 [M. musculus] | | | gi = 4434696 | 1345440 |
| IC11955 | UG75 Expression | EST | Mm.45560 | TITLE ESTs | | | gi = 4484398 | 534030 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11956 | UG75 Expression | EST | Mm.45561 | TITLE ESTs, Weakly similar to legumain [M. musculus] | | | gi = 434381 | 1296023 |
| IC11957 | UG75 Expression | EST | Mm.45562 | TITLE ESTs | | | gi = 1808318 | 636588 |
| IC11958 | UG75 Expression | EST | Mm.45563 | TITLE ESTs | | | gi = 2305806 | 638654 |
| IC11959 | UG75 Expression | EST | Mm.45566 | TITLE ESTs, Moderately similar to PROBABLE RNA-DEPENDENT HELICASE P72 [H. sapiens] | | | gi = 1766844 | 636193 |
| IC11960 | UG75 Expression | EST | Mm.45572 | | | | gi = 3067201 | 1327563 |
| IC11961 | UG75 Expression | EST | Mm.45573 | TITLE ESTs | | | gi = 1542543 | 1264271 |
| IC11962 | UG75 Expression | EST | Mm.45574 | TITLE ESTs, Weakly similar to predicted using Genefinder [C. elegans] | | | gi = 4604072 | 1363156 |
| IC11963 | UG75 Expression | EST | Mm.45578 | TITLE ESTs, Weakly similar to matrin cyclophilin [R. norvegicus] | | | gi = 3683122 | 1921588 |
| IC11964 | UG75 Expression | EST | Mm.45581 | TITLE ESTs | | | gi = 2855533 | 1151585 |
| IC11965 | UG75 Expression | EST | Mm.45582 | TITLE ESTs, Moderately similar to 2-OXOGLUTARATE DEHYDROGENASE E1 COMPONENT PRECURSOR [Homo sapiens] | | | gi = 4967751 | 1380294 |
| IC11966 | UG75 Expression | EST | Mm.45586 | TITLE ESTs | | | gi = 6098632 | 617572 |
| IC11967 | UG75 Expression | EST | Mm.45588 | TITLE ESTs | | | gi = 1755813 | 617213 |
| IC11968 | UG76 LID366 B cell | EST | Mm.45512 | TITLE ESTs | | | gi = 7315566 | 1277744 |
| IC11969 | UG75 Expression | EST | Mm.45644 | TITLE ESTs | | | gi = 1876633 | 1002485 |
| IC11970 | UG75 Expression | EST | Mm.45651 | GLUCOSE:GLYCOPTROTEIN GLUCOSYLTRANSFERASE PRECURSOR [D. melanogaster] | | | gi = 2248728 | 597920 |
| IC11971 | UG75 Expression | EST | Mm.45659 | TITLE ESTs | | | gi = 450516 | 1445870 |
| IC11972 | UG75 Expression | EST | Mm.45678 | TITLE ESTs, Moderately similar to NADH-UBIQUINONE OXIDOREDUCTASE 75 KD SUBUNIT PRECURSOR [H. sapiens] | | | gi = 4298457 | 616715 |
| IC11973 | UG75 Expression | EST | Mm.45681 | TITLE ESTs | | | gi = 2811523 | 1243314 |
| IC11974 | UG75 Expression | EST | Mm.45727 | TITLE ESTs | | | gi = 6638396 | 2331866 |
| IC11975 | UG75 Expression | EST | Mm.45733 | TITLE ESTs | | | gi = 3684477 | 1346183 |
| IC11976 | UG75 Expression | EST | Mm.45736 | TITLE ESTs | | | gi = 2305960 | 583610 |
| IC11977 | UG75 Expression | EST | Mm.45737 | TITLE ESTs | | | gi = 1862367 | 1380221 |
| IC11978 | UG75 Expression | EST | Mm.45738 | TITLE ESTs, Moderately similar to ACYL-COA DEHYDROGENASE, SHORT-CHAIN SPECIFIC PRECURSOR [Homo sapiens] | | | gi = 6631239 | 1294667 |
| IC11979 | UG75 Expression | EST | Mm.45739 | TITLE ESTs | | | gi = 6822682 | 551341 |
| IC11980 | UG75 Expression | EST | Mm.45740 | TITLE ESTs | | | gi = 1937661 | 596232 |
| IC11981 | UG75 Expression | EST | Mm.45741 | TITLE ESTs | | | gi = 4601057 | 597392 |
| IC11982 | UG75 Expression | EST | Mm.45742 | TITLE ESTs | | | gi = 4725764 | 583080 |
| IC11983 | UG75 Expression | EST | Mm.45744 | TITLE ESTs | | | gi = 2076064 | 618433 |
| IC11984 | UG75 Expression | EST | Mm.45745 | TITLE ESTs, Weakly similar to pancortin-1 [M. musculus] | | | gi = 1876084 | 621115 |
| IC11985 | UG75 Expression | EST | Mm.45746 | TITLE ESTs | | | gi = 2140343 | 642324 |
| IC11986 | UG75 Expression | EST | Mm.45747 | TITLE ESTs | | | gi = 4723717 | 637097 |
| IC11987 | UG75 Expression | EST | Mm.45748 | TITLE ESTs, Weakly similar to ZK1128.2 [C. elegans] | | | gi = 4967950 | 638139 |
| IC11988 | UG75 Expression | EST | Mm.45753 | TITLE ESTs | | | gi = 1937284 | 749160 |
| IC11989 | UG75 Expression | EST | Mm.45754 | TITLE ESTs | | | gi = 2743767 | 1749784 |
| IC11990 | UG75 Expression | EST | Mm.45758 | TITLE ESTs | | | gi = 1882297 | 717911 |
| IC11991 | UG75 Expression | EST | Mm.45760 | TITLE ESTs | | | gi = 2349275 | 991279 |
| IC11992 | UG75 Expression | EST | Mm.45763 | TITLE ESTs | | | gi = 2625995 | 717825 |
| IC11993 | UG75 Expression | EST | Mm.45767 | TITLE ESTs | | | gi = 2323832 | 752146 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC11994 | UG75 Expression | EST | Mm.45770 | TITLE ESTs | | | gi = 1776796 | 642472 |
| IC11995 | UG75 Expression | EST | Mm.45771 | TITLE ESTs, Weakly similar to ERG-associated protein ESET [*M. musculus*] | | | gi = 1793334 | 777603 |
| IC11996 | UG75 Expression | EST | Mm.45772 | TITLE ESTs | | | gi = 3370219 | 1378124 |
| IC11997 | UG75 Expression | EST | Mm.45777 | TITLE ESTs | | | gi = 4614842 | 617921 |
| IC11998 | UG75 Expression | EST | Mm.45778 | TITLE ESTs | | | gi = 3692392 | 1226662 |
| IC11999 | UG75 Expression | EST | Mm.45783 | TITLE ESTs | | | gi = 4307475 | 597266 |
| IC12000 | UG75 Expression | EST | Mm.45784 | TITLE ESTs, Moderately similar to Golgi complex autoantigen golgin-97 [*H. sapiens*] | | | gi = 4291200 | 578069 |
| IC12001 | UG75 Expression | EST | Mm.45785 | TITLE ESTs | | | gi = 4304609 | 642291 |
| IC12002 | UG75 Expression | EST | Mm.45786 | TITLE ESTs | | | gi = 4318192 | 749924 |
| IC12003 | UG75 Expression | EST | Mm.45788 | TITLE ESTs | | | gi = 1827008 | 1429421 |
| IC12004 | UG75 Expression | EST | Mm.45795 | TITLE ESTs | | | gi = 2850432 | 1244047 |
| IC12005 | UG75 Expression | EST | Mm.45797 | TITLE ESTs | | | gi = 6008687 | 1001390 |
| IC12006 | UG75 Expression | EST | Mm.45812 | TITLE ESTs | | | gi = 5124824 | 659359 |
| IC12007 | UG75 Expression | EST | Mm.45837 | TITLE ESTs | | | gi = 4299345 | 617234 |
| IC12008 | UG75 Expression | EST | Mm.45849 | TITLE ESTs | | | gi = 5298310 | 734272 |
| IC12009 | UG75 Expression | EST | Mm.45852 | TITLE ESTs | | | gi = 1793080 | 640102 |
| IC12010 | UG75 Expression | EST | Mm.45855 | TITLE ESTs | | | gi = 3731526 | 1395403 |
| IC12011 | UG75 Expression | EST | Mm.45877 | TITLE ESTs | | | gi = 2811475 | 1225264 |
| IC12012 | UG75 Expression | EST | Mm.45889 | TITLE ESTs | | | gi = 5551253 | 621026 |
| IC12013 | UG75 Expression | EST | Mm.45908 | TITLE ESTs | | | gi = 2283576 | 1363239 |
| IC12014 | UG75 Expression | EST | Mm.45927 | TITLE ESTs, Moderately similar to KIFC1 [*M. musculus*] | | | gi = 4613985 | 388628 |
| IC12015 | UG75 Expression | EST | Mm.45950 | TITLE ESTs | | | gi = 4288429 | 619621 |
| IC12016 | UG75 Expression | EST | Mm.45966 | TITLE ESTs | | | gi = 4805066 | 718718 |
| IC12017 | UG75 Expression | EST | Mm.45969 | TITLE ESTs, Weakly similar to KIAA0379 [*H. sapiens*] | | | gi = 6008679 | 597388 |
| IC12018 | UG75 Expression | EST | Mm.45970 | TITLE ESTs | | | gi = 1756127 | 618677 |
| IC12019 | UG75 Expression | EST | Mm.45971 | TITLE ESTs | | | gi = 4571499 | 597211 |
| IC12020 | UG75 Expression | EST | Mm.45972 | TITLE ESTs | | | gi = 2292403 | 958753 |
| IC12021 | UG75 Expression | EST | Mm.45973 | TITLE ESTs | | | gi = 1808271 | 641877 |
| IC12022 | UG75 Expression | EST | Mm.45974 | TITLE ESTs | | | gi = 4785081 | 621506 |
| IC12023 | UG75 Expression | EST | Mm.45975 | TITLE ESTs | | | gi = 1876621 | 642625 |
| IC12024 | UG75 Expression | EST | Mm.45976 | TITLE ESTs | | | gi = 2258669 | 634683 |
| IC12025 | UG75 Expression | EST | Mm.45977 | TITLE ESTs, Moderately similar to CGI-47 protein [*H. sapiens*] | | | gi = 1903556 | 721449 |
| IC12026 | UG75 Expression | EST | Mm.45980 | TITLE ESTs | | | gi = 1464202 | 1446771 |
| IC12027 | UG75 Expression | EST | Mm.45986 | TITLE ESTs, Weakly similar to RSP-1 PROTEIN [*Mus musculus*] | | | gi = 4967317 | 1750080 |
| IC12028 | UG75 Expression | EST | Mm.45987 | TITLE ESTs | | | gi = 4318663 | 973176 |
| IC12029 | UG75 Expression | EST | Mm.45991 | TITLE ESTs | | | gi = 2101163 | 576940 |
| IC12030 | UG75 Expression | EST | Mm.45993 | TITLE ESTs | | | gi = 1863920 | 643373 |
| IC12031 | UG75 Expression | EST | Mm.45994 | TITLE ESTs, Weakly similar to PLATELET-ENDOTHELIAL TETRASPAN ANTIGEN 3 [*M. musculus*] | | | gi = 2411839 | 533937 |
| IC12032 | UG75 Expression | EST | Mm.45995 | TITLE ESTs | | | gi = 1767013 | 1148954 |
| IC12033 | UG75 Expression | EST | Mm.45999 | TITLE ESTs, Moderately similar to protein phosphatase 2A B'alpha3 regularoty subunit [*M. musculus*] | | | gi = 2262739 | 1447142 |
| IC12034 | UG75 Expression | EST | Mm.46001 | TITLE ESTs | | | gi = 1677004 | 1262932 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12035 | UG75 Expression | EST | Mm.46007 | TITLE ESTs, Weakly similar to 78 KD GLUCOSE REGULATED PROTEIN PRECURSOR [*M. musculus*] | | | gi = 2860597 | 972610 |
| IC12036 | UG75 Expression | EST | Mm.46008 | TITLE ESTs | | | gi = 2692307 | 635565 |
| IC12037 | UG75 Expression | EST | Mm.46009 | TITLE ESTs | | | gi = 3054880 | 1328108 |
| IC12038 | UG75 Expression | EST | Mm.46011 | TITLE ESTs | | | gi = 1769383 | 637632 |
| IC12039 | UG75 Expression | EST | Mm.46012 | TITLE ESTs | | | gi = 3100201 | 1281998 |
| IC12040 | UG75 Expression | EST | Mm.46016 | TITLE ESTs, Weakly similar to type 1 procollagen C-proteinase enhancer protein [*M. musculus*] | | | gi = 3160547 | 582169 |
| IC12041 | UG75 Expression | EST | Mm.46018 | TITLE ESTs | | | gi = 6515957 | 1494992 |
| IC12042 | UG75 Expression | EST | Mm.46020 | TITLE ESTs | | | gi = 1794358 | 643146 |
| IC12043 | UG75 Expression | EST | Mm.46021 | TITLE ESTs | | | gi = 3522610 | 1429722 |
| IC12044 | UG75 Expression | EST | Mm.46022 | TITLE ESTs, Moderately similar to hypothetical protein [*H. sapiens*] | | | gi = 6084783 | 973838 |
| IC12045 | UG75 Expression | EST | Mm.46024 | TITLE ESTs | | | gi = 6078046 | 637654 |
| IC12046 | UG75 Expression | EST | Mm.46032 | TITLE ESTs | | | gi = 4968342 | 582466 |
| IC12047 | UG75 Expression | EST | Mm.46036 | TITLE ESTs | | | gi = 2690985 | 577449 |
| IC12048 | UG75 Expression | EST | Mm.46038 | TITLE ESTs | | | gi = 4613266 | 619688 |
| IC12049 | UG75 Expression | EST | Mm.46040 | TITLE ESTs | | | gi = 2990944 | 1265074 |
| IC12050 | UG75 Expression | EST | Mm.46042 | TITLE ESTs, Weakly similar to anti-Fas-induced apoptosis [*H. sapiens*] | | | gi = 4407407 | 750847 |
| IC12051 | UG75 Expression | EST | Mm.46046 | TITLE ESTs | | | gi = 4484851 | 1282110 |
| IC12052 | UG75 Expression | EST | Mm.46063 | TITLE ESTs | | | gi = 1680727 | 596309 |
| IC12053 | UG75 Expression | EST | Mm.46067 | TITLE ESTs | | | gi = 1758937 | 622893 |
| IC12054 | UG75 Expression | EST | Mm.46070 | TITLE ESTs | | | gi = 6939317 | 577137 |
| IC12055 | UG75 Expression | EST | Mm.46078 | TITLE ESTs, Weakly similar to zinc finger protein ZNF216 [*M. musculus*] | | | gi = 1875929 | 641787 |
| IC12056 | UG75 Expression | EST | Mm.46133 | TITLE ESTs | | | gi = 4604337 | 515106 |
| IC12057 | UG75 Expression | EST | Mm.4614 | TITLE ESTs | | | gi = 6633100 | 1225012 |
| IC12058 | UG75 Expression | EST | Mm.46164 | TITLE ESTs | | | gi = 5335564 | 1312403 |
| IC12059 | UG75 Expression | EST | Mm.46172 | TITLE ESTs | | | gi = 1554906 | 722510 |
| IC12060 | UG75 Expression | EST | Mm.46176 | TITLE ESTs, Weakly similar to HYPOTHETICAL 12.3 KD PROTEIN ZK945.8 IN CHROMOSOME II [*Caenorhabditis elegans*] | | | gi = 3164498 | 533467 |
| IC12061 | UG75 Expression | EST | Mm.46179 | TITLE ESTs | | | gi = 4782371 | 572817 |
| IC12062 | UG75 Expression | EST | Mm.46184 | TITLE ESTs, Weakly similar to formin binding protein 11 [*M. musculus*] | | | gi = 6749478 | 644984 |
| IC12063 | UG75 Expression | EST | Mm.46202 | TITLE ESTs | | | gi = 4602942 | 1121795 |
| IC12064 | UG75 Expression | EST | Mm.46206 | TITLE ESTs | | | gi = 5907864 | 598793 |
| IC12065 | UG76 LID366 B cell | EST | Mm.46217 | TITLE ESTs | | | gi = 1287856 | 987078 |
| IC12066 | UG75 Expression | EST | Mm.46218 | TITLE ESTs, Weakly similar to similar to protein kinase C inhibitors [*C. elegans*] | | | gi = 2989080 | 722957 |
| IC12067 | UG75 Expression | EST | Mm.46224 | TITLE ESTs | | | gi = 4030350 | 1920818 |
| IC12068 | UG75 Expression | EST | Mm.46230 | TITLE ESTs | | | gi = 1475033 | 1264287 |
| IC12069 | UG75 Expression | EST | Mm.46242 | TITLE ESTs | | | gi = 1290252 | 573412 |
| IC12070 | UG75 Expression | EST | Mm.46245 | TITLE ESTs | | | gi = 1662898 | 577117 |
| IC12071 | UG75 Expression | EST | Mm.46254 | TITLE ESTs | | | gi = 1888718 | 722537 |
| IC12072 | UG75 Expression | EST | Mm.46262 | TITLE ESTs | | | gi = 1684006 | 595876 |
| IC12073 | 00/02 Literature | EST | Mm.46270 | transcript expressed during hematopoiesis 1 | Tedp1-pending F3-1| | gi = 4315595 | 1479111 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12074 | UG75 Expression | EST | Mm.46272 | TITLE ESTs | | | gi = 3054012 | 622939 |
| IC12075 | UG75 Expression | EST | Mm.46278 | TITLE ESTs | | | gi = 4303677 | 641443 |
| IC12076 | UG75 Expression | EST | Mm.46282 | TITLE ESTs | | | gi = 1476141 | 440233 |
| IC12077 | UG75 Expression | EST | Mm.46292 | homolog of Drosophila female sterile homeotic mRNA [*H. sapiens*] | | | gi = 2283187 | 639354 |
| IC12078 | UG75 Expression | EST | Mm.46299 | TITLE guanine nucleotide binding protein (G protein), gamma transducing activity polypeptide 2 | GENE Gngt2 | | gi = 1494895 | 751431 |
| IC12079 | UG75 Expression | EST | Mm.463 | TITLE ESTs | | | gi = 6822496 | 595923 |
| IC12080 | UG75 Expression | EST | Mm.46307 | TITLE ESTs, Weakly similar to NAD(P)H dehydrogenase [*M. musculus*] | | | gi = 2158076 | 1279427 |
| IC12081 | UG75 Expression | EST | Mm.46333 | TITLE ESTs | | | gi = 2249307 | 718208 |
| IC12082 | UG75 Expression | EST | Mm.46339 | TITLE ESTs, Weakly similar to TRANSIENT RECEPTOR POTENTIAL LOCUS C PROTEIN PRECURSOR [*D. melanogaster*] | | | gi = 5190631 | 334445 |
| IC12083 | UG75 Expression | EST | Mm.46346 | TITLE ESTs | | | gi = 5191595 | 719125 |
| IC12084 | UG75 Expression | EST | Mm.46355 | TITLE ESTs | | | gi = 2720959 | 621066 |
| IC12085 | UG75 Expression | EST | Mm.46366 | TITLE ESTs, Weakly similar to HEAT SHOCK PROTEIN 67B2 [*D. melanogaster*] | | | gi = 6823796 | 582519 |
| IC12086 | UG75 Expression | EST | Mm.46372 | TITLE ESTs | | | gi = 1325858 | 619719 |
| IC12087 | UG75 Expression | EST | Mm.46380 | TITLE ESTs, Weakly similar to /prediction | | | gi = 1643540 | 717784 |
| IC12088 | UG75 Expression | EST | Mm.46382 | TITLE ESTs, Weakly similar to INTERFERON-INDUCED PROTEIN 6-16 PRECURSOR [*Homo sapiens*] | | | gi = 2803142 | 973075 |
| IC12089 | UG75 Expression | EST | Mm.46397 | TITLE ESTs, Weakly similar to cDNA EST CEMSF67FB comes from this gene [*C. elegans*] | | | gi = 3718759 | 1379072 |
| IC12090 | UG75 Expression | EST | Mm.46412 | TITLE ESTs | | | gi = 2989482 | 750133 |
| IC12091 | UG75 Expression | EST | Mm.46415 | TITLE ESTs [*H. sapiens*] | | | gi = 5907821 | 597835 |
| IC12092 | UG75 Expression | EST | Mm.46424 | TITLE ESTs | | | gi = 6638469 | 1363378 |
| IC12093 | UG75 Expression | EST | Mm.46440 | TITLE ESTs | | | gi = 4606023 | 1749588 |
| IC12094 | UG75 Expression | EST | Mm.46444 | TITLE ESTs, Weakly similar to putative membrane associated progesterone receptor component [*M. musculus*] | | | gi = 3519005 | 479552 |
| IC12095 | UG75 Expression | EST | Mm.46449 | TITLE ESTs | | | gi = 6633235 | 621807 |
| IC12096 | UG75 Expression | EST | Mm.46455 | TITLE ESTs | | | gi = 2041949 | 749994 |
| IC12097 | UG75 Expression | EST | Mm.46461 | TITLE ESTs | | | gi = 2256530 | 893933 |
| IC12098 | UG75 Expression | EST | Mm.46466 | TITLE ESTs, Weakly similar to contains similarity to C2H2-type zinc fingers [*C. elegans*] | | | gi = 2305670 | 634448 |
| IC12099 | UG75 Expression | EST | Mm.46473 | TITLE ESTs, Moderately similar to zinc finger protein [*H. sapiens*] | | | gi = 2678374 | 573692 |
| IC12100 | UG75 Expression | EST | Mm.46475 | TITLE ESTs | | | gi = 6516294 | 2102081 |
| IC12101 | UG75 Expression | EST | Mm.46480 | TITLE ESTs, Weakly similar to KIAA0033 [*H. sapiens*] | | | gi = 4537178 | 721994 |
| IC12102 | UG75 Expression | EST | Mm.46482 | TITLE ESTs | | | gi = 4536986 | 636306 |
| IC12103 | UG75 Expression | EST | Mm.46488 | TITLE ESTs | | | gi = 3158647 | 1446613 |
| IC12104 | UG75 Expression | EST | Mm.46491 | TITLE ESTs | | | gi = 5265392 | 1193725 |
| IC12105 | UG75 Expression | EST | Mm.46493 | TITLE ESTs | | | gi = 3683430 | 637482 |
| IC12106 | UG75 Expression | EST | Mm.46494 | TITLE ESTs, Moderately similar to CGI-90 protein [*H. sapiens*] | | | gi = 1682272 | 577065 |
| IC12107 | UG75 Expression | EST | Mm.46497 | TITLE ESTs | | | gi = 1861799 | 760997 |
| IC12108 | UG75 Expression | EST | Mm.46500 | TITLE ESTs | | | gi = 4723738 | 637222 |
| IC12109 | UG75 Expression | EST | Mm.46501 | TITLE ESTs | | | gi = 6756388 | 583471 |

US 6,706,867 B1

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12110 | UG75 Expression | EST | Mm.46503 | TITLE ESTs | | | gi = 2964989 | 636876 |
| IC12111 | UG75 Expression | EST | Mm.46505 | TITLE ESTs | | | gi = 1700736 | 550649 |
| IC12112 | UG75 Expression | EST | Mm.46510 | TITLE ESTs | | | gi = 1539195 | 717783 |
| IC12113 | UG75 Expression | EST | Mm.46512 | TITLE ESTs, Moderately similar to determined by GENSCAN prediction and spliced EST [*H. sapiens*] | | | gi = 3733840 | 620216 |
| IC12114 | UG75 Expression | EST | Mm.46519 | | | | gi = 2625410 | 1001771 |
| IC12115 | UG75 Expression | EST | Mm.46521 | TITLE ESTs | | | gi = 4729824 | 1230756 |
| IC12116 | UG75 Expression | EST | Mm.46528 | TITLE ESTs | | | gi = 2693982 | 1149019 |
| IC12117 | UG75 Expression | EST | Mm.46530 | TITLE ESTs | | | gi = 5476744 | 1149480 |
| IC12118 | UG75 Expression | EST | Mm.46532 | TITLE ESTs | | | gi = 3297055 | 1379806 |
| IC12119 | UG75 Expression | EST | Mm.46539 | TITLE ESTs | | | gi = 1896168 | 1395148 |
| IC12120 | UG75 Expression | EST | Mm.46545 | TITLE ESTs, Weakly similar to growth arrest specific gene [*M. musculus*] | | | gi = 1724419 | 581914 |
| IC12121 | UG75 Expression | EST | Mm.46547 | TITLE ESTs | | | gi = 1931820 | 764228 |
| IC12122 | UG75 Expression | EST | Mm.46548 | TITLE ESTs, Weakly similar to POLYADENYLATE-BINDING PROTEIN [*D. melanogaster*] | | | gi = 1896613 | 1193621 |
| IC12123 | UG75 Expression | EST | Mm.46552 | TITLE ESTs, Weakly similar to (define not available 6010699) [*R. norvegicus*] | | | gi = 5493022 | 1264384 |
| IC12124 | UG75 Expression | EST | Mm.46557 | TITLE ESTs, Weakly similar to RNA binding protein [*M. musculus*] | | | gi = 6083788 | 1001994 |
| IC12125 | UG75 Expression | EST | Mm.46558 | TITLE ESTs | | | gi = 2454776 | 1264062 |
| IC12126 | UG75 Expression | EST | Mm.46580 | TITLE ESTs, Weakly similar to PLATELET-ACTIVATING FACTOR ACETYLHYDROLASE IB ALPHA SUBUNIT [*R. norvegicus*] | | | gi = 4601861 | 635192 |
| IC12127 | UG75 Expression | EST | Mm.46581 | TITLE ESTs, Weakly similar to phospholipase C [*M. musculus*] | | | gi = 1286472 | 765941 |
| IC12128 | UG75 Expression | EST | Mm.46587 | TITLE ESTs [*M. musculus*] | | | gi = 2813646 | 1140288 |
| IC12129 | UG75 Expression | EST | Mm.46595 | TITLE ESTs | | | gi = 448681 | 596431 |
| IC12130 | UG75 Expression | EST | Mm.46600 | TITLE ESTs | | | gi = 1427169 | 1329084 |
| IC12131 | UG75 Expression | EST | Mm.46606 | TITLE ESTs | | | gi = 1794361 | 639651 |
| IC12132 | UG75 Expression | EST | Mm.46614 | TITLE ESTs, Weakly similar to C06G3.8 [*C. elegans*] | | | gi = 1655184 | 551254 |
| IC12133 | UG75 Expression | EST | Mm.46624 | TITLE ESTs, Weakly similar to KIAA0425 [*H. sapiens*] | | | gi = 6078635 | 574032 |
| IC12134 | UG75 Expression | EST | Mm.46627 | TITLE ESTs, Weakly similar to putative retrovirus-related gag protein [*R. norvegicus*] | | | gi = 4765737 | 720866 |
| IC12135 | UG75 Expression | EST | Mm.46628 | TITLE ESTs, Moderately similar to (define not available 6013329) [*M. musculus*] | | | gi = 2978929 | 1281405 |
| IC12136 | UG75 Expression | EST | Mm.46631 | TITLE ESTs, Weakly similar to similar to 4-hydroxybenzoate octaprenyltransferase [*C. elegans*] | | | gi = 1676916 | 598492 |
| IC12137 | UG75 Expression | EST | Mm.46635 | TITLE ESTs | | | gi = 2755968 | 576868 |
| IC12138 | UG75 Expression | EST | Mm.46636 | TITLE ESTs | | | gi = 2081199 | 617290 |
| IC12139 | UG75 Expression | EST | Mm.46641 | TITLE ESTs, Weakly similar to LA PROTEIN HOMOLOG [*Drosophila melanogaster*] | | | gi = 2284279 | 639595 |
| IC12140 | UG75 Expression | EST | Mm.46644 | TITLE ESTs, Weakly similar to Paneth cell enhanced expression PCEE [*M. musculus*] | | | gi = 2101695 | 1294165 |
| IC12141 | UG75 Expression | EST | Mm.46649 | TITLE ESTs, Moderately similar to dJ1163J1.2.1 [*H. sapiens*] | | | gi = 4029587 | 1921390 |
| IC12142 | UG75 Expression | EST | Mm.46653 | TITLE ESTs | | | gi = 1282396 | 597624 |
| IC12143 | UG75 Expression | EST | Mm.46654 | TITLE ESTs | | | gi = 6935970 | 1105806 |
| IC12144 | UG75 Expression | EST | Mm.46656 | TITLE ESTs | | | gi = 4216146 | 1380422 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12145 | UG75 Expression | EST | Mm.46658 | TITLE ESTs | | | gi = 4258719 | 348165 |
| IC12146 | UG75 Expression | EST | Mm.46662 | TITLE ESTs | | | gi = 4302784 | 596156 |
| IC12147 | UG75 Expression | EST | Mm.46673 | TITLE ESTs, Moderately similar to HYPOTHETICAL PROTEIN KIAA0101 [H. sapiens] | | | gi = 2305925 | 719052 |
| IC12148 | UG75 Expression | EST | Mm.46678 | TITLE ESTs | | | gi = 1672495 | 576502 |
| IC12149 | UG75 Expression | EST | Mm.46681 | TITLE ESTs | | | gi = 6167911 | 1296084 |
| IC12150 | UG75 Expression | EST | Mm.46687 | TITLE ESTs | | | gi = 1863616 | 1001668 |
| IC12151 | UG75 Expression | EST | Mm.46698 | TITLE ESTs | | | gi = 6095979 | 1617185 |
| IC12152 | UG75 Expression | EST | Mm.46706 | TITLE ESTs, Weakly similar to RNA binding protein [M. musculus] | | | gi = 4726864 | 1001450 |
| IC12153 | UG75 Expression | EST | Mm.46715 | TITLE ESTs | | | gi = 5343488 | 1225222 |
| IC12154 | UG75 Expression | EST | Mm.46727 | TITLE ESTs | | | gi = 1908514 | 577508 |
| IC12155 | UG75 Expression | EST | Mm.46729 | TITLE ESTs | | | gi = 2978997 | 619107 |
| IC12156 | UG75 Expression | EST | Mm.46732 | TITLE ESTs | | | gi = 1553289 | 476586 |
| IC12157 | UG75 Expression | EST | Mm.46739 | TITLE ESTs, Moderately similar to similar to C. elegans F11A10.5 [H. sapiens] | | | gi = 1825792 | 596529 |
| IC12158 | UG75 Expression | EST | Mm.46740 | TITLE ESTs | | | gi = 1478921 | 468540 |
| IC12159 | UG75 Expression | EST | Mm.46741 | TITLE ESTs | | | gi = 4441028 | 1923113 |
| IC12160 | UG75 Expression | EST | Mm.46742 | TITLE ESTs | | | gi = 2283371 | 643151 |
| IC12161 | UG75 Expression | EST | Mm.46746 | TITLE ESTs | | | gi = 2813446 | 1067701 |
| IC12162 | UG75 Expression | EST | Mm.46748 | TITLE ESTs | | | gi = 4781800 | 1394969 |
| IC12163 | UG75 Expression | EST | Mm.46749 | TITLE ESTs | | | gi = 2334048 | 1345898 |
| IC12164 | UG75 Expression | EST | Mm.46753 | TITLE ESTs | | | gi = 2283482 | 718629 |
| IC12165 | UG75 Expression | EST | Mm.46761 | TITLE ESTs | | | gi = 2859613 | 1226662 |
| IC12166 | UG75 Expression | EST | Mm.46766 | TITLE ESTs | | | gi = 2101891 | 1395601 |
| IC12167 | UG75 Expression | EST | Mm.46769 | TITLE ESTs, Weakly similar to POLYADENYLATE-BINDING PROTEIN 1 [M. musculus] | | | gi = 5861034 | 635864 |
| IC12168 | UG75 Expression | EST | Mm.46776 | TITLE ESTs | | | gi = 2917854 | 894338 |
| IC12169 | UG75 Expression | EST | Mm.46777 | TITLE ESTs, Weakly similar to Ylr239cp [S. cerevisiae] | | | gi = 6096738 | 1445975 |
| IC12170 | UG75 Expression | EST | Mm.46779 | TITLE ESTs, Weakly similar to testis-specific chromodomain Y-like protein [M. musculus] | | | gi = 4968062 | 636600 |
| IC12171 | UG75 Expression | EST | Mm.46782 | TITLE ESTs, Weakly similar to LUPUS LA PROTEIN HOMOLOG [M. spaiens] | | | gi = 6085382 | 638911 |
| IC12172 | UG75 Expression | EST | Mm.46783 | TITLE ESTs | | | gi = 1318348 | 636951 |
| IC12173 | UG75 Expression | EST | Mm.46785 | TITLE ESTs, Weakly similar to DEAD BOX PROTEIN 4 [M. musculus] | | | gi = 2233657 | 550820 |
| IC12174 | UG75 Expression | EST | Mm.46786 | TITLE solute carrier family 31, member 2 | GENE Slc31a2 | | gi = 1917758 | 722534 |
| IC12175 | UG75 Expression | EST | Mm.46787 | TITLE ESTs | | | gi = 1289004 | 575928 |
| IC12176 | UG75 Expression | EST | Mm.46788 | TITLE ESTs, Moderately similar to NY-REN-58 antigen [H. sapiens] | | | gi = 4300601 | 639871 |
| IC12177 | UG75 Expression | EST | Mm.46789 | TITLE ESTs | | | gi = 2646949 | 619885 |
| IC12178 | UG75 Expression | EST | Mm.46790 | TITLE ESTs, Weakly similar to C11D2.4 [C. elegans] | | | gi = 2306083 | 1139948 |
| IC12179 | UG75 Expression | EST | Mm.46822 | TITLE ESTs, Moderately similar to KIAA0895 protein [H. sapiens] | | | gi = 2234777 | 1265419 |
| IC12180 | UG75 Expression | EST | Mm.46824 | TITLE ESTs | | | gi = 2306101 | 639208 |
| IC12181 | UG75 Expression | EST | Mm.46832 | TITLE ESTs | | | gi = 6099401 | 1225001 |
| IC12182 | UG75 Expression | EST | Mm.46833 | TITLE ESTs | | | gi = 4602493 | 1193719 |
| IC12183 | UG75 Expression | EST | Mm.46834 | TITLE ESTs | | | gi = 4440729 | 1226774 |
| IC12184 | UG75 Expression | EST | Mm.46838 | TITLE ESTs | | | gi = 6007932 | 1749656 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12185 | UG75 Expression | EST | Mm.46847 | TITLE ESTs | | | gi = 2591668 | 1362659 |
| IC12186 | UG75 Expression | EST | Mm.46857 | TITLE ESTs | | | gi = 4725751 | 582992 |
| IC12187 | UG75 Expression | EST | Mm.46858 | TITLE ESTs | | | gi = 4300069 | 575727 |
| IC12188 | UG75 Expression | EST | Mm.46859 | TITLE ESTs | | | gi = 4605500 | 582898 |
| IC12189 | UG75 Expression | EST | Mm.46867 | TITLE ESTs | | | gi = 6515660 | 720653 |
| IC12190 | UG75 Expression | EST | Mm.46922 | TITLE ESTs | | | gi = 4318697 | 718807 |
| IC12191 | UG75 Expression | EST | Mm.46932 | TITLE ESTs | | | gi = 2979328 | 1281646 |
| IC12192 | UG75 Expression | EST | Mm.4714 | TITLE ESTs, Weakly similar to Ring1 interactor RYBP [*M. musculus*] | | | gi = 6084432 | 1001366 |
| IC12193 | UG75 Expression | EST | Mm.47306 | TITLE ESTs | | | gi = 1759027 | 621738 |
| IC12194 | 00/04/26 UG#76 17Lid Expansion | EST | Mm.4743 | ESTs, Weakly similar to mCAC [*M. musculus*] | | | gi = 5905273 | 1277342 |
| IC12195 | UG75 Expression | EST | Mm.4748 | TITLE ESTs, Weakly similar to nuclear factor YC [*M. musculus*] | | | gi = 5338431 | 1140324 |
| IC12196 | UG75 Expression | EST | Mm.47539 | TITLE ESTs | | | gi = 2109489 | 750674 |
| IC12197 | UG75 Expression | EST | Mm.47940 | TITLE ESTs | | | gi = 6193609 | 644090 |
| IC12198 | UG75 Expression | EST | Mm.48031 | TITLE ESTs | | | gi = 4409130 | 764809 |
| IC12199 | UG75 Expression | EST | Mm.4810 | TITLE transforming growth factor beta regulated gene 4 | GENE Tbrg4 | TB-12] | gi = 1618871 | 484176 |
| IC12200 | UG75 Expression | EST | Mm.48646 | TITLE ESTs, Weakly similar to orphan G protein-coupled receptor FEX [*M. musculus*] | | | gi = 3175332 | 1361369 |
| IC12201 | UG75 Expression | EST | Mm.48651 | TITLE ESTs | | | gi = 4601853 | 635118 |
| IC12202 | UG75 Expression | EST | Mm.48662 | TITLE ESTs | | | gi = 5910357 | 642276 |
| IC12203 | UG75 Expression | EST | Mm.48691 | TITLE ESTs | | | gi = 3066785 | 1327486 |
| IC12204 | UG75 Expression | EST | Mm.49074 | TITLE ESTs | | | gi = 6520992 | 637393 |
| IC12205 | UG75 Expression | EST | Mm.491 | TITLE ESTs | | | gi = 1853152 | 596538 |
| IC12206 | UG75 Expression | EST | Mm.492 | TITLE ESTs, Weakly similar to APC-binding protein EB1 homolog [*M. musculus*] | | | gi = 1749050 | 618191 |
| IC12207 | UG75 Expression | EST | Mm.4923 | TITLE ESTs | | | gi = 1504489 | 1149493 |
| IC12208 | UG75 Expression | EST | Mm.4927 | TITLE aconitase 1 | GENE Aco1 | Aco-1][rebp][iron responsive element binding protein] | gi = 4725177 | 719234 |
| IC12209 | UG75 Expression | EST | Mm.49270 | TITLE ESTs | | | gi = 4725177 | 765428 |
| IC12210 | UG76 LID366 B cell | EST | Mm.49309 | TITLE ESTs | | | gi = 3683678 | 820416 |
| IC12211 | UG75 Expression | EST | Mm.49389 | TITLE ESTs | | | gi = 3234343 | 643403 |
| IC12212 | UG75 Expression | EST | Mm.4940 | TITLE ESTs, Weakly similar to cartilage-associated protein [*M. musculus*] | | | gi = 4968345 | 1446672 |
| IC12213 | UG75 Expression | EST | Mm.49407 | TITLE ESTs | | | gi = 6078018 | 777557 |
| IC12214 | UG75 Expression | EST | Mm.4948 | TITLE ESTs | | | gi = 2517186 | 621038 |
| IC12215 | UG75 Expression | EST | Mm.49529 | TITLE ESTs | | | gi = 4601809 | 634836 |
| IC12216 | UG75 Expression | EST | Mm.49532 | TITLE EST | | | gi = 4602417 | 1193055 |
| IC12217 | UG75 Expression | EST | Mm.49546 | TITLE ESTs | | | gi = 4605922 | 1139970 |
| IC12218 | UG75 Expression | EST | Mm.49576 | TITLE ESTs | | | gi = 4724561 | 1247666 |
| IC12219 | UG75 Expression | EST | Mm.49580 | TITLE EST | | | gi = 4724865 | 1225515 |
| IC12220 | UG75 Expression | EST | Mm.49582 | TITLE ESTs | | | gi = 4724984 | 1226093 |
| IC12221 | UG75 Expression | EST | Mm.49583 | TITLE ESTs | | | gi = 4725041 | 1226573 |
| IC12222 | UG75 Expression | EST | Mm.49584 | TITLE ESTs | | | gi = 4725069 | 1226782 |
| IC12223 | UG75 Expression | EST | Mm.49611 | TITLE ESTs | | | gi = 4729815 | 616601 |
| IC12224 | UG75 Expression | EST | Mm.4971 | TITLE ESTs | | | gi = 1344400 | 1344400 |
| IC12225 | UG75 Expression | EST | Mm.4975 | TITLE DNA segment, Chr 17, Wayne State University 91, expressed | GENE D17Wsu91e | | gi = 2519520 | 972903 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12226 | UG75 Expression | EST | Mm.50 | TITLE ESTs | | | gi = 3393841 | 1278831 |
| IC12227 | UG75 Expression | EST | Mm.5002 | TITLE ESTs | | | gi = 3168096 | 764968 |
| IC12228 | UG75 Expression | EST | Mm.5018 | TITLE ESTs | | | gi = 2319812 | 1762958 |
| IC12229 | UG75 Expression | EST | Mm.50219 | TITLE ESTs | | | gi = 2411960 | 1002463 |
| IC12230 | UG75 Expression | EST | Mm.5030 | TITLE ESTs | | | gi = 2074390 | 582623 |
| IC12231 | UG75 Expression | EST | Mm.50412 | TITLE ESTs | | | gi = 2646679 | 575276 |
| IC12232 | UG75 Expression | EST | Mm.50582 | TITLE ESTs | | | gi = 1756680 | 623082 |
| IC12233 | UG75 Expression | EST | Mm.50596 | TITLE ESTs | | | gi = 1895648 | 777241 |
| IC12234 | UG75 Expression | EST | Mm.50610 | TITLE ESTs | | | gi = 6097459 | 619950 |
| IC12235 | UG75 Expression | EST | Mm.5063 | TITLE ESTs | | | gi = 6168089 | 1295250 |
| IC12236 | UG75 Expression | EST | Mm.50780 | TITLE ESTs | | | gi = 430483 | 617592 |
| IC12237 | UG75 Expression | EST | Mm.5093 | TITLE ESTs | | | gi = 1504627 | 466888 |
| IC12238 | UG75 Expression | EST | Mm.51079 | TITLE ESTs | | | gi = 4602002 | 1209224 |
| IC12239 | UG75 Expression | EST | Mm.51092 | TITLE ESTs | | | gi = 6280964 | 905872 |
| IC12240 | UG75 Expression | EST | Mm.51130 | TITLE ESTs | | | gi = 1901236 | 618678 |
| IC12241 | UG75 Expression | EST | Mm.51136 | TITLE ESTs | | | gi = 1672666 | 574519 |
| IC12242 | UG75 Expression | EST | Mm.5117 | TITLE ESTs | | | gi = 4444848 | 575876 |
| IC12243 | UG75 Expression | EST | Mm.51179 | TITLE ESTs | | | gi = 4596860 | 1329227 |
| IC12244 | UG75 Expression | EST | Mm.51269 | TITLE ESTs, Weakly similar to myeloid zinc finger protein 2 [*M. musculus*] | | | gi = 2991214 | 1363488 |
| IC12245 | UG75 Expression | EST | Mm.5143 | TITLE ESTs | | | gi = 3684446 | 1477488 |
| IC12246 | UG75 Expression | EST | Mm.51514 | TITLE ESTs | | | gi = 4317072 | 764480 |
| IC12247 | UG75 Expression | EST | Mm.51937 | TITLE ESTs, Weakly similar to golgin-245 [*H. sapiens*] | | | gi = 4441613 | 622365 |
| IC12248 | UG75 Expression | EST | Mm.5197 | TITLE ESTs | | | gi = 4032504 | 1362392 |
| IC12249 | UG75 Expression | EST | Mm.52 | TITLE ESTs, Modeately similar to HSPC009 [*H. sapiens*] | | | gi = 2518347 | 1265058 |
| IC12250 | UG75 Expression | EST | Mm.52043 | TITLE ESTs | | | gi = 2249331 | 777767 |
| IC12251 | UG75 Expression | EST | Mm.52111 | TITLE ESTs | | | gi = 601639 | 336420 |
| IC12252 | UG75 Expression | EST | Mm.52140 | TITLE ESTs | | | gi = 4320462 | 972864 |
| IC12253 | UG75 Expression | EST | Mm.5220 | TITLE ESTs | | | gi = 1724369 | 597578 |
| IC12254 | UG76 LID 366 B cell | EST | Mm.52249 | TITLE ESTs | | | gi = 7066530 | 1399501 |
| IC12255 | UG75 Expression | EST | Mm.52252 | TITLE ESTs | | | gi = 1659936 | 598764 |
| IC12256 | UG75 Expression | EST | Mm.52253 | TITLE ESTs | | | gi = 4601370 | 621452 |
| IC12257 | UG75 Expression | EST | Mm.52254 | TITLE EST | | | gi = 7193990 | 637970 |
| IC12258 | UG75 Expression | EST | Mm.52257 | TITLE ESTs, Moderately similar to PHOSPHATIDYLINOSITOL 4-KINASE PIK1 [*Saccharomyces cerivisiae*] | | | gi = 3686491 | 722503 |
| IC12259 | UG75 Expression | EST | Mm.52259 | TITLE ESTs, Moderately similar to non-ocogenic Rho GTPase-specific GTP exchange factor [*H. sapiens*] | | | gi = 1902446 | 718173 |
| IC12260 | UG75 Expression | EST | Mm.52278 | TITLE ESTs, Weakly similar to KIAA0308 [*H. sapiens*] | | | gi = 2306342 | 893898 |
| IC12261 | UG76 LID366 B cell | EST | Mm.52292 | TITLE ESTs | | | gi = 102988853 | 1230607 |
| IC12262 | UG75 Expression | EST | Mm.52296 | TITLE ESTs | | | gi = 3168095 | 1480422 |
| IC12263 | UG75 Expression | EST | Mm.52297 | TITLE ESTs | | | gi = 3216331 | 958672 |
| IC12264 | UG75 Expression | EST | Mm.5231 | TITLE ESTs | | | gi = 5494919 | 1379823 |
| IC12265 | UG75 Expression | EST | Mm.52322 | TITLE ESTs | | | gi = 6100018 | 643423 |
| IC12266 | UG75 Expression | EST | Mm.52327 | TITLE EST | | | gi = 4404616 | 1002452 |
| IC12267 | UG75 Expression | EST | Mm.5234 | TITLE ESTs | | | gi = 1541347 | 765276 |
| IC12268 | UG75 Expression | EST | Mm.52354 | TITLE ESTs, Weakly similar to putative CAMP protein [*M. musculus*] | | | gi = 3100393 | 596345 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12269 | UG75 Expression | EST | Mm.5242 | TITLE ESTs | | | gi = 1554141 | 622830 |
| IC12270 | UG75 Expression | EST | Mm.5248 | TITLE ESTs | | | gi = 2288404 | 1447137 |
| IC12271 | UG75 Expression | EST | Mm.5258 | TITLE ESTs | | | gi = 2234599 | 1243280 |
| IC12272 | UG75 Expression | EST | Mm.5265 | TITLE ESTs | | | gi = 1326713 | 550948 |
| IC12273 | UG75 Expression | EST | Mm.5269 | TITLE ESTs | | | gi = 2856041 | 1078074 |
| IC12274 | UG75 Expression | EST | Mm.52809 | TITLE ESTs | | | gi = 2989077 | 620838 |
| IC12275 | UG75 Expression | EST | Mm.5293 | TITLE ESTs, Moderately similar to ATP SYNTHASE A CHAIN [Mus musculus] | | | gi = 6084141 | 973639 |
| IC12276 | UG75 Expression | EST | Mm.5294 | TITLE ESTs | | | gi = 849943 | 1379400 |
| IC12277 | UG75 Expression | EST | Mm.53 | TITLE ESTs | | | gi = 1282434 | 597549 |
| IC12278 | UG75 Expression | EST | Mm.531 | TITLE ESTs, Weakly similar to lysophospholipase I [M. musculus] | | | gi = 6100955 | 598381 |
| IC12279 | UG75 Expression | EST | Mm.532 | TITLE ESTs | | | gi = 1772154 | 617732 |
| IC12280 | UG75 Expression | EST | Mm.5326 | TITLE ESTs | | | gi = 4258815 | 749970 |
| IC12281 | UG75 Expression | EST | Mm.5327 | TITLE ESTs | | | gi = 4304286 | 642043 |
| IC12282 | UG75 Expression | EST | Mm.5329 | TITLE ESTs | | | gi = 1767297 | 621995 |
| IC12283 | UG75 Expression | EST | Mm.5357 | TITLE ESTs | | | gi = 3297493 | 574297 |
| IC12284 | UG75 Expression | EST | Mm.5360 | TITLE ESTs | | | gi = 6939447 | 749065 |
| IC12285 | UG75 Expression | EST | Mm.5363 | TITLE ESTs | | | gi = 1663016 | 573404 |
| IC12286 | UG75 Expression | EST | Mm.5366 | TITLE ESTs | | | gi = 1671471 | 576983 |
| IC12287 | UG75 Expression | EST | Mm.5381 | TITLE ESTs | | | gi = 3979017 | 1279260 |
| IC12288 | UG75 Expression | EST | Mm.5383 | TITLE ESTs, Weakly similar to KIAA0594 protein [H. sapiens] | | | gi = 3374272 | 1380465 |
| IC12289 | UG75 Expression | EST | Mm.5390 | TITLE ESTs | | | gi = 2517685 | 1263099 |
| IC12290 | UG75 Expression | EST | Mm.53963 | TITLE ESTs | | | gi = 7119002 | 894081 |
| IC12291 | UG75 Expression | EST | Mm.5409 | TITLE ESTs | | | gi = 2284560 | 619453 |
| IC12292 | UG75 Expression | EST | Mm.54120 | TITLE ESTs | | | gi = 2068481 | 574540 |
| IC12293 | UG75 Expression | EST | Mm.54460 | TITLE ESTs | | | gi = 1682040 | 576656 |
| IC12294 | UG75 Expression | EST | Mm.5458 | TITLE ESTs, Moderately similar to CHROMATIN ASSEMBLY FACTOR I P60 SUBUNIT [H. sapiens] | | | gi = 4275921 | 719225 |
| IC12295 | UG75 Expression | EST | Mm.5466 | TITLE ESTs | | | gi = 2516509 | 974080 |
| IC12296 | UG75 Expression | EST | Mm.5492 | TITLE ESTs | | | gi = 2516768 | 642228 |
| IC12297 | UG75 Expression | EST | Mm.55065 | TITLE ESTs | | | gi = 2572270 | 1139797 |
| IC12298 | UG75 Expression | EST | Mm.55066 | TITLE EST | | | gi = 460599 | 1139888 |
| IC12299 | 00/04/26 UG#76 17Lid Expansion | EST | Mm.55069 | ESTs, Moderately similar to msz1f33 [M. musculus] | — | | gi = 7196272 | 907221 |
| IC12300 | UG75 Expression | EST | Mm.55072 | TITLE EST | | | gi = 4702674 | 1225596 |
| IC12301 | UG75 Expression | EST | Mm.55073 | TITLE EST | | | gi = 4702681 | 1225625 |
| IC12302 | UG75 Expression | EST | Mm.55080 | TITLE EST | | | gi = 421912 | 1225135 |
| IC12303 | UG75 Expression | EST | Mm.55081 | TITLE EST | | | gi = 4721919 | 1225166 |
| IC12304 | UG75 Expression | EST | Mm.55082 | TITLE EST | | | gi = 4721933 | 1225264 |
| IC12305 | UG75 Expression | EST | Mm.55090 | TITLE EST | | | gi = 4722810 | 1243281 |
| IC12306 | UG75 Expression | EST | Mm.55099 | TITLE EST | | | gi = 4724845 | 1225078 |
| IC12307 | UG75 Expression | EST | Mm.5510 | TITLE ESTs, Weakly similar to estrogen-responsive finger protein [M. musculus] | | | gi = 2516906 | 622663 |
| IC12308 | UG75 Expression | EST | Mm.55100 | TITLE EST | | | gi = 4724894 | 1225968 |
| IC12309 | UG75 Expression | EST | Mm.55102 | TITLE ESTs | | | gi = 2456644 | 1226242 |
| IC12310 | UG75 Expression | EST | Mm.55103 | TITLE EST | | | gi = 4725014 | 1226260 |
| IC12311 | UG75 Expression | EST | Mm.55104 | TITLE EST | | | gi = 725021 | 1226302 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12312 | UG75 Expression | EST | Mm.55105 | TITLE EST | | | gi = 4725028 | 1226338 |
| IC12313 | UG75 Expression | EST | Mm.55106 | TITLE EST | | | gi = 4725084 | 1226853 |
| IC12314 | UG75 Expression | EST | Mm.55211 | TITLE ESTs | | | gi = 1514832 | 575132 |
| IC12315 | UG75 Expression | EST | Mm.5532 | TITLE ESTs | | | gi = 2202097 | 718681 |
| IC12316 | UG75 Expression | EST | Mm.55366 | TITLE ESTs | | | gi = 6409713 | 582791 |
| IC12317 | UG75 Expression | EST | Mm.5544 | TITLE ESTs | | | gi = 2517193 | 1225920 |
| IC12318 | UG75 Expression | EST | Mm.55902 | TITLE ESTs | | | gi = 4603204 | 1020635 |
| IC12319 | UG75 Expression | EST | Mm.55967 | TITLE ESTs, Moderately similar to ATP SYNTHASE COUPLING FACTOR B, MITOCHONDRIAL [Bos taurus] | | | gi = 2272002 | 719041 |
| IC12320 | UG75 Expression | EST | Mm.5601 | TITLE ESTs | | | gi = 2517676 | 1225613 |
| IC12321 | UG75 Expression | EST | Mm.56047 | TITLE ESTs | | | gi = 2292420 | 934268 |
| IC12322 | UG75 Expression | EST | Mm.56118 | TITLE ESTs | | | gi = 687177 | 1345449 |
| IC12323 | UG75 Expression | EST | Mm.56175 | TITLE ESTs | | | gi = 1649083 | 643156 |
| IC12324 | UG75 Expression | EST | Mm.5633 | TITLE ESTs | | | gi = 2517992 | 722598 |
| IC12325 | UG76 LID 366 B cell | EST | Mm.56333 | TITLE ESTs | | | gi = 7315368 | 789882 |
| IC12326 | UG75 Expression | EST | Mm.56437 | TITLE ESTs, Weakly similar to NY-REN-25 antigen [H. sapiens] | | | gi = 2307734 | 764996 |
| IC12327 | UG75 Expression | EST | Mm.56455 | TITLE ESTs | | | gi = 2892796 | 1329064 |
| IC12328 | UG75 Expression | EST | Mm.56547 | TITLE ESTs | | | gi = 1776286 | 637177 |
| IC12329 | UG75 Expression | EST | Mm.56565 | TITLE ESTs | | | gi = 326009 | 421672 |
| IC12330 | UG75 Expression | EST | Mm.56579 | TITLE ESTs | | | gi = 1436803 | 959215 |
| IC12331 | UG75 Expression | EST | Mm.56617 | TITLE ESTs | | | gi = 1907464 | 718321 |
| IC12332 | UG75 Expression | EST | Mm.567 | TITLE ESTs, Weakly similar to BACN32G11.d [D. melanogaster] | | | gi = 5907000 | 640166 |
| IC12333 | UG75 Expression | EST | Mm.56731 | TITLE ESTs | | | gi = 2962602 | 1265364 |
| IC12334 | UG75 Expression | EST | Mm.5697 | TITLE ESTs | | | gi = 5905574 | 574152 |
| IC12335 | UG75 Expression | EST | Mm.57256 | TITLE ESTs | | | gi = 1629886 | 551468 |
| IC12336 | UG75 Expression | EST | Mm.57259 | TITLE EST | | | gi = 1682775 | 750940 |
| IC12337 | UG75 Expression | EST | Mm.57264 | TITLE ESTs, Weakly similar to cytochrome c oxidase assembly protein COX11 [H. sapiens] | | | gi = 1595558 | 1345413 |
| IC12338 | UG75 Expression | EST | Mm.5727 | TITLE ESTs | | | gi = 2518951 | 992583 |
| IC12339 | UG75 Expression | EST | Mm.57295 | TITLE ESTs | | | gi = 1904006 | 619206 |
| IC12340 | UG75 Expression | EST | Mm.5749 | TITLE ESTs | | | gi = 4295625 | 637405 |
| IC12341 | UG75 Expression | EST | Mm.5750 | TITLE ESTs, Weakly similar to cDNA EST EMBL:D69907 comes from this gene [C. elegans] | | | gi = 2519114 | 641531 |
| IC12342 | UG75 Expression | EST | Mm.57675 | TITLE ESTs | | | gi = 3234278 | 1378995 |
| IC12343 | UG75 Expression | EST | Mm.57718 | TITLE ESTs | | | gi = 3078486 | 636150 |
| IC12344 | UG75 Expression | EST | Mm.57758 | TITLE ESTs | | | gi = 4791023 | 764413 |
| IC12345 | UG75 Expression | EST | Mm.57792 | TITLE ESTs | | | gi = 5253573 | 1401067 |
| IC12346 | UG75 Expression | EST | Mm.581 | TITLE ESTs | | | gi = 1281951 | 640582 |
| IC12347 | UG75 Expression | EST | Mm.5817 | TITLE ESTs | | | gi = 4375102 | 617871 |
| IC12348 | UG75 Expression | EST | Mm.5833 | TITLE ESTs | | | gi = 2520064 | 574424 |
| IC12349 | UG75 Expression | EST | Mm.58649 | TITLE ESTs, Moderately similar to ENDOSOMAL P24A PROTEIN PRECURSOR [Saccharomyces cerevisiae] | | | gi = 4601278 | 599080 |
| IC12350 | UG75 Expression | EST | Mm.5885 | TITLE ESTs | | | gi = 5125943 | 622290 |
| IC12351 | UG75 Expression | EST | Mm.58882 | TITLE ESTs | | | gi = 1529706 | 478505 |
| IC12352 | UG75 Expression | EST | Mm.5902 | TITLE ESTs | | | gi = 2520366 | 1264370 |
| IC12353 | UG75 Expression | EST | Mm.5915 | TITLE ESTs, Moderately similar to CGI-30 protein [H. sapiens] | | | gi = 3981282 | 1149478 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12354 | UG75 Expression | EST | Mm.5918 | TITLE ESTs, Moderately similar to SHYC [*M. musculus*] | | | gi = 6078368 | 959248 |
| IC12355 | UG75 Expression | EST | Mm.5935 | TITLE ESTs | | | gi = 3161358 | 620653 |
| IC12356 | UG75 Expression | EST | Mm.59477 | TITLE ESTs, Weakly similar to Bassoon [*R. norvegicus*] | | | gi = 1662946 | 597001 |
| IC12357 | UG75 Expression | EST | Mm.5949 | TITLE ESTs | | | gi = 2965969 | 575223 |
| IC12358 | UG75 Expression | EST | Mm.59611 | TITLE ESTs, Weakly similar to heat shock protein hsp40-3 [*M. musculus*] | | | gi = 1504938 | 750486 |
| IC12359 | UG75 Expression | EST | Mm.59645 | TITLE ESTs | | | gi = 3680619 | 1446455 |
| IC12360 | UG75 Expression | EST | Mm.59780 | TITLE ESTs | | | gi = 5335050 | 1924915 |
| IC12361 | UG75 Expression | EST | Mm.5980 | TITLE ESTs | | | gi = 2521079 | 1264145 |
| IC12362 | UG75 Expression | EST | Mm.59800 | TITLE ESTs | | | gi = 1794440 | 639556 |
| IC12363 | UG75 Expression | EST | Mm.59974 | TITLE EST | | | gi = 4721062 | 1226481 |
| IC12364 | UG75 Expression | EST | Mm.59975 | TITLE EST | | | gi = 4721069 | 1226520 |
| IC12365 | UG75 Expression | EST | Mm.59976 | TITLE EST | | | gi = 4721083 | 1226929 |
| IC12366 | UG75 Expression | EST | Mm.59988 | TITLE ESTs | | | gi = 4400854 | 1243314 |
| IC12367 | UG75 Expression | EST | Mm.59989 | TITLE EST | | | gi = 4722829 | 1243376 |
| IC12368 | UG75 Expression | EST | Mm.60001 | TITLE EST | | | gi = 4724976 | 1226082 |
| IC12369 | UG75 Expression | EST | Mm.60002 | TITLE EST | | | gi = 4725026 | 1226317 |
| IC12370 | UG75 Expression | EST | Mm.60003 | TITLE EST | | | gi = 4725061 | 1226736 |
| IC12371 | UG75 Expression | EST | Mm.60122 | TITLE EST | | | gi = 2049107 | 751658 |
| IC12372 | UG75 Expression | EST | Mm.60230 | TITLE ESTs, Weakly similar to SWAP-70 [*M. musculus*] | | | gi = 2906308 | 777593 |
| IC12373 | UG75 Expression | EST | Mm.6053 | TITLE ESTs | | | gi = 3954222 | 893980 |
| IC12374 | UG75 Expression | EST | Mm.6055 | TITLE ESTs | | | gi = 2521564 | 635005 |
| IC12375 | UG75 Expression | EST | Mm.608 | TITLE ESTs | | | gi = 1282039 | 1327640 |
| IC12376 | UG75 Expression | EST | Mm.60887 | TITLE EST | | | gi = 1767407 | 622128 |
| IC12377 | UG75 Expression | EST | Mm.61064 | TITLE ESTs | | | gi = 402473 | 1068230 |
| IC12378 | UG75 Expression | EST | Mm.61080 | TITLE ESTs | | | gi = 1392905 | 1345732 |
| IC12379 | UG75 Expression | EST | Mm.61128 | TITLE ESTs | | | gi = 2291857 | 61747 |
| IC12380 | UG75 Expression | EST | Mm.6128 | TITLE ESTs | | | gi = 2157895 | 1380406 |
| IC12381 | UG75 Expression | EST | Mm.61417 | TITLE ESTs | | | gi = 4442637 | 1853087 |
| IC12382 | UG75 Expression | EST | Mm.6148 | TITLE ESTs | | | gi = 2646534 | 717749 |
| IC12383 | UG75 Expression | EST | Mm.61528 | TITLE ESTs, Weakly similar to unknown [*H. sapiens*] | | | gi = 1776296 | 598868 |
| IC12384 | UG75 Expression | EST | Mm.6156 | TITLE ESTs | | | gi = 2646768 | 622211 |
| IC12385 | UG75 Expression | EST | Mm.6157 | TITLE ESTs | | | gi = 5473731 | 1080060 |
| IC12386 | UG75 Expression | EST | Mm.6161 | TITLE ESTs | | | gi = 6078228 | 638152 |
| IC12387 | UG75 Expression | EST | Mm.61682 | TITLE ESTs | | | gi = 4031751 | 972377 |
| IC12388 | UG75 Expression | EST | Mm.61792 | TITLE ESTs | | | gi = 3299673 | 1379474 |
| IC12389 | UG75 Expression | EST | Mm.61848 | TITLE ESTs | | | gi = 1776302 | 777463 |
| IC12390 | UG75 Expression | EST | Mm.61901 | TITLE ESTs | | | gi = 1650042 | 1225174 |
| IC12391 | UG75 Expression | EST | Mm.61923 | TITLE ESTs | | | gi = 1727132 | 635010 |
| IC12392 | UG75 Expression | EST | Mm.62033 | TITLE ESTs, Weakly similar to retinoblastoma binding protein 1 isoform I [*H. sapiens*] | | | gi = 3682265 | 1344630 |
| IC12393 | UG75 Expression | EST | Mm.62093 | TITLE ESTs | | | gi = 1506464 | 533385 |
| IC12394 | UG75 Expression | EST | Mm.62136 | TITLE ESTs | | | gi = 6078091 | 721216 |
| IC12395 | UG75 Expression | EST | Mm.62186 | TITLE ESTs | | | gi = 6078173 | 1885856 |
| IC12396 | UG75 Expression | EST | Mm.62518 | TITLE ESTs | | | gi = 2192143 | 576078 |
| IC12397 | UG75 Expression | EST | Mm.62580 | TITLE ESTs | | | gi = 6824784 | 749649 |
| IC12398 | UG75 Expression | EST | Mm.62762 | TITLE ESTs | | | gi = 2308267 | 575161 |
| IC12399 | UG75 Expression | EST | Mm.62886 | TITLE ESTs | | | gi = 1816912 | 1379876 |
| IC12400 | UG75 Expression | EST | Mm.63 | TITLE ESTs, Moderately similar to Unknown [*H. sapiens*] | | | gi = 4967670 | 557968 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12401 | UG75 Expression | EST | Mm.63082 | TITLE ESTs | | | gi = 6822548 | 622721 |
| IC12402 | UG75 Expression | EST | Mm.63262 | TITLE ESTs | | | gi = 4484859 | 483753 |
| IC12403 | UG75 Expression | EST | Mm.63425 | TITLE ESTs | | | gi = 4729641 | 643185 |
| IC12404 | UG75 Expression | EST | Mm.63451 | TITLE ESTs | | | gi = 42919 | 638211 |
| IC12405 | UG75 Expression | EST | Mm.63456 | TITLE ESTs | | | gi = 1630202 | 623066 |
| IC12406 | UG75 Expression | EST | Mm.63470 | TITLE ESTs | | | gi = 177202 | 634537 |
| IC12407 | UG75 Expression | EST | Mm.63472 | TITLE ESTs | | | gi = 1756643 | 618975 |
| IC12408 | UG75 Expression | EST | Mm.63473 | TITLE ESTs | | | gi = 1936305 | 752392 |
| IC12409 | UG75 Expression | EST | Mm.63478 | TITLE ESTs, Moderately similar to zinc finger protein 30 [M. musculus] | | | gi = 6101070 | 617510 |
| IC12410 | UG75 Expression | EST | Mm.63479 | TITLE ESTs | | | gi = 4726277 | 638807 |
| IC12411 | UG75 Expression | EST | Mm.63480 | TITLE ESTs | | | gi = 4600885 | 621771 |
| IC12412 | UG75 Expression | EST | Mm.63481 | TITLE ESTs | | | gi = 1800437 | 643917 |
| IC12413 | UG75 Expression | EST | Mm.63482 | TITLE ESTs | | | gi = 610005 | 1312572 |
| IC12414 | UG75 Expression | EST | Mm.63487 | TITLE ESTs, Moderately similar to KIAA0860 protein [H. sapiens] | | | gi = 43777 | 723155 |
| IC12415 | UG75 Expression | EST | Mm.63488 | TITLE ESTs | | | gi = 1882102 | 717902 |
| IC12416 | UG75 Expression | EST | Mm.63496 | TITLE ESTs | | | gi = 212023 | 616674 |
| IC12417 | UG75 Expression | EST | Mm.63508 | TITLE ESTs | | | gi = 405914 | 1139924 |
| IC12418 | UG75 Expression | EST | Mm.6352 | TITLE ESTs | | | gi = 1682344 | 576778 |
| IC12419 | UG75 Expression | EST | Mm.63520 | TITLE ESTs, Moderately similar to phosphoserine aminotransferase [H. sapiens] | | | gi = 2776072 | 1226947 |
| IC12420 | UG75 Expression | EST | Mm.63521 | TITLE ESTs, Weakly similar to (define not available 5921190) [M. musculus] | | | gi = 4967366 | 576852 |
| IC12421 | UG75 Expression | EST | Mm.63523 | TITLE ESTs | | | gi = 3141267 | 1345804 |
| IC12422 | UG75 Expression | EST | Mm.63545 | TITLE ESTs | | | gi = 3517803 | 1395576 |
| IC12423 | UG75 Expression | EST | Mm.63564 | TITLE ESTs | | | gi = 4287708 | 619093 |
| IC12424 | UG75 Expression | EST | Mm.53565 | TITLE EST | | | gi = 4703224 | 617174 |
| IC12425 | UG75 Expression | EST | Mm.63566 | TITLE ESTs | | | gi = 4702891 | 618138 |
| IC12426 | UG75 Expression | EST | Mm.63569 | TITLE ESTs | | | gi = 402605 | 972473 |
| IC12427 | UG75 Expression | EST | Mm.63574 | TITLE ESTs | | | gi = 448841 | 483476 |
| IC12428 | UG75 Expression | EST | Mm.6358 | TITLE ESTs | | | gi = 2516287 | 764766 |
| IC12429 | UG75 Expression | EST | Mm.6374 | TITLE ESTs | | | gi = 2262734 | 596510 |
| IC12430 | UG75 Expression | EST | Mm.638 | TITLE ESTs | | | gi = 3681258 | 583574 |
| IC12431 | UG75 Expression | EST | Mm.6381 | TITLE ESTs | | | gi = 1740028 | 551097 |
| IC12432 | UG75 Expression | EST | Mm.640 | TITLE ESTs | | | gi = 1843299 | 719004 |
| IC12433 | UG75 Expression | EST | Mm.6403 | TITLE ESTs | | | gi = 2519317 | 597858 |
| IC12434 | UG75 Expression | EST | Mm.6407 | TITLE ESTs | | | gi = 2520085 | 1378997 |
| IC12435 | UG75 Expression | EST | Mm.6413 | TITLE ESTs | | | gi = 1768525 | 635623 |
| IC12436 | UG75 Expression | EST | Mm.64409 | TITLE ESTs | | | gi = 2644470 | 638886 |
| IC12437 | UG75 Expression | EST | Mm.6445 | TITLE ESTs | | | gi = 2516481 | 618926 |
| IC12438 | UG75 Expression | EST | Mm.6452 | TITLE ESTs, Moderately similar to unknown protein IT1 [H. sapiens] | | | gi = 4600869 | 621633 |
| IC12439 | UG75 Expression | EST | Mm.6471 | TITLE ESTs | | | gi = 4614753 | 643353 |
| IC12440 | UG75 Expression | EST | Mm.64713 | TITLE ESTs [M. musculus] | | | gi = 1506523 | 636033 |
| IC12441 | UG75 Expression | EST | Mm.6476 | TITLE ESTs, Weakly similar to UBIQUITIN-CONJUGATING ENZYME E2-17 KD 2 [M. musculus] | | | gi = 3979386 | 635972 |
| IC12442 | UG75 Expression | EST | Mm.64866 | TITLE ESTs | | | gi = 1739556 | 749268 |
| IC12443 | UG75 Expression | EST | Mm.6488 | TITLE ESTs | | | gi = 2519519 | 777774 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12444 | UG75 Expression | EST | Mm.64982 | TITLE ESTs, Weakly similar to beta 3-endonexin long form [H. sapiens] | | | gi = 3164329 | 1445674 |
| IC12445 | UG75 Expression | EST | Mm.6499 | TITLE ESTs | | | gi = 2235302 | 644279 |
| IC12446 | UG75 Expression | EST | Mm.65020 | TITLE DNA segment, Chr 14, Wayne State University 171, expressed | GENE D14Wsu171e | | | 638459 |
| IC12447 | UG75 Expression | EST | Mm.6519 | TITLE ESTs | | | gi = 3033083 | 1279035 |
| IC12448 | UG75 Expression | EST | Mm.65264 | TITLE ESTs | | | gi = 2502868 | 597712 |
| IC12449 | UG75 Expression | EST | Mm.65289 | TITLE ESTs | | | gi = 1904238 | 749959 |
| IC12450 | UG75 Expression | EST | Mm.65366 | TITLE Fanconi anemia, complementation group A | GENE Fanca | | gi = 1715534 | 581659 |
| IC12451 | UG75 Expression | EST | Mm.65370 | TITLE ESTs | | | gi = 4765280 | 749370 |
| IC12452 | UG75 Expression | EST | Mm.65392 | TITLE ESTs, Weakly similar to KIAA0713 protein [H. sapiens] | | | gi = 288446 | 1363461 |
| IC12453 | UG75 Expression | EST | Mm.6560 | TITLE ESTs, Moderately similar to hypothetical protein [H. sapiens] | | | gi = 321523 | 1363240 |
| IC12454 | UG75 Expression | EST | Mm.65678 | TITLE ESTs | | | gi = 4616151 | 641737 |
| IC12455 | UG75 Expression | EST | Mm.65874 | TITLE ESTs | | | gi = 3167669 | 750448 |
| IC12456 | UG75 Expression | EST | Mm.66243 | TITLE ESTs | | | gi = 2049006 | 958654 |
| IC12457 | UG75 Expression | EST | Mm.66244 | TITLE ESTs | | | gi = 4600908 | 621941 |
| IC12458 | UG75 Expression | EST | Mm.66248 | TITLE EST | | | gi = 4601245 | 598882 |
| IC12459 | UG75 Expression | EST | Mm.66254 | TITLE ESTs | | | gi = 4602433 | 1193177 |
| IC12460 | UG75 Expression | EST | Mm.66263 | TITLE EST | | | gi = 4603924 | 808994 |
| IC12461 | UG75 Expression | EST | Mm.66273 | TITLE EST | | | gi = 4605910 | 1139900 |
| IC12462 | UG75 Expression | EST | Mm.66274 | TITLE ESTs | | | gi = 4702738 | 1225893 |
| IC12463 | UG75 Expression | EST | Mm.66278 | TITLE ESTs | | | gi = 675690 | 1361425 |
| IC12464 | UG75 Expression | EST | Mm.66279 | TITLE EST | | | gi = 4721228 | 1224894 |
| IC12465 | UG75 Expression | EST | Mm.66628 | TITLE ESTs, Weakly similar to beta-1,4-galactosyltransferase II [M. musculus] | | | gi = 4721242 | 1224966 |
| IC12466 | UG75 Expression | EST | | | | | gi = 3161176 | 718729 |
| IC12467 | UG75 Expression | EST | Mm.66288 | TITLE ESTs | | | gi = 4721948 | 1225343 |
| IC12468 | UG75 Expression | EST | Mm.66289 | TITLE ESTs | | | gi = 4721969 | 1225436 |
| IC12469 | UG75 Expression | EST | Mm.66302 | TITLE EST | | | gi = 4722811 | 1243283 |
| IC12470 | UG75 Expression | EST | Mm.66303 | TITLE EST | | | gi = 4722818 | 1243311 |
| IC12471 | UG75 Expression | EST | Mm.66304 | TITLE EST | | | gi = 4722825 | 1243339 |
| IC12472 | UG75 Expression | EST | Mm.66314 | TITLE EST | | | gi = 4291095 | 1226346 |
| IC12473 | UG75 Expression | EST | Mm.66315 | TITLE EST | | | gi = 4725036 | 1226555 |
| IC12474 | UG75 Expression | EST | Mm.66316 | TITLE ESTs | | | gi = 472578 | 1226830 |
| IC12475 | UG75 Expression | EST | Mm.6635 | TITLE ESTs | | | gi = 6008587 | 721230 |
| IC12476 | UG75 Expression | EST | Mm.6636 | TITLE ESTs | | | gi = 2305728 | 597350 |
| IC12477 | UG75 Expression | EST | Mm.6642 | TITLE ESTs, Weakly similar to retinoblastoma-associated protein HEC [H. sapiens] | | | gi = 2518075 | 721914 |
| IC12478 | UG75 Expression | EST | Mm.666 | TITLE ESTs, Moderately similar to NADH-UBIQUINONE OXIDOREDUCTASE KFYI SUBUNIT PRECURSOR [Bos taurus] | | | gi = 6079184 | 958953 |
| IC12479 | UG75 Expression | EST | Mm.66601 | TITLE ESTs | | | gi = 4402773 | 973866 |
| IC12480 | UG75 Expression | EST | Mm.66667 | TITLE ESTs, Moderately similar to (define not available 5817333) [R. norvegicus] | | | gi = 2256671 | 1225752 |
| IC12481 | UG75 Expression | EST | Mm.6671 | TITLE ESTs | | | gi = 2719461 | 764456 |
| IC12482 | UG75 Expression | EST | Mm.66866 | TITLE ESTs | | | gi = 6079231 | 598247 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12483 | UG75 Expression | EST | Mm.6691 | TITLE ESTs | | | gi = 5125571 | 1294962 |
| IC12484 | UG75 Expression | EST | Mm.67025 | TITLE ESTs | | | gi = 2979144 | 1281530 |
| IC12485 | UG75 Expression | EST | Mm.6703 | TITLE ESTs | | | gi = 1757049 | 619846 |
| IC12486 | UG75 Expression | EST | Mm.6720 | TITLE ESTs | | | gi = 215827 | 973812 |
| IC12487 | UG75 Expression | EST | Mm.6724 | TITLE ESTs | | | gi = 2462035 | 751409 |
| IC12488 | UG75 Expression | EST | Mm.67310 | TITLE ESTs | | | gi = 1475228 | 1140294 |
| IC12489 | UG75 Expression | EST | Mm.67435 | TITLE ESTs | | | gi = 2963267 | 1264816 |
| IC12490 | UG75 Expression | EST | Mm.67527 | TITLE ESTs | | | gi = 3686757 | 639402 |
| IC12491 | UG75 Expression | EST | Mm.67594 | TITLE ESTs | | | gi = 1713642 | 597452 |
| IC12492 | UG75 Expression | EST | Mm.67652 | TITLE ESTs | | | gi = 166258 | 573090 |
| IC12493 | UG75 Expression | EST | Mm.6766 | TITLE ESTs | | | gi = 5819536 | 2182284 |
| IC12494 | UG75 Expression | EST | Mm.6772 | TITLE ESTs | | | gi = 2518912 | 803690 |
| IC12495 | UG75 Expression | EST | Mm.67721 | TITLE ESTs | | | gi = 2272035 | 596746 |
| IC12496 | UG75 Expression | EST | Mm.67848 | TITLE ESTs | | | gi = 6190938 | 718504 |
| IC12497 | UG75 Expression | EST | Mm.6803 | TITLE ESTs, Moderately similar to Hsp70 binding protein HspBP1 [*H. sapiens*] | | | gi = 2520340 | 621268 |
| IC12498 | UG75 Expression | EST | Mm.6807 | TITLE ESTs | | | gi = 2990961 | 764726 |
| IC12499 | UG75 Expression | EST | Mm.68134 | TITLE ESTs | | | gi = 4409122 | 622026 |
| IC12500 | UG75 Expression | EST | Mm.6825 | TITLE ESTs | | | gi = 4374231 | 1282785 |
| IC12501 | UG75 Expression | EST | Mm.68327 | TITLE ESTs, Weakly similar to zinc finger protein [*M. musculus*] | | | gi = 4444728 | 574414 |
| IC12502 | UG75 Expression | EST | Mm.6842 | TITLE ESTs | | | gi = 4508405 | 621763 |
| IC12503 | UG75 Expression | EST | Mm.68427 | TITLE ESTs, Weakly similar to similar to tyrosyl-tRNA synthetase. [*C. elegans*] | | | gi = 2282817 | 573428 |
| IC12504 | UG75 Expression | EST | Mm.68444 | TITLE ESTs, Moderately similar to /prediction [*H. sapiens*] | | | gi = 1853075 | 721519 |
| IC12505 | UG75 Expression | EST | Mm.6847 | TITLE ESTs | | | gi = 1309524 | 1002477 |
| IC12506 | UG75 Expression | EST | Mm.68514 | TITLE ESTs | | | gi = 6632640 | 1329751 |
| IC12507 | UG75 Expression | EST | Mm.68556 | TITLE ESTs | | | gi = 23098 | 874766 |
| IC12508 | UG75 Expression | EST | Mm.68667 | TITLE ESTs, Weakly similar to hypothetical protein [*H. sapiens*] | | | gi = 2042108 | 749871 |
| IC12509 | UG75 Expression | EST | Mm.68777 | TITLE ESTs | | | gi = 4216697 | 599303 |
| IC12510 | UG75 Expression | EST | Mm.68819 | TITLE ESTs, Moderately similar to SLY1 PROTEIN [*Saccharomyces cerevisiae*] | | | gi = 1724720 | 1281328 |
| IC12511 | UG75 Expression | EST | Mm.68827 | TITLE ESTs | | | gi = 2040086 | 1327683 |
| IC12512 | UG75 Expression | EST | Mm.68883 | TITLE ESTs | | | gi = 1917548 | 1002259 |
| IC12513 | UG75 Expression | EST | Mm.68973 | TITLE ESTs pyridoxal (pyridoxine, vitamin B6) kinase | GENE Pdxk | | gi = 4443617 | 1001490 |
| IC12514 | UG75 Expression | EST | Mm.68977 | TITLE ESTs | | | gi = 3079535 | 959000 |
| IC12515 | UG75 Expression | EST | Mm.68985 | TITLE ESTs | | | gi = 6078546 | 573580 |
| IC12516 | UG75 Expression | EST | Mm.68989 | TITLE ESTs, Moderately similar to RRM RNA binding protein GRY-RBP [*M. musculus*] | | | gi = 4605004 | 550708 |
| IC12517 | UG75 Expression | EST | Mm.68991 | TITLE ESTs | | | gi = 1738291 | 540919 |
| IC12518 | UG75 Expression | EST | Mm.68992 | TITLE ESTs | | | gi = 2041713 | 749694 |
| IC12519 | UG75 Expression | EST | Mm.68994 | TITLE ESTs | | | gi = 6100070 | 619809 |
| IC12520 | UG75 Expression | EST | Mm.68996 | TITLE ESTs | | | gi = 1768003 | 622616 |
| IC12521 | UG75 Expression | EST | Mm.68997 | TITLE ESTs | | | gi = 6515673 | 639576 |
| IC12522 | UG75 Expression | EST | Mm.68999 | TITLE ESTs | | | gi = 1808266 | 583737 |
| IC12523 | UG75 Expression | EST | Mm.69001 | TITLE ESTs | | | gi = 2962458 | 618900 |
| IC12524 | UG75 Expression | EST | Mm.69002 | TITLE ESTs | | | gi = 4602566 | 598826 |
| IC12525 | UG75 Expression | EST | Mm.69003 | TITLE EST | | | gi = 1936477 | 750745 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12526 | UG75 Expression | EST | Mm.69013 | TITLE ESTs | | | gi = 5338364 | 1020833 |
| IC12527 | UG75 Expression | EST | Mm.69025 | TITLE ESTs | | | gi = 2247671 | 637808 |
| IC12528 | UG75 Expression | EST | Mm.69033 | TITLE ESTs | | | gi = 2693753 | 582888 |
| IC12529 | UG75 Expression | EST | Mm.69037 | TITLE ESTs | | | gi = 2730589 | 1193445 |
| IC12530 | UG75 Expression | EST | Mm.69038 | TITLE ESTs | | | gi = 775966 | 1226871 |
| IC12531 | UG75 Expression | EST | Mm.69039 | TITLE ESTs | | | gi = 2803531 | 1225036 |
| IC12532 | UG75 Expression | EST | Mm.69042 | TITLE ESTs | | | gi = 2811774 | 1225772 |
| IC12533 | UG75 Expression | EST | Mm.69044 | TITLE ESTs | | | gi = 289760 | 581994 |
| IC12534 | UG75 Expression | EST | Mm.69047 | TITLE ESTs, Weakly similar to coded for by C. elegans cDNA CEESW58F [C. elegans] | | | gi = 1677141 | 574382 |
| IC12535 | UG75 Expression | EST | Mm.69051 | TITLE ESTs | | | gi = 240659 | 1329752 |
| IC12536 | UG75 Expression | EST | Mm.69053 | TITLE ESTs | | | gi = 3068216 | 1328696 |
| IC12537 | UG75 Expression | EST | Mm.69054 | TITLE ESTs | | | gi = 3336277 | 636172 |
| IC12538 | UG75 Expression | EST | Mm.69072 | TITLE ESTs, Moderately similar to spinocerebella ataxia 7 [H. sapiens] | | | gi = 4614825 | 1224916 |
| IC12539 | UG75 Expression | EST | Mm.69074 | TITLE ESTs | | | gi = 156649 | 1226172 |
| IC12540 | UG75 Expression | EST | Mm.69079 | TITLE ESTs | | | gi = 4274670 | 1225734 |
| IC12541 | UG75 Expression | EST | Mm.69081 | TITLE ESTs | | | gi = 4299502 | 573679 |
| IC12542 | UG75 Expression | EST | Mm.69083 | TITLE ESTs | | | gi = 6008159 | 599117 |
| IC12543 | UG75 Expression | EST | Mm.69085 | TITLE ESTs | | | gi = 1725725 | 597487 |
| IC12544 | UG75 Expression | EST | Mm.69086 | TITLE ESTs | | | gi = 4596948 | 573238 |
| IC12545 | UG75 Expression | EST | Mm.69087 | TITLE EST | | | gi = 4281886 | 573631 |
| IC12546 | UG75 Expression | EST | Mm.69088 | TITLE EST | | | gi = 429033 | 577097 |
| IC12547 | UG75 Expression | EST | Mm.69096 | TITLE ESTs | | | gi = 2292530 | 958890 |
| IC12548 | UG75 Expression | EST | Mm.69097 | TITLE ESTs, Weakly similar to kinesin light chain B [R. norvegicus] | | | gi = 4403975 | 973706 |
| IC12549 | UG75 Expression | EST | Mm.6910 | TITLE ESTs | | | gi = 2519356 | 958382 |
| IC12550 | UG75 Expression | EST | Mm.69102 | TITLE ESTs | | | gi = 1896581 | 1361381 |
| IC12551 | UG75 Expression | EST | Mm.69105 | TITLE ESTs | | | gi = 4571692 | 1149384 |
| IC12552 | UG75 Expression | EST | Mm.69166 | TITLE ESTs | | | gi = 1807624 | 644941 |
| IC12553 | UG75 Expression | EST | Mm.69168 | TITLE ESTs | | | gi = 1793062 | 639909 |
| IC12554 | UG75 Expression | EST | Mm.6926 | TITLE ESTs | | | gi = 5496632 | 635198 |
| IC12555 | UG75 Expression | EST | Mm.6929 | TITLE ESTs | | | gi = 2519021 | 639335 |
| IC12556 | UG75 Expression | EST | Mm.69757 | TITLE ESTs, Moderately similar to Ig lambda-2 chain [M. musculus] | | | gi = 5188230 | 622787 |
| IC12557 | UG75 Expression | EST | Mm.70062 | TITLE ESTs | | | gi = 3160557 | 717702 |
| IC12558 | UG75 Expression | EST | Mm.70063 | TITLE ESTs | | | gi = 1794340 | 596132 |
| IC12559 | UG75 Expression | EST | Mm.70065 | TITLE ESTs | | | gi = 3954672 | 639273 |
| IC12560 | UG75 Expression | EST | Mm.70067 | TITLE ESTs | | | gi = 1776746 | 637661 |
| IC12561 | UG75 Expression | EST | Mm.70068 | TITLE ESTs | | | gi = 4729717 | 749718 |
| IC12562 | UG75 Expression | EST | Mm.7012 | TITLE ESTs | | | gi = 2403593 | 597109 |
| IC12563 | UG75 Expression | EST | Mm.7024 | TITLE ESTs | | | gi = 2404294 | 622505 |
| IC12564 | UG75 Expression | EST | Mm.70308 | TITLE ESTs | | | gi = 2692425 | 599259 |
| IC12565 | UG75 Expression | EST | Mm.7033 | TITLE ESTs | | | gi = 2406053 | 1749084 |
| IC12566 | UG75 Expression | EST | Mm.7044 | TITLE ESTs | | | gi = 2962208 | 1363786 |
| IC12567 | UG75 Expression | EST | Mm.70462 | TITLE ESTs | | | gi = 6008761 | 765109 |
| IC12568 | UG75 Expression | EST | Mm.7050 | TITLE ESTs | | | gi = 3955871 | 1345457 |
| IC12569 | UG75 Expression | EST | Mm.70545 | TITLE DNA segment, Chr 10, Wayne State University 183, expressed | GENE D10Wsu183e | | gi = 3955871 | 1294533 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12570 | UG75 Expression | EST | Mm.7066 | TITLE ESTs | | | gi = 1681496 | 617379 |
| IC12571 | UG75 Expression | EST | Mm.70987 | TITLE ESTs | | | gi = 607877 | 1149108 |
| IC12572 | UG75 Expression | EST | Mm.71015 | TITLE ESTs, Weakly similar to F41E6.3 [C. elegans] | | | gi = 4482846 | 1264904 |
| IC12573 | UG75 Expression | EST | Mm.71018 | TITLE ESTs | | | gi = 6097906 | 973076 |
| IC12574 | UG75 Expression | EST | Mm.71055 | TITLE ESTs | | | gi = 1862594 | 1243347 |
| IC12575 | UG75 Expression | EST | Mm.71069 | TITLE ESTs | | | gi = 6101086 | 1263394 |
| IC12576 | UG75 Expression | EST | Mm.7109 | TITLE ESTs, Weakly similar to BcDNA.GH0318 [D. melanogaster] | | | gi = 2521319 | 1279673 |
| IC12577 | UG75 Expression | EST | Mm.71128 | TITLE ESTs, Weakly similar to Src-associated adaptor protein [M. musculus] | | | gi = 1711753 | 598216 |
| IC12578 | UG75 Expression | EST | Mm.7114 | TITLE ESTs, Moderately similar to Mdes protein [M. musculus] | | | gi = 2906979 | 577698 |
| IC12579 | UG75 Expression | EST | Mm.71278 | TITLE ESTs | | | gi = 1796499 | 643581 |
| IC12580 | UG75 Expression | EST | Mm.7153 | TITLE ESTs | | | gi = 1794493 | 637873 |
| IC12581 | UG75 Expression | EST | Mm.71533 | TITLE ESTs | | | gi = 3295083 | 1749662 |
| IC12582 | UG75 Expression | EST | Mm.71547 | TITLE ESTs, Weakly similar to unknown [M. musculus] | | | gi = 1755663 | 617437 |
| IC12583 | UG75 Expression | EST | Mm.71710 | TITLE ESTs | | | gi = 3175482 | 1361800 |
| IC12584 | UG75 Expression | EST | Mm.719 | TITLE ESTs, Weakly similar to coded for by C. elegans cDNA yk157f8.5 [C. elegans] | | | gi = 1282310 | 958604 |
| IC12585 | UG75 Expression | EST | Mm.71913 | TITLE ESTs | | | gi = 2915517 | 596471 |
| IC12586 | UG75 Expression | EST | Mm.71922 | TITLE ESTs | | | gi = 6282462 | 1225350 |
| IC12587 | UG75 Expression | EST | Mm.71923 | TITLE ESTs | | | gi = 4401874 | 1001419 |
| IC12588 | UG75 Expression | EST | Mm.71946 | TITLE ESTs | | | gi = 2288818 | 958442 |
| IC12589 | UG75 Expression | EST | Mm.71947 | TITLE EST | | | gi = 4724854 | 1225469 |
| IC12590 | UG75 Expression | EST | Mm.71948 | TITLE ESTs | | | gi = 4725016 | 1226269 |
| IC12591 | UG75 Expression | EST | Mm.71949 | TITLE EST | | | gi = 2775706 | 1226720 |
| IC12592 | UG75 Expression | EST | Mm.71950 | TITLE ESTs | | | gi = 2775741 | 1226755 |
| IC12593 | UG75 Expression | EST | Mm.71951 | TITLE EST | | | gi = 472072 | 1226792 |
| IC12594 | UG75 Expression | EST | Mm.7196 | TITLE ESTs | | | gi = 2721988 | 621110 |
| IC12595 | UG75 Expression | EST | Mm.7198 | TITLE ESTs, Weakly similar to ZNF127 [M. musculus] | | | gi = 4601356 | 550705 |
| IC12596 | UG75 Expression | EST | Mm.72009 | TITLE ESTs | | | gi = 1714499 | 622757 |
| IC12597 | UG75 Expression | EST | Mm.72105 | TITLE ESTs | | | gi = 1913114 | 764655 |
| IC12598 | UG75 Expression | EST | Mm.72170 | TITLE ESTs | | | gi = 2273304 | 1225579 |
| IC12599 | UG75 Expression | EST | Mm.72235 | TITLE ESTs | | | gi = 4663890 | 643155 |
| IC12600 | UG75 Expression | EST | Mm.72243 | TITLE ESTs, Weakly similar to hydrogen peroxide-inducible protein hic-5 [M. musculus] | | | gi = 3681390 | 622771 |
| IC12601 | UG75 Expression | EST | Mm.7241 | TITLE ESTs, Weakly similar to glucose transport protein, hepatic [M. musculus] | | | gi = 2517858 | 722835 |
| IC12602 | UG75 Expression | EST | Mm.7265 | TITLE ESTs, Weakly similar to KIAA0610 protein [H. sapiens] | | | gi = 2519498 | 573449 |
| IC12603 | UG75 Expression | EST | Mm.7280 | TITLE ESTs | | | gi = 3373183 | 1193424 |
| IC12604 | UG75 Expression | EST | Mm.72845 | TITLE ESTs, Moderately similar to KIAA0944 protein [H. sapiens] | | | gi = 726677 | 1002105 |
| IC12605 | UG75 Expression | EST | Mm.72849 | TITLE ESTs | | | gi = 4765821 | 721508 |
| IC12606 | UG75 Expression | EST | Mm.72946 | TITLE ESTs | | | gi = 1919240 | 777411 |
| IC12607 | UG75 Expression | EST | Mm.72979 | TITLE ESTs | | | gi = 6079287 | 752202 |
| IC12608 | UG75 Expression | EST | Mm.7308 | TITLE DNA segment, Chr 15, Kozak 1 | GENE D15Kz1 | | | 639851 |
| IC12609 | UG75 Expression | EST | Mm.7312 | TITLE DNA segment, Chr 17, human D6S56E 2 | GENE D17H6S56E-2 | | | 596024 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12610 | UG75 Expression | EST | Mm.73153 | TITLE ESTs | | | gi = 461263 | 722445 |
| IC12611 | UG75 Expression | EST | Mm.732 | TITLE ESTs | | | gi = 4441612 | 618991 |
| IC12612 | UG75 Expression | EST | Mm.73234 | TITLE ESTs | | | gi = 1901343 | 598099 |
| IC12613 | UG75 Expression | EST | Mm.73252 | TITLE ESTs | | | gi = 323484 | 1378722 |
| IC12614 | UG75 Expression | EST | Mm.73272 | TITLE ESTs | | | gi = 4721244 | 1224970 |
| IC12615 | UG75 Expression | EST | Mm.73274 | TITLE ESTs | | | gi = 5551195 | 1429504 |
| IC12616 | UG75 Expression | EST | Mm.7328 | TITLE ESTs | | | gi = 2292335 | 621656 |
| IC12617 | UG75 Expression | EST | Mm.73290 | TITLE ESTs | | | gi = 4444742 | 574475 |
| IC12618 | UG75 Expression | EST | Mm.73308 | TITLE ESTs | | | gi = 6099651 | 1001773 |
| IC12619 | UG75 Expression | EST | Mm.73361 | TITLE ESTs | | | gi = 4795804 | 905802 |
| IC12620 | UG75 Expression | EST | Mm.73402 | TITLE ESTs | | | gi = 4724487 | 1383685 |
| IC12621 | UG75 Expression | EST | Mm.73522 | TITLE ESTs | | | gi = 3517966 | 1885643 |
| IC12622 | UG75 Expression | EST | Mm.73550 | TITLE ESTs | | | gi = 185045 | 637263 |
| IC12623 | UG75 Expression | EST | Mm.73598 | TITLE ESTs | | | gi = 2462027 | 637022 |
| IC12624 | UG75 Expression | EST | Mm.7361 | TITLE ESTs, Weakly similar to (define not available 5931573) [*M. musculus*] | | | gi = 2307871 | 1295950 |
| IC12625 | UG75 Expression | EST | Mm.73777 | TITLE ESTs | | | gi = 3680989 | 1149617 |
| IC12626 | UG75 Expression | EST | Mm.7381 | TITLE ESTs, Moderately similar to HSPC010 [*H. sapiens*] | | | gi = 2291685 | 1148920 |
| IC12627 | UG75 Expression | EST | Mm.73856 | TITLE ESTs | | | gi = 4276076 | 1293998 |
| IC12628 | UG75 Expression | EST | Mm.73934 | TITLE ESTs | | | gi = 2504560 | 934833 |
| IC12629 | UG75 Expression | EST | Mm.73959 | TITLE ESTs, Weakly similar to TTF-I interacting peptide 5 [*H. sapiens*] | | | gi = 2040487 | 789799 |
| IC12630 | UG75 Expression | EST | Mm.740 | TITLE ESTs | | | gi = 1715396 | 597341 |
| IC12631 | UG75 Expression | EST | Mm.74084 | TITLE DNA segment, Chr 9, Wayne State University 149, expressed | GENE D9Wsu149e | | | 718956 |
| IC12632 | UG75 Expression | EST | Mm.74129 | TITLE ESTs | | | gi = 5191356 | 765661 |
| IC12633 | UG75 Expression | EST | Mm.74138 | TITLE ESTs, Moderately similar to CGI-05 protein [*H. sapiens*] | | | gi = 3215471 | 1446260 |
| IC12634 | UG75 Expression | EST | Mm.74203 | TITLE ESTs, Weakly similar to KIAA0294 [*H. sapiens*] | | | gi = 2204032 | 722711 |
| IC12635 | UG75 Expression | EST | Mm.74429 | TITLE ESTs | | | gi = 4786666 | 921930 |
| IC12636 | UG75 Expression | EST | Mm.745 | TITLE ESTs, Moderately similar to KIAA1014 protein [*H. sapiens*] | | | gi = 3978677 | 1294209 |
| IC12637 | UG75 Expression | EST | Mm.74539 | TITLE ESTs | | | gi = 5300592 | 638342 |
| IC12638 | UG75 Expression | EST | Mm.74575 | TITLE ESTs | | | gi = 1937120 | 751106 |
| IC12639 | UG75 Expression | EST | Mm.74612 | TITLE ESTs | | | gi = 4032450 | 777789 |
| IC12640 | UG75 Expression | EST | Mm.74615 | TITLE ESTs | | | gi = 6756359 | 576593 |
| IC12641 | UG75 Expression | EST | Mm.74619 | TITLE ESTs | | | gi = 1726082 | 597561 |
| IC12642 | UG75 Expression | EST | Mm.74620 | TITLE ESTs, Weakly similar to cell fate specification homolog MAB21L1 [*M. musculus*] | | | gi = 4601232 | 598801 |
| IC12643 | UG75 Expression | EST | Mm.74622 | TITLE ESTs | | | gi = 4601637 | 619425 |
| IC12644 | UG75 Expression | EST | Mm.74623 | TITLE ESTs | | | gi = 1758761 | 622029 |
| IC12645 | UG75 Expression | EST | Mm.74625 | TITLE ESTs | | | gi = 4601331 | 621150 |
| IC12646 | UG75 Expression | EST | Mm.74626 | TITLE ESTs | | | gi = 1746739 | 598837 |
| IC12647 | UG75 Expression | EST | Mm.74629 | TITLE ESTs | | | gi = 2956151 | 642288 |
| IC12648 | UG75 Expression | EST | Mm.7463 | TITLE ESTs | | | gi = 2520925 | 534091 |
| IC12649 | UG75 Expression | EST | Mm.74630 | TITLE ESTs | | | gi = 1889142 | 722786 |
| IC12650 | UG75 Expression | EST | Mm.74631 | TITLE ESTs | | | gi = 1889452 | 719276 |
| IC12651 | UG75 Expression | EST | Mm.74632 | TITLE ESTs | | | gi = 2756454 | 1149717 |
| IC12652 | UG75 Expression | EST | Mm.74633 | TITLE ESTs | | | gi = 6383246 | 718526 |

| IC ID | IC Selection method | Module | UniGene | UniGene/LocusLink Title | Gene Symbol | Alias | Selected Reference | IMAGE |
|---|---|---|---|---|---|---|---|---|
| IC12653 | UG75 Expression | EST | Mm.74634 | TITLE ESTs | | | gi = 2962460 | 719164 |
| IC12654 | UG75 Expression | EST | Mm.74635 | TITLE ESTs | | | gi = 1681460 | 723120 |
| IC12655 | UG75 Expression | EST | Mm.74639 | TITLE ESTs | | | gi = 1913316 | 621643 |
| IC12656 | UG75 Expression | EST | Mm.74640 | TITLE ESTs | | | gi = 1881853 | 717578 |
| IC12657 | UG75 Expression | EST | Mm.74641 | TITLE ESTs | | | gi = 3235994 | 750972 |
| IC12658 | UG75 Expression | EST | Mm.74642 | TITLE ESTs | | | gi = 1937447 | 749445 |
| IC12659 | UG75 Expression | EST | Mm.74645 | TITLE ESTs, Weakly similar to CCAAT-BINDING TRANSCRIPTIONAL FACTOR SUBUNIT A [M. musculus] | | | gi = 2306145 | 1363562 |
| IC12660 | UG75 Expression | EST | Mm.74654 | TITLE ESTs | | | gi = 2693264 | 750454 |
| IC12661 | UG75 Expression | EST | Mm.74674 | TITLE ESTs | | | gi = 2690960 | 1001924 |
| IC12662 | UG75 Expression | EST | Mm.74677 | TITLE ESTs | | | gi = 2692350 | 577748 |
| IC12663 | UG75 Expression | EST | Mm.74682 | TITLE ESTs, Moderately similar to similar to 5'region of human EXLM1 gene [M. musculus] | | | gi = 2730568 | 1193419 |
| IC12664 | UG75 Expression | EST | Mm.74683 | TITLE ESTs | | | gi = 2730597 | 1193080 |
| IC12665 | UG75 Expression | EST | Mm.74686 | TITLE ESTs | | | gi = 4602465 | 1193548 |
| IC12666 | UG75 Expression | EST | Mm.74687 | TITLE ESTs | | | gi = 4602486 | 1193702 |
| IC12667 | UG75 Expression | EST | Mm.74689 | TITLE ESTs | | | gi = 6295583 | 1225038 |
| IC12669 | UG75 Expression | EST | Mm.74690 | TITLE ESTs | | | gi = 1756938 | 619569 |
| IC12670 | UG75 Expression | EST | Mm.74691 | TITLE ESTs | | | gi = 2811561 | 1225296 |
| IC12671 | UG75 Expression | EST | Mm.74695 | TITLE ESTs | | | gi = 1936307 | 752396 |
| IC12673 | UG75 Expression | EST | Mm.74708 | TITLE ESTs, Weakly similar to actin-binding protein | | | gi = 2404984 | 1295263 |
| IC12674 | UG75 Expression | EST | Mm.74710 | TITLE ESTs | | | gi = 2967277 | 644860 |
| IC12675 | UG75 Expression | EST | Mm.74711 | TITLE ESTs | | | gi = 2855177 | 582841 |
| IC12676 | UG75 Expression | EST | Mm.74713 | TITLE ESTs | | | gi = 3141444 | 1346045 |
| IC12677 | UG75 Expression | EST | Mm.74716 | TITLE ESTs | | | gi = 1555748 | 765047 |
| IC12678 | UG75 Expression | EST | Mm.74718 | TITLE ESTs | | | gi = 3297078 | 1379468 |
| IC12679 | UG75 Expression | EST | Mm.74719 | TITLE EST | | | gi = 3336191 | 1380497 |
| IC12680 | UG75 Expression | EST | Mm.74730 | TITLE ESTs | | | gi = 1937465 | 749312 |
| IC12681 | UG75 Expression | EST | Mm.74735 | TITLE ESTs | | | gi = 440263 | 972653 |
| IC12682 | UG75 Expression | EST | Mm.74737 | TITLE ESTs | | | gi = 6098535 | 643479 |
| IC12683 | UG75 Expression | EST | Mm.74745 | TITLE ESTs | | | gi = 4298965 | 582449 |
| IC12685 | UG75 Expression | EST | Mm.74747 | TITLE ESTs | | | gi = 4290683 | 577423 |
| IC12686 | UG75 Expression | EST | Mm.74754 | TITLE ESTs | | | gi = 4375267 | 894366 |
| IC12687 | UG75 Expression | EST | Mm.74756 | TITLE ESTs | | | gi = 1826782 | 1295808 |
| IC12688 | UG75 Expression | EST | Mm.74761 | TITLE ESTs | | | gi = 4433975 | 1226372 |
| IC12689 | UG75 Expression | EST | Mm.74819 | TITLE ESTs | | | gi = 4729807 | 718349 |
| IC12690 | UG75 Expression | EST | Mm.74842 | TITLE ESTs | | | gi = 4283860 | 777468 |
| IC12691 | UG75 Expression | EST | Mm.74885 | TITLE ESTs | | | gi = 3235834 | 764065 |
| IC12692 | UG75 Expression | EST | Mm.7514 | TITLE ESTs | | | gi = 285742 | 1225142 |
| IC12693 | UG75 Expression | EST | Mm.752 | TITLE ESTs | | | gi = 5492556 | 533951 |
| IC12694 | UG75 Expression | EST | Mm.75467 | TITLE ESTs | | | gi = 5191421 | 1002801 |
| IC12695 | UG75 Expression | EST | Mm.75472 | TITLE ESTs | | | gi = 6078309 | 634704 |
| IC12696 | UG75 Expression | EST | Mm.75489 | TITLE ESTs | | | gi = 1937333 | 617411 |
| IC12697 | UG75 Expression | EST | Mm.756 | TITLE ESTs | | | gi = 4723753 | 637435 |
| IC12698 | UG75 Expression | EST | Mm.7566 | TITLE ESTs | | | gi = 1481100 | 581924 |
| IC12699 | UG75 Expression | EST | Mm.75681 | TITLE ESTs | | | gi = 4602488 | 1001881 |
| | UG75 Expression | EST | Mm.758 | TITLE ESTs | | | gi = 1755347 | 1193705 |
| | | | | | | | | 583508 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12699 | UG75 Expression | EST | Mm.7597 | TITLE ESTs | | | gi = 4409078 | 1329358 |
| IC12700 | UG75 Expression | EST | Mm.760 | TITLE ESTs | | | gi = 4296661 | 641086 |
| IC12701 | UG75 Expression | EST | Mm.76039 | TITLE ESTs | | | gi = 3175576 | 1361975 |
| IC12702 | UG75 Expression | EST | Mm.7604 | TITLE ESTs, Moderately similar to unknown [H. sapiens] | | | gi = 2040525 | 1225336 |
| IC12703 | UG75 Expression | EST | Mm.7605 | TITLE ESTs | | | gi = 1756427 | 617832 |
| IC12704 | UG75 Expression | EST | Mm.7630 | TITLE ESTs | | | gi = 4031939 | 1329869 |
| IC12705 | UG75 Expression | EST | Mm.76356 | TITLE ESTs | | | gi = 4404284 | 1002184 |
| IC12706 | UG75 Expression | EST | Mm.76400 | TITLE ESTs | | | gi = 1896260 | 722511 |
| IC12707 | UG75 Expression | EST | Mm.76453 | TITLE ESTs | | | gi = 472401 | 639076 |
| IC12708 | UG75 Expression | EST | Mm.7649 | TITLE ESTs, Weakly similar to fos39554_1 [H. sapiens] | | | gi = 4442123 | 597931 |
| IC12709 | UG75 Expression | EST | Mm.7654 | TITLE ESTs, Weakly similar to predicted using Genefinder [C. elegans] | | | gi = 1643009 | 1281335 |
| IC12710 | UG75 Expression | EST | Mm.76554 | TITLE ESTs, Weakly similar to /prediction | | | gi = 6649249 | 533663 |
| IC12711 | UG75 Expression | EST | Mm.7664 | TITLE ESTs | | | gi = 6085081 | 1395681 |
| IC12712 | UG75 Expression | EST | Mm.7667 | TITLE ESTs | | | gi = 4723731 | 637184 |
| IC12713 | UG75 Expression | EST | Mm.76727 | TITLE ESTs, Weakly similar to DRPLA [M. musculus] | | | gi = 6098099 | 639085 |
| IC12714 | UG75 Expression | EST | Mm.76794 | TITLE ESTs | | | gi = 2282851 | 777310 |
| IC12715 | UG75 Expression | EST | Mm.7686 | TITLE ESTs, Weakly similar to W06B4.2 [C. elegans] | | | gi = 6826471 | 574282 |
| IC12716 | UG75 Expression | EST | Mm.769 | TITLE ESTs | | | gi = 1715898 | 596670 |
| IC12717 | UG75 Expression | EST | Mm.76991 | TITLE ESTs | | | gi = 1684097 | 575463 |
| IC12718 | UG75 Expression | EST | Mm.77009 | TITLE ESTs | | | gi = 4217291 | 639391 |
| IC12719 | UG75 Expression | EST | Mm.7703 | TITLE ESTs | | | gi = 1487388 | 637901 |
| IC12721 | UG75 Expression | EST | Mm.772 | TITLE ESTs | | | gi = 1715973 | 596701 |
| IC12722 | UG75 Expression | EST | Mm.77471 | TITLE ESTs | | | gi = 2962077 | 737638 |
| IC12723 | UG75 Expression | EST | Mm.77683 | TITLE ESTs | | | gi = 4729933 | 1294579 |
| IC12724 | UG75 Expression | EST | Mm.77692 | TITLE ESTs | | | gi = 4600952 | 622389 |
| IC12725 | UG75 Expression | EST | Mm.77693 | TITLE ESTs | | | gi = 4604507 | 621372 |
| IC12726 | UG75 Expression | EST | Mm.77700 | TITLE EST | | | gi = 4602477 | 1193646 |
| IC12727 | UG75 Expression | EST | Mm.77719 | TITLE ESTs, Moderately similar to hypothetical protein [M. musculus] | | | gi = 2256883 | 894309 |
| IC12728 | UG75 Expression | EST | Mm.77723 | TITLE EST | | | gi = 1725893 | 581793 |
| IC12729 | UG75 Expression | EST | Mm.77727 | TITLE EST | | | gi = 4702691 | 1225687 |
| IC12730 | UG75 Expression | EST | Mm.77728 | TITLE EST | | | gi = 4702719 | 1225797 |
| IC12731 | UG75 Expression | EST | Mm.77729 | TITLE ESTs | | | gi = 1380096 | 1225825 |
| IC12732 | UG75 Expression | EST | Mm.77733 | TITLE EST | | | gi = 471060 | 1226476 |
| IC12733 | UG75 Expression | EST | Mm.77734 | TITLE EST | | | gi = 4721088 | 1226960 |
| IC12734 | UG75 Expression | EST | Mm.77743 | TITLE EST | | | gi = 4721908 | 1225125 |
| IC12735 | UG75 Expression | EST | Mm.77744 | TITLE EST | | | gi = 421922 | 1225194 |
| IC12736 | UG75 Expression | EST | Mm.77745 | TITLE EST | | | gi = 4721936 | 1225278 |
| IC12737 | UG75 Expression | EST | Mm.77746 | TITLE ESTs | | | gi = 5267817 | 1225409 |
| IC12738 | UG75 Expression | EST | Mm.77760 | TITLE EST | | | gi = 472234 | 1243412 |
| IC12739 | UG75 Expression | EST | Mm.77774 | TITLE EST | | | gi = 4724848 | 1225102 |
| IC12740 | UG75 Expression | EST | Mm.77775 | TITLE EST | | | gi = 472869 | 1225547 |
| IC12741 | UG75 Expression | EST | Mm.77778 | TITLE ESTs | | | gi = 4724989 | 1226146 |
| IC12742 | UG75 Expression | EST | Mm.77779 | TITLE EST | | | gi = 2891366 | 1001803 |
| IC12743 | UG75 Expression | EST | Mm.7778 | TITLE ESTs | | | gi = 1739473 | 635704 |
| IC12744 | UG75 Expression | EST | Mm.77784 | TITLE ESTs | | | gi = 4318775 | 719296 |
| | UG75 Expression | EST | Mm.778 | TITLE ESTs | | | gi = 2247868 | 581714 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12745 | UG75 Expression | EST | Mm.7780 | TITLE ESTs, Weakly similar to X-LINKED INHIBITOR OF APOPTOSIS PROTEIN [*M. musculus*] | | | gi = 3955569 | 634780 |
| IC12746 | UG76 LID366 B cell | EST | Mm.77877 | TITLE ESTs | | | gi = 7066601 | 934260 |
| IC12747 | UG75 Expression | EST | Mm.78005 | TITLE ESTs | | | gi = 2956289 | 622930 |
| IC12748 | UG75 Expression | EST | Mm.78025 | TITLE ESTs | | | gi = 2691442 | 620711 |
| IC12749 | UG75 Expression | EST | Mm.78093 | TITLE ESTs | | | gi = 2284202 | 533993 |
| IC12750 | UG75 Expression | EST | Mm.78106 | TITLE ESTs | | | gi = 1863403 | 1617697 |
| IC12751 | UG75 Expression | EST | Mm.78146 | TITLE ESTs | | | gi = 6168586 | 820021 |
| IC12752 | UG75 Expression | EST | Mm.7816 | TITLE ESTs | | | gi = 3981958 | 833478 |
| IC12753 | UG75 Expression | EST | Mm.78250 | TITLE ESTs, Moderately similar to ubiquitin protein ligase [*M. musculus*] | | | gi = 2893748 | 1002729 |
| IC12754 | UG75 Expression | EST | Mm.78312 | TITLE ESTs, Weakly similar to ORF YOR141c [*S. cerevisiae*] | | | gi = 4374286 | 722752 |
| IC12755 | UG75 Expression | EST | Mm.7843 | TITLE ESTs, Weakly similar to Su(var)3-9 homolog [*M. musculus*] | | | gi = 6085560 | 890802 |
| IC12756 | UG75 Expression | EST | Mm.7852 | TITLE ESTs | | | gi = 2919739 | 1002018 |
| IC12757 | UG75 Expression | EST | Mm.78536 | TITLE ESTs, Moderately similar to HYPOTHETICAL PROTEIN HI0376 [*Haemophilus influenzae*] | | | gi = 2861211 | 1294591 |
| IC12758 | UG75 Expression | EST | Mm.78652 | TITLE ESTs | | | gi = 6145503 | 765544 |
| IC12759 | UG75 Expression | EST | Mm.78723 | TITLE ESTs | | | gi = 4318972 | 721433 |
| IC12760 | UG75 Expression | EST | Mm.7884 | TITLE ESTs | | | gi = 4434487 | 973318 |
| IC12761 | UG75 Expression | EST | Mm.78875 | TITLE ESTs | | | gi = 1768391 | 764192 |
| IC12762 | UG75 Expression | EST | Mm.78889 | TITLE ESTs | | | gi = 6262692 | 750175 |
| IC12763 | UG75 Expression | EST | Mm.79198 | TITLE ESTs | | | gi = 4601163 | 598355 |
| IC12764 | UG75 Expression | EST | Mm.79224 | TITLE ESTs | | | gi = 2233576 | 636125 |
| IC12765 | UG75 Expression | EST | Mm.79256 | TITLE ESTs | | | gi = 1905325 | 621914 |
| IC12766 | UG75 Expression | EST | Mm.79348 | TITLE ESTs, Weakly similar to myosin I myr 4 [*R. norvegicus*] | | | gi = 1682067 | 750869 |
| IC12767 | UG75 Expression | EST | Mm.794 | TITLE ESTs, Weakly similar to butyrophilin [*H. sapiens*] | | | gi = 1504172 | 597609 |
| IC12768 | UG75 Expression | EST | Mm.79403 | TITLE ESTs | | | gi = 6289654 | 1225539 |
| IC12769 | UG75 Expression | EST | Mm.796 | TITLE ESTs | | | gi = 6824263 | 597660 |
| IC12770 | UG75 Expression | EST | Mm.79728 | TITLE ESTs | | | gi = 1919391 | 777538 |
| IC12771 | UG75 Expression | EST | Mm.798 | TITLE ESTs | | | gi = 2885653 | 764300 |
| IC12772 | UG75 Expression | EST | Mm.79898 | TITLE ESTs | | | gi = 2962558 | 1265316 |
| IC12773 | UG75 Expression | EST | Mm.80025 | TITLE ESTs | | | gi = 175638 | 618480 |
| IC12774 | UG75 Expression | EST | Mm.801 | TITLE ESTs | | | gi = 2139797 | 749436 |
| IC12775 | UG75 Expression | EST | Mm.80393 | TITLE ESTs | | | gi = 6748759 | 634688 |
| IC12776 | UG75 Expression | EST | Mm.80408 | TITLE ESTs | | | gi = 1700108 | 5777750 |
| IC12777 | UG75 Expression | EST | Mm.80474 | TITLE ESTs | | | gi = 2962474 | 638192 |
| IC12778 | UG75 Expression | EST | Mm.80501 | TITLE ESTs | | | gi = 6278427 | 582430 |
| IC12779 | UG75 Expression | EST | Mm.80519 | TITLE apyrase 1, homolog (*C. lectularius*) | GENE Apy1h | | gi = 4484827 | 1379942 |
| IC12780 | UG75 Expression | EST | Mm.80533 | TITLE ESTs, Weakly similar to transcription repressor [*H. sapiens*] | | | gi = 6757165 | 524182 |
| IC12781 | UG75 Expression | EST | Mm.80535 | TITLE ESTs, Moderately similar to TRAF4 associated factor 1 [*H. sapiens*] | | | gi = 1663009 | 574146 |
| IC12782 | UG75 Expression | EST | Mm.80536 | TITLE ESTs | | | gi = 1675952 | 575085 |
| IC12783 | UG75 Expression | EST | Mm.80539 | TITLE ESTs | | | gi = 5478092 | 575624 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12784 | UG75 Expression | EST | Mm.80542 | TITLE ESTs, Weakly similar to Similarity to Yeast putative mitochondrial carrier protein PET8 [*C. elegans*] | | | gi = 1713559 | 582647 |
| IC12785 | UG75 Expression | EST | Mm.80543 | TITLE ESTs | | | gi = 1738446 | 598846 |
| IC12786 | UG75 Expression | EST | Mm.80544 | TITLE ESTs | | | gi = 5126146 | 598775 |
| IC12787 | UG75 Expression | EST | Mm.80546 | TITLE ESTs | | | gi = 1748893 | 618668 |
| IC12788 | UG75 Expression | EST | Mm.80548 | TITLE ESTs | | | gi = 4601387 | 621548 |
| IC12789 | UG75 Expression | EST | Mm.80549 | TITLE ESTs | | | gi = 4032529 | 620139 |
| IC12790 | UG75 Expression | EST | Mm.80552 | TITLE ESTs | | | gi = 4601351 | 621267 |
| IC12791 | UG75 Expression | EST | Mm.80553 | TITLE ESTs | | | gi = 1749025 | 621054 |
| IC12792 | UG75 Expression | EST | Mm.80554 | TITLE ESTs | | | gi = 609853 | 637809 |
| IC12793 | UG75 Expression | EST | Mm.80556 | TITLE ESTs | | | gi = 4725035 | 1226545 |
| IC12794 | UG75 Expression | EST | Mm.80560 | TITLE ESTs | | | gi = 4602008 | 764342 |
| IC12795 | UG75 Expression | EST | Mm.80561 | TITLE ESTs, Weakly similar to estrogen-responsive finger protein [*M. musculus*] | | | gi = 4804779 | 718628 |
| IC12796 | UG75 Expression | EST | Mm.80562 | TITLE ESTs | | | gi = 6938005 | 720975 |
| IC12797 | UG75 Expression | EST | Mm.80563 | TITLE ESTs | | | gi = 1903573 | 720744 |
| IC12798 | UG75 Expression | EST | Mm.80565 | TITLE ESTs | | | gi = 1919132 | 777119 |
| IC12799 | UG75 Expression | EST | Mm.80566 | TITLE ESTs | | | gi = 4853622 | 751330 |
| IC12800 | UG75 Expression | EST | Mm.80567 | TITLE ESTs | | | gi = 4602336 | 749603 |
| IC12801 | UG75 Expression | EST | Mm.80570 | TITLE ESTs | | | gi = 2885742 | 1020636 |
| IC12802 | UG75 Expression | EST | Mm.80576 | TITLE ESTs | | | gi = 1749246 | 894183 |
| IC12803 | UG75 Expression | EST | Mm.80578 | TITLE ESTs | | | gi = 1917254 | 972715 |
| IC12804 | UG75 Expression | EST | Mm.80579 | TITLE ESTs | | | gi = 2283050 | 1193530 |
| IC12805 | UG75 Expression | EST | Mm.80580 | TITLE ESTs | | | gi = 3067062 | 1282794 |
| IC12806 | UG75 Expression | EST | Mm.80581 | TITLE ESTs | | | gi = 1739286 | 634733 |
| IC12807 | UG75 Expression | EST | Mm.80584 | TITLE ESTs | | | gi = 1749262 | 619168 |
| IC12808 | UG75 Expression | EST | Mm.80590 | TITLE ESTs | | | gi = 4602985 | 1446623 |
| IC12809 | UG75 Expression | EST | Mm.80599 | TITLE ESTs | | | gi = 4968079 | 1312751 |
| IC12810 | UG75 Expression | EST | Mm.80613 | TITLE ESTs | | | gi = 4287666 | 619061 |
| IC12811 | UG75 Expression | EST | Mm.80620 | TITLE ESTs | | | gi = 2730733 | 1193195 |
| IC12812 | UG75 Expression | EST | Mm.80623 | TITLE ESTs | | | gi = 651968 | 1226975 |
| IC12813 | UG75 Expression | EST | Mm.80628 | TITLE ESTs, Moderately similar to tyrosine phosphatase [*M. musculus*] | | | gi = 4274581 | 1225160 |
| IC12814 | UG75 Expression | EST | Mm.80629 | TITLE ESTs | | | gi = 2849555 | 1243393 |
| IC12815 | UG75 Expression | EST | Mm.80636 | TITLE ESTs | | | gi = 297288 | 1281297 |
| IC12816 | UG75 Expression | EST | Mm.80637 | TITLE ESTs | | | gi = 1758699 | 622576 |
| IC12817 | UG75 Expression | EST | Mm.80640 | TITLE ESTs, Weakly similar to (define not available 6016431) [*M. musculus*] | | | gi = 3100367 | 1330013 |
| IC12818 | UG75 Expression | EST | Mm.80643 | TITLE ESTs | | | gi = 5567391 | 1363047 |
| IC12819 | UG75 Expression | EST | Mm.80650 | TITLE ESTs | | | gi = 3299508 | 1379239 |
| IC12820 | UG75 Expression | EST | Mm.80657 | TITLE ESTs | | | gi = 3681994 | 1429214 |
| IC12821 | UG75 Expression | EST | Mm.80671 | TITLE ESTs | | | gi = 3296199 | 1749184 |
| IC12822 | UG75 Expression | EST | Mm.80680 | TITLE ESTs | | | gi = 427467 | 1225780 |
| IC12823 | UG75 Expression | EST | Mm.80687 | [*M. musculus*] | | | gi = 4309651 | 573334 |
| IC12824 | UG75 Expression | EST | Mm.80690 | TITLE ESTs, Moderately similar to NADH-UBIQUINONE OXIDOREDUCTASE B14 SUBUNIT [*H. sapiens*] | | | gi = 460579 | 641893 |
| IC12825 | UG75 Expression | EST | Mm.80700 | TITLE EST | | | gi = 4404641 | 1002600 |
| IC12826 | UG75 Expression | EST | Mm.80701 | TITLE ESTs | | | gi = 4726149 | 750585 |
| IC12827 | UG75 Expression | EST | Mm.80702 | TITLE ESTs | | | gi = 1676539 | 573775 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12828 | UG75 Expression | EST | Mm.80704 | TITLE ESTs | | | gi = 426650 | 1243585 |
| IC12829 | UG75 Expression | EST | Mm.80706 | TITLE ESTs | | | gi = 437577 | 620140 |
| IC12830 | UG75 Expression | EST | Mm.80711 | TITLE ESTs | | | gi = 4600914 | 621999 |
| IC12831 | UG75 Expression | EST | Mm.80714 | TITLE ESTs | | | gi = 4767990 | 1263086 |
| IC12832 | UG75 Expression | EST | Mm.80754 | TITLE ESTs | | | gi = 1765564 | 972843 |
| IC12833 | UG75 Expression | EST | Mm.8100 | TITLE ESTs | | | gi = 1677323 | 576594 |
| IC12834 | UG75 Expression | EST | Mm.8162 | TITLE ESTs | | | gi = 2885716 | 596526 |
| IC12835 | UG75 Expression | EST | Mm.81793 | TITLE ESTs | | | gi = 2754879 | 1749439 |
| IC12836 | UG75 Expression | EST | Mm.8195 | TITLE ESTs | | | gi = 4967715 | 2648751 |
| IC12837 | UG75 Expression | EST | Mm.8217 | TITLE DNA Segment, Chr 6, human D12S2489E | GENE D6H12S2489E | | | 621324 |
| IC12838 | UG75 Expression | EST | Mm.8233 | TITLE ESTs | | | gi = 2891147 | 550633 |
| IC12839 | UG75 Expression | EST | Mm.82435 | TITLE ESTs | | | gi = 352247 | 1225097 |
| IC12840 | UG75 Expression | EST | Mm.82547 | TITLE ESTs, Moderately similar to activin receptor interacting protein 1 [M. musculus] | | | gi = 4571734 | 1149710 |
| IC12841 | UG75 Expression | EST | Mm.82572 | TITLE ESTs | | | gi = 1714613 | 597196 |
| IC12842 | UG75 Expression | EST | Mm.82577 | TITLE ESTs | | | gi = 189550 | 1001461 |
| IC12843 | UG75 Expression | EST | Mm.82584 | TITLE ESTs | | | gi = 1724872 | 1279523 |
| IC12844 | UG75 Expression | EST | Mm.82627 | TITLE ESTs | | | gi = 4804912 | 639366 |
| IC12845 | UG75 Expression | EST | Mm.82751 | TITLE ESTs, Moderately similar to CGI-133 protein [H. sapiens] | | | gi = 1793261 | 750309 |
| IC12846 | UG75 Expression | EST | Mm.8282 | TITLE ESTs | | | gi = 2920197 | 638263 |
| IC12847 | UG75 Expression | EST | Mm.83 | TITLE ESTs | | | gi = 2891430 | 574580 |
| IC12848 | UG75 Expression | EST | Mm.8302 | TITLE ESTs | | | gi = 1814553 | 617187 |
| IC12849 | UG75 Expression | EST | Mm.83021 | TITLE ESTs | | | gi = 4484298 | 1226212 |
| IC12850 | UG75 Expression | EST | Mm.83109 | TITLE ESTs | | | gi = 6758098 | 1110780 |
| IC12851 | UG75 Expression | EST | Mm.8324 | TITLE ESTs | | | gi = 6077529 | 1264074 |
| IC12852 | UG75 Expression | EST | Mm.83277 | TITLE ESTs | | | gi = 2523683 | 751194 |
| IC12853 | UG75 Expression | EST | Mm.83417 | TITLE ESTs | | | gi = 2049076 | 751589 |
| IC12854 | UG75 Expression | EST | Mm.835 | TITLE ESTs, Weakly similar to GLUTAMYL AMINOPEPTIDASE [M. musculus] | | | gi = 2775368 | 1225839 |
| IC12855 | UG75 Expression | EST | Mm.83526 | TITLE ESTs | | | gi = 1800910 | 621560 |
| IC12856 | UG75 Expression | EST | Mm.83528 | TITLE ESTs | | | gi = 4720515 | 1243517 |
| IC12857 | UG75 Expression | EST | Mm.83540 | TITLE ESTs | | | gi = 1758635 | 622529 |
| IC12858 | UG75 Expression | EST | Mm.83541 | TITLE ESTs | | | gi = 4216664 | 635097 |
| IC12859 | UG75 Expression | EST | Mm.83549 | TITLE EST | | | gi = 4602422 | 1193102 |
| IC12860 | UG75 Expression | EST | Mm.8356 | TITLE ESTs | | | gi = 5475587 | 1281641 |
| IC12861 | UG75 Expression | EST | Mm.83573 | TITLE EST | | | gi = 4605927 | 1140094 |
| IC12862 | UG75 Expression | EST | Mm.83582 | TITLE EST | | | gi = 4702685 | 1225662 |
| IC12863 | UG75 Expression | EST | Mm.83583 | TITLE EST | | | gi = 4702699 | 1225719 |
| IC12864 | UG75 Expression | EST | Mm.83584 | TITLE EST | | | gi = 4702706 | 1225760 |
| IC12865 | UG75 Expression | EST | Mm.83587 | TITLE ESTs | | | gi = 5334224 | 764222 |
| IC12866 | UG75 Expression | EST | Mm.83595 | TITLE EST | | | gi = 4721054 | 1226354 |
| IC12867 | UG75 Expression | EST | Mm.83607 | TITLE EST | | | gi = 4721930 | 1225221 |
| IC12868 | UG75 Expression | EST | Mm.83608 | TITLE EST | | | gi = 4721937 | 1225280 |
| IC12869 | UG75 Expression | EST | Mm.83609 | TITLE EST | | | gi = 4721951 | 1225364 |
| IC12870 | UG75 Expression | EST | Mm.83610 | TITLE EST | | | gi = 472198 | 1225375 |
| IC12871 | UG75 Expression | EST | Mm.83615 | TITLE ESTs, Moderately similar to transient receptor potential 2 [M. musculus] | | | gi = 2646443 | 621691 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12872 | UG75 Expression | EST | Mm.83618 | TITLE ESTs | | | gi = 3336155 | 1380456 |
| IC12873 | UG75 Expression | EST | Mm.83623 | TITLE ESTs | | | gi = 1919385 | 777516 |
| IC12874 | UG75 Expression | EST | Mm.83629 | TITLE ESTs | | | gi = 4571920 | 1148887 |
| IC12875 | UG75 Expression | EST | Mm.83630 | TITLE ESTs | | | gi = 723631 | 636252 |
| IC12876 | UG75 Expression | EST | Mm.83632 | TITLE ESTs | | | gi = 4275926 | 777473 |
| IC12877 | UG75 Expression | EST | Mm.83636 | TITLE ESTs | | | gi = 4720894 | 1225530 |
| IC12878 | UG75 Expression | EST | Mm.83639 | TITLE EST | | | gi = 4725067 | 1226760 |
| IC12879 | UG75 Expression | EST | Mm.83641 | TITLE ESTs, Moderately similar to Golgi-associated microtubule-binding protein [H. sapiens] | | | gi = 1796674 | 641508 |
| IC12880 | UG75 Expression | EST | Mm.83646 | TITLE ESTs | | | gi = 4726673 | 719193 |
| IC12881 | UG75 Expression | EST | Mm.83758 | TITLE ESTs | | | gi = 1932125 | 764113 |
| IC12882 | UG75 Expression | EST | Mm.83793 | TITLE ESTs | | | gi = 4725236 | 1281654 |
| IC12883 | UG75 Expression | EST | Mm.83816 | TITLE ESTs | | | gi = 2503068 | 722622 |
| IC12884 | UG75 Expression | EST | Mm.83908 | TITLE ESTs | | | gi = 4725055 | 1226699 |
| IC12885 | UG75 Expression | EST | Mm.8393 | TITLE ESTs, Weakly similar to coded for by C. elegans cDNA CEESS55F [C. elegans] | | | gi = 3680353 | 1140194 |
| IC12886 | UG75 Expression | EST | Mm.840 | TITLE ESTs | | | gi = 1725369 | 583032 |
| IC12887 | UG75 Expression | EST | Mm.84007 | TITLE ESTs | | | gi = 4318958 | 721319 |
| IC12888 | UG75 Expression | EST | Mm.84118 | TITLE ESTs | | | gi = 4307594 | 597371 |
| IC12889 | UG75 Expression | EST | Mm.844 | TITLE ESTs | | | gi = 4614014 | 643857 |
| IC12890 | UG75 Expression | EST | Mm.84539 | TITLE ESTs | | | gi = 6255791 | 1224896 |
| IC12891 | UG75 Expression | EST | Mm.84629 | TITLE ESTs, Moderately similar to PUTATIVE HETEROGENEOUS NUCLEAR RIBONUCLEOPROTEIN X [M. musculus] | | | gi = 4600983 | 622756 |
| IC12892 | UG75 Expression | EST | Mm.84684 | TITLE ESTs | | | gi = 2528167 | 1363075 |
| IC12893 | UG75 Expression | EST | Mm.85101 | TITLE ESTs | | | gi = 3955796 | 1196944 |
| IC12894 | UG75 Expression | EST | Mm.85115 | TITLE ESTs | | | gi = 3926551 | 1396353 |
| IC12895 | UG75 Expression | EST | Mm.85137 | TITLE ESTs | | | gi = 1759843 | 621205 |
| IC12896 | UG75 Expression | EST | Mm.85156 | TITLE ESTs | | | gi = 1699789 | 1263034 |
| IC12897 | UG75 Expression | EST | Mm.85162 | TITLE ESTs | | | gi = 1901907 | 718878 |
| IC12898 | UG75 Expression | EST | Mm.85229 | TITLE ESTs | | | gi = 3732787 | 1430379 |
| IC12899 | UG75 Expression | EST | Mm.85264 | TITLE ESTs | | | gi = 1826395 | 622287 |
| IC12900 | UG75 Expression | EST | Mm.85299 | TITLE ESTs | | | gi = 4766168 | 622584 |
| IC12901 | UG75 Expression | EST | Mm.85343 | TITLE ESTs | | | gi = 4702934 | 618488 |
| IC12902 | UG75 Expression | EST | Mm.85567 | TITLE ESTs | | | gi = 3393956 | 642037 |
| IC12903 | UG75 Expression | EST | Mm.85582 | TITLE ESTs | | | gi = 2308621 | 1003706 |
| IC12904 | UG75 Expression | EST | Mm.85641 | TITLE ESTs, Weakly similar to hypothetical protein [H. sapiens] | | | gi = 3141287 | 1345830 |
| IC12905 | UG75 Expression | EST | Mm.85803 | TITLE ESTs | | | gi = 1757105 | 619685 |
| IC12906 | UG75 Expression | EST | Mm.8581 | TITLE ESTs, Moderately similar to U4/U6 small nuclear ribonucleoprotein hPrp3 [H. sapiens] | | | gi = 2917442 | 618495 |
| IC12907 | UG75 Expression | EST | Mm.85852 | TITLE ESTs | | | gi = 4726644 | 1971294 |
| IC12908 | UG75 Expression | EST | Mm.86090 | TITLE ESTs | | | gi = 4287680 | 619075 |
| IC12909 | UG75 Expression | EST | Mm.8612 | TITLE ESTs, Moderately similar to ADP-RIBOSYLATION FACTOR 1 [Homo sapiens; Bos taurus; Rattus norvegicus] | | | gi = 4057871 | 1378404 |
| IC12910 | UG75 Expression | EST | Mm.86150 | TITLE ESTs | | | gi = 4307363 | 597143 |
| IC12911 | UG75 Expression | EST | Mm.86193 | TITLE ESTs | | | gi = 3054285 | 1225323 |
| IC12912 | UG75 Expression | EST | Mm.86217 | TITLE ESTs | | | gi = 1919403 | 597473 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12913 | UG75 Expression | EST | Mm.86267 | TITLE ESTs, Moderately similar to GTP-binding protein [H. sapiens] | | | gi = 1793165 | 1363069 |
| IC12914 | UG75 Expression | EST | Mm.86318 | TITLE ESTs | | | gi = 1675805 | 574459 |
| IC12915 | UG75 Expression | EST | Mm.86324 | TITLE ESTs | | | gi = 4032469 | 722434 |
| IC12916 | UG75 Expression | EST | Mm.86325 | TITLE ESTs | | | gi = 1684511 | 574645 |
| IC12917 | UG75 Expression | EST | Mm.86327 | TITLE ESTs, Moderately similar to GTP-binding protein [H. sapiens] | | | gi = 1700787 | 596874 |
| IC12918 | UG75 Expression | EST | Mm.86328 | TITLE ESTs | | | gi = 1701678 | 577599 |
| IC12919 | UG75 Expression | EST | Mm.86330 | TITLE ESTs | | | gi = 1702691 | 577779 |
| IC12920 | UG75 Expression | EST | Mm.86332 | TITLE ESTs | | | gi = 6193089 | 1328040 |
| IC12921 | UG75 Expression | EST | Mm.86333 | TITLE ESTs | | | gi = 1714854 | 597075 |
| IC12922 | UG75 Expression | EST | Mm.86338 | TITLE ESTs | | | gi = 1748976 | 618839 |
| IC12923 | UG75 Expression | EST | Mm.86341 | TITLE ESTs | | | gi = 2284477 | 623087 |
| IC12924 | UG75 Expression | EST | Mm.86343 | TITLE ESTs | | | gi = 7026488 | 619804 |
| IC12925 | UG75 Expression | EST | Mm.86344 | TITLE ESTs | | | gi = 1727202 | 620816 |
| IC12926 | UG75 Expression | EST | Mm.86345 | TITLE ESTs | | | gi = 1767111 | 577278 |
| IC12927 | UG75 Expression | EST | Mm.86348 | TITLE ESTs | | | gi = 6193944 | 642561 |
| IC12928 | UG75 Expression | EST | Mm.86350 | TITLE ESTs | | | gi = 1776913 | 636318 |
| IC12929 | UG75 Expression | EST | Mm.86352 | TITLE ESTs | | | gi = 2306176 | 777398 |
| IC12930 | UG75 Expression | EST | Mm.86358 | TITLE ESTs | | | gi = 4442288 | 597331 |
| IC12931 | 00/04/26 UG#76 17Lid Expansion | EST | Mm.86360 | ESTs | | | gi = 2250490 | 860853 |
| IC12932 | UG75 Expression | EST | Mm.86361 | TITLE ESTs | | | gi = 472489 | 1225988 |
| IC12933 | UG75 Expression | EST | Mm.86371 | TITLE ESTs | | | gi = 1889657 | 719337 |
| IC12934 | UG75 Expression | EST | Mm.86374 | TITLE ESTs | | | gi = 1904467 | 718399 |
| IC12935 | UG75 Expression | EST | Mm.86375 | TITLE ESTs | | | gi = 1755977 | 616593 |
| IC12936 | UG75 Expression | EST | Mm.86376 | TITLE ESTs | | | gi = 4602536 | 721996 |
| IC12937 | UG75 Expression | EST | Mm.86377 | TITLE ESTs | | | gi = 1905240 | 722041 |
| IC12938 | UG75 Expression | EST | Mm.86380 | TITLE ESTs | | | gi = 2892308 | 621142 |
| IC12939 | UG75 Expression | EST | Mm.86381 | TITLE ESTs | | | gi = 1915532 | 765533 |
| IC12940 | UG75 Expression | EST | Mm.86383 | TITLE ESTs | | | gi = 1681743 | 596444 |
| IC12941 | UG75 Expression | EST | Mm.86384 | TITLE ESTs | | | gi = 1915776 | 765825 |
| IC12942 | UG75 Expression | EST | Mm.86385 | TITLE ESTs | | | gi = 3054302 | 765796 |
| IC12943 | UG75 Expression | EST | Mm.86387 | TITLE ESTs | | | gi = 6421882 | 777493 |
| IC12944 | UG75 Expression | EST | Mm.86390 | TITLE ESTs | | | gi = 1932515 | 777829 |
| IC12945 | UG75 Expression | EST | Mm.86391 | TITLE ESTs | | | gi = 1681710 | 620810 |
| IC12946 | UG75 Expression | EST | Mm.86394 | TITLE ESTs | | | gi = 5819538 | 1282492 |
| IC12947 | UG75 Expression | EST | Mm.86398 | TITLE ESTs | | | gi = 4294981 | 636665 |
| IC12948 | UG75 Expression | EST | Mm.86399 | TITLE ESTs | | | gi = 382694 | 750944 |
| IC12949 | UG75 Expression | EST | Mm.86401 | TITLE ESTs | | | gi = 2049265 | 751853 |
| IC12950 | UG75 Expression | EST | Mm.86403 | TITLE ESTs | | | gi = 4307079 | 643859 |
| IC12951 | UG75 Expression | EST | Mm.86404 | TITLE ESTs | | | gi = 2248631 | 750151 |
| IC12952 | UG75 Expression | EST | Mm.86405 | TITLE ESTs | | | gi = 1759515 | 620524 |
| IC12953 | UG75 Expression | EST | Mm.86406 | TITLE ESTs | | | gi = 3979890 | 658473 |
| IC12954 | UG75 Expression | EST | Mm.86411 | TITLE ESTs | | | gi = 1902439 | 718150 |
| IC12955 | UG75 Expression | EST | Mm.86415 | TITLE ESTs | | | gi = 2142456 | 819770 |
| IC12956 | UG75 Expression | EST | Mm.86418 | TITLE ESTs | | | gi = 6822720 | 722250 |
| IC12957 | UG75 Expression | EST | Mm.86432 | TITLE ESTs, Weakly similar to SH3 domain-containing adapter protein [M. musculus] | | | gi = 3956357 | 1225311 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC12958 | UG75 Expression | EST | Mm.86437 | TITLE ESTs | | | gi = 2306098 | 973648 |
| IC12959 | UG75 Expression | EST | Mm.86438 | TITLE ESTs | | | gi = 2256912 | 1362636 |
| IC12960 | UG75 Expression | EST | Mm.86439 | TITLE ESTs | | | gi = 2258663 | 1329192 |
| IC12961 | UG75 Expression | EST | Mm.86449 | TITLE ESTs | | | gi = 1776450 | 643082 |
| IC12962 | UG75 Expression | EST | Mm.86451 | TITLE ESTs | | | gi = 6277396 | 959483 |
| IC12963 | UG75 Expression | EST | Mm.86456 | TITLE ESTs | | | gi = 2349914 | 903455 |
| IC12964 | UG75 Expression | EST | Mm.86457 | TITLE ESTs | | | gi = 2350192 | 718486 |
| IC12965 | UG75 Expression | EST | Mm.86473 | TITLE ESTs | | | gi = 1901518 | 598083 |
| IC12966 | UG75 Expression | EST | Mm.86491 | TITLE ESTs, Weakly similar to weak similarity to hemolysins [*C. elegans*] | | | gi = 3372916 | 764572 |
| IC12967 | UG75 Expression | EST | Mm.86502 | TITLE ESTs | | | gi = 1904381 | 721468 |
| IC12968 | UG75 Expression | EST | Mm.86510 | TITLE ESTs | | | gi = 2775456 | 1225955 |
| IC12969 | UG75 Expression | EST | Mm.86513 | TITLE ESTs | | | gi = 1913209 | 765221 |
| IC12970 | UG75 Expression | EST | Mm.86514 | TITLE ESTs | | | gi = 4726285 | 1139855 |
| IC12971 | UG75 Expression | EST | Mm.86521 | TITLE ESTs | | | gi = 2138693 | 1295922 |
| IC12972 | UG75 Expression | EST | Mm.86523 | TITLE ESTs | | | gi = 1914995 | 617424 |
| IC12973 | UG75 Expression | EST | Mm.86528 | TITLE ESTs | | | gi = 2944778 | 1263264 |
| IC12974 | UG75 Expression | EST | Mm.86529 | TITLE ESTs | | | gi = 2962434 | 1265514 |
| IC12975 | UG75 Expression | EST | Mm.86533 | TITLE ESTs | | | gi = 1671636 | 577363 |
| IC12976 | UG75 Expression | EST | Mm.86534 | TITLE ESTs | | | gi = 4725042 | 1226596 |
| IC12977 | UG75 Expression | EST | Mm.86535 | TITLE ESTs | | | gi = 4623739 | 1226813 |
| IC12978 | UG75 Expression | EST | Mm.86545 | TITLE ESTs, Weakly similar to contains similarity to BC-2 protein [*C. elegans*] | | | gi = 3682123 | 619939 |
| IC12979 | UG75 Expression | EST | Mm.86547 | TITLE ESTs, Moderately similar to p85SPR [*M. musculus*] | | | gi = 1796635 | 1294371 |
| IC12980 | UG75 Expression | EST | Mm.86550 | TITLE ESTs | | | gi = 2049031 | 751499 |
| IC12981 | UG75 Expression | EST | Mm.86553 | TITLE ESTs | | | gi = 6268532 | 1263554 |
| IC12982 | UG75 Expression | EST | Mm.86555 | TITLE ESTs, Weakly similar to atopy related autoantigen CALC [*H. sapiens*] | | | gi = 6750982 | 640735 |
| IC12983 | UG75 Expression | EST | Mm.86558 | TITLE ESTs | | | gi = 148549 | 598339 |
| IC12984 | UG75 Expression | EST | Mm.86560 | TITLE ESTs | | | gi = 20772 | 959262 |
| IC12985 | UG75 Expression | EST | Mm.86565 | TITLE ESTs | | | gi = 3161543 | 1579512 |
| IC12986 | UG75 Expression | EST | Mm.86566 | TITLE ESTs | | | gi = 1749116 | 617608 |
| IC12987 | UG75 Expression | EST | Mm.86567 | TITLE ESTs | | | gi = 6278848 | 1361499 |
| IC12988 | UG75 Expression | EST | Mm.86571 | TITLE ESTs | | | gi = 6184567 | 751279 |
| IC12989 | UG75 Expression | EST | Mm.86572 | TITLE ESTs | | | gi = 2333479 | 972930 |
| IC12990 | UG75 Expression | EST | Mm.86574 | TITLE ESTs, Moderately similar to ZINC FINGER PROTEIN 46 [*Homo sapiens*] | | | gi = 1808541 | 1367157 |
| IC12991 | UG75 Expression | EST | Mm.86583 | TITLE ESTs | | | gi = 3295336 | 1749761 |
| IC12992 | UG75 Expression | EST | Mm.86585 | TITLE ESTs | | | gi = 3216030 | 639008 |
| IC12993 | UG75 Expression | EST | Mm.86586 | TITLE ESTs | | | gi = 1676360 | 573486 |
| IC12994 | UG75 Expression | EST | Mm.86587 | TITLE ESTs | | | gi = 3299490 | 1379223 |
| IC12995 | UG75 Expression | EST | Mm.86589 | TITLE ESTs | | | gi = 4721924 | 1225193 |
| IC12996 | UG75 Expression | EST | Mm.86590 | TITLE ESTs, Weakly similar to ZINC FINGER PROTEIN ZFP-38 [*M. musculus*] | | | gi = 6078626 | 721245 |
| IC12997 | UG75 Expression | EST | Mm.86602 | TITLE ESTs | | | gi = 2813768 | 1395545 |
| IC12998 | UG75 Expression | EST | Mm.86603 | TITLE ESTs | | | gi = 1758575 | 621353 |
| IC12999 | UG75 Expression | EST | Mm.86612 | TITLE ESTs | | | gi = 6098447 | 1445788 |
| IC13000 | UG75 Expression | EST | Mm.86615 | TITLE ESTs | | | gi = 3335724 | 972692 |
| IC13001 | UG75 Expression | EST | Mm.86616 | TITLE ESTs | | | gi = 1684119 | 574596 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC13002 | UG75 Expression | EST | Mm.86618 | TITLE ESTs | | | gi = 4482494 | 634849 |
| IC13003 | UG75 Expression | EST | Mm.86622 | TITLE ESTs | | | gi = 460289 | 1193714 |
| IC13004 | UG75 Expression | EST | Mm.86623 | TITLE ESTs | | | gi = 533297 | 639746 |
| IC13005 | UG75 Expression | EST | Mm.86628 | TITLE ESTs | | | gi = 3692721 | 583550 |
| IC13006 | UG75 Expression | EST | Mm.86630 | TITLE ESTs | | | gi = 3731853 | 1394989 |
| IC13007 | UG75 Expression | EST | Mm.86631 | TITLE ESTs | | | gi = 4276050 | 1395000 |
| IC13008 | UG75 Expression | EST | Mm.86632 | TITLE ESTs | | | gi = 1758602 | 621833 |
| IC13009 | UG75 Expression | EST | Mm.86633 | TITLE ESTs | | | gi = 3732320 | 1383826 |
| IC13010 | UG75 Expression | EST | Mm.86638 | TITLE ESTs | | | gi = 3235851 | 1225385 |
| IC13011 | UG75 Expression | EST | Mm.86644 | TITLE DNA segment, Chr 5, Wayne State University 178, expressed | GENE D5Wsu178e | | | 617622 |
| IC13012 | UG75 Expression | EST | Mm.86647 | TITLE ESTs | | | gi = 3068065 | 619639 |
| IC13013 | UG75 Expression | EST | Mm.86650 | TITLE ESTs | | | gi = 3926468 | 1395173 |
| IC13014 | UG75 Expression | EST | Mm.86658 | TITLE ESTs | | | gi = 4216766 | 750542 |
| IC13015 | UG75 Expression | EST | Mm.86665 | TITLE ESTs | | | gi = 1801022 | 641084 |
| IC13016 | UG75 Expression | EST | Mm.86681 | TITLE ESTs | | | gi = 368314 | 581719 |
| IC13017 | UG75 Expression | EST | Mm.86682 | TITLE ESTs | | | gi = 22563870 | 894302 |
| IC13018 | UG75 Expression | EST | Mm.86683 | TITLE ESTs | | | gi = 430342 | 597120 |
| IC13019 | UG75 Expression | EST | Mm.86684 | TITLE ESTs | | | gi = 1744153 | 635597 |
| IC13020 | UG75 Expression | EST | Mm.86687 | TITLE ESTs | | | gi = 4295493 | 637238 |
| IC13021 | UG75 Expression | EST | Mm.86688 | TITLE ESTs | | | gi = 6192478 | 617610 |
| IC13022 | UG75 Expression | EST | Mm.86690 | TITLE ESTs | | | gi = 4300836 | 620853 |
| IC13023 | UG75 Expression | EST | Mm.86694 | TITLE ESTs | | | gi = 633144 | 718087 |
| IC13024 | UG75 Expression | EST | Mm.86698 | TITLE ESTs | | | gi = 431865 | 718604 |
| IC13025 | UG75 Expression | EST | Mm.86699 | TITLE ESTs | | | gi = 4318759 | 719226 |
| IC13026 | UG75 Expression | EST | Mm.86700 | TITLE ESTs | | | gi = 60018 | 721170 |
| IC13027 | UG75 Expression | EST | Mm.86701 | TITLE ESTs | | | gi = 1399482 | 1226253 |
| IC13028 | UG75 Expression | EST | Mm.86712 | TITLE ESTs | | | gi = 3236011 | 1295229 |
| IC13029 | UG76 LID366 B cell | EST | Mm.86715 | TITLE ESTs | | | gi = 7066744 | 373768 |
| IC13030 | UG75 Expression | EST | Mm.86716 | TITLE ESTs | | | gi = 850909 | 622653 |
| IC13031 | UG75 Expression | EST | Mm.86718 | TITLE ESTs | | | gi = 4408473 | 1263602 |
| IC13032 | UG75 Expression | EST | Mm.86720 | TITLE ESTs | | | gi = 4409166 | 765208 |
| IC13033 | UG75 Expression | EST | Mm.86721 | TITLE ESTs | | | gi = 4409202 | 1293606 |
| IC13034 | UG75 Expression | EST | Mm.86723 | TITLE ESTs, Weakly similar to TETRANECTIN PRECURSOR [M. musculus] | | | gi = 4434507 | 1328597 |
| IC13035 | UG75 Expression | EST | Mm.86726 | TITLE ESTs | | | gi = 1808234 | 641645 |
| IC13036 | UG75 Expression | EST | Mm.86731 | TITLE ESTs | | | gi = 4617274 | 722524 |
| IC13037 | UG75 Expression | EST | Mm.86733 | TITLE ESTs | | | gi = 4482804 | 1264661 |
| IC13038 | UG75 Expression | EST | Mm.86738 | TITLE ESTs | | | gi = 4484886 | 1265235 |
| IC13039 | UG75 Expression | EST | Mm.86747 | TITLE ESTs | | | gi = 4403671 | 959072 |
| IC13040 | UG75 Expression | EST | Mm.86752 | TITLE ESTs, Weakly similar to peptidoglycan recognition protein precursor [M. musculus] | | | gi = 4604785 | 1001498 |
| IC13041 | UG75 Expression | EST | Mm.86753 | TITLE ESTs | | | gi = 413421 | 620738 |
| IC13042 | UG75 Expression | EST | Mm.86760 | TITLE ESTs | | | gi = 180051 | 640460 |
| IC13043 | UG75 Expression | EST | Mm.86761 | TITLE ESTs | | | gi = 1808333 | 641707 |
| IC13044 | UG75 Expression | EST | Mm.86768 | TITLE ESTs | | | gi = 2256946 | 894347 |
| IC13045 | UG75 Expression | EST | Mm.86774 | TITLE ESTs | | | gi = 4765813 | 721433 |
| IC13046 | UG75 Expression | EST | Mm.86775 | TITLE ESTs | | | gi = 640766 | 622639 |
| IC13047 | UG75 Expression | EST | Mm.86781 | TITLE ESTs | | | gi = 126021 | 959010 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC13048 | UG75 Expression | EST | Mm.86782 | TITLE ESTs | | | gi = 6243806 | 638744 |
| IC13049 | UG75 Expression | EST | Mm.86783 | TITLE ESTs | | | gi = 404898 | 640292 |
| IC13050 | UG75 Expression | EST | Mm.86786 | TITLE ESTs | | | gi = 1725756 | 597711 |
| IC13051 | UG75 Expression | EST | Mm.868 | TITLE ESTs | | | gi = 1725875 | 599283 |
| IC13052 | UG75 Expression | EST | Mm.8681 | TITLE ESTs | | | gi = 2306559 | 617511 |
| IC13053 | UG75 Expression | EST | Mm.86839 | TITLE ESTs, Weakly similar to similar to RNA binding protein [C. elegans] | | | gi = 5549353 | 1361961 |
| IC13054 | UG75 Expression | EST | Mm.86845 | TITLE ESTs | | | gi = 7026905 | 1224898 |
| IC13055 | UG75 Expression | EST | Mm.8686 | TITLE ESTs | | | gi = 4434023 | 575941 |
| IC13056 | UG75 Expression | EST | Mm.86860 | TITLE ESTs | | | gi = 4726247 | 619207 |
| IC13057 | UG75 Expression | EST | Mm.86871 | TITLE ESTs | | | gi = 187551 | 457307 |
| IC13058 | UG75 Expression | EST | Mm.86878 | TITLE ESTs, Moderately similar to (define not available 6002599) [R. norvegicus] | | | gi = 2307996 | 958545 |
| IC13059 | UG75 Expression | EST | Mm.86884 | TITLE ESTs, Weakly similar to unknown [H. sapiens] | | | gi = 4318888 | 636048 |
| IC13060 | UG75 Expression | EST | Mm.86891 | TITLE ESTs | | | gi = 1902241 | 960785 |
| IC13061 | UG75 Expression | EST | Mm.86909 | TITLE ESTs | | | gi = 4720629 | 598802 |
| IC13062 | UG75 Expression | EST | Mm.86914 | TITLE ESTs | | | gi = 2404013 | 1025469 |
| IC13063 | UG75 Expression | EST | Mm.86921 | TITLE ESTs | | | gi = 3393965 | 908506 |
| IC13064 | UG75 Expression | EST | Mm.86929 | TITLE ESTs | | | gi = 1903617 | 720983 |
| IC13065 | UG75 Expression | EST | Mm.86933 | TITLE ESTs | | | gi = 2591649 | 597400 |
| IC13066 | UG75 Expression | EST | Mm.86937 | TITLE ESTs, Weakly similar to C13F10.7 [C. elegans] | | | gi = 1816868 | 583227 |
| IC13067 | UG75 Expression | EST | Mm.86952 | TITLE ESTs | | | gi = 277608 | 1226934 |
| IC13068 | UG75 Expression | EST | Mm.86987 | TITLE ESTs, Moderately similar to AMSH [H. sapiens] | | | gi = 6631593 | 750984 |
| IC13069 | UG75 Expression | EST | Mm.86989 | TITLE ESTs | | | gi = 1792977 | 1429424 |
| IC13070 | UG75 Expression | EST | Mm.86995 | TITLE ESTs | | | gi = 1792977 | 634069 |
| IC13071 | UG75 Expression | EST | Mm.87002 | TITLE ESTs | | | gi = 4802619 | 1429694 |
| IC13072 | UG75 Expression | EST | Mm.87003 | TITLE ESTs, Weakly similar to antigen NY-CO-1 [H. sapiens] | | | gi = 682459 | 750132 |
| IC13073 | UG75 Expression | EST | Mm.87007 | TITLE ESTs | | | gi = 5819485 | 718373 |
| IC13074 | UG75 Expression | EST | Mm.87012 | TITLE ESTs | | | gi = 6101031 | 634388 |
| IC13075 | UG75 Expression | EST | Mm.87030 | TITLE ESTs | | | gi = 6096093 | 1264851 |
| IC13076 | UG75 Expression | EST | Mm.87037 | TITLE ESTs | | | gi = 6098639 | 636557 |
| IC13077 | UG75 Expression | EST | Mm.87077 | TITLE ESTs | | | gi = 1435866 | 749175 |
| IC13078 | UG75 Expression | EST | Mm.87106 | TITLE ESTs | | | gi = 1744261 | 635624 |
| IC13079 | UG75 Expression | EST | Mm.87115 | TITLE ESTs | | | gi = 6182055 | 634711 |
| IC13080 | UG75 Expression | EST | Mm.87121 | TITLE ESTs | | | gi = 1840201 | 973423 |
| IC13081 | UG75 Expression | EST | Mm.87129 | TITLE ESTs | | | gi = 461597 | 1243922 |
| IC13082 | UG75 Expression | EST | Mm.87141 | TITLE ESTs | | | gi = 2857817 | 1295838 |
| IC13083 | UG75 Expression | EST | Mm.87142 | TITLE ESTs | | | gi = 2041051 | 1279534 |
| IC13084 | UG75 Expression | EST | Mm.87149 | TITLE ESTs | | | gi = 1487533 | 749552 |
| IC13085 | UG75 Expression | EST | Mm.87160 | TITLE ESTs | | | gi = 608693 | 1327610 |
| IC13086 | UG75 Expression | EST | Mm.87169 | TITLE ESTs | | | gi = 7026494 | 1096012 |
| IC13087 | UG75 Expression | EST | Mm.87171 | TITLE ESTs | | | gi = 2402911 | 635170 |
| IC13088 | UG75 Expression | EST | Mm.87180 | TITLE ESTs | | | gi = 4723377 | 1149015 |
| IC13089 | UG75 Expression | EST | Mm.87185 | TITLE ESTs | | | gi = 4724836 | 1225027 |
| IC13090 | UG75 Expression | EST | Mm.87221 | TITLE ESTs | | | gi = 2116181 | 721878 |
| IC13091 | UG75 Expression | EST | Mm.87229 | TITLE ESTs | | | gi = 2520624 | 972791 |
| IC13092 | UG75 Expression | EST | Mm.87280 | TITLE ESTs | | | gi = 4863907 | 567488 |
| IC13093 | UG75 Expression | EST | Mm.87335 | TITLE ESTs | | | gi = 281416 | 750404 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC13094 | UG75 Expression | EST | Mm.87348 | TITLE ESTs, Moderately similar to DNAJ PROTEIN HOMOLOG 1 [Homo sapiens] | | | gi = 2811440 | 1225671 |
| IC13095 | UG75 Expression | EST | Mm.87363 | TITLE ESTs | | | gi = 1919251 | 777458 |
| IC13096 | UG75 Expression | EST | Mm.87370 | TITLE ESTs | | | gi = 2811631 | 1225326 |
| IC13097 | UG76 LID366 B cell | EST | Mm.87395 | TITLE ESTs | | | gi = 7157726 | 820807 |
| IC13098 | UG75 Expression | EST | Mm.87398 | TITLE ESTs, Weakly similar to leukemia/lymphoma related factor LR [M. musculus] | | | gi = 4605170 | 718226 |
| IC13099 | UG75 Expression | EST | Mm.87403 | TITLE ESTs, Weakly similar to KINESIN-LIKE PROTEIN KIF3B [M. musculus] | | | gi = 4600992 | 622823 |
| IC13100 | UG75 Expression | EST | Mm.87437 | TITLE ESTs | | | gi = 6749057 | 597489 |
| IC13101 | UG75 Expression | EST | Mm.87444 | TITLE ESTs, Weakly similar to cationic amino acid transporter 3 [H. sapiens] | | | gi = 155550 | 513868 |
| IC13102 | UG75 Expression | EST | Mm.87451 | TITLE ESTs | | | gi = 2962607 | 1265355 |
| IC13103 | UG75 Expression | EST | Mm.87456 | TITLE ESTs | | | gi = 1726496 | 583238 |
| IC13104 | UG75 Expression | EST | Mm.87457 | TITLE ESTs, Moderately similar to KIAA0373 [H. sapiens] | | | gi = 4571401 | 584770 |
| IC13105 | UG75 Expression | EST | Mm.87459 | TITLE ESTs, Weakly similar to protein phosphatase 1M chain M110 isoform [R. norvegicus] | | | gi = 1827417 | 718700 |
| IC13106 | UG75 Expression | EST | Mm.87463 | TITLE ESTs | | | gi = 4300503 | 576162 |
| IC13107 | UG75 Expression | EST | Mm.87464 | TITLE ESTs | | | gi = 2743629 | 1198153 |
| IC13108 | UG75 Expression | EST | Mm.87465 | TITLE ESTs | | | gi = 1841254 | 670499 |
| IC13109 | UG75 Expression | EST | Mm.87470 | TITLE ESTs | | | gi = 6519482 | 2649627 |
| IC13110 | UG75 Expression | EST | Mm.87483 | TITLE ESTs | | | gi = 2504657 | 934916 |
| IC13111 | UG75 Expression | EST | Mm.87495 | TITLE ESTs, Weakly similar to KIAA0797 protein [H. sapiens] | | | gi = 512613 | 1226696 |
| IC13112 | UG75 Expression | EST | Mm.87496 | TITLE ESTs | | | gi = 1675814 | 958535 |
| IC13113 | UG75 Expression | EST | Mm.87499 | TITLE ESTs | | | gi = 198665 | 642441 |
| IC13114 | UG75 Expression | EST | Mm.87501 | TITLE ESTs | | | gi = 6937459 | 2812301 |
| IC13115 | UG75 Expression | EST | Mm.87505 | TITLE ESTs | | | gi = 1671466 | 641059 |
| IC13116 | UG75 Expression | EST | Mm.87511 | TITLE ESTs | | | gi = 3296694 | 1749366 |
| IC13117 | UG75 Expression | EST | Mm.87525 | TITLE ESTs | | | gi = 1684576 | 641168 |
| IC13118 | UG75 Expression | EST | Mm.87544 | TITLE ESTs | | | gi = 4030031 | 1921906 |
| IC13119 | UG75 Expression | EST | Mm.87546 | TITLE ESTs | | | gi = 4766060 | 622407 |
| IC13120 | UG75 Expression | EST | Mm.87550 | TITLE ESTs | | | gi = 329612 | 1328304 |
| IC13121 | UG75 Expression | EST | Mm.87563 | TITLE ESTs | | | gi = 4601817 | 634891 |
| IC13122 | UG75 Expression | EST | Mm.87570 | TITLE ESTs | | | gi = 4967557 | 634572 |
| IC13123 | UG75 Expression | EST | Mm.87585 | TITLE ESTs, Weakly similar to Lph17p [S. cerevisiae] | | | gi = 1841240 | 658724 |
| IC13124 | UG75 Expression | EST | Mm.87594 | TITLE ESTs, Weakly similar to checkpoint suppressor 1 [H. sapiens] | | | gi = 3374327 | 1198188 |
| IC13125 | UG75 Expression | EST | Mm.87616 | TITLE ESTs | | | gi = 1677009 | 719137 |
| IC13126 | UG75 Expression | EST | Mm.87617 | ISOMERASE-RELATED PROTEIN PRECURSOR [H. sapiens] | | | gi = 2518067 | 972693 |
| IC13127 | UG75 Expression | EST | Mm.87619 | TITLE DNA segment, Chr 17, Wayne State University 76, expressed | GENE D17Wsu76e | | | 721043 |
| IC13128 | UG75 Expression | EST | Mm.87628 | TITLE ESTs | | | gi = 6332879 | 751403 |
| IC13129 | UG75 Expression | EST | Mm.87623 | TITLE ESTs | | | gi = 1701670 | 577575 |
| IC13130 | UG75 Expression | EST | Mm.87634 | TITLE ESTs | | | gi = 4726206 | 636752 |
| IC13131 | UG75 Expression | EST | Mm.87639 | TITLE ESTs | | | gi = 4537240 | 973220 |
| IC13132 | UG75 Expression | EST | Mm.87650 | TITLE ESTs | | | gi = 4407695 | 619642 |
| IC13133 | UG75 Expression | EST | Mm.87657 | TITLE ESTs | | | gi = 678156 | 749941 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC13134 | UG75 Expression | EST | Mm.8766 | TETRAHYDROFOLATE SYNTHASE, CYTOPLASMIC [R. norvegicus] | | | gi = 3124288 | 722264 |
| IC13135 | UG75 Expression | EST | Mm.87660 | TITLE ESTs | | | gi = 4968426 | 640917 |
| IC13136 | UG75 Expression | EST | Mm.87666 | TITLE ESTs | | | gi = 2861368 | 1294700 |
| IC13137 | UG75 Expression | EST | Mm.87672 | TITLE ESTs | | | gi = 1937231 | 749402 |
| IC13138 | UG75 Expression | EST | Mm.87676 | TITLE ESTs, Weakly similar to Abnorman X segregation [D. melanogaster] | | | gi = 425954 | 1429845 |
| IC13139 | UG75 Expression | EST | Mm.87687 | TITLE ESTs | | | gi = 3883824 | 721308 |
| IC13140 | UG75 Expression | EST | Mm.87697 | TITLE ESTs | | | gi = 293310 | 617300 |
| IC13141 | UG75 Expression | EST | Mm.87700 | TITLE ESTs | | | gi = 1767898 | 622736 |
| IC13142 | UG75 Expression | EST | Mm.87705 | TITLE ESTs | | | gi = 262903 | 1002465 |
| IC13143 | UG75 Expression | EST | Mm.87721 | TITLE ESTs | | | gi = 4783065 | 640711 |
| IC13144 | UG75 Expression | EST | Mm.87725 | TITLE ESTs | | | gi = 1286614 | 557633 |
| IC13145 | UG75 Expression | EST | Mm.87727 | TITLE ESTs | | | gi = 6179177 | 1005941 |
| IC13146 | UG75 Expression | EST | Mm.87732 | TITLE ESTs | | | gi = 1656619 | 622772 |
| IC13147 | UG75 Expression | EST | Mm.87735 | TITLE ESTs, Moderately similar to HYPOTHETICAL MYELOID CELL LINE PROTEIN 3 [Home sapiens] | | | gi = 4601808 | 1193651 |
| IC13148 | UG75 Expression | EST | Mm.87736 | TITLE ESTs | | | gi = 1793338 | 640149 |
| IC13149 | UG75 Expression | EST | Mm.87739 | TITLE ESTs, Moderately similar to G protein-coupled receptor kinase 4 [M. musculus] | | | gi = 1662085 | 572876 |
| IC13150 | UG75 Expression | EST | Mm.87740 | TITLE ESTs, Weakly similar to FLI-LRR associated protein-1 [M. musculus] | | | gi = 1662258 | 1366960 |
| IC13151 | UG75 Expression | EST | Mm.87743 | TITLE ESTs | | | gi = 1663115 | 574268 |
| IC13152 | UG75 Expression | EST | Mm.87744 | TITLE ESTs | | | gi = 651572 | 622827 |
| IC13153 | UG75 Expression | EST | Mm.87745 | TITLE ESTs | | | gi = 1671488 | 577054 |
| IC13154 | UG75 Expression | EST | Mm.87747 | TITLE ESTs | | | gi = 4703173 | 616762 |
| IC13155 | UG75 Expression | EST | Mm.87832 | TITLE tumor necrosis factor receptor superfamily, member 10b | GENE Tnfrsf10I | Killer/Dr5|Ly98|MK|Trail Receptor| | gi = 3682747 | 1345564 |
| IC13156 | UG75 Expression | EST | Mm.87951 | TITLE ESTs | | | gi = 2520755 | 621489 |
| IC13157 | UG75 Expression | EST | Mm.88143 | TITLE ESTs | | | gi = 1793221 | 551214 |
| IC13158 | UG75 Expression | EST | Mm.88182 | TITLE solute carrier family 31, member 1 | GENE SIC31a1 | | gi = 3748178 | 642466 |
| IC13159 | UG75 Expression | EST | Mm.88257 | TITLE ESTs | | | gi = 4600870 | 621662 |
| IC13160 | 00/04/26 UG#76 17Lid Expansion | EST | Mm.88265 | testis expressed gene 10 | Tex10 | Tctex-10| | gi = 7201491 | 894573 |
| IC13161 | UG75 Expression | EST | Mm.88314 | TITLE ESTs | | | gi = 4624807 | 973181 |
| IC13162 | UG75 Expression | EST | Mm.88334 | TITLE ESTs | | | gi = 2523353 | 637138 |
| IC13163 | UG75 Expression | EST | Mm.88364 | TITLE tankyrase, TRF1-interacting ankyrin-related ADP-ribose polymerase | GENE Tnks | | gi = 1677371 | 576196 |
| IC13164 | UG75 Expression | EST | Mm.88375 | TITLE expressed sequence tag mouse EST 25 | GENE ESTM25 | | gi = 2860451 | 637500 |
| IC13165 | UG75 Expression | EST | Mm.88389 | TITLE ESTs | | | gi = 4316662 | 751110 |
| IC13166 | UG75 Expression | EST | Mm.88401 | TITLE heparanase | GENE Hpa | endoglycosidase heparanase| | gi = 1527623 | 620141 |
| IC13167 | UG75 Expression | EST | Mm.88433 | TITLE ESTs | | | gi = 4601173 | 598401 |
| IC13168 | UG75 Expression | EST | Mm.88480 | TITLE ESTs | | | gi = 4606309 | 635093 |
| IC13169 | UG75 Expression | EST | Mm.88485 | TITLE retinitis pigmentosa 2 homolog | GENE Rp2h | | gi = 4601588 | 1295265 |
| IC13170 | UG75 Expression | EST | Mm.88548 | TITLE ESTs | | | gi = 4444871 | 582967 |
| IC13171 | UG75 Expression | EST | Mm.88572 | TITLE synaptojanin 2 binding protein | GENE Synj2bp-GENE | OMP25| | gi = 479667 | 1148813 |
| IC13172 | UG75 Expression | EST | Mm.88573 | TITLE ESTM671070 (Roswell Park) | ESTM671070 | | gi = 4967928 | 596501 |
| IC13173 | UG75 Expression | EST | Mm.88597 | TITLE ESTs | | | gi = 2518723 | 1749992 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC13174 | UG75 Expression | EST | Mm.886 | TITLE ESTs | | | gi = 3299382 | 1379066 |
| IC13175 | UG75 Expression | EST | Mm.88641 | TITLE ESTs, Weakly similar to proline-rich protein MP4 [M. musculus] | | | gi = 1793326 | 718138 |
| IC13176 | UG75 Expression | EST | Mm.88656 | TITLE ESTs | | | gi = 460443 | 596549 |
| IC13177 | UG75 Expression | EST | Mm.88682 | TITLE ESTs | | | gi = 1751465 | 619289 |
| IC13178 | UG75 Expression | EST | Mm.88705 | TITLE transcript expressed during hematopoieses 2 | GENE Tedp2-p | F3-2] | gi = 4625079 | 581802 |
| IC13179 | UG75 Expression | EST | Mm.88724 | TITLE heat shock 70 kDa protein 4 | GENE Hspa4 | Hsp70RY] | gi = 1672969 | 1020794 |
| IC13180 | UG75 Expression | EST | Mm.88727 | TITLE ESTs | | | gi = 3681887 | 1329201 |
| IC13181 | UG75 Expression | EST | Mm.88747 | cyclin-dependent kinase 6 | Cdk6 | | gi = 440552 | 760909 |
| IC13182 | UG75 Expression | EST | Mm.88793 | TITLE gamma-fibrinogen | GENE Fgg | | gi = 1282680 | 642982 |
| IC13183 | UG75 Expression | EST | Mm.89031 | TITLE ESTs | | | gi = 1772226 | 637875 |
| IC13184 | UG75 Expression | EST | Mm.89037 | TITLE ESTs, Weakly similar to TYROSINE-PROTEIN KINASE JAK3 [M. musculus] | | CDC2-related kinase 2[Crk2] | gi = 2516395 | 1148527 |
| IC13185 | UG75 Expression | EST | Mm.89108 | TITLE ESTs | | | gi = 1767592 | 621831 |
| IC13186 | UG75 Expression | EST | Mm.89181 | TITLE ESTs | | | gi = 768581 | 750695 |
| IC13187 | 00/02 Literature | EST | Mm.89188 | nuclear factor of kappa light polypeptide gene enhancer in B-cells 2, p49/p100 | Nfkb2 | | gi = 1538392 | 352633 |
| IC13188 | UG75 Expression | EST | Mm.87208 | TITLE immune associated nucleotide 3 | GENE Ian3 | | gi = 2644273 | 639935 |
| IC13189 | UG75 Expression | EST | Mm.87210 | TITLE ESTs | | | gi = 305441 | 1020816 |
| IC13190 | UG75 Expression | EST | Mm.89313 | TITLE ESTs | | | gi = 3518906 | 636723 |
| IC13191 | UG76 LID366 B cell | EST | Mm.89316 | TITLE ESTs, Weakly similar to LARGE PROLINE-RICH PROTEIN BAT2 [Homo sapiens] | | | gi = 7157746 | 423624 |
| IC13192 | UG75 Expression | EST | Mm.89319 | TITLE ESTs | | | gi = 2049026 | 597935 |
| IC13193 | UG75 Expression | EST | Mm.89394 | TITLE ESTs | | | gi = 6557465 | 2654304 |
| IC13194 | UG75 Expression | EST | Mm.89414 | TITLE ESTs | | | gi = 4318876 | 720766 |
| IC13195 | UG75 Expression | EST | Mm.89417 | TITLE ESTs | | | gi = 1919289 | 777484 |
| IC13196 | UG75 Expression | EST | Mm.89548 | TITLE ESTs | | | gi = 1909792 | 1395407 |
| IC13197 | UG75 Expression | EST | Mm.89568 | TITLE ESTs, Weakly similar to female sterile homeotic-related protein Frg-1 [M. musculus] | | | gi = 168162 | 595890 |
| IC13198 | UG75 Expression | EST | Mm.89570 | TITLE ESTs | | | gi = 6633372 | 642307 |
| IC13199 | UG75 Expression | EST | Mm.89572 | TITLE ESTs, Moderately similar to CGI-83 protein [H. sapiens] | | | gi = 3732746 | 534213 |
| IC13200 | UG75 Expression | EST | Mm.89574 | TITLE ESTs, Moderately similar to BRCA1-associated protein 2 [H. sapiens] | | | gi = 1675981 | 574797 |
| IC13201 | UG75 Expression | EST | Mm.89584 | TITLE ESTs, Weakly similar to Similar to S. cerevisiae YD9335.03c protein [H. sapiens] | | | gi = 6757842 | 1446584 |
| IC13202 | UG75 Expression | EST | Mm.89618 | TITLE ESTs | | | gi = 1862670 | 638872 |
| IC13203 | UG75 Expression | EST | Mm.89620 | TITLE ESTs | | | gi = 4723870 | 575508 |
| IC13204 | UG75 Expression | EST | Mm.89634 | TITLE ESTs | | | gi = 6518638 | 764195 |
| IC13205 | UG75 Expression | EST | Mm.89695 | TITLE ESTs | | | gi = 1795745 | 1279178 |
| IC13206 | UG75 Expression | EST | Mm.89697 | TITLE ESTs | | | gi = 1756032 | 617576 |
| IC13207 | UG75 Expression | EST | Mm.89698 | TITLE ESTs | | | gi = 3054125 | 597535 |
| IC13208 | UG75 Expression | EST | Mm.89701 | TITLE ESTs | | | gi = 614375 | 973425 |
| IC13209 | UG75 Expression | EST | Mm.89702 | TITLE ESTs | | | gi = 1801035 | 617193 |
| IC13210 | UG75 Expression | EST | Mm.89722 | TITLE ESTs | | | gi = 2412203 | 1002621 |
| IC13211 | UG75 Expression | EST | Mm.89797 | TITLE ESTs | | | gi = 6521167 | 1148915 |
| IC13212 | UG75 Expression | EST | Mm.89818 | TITLE ESTs | | | gi = 1807680 | 644969 |
| IC13213 | UG75 Expression | EST | Mm.89820 | TITLE ESTs | | | gi = 3518166 | 751171 |
| IC13214 | UG75 Expression | EST | Mm.89821 | TITLE ESTs | | | gi = 7187422 | 764803 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC13215 | UG75 Expression | EST | Mm.89822 | TITLE ESTs | | | gi = 4782926 | 750501 |
| IC13216 | UG75 Expression | EST | Mm.89830 | TITLE ESTs | | | gi = 4613769 | 1361250 |
| IC13217 | UG75 Expression | EST | Mm.89832 | TITLE ESTs, Weakly similar to alternatively spliced [M. musculus] | | | gi = 291894 | 1225414 |
| IC13218 | UG75 Expression | EST | Mm.89847 | TITLE ESTs | | | gi = 1888638 | 617265 |
| IC13219 | UG75 Expression | EST | Mm.89849 | TITLE ESTs | | | gi = 2721701 | 1279173 |
| IC13220 | UG75 Expression | EST | Mm.89851 | TITLE ESTs, Moderately similar to P120 PROTEIN [Mus musculus] | | | gi = 4030939 | 1293693 |
| IC13221 | UG75 Expression | EST | Mm.89858 | TITLE ESTs | | | gi = 6085496 | 1296020 |
| IC13222 | UG75 Expression | EST | Mm.89860 | TITLE ESTs | | | gi = 430614 | 1361891 |
| IC13223 | UG75 Expression | EST | Mm.89873 | TITLE ESTs, Moderately similar to Stra13 [M. musculus] | | | gi = 3235892 | 1395140 |
| IC13224 | UG75 Expression | EST | Mm.89899 | TITLE ESTs | | | gi = 2256745 | 894219 |
| IC13225 | UG75 Expression | EST | Mm.899 | TITLE ESTs | | | gi = 1726423 | 634681 |
| IC13226 | UG75 Expression | EST | Mm.89903 | TITLE ESTs, Weakly similar to plenty-of-prolines-101 [M. musculus] | | | gi = 538259 | 1295636 |
| IC13227 | UG75 Expression | EST | Mm.89906 | TITLE ESTs | | | gi = 1932490 | 637428 |
| IC13228 | UG75 Expression | EST | Mm.89914 | TITLE ESTs | | | gi = 1672660 | 574495 |
| IC13229 | UG75 Expression | EST | Mm.89923 | TITLE ESTs | | | gi = 1814544 | 621386 |
| IC13231 | UG75 Expression | EST | Mm.90017 | TITLE ESTs, Weakly similar to /prediction | | | gi = 4603279 | 974034 |
| IC13232 | UG75 Expression | EST | Mm.90019 | TITLE ESTs | | | gi = 1727128 | 634987 |
| IC13233 | UG75 Expression | EST | Mm.90021 | TITLE ESTs | | | gi = 1903543 | 598697 |
| IC13234 | UG75 Expression | EST | Mm.90022 | TITLE ESTs | | | gi = 1748747 | 617229 |
| IC13235 | UG75 Expression | EST | Mm.90023 | TITLE ESTs | | | gi = 174904 | 616723 |
| IC13236 | UG75 Expression | EST | Mm.90025 | TITLE ESTs | | | gi = 400989 | 622779 |
| IC13237 | UG75 Expression | EST | Mm.90026 | TITLE ESTs | | | gi = 4615043 | 641527 |
| IC13238 | UG75 Expression | EST | Mm.90032 | TITLE ESTs, Weakly similar to contraspin [M. musculus] | | | gi = 2461842 | 719495 |
| IC13239 | UG75 Expression | EST | Mm.90033 | TITLE ESTs | | | gi = 4804766 | 718546 |
| IC13240 | UG75 Expression | EST | Mm.90035 | TITLE EST | | | gi = 1919287 | 777480 |
| IC13241 | UG75 Expression | EST | Mm.90036 | TITLE ESTs | | | gi = 1934493 | 750690 |
| IC13242 | UG75 Expression | EST | Mm.90037 | TITLE EST | | | gi = 1936136 | 752161 |
| IC13243 | UG75 Expression | EST | Mm.90043 | TITLE ESTs | | | gi = 2292479 | 576666 |
| IC13244 | UG75 Expression | EST | Mm.90049 | TITLE ESTs | | | gi = 2412179 | 1002550 |
| IC13245 | UG75 Expression | EST | Mm.90050 | TITLE EST | | | gi = 2894053 | 1296042 |
| IC13246 | UG75 Expression | EST | Mm.90052 | TITLE ESTs | | | gi = 2291754 | 623078 |
| IC13247 | UG75 Expression | EST | Mm.90063 | TITLE ESTs | | | gi = 4601682 | 1148933 |
| IC13248 | UG75 Expression | EST | Mm.90064 | TITLE ESTs | | | gi = 4572203 | 1149119 |
| IC13249 | UG75 Expression | EST | Mm.90068 | TITLE ESTs | | | gi = 2691151 | 582977 |
| IC13250 | UG75 Expression | EST | Mm.90071 | TITLE ESTs | | | gi = 1918936 | 1395431 |
| IC13251 | UG75 Expression | EST | Mm.90079 | TITLE ESTs | | | gi = 4402651 | 972734 |
| IC13252 | UG75 Expression | EST | Mm.90084 | TITLE ESTs | | | gi = 1902734 | 718543 |
| IC13253 | UG75 Expression | EST | Mm.90087 | TITLE ESTs, Weakly similar to EOSINOPHIL CATIONIC PROTEIN PRECURSOR P) [Gorilla gorilla gorilla] | | | gi = 1554796 | 1225262 |
| IC13254 | UG75 Expression | EST | Mm.90112 | TITLE ESTs | | | gi = 419759 | 534373 |
| IC13255 | UG75 Expression | EST | Mm.90114 | TITLE ESTs | | | gi = 2049986 | 777219 |
| IC13256 | UG75 Expression | EST | Mm.90118 | TITLE ESTs | | | gi = 2811474 | 1225262 |
| IC13257 | UG75 Expression | EST | Mm.90158 | TITLE EST | | | gi = 4300307 | 576002 |
| IC13258 | UG75 Expression | EST | Mm.90159 | TITLE EST | | | gi = 4300426 | 576080 |
| IC13259 | UG75 Expression | EST | Mm.90160 | TITLE ESTs | | | gi = 885636 | 617322 |
| IC13260 | UG75 Expression | EST | Mm.90161 | TITLE EST | | | gi = 4304709 | 575383 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC13260 | UG75 Expression | EST | Mm.90162 | TITLE EST | | | gi = 4306657 | 598408 |
| IC13261 | UG75 Expression | EST | Mm.90163 | TITLE EST | | | gi = 4307768 | 597605 |
| IC13262 | UG75 Expression | EST | Mm.90164 | TITLE EST | | | gi = 4307817 | 597647 |
| IC13263 | UG75 Expression | EST | Mm.90165 | TITLE EST | | | gi = 430759 | 597696 |
| IC13264 | UG75 Expression | EST | Mm.90167 | TITLE EST | | | gi = 4287609 | 618999 |
| IC13265 | UG75 Expression | EST | Mm.90168 | TITLE EST | | | gi = 4288443 | 619640 |
| IC13266 | UG75 Expression | EST | Mm.90172 | TITLE ESTs, Moderately similar to ZINC FINGER PROTEIN ZFP-36 [Homo sapiens] | | | gi = 4297842 | 583748 |
| IC13267 | UG75 Expression | EST | Mm.90173 | TITLE EST | | | gi = 4299457 | 617902 |
| IC13268 | UG75 Expression | EST | Mm.90174 | TITLE EST | | | gi = 4300913 | 620916 |
| IC13269 | UG75 Expression | EST | Mm.90175 | TITLE ESTs | | | gi = 1758736 | 621161 |
| IC13270 | UG75 Expression | EST | Mm.90176 | TITLE EST | | | gi = 4304048 | 641841 |
| IC13271 | UG75 Expression | EST | Mm.90179 | TITLE ESTs | | | gi = 1917268 | 764415 |
| IC13272 | UG75 Expression | EST | Mm.90200 | TITLE ESTs | | | gi = 4407660 | 751739 |
| IC13273 | UG75 Expression | EST | Mm.90202 | TITLE EST | | | gi = 4482234 | 1262880 |
| IC13274 | UG75 Expression | EST | Mm.90203 | TITLE EST | | | gi = 4482659 | 1263366 |
| IC13275 | UG75 Expression | EST | Mm.90204 | TITLE EST | | | gi = 4482733 | 1264251 |
| IC13276 | UG75 Expression | EST | Mm.90205 | TITLE EST | | | gi = 4482797 | 1264643 |
| IC13277 | UG75 Expression | EST | Mm.90206 | TITLE EST | | | gi = 442861 | 1264994 |
| IC13278 | UG75 Expression | EST | Mm.90209 | TITLE EST | | | gi = 4484913 | 1265408 |
| IC13279 | UG75 Expression | EST | Mm.90213 | TITLE EST | | | gi = 452101 | 1293979 |
| IC13280 | UG75 Expression | EST | Mm.90216 | TITLE ESTs | | | gi = 1681631 | 595915 |
| IC13281 | UG75 Expression | EST | Mm.90224 | TITLE ESTs | | | gi = 4615115 | 642020 |
| IC13282 | UG75 Expression | EST | Mm.90229 | TITLE ESTs | | | gi = 4617326 | 722927 |
| IC13283 | UG75 Expression | EST | Mm.90233 | TITLE EST | | | gi = 4764855 | 722807 |
| IC13284 | UG75 Expression | EST | Mm.90234 | TITLE ESTs | | | gi = 467319 | 722897 |
| IC13285 | UG75 Expression | EST | Mm.90238 | TITLE ESTs | | | gi = 1937403 | 749107 |
| IC13286 | UG75 Expression | EST | Mm.90239 | TITLE EST | | | gi = 4765262 | 749286 |
| IC13287 | UG75 Expression | EST | Mm.90241 | TITLE ESTs | | | gi = 4315552 | 718040 |
| IC13288 | UG75 Expression | EST | Mm.90243 | TITLE ESTs | | | gi = 2041941 | 749970 |
| IC13289 | UG75 Expression | EST | Mm.90244 | TITLE EST | | | gi = 4766411 | 750159 |
| IC13290 | UG75 Expression | EST | Mm.90245 | TITLE ESTs | | | gi = 1794511 | 639608 |
| IC13291 | UG75 Expression | EST | Mm.90289 | TITLE ESTs | | | gi = 3235687 | 1446401 |
| IC13292 | UG75 Expression | EST | Mm.90292 | TITLE ESTs, Weakly similar to putative CAMP protein [M. musculus] | | | gi = 2990889 | 617787 |
| IC13293 | UG75 Expression | EST | Mm.90353 | TITLE ESTs, Moderately similar to protein URF6 [M. musculus] | | | gi = 2861213 | 1294595 |
| IC13294 | UG75 Expression | EST | Mm.90376 | TITLE ESTs | GENE EST573322 | | gi = 4615755 | 764404 |
| IC13295 | UG75 Expression | EST | Mm.90384 | TITLE DNA segment, EST 573322 | GENE D14Ucla3 | | gi = 1676209 | 573322 |
| IC13296 | UG75 Expression | EST | Mm.90409 | TITLE DNA segment, Chr 14, University of California at Los Angeles 3 | | | gi = 4721929 | 749435 |
| IC13297 | UG75 Expression | EST | Mm.90410 | TITLE dim1 (S. pombe) | GENE Dim1-pe dim1 | (S. pombe)|U5-15kD] | gi = 5549937 | 620056 |
| IC13298 | UG75 Expression | EST | Mm.90422 | TITLE ESTs | | | gi = 4296255 | 640618 |
| IC13299 | UG75 Expression | EST | Mm.90438 | TITLE ESTs, Weakly similar to NEDD-4 PROTEIN [M. musculus] | | | gi = 4600880 | 621710 |
| IC13300 | UG75 Expression | EST | Mm.90439 | TITLE ESTs | | | gi = 4601203 | 598611 |
| IC13301 | UG75 Expression | EST | Mm.90447 | TITLE ESTs | | | gi = 4625076 | 581743 |
| IC13302 | UG75 Expression | EST | Mm.90449 | TITLE ESTs | | | gi = 4721929 | 1225217 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC13303 | UG75 Expression | EST | Mm.90452 | TITLE ESTs | | | gi = 1725828 | 582048 |
| IC13304 | UG75 Expression | EST | Mm.90456 | TITLE ESTs, Moderately similar to synapsin IIb [*M. musculus*] | | | gi = 4724406 | 639128 |
| IC13305 | UG75 Expression | EST | Mm.90457 | TITLE EST | | | gi = 4724835 | 1225017 |
| IC13306 | UG75 Expression | EST | Mm.90458 | TITLE ESTs | | | gi = 277555 | 1226064 |
| IC13307 | UG75 Expression | EST | Mm.90459 | TITLE ESTs | | | gi = 4294932 | 636619 |
| IC13308 | UG75 Expression | EST | Mm.90460 | TITLE ESTs | | | gi = 725130 | 637364 |
| IC13309 | UG75 Expression | EST | Mm.90526 | TITLE ESTs | | | gi = 5336682 | 1001642 |
| IC13310 | UG75 Expression | EST | Mm.90542 | TITLE ESTs | | | gi = 1897305 | 596085 |
| IC13311 | UG75 Expression | EST | Mm.9129 | TITLE ESTs | | | gi = 4485955 | 750564 |
| IC13312 | UG75 Expression | EST | Mm.91405 | TITLE ESTs | | | gi = 939059 | 750567 |
| IC13313 | UG75 Expression | EST | Mm.91717 | TITLE ESTs | | | gi = 3297340 | 1380114 |
| IC13314 | UG75 Expression | EST | Mm.9210 | TITLE EST | | | gi = 6076958 | 2225540 |
| IC13315 | UG75 Expression | EST | Mm.922 | TITLE ESTs | | | gi = 1727013 | 634672 |
| IC13316 | UG75 Expression | EST | Mm.9239 | TITLE ESTs | | | gi = 4374895 | 1314904 |
| IC13317 | UG75 Expression | EST | Mm.92529 | TITLE ESTs | | | gi = 2256557 | 720688 |
| IC13318 | UG75 Expression | EST | Mm.9257 | TITLE DNA segment, Chr 10, Wayne State University 52, expressed | GENE D10Wsu52e | | | 1149725 |
| IC13319 | UG75 Expression | EST | Mm.92871 | TITLE DNA segment, Chr 17, Wayne State University 15, expressed | GENE D17Wsu15e | | | 582853 |
| IC13320 | UG75 Expression | EST | Mm.93266 | TITLE ESTs | | | gi = 1738196 | 598546 |
| IC13321 | UG75 Expression | EST | Mm.9348 | TITLE ESTs | | | gi = 2262287 | 1293684 |
| IC13322 | UG75 Expression | EST | Mm.93774 | TITLE DNA segment, Chr 9, Wayne State University 168, expressed | GENE D9Wse168e | | | 622390 |
| IC13323 | UG75 Expression | EST | Mm.939 | TITLE ESTs | | | gi = 4729572 | 598288 |
| IC13324 | UG75 Expression | EST | Mm.943 | TITLE ESTs | | | gi = 4601795 | 634717 |
| IC13325 | UG75 Expression | EST | Mm.94515 | TITLE ESTs | | | gi = 2411988 | 1002353 |
| IC13326 | UG75 Expression | EST | Mm.94980 | TITLE ESTs | | | gi = 4299731 | 618220 |
| IC13327 | UG75 Expression | EST | Mm.95068 | TITLE ESTs, Moderately similar to NADH-UBIQUINONE OXIDOREDUCTASE CHAIN 2 [*Mus musculus*] | | | gi = 533744 | 973827 |
| IC13328 | UG75 Expression | EST | Mm.95141 | TITLE ESTs | | | gi = 6646230 | 1330113 |
| IC13329 | UG75 Expression | EST | Mm.95270 | TITLE ESTs [*R. norvegicus*] | | | gi = 1282661 | 749283 |
| IC13330 | UG75 Expression | EST | Mm.954 | TITLE ESTs | | | gi = 2518915 | 973911 |
| IC13331 | UG75 Expression | EST | Mm.9559 | TITLE ESTs | | | gi = 1682816 | 718010 |
| IC13332 | UG75 Expression | EST | Mm.9563 | TITLE ESTs | | | gi = 2917061 | 777661 |
| IC13333 | UG75 Expression | EST | Mm.9616 | TITLE ESTs | | | gi = 2917797 | 534037 |
| IC13334 | UG75 Expression | EST | Mm.9621 | TITLE ESTs | | | gi = 4782953 | 573302 |
| IC13335 | UG75 Expression | EST | Mm.9650 | TITLE ESTs | | | gi = 3371816 | 620938 |
| IC13336 | UG75 Expression | EST | Mm.967 | TITLE ESTs | | | gi = 1738176 | 1149229 |
| IC13337 | UG75 Expression | EST | Mm.9671 | TITLE ESTs | | | gi = 2284346 | 777738 |
| IC13338 | UG75 Expression | EST | Mm.96748 | TITLE ESTs | | | gi = 4275705 | 1428892 |
| IC13339 | UG75 Expression | EST | Mm.96828 | TITLE ESTs | | | gi = 175936 | 621017 |
| IC13340 | UG75 Expression | EST | Mm.96867 | TITLE ESTs | | | gi = 3926378 | 596967 |
| IC13341 | UG75 Expression | EST | Mm.969 | TITLE ESTs | | | gi = 1795768 | 638286 |
| IC13342 | UG75 Expression | EST | Mm.9693 | TITLE ESTs | | | gi = 2918712 | 641490 |
| IC13343 | UG75 Expression | EST | Mm.9718 | TITLE ESTs, Moderately similar to hypothetical protein [*H. sapiens*] | | | gi = 2962183 | 777627 |
| IC13344 | UG75 Expression | EST | Mm.9723 | TITLE ESTs | | | gi = 2919070 | 749350 |
| IC13345 | UG75 Expression | EST | Mm.97514 | TITLE ESTs | | | gi = 1748757 | 617849 |

TABLE 1-continued

| IC ID | IC Selection method | Module | UniGene | UniGene/LocusLink Title | Gene Symbol | Alias | Selected Reference | IMAGE |
|---|---|---|---|---|---|---|---|---|
| IC13346 | UG75 Expression | EST | Mm.97694 | TITLE ESTs | | | gi = 3733807 | 1429022 |
| IC13347 | UG75 Expression | EST | Mm.97727 | TITLE ESTs, Moderately similar to protein CO1 [*M. musculus*] | | | gi = 3747304 | 1148992 |
| IC13348 | UG75 Expression | EST | Mm.97794 | TITLE DNA segment, Chr 4, Wayne State University 53, expressed | GENE D4Wsu53e | | | 1002457 |
| IC13349 | UG75 Expression | EST | Mm.9806 | TITLE ESTs | | | gi = 5549663 | 1243842 |
| IC13350 | UG75 Expression | EST | Mm.98071 | TITLE ESTs | | | gi = 4283014 | 573917 |
| IC13351 | UG75 Expression | EST | Mm.98082 | TITLE ESTs | | | gi = 4301758 | 621571 |
| IC13352 | UG75 Expression | EST | Mm.981 | TITLE ESTs | | | gi = 3981441 | 598799 |
| IC13353 | UG75 Expression | EST | Mm.9811 | TITLE ESTs | | | gi = 1289023 | 1295093 |
| IC13354 | UG75 Expression | EST | Mm.9819 | TITLE ESTs | | | gi = 4290319 | 718975 |
| IC13355 | UG75 Expression | EST | Mm.98232 | TITLE ESTs | | | gi = 2042996 | 638307 |
| IC13356 | UG75 Expression | EST | Mm.98244 | TITLE ESTs | | | gi = 4307468 | 597263 |
| IC13357 | UG75 Expression | EST | Mm.9828 | TITLE ESTs | | | gi = 3394711 | 595883 |
| IC13358 | UG75 Expression | EST | Mm.9840 | TITLE ESTs | | | gi = 2918338 | 596656 |
| IC13359 | UG75 Expression | EST | Mm.9852 | TITLE ESTs, Moderately similar to Apg12 [*H. sapiens*] | | | gi = 6085216 | 1149922 |
| IC13360 | UG75 Expression | EST | Mm.9854 | TITLE ESTs | | | gi = 1902442 | 637818 |
| IC13361 | UG75 Expression | EST | Mm.9856 | TITLE ESTs | | | gi = 2918913 | 638372 |
| IC13362 | UG75 Expression | EST | Mm.9859 | TITLE ESTs, Moderately similar to LDLC PROTEIN [*H. sapiens*] | | | gi = 4605222 | 1226935 |
| IC13363 | UG75 Expression | EST | Mm.9860 | TITLE ESTs | | | gi = 6078318 | 1002191 |
| IC13364 | UG75 Expression | EST | Mm.9864 | TITLE ESTs, Weakly similar to ORF YNL091w [*S. cerevisiae*] | | | gi = 2039573 | 761169 |
| IC13365 | UG75 Expression | EST | Mm.9868 | TITLE ESTs, Weakly similar to BONE MARROW STROMAL ANTIGEN 2 [*H. sapiens*] | | | gi = 2918997 | 764061 |
| IC13366 | UG75 Expression | EST | Mm.9870 | TITLE ESTs | | | gi = 2919831 | 1002404 |
| IC13367 | UG75 Expression | EST | Mm.98914 | TITLE ESTs | | | gi = 162645 | 573667 |
| IC13368 | UG75 Expression | EST | Mm.9893 | TITLE ESTs | | | gi = 2516653 | 617749 |
| IC13369 | UG75 Expression | EST | Mm.9908 | TITLE ESTs | | | gi = 2756163 | 619276 |
| IC13370 | UG75 Expression | EST | Mm.9913 | TITLE ESTs | | | gi = 3393878 | 621259 |
| IC13371 | UG75 Expression | EST | Mm.9916 | TITLE ESTs | | | gi = 2917382 | 1226843 |
| IC13372 | UG75 Expression | EST | Mm.9934 | TITLE ESTs | | | gi = 2917301 | 1344336 |
| IC13373 | UG75 Expression | EST | Mm.9953 | TITLE ESTs | | | gi = 3215282 | 1264868 |
| IC13374 | UG75 Expression | EST | Mm.99535 | TITLE ESTs | | | gi = 5549315 | 577029 |
| IC13375 | UG75 Expression | EST | Mm.9954 | TITLE ESTs | | | gi = 1677317 | 576574 |
| IC13376 | UG75 Expression | EST | Mm.9957 | TITLE ESTs | | | gi = 2990667 | 1264466 |
| IC13377 | UG75 Expression | EST | Mm.9984 | TITLE ESTs | | | gi = 1862908 | 1328672 |
| IC13378 | UG75 Expression | EST | Mm.99942 | TITLE ESTs, Moderately similar to G protein-coupled receptor kinase-associated ADP ribosylation factor GTPase-activating protein [*R. norvegicus*] | | | gi = 299080 | 1361222 |
| IC13379 | UG75 Expression | EST | Mm.99962 | TITLE ESTs | | | gi = 295068 | 1263561 |
| IC13380 | UG75 Expression | EST | Mm.99968 | TITLE ESTs | | | gi = 1662011 | 1281322 |
| IC13381 | UG75 Expression | EST | Mm.9997 | TITLE ESTs | | | gi = 3099673 | 1345213 |
| IC13382 | UG75 Expression | EST | Mm.99970 | TITLE ESTs | | | gi = 1660539 | 575299 |
| IC13383 | UG75 Expression | EST | Mm.99978 | TITLE ESTs | | | gi = 180012 | 1312420 |
| IC13384 | UG75 Expression | EST | Mm.99994 | TITLE ESTs | | | gi = 6758423 | 972845 |
| IC13385 | UG75 Expression | EST | Mm.99998 | TITLE ESTs | | | gi = 3375175 | 764345 |

I claim:

1. A composition comprising an array of cDNA probes immobilized on a solid support, said array comprising at least 10 probes selected from SEQ ID NOS: 1–29, wherein at least one of the probes is SEQ ID NO: 1.

2. A composition comprising an array of cDNA probes immobilized on a solid support, said array comprising at least 20 probes selected from SEQ ID NOS: 1–29, wherein at least one of the probes is SEQ ID NO: 1.

3. The array of claim 1, wherein said probes are oligodeoxynucleotides.

4. The array of claim 1, wherein said probes are oligodeoxyribonucleotides.

5. The array of claim 1, wherein said array has between 1,000 and 50,000 probes.

6. The array of claim 1, wherein said array has between 2,000 and 20,000 probes.

7. The array of claim 1, wherein said array has between 5,000 and 15,000 probes.

8. The array of claim 1, wherein said solid support is selected from a group comprising glass, plastic and metal.

* * * * *

SEQUENCE LISTING

<160> NUMBER OF SEQ ID NOS: 29

<210> SEQ ID NO 1
<211> LENGTH: 711
<212> TYPE: DNA
<213> ORGANISM: Mus musculus

<400> SEQUENCE: 1

| atggcgcaag | ccgggagaac | agggtatgat | aaccgggaga | tcgtgatgaa | gtacatacat | 60 |
| tataagctgt | cacagagggg | ctacgagtgg | gatgctggag | atgcggacgc | ggcgccctg | 120 |
| ggggctgccc | ccaccctgg | catcttctcc | ttccagcctg | agagcaaccc | aatgcccgct | 180 |
| gtgcaccggg | agatggctgc | caggacgtct | cctctcaggc | ccctcgttgc | caccgctggg | 240 |
| cctgcgctca | gccctgtgcc | accatgtgtc | catctgaccc | tccgccgggc | tggggatgac | 300 |
| ttctctcgtc | gctaccgtcg | tgacttcgca | gagatgtcca | gtcagctgca | cctgacgccc | 360 |
| ttcaccgcga | ggggacgctt | tgccacggtg | gtggaggaac | tcttcaggga | tggggtgaac | 420 |
| tgggggagga | ttgtggcctt | ctttgagttc | ggtgggtca | tgtgtgtgga | gagcgtcaac | 480 |
| agggagatgt | caccctggt | ggacaacatc | gccctgtgga | tgactgagta | cctgaaccgg | 540 |
| catctgcaca | cctggatcca | ggataacgga | ggctgggatg | cctttgtgga | actatatggc | 600 |
| cccagcatgc | gacctctgtt | tgatttctcc | tggctgtctc | tgaagaccct | gctcagcctg | 660 |
| ccctgggtcg | gggcctgcat | cactctgggt | gcatacctgg | ccacaagtg | a | 711 |

<210> SEQ ID NO 2
<211> LENGTH: 515
<212> TYPE: DNA
<213> ORGANISM: Mus musculus

<400> SEQUENCE: 2

| tagcaaacta | caaactcgac | ttaatttcat | ctgctcaatg | gcccattttg | acccagaatc | 60 |
| cactcacacc | ccaacctgcg | catcttggcc | ttgagatcaa | agcccagact | cattcaacca | 120 |
| gacatgcacc | tacccagcct | ccgttatcct | ggatccaggt | gtgcagatgc | cggttcaggt | 180 |
| actcagtcat | ccacagggcg | atgttgtcca | caggggtga | catctccctg | ttgacgctct | 240 |
| ccacacacat | gaccccaccg | aactcaaaga | aggccacaat | cctcccccag | ttcacccat | 300 |
| ccctgaagag | ttcctccacc | accgtggcaa | agcgtcccct | cgcggtgaag | ggcgtcaggt | 360 |
| gcagctgact | ggacatctct | gcgaagtcac | gacggtagcg | acgagagaag | tcatccccag | 420 |
| cccggcgagg | gtcagatgga | gcacaggtgg | cacagggctg | agcgcaggcc | caagcggtgg | 480 |
| aacgagcggg | ctgagaggag | acgtctggca | gccat | | | 515 |

<210> SEQ ID NO 3
<211> LENGTH: 647
<212> TYPE: DNA
<213> ORGANISM: Mus musculus

<400> SEQUENCE: 3

| atttcagtgg | ctgctactcg | gcgcttcagt | cgcggtcgct | tcagtcgtca | gcatggctcg | 60 |
| ctcggtgacc | ctagtctttc | tggtgcttgt | ctcactgacc | ggcttgtatg | ctatccagaa | 120 |
| aacccctcaa | attcaagtat | actcacgcca | cccaccggag | aatgggaagc | cgaacatact | 180 |
| gaactgctac | gtaacacagt | tccacccgcc | tcacattgaa | atccaaatgc | tgaagaacgg | 240 |
| gaaaaaaatt | cctaaagtag | agatgtcaga | tatgtccttc | agcaaggact | ggtctttcta | 300 |

```
tatcctggct cacactgaat tcacccccac tgagactgat acatacgcct gcagagttaa      360
gcatgacagt atggccgagc ccaagaccgt ctactgggat cgagacatgt gatcaagcat      420
catgatgctc tgaagattca tttgaacctg cttaattaca aatccagttt ctaatatgct      480
atacaattta tgcacgcaga agaaatagc aatgtacaca tcaccttctt tatatcttac       540
tttaaatgtt ttatgcatgt tttcaaaaat tggaaatatc ctagatagct gagcaataaa      600
tcttcaataa gtattttgat cagaataata aatataattt taagaac                    647
```

<210> SEQ ID NO 4
<211> LENGTH: 496
<212> TYPE: DNA
<213> ORGANISM: Mus musculus

<400> SEQUENCE: 4

```
ttttttttt  agttttttat ttttagtaaa agtaacaaaa gcagaagtag ccacagggtt       60
gggggtgaga attgctaagc attgggcaca gtgacagact tcaattaggc ctctttgctt      120
taccaaaagg aaagtatgtc acttatgttg tgatagacca aagatgagta actgcatcca      180
agtaatgaga agtacagagg gtttggcata tgatcaacta ttgttcttaa aattatattt      240
attattctga tcaaaatact tattgaagat ttattgctca gctatctagg atatttccaa      300 tttttttgaaa acatgcataa aatatttaaa gtaagatata agaaggtga tgtgtacatt      360 gctatttctt tctgcgtgca taaattgtat agcatattag aaactggatt tgtaattaag      420
caggttcaaa tgaatcttca gagcatcatg atgcttgatc acatgtctcg atcccagtag      480
acggtcttgg gctcgg                                                      496
```

<210> SEQ ID NO 5
<211> LENGTH: 647
<212> TYPE: DNA
<213> ORGANISM: Mus musculus

<400> SEQUENCE: 5

```
tttcagtggc tgctactcgg cgcttcagtc gcggtcgctt cagtcgtcag catggctcgc       60
tcggtgaccc tggtctttct ggtgcttgtc tcactgaccg gcctgtatgc tatccagaaa      120 accctcaaa ttcaagtata ctcacgccac ccaccggaga atgggaagcc gaacatactg       180
aactgctacg taacacagtt ccacccgcct cacattgaaa tccaaatgct gaagaacggg      240
aaaataattc ctaaagtaga gatgtcagat atgtccttca gcaaggactg gtctttctat      300
atcctggctc acactgaatt caccccccact gagactgata catacgcctg cagagttaag      360
catgccagta tggccgagcc caagaccgtc tactgggatc gagacatgtg atcaagcatc      420
atgatgctct gaagattcat ttgaacctgc ttaattacaa atccagtttc taatatgcta      480
tacaatttat gcacgcagaa agaaatagca atgtacacat caccttcttt atatcttact      540
ttaaatattt tatgcatgtt ttcaaaaaat tggaaatatc ctagatagct gagcaataaa      600
tcttcaataa gtattttgat cagaataata aatataattt taagaac                    647
```

<210> SEQ ID NO 6
<211> LENGTH: 1776
<212> TYPE: DNA
<213> ORGANISM: Mus musculus

<400> SEQUENCE: 6

```
atggaaggga agtggttact gtgtttgctg ctggtccttg gaactgcagc tgttgaggct       60
```

-continued

| | | | | |
|---|---|---|---|---|
| catgatggac | atgatgatga | cgcgattgat | attgaagatg | atcttgatga tgttattgaa | 120 |
| gaggtagaag | attcaaaatc | taaatcagat | gccagcactc | ctccatctcc aaaggtcacc | 180 |
| tacaaagctc | cagttccaac | aggggaggtt | tattttgctg | actcttttga cagagggtct | 240 |
| ctgtcaggt | ggattttatc | taaagccaaa | aaagatgaca | ctgatgatga aattgccaaa | 300 |
| tatgatggaa | agtgggaagt | agatgagatg | aaggaaacaa | agcttccagg ggataaagga | 360 |
| cttgtactga | tgtctcgggc | caagcatcat | gccatctctg | ctaaactgaa taagcccttc | 420 |
| ctgtttgata | ccaagcctct | cattgttcag | tatgaggtta | attttcagaa tggaatagaa | 480 |
| tgtggtggtg | cctatgtgaa | gctgctttcc | aagacggcag | agctcagcct ggatcaattc | 540 |
| cacgacaaga | ctccctatac | tattatgttt | ggtccagata | agtgtggaga ggactacaaa | 600 |
| ctgcatttca | tctttcgaca | caaaaatccc | aagacaggtg | tatatgaaga aaaacatgct | 660 |
| aagaggccag | atgcagatct | gaagacctat | ttcactgaca | agaaaacgca tctttataca | 720 |
| ttaatcttga | atccagacaa | tagttttgaa | atattagttg | accagtctgt tgtgaacagt | 780 |
| ggaaatctgc | taaatgacat | gactcctcct | gtaaacccctt | cacgtgaaat tgaagaccca | 840 |
| gaagaccgga | agcctgaaga | ttgggatgaa | aggcccaaaa | tagcagatcc agatgctgtc | 900 |
| aagccagatg | actgggatga | agacgcccct | tctaagatcc | agatgaaga ggccaccaag | 960 |
| cctgaaggct | ggctagacga | cgaacctgag | tatattccag | accctgatgc agagaagcca | 1020 |
| gaggattggg | atgaggatat | ggacggagaa | tgggaggctc | ctcagattgc aaccccaag | 1080 |
| tgtgagtcag | cccctgggtg | tggtgtctgg | cagcgaccta | tgattgacaa ccccaattat | 1140 |
| aagggcaaat | ggaagcctcc | aatgattgac | aaccctaact | accagggaat ctggaaacca | 1200 |
| aggaaaatac | caaatccaga | tttctttgaa | gacctagaac | cttttaagat gactcctttc | 1260 |
| agtgctattg | gtttggagct | ctggtccatg | acatccgaca | tcttttttga caactttatc | 1320 |
| attagtggta | accgaagagt | agttgatgat | tgggccaatg | atgggtgggg cctgaagaaa | 1380 |
| gctgctgatg | gggctgctga | gccaggtgta | gtgctgcaga | tgctggaggc agctgaagag | 1440 |
| cgtccatggc | tttgggtggt | ctatattttg | actgtagctt | tgccagtgtt ccttgtgatc | 1500 |
| ctcttctgct | gttctggaaa | gaaacagtcc | aatgctatgg | agtacaagaa gacggatgct | 1560 |
| ccccagccag | atgtgaagga | tgaagaaggg | aaggaagaag | agaagaacaa gagggatgaa | 1620 |
| gaggaagaag | aggagaagct | tgaagagaaa | cagaagagtg | atgctgaaga agatggtgtt | 1680 |
| actggcagtc | aagatgagga | agatagcaag | cctaaagcag | aggaggatga aattttgaac | 1740 |
| agatcgccaa | gaaacagaaa | gccacgaaga | gagtga | | 1776 |

<210> SEQ ID NO 7
<211> LENGTH: 575
<212> TYPE: DNA
<213> ORGANISM: Mus musculus

<400> SEQUENCE: 7

| | | | | |
|---|---|---|---|---|
| attcgtcgac | aagctggaaa | gaaacagtcc | aatgctatgg | agtacaagaa gacggatgct | 60 |
| ccccagccag | atgtgaagga | tgaagaaggg | aaggaagaag | agaagaacaa gagggatgaa | 120 |
| gaggaagaag | aggagaagct | tgaagagaaa | cagaagagtg | atgctgaaga agatggtgtt | 180 |
| actggcagtc | aagatgagga | agatagcaag | cctaaagcag | aggaggatga aattttgaac | 240 |
| agatcgccaa | gaaacagaaa | gccacgaaga | gagtgaaaca | atctttaaga acttgatctg | 300 |
| tgatttcctc | tccctccect | tcccctgcaa | atgtggtcct | aggagagggc ctggtgtacc | 360 |
| ttaggtggga | gctcaaaacc | tcaagatgtc | accatccaca | ggttccagtg gatactagcc | 420 |

```
tgtaatttta aacatctagc agtaaataat tgcagttgta atgtaaagga ccctgtttct      480
gtagaaagga aaacatttaa cataatggtt gtgaaatgta acatgaagca actaactagt      540
gttttgttgt ttttaaaatt ttccaggttt gtctt                                 575

<210> SEQ ID NO 8
<211> LENGTH: 2394
<212> TYPE: DNA
<213> ORGANISM: Mus musculus

<400> SEQUENCE: 8
atgccatctc ctctccctgt ctccttcctc ctctttctta ccttagtagg aggcaggccc       60
cagaagtcct tactggtgga ggtagaagag ggaggcaatg ttgtgctgcc atgcctcccg      120
gactcctcac ctgtctcttc tgagaagctg gcttggtatc gaggtaacca gtcaacaccc      180
ttcctggagc tgacccccgg gtccctggcc tgggattgc acgtggggtc cctgggcatc       240
ttgctagtga ttgtcaatgt ctcagaccat atgggggct ctacctgtg ccagaagagg        300 cccccttca aggacatctg gcagcctgcc tggacagtga acgtggagga tagtggggag       360
atgttccggt ggaatgcttc agacgtcagg gacctggact gtgacctaag gaacaggtcc      420
tctgggagcc acaggtccac ttctggttcc cagctgtatg tgtgggctaa agaccatcct      480
aaggtctggg gaacaaagcc tgtatgtgcc cctcggggga gcagtttgaa tcagagtcta      540
atcaaccaag atctcactgt ggcacccggc tccacacttt ggctgtcctg tggggtaccc      600
cctgtcccag tggccaaagc gtccatctcc tggacccatg tgcatcctag agacctaat       660 gtttcactac tgagcctaag ccttggggga gagcacccgg tcagagagat gtgggtttgg      720
gggtctcttc tgcttctgcc ccaagccaca gctttagatg aaggcaccta ttattgtctc      780
cgaggaaacc tgaccatcga gaggcacgtg aaggtcattg caaggtcagc agtgtggctc      840
tggctgttga gaactggtgg atggatagtc ccagtggtga ctttagtata tgtcatcttc      900
tgtatggttt ctctggtggc ttttctctat tgtcaaagag cctttatcct gagaaggaaa      960
aggaagcgaa tgactgaccc cgccaggaga ttcttcaaag tgacgcctcc ctcgggaaac     1020
gggacccaga accagtacgg gaatgtgctc tcccttccta catctaccct ggccaggcc      1080 catgctcagc gttgggctgc tggcctaggg agtgtccctg gtcctatgg aaatccacgc      1140 attcaagtcc aggatactgg agctcagagc catgaaacag gactggaaga agaaggggag     1200
gcctatgaag agccagacag cgaggagggc tctgaattct atgagaacga ctccaacctt     1260
gggcaggacc aggtttccca ggatgggagt ggctatgaga accccgagga tgagcccatg     1320
ggtccagagg aagaagactc cttctccaat gctgagtctt atgaaaatgc agatgaggag     1380
ctggcccaac cagttggcag gatgatggaa ttcctgagcc ccatgggtc tgcgtgggac     1440 cccagccggg aagcatcctc gcttgggtcc cagtcctatg aagatatgag agggatcctc     1500
tatgcagctc ctcagctcca ctcaattcag tccggtccca gtcatgaaga agatgcagac     1560
tcttatgaaa acatggataa gtctgacgac ctagaaccag catgggaagg agagggccac     1620
atggggactt ggggaaccac gtgactccca agtgactagc ctggacttcg ttaggtccca     1680
agaaccacat ctgattctga aatctggaga tcccagatgg tgtcagtcag tgaaatgacc     1740
ttgatcagga tgtgtgctag ctgacacaca cacactcata tgcatgttca agcaaagctt     1800
ccttttgacc ctttgctttc cccaaataaa cccaattagc cactcaaatt ctctgaagcc     1860
ggcccttgtg tgggatagga agatgggtt gaatccagcc ctgagtcacc cagaggaagg     1920
```

| | |
|---|---|
| agaactgagg tctgagtaca tcctggctct agccttccca tggcctggca tttagccacc | 1980 |
| taacatccag tgatgcaaat atgtccagcc gctacattcc atggtgtccc acaagggaga | 2040 |
| gacagtgatg ggactagcag actgtttggt tgtaacccat ccctgctcac cctgcacaaa | 2100 |
| ctgggaaaca ctgtctgcct ctcttttaat cctgcctgct ccaggctaac aggccagtac | 2160 |
| cctcaccttc gagtttctgg caacactacc tgagtgcctg ctcagggggt tcagcttctg | 2220 |
| accatatgta gacaccaccc cagctctgag tttacacatc atcacccctt gcctaagacc | 2280 |
| tgaaaccccc ctttaccttc gcccaggtgt gccatttccc tgctccctcc tggatccttg | 2340 |
| ggacctgtga acctactcaa gtgctgctct caataaatct gcctttatac tttc | 2394 |

<210> SEQ ID NO 9
<211> LENGTH: 491
<212> TYPE: DNA
<213> ORGANISM: Mus musculus

<400> SEQUENCE: 9

| | |
|---|---|
| agcccccatg ggtctgcgtg ggaccccagc cgggaagcat cctcgcttgg gtcccagtcc | 60 |
| tatgaagata tgagagggat cctctatgca gctcctcagc tccactcaat tcagtccggt | 120 |
| cccagtcatg aagaagatgc agactcttat gaaaacatgg ataagtctga cgacctagaa | 180 |
| ccagcatggg aaggagaggg ccacatgggg acttggggaa ccacgtgact cccaagtgac | 240 |
| tagcctggac ttcgttaggt cccaagaacc acatctgatt ctgaaatctg gagatcccag | 300 |
| atggtgtcag tcagtgaaat gaccttgatc aggatgtgtg catgctgaca cacacacact | 360 |
| catatgcatg ttcaagcaaa gcttcctttt gaccctttgc tttccccaaa taaacccaat | 420 |
| tagccactca aattctctga agccggccct gagtcaccca gaggaaggag aactgaggtc | 480 |
| tgagtacatc c | 491 |

<210> SEQ ID NO 10
<211> LENGTH: 497
<212> TYPE: DNA
<213> ORGANISM: Mus musculus
<220> FEATURE:
<221> NAME/KEY: misc_feature
<222> LOCATION: (434)..(434)
<223> OTHER INFORMATION: N at this position can be a, c, t, or g.

<400> SEQUENCE: 10

| | |
|---|---|
| tttagaaagt ataaaggcag atttattgag agcagcactt gagtaggttc acaggtccca | 60 |
| aggatgcagg agggagcagg gaaatggcac acctgggcga aggtaaaggg gggtttcagg | 120 |
| tcttaggcaa ggggtgatga tgtgtaaact cagagctggg gtggtgtcta catatggtca | 180 |
| gaagctgaac cccctgagca ggcactcagg tagtgttgcc agaaactcga aggtgagggt | 240 |
| actggcctgt tagcctggag caggcaggat taaaagagag gcagacagtg tttcccagtt | 300 |
| tgtgcagggt gagcagggat gggttacaac caaacagtct gctagtccca tcactgtctc | 360 |
| tcccttgtgg gacaccatgg aatgtagcgg ctggacatat ttgcatcact ggatgttagg | 420 |
| tggctaaatg ccangccatg ggaaggctag agccaggatg tactcagacc tcagttctcc | 480 |
| ttcctctggg tgactca | 497 |

<210> SEQ ID NO 11
<211> LENGTH: 1492
<212> TYPE: DNA
<213> ORGANISM: Mus musculus

<400> SEQUENCE: 11

-continued

```
acacactctg ccttgctcac agaggagggg ctgcagccct ggccctcatc agaacaatga      60
cactcaggct gctgttcttg gctctcaact tcttctcagt tcaagtaaca gaaaacaaga     120
ttttggtaaa gcagtcgccc ctgcttgtgg tagatagcaa cgaggtcagc ctcagctgca     180
ggtattccta caaccttctc gcaaaggaat tccgggcatc cctgtacaag ggcgtgaaca     240
gcgacgtgga agtctgtgtc gggaatggga attttaccta tcagcccag tttcgctcga     300 atgccgagtt caactgcgac ggggatttcg acaacgaaac agtgacgttc cgtctctgga     360
atctgcacgt caatcacaca gatatttact tctgcaaaat tgagttcatg taccctccgc     420
cttacctaga caacgagagg agcaatggaa ctattattca cataaaagag aaacatcttt     480
gtcatactca gtcatctcct aagctgtttt gggcactggt cgtggttgct ggagtcctgt     540
tttgttatgg cttgctagtg acagtggctc tttgtgttat ctggacaaat agtagaagga     600
acagactcct tcaagtgact accatgaaca tgactccccg gaggcctggg ctcactcgaa     660
agccttacca gccctacgcc cctgccagag actttgcagc gtaccgcccc tgacagggac     720
ccctatccag aagcccgccg gctggtaccc gtctacctgc tcatcatcac tgctctggat     780
aggaaaggac agcctcatct tcagccggcc actttggacc tctactgggc caccaatgcc     840
aactatttta gagtgtctag atctaacatc atgatcatct tgagactctg gaatgaatga     900
cagaagcttc tatggcagga taaagtctgt gtggcttgac ccaaactcaa gcttaataca     960
tttattgact tgattgggga agttagagta gagcaatcaa aaagatcatt cattcagcct    1020
tgggaagtca atttgcaggc tcctggatga gccctgcccc gttttcactt gccagcacat    1080
ttcagtcatg tggtgtgata gccaaagatg ttttggacag agaagaaagg atagaaaaac    1140
cttctctttg gctaagttgg tgtttgggt ggggataggt tagagtatag tacttaacta    1200
tttgaaaaat aatgaaaaca cttttttcac tcatgaaatg agccacttag ctcctaaata    1260
gtgttttcct gttagtttag aaagttgtgg acatattttt ttaatgattt ctgaccattt    1320
ttaatcacat tgactcatgg aatggcctca agcacccccc cagtgcttct ttcctcattc    1380
ccggtcatgg gaactcagta ttattaatag tcacaacatg atttcagaac tagatagccc    1440
tcccacacca agaagaatgt gagaggaagt aaggtcactt tatgtaaaaa cg            1492
```

<210> SEQ ID NO 12
<211> LENGTH: 785
<212> TYPE: DNA
<213> ORGANISM: Mus musculus
<220> FEATURE:
<221> NAME/KEY: misc_feature
<222> LOCATION: (428)..(428)
<223> OTHER INFORMATION: N at this position can be a, c, t, or g.
<221> NAME/KEY: misc_feature
<222> LOCATION: (563)..(563)
<223> OTHER INFORMATION: N at this position can be a, c, t, or g.

<400> SEQUENCE: 12

```
acataaagtg accttacttc ctctcacatt cttcttggtg tgggagggct atctagttct      60
gaaatcatgt tgtgactatt aataatactg agttcccatg accgggaatg aggaaagaag     120
cactgggggg tgctttgagg ccattccatg agtcaatgtg attaaaaatg gtcagaaatc     180
attaaaaaaa tatgtccaca actttctaaa ctaacaggaa aacactattt aggagctaag     240
tggctcattt catgagtgaa aaagtgtttt tcattatttt tcaaatagtt aagtactata     300
ctctaaccta tccccacccc aaacaccaac ttagccaaag agaaggtttt tctatccttt     360
cttctctgtc caaaacatct ttggctatca caccacatga ctgaaatgtg ctggcaagtg     420
```

```
aaaacggngc agggctcatc caggagcctg caaattgact tcccaaggct gaatgaatga    480 tcttttgat tgctctactc taacttcccc aatcaagtca ataaatgtat taagcttgag    540
tttgggtcaa gccacacaga ctntatcctg ccatagaagc ttctgtcatt cattccagag    600
tctcaagatg atcatgatgg tagatctaga cactctaaaa tagttggcat tggtggccca    660
gtagaggtcc aaagtggccg ggctgaagat gaggctgtcc tttcctatcc agagcagtga    720
tgatgagcag gtagccgggt accagccggc cggctttctg gaatagggtt cctgtcaggg    780
gcggt                                                                785
```

<210> SEQ ID NO 13
<211> LENGTH: 900
<212> TYPE: DNA
<213> ORGANISM: Mus musculus
<220> FEATURE:
<221> NAME/KEY: misc_feature
<222> LOCATION: (647)..(647)
<223> OTHER INFORMATION: N at this position can be a, c, t, or g.
<221> NAME/KEY: misc_feature
<222> LOCATION: (741)..(741)
<223> OTHER INFORMATION: N at this position can be a, c, t, or g.
<221> NAME/KEY: misc_feature
<222> LOCATION: (760)..(760)
<223> OTHER INFORMATION: N at this position can be a, c, t, or g.
<221> NAME/KEY: misc_feature
<222> LOCATION: (841)..(841)
<223> OTHER INFORMATION: N at this position can be a, c, t, or g.

<400> SEQUENCE: 13

```
gtgacttcag ttcacaccac actctgcctt gctcacagag gaggggctgc agccctggcc     60
ctcatcagaa caatgacact caggctgctg ttcttggctc tcaacttctt ctcagttcaa    120
gtaacagaaa acaagatttt ggtaaagcag tcgcccctgc ttgtggtaga tagcaacgag    180
gtcagcctca gctgcaggta ttcctacaac cttctcgcaa aggaattccg ggcatccctg    240
tacaagggcg tgaacagcga cgtggaagtc tgtgtcggga atgggaattt tacctatcag    300
ccccagtttc gctcgaatgc cgagttcaac tgcgacgggg atttcgacaa cgaaacagtg    360
acgttccgtc tctggaatct gcacgtcaat cacacagata tttacttctg caaaattgag    420
ttcatgtacc ctccgcctta cctagacaac gagaggagca atggaactat tattcacata    480
aaagagaaac atctttgtca tactcagtca tctcctaagc tgttttggca ctggtcgtgg    540
ttgctggagt cctgttttgt atggcttgct agtgacagtg ggctctttgt gtatctggac    600
caatagtaga aggaaccaga ctctttcaag tgactacatg aacatgnact ccccggagcc    660
tgggctcaac tcgaagcctt accagcccta cgccctgcc agagactttg cagcgtaccc    720
gccctgacaa ggaccctat ncaaaagccc cgcggctggn taccgtctac ctgctcatca    780
tcactgctct tgaaaggaaa ggacagctta tcttcagccc gccactttga acttactgg     840 nccaccaatg caacttattt aagaggctag atccacctta tgacatcttg aaactttgga    900
```

<210> SEQ ID NO 14
<211> LENGTH: 356
<212> TYPE: DNA
<213> ORGANISM: Mus musculus

<400> SEQUENCE: 14

```
cactctgcct tgctcacaga ggaggggctg cagctggcgc ctcatcagaa caatgacact     60
caggctgctg ttcctgggct ctcaacttcc tctcagttca aggtacagga aaccagattt    120
ttggtaaaga gtcgcccttg cttgtggtga tacaacgagg gcagcctaag ttcgaggaat    180
```

```
cctacaaccc tctcgcaaag gaattccggg aatccctgta aaagggcctt aaaagccaag      240
tggaaatttg tgttcgggaa tgggaatttt accttctaac cccggtttgc gccgaatgcc      300
cggttcaact tgaacgggaa tttcggcaca ggaacagtga gctttccgtc tcggaa          356
```

<210> SEQ ID NO 15
<211> LENGTH: 3100
<212> TYPE: DNA
<213> ORGANISM: Mus musculus

<400> SEQUENCE: 15

```
ttttcattta cgaacatctg tgaaggcaaa gcaagactct cttcttcact aggtacctgt       60
ttgcaaagtc tcgagccctc atatacacac acctgtgcaa gaagcagagt gaaggaagga     120
ctggccagag gctcagattc ccaaccaaca agagctcaag gagaccacca tgtgccgagc     180
catctctctt aggcgcttgc tgctgctgct gctgcagctg tcacaactcc tagctgtcac     240
tcaagggaag acgctggtgc tggggaagga aggggaatca gcagaactgc cctgcgagag     300
ttcccagaag aagatcacag tcttcacctg gaagttctct gaccagagga agattctggg     360
gcagcatggc aaaggtgtat taattagagg aggttcgcct tcgcagtttg atcgttttga     420
ttccaaaaaa ggggcatggg agaaaggatc gtttcctctc atcatcaata aacttaagat     480
ggaagactct cagacttata tctgtgagct ggagaacagg aaagaggagg tggagttgtg     540
ggtgttcaaa gtgaccttca gtccgggtac cagcctgttg caaggcagag cctgaccct      600 gaccttggat agcaactcta aggtctctaa ccccttgaca gagtgcaaac acaaaaaggg     660
taaagttgtc agtggttcca aagttctctc catgtccaac ctaagggttc aggacagcga     720
cttctggaac tgcaccgtga ccctggacca gaaaaagaac tggttcggca tgacactctc     780
agtgctgggt tttcagagca cagctatcac ggcctataag agtgagggag agtcagcgga     840
gttctccttc ccactcaact ttgcagagga aaacggggtgg ggagagctga tgtggaaggc     900
agagaaggat tctttcttcc agccctggat ctccttctcc ataaagaaca agaggtgtc      960 cgtacaaaag tccaccaaag acctcaagct ccagctgaag gaaacgctcc cactcaccct    1020
caagataccc caggtctcgc ttcagtttgc tggttctggc aacctgactc tgactctgga    1080
caaagggaca ctgcatcagg aagtgaacct ggtggtgatg aaagtggctc agctcaacaa    1140
tactttgacc tgtgaggtga tgggacctac ctctcccaag atgagactga ccctgaagca    1200
ggagaaccag gaggccaggg tctctgagga gcagaaagta gttcaagtgg tggccctga     1260 gacagggctg tggcagtgtc tactgagtga aggtgataag gtcaagatgg actccaggat    1320
ccaggtttta tccagagggg tgaaccagac agtgttcctg gcttgcgtgc tgggtggctc    1380
cttcggcttt ctgggtttcc ttgggctctg catcctctgc tgtgtcaggt gccggcacca    1440
acagcgccag gcagcacgaa tgtctcagat caagaggctc tcagtgaga agaagacctg     1500 ccagtgcccc caccggatgc agaagagcca taatctcatc tgaggcctag gccccacctg    1560
cagcccacca cctgcgtcct gtctcatcgc ccgaggcctg ggaccagat gaatgtagca     1620 gacacgctgc ctccggcctt ctgctctcct cttccacaac cggccaacgg tttccctccc    1680
tctgttccca agcctgtctg tctgcagagc ttgccctctg cgtttcagac actcaagcac    1740
accccatcag cttatttatt cttcgctgct gcctttctgc cagagcctcg gcccttctcg    1800
gactaaggtc ctggaacctt tttccagctg tctgcttgga tcaaagggca gtgtatagca    1860
cctggcacgg atggtgggac tggtgtctgg aaatacacag cacagtttac gagagggctc    1920
```

```
tgggaccaag ctgagtgggg cagggagggc cgggaggttg tgcatgtcac acatgaagca   1980
tgtcaggggc aaatgaagac tgagaggctg cgggagtcag cctcagcttc ccatgatgcc   2040
tgcttctctt ttgaatttgc aagaccagac tcacattcta accagtgcac caacacacat   2100
ccaagccaca cacctgtcca tatatccaaa cagcatatct taattcataa gccactttaa   2160
tgtcccaggc attcgaccct tacaaaaacc ttacaagtgg ttgagcggta aaaagcctca   2220
tgaactgagt ggaaggagag gattaactct tgaaagttgt cccctatgta tgtaccatga   2280
ccctcatgtg tacagaacac acacacacac acacacacat acacacacac gaacagacgc   2340
atgttgcaca cactgcatcg acgctaaatc ctagcaagct gacagtgatg actaagatgg   2400
cagagataac cagtcatccc tagtgaaatg gcaacttggt gtgaatgact acccaaggtt   2460
acccagctaa caactgctga tgtcagggcc aacccagggc tcctgatccc tagagccaag   2520
ccactacatg gaacacaggg atgaatacca cacagatctg tggagctagt tccaggccct   2580
cggtatacac acacacacac acacacacac acactggagc gcacccctgg cagagatctt   2640
gagaggatgg aggagccatt ctggtttcaa atccctcctt gatcactgct gttctcaccc   2700 cccctcctt cccccaaaac cctagttctc ttagagtgag gctgggagag atgcacagag   2760
acctgccgca gtgtgtgcag agcctgggaa gtggaccatg ctgggtcct ttatggagag   2820 agcattgtgg caggtggctg tgccttccat ccaggaggtc aggggtctaa gggctctccc   2880
tgagagtctt gatctgtttc tcatagatcc acagcctcct ctgcctctgt cgtttgcctg   2940
cttcagcact tccttcccct tttttcctct tttcttccca gctggcctct tctagaaaca   3000
tcccttcccc acttctcttc attattcact tcttattttt gcccactccc cactcctgct   3060
tcctgagctg acagaaaaat aaaggctata aataaaatgc                         3100

<210> SEQ ID NO 16
<211> LENGTH: 492
<212> TYPE: DNA
<213> ORGANISM: Mus musculus

<400> SEQUENCE: 16
gcaagactct cttcttcact aggtacctgt ttgcaaagtc tcgagccctc atatacacac    60
acctgtgcaa gaagcagagt gaaggaagga ctggccagag cgtcagattc ccaaccaaca   120
agagctcaag gagaccacca tgtgccgagc catctctctt aggcgcttgc tgctgctgct   180
gctgcagtgt cacaactcct agctgtcact caagggaaga cgctggtgct ggggtccttt   240
atggagagag cattgtggca ggtggctgtg cttccatcca ggaggtcagg ggtctaaggg   300
ctctccctga gagtcttgat ctgtttctca tagatccaca gcctcctctg cctctgtcgt   360
ttgcctgctt cagcacttcc ttccccttt ttcctctttt cttcccagct ggcctcttct   420
agaaacatcc cttccccact ctcttcatt attcacttct tattttgcc cactccccac   480 tcctgcttcc tg                                                      492

<210> SEQ ID NO 17
<211> LENGTH: 1579
<212> TYPE: DNA
<213> ORGANISM: Mus musculus

<400> SEQUENCE: 17
tgccctgcat ggtgtctttg cctcggctgt gcgcgctatg gggctgcttg ttgacagcgg    60
tccatctagg gcagtgtgtt acgtgcagtg acaaacagta cctccacgat ggccagtgct   120
gtgatttgtg ccagccagga agccgactga caagccactg cacagctctt gagaagaccc   180
```

-continued

```
aatgccaccc atgtgactca ggcgaattct cagcccagtg aacagggag attcgctgtc      240 accagcacag acactgtgaa cccaatcaag ggcttcgggt taagaaggag ggcaccgcag     300
aatcagacac tgtctgtacc tgtaaggaag acaacactg caccagcaag gattgcgagg     360
catgtgctca gcacacgccc tgtatccctg gctttggagt tatggagatg gccactgaga    420
ccactgatac cgtctgtcat ccctgcccag tcggcttctt ctccaatcag tcatcacttt    480
tcgaaaagtg ttatccctgg acaagctgtg aggataagaa cttggaggtc ctacagaaag    540
gaacgagtca gactaatgtc atctgtggtt taaagtcccg gatgcgagcc ctgctggtca    600
ttcctgtcgt gatgggcatc ctcatcacca ttttcggggt gtttctctat atcaaaaagg    660
tggtcaagaa accaaaggat aatgagatgt tacccctgc ggctcgacgg caagatcccc    720
aggagatgga agattatccc ggtcataaca ccgctgctcc agtgcaggag acactgcacg    780
ggtgtcagcc tgtcacacag gaggatggta aagagagtcg catctcagtg caggagcggc    840
aggtgacaga cagcatagcc ttgaggcccc tggtctgaac cctggaactg ctttggaggc    900
gatggctgct gctgaccctt tgaagtttga gatgagccaa gacagagccc agtgcagcta    960
actctcatgc ctgccccctg tcatttctca acttgctttt taaggatgga gggaaagctc    1020
gggcatcggg aggtccacag tgatatctac caagtgcagc agtgcaggac ccagagttgt    1080
cttgctgcgg cgttcactgt aaggagtcgt ggctacagga gtccgtggcc cgcagcttgt    1140
gctcgtagag ggcacctggt tgccatcagc agggtactgg ctaaataaat ctgtaattat    1200
ttatacaatg gcatctcaga aactctagca ggtggggcag aaaacaggta gtggaatgat    1260
gggtagagaa acagctttta aaacacattc caaggcaggt aagatggctt ttgtgggtaa    1320
aggagcttgc tgcccaaacc cggttacctg attttgatcc ctgggacttc atggtaaaag    1380
ggagagaacc aaatccagag ggttgtcatt tgacctccat gtgtgctctg tggtaatgta    1440
ccccgtgtgt gcacatgtgc acatatccta aaatggatgt ggtggtgtat tgtagaaatt    1500
atttaatccg ccctgggttt ctacctgtgt gttaccattt agttcttgaa taaagacaca    1560 ctcaacctt atatttaca                                                  1579
```

<210> SEQ ID NO 18
<211> LENGTH: 469
<212> TYPE: DNA
<213> ORGANISM: Mus musculus

<400> SEQUENCE: 18

```
ttttcgaaaa gtgttatccc tggacaaggt ttaaagtccc ggatgcgagc cctgctggtc     60
attcctgtcg tgatgggcat cctcatcacc attttcgggg tgtttctcta tatcaaaaag    120
gtggtcaaga aaccaaagga taatgagatc ttacccctg cggctcgacg gcaagatccc    180
caggagatgg aagattatcc cggtcataac accgctgctc cagtgcagga gacgctgcac    240
gggtgtcagc ctgtcacaca ggaggatggt aaagagagtc gcatctcagt gcaggagcgg    300
caggtgacag acagcatagc cttgaggccc tggtctgaa cctggaact gctttggagg     360 cgatggctcg gctcgggagc agggcctgg ctctgaggac tgcttgctga cctttgaagt    420
ttgagatgag ccaagacaga acccagtgca gctaactctc atgcctgcc                469
```

<210> SEQ ID NO 19
<211> LENGTH: 192
<212> TYPE: DNA
<213> ORGANISM: Mus musculus

```
<400> SEQUENCE: 19 ttaaagtcc cggatgcgag ccctgcgggt cattcctgtc gtgatgggca tcctcatcac    60
cattttcggg gtgtttctct atatcaaaaa ggtgttcaag atcccaaggt gtaatgagat   120
ttttccccct ggggcttcaa gggcaatttc cccagaagtt gaagtatttc ccgggtaata   180
acacggctgc tc                                                      192

<210> SEQ ID NO 20
<211> LENGTH: 4655
<212> TYPE: DNA
<213> ORGANISM: Mus musculus

<400> SEQUENCE: 20
ttgttcttag ggttagagag taggaaaact tgctccccat ctgataagac agagtgcaaa    60 ggagaccta tttcttaggg gcacagctga tctccagata tgaccatggg tttgtggctc   120
aaacttctgg cctttggatt tgcccttctg gacacagaag tctttgtcac agggcaaaca   180
cctacaccca gtgatggtgc cagcctcaca actcttacac catccactct ggccttgca   240 agcactgacc ctccaagcac aaccatagct accacaacga agcaaacatg tgctgccatg   300
tttgggaaca ttactgtgaa ttacacctat gaatctagta atcagacttt taaggcagac   360
ctcaaagatg tccaaaatgc taagtgtgga aatgaggatt gtgaaaacgt gttaaataat   420
ctagaagaat gctcacagat aaaaaacatc agtgtgtcta atgactcatg tgctccagct   480
acaactatag atttatatgt accaccaggg actgacaagt tttcgctaca tgactgcaca   540
ccaaaagaaa aggctaatac ttcaatttgt ttggagtgga aaacaaaaaa ccttgatttc   600
agaaaatgca acagtgacaa tatttcatat gtactccact gtgagccaga aaataataca   660
aaatgcatta gaagaaatac attcatacct gaaagatgtc agttggacaa ccttcgtgcc   720
caaacaaatt acacatgtgt agcagaaatc ttatatcgcg gtgtaaaact cgtcaaaaat   780
gttataaatg tgcagacaga tttggggatt ccagaaacgc ctaagcctag ttgtgggggat   840 ccagctgcaa gaaaaacgtt agtctcttgg cctgagcctg tatctaaacc tgagtctgca   900
tctaaacccc atggatatgt tttatgctat aagaacaatt cagaaaaatg taaaagtttg   960
cctaataatg tgaccagttt tgaggtggaa agcttgaaac cttataaata ctatgaagtg  1020
tccctacttg cctatgtcaa tgggaagatt caaagaaatg ggactgctga gaagtgcaat  1080
tttcacacaa aagcagatcg tccggacaag gtcaatggaa tgaaaacctc ccggccgaca  1140
gacaatagta taaatgttac atgtggtcct ccttatgaaa ctaatggccc taaaaccttt  1200
tacatttggg tagtcagaag tggaggttct tttgttacaa atacaacaaa gacaaactgt  1260
cagttttatg gagataatct ctactattca actgactatg agtttctggt ctcttttcac  1320
aatggagtgt acgagggaga ttcagttata gaagtgagt caacaaattt taatgctaaa  1380
gcactgatta ttcctggt gtttctgatt attgtgacat caatagcctt gcttgttgtt  1440
ttgtataaaa gctatgatct gcgcaagaaa agatccagca attttagatga caacaggaa  1500 ctcgttgaaa gggatgatga aaagcagctg atggatgtgg agccaatcca ttctgacatt  1560
ttgttggaaa catacaaaag gaagattgct gatgagggca gactgttcct ggctgaattt  1620
cagagcattc cacgggtatt cagcaagttt cccatcaaag atgcccgaaa gccccacaat  1680
cagaataaaa accgttatgt tgacattctt ccctatgatt ataaccgtgt ggaactctct  1740
gaaataaatg gagatgcagg gtccacctac ataaatgcca gctacattga tggcttcaag  1800
gaacccagga aatacattgc tgcacaaggg cccccgggatg agacagttga tgacttctgg  1860
```

```
aggatgatct gggagcaaaa ggccacagtt attgtcatgg tcacacgatg tgaagaagga   1920
aacaggaaca agtgcgcaga atactggcca agcatggagg aaggcactcg ggctttcaaa   1980
gatattgttg tgacaatcaa tgaccacaaa cgatgtcctg attacatcat tcagaagctg   2040
aacgttgcac ataaaaaaga aaaagcaact ggaagagaag tgactcatat ccaattcacc   2100
agctggccag accatggggt tcctgaagac cctcacctgc tcctcaaact tcgacggaga   2160
gttaatgctt ttagcaactt cttcagtggt cccattgtgg tgcactgcag tgctggtgtt   2220
gggcgtacag gtacctacat tggaattgat gccatgctga aaggcctgga agcagagggc   2280
aaagtggatg tctatggtta tgttgtcaag ctaaggcgac agaggtgtct gatggtgcaa   2340
gtggaggcac agtatatcct gattcatcag gctttagtgg aatacaatca gtttggagaa   2400
acacaagtga acttgtctga gttacattca tgcctacaca acatgaagaa gagagatcca   2460
cccagtgacc cctcccctcg tgaggctgaa taccagagac ttccttcata caggagttgg   2520
aggacacagc acattggaaa tcaaggagag aataagaaga agaagaggaa ttctaatgtt   2580
gttccatatg actttaacag agtgccactt aagcatgaac tggagatgag caaagagagt   2640
gagcctgaat cagatgagtc ttcagatgat gacagtgact cagaagaaac cagcaaatac   2700
attaatgcat cctttgtgat gagttactgg aaaccagaaa tgatgattgc tgctcagggg   2760
ccactaaaag aaacgatcgg tgacttttgg cagatgatat tccaaagaaa agtcaaagtt   2820
attgtgatgt tgacagagtt agtgaatgga gaccaggaag tctgtgctca gtactggggc   2880
gaaggaaagc agacttatgg agacatggaa gtggagatga agacacaaa cagagcctca   2940 gcctacactc tccgaacttt tgagctgaga cattccaaga ggaaggagcc cagaactgtg   3000
taccagtacc agtgtaccac atggaaaggg gaagagctcc ctgcagaacc caaagacctg   3060
gtgtctatga ttcaggacct caaacagaag cttcccaagg cttcccccaga agggatgaag   3120 tatcacaagc atgcatccat cctcgtccac tgcagagatg gatcccagca gacagggttg   3180
ttctgtgcct tgttcaatct cttggaaagt gcagaaacag aagatgtggt tgatgttttc   3240
caagtggtaa agtctctacg caaagcacgg cctgggtgtg tgtgcagcta tgagcaatac   3300
cagttcctct atgacatcat cgccagcatc tatcccgccc agaatggaca agtcaagaaa   3360
acaaacagcc aagacaaaat tgaatttcat aatgaagtga tggaggcaa gcaggatgct   3420 aactgtgtcc gtccagatgg tcctctgaat aaagcccagg aagacagcag aggggtggga   3480
accccggagc ctaccaatag tgctgaggaa ccagaacatg ctgccaatgg ttctgcgagc   3540
ccagctccaa cccagagttc ataggaaagg agtcatgtgg gacaacgcag actctcacat   3600
tagttctttc tatttttcta gacctaatga agaacatgc ctgtgcagtg gtttatggaa   3660
tctgtgttca cctttgccac tgtataaaaa tatttaagtt tgtcaaaaca ttttgtacag   3720
ttttatgctt attttaaaag tgtatctatg tcattcagca ggaatgtata tgtgacagag   3780
ggtgtctgtg tgtgtgagag tgtgtttatg tatgagtgac tgtgtgtgtg catgtttgtg   3840
cgtgtgtatg acatctaaat gtgattggag aatactttca agccatttca aatgctttcg   3900
agaaacagtg tgcctttttct cctcttgagg aaactataca ttttatatct aaactgttaa   3960
tttgtttgag ggattaattt tttaaaatcc cattgaaagt ggattcagtt gtaagaataa   4020
caatgtgtac cattctggaa tgacctcaag gtgtcctcct tgtcctgttg atgatcttgt   4080
agtttaagat gctctttttg gatatagata acgtatgta agagtgctgt gggtgtgtac   4140
agctgatctg ggacgtgaac aaaatcaaca tgtgagactt atgttccata tactgtcatt   4200
```

```
tcatcactat ctcttaatgc atatttaatc aaacatgaaa atctcaaggg agactatttt    4260
tgtatccaca tgggaagtag aacattgcaa gtcagttgct gtctacacaa tagataaaaa    4320
ttactagtta atgctcttgg tcatatcgat atatgctatg aacctaaata attgcccttta   4380 gccaaatata atgtatgtta aaaacacata gaataaaaac aggggcatga aaacttgttt    4440
gtactgaata tttacatagg taacctcgta cagttagttc tgttatggaa ttcaccattt    4500
atgggaaatg taaaattgac tatggccatt cctatgctt aagaccatct ttgacttgca     4560
ttactgtgta tttatcttga atttccccac tgttttgttt actcttactg agatataata    4620
ttgataacca aataaacttt tcaactatta tcttc                               4655
```

<210> SEQ ID NO 21
<211> LENGTH: 753
<212> TYPE: DNA
<213> ORGANISM: Mus musculus

<400> SEQUENCE: 21

```
gctttcgaga aacagtgtgc cttttctcct cttgaggaaa ctatacattt tatatctaaa      60
ctgttaattt gtttgaggga ttaatttttt aaaatcccat tgaaagtgga ttcagttgta    120
agaataacaa tgtgtaccat tctggaatga cctcaaggtg tcctccttgt cctgttgatg    180
atcttgtagt ttaagatgct cttttggat atagataagc gtatgtaaga gtgctgtggg     240
tgtgtacagc tgatctggga cgtgaacaaa atcaacatgt gagacttatg ttccatatac    300
tgtcatttca tcactatctc ttaatgcata tttaatcaaa cattaaaatc tcaagggaga    360 ctattttgt atccacatgg gaagtagaac attgcaagtc agttgctgtc tacacaatag      420
ataaaaatta ctagttaatg ctcttggtca tatcgatata tgctatgaac ctaaataatt    480
gcccttagcc aaatataatg tatgttaaaa acacatagaa taaaacagg ggcatgaaaa      540 cttgtttgta ctgaatattt acataggtaa cctcgtacag ttagttctgt tatggaattc    600
accatttatg ggaaatgtaa aattgactat ggcccatttc tatgcttaag accatctttg    660
acttgcatta ctgtgtattt atcctgaatt tgcgcactgt tttgtttact ctactgagat    720
ataatattga tacccataat aacttccact att                                  753
```

<210> SEQ ID NO 22
<211> LENGTH: 1480
<212> TYPE: DNA
<213> ORGANISM: Mus musculus

<400> SEQUENCE: 22

```
gccgcaggct gcccacacag gccgcccgct gttttcccctt gctgcagaca tgctgtggat     60
ctgggctgtc ctgcctctgg tgcttgctgg ctcacagtta agagttcata ctcaaggtac    120
taatagcatc tccgagagtt taaagctgag gaggcgggtt catgaaactg ataaaaactg    180
ctcagaagga ttatatcaag gaggcccatt tgctgtcaa ccatgccaac ctggtaaaaa      240
aaaagttgag gactgcaaaa tgaatggggg tacaccaacc tgtgccccat gcacagaagg    300
gaaggagtac atggacaaga accattatgc tgataaatgc agaagatgca cactctgcga    360
tgaagagcat ggtttagaag tggaaacaaa ctgcacccctg acccagaata ccaagtgcaa   420
gtgcaaacca gacttctact gcgattctcc tggctgtgaa cactgtgttc gctgcgcctc    480
gtgtgaacat ggaacccttg agccatgcac agcaaccagc aatacaaact gcaggaaaca    540
aagtcccaga aatcgcctat ggttgttgac catccttgtt ttgttaattc cacttgtatt    600
tatatatcga agtaccgga aaagaaagtg ctggaaaagg agacaggatg accctgaatc     660
```

| | |
|---|---|
| tagaacctcc agtcgtgaaa ccataccaat gaatgcctca aatcttagct tgagtaaata | 720 |
| catcccgaga attgctgaag acatgacaat ccaggaagct aaaaaatttg ctcgagaaaa | 780 |
| taacatcaag gagggcaaga tagatgagat catgcatgac agcatccaag acacagctga | 840 |
| gcagaaagtc cagctgctcc tgtgctggta ccaatctcat gggaagagtg atgcatatca | 900 |
| agatttaatc aagggtctca aaaagccga atgtcgcaga accttagata aatttcagga | 960 |
| catggtccag aaggaccttg gaaaatcaac cccagacact ggaaatgaaa atgaaggaca | 1020 |
| atgtctggag tgaaaactac ctcagttcca gccatgaaga gaggagagag cctgccaccc | 1080 |
| atgatggaaa caaatgaat gccaactgta ttgacattgg caactcctgg tgtgttctct | 1140 |
| ttgccagcaa atggtagttg atactcagtg agggtcaaat gactagcagg ttccagggac | 1200 |
| tgcttctgtt attctctgca gttgctgaga tgaaccattt tctctgtcta ctgcaatttt | 1260 |
| tacattcaaa tgtccatgaa atttgtatta aatgtgaagt ggaatctgca gtgtttgtgt | 1320 |
| ttatattcat atactatgaa ctgaggagaa ttataaactg aaacaaatac tcgcagttaa | 1380 |
| ttgaagacct tccattgatg gacagttctt ttcctctcta tatggaaatg tataatagaa | 1440 |
| gaaataattt ttaaattaaa gtatctcttt ttgcatttca | 1480 |

<210> SEQ ID NO 23
<211> LENGTH: 545
<212> TYPE: DNA
<213> ORGANISM: Mus musculus

<400> SEQUENCE: 23

| | |
|---|---|
| cgcagaacct tagataaatt tcaggacatg gtccagaagg accttggaaa atcaaccca | 60 |
| gacactggaa atgaaaatga aggacaatgt ctggagtgaa aactacctca gttccagcca | 120 |
| tgaagagagg agagagcctg ccacccatga tggaaacaaa atgaatgcca actgtattga | 180 |
| cattggcaac tcctggtgtg ttctctttgc cagcaaatgg tagttgatac tcagtgaggg | 240 |
| tcaaatgact agcaggttcc aggactgct tctgttattc tctgcagttg ctgagatgaa | 300 |
| ccattttctc tgtctactgc aatttttaca ttcaaatgtc catgaaattt gtattaaatg | 360 |
| tgaagtggaa tctgcagtgt tgtgttat attcatatac tatgaactga ggagaattat | 420 |
| aaactgaaac aaatactcgc agttaattga agaccttcca ttgatggaca gttcttttcc | 480 |
| tctctatgtg gaaatgtata atagaagaga taattttaa attagagtat ctcttttgc | 540 |
| atttc | 545 |

<210> SEQ ID NO 24
<211> LENGTH: 3258
<212> TYPE: DNA
<213> ORGANISM: Mus musculus

<400> SEQUENCE: 24

| | |
|---|---|
| cctgggcccc gccgcggacg cgcggagccg cctgggccgc gccggaggag ggcggggaga | 60 |
| ggaccatgtg aatgtgctcc ggagctgagc gccaagccaa gcagtgtttg aaaggaagca | 120 |
| ggatgctgat ctaatcgtgg caaaaagtca gtccgaccgc tggtttcgaa gacatgtggt | 180 |
| gtatataaag tttgtgatag ttggtggaaa tttgggagct tggataatgg gctgtgtgca | 240 |
| atgtaaggat aaagaagcag cgaaactgac agaggagagg gacggcagcc tgaaccagag | 300 |
| ctctgggtac cgctatggca cagacccac ccctcagcac tacccagct cggcgtgac | 360 |
| ctccatcccg aactacaaca acttccacgc agctgggggc cagggactca ccgtctttgg | 420 |

-continued

```
gggtgtgaac tcctcctctc acactgggac cctacgcacg agaggaggga caggagtgac      480
actgtttgtg gcgctttatg actatgaagc acggacggaa gatgacctga gttttcacaa      540
aggagaaaaa tttcaaatat tgaacagctc ggaaggagat tggtgggaag cccgctcctt      600
gacaaccggg gaaactggtt acattcccag caattacgtg gctccagttg actccatcca      660 ggcagaaagag tggtactttg gaaaacttgg ccgcaaagat gctgagagac agctcctgtc     720
ctttggaaac ccaagaggta ccttcttat ccgcgagagc caaaccacca aggtgccta       780 ctcactttcc atccgtgatt gggatgatat gaaaggggac cacgtcaaac attataaaat     840
ccgcaagctt gacaatggtg gatactatat cacaacgcgg gcccagtttg aaacacttca      900
gcaactggta cagcattact cagagaaagc tgatggtttg tgttttaact taactgtggt      960
ttcatcaagt tgtaccccac aaacttctgg attggctaaa gatgcttggg aagttgcacg     1020
tgactcgttg tttctggaga agaagctggg gcagggtgt ttcgctgaag tgtggcttgg      1080
tacctggaat ggaaatacaa agtagccat aaagaccctt aagccaggca ccatgtctcc      1140
ggagtccttc ctggaggagg cgcagatcat gaagaagctg aagcatgaca agctggtgca     1200
gctctacgcg gtcgtgtctg aggagcccat ttacatcgtc acggagtaca tgagcaaagg     1260
aagtttgctt gacttcttaa aagatggtga aggaagagct ctgaagttgc caaaccttgt    1320
ggacatggcg gcacaggttg ctgcaggaat ggcttacatc gagcgcatga attatatcca     1380
cagagatctg cgatcagcaa acattctagt ggggaatgga ctaatttgca agattgctga     1440
ctttggattg gctcggttga ttgaagacaa tgaatacaca gcaagacaag gtgcgaagtt     1500
tcccattaag tggacagccc ccgaagcggc cctgtatgga aggttcacaa tcaagtctga     1560
cgtatggtct tttggaatct tactcacaga gctggtcacc aaaggaagag tgccataccc     1620
aggcatgaac aaccgggagg tgctggagca ggtggagaga ggctatagga tgccctgccc     1680
acaggactgc ccgatctccc tgcacgagct catgatccac tgctggaaaa aggatccgga     1740
agagcgcccg accttcgagt acttgcaggg cttcctggag gactactttta cggccacaga     1800 gccccagtat cagcccggtg aaaacctgtg agagcctgcg cttcagacgc ctcttcccga     1860
ggcctcccta cccctcccca ttagcttcca attctgtagc cagctgcccc agagcaggag    1920
aaccgtccag gatcagattg catgtgactc ttgaagctga acttccacgg ccctcattaa    1980
tgacacttgt cccccagtcc gaacctcctc tgtgaaccat ctgagacaga agcgtgttat    2040
ttctcagact tggaaatgca ttgtatcgat gttatgtcaa aggccaaacc tctgttcagt    2100
gtaaatagct gctcctgtgc caacaatccc agtgctttcc ttttttaaaa agaaaaagc     2160 aaatcctatg tgatttaac tctgatttca cctgattcaa ctaaaaaaaa aaagtatta      2220 ttttccaaaa gtggcctctt tgtctaaaac aataaaattt tttttcatgt tttaacaaaa    2280
aaatgatcag gacaggtgtt tgggttttt tcccttttt tatacatatg atatatatgt      2340
taacatatgt tcctgtacat acaccatgtg ggtgctacca tggagactgg ccagcgtagg    2400
ccacatagct acaggaccgg agtggggatt actgcagcgt gatcatgcaa gctcaccccc    2460
ttccagcaaa acactggtgt cagcctgcaa gccggtggct cattttttga cttctacgaa    2520
gcatgacgtc ctctccattt ggacttttta ataacctaat catacctata gattgttcat    2580 gtgactttt tcaggtccag ggcctagtca cgagttttag tgccagtttt tagtccagct     2640
caactgtgat tcgtcttgaa acttaggagt gagcatttta gcaaaaagca gccagccagt    2700
tctaccacaa gagctgcaag acggagacca cactaacttc ctgtataaat atgaatgctg    2760
aagggttcag gtgttttcct tttatttaat aaatcttgta accacattta aatggtctaa    2820
```

```
acccatagca ttggtcatgg gcaacctaaa cttttctcat gcaactaaaa ttatgggaag   2880
gctaagggtg gggggttggt acacgtccca ttgtaaaata agtgttttac tgtcctgtac   2940
tgctaatgac tgactctccg tgtcaggagt gctccagtga ataactatgc actactttac   3000
atttcatggg ggtgcacaaa aaaaaaaagg tattacagtt tttagttgct gtttgtacca   3060
acctcgaatt acgtatgttt aacaacaaat caattcctat tctattgagt tttaatactg   3120
actagcaatt ctgaagtctt aattcctttt ttttgttaat gatttacttg tgagtttaca   3180
tttttaaatt gtttaacttt cctaatttag taattaaaaa gagagcattt tacatttgaa   3240
aaaaaaaaaa aaaaaaa                                                  3258
```

<210> SEQ ID NO 25
<211> LENGTH: 515
<212> TYPE: DNA
<213> ORGANISM: Mus musculus

<400> SEQUENCE: 25

```
tttttttttt ttttttttttt tcaaatgtaa aatgctctct ttttaattac taaattagga     60
aagttaaaca atttaaaaat gtaaactcac aagtaaatca ttaacaaaaa aaggaatta     120 agacttcaga attgctagtc agtattaaaa aactcaatag aaataggaat tgatttgttg    180
ttaaacatac gtaattcgag gttggtacaa acagcaacta aaaatgtaat acttttttt    240 ttttgtgcac ccccatgaaa tgtaaagtag tgcatagtta ttcactggag cactcctgac    300
acggagagtc actcattagc agtacaggac agtaaaacac ttattttaca atgggacgtg    360
tacaaccccc caccccttgcc ttcccataat ttttagttgc atgagaaagt ttagtaggtt   420
gccatgacta caatgctatg ggtttagacc atttaaatgt ggttacaaga tttattaaat    480
aaaaggaaaa cacctgaacc cttcagcatt catat                               515
```

<210> SEQ ID NO 26
<211> LENGTH: 459
<212> TYPE: DNA
<213> ORGANISM: Mus musculus

<400> SEQUENCE: 26

```
gccaacaatc ccagtgcttt ccttttttaa aaagaaaag gcaaatccta tgtgatttta     60
actctgtctt cacctgattc aactaaaaaa aaaaagtat tattttccaa aagtggcctc    120
tttgtctaaa acaataaaat tttttttcat gttttaacaa aaaatgatca ggacaggtgt    180
ttgggttttt tttccctttt ttatacatat gatatatatg ttaacatatg ttcctgtaca    240
tacaccatgt gggtgctacc atggagactg gccagcgtag gccacatagc tacaggaccg    300
gagtggggat tactgcagaa ccctgccagc aaagcactgg tgtcagcctg caagccggtg    360
gcctcatttt ttgacttcta cgaagcatga cgtcctctcc atttggactg cactttttg     420 ggtccctaac aaacaccatt agatgggtac atggacttt                           459
```

<210> SEQ ID NO 27
<211> LENGTH: 428
<212> TYPE: DNA
<213> ORGANISM: Mus musculus

<400> SEQUENCE: 27

```
gccaacaatc ccagtgcttt ccttttttaa aaagaaaaa gcaaatccta tgtgatttta      60
actctgtctt cacctgattc aactaaaaaa aaaaaagtat tattttccaa aagtggcctc    120
tttgtctaaa acaataaaat ttttttttcat gttttaacaa aaaatgatca ggacaggtgt   180
ttgggttttt tttccctttt ttatacatat gatatatatg ttaacatatg ttcctgtaca    240
tacaccatgt gggtgctacc atggagactg gccagcgtag gcacatagct acaggaccgg    300
agtggggatt actgcagaac cctgccagca aagcactggt gtcagcctgc aagccggtgg    360 ctcattttt gacttctacg aagcatgacg tcctctccat ttggactgca cttttttggt    420
tcctaatc                                                              428
```

<210> SEQ ID NO 28
<211> LENGTH: 605
<212> TYPE: DNA
<213> ORGANISM: Mus musculus

<400> SEQUENCE: 28

```
ggatccccgg gcagagctgg gggggattt gttagcatct cttgataaac ttaattgtct     60
ctcgtcactg acggcacaga gctattgatg ggtctcaacc cccagctagt tgtcatcctg   120
ctcttctttc tcgaatgtac caggagccat atccacggat gcgacaaaaa tcacttgaga   180
gagatcatcg gcattttgaa cgaggtcaca ggagaaggga cgccatgcac ggagatggat   240
gtgccaaacg tcctcacagc aacgaagaac accacagaga gtgagctcgt ctgtagggct   300
tccaaggtgc ttcgcatatt ttatttaaaa catgggaaaa ctccatgctt gaagaagaac   360
tctagtgttc tcatggagct gcagagactc tttcgggctt ttcgatgcct ggattcatcg   420
ataagctgca ccatgaatga gtccaagtcc acatcactga aagacttcct ggaaagccta   480
aagagcatca tgcaaatgga ttactcgtag tactgagcca ccatgcttta acttatgaat   540
ttttaatggt tttattttaa tatttatata tttataattc ataaaataaa atatttgtat   600
aatgt                                                                605
```

<210> SEQ ID NO 29
<211> LENGTH: 516
<212> TYPE: DNA
<213> ORGANISM: Mus musculus

<400> SEQUENCE: 29

```
acttaattgt ctctcgtcac tgacggcaca gagctataga tgggtctcaa cccccagcta    60
gttgtcatcc tgctcttctt tctcgaatgt accaggagcc atatccacgg atgcgacaaa   120
aatcacttga gagagatcat cggcattttg aacgaggtca caggagaagg gacgccatgc   180
acggagatgg atgtgccaaa cgtcctcaca gcaacgaaga acaccacaga gagtgagctc   240
gtctgtaggg cttccaaggt gcttgcatat tttatttaac atgggaaa actccatgct    300 tgaagaagaa ctctagtgtt ctcatggagc tgcagagact ctttcgggct tttcgatgcc   360
tggattcatc gataagctgc accatgaatg agtcccagtc cacatcactg ttagacttcc   420
tggtaagcct aaatgagctt cctgccaatg gattactcgt agtactgagc acacatggct   480
taacctagtg tattcttaat gggcttaatt ttaata                              516
```